US009212153B2

(12) United States Patent
Cacatian et al.

(10) Patent No.: US 9,212,153 B2
(45) **Date of Patent: *Dec. 15, 2015**

(54) INHIBITORS OF BETA-SECRETASE

(71) Applicants: Vitae Pharmaceuticals, Inc., Fort Washington, PA (US); Boehringer Ingelheim International GmbH, Ingelheim Am Rhein (DE)

(72) Inventors: Salvacion Cacatian, Conshohocken, PA (US); David A. Claremon, Maple Glen, PA (US); Lawrence Wayne Dillard, Yardley, PA (US); Klaus Fuchs, Ingelheim Am Rhein (DE); Niklas Heine, Ingelheim Am Rhein (DE); Lanqi Jia, Horsham, PA (US); Katerina Leftheris, San Diego, CA (US); Brian McKeever, Lake Ronkonkoma, NY (US); Angel Morales-Ramos, Blue Bell, PA (US); Suresh B. Singh, Kendall Park, NJ (US); Shankar Venkatraman, Lansdale, PA (US); Guosheng Wu, Yardley, PA (US); Zhongren Wu, Audubon, PA (US); Zhenrong Xu, Chalfont, PA (US); Jing Yuan, Lansdale, PA (US); Yajun Zheng, Hockessin (DE)

(73) Assignees: Vitae Pharmaceuticals, Inc., Fort Washington, PA (US); Boehringer Ingelheim International GmbH, Ingelheim Am Rheiin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/132,877

(22) Filed: Dec. 18, 2013

(65) Prior Publication Data

US 2014/0200223 A1 Jul. 17, 2014

Related U.S. Application Data

(63) Continuation of application No. 12/723,137, filed on Mar. 12, 2010, now Pat. No. 8,633,212.

(60) Provisional application No. 61/307,542, filed on Feb. 24, 2010, provisional application No. 61/210,146, filed on Mar. 13, 2009.

(51) Int. Cl.

| | |
|---|---|
| *C07D 271/12* | (2006.01) |
| *C07D 235/02* | (2006.01) |
| *C07D 239/70* | (2006.01) |
| *C07D 277/60* | (2006.01) |
| *C07D 403/06* | (2006.01) |
| *C07D 405/12* | (2006.01) |
| *C07D 487/10* | (2006.01) |
| *C07D 491/10* | (2006.01) |
| *C07D 498/10* | (2006.01) |
| *C07D 233/46* | (2006.01) |
| *C07D 405/06* | (2006.01) |
| *C07D 413/04* | (2006.01) |
| *C07D 417/06* | (2006.01) |

(52) U.S. Cl.

CPC ............ *C07D 271/12* (2013.01); *C07D 233/46* (2013.01); *C07D 235/02* (2013.01); *C07D 239/70* (2013.01); *C07D 277/60* (2013.01); *C07D 403/06* (2013.01); *C07D 405/06* (2013.01); *C07D 405/12* (2013.01); *C07D 413/04* (2013.01); *C07D 417/06* (2013.01); *C07D 487/10* (2013.01); *C07D 491/10* (2013.01); *C07D 498/10* (2013.01)

(58) Field of Classification Search

CPC .................................................... C07D 271/12

See application file for complete search history.

(56) References Cited

U.S. PATENT DOCUMENTS

| | | | |
|---|---|---|---|
| 4,874,869 | A | 10/1989 | Ueda et al. |
| 5,430,048 | A | 7/1995 | Gadwood |

(Continued)

FOREIGN PATENT DOCUMENTS

| | | | |
|---|---|---|---|
| WO | WO-9305045 | A1 | 3/1993 |
| WO | WO-9530642 | A1 | 11/1995 |

(Continued)

OTHER PUBLICATIONS

Gadwood et al., "Synthesis and Biological Activity of Spirocyclic Benzopyran Imidazolone Potassium Channel Openers," J. Med. Chem., 36(10):1480-1487 (1993).
International Search Report for related International Application No. PCT/US2009/004686, Feb. 12, 2010.
International Search Report for related International Application No. PCT/US2010/027173, Sep. 6, 2010.
Kobayashi et al., "Preparation of 2-amino-4-phenyl-4, 5-dihydro-5H-1, 3-thiazine derivatives and related compounds for treatment of Alzheimer's disease," Shionogi & Co., Ltd., Japan, pp. 354 [CAPLUS 2008:1339943][Entered STN: Nov. 7, 2008].

(Continued)

*Primary Examiner* — Paul Zarek

(74) *Attorney, Agent, or Firm* — McCarter & English, LLP; Steven G. Davis; Xin Zhang

(57) ABSTRACT

The present invention is directed to a compound represented by the following structural formula

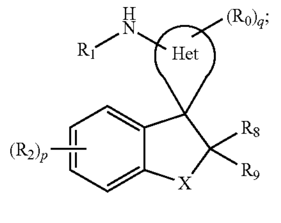

or a pharmaceutically acceptable salt thereof. Pharmaceutical compositions and method of use of the compounds are also described.

23 Claims, No Drawings

(56) References Cited

U.S. PATENT DOCUMENTS

| | | | |
|---|---|---|---|
| 7,423,158 | B2 | 9/2008 | Malamas et al. |
| 7,607,246 | B2 | 10/2009 | Valiyambath Krishnan et al. |
| 7,872,009 | B2 | 1/2011 | Albrecht et al. |
| 8,426,447 | B2 | 4/2013 | White et al. |
| 8,450,308 | B2 | 5/2013 | Dillard et al. |
| 2005/0282825 | A1 | 12/2005 | Malamas et al. |
| 2005/0282826 | A1 | 12/2005 | Malamas et al. |
| 2006/0111370 | A1 | 5/2006 | Zhu et al. |
| 2006/0281730 | A1 | 12/2006 | Zhu et al. |
| 2006/0287294 | A1 | 12/2006 | Zhu et al. |
| 2007/0004730 | A1 | 1/2007 | Zhou et al. |
| 2007/0004786 | A1 | 1/2007 | Malamas et al. |
| 2007/0027199 | A1 | 2/2007 | Malamas et al. |
| 2007/0072925 | A1 | 3/2007 | Malamas et al. |
| 2007/0203116 | A1 | 8/2007 | Quagliato et al. |
| 2007/0287692 | A1 | 12/2007 | Wu et al. |
| 2009/0209529 | A1 | 8/2009 | Andreini et al. |
| 2011/0152253 | A1 | 6/2011 | Motoki et al. |
| 2011/0218192 | A1 | 9/2011 | Dillard et al. |
| 2013/0053377 | A1 | 2/2013 | Dillard et al. |
| 2013/0289050 | A1 | 10/2013 | Bukhtiyarov et al. |

FOREIGN PATENT DOCUMENTS

| | | | |
|---|---|---|---|
| WO | WO-2005058311 | A1 | 6/2005 |
| WO | 2006044497 | A2 | 4/2006 |
| WO | WO-2006065277 | A2 | 6/2006 |
| WO | WO-2007016012 | A2 | 2/2007 |
| WO | WO-2007038271 | A1 | 4/2007 |
| WO | WO-2007049532 | A1 | 5/2007 |
| WO | WO-2007063114 | A2 | 6/2007 |
| WO | WO-2007076284 | A2 | 7/2007 |
| WO | WO-2007078813 | A2 | 7/2007 |
| WO | WO-2007100536 | A1 | 9/2007 |
| WO | WO-2008010481 | A1 | 1/2008 |
| WO | WO-2008030412 | A2 | 3/2008 |
| WO | WO-2008076043 | A1 | 6/2008 |
| WO | WO-2008076044 | A1 | 6/2008 |
| WO | WO-2008076045 | A1 | 6/2008 |
| WO | WO-2008076046 | A1 | 6/2008 |
| WO | WO-2008103351 | A2 | 8/2008 |
| WO | WO-2008115552 | A1 | 9/2008 |
| WO | WO-2008118379 | A2 | 10/2008 |
| WO | WO-2008133273 | A1 | 11/2008 |
| WO | WO-2008133274 | A1 | 11/2008 |
| WO | WO-2008150217 | A1 | 12/2008 |
| WO | WO-2009134617 | A1 | 11/2009 |
| WO | WO-2010013302 | A1 | 2/2010 |
| WO | WO-2010013794 | A1 | 2/2010 |
| WO | WO-2010021680 | A2 | 2/2010 |
| WO | 2010/058333 | A1 | 5/2010 |
| WO | WO-2010105179 | A2 | 9/2010 |
| WO | WO-2011072064 | A1 | 6/2011 |
| WO | WO-2011106414 | A1 | 9/2011 |
| WO | WO-2013134085 | A1 | 9/2013 |

OTHER PUBLICATIONS

Malamas et al., "Aminoimidazoles as Potent and Selective Human Beta-Secretase (BACE1) Inhibitors," J. Med. Chem., 52:6314-6323 (2009).

Malamas et al., "Design and Synthesis of 5,5'-Disubstituted Aminohydantoins as Potent and Selective Human Beta-Secretase (BACE1) Inhibitors," J. Med. Chem., 53:1146-1158 (2010).

Malamas et al., "Di-substituted pyridinyl aminohydantoins as potent and highly selective human beta-secretase (BACE1) inhibitors," Bioorganic & Medicinal Chemistry, 18:630-639 (2010).

Nowak et al., "Discovery and initial optimization of 5,5'-disubstituted aminohydantoins as potent beta-secretase (BACE1) inhibitors," Bioorganic & Medicinal Chemistry Letters, 20:632-635 (2010).

Silvestri, "Boom in the Development of Non-Peptidic Beta-Secretase (BACE1) Inhibitors for the Treatment of Alzheimer's Disease," Medicinal Research Reviews, 29(2):295-338 (2009).

Wang et al., "Application of Fragment-Based NMR Screening, X-ray Crystallography, Structure-Based Design, and Focused Chemical Library Design to Identify Novel μM Leads for the Development of nM BACE-1 (Beta-Site APP Cleaving Enzyme 1) Inhibitors," J. Med. Chem., 53:942-950 (2010).

Written Opinion for related International Application No. PCT/US2010/027173, Sep. 6, 2010.

Written Opinion for related International Application No. PCT/US2009/004686, Feb. 12, 2010.

Zhu et al., "Discovery of Cyclic Acylguanidines as Highly Potent and Selective Beta-Site Amyloid Cleaving Enzyme (BACE) Inhibitors: Part I—Inhibitor Design and Validation," J. Med. Chem., 53:951-965 (2010).

Zhu et al., "Preparation of imidazolidin-2-imines and their analogs as aspartyl protease inhibitors for treating various diseases," Schering Corporation, USA; Pharmacopeia, Inc., pp. 702 [CA 149:307845][Entered STN: Sep. 25, 2008].

Huang et al, "Pharmacaphore Model Construction of β-Secretase Inhibitors", Acta Chimica Sinica, 66(16): 1889-1897 (2008).

Liao et al, "Evolution of design and development of BACE1 inhibitors", Chinese Journal of Medicinal Chemistry, 16(6): 373-379 (2006).

INHIBITORS OF BETA-SECRETASE

RELATED APPLICATIONS

This application is a continuation application of U.S. patent application Ser. No. 12/723,137, filed on Mar. 12, 2010, now issued as U.S. Pat. No. 8,633,212, which claims priority from U.S. Provisional Patent Application Ser. No. 61/307,542, filed on Feb. 24, 2010 and U.S. Provisional Patent Application Ser. No. 61/210,146, filed on Mar. 13, 2009, the contents of which are all incorporated herein by reference in their entireties.

BACKGROUND OF THE INVENTION

β-Amyloid deposits and neurofibrillary tangles are two major pathologic characterizations associated with Alzheimer's disease (AD). Clinically, AD is characterized by the loss of memory, cognition, reasoning, judgment, and orientation. Also affected, as the disease progresses, are motor, sensory and linguistic abilities until global impairment of multiple cognitive functions occurs. These cognitive losses take place gradually, but typically lead to severe impairment and eventual death in 4-12 years.

β-Amyloid deposits are predominantly an aggregate of Aβ peptide, which in turn is a product of the proteolysis of amyloid precursor protein (APP). More specifically, Aβ peptide results from the cleavage of APP at the C-terminals by one or more γ-secretases, and at the N-terminus by β-secretase enzyme (BACE), also known as aspartyl protease, as part of the β-amyloidogenic pathway.

BACE activity is correlated directly to the generation of Aβ peptide from APP, and studies increasingly indicate that the inhibition of BACE inhibits the production of Aβ peptide.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders.

Recently, Amyloid-β (Aβ) has been reported to be implicated in the development of RGC apotosis in glaucoma, with evidence of caspase-3-mediated abnormal amyloid precursor protein processing, increased expression of Aβ in RGCs in experimental glaucoma and decreased vitreous Aβ levels (consistent with retinal Aβ deposition) in patients with glaucoma.

The present invention provides compounds that are BACE inhibitors and are useful as therapeutic agents in the treatment, prevention and amelioration of a disease or disorder characterized by elevated β-amyloid deposits or β-amyloid levels in a patient.

SUMMARY OF THE INVENTION

In one embodiment, the present invention is directed to a compound represented by the following Structural Formula:

(A)

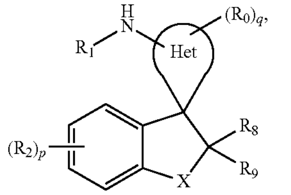

or a pharmaceutically acceptable salt thereof, wherein:

ring Het is a 5 membered monocyclic heterocycle or a 6 membered monocyclic heterocycle;

$R_a$ and $R_b$ are each independently —H, -halogen, $(C_1$-$C_4)$alkyl, methoxy, fluoromethoxy, methoxy$(C_1$-$C_4)$alkyl and fluoro$(C_1$-$C_4)$alkyl;

each $R_0$ is independent selected from —H, =O, =S, =$NR_{15}$, $(C_1$-$C_6)$alkyl, halo$(C_1$-$C_6)$alkyl, —CN, —$NO_2$, halogen, —$OR_5$, —$NR_6R_7$, —$S(O)_iR_5$, —$S(O)_iNR_{12}R_{13}$, —$NR_{11}S(O)_iR_5$, —C(=O)$OR_5$, —OC(=O)$OR_5$, —C(=S)$OR_5$, —O(C=S)$R_5$, —C(=O)$NR_{12}R_{13}$, —$NR_{11}$C(=O)$R_5$, —C(=S)$NR_{12}R_{13}$, —$NR_{11}$C(=S)$R_5$, —$NR_{11}$(C=O)$OR_5$, —O(C=O)$NR_{12}R_{13}$, —$NR_{11}$(C=S)$OR_5$, —O(C=S)$NR_{12}R_{13}$, —$NR_{11}$(C=O)$NR_{12}R_{13}$, —$NR_{11}$(C=S)$NR_{12}R_{13}$, —C(=S)$R_5$, —C(=O)$R_5$, $(C_3$-$C_8)$cycloalkyl, $(C_3$-$C_8)$cycloalkyl$(C_1$-$C_3)$alkyl, $(C_3$-$C_9)$heterocycloalkyl, $(C_3$-$C_9)$heterocycloalkyl$(C_1$-$C_3)$alkyl, aryl, aryl$(C_1$-$C_6)$alkyl, heteroaryl or heteroaryl$(C_1$-$C_6)$alkyl, each of the $(C_1$-$C_6)$alkyl, halo$(C_1$-$C_6)$alkyl, $(C_3$-$C_8)$cycloalkyl, $(C_3$-$C_8)$cycloalkyl$(C_1$-$C_3)$alkyl, $(C_3$-$C_9)$heterocycloalkyl, $(C_3$-$C_9)$heterocycloalkyl$(C_1$-$C_3)$alkyl, aryl, aryl$(C_1$-$C_6)$alkyl, heteroaryl or heteroaryl$(C_1$-$C_6)$alkyl group represented by $R_0$ is optionally substituted with 1 to 5 substituents independently selected from the group consisting of -halogen, —CN, $(C_1$-$C_6)$alkyl, halo$(C_1$-$C_6)$alkyl, $(C_1$-$C_3)$alkoxy, halo$(C_1$-$C_3)$alkoxy, $(C_1$-$C_3)$alkoxy$(C_1$-$C_3)$alkyl, $(C_3$-$C_8)$cycloalkyl, $(C_3$-$C_9)$heterocycloalkyl, aryl, heteroaryl, —$NR_6R_7$, —$NR_{11}S(O)_iR_5$, —C(=O)$NR_{12}R_{13}$, —$NR_{11}$C(=O)$R_5$, —$S(O)_iR_5$—, —$S(O)_iNR_{12}R_{13}$, —$OR_5$, —C(=O)$R_5$, —C(=S)$NR_{12}R_{13}$, —$NR_{11}$C(=S)$R_5$, —C(O)$OR_5$, —OC(=O)$OR_5$, —C(=S)$OR_5$, —O(C=S)$R_5$, —O(C=O)$NR_{12}R_{13}$, (C=O)$OR_5$, (C=S)$OR_5$, —O(C=S)$NR_{12}R_{13}$, —$NR_{11}$(C=O)$NR_{12}R_{13}$, —$NR_{11}$(C=S)$NR_{12}R_{13}$ and —C(=S)$R_5$, wherein the cycloalkyl, heterocycloalkyl, aryl and heteroaryl groups in the substituents on the groups represented by $R_0$ are each optionally substituted with 1 to 3 substituents independently selected from halogen, —CN, $(C_1$-$C_6)$alkyl, halo$(C_1$-$C_6)$alkyl, $(C_1$-$C_3)$alkoxy, halo$(C_1$-$C_3)$alkoxy and $(C_1$-$C_3)$alkoxy$(C_1$-$C_6)$alkyl;

$R_1$ is —H, —OH, —$(C_1$-$C_4)$alkoxy, $(C_1$-$C_6)$alkyl, aryl$(C_1$-$C_6)$alkyl, or heteroaryl$(C_1$-$C_6)$alkyl; wherein each alkyl, aryl and heteroaryl is optionally substituted with 1 to 5 substituents independently selected from halogen, —CN, —OH, $(C_1$-$C_4)$alkyl, halo$(C_1$-$C_4)$alkyl, $(C_1$-$C_3)$alkoxy and halo$(C_1$-$C_3)$alkoxy;

each $R_2$ is independently selected from a) —H, -halogen, —CN, —$NO_2$, —$OR_5$, —$NR_6R_7$, —$S(O)_iR_5$, —$NR_{11}S(O)_iR_5$, —$S(O)_iNR_{12}R_{13}$, C(=O)$OR_5$, —OC(=O)$OR_5$, —C(=S)$OR_5$, —O(C=S)$R_5$, —C(=O)$NR_{12}R_{13}$, C(=O)$R_5$, —C(=S)$NR_{12}R_{13}$, —C(=S)$R_5$, (C=O)$OR_5$, —O(C=O)$NR_{12}R_{13}$, (C=S)$OR_5$, —O(C=S)$NR_{12}R_{13}$, —$NR_{11}$(C=O)$NR_{12}R_{13}$, —$NR_{11}$(C=S)$NR_{12}R_{13}$, —C(=S)$R_5$, and —C(=O)$R_5$; and b) $(C_1$-$C_6)$alkyl, $(C_2$-$C_6)$alkenyl, $(C_2$-$C_6)$alkynyl, $(C_3$-$C_8)$cycloalkyl, $(C_3$-$C_8)$cycloalkyl$(C_1$-$C_6)$alkyl, $(C_3$-$C_8)$cycloalkyl$(C_2$-$C_6)$alkynyl, $(C_4$-$C_8)$cycloalkenyl, $(C_3$-$C_9)$heterocycloalkyl, $(C_3$-$C_9)$heterocycloalkyl($C_1$-$C_6$)alkyl, ($C_3$-$C_9$)heterocycloalkyl($C_2$-$C_6$)alkynyl, aryl, aryl($C_1$-$C_6$)alkyl, aryl($C_2$-$C_6$)alkynyl, heteroaryl, heteroaryl($C_1$-$C_6$)alkyl, and heteroaryl($C_2$-$C_6$)alkynyl, wherein each of the ($C_1$-$C_6$)alkyl, ($C_2$-$C_6$)alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkynyl, ($C_4$-$C_8$)cycloalkenyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkynyl, aryl, aryl($C_1$-$C_6$)alkyl, aryl($C_2$-$C_6$)alkynyl, heteroaryl, heteroaryl($C_1$-$C_6$)alkyl, and heteroaryl($C_2$-$C_6$)alkynyl groups represented by $R_2$ is optionally substituted with 1 to 5 substituents independently selected from the group consisting of -halogen, —CN, —$NO_2$, —$OR_5$, —$SR_5$, —$NR_6R_7$, —$S(O)_iR_5$, —$NR_{11}S(=O)_iR_5$, —$S(O)_iNR_{12}R_{13}$, —C(=O)$OR_5$, —OC(=O)$R_5$, —C(=S)$OR_5$, —OC(=S)$R_5$, —C(=O)$NR_{12}R_{13}$, —$NR_{11}$C(=O)$R_5$, —C(=S)$NR_{12}R_{13}$, —$NR_{11}$C(=S)$R_5$, —C(=O)$R_5$, —C(=S)$R_5$, —OC(=O)$OR_5$, —O(C=O)$NR_{12}R_{13}$, —$NR_{11}$(C=O)$OR_5$, —$NR_{11}$(C=S)$OR_5$, —O(C=S)$NR_{12}R_{13}$, —$NR_{11}$(C=O)$NR_{12}R_{13}$, (C=S)$NR_{12}R_{13}$, —C(=O)$R_5$, —C(=S)$R_5$, ($C_1$-$C_6$)alkyl, ($C_2$-$C_6$)alkynyl, ($C_3$-$C_8$)cycloalkyl, ($C_4$-$C_8$)cycloalkenyl, ($C_3$-$C_9$)heterocycloalkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl, wherein the cycloalkyl, heterocycloalkyl, aryl and heteroaryl groups in the substituents on the groups represented by $R_2$ are each optionally substituted with 1 to 3 substituents independently selected from halogen, —CN, ($C_1$-$C_6$)alkyl, halo($C_1$-$C_6$)alkyl, ($C_1$-$C_3$)alkoxy, halo($C_1$-$C_3$)alkoxy and ($C_1$-$C_3$)alkoxy($C_1$-$C_6$)alkyl;

$R_3$ and $R_4$ are each independently —H, -halogen, —CN, —$NO_2$, —$OR_5$, —$NR_6R_7$, —$S(O)_iR_5$, —$NR_{11}S(O)_iR_5$, —$S(O)_iNR_{12}R_{13}$, —C(=O)$OR_5$, —OC(=O)$OR_5$, —C(=S)$OR_5$, —O(C=S)$R_5$, —C(=O)$NR_{12}R_{13}$, C(=O)$R_5$, —C(=S)$NR_{12}R_{13}$, —C(=S)$R_5$, (C=O)$OR_5$, —O(C=O)$NR_{12}R_{13}$, (C=S)$OR_5$, —O(C=S)$NR_{12}R_{13}$, (C=O)$NR_{12}R_{13}$, —$NR_{11}$(C=S)$NR_{12}R_{13}$, —C(=S)$R_5$, —C(=O)$R_5$, ($C_1$-$C_6$)alkyl, ($C_2$-$C_6$)alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkynyl, aryl, aryl($C_1$-$C_6$)alkyl, aryl($C_2$-$C_6$)alkynyl, heteroaryl, heteroaryl($C_1$-$C_6$)alkyl or heteroaryl($C_1$-$C_6$)alkynyl, wherein each ($C_1$-$C_6$)alkyl, ($C_2$-$C_6$)alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkynyl, aryl, aryl($C_1$-$C_6$)alkyl, aryl($C_2$-$C_6$)alkynyl, heteroaryl, heteroaryl($C_1$-$C_6$)alkyl or heteroaryl($C_1$-$C_6$)alkynyl represented by $R_3$ and $R_4$ is optionally substituted with 1 to 5 substituents independently selected from the group consisting of halogen, —$OR_5$, —$NR_6R_7$, —$S(O)_iR_5$, —$NR_{11}S(O)_iR_5$, —$S(O)_iNR_{12}R_{13}$, —C(=O)$OR_5$, —OC(=O)$OR_5$, —C(=S)$OR_5$, —O(C=S)$R_5$, —C(=O)$NR_{12}R_{13}$, C(=O)$R_5$, —C(=S)$NR_{12}R_{13}$, —C(=S)$R_5$, (C=O)$OR_5$, —O(C=O)$NR_{12}R_{13}$, (C=S)$OR_5$, —O(C=S)$NR_{12}R_{13}$, (C=O)$NR_{12}R_{13}$, —$NR_{11}$(C=S)$NR_{12}R_{13}$, —C(=S)$R_5$, —C(=O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, ($C_3$-$C_8$)cycloalkyl, ($C_3$-$C_9$)heterocycloalkyl, aryl and heteroaryl, wherein the cycloalkyl, heterocycloalkyl, aryl and heteroaryl groups in the substituents on the groups represented by $R_3$ and $R_4$ are each optionally substituted with 1 to 3 substituents independently selected from halogen, —CN, ($C_1$-$C_6$)alkyl, halo($C_1$-$C_6$)alkyl, ($C_1$-$C_3$)alkoxy, halo($C_1$-$C_3$)alkoxy and ($C_1$-$C_3$)alkoxy($C_1$-$C_6$)alkyl;

or $R_3$ and $R_4$, together with the carbon to which they are attached, form ring A, which is a 3-14 membered monocyclic ring, 9-14 membered bicyclic ring or 9-14 membered polycyclic ring, wherein ring A optionally contains 1 to 3 heteroatoms independently selected from O, N, and S and when the heteroatom is nitrogen, the nitrogens is substituted with —H, ($C_1$-$C_3$)alkyl or halo($C_1$-$C_3$)alkyl, and when the heteroatom is sulfur, the sulfurs is optionally mono or di-oxygenated; and ring A is optionally substituted with 1 to 4 substituents independently selected from the group consisting of -halogen, —CN, —$OR_5$, —$NR_6R_7$, —$S(O)_iR_5$, —$NR_{11}S(O)_iR_5$, —$S(O)_iNR_{12}R_{13}$, —C(=O)$OR_5$, —OC(=O)$OR_5$, —C(=S)$OR_5$, —O(C=S)$R_5$, —C(=O)$NR_{12}R_{13}$, —$NR_{11}$C(=O)$R_5$, —C(=S)$NR_{12}R_{13}$, —$NR_{11}$C(=S)$R_5$, —$NR_{11}$(C=O)$OR_5$, —O(C=O)$NR_{12}R_{13}$, —$NR_{11}$(C=S)$OR_5$, —O(C=S)$NR_{12}R_{13}$, —$NR_{11}$(C=O)$NR_{12}R_{13}$, —$NR_{11}$(C=S)$NR_{12}R_{13}$, —C(=S)$R_5$, —C(=O)$R_5$, ($C_1$-$C_6$)alkyl, ($C_2$-$C_6$)alkenyl, halo($C_1$-$C_6$)alkyl, ($C_1$-$C_3$)alkylsulfonylamino($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkynyl, ($C_3$-$C_9$)hetero cycloalkyl, ($C_3$-$C_9$)heterocycloalkyl($C_1$-$C_6$)alkyl, ($C_3$-$C_9$)heterocycloalkyl($C_2$-$C_6$)alkynyl, aryl, aryl($C_1$-$C_6$)alkyl, aryl($C_2$-$C_6$)alkynyl, heteroaryl, heteroaryl($C_1$-$C_6$)alkyl, and heteroaryl($C_2$-$C_6$)alkynyl, wherein the cycloalkyl, heterocycloalkyl, aryl and heteroaryl groups in the substituents on ring A are each optionally substituted with 1 to 3 substituents independently selected from halogen, —CN, ($C_1$-$C_6$)alkyl, halo($C_1$-$C_6$)alkyl, ($C_1$-$C_3$)alkoxy, halo($C_1$-$C_3$)alkoxy and ($C_1$-$C_3$)alkoxy($C_1$-$C_6$)alkyl;

$R_5$ is —H, ($C_1$-$C_6$)alkyl, halo($C_1$-$C_6$)alkyl, ($C_2$-$C_6$)alkenyl, ($C_2$-$C_6$)alkynyl, ($C_1$-$C_3$)alkoxy($C_1$-$C_6$)alkyl, ($C_3$-$C_8$)cycloalkyl, ($C_3$-$C_8$)cycloalkyl($C_1$-$C_6$)alkyl, ($C_3$-$C_9$)heterocycloalkyl, ($C_3$-$C_9$)heterocycloalkyl($C_1$-$C_6$)alkyl, aryl, aryl($C_1$-$C_6$)alkyl, heteroaryl or heteroaryl($C_1$-$C_6$)alkyl, each of the alkyl, alkenyl, alkynyl, cycloalkyl, heterocycloalkyl, aryl and heteroaryl in the groups represented by $R_5$ is optionally substituted with 1 to 5 substituents independently selected from the group consisting of halogen, =O, —$NR_6$C(=NH)$NR_6R_7$, —C(=O)$OR_c$, —$OR_c$, —$SR_c$, —C(=O)$NR_6R_7$, —C(=O)$R_c$, —$S(O)_iR_c$, —$NO_2$, —CN, ($C_1$-$C_6$)alkyl, halo($C_1$-$C_6$)alkyl, ($C_1$-$C_3$)alkoxy($C_1$-$C_6$)alkyl, ($C_1$-$C_3$)alkoxy, halo($C_1$-$C_3$)alkoxy and —$NR_6R_7$;

$R_c$ is —H, ($C_1$-$C_3$)alkyl, halo($C_1$-$C_3$)alkyl or ($C_1$-$C_3$)alkoxy($C_1$-$C_3$)alkyl;

$R_6$ and $R_7$ are each independently —H, ($C_1$-$C_6$)alkyl, hydroxy($C_1$-$C_6$)alkyl, halo($C_1$-$C_6$)alkyl, ($C_3$-$C_8$)cycloalkyl, ($C_3$-$C_8$)cycloalkyl($C_1$-$C_6$)alkyl, ($C_3$-$C_9$)heterocycloalkyl, ($C_3$-$C_9$)heterocycloalkyl($C_1$-$C_6$)alkyl, aryl, aryl($C_1$-$C_6$)alkyl, heteroaryl, or heteroaryl($C_1$-$C_6$)alkyl, all of which groups are optionally substituted with 1 to 3 substituents independently selected from the group consisting of halogen, —CN, ($C_1$-$C_6$)alkyl, halo($C_1$-$C_6$)alkyl, ($C_1$-$C_3$)alkoxy, halo($C_1$-$C_3$)alkoxy and ($C_1$-$C_3$)alkoxy($C_1$-$C_6$)alkyl;

$R_8$ and $R_9$, together with the carbon to which they are attached, form ring A, which is a 3-14 membered monocyclic ring, 9-14 membered bicyclic ring or 9-14 membered polycyclic ring, wherein ring A optionally contains 1 to 3 heteroatoms independently selected from O, N, and S and when the heteroatom is nitrogen, the nitrogen is substituted with —H, ($C_1$-$C_3$)alkyl or halo($C_1$-$C_3$)alkyl, and when the heteroatom is sulfur, the sulfur is optionally mono or di-oxygenated; and ring A is optionally substituted with 1 to 4 substituents independently selected from the group consisting of from halogen, —CN, —$OR_5$, —$NR_6R_7$, —$S(O)_iR_5$, —$NR_{11}S(O)_iR_5$, —$S(O)_iNR_{12}R_{13}$, —C(═O)$OR_5$, —OC(═O)$OR_5$, —C(═S)$OR_5$, —O(C═S)$R_5$, —C(═O)$NR_{12}R_{13}$, —$NR_{11}$C(═O)$R_5$, —C(═S)$NR_{12}R_{13}$, —$NR_{11}$C(═S)$R_5$, —$NR_{11}$(C═O)$OR_5$, —O(C═O)$NR_{12}R_{13}$, —$NR_{11}$(C═S)$OR_5$, —O(C═S)$NR_{12}R_{13}$, —$NR_{11}$(C═O)$NR_{12}R_{13}$, —$NR_{11}$(C═S)$NR_{12}R_{13}$, —C(═S)$R_5$, —C(═O)$R_5$, ($C_1$-$C_6$)alkyl, ($C_2$-$C_6$)alkenyl, halo($C_1$-$C_6$)alkyl, ($C_1$-$C_3$)alkylsulfonylamino($C_1$-$C_6$)alkyl, hydroxy($C_1$-$C_6$)alkyl, cyano ($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, —$C_6$)alkoxy($C_1$-$C_3$)alkyl, ($C_3$-$C_8$)cycloalkyl, ($C_3$-$C_8$)cycloalkyl($C_1$-$C_6$)alkyl, ($C_3$-$C_8$) cycloalkyl($C_2$-$C_6$)alkynyl, ($C_3$-$C_9$)hetero cycloalkyl, ($C_3$-$C_9$)heterocycloalkyl($C_1$-$C_6$)alkyl, ($C_3$-$C_9$)heterocycloalkyl ($C_2$-$C_6$)alkynyl, aryl, aryl($C_1$-$C_6$)alkyl, aryl($C_2$-$C_6$)alkynyl, heteroaryl, heteroaryl($C_1$-$C_6$)alkyl, and heteroaryl($C_2$-$C_6$) alkynyl, wherein the cycloalkyl, heterocycloalkyl, aryl and heteroaryl groups in the substituents on ring A are each optionally substituted with 1 to 3 substituents independently selected from halogen, —CN, ($C_1$-$C_6$)alkyl, halo($C_1$-$C_6$) alkyl, ($C_1$-$C_3$)alkoxy, halo($C_1$-$C_3$)alkoxy and ($C_1$-$C_3$)alkoxy ($C_1$-$C_6$)alkyl, or two substituents attached to the same ring atom of ring A can together with the ring atom to which they are attached form a 3 to 6 membered cycloalkyl, heterocycloalkyl, aryl or heteroaryl ring optionally substituted with 1 to 3 substituents independently selected from -halogen, —CN, —$OR_5$, —$NR_6R_7$, —$S(O)_iR_5$, —$NR_{11}$S(═O)$_iR_5$, —C(═O)$OR_5$, —C(═O)$NR_{12}R_{13}$, —$NR_{11}$C(═O)$R_5$, —C(═S)$NR_{12}R_{13}$, —C(═O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$) alkoxy, ($C_1$-$C_6$)alkoxy($C_1$-$C_3$)alkyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$) alkynyl, heterocycloalkyl, heterocycloalkyl($C_1$-$C_6$)alkyl, heterocycloalkyl($C_2$-$C_6$)alkynyl, aryl, aryl($C_1$-$C_6$)alkyl, aryl ($C_2$-$C_6$)alkynyl, heteroaryl, heteroaryl($C_1$-$C_6$)alkyl, and heteroaryl($C_2$-$C_6$)alkynyl; or when $R_3$ and $R_4$, together with the carbon to which they are attached, form a ring A, $R_8$ and $R_9$ are each independently —H, -halogen, —CN, —$NO_2$, —$OR_5$, —$NR_6R_7$, —$S(O)_iR_5$, —$S(O)_iNR_{12}R_{13}$, —$NR_{11}S(O)_iR_5$, —C(═O)$OR_5$, —OC (═O)$OR_5$, —C(═S)$OR_5$, —O(C═S)$R_5$, —C(═O) $NR_{12}R_{13}$, —$NR_{11}$C(═O)$R_5$, —C(═S)$NR_{12}R_{13}$, —$NR_{11}$C (═S)$R_5$, —$NR_{11}$(C═O)$OR_5$, —O(C═O)$NR_{12}R_{13}$, —$NR_{11}$(C═S)$OR_5$, —O(C═S)$NR_{12}R_{13}$, —$NR_{11}$(C═O) $NR_{12}R_{13}$, —$NR_{11}$(C═S)$NR_{12}R_{13}$, —C(═S)$R_5$, and —C(═O)$R_5$, ($C_1$-$C_6$)alkyl, ($C_2$-$C_6$)alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$) cycloalkyl($C_2$-$C_6$)alkynyl, ($C_3$-$C_9$)heterocycloalkyl, ($C_3$-$C_9$) heterocycloalkyl($C_1$-$C_6$)alkyl, ($C_3$-$C_9$)heterocycloalkyl($C_2$-$C_6$)alkynyl, aryl, aryl($C_1$-$C_6$)alkyl, aryl($C_2$-$C_6$)alkynyl, heteroaryl, heteroaryl($C_1$-$C_6$)alkyl or heteroaryl($C_1$-$C_6$)alkynyl, wherein each ($C_1$-$C_6$)alkyl, ($C_2$-$C_6$)alkenyl, ($C_2$-$C_6$) alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkynyl, aryl, aryl($C_1$-$C_6$)alkyl, aryl($C_2$-$C_6$) alkynyl, heteroaryl, heteroaryl($C_1$-$C_6$)alkyl or heteroaryl($C_1$-$C_6$)alkynyl group represented by $R_8$ and $R_9$ is optionally substituted with 1 to 5 substituents independently selected from the group consisting of -halogen, —CN, —$OR_5$, —$NR_6R_7$, —$S(O)_iR_5$, —$S(O)_iNR_{12}R_{13}$, —$NR_{11}S(O)_iR_5$, —C(═O)$OR_5$, —OC(═O)$OR_5$, —C(═S)$OR_5$, —O(C═S) $R_5$, —C(═O)$NR_{12}R_{13}$, —$NR_{11}$C(═O)$R_5$, —C(═S) $NR_{12}R_{13}$, —$NR_{11}$C(═S)$R_5$, —$NR_{11}$(C═O)$OR_5$, —O(C═O)$NR_{12}R_{13}$, —$NR_{11}$(C═S)$OR_5$, —O(C═S) $NR_{12}R_{13}$, —$NR_{11}$(C═O)$NR_{12}R_{13}$, —$NR_{11}$(C═S) $NR_{12}R_{13}$, —C(═S)$R_5$, —C(═O)$R_5$, ($C_1$-$C_6$)alkyl, ($C_2$-$C_6$) alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$) alkoxy, ($C_1$-$C_6$)alkoxy($C_1$-$C_3$)alkyl, ($C_3$-$C_8$)cycloalkyl, ($C_3$-$C_9$)heterocycloalkyl, aryl and heteroaryl, wherein the cycloalkyl, heterocycloalkyl, aryl and heteroaryl groups in the substituents on the groups represented by $R_8$ and $R_9$ are each optionally substituted with 1 to 3 substituents independently selected from halogen, —CN, ($C_1$-$C_6$)alkyl, halo($C_1$-$C_6$)alkyl, ($C_1$-$C_3$)alkoxy and ($C_1$-$C_3$)alkoxy($C_1$-$C_6$)alkyl;

$R_{11}$ is —H or ($C_1$-$C_6$)alkyl, wherein ($C_1$-$C_6$)alkyl is optionally substituted with 1 to 5 substituents independently selected from halogen, CN, ($C_1$-$C_6$)alkoxy, ($C_2$-$C_6$)alkynyl, ($C_3$-$C_8$)cycloalkyl, ($C_3$-$C_9$)heterocycloalkyl, aryl and heteroaryl, wherein the ($C_1$-$C_6$)alkoxy, ($C_2$-$C_6$)alkynyl, ($C_3$-$C_8$) cycloalkyl, ($C_3$-$C_9$)heterocycloalkyl, aryl and heteroaryl groups are each optionally substituted with 1 to 3 substitutes independently selected from the group consisting of halogen, —CN, ($C_1$-$C_6$)alkyl, halo($C_1$-$C_6$)alkyl, ($C_1$-$C_3$)alkoxy, halo ($C_1$-$C_3$)alkoxy and ($C_1$-$C_3$)alkoxy($C_1$-$C_6$)alkyl;

$R_{12}$ and $R_{13}$ are each independently —H, ($C_1$-$C_6$)alkyl, halo($C_1$-$C_6$)alkyl, ($C_1$-$C_3$)alkoxy($C_1$-$C_6$)alkyl, hydroxy($C_1$-$C_6$)alkyl, cyano($C_1$-$C_6$)alkyl, amino($C_1$-$C_6$)alkyl, ($C_1$-$C_3$) alkylamino($C_1$-$C_6$)alkyl, di($C_1$-$C_3$)alkylamino($C_1$-$C_6$)alkyl, ($C_3$-$C_8$)cycloalkyl, ($C_3$-$C_8$)cycloalkyl($C_1$-$C_6$)alkyl, ($C_3$-$C_9$) heterocycloalkyl, ($C_3$-$C_9$)heterocycloalkyl($C_1$-$C_6$)alkyl, aryl, aryl($C_1$-$C_6$)alkyl, heteroaryl or heteroaryl($C_1$-$C_6$)alkyl, wherein the ($C_3$-$C_8$)cycloalkyl, ($C_3$-$C_8$)cycloalkyl($C_1$-$C_6$) alkyl, ($C_3$-$C_9$)heterocycloalkyl, ($C_3$-$C_9$)heterocycloalkyl($C_1$-$C_6$)alkyl, aryl, aryl($C_1$-$C_6$)alkyl, heteroaryl and heteroaryl ($C_1$-$C_6$)alkyl group is optionally substituted with 1 to 3 substituents independently selected from the group consisting of halogen, —CN, ($C_1$-$C_6$)alkyl, halo($C_1$-$C_6$)alkyl, ($C_1$-$C_3$)alkoxy, halo($C_1$-$C_3$)alkoxy and ($C_1$-$C_3$)alkoxy($C_1$-$C_6$) alkyl;

or $R_{12}$ and $R_{13}$, together with the nitrogen to which they are attached, form a 3-8 membered ring optionally substituted with 1 to 3 substituents independently selected from the group consisting of halogen, —CN, —$OR_5$, —$NR_6R_7$, —$S(O)_iR_5$, —$S(O)_iNR_{12}R_{13}$, —$NR_{11}S(O)_iR_5$, —C(═O) $OR_5$, —OC(═O)$OR_5$, —C(═S)$OR_5$, —O(C═S)$R_5$, —C(═O)$NR_6R_7$, —$NR_{11}$C(═O)$R_5$, —C(═S)$NR_6R_7$, —$NR_{11}$C(═S)$R_5$, —$NR_{11}$(C═O)$OR_5$, —O(C═O)$NR_6R_7$, —$NR_{11}$(C═S)$OR_5$, —O(C═S)$NR_6R_7$, —$NR_{11}$(C═O) $NR_6R_7$, —$NR_{11}$(C═S)$NR_6R_7$, —C(═S)$R_5$, —C(═O)$R_5$, ($C_1$-$C_6$)alkyl, ($C_2$-$C_6$)alkenyl, halo($C_1$-$C_6$)alkyl, ($C_1$-$C_3$) alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$) alkoxy, halo($C_1$-$C_3$)alkoxy and ($C_1$-$C_6$)alkoxy($C_1$-$C_3$)alkyl, wherein the 3-8 membered ring optionally contains 1 to 3 additional heteroatoms, which are independently selected from O, N and S, wherein when the additional heteroatom is nitrogen, the nitrogen is substituted with —H, ($C_1$-$C_3$)alkyl or halo($C_1$-$C_3$)alkyl, and when the additional heteroatom is sulfur, the sulfur is optionally mono or di-oxygenated;

$R_{15}$ is —H or ($C_1$-$C_6$)alkyl optionally substituted with 1 to 5-F.

i is 0, 1 or 2;

p is 1, 2 3 or 4; and q is 1, 2 or 3.

In another embodiment, the compound of the present invention is represented by the following Structural Formula:

(I)

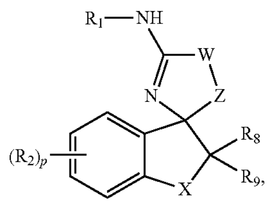

or a pharmaceutically acceptable salt thereof, wherein:

W is —N($R_{14}$)—, —S— or —O—;

Z is —C(═O)—, —C(═S)—, —C(═$NR_{15}$)—, —O—, —C(═O)C($R_{16}R_{17}$)—, —C($R_{16}R_{17}$)C(═O)—, —C(═S)C($R_{16}R_{17}$)—, —C($R_{16}R_{17}$)C(═S)—, —N($R_{18}$)—, —$(CR_{16}R_{17})_m$—, —O—C($R_{16}R_{17}$)— or —C($R_{16}R_{17}$)—O—; provided when W is —S— or —O—, Z is not —O—;

$R_{14}$ is independent selected from —H, ═O, ═S, —$NR_6R_7$, ($C_1$-$C_6$)alkyl, halo($C_1$-$C_6$)alkyl, ($C_3$-$C_8$)cycloalkyl, ($C_3$-$C_8$)cycloalkyl($C_1$-$C_3$)alkyl, ($C_3$-$C_9$)heterocycloalkyl, ($C_3$-$C_9$)heterocycloalkyl($C_1$-$C_3$)alkyl, aryl, aryl($C_1$-$C_6$)alkyl, heteroaryl or heteroaryl($C_1$-$C_6$)alkyl, each ($C_1$-$C_6$)alkyl, halo($C_1$-$C_6$)alkyl, ($C_3$-$C_8$)cycloalkyl, ($C_3$-$C_8$)cycloalkyl($C_1$-$C_3$)alkyl, ($C_3$-$C_9$)heterocycloalkyl, ($C_3$-$C_9$)heterocycloalkyl($C_1$-$C_3$)alkyl, aryl, aryl($C_1$-$C_6$)alkyl, heteroaryl or heteroaryl($C_1$-$C_6$)alkyl represented by $R_{14}$ is optionally substituted with 1 to 5 substituents independently selected from the group consisting of -halogen, —CN, ($C_1$-$C_6$)alkyl, halo($C_1$-$C_6$)alkyl, ($C_1$-$C_3$)alkoxy, —$OR_5$, —$NR_6R_7$, —$S(O)_iR_5$, —$S(O)_iNR_{12}R_{13}$, —$NR_{11}S(O)_iR_5$, —C(═O)$OR_5$, —OC(═O)$OR_5$, —C(═S)$OR_5$, —O(C═S)$R_5$, —C(═O)$NR_{12}R_{13}$, —$NR_{11}$C(═O)$R_5$, —C(═S)$NR_{12}R_{13}$, —$NR_{11}$C(═S)$R_5$, —$NR_{11}$(C═O)$OR_5$, —O(C═O)$NR_{12}R_{13}$, —$NR_{11}$(C═S)$OR_5$, —O(C═S)$NR_{12}R_{13}$, —$NR_{11}$(C═O)$NR_{12}R_{13}$, —$NR_{11}$(C═S)$NR_{12}R_{13}$, —C(═S)$R_5$ and —C(═O)$R_5$;

$R_{16}$ and $R_{17}$ are each independently —H or ($C_1$-$C_3$)alkyl optionally substituted with 1 to 5-F;

$R_{18}$ is —H or ($C_1$-$C_3$)alkyl optionally substituted with 1 to 5-F; and m is 1 or 2.

The remainder of the variables are as described above for Structural Formula (A).

In another embodiment, the compound of the present invention is represented by Structural Formula (I'), wherein:

(I')

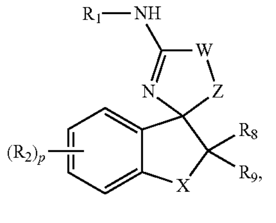

or a pharmaceutically acceptable salt thereof, wherein:

X is —O—, —$CH_2$—C($R_3R_4$)—, or —C($R_3R_4$)—;

W is —N($R_{14}$)—, —S—, —O—;

Z is —C(═O)—, —C(═S)—, —C(═$NR_{15}$)—, —O—, —C(═O)C($R_{16}R_{17}$)—, —C(═S)C($R_{16}R_{17}$)—, —C(═$NR_{15}$)C($R_{16}R_{17}$)—, —N($R_{18}$)—, —$(CR_{16}R_{17})_m$— or —O—($CR_{16}R_{17}$)—; provided when W is —S— or —O—, Z is not —O—;

$R_1$ is —H, ($C_1$-$C_6$)alkyl, aryl($C_1$-$C_6$)alkyl, or heteroaryl($C_1$-$C_6$)alkyl;

each $R_2$ is independently selected from a) —H, -halogen, —CN, —$NO_2$, —$OR_5$, —$NR_6R_7$, —$S(O)_iR_5$, —C(═O)$OR_5$, —C(═O)$NR_{12}R_{13}$, and —C(═O)$R_5$; and b) ($C_1$-$C_6$)alkyl, ($C_2$-$C_6$)alkenyl, ($C_2$-$C_6$)alkynyl, ($C_3$-$C_8$)cycloalkyl, aryl, heteroaryl, phenoxy, and benzyloxy, each optionally substituted with 1 to 3 substituents selected from the group consisting of —F, —Cl, —Br, —CN, —$OR_5$, —$SR_5$, —$NR_6R_7$, —$S(O)_iR_5$, —$NR_{11}$S(═O)$_iR_5$, —C(═O)$OR_5$, —C(═O)$NR_{12}R_{13}$, —$NR_{11}$C(═O)$R_5$, —C(═S)$NR_{12}R_{13}$, —C(═O)$R_5$, ($C_1$-$C_6$)alkyl, ($C_3$-$C_8$)cycloalkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl;

$R_3$ and $R_4$ are each independently —H, -halogen, —CN, —$NO_2$, —$OR_5$, —$NR_6R_7$, —$S(O)_iR_5$, —C(═O)$OR_5$, —C(═O)$NR_{12}R_{13}$, —C(═O)$R_5$, ($C_1$-$C_6$)alkyl, ($C_2$-$C_6$)alkenyl, ($C_2$-$C_6$)alkynyl, ($C_3$-$C_8$)cycloalkyl, aryl, or heteroaryl, wherein each ($C_1$-$C_6$)alkyl, ($C_2$-$C_6$)alkenyl, ($C_2$-$C_6$)alkynyl, ($C_3$-$C_8$)cycloalkyl, aryl, or heteroaryl is optionally substituted with 1 to 3 substituents independently selected from the group consisting of —F, —Cl, —Br, —CN, —$OR_5$, —$NR_6R_7$, —$S(O)_iR_5$, —$NR_{11}$S(═O)$_iR_5$, —C(═O)$OR_5$, —C(═O)$NR_{12}R_{13}$, —$NR_{11}$C(═O)$R_5$, —C(═S)$NR_{12}R_{13}$, —C(═O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl;

or $R_3$ and $R_4$, together with the carbon to which they are attached, form ring A, which is a 3-14 membered monocyclic ring, 9-14 membered bicyclic ring or 9-14 membered polycyclic ring, wherein ring A is optionally substituted with 1 to 4 substituents independently selected from the group consisting of —F, —Cl, —Br, —CN, —$OR_5$, —$NR_6R_7$, —$S(O)_iR_5$, —$NR_{11}$S(═O)$_iR_5$, —C(═O)$OR_5$, —C(═O)$NR_{12}R_{13}$, —$NR_{11}$C(═O)$R_5$, —C(═S)$NR_{12}R_{13}$, —C(═O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl;

$R_5$ is —H, ($C_1$-$C_6$)alkyl, halo($C_1$-$C_6$)alkyl, ($C_2$-$C_6$)alkenyl, ($C_2$-$C_6$)alkynyl, ($C_1$-$C_3$)alkoxy($C_1$-$C_6$)alkyl, ($C_3$-$C_8$)cycloalkyl, ($C_3$-$C_8$)cycloalkyl($C_1$-$C_6$)alkyl, ($C_3$-$C_7$)cycloheteroalkyl, aryl, heteroaryl or benzyl, each of which is optionally substituted with 1 to 3 substituents independently selected from the group consisting of —F, —Cl, —Br, —CN, ($C_1$-$C_6$)alkyl, halo($C_1$-$C_6$)alkyl, and ($C_1$-$C_3$)alkoxy($C_1$-$C_6$)alkyl;

$R_6$ and $R_7$ are each independently —H, ($C_1$-$C_6$)alkyl, hydroxy($C_1$-$C_6$)alkyl, halo($C_1$-$C_6$)alkyl, ($C_3$-$C_8$)cycloalkyl, ($C_3$-$C_8$)cycloalkyl($C_1$-$C_6$)alkyl, each optionally substituted with 1 to 3 substituents independently selected from the group consisting of —F, —Cl, —Br, —CN, ($C_1$-$C_6$)alkyl, halo($C_1$-$C_6$)alkyl and ($C_1$-$C_3$)alkoxy($C_1$-$C_6$)alkyl;

$R_8$ and $R_9$, together with the carbon to which they are attached, form ring A, which is a 3-14 membered monocyclic ring, 9-14 membered bicyclic ring or 9-14 membered polycyclic ring, wherein ring A is optionally substituted with 1 to 4 substituents independently selected from the group consisting of —F, —Cl, —Br, —CN, —$OR_5$, —$NR_6R_7$, —$S(O)_iR_5$, —$NR_{11}$S(═O)$_iR_5$, —C(═O)$OR_5$, —C(═O)$NR_{12}R_{13}$, —$NR_{11}$C(═O)$R_5$, —C(═S)$NR_{12}R_{13}$, —C(═O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$) alkyl, ($C_1$-$C_3$)alkyl carbonylamino($C_1$-$C_6$)alkyl, ($C_1$-$C_3$) alkoxy, halo($C_1$-$C_3$)alkoxy, ($C_1$-$C_6$)alkoxy($C_1$-$C_3$)alkyl, aryl and heteroaryl; or when $R_3$ and $R_4$, together with the carbon to which they are attached, form a ring A, $R_8$ and $R_9$ are each independently —H, -halogen, —CN, —$NO_2$, —$OR_5$, —$NR_6R_7$, —$S(O)_iR_5$, —C(═O)$OR_5$, —C(═O)$NR_{12}R_{13}$, —C(═O)$R_5$, ($C_1$-$C_6$) alkyl, ($C_2$-$C_6$)alkenyl, ($C_2$-$C_6$)alkynyl, ($C_3$-$C_8$)cycloalkyl, aryl, or heteroaryl, wherein each ($C_1$-$C_6$)alkyl, ($C_2$-$C_6$)alkenyl, ($C_2$-$C_6$)alkynyl, ($C_3$-$C_8$)cycloalkyl, aryl, or heteroaryl is optionally substituted with 1 to 3 substituents independently selected from the group consisting of —F, —Cl, —Br, —CN, —$OR_5$, —$NR_6R_7$, —$S(O)_iR_5$, —$NR_{11}S$(═O)$_iR_5$, —C(═O)$OR_5$, —C(═O)$NR_{12}R_{13}$, —$NR_{11}C$(═O)$R_5$, —C(═S)$NR_{12}R_{13}$, —C(═O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$) alkoxy, ($C_1$-$C_6$)alkoxy($C_1$-$C_3$)alkyl, aryl and heteroaryl;

$R_{11}$ is —H, ($C_1$-$C_6$)alkyl or halo($C_1$-$C_6$)alkyl;

$R_{12}$ and $R_{13}$ are each independently —H, ($C_1$-$C_6$)alkyl, ($C_1$-$C_3$)alkoxy($C_1$-$C_6$)alkyl, hydroxy($C_1$-$C_6$)alkyl, cyano ($C_1$-$C_6$)alkyl, amino($C_1$-$C_6$)alkyl, ($C_1$-$C_3$)alkylamino($C_1$-$C_6$)alkyl, or di($C_1$-$C_3$)alkylamino($C_1$-$C_6$)alkyl;

or $R_{12}$ and $R_{13}$, together with the nitrogen to which they are attached, form a 3-8 membered ring optionally substituted with 1 to 3 substituents independently selected from the group consisting of —F, —Cl, —Br, —CN, —$OR_5$, —$NR_6R_7$, —$S(O)_iR_5$, —$NR_{11}S$(═O)$_iR_5$, —C(═O)$OR_5$, —C(═O)$NR_{12}R_{13}$, —$NR_{11}C$(═O)$R_5$, —C(═S)$NR_{12}R_{13}$, —C(═O)$R_5$, ($C_1$-$C_6$)alkyl, ($C_2$-$C_6$)alkenyl, halo($C_1$-$C_6$) alkyl, ($C_1$-$C_3$)alkylsulfonylaminoalkyl, hydroxy($C_1$-$C_6$) alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy and ($C_1$-$C_6$) alkoxy($C_1$-$C_3$)alkyl, wherein the 3-8 membered ring optionally contains 1 to 3 additional heteroatoms, which are independently selected from O, N and S, wherein when the additional heteroatom is nitrogen, the nitrogens is substituted with —H, ($C_1$-$C_3$)alkyl or halo($C_1$-$C_3$)alkyl, and when the additional heteroatom is sulfur, the sulfurs is optionally mono or di-oxygenated;

$R_{14}$ is —H, ($C_1$-$C_6$)alkyl, halo($C_1$-$C_6$)alkyl, ($C_3$-$C_8$)cycloalkyl, cycloheteroalkyl($C_1$-$C_3$)alkyl, ($C_3$-$C_8$)cycloalkyl ($C_1$-$C_3$)alkyl, aryl($C_1$-$C_6$)alkyl, heteroaryl($C_1$-$C_6$)alkyl, each optionally substituted with 1 to 3 substituents independently selected from the group consisting of —F, —Cl, —Br, —CN, ($C_1$-$C_6$)alkyl, halo($C_1$-$C_6$)alkyl and ($C_1$-$C_3$)alkoxy;

$R_{15}$ is —H or ($C_1$-$C_6$)alkyl;

$R_{16}$ and $R_{17}$ are each independently —H or ($C_1$-$C_3$)alkyl;

$R_{18}$ is —H or ($C_1$-$C_3$)alkyl;

i is 0, 1 or 2;

p is 1 or 2; and m is 1 or 2.

One embodiment of the invention is a pharmaceutical composition comprising a pharmaceutically acceptable carrier or diluent and a compound disclosed herein (e.g., a compound represented by Structural Formula (A), (I) or (I'), or a pharmaceutically acceptable salt thereof).

Another embodiment of the invention is a method of inhibiting BACE activity in a subject in need of such treatment. The method comprises administering to the subject an effective amount of a BACE inhibitor disclosed herein (e.g., a compound represented by Structural Formula (A), (I) or (I'), or a pharmaceutically acceptable salt thereof).

Another embodiment of the invention is a method of treating a BACE mediated disorder in a subject. The method comprises administering to the subject an effective amount of a BACE inhibitor disclosed herein (e.g., a compound represented by Structural Formula (A), (I) or (I'), or a pharmaceutically acceptable salt thereof).

Another embodiment of the invention is the use of a BACE inhibitor disclosed herein (e.g., a compound represented by Structural Formula (A), (I) or (I'), or a pharmaceutically acceptable salt thereof) for the manufacture of a medicament for inhibiting BACE activity in a subject.

Another embodiment of the invention is the use of a BACE inhibitor disclosed herein (e.g., a compound represented by Structural Formula (A), (I) or (I'), or a pharmaceutically acceptable salt thereof) for the manufacture of a medicament for treating a BACE mediated disorder in a subject.

Another embodiment of the invention is the use of a BACE inhibitor disclosed herein (e.g., a compound represented by Structural Formula (A), (I) or (I'), or a pharmaceutically acceptable salt thereof for inhibiting BACE activity in a subject in need of such treatment.

Another embodiment of the invention is the use of a BACE inhibitor disclosed herein (e.g., a compound represented by Structural Formula (A), (I) or (I'), or a pharmaceutically acceptable salt thereof for treating a BACE mediated disorder in a subject.

DETAILED DESCRIPTION OF THE INVENTION

The present invention is directed to compounds represented by the Structural Formula (A), (I) or (I'), or a pharmaceutically acceptable salt thereof. Values and alternative values for the variables used in the Structural Formulas described herein are provided in the following paragraphs. It is understood that the invention encompasses all combinations of the substituent variables (i.e., $R^1$, $R^2$, $R^3$, etc.) defined herein. —Values and alternative values for the variables are as follows:

1. $R_1$:

In one embodiment, $R_1$ is as described above for Structural Formula (A). In another embodiment, $R_1$ is as described above for Structural Formula (I').

Alternatively, $R_1$ is —H, ($C_1$-$C_6$)alkyl, aryl($C_1$-$C_6$)alkyl, or heteroaryl($C_1$-$C_6$)alkyl. In another embodiment, $R_1$ is —H, ($C_1$-$C_6$)alkyl or benzyl. Alternatively, $R_1$ is —H or —C(O)—($C_1$-$C_3$)alkyl (e.g., acetyl). In another embodiment, $R_1$ is —H.

2. $R_2$:

In one embodiment, $R_2$ is as described above for Structural Formula (A). In another embodiment, $R_2$ is as described above for Structural Formula (I').

Alternatively, each $R_2$ is —H, halogen, —CN, —$OR_5$, —C(═O)$NR_{12}R_{13}$, —C(═O)$OR_5$, —C(O)$R_5$, ($C_1$-$C_6$) alkyl, ($C_2$-$C_6$)alkenyl, ($C_2$-$C_6$)alkynyl, ($C_3$-$C_6$)cycloalkyl, ($C_3$-$C_6$)cycloalkyl($C_1$-$C_3$)alkyl, ($C_4$-$C_6$)cycloalkenyl, phenyl, phenyl($C_1$-$C_3$)alkyl, heteroaryl, heteroaryl($C_1$-$C_3$)alkyl, ($C_5$-$C_6$)heterocycloalkyl, ($C_5$-$C_6$)heterocycloalkyl($C_1$-$C_3$) alkyl. The heteroaryl is selected from pyridyl, pyridazinyl, pyridinonyl, pyridazinonyl, thiazolyl, oxazolyl, oxadiazolyl, pyrazinyl, pyrimidyl, indolyl, quinolyl, quinoxalinyl, triazole and thiophenyl, the heterocycloalkyl is selected from oxetanyl, tetrahydrafuran, tetrapyran, piperidine, pyrrolidinyl and pyrrolidinonyl. Each of ($C_1$-$C_6$)alkyl, ($C_2$-$C_6$)alkenyl, ($C_2$-$C_6$)alkynyl, ($C_3$-$C_6$)cycloalkyl, ($C_3$-$C_6$)cycloalkyl($C_1$-$C_3$) alkyl, ($C_4$-$C_6$)cycloalkenyl, phenyl, phenyl($C_1$-$C_3$)alkyl, heteroaryl, heteroaryl($C_1$-$C_3$)alkyl, ($C_5$-$C_6$)heterocycloalkyl and ($C_5$-$C_6$)heterocycloalkyl($C_1$-$C_3$)alkyl groups represented by $R_2$ is optionally substituted with 1 to 5 substituents independently selected from halogen, —CN, ($C_1$-$C_3$)alkyl, halo($C_1$-$C_3$)alkyl, ($C_2$-$C_6$)alkynyl, —$NR_6R_7$, —$S(O)_iR_5$, —$C(O)R_5$, —OH, ($C_3$-$C_6$)cycloalkyl, ($C_1$-$C_3$)alkoxy and halo($C_1$-$C_3$)alkoxy.

In another alternative, each $R_2$ is independently selected from the group consisting of —H, —F, —Br, —Cl, —I, —OH, —CN, cyclopropylethyl, 5-propynyl-3-pyridyl, 2-fluoro-3-pyridyl, N,N-dimethylaminoethoxy, cyclopentoxy, cyclopropylmethoxy, 3-methoxypropyl, 3-methoxypropynyl, cyclopropylethynyl, 3-cyanophenyl, trifluoromethoxy, 2-chloro-4-pyridyl, 1-methanesulfonyl-4-piperidinylmethyl, 1-acetyl-4-piperidinylmethyl, 3-methanesulfonylphenyl, 5-trifluoromethyl-3-pyridyl, 2-methoxyethoxy, 2-methyl-5-pyridazin-3-onyl, 1-cyclopropyl-4-pyridin-2-onyl, 1-methyl-2,2,2-trifluoroethyl, 2-cyclopropyl-5-thiazolyl, trifluoromethyl, 2,2,2-trifluoroethyl, methoxy, 3-chloro-5-fluorophenyl, N-methyl-4-pyridin-2-onyl, 4-methylpentyl, 3-methoxyphenoxy, dimethylaminocabonyl, cyclopropyl, 1-hydroxy-2,2,2-trifluoroethyl, pyrrolidinylcarbonyl, 3,3,3-trifluoropropyl, difluoromethoxy, 1,1-dihydroxy-2,2,2-trifluoroethyl, 3-methoxyphenyl, 2,2,2-trifluoroethoxy, phenoxy, 2-methoxy-4-pyridyl, 2-methyl-5-thiazolyl, 3,3,3-trifluoroprop-1-en-2-yl, 5-thiazolyl, 2-thiazolyl, thiophen-3-ylethynyl, 1-hydroxycyclopentan-1-ylethynyl, 5-fluoro-3-pyridyl, pyrrolidinyl, 5-chloro-3-pyridyl, 3,3-dimethylbutyn-1-yl, phenylethynyl, cyclopentylethynyl, 2-pyrazinyl, 3-chlorophenyl, 3-hydroxycyclopent-1-enyl, 3-fluoro-5-trifluoromethylphenyl, 3,5-dicyanophenyl, 3-fluoro-5-cyanophenyl, 3-chloro-4-fluorophenyl, 3,5-difluorophenyl, 3,5-dichlorophenyl, 3-chloro-5-cyanophenyl, 3-pyridazinyl, 3-pyridyl, 3-cyano-4-fluorophenyl, 3-cyano-5-fluorophenyl 6-methoxypyrazin-2-yl, 6-indolyl, 3-chloro-5-methoxyphenyl, 3-trifluoromethoxyphenyl, 3,5-dimethylphenyl, 2-methyl-5-fluorophenyl, 3-trifluoromethylphenyl, phenyl, cyclopentylmethyl, 1-propyl, 2-propyl, 2-methylpropyl, phenylethyl, 1-pentyl, 2-methylbutyl, ethyl, 4-methoxyphenylmethoxy, 1-methylethoxy, methoxycarbonyl, cyclopropyloxy, 5-cyano-3-pyridyl, 4-(propyn-1-yl)-2-thiophenyl, 4-bromo-2-thiazolyl, ethenyl, ethynyl, 4-methylpentyn-1-yl, dimethylaminopropyl, N-methylpyrrolidin-3-ylmethyl, 2,2-difluorocyclopropylmethoxy, 4-bromo-2-thiophenyl, methoxy, methyl, carboxy, 5-propyl-3-pyridyl, 2-methyl-5-fluorophenyl, 2-oxazolyl, propylthio, phenylthio, 2,2-dimethylpropyl, butyl, cyclobutylmethoxy, 2-methyl-5-pyrimidyl, pyrrolidin-2-onyl, 3,3-difluoropyrrolidin-1-yl, cyclopropylethyl, 2-propyloxy, 4-cyano-2-thiophenyl, ethoxymethyl, 4-methoxybenzyloxy, 1-methylethyl, cyclohexylmethyl, 5-chloro-3-pyridyl, 5-methyl-3-pyridyl, 2-methylpropyloxy and 2-chloro-4-pyridyl.

In one embodiment, each $R_2$ is independently selected from a) —H, -halogen, —CN, —$NO_2$, —$OR_5$, —$NR_6R_7$, —$S(O)_iR_5$, —C(=O)$OR_5$, —C(=O)$NR_{12}R_{13}$, and —C(=O)$R_5$; and b) ($C_1$-$C_6$)alkyl, ($C_2$-$C_6$)alkenyl, ($C_2$-$C_6$)alkynyl, ($C_3$-$C_8$)cycloalkyl, aryl, heteroaryl, phenoxy, and benzyloxy, each optionally substituted with 1 to 3 substituents selected from the group consisting of —F, —Cl, —Br, —CN, —$OR_5$, —$SR_5$, —$NR_6R_7$, —$S(O)_iR_5$, —$NR_{11}$S(=O)$_i$ $R_5$, —C(=O)$OR_5$, —C(=O)$NR_{12}R_{13}$, —$NR_{11}$C(=O)$R_5$, —C(=S)$NR_{12}R_{13}$, —C(=O)$R_5$, ($C_1$-$C_6$)alkyl, ($C_3$-$C_8$)cycloalkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkyl carbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl.

In one embodiment, $R_2$ is —H, —Br, —F, —Cl or —CN.

In another embodiment, $R_2$ is ($C_1$-$C_6$)alkyl. In an alternative, $R_2$ is a ($C_1$-$C_3$)alkyl.

In another embodiment, $R_2$ is a ($C_2$-$C_6$)alkynyl optionally substituted with —F, —Cl, —Br, —CN, —$OR_5$, —$SR_5$, —$NR_6R_7$, —$S(O)_iR_5$, —$NR_{11}$S(=O)$_iR_5$, —C(=O)$OR_5$, —C(=O)$NR_{12}R_{13}$, —$NR_{11}$C(=O)$R_5$, —C(=S)$NR_{12}R_{13}$, —C(=O)$R_5$, ($C_1$-$C_6$)alkyl, ($C_3$-$C_8$)cycloalkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$) alkoxy, ($C_1$-$C_6$)alkoxy($C_1$-$C_3$)alkyl, aryl or heteroaryl. Alternatively, $R_2$ is a ($C_2$-$C_6$)alkynyl optionally substituted with a ($C_1$-$C_6$)alkyl or a ($C_3$-$C_8$)cycloalkyl. In another alternative, $R_2$ is a ($C_2$-$C_6$)alkynyl optionally substituted with a cyclopropyl. In yet another alternative, $R_2$ is cyclopropylethynyl. Alternatively, $R_2$ is a ($C_2$-$C_6$)alkynyl optionally substituted with —F, —Cl, —Br, ($C_1$-$C_6$)alkyl, halo($C_1$-$C_6$)alkyl, ($C_1$-$C_6$)alkoxy or ($C_3$-$C_8$)cycloalkyl.

In another embodiment, $R_2$ is a phenyl optionally substituted with 1 to 3 substituents independently selected from the group consisting of —F, —Cl, —Br, —CN, —$OR_5$, —$SR_5$, —$NR_6R_7$, —$S(O)_iR_5$, —$NR_{11}$S(=O)$_iR_5$, —C(=O)$OR_5$, —C(=O)$NR_{12}R_{13}$, —$NR_{11}$C(=O)$R_5$, —C(=S)$NR_{12}R_{13}$, —C(=O)$R_5$, ($C_1$-$C_6$)alkyl, ($C_3$-$C_8$)cycloalkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkyl carbonylamino($C_1$-$C_6$)alkyl, ($C_1$-$C_3$)alkoxy, halo($C_1$-$C_3$) alkoxy, ($C_1$-$C_6$)alkoxy($C_1$-$C_3$)alkyl, aryl and heteroaryl. Alternatively, $R_2$ is a phenyl optionally substituted with 1 to 3 substituents independently selected from the group consisting of —F, —Cl, —Br, —CN, ($C_1$-$C_6$)alkyl, ($C_1$-$C_6$)alkoxy, halo($C_1$-$C_6$)alkyl and halo($C_1$-$C_6$)alkoxy. In another alternative, $R_2$ is phenyl optionally substituted with 1 to 3 substituents independently selected from the group consisting of —F, —Cl, —Br, —CN, -Me, -Et, -OMe, —$CF_3$ and —$OCF_3$.

In another embodiment, $R_2$ is a 5-6 membered heteroaryl optionally substituted with 1 to 3 substituents independently selected from the group consisting of —F, —Cl, —Br, —CN, —$OR_5$, —$SR_5$, —$NR_6R_7$, —$S(O)_iR_5$, —$NR_{11}$S(=O)$_iR_5$, —C(=O)$OR_5$, —C(=O)$NR_{12}R_{13}$, —$NR_{11}$C(=O)$R_5$, —C(=S)$NR_{12}R_{13}$, —C(=O)$R_5$, ($C_1$-$C_6$)alkyl, ($C_3$-$C_8$)cycloalkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, $C_3$)alkyl carbonylamino($C_1$-$C_6$)alkyl, ($C_1$-$C_3$)alkoxy, halo ($C_1$-$C_3$)alkoxy, ($C_1$-$C_6$)alkoxy($C_1$-$C_3$)alkyl and a heteroaryl group. In an alternative, $R_2$ is a pyridinyl, thiophenyl, pyrrolyl, pyrimidinyl, each optionally substituted with 1 to 3 substituents independently selected from the group consisting of —F, —Cl, —Br, —CN, ($C_1$-$C_6$)alkyl, ($C_3$-$C_8$)cycloalkyl, halo($C_1$-$C_6$)alkyl, ($C_1$-$C_3$)alkoxy, halo($C_1$-$C_3$)alkoxy and ($C_1$-$C_6$)alkoxy($C_1$-$C_3$)alkyl.

In another embodiment, $R_2$ is an indolyl, pyridinyl, thiophenyl, pyrrolyl, pyrimidinyl, cyclohexyl, or thiozolyl, each of which is optionally substituted with 1 to 3 substituents independently selected from the group consisting of —F, —Cl, —Br, —CN, —$OR_5$, —$SR_5$, —$NR_6R_7$, —$S(O)_iR_5$, —$NR_{11}$S(=O)$_iR_5$, —C(=O)$OR_5$, —C(=O)$NR_{12}R_{13}$, —$NR_{11}$C(=O)$R_5$, —C(=S)$NR_{12}R_{13}$, —C(=O)$R_5$, ($C_1$-$C_6$)alkyl, ($C_3$-$C_8$)cycloalkyl, ($C_2$-$C_6$)alkenyl, halo($C_1$-$C_6$) alkyl, ($C_1$-$C_3$)alkylsulfonylaminoalkyl, hydroxy($C_1$-$C_6$) alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy ($C_1$-$C_3$)alkyl, aryl and heteroaryl. Alternatively, $R_2$ is an indolyl or pyridinyl optionally substituted with —F, —Cl, —Br, —CN, ($C_1$-$C_6$)alkyl, halo($C_1$-$C_6$)alkyl, ($C_1$-$C_3$)alkoxy or halo($C_1$-$C_3$)alkoxy. In another alternative, $R_2$ is 2-pyridinyl or 6-indolyl.

In another embodiment, $R_2$ is —$OR_5$, wherein $R_5$ is —H, ($C_1$-$C_6$)alkyl, ($C_3$-$C_6$)cycloalkyl, ($C_3$-$C_6$)cycloalkyl($C_1$-$C_3$)

alkyl, phenyl or phenyl($C_1$-$C_3$)alkyl, wherein each of the ($C_1$-$C_6$)alkyl, ($C_3$-$C_6$)cycloalkyl, ($C_3$-$C_6$)cycloalkyl($C_1$-$C_3$)alkyl, phenyl or phenyl($C_1$-$C_3$)alkyl groups is optionally substituted with 1 to 5 substituents independently selected from the group consisting of halogen, —CN, —$NO_2$, ($C_1$-$C_6$)alkyl, halo($C_1$-$C_6$)alkyl, ($C_1$-$C_3$)alkoxy, halo($C_1$-$C_3$)alkoxy, ($C_1$-$C_3$)alkoxy($C_1$-$C_3$)alkyl and —$NR_6R_7$. More specifically, $R_6$ and $R_7$ are each independently selected from —H, ($C_1$-$C_6$)alkyl, halo($C_1$-$C_6$)alkyl and ($C_1$-$C_3$)alkoxy($C_1$-$C_3$)alkyl.

3. $R_3$ and $R_4$

In one embodiment, $R_3$ and $R_4$ are as described above for Structural Formula (A). In another embodiment, $R_3$ and $R_4$ are as described above for Structural Formula (I')

Alternatively, $R_3$ and $R_4$ are each independently —H, -halogen, —CN, —$NO_2$, —$OR_5$, —$NR_6R_7$, —$S(O)_iR_5$, —C(═O)$OR_5$, —C(═O)$NR_{12}R_{13}$, —C(═O)$R_5$, ($C_1$-$C_6$)alkyl, ($C_2$-$C_6$)alkenyl, ($C_2$-$C_6$)alkynyl, ($C_3$-$C_8$)cycloalkyl, aryl, or heteroaryl, wherein each ($C_1$-$C_6$)alkyl, ($C_2$-$C_6$)alkenyl, ($C_2$-$C_6$)alkynyl, ($C_3$-$C_8$)cycloalkyl, aryl, or heteroaryl is optionally substituted with 1 to 3 substituents independently selected from the group consisting of —F, —Cl, —Br, —CN, —$OR_5$, —$NR_6R_7$, —$S(O)_iR_5$, —$NR_{11}S$(═O)$_iR_5$, —C(═O)$OR_5$, —C(═O)$NR_{12}R_{13}$, —$NR_{11}C$(═O)$R_5$, —C(═S)$NR_{12}R_{13}$, —C(═O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl. In one embodiment, $R_3$ and $R_4$ are each independently —H, —F, —Cl, —Br or a ($C_1$-$C_6$)alkyl. In another embodiment, $R_3$ and $R_4$ are both —H.

In another embodiment, $R_3$ and $R_4$, together with the carbon to which they are attached, form ring A, which is a 3-14 membered monocyclic ring, 9-14 membered bicyclic ring or 9-14 membered polycyclic ring, wherein ring A is optionally substituted with 1 to 4 substituents independently selected from the group consisting of —F, —Cl, —Br, —CN, —$OR_5$, —$NR_6R_7$, —$S(O)_iR_5$, —$NR_{11}S$(═O)$_iR_5$, —C(═O)$OR_5$, —C(═O)$NR_{12}R_{13}$, —$NR_{11}C$(═O)$R_5$, —C(═S)$NR_{12}R_{13}$, —C(═O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl.

4. $R_5$:

In one embodiment, $R_5$ is as described above for Structural Formula (A). In another embodiment, $R_5$ is as described above for Structural Formula (I')

Alternatively, $R_5$ is —H, ($C_1$-$C_6$)alkyl, halo($C_1$-$C_6$)alkyl, ($C_2$-$C_6$)alkenyl, ($C_2$-$C_6$)alkynyl, ($C_1$-$C_3$)alkoxy($C_1$-$C_6$)alkyl, ($C_3$-$C_8$)cycloalkyl, ($C_3$-$C_8$)cycloalkyl($C_1$-$C_6$)alkyl, ($C_3$-$C_7$)cycloheteroalkyl, aryl, heteroaryl, or benzyl, each of which is optionally substituted with 1 to 3 substituents independently selected from the group consisting of —Cl, —Br, —CN, ($C_1$-$C_6$)alkyl, halo($C_1$-$C_6$)alkyl, ($C_1$-$C_3$)alkoxy, halo($C_1$-$C_3$)alkoxy and ($C_1$-$C_3$)alkoxy($C_1$-$C_6$)alkyl. In a another alternative, $R_5$ is ($C_1$-$C_6$)alkyl, halo($C_1$-$C_6$)alkyl or ($C_1$-$C_3$)alkoxy($C_1$-$C_6$)alkyl. Alternatively, $R_5$ is methyl, ethyl, propyl, butyl, or trifluoromethyl.

In another embodiment, $R_5$ is selected from the group consisting of —H, ($C_1$-$C_3$)alkyl, halo($C_1$-$C_3$)alkyl, ($C_1$-$C_3$)alkoxy($C_1$-$C_3$)alkyl, ($C_3$-$C_6$)cycloalkyl, ($C_3$-$C_6$)cycloalkyl($C_1$-$C_3$)alkyl, phenyl and phenyl($C_1$-$C_3$)alkyl, wherein the phenyl group in the groups represented by $R_5$ is optionally substituted with 1 to 3 substituents independently selected from —F, —Cl, —Br, —CN, ═O, —$NR_6R_7$, ($C_1$-$C_3$)alkyl, halo($C_1$-$C_3$)alkyl and ($C_1$-$C_3$)alkoxy($C_1$-$C_3$)alkyl.

In another alternative embodiment, $R_5$ is selected from the group consisting of —H, methyl, ethyl, 2-propyl, 2-methylpropyl, cyclopentyl, —$CHF_2$, —$CF_2CHF_2$, —$CH_2CF_3$, —$CF_3$, cyclopropylmethyl, 2,2-difluorocyclopropylmethyl, methoxyethyl, phenyl, 3-methoxyphenyl, (1-amino-2-(4-hydroxyphenyl))ethylcarbonyl, dimethylaminoethyl, cyclobutylmethyl, and 4-methoxybenzyl.

5. $R_6$ and $R_7$:

In one embodiment, $R_6$ and $R_7$ are as described above for Structural Formula (A). In another embodiment, $R_6$ and $R_7$ are as described above for Structural Formula (I')

Alternatively, $R_6$ and $R_7$ are each independently —H, ($C_1$-$C_6$)alkyl, hydroxy($C_1$-$C_6$)alkyl, halo($C_1$-$C_6$)alkyl, ($C_3$-$C_8$)cycloalkyl, ($C_3$-$C_8$)cycloalkyl($C_1$-$C_6$)alkyl, each optionally substituted with 1 to 3 substituents independently selected from the group consisting of —F, —Cl, —Br, —CN, ($C_1$-$C_6$)alkyl, halo($C_1$-$C_6$)alkyl and ($C_1$-$C_3$)alkoxy($C_1$-$C_6$)alkyl. In a alternative embodiment, $R_6$ and $R_7$ are each independently —H or ($C_1$-$C_6$)alkyl. In another alternative embodiment, $R_6$ and $R_7$ are both —H. Alternatively, $R_6$ is —H or ($C_1$-$C_3$)alkyl and $R_7$ is —H, ($C_1$-$C_3$)alkyl, halo($C_1$-$C_3$)alkyl, ($C_3$-$C_6$)cycloalkyl, ($C_3$-$C_6$)cycloalkyl($C_1$-$C_3$)alkyl or ($C_1$-$C_3$)alkoxy($C_1$-$C_3$)alkyl.

In another alternative embodiment, $R_6$ is —H or methyl and $R_7$ is —H, methyl or —$CH_2CF_3$.

6. $R_8$ and $R_9$:

In one embodiment, $R_8$ and $R_9$ are as described above for Structural Formula (A). In another embodiment, $R_8$ and $R_9$ are as described above for Structural Formula (I').

Alternatively, $R_8$ and $R_9$, together with the carbon to which they are attached, form ring A, which is a 3-14 membered monocyclic ring, 9-14 membered bicyclic ring or 9-14 membered polycyclic ring, wherein ring A is optionally substituted with 1 to 4 substituents independently selected from the group consisting of —F, —Cl, —Br, —CN, —$OR_5$, —$NR_6R_7$, —$S(O)_iR_5$, —$NR_{11}S$(═O)$_iR_5$, —C(═O)$OR_5$, —C(═O)$NR_{12}R_{13}$, —$NR_{11}C$(═O)$R_5$, —C(═S)$NR_{12}R_{13}$, —C(═O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl. In one embodiment, ring A is optionally substituted with 1 to 3 substituents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy, halo($C_1$-$C_3$)alkoxy and phenyl, wherein the phenyl is optionally substituted with F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy, halo($C_1$-$C_3$)alkoxy.

Alternatively, when $R_3$ and $R_4$, together with the carbon to which they are attached, form a ring A, $R_8$ and $R_9$ are each independently —H, -halogen, —CN, —$NO_2$, —$OR_5$, —$NR_6R_7$, —$S(O)_iR_5$, —C(═O)$OR_5$, —C(═O)$NR_{12}R_{13}$, —C(═O)$R_5$, ($C_1$-$C_6$)alkyl, ($C_2$-$C_6$)alkenyl, ($C_2$-$C_6$)alkynyl, ($C_3$-$C_8$)cycloalkyl, aryl, or heteroaryl, wherein each ($C_1$-$C_6$)alkyl, ($C_2$-$C_6$)alkenyl, ($C_2$-$C_6$)alkynyl, ($C_3$-$C_8$)cycloalkyl, aryl, or heteroaryl is optionally substituted with 1 to 3 substituents independently selected from the group consisting of —F, —Cl, —Br, —CN, —$OR_5$, —$NR_6R_7$, —$S(O)_iR_5$, —$NR_{11}S$(═O)$_iR_5$, —C(═O)$OR_5$, —C(═O)$NR_{12}R_{13}$, —$NR_{11}C$(═O)$R_5$, —C(═S)$NR_{12}R_{13}$, —C(═O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl. In an alternative embodiment, $R_8$ and $R_9$ are both —H.

7. Ring A:

In one embodiment, ring A is as described above for Structural Formula (A). In another embodiment, ring A is as described above for Structural Formula (I')

Alternatively, ring A is a 5-7 membered monocyclic ring or a 9-14 membered bicyclic or tricyclic fused ring optionally substituted with 1 to 3 substituents independently selected from the group consisting of —F, —Cl, —Br, —CN, —$OR_5$, —$NR_6R_7$, —$S(O)_iR_5$, —$NR_{11}S(=O)_iR_5$, —$C(=O)OR_5$, —$C(=O)NR_{12}R_{13}$, —$NR_{11}C(=O)R_5$, —$C(=S)NR_{12}R_{13}$, —$C(=O)R_5$, $(C_1$-$C_6)$alkyl, $(C_2$-$C_6)$alkenyl, halo$(C_1$-$C_6)$alkyl, $(C_1$-$C_3)$alkylsulfonylaminoalkyl, hydroxy$(C_1$-$C_6)$alkyl, cyano$(C_1$-$C_6)$alkyl, $(C_1$-$C_3)$alkylcarbonylamino$(C_1$-$C_6)$alkyl, $(C_1$-$C_3)$alkoxy, halo$(C_1$-$C_3)$alkoxy, $(C_1$-$C_6)$alkoxy$(C_1$-$C_3)$alkyl, aryl and heteroaryl, wherein ring A contains 0 to 2 heteroatoms, which are independently selected from O, N and S. Alternatively, the substituents are selected from the group consisting of —F, —Cl, —Br, —CN, $(C_1$-$C_6)$alkyl, halo$(C_1$-$C_6)$alkyl, hydroxy$(C_1$-$C_6)$alkyl, $(C_1$-$C_3)$alkoxy, halo$(C_1$-$C_3)$alkoxy and phenyl, wherein the phenyl is optionally substituted with F, —Cl, —Br, —CN, $(C_1$-$C_6)$alkyl, halo$(C_1$-$C_6)$alkyl, hydroxy$(C_1$-$C_6)$alkyl, $(C_1$-$C_3)$alkoxy, halo$(C_1$-$C_3)$alkoxy.

In another alternative embodiment, ring A is selected from tetrahydrofuran, tetrahydropyran, cyclopentane, cyclohexane, cyclohexene, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, 2,3,4,5-tetrahydrobenzo[b]oxepine, and 2,3-dihydro-1H-phenalene, each of which is optionally substituted with 1 to 3 substituents independently selected from the group consisting of —F, —Cl, —Br, —CN, $(C_1$-$C_6)$alkyl, halo$(C_1$-$C_6)$alkyl, hydroxy$(C_1$-$C_6)$alkyl, $(C_1$-$C_3)$alkoxy, halo$(C_1$-$C_3)$alkoxy and phenyl, wherein the phenyl is optionally substituted with F, —Cl, —Br, —CN, $(C_1$-$C_6)$alkyl, halo$(C_1$-$C_6)$alkyl, hydroxy$(C_1$-$C_6)$alkyl, $(C_1$-$C_3)$alkoxy, halo$(C_1$-$C_3)$alkoxy. Alternatively, the substituents are selected from the group consisting of —F, -OMe, -OEt and -Ph.

In another embodiment, ring A is represented by the following Structural Formula:

(B)

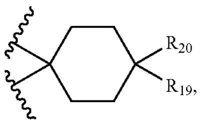

wherein:

$R_{19}$ and $R_{20}$ are each independently selected from —H, halogen, —CN, —$OR_5$, —$NR_6R_7$, —$S(O)_iR_5$, —$NR_{11}S(=O)_iR_5$, —$C(=O)OR_5$, —$C(=O)NR_{12}R_{13}$, —$NR_{11}C(=O)R_5$, —$C(=S)NR_{12}R_{13}$, —$C(=O)R_5$, $(C_1$-$C_6)$alkyl, $(C_2$-$C_6)$alkenyl, aryl, aryl$(C_1$-$C_6)$alkyl, heteroaryl and heteroaryl$(C_1$-$C_6)$alkyl, wherein each of the $(C_1$-$C_6)$alkyl, $(C_2$-$C_6)$alkenyl, aryl, aryl$(C_1$-$C_6)$alkyl, heteroaryl and heteroaryl$(C_1$-$C_6)$alkyl groups represented by $R_{19}$ and $R_{20}$ is optionally substituted with 1 to 5 substituents independently selected from the group consisting of halogen, —CN, —OH, —$NR_{11}SO_2(C_1$-$C_3)$alkyl, —$NR_{11}C(=O)$—$(C_1$-$C_3)$alkyl, $(C_1$-$C_6)$alkyl, halo$(C_1$-$C_6)$alkyl, $(C_1$-$C_3)$alkoxy, halo$(C_1$-$C_3)$alkoxy and $(C_1$-$C_3)$alkoxy$(C_1$-$C_6)$alkyl. Alternatively, $R_{20}$ is —H and $R_{19}$ is —OH, $(C_1$-$C_3)$alkoxy, halo$(C_1$-$C_3)$alkoxy or $(C_1$-$C_3)$alkoxy$(C_1$-$C_3)$alkoxy. In another alternative embodiment, $R_{19}$ and $R_{20}$ are each independently —H or —$NR_6R_7$, wherein $R_6$ and $R_7$ are each independently selected from the group consisting of —H, $(C_1$-$C_6)$alkyl, halo$(C_1$-$C_6)$alkyl, and $(C_1$-$C_3)$alkoxy$(C_1$-$C_3)$alkyl.

In another embodiment, ring A is represented by the following Structural formula:

(C)

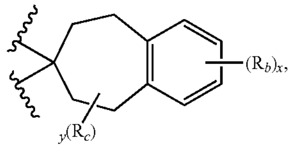

wherein:

$R_g$ and $R_h$, for each occurrence, are independently —H, -halogen, —CN, —$NO_2$, —$OR_5$, —$NR_6R_7$, —$S(O)_iR_5$, —$C(=O)OR_5$, —$C(=O)NR_{12}R_{13}$, —$C(=O)R_5$, $(C_1$-$C_6)$alkyl, $(C_2$-$C_6)$alkenyl, $(C_2$-$C_6)$alkynyl, $(C_3$-$C_8)$cycloalkyl, $(C_3$-$C_9)$heterocycloalkyl, aryl, heteroaryl, each $(C_1$-$C_6)$alkyl, $(C_2$-$C_6)$alkenyl, $(C_2$-$C_6)$alkynyl, $(C_3$-$C_8)$cycloalkyl, $(C_3$-$C_9)$heterocycloalkyl, aryl and heteroaryl represented by $R_b$ is optionally substituted with 1 to 3 substituents selected from the group consisting of —F, —Cl, —Br, —CN, —$OR_5$, —$SR_5$, —$NR_6R_7$, —$S(O)_iR_5$, —$NR_{11}S(=O)_iR_5$, —$C(=O)OR_5$, —$C(=O)NR_{12}R_{13}$, —$NR_{11}C(=O)R_5$, —$C(=S)NR_{12}R_{13}$, —$C(=O)R_5$, $(C_1$-$C_6)$alkyl, $(C_3$-$C_8)$cycloalkyl, $(C_3$-$C_9)$heterocycloalkyl, $(C_2$-$C_6)$alkenyl, halo$(C_1$-$C_6)$alkyl, hydroxy$(C_1$-$C_6)$alkyl, cyano$(C_1$-$C_6)$alkyl, $(C_1$-$C_3)$alkoxy, halo$(C_1$-$C_3)$alkoxy, $(C_1$-$C_6)$alkoxy$(C_1$-$C_3)$alkyl, aryl and heteroaryl;

x is an integer from 1 to 4; and y is an integer from 1 to 6.

In one embodiment, for structural formula (C), each $R_g$ is independently selected from —H, Me and F and each $R_h$ is independently —H, halogen, —CN, —$NO_2$, $(C_1$-$C_6)$alkyl, halo$(C_1$-$C_6)$alkyl, $(C_1$-$C_3)$alkoxy, and halo$(C_1$-$C_3)$alkoxy. Alternatively, for structural formula (C), $R_g$ is —H and each $R_h$ is independently —H, halogen, —CN, —$NO_2$, $(C_1$-$C_6)$alkyl, halo$(C_1$-$C_6)$alkyl, $(C_1$-$C_3)$alkoxy, and halo$(C_1$-$C_3)$alkoxy. In another alternative embodiment, for structural formula (C), $R_g$ and $R_h$ are both —H.

8. $R_{11}$:

In one embodiment, $R_{11}$ is as described above for Structural Formula (A). Alternatively, $R_{11}$ is —H, $(C_1$-$C_6)$alkyl or halo$(C_1$-$C_6)$alkyl. In another alternative embodiment, $R_{11}$ is —H. Alternatively, $R_{11}$ is —H or $(C_1$-$C_3)$alkyl (e.g., methyl).

9. $R_{12}$ and $R_{13}$:

In one embodiment, $R_{12}$ and $R_{13}$ are as described above for Structural Formula (A).

Alternatively, $R_{12}$ and $R_{13}$ are each independently —H, $(C_1$-$C_6)$alkyl, $(C_1$-$C_3)$alkoxy$(C_1$-$C_6)$alkyl, hydroxy$(C_1$-$C_6)$alkyl, cyano$(C_1$-$C_6)$alkyl, amino$(C_1$-$C_6)$alkyl, $(C_1$-$C_3)$alkylamino$(C_1$-$C_6)$alkyl, or di$(C_1$-$C_3)$alkylamino$(C_1$-$C_6)$alkyl. In a alternative embodiment, $R_{12}$ and $R_{13}$ are independently —H, $(C_1$-$C_6)$alkyl, $(C_1$-$C_3)$alkoxy$(C_1$-$C_3)$alkyl, hydroxy$(C_1$-$C_3)$alkyl, cyano$(C_1$-$C_3)$alkyl, or di$(C_1$-$C_3)$alkylamino$(C_1$-$C_3)$alkyl. Alternatively, $R_{12}$ and $R_{13}$ are independently —H, methyl, ethyl, propyl, butyl, methoxyethyl, cyanoethyl, or dimethylaminoethyl.

In another alternative embodiment, $R_{12}$ and $R_{13}$ together with the nitrogen atom to which they are attached forms a pyrrolidine or piperidine ring, optionally substituted with 1 to 3 substituents selected from halogen, —CN, $(C_1$-$C_6)$alkyl, halo$(C_1$-$C_6)$alkyl, $(C_1$-$C_3)$alkoxy and $(C_1$-$C_3)$alkoxy$(C_1$-$C_6)$ alkyl. In another alternative embodiment, $R_{12}$ and $R_{13}$ together with the nitrogen atom to which they are attached forms an unsubstituted pyrrolidine or piperidine ring.

10. $R_{14}$:

In one embodiment, $R_{14}$ is as described above for Structural Formula (I).

Alternatively, $R_{14}$ is —H, $(C_1-C_6)$alkyl, halo$(C_1-C_6)$alkyl, $(C_3-C_8)$cycloalkyl, cycloheteroalkyl$(C_1-C_3)$alkyl, $(C_3-C_8)$cycloalkyl$(C_1-C_3)$alkyl, aryl$(C_1-C_6)$alkyl, heteroaryl$(C_1-C_6)$alkyl, each optionally substituted with 1 to 3 substituents independently selected from the group consisting of —F, —Cl, —Br, —CN, $(C_1-C_6)$alkyl, halo$(C_1-C_6)$alkyl and $(C_1-C_3)$alkoxy. In another alternative embodiment, $R_{14}$ is $(C_1-C_6)$alkyl, halo$(C_1-C_3)$alkyl, $(C_3-C_8)$cycloalkyl$(C_1-C_3)$alkyl or benzyl. In yet another alternative embodiment, $R_{14}$ is ethyl, propyl, cyclohexylmethyl, cyclopropylethyl, trifluoroethyl, or benzyl. In another alternative embodiment, $R_{14}$ is methyl.

In another alternative embodiment, $R_{14}$ is selected from the group consisting of $(C_1-C_6)$alkyl, $(C_3-C_8)$cycloalkyl, $(C_3-C_8)$cycloalkyl$(C_1-C_3)$alkyl, $(C_3-C_7)$heterocycloalkyl and $(C_3-C_7)$heterocycloalkyl$(C_1-C_3)$alkyl, each optionally substituted with 1 to 3 substituents independently selected from the group consisting of —F, —Cl, —Br, —CN, $(C_1-C_6)$alkyl, halo$(C_1-C_6)$alkyl, $(C_1-C_3)$alkoxy, $—NR_6R_7$, $—NR_{11}S(O)_iR_5$, $—S(O)_iR_5—$, —OH and $—C(O)OR_5$.

In another alternative embodiment, $R_{14}$ is selected from $(C_1-C_3)$alkyl, halo$(C_1-C_3)$alkyl, $(C_3-C_6)$cycloalkyl, $(C_3-C_6)$cycloalkyl$(C_1-C_3)$alkyl, $(C_3-C_7)$heterocycloalkyl, $(C_3-C_7)$heterocycloalkyl$(C_1-C_3)$alkyl, wherein each of the group represented by $R_{14}$ is optionally substituted with a substituent selected from $(C_1-C_3)$alkyl, $—CO_2H$, $—SO_2—(C_1-C_3)$alkyl, —CN, —OH and $—(C_1-C_3)$alkoxy and the $(C_3-C_7)$heterocycloalkyl is selected from oxepane, tetrahydrapyran and N—$(C_1-C_3)$alkylpiperidine.

In another alternative embodiment, $R_{14}$ is —H, $—OR_5$, $—NR_6R_7$, $(C_1-C_6)$alkyl, $(C_3-C_6)$cycloalkyl, $(C_3-C_6)$cycloalkyl$(C_1-C_3)$alkyl, $(C_3-C_5)$heterocycloalkyl, $(C_3-C_5)$heterocycloalkyl$(C_1-C_3)$alkyl, heteroaryl, phenyl, phenyl$(C_1-C_3)$alkyl and heteroaryl$(C_1-C_3)$alkyl, wherein the heteroaryl is selected from pyridyl, pyridazinyl, pyridinonyl, pyridazinonyl, thiazolyl, oxazolyl, oxadiazolyl, pyrazinyl, pyrimidyl, indolyl, quinolyl, quinoxalinyl and thiophenyl and triazolyl, the $(C_3-C_5)$heterocycloalkyl is selected from oxetanyl, tetrahydrofuran, tetrahydropyran, piperidinyl and pyrrolidinyl, and each of the $(C_1-C_6)$alkyl, $(C_3-C_6)$cycloalkyl, $(C_3-C_6)$cycloalkyl$(C_1-C_3)$alkyl, $(C_3-C_5)$heterocycloalkyl, $(C_3-C_5)$heterocycloalkyl$(C_1-C_3)$alkyl, heteroaryl, phenyl, phenyl$(C_1-C_3)$alkyl and heteroaryl$(C_1-C_3)$alkyl groups represented by $R_{14}$ is optionally substituted with 1 to 3 substituents independently selected from halogen, $(C_1-C_6)$alkyl, halo$(C_1-C_6)$alkyl, $(C_1-C_3)$alkoxy, $—NR_6R_7$, $—S(O)_iR_5$, $—NR_{11}SO_2R_5$, —OH, $—COOR_5$, $—C(=O)R_5$, $—C(=O)NR_{12}R_{13}$ and thiazolyl.

In another alternative embodiment, $R_{14}$, when present, is selected from the group consisting of —H, methyl, ethyl, 2-propyl, 1-propyl, 1-butyl, benzyl, 2-pyridylmethyl, methoxyethyl, 1-methoxypropan-2-yl, N,N-dimethylaminoethyl, 4-cyanobenzyl, 2-cyanobenzyl, 3-cyanobenzyl, 2-thiazolylethyl, 2-thiazolylmethyl, 6-quinoxalinylmethyl, 1-phenylethyl, 2-propyl, tert-butyl, 3-dimethylaminobenzyl, 3-methanesulfonamidobenzyl, 3-methanesulfonylbenzyl, 2-oxazolylmethyl, 1,1,2,2-tetrafluoroethoxy, 2-oxetanylmethyl, 2-ethylbutyl, 5-fluoro-2-pyridyl, 3-fluorobenzyl, 4-thiazolylmethyl, 2,2-difluoroethyl, 3-tetrahydrofuranylmethyl, 2-tetrahydrofuranyl, 4-fluorobenzyl, 3-methoxybenzyl, 2-fluorobenzyl, 4-methanesulfonylbenzyl, 2-tetrahydrafuranylmethyl, 2,2,2-trifluoroethyl, 5-trifluoromethyl-2-pyridylmethyl, 3,3,3-trifluoropropyl, 2-hydroxyethyl, 2-chlorobenzyl, 2-methoxyethyl, cyclobutylmethyl, 4-tetrahydropyranylmethyl, 2-methylpropyl, phenylethyl, cyclopropyl, cyclobutyl, 1-methylpropyl, 5-pyrimidylmethyl, 2-carboxyethyl, dimethylamino, 4-tetrahydropyranyl, 1-methylpiperidin-4-yl, 2-fluoroethyl, 2-butyl, dimethylaminoethyl, 1-(3-pyridazinyl)ethyl, 1-methoxy-2-propyl, (4-methyl-1,2,4-triazol-3-yl)methyl, (2-methoxy-2-phenyl)ethyl, (1,3,4-oxadiazol-2-yl)methyl, (quinoxalin-2-yl)methyl, 1-phenylethyl, methanesulfonylaminoethyl, aminocarbonylethyl, aminocarbonylmethyl, 3-methoxypropyl and (3-(2-thiazolyl))benzyl, carboxymethyl, 1-methylethoxycarbonylmethyl, 5-methyl-1,3,4-thiadizolyl, 4-pyridazinyl, 5-methyl-2-oxazolylethyl, 2-hydroxyl-2-methylpropyl, 2-hydroxy-1-methylethyl and 2-pyrazinylmethyl.

11. $R_{15}$, $R_{16}$, $R_{17}$ and $R_{18}$:

In one embodiment, $R_{15}$ is as described above for Structural Formula (A). Alternatively, $R_{15}$ is —H or $(C_1-C_6)$alkyl. In another embodiment, $R_{15}$ is —H.

In one embodiment, $R_{16}$ and $R_{17}$ are as described above for Structural Formula (I). Alternatively, $R_{16}$ and $R_{17}$ are each independently —H or $(C_1-C_3)$alkyl. In another embodiment, $R_{16}$ and $R_{17}$ are both —H.

In one embodiment, $R_{18}$ is as described above for Structural Formula (I). Alternatively, $R_{18}$ is —H or $(C_1-C_3)$alkyl. In another embodiment, $R_{18}$ is —H.

12. X, W, Z, i, p, m and q:

In one embodiment, X is as described above for Structural Formula (A). Alternatively, X is —O—, $—CH_2—C(R_3R_4)—$, or $—C(R_3R_4)—$. In one embodiment, X is —O—. In another embodiment, X is $—CH_2—CH_2—$. In another embodiment, X is $—CH_2—$.

In one embodiment, W is as described above for Structural Formula (I). Alternatively, W is $—N(R_{14})—$, —S—, —O—. In one embodiment, W is $—N(CH_3)—$.

In one embodiment, Z is as described above for Structural Formula (I). Alternatively, Z is —C(=O)—, —C(=S)—, $—C(=NR_{15})—$, —O—, $—C(=O)C(R_{16}R_{17})—$, $—C(=S)C(R_{16}R_{17})—$, $—C(=NR_{15})C(R_{16}R_{17})—$, $—N(R_{18})—$, $—(CR_{16}R_{17})_m—$ or $—O—(CR_{16}R_{17})—$. In one embodiment, Z is —C(=O)—. In another embodiment, Z is —O—. In another embodiment, Z is $—C(=O)CH_2—$.

i is 0, 1 or 2;

p is 1 or 2. In one embodiment, p is 1.

m is 1 or 2.

q is 1, 2 or 3.

In a 1st embodiment, the compound of the present invention is represented by Structural Formula (II), (III) or (IV):

(II)

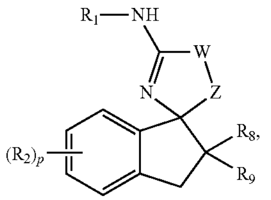

-continued
(III)
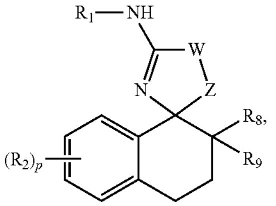
(IV)
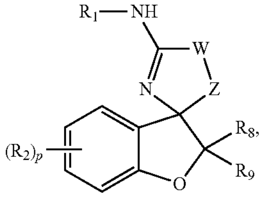
or a pharmaceutically acceptable salt thereof. Values and alternative values for Structural Formulas (II), (III) and (IV) are as described above for Structural Formula (I) or (I').
In a $2^{nd}$ embodiment, the compound of the present invention is represented by Structural Formulas (V)-(XXV):
(V)
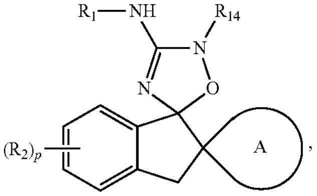
(VI)
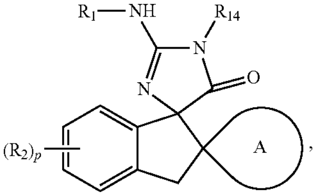
(VII)
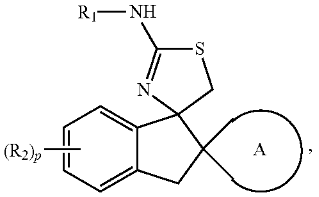
(VIII)
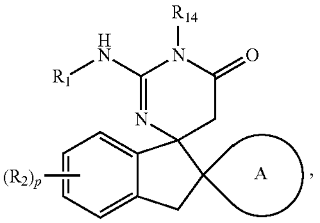
-continued
(IX)
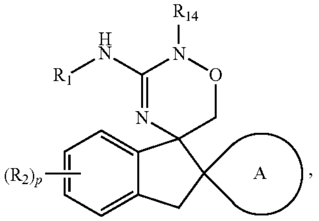
(X)
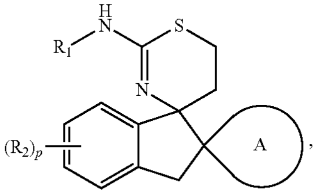
(XI)
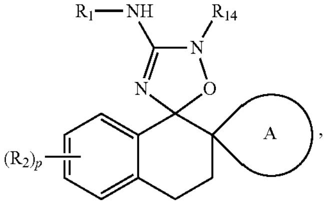
(XII)
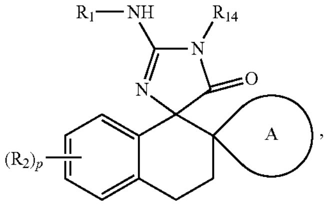
(XIII)
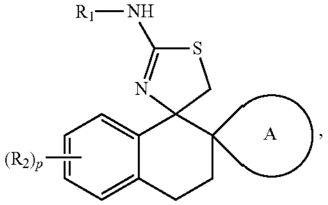
(XIV)
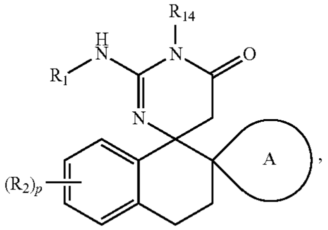
(XV)
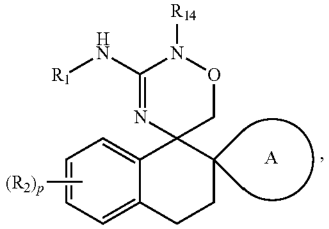

-continued
(XVI)
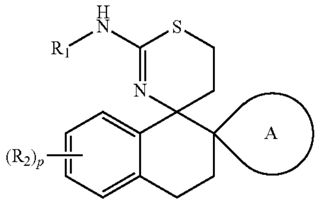
,
(XVII)
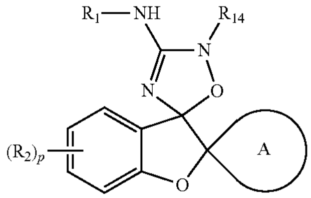
,
(XVIII)
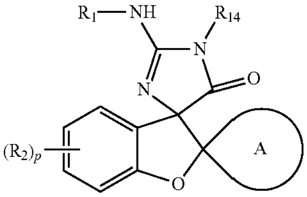
,
(XIX)
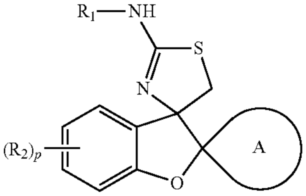
,
(XX)
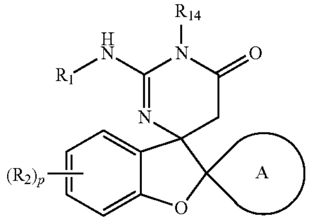
,
(XXI)
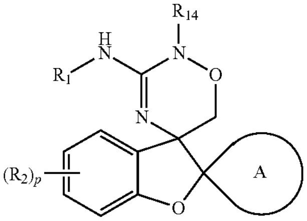
,
(XXII)
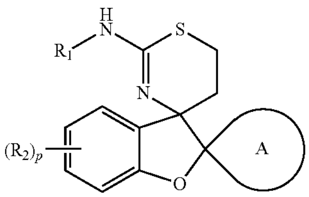
,
-continued
(XXIII)
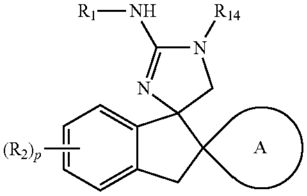
,
(XXIV)
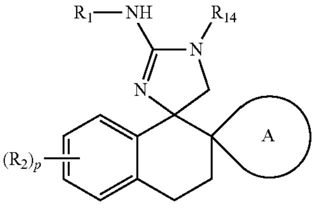
, or
(XXV)
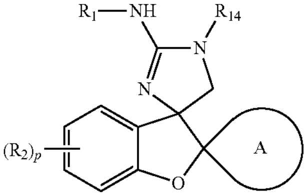
,
or a pharmaceutically acceptable salt thereof. Values or alternative values for the variables in Structural Formulas (V)-(XXV) are as described above for Structural Formula (I) or (I').
In a 3rd embodiment, the compound of the present invention is represented by Structural Formulas (Va)-(XXVa):
(Va)
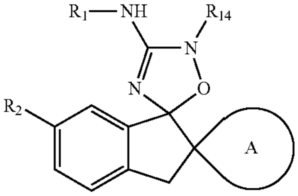
,
(VIa)
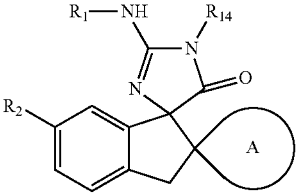
,
(VIIa)
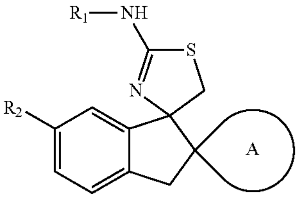
, -continued
(VIIIa)
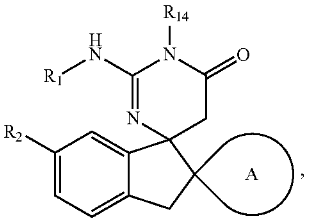
(IXa)
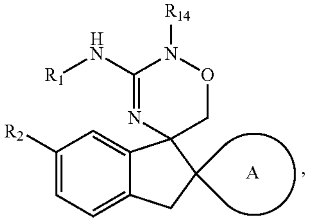
(Xa)
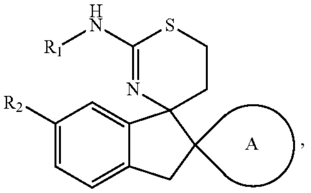
(XIa)
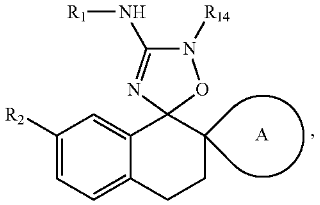
(XIIa)
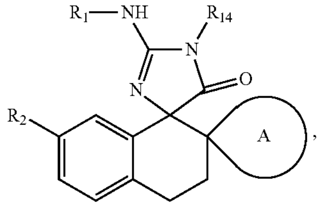
(XIIIa)
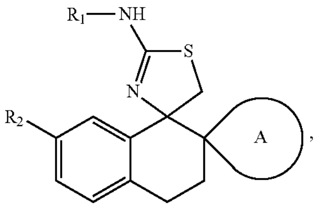
(XIVa)
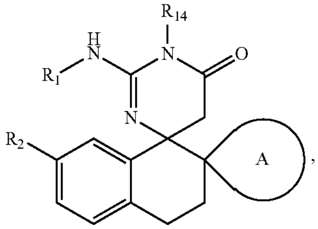
-continued
(XVa)
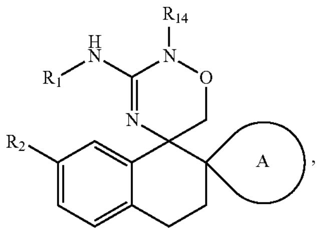
(XVIa)
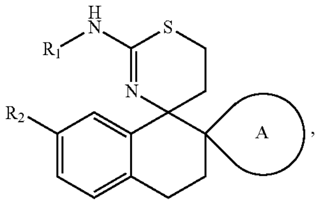
(XVIIa)
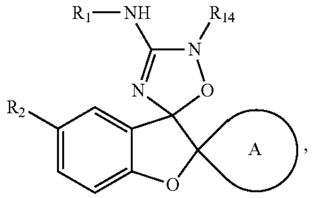
(XVIIIa)
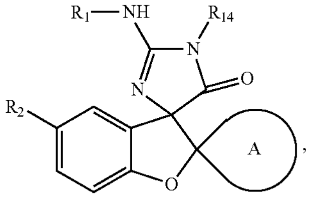
(XIXa)
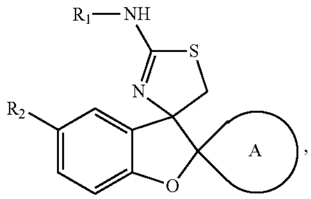
(XXa)
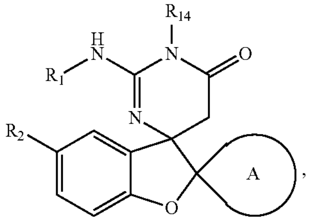
(XXIa)
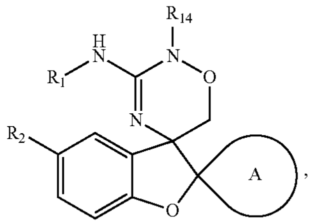

-continued (XXIIa)

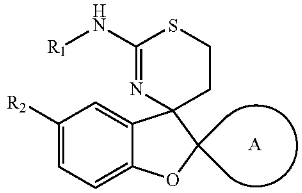, (XXIIIa)

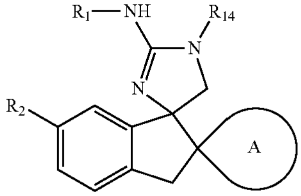, (XXIVa)

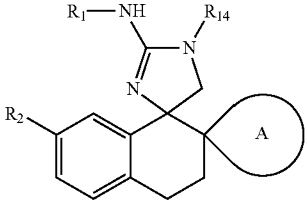, or (XXVa)

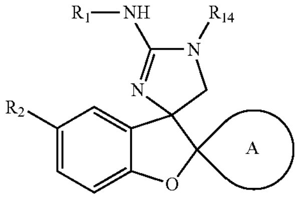, or a pharmaceutically acceptable salt thereof. Values and alternative values for variables in Structural Formulas (Va)-(XXVa) are as described above for Structural Formula (I) or (I').

In one embodiment, ring A is a 5-7 membered monocyclic ring or a 9-14 membered bicyclic or tricyclic fused ring optionally substituted with 1 to 3 substituents independently selected from the group consisting of halogen (e.g., —F, —Cl or —Br), —CN, —$OR_5$, —$NR_6R_7$, —$S(O)_iR_5$, —$NR_{11}S(=O)_iR_5$, —C(=O)$OR_5$, —C(=O)$NR_{12}R_{13}$, —$NR_{11}C(=O)R_5$, —C(=S)$NR_{12}R_{13}$, —C(=O)$R_5$, $(C_1$-$C_6)$alkyl, $(C_2$-$C_6)$alkenyl, halo$(C_1$-$C_6)$alkyl, $(C_1$-$C_3)$alkylsulfonylaminoalkyl, hydroxy$(C_1$-$C_6)$alkyl, cyano$(C_1$-$C_6)$alkyl, $(C_1$-$C_3)$alkylcarbonylamino$(C_1$-$C_6)$alkyl, $(C_1$-$C_3)$alkoxy, halo$(C_1$-$C_3)$alkoxy, $(C_1$-$C_6)$alkoxy$(C_1$-$C_3)$alkyl, aryl and heteroaryl, wherein ring A contains 0 to 2 heteroatoms, which are independently selected from O, N and S. Values and alternative values for the remainder of the variables are as described above for Structural Formula (I) or (I'). More specifically, the substituents are selected from the group consisting of halogen (e.g., —F, —Cl or —Br), —CN, $(C_1$-$C_6)$alkyl, halo$(C_1$-$C_6)$alkyl, hydroxy$(C_1$-$C_6)$alkyl, $(C_1$-$C_3)$alkoxy, halo$(C_1$-$C_3)$alkoxy and phenyl, wherein the phenyl is optionally substituted with F, —Cl, —Br, —CN, $(C_1$-$C_6)$alkyl, halo$(C_1$-$C_6)$alkyl, hydroxy$(C_1$-$C_6)$alkyl, $(C_1$-$C_3)$alkoxy, halo$(C_1$-$C_3)$alkoxy. Even more specifically, $R_1$ is —H and $R_{14}$ is -Me.

In another embodiment, ring A is selected from tetrahydrofuran, tetrahydropyran, cyclopentane, cyclohexane, cyclohexene, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, 2,3,4,5-tetrahydrobenzo[b]oxepine and 2,3-dihydro-1H-phenalene, each of which is optionally substituted with 1 to 3 substituents independently selected from the group consisting of halogen (e.g., —F, —Cl or —Br), —CN, $(C_1$-$C_6)$alkyl, halo$(C_1$-$C_6)$alkyl, hydroxy$(C_1$-$C_6)$alkyl, $(C_1$-$C_3)$alkoxy, halo$(C_1$-$C_3)$alkoxy and phenyl, wherein the phenyl is optionally substituted with halogen (e.g., —F, —Cl or —Br), —CN, $(C_1$-$C_6)$alkyl, halo$(C_1$-$C_6)$alkyl, hydroxy$(C_1$-$C_6)$alkyl, $(C_1$-$C_3)$alkoxy, halo$(C_1$-$C_3)$alkoxy. Values and alternative values for the remainder of the variables are as described above for Structural Formula (I) or (I'). More specifically, the substituents are selected from the group consisting of —F, -OMe, -OEt and -Ph. Even more specifically, $R_1$ is —H and $R_{14}$ is -Me.

In a 4$^{th}$ embodiment, for Structural Formulas (Va)-(XXVa), $R_2$ is —H, —Br, —F, $(C_1$-$C_6)$alkyl, $(C_2$-$C_6)$alkynyl, $(C_3$-$C_8)$cycloalkyl, aryl or heteroaryl, each of the $(C_1$-$C_6)$alkyl, $(C_2$-$C_6)$alkynyl, $(C_3$-$C_8)$cycloalkyl, aryl and heteroaryl represented by $R_2$ is optionally substituted with 1 to 3 substituents independently selected from the group consisting of —F, —Cl, —Br, —CN, —$OR_5$, —$SR_5$, —$NR_6R_7$, —$S(O)_iR_5$, —$NR_{11}S(=O)_iR_5$, —C(=O)$OR_5$, —C(=O)$NR_{12}R_{13}$, —$NR_{11}C(=O)R_5$, —C(=S)$NR_{12}R_{13}$, —C(=O)$R_5$, $(C_1$-$C_6)$alkyl, $(C_3$-$C_8)$cycloalkyl, $(C_2$-$C_6)$alkenyl, halo$(C_1$-$C_6)$alkyl, $(C_1$-$C_3)$alkylsulfonylaminoalkyl, hydroxy$(C_1$-$C_6)$alkyl, cyano$(C_1$-$C_6)$alkyl, $(C_1$-$C_3)$alkylcarbonylamino$(C_1$-$C_6)$alkyl, $(C_1$-$C_3)$alkoxy, halo$(C_1$-$C_3)$alkoxy, $(C_1$-$C_6)$alkoxy$(C_1$-$C_3)$alkyl and a heteroaryl group. Values and alternative values for the remainder of the variables are as described above for Structural Formula (I) or (I').

In a 5$^{th}$ embodiment, for Structural Formulas (Va)-(XXVa), $R_2$ is —H, —Br, —F, —Cl or —CN. Values and alternative values for the remainder of the variables in Structural Formulas (Va)-(XXVa) are as described above in the 3$^{rd}$ embodiment.

In a 6$^{th}$ embodiment, for Structural Formulas (Va)-(XXVa), $R_2$ is $(C_1$-$C_6)$alkyl optionally substituted with —F, —Cl, —Br, $(C_1$-$C_6)$alkyl, halo$(C_1$-$C_6)$alkyl, $(C_1$-$C_6)$alkoxy or $(C_3$-$C_8)$cycloalkyl. Values and alternative values for the remainder of the variables in Structural Formulas (Va)-(XXIIa) are as described above in the 3$^{rd}$ embodiment. Alternatively, $R_2$ is a $(C_1$-$C_3)$alkyl.

In a 7$^{th}$ embodiment, for Structural Formulas (Va)-(XXVa), $R_2$ is a $(C_2$-$C_6)$alkynyl optionally substituted with halogen (e.g., —F, —Cl or —Br), $(C_1$-$C_6)$alkyl, halo$(C_1$-$C_6)$alkyl, $(C_1$-$C_6)$alkoxy or $(C_3$-$C_8)$cycloalkyl with halogen (e.g., —F, —Cl or —Br), $(C_1$-$C_6)$alkyl, halo$(C_1$-$C_6)$alkyl, $(C_1$-$C_6)$alkoxy or $(C_3$-$C_8)$cycloalkyl. Values and values for the remainder of the variables in Structural Formulas (Va)-(XXVa) are as described above in the 3$^{rd}$ embodiment. Alternatively, $R_2$ is a $(C_2$-$C_6)$alkynyl optionally substituted with a cyclopropyl. In another alternative, $R_2$ is cyclopropylethynyl.

In a 8$^{th}$ embodiment, for Structural Formulas (Va)-(XXVa), $R_2$ is a phenyl optionally substituted with 1 to 3 substituents independently selected from the group consisting of halogen (e.g., —F, —Cl or —Br), —CN, —$OR_5$, —$SR_5$, —$NR_6R_7$, —$S(O)_iR_5$, —$NR_{11}S(=O)_iR_5$, —C(=O)$OR_5$, —C(=O)$NR_{12}R_{13}$, —$NR_{11}C(=O)R_5$, —C(=S)$NR_{12}R_{13}$, —C(=O)$R_5$, $(C_1$-$C_6)$alkyl, $(C_3$-$C_8)$cycloalkyl, $(C_2$-$C_6)$alkenyl, halo$(C_1$-$C_6)$alkyl, $(C_1$-$C_3)$alkylsulfonylaminoalkyl, hydroxy$(C_1$-$C_6)$alkyl, cyano$(C_1$-$C_6)$alkyl, $(C_1$-$C_3)$alkylcarbonylamino$(C_1$-$C_6)$alkyl, $(C_1$-$C_3)$alkoxy, halo$(C_1$-$C_3)$alkoxy, $(C_1$-$C_6)$alkoxy$(C_1$-$C_3)$alkyl, aryl and heteroaryl. with halogen (e.g., —F, —Cl or —Br), $(C_1$-$C_6)$alkyl, halo$(C_1$-$C_6)$alkyl, $(C_1$-$C_6)$alkoxy or $(C_3$-$C_8)$cycloalkyl. Values and alternative values for the remainder of the variables in Structural Formulas (Va)-(XXVa) are as described above in the 3rd embodiment. Alternatively, $R_2$ is a phenyl optionally substituted with 1 to 3 substituents independently selected from the group consisting of halogen (e.g., —F, —Cl or —Br), —CN, $(C_1-C_6)$alkyl, $(C_1-C_6)$alkoxy, halo$(C_1-C_6)$alkyl and halo$(C_1-C_6)$alkoxy. In another alternative, $R_2$ is phenyl optionally substituted with 1 to 3 substituents independently selected from the group consisting of halogen (e.g., —F, —Cl or —Br), —CN, -Me, -Et, -OMe, —$CF_3$ and —$OCF_3$.

In a 9th embodiment, for Structural Formulas (Va)-(XXVa), $R_2$ is a 5-6 membered heteroaryl optionally substituted with 1 to 3 substituents independently selected from the group consisting of halogen (e.g., —F, —Cl or —Br), —CN, —$OR_5$, —$SR_5$, —$NR_6R_7$, —$S(O)_iR_5$, —$NR_{11}S(=O)_iR_5$, —C(=O)$OR_5$, —C(=O)$NR_{12}R_{13}$, —$NR_{11}C(=O)R_5$, —C(=S)$NR_{12}R_{13}$, —C(=O)$R_5$, $(C_1-C_6)$alkyl, $(C_3-C_8)$cycloalkyl, $(C_2-C_6)$alkenyl, halo$(C_1-C_6)$alkyl, $(C_1-C_3)$alkylsulfonylaminoalkyl, hydroxy$(C_1-C_6)$alkyl, cyano$(C_1-C_6)$alkyl, $(C_1-C_3)$alkylcarbonylamino$(C_1-C_6)$alkyl, $(C_1-C_3)$alkoxy, halo$(C_1-C_3)$alkoxy, $(C_1-C_6)$alkoxy$(C_1-C_3)$alkyl, aryl and heteroaryl. Values and values for the remainder of the variables in Structural Formulas (Va)-(XXVa) are as described above in the 3rd embodiment. Alternatively, the substituents are independently selected from the group consisting of halogen (e.g., —F, —Cl or —Br), —CN, $(C_1-C_6)$alkyl, halo$(C_1-C_6)$alkyl, $(C_3-C_8)$cycloalkyl, $(C_1-C_3)$alkoxy, halo$(C_1-C_3)$alkoxy and $(C_1-C_6)$alkoxy$(C_1-C_3)$alkyl. In another alternative, $R_2$ is a pyridinyl, thiophenyl, pyrrolyl or pyrimidinyl, each optionally substituted with 1 to 3 substituents independently selected from the group consisting of halogen, —CN, $(C_1-C_6)$alkyl, $(C_3-C_8)$cycloalkyl, halo$(C_1-C_6)$alkyl, $(C_1-C_3)$alkoxy, halo$(C_1-C_3)$alkoxy and $(C_1-C_6)$alkoxy$(C_1-C_3)$alkyl.

In a 10th embodiment, for Structural Formulas (Va)-(XXVa), $R_2$ is an indolyl, pyridinyl, thiophenyl, pyrrolyl, pyrimidinyl, cyclohexyl, or thiozolyl, each of which is optionally substituted with 1 to 3 substituents independently selected from the group consisting of halogen (e.g., —F, —Cl or —Br), —CN, —$OR_5$, —$SR_5$, —$NR_6R_7$, —$S(O)_iR_5$, —$NR_{11}S(=O)_iR_5$, —C(=O)$OR_5$, —C(=O)$NR_{12}R_{13}$, —$NR_{11}C(=O)R_5$, —C(=S)$NR_{12}R_{13}$, —C(=O)$R_5$, $(C_1-C_6)$alkyl, $(C_3-C_8)$cycloalkyl, $(C_2-C_6)$alkenyl, halo$(C_1-C_6)$alkyl, $(C_1-C_3)$alkylsulfonylaminoalkyl, hydroxy$(C_1-C_6)$alkyl, cyano$(C_1-C_6)$alkyl, $(C_1-C_3)$alkylcarbonylamino$(C_1-C_6)$alkyl, $(C_1-C_3)$alkoxy, halo$(C_1-C_3)$alkoxy, $(C_1-C_6)$alkoxy$(C_1-C_3)$alkyl, aryl and heteroaryl. Values and alternative values for the remainder of the variables in Structural Formulas (Va)-(XXVa) are as described above in the 3rd embodiment. Alternatively, $R_2$ is an indolyl or pyridinyl optionally substituted with —F, —Cl, —Br, —CN, $(C_1-C_6)$alkyl, halo$(C_1-C_6)$alkyl, $(C_1-C_3)$alkoxy or halo$(C_1-C_3)$alkoxy. In another alternative, $R_2$ is 2-pyridinyl or 6-indolyl.

In a 11th embodiment, the compound of the present invention is represented by the following Structural Formulas:

(Vb)

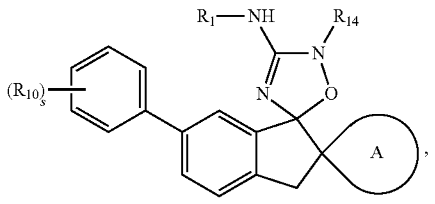

-continued (VIb)

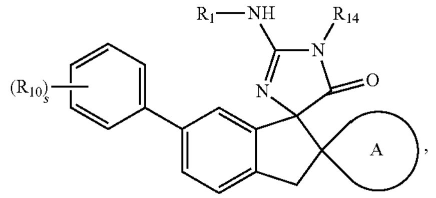

(VIIb)

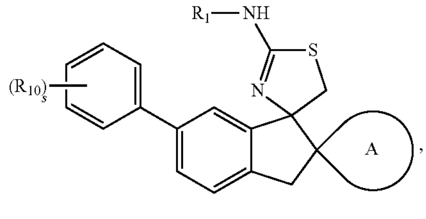

(VIIIb)

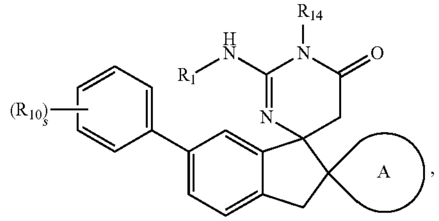

(IXb)

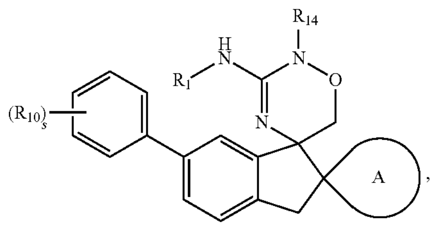

(Xb)

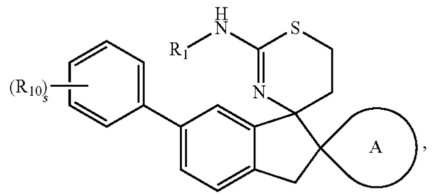

(XIb)

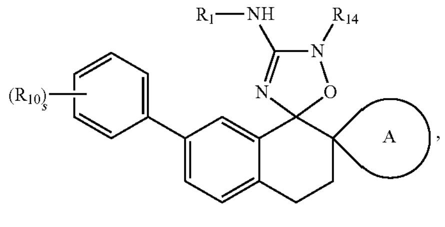

(XIIb)

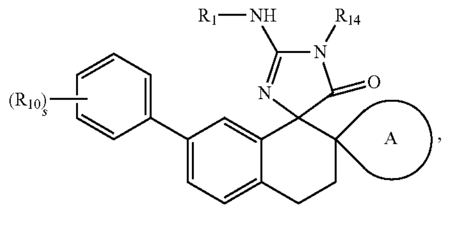

-continued (XIIIb)

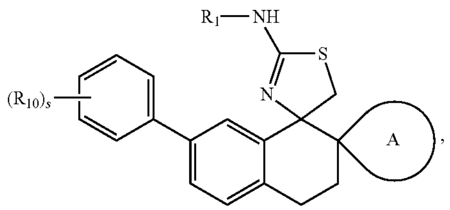, (XIVb)

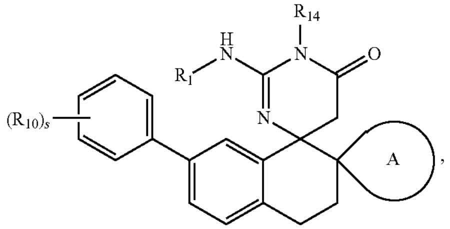, (XVb)

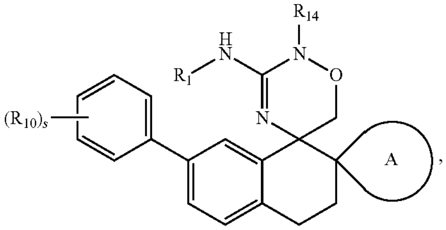, (XVIa)

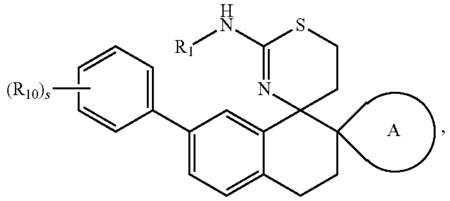, (XVIIb)

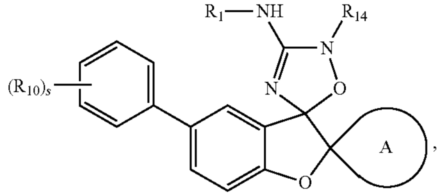, (XVIIIb)

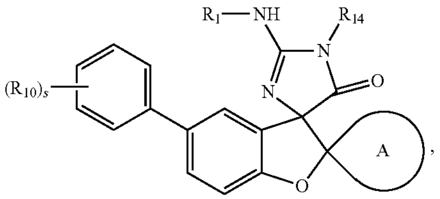, (XIXb)

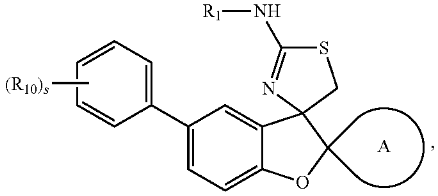,

-continued (XXb)

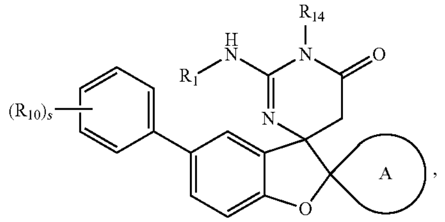, (XXIb)

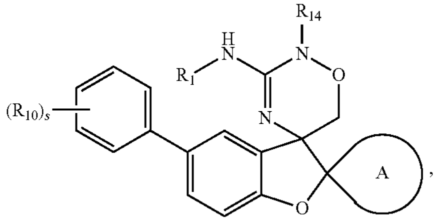, (XXIIb)

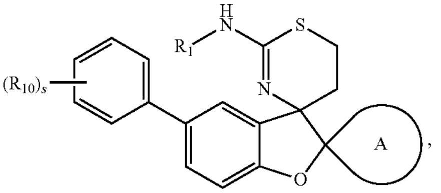, (XXIIIb)

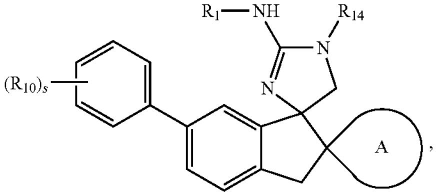, (XXIVb)

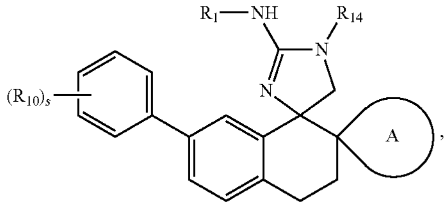, or (XXVb)

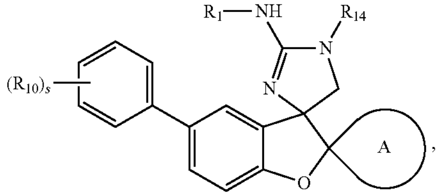, or a pharmaceutically acceptable salt thereof, wherein $R_{10}$ is independently selected from the group consisting of halogen, —CN, —$NO_2$, —$OR_5$, —$SR_5$, —$NR_6R_7$, —$S(O)_tR_5$, —$NR_{11}S(=O)_tR_5$, —$S(O)_tNR_{12}R_{13}$, —$C(=O)OR_5$, —$OC(=O)R_5$, —$C(=S)OR_5$, —$OC(=S)R_5$, —$C(=O)NR_{12}R_{13}$, —$NR_{11}C(=O)R_5$, —$C(=S)NR_{12}R_{13}$, —$NR_{11}C(=S)R_5$, —$C(=O)R_5$, —$C(=S)R_5$, —$OC(=O)OR_5$, —$O(C=O)NR_{12}R_{13}$, —$NR_{11}(C=O)OR_5$, $(C=S)OR_5$, —$O(C=S)NR_{12}R_{13}$, —$NR_{11}(C=O)NR_{12}R_{13}$, —$NR_{11}(C=S)NR_{12}R_{13}$, —$C(=O)R_5$, —$C(=S)R_5$, $(C_1$-$C_6)$alkyl, $(C_2$-$C_6)$alkynyl, $(C_3$-$C_8)$cycloalkyl, $(C_4$-$C_8)$cycloalkenyl, $(C_3$-$C_9)$heterocycloalkyl, $(C_2$-$C_6)$alkenyl, halo$(C_1$-$C_6)$alkyl, $(C_1$-$C_3)$alkylsulfonylaminoalkyl, hydroxy$(C_1$-$C_6)$alkyl, cyano$(C_1$-

$C_6$)alkyl, ($C_1$-$C_3$)alkylcarbonylamino($C_1$-$C_6$)alkyl, ($C_1$-$C_3$) alkoxy, halo($C_1$-$C_3$)alkoxy, ($C_1$-$C_6$)alkoxy($C_1$-$C_3$)alkyl, aryl and heteroaryl, wherein the cycloalkyl, heterocycloalkyl, aryl and heteroaryl groups in the groups represented by $R_{10}$ are each optionally substituted with 1 to 3 substituents independently selected from halogen, —CN, ($C_1$-$C_6$)alkyl, halo($C_1$-$C_6$)alkyl, ($C_1$-$C_3$)alkoxy, halo($C_1$-$C_3$)alkoxy and ($C_1$-$C_3$) alkoxy($C_1$-$C_6$)alkyl and s is 0, 1, 2 or 3. Values and alternative values for the remainder of the variables in Structural Formulas (Vb)-(XXVb) are as described above in Structural Formula (I) or (I'). In one embodiment, s is 1 or 2. Alternatively, $R_{10}$ is independently selected from the group consisting of —F, —Cl, —Br, —CN, ($C_1$-$C_6$)alkyl, ($C_1$-$C_6$)alkoxy, halo ($C_1$-$C_6$)alkyl, halo($C_1$-$C_6$)alkoxy and —$SO_2$($C_1$-$C_3$)alkyl; and s is 0, 1, 2 or 3. In another alternative, $R_{10}$ is independently selected from the group consisting of —F, —Cl, —Br, —CN, ($C_1$-$C_6$)alkyl, ($C_1$-$C_6$)alkoxy, halo($C_1$-$C_6$)alkyl, and halo($C_1$-$C_6$)alkoxy; and s is 0, 1, 2 or 3. In yet another alternative, $R_{10}$ is independently selected from the group consisting of —F, —Cl, —Br, —CN, -Me, -Et, -OMe, —$CF_3$, —$OCF_3$. In another alternative embodiment, $R_{10}$ is independently selected from the group consisting of —F, —Cl, —Br, —CN, -Me, -Et, -OMe, —$CF_3$, —$OCF_3$ and —$SO_2CH_3$.

In one embodiment, ring A is a 5-7 membered monocyclic ring or a 9-14 membered bicyclic or tricyclic fused ring optionally substituted with 1 to 3 substituents independently selected from the group consisting of halogen (e.g., —F, —Cl or —Br), —CN, —$OR_5$, —$NR_6R_7$, —$S(O)_iR_5$, —$NR_{11}S$(═O)$_iR_5$, —C(═O)$OR_5$, —C(═O)$NR_{12}R_{13}$, —$NR_{11}C$(═O)$R_5$, —C(═S)$NR_{12}R_{13}$, —C(═O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$) alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl, wherein ring A contains 0 to 2 heteroatoms, which are independently selected from O, N and S. Values and alternative values for the remainder of the variables are as described in the 11$^{th}$ embodiment. More specifically, the substituents are selected from the group consisting of halogen (e.g., —F, —Cl or —Br), —CN, ($C_1$-$C_6$)alkyl, halo($C_1$-$C_6$)alkyl, hydroxy ($C_1$-$C_6$)alkyl, ($C_1$-$C_3$)alkoxy, halo($C_1$-$C_3$)alkoxy and phenyl, wherein the phenyl is optionally substituted with halogen (e.g., —F, —Cl or —Br), —CN, ($C_1$-$C_6$)alkyl, halo($C_1$-$C_6$) alkyl, hydroxy($C_1$-$C_6$)alkyl, ($C_1$-$C_3$)alkoxy, halo($C_1$-$C_3$) alkoxy. Even more specifically, $R_1$ is —H and $R_{14}$ is -Me.

In another embodiment, for Structural Formulas (Vb)-(XXVb), ring A is selected from tetrahydrofuran, tetrahydropyran, cyclopentane, cyclohexane, cyclohexene, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, 2,3,4,5-tetrahydrobenzo[b]oxepine, and 2,3-dihydro-1H-phenalene, each of which is optionally substituted with 1 to 3 substituents independently selected from the group consisting of halogen (e.g., —F, —Cl or —Br), —CN, ($C_1$-$C_6$)alkyl, halo($C_1$-$C_6$) alkyl, hydroxy($C_1$-$C_6$)alkyl, ($C_1$-$C_3$)alkoxy, halo($C_1$-$C_3$) alkoxy and phenyl, wherein the phenyl is optionally substituted with halogen (e.g., —F, —Cl or —Br), —CN, ($C_1$-$C_6$) alkyl, halo($C_1$-$C_6$)alkyl, hydroxy($C_1$-$C_6$)alkyl, ($C_1$-$C_3$) alkoxy, halo($C_1$-$C_3$)alkoxy. Values and alternative values for the remainder of the variables are as described in the 11$^{th}$ embodiment. More specifically, the substituents are selected from the group consisting of —F, -OMe, -OEt and -Ph. Even more specifically, $R_1$ is —H and $R_{14}$ is -Me.

In a 12$^{th}$ embodiment, for compounds represented by Structural Formulas (A), (I), (I'), (II)-(XXV), (IIa)-(XXVa), (IIb)-(XXVb), ring A is represented by the following structural formula:

(B)

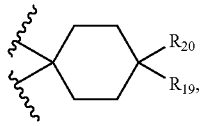

wherein $R_{19}$ and $R_{20}$ are each independently selected from —H, halogen, —CN, —$OR_5$, —$NR_6R_7$, —$S(O)_iR_5$, —$NR_{11}S$(═O)$_iR_5$, —C(═O)$OR_5$, —C(═O)$NR_{12}R_{13}$, —$NR_{11}C$(═O)$R_5$, —C(═S)$NR_{12}R_{13}$, —C(═O)$R_5$, ($C_1$-$C_6$)alkyl, ($C_2$-$C_6$)alkenyl, aryl, aryl($C_1$-$C_6$)alkyl, heteroaryl and heteroaryl($C_1$-$C_6$)alkyl, wherein each of the ($C_1$-$C_6$) alkyl, ($C_2$-$C_6$)alkenyl, aryl, aryl($C_1$-$C_6$)alkyl, heteroaryl and heteroaryl($C_1$-$C_6$)alkyl groups represented by $R_{19}$ and $R_{20}$ is optionally substituted with 1 to 5 substituents independently selected from the group consisting of halogen, —CN, —OH, —$NR_{11}SO_2$($C_1$-$C_3$)alkyl, —$NR_{11}C$(═O)—($C_1$-$C_3$)alkyl, ($C_1$-$C_6$)alkyl, halo($C_1$-$C_6$)alkyl, ($C_1$-$C_3$)alkoxy and ($C_1$-$C_3$) alkoxy($C_1$-$C_6$)alkyl. The remainder of the variables are as described above in the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$ or 11$^{th}$ embodiment. Alternatively, $R_{20}$ is —H and $R_{19}$ is —OH, ($C_1$-$C_3$)alkoxy, halo($C_1$-$C_3$)alkoxy or ($C_1$-$C_3$)alkoxy ($C_1$-$C_3$)alkoxy. In another alternative, $R_{19}$ and $R_{20}$ are each independently —H or —$NR_6R_7$, wherein $R_6$ and $R_7$ are each independently selected from the group consisting of —H, ($C_1$-$C_6$)alkyl, halo($C_1$-$C_6$)alkyl, and ($C_1$-$C_3$)alkoxy($C_1$-$C_3$) alkyl.

In a 13$^{th}$ embodiment, for compounds represented by Structural Formulas (A), (I), (I'), (II)-(XXV), (IIa)-(XXVa), (IIb)-(XXVb), ring A is represented by the following structural formula:

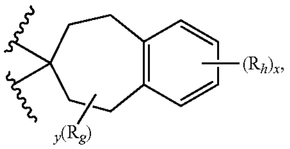

wherein:

$R_g$ and $R_h$, for each occurrence, are independently —H, -halogen, —CN, —$NO_2$, —$OR_5$, —$NR_6R_7$, —$S(O)_iR_5$, —C(═O)$OR_5$, —C(═O)$NR_{12}R_{13}$, —C(═O)$R_5$, ($C_1$-$C_6$) alkyl, ($C_2$-$C_6$)alkenyl, ($C_2$-$C_6$)alkynyl, ($C_3$-$C_8$)cycloalkyl, ($C_3$-$C_9$)heterocycloalkyl, aryl, heteroaryl, each ($C_1$-$C_6$)alkyl, ($C_2$-$C_6$)alkenyl, ($C_2$-$C_6$)alkynyl, ($C_3$-$C_8$)cycloalkyl, ($C_3$-$C_9$) heterocycloalkyl, aryl and heteroaryl represented by $R_b$ is optionally substituted with 1 to 3 substituents selected from the group consisting of —F, —Cl, —Br, —CN, —$OR_5$, —$SR_5$, —$NR_6R_7$, —$S(O)_iR_5$, —$NR_{11}S$(═O)$_iR_5$, —C(═O) $OR_5$, —C(═O)$NR_{12}R_{13}$, —$NR_{11}C$(═O)$R_5$, —C(═S) $NR_{12}R_{13}$, —C(═O)$R_5$, ($C_1$-$C_6$)alkyl, ($C_3$-$C_8$)cycloalkyl, ($C_3$-$C_9$)heterocycloalkyl, ($C_2$-$C_6$)alkenyl, halo($C_1$-$C_6$)alkyl, hydroxy($C_1$-$C_6$)alkyl, cyano($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl;

x is an integer from 1 to 4; and y is an integer from 1 to 6.

The remainder of the variables are as described above in the 1st, 2nd, 3rd, 4th, 5th, 6th, 7th, 8th, 9th, 10th or 11th embodiment. Alternatively, each $R_g$ is independently selected from —H, Me and F and each $R_h$ is independently —H, halogen, —CN, —$NO_2$, ($C_1$-$C_6$)alkyl, halo($C_1$-$C_6$)alkyl, ($C_1$-$C_3$)alkoxy, and halo($C_1$-$C_3$)alkoxy. Alternatively, each $R_g$ is independently selected from —H, Me and F and each $R_h$ is independently —H, halogen, —CN, —$NO_2$, ($C_1$-$C_6$)alkyl, halo($C_1$-$C_6$) alkyl, ($C_1$-$C_3$)alkoxy, and halo($C_1$-$C_3$)alkoxy. In another alternative embodiment, $R_g$ is —H and each $R_h$ is independently —H, halogen, —CN, —$NO_2$, ($C_1$-$C_6$)alkyl, halo($C_1$-$C_6$)alkyl, ($C_1$-$C_3$)alkoxy, and halo($C_1$-$C_3$)alkoxy. In yet another alternative, $R_g$ and $R_h$ are both —H.

In a 14th embodiment, the compounds of the present invention are represented by the following structural formula:

(D)

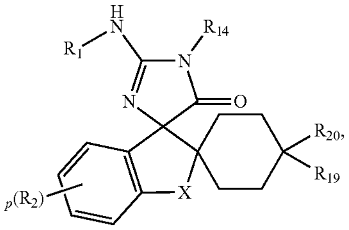

or (E)

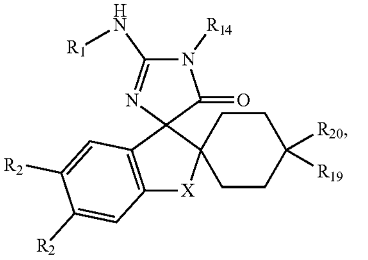

or a pharmaceutically acceptable salt thereof, wherein: $R_{19}$ and $R_{20}$ are each independently selected from —H, halogen, —CN, —$OR_5$, —$NR_6R_7$, —$S(O)_iR_5$, —$NR_{11}S(=O)_iR_5$, —C(=O)$OR_5$, —C(=O)$NR_{12}R_{13}$, —$NR_{11}C(=O)R_5$, —C(=S)$NR_{12}R_{13}$, —C(=O)$R_5$, ($C_1$-$C_6$)alkyl, ($C_2$-$C_6$)alkenyl, aryl, aryl($C_1$-$C_6$)alkyl, heteroaryl and heteroaryl($C_1$-$C_6$)alkyl, wherein each of the ($C_1$-$C_6$)alkyl, ($C_2$-$C_6$)alkenyl, aryl, aryl($C_1$-$C_6$)alkyl, heteroaryl and heteroaryl($C_1$-$C_6$)alkyl groups represented by $R_{19}$ and $R_{20}$ is optionally substituted with 1 to 5 substituents independently selected from the group consisting of halogen, —CN, —OH, —$NR_{11}SO_2$($C_1$-$C_3$)alkyl, —$NR_{11}$C(=O)—($C_1$-$C_3$)alkyl, ($C_1$-$C_6$)alkyl, halo ($C_1$-$C_6$)alkyl, ($C_1$-$C_3$)alkoxy and ($C_1$-$C_3$)alkoxy($C_1$-$C_6$) alkyl; and the remainder of the variables are as described in the 1st, 2nd, 3rd, 4th, 5th, 6th, 7th, 8th, 9th, 10th or 11th embodiment.

In one embodiment, for compounds represented by Structural Formula (D) or (E):

each $R_2$ is independently selected from the group consisting of —H, halogen, —CN, —$OR_5$, —$S(O)_iR_5$, —$NR_6R_7$, ($C_1$-$C_6$)alkyl, ($C_3$-$C_8$)cycloalkyl, ($C_3$-$C_8$)cycloalkyl($C_1$-$C_6$) alkyl, ($C_3$-$C_7$)heterocycloalkyl, ($C_3$-$C_7$)heterocycloalkyl($C_1$-$C_6$)alkyl, ($C_2$-$C_6$)alkynyl, aryl, aryl($C_1$-$C_6$)alkyl, heteroaryl and heteroaryl($C_1$-$C_6$)alkyl, each of ($C_1$-$C_6$)alkyl, ($C_3$-$C_8$) cycloalkyl, ($C_3$-$C_8$)cycloalkyl($C_1$-$C_6$)alkyl, ($C_3$-$C_7$)heterocycloalkyl, ($C_3$-$C_7$)heterocycloalkyl($C_1$-$C_6$)alkyl, ($C_2$-$C_6$) alkynyl, aryl, aryl($C_1$-$C_6$)alkyl, heteroaryl and heteroaryl($C_1$-$C_6$)alkyl are optionally substituted with 1 to 3 substituents independently selected from the group consisting of —F, —Cl, —Br, —CN, —$OR_5$, —$SR_5$, —$NR_6R_7$, —$S(O)_iR_5$, —$NR_{11}S(=O)_iR_5$, —C(=O)$OR_5$, —C(=O)$NR_{12}R_{13}$, —$NR_{11}C(=O)R_5$, —C(=S)$NR_{12}R_{13}$, —C(=O)$R_5$, ($C_1$-$C_6$)alkyl, ($C_2$-$C_6$)alkynyl, ($C_3$-$C_8$)cycloalkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$) alkoxy, ($C_1$-$C_6$)alkoxy($C_1$-$C_3$)alkyl, aryl and heteroaryl, wherein the aryl and heteroaryl groups in the substituents on the groups represented by $R_2$ are each independently optionally substituted with 1 to 3 substituents selected from halogen, —CN, ($C_1$-$C_6$)alkyl, halo($C_1$-$C_6$)alkyl, ($C_1$-$C_3$)alkoxy and ($C_1$-$C_3$)alkoxy($C_1$-$C_6$)alkyl;

$R_{14}$ is selected from the group consisting of ($C_1$-$C_6$)alkyl, ($C_3$-$C_8$)cycloalkyl, ($C_3$-$C_8$)cycloalkyl($C_1$-$C_3$)alkyl, ($C_3$-$C_7$) heterocycloalkyl and ($C_3$-$C_7$)heterocycloalkyl($C_1$-$C_3$)alkyl, each optionally substituted with 1 to 3 substituents independently selected from the group consisting of —F, —Cl, —Br, —CN, ($C_1$-$C_6$)alkyl, halo($C_1$-$C_6$)alkyl, ($C_1$-$C_3$)alkoxy, —$NR_6R_7$, —$NR_{11}S(O)_iR_5$, —$S(O)_iR_5$—, —OH and —C(O) $OR_5$; and $R_{20}$ is —H and $R_{19}$ is —OH, ($C_1$-$C_6$)alkoxy, halo($C_1$-$C_6$) alkoxy or ($C_1$-$C_3$)alkoxy($C_1$-$C_6$)alkoxy.

In a 15th embodiment, for compounds represented by Structural Formulas (I)-(XXV), (Va)-(XXVa) and (Vb)-(XXVb):

$R_1$ is —H or —C(=O)($C_1$-$C_3$)alkyl;

for Structural Formulas (I)-(XXV) and (Va)-(XXVa), $R_2$ is —H, halogen, —CN, —$OR_5$, —C(=O)$NR_{12}R_{13}$, —C(=O) $OR_5$, —C(O)$R_5$, ($C_1$-$C_6$)alkyl, ($C_2$-$C_6$)alkenyl, ($C_2$-$C_6$)alkynyl, ($C_3$-$C_6$)cycloalkyl, ($C_3$-$C_6$)cycloalkyl($C_1$-$C_3$)alkyl, ($C_4$-$C_6$)cycloalkenyl, phenyl, phenyl($C_1$-$C_3$)alkyl, heteroaryl, heteroaryl($C_1$-$C_3$)alkyl, ($C_5$-$C_6$)heterocycloalkyl, ($C_5$-$C_6$) heterocycloalkyl($C_1$-$C_3$)alkyl, wherein the heteroaryl is selected from pyridyl, pyridazinyl, pyridinonyl, pyridazinonyl, thiazolyl, oxazolyl, oxadiazolyl, pyrazinyl, pyrimidyl, indolyl, quinolyl, quinoxalinyl, triazole and thiophenyl, the heterocycloalkyl is selected from oxetanyl, tetrahydrafuran, tetrapyran, piperidine, pyrrolidinyl and pyrrolidinonyl, and each of ($C_1$-$C_6$)alkyl, ($C_2$-$C_6$)alkenyl, ($C_2$-$C_6$)alkynyl, ($C_3$-$C_6$)cycloalkyl, ($C_3$-$C_6$)cycloalkyl($C_1$-$C_3$)alkyl, ($C_4$-$C_6$)cycloalkenyl, phenyl, phenyl($C_1$-$C_3$)alkyl, heteroaryl, heteroaryl($C_1$-$C_3$)alkyl, ($C_5$-$C_6$)heterocycloalkyl and ($C_5$-$C_6$) heterocycloalkyl($C_1$-$C_3$)alkyl groups represented by $R_2$ is optionally substituted with 1 to 5 substituents independently selected from halogen, —CN, ($C_1$-$C_3$)alkyl, halo($C_1$-$C_3$) alkyl, ($C_2$-$C_6$)alkynyl, —$NR_6R_7$, —$S(O)_iR_5$, —C(O)$R_5$, —OH, ($C_3$-$C_6$)cycloalkyl, ($C_1$-$C_3$)alkoxy and halo($C_1$-$C_3$) alkoxy; and $R_{14}$, when present, is —H, —$OR_5$, —$NR_6R_7$, ($C_1$-$C_6$) alkyl, ($C_3$-$C_6$)cycloalkyl, ($C_3$-$C_6$)cycloalkyl($C_1$-$C_3$)alkyl, ($C_3$-$C_5$)hetero cycloalkyl, ($C_3$-$C_5$)heterocycloalkyl($C_1$-$C_3$) alkyl, heteroaryl, phenyl, phenyl($C_1$-$C_3$)alkyl and heteroaryl ($C_1$-$C_3$)alkyl, wherein the heteroaryl is selected from pyridyl, pyridazinyl, pyridinonyl, pyridazinonyl, thiazolyl, oxazolyl, oxadiazolyl, pyrazinyl, pyrimidyl, indolyl, quinolyl, quinoxalinyl and thiophenyl and triazolyl, the ($C_3$-$C_5$)heterocycloalkyl is selected from oxetanyl, tetrahydrofuran, tetrahydropyran, piperidinyl and pyrrolidinyl, and each of the ($C_1$-$C_6$)alkyl, ($C_3$-$C_6$)cycloalkyl, ($C_3$-$C_6$)cycloalkyl($C_1$-$C_3$) alkyl, ($C_3$-$C_5$)heterocycloalkyl, ($C_3$-$C_5$)heterocycloalkyl($C_1$-$C_3$)alkyl, heteroaryl, phenyl, phenyl($C_1$-$C_3$)alkyl and heteroaryl($C_1$-$C_3$)alkyl groups represented by $R_{14}$ is optionally substituted with 1 to 3 substituents independently selected from halogen, ($C_1$-$C_6$)alkyl, halo($C_1$-$C_6$)alkyl, ($C_1$-

$C_3$)alkoxy, $—NR_6R_7$, $—S(O)_iR_5$, $—NR_{11}SO_2R_5$, —OH, $—COOR_5$, $—C(=O)R_5$, $—C(=O)NR_{12}R_{13}$ and thiazolyl; and for Structural Formulas (Vb)-(XXVb), each $R_{10}$ is independently selected from the group consisting of —F, —Cl, —Br, —CN, $(C_1-C_6)$alkyl, $(C_1-C_6)$alkoxy, halo$(C_1-C_6)$alkyl, halo$(C_1-C_6)$alkoxy and $—SO_2(C_1-C_3)$alkyl; and s is 0, 1, 2 or 3.

The remainder of the variables are as described above in the $1^{st}$, $2^{nd}$, $3^{rd}$, $11^{th}$, $12^{th}$ or $13^{th}$ embodiment.

In a $16^{th}$ embodiment, for compounds represented by Structural Formulas (I)-(XXV), (Va)-(XXVa) and (Vb)-(XXVb):

$R_1$ is —H or $—C(=O)CH_3$.

for Structural Formulas (Va)-(XXVa) each $R_2$ is independently selected from the group consisting of —H, —F, —Br, —Cl, —I, —OH, —CN, cyclopropylethyl, 5-propynyl-3-pyridyl, 2-fluoro-3-pyridyl, N,N-dimethylaminoethoxy, cyclopentoxy, cyclopropylmethoxy, 3-methoxypropyl, 3-methoxypropynyl, cyclopropylethynyl, 3-cyanophenyl, trifluoromethoxy, 2-chloro-4-pyridyl, 1-methanesulfonyl-4-piperidinylmethyl, 1-acetyl-4-piperidinylmethyl, 3-methanesulfonylphenyl, 5-trifluoromethyl-3-pyridyl, 2-methoxyethoxy, 2-methyl-5-pyridazin-3-onyl, 1-cyclopropyl-4-pyridin-2-onyl, 1-methyl-2,2,2-trifluoroethyl, 2-cyclopropyl-5-thiazolyl, trifluoromethyl, 2,2,2-trifluoroethyl, methoxy, 3-chloro-5-fluorophenyl, N-methyl-4-pyridin-2-onyl, 4-methylpentyl, 3-methoxyphenoxy, dimethylaminocabonyl, cyclopropyl, 1-hydroxy-2,2,2-trifluoroethyl, pyrrolidinylcarbonyl, 3,3,3-trifluoropropyl, difluoromethoxy, 1,1-dihydroxy-2,2,2-trifluoroethyl, 3-methoxyphenyl, 2,2,2-trifluoroethoxy, phenoxy, 2-methoxy-4-pyridyl, 2-methyl-5-thiazolyl, 3,3,3-trifluoroprop-1-en-2-yl, 5-thiazolyl, 2-thiazolyl, thiophen-3-ylethynyl, 1-hydroxycyclopentan-1-ylethynyl, 5-fluoro-3-pyridyl, pyrrolidinyl, 5-chloro-3-pyridyl, 3,3-dimethylbutyn-1-yl, phenylethynyl, cyclopentylethynyl, 2-pyrazinyl, 3-chlorophenyl, 3-hydroxycyclopent-1-enyl, 3-fluoro-5-trifluoromethylphenyl, 3,5-dicyanophenyl, 3-fluoro-5-cyanophenyl, 3-chloro-4-fluorophenyl, 3,5-difluorophenyl, 3,5-dichlorophenyl, 3-chloro-5-cyanophenyl, 3-pyridazinyl, 3-pyridyl, 3-cyano-4-fluorophenyl, 3-cyano-5-fluorophenyl 6-methoxypyrazin-2-yl, 6-indolyl, 3-chloro-5-methoxyphenyl, 3-trifluoromethoxyphenyl, 3,5-dimethylphenyl, 2-methyl-5-fluorophenyl, 3-trifluoromethylphenyl, phenyl, cyclopentylmethyl, 1-propyl, 2-propyl, 2-methylpropyl, phenylethyl, 1-pentyl, 2-methylbutyl, ethyl, 4-methoxyphenylmethoxy, 1-methylethoxy, methoxycarbonyl, cyclopropyloxy, 5-cyano-3-pyridyl, 4-(propyn-1-yl)-2-thiophenyl, 4-bromo-2-thiazolyl, ethenyl, ethynyl, 4-methylpentyn-1-yl, dimethylaminopropyl, N-methylpyrrolidin-3-ylmethyl, 2,2-difluorocyclopropylmethoxy, 4-bromo-2-thiophenyl, methoxy, methyl, carboxy, 5-propyl-3-pyridyl, 2-methyl-5-fluorophenyl, 2-oxazolyl, propylthio, phenylthio, 2,2-dimethylpropyl, butyl, cyclobutylmethoxy, 2-methyl-5-pyrimidyl, pyrrolidin-2-onyl, 3,3-difluoropyrrolidin-1-yl, cyclopropylethyl, 2-propyloxy, 4-cyano-2-thiophenyl, ethoxymethyl, 4-methoxybenzyloxy, 1-methylethyl, cyclohexylmethyl, 5-chloro-3-pyridyl, 5-methyl-3-pyridyl, 2-methylpropyloxy and 2-chloro-4-pyridyl; and $R_{14}$, when present, is selected from the group consisting of —H, methyl, ethyl, 2-propyl, 1-propyl, 1-butyl, benzyl, 2-pyridylmethyl, methoxyethyl, 1-methoxypropan-2-yl, N,N-dimethylaminoethyl, 4-cyanobenzyl, 2-cyanobenzyl, 3-cyanobenzyl, 2-thiazolylethyl, 2-thiazolylmethyl, 6-quinoxalinylmethyl, 1-phenylethyl, 2-propyl, tert-butyl, 3-dimethylaminobenzyl, 3-methanesulfonamidobenzyl, 3-methanesulfonylbenzyl, 2-oxazolylmethyl, 1,1,2,2-tetrafluoroethoxy, 2-oxetanylmethyl, 2-ethylbutyl, 5-fluoro-2-pyridyl, 3-fluorobenzyl, 4-thiazolylmethyl, 2,2-difluoroethyl, 3-tetrahydrofuranylmethyl, 2-tetrahydrofuranyl, 4-fluorobenzyl, 3-methoxybenzyl, 2-fluorobenzyl, 4-methanesulfonylbenzyl, 2-tetrahydrafuranylmethyl, 2,2,2-trifluoroethyl, 5-trifluoromethyl-2-pyridylmethyl, 3,3,3-trifluoropropyl, 2-hydroxyethyl, 2-chlorobenzyl, 2-methoxyethyl, cyclobutylmethyl, 4-tetrahydropyranylmethyl, 2-methylpropyl, phenylethyl, cyclopropyl, cyclobutyl, 1-methylpropyl, 5-pyrimidylmethyl, 2-carboxyethyl, dimethylamino, 4-tetrahydropyranyl, 1-methylpiperidin-4-yl, 2-fluoroethyl, 2-butyl, dimethylaminoethyl, 1-(3-pyridazinyl)ethyl, 1-methoxy-2-propyl, (4-methyl-1,2,4-triazol-3-yl)methyl, (2-methoxy-2-phenyl)ethyl, (1,3,4-oxadiazol-2-yl)methyl, (quinoxalin-2-yl)methyl, 1-phenylethyl, methanesulfonylaminoethyl, aminocarbonylethyl, aminocarbonylmethyl, 3-methoxypropyl and (3-(2-thiazolyl))benzyl, carboxymethyl, 1-methylethoxycarbonylmethyl, 5-methyl-1,3,4-thiadizolyl, 4-pyridazinyl, 5-methyl-2-oxazolylethyl, 2-hydroxyl-2-methylpropyl, 2-hydroxy-1-methylethyl and 2-pyrazinylmethyl;

for Structural Formula (Vb)-(XXVb), each $R_{10}$ is independently selected from the group consisting of —H, —F, —Cl, —Br, —CN, -Me, -Et, -OMe, $—CF_3$, $—OCF_3$ and $—SO_2CH_3$.

The remainder of the variables are as described above in the $1^{st}$, $2^{nd}$, $3^{rd}$, $11^{th}$, $12^{th}$ or $13^{th}$ embodiment.

In a $17^{th}$ embodiment, for compounds described in the $1^{st}$ to $16^{th}$ embodiment:

$R_5$ is selected from the group consisting of —H, $(C_1-C_3)$alkyl, halo$(C_1-C_3)$alkyl, $(C_1-C_3)$alkoxy$(C_1-C_3)$alkyl, $(C_3-C_6)$cycloalkyl, $(C_3-C_6)$cycloalkyl$(C_1-C_3)$alkyl, phenyl and phenyl$(C_1-C_3)$alkyl, wherein the phenyl group in the groups represented by $R_5$ is optionally substituted with 1 to 3 substituents independently selected from —F, —Cl, —Br, —CN, =O, $—NR_6R_7$, $(C_1-C_3)$alkyl, halo$(C_1-C_3)$alkyl and $(C_1-C_3)$alkoxy$(C_1-C_3)$alkyl;

$R_6$ is —H or $(C_1-C_3)$alkyl;

$R_7$ is —H, $(C_1-C_3)$alkyl, halo$(C_1-C_3)$alkyl, $(C_3-C_6)$cycloalkyl, $(C_3-C_6)$cycloalkyl$(C_1-C_3)$alkyl or $(C_1-C_3)$alkoxy$(C_1-C_3)$alkyl;

$R_{11}$ is —H or $(C_1-C_3)$alkyl;

$R_{12}$ is —H or $(C_1-C_3)$alkyl; and $R_{13}$ is —H, $(C_1-C_3)$alkyl, halo$(C_1-C_3)$alkyl, $(C_3-C_6)$cycloalkyl$(C_1-C_3)$alkyl or $(C_1-C_3)$alkoxy$(C_1-C_3)$alkyl, or $R_{12}$ and $R_{13}$ together with the nitrogen atom to which they are attached forms a pyrrolidine or piperidine ring. In a $18^{th}$ embodiment, for compounds described in the $1^{st}$ to $16^{th}$ embodiments:

$R_5$ is selected from the group consisting of —H, methyl, ethyl, 2-propyl, 2-methylpropyl, cyclopentyl, $—CHF_2$, $—CF_2CHF_2$, $—CH_2CF_3$, $—CF_3$, cyclopropylmethyl, 2,2-difluorocyclopropylmethyl, methoxyethyl, phenyl, 3-methoxyphenyl, (1-amino-2-(4-hydroxyphenyl))ethylcarbonyl, dimethylaminoethyl, cyclobutylmethyl, and 4-methoxybenzyl;

$R_6$ is —H or methyl, $R_7$ is —H, methyl or $—CH_2CF_3$, $R_{11}$ is —H or methyl, $R_{12}$ and $R_{13}$ are each independently —H or methyl, or $R_{12}$ and $R_{13}$ together with the nitrogen atom to which they are attached form a pyrrolidine ring.

GENERAL DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group. For example, $(C_1-C_6)$alkyl means an alkyl group or radical having 1 to 6 carbon atoms. In general, for groups comprising two or more subgroups, the last named subgroup is the radical attachment point. For example, the substituent "aryl$(C_1-C_3)$alkyl" means an aryl group which is bound to a $(C_1-C_3)$alkyl group, the latter of which is bound to the core or to the group to which the substituent is attached.

When a compound of the present invention is depicted in form of a chemical name and as a formula, in case of any discrepancy, the formula shall prevail.

When any variable (e.g. aryl, heterocyclyl, $R^1$, $R^2$ etc.) occurs more than once in a compound, its definition on each occurrence is independent of any other occurrence.

"Alkyl" means a saturated aliphatic branched or straight-chain monovalent hydrocarbon radical having the specified number of carbon atoms. For example, "$(C_1-C_6)$alkyl" means a radical having from 1-6 carbon atoms in a linear or branched arrangement. "$(C_1-C_6)$alkyl" includes methyl, ethyl, propyl, butyl, pentyl, and hexyl.

"Alkenyl" means branched or straight-chain monovalent hydrocarbon radical containing at least one double bond and having specified number of carbon atoms. Alkenyl may be mono or polyunsaturated, and may exist in the E or Z configuration. For example, "$(C_2-C_6)$alkenyl" means a radical having from 2-6 carbon atoms in a linear or branched arrangement.

"Alkynyl" means branched or straight-chain monovalent hydrocarbon radical containing at least one triple bond and having specified number of carbon atoms. For example, "$(C_2-C_6)$alkynyl" means a radical having from 2-6 carbon atoms in a linear or branched arrangement.

"Cycloalkyl" means a saturated aliphatic cyclic hydrocarbon radical having the specified number of carbon atoms. It can be monocyclic, bicyclic, polycyclic (e.g., tricyclic), fused, bridged, or spiro. For example, monocyclic $(C_3-C_8)$cycloalkyl means a radical having from 3-8 carbon atoms arranged in a monocyclic ring. Monocyclic $(C_3-C_8)$cycloalkyl includes but is not limited to cyclopropyl, cyclobutyl, cyclopentyl, cyclohexyl, cycloheptyl and cyclooctane.

Monocyclic ring systems have a single ring structure. They include saturated or unsaturated aliphatic cyclic hydrocarbon rings or aromatic hydrocarbon ring having the specified number of carbon atoms. The monocyclic ring system can optionally contain 1 to 3 heteroatoms in the ring structure and each heteroatom is independently selected from the group consisting O, N and S. When the heteroatom is a ring nitrogen atom connected to other ring atoms only by single bonds, it can be substituted. Exemplary substituents, unless otherwise indicated, include —H, alkyl, cycloalkyl, cycloalkylalkyl, aryl, arylalkyl, heteroaryl, heteroarylalkyl (preferrably, —H, $(C_1-C_6)$alkyl, halo$(C_1-C_6)$alkyl or $(C_1-C_3)$alkylcarbonyl), each of which can be optionally substituted with halogen, hydroxy, alkoxy, haloalkyl, alkyl, etc. When the heteroatom is S, it can be optionally mono- or di-oxygenated (i.e. —S(O)— or —$S(O)_2$—). Examples of monocyclic ring system include, but are not limited to, monocyclic cycloalkyls (e.g., cyclopropyl, cyclobutyl, cyclopentyl, cyclohexyl, cycloheptyl, cyclooctane), partially unsaturated cycloalkyls; monocyclic heterocycloalkyls (e.g., azetidine, pyrrolidine, piperidine, piperazine, hexahydropyrimidine, tetrahydrofuran, tetrahydropyran, oxepane, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, morpholine, thiomorpholine, thiomorpholine 1,1-dioxide, tetrahydro-2H-1,2-thiazine, tetrahydro-2H-1,2-thiazine 1,1-dioxide, and isothiazolidine 1,1-dioxide, tetrahydrothiophene 1-oxide, tetrahydrothiophene 1,1-dioxide, thiomorpholine 1-oxide, thiomorpholine 1,1-dioxide, tetrahydro-2H-1,2-thiazine 1,1-dioxide, and isothiazolidine 1,1-dioxide, pyrrolidin-2-one, piperidin-2-one, piperazin-2-one, and morpholin-2-one); monocyclic aryls (e.g., phenyl) and monocyclic heteroaryls (see descriptions below).

Bicyclic ring systems have two rings that have at least one ring atom in common. Bicyclic ring systems include fused, bridged and spiro ring systems. The two rings can both be aliphatic (e.g., cycloalkyl or cycloheteroalkyl), both be aromatic (e.g., aryl or heteroaryl), or a combination thereof. The bicyclic ring systems can optionally contain 1 to 3 heteroatoms in the ring structure and each heteroatom is independently selected from the group consisting O, N and S. When the heteroatom is a ring nitrogen atom connected to other ring atoms only by single bonds, it can be substituted. Exemplary substituents, unless otherwise indicated, include H, alkyl, cycloalkyl, cycloalkylalkyl, aryl, arylalkyl, heteroaryl, heteroarylalkyl (preferrably, —H, $(C_1-C_6)$alkyl, halo$(C_1-C_6)$alkyl or $(C_1-C_3)$alkylcarbonyl), each of which can be optionally substituted with halogen, hydroxy, alkoxy, haloalkyl, alkyl, etc. When the heteroatom is S, it can be optionally mono- or di-oxygenated (i.e. —S(O)— or —$S(O)_2$—).

A fused bicyclic ring system has two rings which have two adjacent ring atoms in common. The two rings can both be aliphatic (e.g., cycloalkyl or cycloheteroalkyl), both be aromatic (e.g., aryl or heteroaryl), or a combination thereof. For example, the first ring can be monocyclic cycloalkyl or monocyclic cycloheteroalkyl, and the second ring can a cycloalkyl, partially unsaturated carbocycle, aryl, heteroaryl or a monocyclic cycloheteroalkyl. For example, the second ring can be a $(C_3-C_6)$cycloalkyl, such as cyclopropyl, cyclobutyl, cyclopentyl and cyclohexyl. Alternatively, the second ring can be an aryl ring, e.g., phenyl. Examples of fused bicyclic ring systems include, but not limited to, 6,7,8,9-tetrahydro-5H-benzo[7]annulene, 2,3-dihydro-1H-indene, octahydro-1H-indene, tetrahydronaphthalene, decahydronaphthalene, indoline, isoindoline, 2,3-dihydro-1H-benzo[d]imidazole, 2,3-dihydrobenzo[d]oxazole, 2,3-dihydrobenzo[d]thiazole, octahydrobenzo[d]oxazole, octahydro-1H-benzo[d]imidazole, octahydrobenzo[d]thiazole, octahydrocyclopenta[c]pyrrole, 3-azabicyclo[3.1.0]hexane, 3-azabicyclo[3.2.0]heptane, 5,6,7,8-tetrahydroquinoline and 5,6,7,8-tetrahydroisoquinoline and 2,3,4,5-tetrahydrobenzo[b]oxepine.

A Spiro bicyclic ring system has two rings which have only one ring atom in common. The two rings can both be aliphatic (e.g., cycloalkyl or cycloheteroalkyl). For example, the first ring can be a monocyclic cycloalkyl or a monocyclic cycloheteroalkyl and the second ring can be a cycloalkyl, partially unsaturated carbocycle, or a monocyclic cycloheteroalkyl. Examples of spiral bicyclic ring system include, but are not limited to, spiro[2.2]pentane, spiro[2.3]hexane, spiro[3.3]heptane, spiro[2.4]heptane, spiro[3.4]octane, spiro[2.5]octane, azaspiro[4.4]nonane, 7-azaspiro[4.4]nonane, azaspiro[4.5]decane, 8-azaspiro[4.5]decane, azaspiro[5.5]undecane, 3-azaspiro[5.5]undecane and 3,9-diazaspiro[5.5]undecane.

A bridged bicyclic ring system has two rings which have three or more adjacent ring atoms in common. For example, the first ring can be a monocyclic cycloalkyl or a monocyclic cycloheteroalkyl and the other ring is a cycloalkyl, partially unsaturated carbocycle, or a monocyclic cycloheteroalkyl.

Examples of bridged bicyclic ring system include, but are not limited to, bicyclo[1.1.0]butane, bicyclo[1.2.0]pentane, bicyclo[2.2.0]hexane, bicyclo[3.2.0]heptane, bicyclo[3.3.0]octane, bicyclo[4.2.0]octane, bicyclo[2.2.1]heptane, bicyclo [2.2.2]octane, bicyclo[3.2.1]octane, bicyclo[3.2.2]nonane, bicyclo[3.3.1]nonane, bicyclo[3.3.2]decane bicyclo[3.3.3] undecane, azabicyclo[3.3.1]nonane, 3-azabicyclo[3.3.1] nonane, azabicyclo[3.2.1]octane, 3-azabicyclo[3.2.1]octane, 6-azabicyclo[3.2.1]octane and azabicyclo[2.2.2]octane, 2-azabicyclo[2.2.2]octane and 2-oxabicyclo[2.2.2]octane.

Polycyclic ring systems have more than two rings (e.g., three rings resulting in a tricyclic ring system) and adjacent rings having at least one ring atom in common. Polycyclic ring systems include fused, bridged and spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common. Examples of polycyclic ring system include, but not limited to, tricyclo[$3.3.1.0^{3,7}$]nonane (noradamantane) and tricyclo [$3.3.1.1^{3,7}$]decane (adamantane) and 2,3-dihydro-1H-phenalene "Heterocycle" means a saturated, unsaturated, or aromatic mono- or polycyclic-ring systems containing one or more heteroatoms independently selected from N, O or S. When the heteroatom is N, unless otherwise indicated, it can be substituted. Exemplary substituents include H, alkyl, cycloalkyl, cycloalkylalkyl, aryl, arylalkyl, heteroaryl, heteroarylalkyl (preferrably, —H, ($C_1$-$C_6$)alkyl, halo($C_1$-$C_6$)alkyl or ($C_1$-$C_3$) alkylcarbonyl), each of which can be optionally substituted with halogen, hydroxy, alkoxy, haloalkyl, alkyl, etc. When the heteroatom is S, unless otherwise indicated, it can be optionally mono- or di-oxygenated (i.e. —S(O)— or —$S(O)_2$—). A heterocycle can be a heteroaryl ring or heterocycloalkyl ring.

"Cycloheteroalkyl" or "heterocycloalkyl" means a saturated or partially saturated 4-12 membered ring radical having specified number of ring carbon atoms. The cycloheteroalkyl or heterocycloalkyl contains 1 to 4 ring heteroatoms, which may be the same or different, selected from N, O or S. The cycloheteroalkyl or heterocycloalkyl ring optionally contains one or more double bonds. It can be monocyclic, bicyclic, tricyclic, fused, bridged, or spiro. For example, ($C_3$-$C_9$) heterocycloalkyl means a ring radical containing 3-9 ring carbon atoms. The term "cycloheteroalkyl" or "heterocycloalkyl" is intended to include all the possible isomeric forms. When the heteroatom is a ring nitrogen atom connected to other ring atoms only by single bonds, it can be substituted. Exemplary substituents, unless otherwise indicated, include H, alkyl, cycloalkyl, cycloalkylalkyl, aryl, arylalkyl, heteroaryl, heteroarylalkyl (preferrably, —H, ($C_1$-$C_6$) alkyl, halo($C_1$-$C_6$)alkyl or ($C_1$-$C_3$)alkylcarbonyl), each of which can be optionally substituted with halogen, hydroxy, alkoxy, haloalkyl, alkyl, etc. When the heteroatom is S, it can be optionally mono- or di-oxygenated (i.e. —S(O)— or —$S(O)_2$—).

Haloalkyl and halocycloalkyl include mono, poly, and perhaloalkyl groups where the halogens are independently selected from fluorine, chlorine, and bromine.

"Heteroaryl", "heteroaryl group", "heteroaryl ring", "heteroaromatic", "heteroaromatic group" and "heteroaromatic ring" are used interchangeably herein. "Heteroaryl" means a monovalent heteroaromatic monocyclic or polycyclic ring radical. Monocyclic heteroaryl rings are 5- and 6-membered aromatic heterocyclic rings containing 1 to 4 heteroatoms independently selected from N, O, and S, and include, but are not limited to furan, thiophene, pyrrole, imidazole, pyrazole, oxazole, isoxazole, thiazole, isothiazole, 1,2,3-triazole, 1,2,4-triazole, 1,3,4-oxadiazole, 1,2,5-thiadiazole, 1,2,5-thiadiazole 1-oxide, 1,2,5-thiadiazole 1,1-dioxide, 1,3,4-thiadiazole, pyridine, pyridine-N-oxide, pyrazine, pyrimidine, pyridazine, 1,2,4-triazine, 1,3,5-triazine, and tetrazole. Bicyclic heteroaryl rings are bicyclo[4.4.0] and bicyclo[4.3.0] fused ring systems containing 1 to 4 heteroatoms independently selected from N, O, and S, and include indolizine, indole, isoindole, benzo[b]furan, benzo[b]thiophene, indazole, benzimidazole, benzthiazole, purine, 4H-quinolizine, quinoline, isoquinoline, cinnoline, phthalazine, quinazoline, quinoxaline, 1,8-naphthyridine, and pteridine. "Alkoxy" means an alkyl radical attached through an oxygen linking atom. "($C_1$-$C_4$)-alkoxy" includes methoxy, ethoxy, propoxy, and butoxy.

"Aromatic", "aromatic group", "aromatic ring", "aryl", "aryl group" and "aryl ring" are used interchangeable herein.

"Aryl" means an aromatic monocyclic, or polycyclic hydrocarbon ring system. Aryl systems include, but limited to, phenyl, naphthalenyl, fluorenyl, indenyl, azulenyl, and anthracenyl.

"Hetero" refers to the replacement of at least one carbon atom member in a ring system with at least one heteroatom selected from N, S, and O. A hetero ring may have 1, 2, 3, or 4 carbon atom members replaced by a heteroatom.

"Halogen" used herein refers to fluorine, chlorine, bromine, or iodine.

"Carbocycle" means 3-14 membered saturated or unsaturated aliphatic cyclic hydrocarbon ring.

"Cycloalkene" an unsaturated and non-aromatic aliphatic cyclic hydrocarbon radical having the specified number of carbon atoms. It can be monocyclic, bicyclic, tricyclic, fused, bridged, or spiro. Thus, ($C_3$-$C_8$)cycloalkene means a radical having from 3-8 carbon atoms arranged in a ring. ($C_3$-$C_8$) cycloalkene includes cyclobutene, cyclopentene, cyclohexene, cycloheptene and cyclooctene.

The compounds of the invention may be present in the form of pharmaceutically acceptable salts. For use in medicines, the salts of the compounds of the invention refer to non-toxic "pharmaceutically acceptable salts." The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Pharmaceutically acceptable salt forms include pharmaceutically acceptable acidic/anionic or basic/cationic salts. Examples of pharmaceutically acceptable salts include, but are not limited to, mineral or organic acid salts of basic residues such as amines; alkali or organic salts of acidic residues such as carboxylic acids; and the like.

For example, such salts include, the acetate, ascorbate, benzenesulfonate, benzoate, benzylate, bicarbonate, bitartrate, bromide, calcium edetate, camsylate, carbonate, chloride, citrate, dihydrochloride, edetate, edisylate, ethane disulfonate, estolate, esylate, fumarate, glyceptate, gluconate, glutamate, glycolate, glycollylarsanilate, hexylresorcinate, hydrabamine, hydrobromide, hydrochloride, hydroxymaleate, hydroxynaphthoate, iodide, isethionate, lactate, lactobionate, malate, maleate, mandelate, methanesulfonate, mesylate, methylbromide, methylnitrate, methylsulfate, mucate, napsylate, nitrate, oxalate, pamoate, pantothenate, phenylacetate, phosphate/diphosphate, polygalacturonate, propionate, salicylate, stearate, subacetate, succinate, sulfamide, sulfate, tannate, tartrate, teoclate, tosylate, triethiodide, ammonium, benzathine, chloroprocaine, colline, diethanolamine, ethylenediamine, meglumine and procaine salts. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of the compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

When compounds having one or more stereocenters and are depicted with particular stereochemistry for at least one stereocenter, the present invention also include compounds that have the opposite stereochemistry at the corresponding stereocenter(s) and compounds that has no specific stereochemistry at the corresponding stereocenter(s).

The disclosed compounds of the invention are BACE inhibitors for treating, preventing or ameliorating disorders or diseases characterized by elevated β-amyloid deposits or β-amyloid levels in a subject. The present invention also provides a method for the treatment of a disorder related to or associated with excessive BACE activity in a patient in need thereof which comprises administering to said patient an effective amount of a disclosed compound or a pharmaceutically acceptable salt thereof. The present invention also provides methods for inhibiting the activity of BACE in a subject in need thereof, comprising administering to a subject and/or contacting a receptor thereof with an effective amount of at least one disclosed compound or a pharmaceutically acceptable salt thereof. The present invention also provides methods of ameliorating β-amyloid deposits in a subject in need thereof, comprising administering to said subject an effective amount of at least one disclosed compound or a pharmaceutically acceptable salt thereof.

As such, the disclosed BACE inhibitors can be used to treat neurodegenerative disorders, disorders characterized by cognitive decline, cognitive impairment, dementia and diseases characterized by production of β-amyloid deposits or neurofibrillary tangles.

Exemplary diseases or disorders that can be treated by the disclosed BACE inhibitors include Alzheimer's disease, Trisomy 21 (Down's Syndrome), Hereditary Cerebral Hemorrhage with Amyloidosis of the Dutch-typle (HCHWA-D), senile dementia, cerebral amyloid angiopathy, degenerative dementia, dementias of mixed vascular and degenerative origin, dementia associated with Parkinson's disease, dementia associated with progressive supranuclear palsy and dementia associated with cortical basal degeneration, diffuse Lewy body type of Alzheimer's disease and glaucoma.

Accordingly, the present invention relates to a compound described herein or a pharmaceutically acceptable salt thereof as a medicament.

In a further embodiment, the present invention relates to methods for the treatment or prevention of above-mentioned diseases and conditions, which method comprises the administration of an effective amount of a compound described herein or a pharmaceutically acceptable salt thereof.

The invention includes a therapeutic method for treating or ameliorating an BACE mediated disorder in a subject in need thereof comprising administering to a subject in need thereof an effective amount of a compound of Formula I or any other formulas of the invention described herein, or pharmaceutically acceptable salts thereof or composition thereof.

Administration methods include administering an effective amount (i.e., an effective amount) of a compound or composition of the invention at different times during the course of therapy or concurrently in a combination form. The methods of the invention include all known therapeutic treatment regimens.

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be prophylactic or therapeutic, which includes achieving, partially or substantially, one or more of the following results: partially or totally reducing the extent of the disease, disorder or syndrome; ameliorating or improving a clinical symptom or indicator associated with the disorder; delaying, inhibiting or decreasing the likelihood of the progression of the disease, disorder or syndrome; or partially or totally delaying, inhibiting or reducing the likelihood of the onset or development of disease, disorder or syndrome.

"Effective amount" means that amount of active compound agent that elicits the desired biological response in a subject. Such response includes alleviation of the symptoms of the disease or disorder being treated. The effective amount of a compound of the invention in such a therapeutic method is from about 0.01 mg/kg/day to about 1000 mg/kg/day, from about 0.1 mg/kg/day to about 100 mg/kg/day.

"Pharmaceutically acceptable carrier" means compounds and compositions that are of sufficient purity and quality for use in the formulation of a composition of the invention and that, when appropriately administered to an animal or human, do not produce an adverse reaction.

In one embodiment, the present invention includes combination therapy for treating or ameliorating a disease or a disorder described herein. The combination therapy comprises administering a combination of at least one compound represented by structural formula (A), (I) or (I') with another compound selected from the group of, for example, gamma-secretase inhibitors; amyloid aggregation inhibitors (e.g. ELND-005); directly or indirectly acting neuroprotective and/or disease-modifying substances; anti-oxidants (e.g. vitamin E or ginkolide); anti-inflammatory substances (e.g. Cox inhibitors, NSAIDs additionally or exclusively having Abeta lowering properties); HMG-CoA reductase inhibitors (statins); acetylcholinesterase inhibitors (e.g., donepezil, rivastigmine, tacrine, galantamine, memantine; tacrine); NMDA receptor antagonists (e.g. memantine); AMPA receptor agonists; AMPA receptor positive modulators, AMPkines, monoamine receptor reuptake inhibitors, substances modulating the concentration or release of neurotransmitters; substances inducing the secretion of growth hormone (e.g., ibutamoren mesylate and capromorelin); CB-1 receptor antagonists or inverse agonists; antibiotics (e.g., minocyclin or rifampicin); PDE2, PDE4, PDE5, PDE9, PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; histamine H3 antagonists, 5 HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate-receptor 5 positive modulators, antidepressants, such as citalopram, fluoxetine, paroxetine, sertraline and trazodone; anxiolytics, such as lorazepam and oxazepam; antiphychotics, such as aripiprazole, clozapine, haloperidol, olanzapine, quetiapine, risperidone and ziprasidone, and other substances that modulate receptors or enzymes in a manner such that the efficacy and/or safety of the compounds according to the invention is increased and/or unwanted side effects are reduced. The compounds according to the invention may also be used in combination with immunotherapies (e.g., active immunisation with Abeta or parts thereof or passive immunisation with humanised anti-Abeta antibodies or nanobodies) for the treatment of the above-mentioned diseases and conditions.

Combination therapy includes co-administration of the compound of the invention and said other agent, sequential administration of the compound and the other agent, administration of a composition containing the compound and the other agent, or simultaneous administration of separate compositions containing of the compound and the other agent.

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 0.005 to 10% wt.-% of the composition as a whole.

The dosage form containing the composition of the invention contains an effective amount of the active ingredient necessary to provide a therapeutic effect. The composition may contain from about 5,000 mg to about 0.5 mg (preferably, from about 1,000 mg to about 0.5 mg) of a compound of the invention or salt form thereof and may be constituted into any form suitable for the selected mode of administration.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

Methods of Preparation

The compounds of the present invention can be readily prepared according to the following reaction schemes and examples, or modifications thereof, using readily available starting materials, reagents and conventional synthesis procedures. Many of the reactions can also be carried out under microwave conditions or using conventional heating or utilizing other technologies such as solid phase reagents/scavengers or flow chemistry. In these reactions, it is also possible to make use of variants which are themselves known to those of ordinary skill in this art, but are not mentioned in greater detail. Furthermore, other methods for preparing compounds of the invention will be readily apparent to a person of ordinary skill in the art in light of the following reaction schemes and examples. Unless otherwise indicated, all variables are as defined below. The abbreviations used in these experimental details are listed below and additional ones should be known to a person skilled in the art of synthesis. In addition one can refer to the following references for suitable methods of synthesis as described in March, *Advanced Organic Chemistry*, 3rd edition, John Wiley & Sons, 1985 or Greene and Wuts *Protective groups in organic synthesis* $2^{nd}$ edition, John Wiley & sons 1991 and as in Richard Larock, *comprehensive organic transformations*, $4^{th}$ edition, VCH publishers Inc, 1989.

Scheme 1: Synthesis of key intermediate A

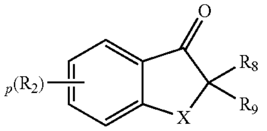

or

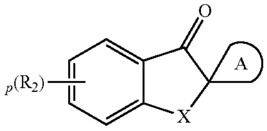

The above shown intermediate can be synthesized by the following methods or by any other methods not detailed here by anyone who is well versed in the art of synthesis.

Method 1

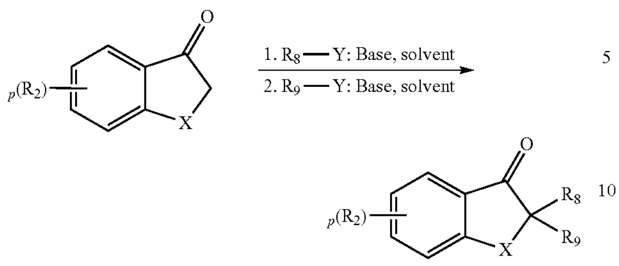

Method 1. Starting with the appropriate ketone one can sequentially alkylate with alkyl halides, triflates and mesylates utilizing bases such as LDA, NaH in various solvents such as THF, DME etc at temperatures varying from −78° C. to 50° C. Each alkylation can be carried out in a sequential fashion with each intermediate being isolated and purified or in one pot in a stepwise fashion. In the event the final product from the above reactions yields a substituent on the alkyl group such as an olefin, sulfone, cyano etc, they can be further manipulated by Dieckman cyclization, RCM or other known reaction such as cycloaddition, nucleophilic substitution etc. to yield highly functionalized spirocyclic intermediates.

Method 2

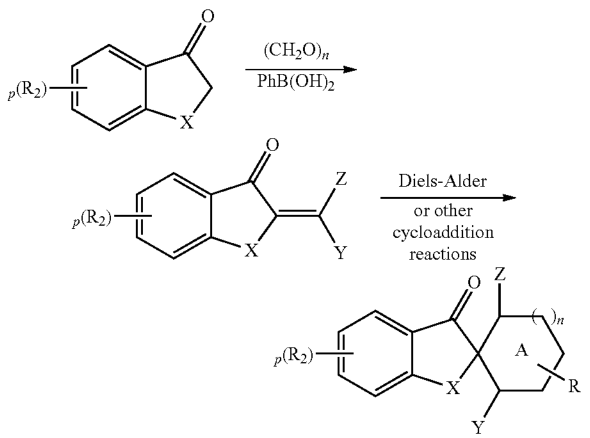

Method 2 represents a specific method for the synthesis of spirocyclic compounds through the Diels Alder reaction or through other cycloaddition reaction such as 1,3-dipolar cycloaddition. The first step involves condensation of ketone with formaldehyde, aldehydes and ketones in presence of any protic acid or boronic acid in solvents such as benzene or toluene at temperatures varying from room temperature to 80° C. The dienophile (or enone) intermediate then can be reacted with various dienes utilizing the Diels-Alder reaction. This reaction can be carried out neat or in presence of non-protic solvents such as benzene, THF in a sealed tube at temperature 30-220° C. In addition one can utilize Lewis acids or any other agents that may assist in the reaction to yield pure enantiomers or diastereomers. The resulting spirocyclic cyclohexyl product may optionally contain one or more alkyl/aryl substituent or functional groups such as a ketone aldehyde, cyano etc. These functional groups can be further elaborated by known functional group transformations. For example the reaction of the dienophile with the Danishefsky diene in refluxing solvents such as benzene or toluene under nitrogen atmosphere yields spirocyclohexanone. The spirocyclohexanone can be further elaborated by reactions such as reduction with hydrides like NaBH4, LAH, DiBAL etc. to yield an alcohol. This alcohol can be further alkylated with various alkyl groups by employing base such as NaH or LiHMDS in solvents such as DMF, THF etc. at room temperature to yield spirocyclic alkyl ethers. The alcohol can also be reacted with aryl/heteroarylhalides in the presence of palladium or copper catalyst along with appropriate bases such as $Cs_2CO_3$ to yield aryl ethers.

Alternatively the ketone functional group can be further modified by known procedures in literature to yield heterocycles or other bicyclic ring systems. In addition the dienophile intermediate can also be reacted with 1,3 ylides to yield 5-membered spirocyclic heterocycles or carbocycles. The utility of these cycloaddition reaction are well documented in literature and are exemplified in these references: Synthesis of heterocycles via cycloadditions, Volume 1 By Alfred Hassner, Topic in heterocyclic chemistry volume 12, 1st edition, springer, 2008 and Cycloaddition reactions in organic synthesis; Kobayashi and Jorgensen, 1st edition, Wiley-VCH, 2002

Method 3

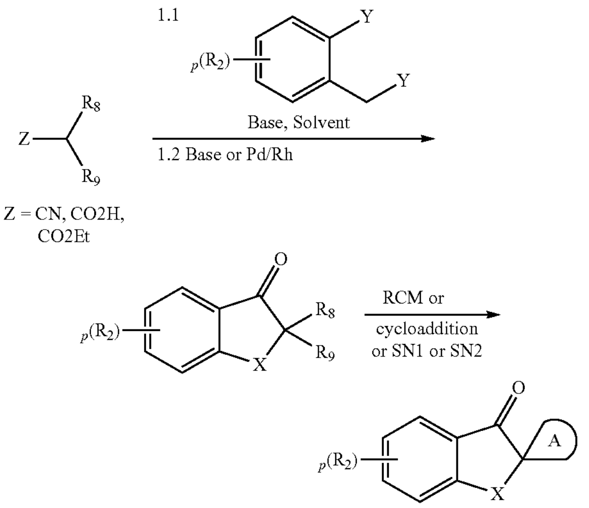

In method 3, starting with alkyl or cycloalkyl or heterocycloalkyl derivatives containing electron withdrawing groups such as cyano or esters, the alkyl/cycloalkyl/heterocycloalkyl groups can be alklylated with optionally substituted ortho-halo benzyl bromides or chlorides utilizing base such as LDA, NaH, or LiHMDS in solvents such as benzene, THF etc. at temperatures ranging from −78° C. to 80° C. The alkylated intermediate can be isolated and further subjected to base such as n-BuLi or LDA in aprotic solvents such as THF, Hexane etc. to effect ring cyclization towards the final intermediate A. Alternatively one can also utilize transition metal based chemistry such as Pd/Cu or Rh containing chelating agents such as phosphine derivatives or amines in solvents such as DMF, DMA, THF and toluene in presence of base (TEA, or $K_2CO_3$) at temperatures varying from room temperature to 80° C. In the event where the final product from the above reactions yields substituent on the alkyl group such as olefins or sulfones, cyano etc, they can be further manipulated by Dieckman cyclization, RCM or other known reactions such as cycloaddition, nucleophilic substitution etc to yield highly functionalized spiro cyclic intermediates.

Method 4

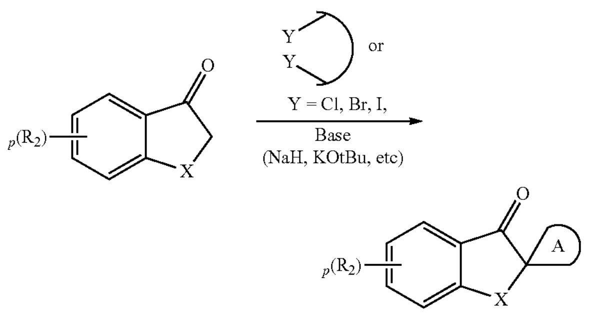

Method 4 represents a one pot reaction towards the synthesis of spirocyclic ketone intermediate A. Starting with appropriate ketone one can utilize alkylation chemistry of internally tethered bis alkyl halides/triflates or mesylates in presence of base such as LDA, LiHMDS and in aprotic solvents such as THF, dioxane, ether etc. at temperature varying from 0° C. to 80° C. to yield spirocyclic intermediate A.

Alternatively ketones can be reacted with acrylates in presence of base such as KOtBu and solvents such as tert-butanol with subsequent decarboxylation of β-keto ester to yield spirocyclic ketone intermediate A.

Scheme 2: Synthesis of Monocyclic Heterocyclic Amines

The ketone intermediate A can be further functionalized and cyclized to yield various monocyclic heterocycles as described in "*Comprehensive Heterocyclic Chemistry: The Structure, Reactions, Synthesis and Uses of Heterocyclic Compounds: The Structure, Reactions, Synthesis and Uses of Heterocyclic Compounds*" by Katritzky and Rees, Wiley and sons, 3rd edition 1991, or as described in *Heterocyclic Chemistry by Joule Keith Mills, 5th* edition by Wiley. Alternatively the methods outlined in WO 2008/103351 can also be utilized in the synthesis of various monocyclic heterocycles. Representative examples of some monocyclic amino heterocycles are shown below.

Scheme 2a: Synthesis of 2,5-dihydro-1,2,4-oxadiazol-3-amine heterocycle.

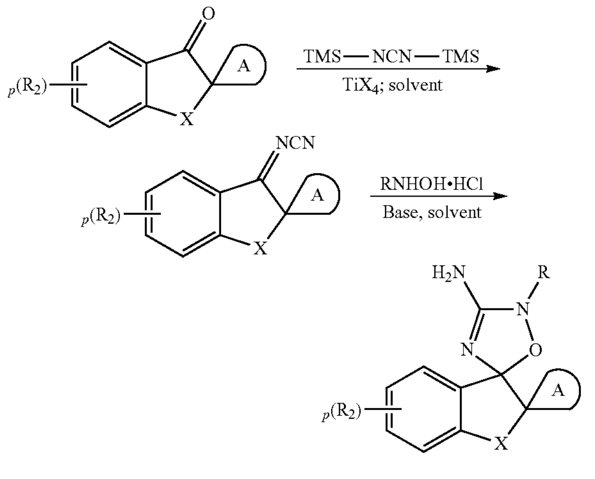

The ketone intermediate is condensed with bis trimethylsilyl carbodimide in presence of Lewis acids such as titanium isopropoxide in solvents such as DCM or THF at room temperature to yield the N-cyanoimine product. The imine is subsequently condensed with hydroxylamine derivative in presence of base such as sodium methoxide in protic solvent such as methanol, t-Butanol etc. at room temperature to yield the desired 1,2,4-oxadiazol-3-amine heterocycle.

Scheme 2b. Synthesis of 2-amino-1H-imidazol-5(4H)-one

1

Error! Objects Cannot be Created from Editing Field Codes

The N-cyano intermediate as described in scheme 2a is reacted with ammonium carbonate and KCN in protic solvent mixture such as ethanol/water and heated to 50-150° C. in a sealed tube overnight. The resulting hydantoin can be alkylated with various alkylating agents in the presence of inorganic bases such as $Cs_2CO_3$ or $K_2CO_3$ or organic bases such as TEA or DBU in various solvents such as ethanol, DMF or dioxane at temperatures ranging from room temperature to 120° C. The resulting alkylated product is reacted with thionating reagents such as Lawesson's reagent or $P_2S_5$ in a solvent such as THF, Dioxane, toluene etc. at temperatures ranging from 50-150° C. The thioimide is then converted to a 2-amino imidazalinone by reacting with tert butyl hydroperoxide in presence of ammonia or alkylamines.

Alternatively the synthesis of 2-amino imidazolinone can be realized from the hydantoin by converting it to a thioimide, followed by bis-alkylation of the thioamide and imide functions in a one pot procedure. Such a bis-alkylated reagent can be reacted with ammonium hydroxide and ammonium iodide in various solvents such as DMF, ethanol, dioxane etc. at temperatures ranging from room temperature to 150° C. in a sealed tube to yield 2-amino-1H-imidazol-5(4H)-one. Similar procedure can also be employed starting with ketone intermediate A.

Scheme 2c. Synthesis of 2-amino-5,6-dihydropyrimidin-4(3H)-one

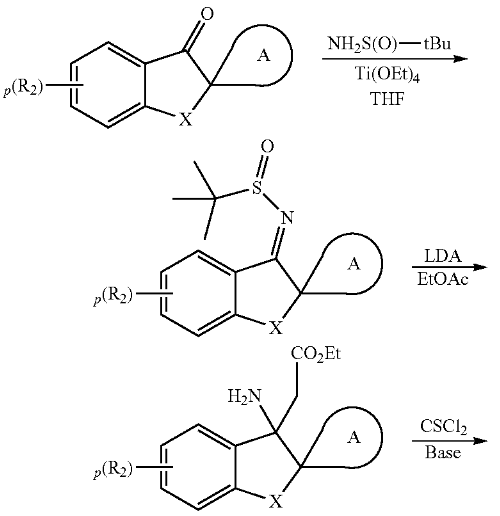

-continued

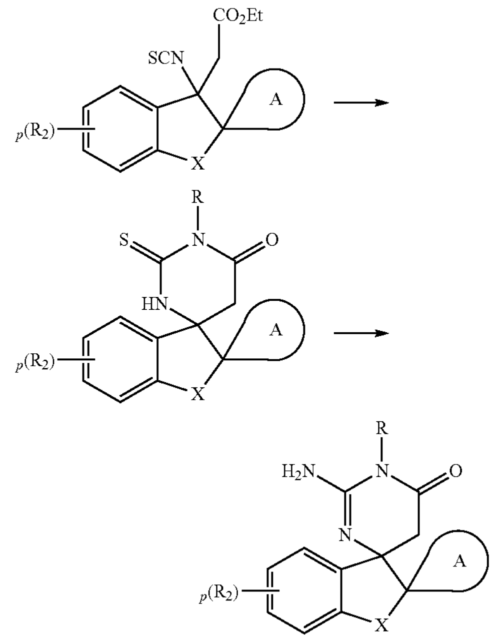

The intermediate ketone A can be condensed with t-butyl sulfonylamine or any other amine such as a-methylbenzylamine under dehydrating conditions as exemplified by use of titanium alkoxide reagents or under a Dean Stark apparatus. The imine is reacted with various nucleophiles as illustrated by lithiated ethylacetate. The deprotection of t-butyl sulfonamide is achieved by reacting with acids such as HCl in protic solvents such as methanol etc. The amino ester intermediate product is then condensed with thiophosgene or its equivalent reagent to convert the amino ester to the thioisocyanate ester. Condensation of thioisocyanate intermediate with various primary/secondary amines yielded thiodihydropyrimidinone. The thiodihydropyrimidnone can be converted to 2-amino dihydropyrimidinone by utilizing methods as described in method 2b.

Scheme 2d Synthesis of 5,6-dihydro-4H-1,3-oxazin-2-amine

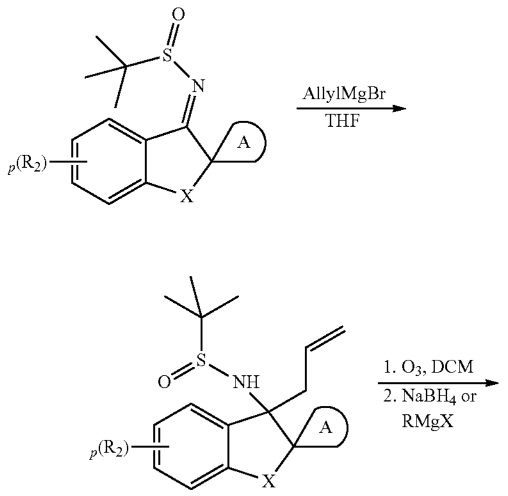

-continued

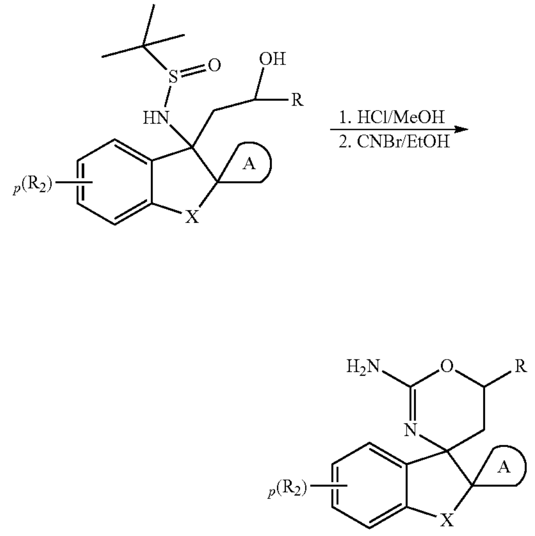

The imine intermediate form above example can also be reacted with carbon neucleophiles such as allylmagnesium bromide to yield sulfonamide. The olefin is subsequently oxidized to aldehyde by ozonolysis or any of its equivalent protocol. The alcohol is obtained from the reaction of aldehyde with reducing agents such as sodium borohydride or utilizing Grignard reagents to yield primary or secondary alcohols. The resulting amino alcohol can be reacted with cyanogen bromide in protic solvents at room temperature to yield 5,6-dihydro-4H-1,3-oxazin-2-amine derivatives.

Scheme 2e. Synthesis of 5,6-dihydro-2H-1,2,4-oxadiazin-3-amine or 1,2,5,6-tetrahydro-1,2,4-triazin-3-amine

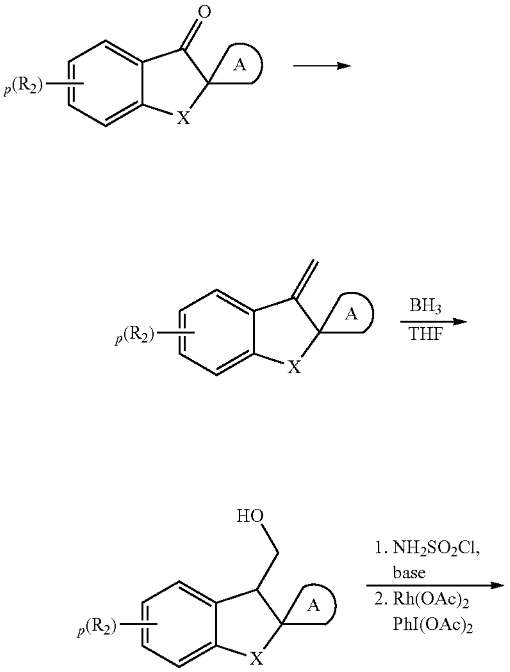

-continued

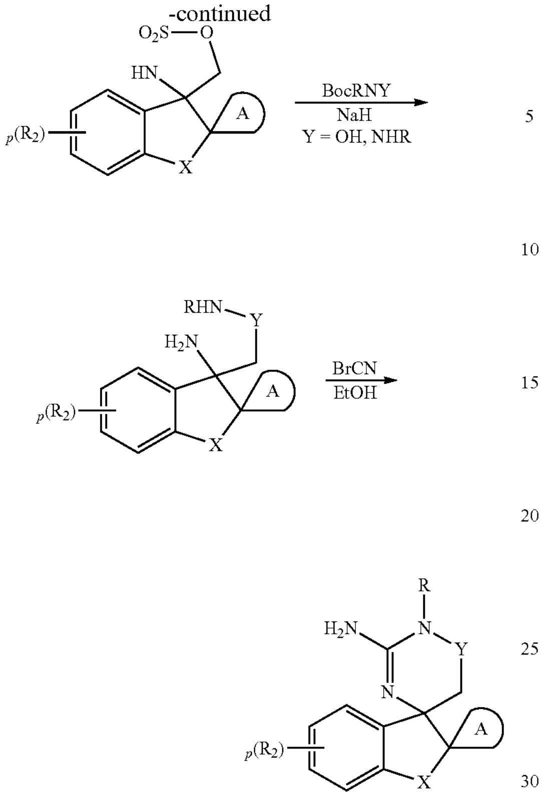

The ketone intermediate A can be converted to an olefin by utilizing the Wittig reaction or any derivation thereof or by other known literature methods. The olefin is hydroborated with borane or equivalent thereof in aprotic solvents such as THF, DCM, diethyl ether etc. at room temperature. The alcohol is condensed with sulfamoyl chloride in presence of base such as NMM, TEA in solvents such as DCM at room temperature. The cyclization of the methylsulfamate can be affected by rhodium catalyst in presence of oxidizing agent such as phenyliodoacetate in solvents such as toluene, acetonitrile, dichloromethane at room temperature to refluxing temperature of the solvent. The cyclic sulfamate is then activated towards neuclophillic attack by reacting with chloroformates followed by addition of a nucleophile such as alkoxide as illustrated by boc protected-N-substituted hydroxylamine. The protecting group such as t-butyl carbamate can be removed and the resulting amino alcohol condensed with cyanogen bromide in solvents such as ethanol to yield 2,4-oxadiazin-3-amine or 1,2,5,6-tetrahydro-1,2,4-triazin-3-amine heterocycles.

Scheme 2f. Synthesis of 5,6-dihydro-4H-1,3-thiazin-2-amine

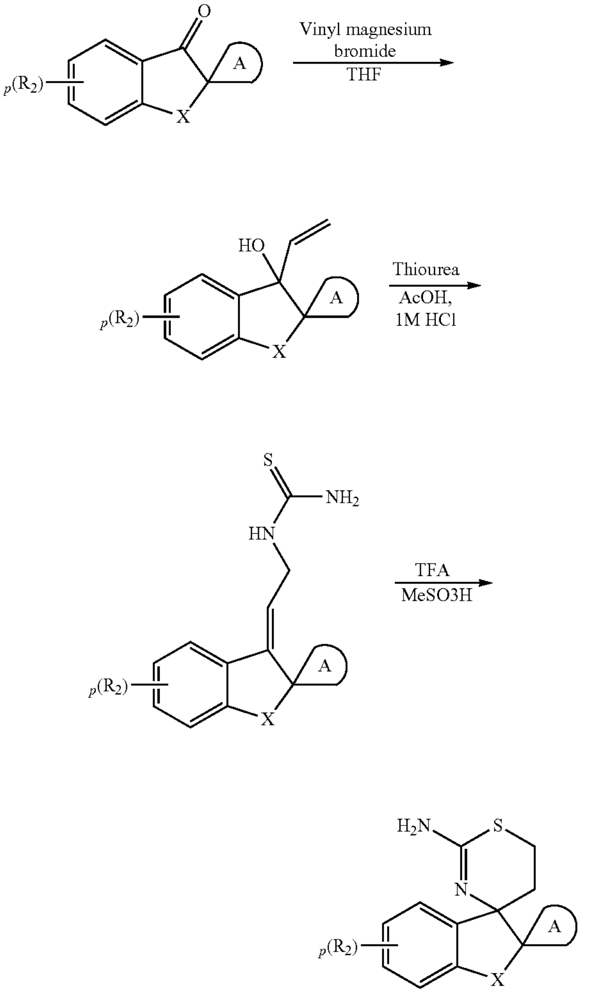

The ketone intermediate A is reacted with a vinyl magnesium derivative or substituted vinyl lithium at room temperature in solvents such as THF, ether, toluene or in hexane to yield a vinylic alcohol. The vinylic alcohol undergoes electrophilic substitution under acidic conditions (such as AcOH/1M HCl or $MeSO_3H$) in presence of thiourea to yield a vinylogous thiourea derivative. This intermediate can be cyclized to 1,3 thiazine-2-amine when exposed to strong acidic conditions as in TFA/$MeSO_3H$ at room temperature overnight.

Scheme 3. Elaboration of monoheteocyclic intermediate

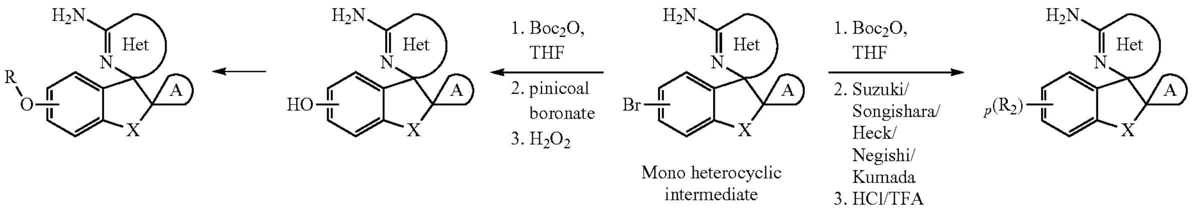

The monoheterocyclic intermediate A containing halogens on the benzene ring can be further elaborated by known organic transformations such as Suzuki couplings of boronates or trifluorborates or with pinacol boronates using various palladium catalyst such as $Pd[P(Ph_3)_3]$ or $Pd(dppf)_2Cl_2$ or any such similar catalyst in presence of inorganic bases such as $K_2CO_3$, $CsCO_3$ in variety of solvents either as single solvent or as combination comprising of Toluene, DMF, Ethanol, water etc. at temperature ranging from 50-100° C. One can utilize copper mediated Sonogashira coupling to introduce alkyne substituent's on the scaffold. Alternatively one can utilize additional transition metal chemistry to introduce alkyne, alkenes, aryls, heterocycles and additional functional groups. Number of such chemical transformations are exemplified in following references: Transition Metals for Organic Synthesis: Building Blocks and Fine Chemicals, by Beller and Bolm, 2nd Edition by Wiley-VCH, 2002 and in *Modern Arylation Methods* by Lutz Ackermann, 1st edition, 2009.

For example, the amino heterocycle of the bromo intermediate is protected as its Boc derivative utilizing Boc anhydride in solvents such as THF, DCM at room temperature. This allows conversion of the bromo to the corresponding pinacolboronate derivative as described in literature. Peroxide oxidation of the pinacolboronate to yield the alcohol is then an available option. The alcohol can be further alkylated with various alkyl/cycloalkyl/heteroalkyl halides in presence of bases such as $Cs_2CO_3$, KOtBu or TEA in solvents such as DMF or dioxane. In addition the alcohol can be arylated under variety of coupling conditions to yield aryl/heteroaryl ethers. The Boc group is further deprotected to yield final compound.

Scheme 4. Synthesis of key intermediate with ring A being cyclohexyl group substituted with —$OR_5$

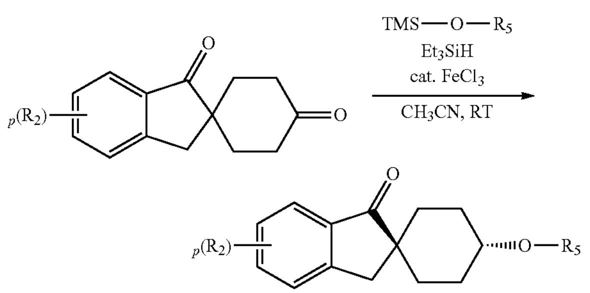

Exemplary reagents and reaction conditions are described in Example 410G.

Scheme 5. Synthesis of key intermediate with ring A being cyclohexyl group substituted with —OH

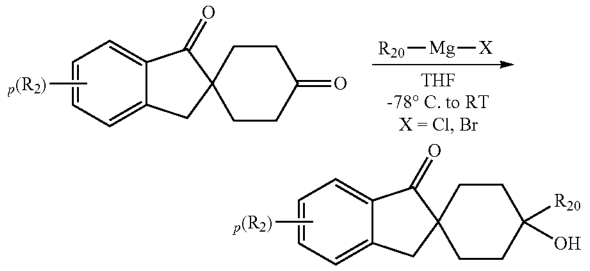

Suitable reagents and reaction conditions for Grignard reaction can be used for the reaction depicted in Scheme. Exemplary reagents and reaction conditions are described in Example 4101.

In cases where the synthetic intermediates and final products of Formula (A), (I') or (I) described below contain potentially reactive functional groups, for example amino, hydroxy, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not usually described explicitly. Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

| Abbreviation | Meaning |
|---|---|
| AcCl | acetyl chloride |
| ACN or $CH_3CN$ | acetonitrile |
| $AlCl_3$ | aluminum chloride |
| Ar | argon |
| $B_2H_6$ | diborane |
| Boc | tert-butoxy carbonyl or t-butoxy carbonyl |
| borax | sodium borate |
| brine | saturated aqueous NaCl |
| CH | cyclohexane |
| $CH_2N_2$ | carbodiimide |
| $Cs_2CO_3$ | cesium carbonate |
| CuBr—$SMe_2$ | cuprous bromide methylsulfide complex |
| CuI | cuprous iodide |
| d | days |
| DCM or $CH_2Cl_2$ | methylene chloride |
| DEA | diethylamine |
| DIBAL-H | diisobutylaluminum hydride |
| DMAP | 4-(dimethylamino)pyridine |
| EtI | ethyl iodide |
| Et | ethyl |
| $Et_2O$ | ethyl ether |
| EtOAc or EA | ethyl acetate |
| EtOH | ethanol |
| $Et_3O^+BF_4^-$ | triethyloxonium tetrafluoroborate |
| h or hr | hour |
| HCl | hydrochloric acid |
| $H_2O$ | water |
| $H_2O_2$ | hydrogen peroxide |
| $HCONH_2$ | formamide |
| HMPA | hexamethylphosphoric triamide |
| HOAc or AcOH | acetic acid |
| HPLC | high performance liquid chromatography |
| HPLC-MS | High performance liquid chromatography with mass detection |
| $K_2CO_3$ | potassium carbonate |
| KCN | potassium cyanide |
| LAH | $LiAlH_4$ = lithium aluminium hydride |
| Lawesson's reagent | 2,4-bis(4-methoxyphenyl)-1,3,2,4-dithiadiphosphetane 2,4-disulfide |
| LC-MS | Liquid chromatography with mass detection |
| LDA | lithium diisopropylamide |
| min | minute |
| MeOH | methanol |
| MeI | methyl iodide |
| Me | methyl |
| MeNHOH | methylhydroxylamine |
| MPLC | Medium pressure liquid chromatography |
| MTBA | 4-(methylthio)benzoic acid |
| $Me_2S$ | methyl sulfide |

-continued

| Abbreviation | Meaning |
|---|---|
| NaOH | sodium hydroxid |
| NaOMe | sodium methoxide |
| $Na_2S_2O_3$ | sodium thiosulfate |
| $Na_2SO_4$ | sodium sulfate |
| NHMDS | Sodium bis(trimethylsilyl)amide |
| $NH_4OH$ | ammonium hydroxide |
| $(NH_4)_2CO_3$ | ammonium carbonate |
| $NH_4I$ | ammonium iodide |
| $Na_2CO_3$ | sodium carbonate |
| $NaHCO_3$ | sodium bicarbonate |
| NaH | sodium hydride |
| $PdCl_2dppf$ | [1,1-bis(diphenylphosphino)ferrocene] dichloropalladium(II) |
| $Pd(OH)_2$ | palladium hydroxide |
| $Pd(PPh_3)_2Cl_2$ | bis(triphenylphosphine)palladium (II) dichloride |
| $Pd(PPh_3)_4$ | tetrakis(triphenylphosphine)palladium(0) |
| PrBr | propyl bromide |
| $PBr_3$ | phosphorous tribromide |
| PCC | pyridinium chlorochromate |
| PE | petroleum ether |
| PPA | polyphosphoric acid |
| $PPh_3$ | triphenyl phosphine |
| RF | heated to reflux |
| Rt | Retention time |
| RT or r.t. | room temperature |
| Selectfluor ™ | 1-chloromethyl-4-fluoro-1,4-diazoniabicyclo[2.2.2]octane bis(tetrafluoroborate) |
| $SOCl_2$ | thionyl chloride |
| TEA | triethylamine |
| TFA | trifluoroacetic acid |
| THF | tetrahydrofuran |
| TLC | thin layer chromatography |
| $TiCl_4$ | titanium chloride |
| TMSCl | trimethylsilyl chloride |
| Triton B | Benzyltrimethylammonium hydroxinde in water |

Compounds of the invention can be prepared employing conventional methods that utilize readily available reagents and starting materials. The reagents used in the preparation of the compounds of this invention can be either commercially obtained or can be prepared by standard procedures described in the literature. Representative compounds of the present invention can be prepared using the following synthetic schemes.

SYNTHETIC METHODS

Example 1

Preparation of 3-(spiro[spiro[2,3-dihydro-indene-2,2'-tetrahydronaphthalene]-1,5'-(3-amino-2-methyl-2H-[1,2,4]oxadiazole)]-6-yl)benzonitrile (compound 45)

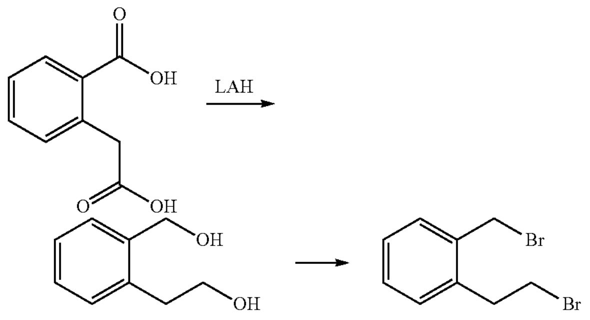

-continued

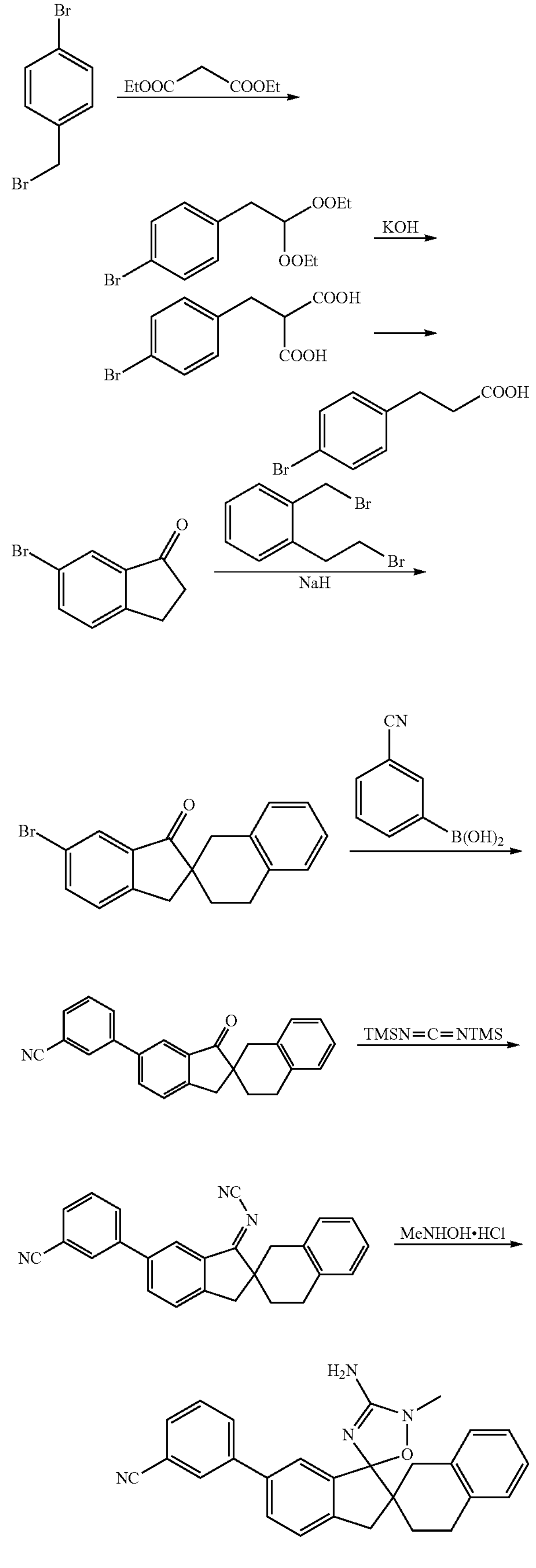

Experimental Data:

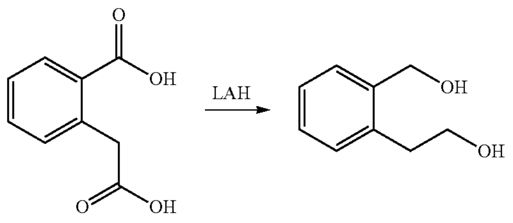 [SMILES: O=C(O)Cc1ccccc1C(=O)O ; OCCc1ccccc1CO]

Step 1. 2-(2-(hydroxymethyl)phenyl)ethanol

To a solution of 2-(carboxymethyl)benzoic acid (9 g, 0.05 mol) in THF (200 mL) was added to LAH in THF (250 mL) dropwise, the mixture was refluxed for 18 hours. The mixture was cooled in ice bath and carefully added water dropwise, followed by 50% NaOH (150 mL), then removed the ice bath and added water slowly with stirring until the gray precipitate turns white. The mixture was filtrated and the filtrate was concentrated to give crude 2-(2-(hydroxymethyl)phenyl) ethanol (6 g, 80%).

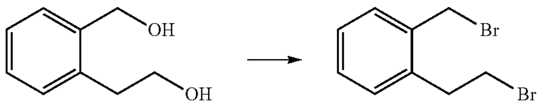 [SMILES: OCCc1ccccc1CO ; BrCCc1ccccc1CBr]

Step 2. 1-(2-Bromoethyl)-2-(bromomethyl)benzene

To a solution of 2-(2-(hydroxymethyl)phenyl)ethanol (2.6 g, 17 mmol), perbromo methane (13.7 g, 41.8 mmol) in DCM (100 mL) was added triphenylphosphine (10.95 g, 41.8 mmol) at 0° C., the mixture was stirred at room temperature for 18 hours. The mixture was concentrated, redissolved by $Et_2O$, filtered, the organic layer was concentrated to give crude 1-(2-bromoethyl)-2-(bromomethyl)benzene (4.2 g, 89%). $^1$H-NMR ($CD_3OD$): 3.69 (m, 2H), 4.05 (m, 2H), 4.97 (m, 2H), 7.64-7.77 (m, 4H).

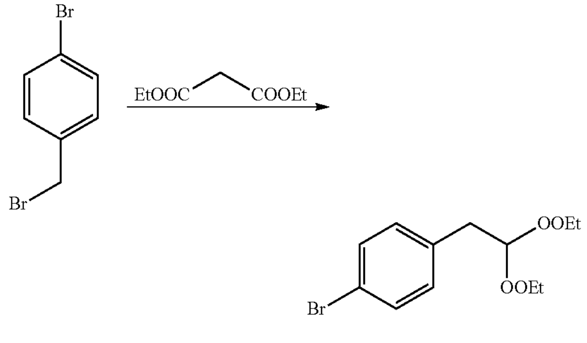

Step 3. Diethyl 2-(4-bromobenzyl)malonate

To a solution of $CH_3CH_2OH$ (240 mL) was added Na (5.82 g, 0.25 mol), the mixture was stirred until Na was disappeared, then 1-bromo-4-bromomethyl-benzenein (37.35 g, 0.15 mol), malonic acid diethyl ester (78 g, 0.49 mol) was added slowly, the mixture was refluxed overnight. The solvent was removed in vacuo, the residue was dissolved with $H_2O$, extracted with ether, the organic layer was washed with 0.5N HCl aqueous, then washed with brine, dried over $Na_2SO_4$, concentrated to give diethyl 2-(4-bromobenzyl)malonate (40 g, 85%).

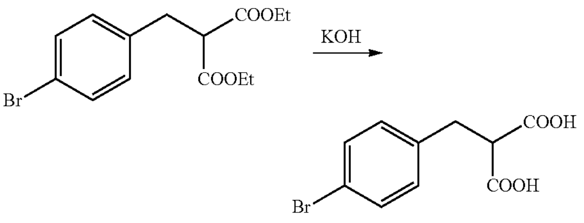

Step 4. 2-(4-Bromobenzyl)malonic acid

Diethyl 2-(4-bromobenzyl)malonate (40 g, 13 mmol) and KOH (42.8 g, 76 mmol) was dissolved in a mixture of HOAc—$H_2O$-THF (1:2:3, 200 mL), the mixture was refluxed for 12 hours. The solvent was removed in vacuo, the residue was added HCl aqueous, then extracted with EtOAc, washed with brine, dried over $Na_2SO_4$, concentrated to give 2-(4-bromobenzyl)malonic acid (31 g, 95%).

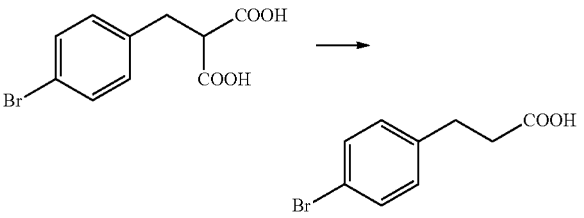

Step 5. 3-(4-Bromophenyl)propanoic acid 2-(4-Bromophenyl)malonic acid (36 g, 11 mmol) was heated at 165° C. until evolution of $CO_2$. the production was crystallized from petrol ether to give 2-(4-bromophenyl)acetic acid (26 g, 87%).

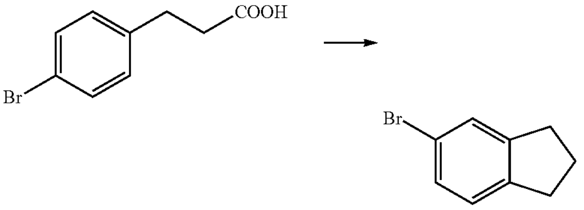

Step 6. 6-Bromo-indan-1-one

A mixture of 3-(4-bromophenyl)propanoic acid (26 g, 12 mmol) in $SOCl_2$ (50 mL) was refluxed overnight, the mixture was concentrated, then added to $AlCl_3$ (80 g, 61 mmol) in DCM (100 mL), the mixture was stirred at room temperature overnight. The mixture was quenched with HCl aqueous, extracted with DCM, washed with brine, dried over $Na_2SO_4$, concentrated to give 6-bromo-indan-1-one (12 g, 48%).

$^1$H-NMR ($CD_3OD$): 2.65 (m, 2H), 3.06 (m, 2H), 7.31 (m, 1H), 7.62 (m, 1H), 7.80 (m, 1H).

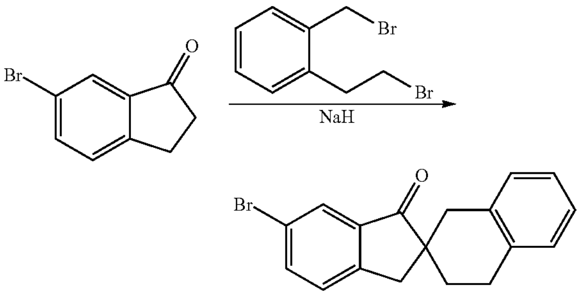

Step 7. 6-Bromo-3',4'-dihydro-1'H-spiro[indene-2,2'-naphthalen]-1(3H)-one

A mixture of 6-bromo-indan-1-one (3.57 g, 17 mmol), 1-(2-bromo-ethyl)-2-bromomethyl-benzene (4.7 g, 17 mmol) in THF (50 mL) was added NaH (816 mg, 34 mmol) at room temperature, the mixture was refluxed for 2 hours. The mixture was quenched with water, concentrated, then extracted with DCM, washed with brine, dried over $Na_2SO_4$, concentrated to 6-bromo-3',4'-dihydro-1'H-spiro[indene-2, 2'-naphthalen]-1(3H)-one (1.8 g, 33%).

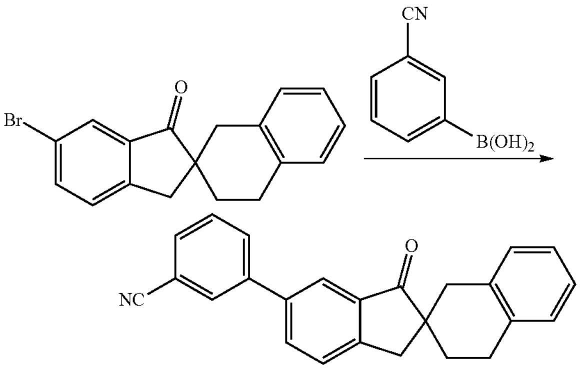

Step 8. 3-(1-oxo-1,3,3',4'-tetrahydro-1'H-spiro[indene-2,2'-naphthalene]-6-yl)benzonitrile 6-Bromo-3',4'-dihydro-1'H-spiro[indene-2,2'-naphthalen]-1(3H)-one (163 mg, 0.5 mmol), 3-cyanophenylboronic acid (147 g, 1 mmol) in [1,4]-dioxane (12 mL), $Cs_2CO_3$ (2 N, 3.2 mL), then $Pd(PPh_3)_2Cl_2$ (5 mg, 0.01 mmol) was added under $Ar_2$, the mixture was refluxed for 30 minutes. The reaction mixture was concentrated in vacuo to give the residue, which was purified by TLC to give 3-(1-oxo-1,3,3',4'-tetrahydro-1'H-spiro[indene-2,2'-naphthalene]-6-yl)benzonitrile (35 mg, 6%).

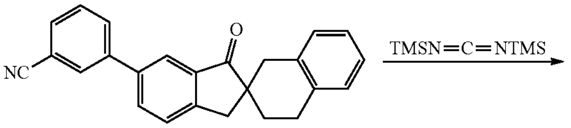

-continued

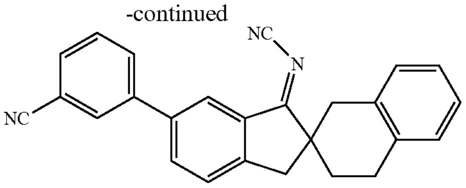

Step 9. (Z)—N-(5-(3-cyanophenyl)-3',4'-dihydro-1'H-spiro[indene-2,2'-naphthalene]-3(1H)-ylidene) cyanamide To a solution of 3-(1-oxo-1,3,3',4'-tetrahydro-1'H-spiro[indene-2,2'-naphthalene]-6-yl)benzonitrile (35 mg, 0.1 mmol) in DCM (5 mL) was added $TiCl_4$ (76 mg, 0.4 mmol) dropwise, the mixture was stirred at 50° C. at $Ar_2$ under microwave for 5 minutes, N,N'-methanediylidenebis(1,1,1-trimethylsilanamine) (74 mg, 0.4 mmol) was added dropwise. The mixture was stirred at 60° C. at $Ar_2$ under microwave for 10 minutes and poured into ice-water (10 mL). The aqueous layer was extracted with $CH_2Cl_2$, which was combined with the organic layer. The organic layer was dried and concentrated to give crude (Z)—N-(5-(3-cyanophenyl)-3',4'-dihydro-1'H-spiro[indene-2,2'-naphthalene]-3(1H)-ylidene)cyanamide (50 mg, 93%).

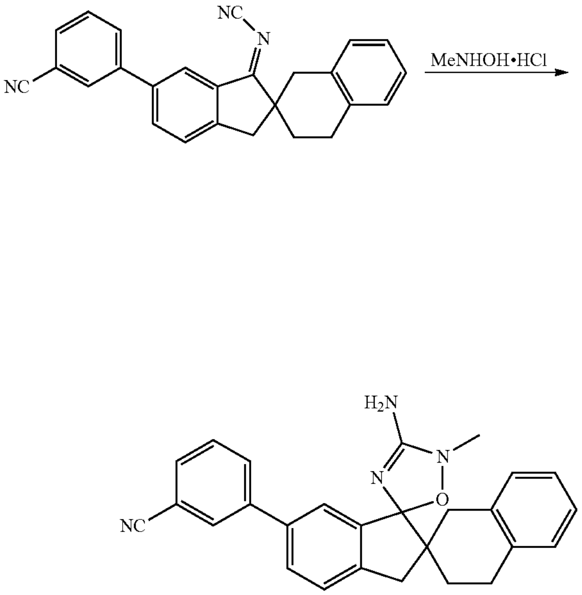

Step 10. Compound 45

To a solution of N-methyl-hydroxylamine hydrochloride (11 mg, 0.134 mmol) in MeOH (5 mL) was added MeONa (0.026 mL, 25% (Wt.) in MeOH), followed by (Z)—N-(5-(3-cyanophenyl)-3',4'-dihydro-1'H-spiro[indene-2,2'-naphthalene]-3(1H)-ylidene)cyanamide (50 mg, 0.13 mmol). After stirred for 10 minutes, the solvent was removed in vacuo. The crude product was purified by preparative HPLC to give the title compound as a TFA salt. $^1$H NMR (400 MHz, $CD_3OD$) δ: 8.05 (m, 1H), 7.99 (m, 2H), 7.84 (m, 1H), 7.79-7.62 (m, 4H), 7.66 (m, 1H), 7.43 (m, 1H), 7.18-7.07 (m, 2H), 3.34 (s, 3H); MS ESI+ve m/z 421 $(M+H)^{30}$.

Example 2

Preparation of 3-(spiro[spiro[2,3-dihydro-indene-2, 1'-(4-oxacyclohexane)]-1,5'-(3-amino-2-methyl-2H-[1,2,4]oxadiazole)]-6-yl)benzonitrile (compound 51)

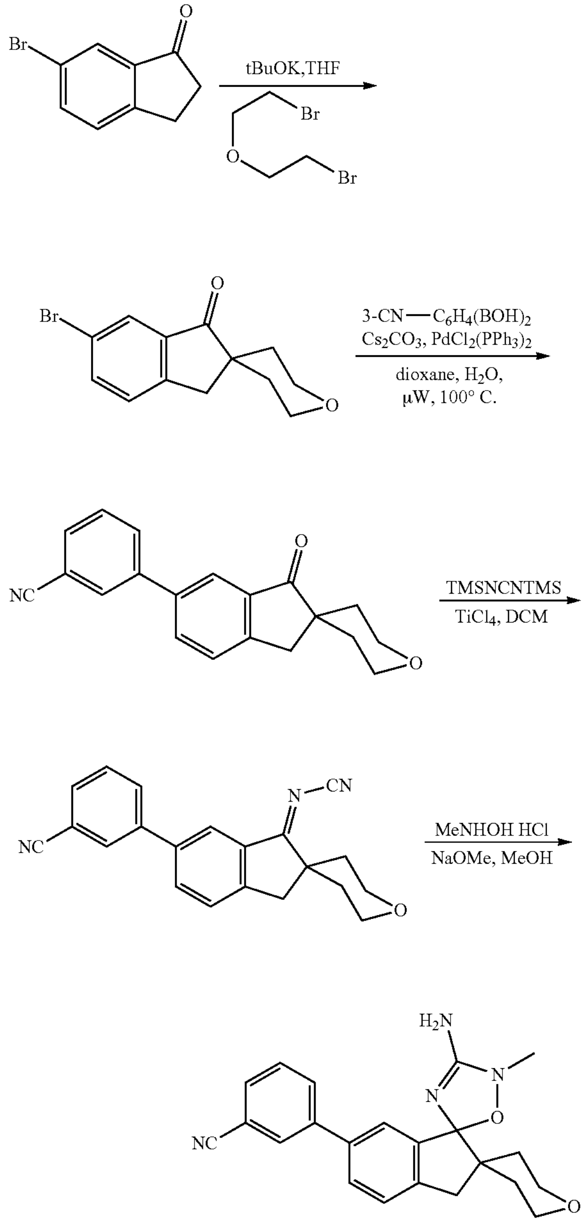

Step 1: Preparation of 6-bromo-2',3',5',6'-tetrahydrospiro[indene-2,4'-pyran]-1(3H)-one To a solution of 6-bromo-1-indanone (1.033 g, 4.89 mmol) in anhydrous THF (100 mL) under $N_2$ atmosphere at room temperature was added a solution of tBuOK in tBuOH (1 M, 10.3 mL, 10.3 mmol) within 30 min (the color turned to deep black upon a drop of tBuOK solution was added), followed by 1-bromo-2-(2-bromoethoxy)ethane (1.134 g, 0.62 mL, 4.89 mmol). The reaction was quenched with saturated aqueous $NH_4Cl$, and extracted with ether two times. The combined organic phases were washed with $H_2O$, brine, and dried over anhydrous $Na_2SO_4$, and filtered, and concentrated to give black tar. It was purified by flash chromatography on silica gel yield 300 mg of the desired product. MS ESI+ve m/z 281 $(M+H)^{30}$.

Step 2: Preparation of 3-(1-oxo-1,2',3,3',5',6'-hexahydrospiro[indene-2,4'-pyran]-6-yl)benzonitrile To a 10 mL CEM microwave test tube was charged with $Cs_2CO_3$ (232 mg, 0.712 mmol), $PdCl_2(PPh_3)_2$ (20 mg, 0.028 mmol), 6-bromo-2',3',5',6'-tetrahydrospiro[indene-2,4'-pyran]-1(3H)-one (100 mg, 0.356 mmol), 3-cyanophenylboronic acid (78 mg, 0.534 mmol), dioxane (4 mL) and $H_2O$ (0.4 mL), the system was swept with $N_2$ and capped, and heated in a CEM microwave reactor at 100° C. for 10 min. The reaction mixture was diluted with DCM, washed with brine, dried over anhydrous $Na_2SO_4$, and filtered, and concentrated. The residue was purified by flash chromatography on silica gel eluting with EA in hexane (0-30%) to give 42 mg of 3-(1-oxo-1,2',3,3',5',6'-hexahydrospiro[indene-2,4'-pyran]-6-yl)benzonitrile. MS ESI+ve m/z 304 $(M+H)^{30}$.

Step 3: Preparation of N-(5-(3-cyanophenyl)-2',3',5',6'-tetrahydrospiro[indene-2,4'-pyran]-3(1H)-ylidene) cyanamide To a solution of 3-(1-oxo-1,2',3,3',5',6'-hexahydrospiro[indene-2,4'-pyran]-6-yl)benzonitrile (42 mg, 0.139 mmol) in anhydrous DCM (10 mL) under $N_2$ atmosphere was added 1 M $TiCl_4$ (in DCM, 0.28 mL, 0.28 mmol) dropwise within 15 min at room temperature. It was stirred another 1 h after the addition. To this mixture was added Bis-trimethylsilylcarbodiimide (0.1 mL, 0.427 mmol) dropwise. The resulting mixture was stirred overnight. The reaction mixture was quenched with ice-water (20 g), and stirred for 20 min, then it was transferred to a separating funnel, the separated aqueous phase was extracted 2 times with DCM. The combined organic phases were dried over anhydrous $Na_2SO_4$, and filtered, and concentrated to give 44 mg of N-(5-(3-cyanophenyl)-2',3',5',6'-tetrahydrospiro[indene-2,4'-pyran]-3(1H)-ylidene)cyanamide as light brown solid which was used for next step without further purification. MS ESI+ve m/z 328 $(M+H)^{30}$.

Step 4: 3-(spiro[spiro[2,3-dihydro-indene-2,1'-(4-oxacyclohexane)]-1,5'-(3-amino-2-methyl-2H-[1,2,4] oxadiazole)]-6-yl)benzonitrile To a suspension of the crude product obtained from previous step in MeOH (5 mL) was added a solution of N-methylhydroxylamine in MeOH (0.373 M, 0.40 mL, prepared from N-methylhydroxylamine HCl salt and 0.9 eq 25 wt % NaOMe/MeOH in MeOH). The mixture was stirred at room temperature for 20 min, followed by adding another portion of N-methylhydroxylamine in MeOH (0.373 M, 1 mL). Solvent was removed under reduced pressure after stirred another 20 min. The residue was purified by preparative PHLC to yield 16.5 mg of the title compound as TFA salt. $^1H$ NMR (400 MHz, $CD_3OD$) δ: 8.02-7.90 (m, 3H), 7.79-7.62 (m, 3H), 7.48 (d, J=7.6 Hz, 1H), 4.05-3.92 (m, 2H), 3.72-3.60 (m, 2H), 3.37 (s, 3H), 3.21 (d, J=16.0 Hz, 1H), 3.11 (d, J=16.0

Hz, 1H), 1.99 (td, J=13.2, 4.8 Hz, 1H), 1.86 (td, J=13.2, 4.8 Hz, 1H), 1.56 (m, 1H), 1.28 (dd, J=13.2, 2.4 Hz, 1H); MS ESI+ve m/z 375 $(M+H)^{30}$.

Example 3

Preparation of 3-(spiro[spiro[2,3-dihydro-indene-3, 1'-(4-oxacyclohexane)]-1,5'-(3-amino-2-methyl-2H-[1,2,4]oxadiazole)]-6-yl)benzonitrile (compound 69)

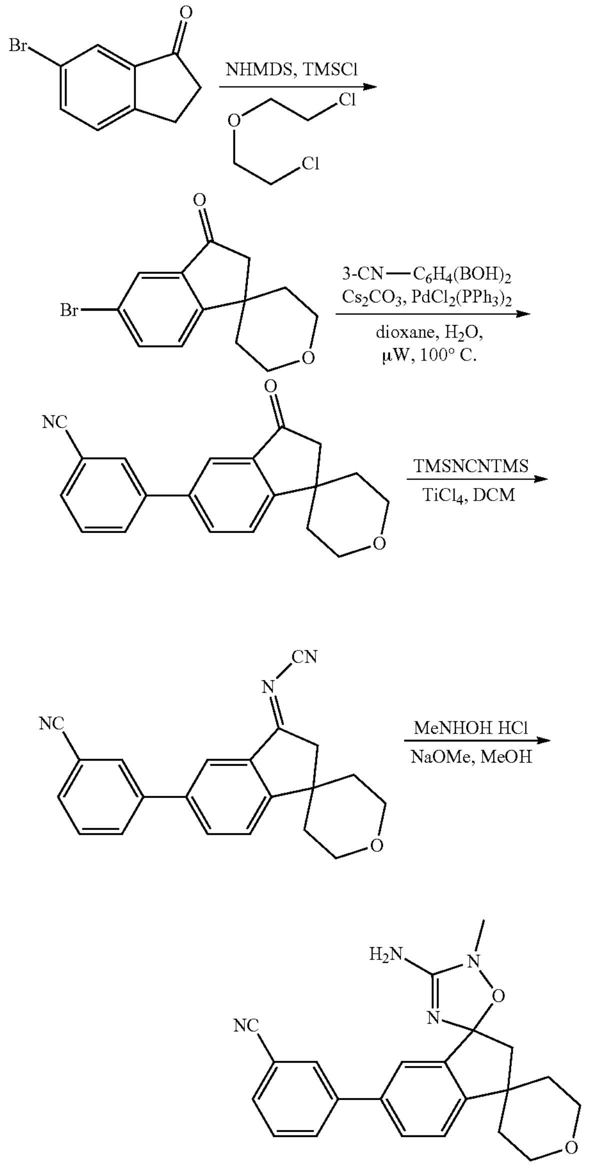

Step 1: Preparation of 5-bromo-2',3',5',6'-tetrahydrospiro[indene-1,4'-pyran]-3(2H)-one To a solution of 6-bromo-1-indanone (0.50 g, 2.35 mmol) in anhydrous THF (40 mL) under $N_2$ atmosphere at −78° C. was added a solution of NHMDS (1 M in THF, 2.5 mL, 2.5 mmol) within 30 min, followed by TMSCl (0.281 g, 0.327 mL 2.59 mmol) after stirred 30 min. To this reaction mixture was added NHMDS (1 M in THF, 6.0 mL, 6.0 mmol) within 30 min at this temperature. The temperature was allowed to warm to −30 to −20° C., after stirred another 30 min, 2,2-dichlorodiethyl ether (336 mg, 0.275 mL, 2.35 mmol) was added. Then the reaction temperature was allowed to warm to room temperature without removing cooling bath, and stirred overnight. The reaction was quenched with saturated aqueous $NH_4Cl$, and extracted with EA two times. The combined organic phases were washed with 1 M HCl, $H_2O$, brine successively, and dried over anhydrous $Na_2SO_4$, and filtered, and concentrated to give black oil. It was purified by flash chromatography on silica gel yield 103 mg of the desired product. MS ESI+ve m/z 281 $(M+H)^{30}$.

Step 2: 3-(3-oxo-2,2',3,3',5',6'-hexahydrospiro[indene-1,4'-pyran]-5-yl)benzonitrile To a 10 mL CEM microwave test tube was charged with $Cs_2CO_3$ (147 mg, 0.45 mmol), $PdCl_2(PPh_3)_2$ (20 mg, 0.028 mmol), 5-bromo-2',3',5',6'-tetrahydrospiro[indene-1,4'-pyran]-3(2H)-one (51 mg, 0.18 mmol), 3-cyanophenylboronic acid (35 mg, 0.24 mmol), dioxane (3 mL) and $H_2O$ (0.1 mL), the system was swept with $N_2$ and capped, and heated in a CEM microwave reactor at 100° C. for 10 min. The reaction mixture was diluted with DCM, washed with brine, dried over anhydrous $Na_2SO_4$, and filtered, and concentrated. The residue was purified by flash chromatography on silica gel eluting with EA in hexane (0-30%) to give 42 mg of 3-(3-oxo-2,2',3,3',5',6'-hexahydrospiro[indene-1,4'-pyran]-5-yl)benzonitrile as white solid. MS ESI+ve m/z 304 $(M+H)^{30}$.

Step 3: Preparation of N-(5-(3-cyanophenyl)-2',3',5',6'-tetrahydrospiro[indene-1,4'-pyran]-3(2H)-ylidene) cyanamide To a solution of 3-(3-oxo-2,2',3,3',5',6'-hexahydrospiro[indene-1,4'-pyran]-5-yl)benzonitrile (42 mg, 0.139 mmol) in anhydrous DCM (10 mL) under $N_2$ atmosphere was added 1 M $TiCl_4$ (in DCM, 0.28 mL, 0.28 mmol) dropwise within 15 min at room temperature. It was stirred another 1 h after the addition. To this mixture was added Bis-trimethylsilylcarbodiimide (0.1 mL, 0.427 mmol) dropwise. The resulting mixture was stirred overnight. The reaction mixture was quenched with ice-water (15 g), and stirred for 30 min, then it was transferred to a separating funnel, the separated aqueous phase was extracted 2 times with DCM. The combined organic phases were dried over anhydrous $Na_2SO_4$, and filtered, and concentrated to give the desired product as white solid, which was used for next step without further purification. MS ESI+ve m/z 328 $(M+H)^{30}$.

Step 4: Preparation of 3-(spiro[spiro[2,3-dihydro-indene-3,1'-(4-oxacyclohexane)]-1,5'-(3-amino-2-methyl-2H-[1,2,4]oxadiazole)]-6-yl)benzonitrile To s suspension of the crude product obtained from previous step in MeOH (6 mL) was added a solution of N-methylhydroxylamine in MeOH (prepared from N-methylhydroxylamine HCl salt (13 mg, 0.153 mmol) in anhydrous MeOH (4 mL) and 25 wt % NaOMe/MeOH (31 μL, 0.138 mmol), stirred 5 min). The mixture was stirred at room temperature for 60 min. Solvent was removed under reduced pressure. The residue was purified by preparative PHLC to yield 2.1 mg of the title compound as TFA salt. $^1H$ NMR (400 MHz, $CD_3OD$) δ: 8.14-7.84 (m, 4H), 7.74 (m, 1H), 7.65 (m, 1H), 7.56 (d, J=8.0 Hz, 1H), 4.06-3.96 (m, 2H), 3.74-3.59 (m, 2H), 3.39 (s, 3H), 2.34-1.48 (m, 6H); MS ESI+ve m/z 375 (M+H)[30].

Example 4

Preparation of 2"-amino-6-bromo-1'"-methyl-1"H-spiro[spiro[2,3-dihydro-indene-2,1'-(trans-4-methoxycyclohexane)]-1,4'-pyrimidin]-6"(5"H)-one (compound 64)

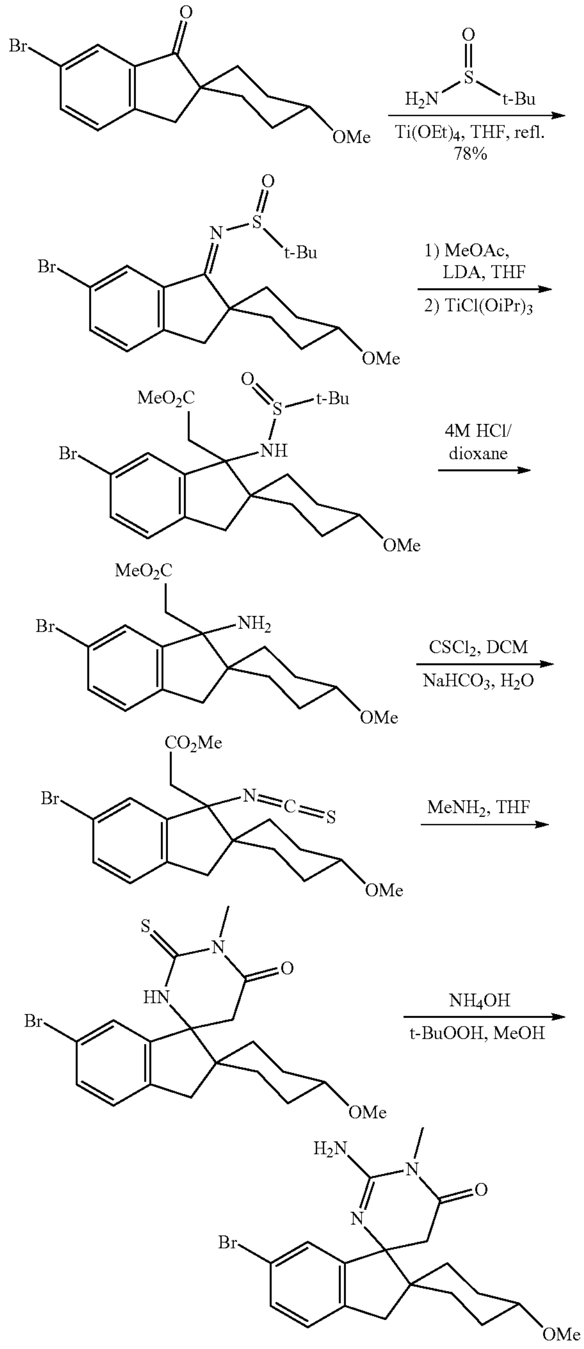

Step 1: Preparation of N-(trans-5'-bromo-4-methoxyspiro[cyclohexane-1,2'-indene]-3'(1'H)-ylidene)-2-methylpropane-2-sulfinamide To a solution of trans-6'-bromo-4-methoxyspiro[cyclohexane-1,2'-inden]-1'(3'H)-one (923 mg, 2.99 mmol) and 2-methyl-2-propane sulfonamide (1.450 g, 11.96 mmol) in anhydrous THF (75 mL) was added $Ti(OEt)_4$ (5.46 g, 4.96 mL, 23.92 mmol). The resulting mixture heated to reflux for 24 h. To this reaction mixture was added 2-methyl-2-propane sulfonamide (0.725 g, 5.98 mmol) and $Ti(OEt)_4$ (2.73 g, 2.48 mL, 11.96 mmol), then reflux another 14 h. After this period of time, 2-methyl-2-propane sulfonamide (0.725 g, 5.98 mmol) and $Ti(OEt)_4$ (2.73 g, 2.48 mL, 11.96 mmol) was added, the mixture was refluxed for another 48 h. The reaction mixture was cooled to room temperature and quenched with brine (3 mL), and stirred vigorously for 30 min. The mixture was filtered through a pad of Celite®, and washed with ethyl acetate (50 mL). The filtrate was concentrated, and the residue was dissolved in DCM, filtered again. The filtrated was concentrated, the residue was purified by flash chromatography on silica gel to afford 0.968 g of the desired product as a light yellow solid. MS ESI+ve m/z 412 $(M+H)^+$ Step 2: Preparation of methyl 2-(trans-6'-bromo-1'-(1,1-dimethylethylsulfinamido)-4-methoxy-1',3'-dihydrospiro[cyclohexane-1,2'-indene]-1'-yl)acetate To a flame dried 50 mL of round bottom flask was charged with of methyl acetate (0.088 mL, 1.11 mmol) and anhydrous THF (10 mL) under $N_2$ atmosphere. The solution was cooled to −78° C. with stirring, 2 M LDA solution in THF (0.551 mL, 1.112 mmol) was added dropwise. The mixture was stirred for another 30 min at the same temperature after the addition. To this mixture was added 1 M solution of $TiCl(OiPr)_3$ in hexane (1.2 mL, 1.2 mmol) dropwise, then stirred another 30 min at −78° C. To this mixture was added a solution of N-(trans-5'-bromo-4-methoxyspiro[cyclohexane-1,2'-indene]-3'(1'H)-ylidene)-2-methylpropane-2-sulfinamide (227.6 mg, 0.55 mmol) in anhydrous THF (10 mL) dropwise within 30 min. The reaction mixture was stirred another 1 h at −78° C. LC-MS shows 10% conversion. Keep this temperature and stirred another 2 h, no improvement in conversion.

In another flame dried 50 mL round bottom, enolate anion was prepared again using the same procedure with bigger scale and higher concentration: methyl acetate (0.44 mL, 1.11 mmol) in anhydrous THF (4 mL); 2 M LDA solution in THF (2.77 mL, 5.55 mmol); 1 M solution of $TiCl(OiPr)_3$ in hexane (6.1 mL, 6.1 mmol). Part of this enolate anion solution (6 mL) was transferred to above reaction flask with a syringe quickly. 70% conversion was achieved after 30 min. More of this Enolate anion solution (2 mL) was added to the reaction system in the same manner. The reaction was quenched after stirred another 30 min. 85% conversion was achieved at this point. The reaction mixture was filtered through a pad of Celite, and washed with EA. The separated aqueous phase was extracted with EA once. The combined organic phases were washed with brine, and dried over anhydrous $Na_2SO_4$, and filtered, and concentrated to dryness. The residue was purified by flash chromatography on silica gel to yield 210 mg of the desired product as white foam. MS ESI+ve m/z 486 (M+H)[30].

Step 3: Preparation of methyl 2-(trans-1'-amino-6'-bromo-4-methoxy-1',3'-dihydrospiro[cyclohexane-1,2'-indene)]-1'-yl)acetate The solution of methyl 2-(trans-6'-bromo-1'-(1,1-dimethylethylsulfinamido)-4-methoxy-1',3'-dihydrospiro[cyclohexane-1,2'-indene]-1'-yl)acetate (190 mg, 0.89 mmol) in MeOH (4 mL) and 4 M HCl solution in 1,4-dioxane (8 mL) was stirred at room temperature for 30 min. The solvent was removed under reduced pressure to give the desired HCl salt as a white foam. It was used for next step without further purification. MS ESI+ve m/z 382 $(M+H)^{30}$.

Step 4: Preparation of methyl 2-(trans-6'-bromo-1'-isothiocyanato-4-methoxy-1',3'-dihydrospiro[cyclohexane-1,2'-indene]-1'-yl)acetate Above crude product was added to a solution of $NaHCO_3$ (328 mg, 3.9 mmol) in $H_2O$ (10 mL) and DCM (1 mL) which was chilled at ° C., to this stirred mixture was added thiophosgene (33 μL, 49.5 mg, 0.93 mmol) and stirred for 1 h at ° C. Thiophosgene (22 μL, 33 mg, 0.62 mmol) was added to the reaction and stirred another 30 min. The reaction was diluted with DCM and brine, and the separated organic phase was washed with saturated brine and dried over anhydrous $Na_2SO_4$, and filtered, and concentrated to produce the desired product as oil. It is used for next step without further purification. MS ESI+ve m/z 365 $(M-NCS)^+$.

Step 5: Preparation of 6-bromo-1'''-methyl-2''-thioxo-2'',3''-dihydro-1''H-spiro[spiro[2,3-dihydroindene-2,1'-(trans-4-methoxycyclohexane)]-1,4'-pyrimidin]-6''(5''H)-one To a solution of above crude product in DCM (3 mL) was added a solution of 2 M $MeNH_2$ in THF (3 mL). The mixture was stirred for 20 min at room temperature. The solvent was removed under reduced pressure and the residue was dissolved in DCM (2 mL) and hexane (2 mL) and evaporated to afford 179 mg of crude product as off-white solid. This product was used for next without further purification. MS ESI+ve m/z 423 $(M+H)^{30}$.

Step 6: Preparation of 2''-amino-6-bromo-1'''-methyl-1''H-spiro[spiro[2,3-dihydro-indene-2,1'-(trans-4-methoxycyclohexane)]-1,4'-pyrimidin]-6''(5''H)-one To a solution of above crude product in MeOH (9 mL) was added concentrated aqueous $NH_4OH$ (4.5 mL), followed by tert-butyl hydroperoxide solution (ca. 5.5 M in nonane, 1 mL). The resulting suspension was stirred overnight. The resulting clear solution was concentrated in vacuum to produce the crude product. 10 mg of the crude product was purified through preparative HPLC to give the desired product as TFA salt. $^1$H NMR (400 MHz, $CD_3OD$) δ: 7.54 (d, J=1.6, 1H), 7.48 (dd, J=8.0, 1.6 Hz, 1H), 7.22 (d, J=8.0 Hz, 1H), 3.34 (s, 3H), 3.30 (s, 3H), 3.20-3.07 (m, 3H), 3.01 (d, J=16.8 Hz, 1H), 2.83 (d, J=16.8 Hz, 1H), 2.03 (m, 2H), 1.74 (m, 1H), 1.44-1.27 (m, 5H); MS ESI+ve m/z 406 $(M+H)^{30}$.

Example 5

Preparation of 3-(2''-amino-1'''-methyl-6''-oxo-5'',6''-dihydro-1''H-spiro[spiro[2,3-dihydro-indene-2,1'-(trans-4-methoxycyclohexane)]-1,4'-pyrimidine]-6-yl)benzonitrile (compound 58)

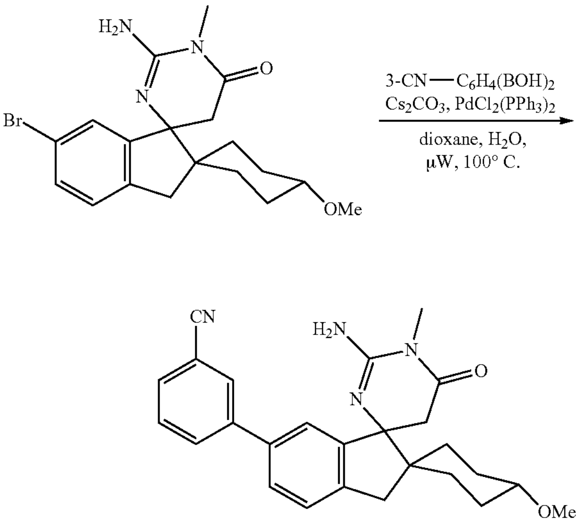

To a solution of crude product of 2''-amino-6-bromo-1'''-methyl-1''H-spiro[spiro[2,3-dihydro-indene-2,1'-(trans-4-methoxycyclohexane)]-1,4'-pyrimidin]-6''(5''H)-one (15 mg, purity 70%, 0.026 mmol), 3-cyanophenylboronic acid (8 mg, 0.055 mmol) and $Cs_2CO_3$ (40 mg, 0.12 mmol) in 1,4-dioxane (2.5 mL) and $H_2O$ (0.2 mL) charged in a 10 mL CEM microwave test tube was added $PdCl_2(PPh_3)_2$ (3 mg, 0.004 mmol), then the system was degassed by sweeping $N_2$. The tube was sealed and heated to 110° C. for 10 min in a CEM microwave reactor. Solvent was removed in vacuum and the residue was purified by preparative HPLC to yield 4 mg of the desired product as a TFA salt. $^1$H NMR (400 MHz, $CD_3OD$) δ: 8.00 (d, J=1.6 Hz, 1H), 7.95 (m, 1H), 7.71 (m, 1H), 7.66-7.61 (m, 3H), 7.42 (d, J=8.4, 1H), 3.36 (s, 3H), 3.35 (s, 3H), 3.21-3.17 (m, 3H), 3.10 (d, J=16.8 Hz, 1H), 2.93 (d, J=16.8 Hz, 1H), 2.04 (m, 2H), 1.79 (m, 1H), 1.48-1.31 (m, 5H); MS ESI+ve m/z 429 $(M+H)^{30}$.

Example 6

Preparation of 2''-amino-1'''-methyl-6-(pyridin-3-yl)-1''H-spiro[spiro[2,3-dihydro-indene-2,1'-(trans-4-methoxycyclohexane)]-1,4'-pyrimidin]-6''(5''H)-one (compound 59)

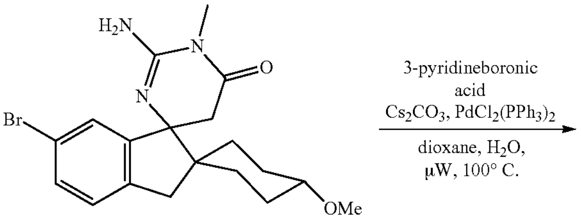

-continued

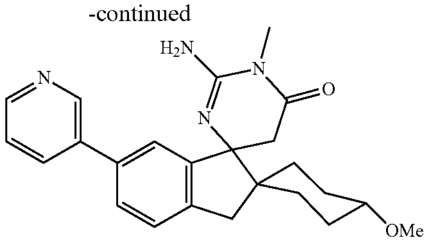

To a solution of crude product of 2"-amino-6-bromo-1'"-methyl-1"H-spiro[spiro[2,3-dihydro-indene-2,1'-(trans-4-methoxycyclohexane)]-1,4'-pyrimidin]-6"(5"H)-one (25 mg, purity 70%, 0.043 mmol), 3-pyridineboronic acid (10 mg, 0.08 mmol) and $Cs_2CO_3$ (40 mg, 0.12 mmol) in 1,4-dioxane (2 mL) and $H_2O$ (0.2 mL) charged in a 10 mL CEM microwave test tube was added $PdCl_2(PPh_3)_2$ (4 mg, 0.005 mmol), then the system was degassed by sweeping $N_2$. The tube was sealed and heated to 110° C. for 10 min in a CEM microwave reactor. Solvent was removed in vacuum and the residue was purified by preparative HPLC to yield 7 mg of the desired product as a TFA salt. $^1$H NMR (400 MHz, $CD_3OD$) δ: 9.14 (s, 1H), 8.82 (m, 2H), 8.10 (dd, J=8.0, 1.6 Hz, 1H), 7.80 (s, 1H), 7.77 (dd, J=9.2, 1.6 Hz, 1H), 7.51 (d, J=8.0 Hz, 1H), 3.36 (s, 3H), 3.35 (s, 3H), 3.25-3.17 (m, 3H), 3.08 (d, J=17.2 Hz, 1H), 2.96 (d, J=17.2 Hz, 1H), 2.05 (m, 2H), 1.81 (dd, J=12.0, 2.8 Hz, 1H), 1.50-1.28 (m, 5H); MS ESI+ve m/z 405 $(M+H)^{30}$.

Example 7

Preparation of 2"-amino-1'"-methyl-6-(3-chloro-5-fluorophenyl)-1"H-spiro[spiro[2,3-dihydro-indene-2,1'-(trans-4-methoxycyclohexane)]-1,4'-pyrimidin]-6"(5"H)-one (Compound 42)

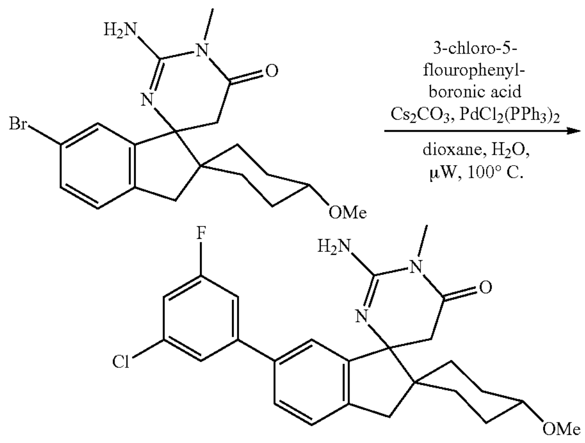

To a solution of crude product of 2"-amino-6-bromo-1'"-methyl-1"H-spiro[spiro[2,3-dihydro-indene-2,1'-(trans-4-methoxycyclohexane)]-1,4'-pyrimidin]-6"(5"H)-one (25 mg, purity 70%, 0.043 mmol), 3-chloro-5-fluorophenylboronic acid (13 mg, 0.07 mmol) and $Cs_2CO_3$ (40 mg, 0.12 mmol) in 1,4-dioxane (2 mL) and $H_2O$ (0.2 mL) charged in a 10 mL CEM microwave test tube was added $PdCl_2(PPh_3)_2$ (4 mg, 0.005 mmol), then the system was degassed by sweeping $N_2$. The tube was sealed and heated to 110° C. for 10 min in a CEM microwave reactor. Solvent was removed in vacuum and the residue was purified by preparative HPLC to yield 6 mg of the desired product as a TFA salt. $^1$H NMR (400 MHz, $CD_3OD$) δ: 7.63 (m, 2H), 7.51 (d, J=1.6 Hz, 1H), 7.40 (m, 1H), 7.36 (m, 1H), 7.19 (m, 1H), 3.36 (s, 3H), 3.35 (s, 3H), 3.20-3.16 (m, 3H), 3.09 (d, J=17.2 Hz, 1H), 2.92 (d, J=16.4 Hz, 1H), 2.03 (m, 2H), 1.79 (m, 1H), 1.48-1.28 (m, 5H); MS ESI+ve m/z 456 $(M+H)^{30}$.

Example 8

Preparation of 2"-amino-1'"-methyl-6-(cyclopropyl-ethynyl)-1"H-spiro[spiro[2,3-dihydro-indene-2,1'-(trans-4-methoxycyclohexane)]-1,4'-pyrimidin]-6"(5"H)-one (compound 55)

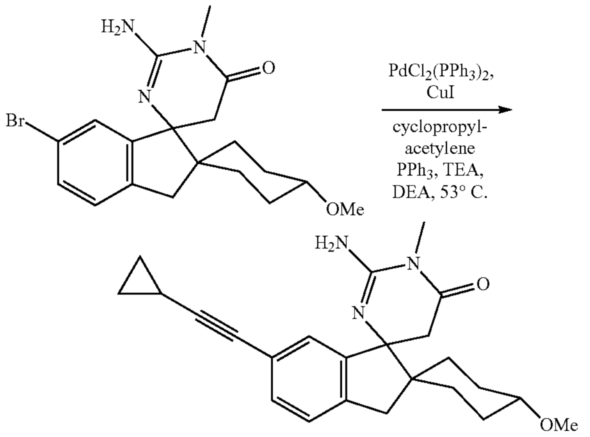

An oven dried 3-necked round bottom flask equipped with condenser was charged with crude product of 2"-amino-6-bromo-1'"-methyl-1"H-spiro[spiro[2,3-dihydro-indene-2,1'-(trans-4-methoxycyclohexane)]-1,4'-pyrimidin]-6"(5"H)-one (25 mg, purity 70%, 0.043 mmol), TEA (3 mL), DEA (0.3 mL) and DMF (1 mL) under $N_2$ atmosphere. To this solution was added CuI (5.7 mg, 0.026 mmol), $PdCl_2(PPh_3)_2$ (5 mg, 0.007 mmol) and $PPh_3$ (4 mg, 0.015 mmol). The system was degas once again, then cyclopropyl acetylene (0.3 mL, excess) added and the mixture was heated to 53° C. (oil bath) with stirring. The reaction was evaporated after 12 h and the residue was filtered and purified by preparative HPLC to yield 3 mg of the desired product as TFA salt. $^1$H NMR (400 MHz, $CD_3OD$) δ: 7.33 (s, 1H), 7.30 (dd, J=7.6, 1.2 Hz, 1H), 7.21 (d, J=7.6 Hz, 1H), 3.33 (s, 3H), 3.32 (s, 3H), 3.21-3.07 (m, 3H), 2.99 (d, J=17.2 Hz, 1H), 2.86 (d, J=16.4 Hz, 1H), 2.04 (m, 2H), 1.71 (m, 1H), 1.46-1.27 (m, 6H), 0.88 (m, 2H), 0.69 (m, 2H); MS ESI+ve m/z 392 $(M+H)^{30}$.

Example 9

Preparation of Compound 50

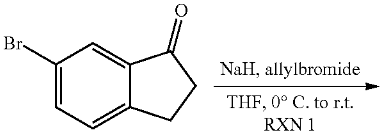

-continued

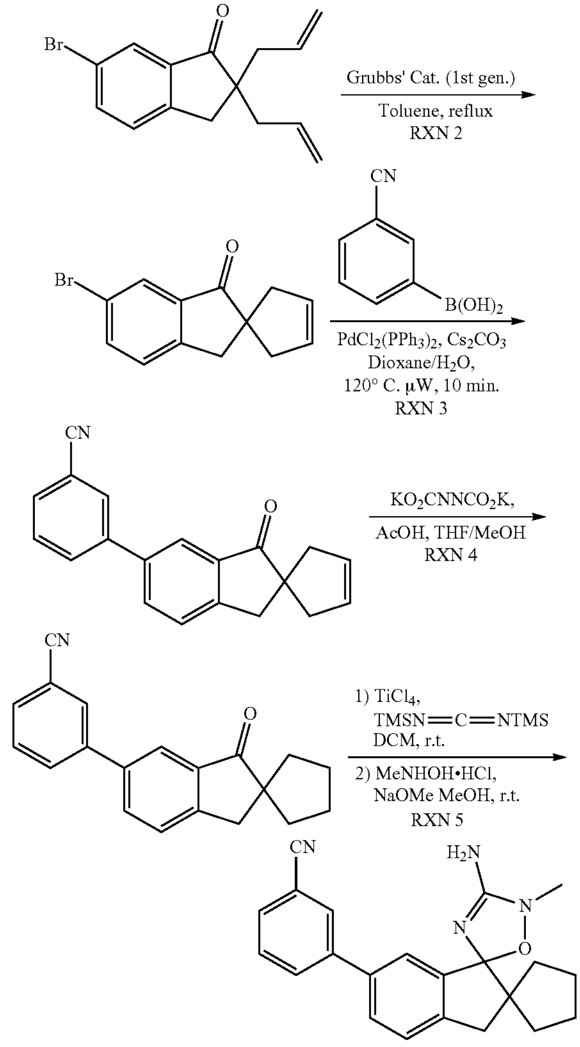

Step 1. Preparation of 2,2-diallyl-6-bromo-2,3-dihydro-1H-inden-1-one (RXN1)

In a heat gun dried 50 mL round bottom flask was placed 6-bromo-1-indanone (500 mg, 2.37 mmol), and it was dissolved in THF (7.9 mL). To this solution was added allylbromide (513 μL, 5.93 mmol) and the solution was cooled down to 0° C. After stirring for 5 minutes, sodium hydride (237 mg, 5.93 mmol, 60% dispersion in mineral oil) was slowly added. The reaction mixture was allowed to stir for 2 hours at 0° C., warmed to room temperature, and stirred for another 2 hours. At that time it was quenched with ethyl acetate (10 mL) and water (10 mL). The phases were separated and the aqueous phase was back-extracted twice with ethyl acetate (5 mL/each). The combined organic phases were dried over $Na_2SO_4$, filtered and concentrated under reduce pressure. The crude material was purified by flash chromatography (ISCO, 40 g $SiO_2$ cartridge, ethyl acetate/hexanes as the eluents). The corresponding fractions were combined and concentrated under reduce pressure yielding the diallyl product (493 mg, 1.70 mmol, 72% yield) as a light yellow oil.

M+H=291.4

$^1$H NMR=($CDCl_3$, 400 MHz) δ 7.85 (dd, J=2.0, 0.4 Hz, 1H), 7.67 (dd, J=8.0, 2.0 Hz, 1H), 7.30 (dd, J=8.0, 0.4 Hz, 1H), 5.62-5.51 (m, 2H), 5.07 (ddd, J=16.8, 3.2, 1.2 Hz, 2H), 4.99 (ddd, J=10.0, 2.0, 0.8 Hz, 2H), 2.97 (s, 2H), 2.45 (m, 2H), 2.30 (m, 2H) ppm.

Step 2. Preparation of 6'-bromospiro[cyclopent[3]ene-1,2'-inden]-1'(3'H)-one (RXN2)

In a heat gun dried 50 mL round bottom flask was placed 2,2-diallyl-6-bromo-2,3-dihydro-1H-inden-1-one (95 mg, 0.328 mmol) and it was dissolved in toluene (15 mL). To this solution was added Grubbs Catalyst 1$^{st}$ generation (40 mg, 0.049 mmol). This solution was purged with a stream of nitrogen for 2 minutes. A condenser was attached to the flask and reaction was heated to reflux overnight (~14 hours). After that time, the reaction was concentrated under reduce pressure. The crude material was purified by flash chromatography (ISCO, 12 g $SiO_2$ cartridge, ethyl acetate/hexanes as the eluents). The corresponding fractions were combined and concentrated under reduce pressure yielding 6'-bromospiro[cyclopent[3]ene-1,2'-inden]-1'(3'H)-one (72 mg, 0.275 mmol, 84% yield) as a white solid.

M+H=262.9, 264.8

$^1$H NMR=($CDCl_3$, 400 MHz) δ 7.89 (dd, J=2.4, 0.4 Hz, 1H), 7.68 (dd, J=8.0, 1.6 Hz, 1H), 7.30 (dd, J=8.0, 0.4 Hz, 1H), 5.71 (s, 2H), 3.10 (s, 2H), 2.87 (m, 2H), 2.33 (m, 2H) ppm.

Step 3. Preparation of 3-(1'-oxo-1',3'-dihydrospiro[cyclopent[3]ene-1,2'-indene]-6'-yl)benzonitrile (RXN3)

In a microwave vial was placed 6'-bromospiro[cyclopent[3]ene-1,2'-inden]-1'(3'H)-one (72 mg, 0.275 mmol), 3-cyanobenzeneboronic acid (52 mg, 0.354 mmol), $PdCl_2(PPh_3)_2$ (19 mg, 0.027 mmol) and cesium carbonate (224 mg, 0.687 mmol). This solid mixture was dissolved in a Dioxane/water mixture (2.7 mL, 6:1 ratio, respectively). The solution was purged with a $N_2$ stream for 1 minute. The vessel was placed in the microwave and heated to 120° C. for 10 minutes. After that time, the mixture was filtered through a Celite plug. The plug was rinsed with dichloromethane (20 mL) and water (20 mL). The phases in the filtrate were separated. The aqueous phase was back-extracted with dichloromethane (5 mL). The combined organic phases were washed with water, brine, dried over $MgSO_4$, filtered and concentrated under reduce pressure. The crude material was purified by flash chromatography (ISCO, 12 g $SiO_2$ cartridge, ethyl acetate/hexanes as the eluents). The corresponding fractions were combined and concentrated under reduce pressure yielding 3-(1'-oxo-1',3'-dihydrospiro[cyclopent[3]ene-1,2'-indene]-6'-yl)benzonitrile (45 mg, 0.158 mmol, 57% yield) as white crystals.

M+H=286.5

$^1$H NMR=($CDCl_3$, 400 MHz) δ 7.97 (bd, J=1.6 Hz, 1H), 7.88 (m, 1H), 7.84 (dt, J=6.4, 1.6 Hz, 1H), 7.81 (ddd, J=8.0, 1.6, 1.2 Hz, 1H), 7.67 (ddd, J=7.6, 1.6, 1.2 Hz, 1H), 7.58 (t, J=8.0 Hz, 2H), 5.75 (s, 2H), 3.23 (s, 2H), 2.93 (d, J=14.8 Hz, 2H), 2.39 (d, J=14.4 Hz, 2H) ppm.

Step 4. Preparation of 3-(1'-oxo-1',3'-dihydrospiro[cyclopentane-1,2'-indene]-6'-yl)benzonitrile (RXN4)

In a 25 mL round bottom flask was placed 3-(1'-oxo-1',3'-dihydrospiro[cyclopent[3]ene-1,2'-indene]-6'-yl)benzonitrile (37 mg, 0.130 mmol) and it was dissolved in THF/MeOH (2.5 mL, 1:1). To this solution was added $KO_2CNNCO_2K$ (378 mg, 1.95 mmol) followed by the dropwise addition of AcOH (334 μL, 5.83 mmol). After 1 hour, more $KO_2CNNCO_2K$ (378 mg, 1.95 mmol) and AcOH (334 μL, 5.83 mmol) were added and this was repeated until complete consumption of the alkene. When the reaction was completed, it was quenched with saturated aqueous $NH_4Cl$ (20 mL) and diluted with ethyl acetate (10 mL). The phases were separated. The aqueous phase was back-extracted with ethyl acetate twice (5 mL/each). The combined organic phases were washed with water, brine, dried over $Na_2SO_4$, filtered and concentrated under reduce pressure. The crude material was purified by flash chromatography (ISCO, 12 g $SiO_2$ cartridge, ethyl acetate/hexanes as the eluents). The corresponding fractions were combined and concentrated under reduce pressure yielding 3-(1'-oxo-1',3'-dihydrospiro[cyclopentane-1,2'-indene]-6'-yl)benzonitrile (17 mg, 0.059 mmol, 45% yield).

M+H=288.4

$^1H$ NMR=($CDCl_3$, 400 MHz) δ 7.95 (bs, 1H), 7.88 (bs, 1H), 7.84 (d, J=8.0 Hz, 1H), 7.79 (dd, J=8.0, 1.6 Hz, 1H), 7.66 (d, J=7.6 Hz, 1H), 7.56 (m, 2H), 3.10 (s, 2H), 2.00 (m, 2H), 1.82 (m, 1H), 1.65 (m, 1H) ppm.

Step 5. Preparation of compound 50 (RXN5)

In a 20 mL vial was placed 3-(1'-oxo-1',3'-dihydrospiro[cyclopentane-1,2'-indene]-6'-yl)benzonitrile (20 mg, 0.070 mmol), and it was azeotroped twice with toluene (2 mL/each). Dichloromethane (4 mL) was added followed by $TiCl_4$ (139 μL, 0.139 mmol, 1M in DCM). The reaction mixture was allowed to stir at room temperature for 1 hour. At that time bis-trimethylsilylcarbodiimide (50 μL, 0.223 mmol) was added and the solution was allowed to stir overnight (14 hours) at room temperature. The reaction was quenched with ice cold water (5 mL). The two phases were separated and the aqueous phase was back-extracted twice with dichloromethane (5 mL/each). The combined organic phases were dried over $MgSO_4$, filtered, concentrated under reduce pressure and azeotroped with toluene (2 mL). In a separate flame dried 4 mL vial was placed MeNH(OH).HCl (7 mg, 0.084 mmol) and it was dissolved in MeOH (2 mL). To this solution was added NaOMe (15 μL, 25% in MeOH) and the solution was stirred for 5 minutes at room temperature. This solution was transferred, via syringe, to the cyanoimine prepared above and stirred at room temperature for 3 hours. After that time, the reaction mixture was concentrated under reduce pressure and the crude material was purified on a HPLC (Gilson, 10-90% $CH_3CN/H_2O$ with 0.1% TFA as the eluent). The corresponding fractions were combined and concentrated yielding the final product (6.5 mg, 0.018 mmol, 26% yield) as a white solid.

M+H=359.1

$^1H$ NMR=($CD_3OD$, 400 MHz) δ 8.02 (bs, 1H), 7.92 (m, 1H), 7.78-7.61 (m, 4H), 7.42 (d, 1H), 3.36 (s, 3H), 2.97 (d, 2H), 2.07-1.51 (m, 4H) ppm.

Example 10

Preparation of Compounds 57 and 62

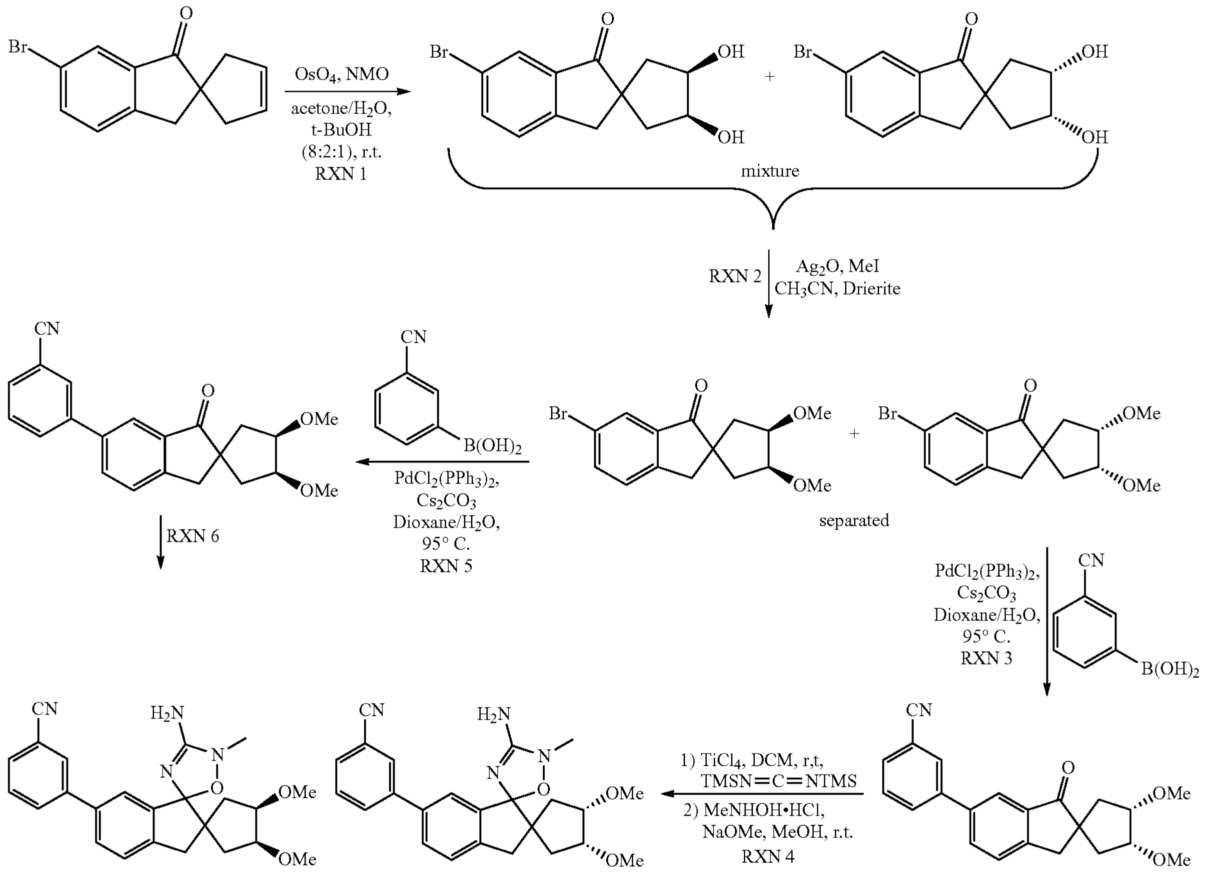

Step 1. Preparation of 6'-bromo-3,4-dihydroxyspiro [cyclopentane-1,2'-inden]-1'(3'H)-one (RXN1)

In a 20 mL vial was placed 6'-bromospiro[cyclopent[3]ene-1,2'-inden]-1'(3'H)-one (100 mg, 0.382 mmol) and it was dissolved in a mixture of acetone, $H_2O$ and t-BuOH (3.8 mL, 8:2:1). To this solution was added NMO (89 mg, 0.760 mmol) and was followed by the addition of aqueous $OsO_4$ (50 μL, 0.153 M in $H_2O$). The reaction was allowed to stir overnight (~14 hours). At that time, the reaction was cooled down to 0° C. and sodium sulfite (50 mg) was added and the mix was stirred for 30 minutes. After that time, water (5 mL) and ethyl acetate (5 mL) were added. The phases were separated and the aqueous phase was back-extracted with ethyl acetate three times (5 mL/each). The combined organic phases were washed with 1M HCl, water, brine, dried over $Na_2SO_4$, filtered and concentrated under reduce pressure. $^1H$ NMR of this crude showed ~1:1 mixture of 6'-bromo-3,4-dihydroxyspiro[cyclopentane-1,2'-inden]-1'(3'H)-one cis-isomers. This crude mixture of isomers was used as it is for the next reaction. 100 mg of crude were obtained.

M+H=296.9, 298.9

Step 2. Preparation of 6'-bromo-3,4-dimethoxyspiro [cyclopentane-1,2'-inden]-1'(3'H)-one (RXN 2)

In a 50 mL round bottom flask was placed 6'-bromo-3,4-dihydroxyspiro[cyclopentane-1,2'-inden]-1'(3'H)-one (100 mg, 0.338 mmol) and it was dissolved in acetonitrile (2 mL). To this heterogenous solution was added $Ag_2O$ (470 mg, 2.028 mmol) followed by freshly grounded Drierite (500 mg). Then MeI (843 μL, 2.97 mmol) was added, the round bottom flask was capped with a plastic cap and it was parafilmed. The reaction was allowed to stir at room temperature. After 2 days stirring the alcohol was consumed. The reaction mixture was filtered through a plug of Celite and the cake was rinsed with ethyl acetate three times (5 mL/each). The filtrate was concentrated under reduce pressure. This crude material was purified by flash chromatography (ISCO, 12 g SiO2 cartridge, using ethyl acetate/hexanes as the eluents). The mixture of cis-isomers was easily separated in the chromatography. The corresponding fractions for each isomer were combined and concentrated under reduce pressure yielding the two cis-isomers of 6'-bromo-3,4-dimethoxyspiro[cyclopentane-1,2'-inden]-1'(3'H)-one (51 mg $1^{st}$ isomer, 23 mg $2^{nd}$ isomer).

M+H=324.9, 327.0 (for both isomers)

$1^{st}$ isomer (51 mg)

$^1H$ NMR=($CDCl_3$, 400 MHz) δ 7.84 (d, J=2.0 Hz, 1H), 7.67 (dd, J=8.0, 2.0 Hz, 1H), 7.29 (d, J=8.0 Hz, 1H), 3.96 (m, 2H), 3.42 (s, 6H), 3.20 (s, 2H), 2.15 (m, 2H), 1.86 (dd, J=14.0, 5.2 Hz, 2H) ppm.

$2^{nd}$ isomer (23 mg)

$^1H$ NMR=($CDCl_3$, 400 MHz) δ 7.88 (d, J=1.6 Hz, 1H), 7.68 (dd, J=8.0, 1.6 Hz, 1H), 7.29 (d, J=8.0 Hz), 3.87 (m, 2H), 3.42 (s, 6H), 3.01 (s, 2H), 2.30 (dd, J=13.2, 6.4 Hz, 2H), 1.80 (dd, J=13.2, 6.0 Hz, 2H) ppm.

Step 3. Preparation of 3-(3,4-dimethoxy-1'-oxo-1',3'-dihydrospiro[cyclopentane-1,2'-indene]-6'-yl)benzonitrile (RXN 3) $1^{st}$ isomer In a microwave vial was placed 6'-bromo-3,4-dimethoxyspiro[cyclopentane-1,2'-inden]-1'(3'H)-one $1^{st}$ isomer (51 mg, 0.157 mmol), 3-cyanobenzeneboronic acid (30 mg, 0.204 mmol), $PdCl_2(PPh_3)_2$ (11 mg, 0.016 mmol) and cesium carbonate (128 mg, 0.393 mmol). This solid mixture was dissolved in a Dioxane/water mixture (2.0 mL, 6:1 ratio, respectively). The solution was purged with a $N_2$ stream for 30 seconds. The vessel was placed in the μwave and heated to 110° C. for 30 minutes. After that time, the mixture was filtered through a Celite plug. The plug was rinsed with dichloromethane (4 mL) and water (4 mL). The phases in the filtrate were separated. The aqueous phase was back-extracted with dichloromethane (2 mL). The combined organic phases were washed with brine, dried over $MgSO_4$, filtered and concentrated under reduce pressure. The crude material was purified by flash chromatography (ISCO, 12 g $SiO_2$ cartridge, ethyl acetate/hexanes as the eluents). The corresponding fractions were combined and concentrated under reduce pressure yielding 3-(3,4-dimethoxy-1'-oxo-1',3'-dihydrospiro[cyclopentane-1,2'-indene]-6'-yl)benzonitrile $1^{st}$ isomer (40 mg, 0.115 mmol, 73% yield).

M+H=347.9

$^1H$ NMR=($CDCl_3$, 400 MHz) δ 7.92 (d, J=2.0 Hz, 1H), 7.87 (dd, J=1.2, 1.2 Hz, 1H), 7.83-7.78 (m, 2H), 7.65 (ddd, J=8.0, 1.2, 1.2 Hz, 1H), 7.58-7.53 (m, 2H), 4.00 (m, 2H), 3.44 (s, 6H), 3.33 (s, 2H), 2.24-2.19 (m, 2H), 1.92 (dd, J=14.0, 5.2 Hz, 2H) ppm.

3-(3,4-dimethoxy-1'-oxo-1',3'-dihydrospiro[cyclopentane-1,2'-indene]-6'-yl)benzonitrile (RXN 5) $2^{nd}$ isomer In a microwave vial was placed 6'-bromo-3,4-dimethoxyspiro[cyclopentane-1,2'-inden]-1'(3'H)-one $1^{st}$ isomer (23 mg, 0.071 mmol), 3-cyanobenzeneboronic acid (14 mg, 0.095 mmol), $PdCl_2(PPh_3)_2$ (5 mg, 0.007 mmol) and cesium carbonate (58 mg, 0.178 mmol). This solid mixture was dissolved in a Dioxane/water mixture (1.0 mL, 6:1 ratio, respectively). The solution was purged with a $N_2$ stream for 30 seconds. The vessel was placed in the microwave and heated to 110° C. for 30 minutes. After that time, the mixture was filtered through a Celite plug. The plug was rinsed with dichloromethane (2 mL) and water (2 mL). The phases in the filtrate were separated. The aqueous phase was back-extracted with dichloromethane (2 mL). The combined organic phases were washed with brine, dried over $MgSO_4$, filtered and concentrated under reduce pressure. The crude material was purified by flash chromatography (ISCO, 12 g $SiO_2$ cartridge, ethyl acetate/hexanes as the eluents). The corresponding fractions were combined and concentrated under reduce pressure yielding 3-(3,4-dimethoxy-1'-oxo-1',3'-dihydrospiro[cyclopentane-1,2'-indene]-6'-yl)benzonitrile $2^{nd}$ isomer (24 mg, 0.069 mmol, 97% yield).

M+H=347.9

$^1H$ NMR=($CDCl_3$, 400 MHz) δ 7.95 (d, J=2.0 Hz, 1H), 7.86 (m, 1H), 7.83-7.78 (2H), 7.67-7.64 (m, 1H), 7.59-7.52 (m, 2H), 3.91 (m, 2H), 3.44 (s, 6H), 3.13 (s, 2H), 2.34 (dd, J=13.2, 6.8 Hz, 2H), 1.85 (dd, J=13.2, 5.6 Hz, 2H) ppm.

Step 4. Preparation of Compound 62 (RXN 4)

In a 20 mL vial was placed 3-(3,4-dimethoxy-1'-oxo-1',3'-dihydrospiro[cyclopentane-1,2'-indene]-6'-yl)benzonitrile $1^{st}$ isomer (40 mg, 0.115 mmol), and it was azeotroped with toluene twice (2 mL/each). Dichloromethane (3 mL) was added followed by $TiCl_4$ (231 μL, 0.231 mmol, 1M in DCM). The reaction mixture was allowed to stir at room temperature for 1 hour. At that time bis-trimethylsilylcarbodiimide (83 μL, 0.370 mmol) was added and the solution was allowed to stir 1 hour at room temperature. The reaction was quenched with ice cold water (5 mL). The two phases were separated and the aqueous phase was back-extracted twice with dichloromethane (2 mL/each). The combined organic phases were dried over $MgSO_4$, filtered, concentrated under reduce pressure and azeotroped with toluene (2 mL). In a separate flame dried 4 mL vial was placed MeNH(OH).HCl (11 mg, 0.132 mmol) and it was dissolved in MeOH (2 mL). To this solution was added NaOMe (26 μL, 25% in MeOH) and the solution was stirred for 5 minutes at room temperature. This solution was transferred, via syringe, to the cyanoimine prepared above and stirred at room temperature for 1 hour. After that time, the reaction mixture was concentrated under reduce pressure. Attempts to purify by HPLC failed due to poor solubility in acetonitrile/water. The white solid was collected and LC/MS analysis showed the desired final compound (9.6 mg, 0.023 mmol, 20% yield)>95% pure. $^1$H NMR confirmed purity.

M+H=419.0

$^1$H NMR=($d_6$-DMSO, 400 MHz) δ 8.03 (s, 1H), 7.90 (d, J=7.6 Hz, 1H), 7.77 (d, J=7.2 Hz, 1H), 7.62 (t, J=8.0 Hz, 1H), 7.55 (dd, J=8.0, 1.6 Hz, 1H), 7.35 (s, 1H), 7.28 (d, J=7.6 Hz, 1H), 3.67-3.62 (m, 2H), 3.25 (s, 3H), 3.20 (s, 3H), 2.88 (s, 3H), 2.91-2.78 (m, 2H), 2.08-1.96 (m, 2H), 1.62 (dd, J=13.6, 4.0 Hz, 1H), 1.30 (dd, J=13.2, 6.4 Hz, 1H) ppm.

Preparation of Compound 57 (RXN 6)

In a 20 mL vial was placed 3-(3,4-dimethoxy-1'-oxo-1',3'-dihydrospiro[cyclopentane-1,2'-indene]-6'-yl)benzonitrile 2$^{nd}$ isomer (24 mg, 0.069 mmol), and it was azeotroped with toluene twice (2 mL/each). Dichloromethane (2 mL) was added followed by $TiCl_4$ (138 μL, 0.138 mmol, 1M in DCM). The reaction mixture was allowed to stir at room temperature for 1 hour. At that time bis-trimethylsilylcarbodiimide (50 μL, 0.223 mmol) was added and the solution was allowed to stir 1 hour at room temperature. Only 50% conversion was observed. The reaction was not forced to completion and it was quenched with ice cold water (5 mL). The two phases were separated and the aqueous phase was back-extracted twice with dichloromethane (2 mL/each). The combined organic phases were dried over $MgSO_4$, filtered, concentrated under reduce pressure and azeotroped with toluene (2 mL). In a separate flame dried 4 mL vial was placed MeNH(OH).HCl (6 mg, 0.072 mmol) and it was dissolved in MeOH (2 mL). To this solution was added NaOMe (16 μL, 25% in MeOH) and the solution was stirred for 5 minutes at room temperature. This solution was transferred, via syringe, to the cyanoimine prepared above and stirred at room temperature for 1 hour. After that time, the reaction mixture was concentrated under reduce pressure and the crude material was purified on a HPLC (Gilson, 10-90% $CH_3CN/H_2O$ with 0.1% TFA as the eluent). The corresponding fractions were combined and concentrated yielding the final product (4.17 mg, 0.010 mmol, 14% yield) as a colorless oil.

M+H=419.0

$^1$H NMR=($CD_3OD$, 400 MHz) δ 8.02 (bs, 1H), 7.97-7.94 (m, 1H), 7.76-7.72 (m, 3H), 7.64 (t, J=8.0 Hz, 1H), 7.43 (d, J=7.6 Hz, 1H), 3.90 (m, 2H), 3.39 (s, 3H), 3.38 (s, 3H), 3.35 (s, 3H), 3.10-2.99 (m, 2H), 2.48 (dd, J=14.8, 4.0 Hz, 1H), 2.06 (m, 1H), 1.83 (dd, J=14.4, 4.8 Hz, 1H), 1.63 (dd, J=12.8, 6.0 Hz, 1H) ppm.

Example 11

Preparation of Compound 49

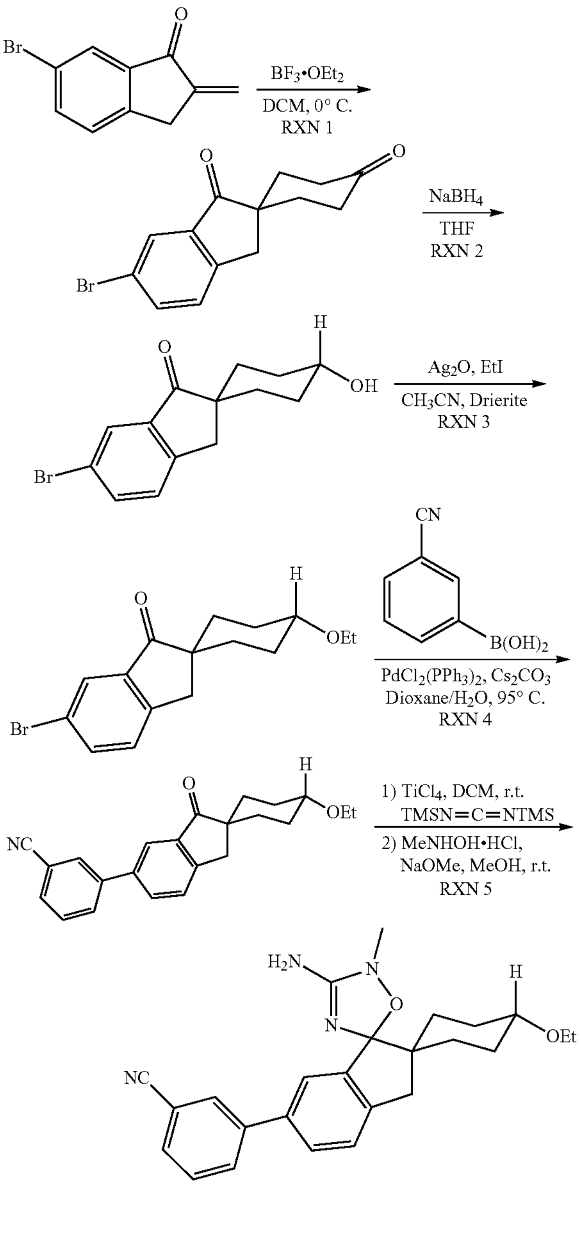

Step 1. Preparation of 6'-bromospiro[cyclohexane-1, 2'-indene]-1',4(3'H)-dione (RXN 1)

In a flame dried 20 mL vial was placed 6-bromo-2-methylene-2,3-dihydro-1H-inden-1-one (98 mg, 0.441 mmol) and it was dissolved in dichloromethane (4.5 mL). To this solution was added 2-trimethylsilyloxy-1,3-butadiene (98 μL, 0.565 mmol) and the solution was cooled down to −78° C. After stirring for 5 minutes, $BF_3.OEt_2$ (27 mL, 0.219 mmol) was slowly added. After 5 minutes of the $BF_3.OEt_2$ addition, TLC indicated consumption of the dienophile. The reaction was quenched with MeOH (300 μL), allowed to stir for 5 minutes at −78° C. and then warmed up to room temperature. Once at room temperature, 2M HCl (7 mL) was added. The phases were separated and the aqueous phase was back-extracted with dichloromethane twice (5 mL/each). The combined organic phases were dried over $MgSO_4$, filtered and concentrated under reduce pressure. The crude material was purified by flash chromatography (ISCO, 12 g $SiO_2$ cartridge, ethyl acetate/hexanes as the eluents). The corresponding fractions were combined and concentrated under reduce pressure yielding 6'-bromospiro[cyclohexane-1,2'-indene]-1',4(3'H)-dione (62 mg, 0.212 mmol, 48% yield).

$^1$H NMR=($CDCl_3$, 400 MHz) δ 7.68 (d, J=2.0 Hz, 1H), 7.51 (dd, J=8.0, 2.0 Hz, 1H), 7.16 (d, J=8.0 Hz, 1H), 2.94 (s, 2H), 2.48 (dt, J=15.2, 5.6 Hz, 2H), 2.22 (ddd, J=15.2, 10.8, 5.6 Hz, 2H), 1.98 (ddd, J=13.6, 11.2, 5.2 Hz, 2H), 1.65 (m, 2H) ppm.

Step 2. Preparation (trans-6'-bromo-4-hydroxyspiro [cyclohexane-1,2'-inden]-1'(3'H)-one (RXN 2)

To a 20 mL vial was added 6'-bromospiro[cyclohexane-1,2'-indene]-1',4(3'H)-dione (102 mg, 0.349 mmol) and it was dissolved in THF (3.49 mL). This solution was cooled down to −78° C. and stirred for 5 minutes at that temperature. Then, $NaBH_4$ (7 mg, 0.184 mmol) were added at −78° C. After 10 minutes more $NaBH_4$ (7 mg, 0.184 mmol) was added. After 5 minutes, LC/MS showed ~70% conversion. Finally, a final portion of $NaBH_4$ (10 mg, 0.263 mmol) was added. After 5 minutes, TLC showed total consumption of the diketone. The excess $NaBH_4$ was quenched immediately with acetone (300 μL). After stirring for 15 minutes at −78° C., the reaction was warmed to room temperature and ethyl acetate (7 mL) and water (7 mL) were added. The phases were separated and the aqueous phase was back-extracted with ethyl acetate twice (5 mL/each). The combined organic phases were washed with brine, dried over $MgSO_4$, filtered and concentrated under reduce pressure. The crude material was purified by flash chromatography (ISCO, 12 g $SiO_2$ cartridge, ethyl acetate/hexanes as the eluents). The fractions corresponding to the isomer shown in the scheme were combined and concentrated under reduce pressure yielding trans-6'-bromo-4-hydroxyspiro[cyclohexane-1,2'-inden]-1'(3'H)-one (71 mg, 0.241 mmol, 69% yield) as a colorless oil.

M+H=294.9, 296.9

$^1$H NMR=($CDCl_3$, 400 MHz) δ 7.84 (bs, 1H), 7.67 (dd, J=8.0, 2.0 Hz, 1H), 7.32 (d, J=8.0 Hz, 1H), 3.73 (m, 1H), 2.96 (s, 2H), 2.04 (m, 2H), 1.94 (s, 1H), 1.77 (m, 2H), 1.47-1.40 (m, 4H) ppm.

Step 3. Preparation of trans-6'-bromo-4-ethoxyspiro [cyclohexane-1,2'-inden]-1'(3'H)-one (RXN 3)

In a 20 mL vial was placed trans-6'-bromo-4-hydroxyspiro [cyclohexane-1,2'-inden]-1'(3'H)-one (295 mg, 1.00 mmol) and it was dissolved in acetonitrile (3 mL). To this heterogenous solution was added $Ag_2O$ (690 mg, 2.98 mmol) followed by freshly grounded Drierite (1 g). Then EtI (1.58 mL, 19.75 mmol) was added, the round bottom flask was capped with a plastic cap and it was parafilmed. The reaction was allowed to stir at 40° C. overnight (~14 hours). The reaction mixture was filtered through a plug of Celite and the cake was rinsed with dichloromethane (15 mL). The filtrate was concentrated under reduce pressure. This crude material was purified by flash chromatography (ISCO, 40 g $SiO_2$ cartridge, using ethyl acetate/hexanes as the eluents). The corresponding fractions were combined and concentrated under reduce pressure yielding trans-6'-bromo-4-ethoxyspiro[cyclohexane-1,2'-inden]-1'(3'H)-one (200 mg, 0.621 mmol, 62% yield).

M+H=322.9, 324.9

$^1$H NMR=($CDCl_3$, 400 MHz) δ 7.79 (bs, 1H), 7.61 (dd, J=8.0 Hz, 2.0 Hz, 1H), 7.27 (d, J=8.0 Hz, 1H), 3.49 (quart., J=7.2 Hz, 2H), 3.28 (m, 1H), 2.90 (s, 2H), 2.05 (m, 2H), 1.69 (ddd, J=13.6, 3.6 Hz, 2H), 1.44-1.27 (m, 4H), 1.15 (t, J=7.2 Hz, 3H) ppm.

Step 4. Preparation of 3-trans-4-ethoxy-1'-oxo-1',3'-dihydrospiro[cyclohexane-1,2'-indene]-6'-yl)benzonitrile (RXN 4)

In a 20 mL vial was placed trans-6'-bromo-4-ethoxyspiro [cyclohexane-1,2'-inden]-1'(3'H)-one (56 mg, 0.174 mmol), 3-cyanobenzeneboronic acid (33 mg, 0.225 mmol), $PdCl_2(PPh_3)_2$ (12 mg, 0.017 mmol) and cesium carbonate (142 mg, 0.436 mmol). This solid mixture was dissolved in a Dioxane/water mixture (2 mL, 6:1 ratio, respectively). The solution was purged with a $N_2$ stream for 20 seconds. The reaction vial was capped and allowed to stir at 95° C. for 1 hour. At this time, the mixture was filtered through a Celite plug. The plug was rinsed with dichloromethane (10 mL) and water (10 mL). The phases in the filtrate were separated. The aqueous phase was back-extracted with dichloromethane twice (5 mL/each). The combined organic phases were washed with brine, dried over $MgSO_4$, filtered and concentrated under reduce pressure. The crude material was purified by flash chromatography (ISCO, 12 g $SiO_2$ cartridge, ethyl acetate/hexanes as the eluents). The corresponding fractions were combined and concentrated under reduce pressure yielding 3-(trans-4-ethoxy-1'-oxo-1',3'-dihydrospiro[cyclohexane-1,2'-indene]-6'-yl)benzonitrile (51 mg, 0.148 mmol, 66% yield) as a yellow solid.

M+H=346.0

$^1$H NMR=($CDCl_3$, 400 MHz) δ 7.92 (d, J=1.6 Hz, 1H), 7.86 (dd, J=1.6, 1.6 Hz, 1H), 7.83-7.78 (m, 2H), 7.65 (dt, J=7.6, 1.6 Hz, 1H), 7.58-7.54 (m, 2H), 3.57 (quart., J=6.8 Hz, 2H), 3.37 (m, 1H), 3.08 (s, 2H), 2.14 (m, 2H), 1.80 (ddd, J=14.0, 3.6 Hz, 2H), 1.54-1.37 (m, 4H), 1.22 (t, J=6.8 Hz, 3H) ppm.

Step 5. Preparation of Compound 11 (RXN 5)

In a 20 mL vial was placed 3-(trans-4-ethoxy-1'-oxo-1',3'-dihydrospiro[cyclohexane-1,2'-indene]-6'-yl)benzonitrile (51 mg, 0.148 mmol), and it was azeotroped with toluene (2 mL). Dichloromethane (4 mL) was added followed by $TiCl_4$ (296 μL, 0.296 mmol, 1M in DCM). The reaction mixture was allowed to stir at room temperature for 1 hour. At that time bis-trimethylsilylcarbodiimide (106 μL, 0.472 mmol) was added and the solution was allowed to stir for 1 hour at room temperature. The reaction was quenched with ice cold water (5 mL). The two phases were separated and the aqueous phase was back-extracted twice with dichloromethane (2 mL/each). The combined organic phases were dried over $MgSO_4$, filtered, concentrated under reduce pressure and azeotroped with toluene (2 mL). In a separate flame dried 4 mL vial was placed MeNH(OH).HCl (14 mg, 0.167 mmol) and it was dissolved in MeOH (3 mL). To this solution was added NaOMe (33 μL, 25% in MeOH) and the solution was stirred for 5 minutes at room temperature. This solution was transferred, via syringe, to the cyanoimine prepared above and stirred at room temperature overnight (~14 hours). After that time, the reaction mixture was concentrated under reduce pressure and the crude material was purified on a HPLC (Gilson, 5-90% CH₃CN/H₂O with 0.1% TFA as the eluent). The corresponding fractions were combined and concentrated. The oil obtained was lyophilized yielding the final product (14 mg, 0.034 mmol, 23% yield) as white solid.

M+H=417.1

¹H NMR=(CD₃OD, 400 MHz) δ 8.00 (bs, 1H), 7.95-7.93 (m, 1H), 7.78-7.61 (m, 4H), 7.45 (m, 1H), 3.57 (quart., J=7.2 Hz, 2H), 3.34 (s, 3H), 3.09-2.97 (m, 2H), 2.17-2.03 (m, 2H), 1.82-1.67 (m, 2H), 1.57-1.37 (m, 4H), 1.18 (t, J=7.2 Hz, 3H) ppm.

Example 12

Preparation of Compounds 47 and 53

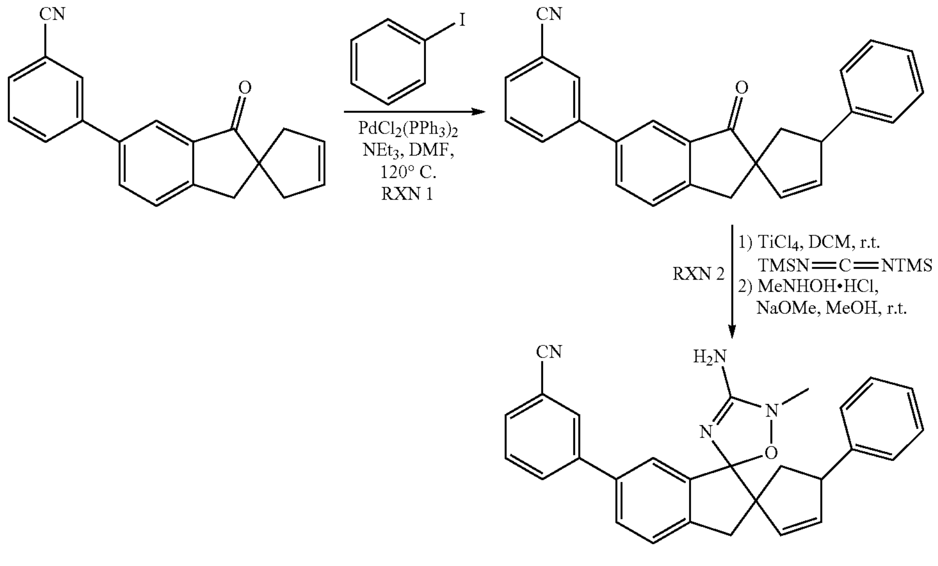

Step 1. Preparation of 3-(1'-oxo-4-phenyl-1',3'-dihydrospiro[cyclopent[2]ene-1,2'-indene]-6'-yl)benzonitrile (RXN1)

In to a 4 mL vial was placed 3-(1'-oxo-1',3'-dihydrospiro[cyclopent[3]ene-1,2'-indene]-6'-yl)benzonitrile (99 mg, 0.347 mmol) and PdCl₂(PPh₃)₂ (12 mg, 0.017 mmol). They were dissolved in DMF (1 mL). To this solution was added NEt₃ (72 μL, 0.518 mmol) followed by iodobenzene (47 μL, 0.420 mmol). The vial was capped and heated in an oil bath at 120° C. overnight (~14 hours). After that time, the mixture was filtered through a Celite plug and rinsed with dichloromethane twice (5 mL/each). To the filtrate was added water (5 mL). The phases were separated and the aqueous phase was back-extracted with dichloromethane twice (2 mL/each). The combined organic phases were washed with water, brine, dried over MgSO₄, filtered and concentrated under reduce pressure. The crude material was purified by flash chromatography (ISCO, 12 g SiO₂ cartridge, ethyl acetate/hexanes as the eluents). The corresponding fractions were combined and concentrated under reduce pressure yielding 3-(1'-oxo-4-phenyl-1',3'-dihydrospiro[cyclopent[2]ene-1,2'-indene]-6'-yl)benzonitrile (43 mg, 0.119 mmol, 34% yield).

¹H NMR=(CDCl₃, 400 MHz) δ 7.96 (bs, 1H), 7.87 (bs, 1H), 7.84-7.80 (m, 2H), 7.66 (dd, J=7.6, 1.2 Hz, 1H) 7.60-7.54 (m, 2H), 7.43-7.30 (m, 3H), 7.26-7.21 (2H), 6.10 (ddd, J=5.6, 2.4, 0.8 Hz, 1H), 5.69 (dd, J=5.6, 2.4 Hz, 1H), 4.37 (m, 1H), 3.45 (d, J_{A,B}=17.6 Hz, 1H), 3.15 (d, J_{A,B}=17.6 Hz, 1H), 2.92 (dd, J=12.8, 8.4 Hz, 1H), 1.85 (dd, J=12.8, 6.4 Hz, 1H) ppm.

Step 2. Preparation and separation of compounds 47 and 53

In a 20 mL vial was placed 3-(1'-oxo-4-phenyl-1',3'-dihydrospiro[cyclopent[2]ene-1,2'-indene]-6'-yl)benzonitrile (43 mg, 0.119 mmol), and it was azeotroped with toluene twice (2 mL/each). Dichloromethane (4 mL) was added followed by TiCl₄ (238 μL, 0.238 mmol, 1M in DCM). The reaction mixture was allowed to stir at room temperature for 1 hour. At that time bis-trimethylsilylcarbodiimide (86 μL, 0.383 mmol) was added and the solution was allowed to stir for 1 hour at room temperature. The reaction was quenched with ice cold water (5 mL). The two phases were separated and the aqueous phase was back-extracted twice with dichloromethane (2 mL/each). The combined organic phases were washed with brine, dried over MgSO₄, filtered, concentrated under reduce pressure and azeotroped with toluene (2 mL). In a separate flame dried 4 mL vial was placed MeNH(OH).HCl (11 mg, 0.167 mmol) and it was dissolved in MeOH (3 mL). To this solution was added NaOMe (26 μL, 25% in MeOH) and the solution was stirred for 5 minutes at room temperature. This solution was transferred, via syringe, to the cyanoimine prepared above and stirred at room temperature overnight (~14 hours). After that time, the reaction mixture was concentrated under reduce pressure and the crude material was purified on a HPLC (Gilson, 10-90% CH₃CN/H₂O with 0.1% TFA as the eluent). Two diastereomers were separated by the HPLC. The corresponding fractions for each respective diastereomer were combined and concentrated yielding two final diastereomeric products (1.1 mg, 0.034 mmol, FRACTION A, 1.64 mg, 0.000 mmol, FRACTION B, 23% yield).

M+H=433.0 (ISOMER A)
M+H=433.0 (ISOMER B)

Fraction A

¹H NMR=(CD₃OD, 400 MHz) δ 8.03 (bs, 1H), 7.98-7.95 (m, 1H), 7.82-7.72 (m, 3H), 7.65 (t, J=8.0 Hz, 1H), 7.47 (d, J=8.0 Hz, 1H), 7.34-7.27 (m, 2H), 7.23-7.19 (m, 3H), 6.10

(dd, J=5.6, 1.6 Hz, 1H), 5.71 (dd, J=5.6 Hz, 2.4 Hz, 1H), 4.12 (m, 1H), 3.41 (s, 3H), 3.25 (d, $J_{A,B}$=16.4 Hz, 1H), 3.09 (d, $J_{A,B}$=16.4 Hz, 1H), 3.05 (dd, J=14.0, 7.6 Hz, 1H), 1.78 (dd, J=14.0, 7.6 Hz, 1H) ppm.

Fraction B $^1$H NMR=($CD_3OD$, 400 MHz) δ 8.03 (m, 1H), 7.98-7.95 (m, 1H), 7.82-7.72 (m, 3H), 7.64 (t, J=7.6 Hz, 1H), 7.46 (t, J=7.6 Hz, 1H), 7.32-7.27 (m, 2H), 7.23-7.17 (m, 3H), 6.08 (m, 2H), 4.12 (t, J=4.0 Hz, 1H), 3.46 (d, $J_{A,B}$=16.0 Hz, 1H), 3.34 (s, 3H), 2.91 (d, $J_{A,B}$=16.0 Hz, 1H), 2.65 (dd, J=14.0, 8.4 Hz, 1H), 1.63 (dd, J=14.0, 7.6 Hz) ppm.

Example 13

Preparation of Compounds 34 and 44 luoro analog. The reaction mixture was directly transferred to a 12 g SiO2 cartridge packed in 100% hexanes and purified by flash chromatography (ISCO, using ethyl acetate/hexanes as the eluents. The corresponding fractions for each individual compound were combined and concentrated under reduce pressure yielding 6'-bromo-4-fluorospiro[cyclohex[3]ene-1,2'-inden]-1'(3'H)-one (14 mg, 0.048 mmol) as a white solid, and 6'-bromo-4,4-difluorospiro[cyclohexane-1,2'-inden]-1'(3'H)-one (37 mg, 0.118 mmol) as a white solid.

M+H=294.9 and 296.9 (VINYL FLUORIDE)

M+H=314.9 and 316.9 (GEMINAL DIFLUORIDE)

6'-bromo-4-fluorospiro[cyclohex[3]ene-1,2'-inden]-1'(3'H)-one $^1$H NMR=($CDCl_3$, 400 MHz) δ 7.88 (d, J=1.6 Hz, 1H), 7.70 (dd, J=8.0, 1.6 Hz, 1H), 7.33 (d, J=8.0 Hz, 1H), 5.25 (m,

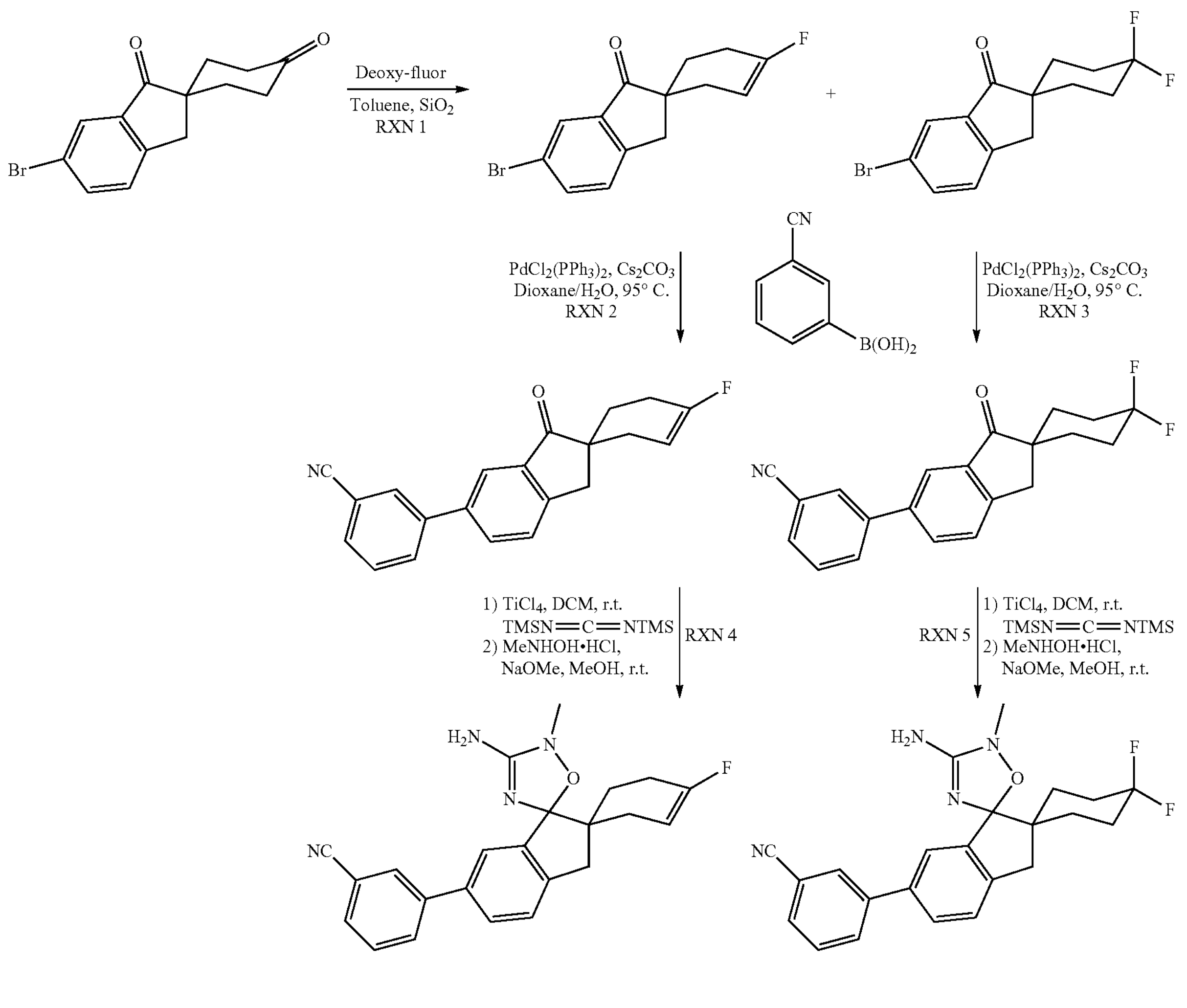

Step 1: Preparation of 6'-bromo-4-fluorospiro[cyclohex[3]ene-1,2'-inden]-1'(3'H)-one and 6'-bromo-4,4-difluorospiro[cyclohexane-1,2'-inden]-1'(3'H)-one (RXN 1)

In a 15 mL plastic tube was placed 6'-bromospiro[cyclohexane-1,2'-indene]-1',4(3'H)-dione (100 mg, 0.340 mmol) and dry silica gel (50 mg). To the mixture was slowly added Deoxy-fluor (2 mL, 50% in toluene). The reaction was allowed to stir for 2 hours. LC/MS analysis indicated formation of the vinyl fluoride adduct along with the geminal dif- 1H), 3.00 (d, $J_{A,B}$=17.2 Hz, 1H) 2.90 (d, $J_{A,B}$=17.2 Hz, 1H), 2.52 (m, 1H), 2.39-2.35 (m, 2H), 2.09-2.02 (m, 1H), 1.87-1.81 (m, 1H), 1.63-1.58 (m, 1H) ppm.

6'-bromo-4,4-difluorospiro[cyclohexane-1,2'-inden]-1'(3'H)-one $^1$H NMR=($CDCl_3$, 400 MHz) δ 7.88 (d, J=2.0 Hz), 7.70 (dd, J=8.0 Hz, 2.0 Hz), 7.33 (d, J=8.0 Hz, 1H), 2.99 (s, 2H), 2.34-2.25 (m, 2H), 2.06-1.99 (m, 2H), 1.96-1.81 (m, 2H), 1.63-1.58 (m, 2H) ppm.

Step 2. Preparation of 3-(4-fluoro-1'-oxo-1',3'-dihydrospiro[cyclohex[3]ene-1,2'-indene]-6'-yl)benzonitrile (RXN 2)

In a 20 mL vial was placed 6'-bromo-4-fluorospiro[cyclohex[3]ene-1,2'-inden]-1'(3'H)-one (11 mg, 0.037 mmol), 3-cyanobenzeneboronic acid (7 mg, 0.048 mmol), $PdCl_2(PPh_3)_2$ (3 mg, 0.004 mmol) and cesium carbonate (30 mg, 0.092 mmol). This solid mixture was dissolved in a Dioxane/water mixture (1 mL, 6:1 ratio, respectively). The reaction vial was capped and allowed to stir at 95° C. for 1 hour. At this time, the mixture was filtered through a Celite plug. The plug was rinsed with dichloromethane (1 mL) and water (1 mL). The filtrate was diluted with dichloromethane (2 mL) and water (2 mL). The phases in the filtrate were separated. The aqueous phase was back-extracted with dichloromethane twice (2 mL/each). The combined organic phases were washed with brine, dried over $MgSO_4$, filtered and concentrated under reduce pressure. The crude material was purified by flash chromatography (ISCO, 4 g $SiO_2$ cartridge, ethyl acetate/hexanes as the eluents). The corresponding fractions were combined and concentrated under reduce pressure yielding 3-(4-fluoro-1'-oxo-1',3'-dihydrospiro[cyclohex[3]ene-1,2'-indene]-6'-yl)benzonitrile (15 mg, 0.047 mmol, quantitative).

M+H=318.0

$^1$H NMR=($CDCl_3$, 400 MHz) δ 7.95 (bs, 1H), 7.87 (bs, 1H), 7.84-7.80 (m, 2H), 7.66 (d, J=8.0 Hz, 1H), 7.59-7.55 (m, 2H), 5.31-5.25 (m, 1H), 3.12 (d, $J_{A,B}$=17.6 Hz, 1H), 3.03 (d, $J_{A,B}$=17.6 Hz, 1H), 2.60-2.54 (m, 1H), 2.40 (m, 2H), 2.14-2.06 (m, 1H), 1.91-1.87 (m, 1H), 1.68-1.63 (m, 1H) ppm.

Preparation of 3-(4,4-difluoro-1'-oxo-1',3'-dihydrospiro[cyclohexane-1,2'-indene]-6'-yl)benzonitrile (RXN 3)

In a 20 mL vial was placed 6'-bromo-4,4-difluorospiro[cyclohexane-1,2'-inden]-1'(3'H)-one (35 mg, 0.111 mmol), 3-cyanobenzeneboronic acid (23 mg, 0.157 mmol), $PdCl_2(PPh_3)_2$ (8 mg, 0.011 mmol) and cesium carbonate (91 mg, 0.279 mmol). This solid mixture was dissolved in a Dioxane/water mixture (1.1 mL, 6:1 ratio, respectively). The reaction vial was capped and allowed to stir at 90° C. for 1 hour. At this time, the mixture was filtered through a Celite plug. The plug was rinsed with dichloromethane (5 mL) and water (5 mL). The phases in the filtrate were separated. The aqueous phase was back-extracted with dichloromethane twice (3 mL/each). The combined organic phases were washed with brine, dried over $MgSO_4$, filtered and concentrated under reduce pressure. The crude material was purified by flash chromatography (ISCO, 12 g $SiO_2$ cartridge, ethyl acetate/hexanes as the eluents). The corresponding fractions were combined and concentrated under reduce pressure yielding 3-(4,4-difluoro-1'-oxo-1',3'-dihydrospiro[cyclohexane-1,2'-indene]-6'-yl)benzonitrile (30 mg, 0.089 mmol, 80% yield) as a white solid.

M+H=338.0

$^1$H NMR=($CDCl_3$, 400 MHz) δ 7.94 (d, J=2.0 Hz, 1H), 7.87 (m, 1H), 7.84-7.80 (m, 2H), 7.72-7.66 (m, 1H), 7.61-7.55 (m, 2H), 3.11 (s, 2H), 2.34-2.28 (m, 2H), 2.12-2.04 (m, 2H), 1.99-1.89 (m, 2H), 1.64 (m, 2H) ppm.

Step 3. Preparation of Compound 34

In a 20 mL vial was placed 3-(4-fluoro-F-oxo-1',3'-dihydrospiro[cyclohex[3]ene-1,2'-indene]-6'-yl)benzonitrile (15 mg, 0.047 mmol), and it was azeotroped with toluene (2 mL). Dichloromethane (3 mL) was added followed by $TiCl_4$ (94 μL, 0.094 mmol, 1M in DCM). The reaction mixture was allowed to stir at room temperature for 1 hour. At that time bis-trimethylsilylcarbodiimide (34 μL, 0.151 mmol) was added and the solution was allowed to stir for 1 hour at room temperature. The reaction was quenched with ice cold water (5 mL). The two phases were separated and the aqueous phase was back-extracted twice with dichloromethane (3 mL/each). The combined organic phases were washed with brine, dried over $MgSO_4$, filtered, concentrated under reduce pressure and azeotroped with toluene (2 mL). In a separate flame dried 4 mL vial was placed MeNH(OH).HCl (4.3 mg, 0.051 mmol) and it was dissolved in MeOH (2 mL). To this solution was added NaOMe (11 μL, 25% in MeOH) and the solution was stirred for 5 minutes at room temperature. This solution was transferred, via syringe, to the cyanoimine prepared above and stirred at room temperature overnight (~14 hours). After that time, the reaction mixture was concentrated under reduce pressure and the crude material was purified on a HPLC (Gilson, 5-90% $CH_3CN/H_2O$ with 0.1% TFA as the eluent). The corresponding fractions were combined and concentrated yielding the final product (0.78 mg, 0.002 mmol, 4% yield).

M+H=389.0

$^1$H NMR=($CD_3OD$, 400 MHz) δ 8.02 (m, 1H), 7.97-7.95 (m, 1H), 7.80-7.77 (m, 2H), 7.75-7.72 (m, 1H), 7.68-7.63 (m, 1H), 7.48-7.45 (m, 1H), 5.28-5.16 (m, 1H), 3.35 (s, 3H), 3.07 (d, $J_{A,B}$=16.4 Hz, 1H), 2.93 (d, $J_{A,B}$=16.4 Hz, 1H), 2.57-2.32 (m, 3H), 2.10-1.81 (m, 3H) ppm.

Preparation of Compound 44 (RXN 5)

In a 20 mL vial was placed 3-(4,4-difluoro-1'-oxo-1',3'-dihydrospiro[cyclohexane-1,2'-indene]-6'-yl)benzonitrile (30 mg, 0.089 mmol), and it was azeotroped with toluene (2 mL). Dichloromethane (3 mL) was added followed by $TiCl_4$ (178 μL, 0.178 mmol, 1M in DCM). The reaction mixture was allowed to stir at room temperature for 1 hour. At that time bis-trimethylsilylcarbodiimide (64 μL, 0.285 mmol) was added and the solution was allowed to stir for 1 hour at room temperature. The reaction was quenched with ice cold water (5 mL) and diluted with dichloromethane (3 mL). The two phases were separated and the aqueous phase was back-extracted twice with dichloromethane (3 mL/each). The combined organic phases were washed with brine, dried over $MgSO_4$, filtered, concentrated under reduce pressure and azeotroped with toluene (2 mL). In a separate flame dried 4 mL vial was placed MeNH(OH).HCl (8 mg, 0.096 mmol) and it was dissolved in MeOH (2.5 mL). To this solution was added NaOMe (20 μL, 25% in MeOH) and the solution was stirred for 5 minutes at room temperature. This solution was transferred, via syringe, to the cyanoimine prepared above and stirred at room temperature overnight (~14 hours). After that time, the reaction mixture was concentrated under reduce pressure and the crude material was purified on a HPLC (Gilson, 10-90% $CH_3CN/H_2O$ with 0.1% TFA as the eluent). The corresponding fractions were combined and concentrated. The glace product was lyophilized yielding the final product (3.01 mg, 0.007 mmol, 8% yield).

M+H=409.0

$^1$H NMR=($CD_3OD$, 400 MHz) δ 8.01 (bs, 1H), 7.96-7.94 (m, 1H), 7.79-7.76 (m, 2H), 7.73-7.71 (m, 1H), 7.67-7.62 (m, 1H), 7.48 (d, J=8.0 Hz, 1H), 3.36 (s, 3H), 3.14 (d, $J_{A,B}$=16.0 Hz, 1H), 3.06 (d, $J_{A,B}$=16.0 Hz, 1H), 2.13-2.07 (m, 3H), 2.00-1.76 (m, 4H), 1.52 (m, 1H) ppm.

Example 14

Preparation of Compound 24

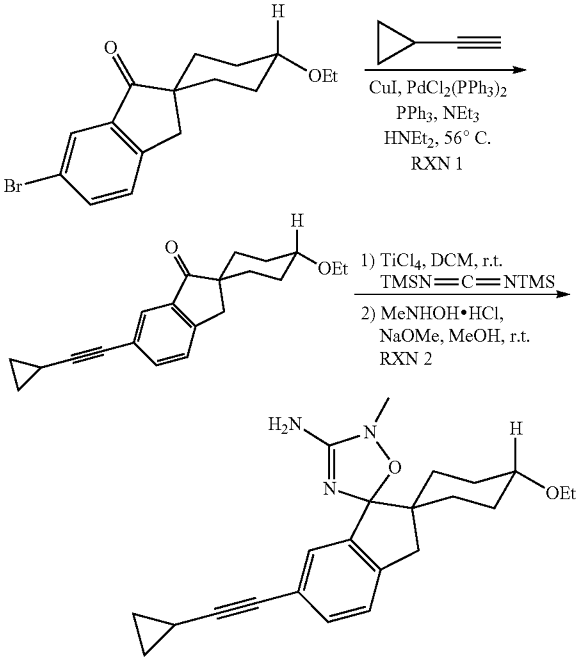

Step 1. Preparation of 6'-(cyclopropylethynyl)-4-ethoxyspiro[cyclohexane-1,2'-inden]-1'(3'H)-one (RXN 1)

In a 25 mL round bottom flask was placed 6'-bromo-4-ethoxyspiro[cyclohexane-1,2'-inden]-1'(3'H)-one (200 mg, 0.621 mmol) and it was azeotroped twice with toluene (5 mL/each). Triethylamine (3.0 mL) and diethylamine (0.8 mL) were added and this solution was bubbled with a nitrogen stream for 1 minute. Then $PdCl_2(PPh_3)_2$ (22 mg, 0.031 mmol) and CuI (6 mg, 0.032 mmol) were added and again the solution was bubbled with a stream of nitrogen for 1 minute. Then, $PPh_3$ (16 mg, 0.061 mmol) was added followed by the addition of cyclopropyl acetylene (600 μL, excess) and one more time the solution was bubbled with a stream of nitrogen for 1 minute. The flask was capped with a septum and allowed to stir overnight (~14 hours) at 56° C. At that time, the solvent was removed under reduce pressure and the crude material was purified by flash chromatography (ISCO, 40 g $SiO_2$ cartridge, using ethyl acetate/hexanes as the eluents). The corresponding fractions were combined and concentrated under reduce pressure yielding 6'-(cyclopropylethynyl)-4-ethoxyspiro[cyclohexane-1,2'-inden]-1'(3'H)-one (180 mg, 0.584 mmol, 94% yield).

M+H=309.0

$^1$H NMR=($CDCl_3$, 400 MHz) δ 7.72 (s, 1H), 7.56 (d, J=8.0 Hz, 1H), 7.34 (d, J=8.0 Hz, 1H), 3.55 (quart., J=7.2 Hz, 2H), 3.34 (m, 1H), 2.99 (s, 2H), 2.11 (m, 2H), 1.75 (ddd, J=13.6, 13.6, 2.8 Hz, 2H), 1.48-1.33 (m, 4H), 1.21 (t, J=7.2 Hz, 3H), 0.90-0.83 (m, 2H), 0.82-0.77 (m, 2H) ppm.

Step 2. Preparation of compound 24 (RXN 2)

In a 50 mL round bottom flask was placed 6'-(cyclopropylethynyl)-4-ethoxyspiro[cyclohexane-1,2'-inden]-1'(3'H)-one (180 mg, 0.584 mmol), and it was azeotroped with toluene twice (2 mL/each). Dichloromethane (20 mL) was added followed by $TiCl_4$ (1.17 mL, 1.17 mmol, 1M in DCM). The reaction mixture was allowed to stir at room temperature for 1 hour. At that time bis-trimethylsilylcarbodiimide (420 μL, 1.87 mmol) was added and the solution was allowed stir overnight (~14 hours). The reaction was quenched with ice cold water (20 mL). The two phases were separated and the aqueous phase was back-extracted with dichloromethane (10 mL). The combined organic phases were dried over $MgSO_4$, filtered, concentrated under reduce pressure and azeotroped with toluene (2 mL). In a separate flame dried 20 mL vial was placed MeNH(OH).HCl (54 mg, 0.647 mmol) and it was dissolved in MeOH (15 mL). To this solution was added NaOMe (118 μL, 25% in MeOH) and the solution was stirred for 5 minutes at room temperature. This solution was transferred, via syringe, to the cyanoimine prepared above and stirred at room temperature for 1 hour. After that time, the reaction mixture was concentrated under reduce pressure and the crude material was purified on a HPLC (Gilson, 10-90% MeOH/$H_2O$ with 0.1% TFA as the eluent). The corresponding fractions were combined and concentrated. The concentrated product was lyophilized yielding the final product (90 mg, 0.237 mmol, 41% yield).

M+H=380.1

$^1$H NMR ($CD_3OD$, 400 MHz): δ 7.41 (bs, 1H), 7.38 (m, 1H), 7.26 (d, J=7.6 Hz, 1H), 3.57 (m, 2H), 3.27 (s, 3H), 2.99 (d, $J_{A,B}$=16.0 Hz, 1H), 2.93 (d, $J_{A,B}$=16.0 Hz, 1H), 2.14-2.01 (m, 2H), 1.71-1.62 (m, 2H), 1.51-1.34 (m, 4H), 1.17 (t, J=7.2 Hz, 3H), 0.92-0.85 (m, 2H), 0.75-0.71 (m, 2H) ppm.

Example 15

Preparation of Compounds 26, 29 and 56

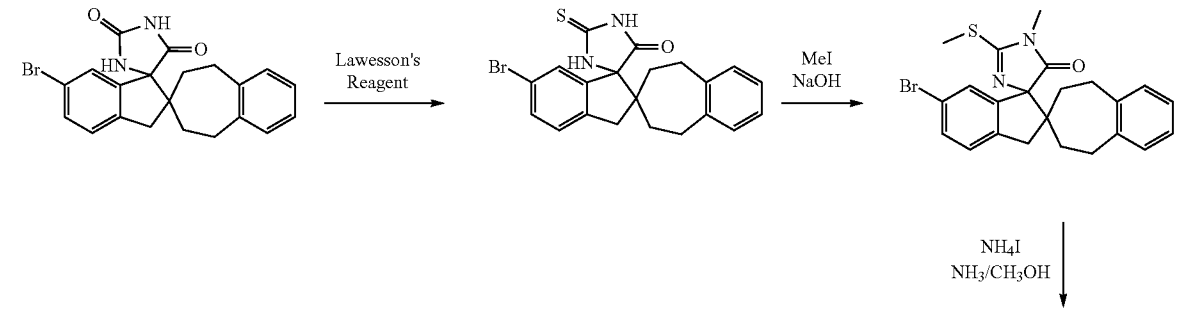

-continued

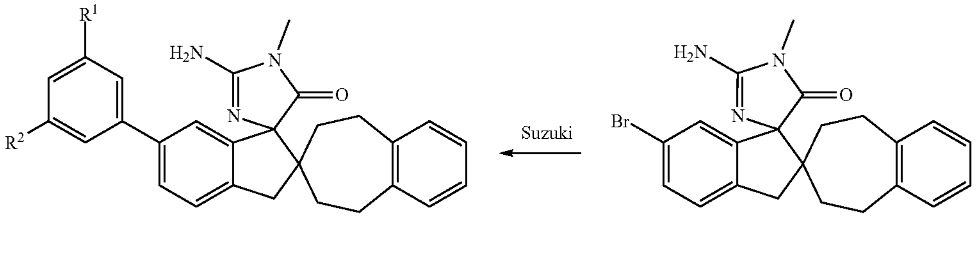

$R^1$ = CN, $R^2$ = H
$R^1$ = Cl, $R^2$ = F

Step 1

A 10 mL microwave tube was charged with Lawesson's reagent (0.0745 g, 0.184 mmol), hydantoin (0.0758 g, 0.184 mmol), and 1,4-dioxane (3 mL). The tube was heated in a CEM microwave reactor for three times, at 110° C. for 30 min, 140° C. for 30 min, and 140° C. for 30 min, respectively. After the solvent was evaporated under reduced pressure, the residue was purified by chromatography on silica gel eluted with hexanes/ethyl acetate to afford 0.0339 g (43%) of 2-thiohydantoin as a solid. LC-MS $t_R$=1.88 min in 3 min chromatography, m/z 427, 429 ($MH^+$).

Step 2

A 10 mL microwave tube was charged with 2-thiohydantoin (0.0339 g), MeOH (3 mL), and 1 N NaOH (0.5 mL). After stirring at room temperature for 10 min, MeI (0.5 mL) was added. The reaction mixture was heated in a CEM microwave reactor at 60° C. for 10 min and then purified by reversed-phase HPLC (SunFire™ Prep $C_{18}$ OBD™ 5 μm 19×50 mm column, 10%→90% $CH_3CN/H_2O$, 0.1% $CF_3COOH$ over 8 min and then 90% $CH_3CN/H_2O$, 0.1% $CF_3COOH$ over 2 min, flow rate 20 mL/min) to afford 0.0180 g (50%) of 3-methyl-2-(methylthio)-3,5-dihydroimidazole-4-one. LC-MS $t_R$=2.17 min in 3 min chromatography, m/z 455, 457 ($MH^+$).

Step 3. Preparation of Compound 56

A 10 mL microwave tube was charged with 3-methyl-2-(methylthio)-3,5-dihydroimidazole-4-one (0.0180 g), $NH_4I$ (0.600 g), 1,4-dioxane (1 mL), and 7 M $NH_3$ in MeOH (4 mL). The tube was heated in a CEM microwave reactor at 120° C. for 1 h. The reaction mixture was purified by reversed-phase HPLC (SunFire™ Prep $C_{18}$ OBD™ 5 μm 19×50 mm column, 10%→90% $CH_3CN/H_2O$, 0.1% $CF_3COOH$ over 8 min and then 90% $CH_3CN/H_2O$, 0.1% $CF_3COOH$ over 2 min, flow rate 20 mL/min) to afford TFA salt of compound 56. LC-MS $t_R$=1.80 min in 3 min chromatography, m/z 424, 426 ($MH^1$); $^1H$ NMR (400 MHz, $CD_3OD$) δ 7.46-6.89 (m, 7H), 5.62-5.56 (m, 1H), 5.26-5.22 (m, 1H), 3.11 (s, 3H), 2.90-2.58 (m, 6H), 1.74-1.67 (m, 2H).

Step 4. Preparation of Compounds 26 and 29

A 10 mL microwave tube was charged with compound 56 (0.0040 g), 3-cyanophenylboronic acid (0.0462 g), $Cs_2CO_3$ (0.2225 g), $PdCl_2(PPh_3)_2$ (0.0142 g), 1,4-dioxane (4 mL), and $H_2O$ (0.5 mL). The tube was heated in a CEM microwave reactor at 110° C. for 30 min. The reaction mixture was purified by reversed-phase HPLC (SunFire™ Prep $C_{18}$ OBD™ 5 μm 19×50 mm column, 10%→90% $CH_3CN/H_2O$, 0.1% $CF_3COOH$ over 8 min and then 90% $CH_3CN/H_2O$, 0.1% $CF_3COOH$ over 2 min, flow rate 20 mL/min) to afford TFA salt of compound 29. LC-MS $t_R$=1.86 min in 3 min chromatography, m/z 447 ($MH^+$); $^1H$ NMR (400 MHz, $CD_3OD$) δ 7.93-6.92 (m, 11H), 5.63-5.58 (m, 1H), 5.28-5.24 (m, 1H), 3.13 (s, 3H), 3.02-2.59 (m, 6H), 1.82-1.70 (m, 2H).

A 10 mL microwave tube was charged with compound 56 (0.0068 g), 3-chloro-5-fluorophenylboronic acid (0.0782 g), $Cs_2CO_3$ (0.2277 g), $PdCl_2(PPh_3)_2$ (0.0127 g), 1,4-dioxane (4 mL), and $H_2O$ (0.5 mL). The tube was heated in a CEM microwave reactor at 110° C. for 30 min. The reaction mixture was purified by reversed-phase HPLC (SunFire™ Prep $C_{18}$ OBD™ 5 μm 19×50 mm column, 10%→90% $CH_3CN/H_2O$, 0.1% $CF_3COOH$ over 8 min and then 90% $CH_3CN/H_2O$, 0.1% $CF_3COOH$ over 2 min, flow rate 20 mL/min) to afford TFA salt of compound 26. LC-MS $t_R$=2.27 min in 3 min chromatography, m/z 474, 476 ($MH^+$); $^1H$ NMR (400 MHz, $CD_3OD$) δ 7.62-6.75 (m, 10H), 5.62-5.56 (m, 1H), 5.27-5.23 (m, 1H), 3.12 (s, 3H), 3.00-2.56 (m, 6H), 1.77-1.68 (m, 2H); $^{19}F$ NMR (376 MHz, $CD_3OD$) δ −113.11 (m).

Example 16

Preparation of Compound 67

−113.01; $^{13}C$ NMR (100 MHz, $CDCl_3$) δ 205.59, 157.47 (d, J=249.2 Hz), 142.18, 134.95 (d, J=8.4 Hz), 131.18 (d, J=3.8 Hz), 128.93, 128.24 (d, J=19.9 Hz), 126.40, 117.89 (d, J=24.5 Hz), 116.81 (d, J=3.1 Hz), 81.65, 35.21, 35.19, 29.25.

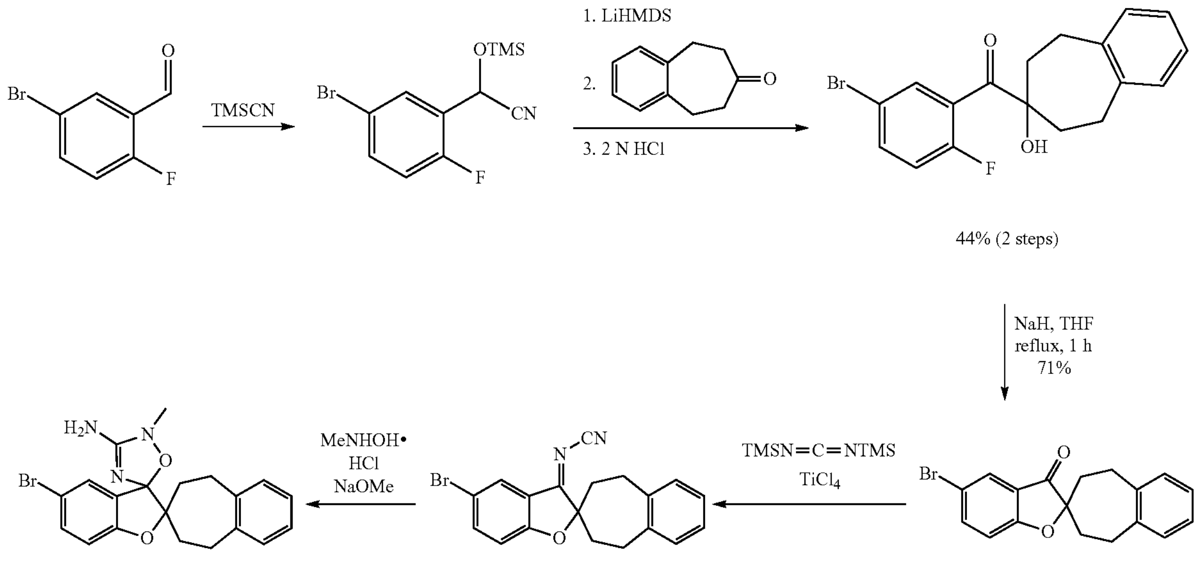

Step 1. 2-(5-bromo-2-fluorophenyl)-2-(trimethylsilyloxy)acetonitrile

To a solution of 5-bromo-2-fluorobenzaldehyde (2.1385 g, 10.53 mmol) and DMAP (0.0146 g, 0.12 mmol, 0.011 equiv) in $CH_3CN$ (20 mL) was added TMSCN (1.4086 g, 14.20 mmol, 1.35 equiv) dropwise via a syringe under nitrogen at room temperature. After 4 h, the solvent was removed under reduced pressure. The crude product was directly used in the next step without further purification.

Step 2. (5-bromo-2-fluorophenyl)(7-hydroxy-6,7,8,9-tetrahydro-5H-benzo[7]annulen-7-yl)methanone To a solution of 2-(5-bromo-2-fluorophenyl)-2-(trimethylsilyloxy)acetonitrile (10.53 mmol), obtained as described above, in THF (10 mL) was added LiHMDS (1.0 M in THF, 11 mL, 11 mmol, 1.05 equiv) via a syringe under nitrogen at −78° C. After 1.25 h, a solution of 5,6,8,9-tetrahydro-7H-benzocyclohepten-7-one (1.6550 g, 10.33 mmol, 0.98 equiv) in THF (16 mL) was added dropwise via a cannula. The resulting mixture was allowed to slowly warm to 7° C. over 16 h. The mixture was then treated with 2 N HCl (25 mL) and MeOH (75 mL). The resulting solution was vigorously stirred at room temperature for 22 h and the solvents were removed under reduced pressure. The residue was extracted twice with $CH_2Cl_2$, dried over $Na_2SO_4$. After the solvent was evaporated under reduced pressure, the residue was purified by chromatography on silica gel eluted with hexanes/ethyl acetate to afford 1.6570 g (44% in two steps) of (5-bromo-2-fluorophenyl)(7-hydroxy-6,7,8,9-tetrahydro-5H-benzo[7]annulen-7-yl)methanone as a solid. LC-MS $t_R$=2.02 min in 3 min chromatography, m/z 345, 347 $(M-H_2O)^+$; $^1H$ NMR (400 MHz, $CDCl_3$) δ 7.54-7.49 (m, 1H), 7.41-7.38 (m, 1H), 7.13 (m, 4H), 7.01-6.97 (m, 1H), 3.43-3.36 (m, 2H), 3.31 (s, 1H), 2.64-2.59 (m, 2H), 2.00-1.88 (m, 4H); $^{19}F$ NMR (376 MHz, $CDCl_3$) δ

Step 3. 5'-bromo-5,6,8,9-tetrahydro-3'H-spiro[benzo[7]annulene-7,2'-benzofuran]-3'-one A mixture of (5-bromo-2-fluorophenyl)(7-hydroxy-6,7,8,9-tetrahydro-5H-benzo[7]annulen-7-yl)methanone (1.3739 g, 3.78 mmol) and 60% NaH (0.5900 g, 14.75 mmol) in THF (20 mL) was heated at 100° C. for 1 h. The reaction mixture was then cooled with an ice bath and quenched with 2 N HCl (5 mL), extracted with ethyl acetate, dried over $Na_2SO_4$. After the solvents were evaporated, the residue was purified by chromatography on silica gel eluted with hexanes/ethyl acetate to afford 0.9170 g (71%) of 5'-bromo-5,6,8,9-tetrahydro-3'H-spiro[benzo[7]annulene-7,2'-benzofuran]-3'-one as a solid. LC-MS $t_R$=2.31 min in 3 min chromatography, m/z 343, 345 $(MH^+)$; $^1H$ NMR (400 MHz, $CDCl_3$) δ 7.79-7.78 (m, 1H), 7.73-7.71 (m, 1H), 7.17 (m, 4H), 7.11-7.09 (m, 1H), 3.41-3.35 (m, 2H), 2.78-2.75 (m, 2H), 1.95-1.85 (m, 4H); $^{13}C$ NMR (100 MHz, $CDCl_3$) δ 201.53, 169.46, 141.50, 140.56, 128.93, 127.47, 126.62, 121.63, 115.61, 114.15, 92.58, 32.98, 29.67.

Step 4. N-(5'-bromo-5,6,8,9-tetrahydro-3'H-spiro[benzo[7]annulene-7,2'-benzofuran]-3'-ylidene)cyanamide To a solution of 5'-bromo-5,6,8,9-tetrahydro-3'H-spiro[benzo[7]annulene-7,2'-benzofuran]-3'-one (0.1660 g, 0.48 mmol) in $CH_2Cl_2$ (5 mL) was added $TiCl_4$ (1.0 M in $CH_2Cl_2$, 1.0 mL, 1.0 mmol) dropwise at room temperature. The reaction mixture was turned into orange precipitates in a few minutes. After 1 h, 1,3-bis(trimethylsilyl)carbodiimide (0.30 mL, 1.32 mmol) was added via a syringe. The precipitates were disappeared and the reaction mixture was turned into a red solution. The mixture was stirred at room temperature for 15 h and then quenched with ice, extracted with $CH_2Cl_2$, dried over $Na_2SO_4$. After the solvent was removed under reduced pressure, the crude product was directly used in the next step without further purification. LC-MS $t_R$=2.27 min in 3 min chromatography, m/z 367, 369 ($MH^+$).

Step 5. Preparation of Compound 67

To a suspension of N-(5'-bromo-5,6,8,9-tetrahydro-3'H-spiro[benzo[7]annulene-7,2'-benzofuran]-3'-ylidene)cyanamide (0.48 mmol), obtained as described above, in EtOH (20 mL) was added a mixture of methylhydroxyamine.HCl salt (0.0986 g, 1.18 mmol) and $CH_3ONa$ (25 wt. % in MeOH, 0.25 mL, 1.10 mmol) in MeOH (10 mL). After 16 h, the reaction mixture was purified by reversed-phase HPLC (SunFire™ Prep $C_{18}$ OBD™ 5 μm 19×50 mm column, 10%→90% $CH_3CN/H_2O$, 0.1% $CF_3COOH$ over 8 min and then 90% $CH_3CN/H_2O$, 0.1% $CF_3COOH$ over 2 min, flow rate 20 mL/min) to afford TFA salt of compound 67. LC-MS $t_R$=1.43, 1.58 min in 3 min chromatography, m/z 414, 416 ($MH^+$); $^1H$ NMR (400 MHz, $CD_3OD$) δ 7.81-6.83 (m, 7H), 3.37-3.30 (m, 2H), 2.70-2.64 (m, 2H), 2.07-2.02 (m, 2H), 1.78-1.72 (m, 2H).

Example 17

Preparation of Compound 25

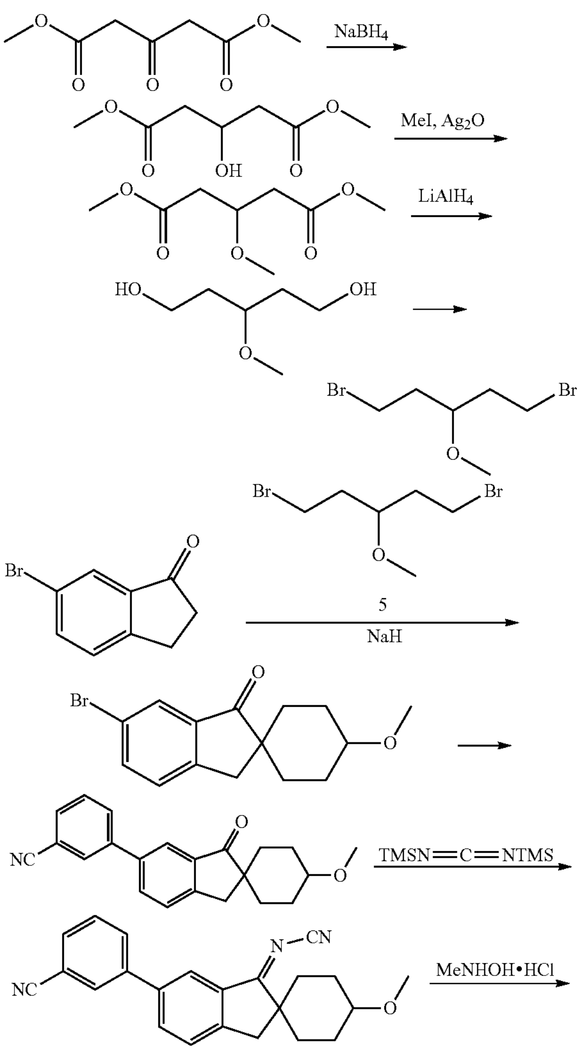

-continued

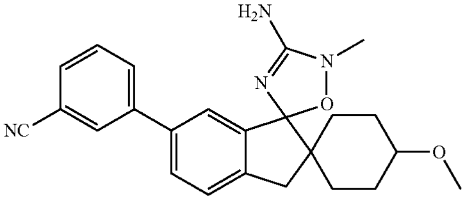

Experimental Data:

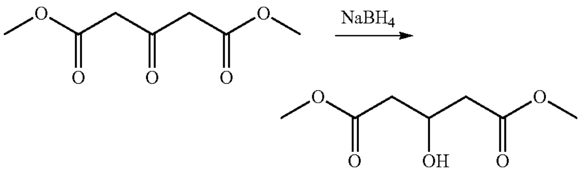

Step 1. dimethyl 3-hydroxypentanedioate

To a mixture of dimethyl 3-oxopentanedioate (20 g, 115 mmol) in anhydrous MeOH (140 mL) was added $NaBH_4$ (2.33 g, 63.18 mmol) in small portions over 10 minutes. The mixture was stirred for 1 h at room temperature and concentrated. Water and EtOAc was added and the organic phase was separated and dried. The combined organic layer was concentrated to give the crude product, which was purified by column chromatography to give dimethyl 3-hydroxypentanedioate (9 g, 44%). $^1H$-NMR ($CDCl_3$): 2.51 (m, 4H), 3.43 (m, 1H), 3.70 (m, 6H), 4.45 (m, 1H).

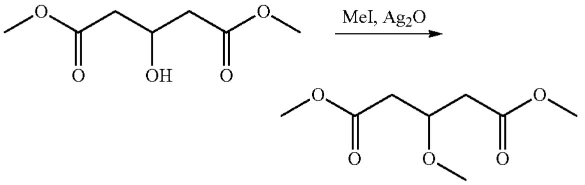

Step 2. dimethyl 3-methoxypentanedioate

To a solution of dimethyl 3-hydroxypentanedioate (9 g, 51.1 mmol) in DMF (70 mL) was added $Ag_2O$ (35.5 g, 154.3 mmol) and iodomethane (48.2 g, 339.2 mmol) under ice-cooling. The mixture was stirred at room temperature overnight. The mixture was filtrated and the filtrate was washed with water. Ether was added and the organic layer was dried and concentrated to give the crude product, which was purified by column chromatography to give dimethyl 3-methoxypentanedioate (8 g, 82%). $^1H$-NMR ($CDCl_3$): 2.48 (m, 4H), 3.21 (m, 3H), 3.50 (m, 6H), 3.85 (s, 1H).

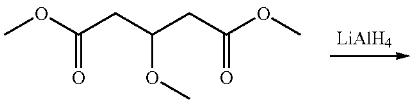

-continued

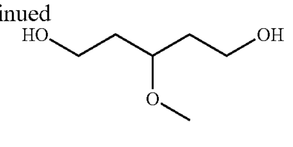

Step 3. 3-methoxypentane-1,5-diol

To a stirred suspension of LAH (1.77 g, 46.6 mmol) in THF (40 mL) under $N_2$ was cooled to 0° C. and was added dimethyl 3-methoxypentanedioate (3.7 g, 19.5 mmol). The mixture was stirred overnight. Aqueous NaOH (1 N, 12 mL) was added at 0° C. The mixture was filtered and the cake was washed with EtOAc 3 times. The filtrate was dried and concentrated to give 3-methoxypentane-1,5-diol (1 g, 38%). $^1$H-NMR ($CDCl_3$): 1.75 (m, 4H), 2.62 (s, 2H), 3.37 (m, 3H), 3.6 (m, 2H), 3.7 (m, 4H).

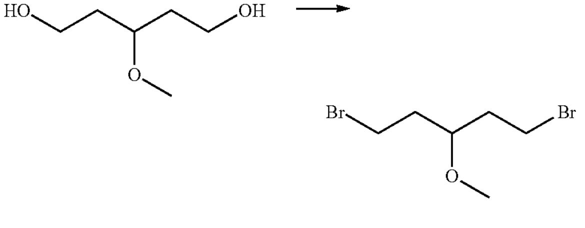

Step 4. 1,5-dibromo-3-methoxypentane

To a solution of 3-methoxypentane-1,5-diol (1 g, 7.46 mmol) in DCM (10 mL) was added $PPh_3$ (5.77 g, 22.05 mmol) and $CBr_4$ (4.87 g, 14.7 mmol) at 0° C. The mixture was stirred at 0° C. for 2 h. The mixture was filtrated and the filtrate was concentrated to give the residue, which was purified by column chromatography to give 1,5-dibromo-3-methoxypentane (1.2 g, 62%). $^1$H-NMR ($CDCl_3$): 2.0 (m, 4H), 3.3 (m, 3H), 3.37 (m, 4H), 3.5 (m, 1H), 3.7 (m, 4H).

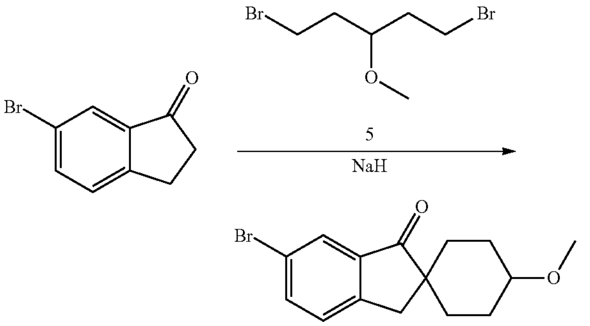

Step 5. 6'-bromo-4-methoxyspiro[cyclohexane-1,2'-inden]-1'(3'H)-one

A mixture of 6-bromo-2,3-dihydro-1H-inden-1-one (1.037 g, 4.94 mmol) and 1,5-dibromo-3-methoxypentane (1.2 g, 4.94 mmol) in THF (16 mL) was added NaH (237.12 mg, 60%, 9.88 mmol) at room temperature. The mixture was refluxes for 3 h. The mixture was quenched with water and extracted with EtOAc. The organic layer was dried and concentrated to give the residue, which was purified by column chromatography to give 6'-bromo-4-methoxyspiro[cyclohexane-1,2'-inden]-1'(3'H)-one (60 mg, 4%).

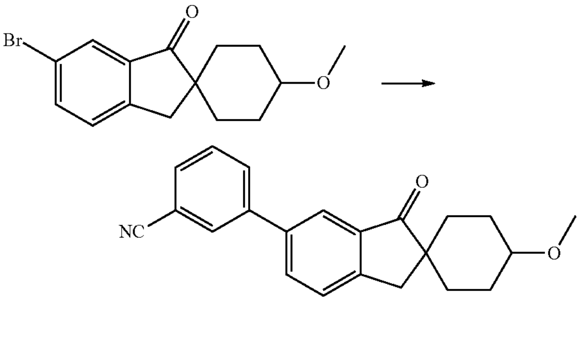

Step 6. 3-(4-methoxy-1'-oxo-1',3'-dihydrospiro[cyclohexane-1,2'-indene]-6'-yl)benzonitrile To a solution of 6'-bromo-4-methoxyspiro[cyclohexane-1,2'-inden]-1'(3'H)-one (40 mg, 0.130 mmol) and 3-cyanophenylboronic acid (30.5 mg, 0.208 mmol) in $Cs_2CO_3$ (2 M, 0.247 mL) and 1,4-dioxane (1.2 mL) under $N_2$ was added $Pd(PPh_3)_2Cl_2$ (7.5 mg). The mixture was stirred at 100° C. for 6 minutes. After cooled to room temperature, the organic layer was dried and concentrated to give the residue, which was purified by TLC to give 3-(4-methoxy-1'-oxo-1',3'-dihydrospiro[cyclohexane-1,2'-indene]-6'-yl)benzonitrile (20 mg, 46%).

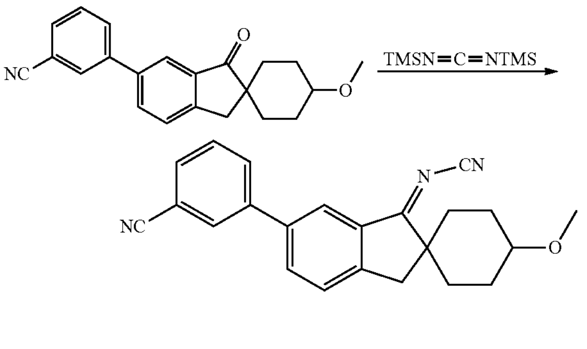

Step 7. (E)-N-(5'-(3-cyanophenyl)-4-methoxyspiro[cyclohexane-1,2'-indene]-3'(1'H)-ylidene)cyanamide To a solution of 3-(4-methoxy-1'-oxo-1',3'-dihydrospiro[cyclohexane-1,2'-indene]-6'-yl)benzonitrile (30 mg, 0.09 mmol) in $CH_2Cl_2$ (3 mL) was added $TiCl_4$ (0.2 mL). It was stirred in microwave at 50° C. for 5 minutes. Then bis-trimethylsilylcarbodiimide (0.2 mL, 0.146 mmol) was added. The resulting mixture was stirred in microwave at 60° C. for 10 minutes. The reaction mixture was poured into ice-water, extracted with DCM. The combined organic phases were dried over anhydrous $Na_2SO_4$, and filtered. The filtrate was concentrated to give (E)-N-(5'-(3-cyanophenyl)-4-methoxyspiro[cyclohexane-1,2'-indene]-3'(1'H)-ylidene)cyanamide (30 mg, crude).

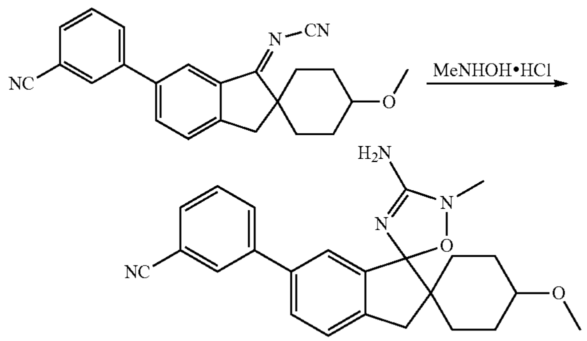

Step 8. Preparation of Compound 25

To a solution of methylhydroxylamine HCl salt (7 mg, 0.085 mmol) in anhydrous MeOH (1 mL) was added NaOMe (25% in MeOH (Wt %), 0.017 mL), followed by (E)-N-(5'-(3-cyanophenyl)-4-methoxyspiro[cyclohexane-1,2'-indene]-3'(1'H)-ylidene)cyanamide (30 mg, 0.085 mmol). After stirred for 15 minutes, the solvent was removed in vacuo. The residue was redissolved in DCM (5 mL). The mixture was filtered, and the solvent was removed to give the residue, which was purified by preparative HPLC to give compound 25 (2.35 mg, 7%). $^1$H-NMR (MeOD): 1.37 (m, 4H), 1.77 (m, 3H), 2.09 (m, 2H), 3.03 (m, 1H), 3.23 (m, 1H), 3.32 (m, 3H), 3.45 (m, 3H), 7.45 (m, 1H), 7.75 (m, 4H), 8.0 (m, 2H).

Example 18

Preparation of Compound 46

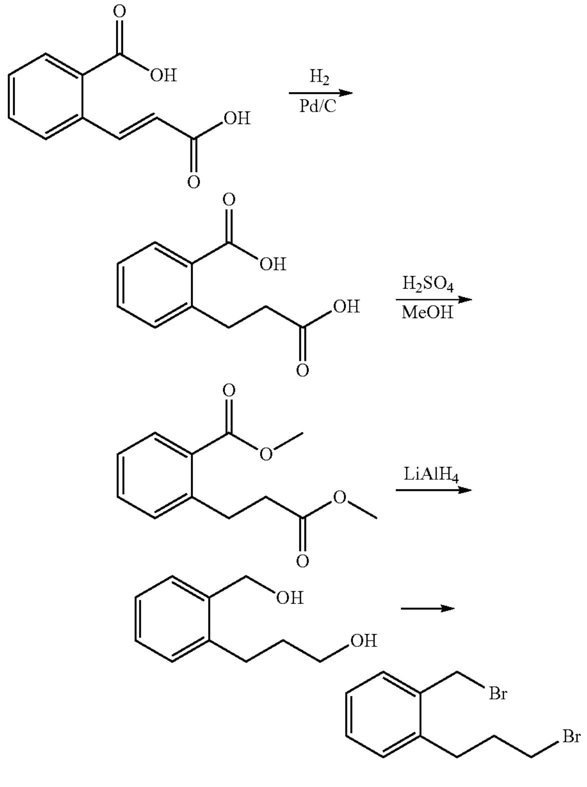

-continued

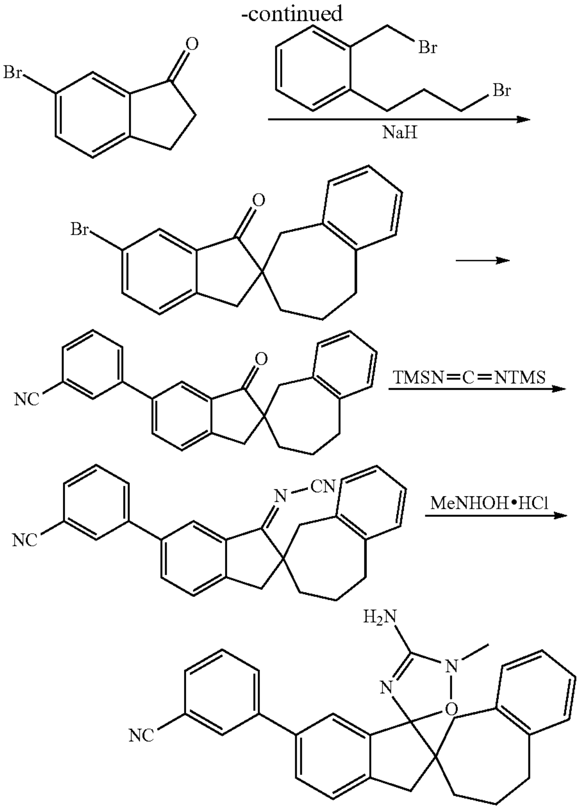

Experimental Data:

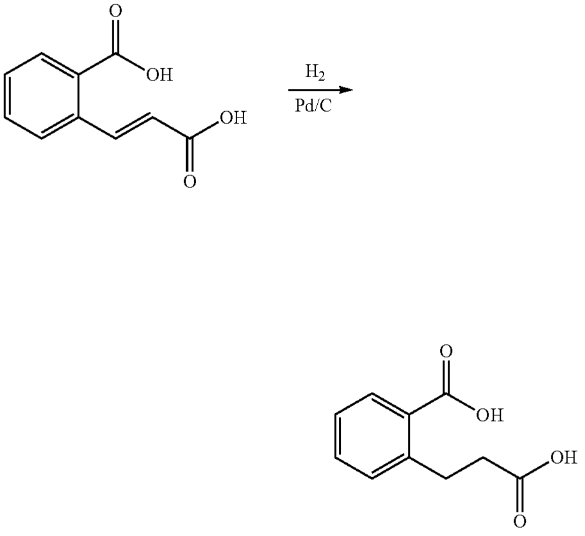

Step 1. 2-(2-carboxyethyl)benzoic acid

A mixture of 2-(2-carboxyvinyl)benzoic acid (5 g, 26 mmol) in MeOH (45 mL) was bubbled with $H_2$ (10 psi) at room temperature overnight. The mixture was filtered and the filtrate was concentrated to give 2-(2-carboxyethyl)benzoic acid (5.2 g, 100%). $^1$H-NMR ($CDCl_3$): 2.61 (m, 2H), 3.21 (m, 2H), 7.22 (m, 2H), 7.38 (m, 1H), 7.88 (m, 1H).

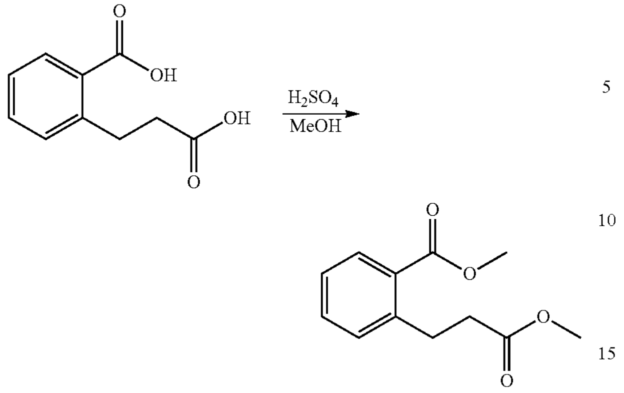

Step 2. methyl 2-(3-methoxy-3-oxopropyl)benzoate

Concentrated $H_2SO_4$ (1.7 mL) was added dropped into a mixture of 2-(2-carboxyethyl)benzoic acid (5 g, 25.9 mmol) in MeOH (21 mL) under ice-cooling. The mixture was refluxed overnight. The mixture was concentrated and EtOAc was added. The organic layer was dried and concentrated to give methyl 2-(3-methoxy-3-oxopropyl)benzoate (5.75 g, 100%). $^1$H-NMR ($CDCl_3$): 2.67 (m, 2H), 3.28 (m, 2H), 3.57 (s, 3H), 3.91 (s, 3H), 7.27 (m, 2H), 7.44 (m, 1H), 7.92 (m, 1H).

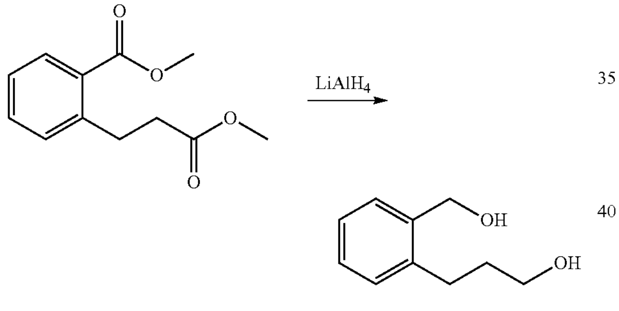

Step 3. 3-(2-(hydroxymethyl)phenyl)propan-1-ol

To a stirred solution of LAH (1.89 g, 49.77 mmol) in $Et_2O$ (40 mL) under $N_2$ was cooled to 0° C. and was added $AlCl_3$ (1.6 g, 11.8 mmol). The mixture was allowed to warm to room temperature and stirred for 30 minutes. A mixture of methyl 2-(3-methoxy-3-oxopropyl)benzoate (2 g, 9 mmol) in $Et_2O$ was added dropwise. The mixture was stirred overnight. Aqueous NaOH (1 N, 12 mL) was added at 0° C. The mixture was filtered and the cake was washed with EtOAc 3 times. The filtrate was dried and concentrated to give 3-(2-(hydroxymethyl)phenyl)propan-1-ol (1.46 g, 98%). $^1$H-NMR ($CDCl_3$): 1.85 (m, 2H), 2.77 (m, 2H), 3.52 (m, 2H), 4.62 (s, 2H), 7.23 (m, 2H), 7.27 (m, 2H).

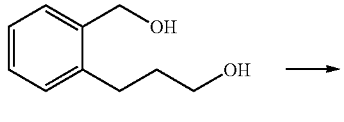

-continued

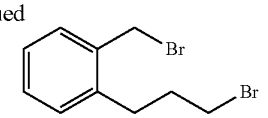

Step 4. 1-(bromomethyl)-2-(3-bromopropyl)benzene

To a solution of 3-(2-(hydroxymethyl)phenyl)propan-1-ol (1.46 g, 8.85 mmol) in DCM (40 mL) was added $PPh_3$ (6.95 g, 26.5 mmol) and $CBr_4$ (5.86 g, 17.7 mmol) at 0° C. The mixture was stirred at room temperature overnight. The mixture was concentrated to give the residue, which was purified by column chromatography to give 1-(bromomethyl)-2-(3-bromopropyl)benzene (2.27 g, 88%).

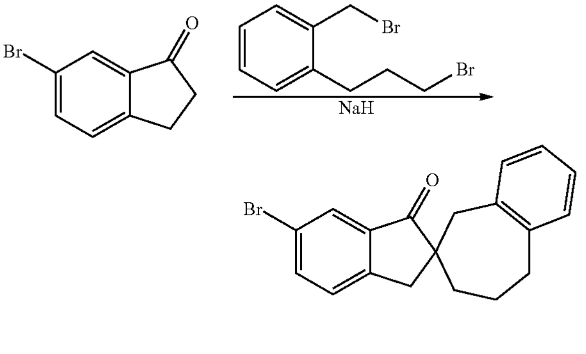

Step 5. 6'-bromo-5,7,8,9-tetrahydrospiro[benzo[7]annulene-6,2'-inden]-1'(3'H)-one A mixture of 6-bromo-2,3-dihydro-1H-inden-1-one (1.2 g, 5.71 mmol) and 1-(bromomethyl)-2-(3-bromopropyl)benzene (1.66 g, 5.71 mmol) in THF (40 mL) was added NaH (457 mg, 60%, 11.42 mmol) at room temperature. The mixture was refluxes for 2 h. The mixture was quenched with water and extracted with EtOAc. The organic layer was dried and concentrated to give the residue, which was purified by column chromatography to give 6'-bromo-5,7,8,9-tetrahydrospiro[benzo[7]annulene-6,2'-inden]-1'(3'H)-one (420 mg, 22%).

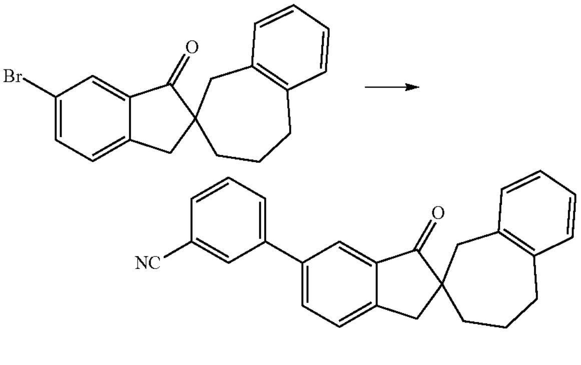

Step 6. 3-(1'-oxo-1',3',5,7,8,9-hexahydrospiro[benzo[7]annulene-6,2'-indene]-6'-yl)benzonitrile To a solution of 6'-bromo-5,7,8,9-tetrahydrospiro[benzo[7]annulene-6,2'-inden]-1'(3'H)-one (200 mg, 0.59 mmol)

and 3-cyanophenylboronic acid (130 mg, 0.885 mmol) in $Cs_2CO_3$ (2 M, 1 mL) and 1,4-dioxane (4.2 mL) under $N_2$ was added $Pd(PPh_3)_2Cl_2$ (20 mg). The mixture was stirred at 100° C. for 0.7 h. After cooled to room temperature, the organic layer was dried and concentrated to give the residue, which was purified by TLC to give 3-(1'-oxo-1',3',5,7,8,9-hexahydrospiro[benzo[7]annulene-6,2'-indene]-6'-yl)benzonitrile (120 mg, 56%).

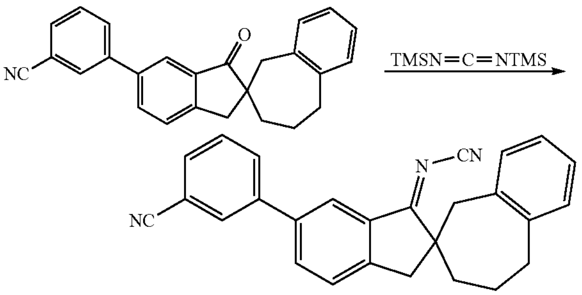

Step 7. N-(5'-(3-cyanophenyl)-5,7,8,9-tetrahydrospiro[benzo[7]annulene-6,2'-indene]-3'(1'H)-ylidene)cyanamide To a solution of 3-(1'-oxo-1',3',5,7,8,9-hexahydrospiro[benzo[7]annulene-6,2'-indene]-6'-yl)benzonitrile (31 mg, 0.086 mmol) in $CH_2Cl_2$ (2 mL) was added $TiCl_4$ (66 mg). It was stirred in microwave at 50° C. for 5 minutes. Then bis-trimethylsilylcarbodiimide (112 mg, 0.6 mmol) was added. The resulting mixture was stirred in microwave at 60° C. for 10 minutes. The reaction mixture was poured into ice-water, extracted with DCM. The combined organic phases were dried over anhydrous $Na_2SO_4$, and filtered. The filtrate was concentrated to give N-(5'-(3-cyanophenyl)-5,7,8,9-tetrahydrospiro[benzo[7]annulene-6,2'-indene]-3'(1'H)-ylidene)cyanamide (50 mg, crude).

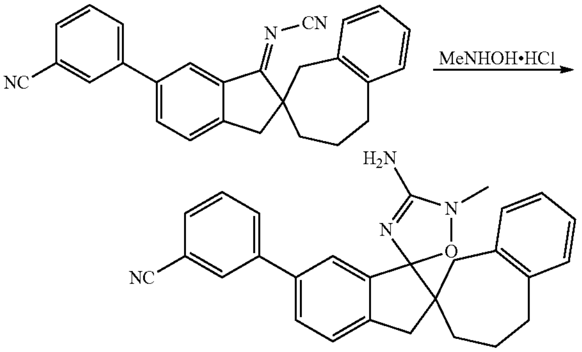

Step 8. Preparation of Compound 46

To a solution of methylhydroxylamine HCl salt (13 mg, 0.13 mmol) in anhydrous MeOH (2 mL) was added NaOMe (25% in MeOH (Wt. %), 5 drops), followed by N-(5'-(3-cyanophenyl)-5,7,8,9-tetrahydrospiro[benzo[7]annulene-6,2'-indene]-3'(1'H)-ylidene)cyanamide (50 mg, 0.13 mmol). After stirred for 10 minutes, the solvent was removed in vacuo. The residue was redissolved in DCM (5 mL). The mixture was filtered, and the solvent was removed to give the residue, which was purified by preparative HPLC to give compound 46 (2.38 mg, 4%). $^1$H-NMR (MeOD): 1.41 (m, 1H), 1.72-2.23 (m, 3H), 2.46 (m, 2H), 2.81 (m, 3H), 3.08 (m, 1H), 3.32 (m, 3H), 6.62 (m, 1H), 7.02 (m, 3H), 7.21 (m, 1H), 7.62 (m, 4H), 7.92 (m, 2H).

Example 19

Preparation of Compound 48

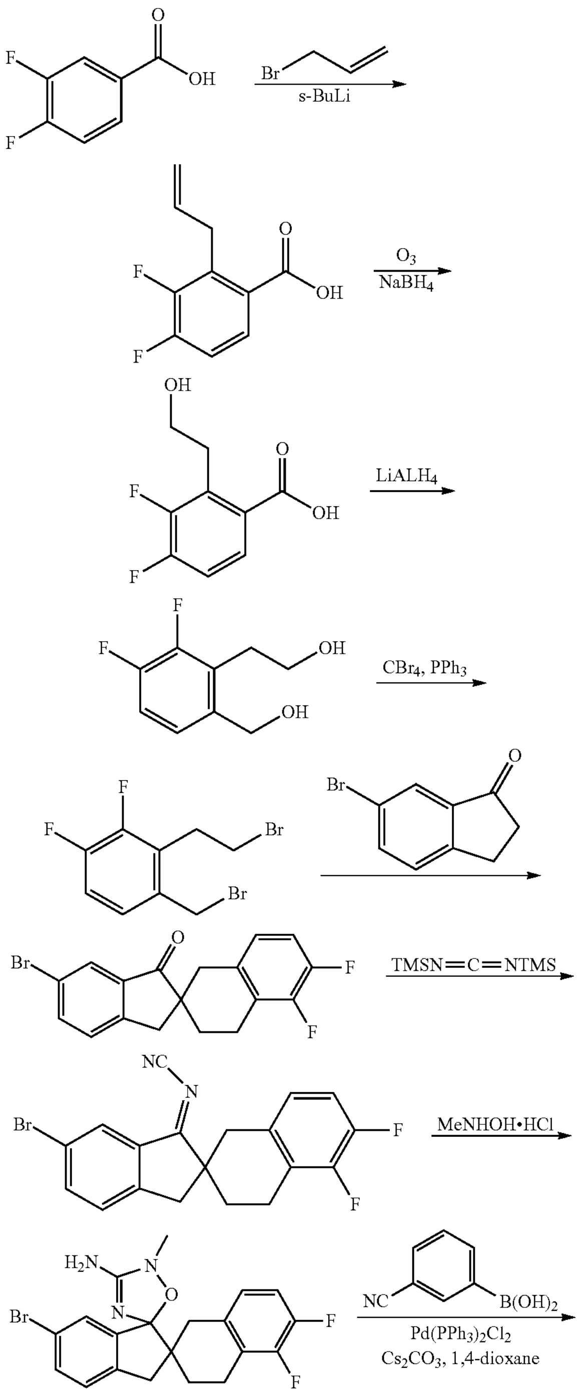

-continued

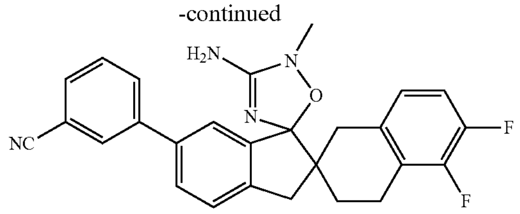

Experimental Data:

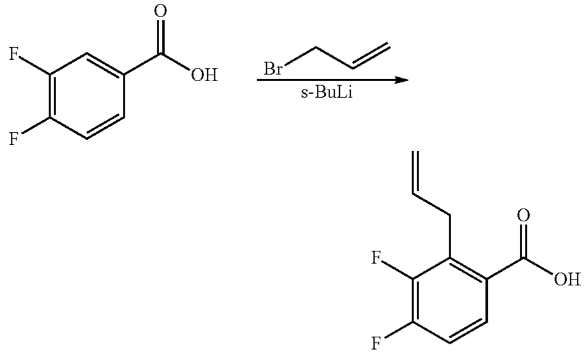

Step 1. 2-allyl-3,4-difluorobenzoic acid

To a solution of TMEDA (32.2 g, 0.278 mol) in dry THF (150 mL) was added s-BuLi (1.3 M, 0.278 mol, 214 mL) at −78° C. The mixture was stirred at this temperature for 0.5 hour, and then a solution of 3,4-difluorobenzoic acid (20 g, 0.127 mol) in THF (100 mL) was added dropwise. After stirring for 1 hour, CuBr.DMS (3.9 g, 0.019 mol, 15% mol) was added, followed by 3-bromoprop-1-ene (46 g, 0.38 mol) in 50 mL of THF. The reaction mixture was allowed to warm to room temperature and was quenched with water. The aqueous layer was washed with $Et_2O$, and acidified with 4 N HCl. The mixture was extracted with $Et_2O$. The organic layer was washed with brine, dried over $Na_2SO_4$, filtered and concentrated to give 2-allyl-3,4-difluorobenzoic acid (22 g, 55%). $^1H$ NMR ($CDCl_3$): 3.91 (d, 2H), 5.06 (m, 2H), 6.01 (m, 1H), 7.12 (m, 1H), 7.90 (m, 1H).

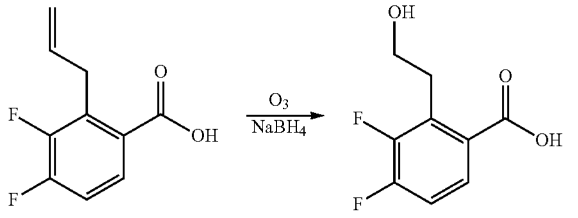

Step 2. 3,4-difluoro-2-(2-hydroxyethyl)benzoic acid

A steam of $O_3$ was bubbled through a solution of 2-allyl-3,4-difluorobenzoic acid (13 g, 0.065 mol) in absolute $CH_2Cl_2$ (200 mL) at −78° C. until the mixture was turned blue. Then $NaBH_4$ (7.25 g, 0.196 mol) in was added to the above mixture, and the final mixture was stirred at room temperature overnight. The solution was concentrated. Water was added at 0° C., and the mixture was acidified by adding 6 N HCl, and was extracted with EtOAc. The organic layer was washed with brine, dried over $Na_2SO_4$, filtered and concentrated to give 3,4-difluoro-2-(2-hydroxyethyl)benzoic acid (8.2 g, crude).

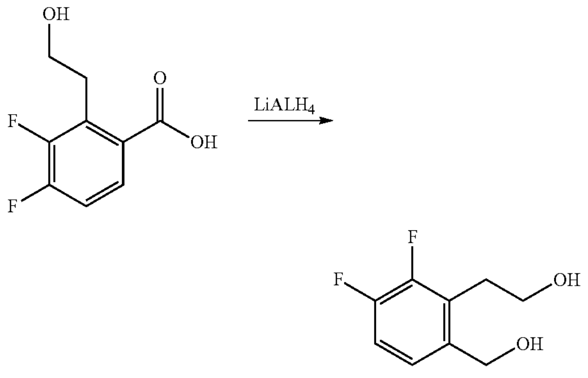

Step 3. 2-(2,3-difluoro-6-(hydroxymethyl)phenyl)ethanol

To a solution of $LiAlH_4$ (2.45 g, 0.065 mol) in THF (30 mL) was added 3,4-difluoro-2-(2-hydroxyethyl)benzoic acid (8.7 g, 0.043 mol) in THF (60 mL) at 0° C. The mixture was stirred at room temperature overnight. The reaction was quenched with 3 mL of $H_2O$, followed by aqueous NaOH solution (3 mL, 10%). The solution was filtered and the filtrated was concentrated to give the residue, which was purified by chromatography to give 2-(2,3-difluoro-6-(hydroxymethyl)phenyl)ethanol (2.5 g, 31%). $^1H$ NMR ($CDCl_3$): 2.99 (m, 2H), 3.58 (s, 2H), 3.83 (t, 2H), 4.52 (s, 2H), 7.03 (m, 2H).

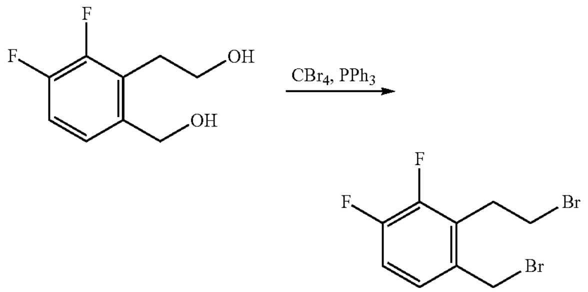

Step 4. 2-(2-bromoethyl)-1-(bromomethyl)-3,4-difluorobenzene

To a solution of 2-(2,3-difluoro-6-(hydroxymethyl)phenyl)ethanol (2.5 g, 13.3 mmol) and $CBr_4$ (10.9 g, 33 mmol) in DCM (100 mL) was added $PPh_3$ (8.65 g, 33 mmol) at 0° C. in portions. The mixture was stirred at room temperature overnight. The solution was concentrated. The residue was redissolved in $Et_2O$ and filtered. The filtrated was concentrated to give the crude product, which was purified by chromatography to afford 2-(2-bromoethyl)-1-(bromomethyl)-3,4-difluorobenzene (3.2 g, 77%). $^1H$ NMR ($CDCl_3$): 3.37 (t, 2H), 3.63 (t, 2H), 4.53 (s, 2H), 7.11 (m, 2H).

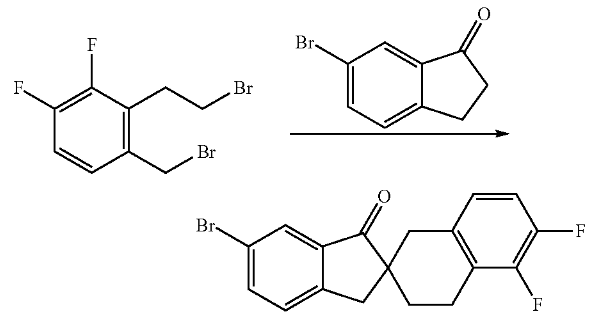

Step 5 6-bromo-5',6'-difluoro-3',4'-dihydro-1'H-spiro[indene-2,2'-naphthalen]-1(3H)-one To a solution of 2-(2-bromoethyl)-1-(bromomethyl)-3,4-difluorobenzene (3 g, 9.62 mmol) and 6-bromo-2,3-dihydro-1H-inden-1-one (2.03 mg, 9.62 mmol) in THF (20 mL) was added NaH (0.58 mg, 14.43 mmol), and the mixture was refluxed for 2 hour. The reaction was cooled and quenched with ice-water. The mixture was extracted with EtOAc. The organic layer was washed with brine, dried over $Na_2SO_4$, filtered and concentrated to give the residue, which was purified by preparative TLC to afford 6-bromo-5',6'-difluoro-3',4'-dihydro-1'H-spiro[indene-2,2'-naphthalen]-1(3H)-one (1.6 g, 46%). $^1H$ NMR ($CDCl_3$): 1.68 (m, 1H), 2.01 (m, 1H), 2.47 (d, 1H), 2.72 (m, 2H), 2.89 (d, 1H), 3.07 (m, 2H), 6.71 (m, 1H), 6.86 (m, 1H), 7.22 (d, 1H), 7.63 (d, 1H), 7.92 (s, 1H).

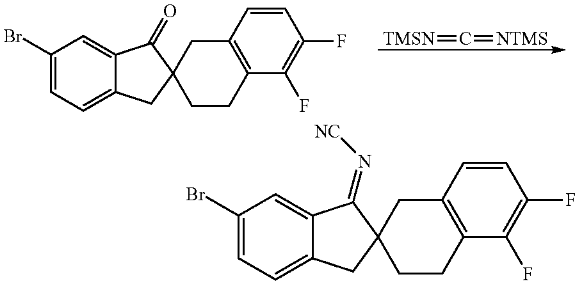

Step 6. (Z)—N-(5-bromo-5',6'-difluoro-3',4'-dihydro-1'H-spiro[indene-2,2'-naphthalene]-3(1H)-ylidene)cyanamide To a solution of 6-bromo-5',6'-difluoro-3',4'-dihydro-1'H-spiro[indene-2,2'-naphthalen]-1(3H)-one (150 mg, 0.41 mmol) in dried $CH_2Cl_2$ (1 mL) was added $TiCl_4$ (1 M solution in DCM, 0.1.24 mmol) dropwise within 15 minutes, and stirred for 1 h. Then to this mixture was added bis-trimethlysilylcarbodiimide (234 mg, 1.24 mmol) dropwise. The resulting mixture was stirred overnight. The reaction mixture was poured into ice-water, extracted with $CH_2Cl_2$. The combined organic layer was washed with brine, dried over $Na_2SO_4$, filtered and concentrated to give (Z)—N-(5-bromo-5',6'-difluoro-3',4'-dihydro-1'H-spiro[indene-2,2'-naphthalene]-3(1H)-ylidene)cyanamide (180 mg, crude), which was used for the next step without further purification.

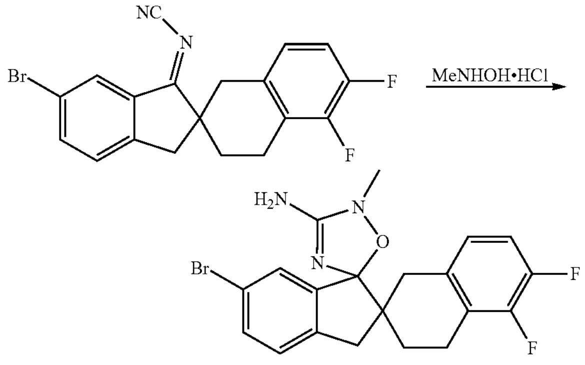

48a

Step 7. Compound 48a

To a solution of MeNHOH.HCl (39 mg, 0.47 mmol) in anhydrous MeOH (5 mL) was added NaOMe (25 wt % in MeOH, 91 mg, 0.42 mmol), followed by (Z)—N-(5-bromo-5',6'-difluoro-3',4'-dihydro-1'H-spiro[indene-2,2'-naphthalene]-3(1H)-ylidene)cyanamide (180 mg, 0.47 mmol). After stirring for 5 minutes, the solvent was removed in vacuum. The residue was re-dissolved in $CH_2Cl_2$ and filtered. The filtrate was concentrated to give the residue, which was purified by preparative TLC to afford the compound 48a (50 mg, 24%). $^1H$ NMR (MeOD): 1.72 (m, 1H), 2.09 (m, 1H), 2.32 (d, 1H), 2.53 (m, 1H), 2.69 (m, 2H), 2.97 (m, 2H), 3.06 (d, 3H), 6.76 (m, 1H), 6.88 (m, 1H), 6.98 (m, 1H), 7.37 (d, 1H), 7.43 (m, 1H).

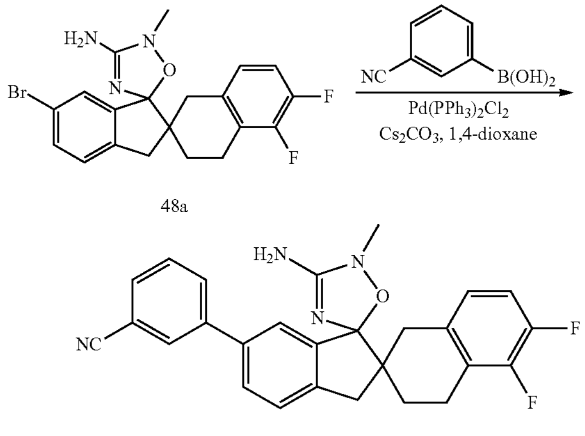

48a

Step 8. Compound 48

$Pd(PPh_3)_2Cl_2$ (10 mg) in a 10 mL of flask under $N_2$ was treated sequentially with the compound 48a (50 mg, 0.146 mmol) in 1,4-dioxane (1 mL), $Cs_2CO_3$ (2 N, 0.2 mL) and 3-cyanophenylboronic acid (43 mg, 0.29 mmol). The mixture was heated under 110° C. at $N_2$ under microwave for 20 minutes. The reaction mixture was concentrated in vacuo to give the residue, which was purified by preparative TLC and HPLC to give compound 48 (6.73 mg, 10%). $^1H$ NMR (MeOD): 1.48 (m, 1H), 2.03 (m, 1H), 2.51 (d, 1H), 2.77 (m, 2H), 2.93-3.13 (m, 3H), 3.37 (m, 3H), 6.88 (m, 1H), 7.03 (m, 1H), 7.39 (m, 1H), 7.62-7.83 (m, 4H), 7.97 (m, 2H).

Example 20

Preparation of Compound 22

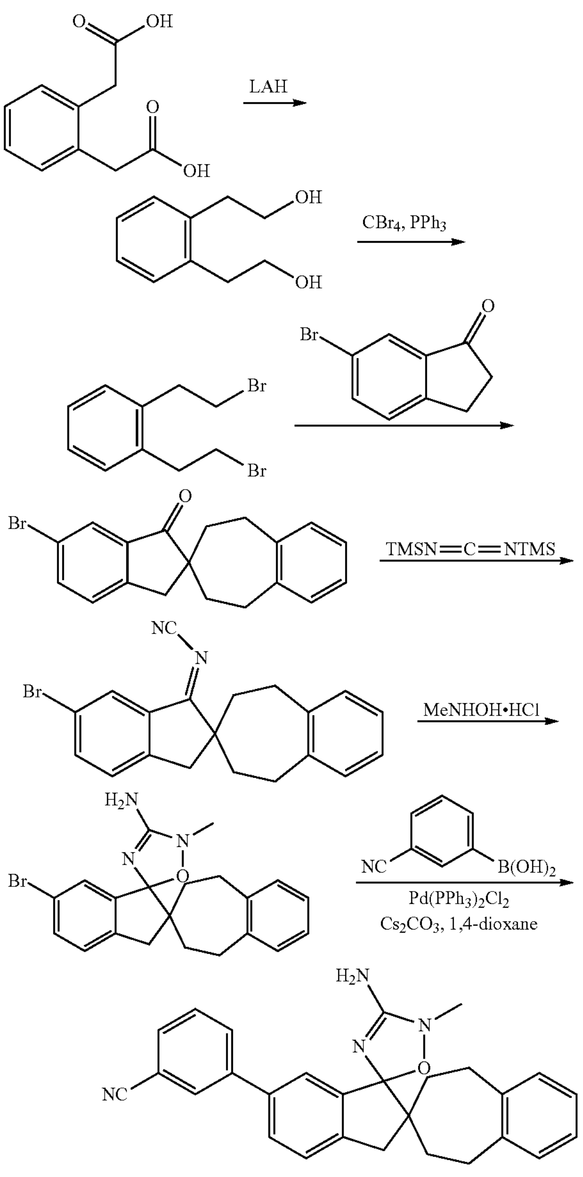

Experimental Data:

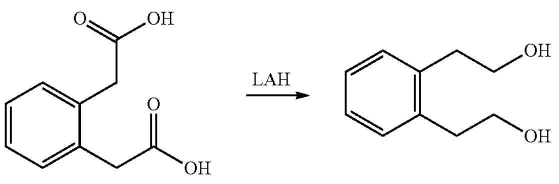 [SMILES: O=C(O)Cc1ccccc1CC(=O)O ; OCCc1ccccc1CCO]

Step 1. 2,2'-(1,2-phenylene)diethanol

To a solution of 2,2'-(1,2-phenylene)diacetic acid (10 g, 51.5 mmol) in THF (100 mL) was added to LAH in THF (90 mL) dropwise, the mixture was refluxed for 18 hours. The mixture was cooled in ice bath and carefully added water (8 mL) dropwise, followed by 1 N NaOH (8 mL), then removed the ice bath added water slowly with stirring until the gray precipitate turns white. The mixture was filtrated and the filtrate was concentrated to give crude 2,2'-(1,2-phenylene) diethanol (8 g, 94%). $^1$H-NMR ($CDCl_3$): 2.02 (s, 3H), 2.97 (m, 4H), 3.83 (m, 2H), 4.12 (m, 1H), 4.24 (t, 1H), 7.19 (m, 4H).

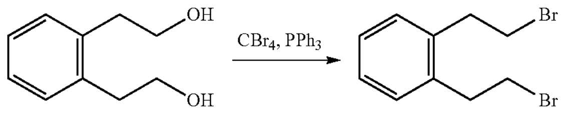 [SMILES: OCCc1ccccc1CCO ; BrCCc1ccccc1CCBr]

Step 2. 1,2-bis(2-bromoethyl)benzene

To a solution of 2,2'-(1,2-phenylene)diethanol (5 g, 30.1 mmol), perbromo methane (24.7 g, 75.3 mmol) in DCM (200 mL) was added triphenylphosphine (19.73 g, 75.3 mmol) at 0° C., the mixture was stirred at room temperature for 18 hours. The mixture was concentrated, redissolved by $Et_2O$, filtered, the organic layer was concentrated to give crude product, which was purified by column chromatography to give 1,2-bis(2-bromoethyl)-benzene (2.3 g, 26%). $^1$H-NMR ($CDCl_3$): 3.12 (t, 4H), 3.47 (t, 4H), 7.16 (m, 4H).

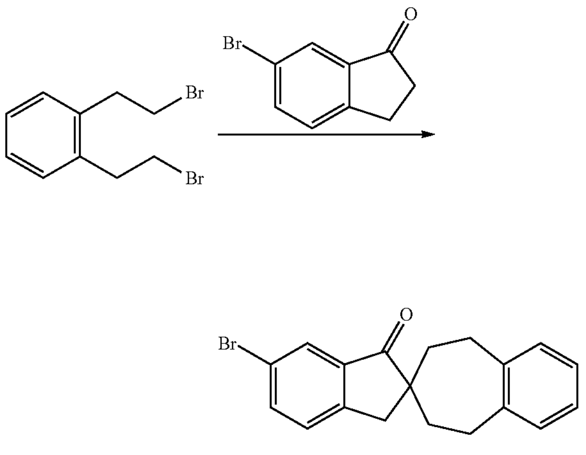

Step 3. 6'-bromo-5,6,8,9-tetrahydrospiro[benzo[7]annulene-7,2'-inden]-1'(3'H)-one A mixture of 6-bromo-indan-1-one (300 mg, 1.43 mmol), 1,2-bis(2-bromoethyl)-benzene (414.3 mg, 1.43 mmol) in THF (10 mL) was added NaH (114 mg, 2.86 mmol) at room temperature, the mixture was refluxed for 2 hours. The mixture was quenched with water, concentrated, then extracted with DCM, washed with brine, dried over $Na_2SO_4$, concentrated to 6'-bromo-5,6,8,9-tetrahydrospiro[benzo[7]annulene-7,2'-inden]-1'(3'H)-one (20 mg, 5%).

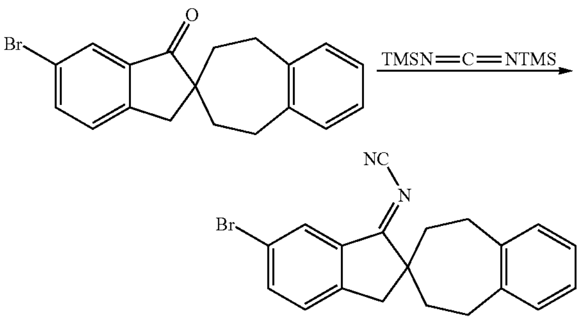

Step 4. (Z)—N-(5'-bromo-5,6,8,9-tetrahydrospiro[benzo[7]annulene-7,2'-indene]-3'(1'H)-ylidene)cyanamide To a solution of 6'-bromo-5,6,8,9-tetrahydrospiro[benzo[7]annulene-7,2'-inden]-1'(3'H)-one (20 mg, 0.059 mmol) in DCM (2 mL) was added $TiCl_4$ (44.7 mg, 0.235 mmol) dropwise, the mixture was stirred at 50° C. at $Ar_2$ under microwave for 20 minutes, N,N'-methanediylidenebis(1,1,1-trimethylsilanamine) (43.8 mg, 0.235 mmol) was added dropwise. The mixture was stirred at 60° C. at $Ar_2$ under microwave for 10 minutes and repeated the same operation for one time and then poured into ice-water (10 mL). The aqueous layer was extracted with $CH_2Cl_2$, which was combined with the organic layer. The organic layer was dried and concentrated to give crude (Z)—N-(5'-bromo-5,6,8,9-tetrahydrospiro[benzo[7]annulene-7,2'-indene]-3'(1'H)— ylidene)cyanamide (20 mg, 4%).

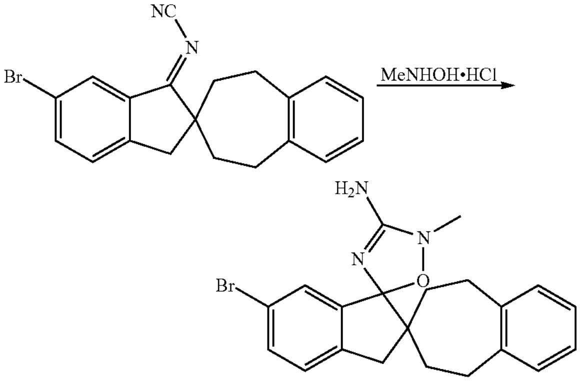

22a

Step 5. The compound 22a

To a solution of N-methyl-hydroxylamine hydrochloride (4.59 mg, 0.055 mmol) in MeOH (3 mL) was added MeONa (0.02 mL, 25% (Wt.) in MeOH), followed by (Z)—N-(5'-bromo-5,6,8,9-tetrahydrospiro[benzo[7]annulene-7,2'-indene]-3'(1'H)-ylidene)cyanamide (20 mg, 0.055 mmol). After stirring for 10 minutes, the solvent was removed in vacuo to give the crude compound 22a (20 mg).

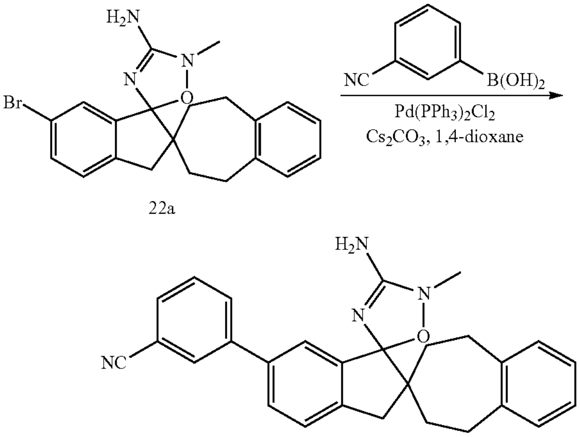

22a

Step 6. Compound 22

$Pd(PPh_3)_2Cl_2$ (10 mg) in a 10 mL of tube under $Ar_2$ was treated sequentially with compound 1 (20 mg, 0.049 mmol) in 1,4-dioxane (1 mL), $Cs_2CO_3$ (2 N, 0.3 mL) and 3-cyanophenylboronic acid (14.4 mg, 0.097 mmol). The mixture was heated under microwave at 120° C. for 25 minutes. The reaction mixture was concentrated in vacuo to give the residue, which was purified by preparative TLC and then by preparative HPLC to give pure compound 22 (1.12 mg, 5%). $^1$H-NMR (MeOD): 1.53 (t, 0.7H), 1.71 (m, 1H), 1.89 (m, 1.5H), 2.16 (m, 0.6H), 2.79 (m, 2H), 3.12 (m, 3H), 3.27 (m, 3H), 3.49 (m, 1H), 3.63 (s, 1H), 7.12 (m, 4H), 7.52 (d, 0.6H), 7.71 (m, 1.5H), 7.79 (m, 2H), 7.97 (m, 1H), 8.03 (m, 1H).

Example 21

Preparation of Compound 30

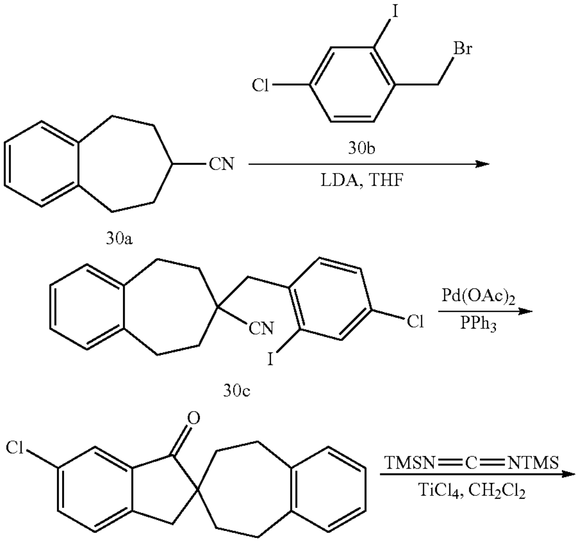

30a

30c

30d

-continued

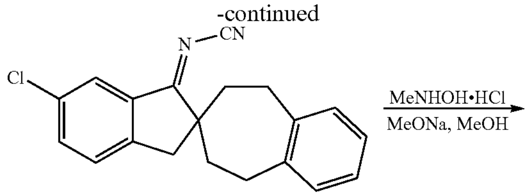

30e

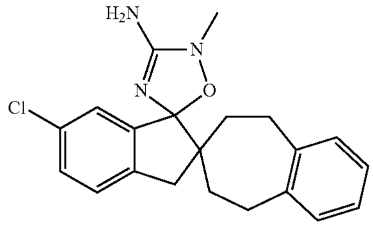

30

Step 1: Preparation compound 30c

To a solution of LDA (5.2 mL, 9.36 mmol, 1.8 M in THF) in THF (10 mL) was added the solution of compound 30a (800 mg, 4.68 mmol) in THF (15 mL) slowly at −60° C. It was stirred at −60° C. for 30 min. To the resulting mixture the solution of compound 30b (1.38 g, 4.21 mmol) in THF (4 mL) was added slowly. The resulting mixture was stirred at −60° C. for 1.5 h. The reaction mixture was quenched with water (10 mL). The aqueous layer was extracted with EtOAc (2×30 mL). The combined organic layers were washed with brine (20 mL), dried over $Na_2SO_4$ and concentrated to dryness to give the crude product, which was purified by chromatography to give compound 30c (750 mg, yield 38%) as yellow solid.

$^1$H NMR ($CDCl_3$ 400 MHz): δ 7.74 (s, 1H), 7.58-7.73 (m, 1H), 7.43 (m, 1H), 7.11 (m, 4H), 2.99-3.13 (m, 2H), 2.97 (s, 2H), 2.66 (m, 2H), 2.04-2.10 (m, 2H), 1.52-1.61 (m, 2H).

Step 2: Preparation of Compound 30d

An 100 mL flask was charged with compound 30c (0.75 g, 1.78 mmol), $Pd(OAc)_2$ (0.0523 g, 0.23 mmol), $Ph_3P$ (0.136 g, 0.52 mmol), DMF (28 mL) and $H_2O$ (3.13 mL). The resulting mixture was degassed and then $Et_3N$ (0.216 g, 2.14 mmol) was added under nitrogen. The reaction mixture was stirred at 130° C. for 4 h. Then the mixture was cooled to room temperature, diluted with water (10 mL). The solution was extracted with EtOAc (2×30 mL). The combined organic layers were washed with brine (10 mL), dried over $Na_2SO_4$ and concentrated to dryness to give the crude product, which was purified by chromatography to give compound 30d (30 mg, yield 8%) as a white solid. $^1$H NMR ($CDCl_3$ 400 MHz): δ 7.74 (s, 1H), 7.58-7.73 (m, 1H), 7.45 (d, J=8.2 Hz, 1H), 7.14 (m, 4H), 3.16 (s, 2H), 3.04-2.97 (m, 2H), 2.89 (br s, 2H), 1.91-1.85 (m, 2H), 1.69-1.63 (m, 2H).

Step 3: Preparation of Compound 30e

To a solution of compound 30d (30 mg, 0.102 mmol) in $CH_2Cl_2$ (2 mL) was added $TiCl_4$ (0.408 mL, 0.408 mmol). It was stirred at 50° C. for 6 min in microwave. To the resulting mixture bis-trimethylsilylcarbodiimide (0.05 mL, 0.224 mmol) was added. The resulting mixture was stirred at 60° C. for 12 min in microwave. TLC showed that the reaction was completed. The reaction mixture was poured into ice-water (10 mL). The solution was extracted with $CH_2Cl_2$ (2×15 mL). The combined organic layers were washed with brine (10 mL), dried over $Na_2SO_4$ and concentrated to dryness to give compound 30e (30 mg, 93% crude yield) as yellow solid, which was used directly for the next step without purification.

Step 4: Preparation of Compound 30

To a solution of methylhydroxylamine HCl salt (7.9 mg, 0.094 mmol) in anhydrous MeOH (2 mL) was added a solution of NaOMe (10 wt %, 0.048 mL, 0.0846 mmol) in methanol followed by compound 30e (30 mg, 0.094 mmol). After being stirred for 20 min, the solvent was removed in vacuo. The residue was dissolved in $CH_2Cl_2$ (20 mL). The mixture was filtered, and the solvent was removed under reduce pressure to give the residue, which was purified by HPLC to give compound 30 (4.9 mg, yield 14%) as a white solid. LC-MS $t_R$=1.017 min and 1.078 min in 2 min chromatography, MS (ESI) m/z 368[M+H]$^+$; $^1$H NMR ($CD_3OD$ 400 MHz): δ 7.63-7.77 (m, 1H), 7.51 (m, 1H), 7.40-7.48 (m, 1H), 7.10-7.14 (m, 4H) 3.32 (s, 3H), 2.97-3.12 (m, 3H), 2.77-2.84 (s, 2H), 2.05 (m, 1H), 1.83-1.92 (m, 2H), 1.55-1.69 (m, 2H).

Example 22

Preparation of Compound 61

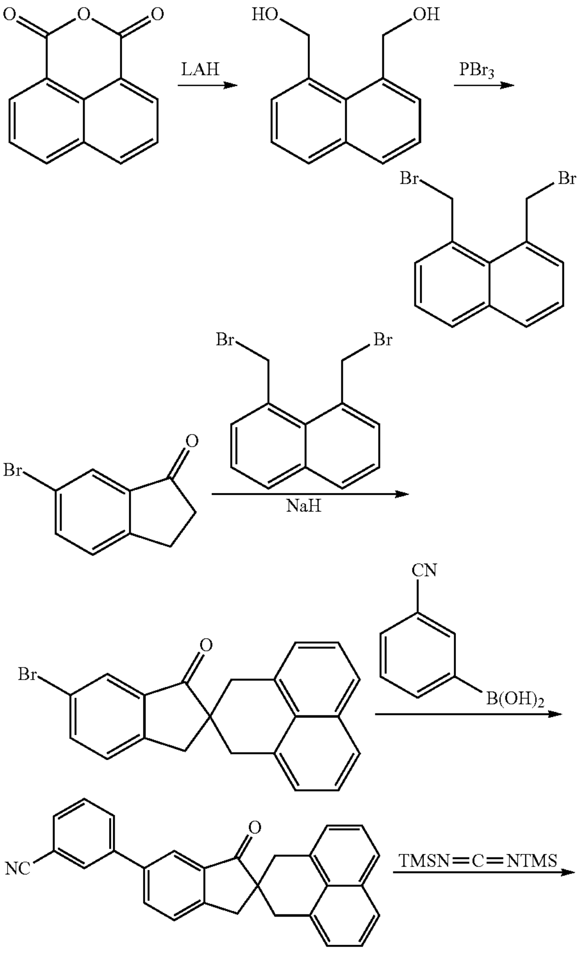

-continued

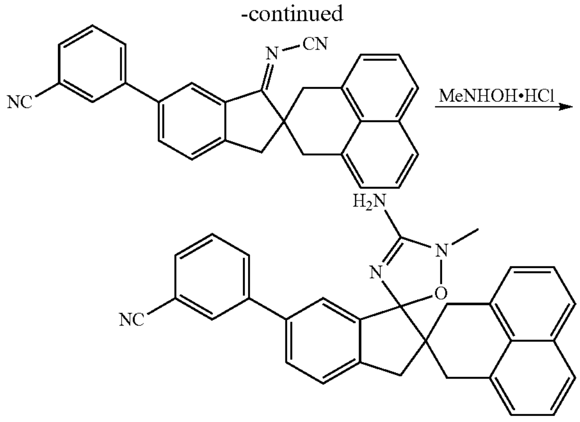

Experimental Data:

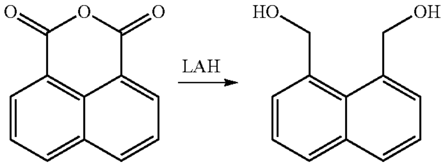 [SMILES: O=C1OC(=O)c2cccc3cccc1c23 ; OCc1cccc2cccc(CO)c12]

Step 1. (8-hydroxymethyl-naphthalen-1-yl)-methanol

Benzo[de]isochromene-1,3-dione (30 g, 0.15 mol) in anhydrous THF (300 mL) was added dropwise to a solution of LAH (10 g, 0.38 mol) in anhydrous THF (200 mL). The result reaction mixture was refluxed for 3 h, then allowed to cool and stand overnight at room temperature. Water and 10% aq. NaOH was added dropwise, filtered. The filtrate was concentrated in vacuum to give the crude product, which was used directly without purification (1.15 g, crude). $^1$H-NMR ($CDCl_3$): 5.06 (m, 4H), 5.23 (m, 2H), 7.42 (m, 2H), 7.60 (m, 2H), 7.82 (m, 2H).

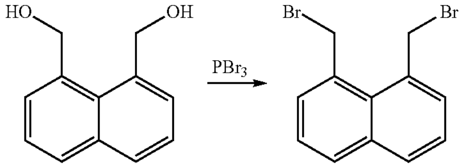

Step 2. 1,8-bis-bromomethyl-naphthalene

A mixture of naphthalene-1,8-diyldimethanol (1.15 g, 6 mmol) and $CH_2Cl_2$ (10 mL) was stirred mechanically and $PBr_3$ (1.2 mL) added dropwise over 20 mins. During the first half of the addition the solution refluxed spontaneously. After stirring overnight at room temperature, water was added dropwise with stirring over 20 min, which again caused refluxing and evolution of much HBr. After stirring for an additional 2 h, water was added and the layers separated and the organic layer washed with water. The organic layer was evaporated in vacuum to give the crude product, which was used directly without purification (1.6 g, 84%). $^1$H-NMR ($CDCl_3$): 5.30 (s, 4H), 7.44 (m, 2H), 7.62 (m, 2H), 7.87 (m, 2H).

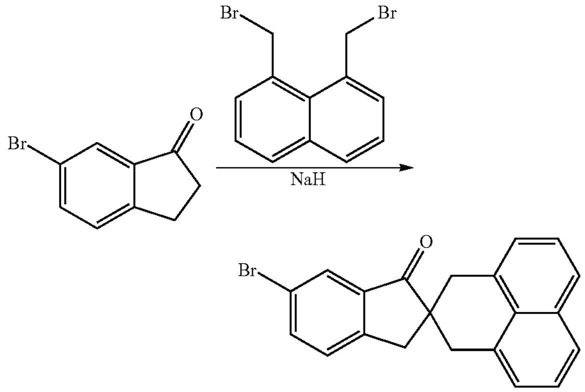

Step 3. 6-bromo-1',3'-dihydrospiro[indene-2,2'-phenalen]-1(3H)-one

A mixture of 6-bromo-2,3-dihydro-1H-inden-1-one (400 mg, 1.9 mmol) and 1,8-bis(bromomethyl)naphthalene (596 mg, 1.9 mmol) in THF (20 mL) was added NaH (152 mg, 3.8 mmol) at room temperature, the mixture was heated under reflux for 2 h. The mixture was quenched with water, concentrated, then extracted with $CH_2Cl_2$, washed with brine, dried over $Na_2SO_4$ and concentrated to give 6-bromo-1',3'-dihydrospiro[indene-2,2'-phenalen]-1(3H)-one (386 mg, 56%). $^1$H-NMR ($CDCl_3$): 2.79 (d, 2H), 3.50 (d, 2H), 7.12 (m, 1H), 7.18 (m, 2H), 7.36 (m, 2H), 7.60 (m, 1H), 7.71 (m, 1H), 7.92 (m, 1H).

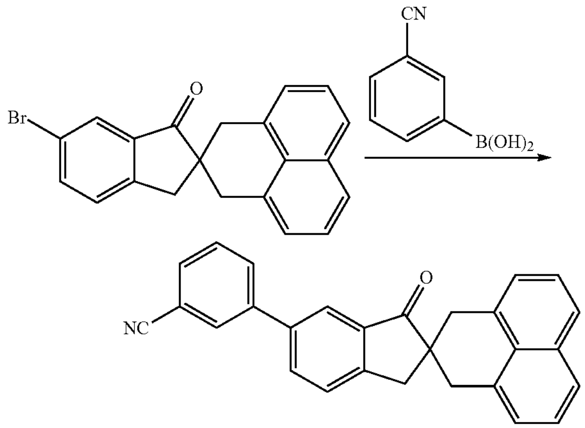

Step 4. 3-(1-oxo-1,1',3,3'-tetrahydrospiro[indene-2,2'-phenalene]-6-yl)benzonitrile 6-Bromo-1',3'-dihydrospiro[indene-2,2'-phenalen]-1(3H)-one (200 mg, 0.57 mmol) and 3-cyanophenylboronic acid (168 mg, 1.17 mmol) was dissolved in 1,4-dioxane (5 mL), $Cs_2CO_3$ (0.6 mL, 2 M) was added. Then $Pd(PPh_3)_2Cl_2$ (10 mg) was added under $N_2$. The mixture was heated at 100° C. for 10 minutes under microwave. The solvent was removed in vacuum. The crude product was purified by preparative TLC to give 3-(1-oxo-1,1',3,3'-tetrahydrospiro[indene-2,2'-phenalene]-6-yl)benzonitrile (130 mg, 60%).

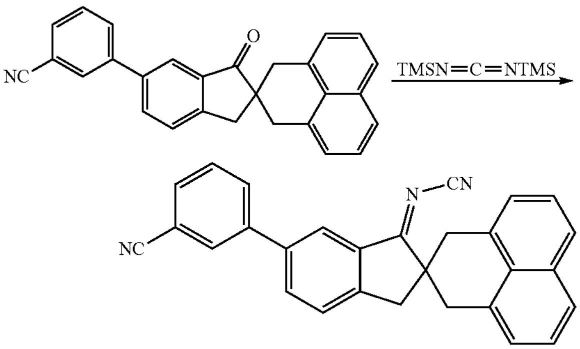

Step 5. (E)-N-(5-(3-cyanophenyl)-1',3'-dihydrospiro[indene-2,2'-phenalene]-3(1H)-ylidene)cyanamide To a solution of 3-(1-oxo-1,1',3,3'-tetrahydrospiro[indene-2,2'-phenalene]-6-yl)benzonitrile (130 mg, 0.34 mmol) in DCM (2 mL) was $TiCl_4$ (257 mg, 1.35 mmol), then the mixture was heated at 50° C. for 5 minutes under microwave. Then the reagent was added, and it was heated at 60° C. for 10 minutes. The reaction mixture was poured into ice-water, and then extracted with DCM. The organic layer was washed with brine, dried and concentrated to give the crude product. The crude product was used directly without purification (70 mg, crude).

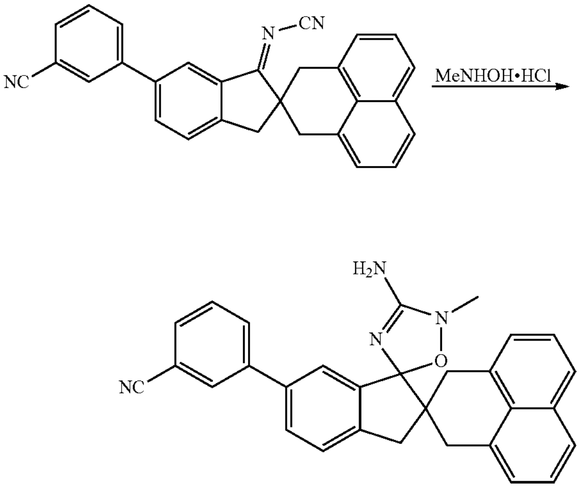

Step 6. Compound 61

To a solution of MeNHOH.HCl in anhydrous MeOH was added NaOMe (25% in MeOH) followed by (E)-N-(5-(3-cyanophenyl)-1',3'-dihydrospiro[indene-2,2'-phenalene]-3(1H)-ylidene)cyanamide (35 mg, 0.085 mmol). After stirring for 10 minutes, the solvent was removed in vacuum. The residue was dissolved in DCM. The mixture was filtered and the solvent was removed in vacuum. The crude product was purified by preparative HPLC to give compound 61 (1.02 mg, 3%). $^1$H-NMR (MeOD): 2.76 (m, 1H), 2.97 (m, 1H), 3.06 (s, 2H), 3.28 (m, 3H), 3.41 (m, 1H), 3.58 (m, 1H), 7.18 (m, 1H), 7.26 (m, 1H), 7.36 (m, 2H), 7.58 (m, 1H), 7.68 (m, 2H), 7.72 (m, 1H), 7.81 (m, 1H), 7.90 (m, 1H), 7.98 (m, 1H)

Example 23

Preparation of Compound 40

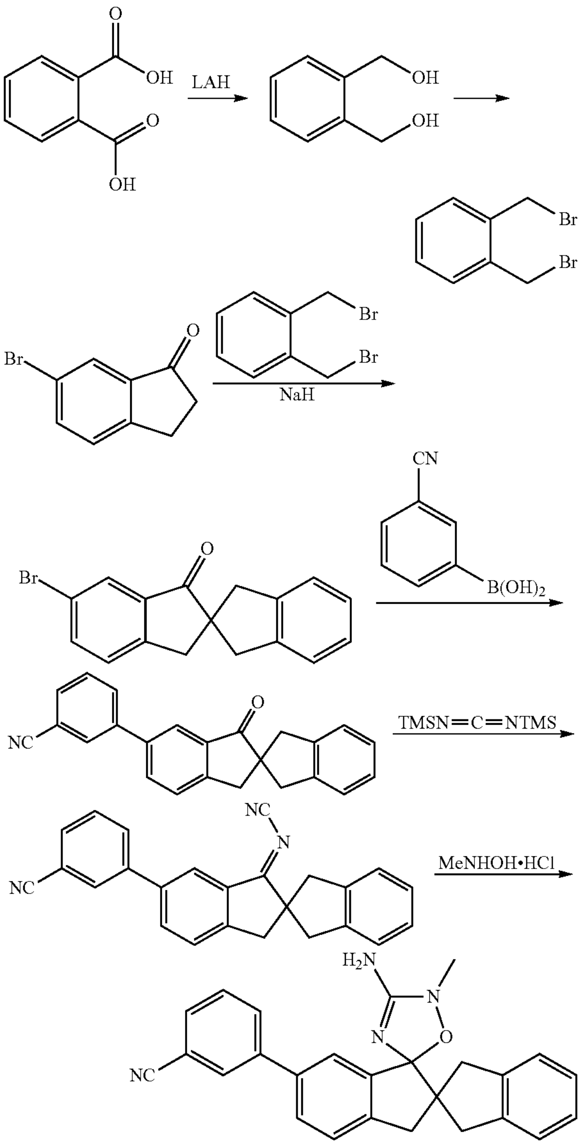

Experimental Data:

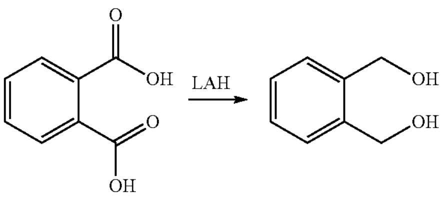 [SMILES: O=C(O)c1ccccc1C(=O)O ; OCc1ccccc1CO]

Step 1. 1,2-phenylenedimethanol

A solution of phthalic acid (9 g, 0.05 mol) in anhydrous THF (200 mL) was added to LAH (7.6 g, 0.2 mol) in THF (250 mL) dropwise, and the mixture was refluxed for 18 hours. The mixture was cooled in ice bath and carefully added water dropwise, followed by 50% NaOH (150 mL), and then removed the ice bath added water slowly with stirring until the gray precipitate turns white. The mixture was filtrated and the filtrate was concentrated to give crude 1,2-phenylene-dimethanol (7 g, 92%).

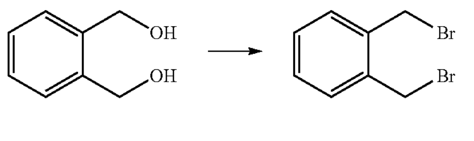 [SMILES: OCc1ccccc1CO ; BrCc1ccccc1CBr]

Step 2. 1,2-bis(bromomethyl)benzene

To a solution of 1,2-phenylenedimethanol (2.6 g, 17 mmol), perbromo methane (13.7 g, 41.8 mmol) in DCM (100 mL) was added triphenylphosphine (10.95 g, 41.8 mmol) at 0° C., the mixture was stirred at room temperature for 18 hours. The mixture was concentrated, redissolved by $Et_2O$, filtered, the organic layer was concentrated to give crude 1,2-bis(bromomethyl)benzene (4.2 g, 89%).

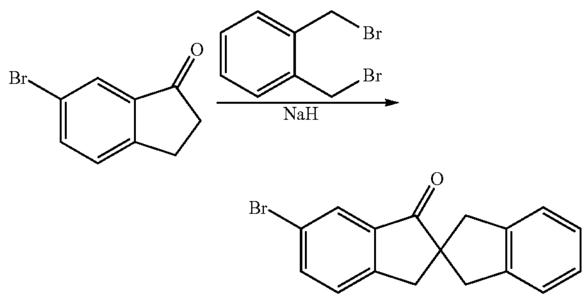

Step 3. 6-bromo-1',3'-dihydro-2,2'-spirobi[inden]-1 (3H)-one

A mixture of 6-bromo-indan-1-one (1.05 g, 5 mmol), 1,2-bis(bromomethyl)benzene (1.31 g, 5 mmol) in THF (50 mL) was added NaH (240 mg, 10 mmol) at room temperature, the mixture was refluxed for 2 hours. The mixture was quenched with water, concentrated, then extracted with DCM, washed with brine, dried over $Na_2SO_4$, concentrated to 6-bromo-1',3'-dihydro-2,2'-spirobi[inden]-1(3H)-one (1.8 g, 33%).

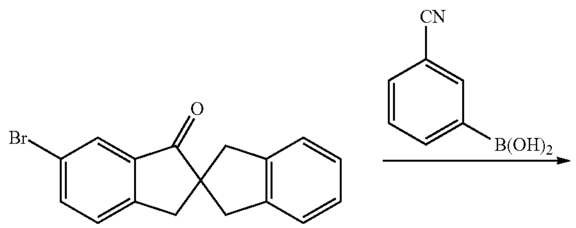

-continued

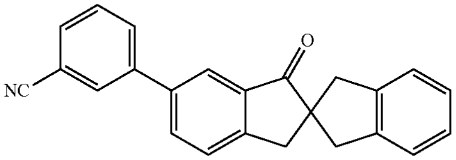

Step 4. 3-(1-oxo-1,1',3,3'-tetrahydro-2,2'-spirobi[indene]-6-yl)benzonitrile

6-Bromo-1',3'-dihydro-2,2'-spirobi[inden]-1(3H)-one (314 mg, 1 mmol), 3-cyanophenylboronic acid (294 g, 2 mmol) in [1,4]-dioxane (12 mL), $Cs_2CO_3$ (2 N, 3.2 mL), then $Pd(PPh_3)_2Cl_2$ (5 mg, 0.01 mmol) was added under $Ar_2$, the mixture was stirred at 100° C. for 5 minutes under microwave. The reaction mixture was concentrated in vacuo to give the residue, which was purified by TLC to give 3-(1-oxo-1,1',3,3'-tetrahydro-2,2'-spirobi[indene]-6-yl)benzonitrile (34 mg, 10%). $^1$H-NMR ($CDCl_3$): 3.00 (d, 2H), 3.33 (s, 2H), 3.62 (d, 2H), 7.31 (m, 3H), 7.67 (m, 2H), 7.78 (m, 1H), 7.96 (m, 2H), 8.02 (m, 1H), 8.11 (m, 1H).

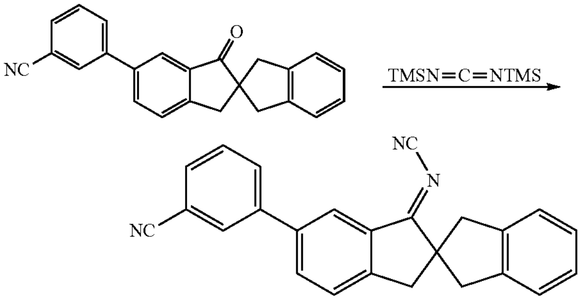

Step 5. (Z)—N-(5-(3-cyanophenyl)-1',3'-dihydro-2,2'-spirobi[indene]-3(1H)-ylidene)cyanamide To a solution of 3-(1-oxo-1,1',3,3'-tetrahydro-2,2'-spirobi[indene]-6-yl)benzonitrile (34 mg, 0.1 mmol) in DCM (5 mL) was added $TiCl_4$ (76 mg, 0.4 mmol) dropwise, the mixture was stirred at 50° C. at $Ar_2$ under microwave for 5 minutes, N,N'-methanediylidenebis(1,1,1-trimethylsilanamine) (74 mg, 0.4 mmol) was added dropwise. The mixture was stirred at 60° C. at $Ar_2$ under microwave for 10 minutes and poured into ice-water (10 mL). The aqueous layer was extracted with $CH_2Cl_2$, which was combined with the organic layer. The organic layer was dried and concentrated to give crude ((Z)—N-(5-(3-cyanophenyl)-1',3'-dihydro-2,2'-spirobi[indene]-3(1H)-ylidene)cyanamide (36 mg, 99%).

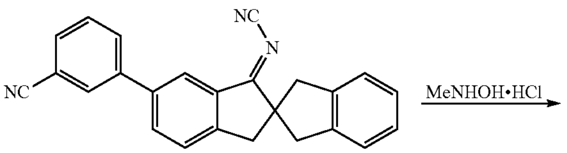

-continued

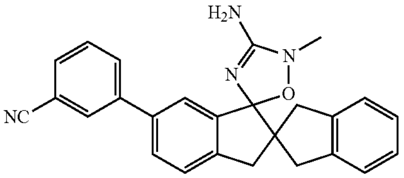

Step 10. Compound 40

To a solution of N-methyl-hydroxylamine hydrochloride (11 mg, 0.134 mmol) in MeOH (5 mL) was added MeONa (0.026 mL, 25% (Wt.) in MeOH), followed by (Z)—N-(5-(3-cyanophenyl)-3',4'-dihydro-1'H-spiro[indene-2,2'-naphthalene]-3(1H)-ylidene)cyanamide (50 mg, 0.13 mmol). After stirred for 10 minutes, the solvent was removed in vacuo. The residue was purified by preparative TLC, and then HPLC to give compound 40 (2.19 mg, 5%). $^1$H-NMR (MeOD): 2.79 (m, 1H), 2.91 (m, 1H), 3.02-3.19 (m, 3H), 3.25 (s, 3H), 3.48 (m, 1H), 7.17 (m, 4H), 7.45 (m, 1H), 7.63 (m, 1H), 7.75 (m, 3H), 8.02 (m, 2H).

Example 24

Preparation of Compound 54

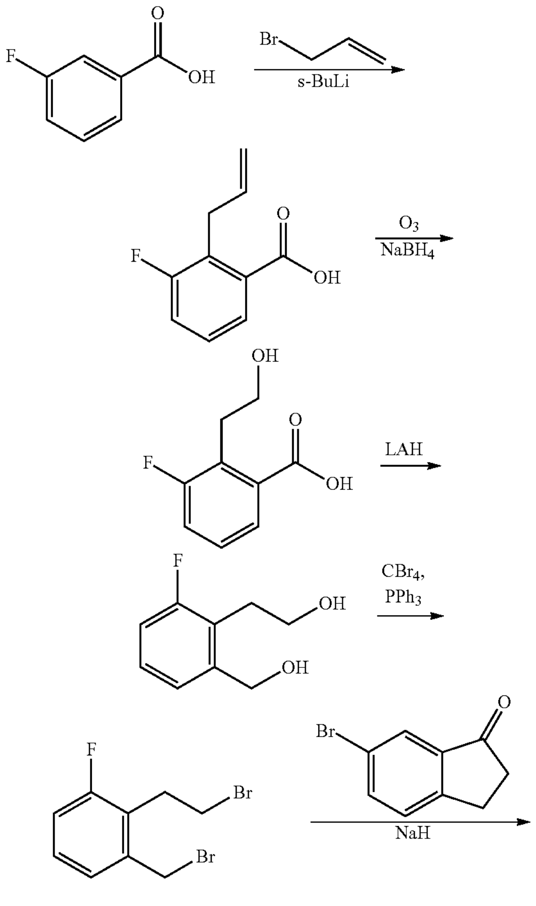

-continued

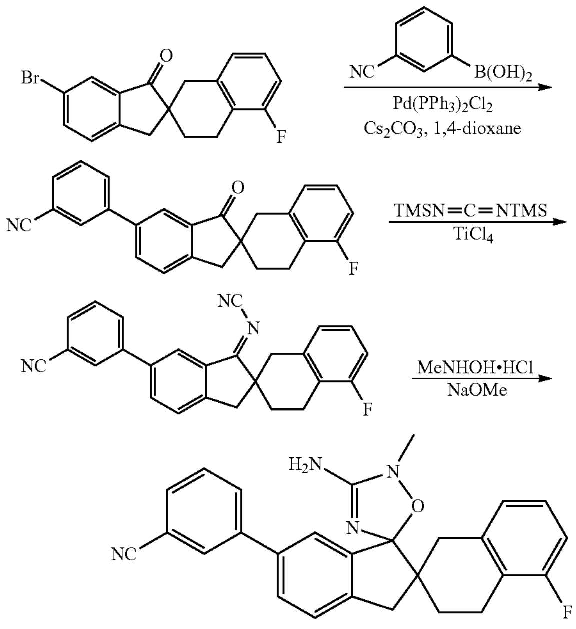

Experimental Data:

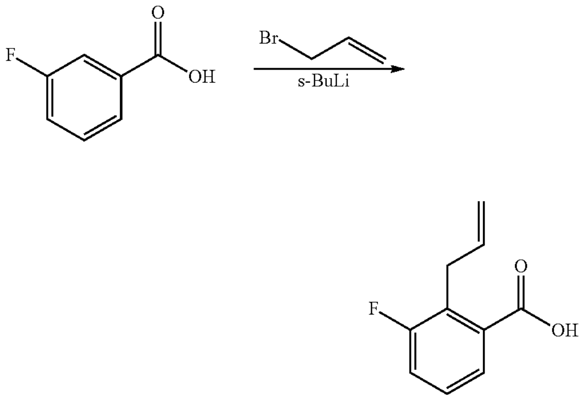

54a

Preparation of Compound 54a

To a solution of TMEDA (25.5 g, 0.22 mol) in dry THF (150 mL) was added s-BuLi (1.3 M, 0.22 mol, 169 mL) at −78° C. The mixture was stirred at this temperature for 0.5 hour, and a solution of 3-fluorobenzoic acid (14 g, 0.1 mol) in THF (50 mL) was added dropwise. After being stirred for 1 hour, CuBr/DMS (3.09 g, 0.015 mol, 15% mol) was added, followed by addition of 3-bromoprop-1-ene (36 g, 0.3 mol) in 50 mL of THF. The reaction mixture was warmed to room temperature, and quenched with water. The aqueous layer was washed with $Et_2O$, and acidified with 4 N HCl. The mixture was extracted with $Et_2O$. The organic layer was washed with brine, dried over $Na_2SO_4$, filtered, and concentrated to give compound 54a (14.2 g, 79%). $^1$H NMR (400 MHz $CDCl_3$): δ7.87 (d, 1H), 7.35 (m, 2H), 6.03 (m, 1H), 5.06 (d, 1H), 5.03 (s, 1H), 3.87 (d, 2H).

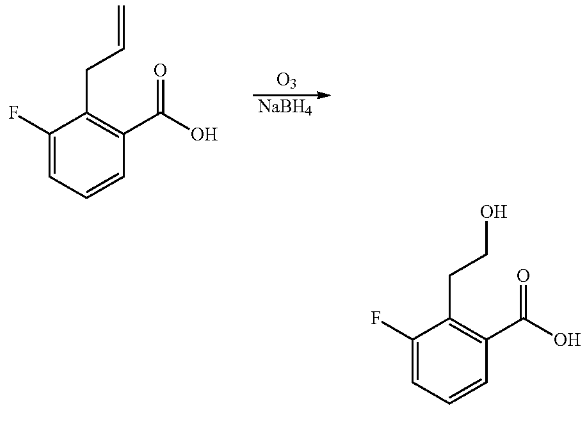

54b

Preparation of Compound 54b

A steam of $O_3$ was bubbled through a solution of 2-allyl-3-fluorobenzoic acid (8.0 g, 0.044 mol) in absolute methanol (50 mL) at −78° C. until the mixture was turned to blue. The ozonide solution was added dropwise to an ice-cold solution of NaOH (0.066 mol, 2.64 g) and $NaBH_4$ (0.22 mol, 8.2 g) in 50% aqueous ethanol (50 mL). The mixture was stirred at room temperature overnight, and concentrated. Water was added at 0° C., and the mixture was acidified by adding 6 N HCl, and extracted with EtOAc. The organic layer was washed with brine, dried over $Na_2SO_4$, filtered, and concentrated to give the compound 54b (6 g, crude).

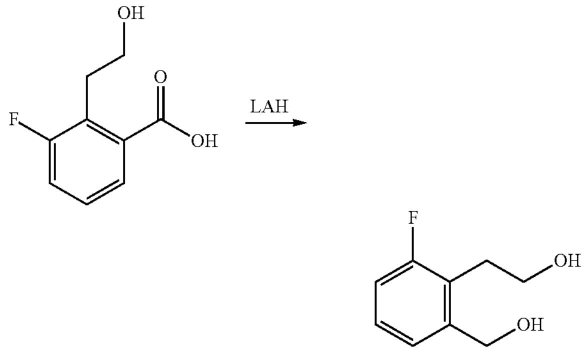

54c

Preparation of Compound 54c

To a solution of $LiAlH_4$ (2.76 g, 0.072 mol) in THF (50 mL) was added 3-fluoro-2-(2-hydroxyethyl)-benzoic acid (6 g, 0.036 mol) in THF (30 mL) at 0° C. The mixture was stirred at room temperature overnight, quenched with 3 mL of $H_2O$, followed by addition of 3 mL of 10% aqueous NaOH solution. The solution was filtered, and the filtrate was concentrated, the residue was purified by chromatography to give the compound 54c (2.5 g, 41%). $^1H$ NMR (400 MHz $CDCl_3$): δ7.24 (m, 1H), 7.13 (m, 1H), 7.03 (m, 1H), 4.59 (s, 2H), 3.86 (t, 2H), 3.02 (m, 4H).

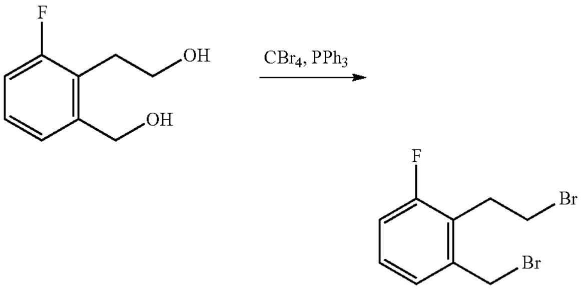

54d

Preparation of Compound 54d

To a solution of 2-(2-fluoro-6-(hydroxymethyl)phenyl) ethanol (3 g, 17.5 mmol) and $CBr_4$ (14.4 g, 43.9 mmol) in DCM (10 mL) was added $PPh_3$ (11.5 g, 43.9 mmol) at 0° C. in portions. The mixture was stirred at room temperature overnight, and concentrated. The residue was dissolved in $Et_2O$ and filtered. The filtrate was concentrated to give the crude product, which was purified by chromatography to afford the compound 54d (2.5 g, 48%). $^1H$ NMR (400 MHz $CDCl_3$): δ7.23 (m, 1H), 7.17 (m, 1H), 7.04 (m, 1H), 4.58 (s, 2H), 3.62 (t, 2H), 3.33 (t, 2H).

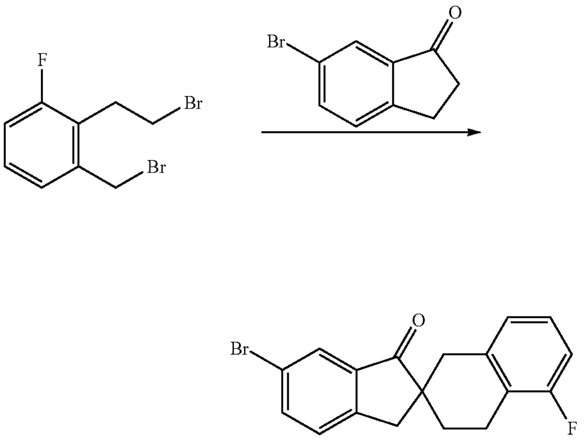

54e

Preparation of Compound 54e

To a solution of 2-(2-bromoethyl)-1-(bromomethyl)-3-fluorobenzene (500 mg, 1.69 mmol) and 6-bromo-2,3-dihydro-1H-inden-1-one (356 mg, 1.69 mmol) in THF (20 mL) was added NaH (102 mg, 2.54 mmol), and the mixture was refluxed for 2 hour. The reaction was cooled, and quenched with ice-water. The mixture was extracted with EtOAc. The organic layer was washed with brine, dried over $Na_2SO_4$, filtered, and concentrated, the residue was purified by preparative TLC to afford the compound 54e (210 mg, 36%). $^1H$ NMR (400 MHz $CDCl_3$): δ7.79 (s, 1H), 7.62 (d, 1H), 7.24 (m, 1H), 7.03 (m, 1H), 6.79 (m, 2H), 2.95-3.13 (m, 3H), 2.76 (m, 2H), 2.49 (d, 1H), 2.02 (m, 1H), 1.71 (m, 1H).

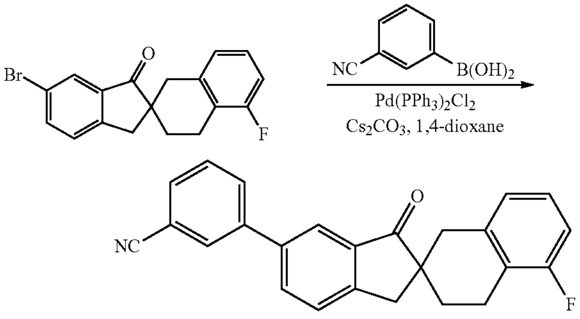

54f

Preparation of Compound 54f $Pd(PPh_3)_2Cl_2$ (10 mg) in a 10 mL of flask under $N_2$ was treated sequentially with a solution 6-bromo-5'-fluoro-3',4'-dihydro-1'H-spiro[indene-2,2'-naphthalen]-1(3H)-one (100 mg, 0.29 mmol) in 1,4-dioxane (1 mL), $Cs_2CO_3$ (2 N, 0.3 mL), and 3-cyanophenylboronic acid (64 mg, 0.43 mmol). The mixture was heated at 100° C. under $N_2$ in microwave for 10 minutes, concentrated in vacuo, and purified by preparative TLC to give the compound 54f (100 mg, 94%). $^1$H NMR (400 MHz $CDCl_3$): δ7.94 (s, 1H), 7.82 (m, 1H), 7.77 (m, 2H), 7.63 (m, 1H), 7.51 (m, 2H), 7.04 (m, 1H), 6.82 (m, 2H), 3.11 (m, 3H), 2.88 (d, 1H), 2.76 (m, 1H), 2.52 (d, 1H), 2.08 (m, 1H), 1.73 (m, 1H).

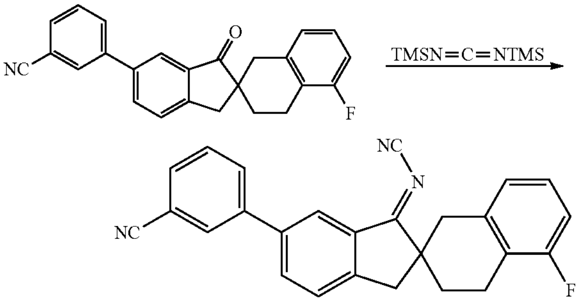

54g

Preparation of Compound 54g

To a solution of 3-(5'-fluoro-1-oxo-1,3,3',4'-tetrahydro-1'H-spiro[indene-2,2'-naphthalene]-6-yl)benzonitrile (100 mg, 0.29 mmol) in dried $CH_2Cl_2$ (1 mL) was added $TiCl_4$ (1 M solution in DCM, 0.817 mmol) dropwise within 15 minutes. This mixture was heated at 50° C. under $N_2$ in microwave for 10 minutes, added bis-trimethlysilylcarbodiimide (206 mg, 1.09 mmol) dropwise, heated at 60° C. under $N_2$ in microwave for another 10 minutes, poured into ice-water, and extracted with $CH_2Cl_2$. The combined organic layer was washed with brine, dried over $Na_2SO_4$, filtered, and concentrated to give the compound 54g (105 mg, crude), which was used for the next step without further purification.

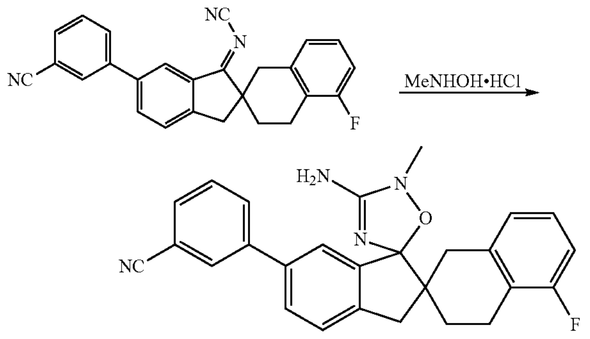

Preparation of Compound 54

To a solution of MeNHOH.HCl (22.5 mg, 0.269 mmol) in anhydrous MeOH (5 mL) was added NaOMe (25 wt % in MeOH, 53 mg, 0.242 mmol) and (Z)—N-(5-(3-cyanophenyl)-5'-fluoro-3',4'-dihydro-1'H-spiro[indene-2,2'-naphthalene]-3(1H)-ylidene)cyanamide (105 mg, 0.269 mmol). After being stirred for 20 minutes, the solvent was removed in vacuum, and the residue was dissolved in $CH_2Cl_2$. After filteration, the filtrate was concentrated, and the residue was purified by preparative TLC and preparative HPLC to afford compound 54 (25 mg, 21%). $^1$H NMR (400 MHz $CD_3OD$): δ7.92-8.01 (m, 2H), 7.62-7.83 (m, 4H), 7.39 (m, 1H), 7.14 (m, 1H), 6.88 (m, 2H), 3.38 (d, 3H), 3.28 (m, 1H), 3.02 (m, 2H), 2.48-2.84 (m, 3H), 1.89-2.23 (m, 2H); ESI MS: m/z 439 $[M+H]^+$.

Example 25

Preparation of Compound 43

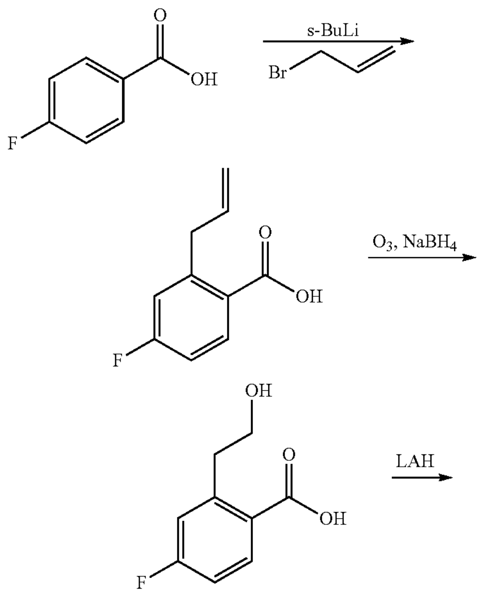

-continued

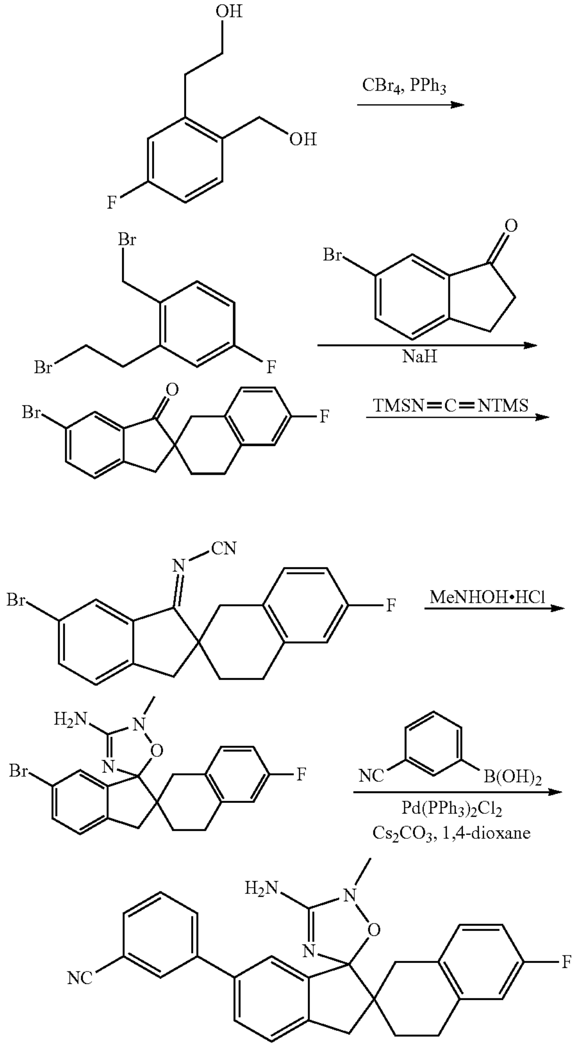

Experimental Data:

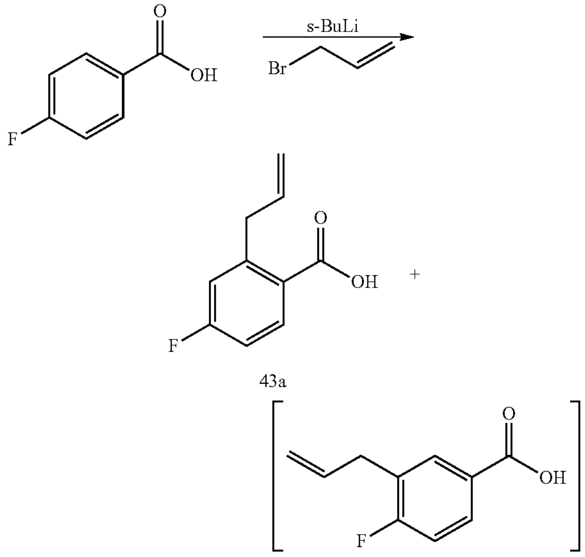

43a

43aA

Preparation of Compound 43a

To a solution of TMEDA (33 mL, 0.22 mol) in dry THF (150 mL) was added s-BuLi (1.3 M, 0.22 mol, 169 mL) at −78° C. The mixture was stirred at this temperature for 0.5 hour, and a solution of 4-fluorobenzoic acid (14 g, 0.1 mol) in THF (50 mL) was added dropwise. After being stirred for 1 hour, CuBr.DMS (3.09 g, 0.015 mol, 15% mol) was added, followed addition of 3-bromoprop-1-ene (36 g, 0.3 mol) in 50 mL of THF. The reaction mixture was warmed to room temperature, and quenched with water. The aqueous layer was washed with $Et_2O$, acidified with 4 N HCl, and extracted with $Et_2O$. The organic layer was washed with brine, dried over $Na_2SO_4$, filtered, and concentrated to give the mixture of compound 43a and compound 43aA (10 g, 55%).

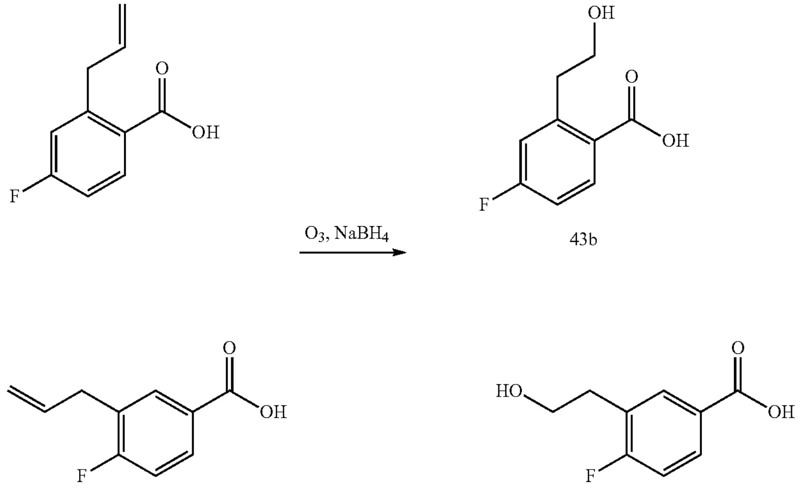

43b

43bA

Preparation of Compound 43b

A steam of $O_3$ was bubbled through a solution of 2-allyl-4-fluoro-benzoic acid (5.0 g, 27.6 mmol) in absolute methanol (30 mL) at −78° C. until the mixture was turned to blue. $NaBH_4$ (3 g, 82.9 mmol) was added, and the mixture was stirred at room temperature overnight. The solution was concentrated, water was added at 0° C., and the mixture was acidified by adding 6 N HCl. The mixture was extracted with EtOAc, and the organic layer was washed with brine, dried over $Na_2SO_4$, filtered, and concentrated to give the mixture of compounds 43b and 43bA (3.8 g, crude).

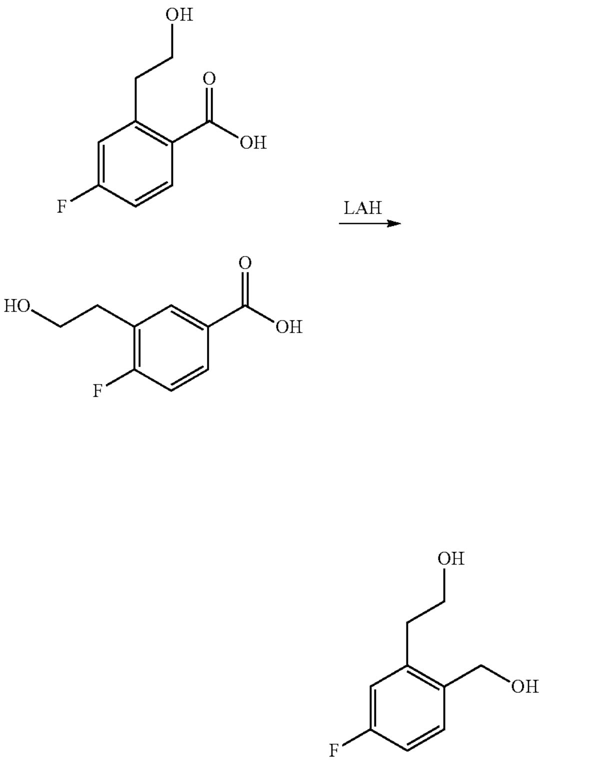

43c

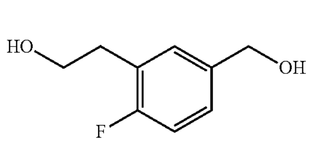

43cA

Preparation of Compound 43c

To a solution of $LiAlH_4$ (1.2 g, 31 mmol) in THF (15 mL) was added 4-fluoro-2-(2-hydroxy-ethyl)-benzoic acid (3.8 g, 20.7 mmol) in THF (30 mL) at 0° C. The mixture was stirred at room temperature overnight, quenched with 1.2 mL of $H_2O$, followed by addition of 1.2 mL of 10% aqueous NaOH solution. The solution was filtered, and the filtrate was concentrated, the residue was purified by chromatography to give the mixture of compounds 43c and 43cA (1.1 g, 31%). $^1H$ NMR (400 MHz $CDCl_3$): δ7.21 (m, 0.5H), 7.12 (m, 1H), 6.94 (m, 0.5H), 6.84 (m, 2H), 4.53 (m, 1H), 4.51 (m, 2H), 3.77 (m, 2H), 3.75 (m, 1H), 2.87 (m, 2H), 2.81 (m, 1H).

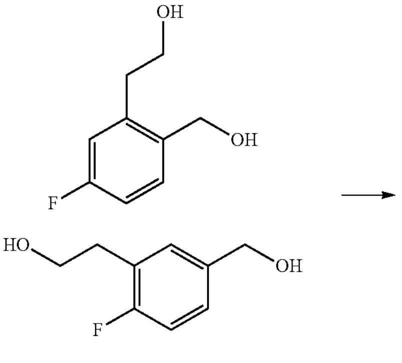

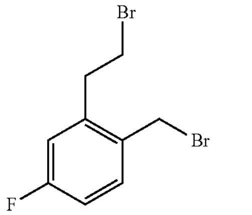

43d

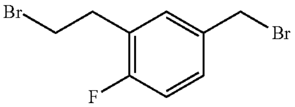

43dA

Preparation of Compound 43d

To a solution of 2-(5-fluoro-2-hydroxymethyl-phenyl)-ethanol (1.1 g, 6.5 mmol) and $CBr_4$ (5.3 g, 16.2 mmol) in DCM (30 mL) was added $PPh_3$ (4.2 g, 16.2 mmol) at 0° C. in portions. The mixture was stirred at room temperature overnight, and concentrated. The residue was dissolved in $Et_2O$, and filtered. The filtrate was concentrated to give the crude product, which was purified by chromatography to afford the mixture of compounds 43d and 43dA (2.5 g, 48%). $^1H$ NMR (400 MHz $CDCl_3$): δ7.36 (m, 1H), 7.26 (m, 1H), 7.04 (m, 0.5H), 6.98 (m, 2H), 4.54 (s, 2H), 4.46 (s, 1H), 3.66 (t, 2H), 3.58 (t, 1H), 3.29 (t, 2H), 3.20 (t, 1H).

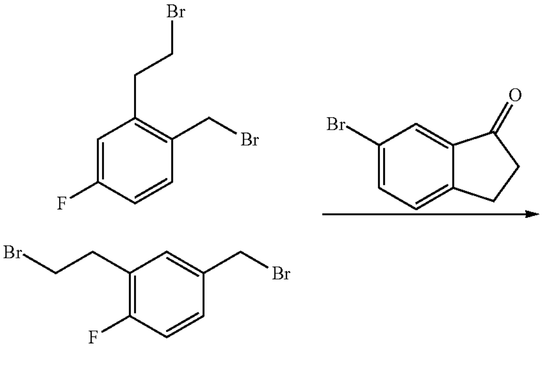

-continued

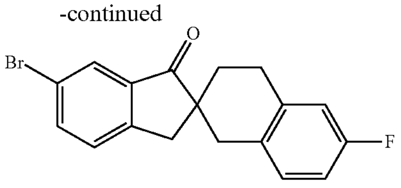

43e

Preparation of Compound 43e

To a solution of 2-(2-bromo-ethyl)-1-bromomethyl-4-fluoro-benzene (500 mg, 1.7 mmol) and 6-bromo-2,3-dihydro-1H-inden-1-one (360 mg, 1.7 mmol) in THF (60 mL) was added NaH (102 mg, 2.6 mmol), and the mixture was refluxed for 1.5 hour. The reaction was cooled, quenched with ice-water, and extracted with EtOAc. The organic layer was washed with brine, dried over $Na_2SO_4$, filtered, and concentrated, the residue was purified by preparative TLC to afford the compound 43e (280 mg, 47%). $^1H$ NMR (400 MHz $CDCl_3$): δ7.89 (s, 1H), 7.62 (d, 1H), 7.23 (m, 1H), 6.95 (m, 1H), 6.76 (m, 2H), 3.04 (m, 2H), 2.90 (m, 3H), 2.77 (m, 1H), 2.42 (m, 1H), 2.04 (m, 1H), 1.64 (m, 1H).

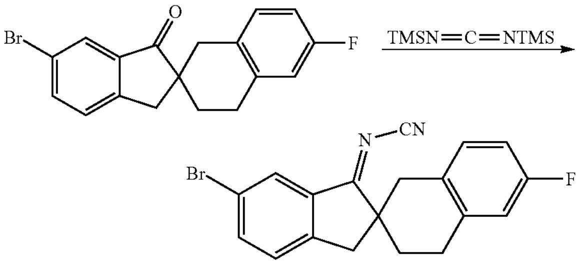

43f

Preparation of Compound 43f

To a solution of 6-bromo-6'-fluoro-3',4'-dihydro-1'H-spiro[indene-2,2'-naphthalen]-1(3H)-one (100 mg, 0.29 mmol) in dried $CH_2Cl_2$ (3 mL) was added $TiCl_4$ (0.87 mL, 1 M solution in DCM, 0.87 mmol) dropwise within 15 minutes at room temperature. After the mixture was stirred for another 1 h, bis-trimehtlysilylcarbodiimide (220 mg, 1.16 mmol) was added dropwise. The resulting mixture was stirred overnight, poured into ice-water, and extracted with $CH_2Cl_2$. The combined organic layer was washed with brine, dried over $Na_2SO_4$, filtered, and concentrated to give the compound 43f (170 mg, crude), which was used for the next step without further purification.

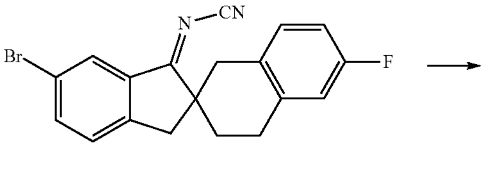

-continued

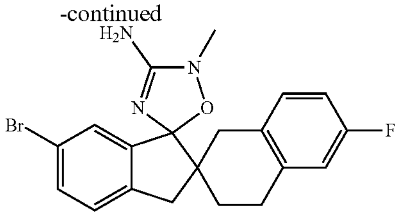

43g

Preparation of Compound 43g

To a solution of MeNHOH.HCl (19.5 mg, 0.23 mmol) in anhydrous MeOH (5 mL) was added NaOMe (25 wt % in MeOH, 45 μL, 0.21 mmol) and (E)-N-(5-bromo-6'-fluoro-3',4'-dihydro-1'H-spiro[indene-2,2'-naphthalene]-3(1H)-ylidene)cyanamide (85 mg, 0.23 mmol). After being stirred for 10 minutes, the solvent was removed in vacuum. The residue was dissolved in $CH_2Cl_2$. After filteration, the filtrate was concentrated, and the residue was purified by preparative TLC and preparative HPLC to afford the compound 43g (30 mg, 32%). $^1H$ NMR (400 MHz $CD_3OD$): δ7.92-8.01 (m, 2H), 7.62-7.83 (m, 4H), 7.39 (m, 1H), 7.14 (m, 1H), 6.88 (m, 2H), 3.38 (d, 3H), 3.28 (m, 1H), 3.02 (m, 2H), 2.48-2.84 (m, 3H), 1.89-2.23 (m, 2H).

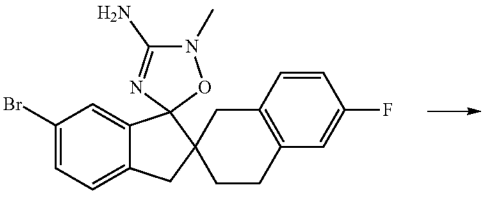

43g

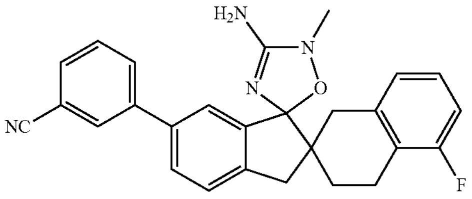

Preparation of Compound 43

$Pd(PPh_3)_2Cl_2$ (10 mg) in a 10 mL of flask under $N_2$ was treated sequentially with the solution of compound 43g (30 mg, 0.07 mmol) in dioxane (1 mL), $Cs_2CO_3$ (2 N, 0.09 mL), and 3-cyanophenylboronic acid (18 mg, 0.12 mmol). The mixture was heated at 100° C. under $N_2$ in microwave for 10 minutes, concentrated, and purified by preparative TLC to give compound 43 (4.69 mg, 15%). $^1H$ NMR (400 MHz $CDCl_3$): δ7.94 (m, 2H), 7.62-7.81 (m, 4H), 7.41 (m, 1H), 7.04 (m, 1H), 6.86 (m, 2H), 3.46 (m, 3H), 3.08 (m, 1H), 3.01 (m, 2H), 2.67-2.81 (m, 2H), 2.45 (m, 0.5H), 2.12 (m, 0.5H), 2.00 (m, 1H), 1.84 (m, 1H); ESI MS: m/z 439 $[M+H]^+$.

Example 26

Preparation of Compound 33

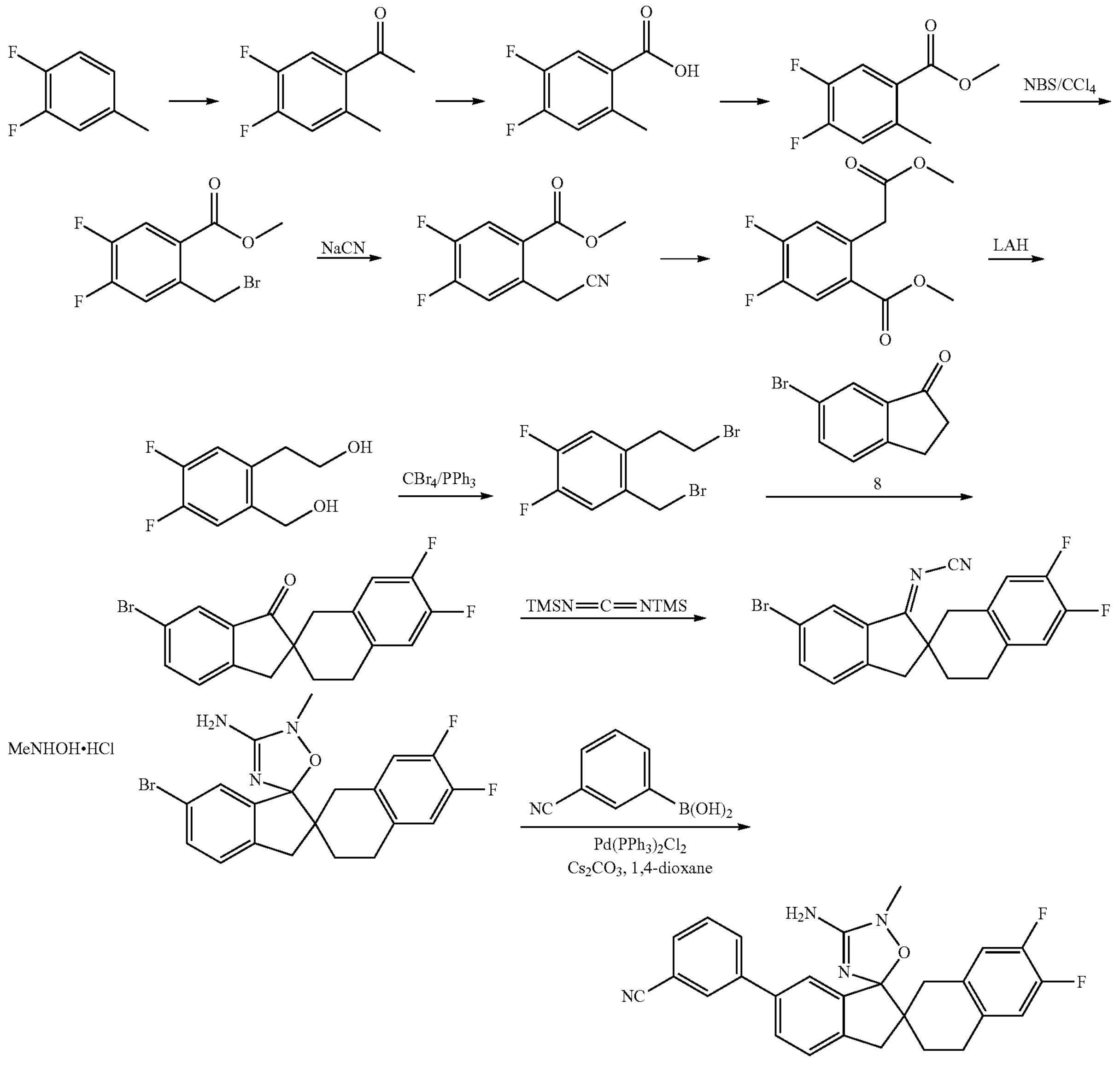

Experimental Data:

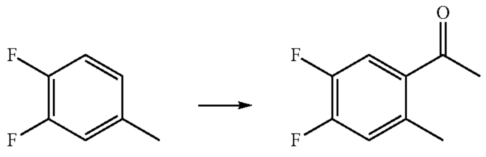

33a

Preparation of Compound 33a

To a solution of $AlCl_3$ (195 g, 1.48 mol) in dichloroethane (200 mL) was added acetyl chloride (103 g, 1.56 mol) and 1,2-difluoro-4-methylbenzene (100 g, 0.78 mol) dropwise in cooling ice bath. After the completion of the addition, the mixture was stirred at room temperature for 5 hours, added to ice water, extracted with DCM, washed with aqueous 5% HCl and saturated $NaHCO_3$ aqueous solution, dried with $Na_2SO_4$, and concentrated to give the crude compound 33a (80 g, crude). $^1$H-NMR (400 MHz $CD_3OD$): δ7.50 (m, 1H), 6.91 (m, 1H), 2.51 (s, 3H), 2.48 (s, 3H).

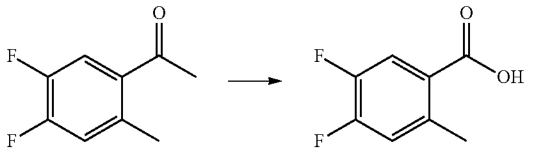

33b

Preparation of Compound 33b

To a solution of 1-(4,5-difluoro-2-methylphenyl)ethanone (44 g, 256 mmol) in dioxane (500 mL) was added NaOCl (63%, 7.3 mmol) at 5° C., and the mixture was stirred in iced water bath for 2 hours. $Na_2SO_3$ was added, and the reaction mixture was extracted with DCM, washed with 20% HCl, dried over $Na_2SO_4$, and filtered. The organic layer was concentrated to give the crude compound 33b (40 g, 90%). $^1$H-NMR (400 MHz $CD_3OD$): δ7.86 (m, 1H), 7.08 (m, 1H), 2.56 (s, 3H), 2.11 (s, 3H).

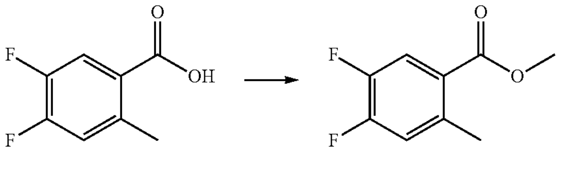

33c

Preparation of Compound 33c

To a solution of 4,5-difluoro-2-methylbenzoic acid (10 g, 0.1 mol) in MeOH (30 mL) was added $H_2SO_4$ (5 mL) dropwise at 0° C., and the mixture was stirred at room temperature overnight. The mixture was acidified to PH=8 with $NaHCO_3$, and the residue was extracted with EA. The organic layer was washed brine, dried over $Na_2SO_4$, and concentrated to give the compound 33c (8.9 g, 82%).

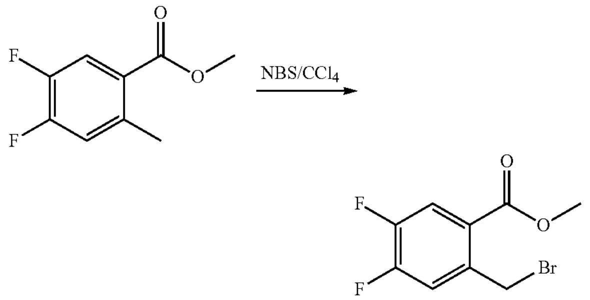

33d

Preparation of Compound 33d

The mixture of methyl 4,5-difluoro-2-methylbenzoate (8.9 g, 48 mmol), NBS (9.35 g, 52.8 mmol) and AIBN (790 mg, 4.8 mmol) in $CCl_4$ (100 mL) was stirred at 80° C. for overnight, and filtrated. The filtrate was extracted with $CHCl_3$, washed with aqueous $NaHCO_3$ and brine, dried over $Na_2SO_4$, and concentrated to give the compound 33d (12.8 g, crude). $^1$H-NMR (400 MHz $CD_3OD$): δ7.84 (m, 1H), 7.32 (m, 1H), 4.91 (s, 2H), 3.95 (s, 3H).

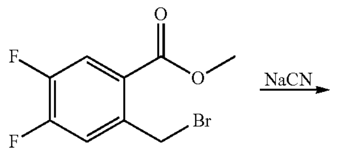

-continued

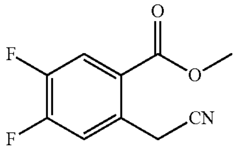

33e

Preparation of Compound 33e

To a solution of methyl 2-(bromomethyl)-4,5-difluorobenzoate (12.8 g, 48 mmol) in MeOH (100 mL) was added NaCN (4.2 N, 11.4 mL) dropwise, and the mixture was stirred at 50° C. for 2 hours. After concentration, the residue was dissolved in EA. The solution was washed with $H_2O$ and brine, dried over $Na_2SO_4$, and concentrated to give the compound 33e (5 g, 50%). $^1$H-NMR (400 MHz $CD_3OD$): δ7.95 (m, 1H), 7.48 (m, 1H), 4.21 (s, 2H), 3.91 (s, 3H).

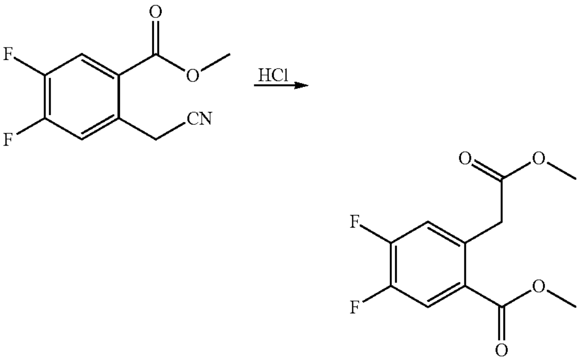

33f

Preparation of Compound 33f

A mixture of methyl 2-(cyanomethyl)-4,5-difluorobenzoate (5 g, 24 mmol) in $H_2SO_4$ (50 mL) was stirred at 100° C. under $N_2$ overnight, cooled to 65° C., added MeOH (50 mL), and stirred for 4 hours. The mixture was cooled, acidified to PH 7-8 with $NaHCO_3$, extracted with EA, washed brine, dried over $Na_2SO_4$, and concentrated to give the compound 33f (5 g, 87%).

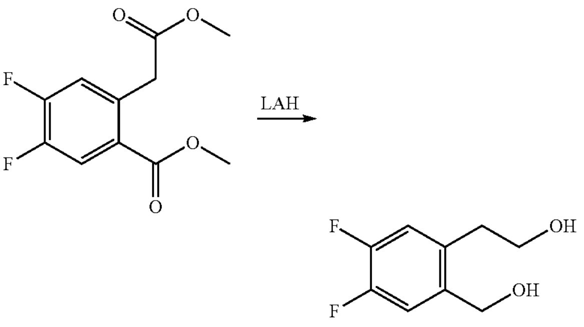

33g

Preparation of Compound 33g

To a solution of 2-(carboxymethyl)-4,5-difluorobenzoic acid (5 g, 20 mmol) in ether (250 mL) was added LAH (3.04 g, 82 mmol), and the mixture was refluxed overnight. The mixture was cooled in ice bath, added water (3 mL) carefully, and followed by addition of 2N NaOH (3 mL). The mixture was filtrated, and the filtrate was concentrated to give the crude compound 33g (3.5 g, 90%).

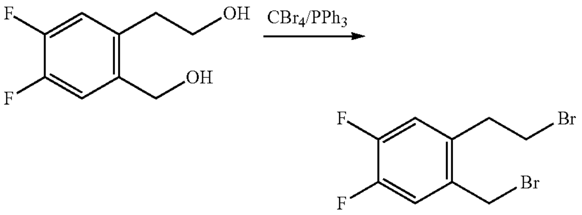

33h

Preparation of Compound 33h

To a solution of 2-(4,5-difluoro-2-(hydroxymethyl)phenyl)ethanol (3.5 g, 18.5 mmol) and tetrabromomethane (15 g, 46.3 mmol) in DCM (100 mL) was added triphenylphosphine (12 g, 46.3 mmol) at 0° C., and the mixture was stirred at room temperature for 18 hours. After concentration, the residue was dissolved in $Et_2O$, the organic layer was concentrated to give the crude compound 33h (2.3 g, 40%). $^1$H-NMR (400 MHz $CD_3OD$): δ7.19 (m, 1H), 7.05 (m, 1H), 4.46 (s, 2H), 3.62 (t, 2H), 3.21 (t, 2H).

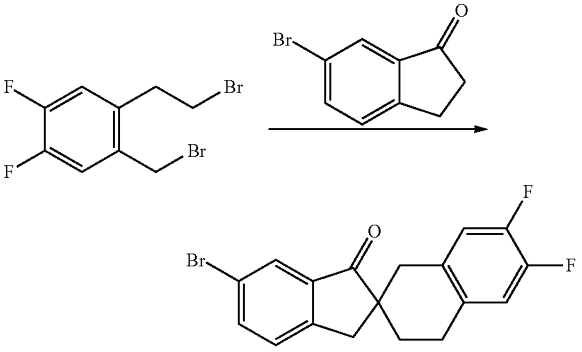

33i

Preparation of Compound 33i

A mixture of 6-bromo-indan-1-one (1.6 g, 7.4 mmol), 1-(2-bromoethyl)-2-(bromomethyl)-4,5-difluorobenzene (2.3 g, 7.4 mmol) in THF (50 mL) was added NaH (360 mg, 15 mmol) at room temperature, and the mixture was refluxed for 2 hours. The mixture was quenched with water, concentrated, extracted with DCM, washed with brine, dried over $Na_2SO_4$, and concentrated to give the compound 33i (600 mg, 22%). $^1$H-NMR (400 MHz $CD_3OD$): δ7.88 (s, 1H), 7.63 (s, 1H), 7.30 (m, 1H), 7.21 (m, 1H), 6.87 (m, 1H), 6.75 (m, 1H), 3.03 (m, 2H), 2.85 (m, 2H), 2.38 (m, 1H), 2.00 (m, 1H), 1.66 (m, 1H), 1.55 (m, 1H).

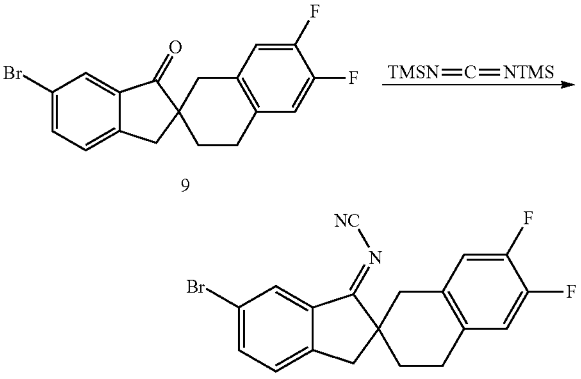

9

33j

Preparation of Compound 33j

To a solution of 3-(6',7'-difluoro-1-oxo-1,3,3',4'-tetrahydro-1'H-spiro[indene-2,2'-naphthalene]-6-yl)benzonitrile (150 mg, 0.41 mmol) in DCM (2 mL) was added $TiCl_4$ (151 mg, 0.83 mmol) dropwise. After the mixture was stirred at 50° C. under $Ar_2$ under microwave for 10 minutes, N,N-methanediylidenebis(1,1,1-trimethylsilanamine) (157 mg, 0.83 mmol) was added dropwise. After being stirred at 60° C. under $Ar_2$ in microwave for 10 minutes, the mixture was poured into ice-water (10 mL). The aqueous layer was extracted with $CH_2Cl_2$, the organic layer was dried and concentrated to give the crude compound 33j (100 mg, 63%).

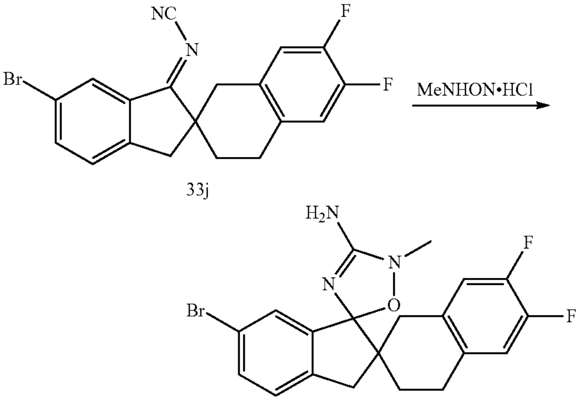

33j

33k

Preparation of Compound 33k

To a solution of N-methyl-hydroxylamine hydrochloride (19 mg, 0.23 mmol) in MeOH (5 mL) was added MeONa (0.05 mL, 25% (Wt.) in MeOH) and compound 33j (100 mg, 0.26 mmol). After being stirred for 10 minutes, the mixture was concentrated in vacuo. The residue was dissolved with DCM, after filtration and concentration, the crude product was purified by preparative TLC to give the compound 33k (58 mg, 52%).

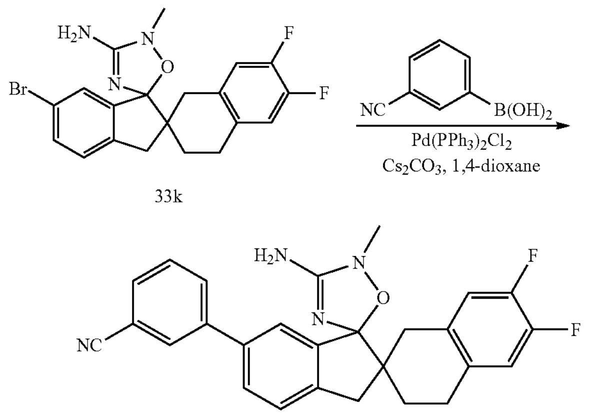

33k

Preparation of Compound 33

The mixture of compound 33k (58 mg, 0.13 mmol), 3-cyanophenylboronic acid (39 mg, 0.26 mmol), $Cs_2CO_3$ (2 N, 0.5 mL), $Pd(PPh_3)_2Cl_2$ (5 mg, 0.01 mmol) in dioxane (2 mL) was refluxed under $Ar_2$ for 30 minutes. After concentration in vacuo, the residue was purified by TLC and HPLC to give compound 33 (2.53 mg, 4.15%). $^1$H-NMR (400 MHz $CD_3OD$): δ7.98 (m, 2H), 7.63-7.82 (m, 4H), 7.40 (m, 1H), 6.89-7.12 (m, 2H), 3.33 (s, 3H), 3.08 (m, 2H), 2.96 (m, 2H), 2.68-2.87 (m, 1.7H), 2.44 (m, 0.6H), 1.75-2.16 (m, 2H); ESI MS: m/z 457 $[M+H]^+$.

Example 27

Preparation of Compound 4

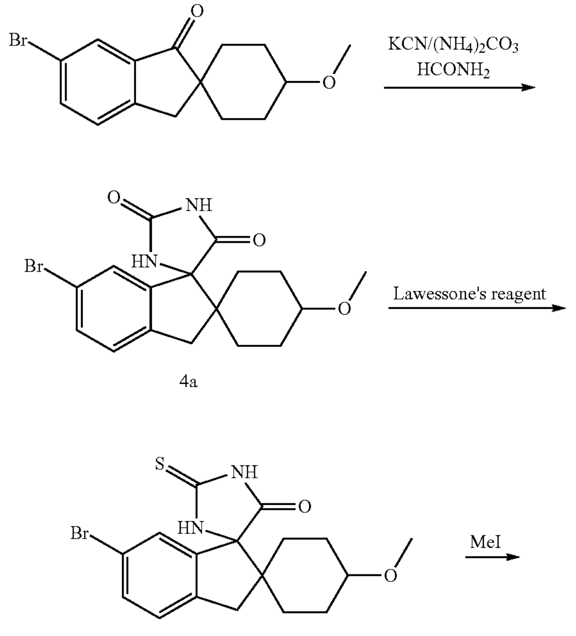

4a

4b

-continued

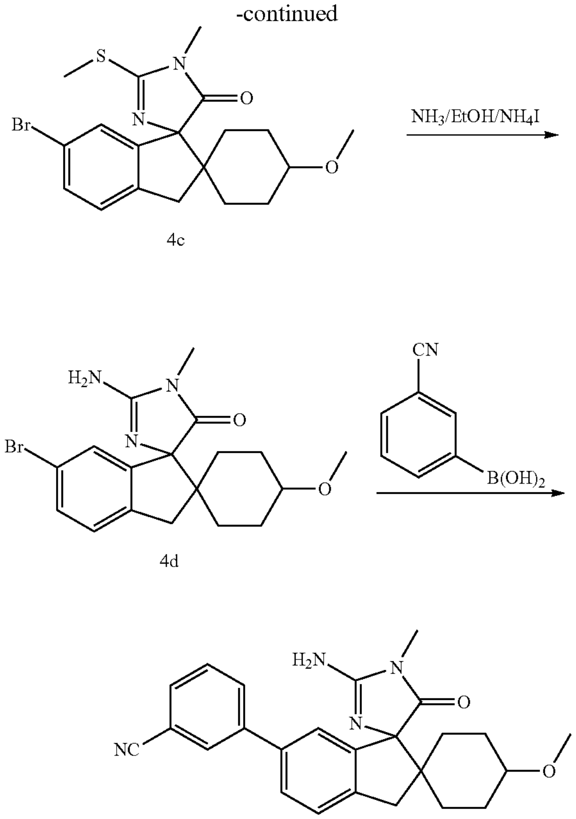

4c

4d

Experimental Data:

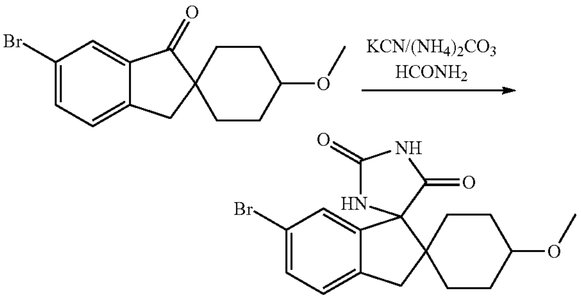

4a

Preparation of Compound 4a

A steel clave was charged with 6'-bromo-4-methoxyspiro [cyclohexane-1,2'-inden]-1'(3'H)-one (500 mg, 1.62 mmol), KCN (211 mg, 3.25 mol), and $(NH_4)_2CO_3$ (1.67 g, 12.15 mol). Formamide (25 mL) was added to fill the tube completely. The mixture was heated at 80° C. for 72 h, cooled, and poured into ice. After acidification with concentrated HCl solution, the mixture was filtrated, the solid was dissolved in ethyl acetate, and washed with water for 2 times. The combined organic phases were dried, and concentrated to give compound 4a (500 mg, 81%), which was used for the next step without purification. $^1$H-NMR ($CDCl_3$): δ7.32 (m, 1H), 7.20 (m, 1H), 7.10 (m, 1H), 3.33 (m, 3H), 3.00 (m, 3H), 2.00 (m, 3H), 1.21-1.41 (m, 5H).

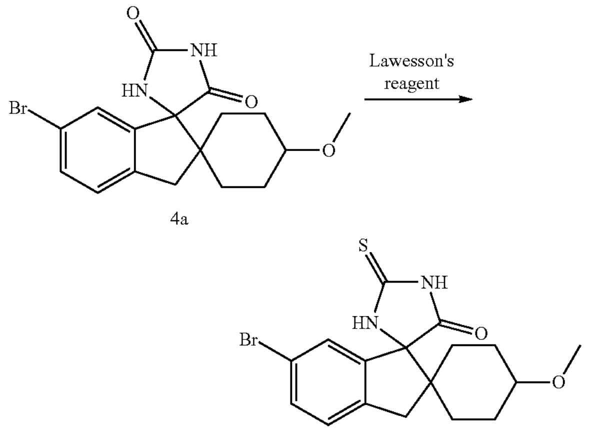

4a

4b

Preparation of Compound 4b

A suspension of compound 4a (450 mg, 1.19 mmol) and Lawesson's Reagent (481 mg, 1.19 mmol) in dry 1,4-dioxane (9 mL) was heated under 120° C. for 35 minutes in CEM microwave reactor. The mixture was concentrated in vacuo, and the residue was purified by column to give the compound 4b (220 mg, 47%).

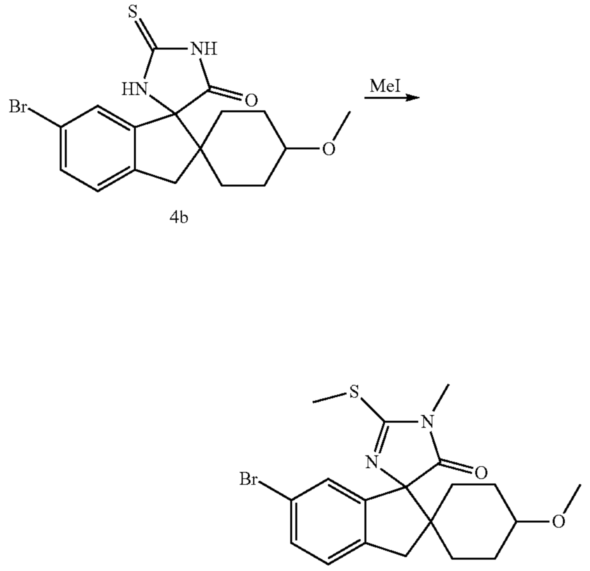

4b

4c

Preparation of Compound 4c

To a solution of compound 4b (150 mg, 0.381 mmol) in MeOH (9 mL) was added a solution of NaOH (1.143 mL, 0.6 N). After being stirred for 5 min., MeI (0.27 mL) was added, and the reaction mixture was heated at 60° C. for 15 minutes in microwave. The mixture was concentrated in vacuo, and the residue was purified by preparative TLC to give the compound 4c (50 mg, 31%).

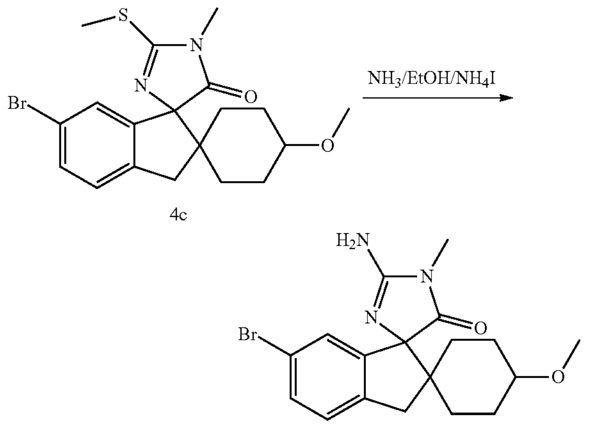

4c

4d

Preparation of Compound 4d

A solution of compound 4c (70 mg, 0.166 mmol), $NH_4$I (60 mg, 0.415 mmol) in a solution of $NH_3$/EtOH (6 mL, 5 N) was heated at 120° C. in a CEM tube in a microwave reactor for 3 h. After being cooled, the mixture was concentrated in vacuum. The residue was dissolved in DCM, filtrated, and the filtrate was concentrated in vacuum to give the compound 4d (20 mg, 31%), which was used for the next step without purification. $^1$H-NMR ($CDCl_3$): δ7.42 (m, 1H), 7.42 (m, 1H), 7.30 (m, 1H), 7.22 (m, 1H), 3.33 (m, 3H), 3.20 (m, 3H), 3.01 (m, 3H), 2.00 (m, 3H), 1.51-1.70 (m, 3H), 1.32 (m, 2H).

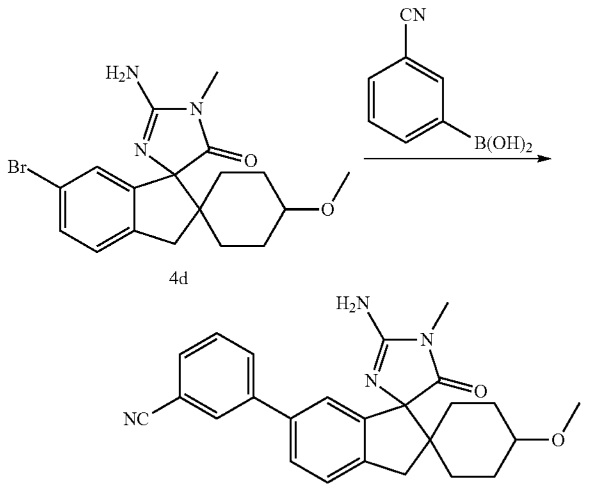
4d

Preparation of Compound 4

A mixture of compound 4d (20 mg, 0.051 mmol), 3-cyanophenylboronic acid (15 mg, 0.102 mmol), $Cs_2CO_3$ (2 M, 0.30 mL) and $Pd(PPh_3)_2Cl_2$ (5 mg) in 1,4-dioxane (1 mL) under $Ar_2$ was stirred in microwave at 120° C. for 35 minutes. The reaction mixture was concentrated in vacuum, the residue was purified by preparative TLC and HPLC to give compound 4 (2.81 mg, 13%). $^1$H-NMR ($CD_3OD$): δ8.00 (m, 2H), 7.61-7.71 (m, 4H), 7.50 (m, 1H), 3.33-3.41 (m, 4H), 3.25 (m, 3H), 3.21 (m, 2H), 2.04 (m, 2H), 1.92 (m, 1H), 1.50 (m, 2H), 1.30 (m, 3H); ESI MS: m/z=415 $[M+H]^+$.

Example 28

Preparation of Compound 49

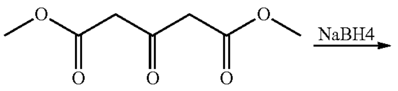

49a

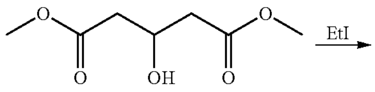

49b

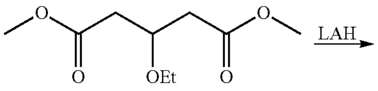

49c

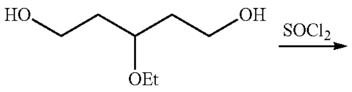

49d

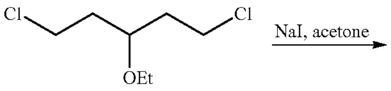

49e

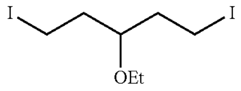

49f

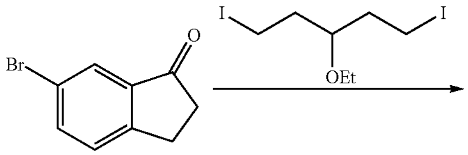

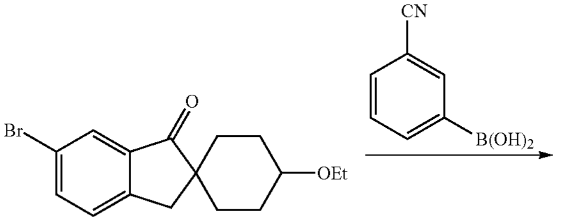

49g

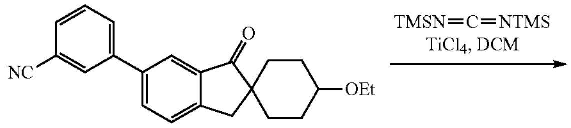

49h

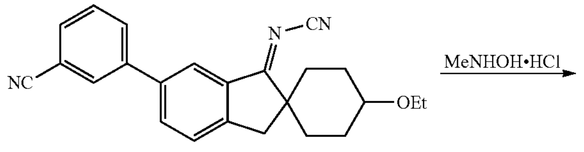

49i

-continued

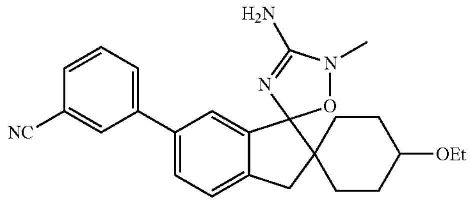

Experimental Data:

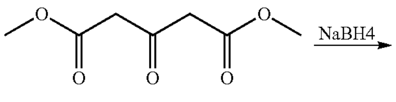

49a

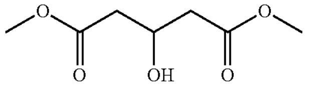

49b

Preparation of Compound 49b

To a solution of dimethyl compound 49a (240 g, 1.37 mol) in anhydrous MeOH (1000 mL) was added $NaBH_4$ (28 g, 0.73 mmol) 0° C. The temperature was rised to room temperature, and the mixture was stirred at this temperature for 1.5 hr. The solvent was removed in vacuo, the crude product was purified by silica gel column to give the compound 49b (150 g, 60%). $^1H$ NMR ($CDCl_3$, 400 MHz): δ4.55-4.96 (m. 1H), 3.70-3.74 (s, 6H), 2.60-2.55 (m, 4H).

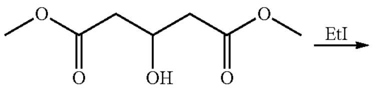

49b

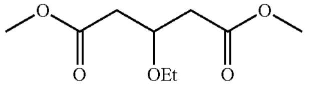

49c

Preparation of Compound 49c

A solution of dimethyl compound 49b (20 g, 106 mmol), $Ag_2O$ (40 g, 169 mmol) and EtI (40 g, 254 mmol) in MeCN (15 mL) was refluxed overnight. The mixture was filtered, and concentrated in vacuo, and purified by silica gel column to give the compound 49c (20.6 g, 30%).

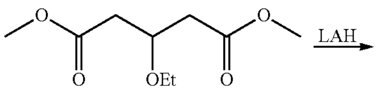

49c

-continued

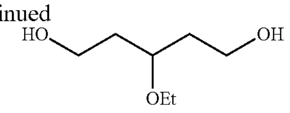

49d

Preparation of Compound 49d

To a solution of LAH (13.7 g, 404 mmol) in anhydrous THF (150 mL) was added dropwise a solution of dimethyl compound 49c (20.6 g, 101 mmol) in anhydrous THF (50 mL) under $N_2$ at 0° C. The temperature was rised to room temperature, and the mixture was stirred overnight. 2 N NaOH (100 mL) was added dropwise, and the mixture was extracted with ethyl acetate (100 mL×3). The organic layer was dried over $Na_2SO_4$ and concentrated in vacuo to give the compound 49d (10.6 g, 71%). $^1$H NMR ($CDCl_3$, 400 MHz): δ3.71-3.82 (m, 4H), 3.52-3.60 (m, 2H), 2.11-2.21 (s, 1H), 1.69-1.75 (m, 4H), 1.11-1.22 (m, 3H).

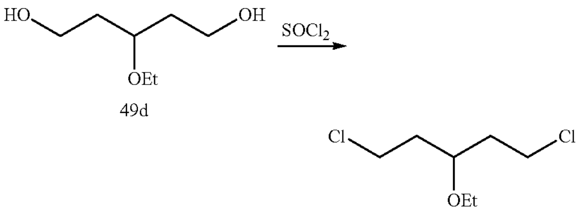

49d

49e

Preparation of Compound 5

A solution of compound 49d (10.6 g, 71.6 mmol) in DCM (6 mL) was added $SOCl_2$ (34.1 g, 296.4 mmol) at 0° C. The mixture was refluxed overnight, and the solvent was removed in vacuo to give the compound 49e (13 g, 100%). $^1$H NMR ($CDCl_3$, 400 MHz): δ3.39-3.65 (m, 6H), 1.70-1.95 (m, 4H), 1.05-1.12 (m, 3H).

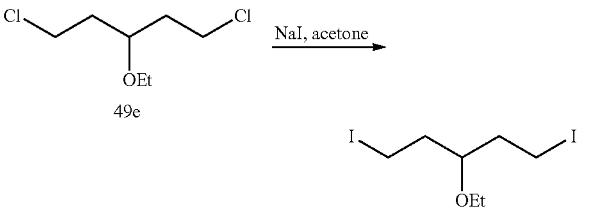

49e

49f

Preparation of Compound 49f

A solution of compound 49e (13 g, 70.6 mmol) and NaI (42.3 g, 282.4 mmol) in acetone (130 mL) was refluxed overnight. The mixture was filtered, and concentrated to give the compound 49f (crude 28 g), which was used for the next step directly.

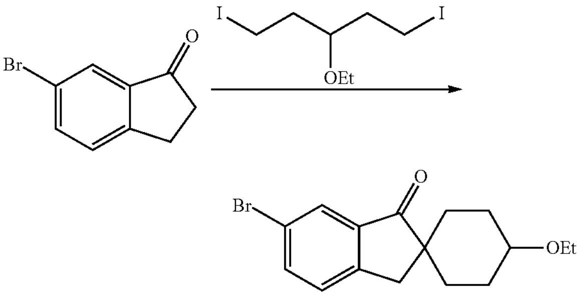

49g

Preparation of Compound 49g

To a solution of 6-bromo-2,3-dihydro-1H-inden-1-one (3.5 g, 16.7 mmol) in DMF (15 mL) was added NaH (1.2 g, 50.1 mmol) at 0° C. After being stirred for 15 minutes, the mixture was added 3-ethoxy-1,5-diiodopentane (8.8 g, 16.7 mmol) 0° C., and stirred at room temperature overnight. Water (100 mL) was added, and the mixture was extracted with ethyl acetate (150 mL×3). The organic layer was washed by water (50 mL×3), and organic layer was dried over $Na_2SO_4$, and concentrated in vacuo, and purified by silica gel column to give the compound 49g (700 mg, 10%). $^1$H NMR ($CDCl_3$, 400 MHz): δ7.78-7.82 (s, 1H), 7.55-7.67 (t, 1H), 7.25-7.29 (d, 1H), 3.50-3.55 (s, 1H), 3.35-3.40 (m, 2H), 2.85-2.95 (s, 2H), 1.89-2.15 (m, 4H).

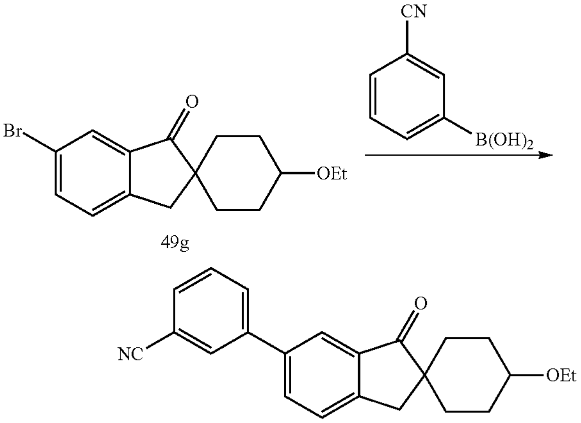

49g

49h

Preparation of Compound 49g

A mixture of compound 49g (120 mg, 0.37 mmol), 3,5-dicyanophenylboronic acid (110 mg, 0.75 mmol), $Cs_2CO_3$ (0.5 mL) and Pd(dppf)$Cl_2$ (25 mg) in 1,4-dioxane (2 mL) was heated at 110° C. for 20 minutes. The separated organic layer was concentrated in vacuo and purified by prepare TLC to give the compound 49h (108 mg, 84%). $^1$H NMR ($CDCl_3$, 400 MHz): δ7.50-7.95 (m, 7H), 3.50-3.55 (1, H), 3.39-3.45 (m, 2H), 2.85-2.95 (s, 2H), 1.90-2.20 (m, 4H).

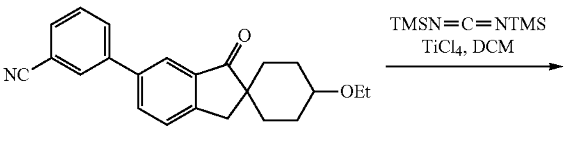

49h

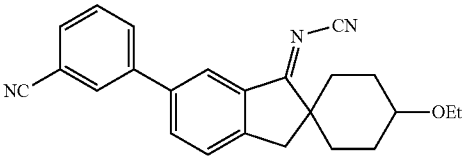

49i

Preparation of Compound 49i

To a solution of compound 49h (100 mg, 0.3 mmol) in anhydrous DCM (2 mL) was added $TiCl_4$ (0.6 mL, 1 mol/L) dropwise in 15 minutes at room temperature. The mixture was stirred for 1 h, added N,N'-methanediylidenebis(1,1,1-trimethylsilanamine) (123 mg, 0.6 mmol), and stirred at room temperature for another 18 hr. Ethyl acetate (2 mL) was added, and the mixture was filtered and purified by prep TLC to give the crude compound 49i (90 mg, 84%).

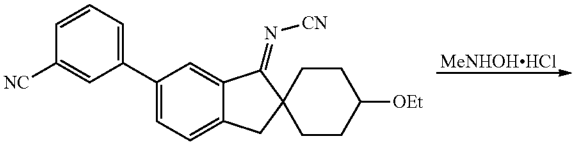

49i

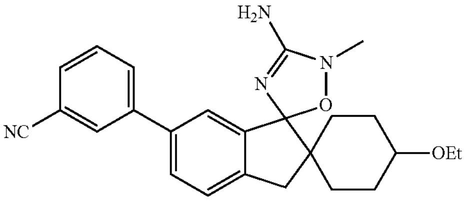

Preparation of Compound 49

To a solution of MeNHOH.HCl (19 mg 0.23 mmol) in anhydrous MeOH (1 ml) was added NaOMe (0.21 mmol) and compound 9 (84 mg, 0.23 mmol). The mixture was stirred for 5 minutes and purified by preparative TLC and HPLC to give compound 49 (2.52 mg, 3%). $^1H$ NMR (400 MHz $CD_3OD$): δ7.91-8.15 (m, 2H), 7.62-7.80 (m, 4H), 7.42-7.48 (m, 1H), 3.60-3.63 (s, 1H), 3.45-3.54 (m, 2H), 3.30-3.35 (s, 3H), 1.40-2.25 (m, 7H); ESI MS: m/z=417 $[M+H]^+$.

Example 29

Preparation of Compound 11

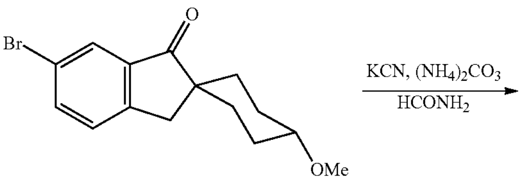

11a

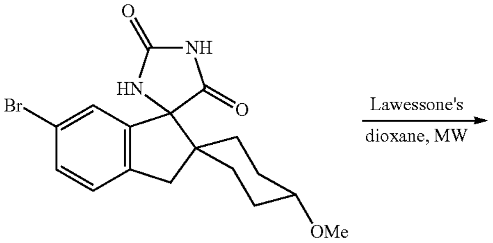

11b

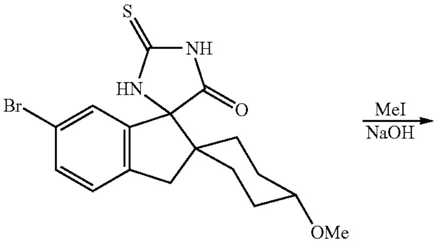

11c

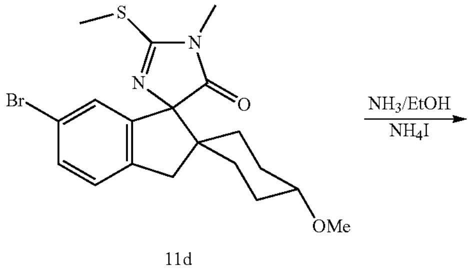

11d

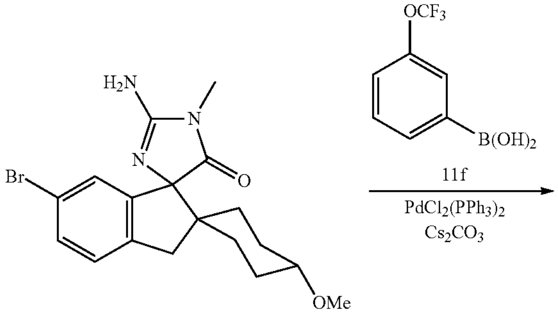

11e

-continued

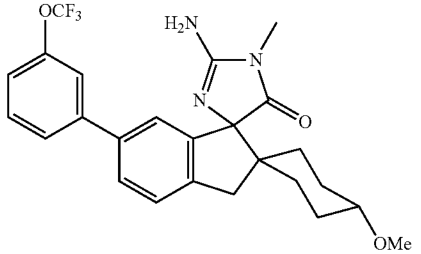

Experimental Data

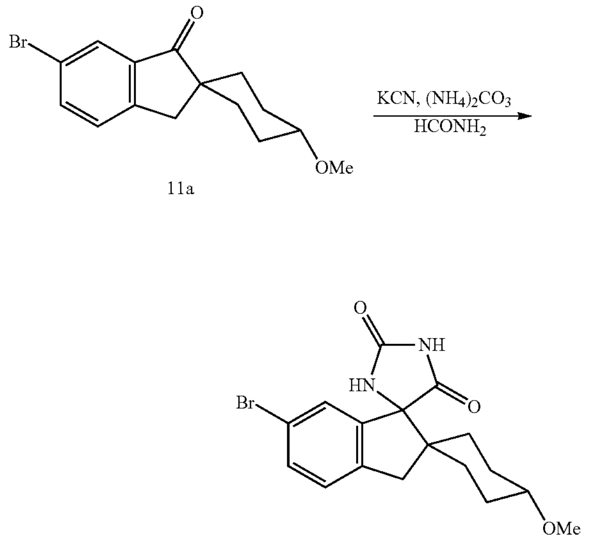

11a

11b

A steel autoclave was charged with compound 11a (700 mg, 2.27 mmol), KCN (294 mg, 4.53 mmol), and $(NH_4)_2CO_3$ (1.63 g, 16.98 mmol). Formamide (25 mL) was added to fill the tube completely. The mixture was heated at 80° C. for 72 h, cooled, and poured into ice. After acidification with concentrated HCl solution (30 mL), the mixture was filtrated. The solid was dissolved in ethyl acetate (600 mL), and washed with water (2×150 mL). The organic layer was dried over $Na_2SO_4$ and concentrated to give the compound 11b (550 mg, yield 61%) as a white solid, which was used for the next step directly without purification. $^1H$ NMR ($CDCl_3$ 300 MHz): δ7.80 (s, 1H), 7.62 (m, 1H), 7.25 (m, 1H), 3.33 (m, 3H), 3.05-3.21 (m, 2H), 2.92 (s, 1H), 1.91-2.26 (m, 3H), 1.67 (m, 2H), 1.43 (m, 1H), 1.33 (m, 2H), 1.21 (m, 3H), 0.80 (m, 1H).

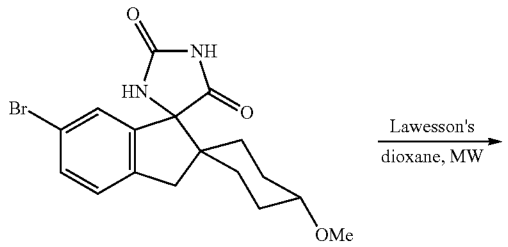

11b

-continued

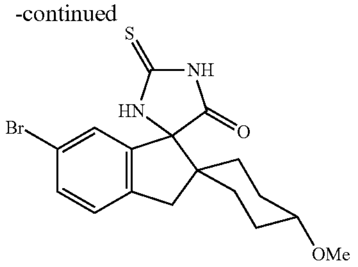

11c

A suspension of compound 11b (1 g, 2.64 mmol) and Lawesson's Reagent (1.68 g, 2.64 mmol) in dry 1,4-dioxane (18 mL) was heated at 120° C. for 35 min. in a CEM microwave reactor. The mixture was concentrated in vacuo, and purified by column (petroleum ether/EA=8/1-5/1) to give the compound 11e as a yellow solid (390 mg, yield 37%).

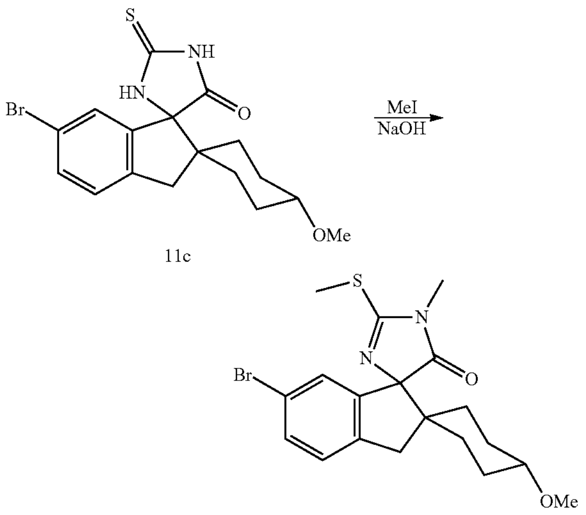

11c

11d

To a solution of compound 11c (200 mg, 0.51 mmol) in MeOH (20 mL) was added NaOH solution (1.5 mL, 0.6 N). After being stirred for 5 min., the mixture was added MeI (0.36 mL), and stirred at room temperature for another 10 minutes and at 60° C. for 15 minutes in a CEM microwave reactor. The mixture was concentrated in vacuo, and purified by preparative TLC (petroleum ether/EA=5/1) to give the compound 11d (80 mg, yield 37%) as a white solid. $^1H$-NMR ($CDCl_3$ 300 MHz): δ7.31 (d, J=8.1 Hz, 1H), 7.12 (d, J=7.8 Hz, 1H), 6.88 (s, 1H), 3.29 (s, 3H), 3.13-2.92 (m, 6H), 2.61 (s, 3H), 1.94-1.78 (m, 3H), 1.69 (t, 1H), 1.51 (m, 1H), 1.39-1.26 (m, 3H), 1.08 (m, 1H).

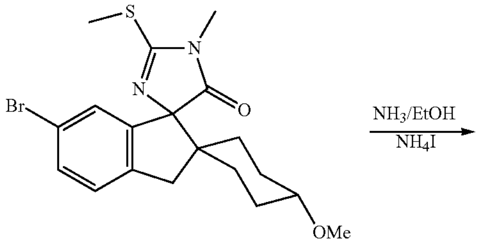

11d

-continued

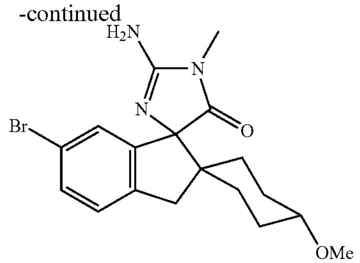

11e

A solution of compound 11d (45 mg, 0.107 mmol) and $NH_4I$ (78 mg, 0.535 mmol) in $NH_3$/EtOH (5 mL, 5 N) was heated at 120° C. in a CEM microwave reactor for 3 h. After being cooled, the mixture was concentrated in vacuum, and the residue was dissolved in $CH_2Cl_2$. After filtration, the filtrate was concentrated in vacuo to give the compound 11e (25 mg, 60%) as a white solid, which was used for the next step directly without purification. $^1$H-NMR ($CDCl_3$ 400 MHz): δ7.51 (d, 1H), 7.22 (m, 2H), 3.39 (m, 5H), 3.15 (4, 2H), 2.96 (s, 3H), 2.11 (m, 2H), 1.93 (m, 1H), 1.55 (m, 2H), 1.42 (m, 3H).

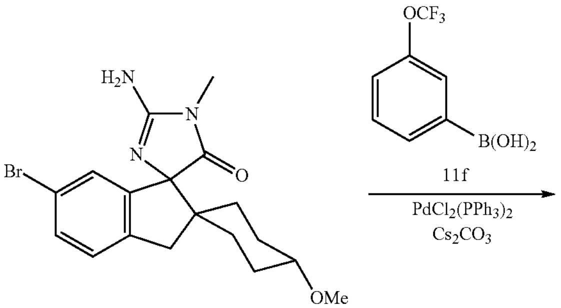

11e

11f

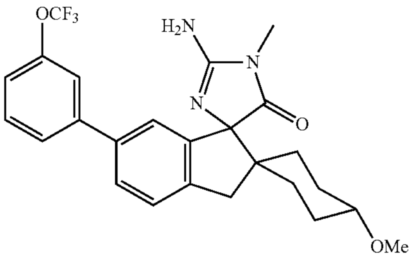

A 10 mL flask was charged with a solution of compound 11e (20 mg, 0.051 mmol) in 1,4-dioxane (1 mL), $Cs_2CO_3$ solution (2 N, 0.1 mL), 3-(trifluoromethoxy)phenylboronic acid (21 mg, 0.102 mmol) and $Pd(PPh_3)_2Cl_2$ (5 mg) under $N_2$ atmosphere. The mixture was heated at 120° C. in a CEM microwave reactor for 15 minutes, and concentrated in vacuo. The residue was purified by preparative TLC ($CH_2Cl_2$/MeOH=10/1) and HPLC to give compound 11 (2.25 mg, yield 9%). $^1$H-NMR ($CD_3OD$, 400 MHz): δ7.66 (m, 2H), 7.54 (m, 4H), 7.27 (m, 1H), 3.41 (s, 3H), 3.29-3.11 (m, 6H), 2.09 (m, 2H), 1.94 (m, 1H), 1.54-1.31 (m, 5H); ESI MS: m/z 474 $[M+H]^+$.

Example 30

Preparation of Compound 14

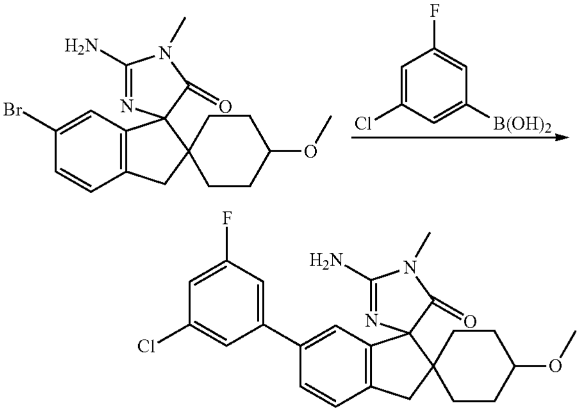

By using the same synthetic strategy as compound 4 described in example 27, compound 14 (3.5 mg, yield 13%) was obtained. $^1$H NMR ($CD_3OD$ 400 MHz): δ7.68 (m, 1H), 7.60-7.45 (m, 3H), 7.48 (m, 1H), 7.21 (m, 1H), 3.49 (s, 3H), 3.32-3.14 (m, 6H), 2.21 (m, 2H), 1.89 (m, 1H), 1.53-1.26 (m, 5H); ESI MS: m/z=441 $[M+H]^+$.

Example 31

Preparation of Compound 52

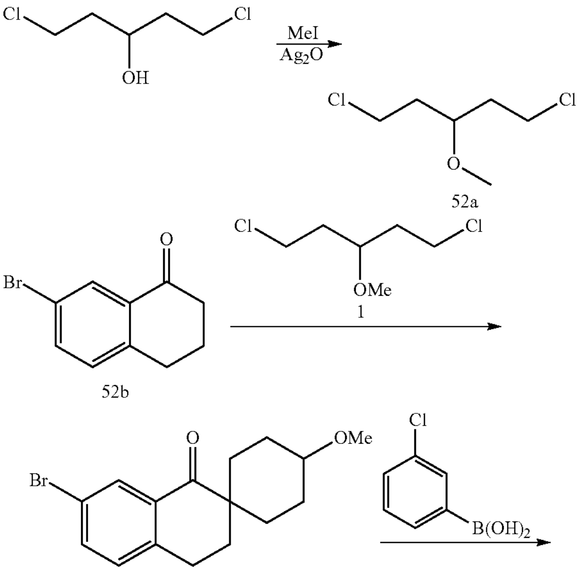

52a

1

52b

53c

-continued

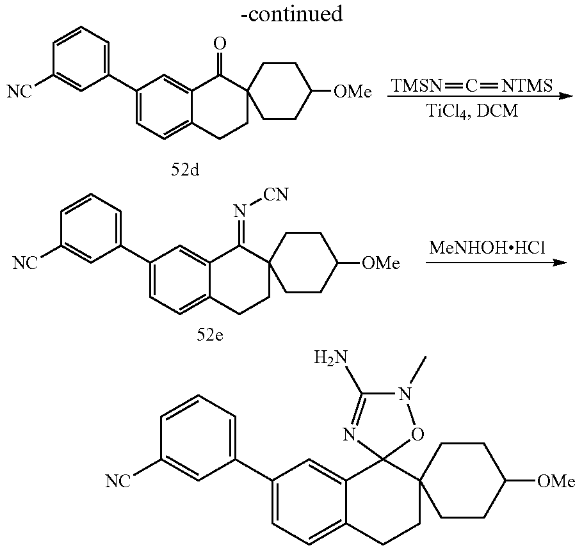

52d

52e

Experimental Data:

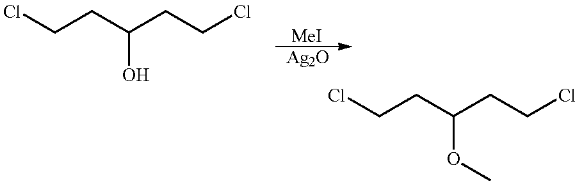

52a

Preparation of Compound 52a

MeI (4.46 mL, 71.6 mmol) was added to a solution of 1,5-dichloropentan-3-ol (1.9 g, 12.2 mmol) and $Ag_2O$ (7.5 g, 32.3 mmol) in DMF (25 mL) at 20-30° C. The mixture was stirred at room temperature overnight, and filtered. The filtrate was extracted with $Et_2O$ for 3 times, and the combined organic layers were washed with $H_2O$, dried, and concentrated to give the crude compound 52a (1.3 g, 63%), which was used directly without further purification.

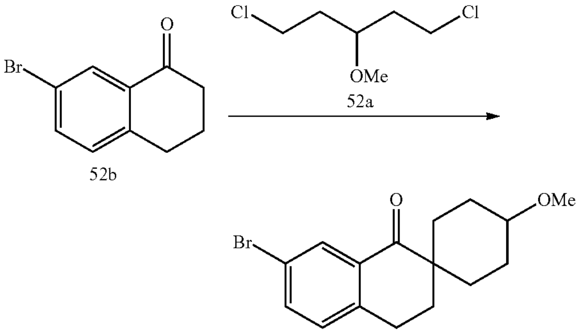

52a

52b

52c

Preparation of Compound 52c

To a solution of compound 52b (336 mg, 1.5 mmol) in DMF was added NaH (150 mg, 60%, 3.75 mmol) at 0° C., and the mixture was stirred for 1 h at the same temperature. Compound 52a (510 mg, 3 mmol) was added, and the mixture was stirred at room temperature overnight. The mixture was quenched with ice water, and extracted with EtOAc. The organic layer was concentrated, the residue was purified with preparative TLC to give the compound 52c (50 mg, 10%).

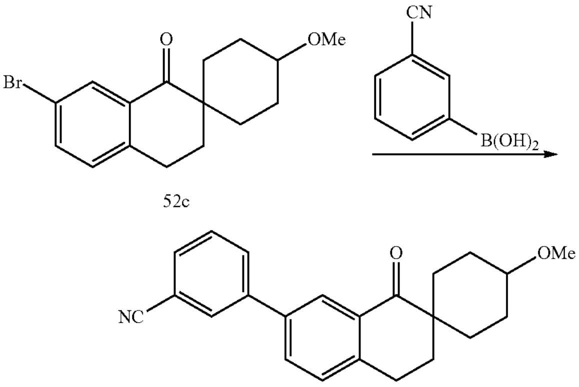

52c

52d

Preparation of Compound 52d

To a solution of compound 52c (34 mg, 0.23 mmol) and $Cs_2CO_3$ (2 M, 0.8 mL) in 1,4-dioxane (1.5 mL) under $N_2$ was added $Pd(PPh_3)_2Cl_2$ (15 mg). The mixture was stirred at 100° C. for 6 h. After being cooled to room temperature, the organic layer was dried, and concentrated. The residue was purified by TLC to give the compound 52d (25 mg, 47%).

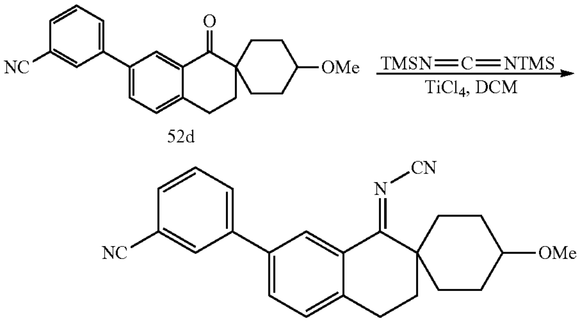

52d

52e

Preparation of Compound 52e

To a solution of compound 52d (25 mg, 0.07 mmol) in $CH_2Cl_2$ (1.5 mL) was added $TiCl_4$ (28 mg). The mixture was stirred at 50° C. in a microwave reactor for 6 minutes, and bis-trimethylsilylcarbodiimide (30 mg, 0.16 mmol) was added. The resulting mixture was stirred at 60° C. in a microwave reactor for 10 minutes. The reaction mixture was poured into ice-water, and extracted with DCM. The combined organic phases were dried over anhydrous $Na_2SO_4$, filtered, and the filtrate was concentrated to give the crude compound 52e (30 mg, 116% crude).

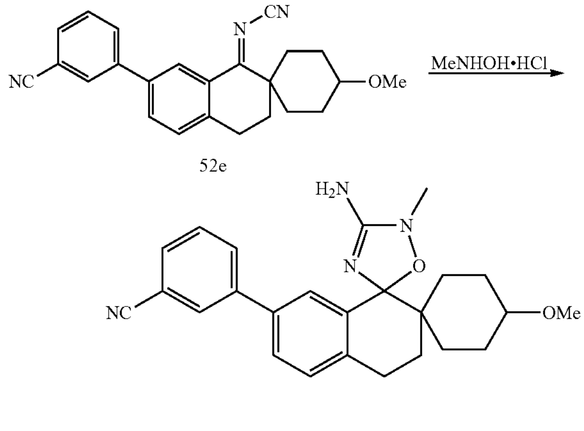

52e

Preparation of Compound 52

To a solution of methylhydroxylamine HCl salt (7 mg, 0.08 mmol) in anhydrous MeOH (1 mL) was added NaOMe (25% in MeOH, 6 drops) and compound 52e (30 mg, 0.08 mmol). After being stirred for 10 minutes, the solvent was removed in vacuo. The residue was purified by preparative HPLC to give compound 52 (1.07 mg, 3%). $^1$H-NMR (400 MHz $CD_3OD$): δ7.95 (m, 2H), 7.74 (m, 2H), 7.64 (m, 2H), 7.35 (m, 1H), 3.45 (d, 6H), 2.92 (m, 1H), 2.13 (m, 1H), 2.03 (m, 3H), 1.63 (m, 1H), 1.52 (m, 3H), 1.43 (m, 1H), 1.35 (m, 1H); ESI MS: m/z=417 $[M+H]^+$.

Example 32

Preparation of Compound 13

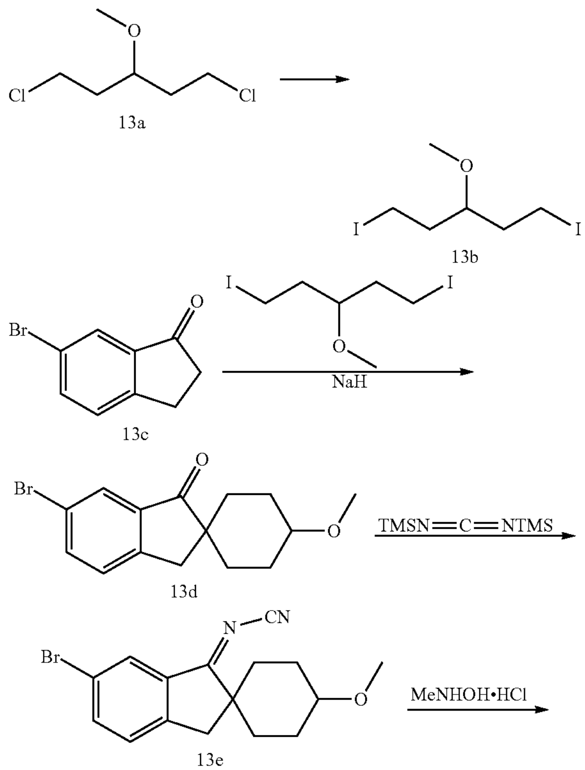

13a

13b

13c

13d

13e

-continued

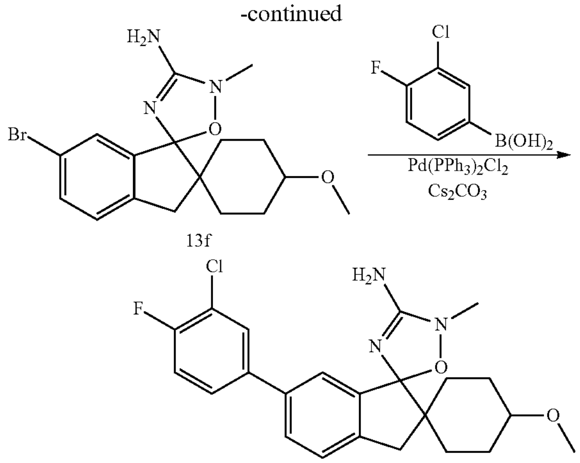

13f

Experimental Data:

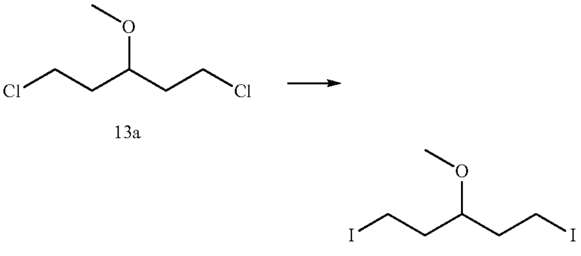

13a

13b

Preparation of Compound 13a

To the solution of compound 13a (5 g, 29.4 mmol) in acetone (62.5 mL) was added sodium iodide (17.64 g, 117.6 mmol). The mixture was refluxed overnight, and filtered. The filtrate was concentrated, and the residue was dissolved in DCM (100 mL). After filtration, the filtrate was concentrated to give the compound 13b (9.6 g, 93%). $^1$H-NMR (400 Hz $CDCl_3$): δ3.39 (m, 3H), 3.22-3.30 (m, 5H), 1.95-2.00 (m, 4H).

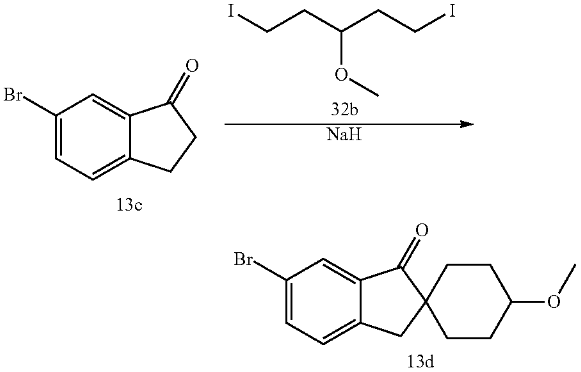

13c

13d

Preparation of Compound 13d

A solution of compound 13c (4.75 g, 22.6 mmol) and compound 13b (9.6 g, 27.1 mmol) in DMF (80 mL) was added NaH (2.71 g, 60%, 67.8 mmol) at 0° C. The mixture was stirred at room temperature for 2 h, quenched with water, and extracted with EtOAc. The organic layer was dried, and concentrated. The residue was purified by column chromatography to give the compound 13d (900 mg, 12%). $^1$H-NMR ($CDCl_3$): δ7.80 (m, 1H), 7.62 (m, 1H), 7.25 (m, 1H), 3.34 (m, 3H), 3.22 (m, 1H), 2.91 (m, 2H), 2.10 (m, 2H), 1.75 (m, 2H), 1.44 (m, 2H), 1.20-1.30 (m, 2H).

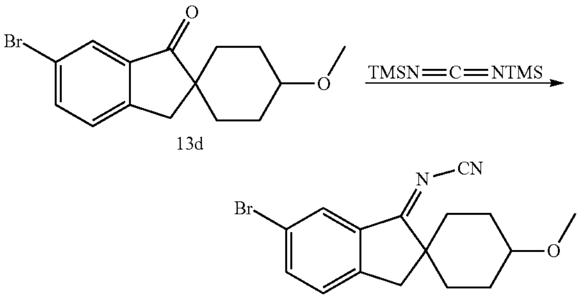

13d

13e

Preparation of Compound 13e

To a solution of compound 13d (700 mg, 2.27 mmol) in $CH_2Cl_2$ (18 mL) was added $TiCl_4$ (4.55 mL, 4.55 mmol). The mixture was stirred for 1 h at room temperature, and bis-trimethylsilylcarbodiimide (1.12 mL, 5.00 mmol) was added. The resulting mixture was stirred overnight, poured into ice-water, and extracted with DCM. The combined organic phases were dried over anhydrous $Na_2SO_4$, and filtered. The filtrate was concentrated to give the crude compound 13e (700 mg, 93%).

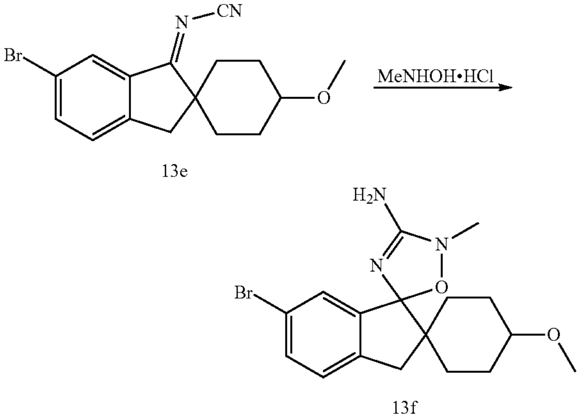

13e

13f

Preparation of Compound 13f

To a solution of methylhydroxylamine HCl salt (177 mg, 2.11 mmol) in anhydrous MeOH 35 mL) was added NaOMe (10% in MeOH, 1.05 mL) and compound 13e (700 mg, 2.11 mmol). After being stirred for 25 minutes, the solvent was removed, and the residue was dispended in DCM (50 mL), and the precipitate was filtered off. The solvent was removed, and the residue was purified by TLC to give the compound 13f (1 g, 125% crude). $^1$H-NMR (400 Hz $CDCl_3$): δ7.45 (m, 2H), 7.10 (m, 1H), 3.40 (m, 3H), 3.20 (m, 1H), 3.00 (m, 3H), 2.70-2.88 (m, 2H), 2.00 (m, 2H), 1.75 (m, 1H), 1.45-1.62 (m, 3H), 1.35 (m, 2H).

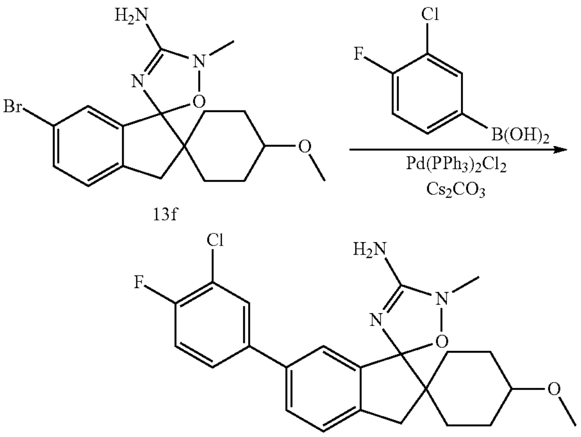

13f

Preparation of Compound 13

A mixture of compound 13f (20 mg, 0.053 mmol), 3-chloro-4-fluorophenylboronic acid (14 mg, 0.08 mmol), $Cs_2CO_3$ (2 M, 0.300 mL) and $Pd(PPh_3)_2Cl_2$ (5 mg) in 1,4-dioxane (1 mL) under $Ar_2$ was stirred in a microwave reactor at 120° C. for 18 minutes. The reaction mixture was concentrated under vacuum, and the residue was purified by preparative TLC and HPLC to give the compound compound 13 (2.67 mg, 12%). $^1$H-NMR (400 Hz $CD_3OD$): δ7.90-8.00 (m, 0.3H), 7.55-7.65 (m, 3H), 7.50-7.60 (m, 1H), 7.30-7.45 (m, 2H), 3.35-3.40 (m, 6H), 3.30-3.35 (m, 1H), 3.15-3.25 (m, 1H), 2.95-3.05 (m, 1H), 2.00-2.20 (m, 2H), 1.64-1.95 (m, 3H), 1.30-1.55 (m, 3H); ESI MS: m/z=430 $[M+H]^+$.

Example 33

Preparation of Compound 5

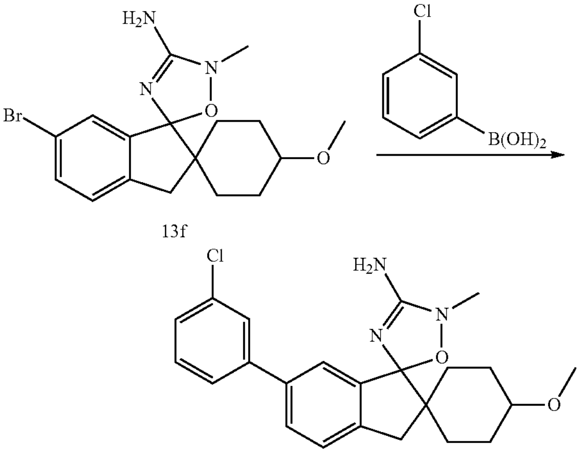

13f

By using the same synthetic strategy as compound 13 described in Example 32, compound 5 (1.79 mg, 8%) was obtained. $^1$H NMR (400 Hz $CD_3OD$): δ7.90-8.00 (m, 1H), 7.65-7.75 (m, 2H), 7.50-7.65 (m, 4H), 7.35-7.50 (m, 1H), 3.35-3.45 (m, 6H), 3.15-3.30 (m, 2H), 3.00-3.10 (d, 1H), 2.00-2.20 (m, 2H), 1.60-1.90 (m, 3H), 1.35-1.55 (m, 3H); ESI MS: m/z=412 $[M+H]^+$.

Example 34

Preparation of Compound 19

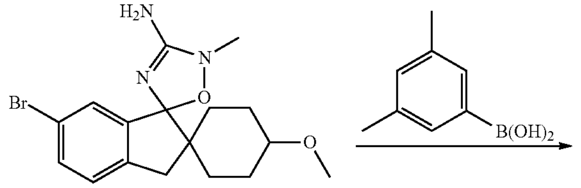

13f

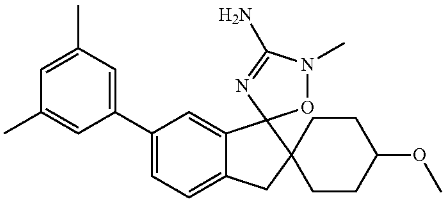

By using the same synthetic strategy as compound 13 described in Example 32, compound 19 (2.16 mg, 10%) was obtained. $^1$H-NMR (400 Hz $CD_3OD$): δ7.90-8.00 (m, 1H), 7.60-7.75 (m, 2H), 7.30-7.40 (m, 1H), 7.10-7.20 (m, 2H), 6.95-7.05 (m, 1H), 3.35-3.45 (m, 6H), 3.15-3.25 (m, 1H), 2.95-3.05 (m, 2H), 2.30-2.45 (d, 6H), 2.00-2.20 (m, 2H), 1.64-1.95 (m, 3H), 1.30-1.55 (m, 3H); ESI MS: m/z=406 $[M+H]^+$.

Example 35

Preparation of Compound 6

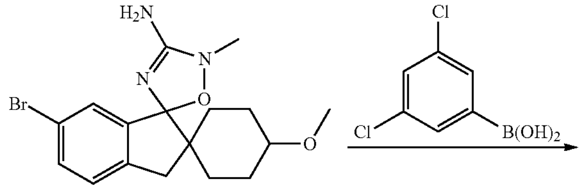

13f

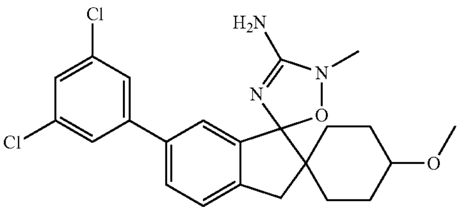

By using the same synthetic strategy as compound 13 described in Example 32, compound 6 (1.82 mg, 8%) was obtained. $^1$H-NMR (400 Hz $CD_3OD$): δ7.65-7.75 (m, 2H), 7.50-7.65 (m, 2H), 7.40-7.50 (m, 2H), 3.35-3.45 (m, 6H), 3.15-3.25 (m, 2H), 2.95-3.05 (m, 2H), 2.00-2.20 (m, 2H), 1.64-1.95 (m, 3H), 1.30-1.55 (m, 3H); ESI MS: m/z=446 $[M+H]^+$.

Example 36

Preparation of Compound 20

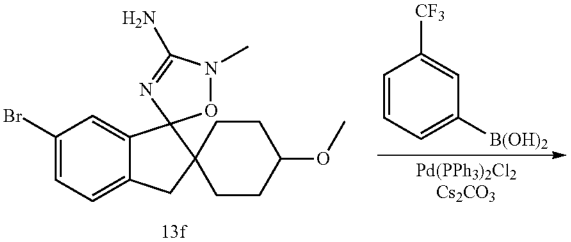

13f

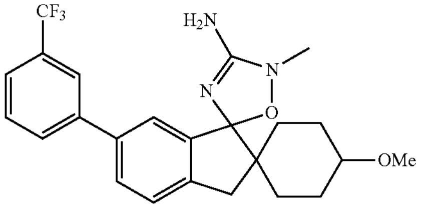

By using the same synthetic strategy as compound 13 described in Example 32, compound 20 (2.06 mg, 10%) was obtained. $^1$H-NMR (400 Hz $CD_3OD$): δ 7.80-8.00 (m, 2H), 7.60-7.80 (m, 4H), 7.40-7.50 (m, 1H), 3.35-3.45 (m, 6H), 3.15-3.25 (m, 1H), 2.95-3.05 (m, 2H), 2.00-2.20 (m, 2H), 1.64-1.95 (m, 3H), 1.30-1.55 (m, 3H); ESI MS: m/z=446 $[M+H]^+$.

Example 36a Preparation of Compound 32

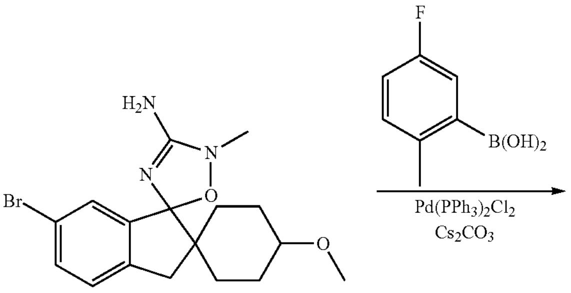

13f

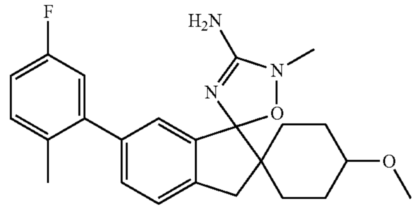

By using the same synthetic strategy as compound 13 described in Example 35, compound 32 (9.28 mg, 42%) was. $^1$H-NMR (400 Hz $CD_3OD$): δ7.60-7.70 (m, 1H), 7.30-7.40 (m, 2H), 7.20-7.30 (m, 1H), 6.85-7.05 (m, 2H), 3.23-3.45 (m, 6H), 3.15-3.25 (m, 1H), 2.95-3.05 (m, 2H), 2.10-2.18 (m, 4.3H), 2.00-2.10 (m, 1H), 1.64-1.95 (m, 3H), 1.30-1.55 (m, 3H); ESI MS: m/z=410 $[M+H]^+$.

Example 37

Preparation of Compound 9

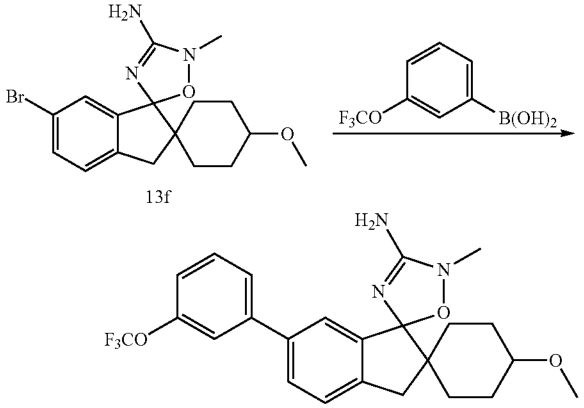

13f

By using the same synthetic strategy as compound 13 described in Example 32, compound 9 (2.46 mg, 10%) was obtained. $^1$H-NMR (400 Hz $CD_3OD$): δ7.65-8.00 (m, 1H), 7.50-7.65 (m, 2H), 7.40-7.50 (m, 2H), 7.20-7.40 (m, 1H), 3.23-3.45 (m, 6H), 3.15-3.25 (m, 1H), 2.95-3.05 (m, 2H), 2.10-2.18 (m, 4.3H), 2.00-2.10 (m, 1H), 1.64-1.95 (m, 3H), 1.30-1.55 (m, 3H); ESI MS: m/z=462 $[M+H]^+$.

Example 38

Preparation of Compound 8

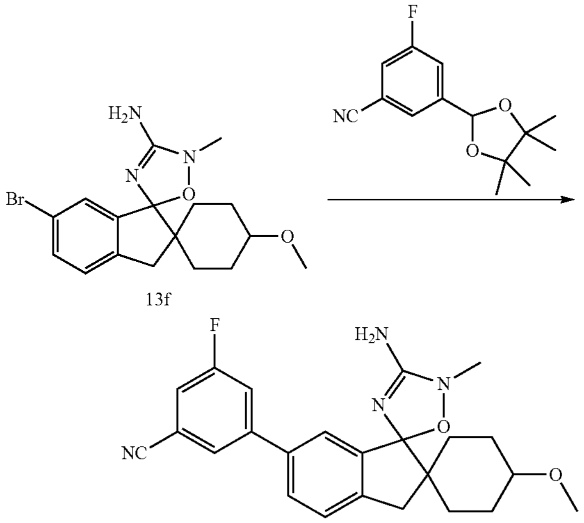

13f

A mixture of compound 13f (20 mg, 0.053 mmol), 3-fluoro-5-(4,4,5,5-tetramethyl-1,3-dioxolan-2-yl)benzonitrile (20 mg, 0.08 mmol), $Cs_2CO_3$ (2 M, 0.300 mL), and $Pd(PPh_3)_2Cl_2$ (5 mg) in 1,4-dioxane (1 mL) under $Ar_2$ was stirred at 100° C. for 90 minutes. The reaction mixture was concentrated in vacuum, the residue was purified by preparative TLC and HPLC to give compound 8 (1.85 mg, 8%). $^1$H-NMR (400 Hz $CD_3OD$): δ 7.85-8.00 (m, 1H), 7.70-7.85 (m, 3H), 7.50-7.65 (m, 1H), 7.40-7.50 (m, 1H), 3.23-3.45 (m, 6H), 3.15-3.25 (m, 1H), 2.95-3.05 (m, 2H), 2.00-2.20 (m, 2H), 1.64-1.95 (m, 2H), 1.30-1.55 (m, 4H); ESI MS: m/z=421 $[M+H]^+$.

Example 39

Preparation of Compound 12

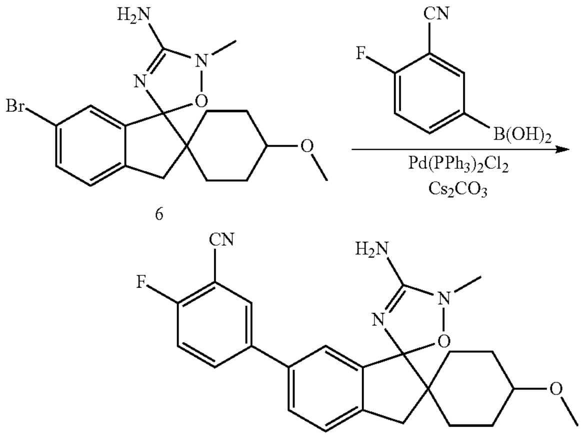

6

VT_B060608_09

By using the same synthetic strategy as compound 13 described in Example 35, compound 12 (2.73 mg, 12%) was obtained. $^1$H-NMR (400 Hz $CD_3OD$): δ7.90-8.10 (m, 2H), 7.70-7.80 (m, 2H), 7.40-7.50 (m, 2H), 3.23-3.45 (m, 6H), 3.15-3.25 (m, 1H), 2.95-3.05 (m, 2H), 2.00-2.20 (m, 2H), 1.64-1.95 (m, 3H), 1.30-1.55 (m, 3H); ESI MS: m/z=421 $[M+H]^+$.

Example 40

Preparation of Compound 68

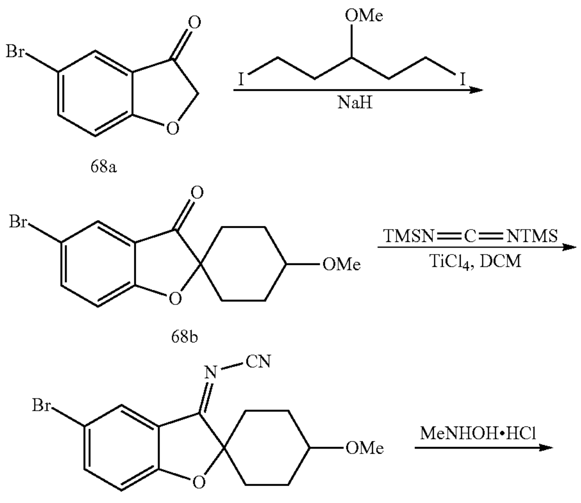

68a

68b

68c

-continued

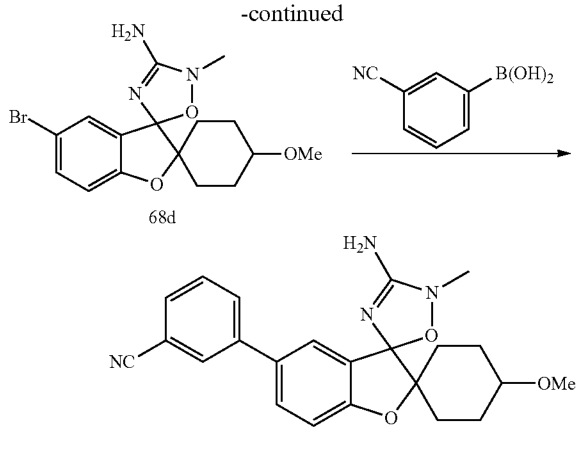

68d

Experimental Data:

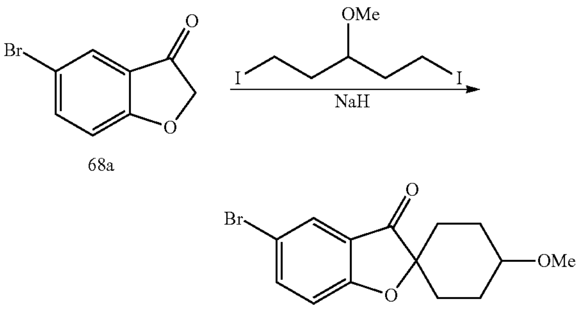

68a

68b

Preparation of Compound 68b

To a solution of NaH (5.4 g, 0.135 mol) in dry THF (150 mL) was added dropwise a solution of compound 68a (9.48 g, 0.045 mol) in THF (20 mL) at −30° C. The mixture was stirred at −30° C. for 0.5 h, 1,5-diiodo-3-methoxypentane (15.8 g, 0.045 mol) was added dropwise, and the mixture was stirred at ambient temperature overnight. The mixture was concentrated in vacuo, and purified by preparative TLC and HPLC to give the compound 68b (220 mg, 2%).

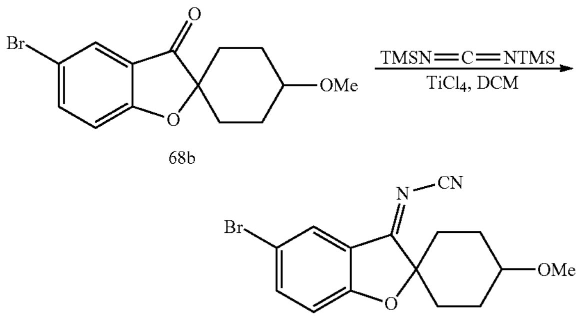

68b

68c

Preparation of Compound 68c

To a solution of compound 68b (100 mg, 0.32 mmol) in DCM (10 ml) was added $TiCl_4$ (0.8 mL, 0.8 mmol) dropwise. The mixture was stirred for 1 h, $(TMSN)_2C$ (150 mg, 0.8 mmol) was added, and the mixture was stirred at ambient temperature overnight. The mixture was quenched with water, extracted by DCM, dried over $Na_2SO_4$, and concentrated in vacuo to give the compound 68c (96 mg, 95%).

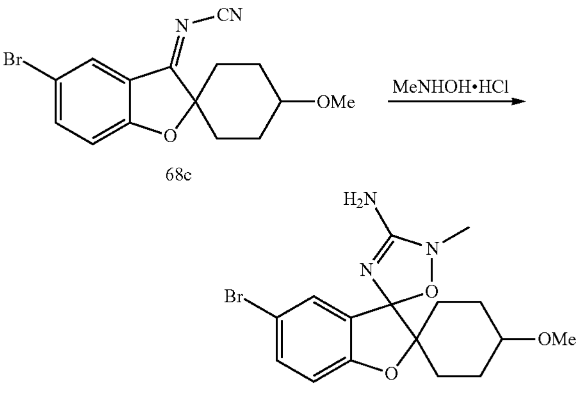

68c

68d

Preparation of Compound 68d

To a solution of MeNHOH.HCl (24 mg, 0.284 mmol) in anhydrous MeOH (10 ml) was added NaOMe (138 mg) and compound 68c (95 mg, 0.284 mol). The mixture was stirred at ambient temperature for 1 h, quenched with water, extracted by DCM, and concentrated in vacuo to give the compound 68d without other purification (60 mg, 50%).

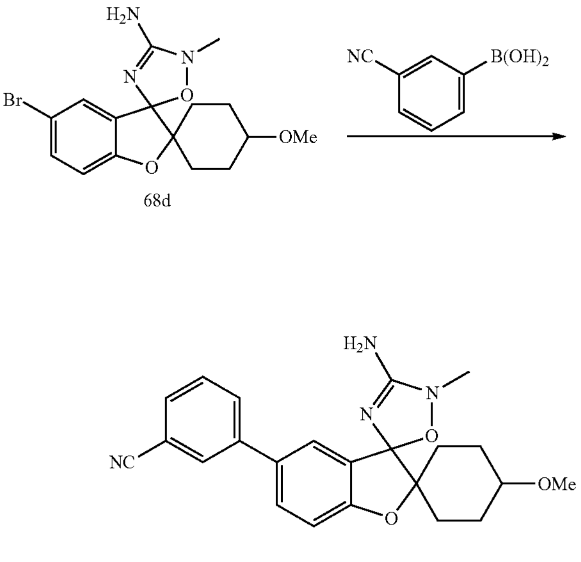

68d

Preparation of Compound 68

By using the same synthetic strategy as compound 13 described in Example 35, compound 68 (2.11 mg, 3%) was obtained. $^1$H-NMR (400 Hz $CD_3OD$): δ8.00-8.10 (m, 1H), 7.85-8.00 (m, 2H), 7.70-7.80 (m, 2H), 7.60-7.70 (m, 1H), 7.30-7.40 (m, 1H), 3.50-3.70 (m, 1H), 3.30-3.40 (m, 6H), 2.10-2.25 (m, 2H), 2.00-2.10 (m, 2H), 1.85-2.00 (m, 2H), 1.65-1.75 (m, 2H); ESI MS: m/z=405 [M+H]$^+$.

Example 41

Preparation of Compound 38

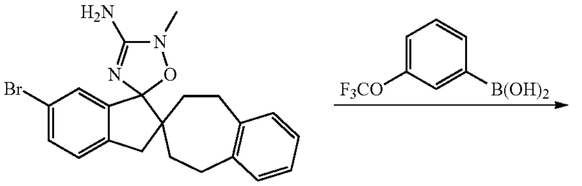

38a

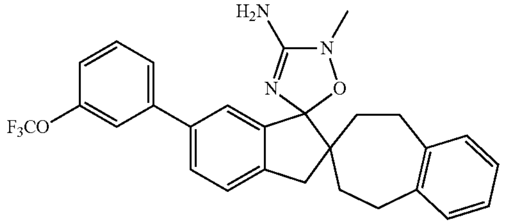

$Pd(PPh_3)_2Cl_2$ (10 mg, 0.014 mmol), $Cs_2CO_3$ (2 N, 0.3 mL) and 3-(trifluoromethoxy)phenylboronic acid (15 mg, 0.073 mmol) were added to a solution of compound 1 (15 mg, 0.036 mmol) in 1,4-dioxane (2 mL) in a 10 mL tube under $Ar_2$. The mixture was heated at 120° C. in a microwave reactor for 20 min. The reaction mixture was concentrated in vacuo, and the residue was purified by preparative TLC and HPLC to give compound 38 (4.59 mg, 28%). $^1$H NMR (400 Hz $CD_3OD$): δ7.95-8.05 (m, 0.4H), 7.70-7.80 (m, 2H), 7.60-7.65 (m, 0.6H), 7.45-7.60 (m, 3H), 7.25-7.40 (m, 1H), 7.05-7.15 (m, 4H), 3.35-3.50 (m, 2H), 3.20-3.30 (m, 3H), 2.95-3.20 (m, 2H), 2.65-2.90 (m, 2H), 1.75-2.20 (m, 2H), 1.50-1.75 (m, 2H); ESI MS: m/z=494 [M+H]$^+$.

Example 42

Preparation of Compound 39

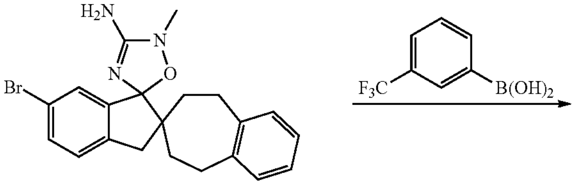

1

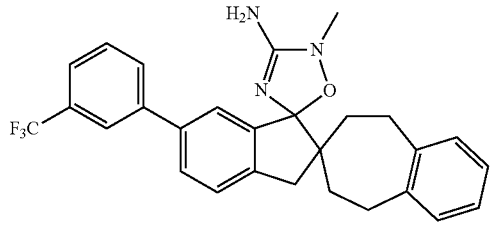

By using the same synthetic strategy as compound 38 described in Example 41, compound 39 (1.40 mg, 27%) was obtained. $^1$H NMR (400 Hz $CD_3OD$): δ7.95-8.05 (m, 0.4H), 7.75-7.90 (m, 2H), 7.60-7.75 (m, 4H), 7.40-7.50 (m, 0.6H), 7.05-7.15 (m, 4H), 3.30-3.50 (m, 2H), 3.15-3.25 (m, 3H), 2.95-3.15 (m, 2H), 2.65-2.85 (m, 2H), 1.75-2.20 (m, 2H), 1.40-1.70 (m, 2H); ESI MS: m/z=478 [M+H]$^+$.

Example 43

Preparation of Compound 17

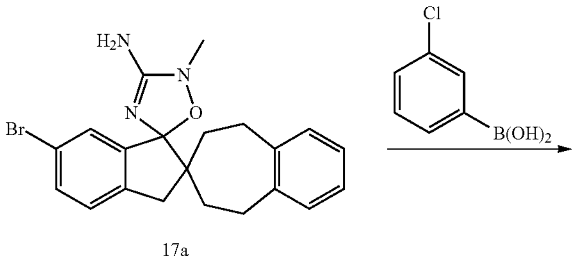

17a

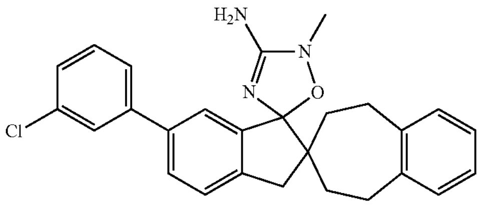

By using the same synthetic strategy as compound 38 described in Example 41, compound 17 (2.78 mg, 8%) was obtained. $^1$H NMR (400 Hz $CD_3OD$): δ7.70-8.00 (m, 2H), 7.50-7.70 (m, 2H), 7.35-7.50 (m, 3H), 7.05-7.15 (m, 4H), 3.40-3.50 (m, 2H), 3.20-3.30 (m, 3H), 2.95-3.20 (m, 2H), 2.65-2.85 (m, 2H), 1.75-2.20 (m, 2.5H), 1.45-1.70 (m, 1.6H); ESI MS: m/z=444 [M+H]$^+$.

Alternatively, a solution containing compound 17a (105 mg, 0.255 mmol) and compound 1A (60 mg, 0.384 mmol) in dioxane (5 mL), and aqueous Cs2CO3 (2 M, 1.8 mL) was deoxygenated by bubbling a stream of nitrogen through the reaction mixture for 5 min. Then, PdCl12$(PPh_3)_2$ (18 mg) was added. The reaction vial was sealed and placed into CEM microwave reactor and irradiated at 120° C. for 15 min. After being cooled to room temperature, the mixture was diluted with EtOAc and filtered through a short Celite pad. The solution was concentrated in vacuo and the residue was purified by preparative TLC and HPLC to give compound 17 (48.2 mg, 42%) as a white solid. LC-MS tR=1.178, 1.241 min in 2 min chromatography, MS (ESI) m/z 444 [M+H]+; 1H-NMR (CD3OD 400 MHz): δ 7.62-7.90 (m, 2H), 7.47-

7.55 (m, 2H), 7.27-7.45 (m, 3H), 7.00-7.27 (m, 4H), 3.27 (s, 3H), 2.90-3.10 (m, 3H), 2.61-2.75 (m, 2H), 1.77-2.08 (m, 3H), 1.41-1.84 (m, 2H).

Example 44

Preparation of Compound 23

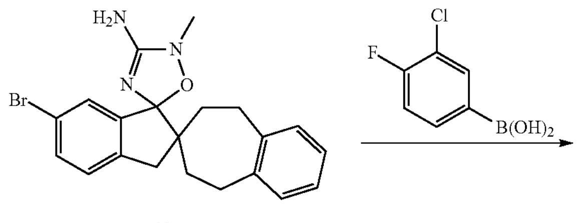

23a

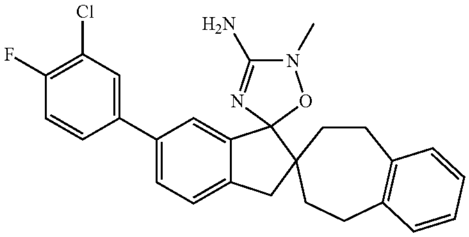

By using the same synthetic strategy as compound 38 described in Example 41, compound 23 (1.57 mg, 10%) was obtained. $^1$H NMR (400 Hz $CD_3OD$): δ7.90-8.00 (m, 0.4H), 7.65-7.80 (m, 2H), 7.45-7.60 (m, 1.6H), 7.30-7.40 (m, 1H), 7.05-7.15 (m, 4H), 3.40-3.50 (m, 2H), 3.20-3.30 (m, 3H), 2.95-3.20 (m, 2H), 2.65-2.85 (m, 2H), 1.80-2.20 (m, 2H), 1.45-1.75 (m, 2H); ESI MS: m/z=462 $[M+H]^+$.

Example 45

Preparation of Compound 15

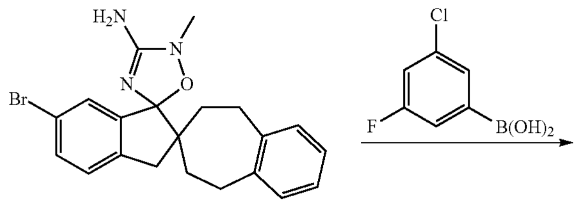

15a

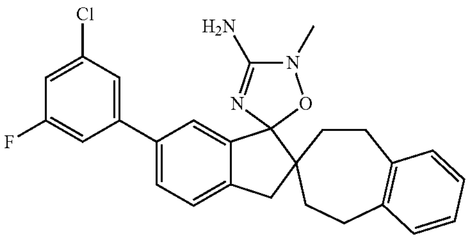

By using the same synthetic strategy as compound 38 described in Example 41, compound 15 (1.51 mg, 10%) was obtained. $^1$H NMR (400 Hz $CD_3OD$): δ7.90-8.00 (m, 0.3H), 7.70-7.80 (m, 2H), 7.45-7.55 (m, 1.6H), 7.20-7.40 (m, 2H), 7.05-7.15 (m, 4H), 3.40-3.50 (m, 2H), 3.20-3.30 (m, 3H), 2.95-3.20 (m, 2H), 2.65-2.85 (m, 2H), 1.80-2.20 (m, 2H), 1.50-1.75 (m, 2H); ESI MS: m/z=462 $[M+H]^+$.

Example 46

Preparation of Compound 21

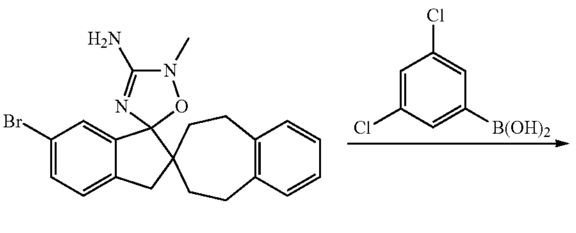

21a

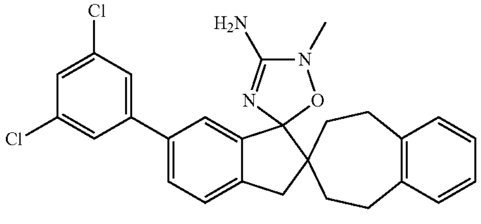

By using the same synthetic strategy as compound 38 described in Example 41, compound 21 (1.51 mg, 10%) was obtained. $^1$H NMR (400 Hz $CD_3OD$): δ7.90-8.00 (m, 0.3H), 7.70-7.80 (m, 1.7H), 7.55-7.65 (s, 1H), 7.45-7.55 (m, 2H), 7.05-7.15 (m, 4H), 3.40-3.50 (m, 1H), 3.20-3.30 (m, 4H), 2.95-3.20 (m, 2H), 2.65-2.85 (m, 2H), 1.80-2.20 (m, 2H), 1.50-1.75 (m, 2H); ESI MS: m/z=478 $[M+H]^+$.

Example 47

Preparation of Compound 10

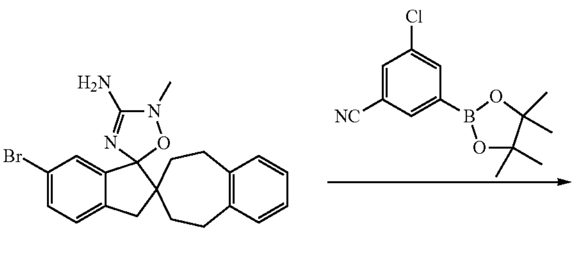

10a

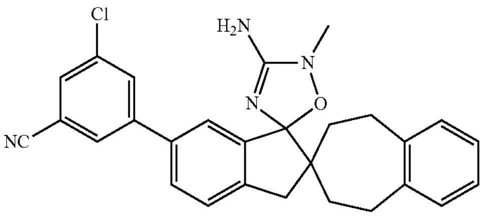

A mixture of compound 10a (20 mg, 0.049 mmol), 3-chloro-5-(4,4,5,5-tetramethyl-1,3,2-dioxaborolan-2-yl) benzonitrile (19.20 mg, 0.073 mmol), $Cs_2CO_3$ (2 M, 0.300 mL) and $Pd(PPh_3)_2Cl_2$ (5 mg) in 1,4-dioxane (1 mL) under $Ar_2$ was stirred at 120° C. in a microwave reactor for 20 minutes. The reaction mixture was concentrated in vacuum, the residue was purified by preparative TLC and HPLC to give compound 10 (2.10 mg, 9%). $^1H$ NMR (400 Hz $CD_3OD$): δ7.90-8.00 (m, 0.3H), 7.85-8.10 (m, 2.6H), 7.75-7.85 (m, 2H), 7.45-7.55 (m, 0.7H), 7.05-7.15 (m, 4H), 3.40-3.50 (m, 2H), 3.20-3.30 (m, 3H), 2.95-3.20 (m, 2H), 2.65-2.85 (m, 2H), 1.80-2.20 (m, 2H), 1.50-1.75 (m, 2H); ESI MS: m/z=469 $[M+H]^+$.

Example 48

Preparation of Compound 27

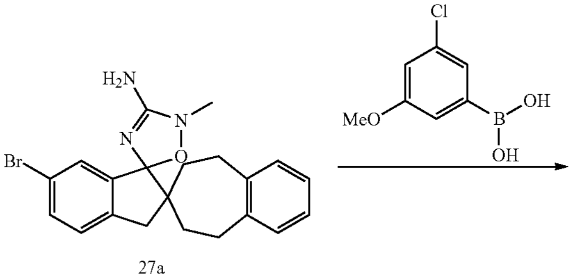

27a

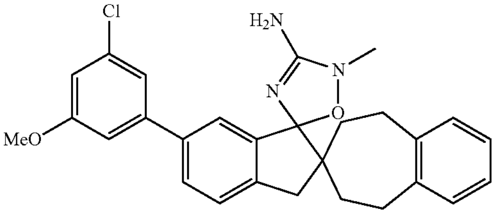

By using the same synthetic strategy as compound 38 described in Example 41, compound 27 (1.08 mg, 3%) was obtained. $^1H$ NMR (400 Hz $CD_3OD$): δ7.85-7.95 (m, 0.5H), 7.55-7.75 (m, 2H), 7.35-7.45 (m, 0.6H), 6.85-7.20 (m, 7H), 3.75-3.80 (s, 3H), 3.40-3.50 (m, 2H), 3.20-3.30 (m, 3H), 2.95-3.20 (m, 2H), 2.65-2.85 (m, 2H), 1.80-2.20 (m, 2H), 1.50-1.75 (m, 2H); ESI MS: m/z=474 $[M+H]^+$.

Example 49

Preparation of Compound 1

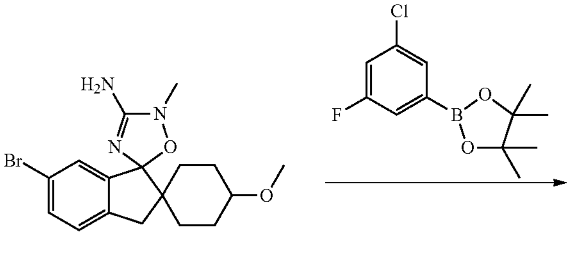

1a

-continued

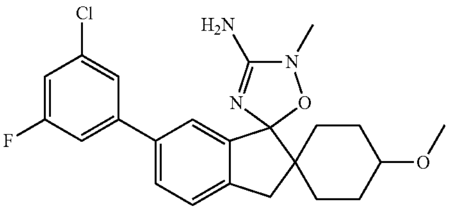

By using the same synthetic strategy as compound 10 described in Example 47, compound 1 (2.8 mg, 14%) was obtained. $^1H$ NMR (400 Hz $CD_3OD$): δ7.85-7.95 (m, 0.3H), 7.65-7.75 (m, 2H), 7.20-7.55 (m, 3.5H), 3.30-3.40 (m, 6H), 3.15-3.25 (m, 1H), 3.20-3.30 (m, 3H), 2.95-3.10 (m, 2H), 2.00-2.20 (m, 2H), 1.65-1.95 (m, 2H), 1.30-1.60 (m, 4H); ESI MS: m/z=430 $[M+H]^+$.

Example 50

Preparation of Compound 2

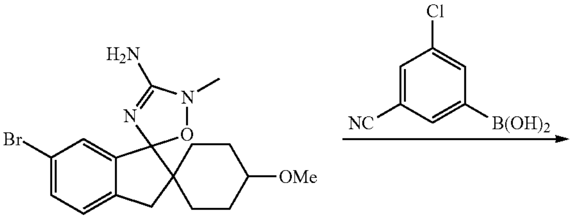

2a

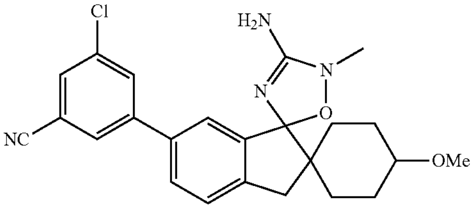

By using the same synthetic strategy as compound 38 described in Example 41, compound 2 (2.8 mg, 14%) was obtained. $^1H$ NMR (400 Hz $CD_3OD$): δ7.85-7.95 (m, 0.3H), 7.65-7.75 (m, 2H), 7.20-7.55 (m, 3.5H), 3.30-3.40 (m, 6H), 3.15-3.25 (m, 1H), 3.20-3.30 (m, 3H), 2.95-3.10 (m, 2H), 2.00-2.20 (m, 2H), 1.65-1.95 (m, 2H), 1.30-1.60 (m, 4H); ESI MS: m/z=430 [M+H]$^+$.

Example 51

Preparation of Compound 7

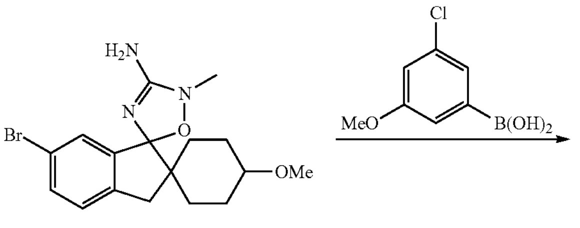

7a

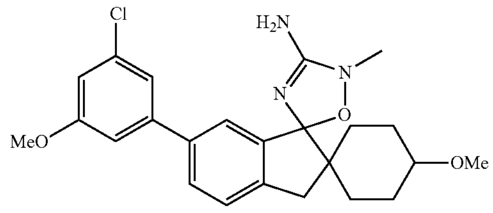

By using the same synthetic strategy as compound 38 described in Example 41, compound 7 (1.23 mg, 4.1%) was obtained. $^1$H NMR (400 Hz $CD_3OD$): δ7.90-8.00 (m, 0.5H), 7.65-7.75 (m, 2H), 7.35-7.45 (m, 0.6H), 7.10-7.20 (m, 1H), 6.95-7.05 (m, 2H), 3.80-3.90 (s, 3H), 3.30-3.45 (m, 6H), 3.00-3.25 (m, 3H), 2.00-2.20 (m, 2H), 1.65-1.95 (m, 3H), 1.35-1.55 (m, 3H); ESI MS: m/z=442 [M+H]$^+$.

Example 52

Preparation of Compound 36

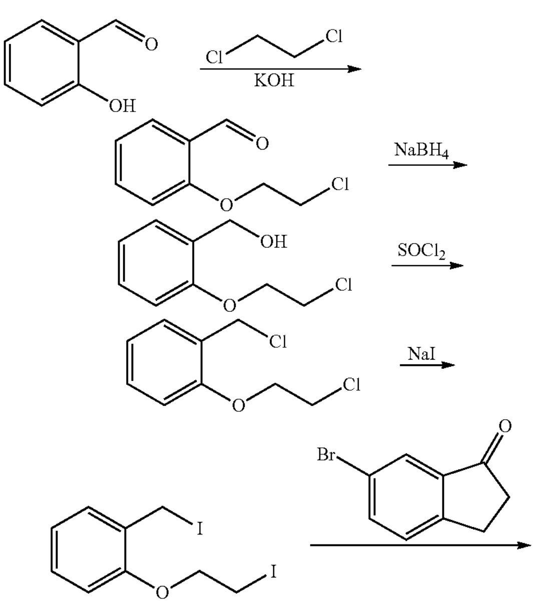

-continued

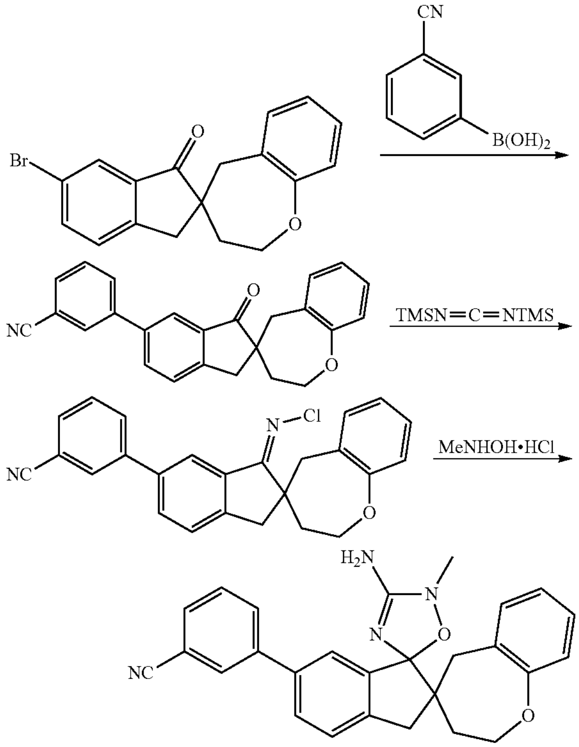

Experimental Data:

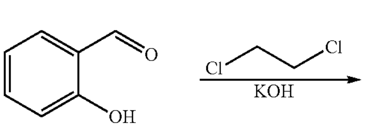

36a

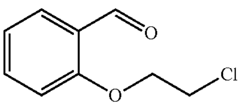

36b

Preparation of Compound 36b

A mixture of compound 36a (50 g, 410 mmol), 1,2-dichloroethane (50 mL), and KOH (25 g, 445 mmol) in $H_2O$ (50 mL) was refluxed for three days. The organic layer was separated, diluted with $CH_2Cl_2$, washed with aqueous NaOH solution and with water, and concentrated to give the compound 36b (47 g, 63%). $^1$H NMR (400 MHz $CDCl_3$): δ7.82 (m, 1H), 7.53 (m, 1H), 7.06 (m, 1H) 6.94 (d, 1H), 4.33 (t, 2H), 3.87 (t, 2H).

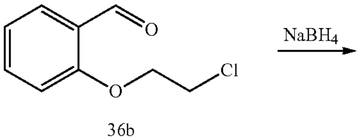

36b

-continued

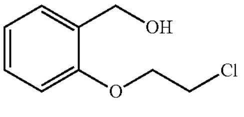

36c

Preparation of Compound 36c

To a solution of compound 36b (10 mg, 54.3 mmol) in MeOH (50 mL) was added $NaBH_4$ (3.0 g, 81.5 mmol) at 0° C. The reaction mixture was stirred at room temperature for 1 h, and concentrated. Water (100 mL) was added at 0° C., and the mixture was extracted with EtOAc (100 mL×3). The organic layer was washed with brine, dried over $Na_2SO_4$, filtered, and concentrated to give the compound 36c (10 g, 99%). $^1$H NMR ($CDCl_3$): δ7.28 (m, 2H), 6.98 (m, 1H), 6.83 (m, 1H), 4.69 (m, 2H), 4.38 (t, 2H), 3.83 (t, 2H).

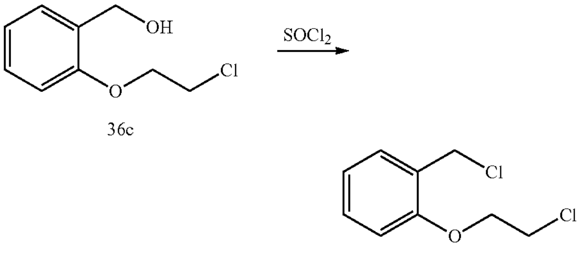

36c

36d

Preparation of Compound 36d

To a solution of compound 36c (10 g, 53.7 mmol) in DCM (30 mL) was added $SOCl_2$ (51 g, 430 mmol) dropwise at 0° C., and the reaction mixture was refluxed overnight. The solution was concentrated, and the residue was diluted $NH_4OH$ and extracted with EtOAc. The organic layer was dried, and concentrated. The residue was purified by flash chromatography to afford the compound 36d (3.8 g, 35%). $^1$H NMR (400 MHz $CDCl_3$): δ7.73 (m, 1H), 7.36 (m, 1H), 7.06 (t, 1H), 6.88 (d, 1H), 4.72 (s, 2H), 4.33 (t, 2H), 3.89 (t, 2H).

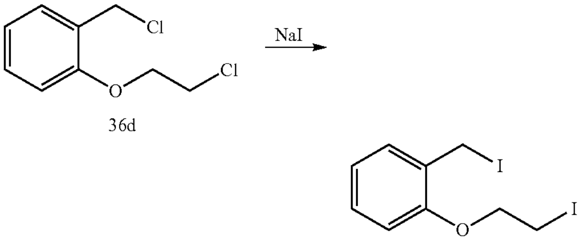

36d

36e

Preparation of Compound 36e

To a solution of compound 36d (1 g, 4.88 ooml) in propan-2-one (25 mL) was added NaI (2.2 g, 14.63 mmol), and the mixture was refluxed for 2 hour. The mixture was filtered, and concentrated. The residue was dissolved in EtOAc (50 mL), and the solution was washed with water (30 mL). The organic layer was dried, and concentrated to give the compound 36e (1.5 g, 79%). $^1$H NMR (400 MHz $CDCl_3$): δ7.34 (d, 1H), 7.25 (m, 1H), 6.93 (t, 1H), 6.81 (d, 1H), 4.51 (s, 2H), 4.31 (m, 2H), 3.92 (t, 2H).

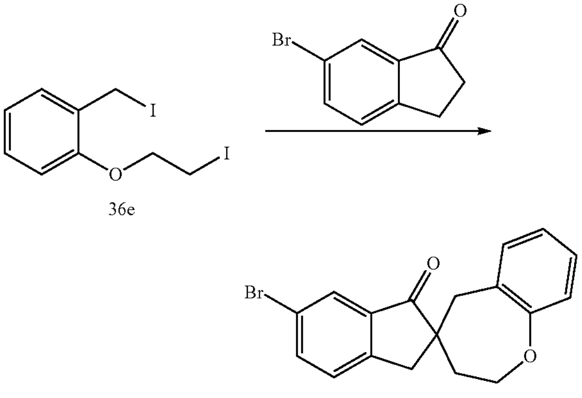

36e

36f

Preparation of Compound 36f

To a solution of 6-bromo-indan-1-one (500 mg, 2.37 mmol) in DMF (15 mL) was added NaH (190 mg, 4.74 mmol) at 0° C. After being stirred for 30 minutes, compound 36e (919 mg, 2.37 mmol) was added, and the mixture was stirred at room temperature overnight. The reaction was quenched with water, and extracted with TBME. The organic layer was washed with water, brine, dried over $Na_2SO_4$, filtered, and concentrated. The residue was purified by preparative TLC to afford the compound 36f (145 mg 18%). $^1$H NMR (400 MHz $CDCl_3$): δ7.88 (s, 1H), 7.64 (m, 1H), 7.16 (m, 1H), 7.01 (d, 4H), 6.88 (m, 1H), 4.48 (m, 2H), 4.07 (m, 1H), 3.69 (m, 2H), 3.38 (d, 1H), 3.22 (m, 1H), 2.68-2.92 (m, 3H), 2.51 (t, 1H), 2.36 (d, 1H), 1.61 (d, 1H).

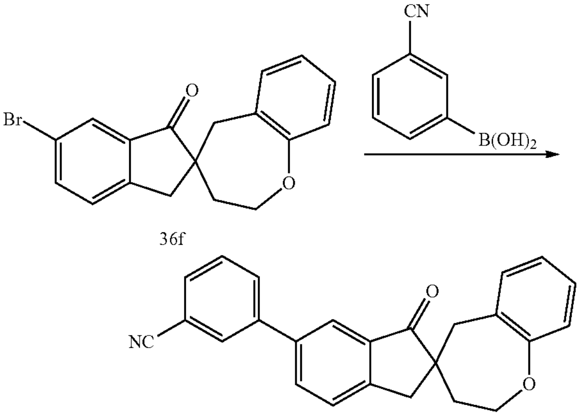

36f

36g

Preparation of Compound 36g $Pd(PPh_3)_2Cl_2$ (10 mg) in a 10 mL of flask under $N_2$ was treated sequentially with the solution of the compound 36f (105 mg, 0.305 mmol) in 1,4-dioxane (2 mL), $Cs_2CO_3$ solution (2 N, 0.3 mL), and 3-cyanophenylboronic acid (90 mg, 0.61 mmol). The mixture was heated at 100° C. under $N_2$ in microwave for 10 minutes. The organic layer was concentrated in vacuo, and the residue was purified by preparative TLC to give the compound 36g (98 mg, 96%). $^1$H NMR (400 MHz $CDCl_3$): δ7.95 (s, 1H), 7.80 (m, 4H), 7.63 (m, 1H), 7.51 (m, 3H), 7.16 (m, 1H), 6.98 (m, 4H), 4.48 (m, 1H), 3.72 (m, 1H), 3.43 (d, 2H), 3.21 (m, 1H), 2.88 (m, 2H), 2.53 (t, 1H), 2.41 (d, 1H).

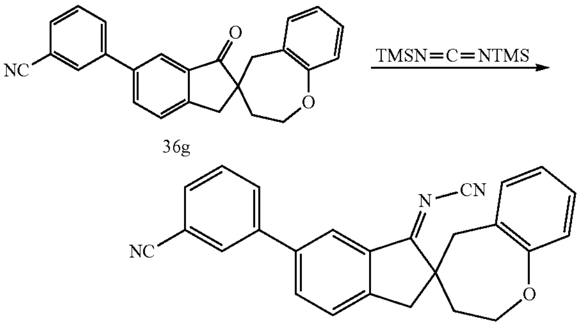

36g

36h

Preparation of Compound 36h

To a solution of compound 36g (70 mg, 0.19 mmol) in drying $CH_2Cl_2$ (3 mL) was added $TiCl_4$ (1 M solution in DCM, 0.38 mL) at room temperature dropwise within 15 minutes. The mixture was stirred for 1 h, added bis-trimehtl-ysilylcarbodiimide (109 mg, 0.58 mmol) dropwise, stirred overnight, poured into ice-water, and extracted with $CH_2Cl_2$. The combined organic layer was washed with brine, dried over $Na_2SO_4$, filtered, and concentrated to give the compound 36h (80 mg, crude), which was used for the next step without further purification.

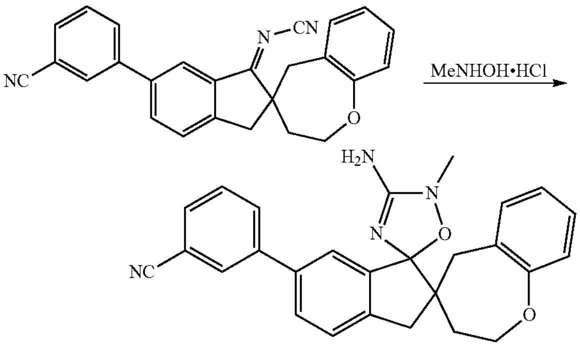

Preparation of Compound 36

To a solution of MeNHOH.HCl (17 mg, 0.206 mmol) in anhydrous MeOH (3 mL) was added NaOMe (10% in MeOH, 100 mg, 0.185 mmol) and compound 36h (80 mg, 0.206 mmol) at room temperature. After being stirred for 10 minutes, the solvent was removed in vacuum, the residue was dissolved in $CH_2Cl_2$. After filtration, the filtrate was concentrated, and the residue was purified by preparative TLC and HPLC to afford the compound 36 (5.08 mg, 6%). $^1$H NMR (400 MHz $CD_3OD$): δ8.02 (m, 2H), 7.52-7.93 (m, 4H), 7.38 (m, 1H), 7.21 (m, 1H), 7.03 (m, 3H), 4.48 (m, 1H), 3.7 (m, 1H), 3.48 (m, 3H), 3.19 (m, 2H), 2.52-2.78 (m, 2H), 2.46 (m, 1H), 1.73-2.11 (m, 1H); ESI MS: m/z 437 $[M+H]^+$.

Example 53

Preparation of Compound 63

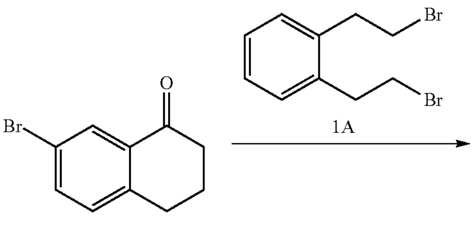

63a

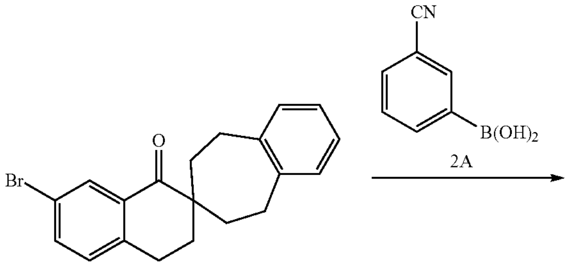

63b

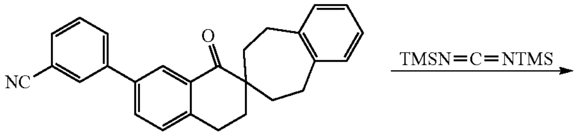

63c

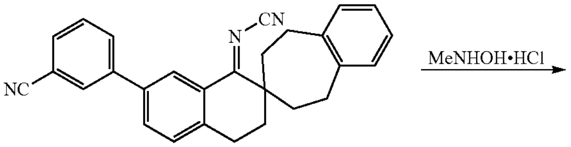

63d

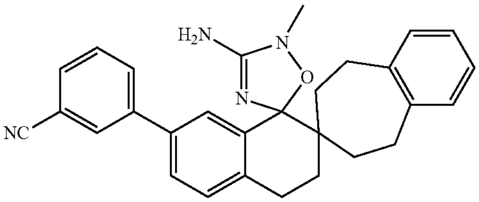

Experimental Data:

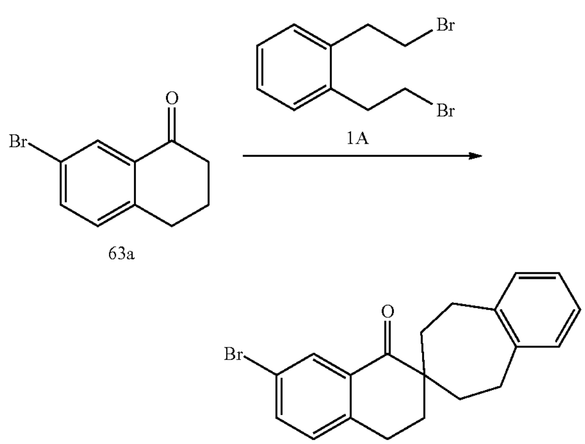

63a

63b

Preparation of Compound 63b

A solution of compound 63a (1 g, 4.46 mmol) in DMF (20 mL) was added NaH (393 mg, 9.81 mmol) in ice water bath, and the mixture was stirred at room temperature for 30 min., and compound 1A was added dropwise. The mixture was stirred overnight, quenched with water, and extracted with $CH_2Cl_2$. The organic layer was washed with brine, dried over $Na_2SO_4$, and concentrated to give the compound 63b (100 mg, 5%).

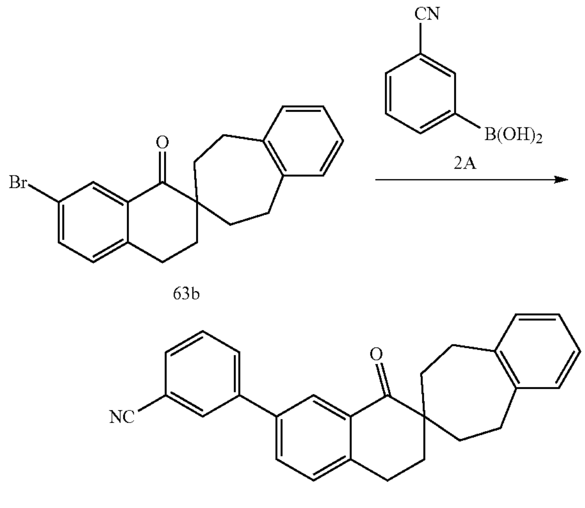

63b

63c

Preparation of Compound 63c $Pd(PPh_3)_2Cl_2$ (30 mg) in a 10 mL of tube was treated sequentially with a solution of compound 63b (100 mg, 354 mmol) in 1,4-dioxane (3 mL), $Cs_2CO_3$ solution (2 N, 0.6 mL), and 3-cyanophenylboronic acid (83 mg, 147 mmol) under $Ar_2$ atmosphere. The mixture was heated in microwave at 120° C. for 25 min. The reaction mixture was concentrated in vacuo, the residue was purified by preparative TLC to give the compound 63c (20 mg, 18%).

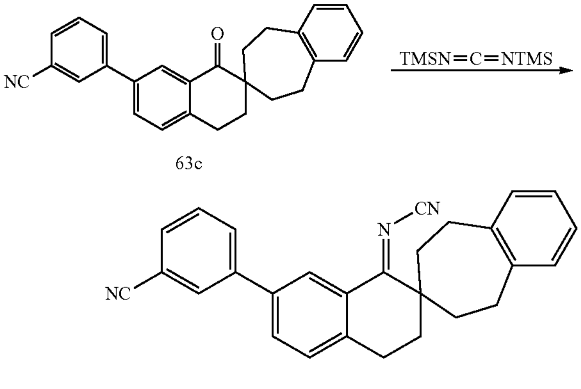

63c

63d

Preparation of Compound 63d

To a solution of compound 63c (20 mg, 0.053 mmol) in $CH_2Cl_2$, (3 mL) was added $TiCl_4$ (39.5 mg, 0.2 mmol) dropwise, and the mixture was stirred at 50° C. at $Ar_2$ in microwave for 20 minutes, N,N'-methanediylidenebis(1,1,1-trimethylsilanamine) (18 mg, 0.096 mmol) was added dropwise. The mixture was stirred at 60° C. under $Ar_2$ in microwave for 10 minutes, and poured into ice-water (10 mL). The aqueous layer was extracted with $CH_2Cl_2$. The organic layer was dried, and concentrated to give the crude compound 63d (20 mg), which was used for the next step directly without purification.

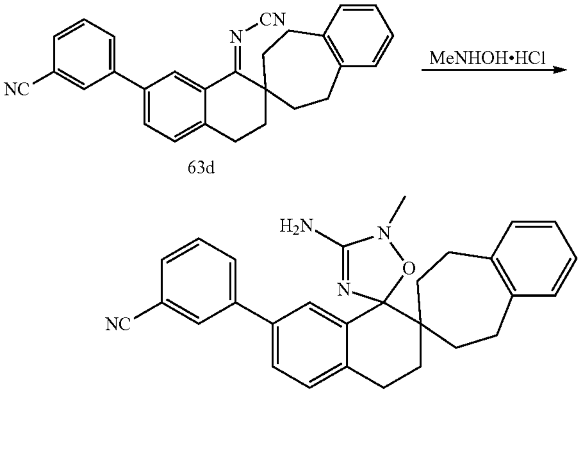

63d

Preparation of Compound 63

To a solution of N-methyl-hydroxylamine hydrochloride (4.2 mg, 0.05 mmol) in MeOH (5 mL) was added MeONa (2.43 mg, 25% in MeOH) and (E)-N-(7'-(3-cyanophenyl)-3',4',5,6,8,9-hexahydro-1'H-spiro[benzo[7]annulene-7,2'-naphtha-lene]-1'-ylidene)cyanamide (20 mg, 0.053 mmol). After being stirred for 10 minutes, the solvent was removed in vacuo to give the crude compound, which was purified by preparative TLC and HPLC to give compound 63 (0.41 mg, 2%). $^1$H-NMR ($CD_3OD$ 400 MHz): 7.92 (t, 2H), 7.60-7.74 (m, 4H), 7.41 (t, 1H), 7.09 (m, 4H), 3.33 (d, 3H), 3.12 (m, 2H), 3.00 (t, 2H), 2.69 (d, 2H), 2.32 (t, 2H), 1.58 (t, 2H), 1.47 (d, 2H); ESI MS: m/z 449 $[M+H]^+$.

Example 54

Preparation of Compound 3

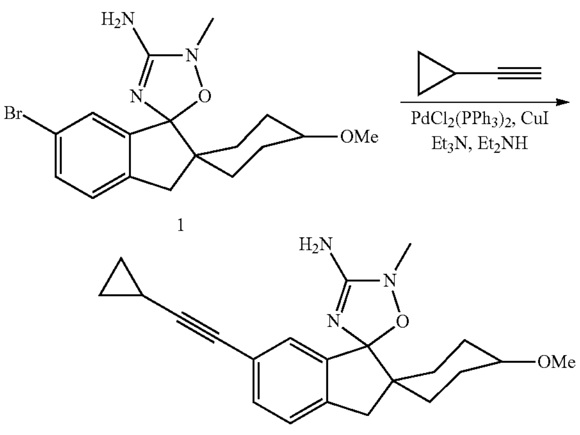

1

By using the same synthetic procedure as compound 76a in Example 56, compound 3 (4.5 mg, 12%) was obtained as a white solid. $^1$H-NMR (400 MHz $CD_3OD$): δ7.59 (m, 1H), 7.42 (d, J=9.6 Hz, 1H), 7.27 (d, J=7.6 Hz, 1H), 3.38 (d, J=12.0 Hz, 3H), 3.31 (m, 3H), 3.17 (m, 1H), 2.97 (m, 1H), 2.16 (m, 2H), 1.72 (m, 3H), 1.46 (m, 4H), 0.91 (m, 2H), 0.76 (m, 2H); ESI MS: 366 $[M+H]^+$.

Alternatively, compound 3 can be prepared according to the following scheme:

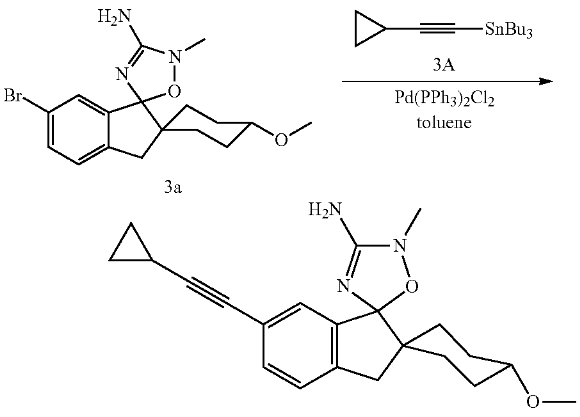

3a

3

A solution containing compound 3a (300 mg, 0.789 mmol) and compound 3A (560 mg, 1.58 mmol) in toluene (20 mL) was deoxygenated by bubbling a stream of nitrogen through the reaction mixture for 5 min. Then, $PdCl_2(PPh_3)_2$ (5 mg) was added. The reaction vial was sealed and placed into CEM microwave reactor and irradiated at 130° C. for 30 min. After being cooled to room temperature, the mixture was partitioned between EtOAc (50 mL) and aqueous CsF (4.0 M, 50 mL), and the aqueous layer was extracted with EtOAc (3×50 mL). The combined organic layers were washed with brine (50 mL), dried over anhydrous $Na_2SO_4$, filtered, and concentrated in vacuo. The residue was purified by preparative HPLC to afforded compound 3 (93 mg, 31%) as a white solid. LC-MS $t_R$=1.084 min and 1.143 min in 2 min chromatography, MS (ESI) m/z 366.2 $[M+H]^+$. $^1$H NMR ($CD_3OD$, 400 MHz): δ 7.22-7.26 (t, J=7.6 Hz, 2H), 7.13-7.15 (d, J=7.6 Hz, 1H), 3.37 (s, 3H), 3.12-3.20 (m, 1H), 3.03 (s, 3H), 2.78-2.88 (q, J=16.0 Hz, J=10.4 Hz, 2H), 1.99-2.06 (m, 2H), 1.65-1.68 (m, 1H), 1.52-1.60 (m, 2H), 1.41-1.49 (m, 2H), 1.27-1.37 (m, 2H), 0.86-0.92 (m, 2H), 0.70-0.75 (m, 2H).

Example 55

Preparation of Compound 16

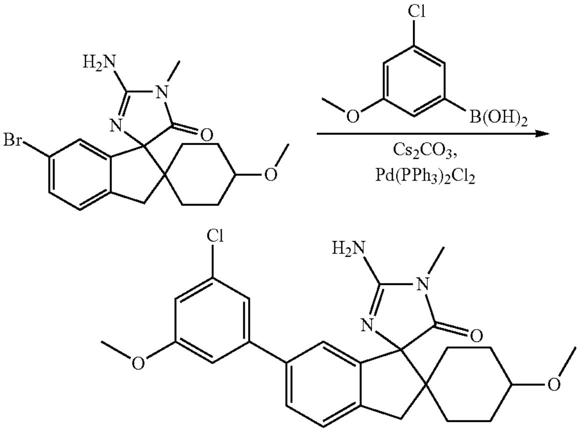

By using the same synthetic procedure as compound 4 described in Example 27, compound 16 (2.3 mg, yield 8%) was obtained. $^1$H-NMR ($CD_3OD$, 400 MHz): δ7.53 (d, 1H), 7.38 (m, 2H), 7.12 (m, 1H), 6.99 (m, 1H), 6.83 (m, 1H), 3.72 (s, 3H), 3.26 (m, 3H), 3.05-3.12 (m, 6H), 1.88-2.06 (m, 2H), 1.76 (d, 1H), 1.38 (m, 3H), 1.22 (m, 2H); ESI MS: m/z 454 $[M+H]^+$.

Example 56

Preparation of Compound 76

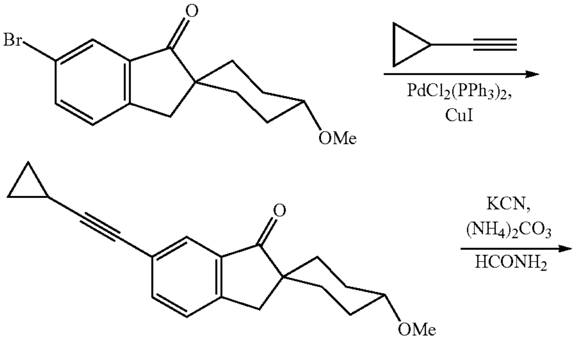

76a

-continued

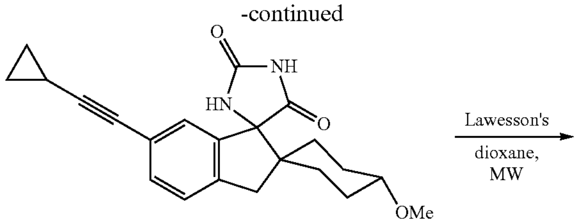

76b

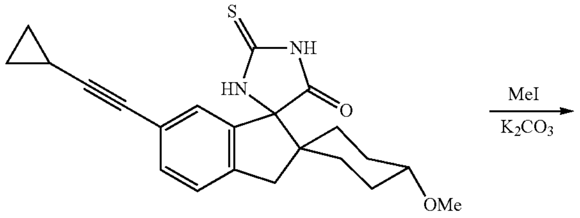

76c

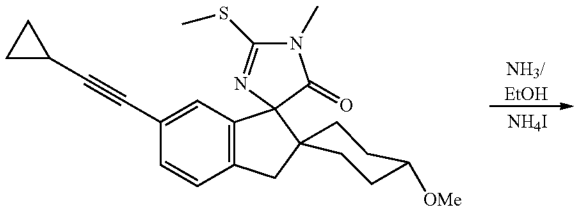

76d

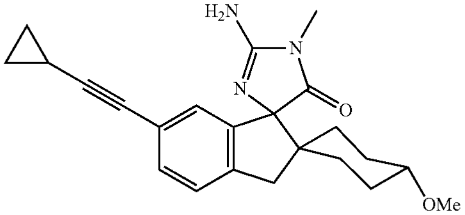

Procedure for Preparation of the Compound 76a

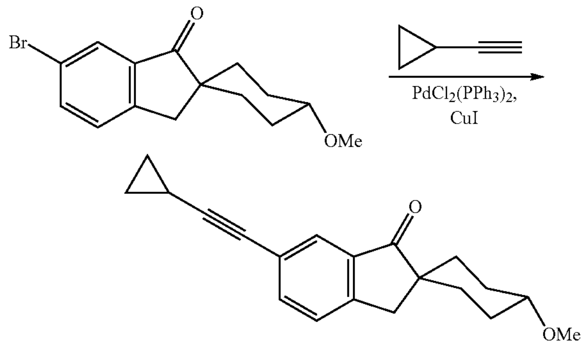

76a

A dry three-necked round bottom flask equipped with a condenser was charged with 6'-bromo-4-methoxyspiro[cyclohexane-1,2'-inden]-1'(3'H)-one (1.8 g, 5.8 mmol), TEA (30 mL) and DEA (6 mL) under $N_2$ atmosphere. To this solution was added CuI (60 mg, 0.3 mmol), and $PdCl_2(PPh_3)_2$ (210 mg, 0.3 mmol). After being degassed once again, the cyclopropyl acetylene (3 mL, excess) was added, and the mixture was heated at 50° C. (oil bath) with stirring for 15 hours. After evaporation, the residue was partitioned with EtOAC (50 mL) and water (30 mL), and the aqueous layer was extracted with EtOAc (2x30 mL). The combined organic layers were washed with brine (30 mL), dried over $Na_2SO_4$, and concentrated under reduced pressure, and the crude product was purified by column chromatography on silica gel eluting with 5%-20% EtOAc in hexane to afford the compound 76a (1.55 g, 87% purity), which was purified by preparative HPLC to yield give the pure compound 1 (0.88 g, 51%) as a white solid. $^1$H-NMR ($CDCl_3$, 400 MHz): δ7.66 (s, 1H), 7.50 (d, J=8.0 Hz, 1H), 7.29 (d, J=8.0 Hz, 1H), 3.32 (s, 3H), 3.18 (m, 1H), 2.93 (s, 2H), 2.08 (m, 2H), 1.69 (m, 2H), 1.52 (s, 1H), 1.38 (m, 5H), 0.82 (m, 2H), 0.71 (m, 2H).

Procedure for Preparation of the Compound 76b

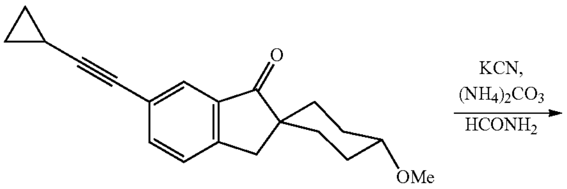

76a

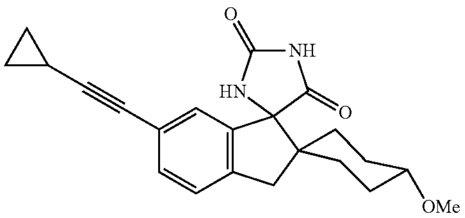

76b

A steel clave was charged with a mixture of 6'-(cyclopropylethynyl)-4-methoxyspiro [cyclohexane-1,2'-inden]-1'(3'H)-one (600 mg, 2.04 mmol), KCN (266 mg, 4.08 mmol), and $(NH_4)_2CO_3$ (689 mg, 15.29 mmol). Formamide (20 mL) was added to fill tube completely. The mixture was heated at 100° C. for 72 h, and the reaction mixture was cooled, and poured into ice. After acidification with concentrated aqueous HCl solution (20 mL), the mixture was filtrated to give the solid, which was dissolved in ethyl acetate (600 mL) and washed with water (150 mLx2). The organic phase was dried over $Na_2SO_4$ and concentrated to give the compound 76b (660 mg, 80%) as a white solid, which was used for the next step directly without purification. $^1$H-NMR ($CDCl_3$ 400 MHz): δ7.59 (s, 1H), 7.23 (m, 1H), 7.16 (m, 2H), 3.29 (s, 3H), 2.92-3.11 (m, 3H), 2.06 (m, 1H), 1.88-1.97 (m, 2H), 1.59 (m, 1H), 1.43 (m, 1H), 1.32-1.38 (m, 2H), 1.25 (m, 2H), 0.82 (m, 2H), 0.73 (m, 2H).

Procedure for Preparation of the Compound 76c

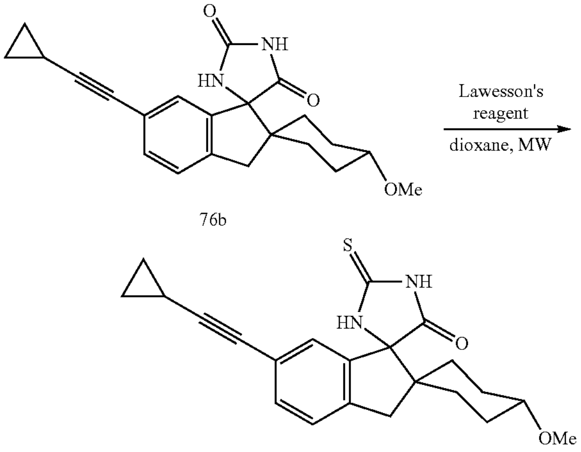

76b

76c

A suspension of compound 76b (660 mg, 1.81 mmol) and Lawesson's Reagent (730 mg, 1.81 mmol) in dry 1,4-dioxane (60 mL) was heated at 120° C. for 35 minutes in a CEM microwave reactor. The mixture was concentrated in vacuo, and the residue was purified by column chromatography on silica gel eluting with PE/EA=5/1 to give the compound 76c as a yellow solid (330 mg, 47%). $^1$H-NMR ($CDCl_3$ 400 MHz): δ7.96 (s, 1H), 7.27 (m, 1H), 7.08-7.14 (m, 2H), 6.92 (m, 1H), 3.63-3.79 (m, 1H), 3.28 (s, 3H), 2.92-3.11 (m, 3H), 2.04 (m, 1H), 1.97 (m, 1H), 1.35 (m, 5H), 1.26 (m, 1H), 0.81 (m, 2H), 0.72 (m, 2H).

2. Procedure for Preparation of Compound 76d

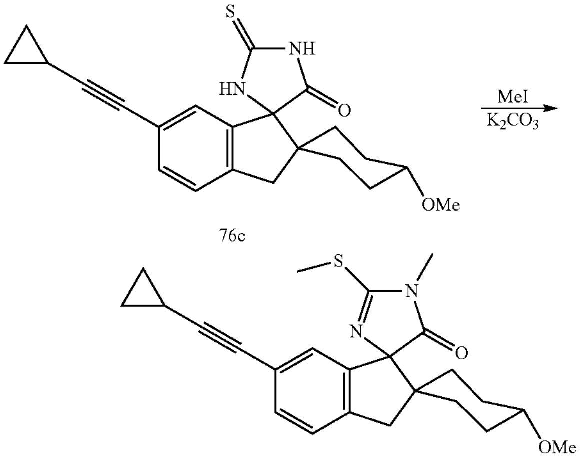

76c

76d

To a solution of compound 76c (300 mg, 0.786 mmol) in $CH_3CN$ (30 mL) was added $K_2CO_3$ (434 mg, 3.14 mmol). After being stirred for 5 minutes, MeI (462 mg, 3.14 mmol) was added, and the reaction mixture was heated at 60° C. for 10 minutes in microwave, and at 100° C. for another 10 minutes. The mixture was filtered, and the filtrate was concentrated in vacuo. The residue was purified by preparative TLC (PE/EA=5/1) to give the compound 76d (150 mg, 47%) as a white solid. $^1$H-NMR ($CDCl_3$ 400 MHz): δ7.18 (m, 1H), 7.16 (d, J=7.6 Hz, 1H), 6.78 (s, 1H), 3.27 (s, 3H), 3.14 (m, 1H), 2.98-3.04 (m, 2H), 2.92 (s, 3H), 2.58 (s, 3H), 1.78-1.92 (m, 3H), 1.65 (t, 1H), 1.46 (m, 1H), 1.22-1.36 (m, 3H), 1.08 (m, 1H), 0.74 (m, 2H), 0.67 (m, 2H).

3. Procedure for Preparation of Compound 76

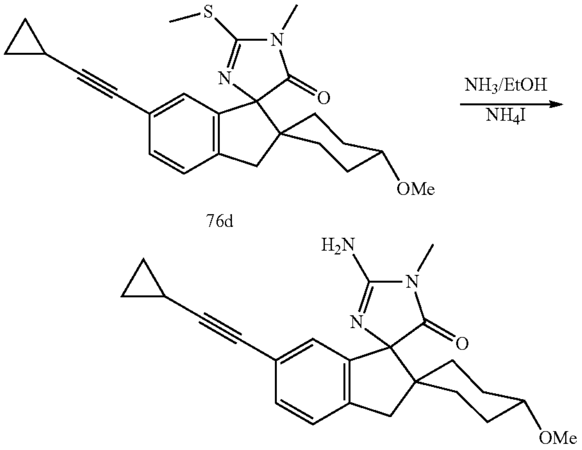

76d

A solution of compound 76d (150 mg, 0.37 mmol), $NH_4I$ (531 mg, 3.7 mmol) in $NH_3$/EtOH (15 mL, 5 N) was heated at 120° C. in a CEM microwave reactor for 3 h. After being cooled, the mixture was concentrated in vacuum, and the residue was purified by preparative TLC (DCM/MeOH=10/1) and preparative HPLC to give compound 76 (92 mg, 66%) as a white solid. $^1$H-NMR ($CD_3OD$ 400 MHz): δ7.19 (m, 2H), 6.88 (s, 1H), 3.32 (s, 3H), 3.2.98-3.12 (m, 6H), 1.91-2.04 (m, 2H), 1.82 (m, 1H), 1.57 (m, 1H), 1.21-1.43 (m, 5H), 0.82 (m, 2H), 0.68 (m, 2H); ESI MS: m/z 378 $[M+H]^+$.

Example 57

Preparation of Compound 31

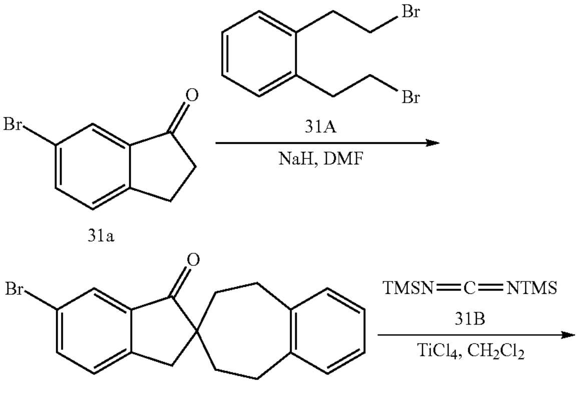

31a

31b

-continued

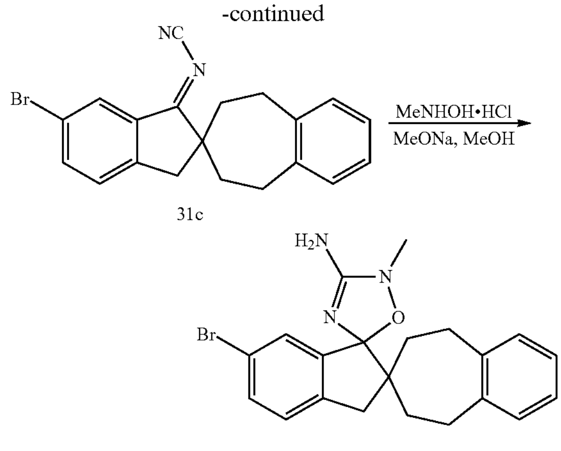

31c

Experimental Data

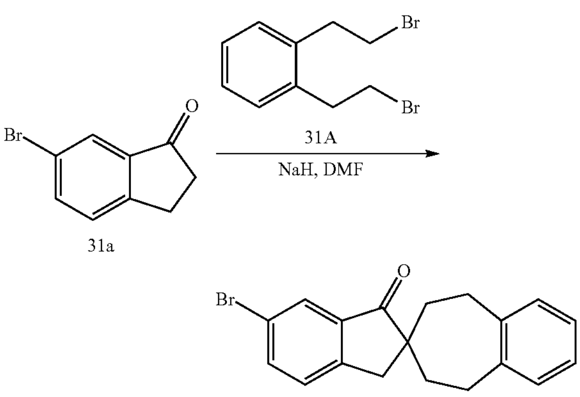

31A

31a

31b

A mixture of compound 31a (2.17 g, 10.35 mmol) and compound 31A (6 g, 20.7 mmol) in DMF (17.5 mL) was added NaH (910 mg, 60%, 22.75 mmol) at 0° C. The mixture was stirred at room temperature overnight, quenched with water (5 mL), and extracted with EtOAc (3x50 mL). The organic layer was dried, and concentrated. The residue was purified by column chromatography to give the compound 31b (250 mg, yield 7%) as a yellow solid.

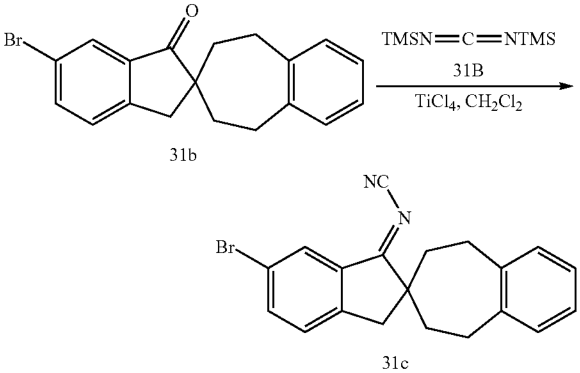

31b

31c

To a solution of compound 31b (200 mg, 0.59 mmol) in $CH_2Cl_2$ (26 mL) was added $TiCl_4$ (2.35 mL, 2.35 mmol). The mixture was stirred at room temperature for 1 h, and compound 31B (245.7 mg, 1.3 mmol) was added. The mixture was stirred at room temperature overnight, poured into ice-water (5 mL), and extracted with $CH_2Cl_2$ (2x20 mL). The combined organic phases were dried over anhydrous $Na_2SO_4$, filtered, and concentrated to give the compound 31c (200 mg, crude) as a yellow solid.

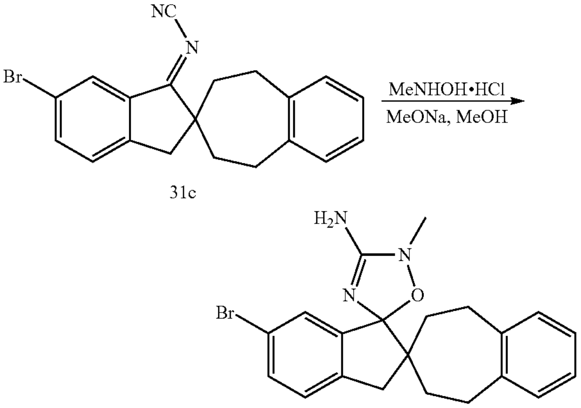

31c

To a solution of methylhydroxylamine HCl salt (11.5 mg, 0.137 mmol) in anhydrous MeOH (2.5 mL) was added NaOMe (10% in MeOH, 0.07 mL) and compound 31c (50 mg, 0.137 mmol). After being stirred for 20 minutes, the solvent was removed in vacuo, and the residue was dissolved in $CH_2Cl_2$ (10 mL). The mixture was filtered, concentrated, and purified by pre-TLC and HPLC to give the compound 31 (4.99 mg, yield 9%) as a white solid. $^1H$-NMR ($CD_3OD$ 400 MHz): δ7.60-7.87 (m, 2H), 7.32 (d, J=8.0 Hz, 1H), 7.10-7.13 (m, 4H), 3.32 (m, 3H), 2.97-3.11 (m, 3H), 2.70-2.78 (m, 2H), 2.05-2.10 (m, 1H), 1.67-1.70 (m, 1H), 1.47-1.68 (m, 3H); ESI MS: m/z 412 $[M+H]^+$.

Example 58

Preparation of Compound 35

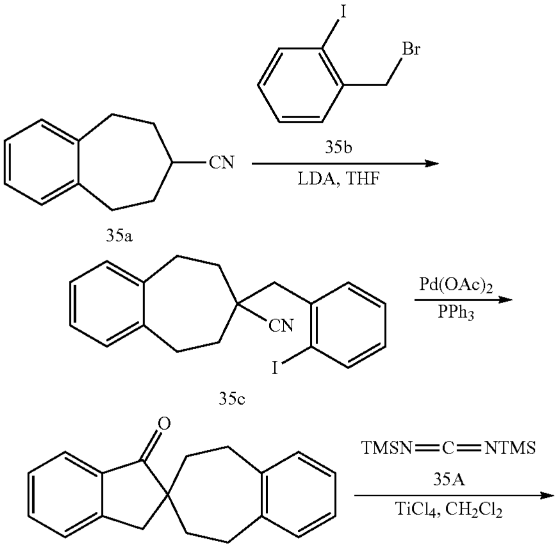

35a

35c

35d

-continued

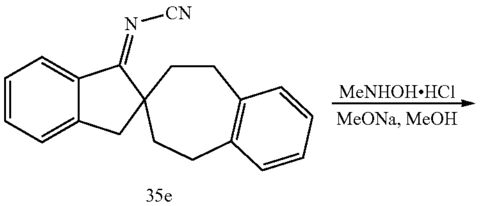

35e

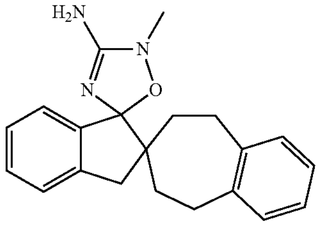

Experimental Data

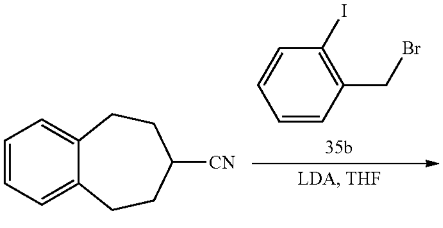

35a

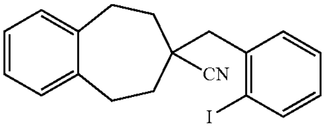

35c

The solution of LDA (6.5 mL, 11.7 mmol, 1.8M in THF) in THF (12.5 mL) was added the solution of compound 35a (1 g, 5.85 mmol) in THF (6 mL) slowly at −60° C. The mixture was stirred at −60° C. for 30 min., the solution of compound 35b (1.55 g, 5.26 mmol)) in THF (5 mL) was added slowly. The resulting mixture was stirred at −60° C. for 1.5 h, quenched with water (10 mL), and extracted with EtOAc (2×30 mL). The combined organic layers were washed with brine (20 mL), dried over $Na_2SO_4$, concentrated, and purified by chromatography to give the compound 35c (1.85 g, yield 82%) as a yellow solid. $^1$H-NMR ($CDCl_3$ 400 MHz): δ7.81 (m, 1H), 7.52 (m, 1H), 7.26-7.49 (m, 1H), 7.19 (m, 4H), 6.92 (m, 1H), 2.99-3.13 (m, 2H), 2.97 (s, 2H), 2.66 (m, 2H), 2.04-2.10 (m, 2H), 1.52-1.61 (m, 2H).

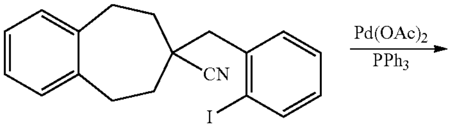

35c

-continued

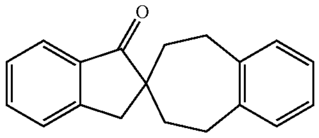

35d

A 100 mL flask was charged with compound 35c (1.85 g, 4.77 mmol), $Pd(OAc)_2$ (0.140 g, 0.62 mmol), $Ph_3P$ (0.363 g, 1.38 mmol), DMF (75 mL) and $H_2O$ (8.33 mL). The resulting mixture was degassed, and $Et_3N$ (0.578 g, 5.72 mmol) was added under nitrogen. The reaction mixture was stirred at 130° C. for 4 h, cooled to room temperature, diluted with water (20 mL), and extracted with EtOAc (2×40 mL). The combined organic layers were washed with brine (20 mL), dried over $Na_2SO_4$, concentrated, and purified by chromatography to give the compound 35d (650 mg, yield 52%) as a white solid. $^1$H-NMR ($CDCl_3$ 400 MHz): δ7.74 (m, J=8.2 Hz, 1H), 7.58-7.73 (m, 1H), 7.41-7.43 (m, 1H), 7.31-7.33 (m, 1H), 7.03-7.09 (m, 4H), 3.15 (s, 2H), 2.93-3.00 (m, 2H), 2.80 (br s, 2H), 1.79-1.86 (m, 2H), 1.57-1.62 (m, 2H).

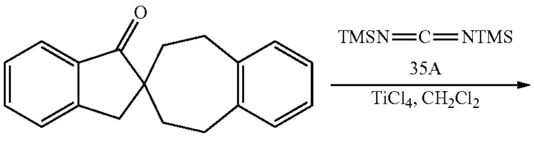

35d

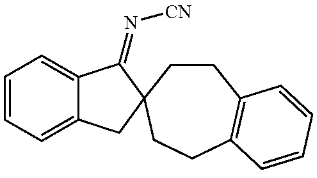

35e

To a solution of compound 35d (100 mg, 0.38 mmol) in $CH_2Cl_2$ (7 mL) was added $TiCl_4$ (1.53 mL, 1.53 mmol). This mixture was stirred at 50° C. for 10 min in microwave, and added bis-trimethylsilylcarbodiimide (0.187 mL, 0.836 mmol). The resulting mixture was stirred at 60° C. for 12 min. in microwave, TLC showed that the reaction was completed, the mixture was poured into the ice-water (20 mL). The solution was extracted with $CH_2Cl_2$ (2×30 mL). The combined organic layers were washed with brine (10 mL), dried over $Na_2SO_4$ and concentrated to give the compound 35e (100 mg, yield 93%) as a yellow solid, which was used directly for the next step without purification.

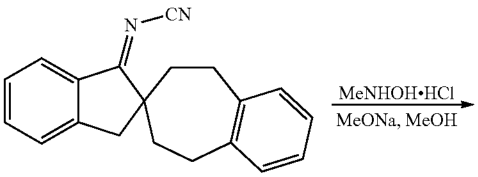

35e

-continued

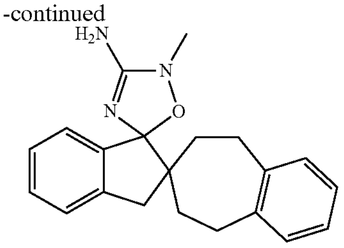

To a solution of methylhydroxylamine HCl salt (14.5 mg, 0.175 mmol) in anhydrous MeOH (3 mL) was added NaOMe (10% in MeOH, 0.090 mL, 0.157 mmol) and compound 35e (50 mg, 0.175 mmol). After being stirred for 25 minutes, the solvent was removed in vacuo, and residue was dissolved in $CH_2Cl_2$ (20 mL). The mixture was filtered, and the solvent was removed, the residue was purified by HPLC to give the compound 35 (3.4 mg, yield 6%) as a white solid. $^1$H-NMR ($CD_3OD$ 400 MHz): δ7.51-7.77 (m, 2H), 7.47 (m, 1H), 7.40 (m, 1H), 7.11-7.17 (m, 4H) 3.34 (s, 3H), 2.97-3.12 (m, 3H), 2.73-2.85 (s, 2H), 2.09-2.67 (m, 3H), 1.66-1.69 (m, 1H), 1.49-1.56 (m, 1H); ESI MS: 515 [M+H]$^+$.

Example 59

Preparation of Compound 18

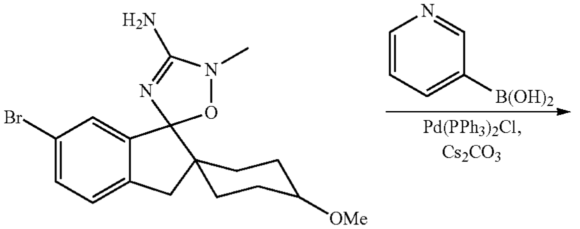

18a

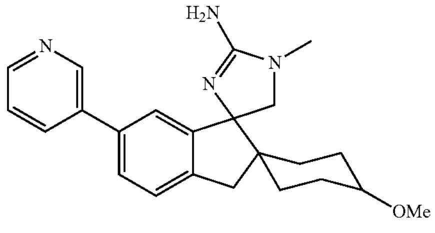

A solution of compound 18a (25 mg, 0.065 mmol) in 1,4-dioxane (2 mL) was added 3-pyridinylboronic acid (12 mg, 0.098 mmol), $Cs_2CO_3$ (2N, 0.5 mL), and $Pd(PPh_3)_2Cl_2$ (4.3 mg, 0.00065 mmol, under nitrogen atmosphere. The mixture was stirred in microwave at 120° C. for 15 min., TLC showed the reaction was completed, and the reaction mixture was concentrated, and purified by Prep-TLC and Prep-HPLC to give compound 18 (5 mg, 20%) as a white solid. $^1$H-NMR: δ8.78 (s, 1H), 8.51 (d, 1H), 8.10 (m, 1H), 7.61 (m, 1H), 7.54

(m, 2H), 7.39 (m, 1H), 3.51 (s, 3H), 3.15 (s, 3H), 2.94 (m, 2H), 2.09 (m, 2H), 1.76 (m, 1H), 1.64 (m, 2H), 1.32-1.49 (m, 4H); ESI MS: 379 [M+H]$^+$.

Example 60

Preparation of Compound 37

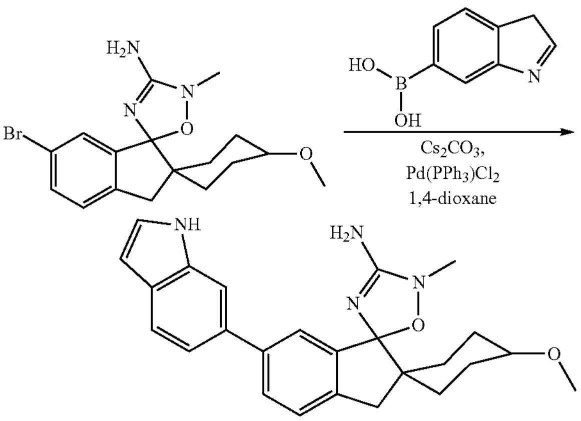

By using the same synthetic strategy as compound 18 described in Example 59, compound 37 (3.9 mg, yield 11%) was obtained as a white solid. $^1$H-NMR ($CD_3OD$ 400 MHz): δ7.71-7.92 (m, 1H), 7.30-7.69 (m, 4H), 7.11-7.29 (m, 2H), 3.25-3.36 (m, 6H), 3.11-3.15 (m, 2H), 2.88-2.90 (d, 1H), 1.95-2.15 (m, 2H), 1.57-1.85 (m, 3H), 1.26-1.50 (m, 3H); ESI MS: 417 [M+H]$^+$.

Specific stereochemistry shown in Examples 1-60 was determined based on spectroscopic data and/or computer modeling study.

LCMS Method for Examples 61-409 and 411-433

LCMS Chromatographic method: (2 min)
Column: Welch Xtimate C18 2.1*30 mm, 3 um

| | | | |
|---|---|---|---|
| Mobile Phase | A 4 L $H_2O$ (1.5 mL TFA)<br>B 4 L MeCN (0.75 mL TFA) | | |
| | TIME(min) | A % | B % |
| | 0 | 90 | 10 |
| | 1.5 | 20 | 80 |
| | 1.51 | 20 | 80 |
| | 2 | 90 | 10 |
| Flow Rate | 1.2 mL/min | | |
| Wavelength | UV220 | | |
| Oven Tem. | 50° C. | | |
| MS | ESI | | |

LCMS Chromatographic method: (3 min)
Column: Welch Xtimate C18 2.1*30 mm, 3 um

| | | | |
|---|---|---|---|
| Mobile Phase | A 4 L $H_2O$ (1.5 mL TFA)<br>B 4 L MeCN (0.75 mL TFA) | | |
| | TIME(min) | A % | B % |
| | 0 | 90 | 10 |
| | 1.35 | 20 | 80 |
| | 2.25 | 20 | 80 |

-continued

| | | | |
|---|---|---|---|
| | 2.26 | 90 | 10 |
| | 3.00 | 90 | 10 |
| Flow Rate | 0.8 mL/min | | |
| Wavelength | UV220 | | |
| Oven Tem. | 50° C. | | |
| MS | ESI | | |

LCMS Chromatographic method: (7 min)

Column: Welch Xtimate C18 2.1*30 mm, 3 um

| Mobile Phase | A 4 L $H_2O$ (1.5 mL TFA)<br>B 4 L MeCN (0.75 mL TFA) | | |
|---|---|---|---|
| | TIME(min) | A % | B % |
| | 0 | 90 | 10 |
| | 6 | 20 | 80 |
| | 6.5 | 20 | 80 |
| | 6.51 | 90 | 10 |
| | 7 | 90 | 10 |
| Flow Rate | 0.8 mL/min | | |
| Wavelength | UV220 | | |
| Oven Tem. | 50° C. | | |
| MS | ESI | | |

Example 61

Preparation of Compound 94

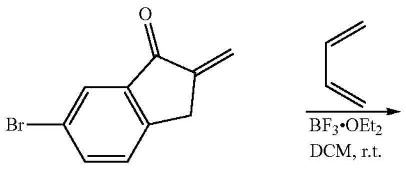

94a

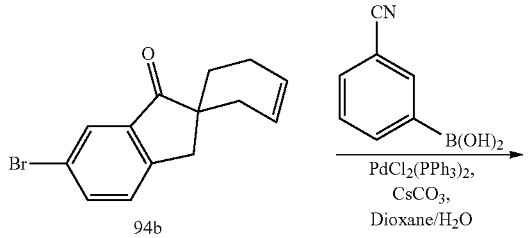

94b

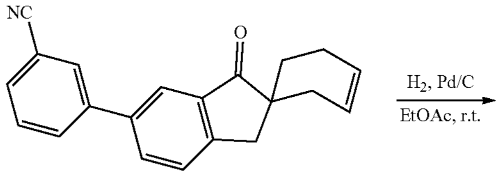

94c

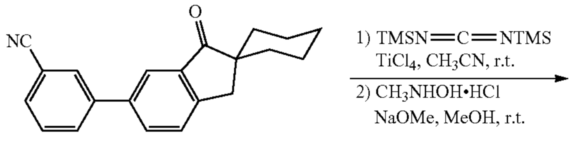

94d

-continued

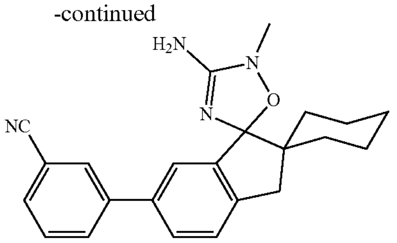

94

Step 1: preparation of 6'-bromospiro[cyclohex[3]ene-1,2'-inden]-1'(3'H)-one (94b)

In a flame dried 50 mL round bottom flask was placed 6-bromo-2-methylene-2,3-dihydro-1H-inden-1-one (500 mg, 2.252 mmol) and it was dissolved in dichloromethane (7.5 mL). To this solution was bubbled 1,3-butadiene (excess). After stirring for 5 minutes, $BF_3.OEt_2$ (414 μL, 3.377 mmol) was slowly added and the 1,3-butadiene still bubbling (2-3 bubbles per second; for 2 minutes). After the 2 minutes, the reaction was quenched with saturated $NaHCO_3$ aq. (10 mL), and diluted with DCM (10 mL). The phases were separated and the aqueous phase was back-extracted with dichloromethane (10 mL). The combined organic phases were washed with brine, dried over $MgSO_4$, filtered and concentrated under reduce pressure. The crude material was purified by flash chromatography (ISCO, 40 g $SiO_2$ cartridge, ethyl acetate/hexanes as the eluents). The corresponding fractions were combined and concentrated under reduce pressure yielding 6'-bromospiro[cyclohex[3]ene-1,2'-inden]-1'(3'H)-one (317 mg, 1.149 mmol, 51% yield). M+H=276.9, 278.9 (bromine ion effect). $^1$H NMR=($CDCl_3$, 400 MHz) δ 7.88 (d, J=2.0 Hz, 1H), 7.67 (dd, J=8.0, 2.0 Hz, 1H), 7.31 (d, J=8.0 Hz, 1H), 5.81-5.72 (m, 2H), 2.98 (d, $J_{A,B}$=17.6 Hz, 1H), 2.86 (d, $J_{A,B}$=17.2 Hz, 1H), 2.48-2.42 (m, 1H), 2.28-2.16 (m, 2H), 1.93-1.85 (m, 1H), 1.81-1.75 (m, 1H), 1.51-1.46 (m, 1H).

Step 2: Preparation of 3-(1'-oxo-1',3'-dihydrospiro[cyclohex[3]ene-1,2'-indene]-6'-yl)benzonitrile (94c)

In a 20 mL vial was placed 6'-bromospiro[cyclohex[3]ene-1,2'-inden]-1'(3'H)-one (155 mg, 0.562 mmol), 3-cyanobenzeneboronic acid (107 mg, 0.728 mmol), $PdCl_2(PPh_3)_2$ (39 mg, 0.056 mmol) and cesium carbonate (457 mg, 1.403 mmol). This solid mixture was dissolved in a Dioxane/water mixture (5.6 mL, 6:1 ratio, respectively). The reaction vial was capped and allowed to stir at 90° C. for 1 hour. At this time, the mixture was filtered through a Celite plug. The plug was rinsed with dichloromethane (15 mL) and water (15 mL). The phases in the filtrate were separated. The aqueous phase was back-extracted with dichloromethane (5 mL). The combined organic phases were dried over $MgSO_4$, filtered and concentrated under reduce pressure. The crude material was purified by flash chromatography (ISCO, 40 g $SiO_2$ cartridge, ethyl acetate/hexanes as the eluents). The corresponding fractions were combined and concentrated under reduce pressure yielding 3-(1'-oxo-1',3'-dihydrospiro[cyclohex[3]ene-1,2'-indene]-6'-yl)benzonitrile (125 mg, 0.418 mmol, 74% yield). M+H=299.9 $^1$H NMR=($CDCl_3$, 400 MHz) δ 7.94 (d, J=1.6 Hz, 1H), 7.87 (s, 1H), 7.83-7.78 (m, 2H), 7.65 (d, J=8.0 Hz, 1H), 7.58-7.54 (m, 2H), 5.83-5.75 (m, 2H), 3.10 (d, $J_{A,B}$=17.6 Hz, 1H), 2.97 (d, $J_{A,B}$=17.6 Hz, 1H), 2.49 (d, J=9.2 Hz, 1H), 2.25-2.20 (m, 2H), 1.97-1.89 (m, 1H), 1.84-1.79 (m, 1H), 1.55-1.50 (m, 1H)

Step 3: Preparation of 3-(1'-oxo-1',3'-dihydrospiro[cyclohexane-1,2'-indene]-6'-yl)benzonitrile (94d)

To a 100 mL round bottom flask was placed 3-(1'-oxo-1',3'-dihydrospiro[cyclohex[3]ene-1,2'-indene]-6'-yl)benzonitrile (52 mg, 0.174 mmol) and it was dissolved in Ethyl Acetate (5 mL). To this solution was added Pearlmann's catalyst (10 mg, Pd/C). A three way adapter was attached and one of the lines had a $H_2$ filled balloon attached. The system was flushed with $H_2$ and evacuated under vacuum for 3 cycles. After 1 hour stirring at room temperatures, the starting alkene was consumed. The reaction was filtered through a celite cake and the cake was rinsed with ethyl acetate (5 mL). The filtrate was concentrated yielding 3-(1'-oxo-1',3'-dihydrospiro[cyclohexane-1,2'-indene]-6'-yl)benzonitrile (49 mg, 0.163 mmol, 94% yield) and use as it is for the next reaction. M+H=302.1. $^1$H NMR ($CDCl_3$, 400 MHz) δ 7.94 (s, 1H), 7.87 (s, 1H), 7.84-7.78 (m, 2H), 7.65 (dd, J=7.6, 1.2 Hz, 1H), 7.59-7.55 (m, 2H), 3.08 (s, 2H), 1.85-1.80 (m, 2H), 1.77-1.71 (m, 3H), 1.50-1.36 (m, 5H).

Step 4: Preparation of Compound 94

In a 20 mL vial was placed 3-(1'-oxo-1',3'-dihydrospiro[cyclohexane-1,2'-indene]-6'-yl)benzonitrile (49 mg, 0.163 mmol), and it was azeotroped with toluene (2 mL). Dichloromethane (3 mL) was added followed by $TiCl_4$ (326 μL, 0.326 mmol, 1M in DCM). The reaction mixture was allowed to stir at room temperature for 1 hour. At that time bis-trimethylsilylcarbodiimide (117 μL, 0.521 mmol) was added and the solution was allowed to stir overnight (~14 hours) at room temperature. The reaction was quenched with ice cold water (5 mL). The two phases were separated and the aqueous phase was back-extracted twice with dichloromethane (3 mL/each). The combined organic phases were dried over $MgSO_4$, filtered, concentrated under reduce pressure and azeotroped with toluene (2 mL). In a separate flame dried 4 mL vial was placed MeNH(OH).HCl (15 mg, 0.180 mmol) and it was dissolved in MeOH (3 mL). To this solution was added NaOMe (35 μL, 25% in MeOH) and the solution was stirred for 5 minutes at room temperature. This solution was transferred, via syringe, to the cyanoimine prepared above and stirred at room temperature for 1 hour. After that time, the reaction mixture was concentrated under reduce pressure and the crude material was purified on a HPLC (Gilson, 10-90% MeOH/$H_2O$ with 0.1% TFA as the eluent). The corresponding fractions were combined and concentrated. The obtained oil was lyophilized yielding the final product (1.65 mg, 0.004 mmol, 2% yield) as white solid. M+H=373.1. $^1$H NMR=($CD_3OD$, 400 MHz) δ 8.01-7.90 (m, 2H), 7.80-7.62 (m, 4H), 7.45 (d, J=8.4 Hz, 1H), 3.35 (s, 3H), 3.09-2.96 (m, 2H), 1.83-1.42 (m, 10H).

Example 62

Preparation of Compound 95

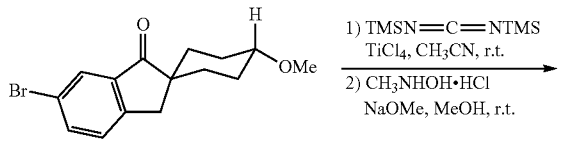

-continued

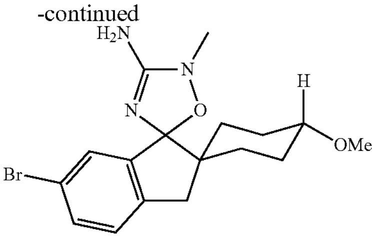

95

In a 4 mL vial was placed 6'-bromo-4-methoxyspiro[cyclohexane-1,2'-inden]-1'(3'H)-one (26 mg, 0.084 mmol), and it was azeotroped with toluene twice (1 mL/each). Dichloromethane (3 mL) was added followed by $TiCl_4$ (177 μL, 0.177 mmol, 1M in DCM). The reaction mixture was allowed to stir at room temperature for 1 hour. At that time bis-trimethylsilylcarbodiimide (61 μL, 0.272 mmol) was added. The solution was allowed to stir 2 hours at room temperature. The reaction was quenched with ice cold water (5 mL) and diluted with DCM (5 mL). The two phases were separated and the aqueous phase was back-extracted twice with dichloromethane (3 mL/each). The combined organic phases were washed with brine, dried over $MgSO_4$, filtered, concentrated under reduce pressure and azeotroped with toluene (2 mL). In a separate flame dried 4 mL vial was placed MeNH(OH).HCl (8 mg, 0.096 mmol) and it was dissolved in MeOH (2 mL). To this solution was added NaOMe (22 μL, 25% in MeOH) and the solution was stirred for 5 minutes at room temperature. This solution was transferred, via syringe, to the cyanoimine prepared above and stirred at room temperature for 1 hour. After that time, the reaction mixture was concentrated under reduce pressure and the crude material was purified on a HPLC (Gilson, 10-90% MeOH/$H_2O$ with 0.1% TFA as the eluent). The corresponding fractions were combined and concentrated. The obtained oil was lyophilized yielding the final product (1.05 mg, 0.003 mmol, 3% yield) as white solid. M+H=381.9. $^1$H NMR=($CD_3OD$, 400 MHz) δ 7.64-7.54 (m, 2H), 7.27 (d, J=8.4 Hz, 1H), 3.37 (s, 3H), 3.33 (s, 3H), 3.17 (m, 1H), 2.94 (m, 2H), 2.18-2.05 (m, 2H), 1.73-1.33 (m, 6H).

Example 63

Preparation of Compound 96

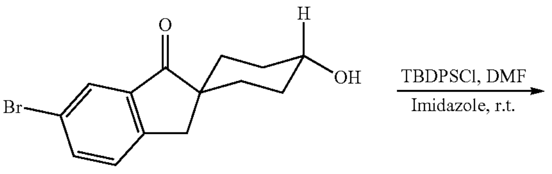

96a

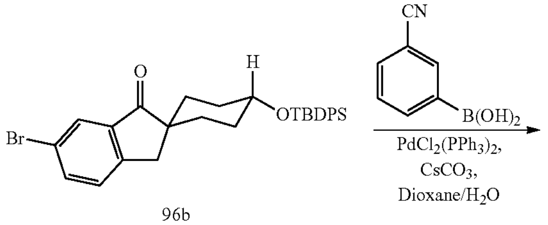

96b

-continued

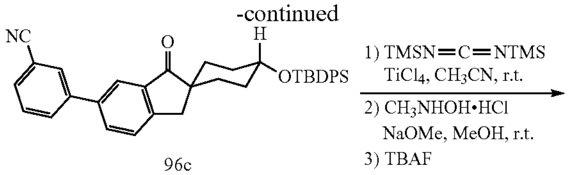

96c

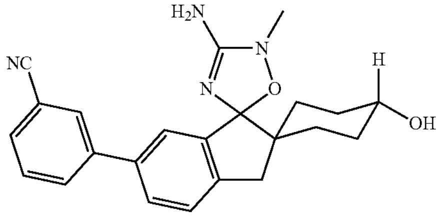

96

Step 1: Preparation of 6'-bromo-4-(tert-butyldiphenylsilyloxy)spiro[cyclohexane-1,2'-inden]-1'(3'H)-one (96b)

To a 4 mL vial was placed 6'-bromo-4-hydroxyspiro[cyclohexane-1,2'-inden]-1'(3'H)-one (41 mg, 0.139 mmol) and it was azeotroped with toluene twice (1 mL/each). The solid was dissolved in DMF (1.5 mL). To this solution was added TBDPS-Cl (40 μL, 0.154 mmol) followed by imidazole (24 mg, 0.353 mmol). The reaction was allowed to stir overnight (~14 hours) at room temperature. The reaction was quenched with $H_2O$ (1 mL) and diluted with diethyl ether (1 mL). The phases were separated and the aqueous phase was back extracted twice with diethyl ether (2 mL/each). The combined organic phases were washed with $H_2O$, brine, dried over $Na_2SO_4$, filtered and concentrated. The crude material was purified by flash chromatography (ISCO, 12 g $SiO_2$ cartridge, ethyl acetate/hexanes as the eluents). The corresponding fractions were combined and concentrated under reduce pressure yielding 6'-bromo-4-(tert-butyldiphenylsilyloxy)spiro[cyclohexane-1,2'-inden]-1'(3'H)-one (58 mg, 0.109 mmol, 78% yield). M+H=did not ionized. $^1H$ NMR=($CDCl_3$, 400 MHz) δ 7.83 (d, J=1.6 Hz 1H), 7.69-7.66 (m, 5H), 7.45-7.32 (m, 7H), 3.73 (m, 1H), 2.98 (s, 2H), 1.93-1.89 (m, 2H), 1.62-1.47 (m, 4H), 1.37 (m, 2H), 1.08 (s, 9H).

Step 2: 4-(tert-butyldiphenylsilyloxy)-1'-oxo-1',3'-dihydrospiro[cyclohexane-1,2'-indene]-6'-yl)benzonitrile (96c)

In a 50 mL round bottom flask was placed 6'-bromo-4-(tert-butyldiphenylsilyloxy)spiro[cyclohexane-1,2'-inden]-1'(3'H)-one (58 mg, 0.109 mmol), 3-cyanobenzeneboronic acid (21 mg, 0.143 mmol), $PdCl_2(PPh_3)_2$ (8 mg, 0.011 mmol) and cesium carbonate (89 mg, 0.273 mmol). This solid mixture was dissolved in a Dioxane/water mixture (1.1 mL, 6:1 ratio, respectively). The flask was capped and allowed to stir at 90° C. for 1 hour. At this time, the mixture was filtered through a Celite plug. The plug was rinsed with dichloromethane (5 mL) and water (5 mL). The phases in the filtrate were separated. The aqueous phase was back-extracted with dichloromethane twice (2 mL/each). The combined organic phases were washed with brine, dried over $MgSO_4$, filtered and concentrated under reduce pressure. The crude material was purified by flash chromatography (ISCO, 12 g $SiO_2$ cartridge, ethyl acetate/hexanes as the eluents). The corresponding fractions were combined and concentrated under reduce pressure yielding 4-(tert-butyldiphenylsilyloxy)-1'-oxo-1',3'-dihydrospiro[cyclohexane-1,2'-indene]-6'-yl)benzonitrile (24 mg, 0.043 mmol, 39% yield). M+H=556.0. $^1H$ NMR=($CDCl_3$, 400 MHz) δ 7.90-7.78 (m, 4H), 7.71-7.64 (m, 5H), 7.58-7.54 (m, 2H), 7.46-7.36 (m, 5H), 3.75 (m, 1H), 3.10 (s, 2H), 1.94 (m, 2H), 1.67-1.51 (m, 4H), 1.41 (m, 2H), 1.08 (s, 9H).

Step 3: Preparation of Compound 96

In a 20 mL vial was placed 4-(tert-butyldiphenylsilyloxy)-1'-oxo-1',3'-dihydrospiro[cyclohexane-1,2'-indene]-6'-yl) benzonitrile (24 mg, 0.043 mmol), and it was azeotroped with toluene twice (1 mL/each). Dichloromethane (2 mL) was added followed by $TiCl_4$ (86 μL, 0.086 mmol, 1M in DCM). The reaction mixture was allowed to stir at room temperature for 1 hour. At that time bis-trimethylsilylcarbodiimide (31 μL, 0.138 mmol) was added. The solution was allowed to stir 1 hour at room temperature. The reaction was quenched with ice cold water (5 mL) and diluted with DCM (5 mL). The two phases were separated and the aqueous phase was back-extracted with dichloromethane (5 mL). The combined organic phases were dried over $MgSO_4$, filtered, concentrated under reduce pressure and azeotroped with toluene (2 mL). In a separate flame dried 4 mL vial was placed MeNH(OH).HCl (4 mg, 0.048 mmol) and it was dissolved in MeOH (2 mL). To this solution was added NaOMe (10 μL, 25% in MeOH) and the solution was stirred for 5 minutes at room temperature. This solution was transferred, via syringe, to the cyanoimine prepared above and stirred at room temperature for 1 hour. After that time, the solvent was removed under reduced pressure. TBAF (1 mL of a 1M THF sol'n) was added and the reaction was stirred for 1 hour at room temperature. The reaction mixture was concentrated under reduce pressure and the crude material was purified on a HPLC (Gilson, 10-90% $MeOH/H_2O$ with 0.1% TFA as the eluent). The corresponding fractions were combined and concentrated. The obtained material was lyophilized yielding the final product (2.1 mg, 0.005 mmol, 12% yield) as white solid. M+H=389.0. $^1H$ NMR=($CD_3OD$, 400 MHz) δ 8.01-7.90 (m, 2H), 7.77-7.62 (m, 4H), 7.47 (m, 1H), 3.57 (m, 1H), 3.45 (s, 3H), 3.04 (m, 2H), 2.06-1.96 (m, 2H), 1.80-1.68 (m, 2H), 1.61-1.44 (m, 4H).

Example 64

Preparation of Compounds 97 and 98

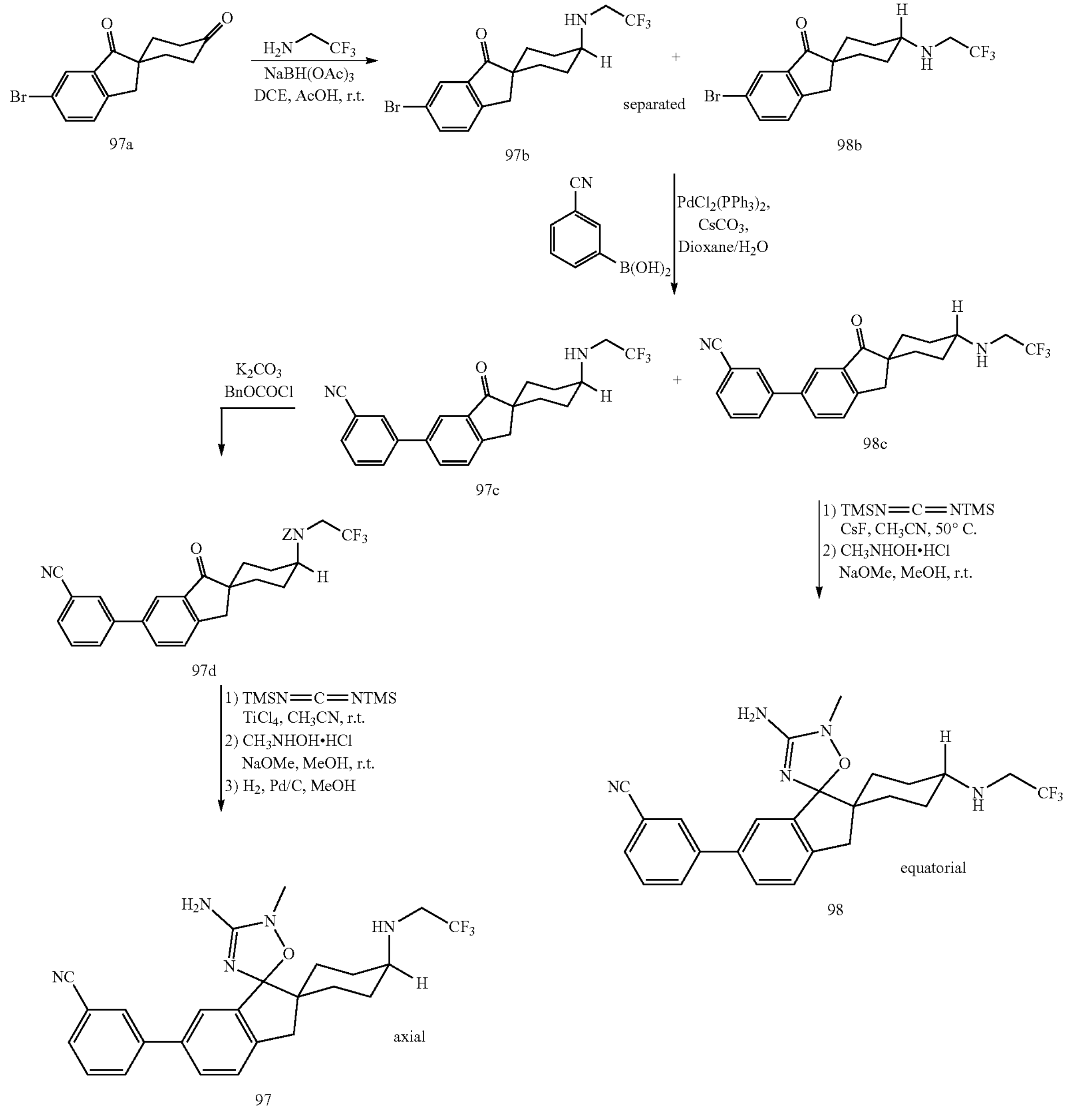

Step 1: Preparation of Compound 97b and 98b

In a 25 mL round bottom flask was placed 6'-bromospiro[cyclohexane-1,2'-indene]-1',4(3'H)-dione (501 mg, 1.716 mmol) and it was dissolved in dichloroethane (5.7 mL). To this solution was added the trifluoro ethylamine (162 μL, 2.059 mmol), AcOH (124 μL, 2.059 mmol), and NaBH$(OAc)_3$ (582 mg, 2.746 mmol) at last. The reaction was stirred at room temperature. When the reaction was completed it was quenched with saturated $NaHCO_3$ (aq) (20 mL) and diluted with ethyl acetate (20 mL). The phases were separated and the aqueous phase was back-extracted with ethyl acetate twice (5 mL/each). The combined organic phases were dried over $Na_2SO_4$, filtered and concentrated under reduce pressure. The crude material was purified by flash chromatography (ISCO, 40 g $SiO_2$ cartridge, ethyl acetate/hexanes as the eluents). At the end, two isomers were obtained and their corresponding fractions were combined separately and concentrated under reduce pressure yielding 6'-bromo-4-(2,2,2-trifluoroethylamino)spiro[cyclohexane-1,2'-inden]-1'(3'H)-one (axial, 97b) (420 mg, 1.120 mmol) and 6'-bromo-4-(2,2,2-trifluoroethylamino)spiro[cyclohexane-1,2'-inden]-1'(3'H)-one (equatorial, 98b) (108 mg, 0.288 mmol) (82% yield). Compound 97b: M+H=375.9, $^1H$ NMR=($CDCl_3$, 400 MHz) δ

7.85 (d, J=1.6 Hz, 1H), 7.67 (dd, J=8.0, 1.6 Hz, 1H), 7.29 (d, J=8.0 Hz, 1H), 3.21 (q, J=9.2 Hz, 2H), 2.93 (s, 2H), 2.90 (m, 1H), 2.01-1.94 (m, 2H), 1.87-1.81 (m, 2H), 1.75-1.68 (m, 2H), 1.38-1.29 (m, 2H). Compound 98b: M+H=375.8, $^1$H NMR=($CDCl_3$, 400 MHz) δ 7.86 (d, J=1.6 Hz, 1H), 7.68 (dd, J=8.0, 1.6 Hz, 1H), 7.32 (d, J=8.0 Hz, 1H), 3.24 (q, J=9.6 Hz, 2H), 2.95 (s, 2H), 2.68 (m, 1H), 2.03-1.97 (m, 2H), 1.81-1.74 (ddd, J=14.0, 14.0, 3.6 Hz, 2H), 1.46 (m, 2H), 1.31-1.21 (m, 2H).

Step 2: Preparation of Compound 97c and 98c

To a microwave vial was placed was placed 6'-bromo-4-(2,2,2-trifluoroethylamino)spiro[cyclohexane-1,2'-inden]-1'(3'H)-one (axial) (50 mg, 0.133 mmol), 3-cyanobenzeneboronic acid (25 mg, 0.170 mmol), $PdCl_2(PPh_3)_2$ (5 mg, 0.007 mmol) and cesium carbonate (109 mg, 0.335 mmol). This solid mixture was dissolved in a Dioxane/water mixture (1.5 mL, 6:1 ratio, respectively). The vial was capped and heated in the microwave at 110° C. for 10 minutes. At this time, the mixture was filtered through a Celite plug. The plug was rinsed with dichloromethane (5 mL) and water (5 mL). The phases in the filtrate were separated. The aqueous phase was back-extracted with dichloromethane (2 mL). The combined organic phases were dried over $MgSO_4$, filtered and concentrated under reduce pressure. The crude material was purified by flash chromatography (ISCO, 12 g $SiO_2$ cartridge, ethyl acetate/hexanes as the eluents). The corresponding fractions were combined and concentrated under reduce pressure yielding 1'-oxo-4-(2,2,2-trifluoroethylamino)-1',3'-dihydrospiro[cyclohexane-1,2'-indene]-6'-yl)benzonitrile (axial, 97c) (50 mg, 0.126 mmol, 74% yield). M+H=399.0

In a 20 mL vial was placed 6'-bromo-4-(2,2,2-trifluoroethylamino)spiro[cyclohexane-1,2'-inden]-1'(3'H)-one (axial) (43 mg, 0.115 mmol), 3-cyanobenzeneboronic acid (22 mg, 0.150 mmol), $PdCl_2(PPh_3)_2$ (4 mg, 0.006 mmol) and cesium carbonate (93 mg, 0.285 mmol). This solid mixture was dissolved in a Dioxane/water mixture (1.2 mL, 6:1 ratio, respectively). The vial was capped and allowed to stir at 95° C. for 1 hour. At this time, the mixture was filtered through a Celite plug. The plug was rinsed with dichloromethane (10 mL) and water (10 mL). The phases in the filtrate were separated. The aqueous phase was back-extracted with dichloromethane twice (3 mL/each). The combined organic phases were dried over $MgSO_4$, filtered and concentrated under reduce pressure. The crude material was purified by flash chromatography (ISCO, 12 g $SiO_2$ cartridge, ethyl acetate/hexanes as the eluents). The corresponding fractions were combined and concentrated under reduce pressure yielding 1'-oxo-4-(2,2,2-trifluoroethylamino)-1',3'-dihydrospiro[cyclohexane-1,2'-indene]-6'-yl)benzonitrile (equatorial, 98c) (48 mg, 0.121 mmol, quantitative). M+H=399.0

Step 3: Preparation of benzyl 6'-(3-cyanophenyl)-1'-oxo-1',3'-dihydrospiro[cyclohexane-1,2'-indene]-4-yl (2,2,2-trifluoroethyl)carbamate (axial) (97d)

To two separate 4 mL vials were placed 1'-oxo-4-(2,2,2-trifluoroethylamino)-1',3'-dihydrospiro[cyclohexane-1,2'-indene]-6'-yl)benzonitrile (axial) (25 mg/each, 0.063 mmol/each). To vial #1 was added NaOH (100 mg of a cruch pellet, excess), DCM (1 mL) and $H_2O$ (1 mL). To vial #2 was added $K_2CO_3$ (270 mgs, excess), DCM (1 mL) and $H_2O$ (1 mL). To each vial was added benzyl chloroformate (50 μL, 1.5 equivalents) and they were allowed to stir overnight (~14 hours) at room temperature. At that time, both reactions were completed. The $K_2CO_3$ was cleaner than the NaOH one (judge by LC/MS). The reactions were combined and diluted with $H_2O$ (5 mL) and DCM (5 mL). The phases were separated and the aqueous phase was back-extracted with dichloromethane (5 mL). The combined organic phases were dried over $MgSO_4$, filtered and concentrated under reduce pressure. The crude material was purified by flash chromatography (ISCO, 12 g $SiO_2$ cartridge, ethyl acetate/hexanes as the eluents). The corresponding fractions were combined and concentrated under reduce pressure yielding benzyl 6'-(3-cyanophenyl)-1'-oxo-1',3'-dihydrospiro[cyclohexane-1,2'-indene]-4-yl(2,2,2-trifluoroethyl)carbamate (axial, 97d) (50 mg, 0.094 mmol, 75% yield). M+H=533.0, $^1$H NMR=($CDCl_3$, 400 MHz) δ 7.86-7.75 (m, 4H), 7.66-7.48 (m, 3H), 7.36-7.31 (m, 5H), 5.18 (bs, 2H), 4.19 (bs, 1H), 3.96 (bs, 2H), 2.97 (s, 2H), 2.31 (m, 2H), 1.94 (d, J=14.0 Hz, 2H), 1.75 (m, 2H), 1.65 (d, J=10.4 Hz, 2H).

Step 4: Preparation of Compound 97

In a 20 mL vial was placed benzyl 6'-(3-cyanophenyl)-1'-oxo-1',3'-dihydrospiro[cyclohexane-1,2'-indene]-4-yl(2,2,2-trifluoroethyl)carbamate (axial) (50 mg, 0.094 mmol), and it was azeotroped with toluene twice (2 mL/each). Dichloromethane (3 mL) was added followed by $TiCl_4$ (188 μL, 0.188 mmol, 1M in DCM). The reaction mixture was allowed to stir at room temperature for 1 hour. At that time bis-trimethylsilylcarbodiimide (68 μL, 0.303 mmol) was added. The solution was allowed to stir 20 minutes at room temperature. The reaction was quenched with ice cold water (7 mL) and diluted with DCM (7 mL). The two phases were separated and the aqueous phase was back-extracted with dichloromethane twice (3 mL/each). The combined organic phases were dried over $MgSO_4$, filtered, concentrated under reduce pressure and azeotroped with toluene (1 mL). In a separate flame dried 4 mL vial was placed MeNH(OH).HCl (9 mg, 0.108 mmol) and it was dissolved in MeOH (3 mL). To this solution was added NaOMe (24 μL, 25% in MeOH) and the solution was stirred for 5 minutes at room temperature. This solution was transferred, via syringe, to the cyanoimine prepared above and stirred at room temperature for 20 minutes. After that time, the solvent was removed under reduced pressure. The crude was dissolved in MeOH (2 mL) and Pd/C (<1 mg) was added. A balloon filled with $H_2$ was attached to the flask and the mixture was stirred for 5 minutes. The reaction mixture was filtered through Celite and the filtrate was directly purified on a HPLC (Gilson, 10-90% MeOH/$H_2O$ with 0.1% TFA as the eluent). The corresponding fractions were combined and concentrated yielding the final product (0.5 mg, 0.001 mmol, 11% yield). M+H=470.1; $^1$H NMR ($CD_3OD$, 400 MHz) δ 8.00-7.89 (m, 2H), 7.80-7.62 (m, 4H), 7.43 (d, J=7.6 Hz, 1H), 3.78 (m, 1H), 3.63 (m, 2H), 3.40 (s, 3H), 3.06-2.90 (m, 2H), 2.19-2.10 (m, 2H), 2.00-1.89 (m, 4H), 1.78 (m, 2H) ppm.

Step 4: Preparation of Compound 98

In a 20 mL vial was placed 1'-oxo-4-(2,2,2-trifluoroethylamino)-1',3'-dihydrospiro[cyclohexane-1,2'-indene]-6'-yl) benzonitrile (equatorial) (48 mg, 0.121 mmol) and it was azeotroped with acetonitrile twice (2 mL/each). Acetonitrile (2.5 mL) was added. To this solution was added bis-trimethylsilylcarbodiimide (111 μL, 0.494 mmol) was added followed by cesium fluoride (75 mg, 0.494 mmol). The vial was tightly capped and heated overnight (~14 hours) at 50° C. The reaction was quenched with water (5 mL) and diluted with DCM (10 mL). The two phases were separated and the aqueous phase was back-extracted with dichloromethane twice (3 mL/each). The combined organic phases were dried over $MgSO_4$, filtered, concentrated under reduce pressure and azeotroped with toluene (2 mL). In a separate flame dried 4 mL vial was placed MeNH(OH).HCl (11 mg, 0.132 mmol) and it was dissolved in MeOH (2 mL). To this solution was added NaOMe (20 μL, 25% in MeOH) and the solution was stirred for 5 minutes at room temperature. This solution was transferred, via syringe, to the cyanoimine prepared above and stirred at room temperature for 1 hour. After that time, the solvent was removed under reduced pressure. The crude was dissolved in MeOH (2 mL), the solution filtered and purified on a HPLC (Gilson, 10-90% MeOH/$H_2O$ with 0.1% TFA as the eluent). The corresponding fractions were combined and concentrated under reduced pressure. The material was lyophilized yielding the final product (1.4 mg, 0.003 mmol, 2% yield) as a white fluffy solid. M+H=470.1, $^1H$ NMR=($CD_3OD$, 400 MHz) δ 8.03-7.90 (m, 2H), 7.80-7.62 (m, 4H), 7.47 (d, J=7.6 Hz, 1H), 3.93 (m, 2H), 3.36 (s, 3H), 3.30-3.20 (m, 2H), 3.06 (m, 1H), 2.25-2.18 (m, 2H), 1.94-1.80 (m, 2H), 1.66-1.58 (m, 2H).

Example 65

Preparation of Compound 99

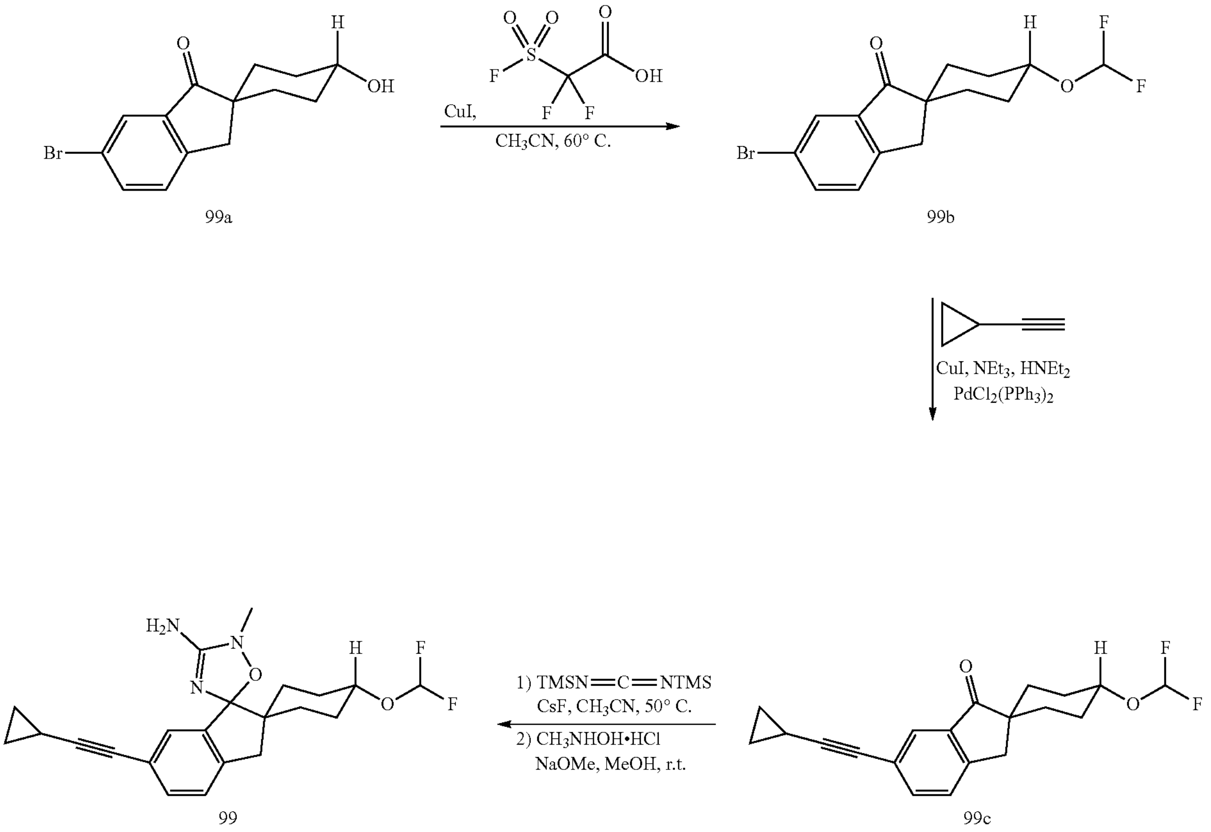

Step 1: Preparation of 6'-bromo-4-(difluoromethoxy)spiro[cyclohexane-1,2'-inden]-1'(3'H)-one (99b)

In a 25 mL round bottom flask was placed 6'-bromo-4-hydroxyspiro[cyclohexane-1,2'-inden]-1'(3'H)-one (368 mg, 1.252 mmol) and it was azeotroped twice with acetonitrile (2 mL/each). CuI (24 mg, 0.126 mmol) was added followed by acetonitrile (2.5 mL). This solution was purged under a stream of $N_2$ for 30 seconds. The solution was heated to 60° C. under a nitrogen atmosphere. After being 5 minutes at 60° C., $FSO_2CF_2CO_2H$ (136 mL, 1.316 mmol) was added dropwise. After 1 hour, the reaction was quenched with H2O (10 mL) and diluted with diethyl ether (10 mL). The phases were separated and the aqueous phase was back-extracted with diethyl ether (5 mL). The combined organic phases were dried over $Na_2SO_4$, filtered and concentrated under reduce pressure. The crude material was purified by flash chromatography (ISCO, 40 g $SiO_2$ cartridge, ethyl acetate/hexanes as the eluents). The corresponding fractions were combined and concentrated under reduce pressure yielding benzyl 6'-bromo-4-(difluoromethoxy)spiro[cyclohexane-1,2'-inden]-1'(3'H)-one (137 mg, 0.398 mmol, 32% yield). M+H=344.9, $^1H$ NMR ($CDCl_3$, 400 MHz) δ 7.86 (d, J=1.2 Hz, 1H), 7.69 (dd, J=8.0, 1.6 Hz, 1H), 7.33 (d, J=8.4 Hz, 1H), 6.26 (t, J=75.2 Hz, 1H), 4.20 (m, 1H), 2.98 (s, 2H), 2.14 (m, 2H), 1.80 (m, 2H), 1.65-1.52 (m, 4H).

Step 2: Preparation of 6'-(cyclopropylethynyl)-4-(difluoromethoxy)spiro[cyclohexane-1,2'-inden]-1'(3'H)-one (99c)

In a 20 mL vial was placed 6'-bromo-4-(difluoromethoxy)spiro[cyclohexane-1,2'-inden]-1'(3'H)-one (51 mg, 0.148 mmol) and it was azeotroped twice with toluene (2 mL/each). Triethylamine (1.5 mL) and diethylamine (0.4 mL) were added and this solution was bubbled with a nitrogen stream for 1 minute. Then $PdCl_2(PPh_3)_2$ (5 mg, 0.007 mmol) and CuI (1.5 mg, 0.008 mmol) were added and again the solution was bubbled with a stream of nitrogen for 1 minute. Then, $PPh_3$ (4 mg, 0.015 mmol) was added followed by the addition of cyclopropyl acetylene (300 μL, excess, 70% toluene solution) and one more time the solution was bubbled with a stream of nitrogen for 1 minute. The vial was capped and allowed to stir overnight (~14 hours) at 56° C. At that time, the solvent was removed under reduce pressure and the crude material was purified by flash chromatography (ISCO, 12 g $SiO_2$ cartridge, using ethyl acetate/hexanes as the eluents). The corresponding fractions were combined and concentrated under reduce pressure yielding 6'-(cyclopropylethynyl)-4-(difluoromethoxy)spiro[cyclohexane-1,2'-inden]-1'(3'H)-one (44 mg, 0.133 mmol, 90% yield) as an off-white solid. M+H=331.0, 1H NMR=($CDCl_3$, 400 MHz) δ 7.71 (s, 1H), 7.56 (d, J=6.8 Hz, 1H), 7.34 (d, J=8.0 Hz, 1H), 6.25 (t, J=75.6 Hz, 1H), 4.18 (m, 1H), 3.00 (s, 2H), 2.12 (m, 2H), 1.78 (m, 2H), 1.64-1.41 (m, 5H), 0.89-0.77 (m, 4H).

Step 3: Preparation of Compound 99

In a 20 mL vial was placed 6'-(cyclopropylethynyl)-4-(difluoromethoxy)spiro[cyclohexane-1,2'-inden]-1'(3'H)-one (44 mg, 0.133 mmol) and it was azeotroped with acetonitrile twice (2 mL/each). Acetonitrile (2 mL) was added. To this solution was added bis-trimethylsilylcarbodiimide (120 μL, 0.534 mmol) was added followed by cesium fluoride (81 mg, 0.533 mmol). The vial was tightly capped and heated for 3 hours at 50° C. The reaction was quenched with water (7 mL) and diluted with DCM (10 mL). The two phases were separated and the aqueous phase was back-extracted with dichloromethane twice (5 mL/each). The combined organic phases were dried over $MgSO_4$, filtered, concentrated under reduce pressure and azeotroped with toluene (2 mL). In a separate flame dried 4 mL vial was placed MeNH(OH).HCl (12 mg, 0.144 mmol) and it was dissolved in MeOH (2 mL). To this solution was added NaOMe (21 μL, 25% in MeOH) and the solution was stirred for 3 minutes at room temperature. This solution was transferred, via syringe, to the cyanoimine prepared above and stirred at room temperature for 30 minutes. After that time, the solvent was removed under reduced pressure. The crude was dissolved in MeOH (2 mL) and $H_2O$ (500 μL). The solution was filtered and purified on a HPLC (Gilson, 10-90% MeOH/$H_2O$ with 0.1% TFA as the eluent). The corresponding fractions were combined and concentrated under reduced pressure. The obtained material was lyophilized yielding the final product (1.24 mg, 0.003 mmol, 2% yield). M+H=402.0; $^1H$ NMR=($CD_3OD$, 400 MHz) δ 7.66-7.26 (m, 3H), 6.41 (t, J=75.6 Hz, 1H), 4.08 (m, 1H), 3.33 (s, 3H), 2.99 (m, 2H), 2.12-1.91 (m, 3H), 1.75-1.43 (m, 6H), 0.93-0.86 (m, 2H), 0.77-0.71 (m, 2H).

Example 66

Preparation of Compound 100

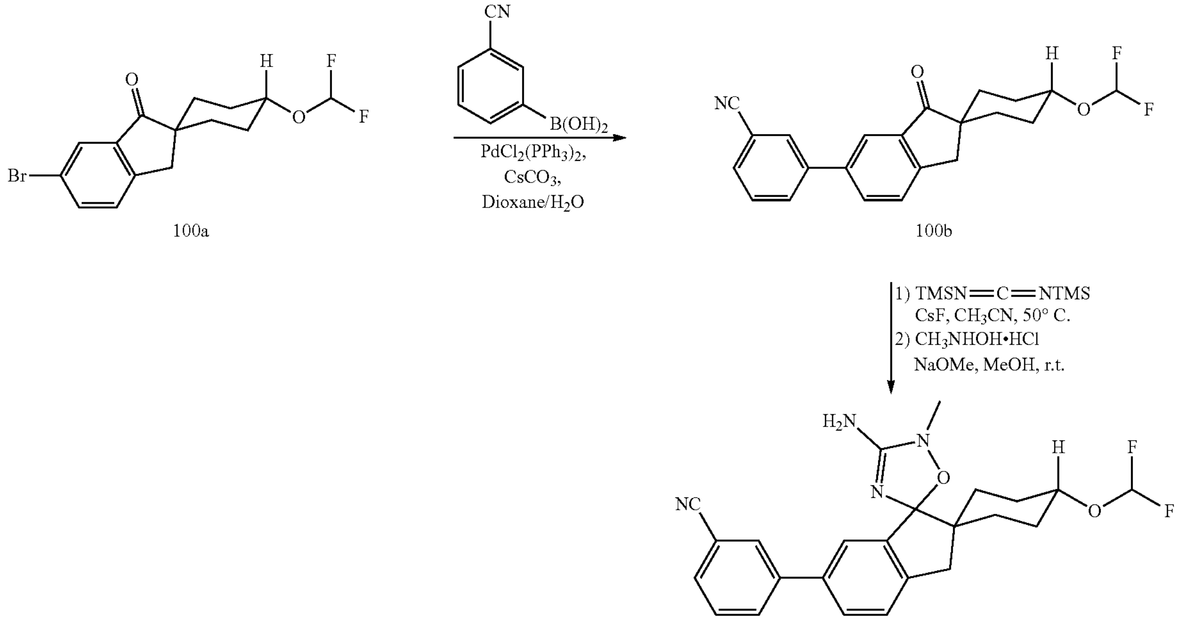

100a

100b

100

Step 1: Preparation of 4-(difluoromethoxy)-1'-oxo-1',3'-dihydrospiro[cyclohexane-1,2'-indene]-6'-yl)benzonitrile (100b)

In a 20 mL vial was placed 6'-bromo-4-(difluoromethoxy)spiro[cyclohexane-1,2'-inden]-1'(3'H)-one (51 mg, 0.148 mmol), 3-cyanobenzeneboronic acid (28 mg, 0.1910 mmol), $PdCl_2(PPh_3)_2$ (5 mg, 0.007 mmol) and cesium carbonate (121 mg, 0.371 mmol). This solid mixture was dissolved in a Dioxane/water mixture (1.5 mL, 6:1 ratio, respectively). The vial was capped and allowed to stir at 95° C. for 1 hour. At this time, the mixture was filtered through a Celite plug. The plug was rinsed with dichloromethane (10 mL) and water (5 mL). The phases in the filtrate were separated. The aqueous phase was back-extracted with dichloromethane (5 mL). The combined organic phases were dried over $MgSO_4$, filtered and concentrated under reduce pressure. The crude material was purified by flash chromatography (ISCO, 12 g $SiO_2$ cartridge, ethyl acetate/hexanes as the eluents). The corresponding fractions were combined and concentrated under reduce pressure yielding 4-(difluoromethoxy)-1'-oxo-1',3'-dihydrospiro[cyclohexane-1,2'-indene]-6'-yl)benzonitrile (equatorial) (48 mg, 0.131 mmol, 88% yield). M+H=368.0

Step 2: Preparation of Compound 100

In a 20 mL vial was placed 4-(difluoromethoxy)-1'-oxo-1',3'-dihydrospiro[cyclohexane-1,2'-indene]-6'-yl)benzonitrile (equatorial) (48 mg, 0.131 mmol) and it was azeotroped with acetonitrile twice (1 mL/each). Acetonitrile (1.3 mL) was added. To this solution was added bis-trimethylsilylcarbodiimide (118 μL, 0.525 mmol) was added followed by cesium fluoride (80 mg, 0.526 mmol). The vial was tightly capped and heated overnight (~14 hours) at 50° C. The reaction was quenched with water (5 mL) and diluted with DCM (5 mL). The two phases were separated and the aqueous phase was back-extracted with dichloromethane twice (3 mL/each). The combined organic phases were dried over $MgSO_4$, filtered, concentrated under reduce pressure and azeotroped with toluene (2 mL). In a separate flame dried 4 mL vial was placed MeNH(OH).HCl (12 mg, 0.144 mmol) and it was dissolved in MeOH (2 mL). To this solution was added NaOMe (21 μL, 25% in MeOH) and the solution was stirred for 5 minutes at room temperature. This solution was transferred, via syringe, to the cyanoimine prepared above and stirred at room temperature for 1 hour. After that time, the solvent was removed under reduced pressure. The crude was dissolved in MeOH (2 mL) and $H_2O$ (500 μL). The solution was filtered and purified on a HPLC (Gilson, 10-90% MeOH/$H_2O$ with 0.1% TFA as the eluent). The corresponding fractions were combined and concentrated under reduced pressure. The obtained material was lyophilized yielding the final product (5 mg, 0.011 mmol, 9% yield). M+H=439.1 $^1H$ NMR=($CD_3OD$, 400 MHz) δ 8.00 (m, 2H), 7.76-7.60 (m, 3H), 7.45 (d, J=8.8 Hz, 1H), 6.40 (t, J=75.6 Hz, 1H), 4.09 (m, 1H), 3.33 (s, 3H), 3.09 (d, $J_{A,B}$=16.0 Hz, 1H), 3.02 (d, $J_{A,B}$=16.4 Hz, 1H), 2.12-1.92 (m, 2H), 1.79-1.51 (m, 6H).

Example 67

Synthesis of Compound 101

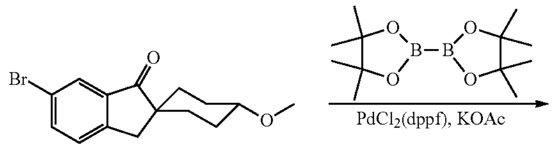

101a

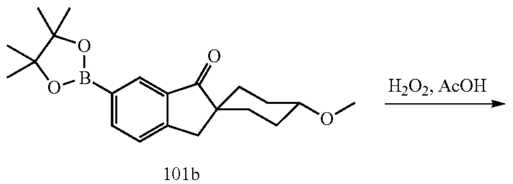

101b

-continued

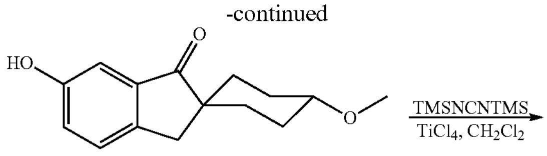

101c

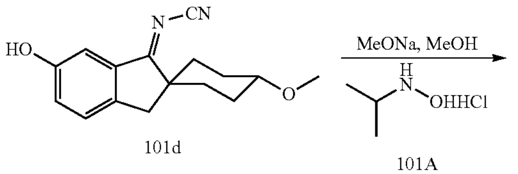

101d

101A

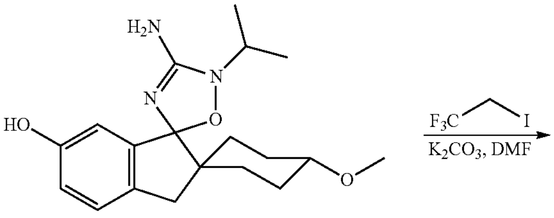

101e

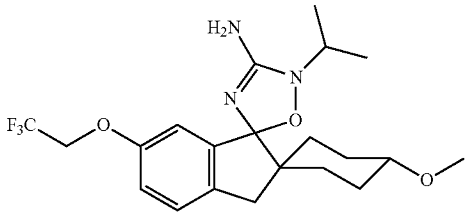

101

Step 1: Preparation of Compound 101b

To a solution of compound 101a (4 g, 12.9 mmol) in 1,4-dioxane (40 mL), was added KOAc (3.67 g, 37.4 mmol), bis(pinacolato)diboron (3.6 g, 14.2 mmol) and Pd(dppf)$Cl_2$ (1.2 g, 1.8 mmol) under nitrogen, the mixture was stirred at 100° C. in a CEM microwave reactor for 1 h, LCMS showed the complete consumption of compound 101a. Water (20 mL) was added to the mixture, and the precipitate was filtered off through a pad of celite, and then was washed with EtOAc (20 mL×3). The combined organic fractions were washed with brine (50 mL), dried over $Na_2SO_4$ and concentrated to give compound 101b (4.1 g, crude 90%) which was used in the next step without further purification as a black solid. $^1H$ NMR ($CDCl_3$ 300 MHz): δ 8.15 (s, 1H), 7.94 (d, J=7.8 Hz, 1H), 7.38 (d, J=8.0 Hz, 1H), 3.45 (s, 3H), 3.26-3.19 (m, 1H), 3.07 (s, 2H), 2.08 (m, 2H), 1.73-1.96 (m, 2H), 1.65-1.70 (m, 2H), 1.42-1.65 (m, 2H), 1.26 (s, 12H).

Step 2: Preparation of Compound 101c

To a solution of compound 101b (4 g, 11.5 mmol) in THF (40 mL) was added HOAc (4 mL) and $H_2O_2$ (20 mL) under nitrogen, the mixture was stirred at room temperature overnight. The mixture was quenched with $NaHSO_3$ solution (20 mL), and then was extracted with EtOAc (10 mL×3). The combined organic layers were washed with brine (30 mL), dried over $Na_2SO_4$ and concentrated to afford the crude product which was purified by column chromatography on silica gel eluting with hexane:EtOAc (100:10 to 30:10) to give compound 101c (2 g, 71%) as a white solid. $^1H$ NMR ($CDCl_3$ 400 MHz): δ:7.31 (s, 1H), 7.21 (d, J=8.0 Hz, 2H), 3.33 (s, 3H), 3.23-3.27 (m, 1H), 2.86 (s, 2H), 2.05-2.09 (m, 2H), 1.85-1.94 (m, 2H), 1.39-1.47 (m, 2H), 1.28-1.34 (m, 2H).

Step 3: Preparation of Compound 101d

To a solution of compound 101c (100 mg, 0.40 mmol) in anhydrous $CH_2Cl_2$ (2 mL) was added $TiCl_4$ (1.2 mL) under nitrogen, the mixture was stirred at 50° C. in a CEM microwave reactor for 15 min, then bis-trimethylsilylcarbodiimide (189 mg, 1.0 mmol) was added. The mixture was stirred at 60° C. in a CEM microwave reactor for 15 min. The mixture was poured into ice-water (5 mL) and the aqueous layer was extracted with $CH_2Cl_2$ (20 mL×2). The combined organic layers were washed with brine (50 mL), dried over $Na_2SO_4$ and concentrated to give compound 101d (90 mg, crude, 83%) as a yellow solid which was used directly for the next step without purification. LCMS: $t_R$=1.198 min in 2 min chromatography, MS (ESI) m/z=271.1 $[M+H]^+$.

Step 4: Preparation of Compound 101e

To a solution of compound 101A (20.6 mg, 0.19 mmol) in MeOH (2 mL) was added MeONa (99.9 mg, 0.19 mmol, 10% (Wt.) in MeOH, followed by compound 101d (50 mg, 0.185 mmol). After stirring for 10 min, LCMS showed the complete consumption of compound 101d. The solvent was removed in vacuo to give the crude product which was purified by preparative TLC on silica gel eluting with hexane:EtOAc=1:1 to afford compound 101e (26 mg, 41%) as a yellow solid.

LCMS: $t_R$=1.016 min in 2 min chromatography, MS (ESI) m/z=346.2 $[M+H]^+$.

Step 5: Preparation of Compound 101

To a solution of compound 101e (26 mg, 0.075 mmol) in DMF (2 mL) was added $K_2CO_3$ (20.7 mg, 0.15 mmol), and 1,1,1-trifluoro-2-iodo-ethane (19.2 mg, 0.082 mmol), the mixture was stirred at room temperature overnight. The reaction was added brine (5 mL), and was extracted with EtOAc (10 mL×2). The combined organic layers were washed with brine (30 mL), dried over $Na_2SO_4$ and concentrated to give the crude product which was purified by preparative TLC on silica gel eluting with dichloromethane:methanol=10:1 followed by preparative HPLC to afford compound 101 (2.0 mg, 6.2%) as a white solid. $^1H$ NMR ($CD_3OD$, 400 MHz): δ 7.35 (d, J=8.4 Hz, 1H), 7.07 (d, J=6.0 Hz, 1H), 6.94 (s, 1H), 4.52 (dd, J=8.4, 16.4 Hz, 2H), 3.50-3.60 (m, 1H), 3.37 (s, 3H), 3.09-3.19 (m, 1H), 2.87 (dd, J=15.2, 31.2 Hz, 2H), 1.97-2.15 (m, 2H), 1.70-1.97 (m, 1H), 1.56-1.70 (m, 2H), 1.56-1.20 (m, 3H), 1.20-1.16 (d, J=7.2 Hz, 6H).

LCMS: $t_R$=2.053 min in 3 min chromatography, MS (ESI) m/z=428.2 $[M+H]^+$.

$^{19}F$ NMR ($CD_3OD$ 400 MHz) δ −75.784

Example 68

Preparation of Compound 102

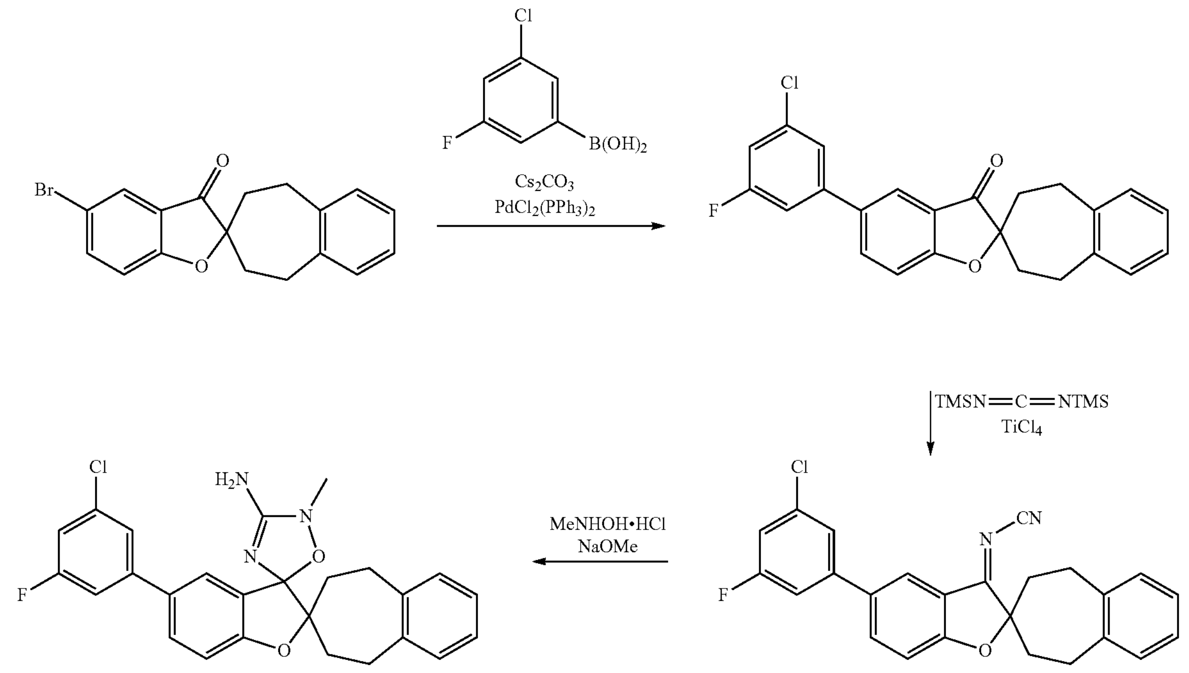

102

Step 1. 5'-(3-chloro-5-fluorophenyl)-5,6,8,9-tetrahydro-3'H-spiro[benzo[7]annulene-7,2'-benzofuran]-3'-one A 10 mL microwave tube was charged with 5'-bromo-5,6,8,9-tetrahydro-3'H-spiro[benzo[7]annulene-7,2'-benzofuran]-3'-one (0.0573 g, 0.167 mmol), 3-chloro-5-fluorophenylboronic acid (0.0930 g, 0.53 mmol), $Cs_2CO_3$ (0.2537 g, 0.78 mmol), 1,4-dioxane (4 mL), water (1 mL), and $PdCl_2(PPh_3)_2$ (0.0118 g, 0.0168 mmol). The tube was heated in a CEM microwave reactor at 110° C. for 30 min. The reaction mixture was diluted with $CH_2Cl_2$ and dried over $Na_2SO_4$. After the solvent was evaporated under reduced pressure, the residue was purified by chromatography on silica gel eluted with hexanes/ethyl acetate to afford 0.0607 g (92%) of 5'-(3-chloro-5-fluorophenyl)-5,6,8,9-tetrahydro-3'H-spiro[benzo[7]annulene-7,2'-benzofuran]-3'-one. LC-MS $t_R$=2.55 min in 3 min chromatography, m/z 393, 395 ($MH^+$).

Step 2. N-(5'-(3-chloro-5-fluorophenyl)-5,6,8,9-tetrahydro-3'H-spiro[benzo[7]annulene-7,2'-benzofuran]-3'-ylidene)cyanamide To a solution of 5'-(3-chloro-5-fluorophenyl)-5,6,8,9-tetrahydro-3'H-spiro[benzo[7]annulene-7,2'-benzofuran]-3'-one (0.0607 g, 0.155 mmol) in $CH_2Cl_2$ (5 mL) was added 0.7 mL of 1.0 M $TiCl_4$ in $CH_2Cl_2$ at room temperature. After 1 h, 0.28 mL of bis(trimethylsilyl)carbodiimide was added to the red solution. The resulting mixture was then stirred at room temperature for 18 h. The mixture was quenched with ice, diluted with $CH_2Cl_2$, and dried over $Na_2SO_4$. After the solvent was removed under reduced pressure, the crude product was directly used in the next step without further purification.

Step 3. Preparation of compound 102

A 50 mL flask was charged with 10 mL of EtOH, 0.2365 g of sodium methoxide (25 wt. % solution in MeOH), and 0.1050 g of N-methylhydroxylamine hydrochloride. The suspension was filtered through HPLC filter and the filtrate was added to N-(5'-(3-chloro-5-fluorophenyl)-5,6,8,9-tetrahydro-3'H-spiro[benzo[7]annulene-7,2'-benzofuran]-3'-ylidene)cyanamide, obtained as described above. The resulting mixture was stirred at room temperature overnight. The mixture was purified by reversed-phase HPLC (SunFire™ Prep $C_{18}$ OBD™ 5 μm 19×50 mm column, 10%→90% $MeOH/H_2O$, 0.1% $CF_3COOH$ over 8 min and then 90% $MeOH/H_2O$, 0.1% $CF_3COOH$ over 2 min, flow rate 20 mL/min) to afford compound 102 as a TFA salt. LC-MS $t_R$=1.72, 2.00 min in 3 min chromatography, m/z 464, 466 ($MH^+$); $^1H$ NMR (400 MHz, $CD_3OD$) δ 8.07-7.75 (m, 2H), 7.48-7.08 (m, 8H), 3.48 (t, J=13.6 Hz, 2H), 2.80 (dd, J=14.6, 6.1 Hz, 2H), 2.18 (dd, J=14.5, 6.0 Hz, 2H), 1.90 (t, J=13.5 Hz, 2H); $^{19}F$ NMR (376 MHz, $CD_3OD$) δ −112.40 (t, J=9.2 Hz), −112.97 (t, J=9.2 Hz).

Example 69

Preparation of Compound 103

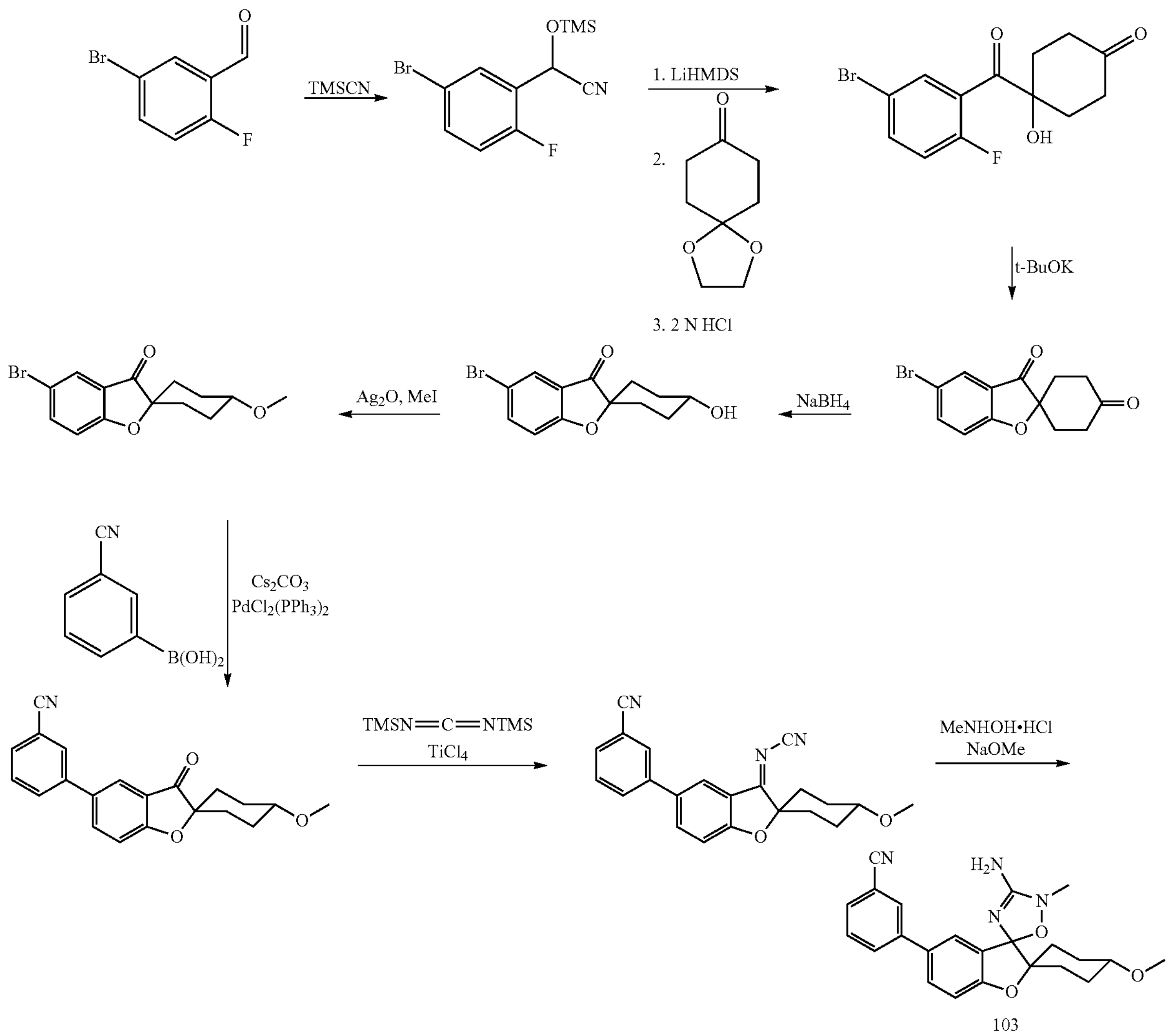

103

Step 1. 2-(5-bromo-2-fluorophenyl)-2-(trimethylsilyloxy)acetonitrile

To a solution of 5-bromo-2-fluorobenzaldehyde (3.4160 g, 16.8 mmol) and DMAP (0.0256 g, 0.21 mmol, 0.012 equiv) in $CH_3CN$ (35 mL) was added TMSCN (1.8885 g, 19.0 mmol, 1.13 equiv) dropwise via a syringe under nitrogen at room temperature. After 3.75 h, the solvent was removed under reduced pressure. The crude product was directly used in the next step without further purification.

Step 2. 4-(5-bromo-2-fluorobenzoyl)-4-hydroxycyclohexanone

To a solution of 2-(5-bromo-2-fluorophenyl)-2-(trimethylsilyloxy)acetonitrile (16.8 mmol), obtained as described above, in THF (10 mL) was added LiHMDS (1.0 M in THF, 18 mL, 18 mmol, 1.07 equiv) via a syringe under nitrogen at −78° C. After 1.25 h, a solution of 1,4-cyclohexanedione mono-ethylene ketal (2.6310 g, 16.8 mmol, 1.0 equiv) in THF (20 mL) was added dropwise via a cannula. The resulting mixture was allowed to slowly warm to 10° C. over 16 h. The mixture was then quenched with saturated $NH_4Cl$ (10 mL) and $H_2O$ (10 mL), extracted twice with ethyl acetate, and dried over $Na_2SO_4$. After the solvent was evaporated under reduced pressure, the residue was treated with MeOH (120 mL) and 2 N HCl (40 mL). The resulting solution was vigorously stirred at room temperature for 24 h and the solvents were removed under reduced pressure. The residue was extracted twice with $CH_2Cl_2$, dried over $Na_2SO_4$. After the solvent was evaporated under reduced pressure, the residue was purified by chromatography on silica gel eluted with hexanes/ethyl acetate to afford 2.9319 g (55% in two steps) of 4-(5-bromo-2-fluorobenzoyl)-4-hydroxycyclohexanone. LC-MS $t_R$=1.39 min in 3 min chromatography, m/z 315, 317 ($MH^+$); $^1H$ NMR (400 MHz, $CDCl_3$) δ 7.62-7.57 (m, 1H), 7.50-7.47 (m, 1H), 7.08-7.03 (m, 1H), 3.41 (s, 1H), 2.83-2.74 (m, 2H), 2.42-2.36 (m, 2H), 2.31-2.23 (m, 2H), 2.14-2.09 (m, 2H); $^{13}C$ NMR (100 MHz, $CDCl_3$) δ 209.51, 204.88 (d, J=2.30 Hz), 157.68 (d, J=248.44 Hz), 135.66 (d, J=8.44 Hz), 131.55 (d, J=3.83 Hz), 127.54 (d, J=19.17 Hz), 118.07 (d, J=24.53 Hz), 117.19 (d, J=3.84 Hz), 78.07, 36.37, 33.89, 33.87; $^{19}F$ NMR (376 MHz, $CDCl_3$) δ −112.90.

Step 3. 5-bromo-3H-spiro[benzofuran-2,1'-cyclohexane]-3,4'-dione

To a solution of 4-(5-bromo-2-fluorobenzoyl)-4-hydroxycyclohexanone (1.0055 g, 3.19 mmol, 1.0 equiv) in THF (30 mL) was added 95% t-BuOK (0.3440 g, 2.91 mmol, 0.9 equiv) portionwise. The resulting mixture was heated at 100° C. for 1 h. The reaction mixture was then cooled with an ice bath and quenched with $H_2O$, extracted with ethyl acetate, dried over $Na_2SO_4$. After the solvents were evaporated, the residue was purified by chromatography on silica gel eluted with hexanes/ethyl acetate to afford 0.3889 g (41%) of 5-bromo-3H-spiro[benzofuran-2,1'-cyclohexane]-3,4'-dione as a white solid. LC-MS $t_R$=1.58 min in 3 min chromatography, m/z 295, 297 ($MH^+$); $^1H$ NMR (400 MHz, $CDCl_3$) δ 7.82-7.81 (m, 1H), 7.76-7.73 (m, 1H), 7.10-7.07 (m, 1H), 2.81-2.72 (m, 2H), 2.60-2.55 (m, 2H), 2.29-2.21 (m, 2H), 2.08-2.03 (m, 2H); $^{13}C$ NMR (100 MHz, $CDCl_3$) δ 208.25, 200.80, 169.71, 140.99, 127.47, 121.58, 115.55, 114.81, 88.10, 36.68, 31.86.

Step 4. cis-5-bromo-4'-hydroxy-3H-spiro[benzofuran-2,1'-cyclohexan]-3-one and trans-5-bromo-4'-hydroxy-3H-spiro[benzofuran-2,1'-cyclohexan]-3-one To a solution of 5-bromo-3H-spiro[benzofuran-2,1'-cyclohexane]-3,4'-dione (0.2281 g, 0.77 mmol) in THF (15 mL) was added $NaBH_4$ (0.0266 g, 0.70 mmol) portionwise at −78° C. After 15 min, additional $NaBH_4$ (0.0138 g, 0.36 mmol) was added at −78° C. After 25 min, the reaction mixture was quenched with acetone and stirred at room temperature for 1 h. After the solvents were evaporated, the residue was purified by chromatography on silica gel eluted with hexanes/ethyl acetate to afford 0.0108 g (5%) of trans-5-bromo-4'-hydroxy-3H-spiro[benzofuran-2,1'-cyclohexan]-3-one and 0.1424 g (62%) of cis-5-bromo-4'-hydroxy-3H-spiro[benzofuran-2,1'-cyclohexan]-3-one.

For trans-5-bromo-4'-hydroxy-3H-spiro[benzofuran-2,1'-cyclohexan]-3-one, LC-MS $t_R$=1.56 min in 3 min chromatography, m/z 297, 299 ($MH^+$), 279, 281; $^1H$ NMR (400 MHz, $CDCl_3$) δ 7.78-7.77 (m, 1H), 7.70-7.66 (m, 1H), 7.02-6.99 (m, 1H), 4.18-4.17 (m, 1H), 2.23-2.14 (m, 2H), 2.03-1.87 (m, 4H), 1.53-1.49 (m, 2H).

For cis-5-bromo-4'-hydroxy-3H-spiro[benzofuran-2,1'-cyclohexan]-3-one, LC-MS $t_R$=1.47 min in 3 min chromatography, m/z 297, 299 ($MH^+$); $^1H$ NMR (400 MHz, $CDCl_3$) δ 7.77-7.76 (m, 1H), 7.70-7.67 (m, 1H), 7.05-7.02 (m, 1H), 3.83-3.78 (m, 1H), 2.08-2.03 (m, 2H), 1.88-1.72 (m, 6H); $^{13}C$ NMR (100 MHz, $CDCl_3$) δ 202.30, 169.84, 140.60, 127.21, 121.81, 115.54, 114.20, 89.12, 68.73, 30.67, 30.37.

Step 5. cis-5-bromo-4'-methoxy-3H-spiro[benzofuran-2,1'-cyclohexan]-3-one

A mixture of cis-5-bromo-4'-hydroxy-3H-spiro[benzofuran-2,1'-cyclohexan]-3-one (0.1424 g, 0.48 mmol), $Ag_2O$ (0.3800 g, 1.64 mmol), MeI (0.85 mL, 13.6 mmol), and Drierite® (0.78 g) in $CH_3CN$ (5 mL) was vigorously stirred at room temperature for 66 h. The reaction mixture was filtered. After the solvents were evaporated, the residue was purified by chromatography on silica gel eluted with hexanes/ethyl acetate to afford 0.1232 g (83%) of cis-5-bromo-4'-methoxy-3H-spiro[benzofuran-2,1'-cyclohexan]-3-one and recover 0.0220 g (15%) of cis-5-bromo-4'-hydroxy-3H-spiro[benzofuran-2,1'-cyclohexan]-3-one.

For cis-5-bromo-4'-methoxy-3H-spiro[benzofuran-2,1'-cyclohexan]-3-one, LC-MS $t_R$=1.86 min in 3 min chromatography, m/z 311, 313 ($MH^+$); $^1H$ NMR (400 MHz, $CDCl_3$) δ 7.68-7.67 (m, 1H), 7.63-7.60 (m, 1H), 6.97 (d, J=8.8 Hz, 1H), 3.33 (s, 3H), 3.29-3.22 (m, 1H), 2.08-2.04 (m, 2H), 1.77-1.57 (m, 6H); $^{13}C$ NMR (100 MHz, $CDCl_3$) δ 202.15, 169.74, 140.44, 127.07, 121.77, 115.48, 114.04, 89.32, 55.70, 30.09, 26.95.

Step 6. 3-(cis-4'-methoxy-3-oxo-3H-spiro[benzofuran-2,1'-cyclohexan]-5-yl)benzonitrile A 10 mL microwave tube was charged with cis-5-bromo-4'-methoxy-3H-spiro[benzofuran-2,1'-cyclohexan]-3-one (0.0446 g, 0.143 mmol), 3-cyanophenylboronic acid (0.1239 g, 0.84 mmol), $Cs_2CO_3$ (0.4314 g, 1.3 mmol), 1,4-dioxane (4 mL), water (1 mL), and $PdCl_2(PPh_3)_2$ (0.0286 g, 0.04 mmol). The tube was heated in a CEM microwave reactor at 110° C. for 30 min. The reaction mixture was diluted with $CH_2Cl_2$ and dried over $Na_2SO_4$. After the solvent was evaporated under reduced pressure, the residue was purified by chromatography on silica gel eluted with hexanes/ethyl acetate to afford 0.0400 g (84%) of 3-(cis-4'-methoxy-3-oxo-3H-spiro[benzofuran-2,1'-cyclohexan]-5-yl)benzonitrile. LC-MS $t_R$=1.86 min in 3 min chromatography, m/z 334 ($MH^+$).

Step 7. N-(cis-5-(3-cyanophenyl)-4'-methoxy-3H-spiro[benzofuran-2,1'-cyclohexan]-3-ylidene)cyanamide To a solution of 3-(cis-4'-methoxy-3-oxo-3H-spiro[benzofuran-2,1'-cyclohexan]-5-yl)benzonitrile (0.0400 g, 0.12 mmol) in $CH_2Cl_2$ (5 mL) was added 0.5 mL of 1.0 M $TiCl_4$ in $CH_2Cl_2$ at room temperature. After 1.5 h, 0.2 mL of bis(trimethylsilyl)carbodiimide was added to the red solution. The resulting mixture was then stirred at room temperature for 21 h. The mixture was quenched with ice, diluted with $CH_2Cl_2$, and dried over $Na_2SO_4$. After the solvent was removed under reduced pressure, the crude product (0.0584 g) was directly used in the next step without further purification. LC-MS $t_R$=1.90 min in 3 min chromatography, m/z 358 ($MH^+$)

Step 8. Preparation of compound 103

A 50 mL flask was charged with 10 mL of EtOH, 0.2552 g of sodium methoxide (25 wt. % solution in MeOH), and 0.1314 g of N-methylhydroxylamine hydrochloride. The suspension was filtered through HPLC filter and the filtrate was added to N-(cis-5-(3-cyanophenyl)-4'-methoxy-3H-spiro[benzofuran-2,1'-cyclohexan]-3-ylidene)cyanamide, obtained as described above. The resulting mixture was stirred at room temperature for 2 h. The mixture was purified by reversed-phase HPLC (SunFire™ Prep $C_{18}$ OBD™ 5 μm 19×50 mm column, 10%→90% MeOH/$H_2O$, 0.1% $CF_3COOH$ over 8 min and then 90% MeOH/$H_2O$, 0.1% $CF_3COOH$ over 2 min, flow rate 20 mL/min) to afford compound 103 as a TFA salt. LC-MS $t_R$=1.25, 1.41 min in 3 min chromatography, m/z 405 ($MH^+$); $^1H$ NMR (400 MHz, $CD_3OD$) δ 8.08-7.03 (m, 7H), 3.43-3.35 (m, 7H), 2.22-1.65 (m, 8H).

Example 70

Synthesis of Compound 104

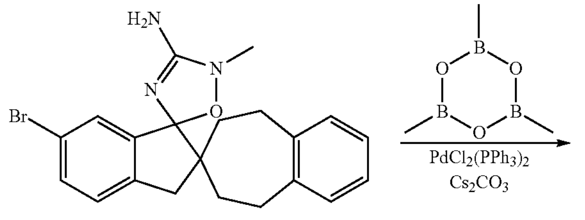

104a

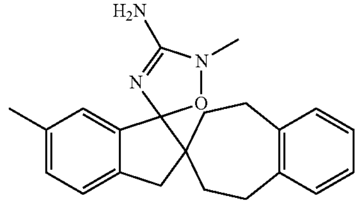

104

A solution containing compound 104a (50 mg, 0.12 mmol) and 2,4,6-trimethyl-cyclotriboroxane (153 mg, 1.2 mmol) in dioxane (3 mL), and aqueous $Cs_2CO_3$ (2 M, 0.85 mL) was deoxygenated by bubbling a stream of nitrogen through the reaction mixture for 5 min. Then, $PdCl_2(PPh_3)_2$ (8.5 mg) was added. The reaction vial was sealed and placed into CEM microwave reactor and irradiated at 120° C. for 15 min. After being cooled to room temperature, the mixture was diluted with EtOAc and filtered through a short Celite pad. The solution was concentrated in vacuo and the residue was purified by preparative TLC ($CH_2Cl_2$:MeOH, 10:1) and HPLC to give compound 104 (1.5 mg, yield 4%) as a white solid. LC-MS $t_R$=1.016 min and 1.066 min in 2 min chromatography, MS (ESI) m/z 348 $[M+H]^+$; $^1H$ NMR ($CD_3OD$ 400 MHz): δ 7.46 (m, 1H), 7.39 (m, 1H), 7.18 (m, 1H), 7.02 (m, 4H), 3.17 (s, 3H), 2.94-2.99 (m, 3H), 3.65 (m, 2H), 2.56-2.70 (m, 2H); 2.28-2.31 (m, 3H), 1.73-1.84 (m, 3H), 1.56-1.70 (m, 1H); 1.19-1.60 (m, 1H).

Example 71

Synthesis of Compound 105

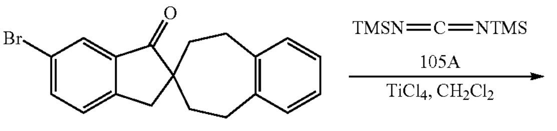

105a

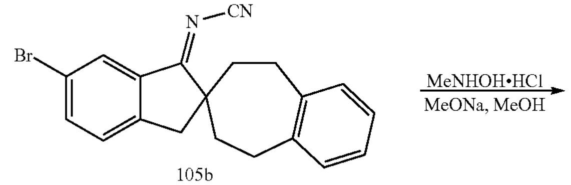

105b

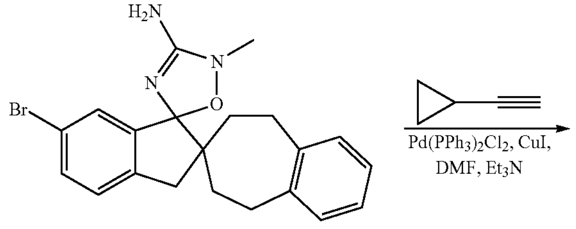

105c

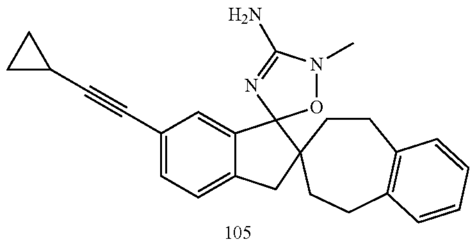

105

Step 1: Preparation of Compound 105b

To a solution of compound 105a (200 mg, 0.58 mmol) in anhydrous $CH_2Cl_2$ (14 mL) was added $TiCl_4$ (1 M in $CH_2Cl_2$, 2.36 mL, 2.36 mmol) at room temperature. After being stirred in microwave at 50° C. for 15 min., bis(trimethylsilyl)carbodiimide (236 mg, 1.28 mmol) was added, and the mixture was stirred in microwave at 60° C. for another 22 min. TLC showed the reaction was completed, and the mixture was poured into ice-water (20 mL), and extracted with $CH_2Cl_2$ (3×30 mL). The combined organic layers were washed with brine (20 mL), dried over $Na_2SO_4$, concentrated under reduced pressure to give compound 105b (200 mg, yield 93%) as a yellow solid.

Step 2: Preparation of Compound 105c

To a solution of N-methylhydroxylamine hydrochloride (92 mg, 1.08 mmol) in anhydrous MeOH (28 mL) was added a solution of NaOMe (10 wt %, 0.56 mL, 0.972 mmol) in methanol followed by compound 105b (400 mg, 1.08 mmol). After being stirred at room temperature for 50 min., the solvent was removed under reduced pressure, and the residue was dissolved in $CH_2Cl_2$ (20 mL). The mixture was filtered, concentrated under reduced pressure. The residue was purified by chromatograph silica gel ($CH_2Cl_2$:MeOH, 10:1) to give compound 105c (80 mg, yield 18%) as a yellow solid.

Step 3: Preparation of Compound 105

To a stirred solution of compound 105c (30 mg, 0.073 mmol) and CuI (10 mg, 0.05) in anhydrous $Et_3N$ (0.5 mL) and DMF (2 mL) was added cyclopropane acetylene (0.5 mL) and $Pd(PPh_3)_2Cl_2$ (10 mg, 0.011 mmol) under a $N_2$ atmosphere. The mixture was stirred at 55° C. overnight. The mixture was concentrated under reduced pressure to dryness. The residue was dissolved in $CH_2Cl_2$ (10 mL) and then filtered. The filtrate was concentrated under reduced pressure to give the crude product, which was purified by preparative TLC ($CH_2Cl_2$:MeOH, 10:1) and preparative HPLC (basic) in sequence to give compound 105 (3.5 mg, yield 12%) as a white solid. LC-MS $t_R$=1.075 min and 1.142 min in 2 min chromatography, MS (ESI) m/z 398 $[M+H]^+$; $^1H$ NMR ($CD_3OD$, 400 MHz): δ 7.25 (d, J=6.4 Hz, 1H), 7.18 (m, 2H), 7.05 (d, J=10 Hz, 2H), 3.16 (m, 3H), 2.91 (m, 3H), 2.66 (m, 2H), 1.94 (m, 2H), 1.68 (m, 1H), 1.55 (t, J=26.4 Hz, 2H), 1.45 (m, 1H), 0.88 (m, 2H), 0.73 (m, 1H).

Example 72

Synthesis of Compound 106

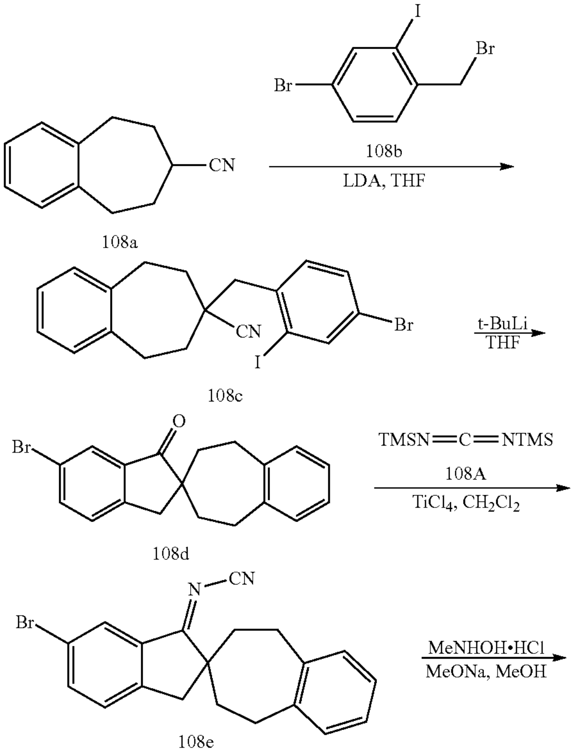

108a

108c

108d

108e

-continued

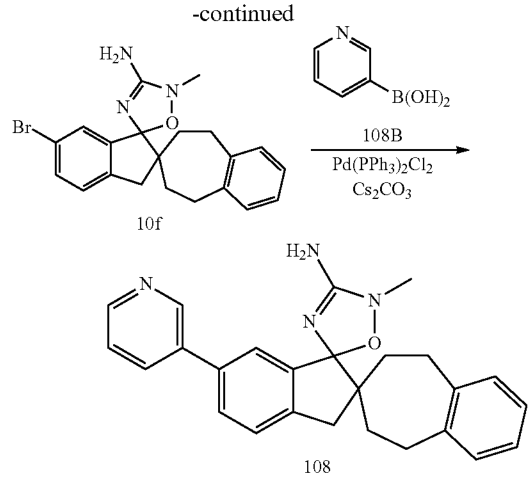

10f

108

Step 1: Preparation of Compound 108c

To a solution of LDA (23.4 mL, 42.1 mmol, 1.8 M in THF) in THF (150 mL) was added slowly a solution of compound 108a (3.6 g, 21.05 mmol) in THF (77 mL) at −60° C. under a $N_2$ atmosphere. After being stirred at −60° C. for 1 h, a solution of compound 108b (7.05 g, 18.9 mmol)) in THF (23 mL) was added slowly to the above solution. The resulting mixture was stirred at −60° C. for 2 h. The reaction mixture was quenched with water (15 mL). The aqueous layer was extracted with EtOAc (3×40 mL). The combined organic layers were washed with brine (20 mL), dried over $Na_2SO_4$ and concentrated under reduced pressure to dryness. The residue was purified by column chromatography on silica gel (petroleum:ethyl acetate, 10:1) to give compound 108c (2.5 g, yield 26%) as a yellow solid.

Step 2: Preparation of Compound 108d

A flame dried 100 mL RBF was charged with compound 108c (2.11 g, 4.5 mmol) and anhydrous THF (80 mL) under $N_2$ atmosphere. The resulting solution was stirred and chilled to −70° C., and t-BuLi (1.3 M, in hexane 6.95 mL, 9 mmol, 2 eq.) was added dropwise. Deep red was observed during the addition. The reaction was stirred another 1 h after the addition. The reaction was quenched with MeOH (0.4 mL), and followed by aq. HCl solution (2 M, 8 mL). The resulting solution was concentrated to remove organic solvent. The residue was stirred in 0.5 M aq. HCl solution (40 mL). The suspension was heated to reflux (oil bath 105° C.). The reaction was cooled down to room temperature and filter. The cake was washed with $H_2O$. The light yellow solid was collected and co-evaporated with MeOH two times to remove water to give crude product, which was purified by chromatography to give compound 108d (450 mg, yield 35%) as a white solid. $^1H$ NMR ($CDCl_3$ 400 MHz): δ 7.80-8.01 (m, 1H), 7.63-7.66 (m, 1H), 7.30-7.32 (m, 1H), 7.00-7.18 (m, 4H), 3.10 (s, 2H), 2.91-2.97 (m, 2H), 2.81 (brs, 2H), 1.78-1.85 (m, 2H), 1.57-1.62 (m, 2H).

Step 3: Preparation of Compound 108e

To a solution of compound 108d (100 mg, 0.29 mmol) in $CH_2Cl_2$ (7 mL) was added $TiCl_4$ (1.0 M in $CH_2Cl_2$, 1.18 mL, 1.18 mmol). After being stirred at 50° C. for 15 min in microwave, bis-trimethylsilylcarbodiimide (0.143 mL, 0.638 mmol) was added to above solution. The resulting mixture was stirred at 60° C. for 22 min in microwave. TLC showed that the reaction was completed. The reaction mixture was poured into ice-water (20 mL). The solution was extracted with $CH_2Cl_2$ (2×30 mL). The combined organic layers were washed with brine (10 mL), dried over $Na_2SO_4$ and concentrated under reduced pressure to dcrude compound 108e (100 mg, yield 93%) as a yellow solid, which was used directly for the next step without purification.

Step 4: Preparation of Compound 108f

To a solution of methylhydroxylamine HCl salt (46 mg, 0.55 mmol) in anhydrous MeOH (14 mL) was added a solution of NaOMe (10 wt %, 0.280 mL, 0.5 mmol) in methanol followed by compound 108e (200 mg, 0.55 mmol). After addition, the reaction mixture was stirred for 30 min, and the solvent was removed in vacuo. The residue was dissolved in $CH_2Cl_2$ (20 mL). The mixture was filtered, and the solvent was removed under reduced pressure to give the residue, which was purified by chromatography to give compound 108f (50 mg, yield 22%) as a yellow solid.

Step 5: Preparation of Compound 108

A solution containing compound 108f (25 mg, 0.061 mmol) and compound 108B (11.2 mg, 0.091 mmol) in dioxane (1.5 mL), and aqueous $Cs_2CO_3$ (2 M, 0.43 mL) was deoxygenated by bubbling a stream of nitrogen through the reaction mixture for 5 min. Then, $PdCl_2(PPh_3)_2$ (4.3 mg) was added. The reaction vial was sealed and placed into CEM microwave reactor and irradiated at 120° C. for 15 min. After being cooled to room temperature, the mixture was diluted with EtOAc and filtered through a short Celite pad. The solution was concentrated in vacuo and the residue was purified by preparative TLC and HPLC to give compound 108 (1.5 mg, yield 6%) as a white solid. LC-MS $t_R$=0.943 min in 2 min chromatography, MS (ESI) m/z 411 $[M+H]^+$; $^1H$ NMR ($CD_3OD$ 400 MHz): δ 7.68 (s, 1H), 8.40-8.68 (m, 1H), 7.97-8.00 (m, 1H), 7.52-7.54 (m, 1H), 7.40-7.46 (m, 2H), 7.31-7.40 (m, 1H), 6.96-7.05 (m, 4H), 3.10-3.22 (m, 2H), 2.97 (s, 3H), 2.92-2.95 (m, 2H), 2.53-2.65 (m, 2H), 1.87-1.96 (m, 2H), 1.53-1.64 (m, 1H), 1.46-1.50 (m, 2H).

Example 73

Synthesis of Compound 107

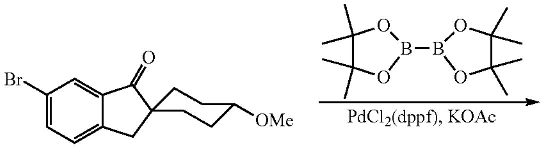

107a

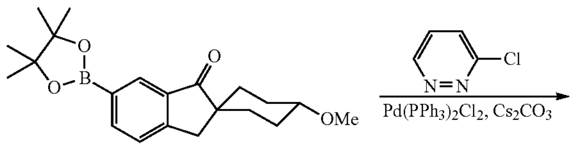

107b

-continued

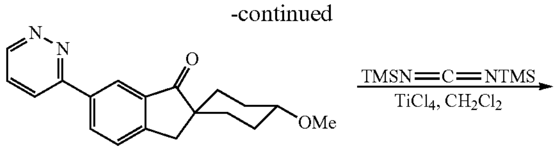

107c

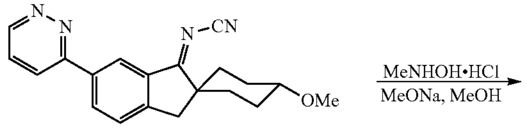

107d

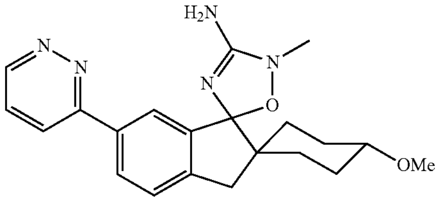

107

Step 1: Preparation of Compound 107b

To a solution of compound 107a (500 mg, 1.61 mmol) in 1,4-dioxane (10 mL), was added KOAc (0.46 g, 4.69 mmol), 4,4,5,5-tetramethyl-2-(4,4,5,5-tetramethyl-1,3,2-dioxaborolan-2-yl)-1,3,2-dioxaborolane (450 mg, 1.77 mmol) and $PdCl_2$(dppf) (150 mg, 0.18 mmol) under nitrogen, the mixture was stirred at 100° C. in a CEM microwave reactor for 1 h, LCMS showed the complete consumption of compound 107a. Water (5 mL) was added to the mixture, and the precipitate was filtered off through a pad of celite, and then was washed with EtOAc (10 mL x 3). The combined organic fractions were washed with brine (20 mL), dried over $Na_2SO_4$ and concentrated to give compound 107b (284 mg, 50%) as a black solid, which was used in the next step without further purification. $^1H$ NMR ($CDCl_3$ 400 MHz): δ 8.16 (s, 1H), 7.92 (d, J=6.4 Hz, 1H), 7.39 (d, J=7.6 Hz, 1H), 3.32 (s, 3H), 3.20 (m, 1H), 2.97 (m, 2H), 2.08 (m, 2H), 1.67 (m, 2H), 1.58 (m, 2H), 1.42 (m, 2H), 1.33 (s, 12H).

Step 2: Preparation of Compound 107c

To a solution of compound 107b (400 mg, 1.1 mmol) in dioxane (10 mL) was added 3-chloropyridazine (193 mg, 1.65 mmol), $Cs_2CO_3$ (2 N, 8 mL) and $Pd(PPh_3)_2Cl_2$ (7.4 mg, 0.011 mmol) under nitrogen, the mixture was stirred at 120° C. in a CEM microwave reactor for 15 min. Water (5 mL) was added to the mixture, and the precipitate was filtered off through a pad of celite, and then was washed with EtOAc (10 mL×3). The combined organic fractions were washed with brine (20 mL), dried over $Na_2SO_4$ and concentrated to give the crude product which was purified by preparative TLC on silica gel eluting with hexane:EtOAc=1:1 to give compound 109c (100 mg, 29%) as a yellow solid. $^1H$ NMR ($CDCl_3$ 400 MHz): δ 9.11 (d, J=4.8 Hz, 1H), 8.49 (d, J=7.2 Hz, 1H), 8.21 (s, 1H), 7.87 (d, J=7.2 Hz, 1H), 7.84 (d, J=4.4 Hz, 1H), 7.84 (m, 1H) 3.41 (s, 3H), 3.29 (m, 1H), 3.05 (s, 2H), 1.78 (m, 2H), 1.72 (m, 2H), 1.51 (m, 2H). 1.41-1.21 (m, 2H).

Step 3: Preparation of Compound 107d

To a solution of compound 107c (80 mg, 0.25 mmol) in anhydrous $CH_2Cl_2$ (2 mL) was added $TiCl_4$ (2.5 mL) under $N_2$, the mixture was stirred at 50° C. in a CEM microwave reactor for 15 min, then bistrimethylsilylcarbodiimide (105.3 mg, 0.56 mmol) was added. The mixture was stirred at 60° C. in a CEM microwave reactor for 15 min. TLC (hexane:EtOAc=3:1) showed the complete consumption of compound 107c. The mixture was poured into ice-water (5 mL) and the aqueous layer was extracted with $CH_2Cl_2$ (10 mL×3). The combined organic layers were washed with brine (50 mL), dried over $Na_2SO_4$ and concentrated to give compound 107d (82 mg, crude 95%) as a yellow solid which was used directly in the next step without purification.

Step 4: Preparation of Compound 107

To a solution of N-methylhydroxylamine hydrochloride (12.6 mg, 0.15 mmol) in MeOH (4 mL) was added MeONa (81 mg, 0.15 mmol, 10 wt % in MeOH), followed by compound 109d (50 mg, 0.15 mmol). The mixture was stirred at room temperature for 10 min, LCMS showed the complete consumption of compound 107d. The solvent was removed in vacuo to give the crude product, which was purified by preparative TLC on silica gel eluting with dichloromethane: methanol=10:1 followed by preparative HPLC to afford compound 107 (5.6 mg, 10% for 2 steps) as a white solid. $^1H$ NMR ($CD_3OD$ 400 MHz): δ 9.13 (d, J=4.4 Hz, 1H), 8.18 (d, J=8.4 Hz, 1H), 7.81 (m, 2H), 7.44 (d, J=8.8 Hz, 1H), 7.44 (d, J=7.6 Hz, 1H), 3.43 (s, 3H), 3.23 (m, 1H), 3.15 (s, 3H), 3.0 (m, 2H), 2.09 (m, 2H), 1.75 (m, 1H) 1.65 (m, 2H), 1.52 (m, 1H), 1.38 (m, 2H). LCMS: 663-148-1, $t_R$=0.810 min in 2 min chromatography, MS (ESI) m/z 380.1 $[M+H]^+$.

Example 74

Synthesis of Compound 108

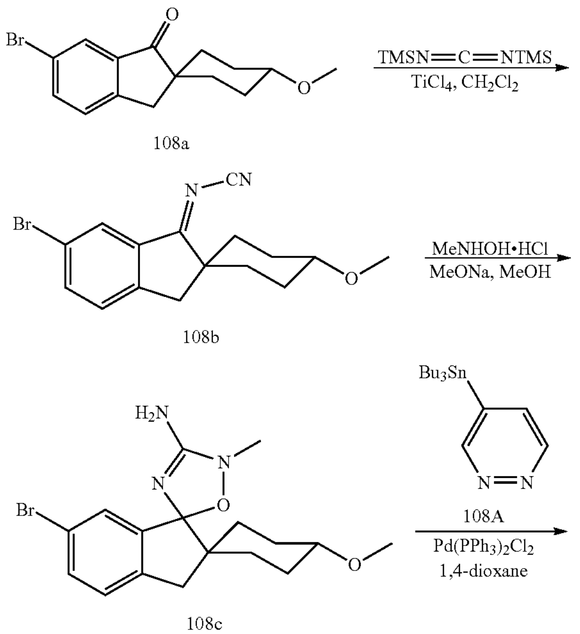

108c

-continued

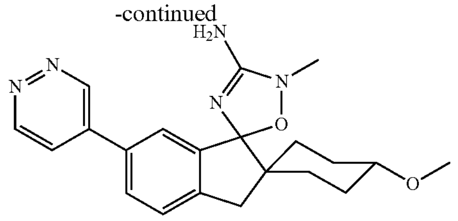

108

Step 1: Preparation of Compound 108b

To a solution of compound 108a (2 g, 6.5 mmol) in anhydrous $CH_2Cl_2$ (70 mL) was added $TiCl_4$ (1 M in $CH_2Cl_2$, 14.3 mL, 14.3 mol). After stirring at room temperature for 1 h under nitrogen, bis-trimethylsilylcarbodiimide (2.47 g, 3.0 mL, 13.3 mmol) was added. After addition, the mixture was stirred at room temperature overnight. TLC showed that the reaction was completed. The reaction mixture was poured into ice-water (100 g) and stirred 30 min. The separated aqueous phase was extracted with $CH_2Cl_2$ (2×100 mL). The combined organic layers were washed with brine (2×100 mL), dried over $Na_2SO_4$ and filtered. The filtrate was concentrated to give compound 108b (2.3 g, crude, 100%) as a white solid, which was used for the next step directly without purification.

Step 2: Preparation of Compound 108c

To a solution of methylhydroxylamine HCl salt (0.546 g, 6.5 mmol) in anhydrous MeOH (300 mL) was added NaOMe (10 wt % in MeOH, 3.16 g, 5.85 mmol), followed by compound 108b (2.15 g, 6.5 mmol). After stirring at room temperature for 40 min, the solvent was removed in vacuo. The residue was re-dissolved in $CH_2Cl_2$ (100 mL). The mixture was filtered and the solvent was removed to give the residue, which was purified by column chromatography ($CH_2Cl_2$: MeOH=20:1 to 5:1) to give compound 108c (1.7 g, 69%) as a white solid.

Step 3: Preparation of Compound 108

A solution containing compound 108A (97 mg, 0.26 mmol) and compound 108c (40 mg, 0.105 mmol) in 1,4-dioxane (3 mL) was deoxygenated by bubbling a stream of nitrogen through the reaction mixture for 5 min. Then, $PdCl_2(PPh_3)_2$ (4 mg) was added. The reaction vial was sealed and placed into CEM microwave reactor and irradiated at 125° C. for 45 min. After being cooled to room temperature, the mixture was partitioned between EtOAc (10 mL) and aqueous CsF (4 M, 10 mL), and the aqueous layer was extracted with EtOAc (3×10 mL). The combined organic layers were washed with brine (15 mL), dried over anhydrous $Na_2SO_4$, filtered, and concentrated in vacuo. The residue was purified by preparative TLC ($CH_2Cl_2$:MeOH=10:1) and preparative HPLC to afford product compound 108 (7.3 mg, 18%) as a white solid.

LC-MS $t_R$=0.843 min in 2 min chromatography, MS (ESI) m/z 380.0 $[M+H]^+$ $^1H$ NMR ($CD_3OD$ 300 MHz): δ 9.55-9.68 (d, J=50.8 Hz, 1H), 9.32 (s, 1H), 8.18-8.23 (m, 1H), 7.96-8.07 (m, 2H), 7.58-7.61 (d, J=10.8 Hz, 1H), 3.35-3.42 (m, 7H), 3.03-3.17 (q, 2H), 2.01-2.22 (m, 2H), 1.65-1.84 (m, 2H), 1.33-1.64 (m, 4H).

Example 75

Synthesis of Compound 109

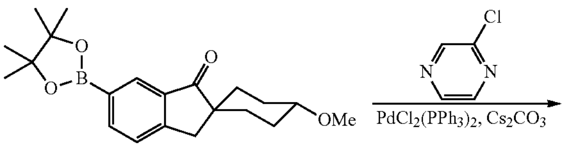

109a

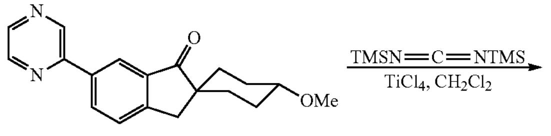

109b

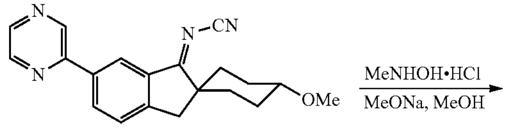

109c

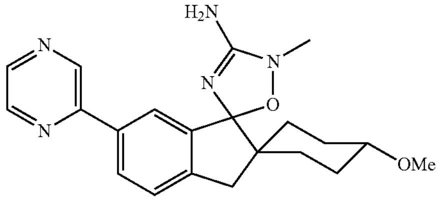

109

Step 1: Preparation of Compound 109b

To a solution of compound 109a (400 mg, 1.1 mmol) in dioxane (10 mL) were added 2-chloropyrazine (135 mg, 1.17 mmol), $Cs_2CO_3$ (2 N, 8 mL) and $PdCl_2(PPh_3)_2$ (5.2 mg, 0.0078 mmol) under nitrogen, the mixture was stirred at 120° C. in a CEM microwave reactor for 15 min. Water (5 mL) was added to the mixture, and the precipitate was filtered off through a pad of celite, and then was washed with EtOAc (10 mL×3). The combined organic fractions were washed with brine (20 mL), dried over $Na_2SO_4$ and concentrated to give the crude product which was purified by preparative TLC on silica gel eluting with hexane:EtOAc=1:1 to give compound 109b (100 mg, 41%) as a yellow solid. $^1$H NMR ($CDCl_3$ 400 MHz): δ 9.10 (s, 1H), 8.69 (d, J=8.0 Hz, 1H), 8.38 (s, 1H), 7.63 (d, J=9.2 Hz, 2H), 7.63 (d, J=8.0 Hz, 1H), 3.43 (s, 3H), 3.37 (m, 1H), 3.13 (s, 2H), 2.2 (m, 2H), 1.87 (m, 2H), 1.56 (m, 2H), 1.47 (m, 2H).

Step 2: Preparation of Compound 109c

To a solution of compound 109b (66 mg, 0.21 mmol) in anhydrous $CH_2Cl_2$ (2 mL) was added $TiCl_4$ (2 mL, 1 M in $CH_2Cl_2$, 2 mmol) under nitrogen, the mixture was stirred at 50° C. in a CEM microwave reactor for 15 min, then bistrimethylsilylcarbodiimide (87.6 mg, 0.45 mmol) was added. The mixture was stirred at 60° C. in a CEM microwave reactor for 15 min, TLC (hexane:EtOAc=1:1) showed the complete consumption of compound 109b. The mixture was poured into ice-water (5 mL) and the aqueous layer was extracted with $CH_2Cl_2$ (10 mL×3). The combined organic layers were washed with brine (30 mL), dried over $Na_2SO_4$ and concentrated to give compound 109c (47 mg, 66%) as a yellow solid which was used directly in the next step without purification.

Step 3: Preparation of Compound 109

To a solution of N-methylhydroxylamine hydrochloride (11.8 mg, 0.14 mmol) in MeOH (2 mL) was added MeONa (76.4 mg, 0.14 mmol, 10 wt % in MeOH), followed by compound 111c (47 mg, 0.14 mmol), the mixture was stirred for 10 min. The solvent was removed in vacuo to give the crude product which was purified by preparative TLC on silica gel eluting with dichloromethane:methanol=10:1 followed by preparative HPLC to afford compound 109 (1.2 mg, 2.2%) as a white solid.

$^1$H NMR ($CDCl_3$ 400 MHz): δ 9.09 (s, 1H), 8.67 (d, J=8.0 Hz, 1H), 8.52 (s, 1H), 8.02 (d, J=7.6 Hz, 2H), 7.42 (d, J=7.6 Hz, 1H), 3.49 (s, 3H), 3.2 (m, 1H), 3.14 (s, 3H), 2.95 (m, 2H), 2.17 (m, 2H), 1.71 (m, 1H), 1.61 (m, 2H), 1.58 (m, 1H), 1.37 (m, 2H).

LCMS: $t_R$=0.855 min in 2 min chromatography, MS (ESI) m/z 380.1 $[M+H]^+$.

Example 76

Synthesis of Compound 110

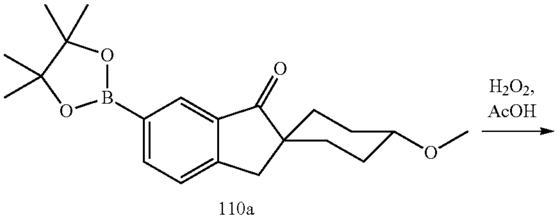

110a

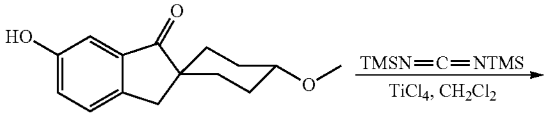

110b

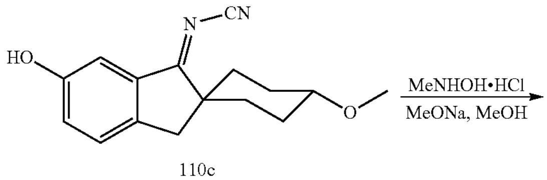

110c

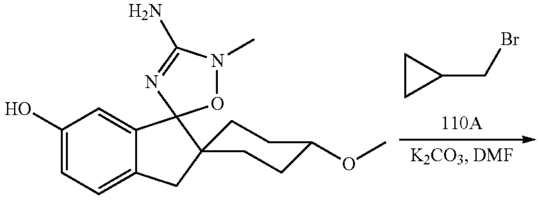

475

-continued

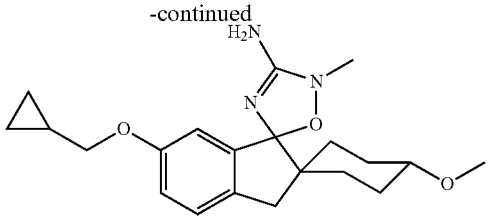

110

Step 1: Preparation of Compound 110b

To a solution of compound 110a (150 mg, 0.42 mmol) in THF (10 mL) was added HOAc (0.2 mL) and $H_2O_2$ (1 mL) under nitrogen, the mixture was stirred at room temperature overnight. The mixture was quenched with $NaHSO_3$ solution (10 mL), and then was extracted with EtOAc (10 mL×3). The combined organic layers were washed with brine (30 mL), dried over $Na_2SO_4$ and concentrated to afford the crude product which was purified by column chromatography on silica gel eluting with hexane:EtOAc (100:10~30:10) to give compound 110b (100 mg, 97%) as a white solid. $^1$H NMR ($CDCl_3$ 400 MHz): δ 7.31 (s, 1H), 6.91-7.15 (d, J=8.0 Hz, 2H), 3.43 (s, 3H), 3.26 (m, 1H), 2.97 (s, 2H), 1.98-2.09 (m, 2H), 1.86-1.98 (m, 2H), 1.41-1.65 (m, 2H), 1.20-1.41 (m, 2H).

Step 2: Preparation of Compound 110c

To a solution of compound 110b (100 mg, 0.40 mmol) in anhydrous $CH_2Cl_2$ (2 mL) was added $TiCl_4$ (1.2 mL, 1.0 M in $CH_2Cl_2$, 1.2 mmol) under nitrogen, the mixture was stirred at 50° C. in a CEM microwave reactor for 15 min, then bistrimethylsilylcarbodiimide (187.8 mg, 1.01 mmol) was added. The mixture was stirred at 60° C. in a CEM microwave reactor for 15 min, TLC (hexane:EtOAc=1:1) analysis showed the complete consumption of compound 110b. The mixture was poured into ice-water (5 mL) and the aqueous layer was extracted with $CH_2Cl_2$ (10 mL×2). The combined organic layers were washed with brine (40 mL), dried over $Na_2SO_4$ and concentrated to give compound 110c (85 mg, 77%) as a yellow solid which was used directly in the next step without purification.

Step 3: Preparation of Compound 475

To a solution of N-methylhydroxylamine hydrochloride (26.4 mg, 0.31 mmol) in MeOH (2 mL) was added MeONa (169 mg, 0.31 mmol, 10 wt % in MeOH), followed by compound 110c (85 mg, 0.31 mmol), the mixture was stirred for 10 min at room temperature, TLC (dichloromethane:methanol=10:1) analysis showed the complete consumption of compound 110c. the solvent was removed in vacuo to give the crude product which was purified by preparative TLC on silica gel eluting with dichloromethane:methanol=10:1 to afford compound 475 (50 mg, 51%) as a white solid.

Step 4: Preparation of Compound 110

To a solution of compound 475 (21 mg, 0.066 mmol) in DMF (2 mL) were added $K_2CO_3$ (36.5 mg, 0.26 mmol), and compound 110A (17.8 mg, 0.132 mmol), the mixture was stirred at 50° C. for 3 h, LCMS showed the complete consumption of compound 475. The reaction was added with $H_2O$ (5 mL), and the aqueous layer was extracted with EtOAC (10 mL×3). The combined organic layers were washed with brine (30 mL), dried over $Na_2SO_4$ and concentrated to give the crude product which was purified by preparative TLC on silica gel eluting with dichloromethane:methanol=10:1 followed by preparative HPLC to afford compound 110 (1.7 mg, 5%) as a white solid. $^1$H NMR ($CD_3OD$ 400 MHz): δ 6.93 (s, 1H), 6.71-6.93 (d, J=8.4 Hz, 2H), 3.73 (d, J=6.8 Hz, 2H), 3.38 (s, 3H), 3.09 (m, 1H), 2.95 (s, 3H), 2.62-2.72 (m, 2H), 1.94-2.07 (m, 2H), 1.78 (m, 1H), 1.59 (m, 1H), 1.39-1.56 (m, 2H), 1.19-1.31 (m, 1H), 1.13-1.19 (m, 2H), 0.47-0.53 (m, 2H), 0.23-0.43 (m, 2H). LCMS: $t_R$=0.967 min in 2 min chromatography, MS (ESI) m/z 372 $[M+H]^+$.

Example 77

Synthesis of Compound 111

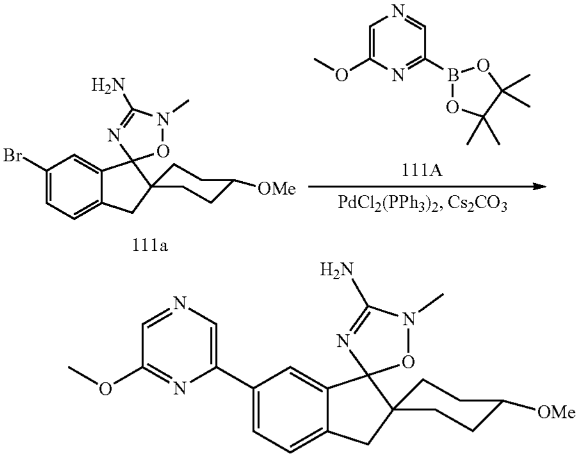

111a

111

A mixture of compound 111a (30 mg, 0.0792 mmol), compound 111A (28 mg, 0.1196 mmol), $Cs_2CO_3$ (0.567 mL, 1.134 mmol, 2 M in water) and $PdCl_2(PPh_3)_2$ (8 mg) in 1,4-dioxane (2.0 mL) was irradiated in microwave at 120° C. for 15 min under nitrogen. The mixture was concentrated to give crude compound 111, which was purified by preparative HPLC to afford compound 111 (1.8 mg, 5%) as a white solid. LCMS: $t_R$=0.953 min in 2 min chromatography, MS (ESI) m/z 410.1 $[M+H]^+$. $^1$H NMR ($CD_3OD$ 400 MHz TMS): δ 8.59 (s, 1H), 8.32 (s, 1H), 8.10-8.12 (m, 2H), 7.38-7.67 (m, 1H), 3.08-4.92 (m, 3H), 3.31-3.32 (m, 6H), 3.14-3.17 (m, 1H), 2.95-2.98 (m, 2H), 1.91-2.22 (m, 2H), 1.61-1.85 (m, 2H), 1.22-1.48 (m, 4H).

Example 78

Synthesis of Compound 112

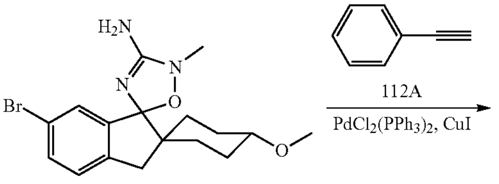

112a

-continued

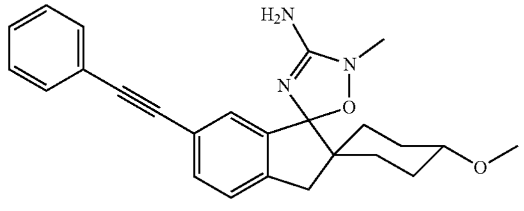

112

Compound 112a (50 mg, 0.13 mmol) was dissolved in $Et_3N$ (5 mL) and $Et_2NH$ (1 mL), the resulting mixture was degassed and purged with $N_2$ for three times. $Pd(PPh_3)_2Cl_2$ (5 mg) and CuI (4 mg) were added under $N_2$ atmosphere and the system was degassed again. Ethynylbenzene (0.3 mL, excess) was added by syringe. The system was degassed one more time. The reaction was heated to 75~85° C. for 12 h. LCMS showed that the reaction was completed; the solvent was removed under reduced pressure. The residue was partitioned by $CH_2Cl_2$ (10 mL) and water (10 mL). The aqueous layer was extracted with $CH_2Cl_2$ (2×10 mL), the combined organic layers were washed with brine (2×10 mL), dried over $Na_2SO_4$ and concentrated to dryness. Purification of this residue by preparative TLC ($CH_2Cl_2$:MeOH=5:1) and RP-HPLC (basic) afforded compound 112 (4.6 mg, 9%) as a white solid. LC-MS $t_R$=1.168 min in 2 min chromatography, MS (ESI) m/z 402.2 $[M+H]^+$. $^1H$ NMR ($CD_3OD$ 400 MHz): δ 7.51-7.53 (m, J=7.2 Hz, 2H), 7.37-7.45 (m, J=8.0 Hz, 5H), 7.24-7.26 (d, J=7.6 Hz, 1H), 3.38 (s, 3H), 3.15-3.25 (m, 1H), 3.06 (s, 3H), 2.83-2.94 (q, 2H), 2.02-2.08 (t, J=12.8 Hz, 2H), 1.68-1.71 (d, J=11.6 Hz, 1H), 1.56-1.63 (t, J=14.0 Hz, 2H), 1.18-1.48 (m, 3H).

Example 79

Synthesis of Compound 113

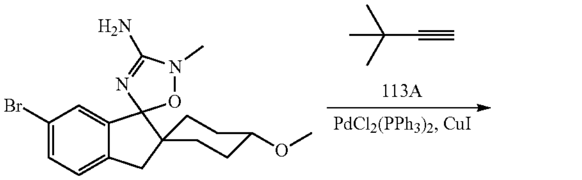

113a

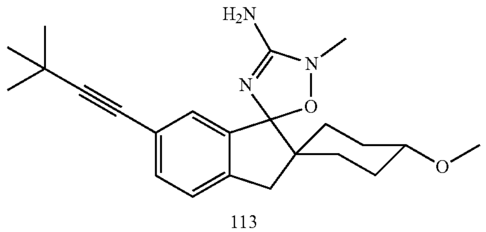

113

The compound 113a (50 mg, 0.13 mmol) was dissolved in $Et_3N$ (106 mg, 1.05 mmol 1) and DMF (4 mL), the resulting mixture was degassed and purged with $N_2$ for three times. $Pd(PPh_3)_2Cl_2$ (5 mg) and CuI (4 mg) were added under a $N_2$ atmosphere and the system was degassed again. 3,3-dimethylbut-1-yne (0.5 mL, excess) was added by syringe. The system was degassed one more time. The reaction was heated to 90~100° C. for 12 h. LCMS showed that the reaction was completed. The solvent was removed under reduced pressure. The residue was partitioned between $CH_2Cl_2$ (10 mL) and water (10 mL). The aqueous layer was extracted with $CH_2Cl_2$ (2×10 mL); the combined organic layers were washed with brine (2×10 mL), dried over $Na_2SO_4$ and concentrated to dryness. Purification of this residue by preparative TLC ($CH_2Cl_2$:MeOH=5:1) and pre-HPLC (basic) afforded compound 113 (6.7 mg, 13%) as a white solid. LC-MS $t_R$=1.184 min in 2 min chromatography, MS (ESI) m/z 382.2 $[M+H]^+$. $^1H$ NMR ($CD_3OD$ 400 MHz): δ 7.10-7.14 (t, J=7.6 Hz, 2H), 7.03-7.04 (d, J=7.6 Hz, 1H), 3.26 (s, 3H), 3.01-3.09 (m, 1H), 2.91 (s, 3H), 2.67-2.77 (m, 2H), 1.88-1.94 (m, 3H), 1.54-1.57 (d, J=14.0 Hz, 1H), 1.25-1.48 (m, 4H), 1.25 (s, 9H).

Example 80

Synthesis of Compound 114

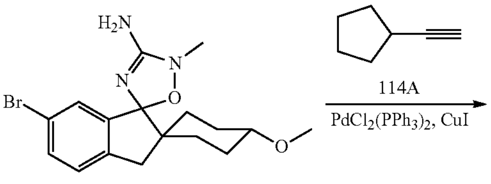

114a

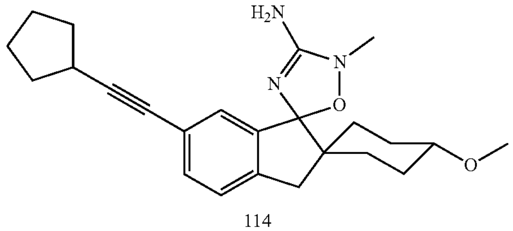

114

The titled compound was synthesized as described in example 77, compound 114 in 7% yield starting from compound 114a and Ethynylcyclopentane. LC-MS $t_R$=1.078 min in 2 min chromatography, MS (ESI) m/z 394.1 $[M+H]^+$. $^1H$ NMR ($CD_3OD$ 400 MHz): δ 7.20-7.24 (t, J=8.0 Hz, 2H), 7.12-7.14 (d, J=8.0 Hz, 1H), 3.38 (s, 3H), 3.13-3.20 (m, 1H), 3.01 (s, 3H), 2.80-2.83 (m, 3H), 1.96-2.03 (m, 4H), 1.76-1.79 (m, 2H), 1.61-1.69 (m, 5H), 1.50-1.58 (m, 2H), 1.24-1.43 (m, 3H).

Example 81

Synthesis of Compound 115

Method 1

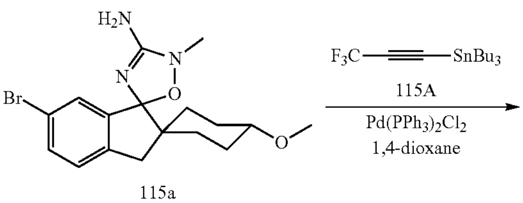

115a

-continued

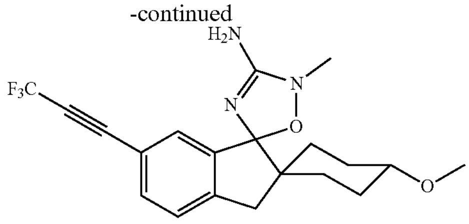

115

Method 2

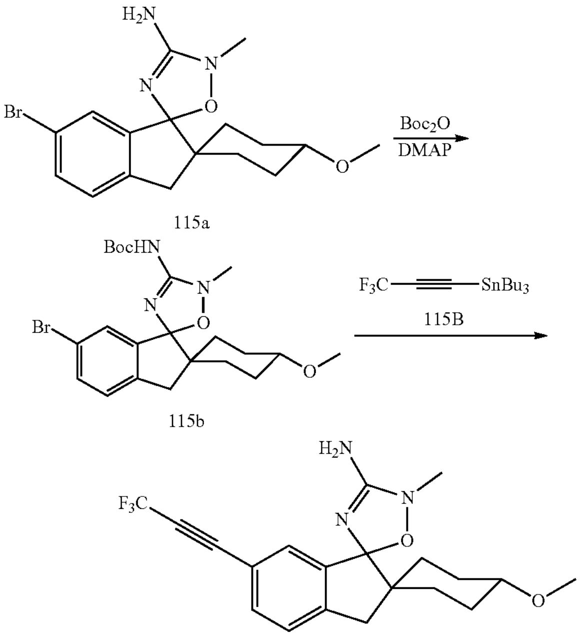

115a
115b
115

Method 1

A solution containing compound 115A (126 mg, 0.33 mmol) and compound 115a (50 mg, 0.13 mmol) in 1,4-dioxane (4 mL) was deoxygenated by bubbling a stream of nitrogen through the reaction mixture for 5 min. Then, $Pd(PPh_3)_2Cl_2$ (5 mg) was added. The reaction vial was sealed and placed into a CEM microwave reactor and irradiated at 125° C. for 45 min. After being cooled to room temperature, the mixture was partitioned between EtOAc (10 mL) and aqueous CsF (4 M, 10 mL), and the aqueous layer was extracted with EtOAc (3×10 mL). The combined organic layers were washed with brine (15 mL), dried over anhydrous $Na_2SO_4$, filtered, and concentrated in vacuo. The residue was purified by preparative TLC ($CH_2Cl_2$: MeOH=10:1) and preparative HPLC (basic) to afford product compound 115 (3 mg, 6%) as a white solid. LC-MS $t_R$=1.140 min in 2 min chromatography, MS (ESI) m/z 394.2 $[M+H]^+$. $^1H$ NMR ($CD_3OD$ 400 MHz): δ 7.42-7.44 (d, J=7.6 Hz, 1H), 7.37 (s, 1H), 7.22-7.24 (d, J=7.6 Hz, 1H), 3.26 (s, 3H), 3.02-3.10 (m, 1H), 2.93 (s, 3H), 2.75-2.85 (q, 2H), 1.87-1.96 (m, 2H), 1.43-1.59 (m, 3H), 1.16-1.36 (m, 3H).

Method 2 step 1: Preparation of Compound 115b

Compound 115a (280 mg, 0.74 mmol) and $(Boc)_2O$ (241 mg, 1.1 mmol) was dissolved in THF (8 mL), this solution was added DMAP (135 mg, 1.1 mmol) and $Et_3N$ (0.2 mL, 1.47 mmol), the reaction mixture was stirred at room temperature overnight. LCMS showed that the reaction was completed. The reaction mixture was concentrated under reduced pressure to give the residue, which was purified by preparative TLC (petroleum ether:ethyl acetate=5:1) to give 115b (300 mg, 85%) as a white solid.

Method 2 Step 2: Preparation of Compound 115

A solution containing compound 115B (120 mg, 0.312 mmol) and compound 115b (100 mg, 0.208 mmol) in toluene (5 mL) was deoxygenated by bubbling a stream of nitrogen through the reaction mixture for 5 min. Then, $PdCl_2(PPh_3)_2$ (7 mg, 0.010 mmol) was added. The reaction vial was sealed and placed into CEM microwave reactor and irradiated at 125° C. for 45 min. After being cooled to room temperature, the mixture was partitioned between EtOAc (10 mL) and aqueous CsF (4 M, 10 mL), and the aqueous layer was extracted with EtOAc (3×10 mL). The combined organic layers were washed with brine (15 mL), dried over anhydrous $Na_2SO_4$, filtered, and concentrated in vacuo. The residue was purified by preparative TLC ($CH_2Cl_2$:MeOH=10:1) and preparative HPLC (basic) to afford product compound 115 (9.3 mg, 6%) as a white solid. LC-MS $t_R$=1.011 min in 2 min chromatography, MS (ESI) m/z 394.2 [M+H]NMR ($CD_3OD$ 400 MHz): δ 7.41-7.43 (d, J=8.0 Hz, 1H), 7.37 (s, 1H), 7.22-7.24 (d, J=7.6 Hz, 1H), 3.30 (s, 3H), 3.04-3.10 (m, 1H), 2.93 (s, 3H), 2.75-2.85 (q, 2H), 1.89-1.95 (m, 2H), 1.42-1.56 (m, 3H), 1.17-1.34 (m, 3H).

Example 82

Synthesis of Compound 116

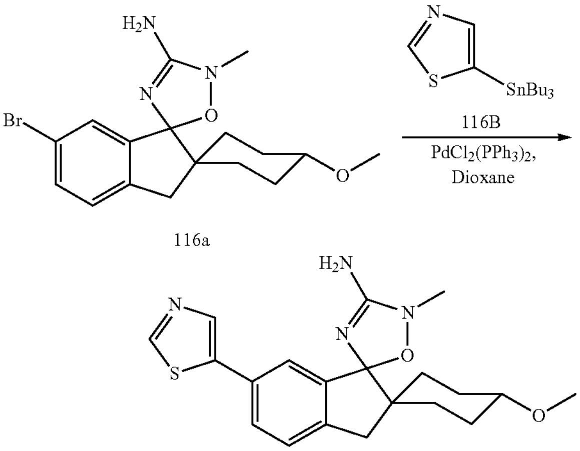

116a
116

A solution containing compound 116B (124 mg, 0.33 mmol) and compound 116a (50 mg, 0.13 mmol) in anhydrous 1,4-dioxane (10 mL) was deoxygenated by bubbling a stream of nitrogen through the reaction mixture for 5 min. Then, $PdCl_2(PPh_3)_2$ (4 mg) was added. The reaction vial was sealed and placed into CEM microwave reactor and irradiated at 125° C. for 45 min. After being cooled to room temperature, the mixture was partitioned between EtOAc (10 mL) and aqueous CsF (4 M, 10 mL), and the aqueous layer was extracted with EtOAc (3×10 mL). The combined organic layers were washed with brine (15 mL), dried over anhydrous $Na_2SO_4$, filtered, and concentrated in vacuo. The residue was purified by preparative TLC ($CH_2Cl_2$:MeOH=10:1) and preparative HPLC (basic) to afford product compound 116 (2.2 mg, 4.3%) as a white solid. LC-MS $t_R$=0.996 min in 2 min chromatography, MS (ESI) m/z 384.2 $[M+H]^+$. $^1H$ NMR ($CD_3OD$ 300 MHz): δ 8.83 (s, 1H), 8.03 (s, 1H), 7.49-7.51 (d, J=8.0 Hz, 1H), 7.42 (s, 1H), 7.20-7.22 (d, J=10.4 Hz, 1H), 3.26 (s, 3H), 3.21 (m, 1H), 2.95 (s, 3H), 2.78 (m, 2H), 1.92 (s, 2H), 1.21-1.47 (m, 6H).

Example 83

Synthesis of Compound 117

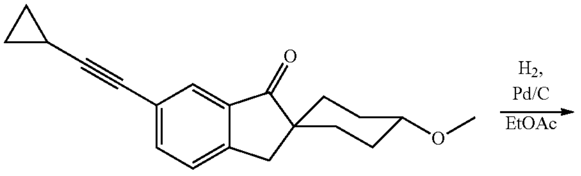

117a

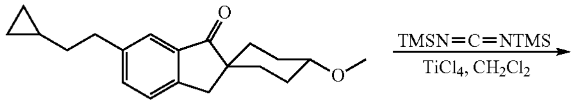

117b

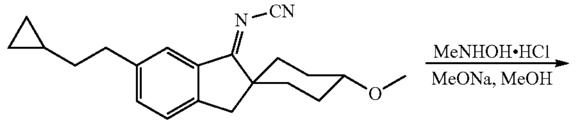

117b

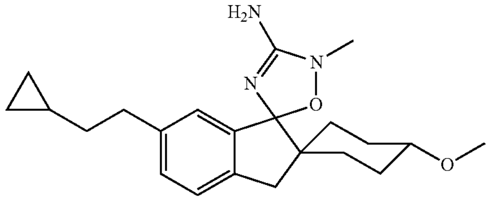

117

Procedure for Preparation of Compound 117b

To a solution of compound 117a (0.15 g, 0.51 mmol) in EtOAc (10 mL) was added Pd/C (15 mg, 10 wt %). The resulting mixture was stirred at room temperature under $H_2$ atmosphere (30 Psi) for 1 h, LC-MS showed that the reaction was completed. The reaction mixture was filtered and the filtrate was concentrated to give compound 117b (0.14 g, 92% crude yield) as a red oil, which was used for next step directly without purification without purification.

Procedure for Preparation of Compound 117c

To a solution of compound 117b (50 mg, 0.167 mmol) in anhydrous $CH_2Cl_2$ (4 mL) was added $TiCl_4$ (1 M in $CH_2Cl_2$, 0.4 mL, 0.4 mmol). The resulting mixture was stirred at room temperature for 1 h under a nitrogen atmosphere, and then bis-trimethylsilylcarbodiimide (64 mg/0.076 mL, 0.34 mmol) was added. After addition, the mixture was stirred at room temperature overnight. LC-MS showed that the reaction was completed. The reaction mixture was poured into ice-water (10 g) and stirred for 30 min. The separated aqueous phase was extracted with $CH_2Cl_2$ (2×10 mL). The combined organic layers were washed with brine (2×10 mL), dried over $Na_2SO_4$ and filtered. The filtrate was concentrated to give compound 117c (54 mg, 100% crude yield) as a white solid, which was used directly for the next step without purification.

Procedure for Preparation of Compound 117

To a solution of methylhydroxylamine HCl salt (14 mg, 0.167 mmol) in anhydrous MeOH (5 mL) was added NaOMe (10 wt % in MeOH, 0.08 g, 0.15 mmol), followed by compound 117c (54 mg, 0.17 mmol). After stirred for 40 min, the solvent was removed under reduced pressure. The residue was purified by preparative TLC ($CH_2Cl_2$:MeOH=10:1) and preparative RP-HPLC to give compound 117 (4.8 mg, 8%) as a white solid. LC-MS $t_R$=1.109 min and 1.175 min in 2 min chromatography, MS (ESI) m/z 370.2 $[M+H]^+$. $^1H$ NMR ($CD_3OD$ 400 MHz): δ 7.48-7.56 (d, J=8.4 Hz, 1.4H), 7.38 (s, 0.6H), 7.18-7.27 (m, 1H), 3.66 (s, 1H), 3.37 (s, 2H), 3.34 (s, 1H), 3.24 (s, 3H), 3.11 (s, 1H), 2.90 (s, 1H), 2.70-2.80 (m, 2H), 2.05-2.15 (m, 2H), 1.75-1.88 (m, 1H), 1.57-1.73 (m, 2H), 1.30-1.51 (m, 5H), 0.60-0.68 (m, 1H), 0.37-0.42 (m, 2H), 0.02-0.03 (m, 2H).

Example 84

Synthesis of Compound 118

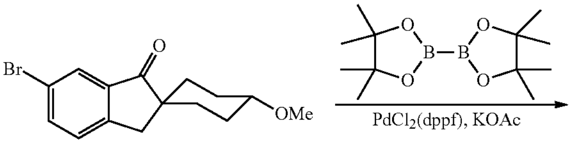

118a

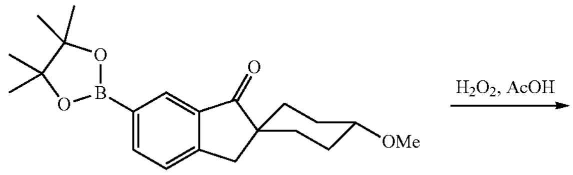

118b

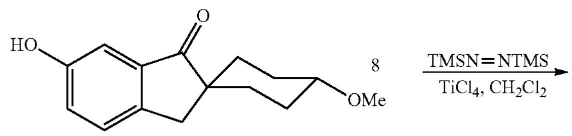

118c

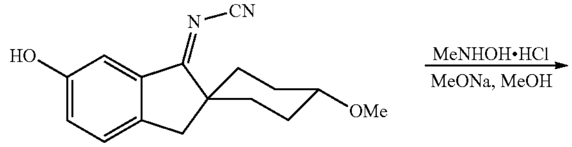

118d

-continued

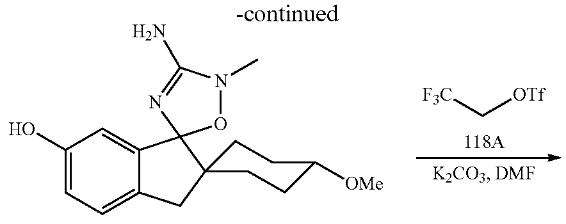

118e

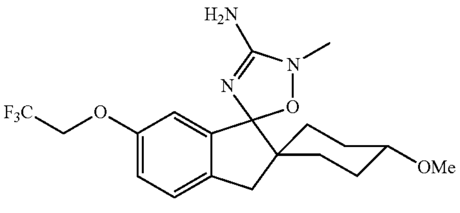

118

Procedure for Preparation of Compound 118b

To a solution of compound 118a (500 mg, 1.61 mmol) in 1,4-dioxane (10 mL), was added KOAc (0.46 g, 4.69 mmol), 4,4,5,5-tetramethyl-2-(4,4,5,5-tetramethyl-1,3,2-dioxaborolan-2-yl)-1,3,2-dioxaborolane (450 mg, 1.77 mmol) and $PdCl_2$(dppf) (150 mg, 0.18 mmol) under a nitrogen atmosphere, the mixture was stirred at 100° C. in a CEM microwave reactor for 1 h. LCMS showed the complete consumption of compound 118a. Water (5 mL) was added to the mixture, and the precipitate was filtered off through a pad of celite, and then was washed with EtOAc (3×10 mL). The combined organic fractions were washed with brine (20 mL), dried over $Na_2SO_4$ and concentrated to give compound 118b (284 mg, 50%) as a black solid which was used in the next step without further purification. $^1$H NMR ($CDCl_3$ 400 MHz): δ 8.20 (s, 1H), 7.97 (d, J=8.0 Hz, 2H), 3.41 (s, 3H), 3.21 (m, 1H), 2.96 (s, 2H), 2.06 (m, 2H), 1.64 (m, 2H), 1.56 (m, 2H), 1.44 (m, 2H), 1.31 (s, 12H).

Procedure for Preparation of Compound 118c

To a solution of compound 118b (100 mg, 0.28 mmol) in THF (10 mL) was added HOAc (0.2 mL) and $H_2O_2$ (1 mL) under a nitrogen atmosphere, the mixture was stirred at room temperature overnight. The mixture was quenched by addition of $NaHSO_3$ solution (10 mL), and then was extracted with EtOAc (3×10 mL). The combined organic layers were washed with brine (30 mL), dried over $Na_2SO_4$ and concentrated to afford the crude product which was purified by column chromatography on silica gel eluting with hexane: EtOAc (100:10 to 30:10) to afford compound 118c (50 mg, 72%) as a yellow oil. $^1$H NMR ($CDCl_3$ 400 MHz): δ 7.24 (s, 1H), 7.10 (d, J=8.0 Hz, 2H), 3.33 (s, 3H), 3.26 (m, 1H), 2.86 (s, 2H), 2.20-2.21 (m, 2H), 1.68-1.69 (m, 2H), 1.44-1.65 (m, 2H), 1.20-1.40 (m, 2H).

Procedure for Preparation of Compound 118d

To a solution of compound 118c (50 mg, 0.20 mmol) in anhydrous $CH_2Cl_2$ (2 mL) was added $TiCl_4$ (1.2 mL, 1.2 mmol, 1 M in $CH_2Cl_2$) under a nitrogen atmosphere, the mixture was stirred at 50° C. in a CEM microwave reactor for 15 min, then bis-trimethylsilylcarbodiimide (15.1 mg, 0.40 mmol) was added. The mixture was stirred at 60° C. in a CEM microwave reactor for 15 min. The mixture was poured into ice-water (5 mL) and the aqueous layer was extracted with $CH_2Cl_2$ (2×20 mL). The combined organic layers were washed with brine (40 mL), dried over $Na_2SO_4$ and concentrated to give compound 118d (40 mg, 73%) as a yellow solid which was used directly for the next step without purification.

Procedure for Preparation of Compound 118e

To a solution of MeNHOH.HCl (12.4 mg, 0.14 mmol) in MeOH (2 mL) was added MeONa (80 mg, 0.14 mmol, 10 wt % in MeOH), followed by compound 118d (40 mg, 0.14 mmol). The mixture was stirred for 10 min at room temperature, LCMS analysis showed the complete consumption of compound 118d. The solvent was removed by evaporation in vacuo to give the crude product, which was purified by preparative TLC eluting with dichloromethane: methanol=10:1 to afford compound 118e (10 mg, 22%) as a white solid. $^1$H NMR ($CD_3OD$ 400 MHz): δ 6.99 (s, 1H), 6.80 (d, J=6.4 Hz, 2H), 3.41 (s, 3H), 3.25 (m, 1H), 2.94 (s, 3H), 1.92-2.08 (m, 2H), 1.86-1.93 (m, 2H), 1.58-1.75 (m, 2H), 1.42-1.59 (m, 2H), 1.21-1.41 (m, 2H).

Procedure for Preparation of Compound 118

To a solution of compound 118e (10 mg, 0.031 mmol) in DMF (2 mL) was added $K_2CO_3$ (8.5 mg, 0.062 mmol) and compound 118A (8.0 mg, 0.034 mmol), the mixture was stirred at 50° C. for 3 h, LCMS analysis showed the complete consumption of compound 118e. The reaction was added with $H_2O$ (5 mL), and the aqueous layer was extracted with EtOAc (3×10 mL). The combined organic layers were washed with brine (30 mL), dried over $Na_2SO_4$ and concentrated to give the crude product which was purified by preparative TLC eluting with dichloromethane:methanol=10:1 followed by preparative RP-HPLC to afford compound 118 (2 mg, 14%) as a white solid. $^1$H NMR ($CD_3OD$ 400 MHz): δ 7.15 (d, J=8.0 Hz, 1H), 6.95 (dd, J=2.4, 8.0 Hz, 1H), 6.89 (d, J=2.0 Hz, 1H), 4.53 (m, 2H), 3.40 (s, 3H), 3.24 (m, 1H), 3.04 (s, 3H), 2.80-2.84 (d, J=15.2 Hz, 1H), 2.75-2.80 (d, J=15.2, Hz, 1H), 1.98-2.01 (m, 2H), 1.70 (m, 1H), 1.66-1.70 (m, 2H), 1.46 (m, 1H), 1.36-1.46 (m, 2H). LCMS: $t_R$=1.80 min in 2 min chromatography, MS (ESI) m/z 400.2 $[M+H]^+$.

Example 85

Synthesis of Compound 119

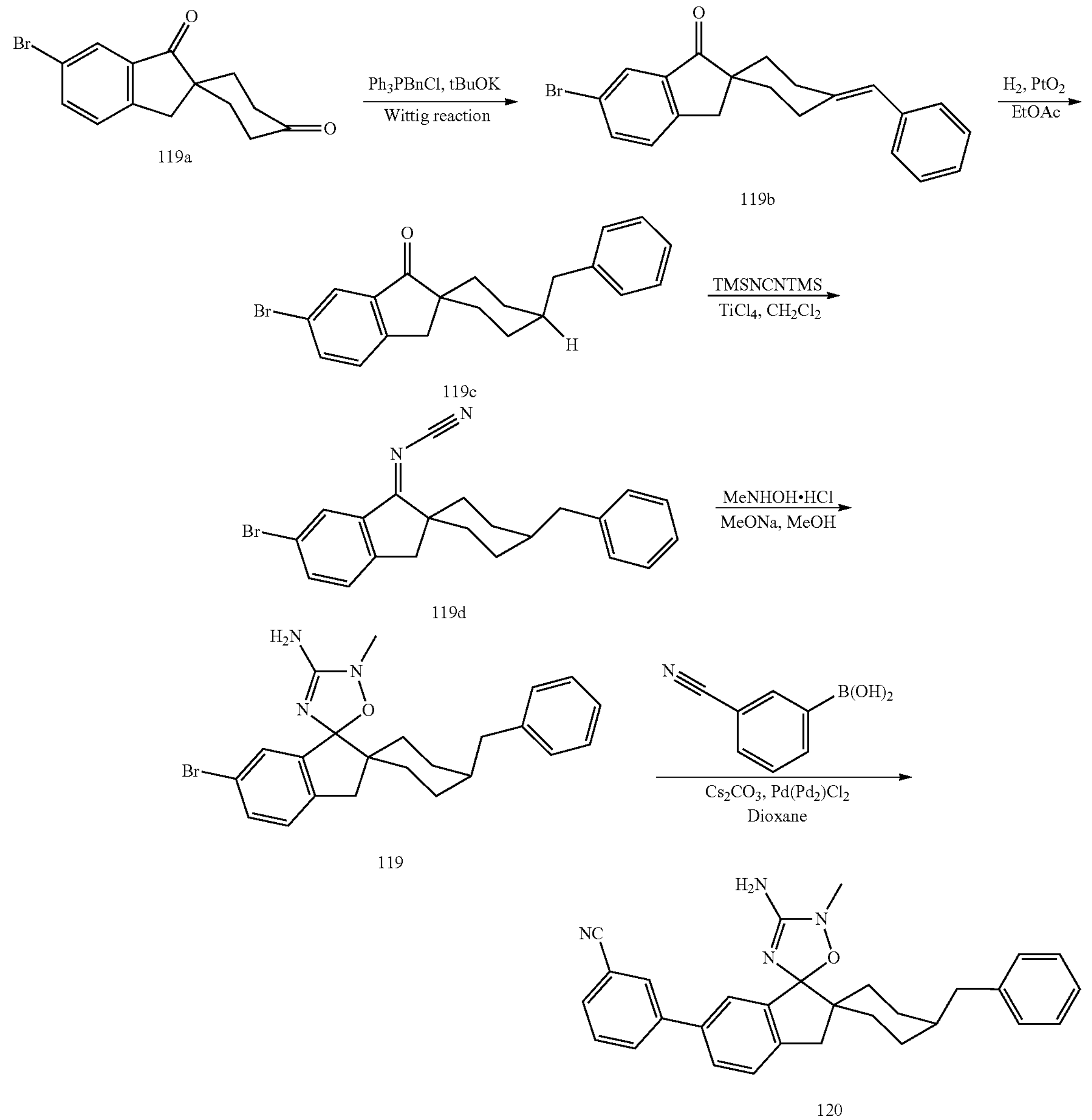

Procedure for Preparation of Compound 119b

To a solution of potassium tert-butoxide (0.89 g, 7.7 mmol) in tert-butyl alcohol (30 mL) was added benzyl triphenyl phosphonium chloride (2.4 g, 6.1 mmol). The mixture was stirred at ambient temperature for 3 h. Compound 1 (1.5 g, 5.1 mmol) was added under a nitrogen atmosphere. The reaction mixture was stirred at ambient temperature overnight. The solvent was removed by evaporation in vacuo. The residue was added $H_2O$ (100 mL) and then was extracted with ethyl acetate (3×50 mL), the combined organic layers were washed with brine (2×50 mL). The separated organic phase was dried over $Na_2SO_4$ and concentrated in vacuo. The residue was purified by column chromatography over silica gel eluting with petroleum ether:ethyl acetate=100:1 to 10:1 to give compound 119b (1.0 g, 53%) as a yellow solid. LC-MS: $t_R$=2.83 min in 3 min chromatography, MS (ESI) m/z 367.28 $[M+H]^+$.

Procedure for Preparation of Compound 119c

A mixture of compound 119b (1.0 g, 2.7 mmol), ethyl acetate (100 mL) and $PtO_2$ (0.10 g, 0.44 mmol) was stirred at temperature under hydrogen (1 atm) atmosphere overnight. The precipitate was filtered off and washed with ethyl acetate (2×50 mL). The filtrate and washings were concentrated by evaporation in vacuo. The residue was purified by column chromatography over silica gel eluting with petroleum ether: ethyl acetate=100:1 to 10:1 to give compound 119c (0.35 g, 35%) as a white solid. $^1H$ NMR: ($CD_3OD$ 400 MHz): δ 7.60-7.70 (m, 2H), 7.30-7.35 (d, J=8.0 Hz, 1H), 7.10-7.20 (m, 2H), 7.00-7.10 (m, 3H), 2.80-2.90 (s, 2H), 2.50-2.60 (d, J=7.2 Hz, 2H), 1.75-1.85 (m, 2H), 1.65-1.75 (m, 1H), 1.55-1.65 (m, 2H), 1.35-1.45 (m, 2H). LC-MS: $t_R$=2.46 min in 3 min chromatography, MS (ESI) m/z 369.29 $[M+H]^+$.

Procedure for Preparation of Compound 119d

A sealed tube was charged with compound 119c (0.15 g, 0.41 mmol), anhydrous dichloromethane (3 mL) and $TiCl_4$ (0.82 mL, 0.82 mmol, 1 M in $CH_2Cl_2$). The tube was heated at 50° C. in a CEM microwave reactor for 15 min. After cooling down, N,N'-methanediylidene bis(1,1,1-trimethylsilianamine) (0.15 g, 0.82 mmol) was added. The tube was heated at 60° C. in a CEM reactor for 15 min again. After cooling down, the mixture was quenched by addition of ice-water (2 mL) carefully with stirring. Brine (10 mL) was added, and the mixture was extracted with dichloromethane (3×10 mL). The combined organic layers were washed with brine (2×10 mL). The separated organic phase was dried over $Na_2SO_4$, filtered and concentrated in vacuo to give crude compound 119d (0.17 g, 106% crude yield) as a pale yellow solid, which was used directly in next step without further purification.

Procedure for Preparation of Compound 119

A solution of sodium methanolate in methanol (0.4 mL, 0.74 mmol, 10% in MeOH) was added to a flask was charged with compound 119d (0.17 g, 0.41 mmol, crude), anhydrous methanol (10 mL) and N-methyl hydroxylamine hydrochloride (41 mg, 0.49 mmol). The reaction mixture was stirred at ambient temperature overnight. The solvent was removed by evaporation in vacuo. Brine (20 mL) was added and the mixture was extracted with ethyl acetate (contained 10% methanol) (3×20 mL). The combined organic layers were washed with brine (2×10 mL). The separated organic phase was dried over $Na_2SO_4$, filtered and concentrated in vacuo and the resulting residue was purified by preparative RP-HPLC to give compound 119 (60 mg, 33%) with 99% purity based on LC-MS as a pale yellow solid. $^1H$ NMR: ($CD_3OD$, 300 MHz): δ 7.35-7.40 (m, 2H), 7.20-7.30 (m, 2H), 7.05-7.20 (m, 4H), 3.00-3.10 (s, 3H), 2.70-2.80 (d, J=20.8 Hz, 1H), 2.65-2.70 (d, J=20.8 Hz, 1H), 2.60-2.65 (d, J=10.0 Hz, 2H), 1.85-2.00 (m, 2H), 1.75-1.85 (m, 1H), 1.50-1.60 (m, 4H), 1.30-1.40 (m, 1H), 1.15-1.25 (m, 1H). LC-MS: $t_R$=2.54 min in 3 min chromatography, MS (ESI) m/z 439.13 $[M+H]^+$.

Procedure for Preparation of Compound 120

A mixture of compound 119 (30 mg, 0.053 mmol), 3-cyanophenylboronic acid (10 mg, 0.068 mmol), $Cs_2CO_3$ (0.2 mL, 0.40 mmol, 2M in water) and $Pd(PPh_3)_2Cl_2$ (1 mg, 0.0014 mmol) in 1,4-dioxane (5 mL) was stirred in at 80° C. for 3 h under a nitrogen atmosphere. After cooling down, brine (10 mL) was added and the mixture was extracted with ethyl acetate (3×10 mL). The combined organic layers were washed with brine (2×10 mL), dried over $Na_2SO_4$, filtered and concentrated in vacuo, the resulting crude product was purified by preparative TLC eluting with petroleum ether: ethyl acetate=2:1 and then by preparative RP-HPLC to give compound 120 (10.2 mg, 42%) with 99% purity based on LC-MS as a pale yellow solid. $^1H$ NMR: ($CD_3OD$ 300 MHz): δ 7.90-8.00 (m, 2H), 7.50-7.75 (m, 4H), 7.10-7.45 (m, 6H), 3.05-3.10 (s, 3H), 2.84-2.90 (d, J=20.8 Hz, 1H), 2.65-2.82 (d, J=20.8 Hz, 1H), 2.60-2.70 (d, J=10.0 Hz, 2H), 1.90-2.00 (m, 2H), 1.80-1.90 (m, 1H), 1.50-1.70 (m, 4H), 1.35-1.45 (m, 1H), 1.20-1.30 (m, 1H). LC-MS: $t_R$=2.53 min in 3 min chromatography, MS (ESI) m/z 463.3 $[M+H]^+$.

Example 86

Synthesis of Compound 121

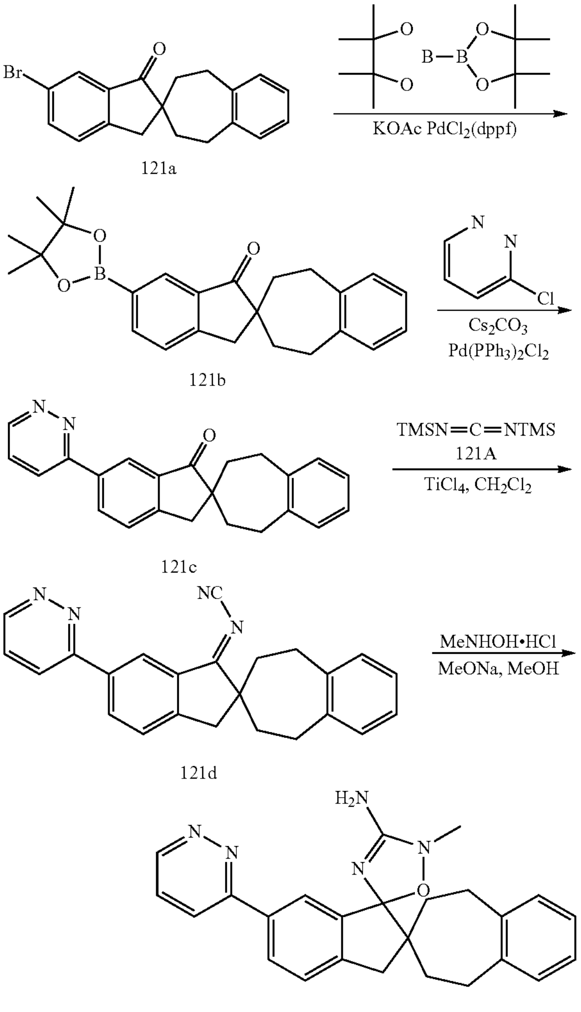

121a

121b

121c

121d

121

Procedure for Preparation of Compound 121b

The mixture of $Pd(dppf)Cl_2$ (54 mg), compound 121a (200 mg, 0.588 mmol), bispinacolatodiboron (164.3 mg, 0.647 mmol) and KOAc (167.1 mg, 1.71 mmol) in dioxane (3.5 mL) was placed into CEM microwave reactor and irradiated at 100° C. for 1 h under nitrogen. The solution was concentrated in vacuo, and the residue was purified by preparative TLC (petroleum:ethyl acetate, 10:1) to give compound 121b (120 mg, 53%) as a white solid. $^1H$-NMR ($CDCl_3$ 400 MHz): δ 8.17 (s, 1H), 7.64-7.97 (m, 1H), 7.41-7.43 (m, 1H), 7.06 (d, J=3.6 Hz, 4H), 3.10-3.16 (m, 2H), 2.93-2.99 (m, 2H), 2.80 (s, 2H), 1.79-1.87 (m, 4H), 1.55-1.61 (m, 2H); 1.17-1.23 (m, 12H).

Procedure for Preparation of Compound 121c

A solution containing compound 121b (60 mg, 0.155 mmol), 3-chloro-pyridazine (27 mg, 0.233 mmol) in dioxane (4 mL), and aqueous $Cs_2CO_3$ (2 M, 1.1 mL) was deoxygenated by bubbling a stream of nitrogen through the reaction mixture for 5 min. Then $PdCl_2(PPh_3)_2$ (11 mg) was added. The reaction vial was sealed and placed into CEM microwave reactor and irradiated at 120° C. for 15 min. After being cooled to room temperature, the mixture was diluted with EtOAc and filtered through a short Celite pad. The solution was concentrated in vacuo and the residue was purified by preparative HPLC (acidic) to afford compound 121c (15 mg, 29%) as a yellow solid.

Procedure for Preparation of Compound 121d

To a solution of compound 121c (15 mg, 0.044 mmol) in anhydrous $CH_2Cl_2$ (1 mL) was added a solution of $TiCl_4$ in $CH_2Cl_2$ (1 M, 0.44 mL, 0.44 mmol) at room temperature. The mixture placed into CEM microwave reactor and irradiated at 50° C. for 15 min, bistrimethylsilylcarbodiimide (18 mg, 0.10 mmol) was added. The resulting mixture was irradiated in microwave at 60° C. for 15 min and 70° C. for 1 h. After being cooled to room temperature, the mixture was poured into ice-water (2 mL), and extracted with $CH_2Cl_2$ (3×10 mL). The combined organic layers were washed with brine (10 mL), dried over $Na_2SO_4$, concentrated to give compound 121d (20 mg, 100%) as a yellow solid, which was used for next step without purification.

Procedure for Preparation of Compound 121

To a solution of N-methylhydroxylamine hydrochloride (4.6 mg, 0.055 mmol) in anhydrous MeOH (1.5 mL) was added NaOMe (10 wt % in MeOH, 0.028 mL, 0.05 mmol), and compound 121d (20 mg, 0.055 mmol). After being stirred at room temperature for 30 min, the solvent was removed under reduced pressure, and the residue was dissolved in $CH_2Cl_2$ (20 mL). The mixture was filtered and the filtrate was concentrated in vacuo to dryness. The residue was purified by preparative HPLC (basic) to give compound 121 (1.7 mg, 8%) as a white solid. LC-MS $t_R$=1.086 min in 2 min chromatography, MS (ESI) m/z 412 $[M+H]^+$, $^1H$ NMR ($CD_3OD$ 400 MHz): δ 9.02 (d, J=4.4 Hz, 4H), 8.06 (d, J=9.2 Hz, 1H), 7.92-7.94 (m, 2H), 7.67-7.71 (m, 1H), 7.36-7.38 (m, 1H), 6.97-7.04 (m, 4H), 3.03-3.11 (m, 3H), 2.91 (s, 3H), 2.60-2.65 (m, 2H), 1.89-1.91 (m, 2H), 1.64 (m, 1H), 1.48-1.54 (m, 2H).

Example 87

Synthesis of Compound 122

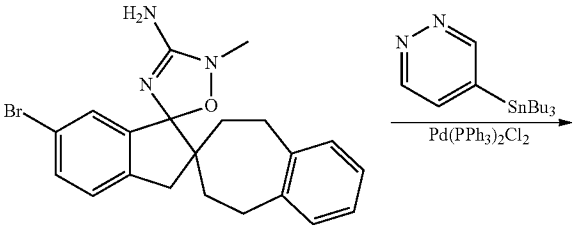

122a

-continued

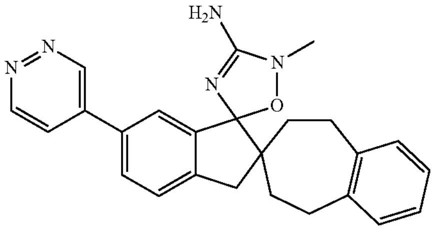

122

A solution containing 4-tributylstannanyl-pyridazine (78 mg, 0.213 mmol) and compound 1 (35 mg, 0.085 mmol) in dioxane (2 mL) was deoxygenated by bubbling a stream of nitrogen through the reaction mixture for 5 min. Then $PdCl_2(PPh_3)_2$ (6.1 mg) was added. The reaction vial was sealed and placed into CEM microwave reactor and irradiated at 125° C. for 45 min. After being cooled to room temperature, the mixture was partitioned between EtOAc (20 mL) and aqueous CsF (4 M, 20 mL), and the aqueous layer was extracted with EtOAc (3×20 mL). The combined organic layers were washed with brine (15 mL), dried over anhydrous $Na_2SO_4$, filtered, and concentrated in vacuo. The residue was purified by RP-HPLC (basic) to yield compound 122 (3.4 mg, 10%) as a white solid. LC-MS $t_R$=1.009 min in 2 min chromatography, MS (ESI) m/z 412 $[M+H]^+$; $^1H$ NMR ($CD_3OD$ 400 MHz): δ 9.54-9.63 (m, 1H), 9.27-9.32 (m, 1H), 7.95-8.11 (m, 3H), 7.64-7.66 (m, 1H), 7.13-7.17 (m, 4H), 3.27 (s, 3H), 3.12-3.25 (m, 3H), 2.72-3.06 (m, 2H), 2.11-2.20 (m, 1H), 1.87-2.05 (m, 1H), 1.58-1.74 (m, 3H).

Example 88

Synthesis of Compound 123

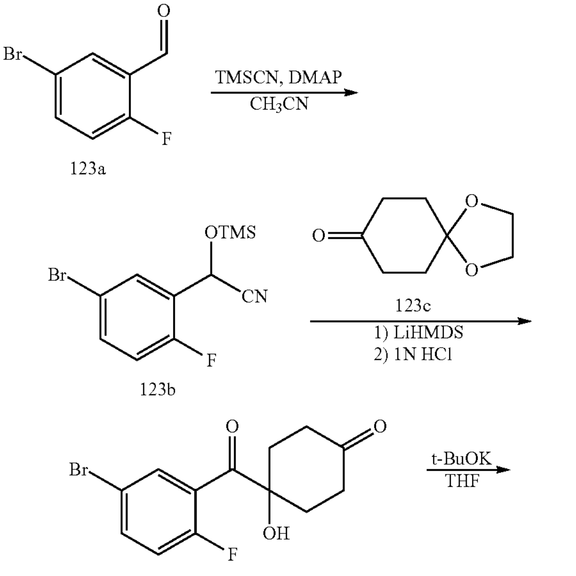

123a

123b

123d

-continued

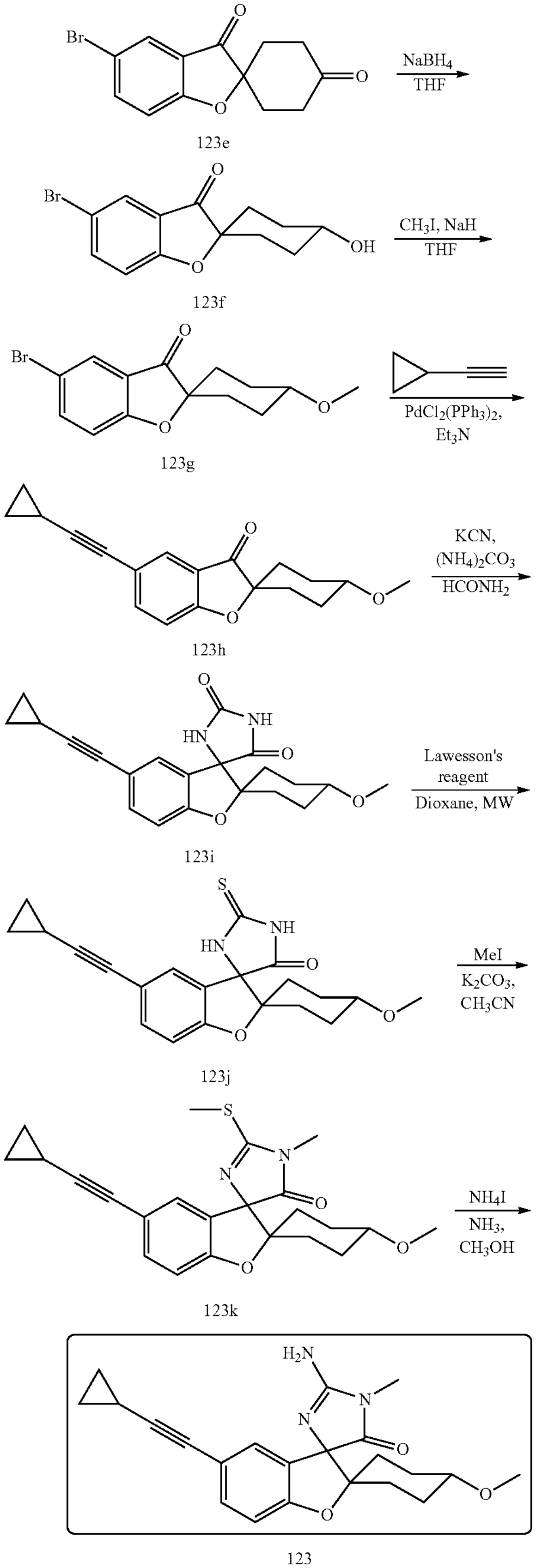

123e

123f

123g

123h

123i

123j

123k

123

Procedure for Preparation of Compound 123b

A flask was charged with compound 123a (30 g, 147.7 mmol), $CH_3CN$ (250 mL), TMSCN (18 g, 181.5 mmol) and DMAP (0.20 g, 1.7 mmol) in turn. The reaction mixture was stirred at ambient temperature for 4 h. The solvent was removed by evaporation in vacuo (lower than 25° C.) to give crude compound 123b (48.5 g, 101% crude yield) as a yellow oil, which was used directly in next step without further purification.

Procedure for Preparation of Compound 123d

To a solution of compound 123b (23.7 g, 78.48 mmol) in anhydrous THF (150 mL) was added LiHMDS (1.0 M in THF, 86.3 mL, 86.3 mmol) dropwise via an addition funnel at −78° C. under a nitrogen atmosphere. After 1.5 h, a solution of compound 123c (13.5 g, 86.3 mmol) in anhydrous THF was added dropwise via an addition funnel at −78° C. under a nitrogen atmosphere. After addition, the reaction mixture was stirred at −78° C. for 3 h. 1 N HCl (200 mL) was added via an addition funnel at −78° C. carefully. After that, the reaction mixture was allowed to warm to ambient temperature and kept at this temperature overnight. The mixture was separated and the aqueous layer was extracted with EtOAc (3×150 mL). The combined organic layers were washed with brine (2×200 mL), dried over $Na_2SO_4$, and concentrated in vacuo. The residue was purified by column chromatography over silica gel (eluent:petroleum ether:EtOAc=50:1 to 3:1) to give pure compound 123d (7.8 g, 31.6%) as a white solid. $^1H$ NMR ($CDCl_3$ 300 MHz): δ 7.55-7.65 (m, 1H), 7.50-7.55 (m, 1H), 7.05-7.15 (m, 1H), 2.70-2.90 (m, 2H), 2.20-2.50 (m, 4H), 2.05-2.15 (m, 2H).

Procedure for Preparation of Compound 123e

A suspension of compound 123d (14.5 g, 46 mmol) and t-BuOK (5.6 mg, 50 mmol) in THF (150 mL) was heated at 70° C. for 30 min in a CEM microwave reactor. The mixture was partitioned between EtOAc (150 mL) and water (100 mL). The aqueous layer was extracted with EtOAc (2×100 mL). The combined organic layer was washed with brine (100 mL) and concentrated in vacuo. The residue was purified by chromatography column on silica gel (eluent:petroleum ether:ethyl acetate from 50:1 to 20:1) to afford compound 123e (2.5 g, 20%) as a yellow solid.

Procedure for Preparation of Compound 123f

To a mixture of compound 123e (2.5 g, 8.47 mmol) in THF (70 mL) was added $NaBH_4$ (0.35 g, 9.3 mmol) at −78° C. under a nitrogen atmosphere. The mixture kept stirring at −78° C. for 15 min. The mixture was quenched by addition of MeOH (1 mL). The solvent was removed to afford crude compound 123f (2.5 g, 100% crude yield) as a yellow solid, which was used directly to the next step.

Procedure for Preparation of Compound 123g

To a round bottle flask were added compound 123f (2.5 g, 8.4 mmol) and NaH (0.40 g, 16.5 mmol) in THF (70 mL) at 0° C., and then $CH_3I$ (2.4 g, 6.5 mmol) was added. The mixture was warmed to 60° C. and stirred for 5 h. The mixture was cooled to 0° C. and quenched by addition of water (1 mL). The mixture was concentrated, the residue was purified by column chromatography on silica gel (eluent:petroleum ether:ethyl acetate=30:1) to afford compound 123g (1.6 g, 62%) as a yellow solid.

Procedure for Preparation of Compound 123h

An oven dried three-necked round bottom flask equipped with a condenser was charged with compound 123f (1.45 g, 4.7 mmol), $Et_3N$ (30 mL) and $Et_2NH$ (30 mL) under a nitrogen atmosphere. To this solution was added CuI (35 mg, 0.2 mmol), $PdCl_2(PPh_3)_2$ (50 mg, 0.07 mmol) under a nitrogen atmosphere. The system was degassed once again, then cyclopropyl acetylene (5 mL, excess) was added and the mixture was heated at 60° C. for 15 h. The solvent was evaporated and the residue was separated between EtOAc (50 mL) and water (30 mL). The aqueous layer was extracted with EtOAc (2×30 mL), and the combined organic layers were washed with brine (30 mL), dried over $Na_2SO_4$ and concentrated under reduced pressure to dryness. The crude product was purified by column chromatography on silica gel (eluent: petroleum ether:ethyl acetate=50:1 to 20:1) to afford compound 123h (630 mg, 40% purity) as a white solid.

Procedure for Preparation of Compound 123i

A steel autoclave was charged with a mixture of compound 123h (300 mg, 1 mmol), KCN (130 mg, 2 mmol), $(NH_4)_2CO_3$ (700 mg, 7 mmol) and formamide (20 mL). The mixture was heated at 100° C. for 72 h. The reaction mixture was then cooled and poured over ice. After acidification with concentrated HCl (20 mL), the mixture was filtered to collect the solid, which was dissolved in ethyl acetate (600 mL) and washed with water (2×150 mL). The separated organic phase was dried over $Na_2SO_4$ and concentrated to give compound 123i (170 mg, 35%) as a grey solid, which was used in next step without purification.

Procedure for Preparation of Compound 123j

A suspension of compound 123i (50 mg, 0.14 mmol) and Lawesson's Reagent (60 mg, 0.15 mmol) in anhydrous toluene (60 mL) was heated at 120° C. for one hour in a CEM microwave reactor. The mixture was concentrated in vacuo and the residue was purified by preparative TLC (eluent: petroleum ether:ethyl acetate=3:1) to give compound 123j (22 mg, 40%) as a white solid.

Procedure for Preparation of Compound 123k

To a solution of compound 123j (22 mg, 0.058 mmol) in DMF (3 mL) was added $K_2CO_3$ (15 mg, 0.1 mmol). After stirring for 5 min, MeI (10 mg, 0.11 mmol) was added and the reaction mixture was heated at 30° C. for 2 h. The mixture was filtered and the filtrate was concentrated in vacuo to give the residue, which was purified by preparative TLC (eluent:petroleum ether:ethyl acetate=3:1) to give compound 123k (10 mg, 40%) as a white solid.

Procedure for Preparation of Compound 123

A solution of compound 123k (10 mg, 0.024 mmol), $NH_4I$ (75 mg, 0.66 mmol) in a solution of $NH_3$-EtOH (2 mL, 5 N) was heated at 120° C. in a CEM microwave reactor for 2 h. After cooling, the mixture was concentrated in vacuo to give the residue, which was purified by preparative RP-HPLC to give compound 123 (0.9 mg, 10%) as a white solid. $^1H$ NMR ($CD_3OD$ 400 MHz): δ 7.35-7.37 (d, J=8.4 Hz, 1H), 7.32 (s, 1H), 6.88-6.90 (d, J=8.4 Hz, 1H), 3.38 (s, 3H), 3.25 (m, 4H), 2.24-2.27 (m, 1H), 1.99-2.08 (m, 3H), 1.51-1.68 (m, 4H), 1.42-1.46 (m, 1H), 0.86-0.87 (m, 2H), 0.68-0.69 (m, 2H). LCMS: $t_R$=1.62 min in 3 min chromatography, MS (ESI) m/z 380.2 $[M+H]^+$.

Example 89

Synthesis of Compound 124

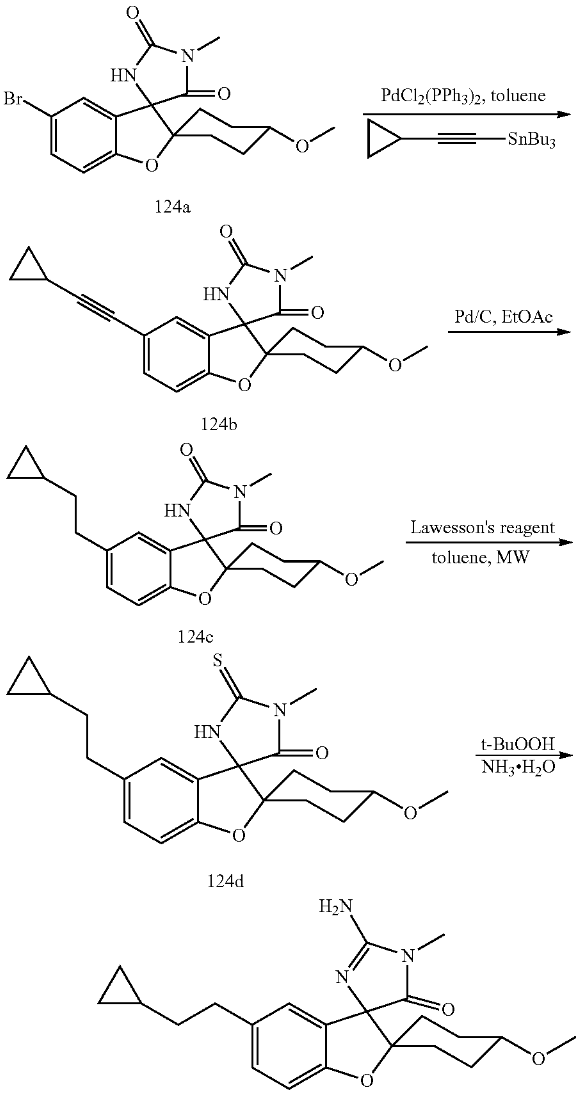

124a

124b

124c

124d

124

Procedure for Preparation of the Compound 124b

A suspension of compound 124a (250 mg, 0.6 mmol), tributyl-cyclopropylethynyl-stannane (1.3 g, 3 mmol) and $PdCl_2(PPh_3)_2$ (40 mg, 0.06 mmol) in anhydrous toluene (5 mL) was heated at 130° C. for 30 min in a CEM microwave reactor. The mixture was concentrated in vacuo, the residue was purified by preparative TLC on silica gel (petroleum ether:ethyl acetate=2:1) to give compound 124b (99 mg, 40%) as a yellow oil.

Procedure for Preparation of the Compound 124c

A solution of compound 124b (95 mg, 0.25 mmol) and Pd/C (10 mg) in EtOAc (10 mL) was stirred at 25° C. under $H_2$ (10 psi) atmosphere for 5 h. The mixture was filtered and the filtrate was concentrated in vacuo to give the residue which was purified by preparative TLC on silica gel (eluent:petroleum ether:ethyl acetate=2:1) to give compound 124c (77 mg, 80%) as a white solid.

Procedure for Preparation of the Compound 124d

A suspension of compound 124c (30 mg, 0.078 mmol) and Lawesson's Reagent (30 mg, 0.085 mmol) in anhydrous toluene (1 mL) was heated under 130° C. for 30 min in a CEM microwave reactor. The mixture was concentrated in vacuo, the residue was purified by preparative TLC on silica gel (petroleum ether:ethyl acetate=2:1) to give compound 124d (16 mg, 50%) as a white solid.

Procedure for Preparation of Compound 124

A solution of compound 124d (16 mg, 0.04 mmol), t-BuOOH (0.5 mL), $NH_3.H_2O$ (0.5 mL) in EtOH (2 mL) was stirred at 25° C. for 10 h. The mixture was concentrated in vacuo to give the residue, which was purified by preparative HPLC to give compound 124 (9 mg, 60%) as a white solid. $^1$H NMR ($CD_3OD$ 400 MHz): δ 7.15-7.20 (d, J=8.4 Hz, 1H), 7.05-7.10 (s, 1H), 6.80-6.85 (d, J=8.4 Hz, 1H), 3.35-3.40 (s, 3H), 3.20-3.25 (m, 1H), 3.15-3.20 (s, 3H), 2.60-2.70 (m, 2H), 2.20-2.30 (m, 1H), 1.90-2.10 (m, 3H), 1.60-1.70 (m, 3H), 1.40-1.55 (m, 3H), 0.60-0.70 (m, 1H), 0.35-0.45 (m, 2H), 0.05-0.10 (m, 2H). LCMS: $t_R$=1.86 min in 3 min chromatography, MS (ESI) m/z=384.2 $[M+H]^+$.

Example 90

Synthesis of Compound 125

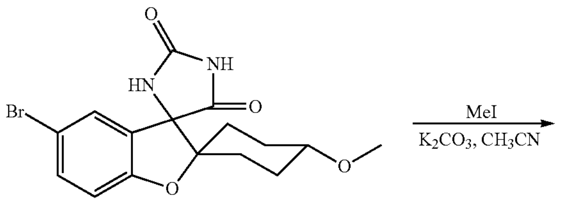

125a

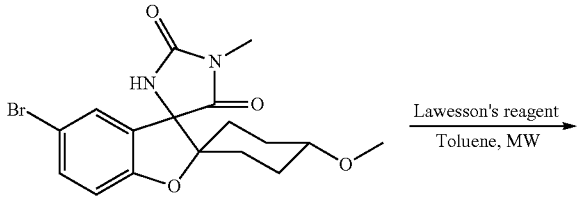

125b

-continued

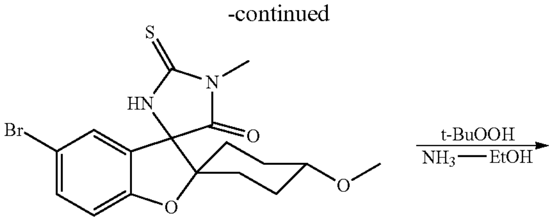

125c

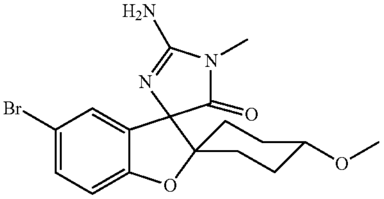

125

Procedure for Preparation of Compound 125b

To a solution of compound 125a (190 mg, 0.5 mmol) in DMF (5 mL) was added $K_2CO_3$ (138 mg, 1.0 mmol) and MeI (73.5 mg, 0.5 mmol), the mixture was stirred at room temperature for 3 h. $H_2O$ (10 mL) was added and the mixture was extracted with EtOAc (10 mL×3). The combined organic layers were washed with brine (30 mL), dried over $Na_2SO_4$ and concentrated to give compound 125b (170 mg, 86%) as a yellow solid. which was used in next step without further purification. LCMS: $t_R$=1.215 min in 2 min chromatography, MS (ESI) m/z=397 $[M+H]^+$.

Procedure for Preparation of Compound 125c

To a solution of compound 125b (170 mg, 0.43 mmol) in anhydrous toluene (5 mL) was added Lawesson's Reagent (173.8 mg, 0.43 mmol) under $N_2$, the mixture was stirred at 130° C. for 30 min in microwave, the solvent was removed in vacuo to give the crude product which was purified by preparative TLC on silica gel eluting with hexane:EtOAc=3:1 to afford compound 125c (110 mg, 62%) as a white solid. LCMS: $t_R$=1.345 min in 2 min chromatography, MS (ESI) m/z=411 $[M+H]^+$.

Procedure for Preparation of Compound 125

To a solution of compound 125c (110 mg, 0.26 mmol) in EtOH (10 mL) was added t-BuOOH (1 mL) and $NH_3$—$H_2O$ (3 mL) under $N_2$, the mixture was stirred at room temperature overnight. The solvent was removed in vacuo to give the crude product which was purified by preparative TLC on silica gel eluting with dichloromethane:methanol=10:1 to afford compound 125 (60 mg, 57%) as a white solid. LCMS: $t_R$=1.018 min in 2 min chromatography, MS (ESI) m/z=394.0 $[M+H]^+$.

Example 91

Synthesis of Compound 126

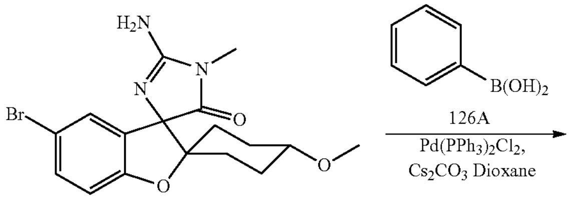

125

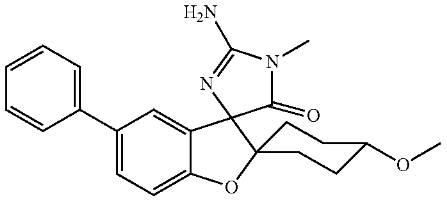

126

To a solution of compound 125 (20 mg, 0.05 mmol) in 1,4-dioxane (2 mL) was added compound 126A (11.1 mg, 0.076 mmol), $Cs_2CO_3$ (2 N, 0.2 mL) and $Pd(PPh_3)_2Cl_2$ (5 mg) under nitrogen, the mixture was stirred at 120° C. in a CEM microwave reactor for 15 min, LCMS showed the complete consumption of compound 125. Water (2 mL) was added and the precipitate was filtered off through a pad of celite, and was washed with EtOAc (10 mL×3). The combined organic fractions were washed with brine (20 mL), dried over $Na_2SO_4$ and concentrated to give the crude product which was purified by preparative TLC on silica gel eluting with dichloromethane: methanol=10:1 followed by preparative HPLC to afford compound 126 (3.0 mg, 15%) as a white solid. $^1H$ NMR ($CD_3OD$ 400 MHz): δ 7.67 (d, J=7.8 Hz, 2H), 7.61 (d, J=7.6 Hz, 2H), 7.55 (d, J=7.6 Hz, 2H), 7.33 (d, J=7.6 Hz, 1H), 7.05 (d, J=8.4 Hz, 1H) 3.40 (s, 3H), 3.33-3.27 (m, 1H), 3.25-3.15 (s, 3H), 2.32-2.29 (m, 1H), 2.29-2.05 (m, 3H), 1.71-1.56 (m, 4H). LCMS: $t_R$=1.018 min in 2 min chromatography, MS (ESI) m/z=394.0 $[M+H]^+$.

Example 92

Synthesis of Compound 127

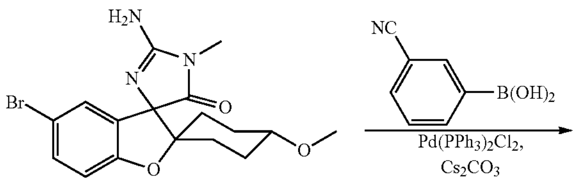

125

-continued

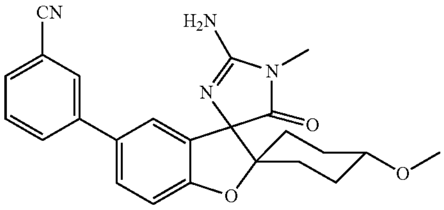

127

A suspension of compound 125 (10 mg, 0.03 mmol), 3-cyanophenylboronic acid (7 mg, 0.03 mmol), $PdCl_2(PPh_3)_2$ (1 mg, 0.003 mmol) and $Cs_2CO_3$ (0.1 mL, 2 N in water) in 1,4-dioxane (2 mL) was heated under 120° C. for 15 min in a CEM microwave reactor. The mixture was concentrated in vacuo, the residue was purified by preparative HPLC to give compound 127 (5.8 mg, 60%) as a white solid. $^1H$ NMR ($CD_3OD$ 400 MHz): δ 7.98-8.05 (s, 1H), 7.95-8.00 (d, J=2.0 Hz, 1H), 7.55-7.80 (m, 4H), 7.05-7.10 (s, 1H), 3.40 (s, 3H), 3.20-3.35 (m, 4H), 2.20-2.30 (m, 1H), 2.00-2.10 (m, 3H), 1.55-1.80 (m, 4H). LCMS: $t_R$=1.60 min in 3 min chromatography, MS (ESI) m/z=416 $[M+H]^+$.

Example 93

Synthesis of Compound 128

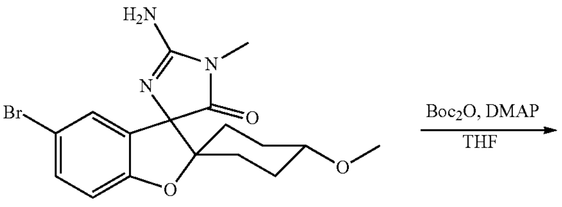

125

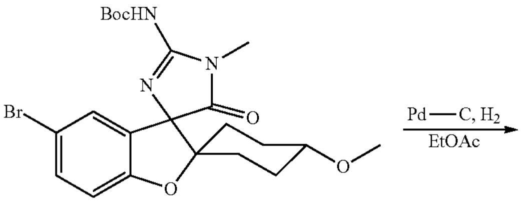

128a

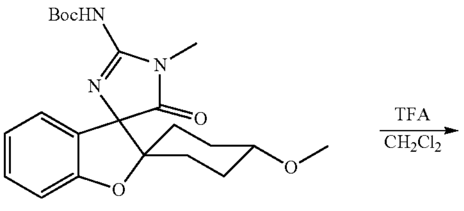

128b

-continued

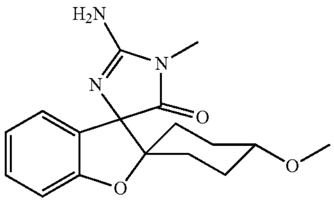

128

Procedure for Preparation of the Compound 128a

To a solution of compound 125 (45 mg, 0.11 mmol) in THF (3 mL) was added $(Boc)_2O$ (50 mg, 0.23 mmol) and DMAP (2 mg, 0.011 mmol). The reaction mixture was stirred at 30° C. for 1 h. The mixture was concentrated in vacuo to give the residue, which was purified by preparative TLC on silica gel (petroleum ether:ethyl acetate=2:1) to give compound 128a (46 mg, 70%) as a colorless oil.

Procedure for Preparation of the Compound 128b

To a solution of compound 128a (10 mg, 0.02 mmol) in EtOAc (3 mL) was added Pd/C (2 mg). The reaction mixture was stirred at 30° C. at $H_2$ atmosphere (1 atm) condition overnight. The mixture was filtered and concentrated in vacuo to give compound 128b (10 mg, 100% crude yield) as a colorless oil.

Procedure for Preparation of Compound 128

To a solution of compound 128b (10 mg, 0.024 mmol) in $CH_2Cl_2$ (2 mL) was added TFA (1 mL). After stirring for 10 min, the mixture was concentrated in vacuo to give the residue, which was purified by preparative HPLC to give compound 128 (1.6 mg, 20%) as a white solid. $^1H$ NMR ($CD_3OD$ 400 MHz): δ 7.35-7.40 (t, J=9.2 Hz, 1H), 7.25-7.30 (d, J=10.4 Hz, 1H), 7.40-7.55 (m, 2H), 3.35-3.40 (s, 3H), 3.20-3.30 (m, 4H), 2.20-2.30 (m, 1H), 1.95-2.05 (m, 3H), 1.50-1.75 (m, 4H). LCMS: $t_R$=0.792 min in 2 min chromatography, MS (ESI) m/z=316.1 $[M+H]^+$

Example 94

Synthesis of Compound 129

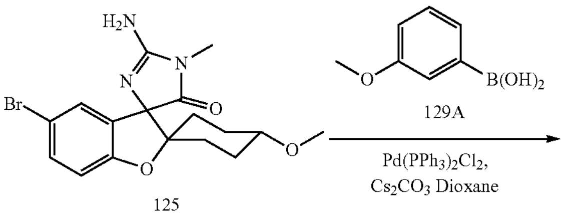

125

129A

-continued

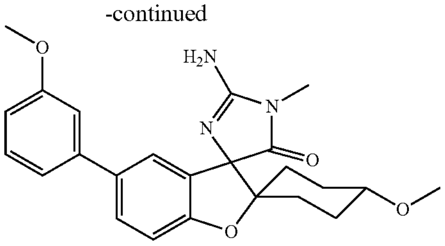

129

Synthesized by a route analogously to compound 126 from compound 125 (20 mg, 0.05 mol) and purified by preparative TLC on silica gel eluting with petroleum ether:ethyl acetate=1:1 to give compound 129 (2.5 mg, 11%) as a white solid. $^1H$ NMR ($CD_3OD$ 400 MHz): δ 7.67 (d, J=8.4 Hz, 1H), 7.64 (s, 1H), 7.35 (d, J=8.0 Hz, 1H), 7.20 (d, J=8.0 Hz, 2H), 7.02 (d, J=8.4 Hz, 1H), 6.90 (d, J=8.4 Hz, 1H), 3.84 (s, 3H), 3.40 (s, 3H), 3.33-3.27 (m, 1H), 3.27-3.15 (s, 3H), 2.40-2.29 (m, 1H), 2.27-2.05 (m, 3H), 1.70-1.56 (m, 4H). LCMS: $t_R$=1.116 min in 2 min chromatography, MS (ESI) m/z=422.1 $[M+H]^+$.

Example 95

Synthesis of Compound 130

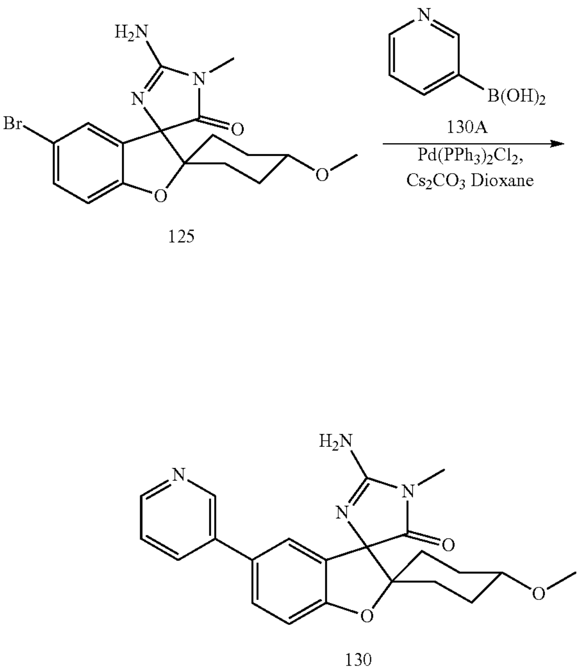

125

130A

130

Synthesized by a route analogously to compound 126 from compound 125 (20 mg, 0.05 mol) and purified by preparative TLC on silica gel eluting with dichloromethane:methanol=10:1 followed by preparative HPLC to afford compound 130 (2.1 mg, 11%) as a white solid. $^1H$ NMR ($CD_3OD$ 400 MHz): δ 8.91 (s, 1H), 8.70 (s, 1H), 8.38 (d, J=8.0 Hz, 1H), 7.81 (d, J=7.2 Hz, 3H), 7.16 (d, J=8.8 Hz, 1H), 3.40 (s, 3H), 3.34-3.27 (m, 1H), 3.28-3.15 (s, 3H), 2.45-2.24 (m, 1H), 2.25-2.06 (m, 3H), 1.72-1.57 (m, 4H); LCMS: $t_R$=0.846 min in 2 min chromatography, MS (ESI) m/z=393.1 $[M+H]^+$.

Example 96

Synthesis of Compound 131

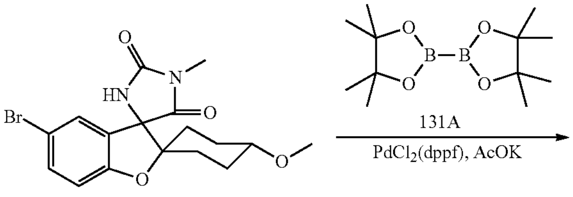

131a

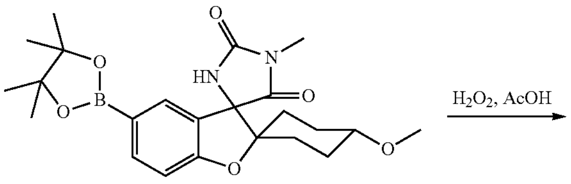

131b

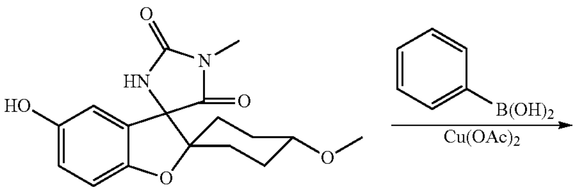

131c

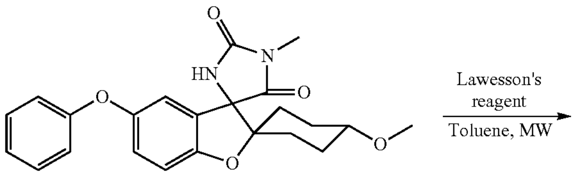

131d

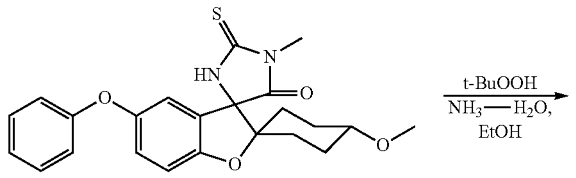

131e

-continued

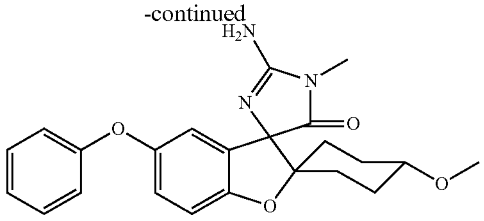

131

Procedure for Preparation of Compound 131b

A suspension of compound 131a (270 mg, 0.68 mmol), compound 131A (190 mg, 0.75 mmol), $PdCl_2$(dppf) (60 mg, 0.08 mmol) and KOAc (200 mg, 2 mmol) in anhydrous 1,4-dioxane (5 mL) was heated at 100° C. for 60 min in a CEM microwave reactor. The mixture was concentrated in vacuo and the residue was purified by column on silica gel (eluent: petroleum ether:ethyl acetate=3:1) to give compound 131b (300 mg, yield 88%, 67% purity) as a yellow solid.

Procedure for Preparation of Compound 131c

To a solution of compound 131b (300 mg, 0.7 mmol) in THF (10 mL) was added AcOH (1 mL) and $H_2O_2$ (3 mL). The reaction mixture was stirred at 30° C. for 10 h. The mixture was quenched with saturated $NaHSO_3$ (6 mL) and then balanced between EtOAc (20 mL×2) and water (10 mL). The organic layers were collected and concentrated in vacuo to give the residue, which was purified by preparative TLC on silica gel (eluent:petroleum ether:ethyl acetate=1:2) to give compound 131c (123 mg, 40% for two steps) as a colorless oil.

Procedure for Preparation of Compound 131d

To a solution of compound 131c (30 mg, 0.09 mmol) in $CH_2Cl_2$ (8 mL) was added phenyl boronic acid (14 mg, 0.11 mmol), $Cu(OAc)_2$ (36 mg, 0.18 mmol) and $EtN_3$ (18 mg, 0.18 mmol). The reaction mixture was stirred in the open air at 30° C. for 10 h. The precipitate was filtered off and washed with ethyl acetate (10 mL×2), the filtrate was concentrated in vacuo to give the residue, which was purified by preparative TLC on silica gel (eluent:petroleum ether:ethyl acetate=2:1) to give compound 131d (15 mg, 50%) as a white solid.

Procedure for Preparation of Compound 131e

A suspension of compound 131d (13 mg, 0.03 mmol) and Lawesson's Reagent (14 mg, 0.03 mmol) in anhydrous toluene (1 mL) was heated at 130° C. for 40 min in a CEM microwave reactor. The mixture was concentrated in vacuo, the residue was purified by preparative TLC on silica gel (eluent:petroleum ether:ethyl acetate=5:1) to give compound 131e (8 mg, 65%) as a white solid.

Procedure for Preparation of Compound 131

A solution of compound 131e (8 mg, 0.02 mmol), t-BuOOH (0.2 mL), $NH_3$—$H_2O$ (0.3 mL) in EtOH (2 mL) was stirred at 30° C. for 10 h. Then, the mixture was concentrated in vacuo to give the residue, which was purified by preparative HPLC to give compound 131 (2.0 mg, 25%) as a white solid. $^1H$ NMR ($CD_3OD$ 400 MHz): δ 7.35-7.45 (m, 2H,), 7.00-7.10 (m, 1H), 6.85-6.95 (m, 4H), 6.63 (s, 1H), 3.35 (s, 3H), 3.20-3.30 (m, 1H), 3.08 (s, 3H), 2.25-2.30 (m, 1H), 1.90-2.10 (m, 3H), 1.45-1.70 (m, 3H), 1.30-1.45 (m, 1H). LCMS: $t_R$=1.66 min in 3 min chromatography, MS (ESI) m/z=408.2 $[M+H]^+$.

Example 97

Synthesis of Compound 132

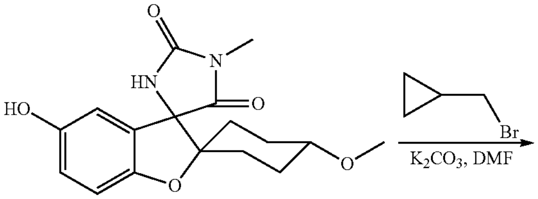

132a

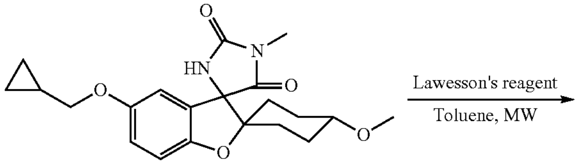

132b

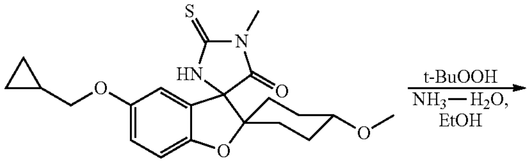

132c

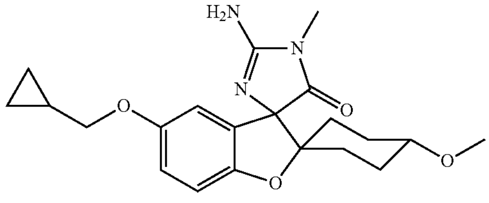

132

Procedure for Preparation of Compound 132b

To a solution of compound 132a (35 mg, 0.1 mmol) in DMF (3 mL) was added $K_2CO_3$ (40 mg, 0.3 mmol). After stirring for 5 min, bromomethyl-cyclopropane (20 mg, 0.12 mmol) was added and the reaction mixture was stirred at 25° C. for 10 h. The mixture was filtered and the filtrate was concentrated in vacuo to give the residue, which was purified by preparative TLC on silica gel (eluent:petroleum ether: ethyl acetate=2:1) to give compound 132b (13 mg, 35%) as a white solid.

Procedure for Preparation of Compound 132c

A suspension of compound 132b (13 mg, 0.03 mmol) and Lawesson's Reagent (13 mg, 0.04 mmol) in anhydrous toluene (1 mL) was heated at 130° C. for 40 min in a CEM microwave reactor. The mixture was concentrated in vacuo, the residue was purified by preparative TLC on silica gel (eluent:petroleum ether:ethyl acetate=2:1) to give compound 132c (7 mg, 45%) as a white solid.

Procedure for Preparation of Compound 132

A solution of compound 132c (7 mg, 0.017 mmol), t-BuOOH (0.5 mL), $NH_3.H_2O$ (0.5 mL) in EtOH (2 mL) was stirred at 30° C. for 10 h. The mixture was concentrated in vacuum to give the residue, which was purified by preparative HPLC to give compound 132 (2.9 mg, 40%) as a white solid. $^1H$ NMR ($CD_3OD$ 400 MHz): δ 6.60-6.75 (m, 2H), 6.40-6.45 (s, 1H), 3.50-3.55 (d, J=6.9 Hz, 2H), 3.20-3.30 (s, 3H), 3.05-3.15 (m, 1H), 2.95-3.00 (s, 3H), 2.05-2.10 (d, J=13.8 Hz, 1H), 1.80-1.90 (m, 3H), 1.40-1.60 (m, 2H), 1.15-1.30 (m, 2H), 1.00-1.10 (m, 1H), 0.40-0.50 (m, 2H), 0.15-0.25 (m, 2H). LCMS: $t_R$=1.56 min in 3 min chromatography, MS (ESI) m/z=386.1 $[M+H]^+$.

Example 98

Synthesis of Compound 133

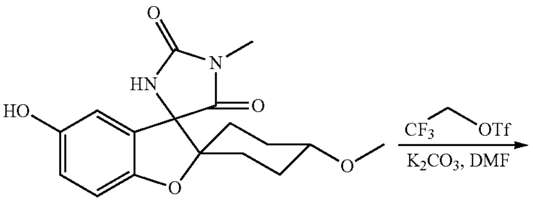

133a

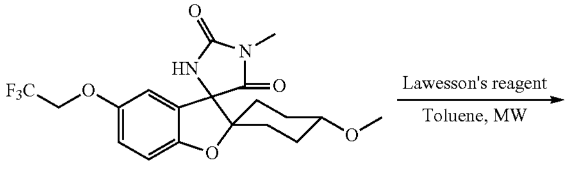

133b

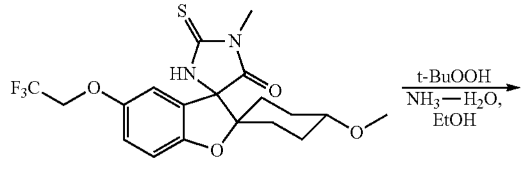

133c

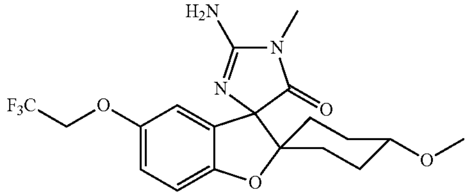

133

Procedure for Preparation of Compound 133b

To a solution of compound 133a (35 mg, 0.1 mmol) in DMF (3 mL) was added $K_2CO_3$ (40 mg, 0.3 mmol). After stirring for 5 min, trifluoro-methanesulfonic acid 2,2,2-trifluoro-ethyl ester (23 mg, 0.13 mmol) was added and the reaction mixture was stirred at 25° C. for 10 h. The mixture was filtered and filtrate was concentrated in vacuo to give the residue, which was purified by preparative TLC on silica gel (eluent:petroleum ether:ethyl acetate=2:1) to give compound 133b (14 mg, 35%) as a white solid.

Procedure for Preparation of Compound 133c

A suspension of compound 133b (14 mg, 0.03 mmol) and Lawesson's Reagent (14 mg, 0.03 mmol) in anhydrous toluene (1 mL) was heated at 130° C. for 40 min in a CEM microwave reactor. The mixture was concentrated in vacuo and the residue was purified by preparative TLC on silica gel (eluent:petroleum ether:ethyl acetate=2:1) to give compound 133c (8 mg, 55%) as a white solid.

Procedure for Preparation of Compound 133

A solution of compound 133c (8 mg, 0.018 mmol), t-BuOOH (0.5 mL), $NH_3.H_2O$ (0.5 mL) in EtOH (1 mL) was stirred at 30° C. for 10 h. Then, the mixture was concentrated in vacuo to give the residue, which was purified by preparative HPLC to give compound 133 (7.0 mg, 75%) as a white solid. $^1H$ NMR ($CD_3OD$ 400 MHz): δ 6.75-6.85 (d, J=8.2 Hz, 1H), 6.65-6.70 (d, J=8.8 Hz, 1H), 6.55-6.60 (s, 1H), 4.25-4.35 (m, 2H), 3.20-3.30 (s, 3H), 3.05-3.15 (m, 1H), 2.95-3.00 (s, 3H), 2.05-2.10 (d, J=13.8 Hz, 1H), 1.80-1.95 (m, 3H), 1.40-1.60 (m, 3H), 1.15-1.30 (m, 1H). LCMS: $t_R$=1.57 min in 3 min chromatography, MS (ESI) m/z=415.1 $[M+H]^+$.

Example I-0

Synthesis of (1r,4r)-6'-bromo-4-methoxyspiro[cyclohexane-1,2'-inden]-1'(3'H)-one A. Synthesis of 6'-bromospiro[cyclohexane-1,2'-indene]-1',4(3'H)-dione (4)—Method 1

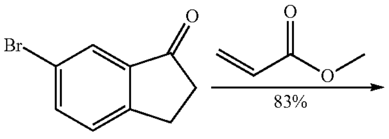

1

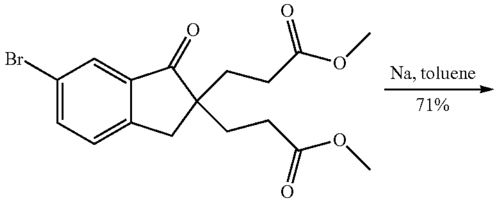

2

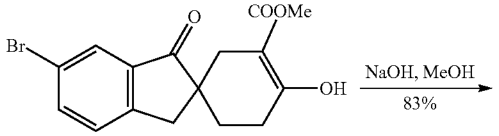

3

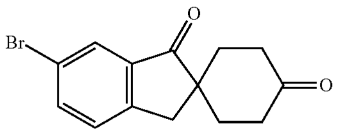

4

Procedure for Preparation of Compound 2

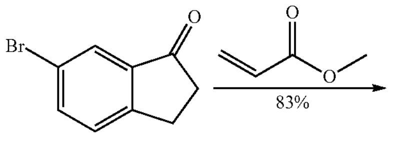

1

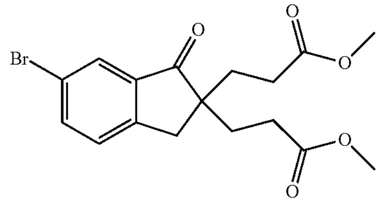

2

Under $N_2$, triton B (benzyl(tri-methyl)-ammonium hydroxide, 40% in MeOH, 2.48 mL) was added to a solution of 6-bromo-indan-1-one (1) (26.1 g, 0.124 mol) in toluene (200 mL), and the mixture was stirred at 50° C. for 10 minutes. Acrylic methyl ester (31 mL, 0.286 mol) was added at 50° C., and the mixture was stirred at 50° C. overnight. After being cooled to room temperature, the mixture was poured into water (150 mL), and extracted with DCM (100 mL×4). The combined organic phases were dried over $Na_2SO_4$, and evaporated, and purified by column chromatography on silica gel (PE/EA=10:1) to give compound 2 (39 g, 83%) as a yellow oil. $^1H$ NMR ($CDCl_3$ 400 MHz): δ 7.75-7.81 (s, 1H), 7.55-7.58 (d, 1H), 7.22-7.28 (d, 1H), 3.51-3.55 (s, 3H), 2.85-2.99 (s, 2H), 2.10-2.25 (m, 4H), 1.80-1.95 (m, 4H).

Procedure for Preparation of Compound 3

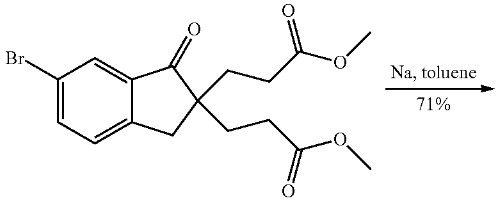

2

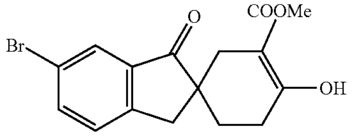

3

A solution of compound 2 (34 g, 88.7 mmol) in toluene (400 mL) was added dropwise to a flask containing Na (2.24 g, 97.6 mmol) and dry toluene (100 mL) at refluxing at 120° C. The reaction mixture was heated at 120° C. for 28 hours, cooled to room temperature, and poured into a mixture $H_2O$ (370 mL) and 4N HCl solution (37 mL) to afford a white suspension. This mixture was extracted with AcOEt (100 mL×4), evaporated, and purified by column chromatography on silica gel (PE/EA=10:1) to give compound 3 (22.11 g, 71%) as white solid. $^1H$ NMR: ($CDCl_3$ 400 MHZ): δ12.1 (s, 1H), 7.82-7.85 (s, 1H), 7.61-7.65 (d, 1H), 7.22-7.25 (d, 1H), 3.60-3.65 (s, 3H), 2.91-2.85 (d, 2H), 2.35-2.50 (m, 3H), 2.10-2.15 (d, 1H), 1.90-2.01 (m, 1H), 1.50-1.52 (m, 1H).

Procedure for Preparation of Compound 4

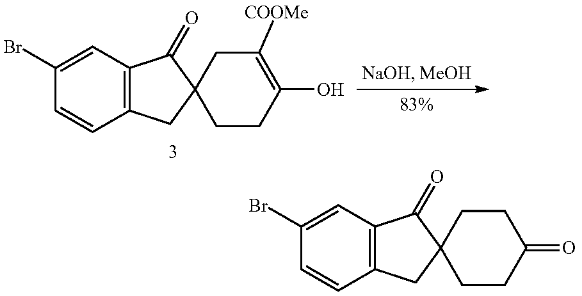

3

4

To a suspension of compound 3 (22.1 g, 63.0 mmol) in MeOH (221 mL) was added a solution of NaOH (10.20 g, 0.255 mol) in $H_2O$ (331 mL) at room temperature. The reaction mixture was heated at 60° C. overnight. The solvent was removed in vacuo, and extracted with DCM (250 mL×3). The combined organic layer was dried over $Na_2SO_4$ and concentrated in vacuo to afford compound 4 (15.33 g, 83%) as a white solid, which was used for the next step directly without purification. $^1H$ NMR (300 MHz, $CDCl_3$) δ 7.84 (s, 1H), 7.60-7.71 (d, 1H), 7.25-7.36 (d, 1H), 3.11 (s, 2H), 2.60-2.71 (m, 2H), 2.35-2.46 (m, 2H), 2.10-2.23 (m, 2H), 1.75-1.87 (m, 2H).

Note: 1. this reaction was completed under reflux at 120° C. (oil bath) for 2 h. 2. Compound 3 couldn't be dissolved in MeOH completely, which didn't affect the reaction.

After the reaction was completed, the reaction mixture was a suspension.

B. Synthesis of 6'-bromospiro[cyclohexane-1,2'-indene]-1',4(3'H)-dione (4)—Method 2

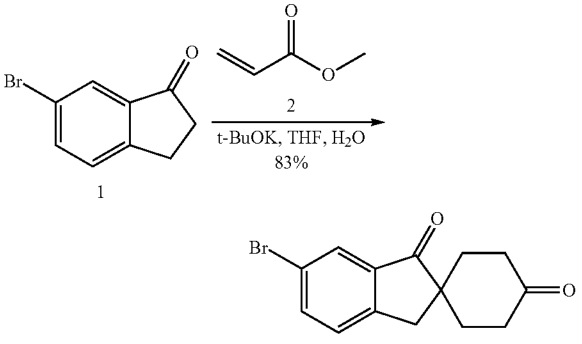

1

4

To a solution of compound 1 (20 g, 95 mmol) and methyl acrylate (18 g, 201 mmol) in anhydrous THF (200 mL) was added t-BuOK (16 g, 114 mmol) portionwise at room temperature. The reaction mixture was stirred at room temperature for 1 hour. Water (400 mL) and KOH (5.32 g, 95 mmol) were added. The resulting mixture was heated to reflux overnight. 3 N HCl (150 mL) was added and extracted with $CH_2Cl_2$ (500 mL×2). The organic layers were washed with $NaHCO_3$ (150 mL), brine (150 mL) and dried over $Na_2SO_4$, concentrated in vacuo to give compound 4 as a grey solid (23 g, 83% yield), which was used for next step without purification. $^1H$ NMR (300 MHz, $CDCl_3$) δ 7.84 (s, 1H), 7.60-7.71 (d, 1H), 7.25-7.36 (d, 1H), 3.11 (s, 2H), 2.60-2.71 (m, 2H), 2.35-2.46 (m, 2H), 2.10-2.23 (m, 2H), 1.75-1.87 (m, 2H).

C. Synthesis of (1r,4r)-6'-bromo-4-methoxyspiro[cyclohexane-1,2'-inden]-1'(3'H)-one (6)

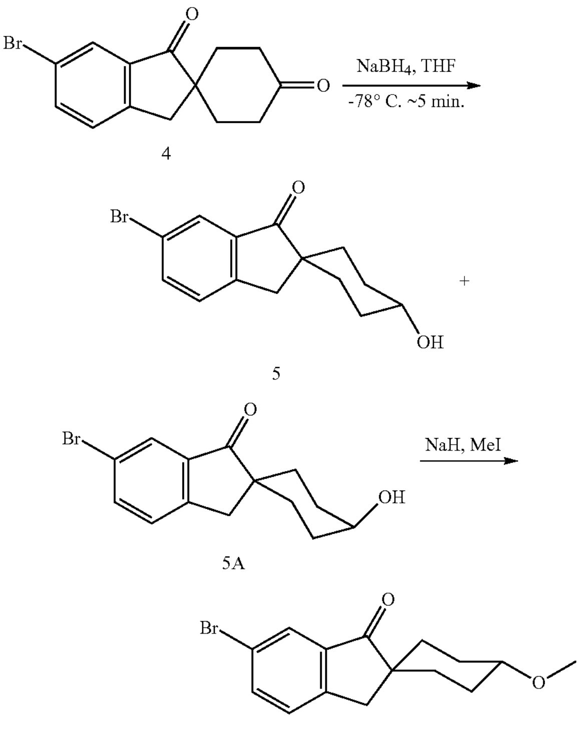

4

5

5A

6

Procedure for Preparation of Compound 5

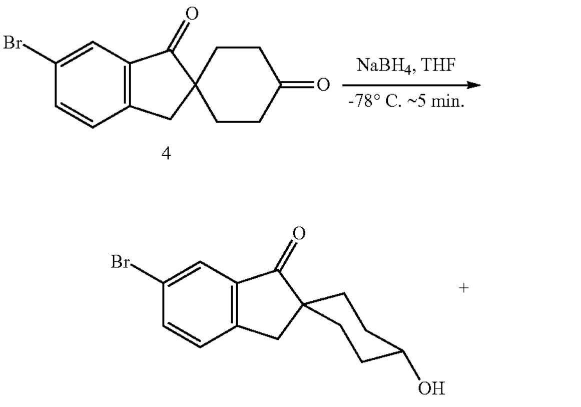

4

5

-continued

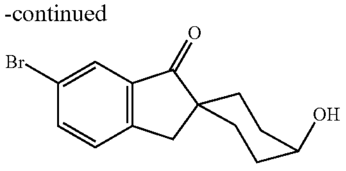

5A

6'-bromospiro[cyclohexane-1,2'-indene]-1',4 (3'H)-dione (4) (19 g, 62.9 mmol, 97% purity in HPLC) was dissolved in anhydrous THF (600 mL) and was cooled to −78° C. $NaBH_4$ (0.951 g, 25.1 mmol) was added portionwise to the reaction mixture at −78° C. No more than 5 min, TLC (Hexane: EtOAc=1:1) showed the starting material 4 was consumed. $CH_3OH$ (140 mL) and EtOAc (280 mL) was added and the resulting mixture was allowed to warm to room temperature. Water (280 mL) was added and the solution was concentrated in vacuo to remove THF and $CH_3OH$. EtOAc (200 mL) was added to dissolve the residue. The organic layer was separated and the aqueous layer was extracted with EtOAc (3×100 mL). The combined organic layers were washed with brine (600 mL), dried over $Na_2SO_4$ and concentrated in vacuo to give the mixture of compound 5 and compound 5A (21 g), which was used for the next step without purification.

Procedure for preparation of (1r,4r)-6'-bromo-4-methoxyspiro[cyclohexane-1,2'-inden]-1'(3'H)-one

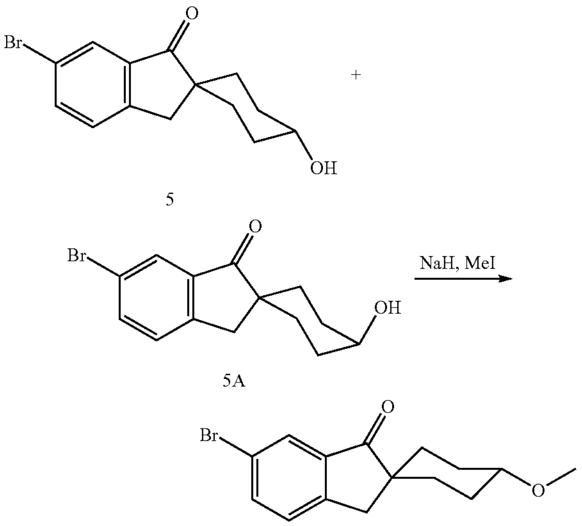

5

5A

6

The mixture of compound 5 and compound 5A (21 g, 71.1 mmol) was dissolved in anhydrous THF (300 mL) and was cooled to 0° C. NaH (11.38 g, 474 mmol, 60% in mineral oil) was added portionwise to the reaction mixture at 0° C. After being stirred for 15 min at the same temperature, MeI (121.2 g, 854 mmol) was added dropwise to the reaction mixture at 0° C. The reaction mixture was stirred at 0° C. for 1 h and stirred at room temperature overnight. TLC (Hexane: EtOAc=5:1) showed the starting material was consumed. EtOH (200 mL) and brine (400 mL) was added. The organic layer was separated and the aqueous layer was extracted with EtOAc (3×200 mL). The combined organic layers were washed with brine (100 mL), dried over $Na_2SO_4$ and concentrated in vacuo to give crude product (31 g), which was purified by column chromatography on silica gel (Hexane: EtOAc=100:1~30:1) to give pure 1r,4r)-6'-bromo-4-methoxyspiro[cyclohexane-1,2'-inden]-1'(3'H)-one (6) (9.43 g, 62%) as a yellowish solid. LCMS: $t_R$=4.749 min in 7 min chromatography MS (ESI) m/z 309.1 $[M+H]^+$; $^1H$ NMR ($CDCl_3$ 400 MHz): δ 7.87 (s, 1H), 7.69 (d, J=8.0 Hz, 1H), 7.34 (d, J=8.0 Hz, 1H), 3.39 (s, 3H), 3.27 (m, 1H), 2.97 (s, 2H), 2.16 (m, 2H), 1.76 (m, 2H), 1.52 (m, 2H), 1.36 (m, 2H).

Example I-1

Synthesis of hydantoin—Method 1

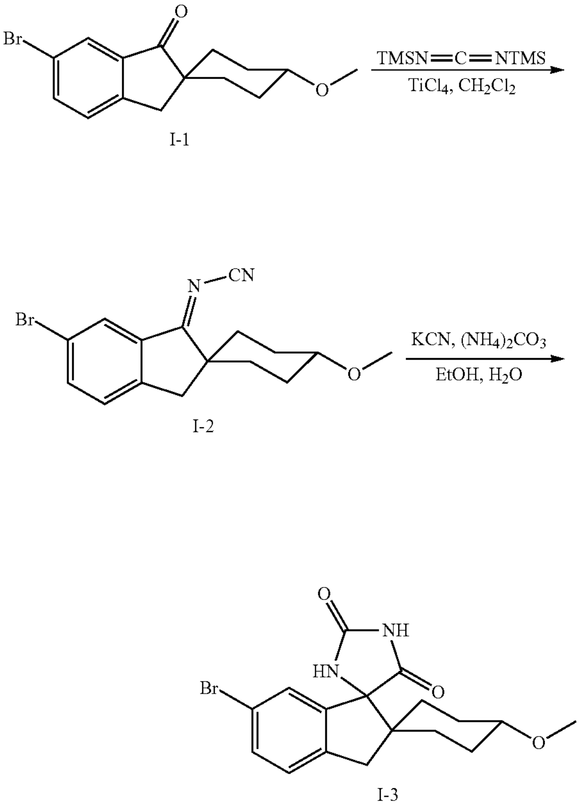

I-1

I-2

I-3

To a solution of compound I-1 (3.1 g, 10 mmol) in $CH_2Cl_2$ (100 mL) was added $TiCl_4$ (22 mL, 22 mmol, 1 M in $CH_2Cl_2$) under a nitrogen atmosphere. After stirring at room temperature for 1 h, bis-trimethylsilylcarbodiimide (4.5 mL, 20 mmol) was added. After addition, the reaction mixture was stirred at room temperature overnight. Then the mixture was poured into ~200 g crashed ice, the organic layer was separated and the aqueous layer was extracted with CH2C12, the combined organic layers were dried over anhydrous MgSO4, filtered and evaporated, the crude product was used directly for the next step without purification. The crude product of compound I-2 (3.3 g, 10 mmol), KCN (2.6 g, 40 mmol), $(NH_4)_2CO_3$ (9.7 g, 100 mmol) were dissolved in EtOH (20 mL) and $H_2O$ (20 mL). After heated at 75° C. in a steel autoclave overnight, the reaction mixture was cooled to room temperature and poured into $H_2O$. The precipitate was collected by filtration then washed with $H_2O$ and EtOH. The yellow solid obtained was dried under vacuum and used in next step directly without purification.

Example I-2

Synthesis of Acylguanidine I-6

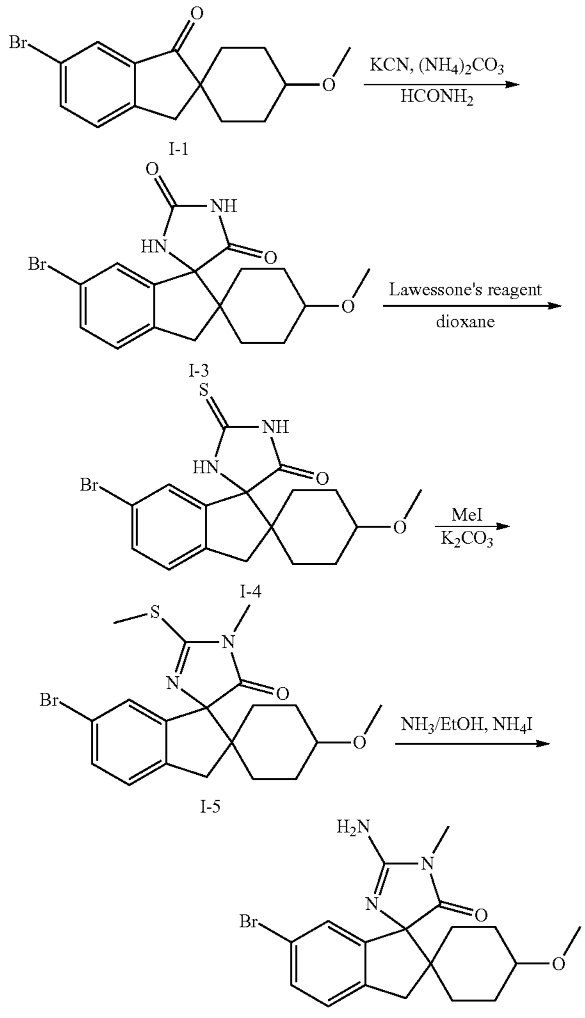

I-1, I-3, I-4, I-5, I-6

Procedure for Preparation of Hydantoin I-3—Method 2

A steel autoclave was charged with a mixture of 6'-bromo-4-methoxyspiro[cyclohexane-1,2'-inden]-1'(3'H)-one (700 mg, 2.27 mmol), KCN (294 mg, 4.53 mmol), $(NH_4)_2CO_3$ (1.63 g, 16.98 mmol) and formamide (25 mL). The mixture was heated at 80° C. for 72 h. The reaction mixture was then cooled and poured over ice. After acidification with concentrated HCl (30 mL), the mixture was filtrated to collect the solid, which was dissolved in ethyl acetate (600 mL) and washed with water (2×150 mL). The combined organic phase was dried and concentrated to give compound I-3 (550 mg, 61%) as a white solid, which was used for the next step without purification. $^1$H NMR ($CDCl_3$ 300 MHz): δ 7.80 (s, 1H), 7.62 (m, 1H), 7.25 (m, 1H), 3.33 (m, 3H), 3.05-3.21 (m, 2H), 2.92 (s, 1H), 1.91-2.26 (m, 3H), 1.67 (m, 2H), 1.43 (m, 1H), 1.33 (m, 2H), 1.21 (m, 3H), 0.80 (m, 1H).

Procedure for Preparation of Compound I-4

A suspension of compound I-3 (1 g, 2.64 mmol) and Lawesson's Reagent (1.68 g, 2.64 mmol) in anhydrous 1,4-dioxane (18 mL) was heated at 150° C. for 35 min in a CEM microwave reactor. The mixture was concentrated in vacuo and the residue was purified by column (petroleum ether: EtOAc=8:1 to 5:1) to give compound I-4 as a yellow solid (390 mg, 37%).

Procedure for Preparation of Compound I-5

To a solution of compound I-4 (300 mg, 0.76 mmol) in $CH_3CN$ (20 mL) was added a solution of $K_2CO_3$ (423 mg, 3.04 mmol) and MeI (447 mg, 3.04 mmol). The reaction mixture was heated at 60° C. for 10 min in a CEM microwave reactor. Then MeI (447 mg, 3.04 mmol) was added and the reaction mixture was heated at 60° C. for another 10 min. The solution was filtered and the filtrate was concentrated to give the residue, which was purified by chromatography on silica gel (petroleum ether:EtOAc=10:1) to afford compound I-5 (151 mg, 47%) as a white solid. $^1$H NMR ($CDCl_3$ 400 MHz): δ 7.28 (d, J=8.0 Hz, 1H), 7.10 (d, J=8.0 Hz, 1H), 6.88 (s, 1H), 3.26 (s, 3H), 3.16-2.91 (m, 6H), 2.59 (s, 3H), 1.99-1.78 (m, 3H), 1.67 (t, 1H), 1.49 (m, 1H), 1.38-1.27 (m, 1H), 1.08 (m, 1H).

Procedure for Preparation of Compound I-6

A solution of compound I-5 (45 mg, 0.10 mmol), $NH_4I$ (78 mg, 0.53 mmol) in a solution of $NH_3$/EtOH (5 mL, 5 N) was heated at 120° C. in a CEM tube in a microwave reactor for 3 h. After cooling, the mixture was concentrated in vacuo to give the residue, which was dissolved in $CH_2Cl_2$, filtrated and the filtrate was concentrated in vacuo to give compound I-6 (25 mg, 60%) as a white solid, which was used for the next step without purification. $^1$H NMR ($CDCl_3$ 400 MHz): δ 7.53 (m, 1H), 7.22 (m, 2H), 3.39 (m, 6H), 3.15 (4, 2H), 2.96 (s, 3H), 2.55 (s, 2H), 2.11 (m, 4H), 1.93 (m, 2H), 1.55 (m, 3H), 1.42 (m, 4H).

Example 99

Synthesis of Compound 134

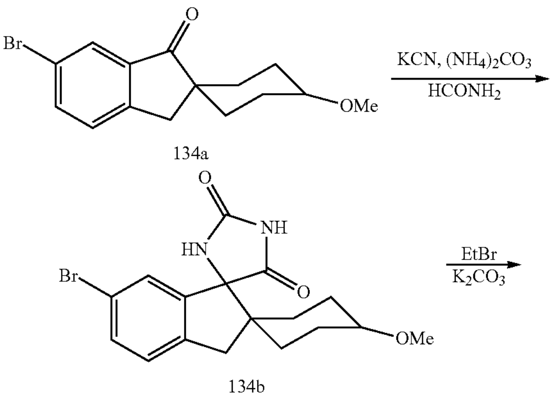

134a, 134b

-continued

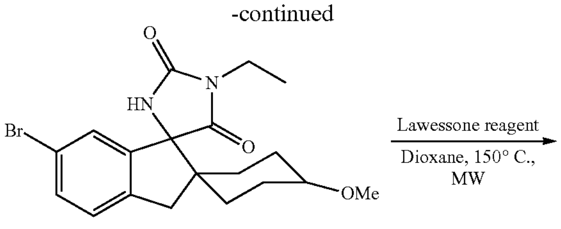

134c

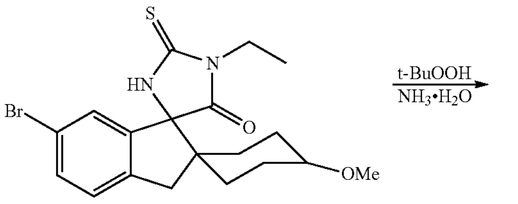

134d

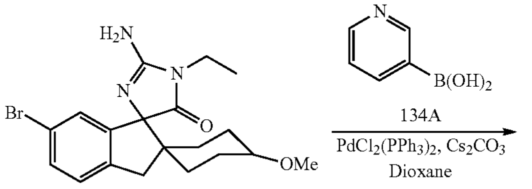

134e

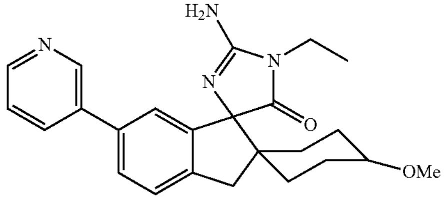

134

Procedure for Preparation of Compound 134b

To a solution of compound 134a (1.2 g, 3.88 mmol) in $HCONH_2$ (15 mL) was added KCN (0.52 g, 7.76 mmol), $(NH_4)_2CO_3$ (3.68 g, 38.8 mmol) at room temperature. The mixture was stirred in a steel autoclave at 90° C. for 72 h. TLC showed that the reaction was completed. The reaction mixture was then cooled and poured into ice water (25 mL). After acidification with concentrated HCl (5 mL), the mixture was filtrated to give the solid product (0.9 g yield 62%), which was used for the next step without purification. $^1$H NMR (DMSO-$d_6$ 400 MHz): δ 10.75 (s, 1H), 8.43 (s, 1H), 7.48 (d, 1H), 7.25 (dd, J=8.4 Hz, 2H), 3.25 (s, 3H), 3.09 (s, 1H), 2.95 (s, 1H), 2.81 (d, 1H), 1.97 (d, 1H), 1.80 (m, 2H), 1.42 (m, 3H), 1.15 (m, 2H).

Procedure for Preparation of Compound 134c

To a solution of compound 134b (200 mg, 0.52 mmol) in DMF (10 mL) was added ethyl bromide (60 mg, 0.56 mmol) and $K_2CO_3$ (72 mg, 0.8 mmol). The reaction mixture was stirred at room temperature overnight. TLC showed that the reaction was completed. The solution was extracted with EtOAc (2×15 mL). The combined organic layers were washed with brine (10 mL), dried over $Na_2SO_4$ and concentrated under reduced pressure. The residue was purified by preparative TLC to give compound 134c (140 mg, 66%) as a yellow solid.

Procedure for Preparation of Compound 134d

To a solution of compound 134c (40 mg, 0.10 mmol) and Lawesson's reagent (40 mg, 0.10 mmol) in anhydrous dioxane (5 mL) was stirred in microwave at 150° C. for 50 min. TLC showed that the reaction was completed. The mixture was concentrated under reduced pressure. The residue was purified by preparative TLC to give compound 134d (12 mg, 29%). $^1$H NMR ($CDCl_3$ 400 MHz): δ 7.39 (d, 1H), 7.15 (d, 1H), 6.95 (s, 1H), 3.75 (m, 3H), 3.30 (s, 3H), 3.08 (s, 1H), 2.95 (s, 1H), 1.97 (m, 3H), 1.25 (m, 8H).

Procedure for Preparation of Compound 134e

To a solution of compound 134d (20 mg, 0.047 mmol) in MeOH (5 mL) and $NH_3.H_2O$(1 mL) was added t-BuOOH (0.4 g, 65 wt % in water). The reaction mixture was stirred at room temperature overnight. TLC showed that the reaction was completed. The solution was concentrated under reduced pressure and water was added. The mixture was extracted with EtOAc (2×15 mL). The combined organic layers were washed with brine (10 mL), dried over $Na_2SO_4$ and concentrated under reduced pressure to give compound 134e (15.3 mg, 80%) as solid, which was used for the next step without purification.

Procedure for Preparation of Compound 134

To a solution of compound 134e (36 mg, 0.089 mmol) and compound 134A (16.4 mg, 0.133 mmol) in anhydrous dioxane (5 mL) was added $CS_2CO_3$ (0.7 mL, 2 mol/L) and $PdCl_2(PPh_3)_2$ (0.36 mg) under nitrogen. The mixture was stirred in microwave at 120° C. for 15 min. TLC showed that the reaction was completed. The mixture was concentrated under reduced pressure. The residue was purified by preparative TLC ($CH_2Cl_2$:MeOH=10:1) and RP-HPLC to give compound 134 (4.7 mg, 13%) as a white solid. LC-MS $t_R$=0.866 min in 2 min chromatography, MS (ESI) m/z 405.2 [MH+]; $^1$H NMR ($CD_3OD$ 400 MHz): δ 9.1 (s, 1H), 8.75 (s, 1H), 8.62 (d, 1H), 7.95 (t, 1H), 7.81 (d, 1H), 7.69 (s, 1H), 7.60 (d, 1H), 3.75 (m, 2H), 3.42 (s, 3H), 3.31 (s, 1H), 3.25 (m, 2H), 2.12 (m, 2H), 1.95 (d, 1H), 1.48 (m, 5H), 1.25 (t, 3H).

Example 100

Synthesis of Compound 135

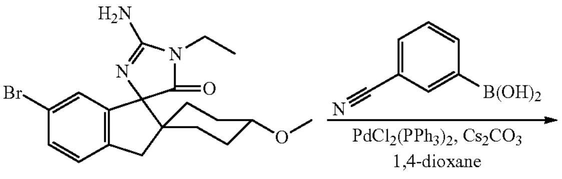

134e

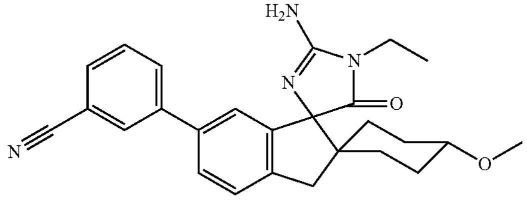

135

According to a similar synthesis of compound 134, compound 134e (25 mg, 0.06 mmol) was reacted with 3-cyanophenylboronic acid (10 mg, 0.08 mmol) to give compound 135 (7.6 mg, 30%) as a white solid. LCMS: $t_R$=1.63 min in 3 min chromatography, MS (ESI) m/z 429 $[M+H]^+$. $^1H$ NMR ($CD_3OD$ 400 MHz): δ 7.9 (s, 1H), 7.85 (d, J=7.6 Hz, 1H), 7.6 (m, 2H), 7.55 (m, 1H), 7.47 (s, 1H), 7.40 (m, 2H), 3.55-3.70 (m, 2H), 3.30 (s, 3H), 3.05-3.20 (m, 3H), 1.95-2.04 (m, 2H), 1.85 (m, 1H), 1.15-1.55 (m, 8H).

Example 101

Synthesis of Compound 136

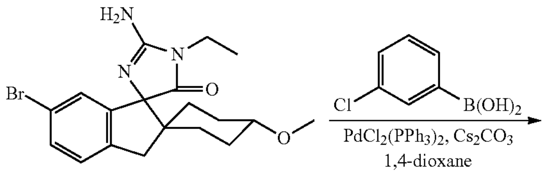

134e

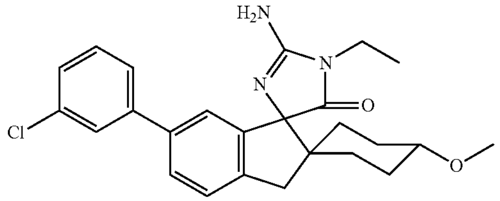

136

According to a similar synthesis of compound 134, compound 134e (25 mg, 0.06 mmol) was coupled with 3-chlorophenylboronic acid (10 mg, 0.08 mmol) to give compound 136 (7.1 mg, 28%) as a white solid. LCMS: $t_R$=1.73 min in 3 min chromatography, MS (ESI) m/z 439.2 $[M+H]^+$. $^1H$ NMR ($CD_3OD$ 400 MHZ): δ 7.55-7.72 (m, 2H), 7.43-7.45 (d, J=7.6 Hz, 1H), 7.36-7.38 (d, J=6.8 Hz, 2H), 7.31-7.33 (m, 1H), 7.20-7.25 (d, J=8.0 Hz, 1H), 3.70-3.80 (m, 1H), 3.60-3.70 (m, 1H), 3.26 (s, 3H), 3.10-3.20 (m, 3H), 1.93-2.05 (m, 2H), 1.79-1.82 (m, 1H), 1.21-1.38 (m, 5H), 1.12-1.19 (m, 3H).

Example 102

Synthesis of Compound 137

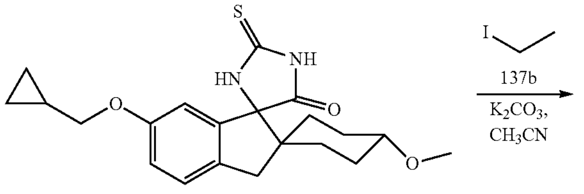

137a

-continued

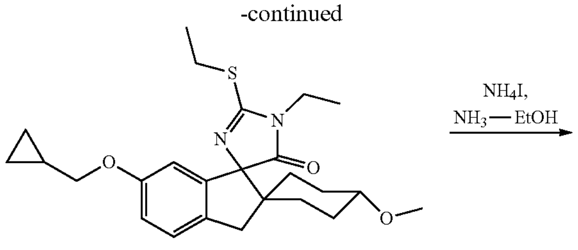

137c

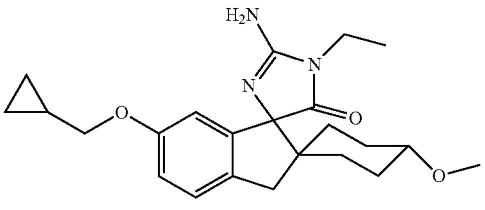

137

Procedure for Preparation of Compound 137c

To a solution of compound 137a (30 mg, 0.077 mmol) in $CH_3CN$ (5 mL) was added $K_2CO_3$ (42.9 mg, 0.31 mmol) and compound 137b (48.4 mg, 0.31 mmol), the reaction mixture was stirred at 60° C. for 10 min and at 100° C. for another 10 min in a CEM microwave reactor. The precipitate was filtered off and the filtrate was concentrated to give the crude product which was purified by preparative TLC on silica gel eluting with hexane:EtOAc=3:1 to give compound 137c (20 mg, 59%) as a white solid. LC-MS $t_R$=1.511 min in 2 min chromatography, MS (ESI) m/z=442.3 $[M+H]^+$.

Procedure for Preparation of Compound 137

A solution of compound 137c (20 mg, 0.045 mmol), $NH_4I$ (54.9 mg, 0.45 mmol) in $NH_3$-EtOH (2 mL, 5 N) was heated at 120° C. in a CEM microwave reactor for 3 h. After being cooled, the mixture was concentrated in vacuo, and the residue was purified by preparative TLC on silica gel eluting with dichloromethane:methanol=10:1 and preparative HPLC to give compound 137 (4.60 mg 25%) as a white solid. LC-MS $t_R$=0.864 min in 2 min chromatography, MS (ESI) m/z 398.1 $[M+H]^+$. $^1H$ NMR ($CD_3OD$ 400 MHz): δ 7.30 (d, J=8.4 Hz, 1H), 6.90 (d, J=8.4 Hz, 1H), 6.6 (s, 1H), 3.79 (d, J=8.0 Hz, 2H), 3.63 (d, J=7.2 Hz, 2H), 3.35 (s, 3H), 3.20-3.11 (m, 1H), 3.10-2.92 (m, 2H), 2.1-1.9 (m, 2H), 1.9-1.8 (m, 1H), 1.74-

1.56 (m, 1H), 1.51-1.32 (m, 2H), 1.32-1.25 (m, 3H), 1.22-1.15 (t, J=8.0 Hz, 3H), 0.70-0.50 (m, 2H), 0.41-0.22 (m, 2H).

Example 103

Synthesis of Compound 138

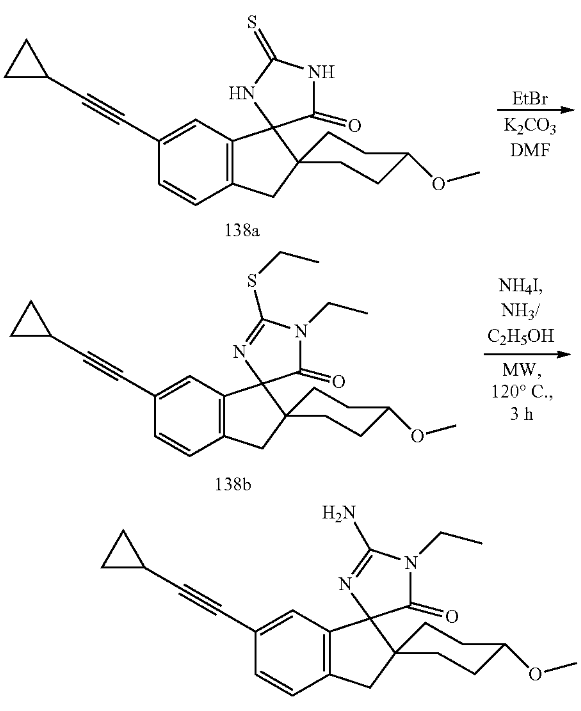

138a

138b

138

Procedure for Preparation of the Compound 138b

To a solution of compound 138a (45 mg, 0.12 mmol) in DMF (3 mL) was added $K_2CO_3$ (50 mg, 0.36 mmol) and EtBr (33 mg, 0.3 mmol). The reaction mixture was stirred at 20° C. for 10 h. The mixture was filtered and filtrate was concentrated in vacuo to give the residue, which was purified by preparative TLC on silica gel (petroleum ether:ethyl acetate=4:1) to give compound 138b (40 mg, 80%) as a white solid.

Procedure for Preparation of Compound 138

A suspension of compound 138b (40 mg, 0.09 mmol) and $NH_4I$ (100 mg, 0.7 mmol) in $NH_3$/EtOH (3 mL) was heated under 120° C. for 3 h in a CEM microwave reactor. The mixture was concentrated in vacuo, the residue was purified by preparative TLC on silica gel ($CH_2Cl_2$:$CH_3OH$=20:1) to give compound 138 (29 mg, 70%) as a white solid. LCMS: $t_R$=1.65 min in 3 min chromatography, MS (ESI) m/z 392.2 $[M+H]^+$. $^1$H NMR ($CD_3OD$ 400 MHZ): δ 7.11-7.18 (m, 2H), 6.87 (s, 1H), 3.48-3.55 (m, 2H), 3.21-3.28 (m, 3H), 3.02-3.06 (m, 1H), 2.93 (m, 1H), 1.81-1.97 (m, 2H), 1.70-1.80 (m, 1H), 1.41-1.49 (m, 1H), 1.15-1.40 (m, 5H), 1.05-1.10 (m, 3H), 0.72-0.78 (m, 2H), 0.54-0.61 (m, 2H).

Example 104

Synthesis of Compound 139

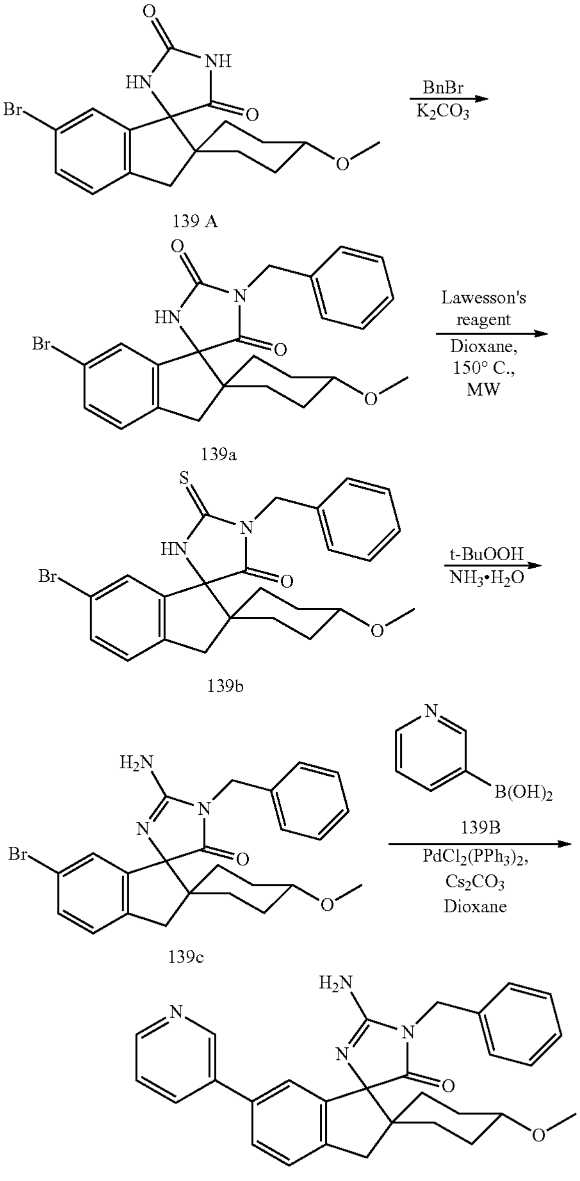

139 A

139a

139b

139c

139

Procedure for Preparation of the Compound 139a

To a solution of compound 139A (300 mg, 0.8 mmol) in DMF (5 mL) was added $K_2CO_3$ (140 mg, 1 mmol) and BnBr (150 mg, 0.9 mmol). The reaction mixture was stirred at 20° C. for 10 h. The mixture was filtered and the filtrate was concentrated in vacuo to give the residue, which was purified by preparative TLC on silica gel (petroleum ether:ethyl acetate=2:1) to give compound 139a (270 mg, 73%) as a white solid.

Procedure for Preparation of the Compound 2

A suspension of compound 139a (260 mg, 0.55 mmol) and Lawesson's Reagent (250 mg, 0.61 mmol) in anhydrous 1,4-dioxane (6 mL) was heated at 150° C. for 180 min in a CEM microwave reactor. The mixture was concentrated in vacuo and the residue was purified by preparative TLC on silica gel ($CH_2Cl_2$:$CH_3OH$=15:1) to give compound 139b (122 mg, 46%) as a yellow solid.

Procedure for Preparation of the Compound 139c

A solution of compound 139b (120 mg, 0.25 mmol), t-BuOOH (450 mg, 5 mmol), $NH_3.H_2O$ (1 mL) in EtOH (4 mL) was stirred at 20° C. for 10 h. The mixture was concentrated in vacuo to give the residue, which was purified by preparative TLC on silica gel ($CH_2Cl_2$:$CH_3OH$=12:1) to give compound 139c (37 mg, 31%) as a white solid.

Procedure for Preparation of Compound 139

A suspension of compound 139c (35 mg, 0.07 mmol), pyridine-3-boronic acid (10 mg, 0.09 mmol), $PdCl_2(PPh_3)_2$ (5 mg) and $Cs_2CO_3$ (0.1 mL, 2 N in water) in 1,4-dioxane (2 mL) was heated under 120° C. for 15 min in CEM microwave reactor. The mixture was concentrated in vacuo, the residue was purified by preparative HPLC to give compound 139 (11 mg, 31%) as a white solid. LCMS: $t_R$=1.42 min in 3 min chromatography, MS (ESI) m/z 467 $[M+H]^+$. $^1H$ NMR ($CD_3OD$ 400 MHz): δ 8.85 (s, 1H), 8.58 (s, 1H), 8.30-8.40 (m, 1H), 7.66 (s, 1H), 7.62 (d, J=7.2 Hz, 1H), 7.20-7.35 (m, 5H), 4.84-4.90 (m, 2H), 3.29-3.37 (m, 3H), 3.02-3.19 (m, 3H), 1.85-1.95 (m, 2H), 1.65 (m, 2H), 1.30-1.42 (m, 3H), 1.10-1.30 (m, 2H).

Example 105

Synthesis of Compound 140

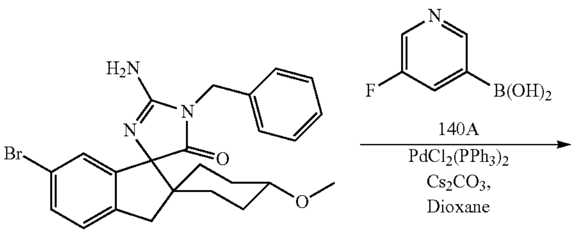

139c

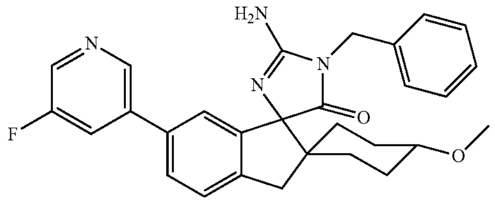

140

According to a similar synthesis of compound 139, compound 139c (15 mg, 0.032 mmol) was coupled with compound 140A (10 mg, 0.064 mmol) to give compound 140 (4.5 mg, 30%) as a white solid. LC-MS: $t_R$=0.997 min in 2 min chromatography, MS (ESI) m/z=485 $[M+H]^+$. $^1H$ NMR ($CD_3OD$ 400 MHz): δ 8.68 (s, 1H), 8.50 (d, J=2.4 Hz, 1H), 7.93 (m, 1H), 7.76 (dd, J=2.4, 8.0 Hz, 1H), 7.56 (m, 2H), 7.38 (m, 5H), 4.96 (m, 2H), 3.36 (s, 3H), 3.29 (m, 2H), 3.23 (m, 1H), 2.01 (m, 3H), 1.79 (m, 1H), 1.46 (m, 3H), 1.31 (m, 2H).

Example 106

Synthesis of Compound 141

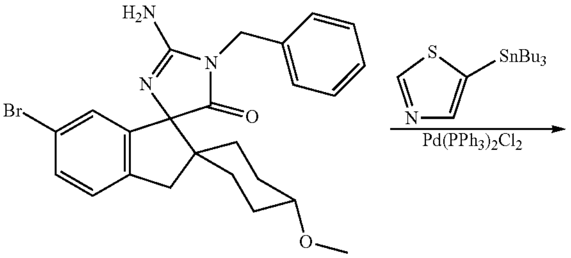

139c

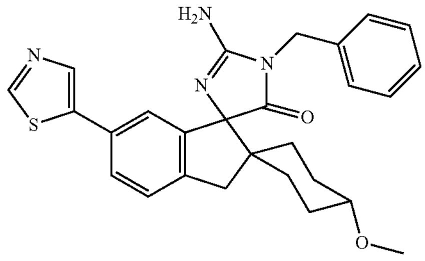

141

A suspension of compound 139c (10 mg, 0.02 mmol), 5-tributylstannanyl-thiazole (4 mg, 0.1 mmol), $PdCl_2(PPh_3)_2$ (2 mg, 0.003 mmol) in 1,4-dioxane (3 mL) was heated at 130° C. for 30 min in a CEM microwave reactor. The mixture was concentrated in vacuo, the residue was purified by preparative RP-HPLC to give compound 141 (2.5 mg, 25%) as a white solid. LCMS: $t_R$=1.79 min in 3 min chromatography, MS (ESI) m/z 473 $[M+H]^+$. $^1H$ NMR ($CD_3OD$ 400 MHz): δ 9.0 (s, 1H), 8.22 (s, 1H), 7.70-7.72 (dd, J=1.6, 9.2 Hz, 1H), 7.50-7.52 (m, 2H), 7.36-7.43 (m, 5H), 4.95 (m, 2H), 3.36 (s, 3H), 3.14-3.26 (m, 3H), 1.96 (m, 2H), 1.73-1.78 (m, 1H), 1.45-1.48 (m, 3H), 1.25-1.33 (m, 2H).

Example 107

Synthesis of Compound 142

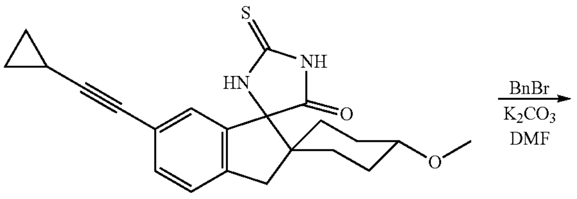

142a

-continued

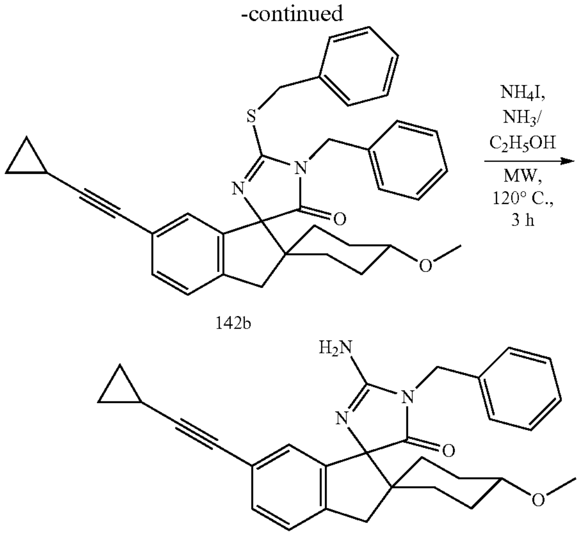

142b

142

Procedure for Preparation of the Compound 142b

To a solution of compound 142a (45 mg, 0.12 mmol) in DMF (3 mL) was added $K_2CO_3$ (50 mg, 0.36 mmol) and BnBr (50 mg, 0.3 mmol). The reaction mixture was stirred at room temperature for 10 h. The mixture was filtered and the filtrate was concentrated in vacuo to give the residue, which was purified by preparative TLC on silica gel (petroleum ether:ethyl acetate=5:1) to give compound 142b (70 mg, 95%) as a white solid.

Procedure for Preparation of Compound 142

A suspension of compound 142b (70 mg, 0.125 mmol) and $NH_4I$ (145 mg, 1 mmol) in $NH_3$/EtOH (4 mL) was heated under 120° C. for 3 h in a CEM microwave reactor. The mixture was concentrated in vacuo, the residue was purified by preparative HPLC to give compound 142 (15.4 mg, 45%) as a white solid. LCMS: $t_R$=1.72 min in 3 min chromatography, MS (ESI) m/z 454.2 $[M+H]^+$. $^1H$ NMR ($CD_3OD$ 400 MHz): δ 7.30-7.44 (m 7H), 7.16 (s, 1H), 4.92 (s, 2H), 3.32-3.39 (m, 3H), 3.08-3.19 (m, 3H), 1.99 (m, 2H), 2.76 (m, 1H), 1.41-1.49 (m, 4H), 1.25-1.35 (m, 2H), 0.85-0.94 (m, 2H), 0.69-0.74 (m, 2H).

Example 108

Synthesis of Compounds 142, 143 and 144

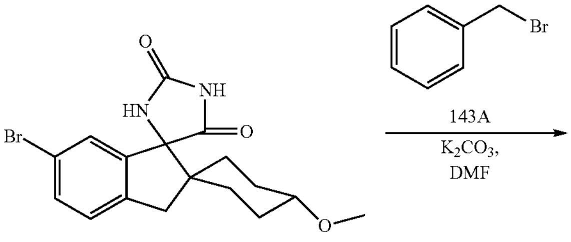

143a

-continued

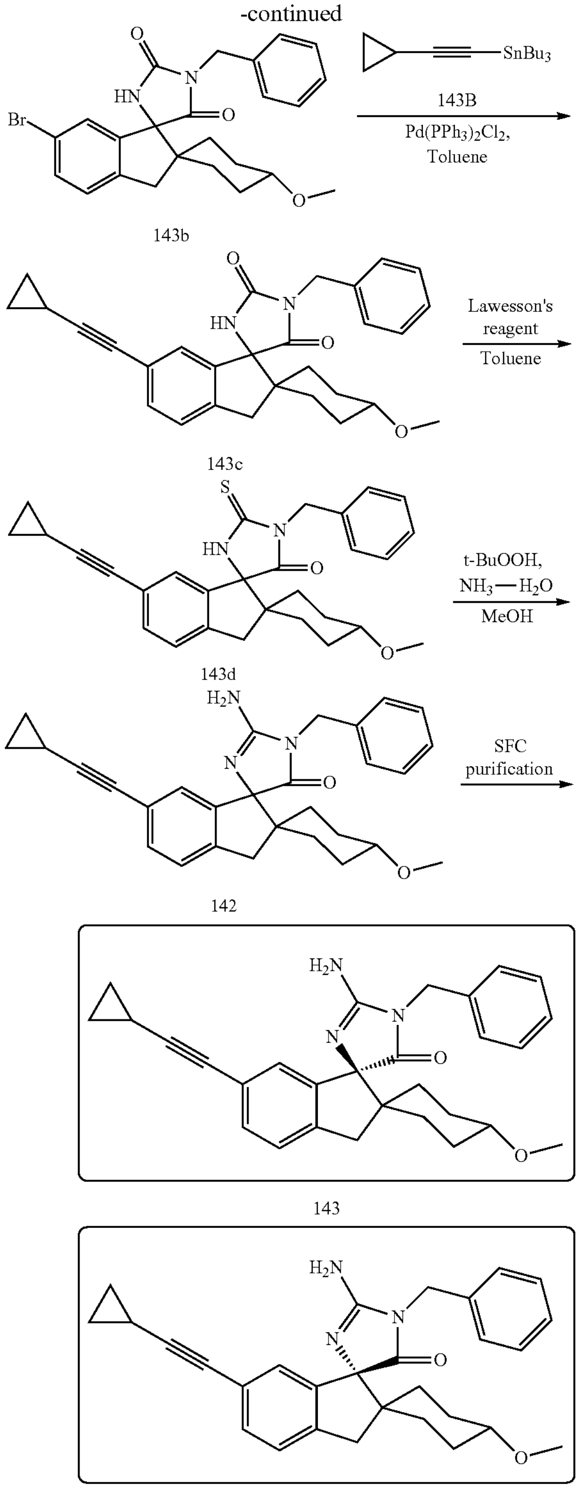

143b

143c

143d

142

143

144

Procedure for Preparation of Compound 143b

To a solution of compound 143a (1.5 g, 2.74 mmol) in DMF (20 mL) was added $K_2CO_3$ (756 mg, 5.48 mmol) and compound 143A (465 mg, 2.74 mmol). The mixture was stirred at room temperature for 3 h. The solution was added water (100 mL), the mixture was filtered to collect the solid and dried in vacuo to give compound 143b (0.7 g, 38%) as a white solid, which was used in next step directly.

Procedure for Preparation of Compound 143c

To a solution of compound 143b (470 mg, 1.0 mmol) in toluene (16 mL) was added compound 143B (1.0 mL, 2.0 mmol) and $Pd(PPh_3)_2Cl_2$ (20 mg) under nitrogen. The mixture was stirred at 135° C. for 45 min in microwave. LCMS showed that the reaction was completed. The reaction mixture was concentrated in vacuo to give the residue. The residue was partitioned by EtOAc (50 mL) and aqueous CsF (4M, 50 mL). The separated aqueous layer was extracted with EtOAc (2×50 mL), the combined organic layers were washed with brine (2×50 mL), dried over anhydrous $Na_2SO_4$ and concentrated to dryness. Purification of this residue by preparative TLC on silica gel (petroleum ether:ethyl acetate=3:1) afforded compound 143c (400 mg, 61.4%).

Procedure for Preparation of Compound 143d

To solution of compound 143c (400 mg, 0.88 mmol) and Lawesson'reagent (356 mg, 0.88 mmol) in toluene (20 mL) was heated under 130° C. for 30 min in a CEM microwave reactor. The mixture was cooled, and concentrated in vacuo. The residue was purified by preparative TLC on silica gel (petroleum ether:ethyl acetate=3:1 to give compound 143d (180 mg, 43.4%).

Procedure for Preparation of Compound 142

To a solution of compound 143d (180 mg, 0.382 mmol) in a mixture of MeOH (25 mL) and $NH_4OH$ (5 mL) was added t-BuOOH (690 mg, 7.65 mmol, 65% in water). The mixture was stirred at room temperature overnight, and was concentrated in vacuo. Water (15 mL) was added, the mixture was extracted with EtOAc (20 mL×3). The combined organic layer were dried over $Na_2SO_4$ and concentrated to give the residue which was purified by HPLC to give compound 142 (120 mg, 68%) as a white solid, which was purified by prep-SFC to give compound 143 (25 mg, 21%); LC-MS: $t_R$=1.102 min in 2 min chromatography, MS (ESI) m/z 453, 454 $[M+H]^+$; SFC:ee=99.7%; $^1H$ NMR ($CD_3OD$ 400 MHz): δ 7.35 (m, 7H), 6.92 (s, 1H), 4.74 (s, 2H), 4.62 (s, 2H), 3.32 (s, 3H), 3.09 (m, 3H), 1.96 (m, 2H), 1.82 (m, 1H), 1.60 (m, 1H), 1.45 (m, 1H), 1.38 (m, 2H), 1.24 (m, 2H), 0.88 (m, 2H), 0.72 (m, 2H). And compound 144 (40 mg, 33%); LC-MS: $t_R$=1.104 min in 2 min chromatography, MS (ESI) m/z 453, 454 $[M+H]^+$; SFC ee=99.0%; $^1H$ NMR ($CD_3OD$ 400 MHz): δ 7.21 (m, 7H), 6.98 (s, 1H), 4.75 (m, 2H), 3.23 (s, 3H), 3.01 (m, 3H), 1.86 (m, 2H), 1.65 (m, 1H), 1.33 (m, 4H), 1.18 (m, 2H), 0.77 (m, 2H), 0.60 (m, 2H).

Example 109

Synthesis of Compound 145

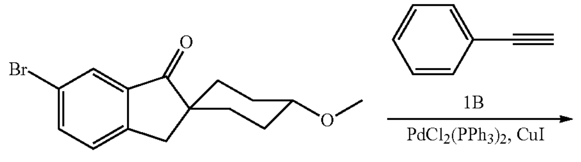

1A

1B

-continued

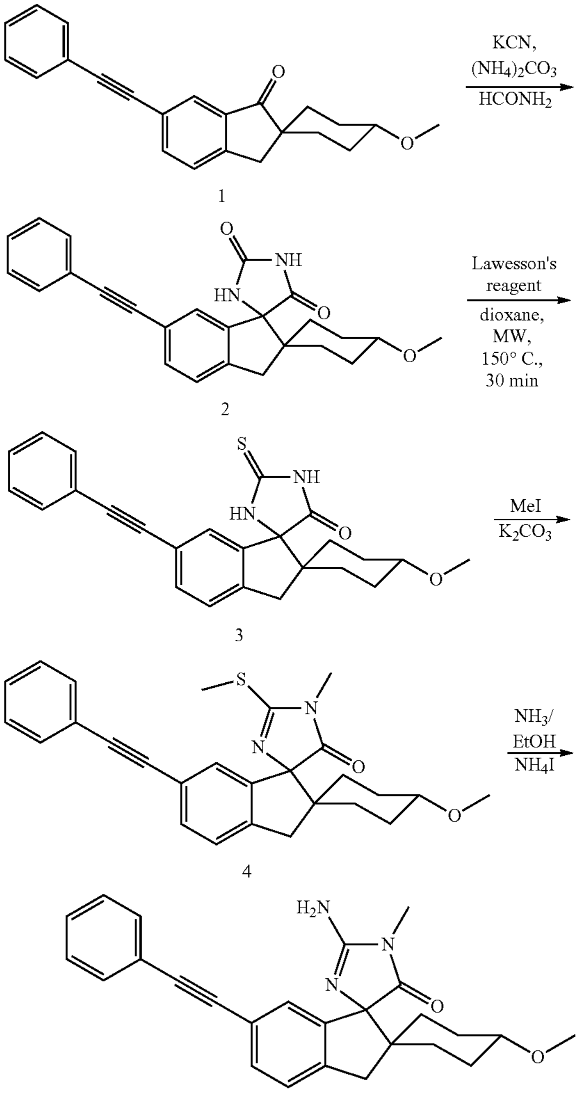

1

2

3

4

VT_B022409_04

Procedure for Preparation of Compound 145a

An oven dried three-necked round bottom flask equipped with condenser was charged with 6'-bromo-4-methoxyspiro [cyclohexane-1,2'-inden]-1'(3'H)-one (145A) (500 mg, 1.62 mmol), $Et_3N$ (40 mL) and $Et_2NH$ (8 mL) under $N_2$ atmosphere. To this solution was added CuI (60 mg, 0.3 mmol), $PdCl_2(PPh_3)_2$ (115 mg, 0.16 mmol). The system was degassed once again, then ethynylbenzene (145B) (1.65 g, excess) was added and the mixture was heated to 80° C. (oil bath) for 12 h. The reaction was evaporated under reduced pressure and the residue was partitioned between EtOAc (50 mL) and water (30 mL). The aqueous layer was extracted with EtOAc (2×30 mL), and the combined organic layers were washed with brine (30 mL), dried over $Na_2SO_4$, and concentrated under reduced pressure to dryness. The crude product was purified by column chromatography on silica gel eluting with 5%-20% EtOAc in hexane to afford compound 145a (0.5 g, 93%) as a brown oil.

Procedure for Preparation of Compound 145b

A steel autoclave was charged with a mixture of compound 145a (500 mg, 1.5 mmol), KCN (200 mg, 3.0 mmol), and $(NH_4)_2CO_3$ (1.1 g, 11.3 mmol), formamide (15 mL) was added. The mixture was heated at 100° C. for 72 h. The reaction mixture was then cooled and poured over ice. After acidification with concentrated HCl (20 mL), the mixture was filtrated to give the solid, which was dissolved in ethyl acetate (600 mL) and washed with water (150 mL) for 2 times. The combined organic layers were dried over $Na_2SO_4$, and concentrated under reduced pressure to dryness. The crude product was purified by column chromatography on silica gel eluting with 10%~33% EtOAc in hexane to afford compound 145b (0.1 g, 82%) as a white solid.

Procedure for Preparation of the Compound 145c

A suspension of compound 145b (100 mg, 0.25 mmol) and Lawesson's Reagent (101 mg, 0.25 mmol) in dry 1,4-dioxane (10 mL) was heated under 150° C. for 35 min in CEM microwave reactor. The mixture was concentrated under reduced pressure and the residue was purified by preparative TLC (petroleum ether:EtOAc=3:1) to give compound 145c (50 mg, 80%) as a yellow solid.

Procedure for Preparation of Compound 145d

To a solution of compound 145c (50 mg, 0.12 mmol) in $CH_3CN$ (3.0 mL) was added $K_2CO_3$ (67 mg, 0.48 mmol). After stirring for 5 min, MeI (68 mg, 0.48 mmol) was added and the reaction mixture was heated at 60° C. for 10 min in microwave and then at 100° C. for another 10 min. The mixture was filtered and filtrate was concentrated under reduced pressure to give compound 145d (50 mg, 80%) as a brown oil, which was used for the next step directly without further purification.

Procedure for Preparation of Compound 145

A solution of compound 145d (50 mg, 0.113 mmol), $NH_4I$ (164 mg, 1.13 mmol) in a solution of $NH_3$/EtOH (5 mL, 5 N) was heated at 120° C. in a CEM tube under microwave reactor for 3.5 h. After cooling, the mixture was concentrated under vacuum to give the residue, which was purified by pre-HPLC (basic) to give compound 145 (3.7 mg, 3%) as a white solid. LC-MS $t_R$=1.162 min in 2 min chromatography, MS (ESI) m/z 414.2 $[M+H]^+$. $^1$H NMR ($CDCl_3$ 400 MHz): δ 7.51-7.55 (m, 2H), 7.50 (d, J=7.6 Hz, 1H), 7.35 (m, 3H), 7.30 (m, 2H), 3.39 (s, 3H), 3.3 (d, J=16.0 Hz, 1H), 3.2-3.15 (m, 1H), 3.14 (s, 3H), 3.1 (s, 1H), 1.86-2.1 (m, 3H), 1.3-1.5 (m, 3H).

Example 110

Synthesis of Compound 146

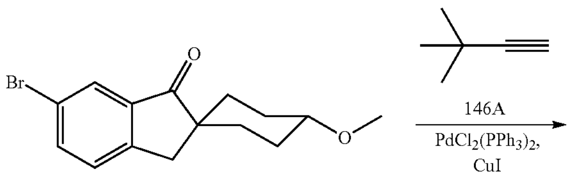

146a

-continued

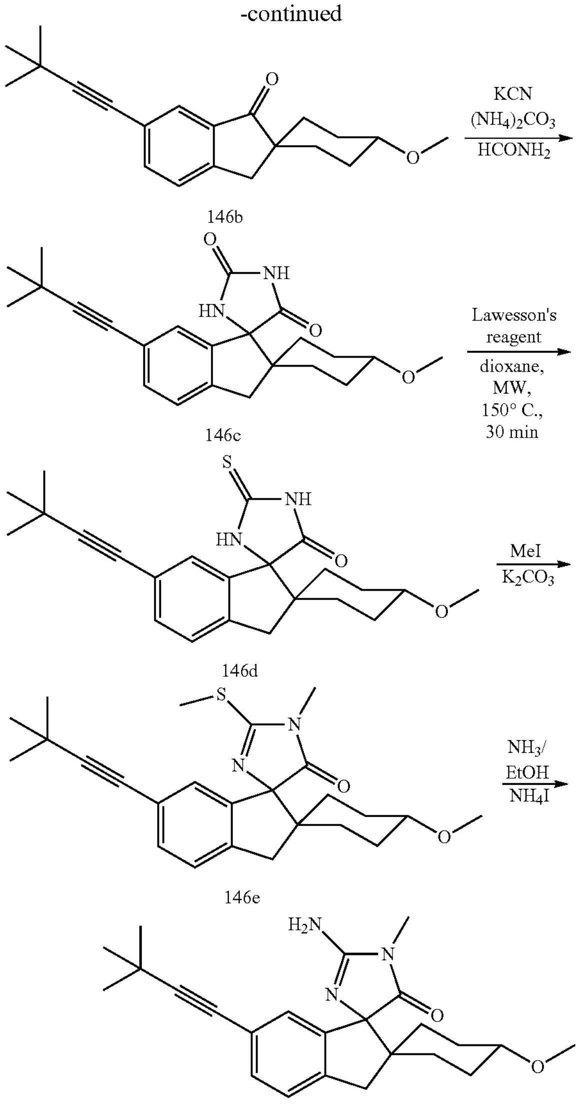

146b

146c

146d

146e

146

Applying the same reaction sequence as compound 145, compound 146a (0.5 g, 1.61 mmol) was coupled with 3,3-Dimethyl-but-1-yne (146A) (3 mL, excess) to afford compound 146b (300 mg, 50%) as a yellow oil. $^1$H NMR ($CDCl_3$ 400 MHz): δ 7.68 (s, 1H), 7.50 (d, J=7.6 Hz, 1H), 7.29 (d, J=8.4 Hz, 1H), 3.42 (s, 3H), 3.28 (m, 1H), 2.95 (s, 2H), 2.07 (m, 2H), 1.68 (m, 2H), 1.43 (m, 2H), 1.33 (m, 2H), 1.24 (s, 9H).

Compound 146b (300 mg, 0.96 mmol) then condensed to hydantoin 146c (100 mg, 27%) as a white solid, $^1$H NMR ($CDCl_3$ 400 MHz): δ 7.27 (s, 1H), 7.14 (d, J=7.8 Hz, 1H), 7.05 (d, J=7.6 Hz, 1H), 3.29 (s, 3H), 3.07 (m, 1H), 2.95 (s, 2H), 2.07 (m, 2H), 1.86 (m, 2H), 1.68 (m, 2H), 1.35 (m, 2H), 1.24 (s, 9H).

Hydantoin 146c (80 mg, 0.21 mmol) reacted with Lawesson's Reagent (85 mg, 0.21 mmol) in dry 1,4-dioxane (10 mL) to afford compound 146d (42 mg, 50%) as a white solid, which was methylated to give compound 146e (30 mg, 66%) as a white solid. $^1$H NMR ($CDCl_3$ 400 MHz): δ 7.31 (s, 1H), 7.13 (d, J=8.0 Hz, 1H), 6.76 (d, J=7.6 Hz, 1H), 3.43 (s, 3H), 3.26 (m, 1H), 3.21 (m, 2H), 2.94 (s, 3H), 2.59 (s, 3H), 1.77-1.81 (m, 2H), 1.81-1.99 (m, 2H), 1.26-1.31 (m, 2H), 1.31-1.41 (m, 2H), 1.26 (s, 9H).

Finally, compound 146e (30 mg, 0.073 mmol) was converted to compound 146 (1.7 mg, 6%) as a white solid. LCMS: $t_R$=1.271 min in 2 min chromatography, MS (ESI) m/z 394 $[M+H]^+$. $^1H$ NMR ($CD_3OD$ 400 MHz): δ 7.14 (d, J=8 Hz, 2H), 6.87 (s, 1H), 3.38 (s, 3H), 3.24 (m, 1H), 2.96 (s, 3H), 2.78 (s, 2H) 1.83-1.91 (m, 2H), 1.72-1.83 (m, 2H), 1.45-1.72 (m, 2H), 1.28-1.45 (m, 2H), 1.18 (s, 9H).

Example 111

Synthesis of Compound 147

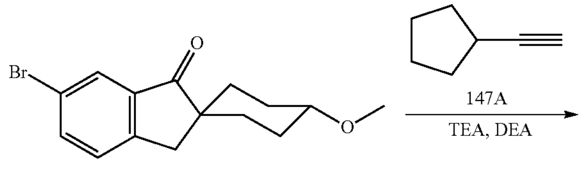

147a

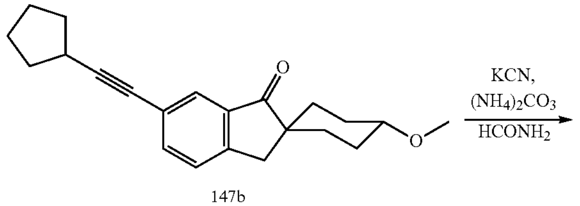

147b

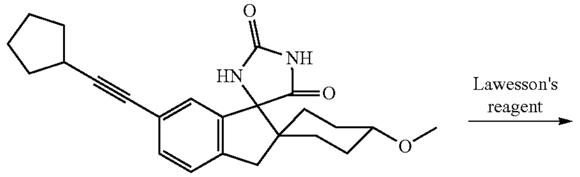

147c

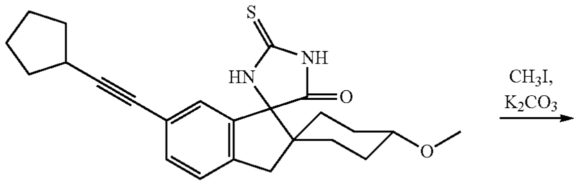

147d

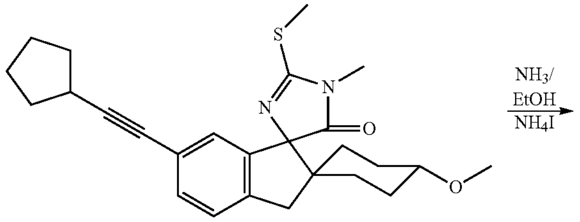

147e

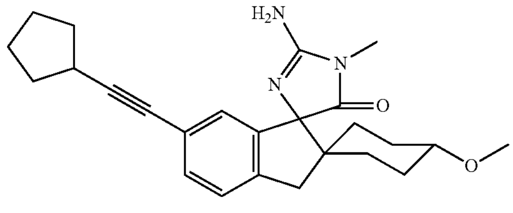

147

According to a similar synthesis of compound 145, compound 147a (500 mg, 1.6234 mmol) was coupled with compound 147A (11.2 g, 56.08 mmol) to afford compound 147b (370 mg, 71%) as a white solid. Compound 147b (370 mg, 1.1491 mmol) was then condensed to hydantoin 147c (100 mg, 23%) as a white solid.

Hydantoin 147c (50 mg, 0.1276 mmol) then was reacted with Lawessons reagent (58 mg, 0.1531 mmol) to give compound 147d (35 mg, 34%), which was methylated to give compound 147e (27 mg, 72%) as a white solid.

Finally, compound 147e (27 mg, 0.06193 mmol) was converted to compound 147 (13.0 mg, 52%) as a white solid. LC-MS $t_R$=1.036 min in 2 min chromatography, MS (ESI) m/z 405.9 $[M+H]^+$; $^1H$ NMR ($CD_3OD$ 400 MHz): δ 7.36 (m, 2H), 7.23 (s, 1H), 8.11 (m, 1H), 3.38 (s, 3H), 3.23-3.07 (m, 6H), 3.79-3.88 (m, 1H), 1.94-2.14 (m, 4H), 1.56-1.93 (m, 7H), 1.23-1.55 (m, 5H).

Example 112

Synthesis of Compound 148

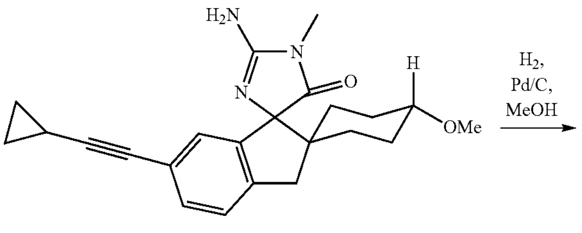

148a

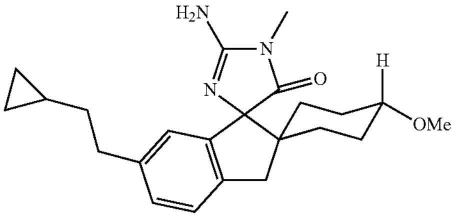

148

To a 25 mL round bottom flask was placed the alkyne 148a (6 mg, 0.016 mmol) and it was dissolved in MeOH (2 mL). To this solution was added Pd/C (<1 mg) and a ballon containing $H_2$ was attached to the flask. The reaction atmosphere was flushed twice with $H_2$ and then allowed to stir at room temperature for 20 minutes. The reaction was filtered through Celite and the filtrate concentrated under reduce pressure. The crude material was purified on a HPLC (Gilson, 10-90% $MeOH/H_2O$ with 0.1% TFA as the eluent). The corresponding fractions were combined and concentrated yielding the final product compound 148 (2.7 mg, 0.007 mmol, 44% yield). LCMS: M+H=382.1; $^1H$ NMR ($CD_3OD$, 400 MHz) δ 7.26-7.21 (m, 2H), 7.02 (s, 1H), 3.34 (s, 3H), 3.19 (s, 3H), 3.12 (m, 2H), 2.70 (m, 2H), 1.99-1.83 (m, 3H), 1.47-1.28 (m, 9H), 0.67 (m, 1H), 0.40 (m, 2H), 0.01 (m, 2H) ppm.

Example 113

Synthesis of Compound 149

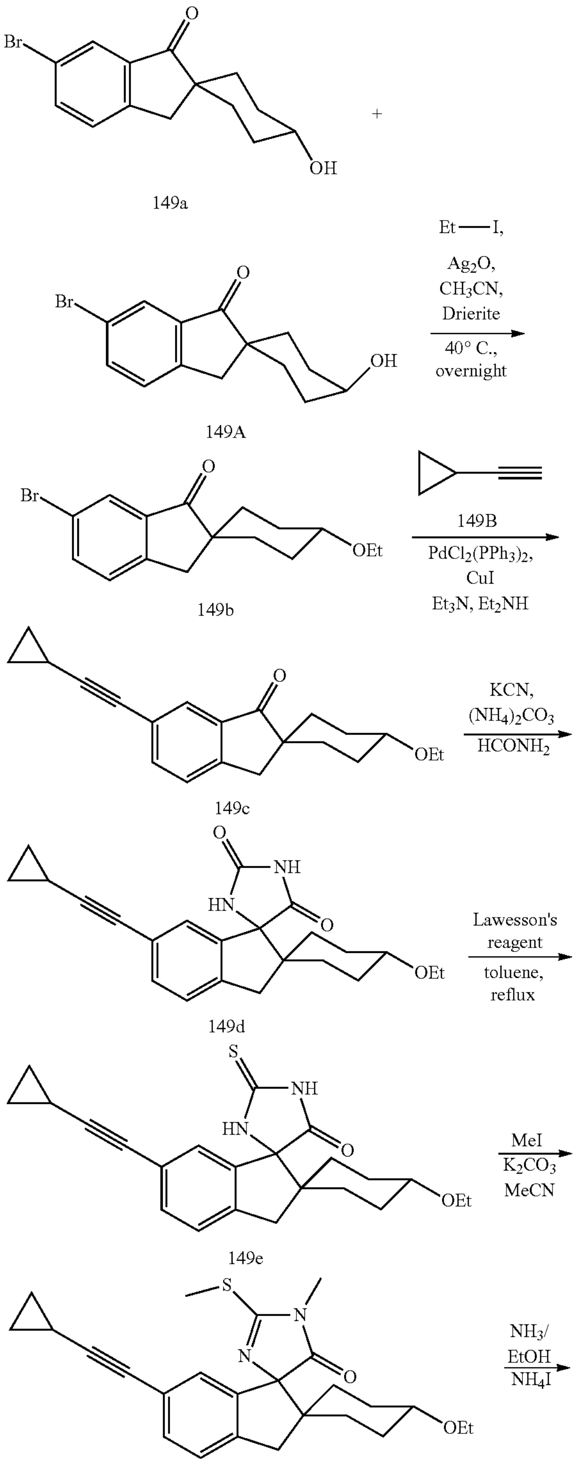

149a

149A

149b

149c

149d

149e

149f

-continued

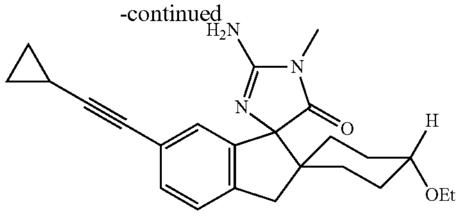

149

Procedure for Preparation of Compound 149b

A mixture containing compound 149a and compound 149A (4 g, 13.6 mmol, 60% purity) in $CH_3CN$ (40 mL) was added $Ag_2O$ (9.5 g, 40.8 mmol) and $MgSO_4$ (10 g) at room temperature. After the mixture was stirred for 10 min at room temperature, EtI (42 g, 172 mmol) was added dropwise to the former solution. The reaction mixture was heated overnight at 40° C. The mixture was filtered and the filtrate was dried over $Na_2SO_4$ and concentrated in vacuo to afford crude compound 2, which was purified by column chromatography on silica gel eluting with Hexane:EtOAc=30:1 to 5:1 to give compound 149b (0.81 g, 40%) as yellow solid. $^1$H NMR ($CDCl_3$ 400 MHz): δ 7.75-7.81 (s, 1H), 7.50-7.55 (d, 1H), 7.25-7.28 (m, 1H), 3.46-3.54 (m, 2H), 3.20-3.30 (m, 1H), 2.85-2.90 (s, 2H), 2.00-2.09 (m, 2H), 1.55-1.62 (m, 2H), 1.20-1.40 (m, 4H), 1.10-1.19 (t, 3H).

Procedure for Preparation of Compound 149

According to a similar synthesis of compound 145, compound 149b (0.8 g, 2.48 mmol) was coupled compound 149B (2 mL, excessive) under a nitrogen atmosphere to give compound 149c (0.51 g, 67%) as a brown solid. $^1$H NMR: ($CDCl_3$ 400 MHz): δ 7.67 (s, 1H), 7.52-7.49 (d, J=8 Hz, 1H), 7.29 (d, J=7.6 Hz, 1H), 3.53-3.45 (m, 2H), 3.32-3.25 (m, 1H), 2.93 (s, 2H), 2.11-2.03 (m, 2H), 1.73-1.65 (m, 2H), 1.42-1.27 (m, 5H), 1.17-1.12 (m, 3H), 0.83 (m, 2H), 0.74 (m, 2H).

Compound 149c (0.51 g, 1.65 mmol) was then condensed to hydantoin 149d (160 mg, 25%) as a gray solid. $^1$H NMR: (DMSO-$d_6$ 400 MHz): δ 10.75 (s, 1H), 8.39 (s, 1H), 7.24 (m, 2H), 6.99 (s, 1H), 3.43-3.39 (m, 2H), 3.15 (m, 1H), 2.99-2.86 (m, 2H), 1.97 (m, 1H), 1.78 (m, 2H), 1.49 (m, 1H), 1.36-1.14 (m, 5H), 1.07-1.02 (m, 3H), 0.87-0.82 (m, 2H), 0.73-0.68 (m, 2H).

And Compound 149d (130 mg, 0.34 mmol) was reacted with Lawesson's reagent (139 mg, 0.34 mmol) in toluene (8 mL) to give compound 149e (100 mg, 74%) as a white solid. $^1$H NMR: ($CDCl_3$ 400 MHz): δ 8.03 (s, 1H), 7.27 (d, J=7.6 Hz, 1H), 7.14 (d, J=7.6 Hz, 1H), 7.09 (s, 1H), 3.48-3.43 (m, 2H), 3.18-3.13 (m, 1H), 3.09-2.96 (m, 2H), 2.10 (s, 1H), 2.01-1.89 (m, 3H), 1.40-1.23 (m, 5H), 1.13 (m, 3H), 0.80 (m, 2H), 0.72 (m, 2H).

Compound 149e (100 mg, 0.25 mmol) was dimethylated with MeI (2 mL, excessive) to give compound 149f (85 mg, 79%) as a white solid. $^1$H NMR: ($CDCl_3$ 400 MHz): δ 7.18 (d, J=10 Hz, 1H), 7.12 (d, J=7.6 Hz, 1H), 6.77 (s, 1H), 3.46-3.40 (m, 2H), 3.16-3.09 (m, 2H), 2.99-2.95 (m, 1H), 2.93 (s, 3H), 2.58 (s, 3H), 1.92-1.78 (m, 3H), 1.65 (m, 1H), 1.50 (m, 1H), 1.38-1.17 (m, 4H), 1.13-1.06 (m, 4H), 0.77-0.74 (m, 2H), 0.72-0.66 (m, 2H).

Finally, compound 149f (30 mg, 0.071 mmol) was converted to compound 149 (8 mg, 29%) as a white solid. LC-MS: $t_R$=1.124 min in 2 min chromatography, MS (ESI) m/z 392.2 $[M+H]^+$. $^1$H NMR: ($CD_3OD$ 400 MHz): δ 7.13 (m, 2H), 6.82 (s, 1H), 3.48-3.43 (m, 2H), 3.15-3.12 (m, 1H), 3.03-2.96 (m, 2H), 2.93 (s, 3H), 1.91-1.82 (m, 2H), 1.74-1.71 (m, 1H), 1.55-1.45 (m, 1H), 1.36-1.15 (m, 5H), 1.12-1.06 (m, 3H), 0.79-0.76 (m, 2H), 0.63-0.57 (m, 2H).

Example 114

Synthesis of Compounds 150 and 151

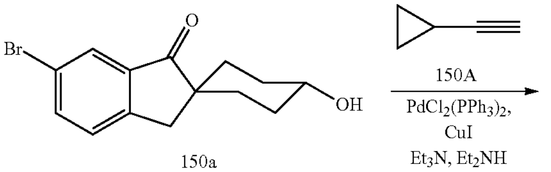

150a

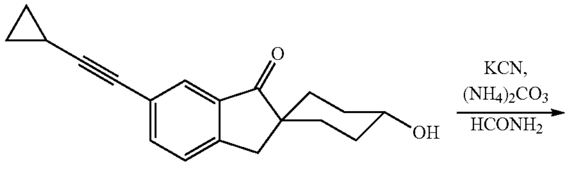

150b

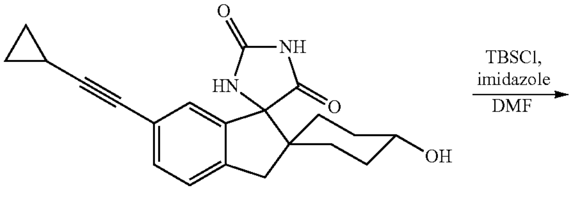

150c

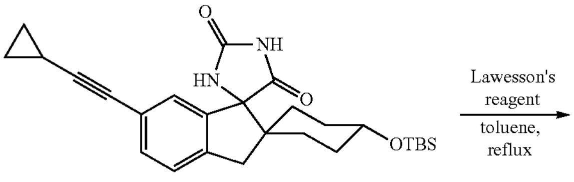

150d

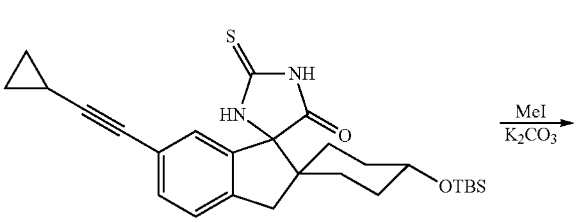

150e

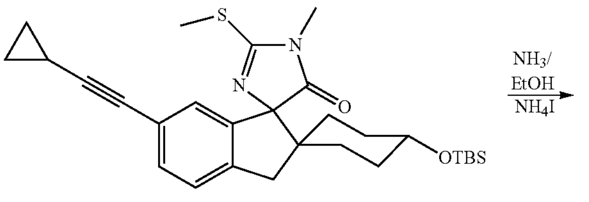

150f

-continued

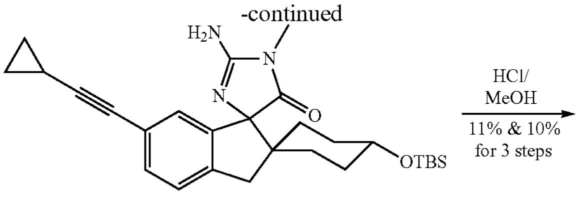

150g

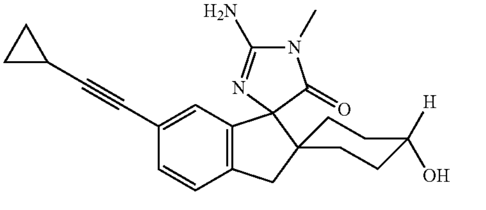

+

150

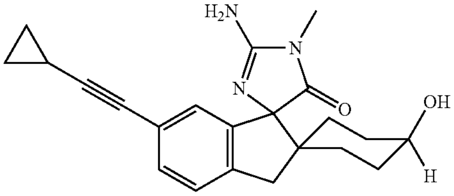

151

According to a similar synthesis of compound 145, compound 150a (0.7 g, 2.38 mmol) was coupled with compound 150A (2 mL, excessive) to give compound 150b (0.53 g, 79%) as a brown solid. $^1$H NMR: ($CDCl_3$ 400 MHz): δ 7.67 (s, 1H), 7.52-7.49 (dd, J=8 Hz, 1H), 7.38-7.26 (m, 1H), 3.69 (m, 1H), 2.94 (s, 2H), 2.00-1.90 (m, 2H), 1.76-1.65 (m, 2H), 1.50-1.47 (m, 1H), 1.44-1.31 (m, 5H), 0.86-0.77 (m, 2H), 0.76-0.71 (m, 2H).

Compound 150b (0.53 g, 1.89 mmol) was then condensed to hydantoin 150c (0.27 g, 41%) as a gray solid. $^1$H NMR: (DMSO-$d_6$ 400 MHz): δ 10.74 (s, 1H), 8.39 (s, 1H), 7.27 (m, 2H), 7.01 (s, 1H), 4.58 (m, 1H), 2.99-2.88 (m, 2H), 1.84-1.63 (m, 3H), 1.57-1.45 (m, 1H), 1.38-1.16 (m, 5H), 1.06-0.98 (m, 1H), 0.87-0.86 (m, 2H), 0.77-0.69 (m, 2H).

A mixture of compound 150c (160 mg, 0.46 mmol), TBSCl (104 mg, 0.69 mmol) and imidazol (78 mg, 1.15 mmol) in DMF (2 mL) was stirred at room temperature for 20 h. The reaction mixture was diluted with water (10 mL) and extracted with EtOAc (15 mL×3). The combined organic layers were washed with brine (20 mL), dried over $Na_2SO_4$ and concentrated to dryness. The crude product was purified by prep-TLC (petroleum ether:EtOAc=2:1) to give compound 150d (94 mg, 44%) as a white solid. $^1$H NMR: ($CDCl_3$ 400 MHz): δ 7.36-7.34 (d, J=9.2 Hz, 1H), 7.28-7.19 (m, 2H), 3.64-3.51 (m, 1H), 3.20-3.02 (m, 2H), 2.05-1.86 (m, 2H), 1.86-1.57 (m, 2H), 1.55-1.42 (m, 3H), 1.41-1.21 (m, 2H), 0.91 (s, 9H), 0.88-0.86 (m, 2H), 0.85-0.79 (m, 2H), 0.09 (s, 6H).

Then compound 150d (60 mg, 0.129 mmol) was reacted with Lawesson's reagent (52 mg, 0.129 mmol) in toluene (5 mL) to give compound 150e (38 mg, 61%) as a yellow solid. $^1$H NMR: ($CDCl_3$ 400 MHz): δ 7.29-7.26 (m, 1H), 7.17-7.09 (m, 2H), 3.49 (m, 1H), 3.06-2.93 (m, 2H), 1.95-1.29 (m, 10H), 0.88-0.76 (m, 11H), 0.75-0.70 (m, 2H), 0.01 (s, 6H).

Compound 150e (40 mg, 0.083 mmol) was dimethylated with MeI (1 mL, excessive) and $K_2CO_3$ (46 mg, 0.33 mmol) in MeCN (2 mL) to give compound 150f (25 mg, impure), which was converted to compound 150g (20 mg), which was used in next step directly without purification.

Finally, compound 150g (20 mg, 0.042 mmol) in HCl/MeOH (5 N, 5 mL) was stirred at room temperature for 2 h. The reaction mixture was concentrated under reduced pressure to dryness. The residue was purified by prep-HPLC (basic) to give compound 150 (2.4 mg, 11% for 3 steps), LC-MS: $t_R$=1.025 min in 2 min chromatography, MS (ESI) m/z 364.2 $[M+H]^+$. $^1H$ NMR: ($CD_3OD$ 400 MHz): δ 7.27-7.21 (m, 2H), 6.95 (s, 1H), 3.49-3.41 (m, 1H), 3.09 (s, 2H), 3.06 (s, 3H), 1.94-1.77 (m, 3H), 1.62-1.24 (m, 7H), 0.91-0.83 (m, 2H), 0.73-0.67 (m, 2H); and compound 151 (2.3 mg, 10% for 3 steps), LC-MS: $t_R$=1.073 min in 2 min chromatography, MS (ESI) m/z 364.2 $[M+H]^+$. $^1H$ NMR: ($CD_3OD$ 400 MHZ): δ 7.28-7.21 (m, 2H), 6.98 (s, 1H), 3.95 (m, 1H), 3.15-3.03 (m, 5H), 1.98-1.89 (m, 1H), 1.82-1.60 (m, 5H), 1.57-1.39 (m, 2H), 1.12-1.04 (m, 1H), 0.91-0.81 (m, 2H), 0.73-0.68 (m, 2H).

Example 115

Synthesis of Compound 152

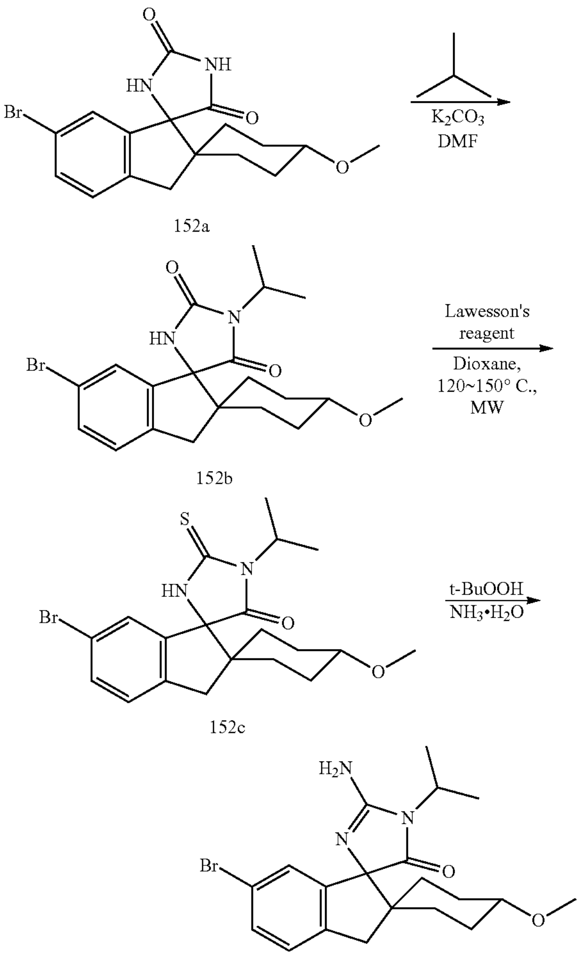

152a

152b

152c

152

Procedure for Preparation of Compound 152b

To a solution of compound 152a (300 mg, 0.8 mmol) in DMF (6 mL) was added $K_2CO_3$ (220 mg, 0.95 mmol) and 2-iodo-propane (160 mg, 0.9 mmol). The reaction mixture was stirred at 20° C. for 10 h. The mixture was filtered and the filtrate was concentrated in vacuo to give the residue, which was purified by preparative TLC on silica gel (petroleum ether:ethyl acetate=2:1) to give compound 152b (300 mg, 90%) as a white solid.

Procedure for Preparation of Compound 152c

A suspension of compound 152b (120 mg, 0.3 mmol) and Lawesson's Reagent (240 mg, 0.6 mmol) in anhydrous 1,4-dioxane (5 mL) was heated at 150° C. for 60 min in a CEM microwave reactor. The mixture was concentrated in vacuo, the residue was purified by preparative TLC on silica gel (petroleum ether:ethyl acetate=3:1) to give compound 152c as a yellow solid (63 mg, 50%).

Procedure for Preparation of Compound 152

A solution of compound 152c (40 mg, 0.09 mmol), t-BuOOH (180 mg, 1.9 mmol) and $NH_3.H_2O$ (1 mL) in EtOH (4 mL) was stirred at 20° C. for 10 h. The mixture was concentrated in vacuo to give the residue, which was purified by preparative TLC on silica gel ($CH_2Cl_2$:$CH_3OH$=15:1) to give compound 152 (23 mg, 60%) as a white solid.

Example 116

Synthesis of Compound 153

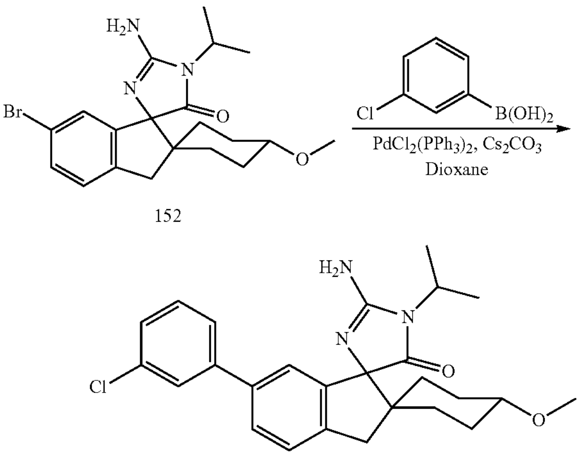

152

153

A suspension of compound 152 (20 mg, 0.05 mmol), 3-chrolophenylboronic acid (10 mg, 0.06 mmol), $PdCl_2(PPh_3)_2$ (5 mg) and $Cs_2CO_3$ (0.1 mL, 2 N in water) in 1,4-dioxane (3 mL) was heated under 120° C. for 15 min in a CEM microwave reactor. The mixture was concentrated in vacuo, the residue was purified by preparative HPLC to give compound 153 (7.9 mg, 55%) as a white solid. LCMS: $t_R$=1.79 min in 3 min chromatography, MS (ESI) m/z 452.2 $[M+H]^+$. $^1H$ NMR ($CD_3OD$ 400 MHz): δ 7.60-7.67 (d, 2H), 7.50-7.56 (d, 1H), 7.45-7.50 (d, 2H), 7.43-7.48 (m, 1H), 7.35-7.38 (s, 1H), 4.27-4.35 (m, 1H), 3.38 (s, 3H), 3.14-3.25 (m, 3H), 1.94-2.13 (m, 3H), 1.33-1.53 (m, 11H).

Example 117

Synthesis of Compound 154

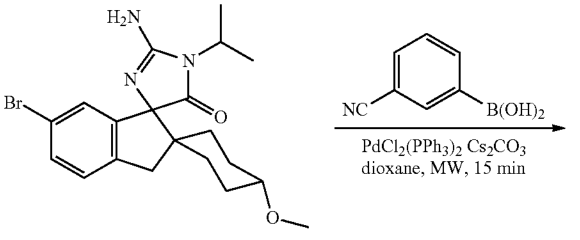

152

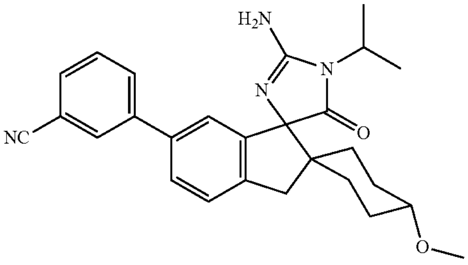

154

According to a similar synthesis of compound 153, compound 152 (10 mg, 0.024 mmol) was coupled with 3-cyanophenylboronic acid (4 mg, 0.024 mmol) to give compound 154 (4.3 mg, 45%) as a white solid. LCMS: $t_R$=1.71 min in 3 min chromatography, MS (ESI) m/z 443 $[M+H]^+$. $^1$H NMR ($CD_3OD$ 400 MHz): δ 7.94 (s, 1H), 7.88-7.90 (m, 2H), 7.66-7.70 (m, 1H), 7.57-7.63 (m, 2H), 7.42-7.45 (d, J=7.6 Hz, 1H), 7.26 (s, 1H), 4.20-4.28 (m, 1H), 3.37 (s, 3H), 3.08-3.20 (m, 3H), 1.91-2.08 (m, 3H), 1.64-1.66 (m, 1H), 1.30-1.45 (m, 10H).

Example 118

Synthesis of Compound 155

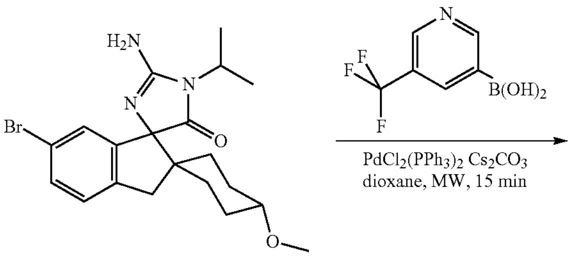

152

-continued

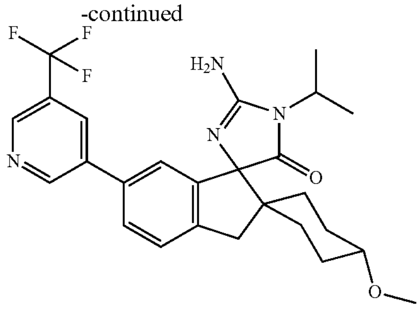

155

According to a similar synthesis of compound 153, compound 152 (10 mg, 0.024 mmol) was coupled with 3-trifluoromethyl-5-pyridineboronic acid (6 mg, 0.024 mmol) to give compound 155 (5.3 mg, 52%) as a white solid. LCMS: $t_R$=1.71 min in 3 min chromatography, MS (ESI) m/z 487 $[M+H]^+$. $^1$H NMR ($CD_3OD$ 400 MHz): δ 9.04 (s, 1H), 8.86 (s, 1H), 8.55 (s, 2H), 7.66-7.68 (m, 1H), 7.50-7.52 (d, J=7.2 Hz, 1H), 7.15 (s, 1H), 4.21-4.26 (m, 1H), 3.37 (s, 3H), 3.11-3.22 (m, 3H), 1.94-2.10 (m, 3H), 1.61-1.70 (m, 1H), 1.31-1.47 (m, 10H).

Example 119

Synthesis of Compound 156

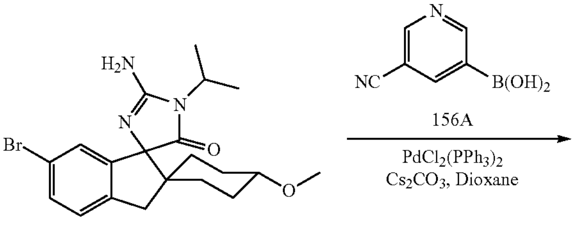

152

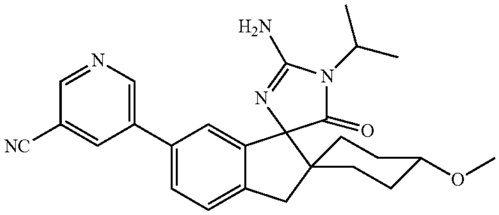

156

According to a similar synthesis of compound 153, compound 152 (10 mg, 0.024 mmol) was coupled with compound 156A (17 mg, 0.0714 mmol) to give product compound 156 (6 mg, 29%) as a white solid. LC-MS $t_R$=0.977 min in 2 min chromatography, MS (ESI) m/z 444 $[M+H]^+$. $^1$H NMR ($CD_3OD$ 300 MHz): δ 9.06 (s, 1H), 8.87 (s, 1H), 8.46 (s, 1H), 7.76 (d, J=7.8 Hz, 1H), 7.63 (s, 1H), 7.54 (d, J=7.8 Hz, 1H), 4.28 (m, 1H), 3.34 (s, 3H), 3.17 (m, 3H), 2.01 (m, 1H), 2.89 (m, 2H), 1.52 (m, 3H), 1.46 (m, 6H), 1.33 (m, 2H).

Example 120

Synthesis of Compound 157

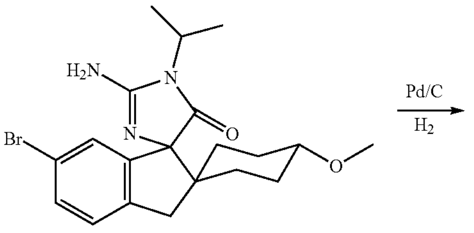

152

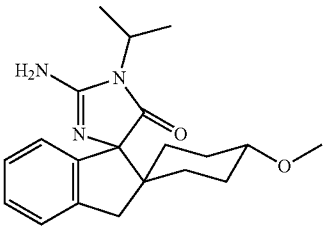

157

To a solution of compound 152 (20 mg, 0.048 mmol) in MeOH (2 mL) was added Pd/C (10 mg). The reaction mixture was stirred at room temperature for 2 h. The solution was filtered and the filtrate was concentrated to give the residue, which was purified by preparative HPLC to give compound 157 (3.0 mg, 19%) as a white solid. LC-MS $t_R$=0.935 min in 2 min chromatography, MS (ESI) m/z 342 $[M+H]^+$. $^1H$ NMR ($CD_3OD$ 300 MHz): δ 7.41 (s, 2H), 7.38 (m, 1H), 7.17 (d, J=7.5 Hz, 1H), 4.29 (m, 1H), 3.38 (s, 3H), 3.15 (m, 3H), 2.17-1.99 (m, 2H), 1.82 (m, 1H), 1.58 (m, 3H), 1.48-1.23 (m, 8H).

Example 121

Synthesis of Compound 158

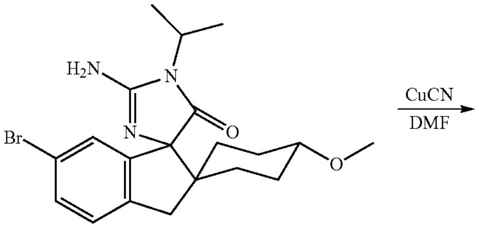

152

-continued

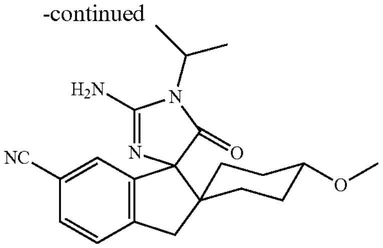

158

A suspension of compound 152 (20 mg, 0.048 mmol), CuCN (30 mg, excess) and $Pd(PPh_3)_4$ (8 mg) in dry DMF (2 mL) was heated under 180° C. for 45 min in a CEM microwave reactor. Water (10 mL) was added and the mixture was extracted with EtOAc (10 mL*3). The organic layer was washed with water, brine, dried over $Na_2SO_4$ and concentrated. The residue was purified by preparative HPLC to give compound 158 (8.0 mg, 51%) as a white solid. LC-MS $t_R$=0.916 min in 2 min chromatography, MS (ESI) m/z 367 $[M+H]^+$. $^1H$ NMR ($CD_3OD$ 400 MHz): δ 7.65 (d, J=8.0 Hz, 1H), 7.51 (d, J=7.6 Hz, 1H), 7.32 (s, 1H), 4.21 (m, 1H), 3.39 (s, 3H), 3.16 (m, 3H), 2.07 (m, 1H), 2.01-1.89 (m, 2H), 1.66 (m, 1H), 1.43 (m, 3H), 1.38 (m, 4H), 1.34-1.22 (m, 3H).

Example 122

Synthesis of Compound 159

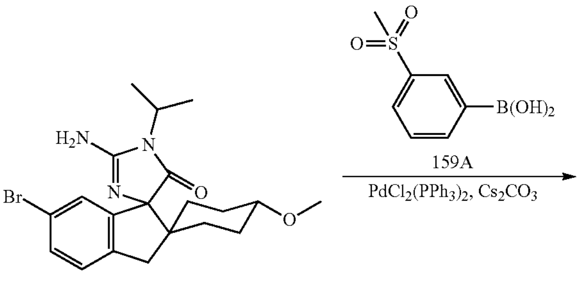

152

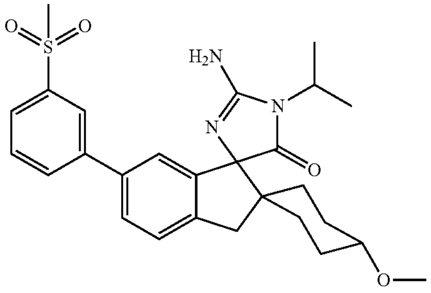

159

According to a similar synthesis of 153, compound 152 (20 mg, 0.047 mmol) was coupled with compound 159A (12 mg, 0.094 mmol) to give compound 159 (10.6 mg, 30%) as a white solid. LC-MS $t_R$=1.118 min in 2 min chromatography, MS (ESI) m/z 496 $[M+H]^+$. $^1H$ NMR ($CD_3OD$ 400 MHz): δ 8.16 (s, 1H), 7.95-8.00 (m, 2H), 7.72-7.75 (m, 2H), 7.53-7.57 (m, 2H), 4.29-4.36 (m, 1H), 3.38 (s, 3H) 3.26-3.27 (m, 1H), 3.20-3.23 (d, 2H), 3.19 (s, 3H), 2.11-2.14 (m, 1H), 2.04 (m, 1H), 1.94-1.97 (m, 1H), 1.49-1.54 (m, 3H), 1.45-1.49 (m, 6H), 1.31-1.41 (m, 2H).

Example 123

Synthesis of Compound 160

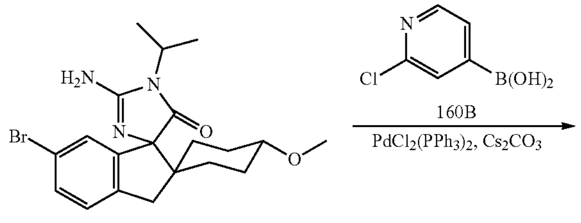

152

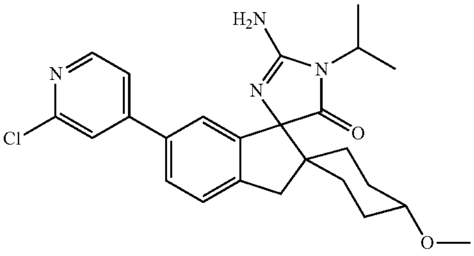

160

According to a similar synthesis of 153, compound 152 (40 mg, 0.095 mmol) was coupled with compound 160A (30 mg, 0.19 mmol) to give compound 160 (15.0 mg, 35%) as a white solid. LC-MS $t_R$=1.026 min in 2 min chromatography, MS (ESI) m/z 453 $[M+H]^+$. $^1$H NMR ($CD_3OD$ 400 MHz): δ 8.41 (d, J=5.2. Hz, 1H), 7.82 (d, J=10.0 Hz, 2H), 7.69 (m, 2H), 7.58 (d, J=8.0 Hz, 1H), 4.33 (m, 1H), 3.38 (s, 3H), 3.22 (m, 3H), 2.23 (m, 1H), 2.04 (m, 1H), 1.96 (m, 1H), 1.49 (m, 10H), 1.37 (m, 1H).

Example 124

Synthesis of Compounds 161 and 162

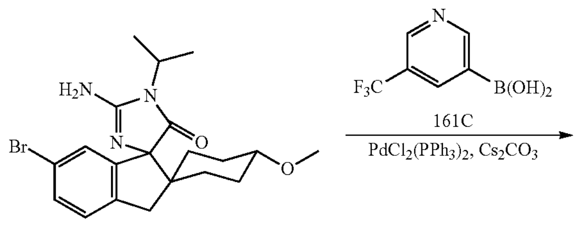

152

-continued

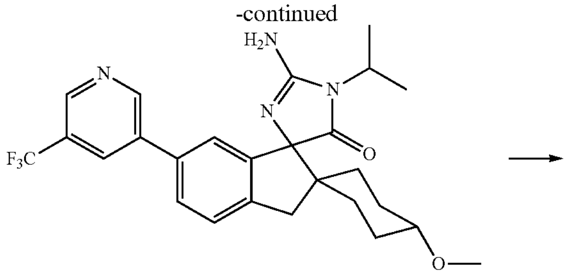

155

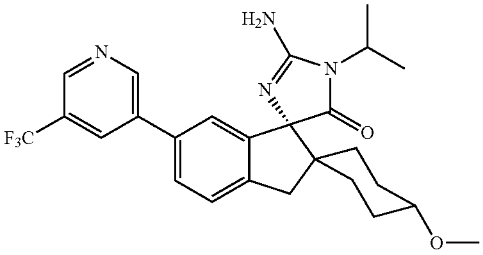

161

+

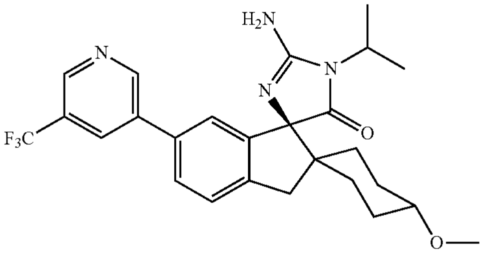

162

According to a similar synthesis of compound 153, compound 152 (200 mg, 0.476 mmol) was coupled with compound 161C (137 mg, 0.714 mmol) to give compound 155 (105 mg, 47%) as a white solid. LC-MS $t_R$=1.164 min in 2 min chromatography, MS (ESI) m/z 487 $[M+H]^+$. $^1$H NMR ($CD_3OD$ 400 MHz): δ 9.01 (s, 1H), 8.88 (s, 1H), 8.39 (s, 1H), 7.82-7.58 (m, 3H), 4.33 (m, 1H), 3.38 (s, 3H), 3.21 (m, 3H), 2.17-1.94 (m, 3H), 1.57 (m, 10H), 1.37 (m, 1H). $^{19}$F NMR ($CD_3OD$ 19F 400 MHz): δ -63.915

Compound 155 (50 mg) was separated by SFC to give compound 162 (10.30 mg) LC-MS $t_R$=1.169 min in 2 min chromatography, MS (ESI) m/z 487 $[M+H]^+$. SFC: $t_R$=5.16 min in 15 min chromatography, ee=100%; $^1$H NMR ($CD_3OD$ 400 MHz): δ 9.04 (s, 1H), 8.86 (s, 1H), 8.32 (s, 1H), 7.68 (d, J=7.8 Hz, 1H), 7.51 (d, J=7.8 Hz, 1H), 7.34 (s, 1H), 4.25 (m, 1H), 3.38 (s, 3H), 3.17 (m, 3H), 2.09 (m, 1H), 1.95 (m, 2H), 1.66 (m, 1H), 1.47 (m, 4H), 1.38 (m, 4H), 1.31 (m, 2H). $^{19}$F NMR ($CD_3OD$ 19F 400 MHz): δ -63.96.

and compound 161 (11.30 mg) as a white solid; LC-MS $t_R$=1.169 min in 2 min chromatography, MS (ESI) m/z 487 $[M+H]^+$. SFC: $t_R$=6.77 min in 15 min chromatography, ee=100%; $^1$H NMR ($CD_3OD$ 400 MHz): δ 9.06 (s, 1H), 8.87 (s, 1H), 8.32 (s, 1H), 7.68 (d, J=8.0 Hz, 1H), 7.51 (d, J=8.0 Hz, 1H), 7.35 (s, 1H), 4.23 (m, 1H), 3.38 (s, 3H), 3.18 (m, 3H), 2.10 (m, 1H), 1.95 (m, 2H), 1.67 (m, 1H), 1.46 (m, 4H), 1.39 (m, 4H), 1.30 (m, 2H). $^{19}$F NMR ($CD_3OD$ 19F 400 MHz): δ −63.96.

Example 125

Synthesis of Compound 163

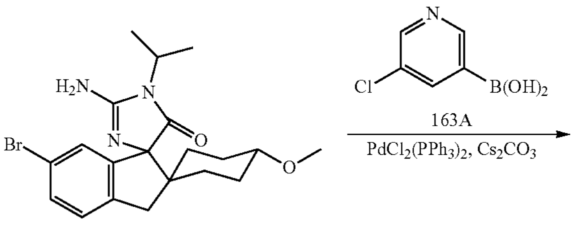

152

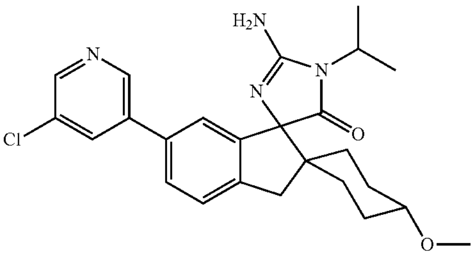

163

According to a similar synthesis of compound 153, compound 152 (20 mg, 0.048 mmol) was coupled with compound 163A (12 mg, 0.071 mmol) to give compound 163 (10.0 mg, 47%) as a white solid. LC-MS $t_R$=0.973 min in 2 min chromatography, MS (ESI) m/z 453 $[M+H]^+$. $^1$H NMR ($CD_3OD$ 400 MHz): δ 8.77 (s, 1H), 8.56 (s, 1H), 8.19 (s, 1H), 7.73 (d, J=8.0 Hz, 1H), 7.61 (s, 1H), 7.55 (d, J=8.0 Hz, 1H), 4.33 (m, 1H), 3.38 (s, 3H), 3.24 (m, 3H), 2.17 (m, 1H), 2.08 (m, 1H), 1.97 (m, 1H), 1.53-1.45 (m, 10H), 1.38 (m, 1H).

Example 126

Synthesis of Compound 164

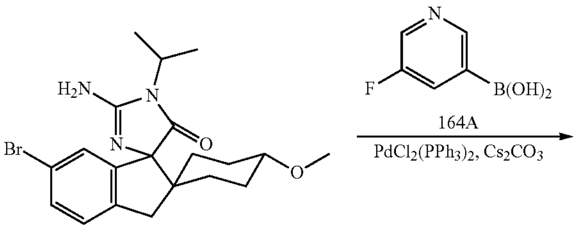

152

-continued

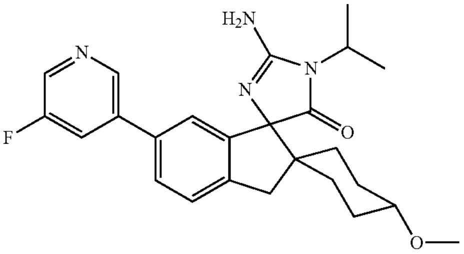

164

According to a similar synthesis of compound 153, compound 152 (20 mg, 0.048 mmol) was coupled with compound 164A (14 mg, 0.095 mmol) to give compound 164 (5.1 mg, 31%) as a white solid. LC-MS $t_R$=0.990 min in 2 min chromatography, MS (ESI) m/z 437 $[M+H]^+$. $^1$H NMR ($CD_3OD$ 300 MHz): δ 8.69 (s, 1H), 8.47 (s, 1H), 7.96 (d, J=10.2 Hz, 1H), 7.73 (d, J=7.8 Hz, 1H), 7.62 (s, 1H), 7.53 (d, J=7.8 Hz, 1H), 4.32 (m, 1H), 3.39 (s, 3H), 3.19 (m, 3H), 2.13 (m, 1H), 2.08-1.91 (m, 2H), 1.58-1.45 (m, 10H), 1.36 (m, 1H). $^{19}$F NMR ($CD_3OD$ 19F 400 MHz): δ −128.30.

Example 127

Synthesis of Compound 165

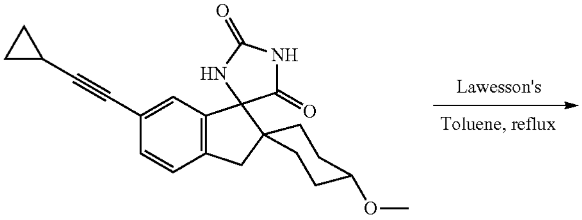

165a

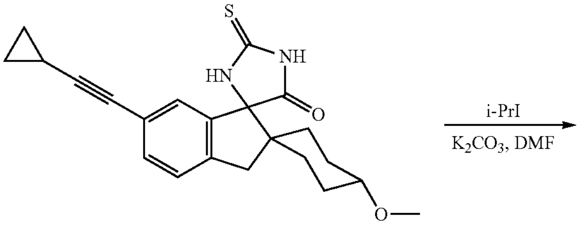

165b

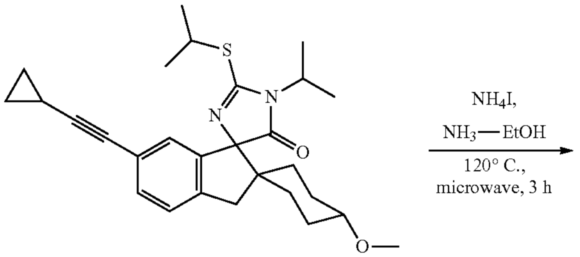

165c

-continued

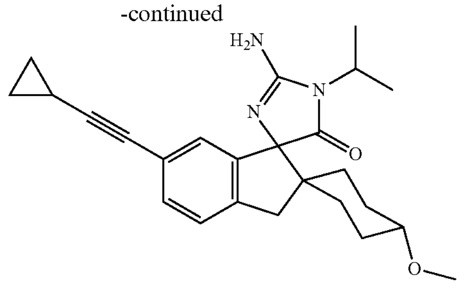

165

Procedure for Preparation of Compound 165b

A flask equipped with a condenser and a nitrogen balloon was charged with a mixture of compound 165a (0.50 g, 1.4 mmol), Lawesson's reagent (0.60 g, 1.5 mmol) in toluene (30 mL) was heated at 130° C. for 4 h. After cooling down, the precipitate was filtered off and washed with ethyl acetate (2×40 mL). The filtrate and the washing were concentrated in vacuo and the residue was purified by column chromatography on silica gel eluting with petroleum ether: EtOAc (20:1 to 5:1) to give compound 165b (0.34 g, 64%) with 80% purity as a pale brown solid.

LC-MS: $t_R$=1.94 min in 3 min chromatography, MS (ESI) m/z 381.1 $[M+H]^+$.

Procedure for Preparation of Compound 165c

A flask was charged with compound 165b (40 mg, 0.11 mmol), 2-iodopropane (75 mg, 0.44 mmol), $K_2CO_3$ (0.10 g, 0.72 mmol) and DMF (2 mL). The reaction mixture was stirred at ambient temperature overnight. The precipitate was filtered of and washed with $CH_2Cl_2$ (10 mL), and the filtrate and washings were concentrated under vacuum and the residue was dissolved in $CH_2Cl_2$ (50 mL). The mixture was washed with brine (2×20 mL). The separated organic layer was dried over $Na_2SO_4$ and concentrated in vacuo to give crude compound 165c (40 mg, 78% crude yield) as a yellow oil, which was used directly in next step without purification.

Procedure for Preparation of Compound 165

A sealed tube was charged with a mixture of compound 165c (40 mg, 0.086 mmol), $NH_4I$ (0.10 g, 0.69 mmol) and a solution of $NH_3$ in ethanol (2 mL). The mixture was heated at 120° C. in a CEM microwave reactor for 3 h. After cooling down, the solvent was removed by evaporation in vacuo and the resulting residue was purified by preparative RP-HPLC to give compound 165 (19.0 mg, 54.3%) with the purity of 99% as a white solid. LC-MS: $t_R$=1.75 min in 3 min chromatography, MS (ESI) m/z 406.2 $[M+H]^+$. $^1H$ NMR: ($CD_3OD$ 400 MHz): δ 7.30-7.35 (d, J=8.0 Hz, 1H), 7.25-7.30 (d, J=8.0 Hz, 1H), 7.10-7.15 (s, 1H), 4.20-4.30 (m, 1H), 3.30-3.35 (s, 3H), 3.10-3.20 (m, 2H), 3.00-3.10 (d, J=16.0 Hz, 1H), 2.00-2.10 (m, 1H), 1.90-2.00 (m, 1H), 1.80-1.90 (m, 1H), 1.20-1.50 (m, 11H), 0.80-0.90 (m, 2H), 0.60-0.70 (m, 2H).

Example 128

Synthesis of Compound 166

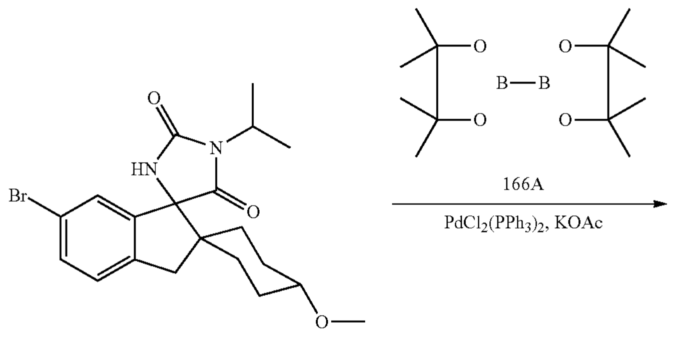

166a

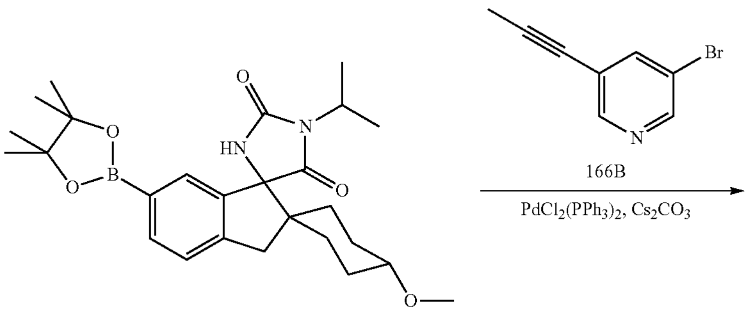

166b

-continued

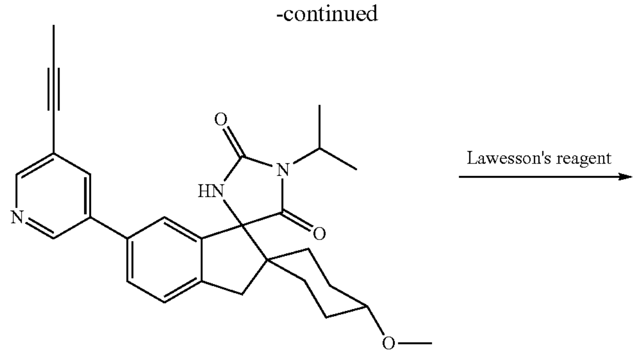

166c

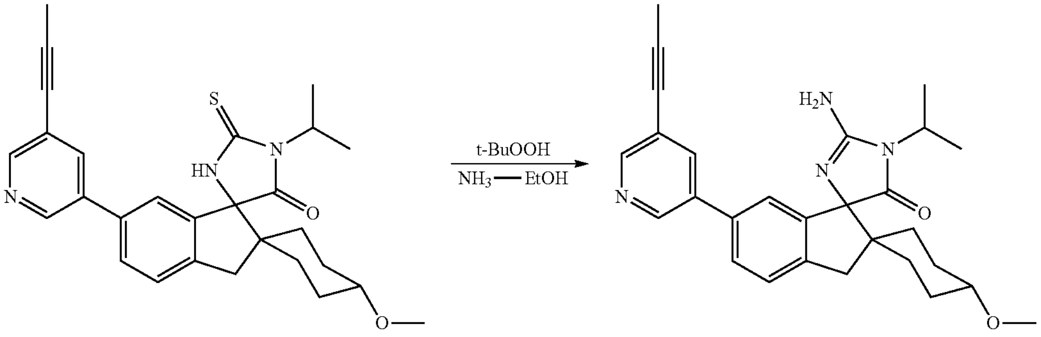

166d 166

Procedure for Preparation of Compound 166b

To a solution of compound 166a (263 mg, 0.62 mmol) in 1,4-dioxane (10 mL) was added compound 166A (190 mg, 0.75 mmol), $PdCl_2$(dppf) (79 mg), KOAc (182.3 mg, 1.86 mmol), the mixture was carried under microwave at 100° C. for 1 h under $N_2$. Then filtered, the filtrate was concentrated to give the residue which was purified by preparative TLC (hexanes:EtOAc=1:1) to give compound 166b (238.9 mg, 95%) as a white solid.

Procedure for Preparation of Compound 166c

Compound 166b (238.9 mg, 0.51 mmol) in a 10 mL of flask under $N_2$ was treated sequentially with compound 3A (50 mg, 0.255 mmol) in 1,4-dioxane (2 mL), $Cs_2CO_3$ (2 N, 0.38 mL, 0.765 mmol) and $Pd(PPh_3)_2Cl_2$ (10 mg). The mixture was heated under 120° C. under $N_2$ in a CEM microwave for 15 min. The reaction mixture was concentrated in vacuo to give the residue, which was purified by preparative TLC (hexanes: EtOAc=1:1) to give compound 166c (100 mg, 97%) as a white solid.

Procedure for Preparation of Compound 166d

A suspension of compound 166c (100 mg, 0.22 mmol) and Lawesson's reagent (88 mg, 0.22 mmol) in anhydrous toluene (2 mL) was heated 130° C. for 60 minis in a CEM microwave reactor. The reaction mixture was concentrated under reduced pressure, and purified by preparative TLC with petroleum ether:EtOAc=1:1 to give compound 166d (56 mg, 54%) as a yellow solid.

Procedure for Preparation of Compound 166

To a solution of compound 166d (56 mg, 0.12 mmol) in a mixture of MeOH (3 mL) and $NH_4OH$ (0.6 mL) was added t-BuOOH (346 mg, 2.4 mmol, 65% in water). The mixture was stirred at room temperature overnight, and concentrated. Water (15 mL) and EtOAc (3×10 mL) were added, and the organic layer was dried over $Na_2SO_4$ and concentrated to give the residue which was purified by HPLC to give compound 166 (5.8 mg, 11%) as a white solid. LC-MS $t_R$=1.014 min in 2 min chromatography, MS (ESI) m/z 457 $[M+H]^+$. $^1H$ NMR ($CD_3OD$ 400 MHz): δ 8.60 (d, J=2.0 Hz, 1H), 8.41 (d, J=1.6 Hz, 1H), 8.00 (t, J=1.6 Hz, 1H), 7.60 (m, 1H), 7.45 (m, 2H), 4.20 (m, 2H), 3.26 (s, 3H), 3.20 (m, 1H), 3.15 (m, 2H), 1.99 (m, 4H), 1.85 (m, 2H), 1.40 (m, 3H), 1.36 (m, 7H), 1.21 (m, 1H).

Example 129

Synthesis of Compound 167

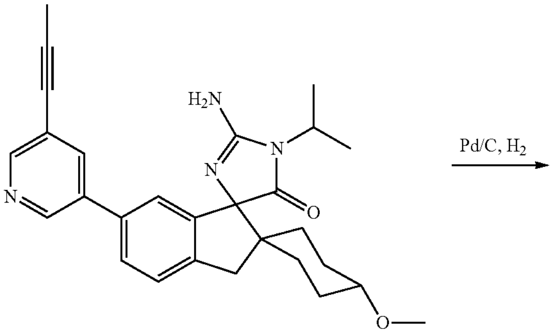

166

-continued

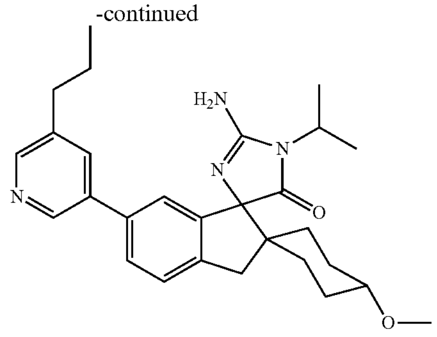

167

A solution of compound 166 (14 mg, 0.03 mmol) and Pd/C (3 mg) in MeOH (5 mL) was stirred at room temperature for 1 h. The reaction mixture was concentrated, added $CH_2Cl_2$ (20 mL), filtered, concentrated, and purified by preparative HPLC (0.1% TFA as additive) to give compound 167 (3.0 mg, 21%) as a TFA salt. LC-MS $t_R$=0.917 min in 2 min chromatography, MS (ESI) m/z 461 $[M+H]^+$. $^1H$ NMR ($CD_3OD$ 400 MHz): δ 8.82 (s, 1H), 8.57 (s, 1H), 8.38 (s, 1H), 7.80 (m, 1H), 7.66 (m, 1H), 7.57 (m, 1H), 4.36 (m, 2H), 3.46 (s, 3H), 3.20 (m, 1H), 3.15 (m, 2H), 2.86 (m, 2H), 2.14 (m, 1H), 2.05 (m, 1H), 1.97 (m, 1H), 1.79 (m, 2H), 1.54 (m, 4H), 1.48 (m, 6H), 1.37 (m, 1H), 1.05 (m, 3H).

Example 130

Synthesis of Compound 168

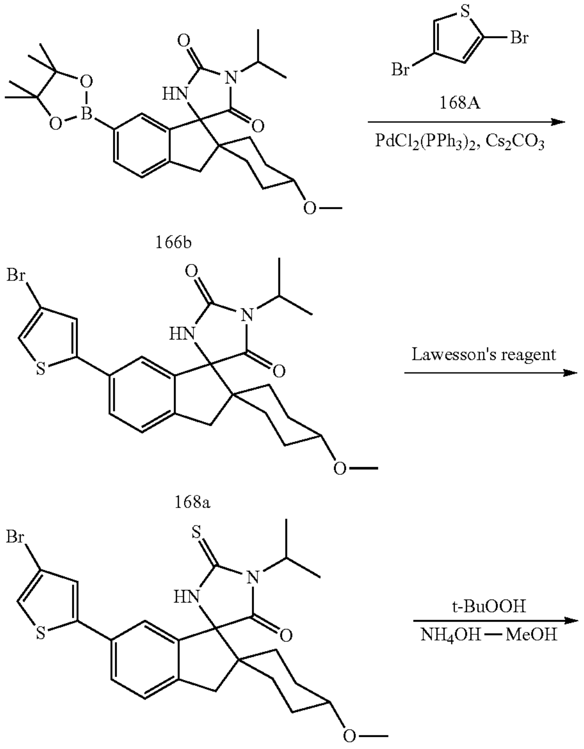

166b

168a

168b

-continued

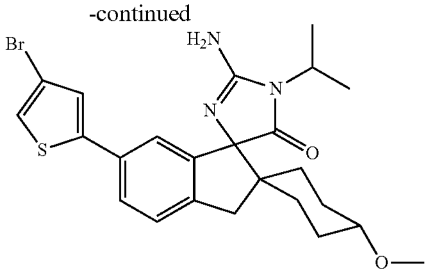

168

According to a similar synthesis of compound 166, compound 166b (100 mg, 0.213 mmol) was coupled with compound 168A (103 mg, 0.426 mmol) to give compound 168a (60 mg, 56%) as a white solid. LC-MS: $t_R$=1.326 min in 2 min chromatography, MS (ESI) m/z=503.1, 506.0 $[M+H]^+$. $^1H$ NMR ($CD_3CN$ 400 MHz): δ 7.45-7.48 (m, 1H), 7.28-7.29 (m, 1H), 7.20-7.26 (m, 2H), 4.07-4.15 (m, 1H), 3.18 (s, 3H), 2.97-3.05 (m, 3H), 2.07-2.10 (m, 2H), 1.74-1.83 (m, 6H), 1.23-1.27 (m, 6H).

Compound 168a (114 mg, 0.227 mmol) was reacted with Lawesson's reagent (92 mg, 0.227 mmol) to give compound 168b (80 mg, 68%) as a yellow solid. LC-MS: $t_R$=1.401 min in 2 min chromatography, MS (ESI) m/z=519.0, 521.0 $[M+H]^+$. Compound 168b (80 mg, 0.154 mmol) was then converted to compound 168 (3.4 mg, 34%) as a white solid. LC-MS: $t_R$=1.070 min in 2 min chromatography, MS (ESI) m/z=502.0 $[M+H]^+$. $^1H$ NMR ($CD_3OD$ 400 MHz): δ 7.53-7.56 (dd, J=1.6, 8.0 Hz, 1H), 7.41-7.41 (d, J=1.2 Hz, 1H), 7.32-7.34 (d, J=8.0 Hz, 1H), 7.29-7.30 (d, J=1.6 Hz, 2H), 4.19-4.25 (m, 1H), 3.27 (s, 3H), 3.01-3.12 (m, 3H), 1.99-2.02 (m, 1H), 1.81-1.93 (m, 2H), 1.38-1.43 (m, 6H), 1.18-1.36 (m, 5H).

Example 131

Synthesis of Compound 169

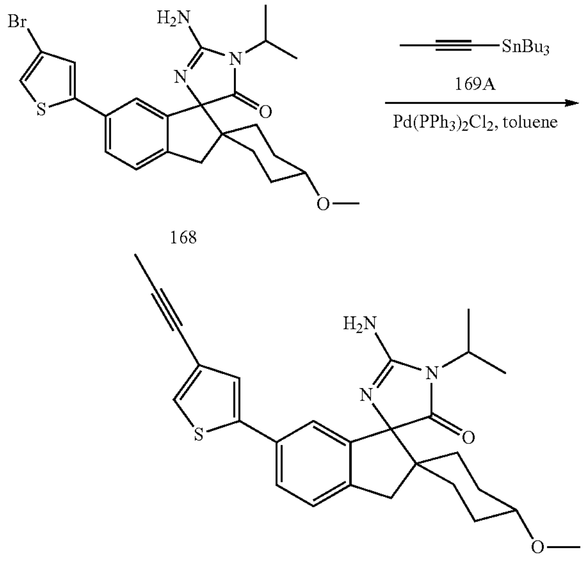

168

169

A solution containing compound 168 (45 mg, 0.09 mmol) and compound 169A (89 mg, 0.27 mmol) in toluene (1 mL) was deoxygenated by bubbling a stream of nitrogen through the reaction mixture for 5 min. Then, $Pd(PPh_3)_2Cl_2$ (5 mg) was added. The mixture was stirred at 135° C. for 45 min in microwave. LCMS showed that the reaction was completed. The reaction mixture was concentrated in vacuo to give the residue. The residue was partitioned by EtOAc (50 mL) and aqueous of CsF (4M, 50 mL). The aqueous layer was extracted by EtOAc (2×50 mL), the combined organic layers were washed with brine (2×50 mL), dried over anhydrous $Na_2SO_4$ and concentrated to dryness. Purification of this residue by preparative TLC ($CH_2Cl_2$: MeOH=10:1) and preparative HPLC afforded compound 169 (3.4 mg, 8%) as a white solid. LC-MS: $t_R$=1.114 min in 2 min chromatography, MS (ESI) m/z=462.2 $[M+H]^+$. $^1$H NMR ($CD_3OD$ 400 MHz): δ 7.91-7.93 (dd, J=1.6, 8.0 Hz, 1H), 7.83 (s, 1H), 7.12 (s, 1H), 7.51-7.53 (d, J=7.6 Hz, 1H), 4.30-4.37 (m, 1H), 3.38 (s, 3H), 3.19-3.28 (m, 3H), 2.03-2.13 (m, 4H), 1.94-1.98 (m, 2H), 1.48-1.54 (m, 3H), 1.33-1.42 (m, 8H).

Example 132

Synthesis of Compound 170

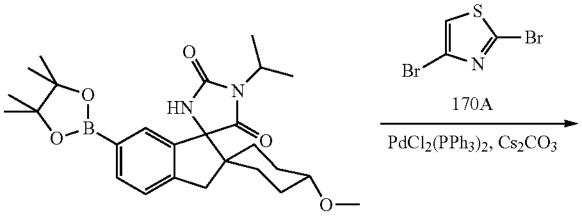

166b

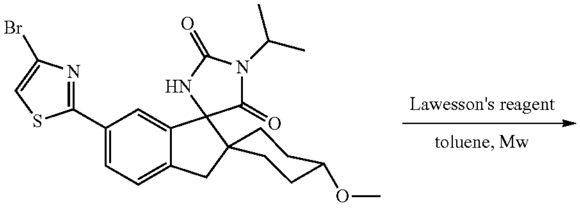

170a

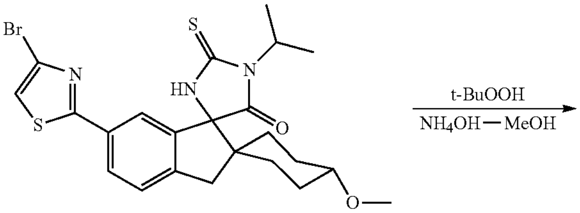

170b

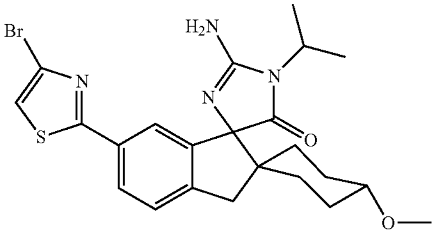

170

According to a similar synthesis of compound 166, compound 166b (50 mg, 0.107 mmol) was coupled with compound 170A (52 mg, 0.213 mmol) to give compound 170a (40 mg, 74%) as a white solid. LC-MS: $t_R$=1.260 min in 2 min chromatography, MS (ESI) m/z=504.1, 506.1 $[M+H]^+$.

Compound 170a (100 mg, 0.20 mmol) was reacted with Lawesson's reagent (81 mg, 0.20 mmol) to give compound 170b (80 mg, 78%) as a yellow solid. LC-MS: $t_R$=1.593 min in 2 min chromatography, MS (ESI) m/z=522.2 $[M+H]^+$. Compound 170b (80 mg, 0.154 mmol) was then converted to compound 170 with 60% purity (60 mg, 46%) as a white solid. 15 mg of the product was further purified by preparative HPLC to give compound 170 (5.3 mg, 58%) as a white solid. LC-MS: $t_R$=1.044 min in 2 min chromatography, MS (ESI) m/z=503.1, 505.1 $[M+H]^+$. $^1$H NMR ($CD_3OD$ 400 MHz): δ 7.93-7.95 (dd, J=1.6, 8.0 Hz, 1H), 7.86 (s, 1H), 7.60 (s, 1H), 7.52-7.54 (d, J=8.0 Hz, 1H), 4.29-4.35 (m, 1H), 3.37 (s, 3H), 3.20-3.27 (m, 3H), 2.10-2.13 (m, 1H), 1.94-2.03 (m, 2H), 1.52-1.54 (m, 3H), 1.47-1.50 (m, 3H), 1.32-1.39 (m, 5H).

Example 133

Synthesis of Compound 171

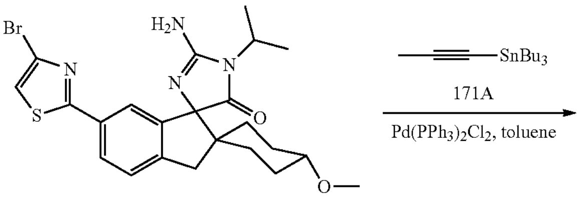

170

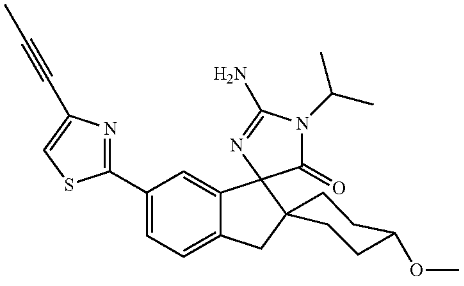

171

According to a similar synthesis of compound 169, compound compound 170 (50 mg, 0.1 mmol) was coupled with compound 171A (99 mg, 0.3 mmol) to give compound 171 (9.4 mg, 20%) as a white solid. LC-MS: $t_R$=1.158 min in 2 min chromatography, MS (ESI) m/z=463.3 $[M+H]^+$. $^1$H NMR ($CD_3OD$ 400 MHz): δ 7.40-7.42 (dd, J=1.6, 8.0 Hz, 1H), 7.20-7.22 (d, J=9.6 Hz, 2H), 7.12 (s, 1H), 7.06 (s, 1H), 4.10-4.14 (m, 1H), 3.24 (s, 3H), 3.01-3.06 (m, 1H), 2.91-2.99 (m, 2H), 1.92-1.94 (m, 1H), 1.87-1.89 (m, 3H), 1.80-1.83 (m, 2H), 1.45-1.52 (m, 1H), 1.29-1.33 (m, 3H), 1.19-1.27 (m, 5H), 1.13-1.17 (m, 2H).

Example 134
Synthesis of Compound 172
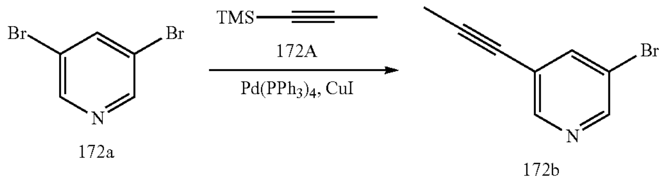
172a 172b
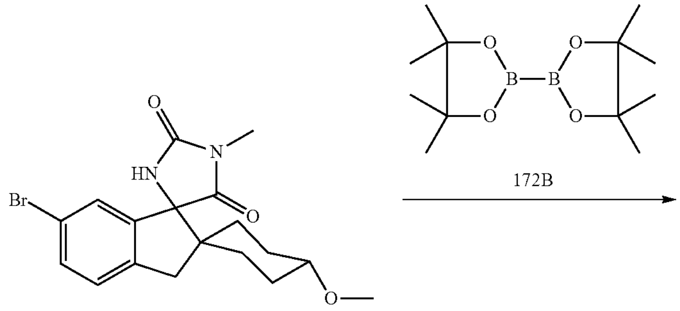
172c
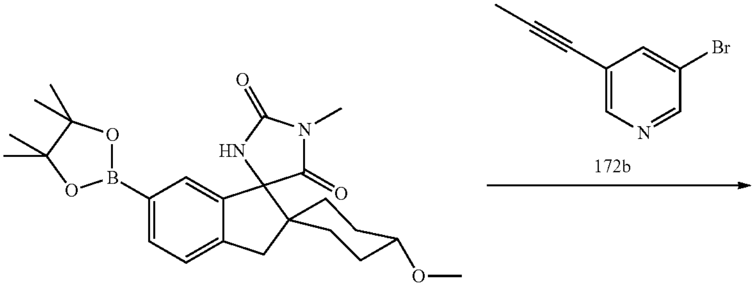
172d
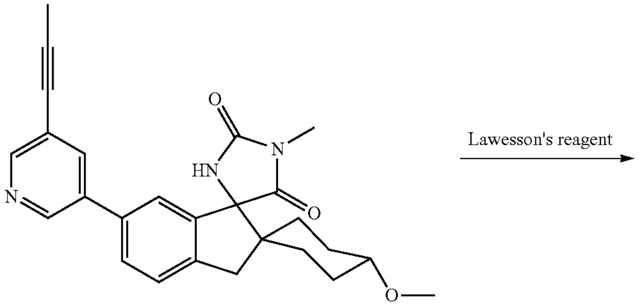
172e
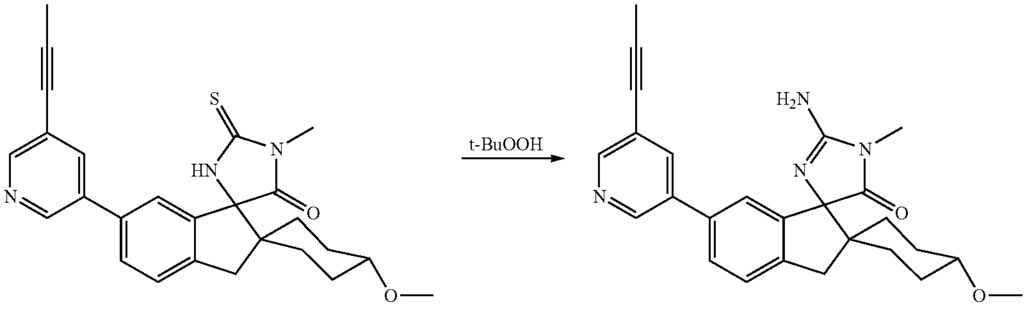
172f 172

Procedure for Preparation of Compound 172b

A mixture of compound 172a (1 g, 4.22 mmol), compound 172A (474 mg, 4.22 mmol), CuI (241 mg, 1.27 mmol), $Et_3N$ (1.4 g, 13.9 mmol), $Pd(PPh_3)_4$ (244 mg, 0.21 mmol) in toluene (200 mL) was stirred at room temperature for 3 h before it was extracted with $CH_2Cl_2$ (3×100 mL) and water (200 mL). The organic layer was dried, evaporated and the residue was purified by column chromatography (hexanes: EtOAc=100:1) to give compound 172b (200 mg, 24%) as a white solid. $^1$H NMR ($CDCl_3$ 400 MHz): δ 8.48 (d, J=12.4 Hz, 2H), 7.74 (t, J=2.0 Hz, 1H), 2.00 (s, 3H).

Procedure for Preparation of Compound 172d

To a solution of compound 172c (120 mg, 0.31 mmol) in 1,4-dioxane (3 mL) was added compound 172B (93.3 mg, 0.37 mmol), $PdCl_2$(dppf) (36 mg), KOAc (91.1 mg, 0.93 mmol), the mixture was carried under microwave at 100° C. for 1 h under $N_2$. Then filtered, the filtrate was concentrated to give the residue which was purified by preparative TLC (hexanes:EtOAc=3:1) to give compound 172d (100 mg, 74%) as a white solid.

Procedure for Preparation of Compound 172e $PdCl_2(PPh_3)_2$ (10 mg) in a 10 mL of flask under $N_2$ was treated sequentially with compound 172d (224.6 mg, 0.51 mmol), in 1,4-dioxane (2 mL), and compound 172b (50 mg, 0.225 mmol), $Cs_2CO_3$ (2 N, 0.38 mL, 0.765 mmol). The mixture was heated under 120° C. at $N_2$ under microwave for 15 min. The reaction mixture was concentrated in vacuo to give the residue, which was purified by preparative TLC (hexanes:EtOAc=1:1) to give compound 172e (100 mg, 91%) as a white solid.

Procedure for Preparation of Compound 172f

A suspension of compound 172e (49 mg, 0.11 mmol) and Lawesson's reagent (46 mg, 0.11 mmol) in anhydrous toluene (2 mL) was heated 140° C. for 40 min in a CEM microwave reactor. The reaction mixture was concentrated under reduced pressure, and purified by preparative TLC (hexanes: EtOAc=3:1) to give compound 172f (30 mg, 59%) as a white solid.

Procedure for Preparation of Compound 172

To a solution of compound 172f (30 mg, 0.067 mmol) in a mixture of MeOH (3 mL) and $NH_4OH$ (0.6 mL) was added t-BuOOH (128 mg, 1.35 mmol, 65% in water). The mixture was stirred at room temperature overnight, and concentrated. Water (15 mL) and EtOAc (3×10 mL) were added, and the organic layer was dried over $Na_2SO_4$ and concentrated to give the residue which was purified by HPLC to give compound 172 (13.4 mg, 46%) as a white solid. LC-MS: $t_R$=0.894 min in 2 min chromatography, MS (ESI) m/z 429 $[M+H]^+$. $^1$H NMR ($CD_3OD$ 400 MHz): δ 8.72 (d, J=2.0 Hz, 1H), 8.53 (d, J=1.2 Hz, 1H), 8.13 (s, 1H), 7.71 (m, 1H), 7.55 (m, 2H), 3.50 (s, 3H), 3.25 (m, 1H), 3.22 (s, 3H), 3.15 (m, 2H), 2.11 (s, 3H), 2.04 (m, 1H), 1.89 (m, 1H), 1.43 (m, 6H).

Example 135

Synthesis of Compound 173

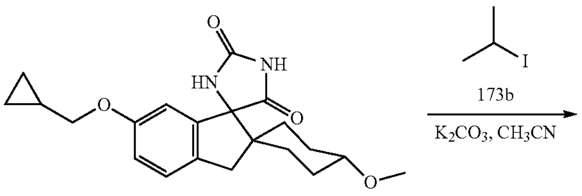

173a

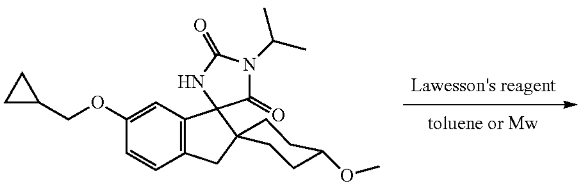

173c

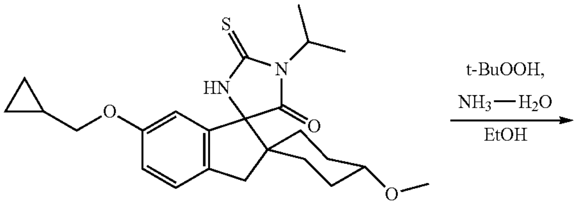

173d

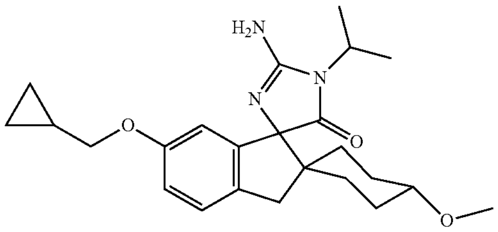

173

Procedure for Preparation of Compound 173c

To a solution of compound 173a (30 mg, 0.08 mmol) in $CH_3CN$ (2 mL) was added $K_2CO_3$ (22.3 mg, 0.16 mmol), and compound 173b (9.6 mg, 0.08 mmol), the mixture was stirred at 80° C. for 15 min in microwave, the precipitate was filtered off, the filtrate was concentrated to give the crude product which was purified by preparative TLC on silica gel eluting with hexane:EtOAc=3:1 to afford compound 173c (23 mg, 68%) as a white solid. $^1$H NMR ($CDCl_3$ 400 MHz): δ 7.19 (d, J=8.0 Hz, 1H), 6.75 (m, J=8.4 Hz, 1H), 6.54 (s, 1H), 4.25-4.22 (m, 1H), 3.67-3.65 (d, J=6.8 Hz, 2H), 3.44 (s, 3H), 3.04-2.91 (m, 2H), 2.91-2.87 (m, 1H), 2.0-1.90 (m, 2H), 1.49-1.39 (m, 6H), 1.39-1.32 (m, 1H), 1.26-1.18 (d, J=6.0 Hz, 6H), 0.68-0.58 (m, 2H), 0.38-0.27 (m, 2H).

Procedure for Preparation of Compound 173d

To a solution of compound 173c (23 mg, 0.055 mmol) in anhydrous toluene (2 mL) was added Lawesson's Reagent (24.7 mg, 0.06 mmol) under $N_2$, the mixture was stirred at 130° C. in a CEM microwave reactor for 40 min. After cooling, the solvent was removed by evaporation in vacuo to give the crude product which was purified by preparative TLC on silica gel eluting with hexane:EtOAc=3:1 to afford compound 173d (15 mg, 63%) as a white solid. LCMS: $t_R$=1.504 min in 2 min chromatography, MS (ESI) m/z=429.2 $[M+H]^+$.

Procedure for Preparation of Compound 173

To a solution of compound 173d (15 mg, 0.035 mmol) in EtOH (5 mL) was added t-BuOOH (0.5 mL) and $NH_3.H_2O$ (1.5 mL), the mixture was stirred at room temperature overnight, the reaction was completed detecting by LCMS. The mixture was concentrated in vacuo, and the residue was purified by preparative TLC on silica gel eluting with dichloromethane:methanol=10:1 and then by preparative HPLC to give compound 173 (3.0 mg, 20%) as a white solid. LCMS: $t_R$=1.867 min in 2 min chromatography, MS (ESI) m/z=412.3 $[M+H]^+$. $^1H$ NMR ($CD_3OD$ 400 MHz): δ 7.18 (d, J=8.0 Hz, 1H), 6.83 (d, J=8.4 Hz, 1H), 6.51 (s, 1H), 4.24 (m, 1H), 3.78 (d, J=7.2 Hz, 2H), 3.35 (s, 3H), 3.15-3.04 (m, 1H), 3.04-2.93 (m, 2H), 2.10-1.90 (m, 3H), 1.56-1.53 (m, 1H), 1.53-1.44 (d, J=6.8 Hz, 3H), 1.44-1.39 (d, J=8.0 Hz, 3H), 1.39-1.37 (m, 1H), 1.37-1.22 (m, 4H), 0.60-0.58 (m, 2H), 0.33-0.32 (m, 2H)

Example 136

Synthesis of Compounds 174 and 175

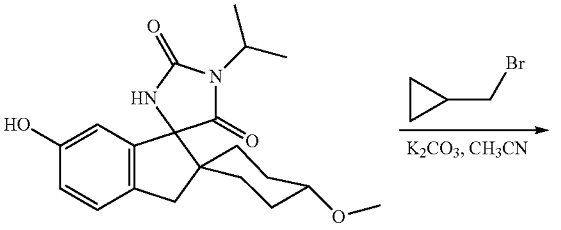

174a

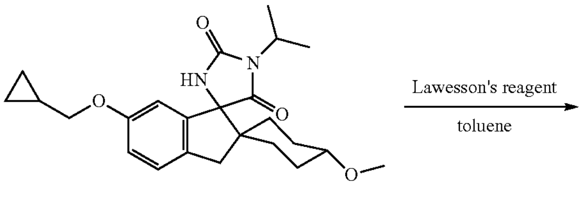

174b

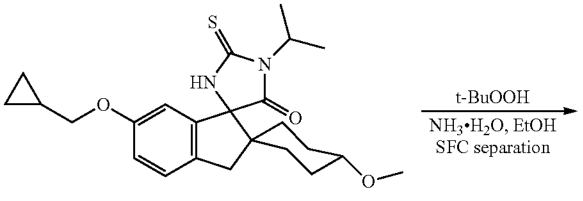

174c

-continued

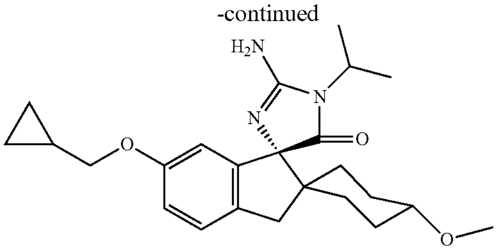

+

174

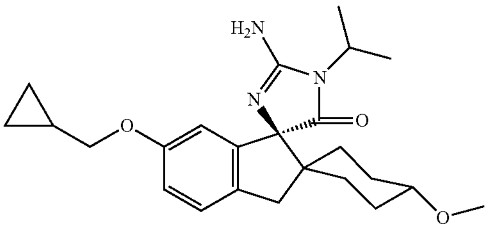

175

Procedure for Preparation of Compound 174b

To a solution of compound 174a (150 mg, 0.41 mmol) in anhydrous $CH_3CN$ (10 mL) was added $K_2CO_3$ (115.6 mg, 0.82 mmol) and bromomethyl-cyclopropane (62.6 mg, 0.46 mmol). The resulting suspension was stirred at 60° C. for 5 h. The precipitate was filtered off and the filtrate was concentrated to give the crude product which was purified by preparative TLC on silica gel eluting with petroleum ether:ethyl acetate=3:1 to give compound 174b (100 mg, 55%); LC-MS: $t_R$=1.216 min in 2 min chromatography, MS (ESI) m/z=413.2 $[M+H]^+$.

Procedure for Preparation of Compounds 174 and 175

The same synthesis for compound 173 was applied for this synthesis, and compound 174b (100 mg, 0.24 mmol) gave compound 174c (67 mg, 65%), which was converted to compound 173. Preparative SFC to give compound 174 (12.8 mg, 11%); LC-MS: $t_R$=0.988 min in 2 min chromatography, MS (ESI) m/z=412.1 $[M+H]^+$. SFC: $t_R$=6.26 min in 16 min chromatography, ee %=100%. $^1H$ NMR ($CD_3OD$, 400 MHz): δ 7.25-7.08 (d, J=8.4 Hz, 1H), 6.90-6.82 (dd, J=2.0, 8.0 Hz, 1H), 6.46 (s, 1H), 4.40-4.10 (m, 1H), 3.80-3.74 (d, J=6.8 Hz, 2H), 3.35 (s, 3H), 3.14 (m, 1H), 3.10-2.90 (m, 2H), 2.10-2.01 (m, 1H), 2.01-1.85 (m, 2H), 1.60-1.50 (m, 1H), 1.50-1.40 (d, J=6.8 Hz, 3H), 1.40-1.35 (d, J=6.8 Hz, 3H), 1.35-1.15 (m, 5H), 0.70-0.50 (m, 2H), 0.40-0.30 (m, 2H); and compound 175 (10.0 mg, 15%), LC-MS: $t_R$=0.992 min in 2 min chromatography, MS (ESI) m/z=412.1 $[M+H]^+$. SFC: $t_R$=7.76 min in 16 min chromatography, ee %=98%. $^1H$ NMR ($CD_3OD$, 400 MHz): δ 7.13-7.06 (d, J=8.4 Hz, 1H), 6.83-6.74 (dd, J=2.0, 8.0 Hz, 1H), 6.44 (s, 1H), 4.20-4.00 (m, 1H), 3.70-3.60 (d, J=6.8 Hz, 2H), 3.36 (s, 3H), 3.10-3.01 (m, 1H), 3.00-2.81 (m, 2H), 2.00-1.91 (m, 1H), 1.90-1.75 (m, 2H), 1.50-1.35 (m, 1H), 1.35-1.30 (d, J=6.4 Hz, 3H), 1.30-1.25 (d, J=6.8 Hz, 3H), 1.25-1.05 (m, 1H), 1.10-1.00 (m, 4H), 0.60-0.40 (m, 2H), 0.30-0.11 (m, 2H).

Example 137

Synthesis of Compound 176

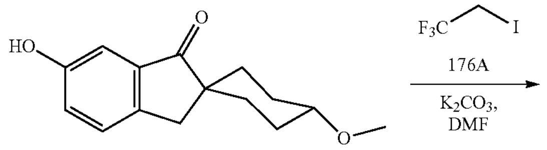

176a

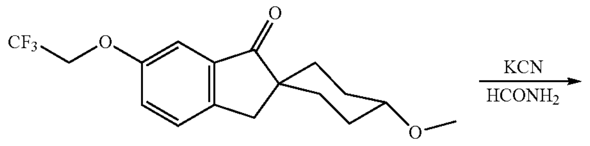

176b

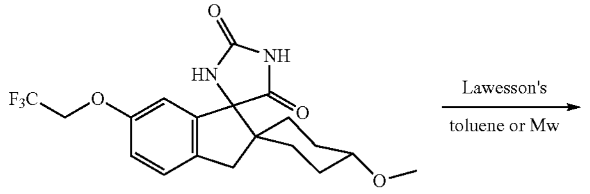

176c

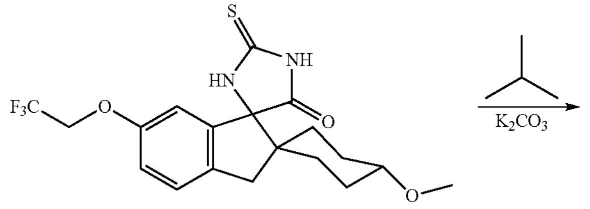

176d

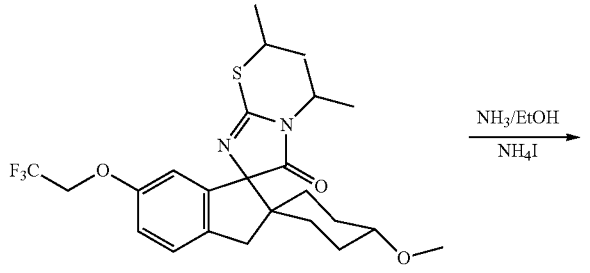

176e

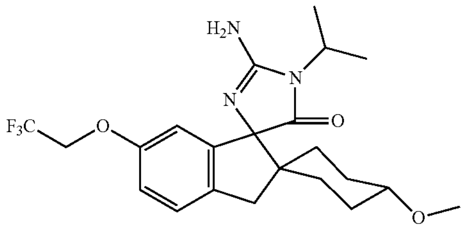

176

Procedure for Preparation of Compound 176b

To a solution of compound 176a (500 mg, 2.02 mmol) in DMF (2 mL) was added $K_2CO_3$ (559 mg, 4.04 mmol), and compound 176A (516.6 mg, 2.22 mmol), the mixture was stirred at ambient temperature overnight. The reaction was added with $H_2O$ (10 mL), and the aqueous layer was extracted with EtOAc (10 mL×3). The combined organic layers were washed with brine (30 mL), dried over $Na_2SO_4$ and concentrated to give compound 176b (400 mg, 60%) as a white solid, which was used in the next step without further purification. $^1$H NMR ($CDCl_3$ 400 MHz): δ 7.34 (d, J=8.4 Hz, 1H), 7.27 (d, J=8.4 Hz, 1H), 7.19 (s, 1H), 4.33 (dd, J=8.0, 40.4 Hz, 2H), 3.43 (s, 3H), 3.18-3.22 (m, 1H), 2.96 (s, 2H), 1.97-2.06 (m, 2H), 1.73-1.85 (m, 2H), 1.45-1.52 (m, 2H), 1.34-1.45 (m, 2H).

Procedure for Preparation of Compound 176

According to a similar synthesis for Acylguanidine 1-6 described in Example I-2, compound 176b (400 mg, 1.21 mmol), was condensed to hydantoin 176c (80 mg, 16%) as a white solid. LCMS: $t_R$=1.080 min in 2 min chromatography, MS (ESI) m/z=399.1[M+H]$^+$.

Compound 176c (50 mg, 0.12 mmol) was reacted with Lawesson's Reagent (50.7 mg, 0.12 mmol) to afford compound 176d (25 mg, 50%) as a white solid. LCMS: $t_R$=1.250 min in 2 min chromatography, MS (ESI) m/z=415.1[M+H]

Compound 176d (25 mg, 0.06 mmol) was then dialkylated with 2-iodo-propane (40.7 mg, 0.24 mmol) to give compound 176e (15 mg, 50%) as a white solid. LCMS: $t_R$=1.726 min in 2 min chromatography, MS (ESI) m/z=499.2 [M+H]

Finally, compound 176e (15 mg, 0.03 mmol) was converted to compound 176 (0.8 mg, 6%) as a white solid. LCMS: 694-139-1 $t_R$=1.936 min in 3 min chromatography, MS (ESI) m/z=440.2 [M+H]$^+$. $^1$H-NMR ($CD_3OD$ 400 MHz): δ 7.27 (d, J=8.0 Hz, 1H), 6.94 (d, J=6.0 Hz, 1H), 6.65 (s, 1H), 4.50 (dd, J=6.4, 8.4 Hz, 2H), 4.46 (m, 1H), 3.36 (s, 3H), 3.07-3.15 (m, 1H), 2.98-3.03 (m, 2H), 1.98-2.05 (m, 4H), 1.89 (m, 2H), 1.54 (d, J=11.2 Hz, 3H), 1.45 (d, J=6.8 Hz, 3H), 1.27-1.32 (m, 2H). $^{19}$FNMR: ($CD_3OD$ 400 MHz): δ −75.806

Example 138

Synthesis of Compound 177

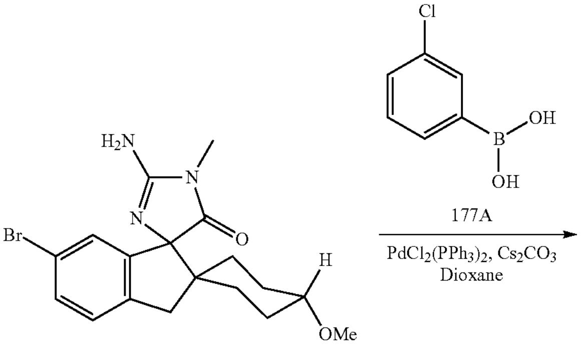

I-6

-continued

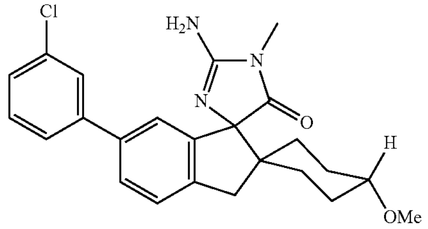

177

According to a similar synthesis of compound 4 described in Example 27, compound I-6 (30 mg, 0.076 mmol) was coupled with compound 177A (24 mg, 0.153 mmol) to give compound 177 (15 mg, yield 47%). LC-MS $t_R$=1.025 min in 2 min chromatography, MS (ESI) m/z 424.0.1 $[M+H]^+$; $^1H$ NMR ($CD_3OD$ 400 MHz): δ 7.58 (s, 2H), 7.47 (m, 2H), 7.13-7.39 (m, 3H), 3.28 (s, 3H), 3.05-3.17 (m, 6H), 1.92-2.07 (m, 2H), 1.81 (d, 1H), 1.19-1.45 (m, 5H).

Example 139

Synthesis of Compound 178

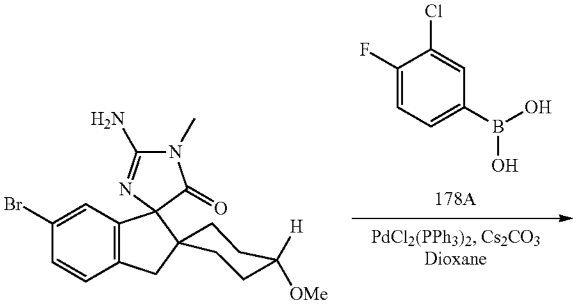

I-6

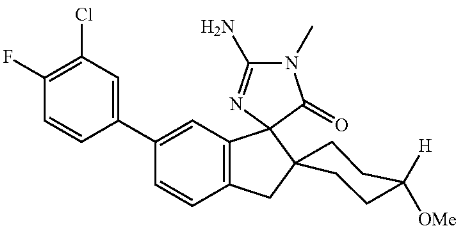

178

According to a similar synthesis of compound 4 described in Example 27, compound I-6 (25 mg, 0.06 mmol) was coupled with compound 178A (21 mg, 0.12 mmol) to give compound 178 (9.1 mg, 32%) as a white solid. LC-MS $t_R$=1.012 min in 2 min chromatography, MS (ESI) m/z 442.1 $[M+H]^+$; $^1H$ NMR ($CD_3OD$ 400 MHz): δ 7.56 (m, 1H), 7.37-7.43 (m, 2H), 7.27 (m, 1H), 7.17 (m, 1H), 7.05 (m, 1H), 3.24 (s, 3H), 2.96-3.07 (m, 3H), 2.93 (s, 3H), 1.74-1.93 (m, 3H), 1.51 (m, 1H), 1.17-1.30 (m, 4H).

Example 140

Synthesis of Compound 179

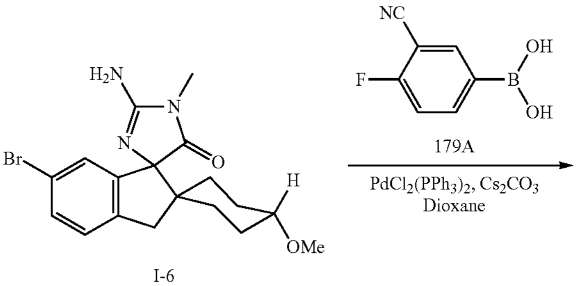

I-6

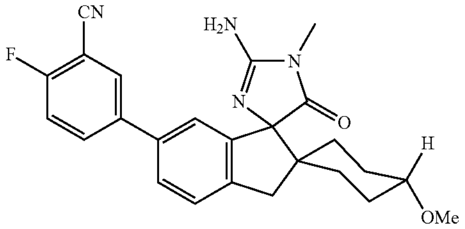

179

According to a similar synthesis of compound 4 described in Example 27, compound I-6 was coupled with compound 179A (17 mg, 0.103 mmol) to give compound 179 (5.6 mg, yield 25%). LC-MS $t_R$=0.956 min in 2 min chromatography, MS (ESI) m/z 433.1 $[M+H]^+$; $^1H$ NMR ($CD_3OD$ 400 MHz): δ 7.91 (m, 1H), 7.83 (m, 1H), 7.44 (m, 1H), 7.32 (m, 2H), 7.13 (s, 1H), 3.28 (s, 3H), 3.17 (m, 3H), 2.94 (s, 3H), 2.01-1.84 (m, 2H), 1.78 (m, 1H), 1.57 (m, 1H), 1.42-1.17 (m, 4H)

Example 141

Synthesis of Compound 180

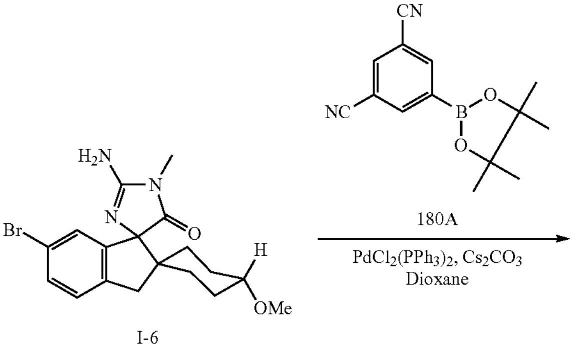

I-6

-continued

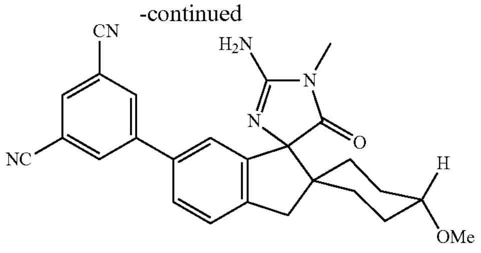

180

According to a similar synthesis of compound 4 described in Example 27, compound I-6 was coupled with compound 180A (32 mg, 0.128 mmol) to give compound 180 (4.4 mg, yield 20%). LC-MS $t_R$=1.056 min in 2 min chromatography, MS (ESI) m/z 440.2 $[M+H]^+$; $^1H$ NMR ($CD_3OD$ 400 MHz): δ 8.19 (s, 2H), 8.02 (s, 1H), 7.55-7.53 (m, 1H), 7.38-7.36 (d, J=8.0 Hz, 1H), 7.25 (s, 1H), 3.43-3.32 (m, 3H), 3.26-3.22 (m, 2H), 3.08-3.05 (m, 1H), 2.97 (s, 3H), 1.95-1.87 (m, 2H), 1.76 (m, 1H), 1.56-1.52 (m, 1H), 1.35-1.29 (m, 2H), 1.23-1.20 (m, 2H).

Example 142

Synthesis of Compound 181

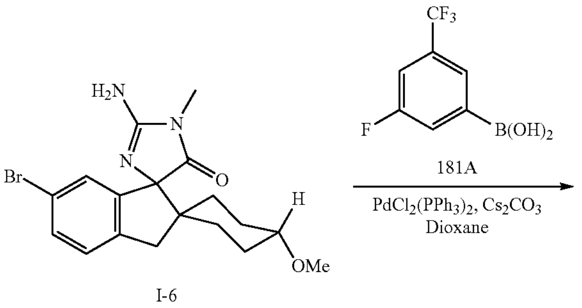

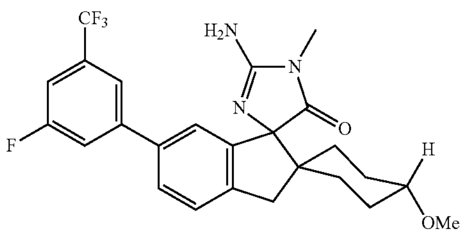

181

According to a similar synthesis of compound 4 described in Example 27, compound I-6 (20 mg, 0.051 mmol) was coupled with compound 181A (21.2 mg, 0.102 mmol) to give compound 181 (5.6 mg, yield 25%). LC-MS $t_R$=1.035 min in 2 min chromatography, MS (ESI) m/z 476.1 $[M+H]^+$; $^1H$ NMR ($CD_3OD$ 300 MHz): δ 7.69-7.57 (m, 3H), 7.46-7.40 (m, 2H), 7.25 (s, 1H), 3.36 (s, 3H), 3.22-3.08 (m, 3H), 3.05 (s, 3H), 2.04-1.85 (m, 3H), 1.72-1.63 (m, 1H), 1.46-1.18 (m, 4H).

Example 143

Synthesis of Compound 182

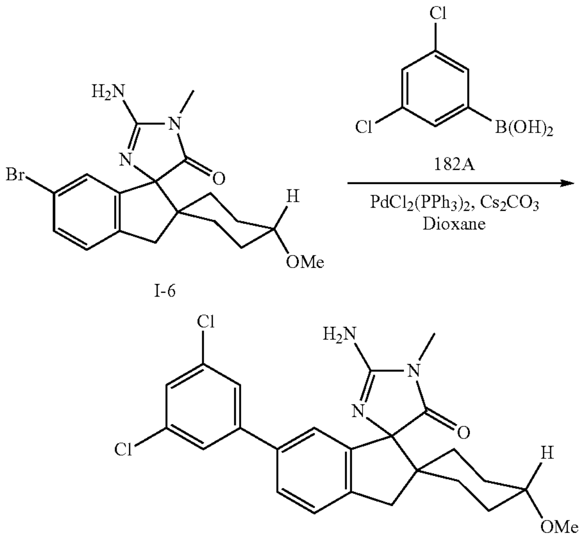

182

According to a similar synthesis of compound 4 described in Example 27, compound I-6 (20 mg, 0.051 mmol) was coupled with compound 182A (19 mg, 0.102 mmol) to give compound 182 (1.56 mg, yield 7%). LC-MS $t_R$=1.071 min in 2 min chromatography, MS (ESI) m/z 458.0 $[M+H]^+$; $^1H$ NMR ($CDCl_3$ 400 MHz): δ 7.38-7.31 (m, 4H), 7.23 (s, 1H), 7.11 (s, 1H), 3.29 (s, 3H), 3.18 (d, J=15.6 Hz, 1H), 3.04 (m, 5H), 1.85-1.98 (m, 3H), 1.45 (m, 1H), 1.34 (m, 2H), 1.27 (m, 2H).

Example 144

Synthesis of Compound 183

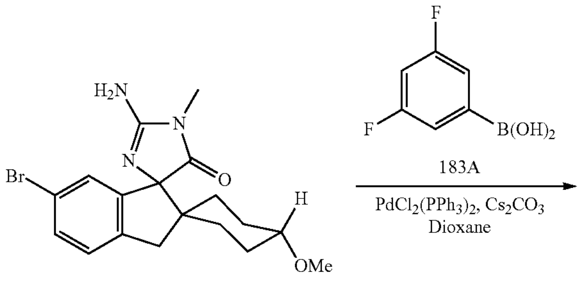

I-6

-continued

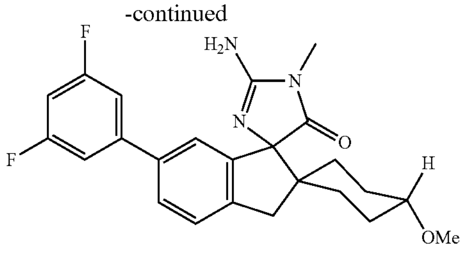

183

According to a similar synthesis of compound 4 described in Example 27, compound I-6 (20 mg, 0.051 mmol) was coupled with compound 183A (16 mg, 0.102 mmol) to give compound 183 (3.8 mg, yield 18%). LC-MS $t_R$=0.989 min in 2 min chromatography, MS (ESI) m/z 426.1 $[M+H]^+$; $^1H$ NMR ($CD_3OD$ 400 MHz): δ 7.58 (d, J=7.6 Hz, 1H), 7.42 (d, J=8.0 Hz, 1H), 7.21 (m, 3H), 6.90 (m, 1H), 3.39 (s, 3H), 3.16 (m, 3H), 3.08 (s, 3H), 2.12 (m, 2H), 1.88 (m, 1H), 1.69 (m, 1H), 1.29-1.45 (m, 4H).

Example 145

Synthesis of Compound 184

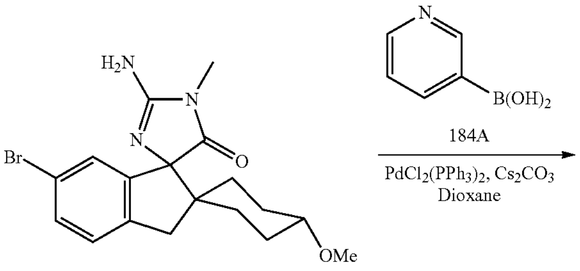

I-6 184A

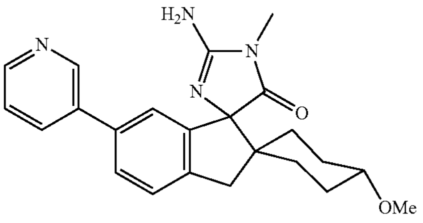

184

According to a similar synthesis of compound 4 described in Example 27, compound I-6 (20 mg, 0.051 mmol) was coupled with compound 184A (13 mg, 0.102 mmol) to give compound 184 (3.9 mg, yield 20%). LC-MS $t_R$=0.737 min in 2 min chromatography, MS (ESI) m/z 391.0 $[M+H]^+$; $^1H$ NMR ($CD_3OD$ 400 MHz): δ 8.76 (s, 1H), 7.49 (d, J=3.6 Hz, 1H), 8.06 (d, J=8.8 Hz, 1H), 7.59-7.44 (m, 3H), 7.25 (s, 1H), 3.37 (s, 3H), 3.11-3.22 (m, 3H), 3.05 (s, 3H), 1.95-2.09 (m, 2H), 1.86 (m, 1H), 1.68 (m, 1H), 1.29-1.42 (m, 4H).

Example 146

Synthesis of Compound 185

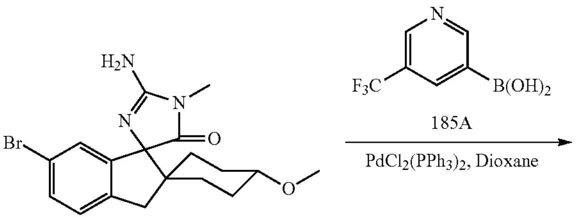

I-6 185A

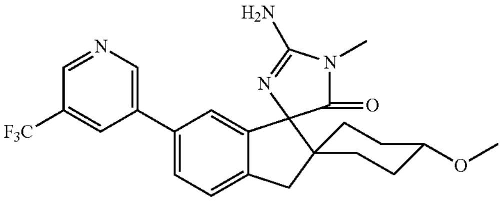

185

According to a similar synthesis of compound 4 described in Example 27, compound I-6 (25 mg, 0.064 mmol) was coupled with compound 185A (24 mg, 0.13 mmol) in 1,4-dioxane (1 mL) to give compound 185 (15 mg, 51%) as a white solid. LC-MS $t_R$=1.072 min in 2 min chromatography, MS (ESI) m/z 459.2 $[M+H]^+$. $^1H$ NMR ($CD_3OD$ 400 MHz): δ 9.10 (s, 1H), 8.88 (s, 1H), 8.39 (s, 1H), 7.79 (d, J=8.0 Hz, 1H), 7.69 (s, 1H), 7.58 (d, J=8.0 Hz, 1H), 3.38 (s, 3H), 3.12-3.29 (m, 6H), 2.11 (m, 2H), 1.92 (m, 1H), 1.33-1.50 (m, 5H).

Example 147

Synthesis of Compound 186

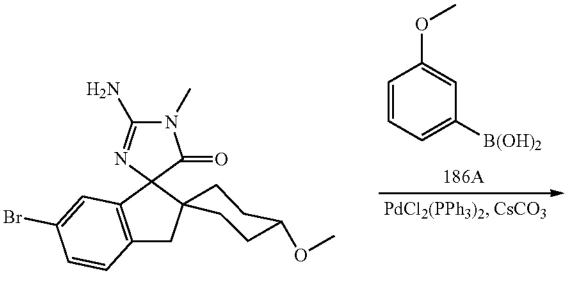

I-6 186A

-continued

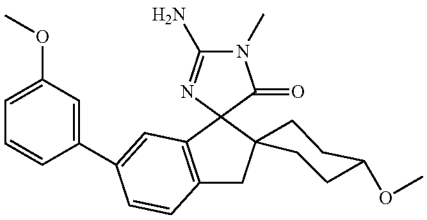

186

According to a similar synthesis of compound 4 described in Example 27, compound I-6 (25 mg, 0.064 mmol) was couple with compound 186A (15 mg, 0.095 mmol) to afford compound 186 (7.2 mg, 28%) as a white solid. LC-MS $t_R$=0.969 min in 2 min chromatography, MS (ESI) m/z 419.2 $[M+H]^+$. $^1H$ NMR ($CD_3OD$ 300 MHz): δ 7.65-7.62 (d, J=7.5 Hz, 1H), 7.46-7.43 (d, J=9.0 Hz, 2H), 7.34 (t, J=8.1 Hz, 1H), 7.16 (t, J=8.1 Hz, 2H), 6.90 (d, J=8.7 Hz, 1H), 3.84 (s, 3H), 3.52 (s, 3H), 3.20 (s, 6H), 3.06-1.82 (m, 3H), 1.49-1.39 (m, 5H).

Example 148

Synthesis of Compound 187

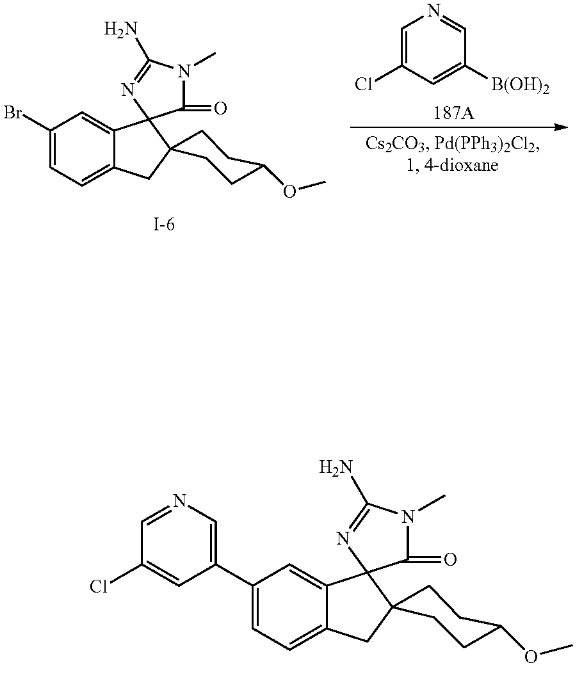

I-6

187A

187

According to a similar synthesis of compound 4 described in Example 27, compound I-6 (20 mg, 0.05 mmol) was coupled with compound 187A (15.7 mg, 0.10 mmol) to afford compound 187 (2 mg, 10%) as a white solid. LC-MS $t_R$=1.047 min in 2 min chromatography, MS (ESI) m/z 425.1 $[M+H]^+$. $^1H$ NMR ($CD_3OD$ 400 MHz): δ 8.70 (s, 1H), 7.48-8.49 (s, 1H), 8.09 (s, 1H), 7.61-7.63 (m, 1H), 7.52-7.60 (m, 1H), 7.42-7.44 (m, 1H), 3.32 (s, 3H), 3.05-3.10 (m, 1H), 1.90-2.05 (m, 2H), 1.75-1.80 (m, 1H), 1.30-1.42 (m, 4H), 1.15-1.25 (m, 1H).

Example 149

Synthesis of Compound 188

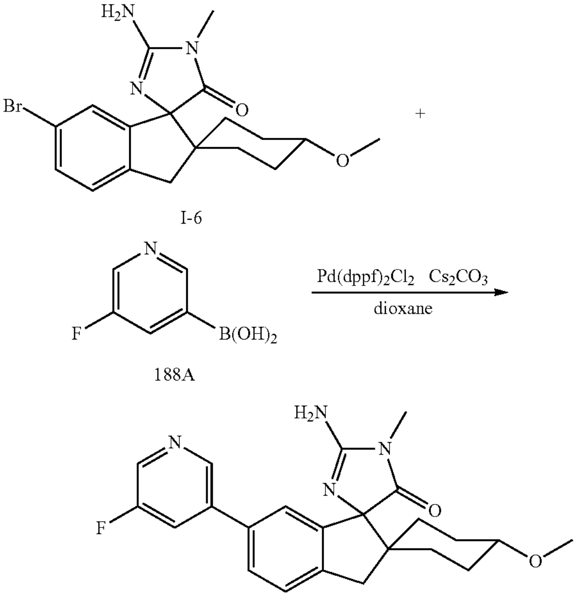

I-6

188A

188

According to a similar synthesis of compound 4 described in Example 27, compound I-6 (20 mg, 0.052 mmol) was coupled with compound 188A (7 mg, 0.052 mmol) to afford product compound 188 (10.0 mg, 48%) as a white solid. LC-MS $t_R$=3.580 min in 7 min chromatography, MS (ESI) m/z 409.3 $[M+H]^+$. $^1H$ NMR ($CD_3OD$ 400 MHz): δ 8.72 (s, 1H), 8.48 (d, J=1.6 Hz, 1H), 7.97 (d, J=9.2 Hz, 1H), 7.75 (dd, J=1.2, 7.6 Hz, 1H), 7.69 (s, 1H), 7.56 (m, 1H), 3.8043 (s, 3H), 3.26-3.38 (m, 6H), 2.00-2.15 (m, 2H), 1.90 (m, 1H), 1.32-1.52 (m, 5H).

Example 150

Synthesis of Compound 189

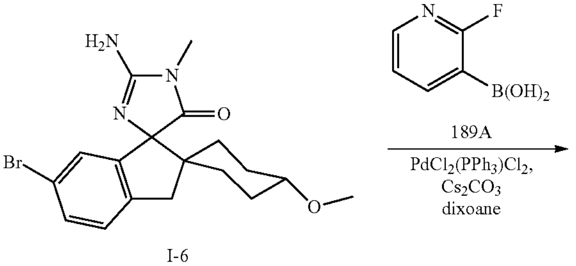

I-6

189A

-continued

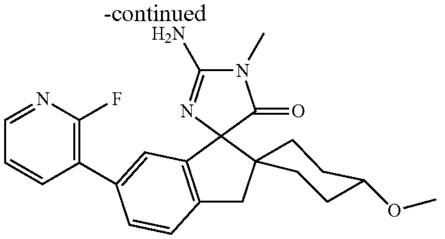

189

According to a similar synthesis of compound 4 described in Example 27, compound I-6 (20 mg, 0.051 mmol) was coupled with compound 189A (18 mg, 0.13 mmol) to give compound 189 (2.9 mg, 14%). LC-MS: $t_R$=0.922 min in 2 min chromatography, MS (ESI) m/z 409.1 $[M+H]^+$. $^1H$ NMR ($CD_3OD$ 400 MHz): δ 8.07-8.06 (d, J=4.4 Hz, 1H), 7.94-7.90 (m, 1H), 7.43-7.41 (d, J=8.0 Hz, 1H), 7.36-7.28 (d, J=7.6 Hz, 2H), 7.12 (s, 1H), 3.26-3.23 (s, 3H), 3.12-3.05 (m, 3H), 3.02-2.96 (s, 3H), 1.95-1.76 (m, 4H), 1.58-1.51 (t, 1H), 1.37-1.27 (m, 1.5H), 1.21-1.16 (m, 1.7H).

Example 151

Synthesis of Compound 190

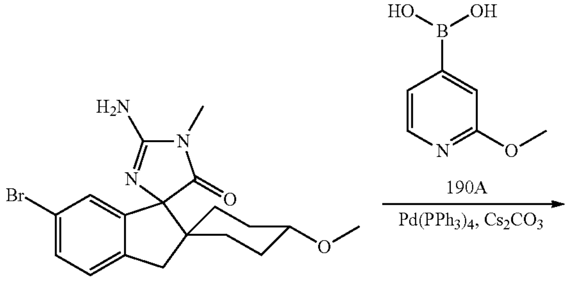

I-6

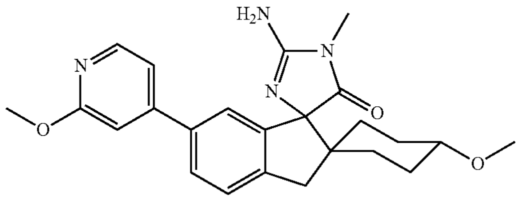

190

According to a similar synthesis of compound 4 described in Example 27, compound I-6 (20 mg, 0.05 mmol) was coupled with compound 190A (12 mg, 0.08 mmol) to give compound 190 (8 mg, 37%) as a white solid. LC-MS $t_R$=0.846 min in 2 min chromatography, MS (ESI) m/z 421.1 $[M+H]^+$. $^1H$ NMR (methanol-$d_4$ 400 MHz TMS): δ 8.20 (d, J=4.8 Hz, 1H), 7.78 (d, J=8.0 Hz, 1H), 7.66 (s, 1H), 7.53 (d, J=8.0 Hz, 1H), 7.32 (br, 1H), 7.17 (br, 1H), 4.00 (s, 3H), 3.37

(s, 3H), 3.25-3.23 (m, 4H), 3.01 (s, 1H), 2.88 (s, 1H), 2.11-2.05 (m, 2H), 1.91-1.88 (m, 1H), 1.53-1.31 (m, 5H).

Example 152

Synthesis of Compound 191

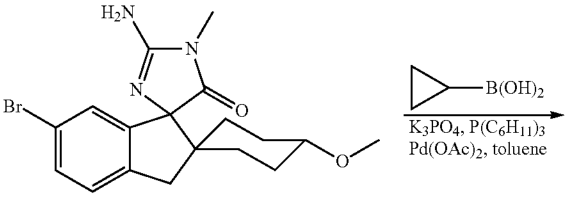

I-6

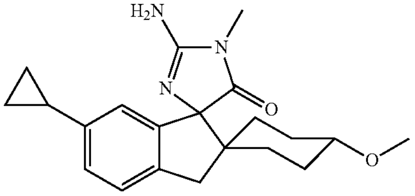

191

To a suspension of compound I-6 (39.1 mg, 0.1 mmol), cyclopropylboronic acid (11.2 mg, 0.13 mmol), $K_3PO_4$ (75 mg, 0.35 mmol) and tricyclohexylphosphine (5.6 mg, 0.02 mmol) in toluene and water (3 mL/100 uL) was added $Pd(OAc)_2$ (3.0 mg, 0.01 mmol) under a $N_2$ atmosphere, the resulting mixture was heated in a sealed tube at 100° C. for 1 day. After cooling to room temperature, the mixture was extracted with ethyl acetate (3×10 mL) and washed with brine (10 mL). The separated organic phase was dried over anhydrous $Na_2SO_4$, filtered and concentrated under reduced pressure. The residue was purified by preparative HPLC (basic) to give compound compound 191 (2.3 mg, 6%) as a white solid. LC-MS $t_R$=0.925 min in 2 min chromatography, MS (ESI) m/z 354.0 $[M+H]^+$. $^1H$ NMR ($CDCl_3$, 400 MHz): δ 7.07-7.09 (d, J=8.0 Hz, 1H), 6.88-6.90 (d, J=8.0 Hz, 1H), 6.68 (s, 1H), 3.36 (s, 3H), 3.11 (t, J=10.8 Hz, 2H), 3.05 (s, 3H), 2.90-2.92 (d, J=9.2 Hz, 1H), 1.95-1.72 (m, 3H), 1.75 (m, 2H), 1.32 (m, 3H), 1.26 (m, 3H), 0.85 (q, 2H), 0.55 (q, 2H).

Example 153

Synthesis of Compound 192

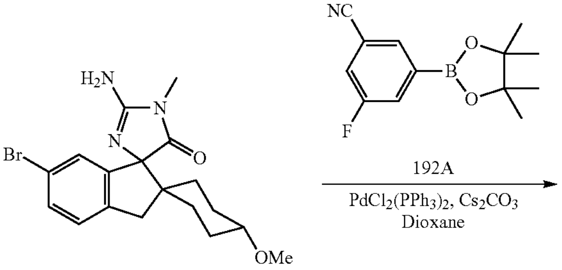

I-6

-continued

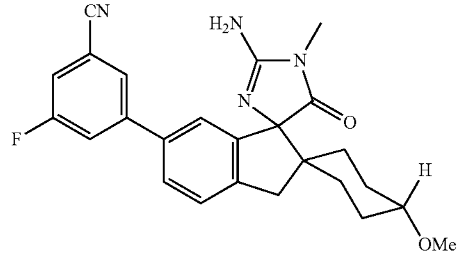

192

$Pd(PPh_3)_2Cl_2$ (5 mg) in a 10 mL of flask under a nitrogen atmosphere was treated sequentially with compound I-6 (25 mg, 0.06 mmol) in 1,4-dioxane (2 mL), $Cs_2CO_3$ (2 N, 0.09 mL, 0.18 mmol) and compound 192A (31.5 mg, 0.12 mmol). The mixture was heated at 120° C. in a CEM microwave reactor under a nitrogen atmosphere for 15 min. The reaction mixture was concentrated in vacuo to give the residue, which was purified by preparative TLC ($CH_2Cl_2$:MeOH=10:1) and preparative HPLC to give compound 192 (5.6 mg, 20%) as a white solid. LC-MS $t_R$=0.958 min in 2 min chromatography, MS (ESI) m/z 433.1 $[M+H]^+$; $^1$H NMR ($CD_3OD$ 400 MH): δ 7.83 (s, 1H), 7.70-7.77 (m, 1H), 7.59 (m, 1H), 7.50 (m, 1H), 7.43 (m, 1H), 7.27 (s, 1H), 3.26 (s, 3H), 3.13 (m, 3H), 3.05 (s, 3H), 1.81-2.04 (m, 3H), 1.64 (m, 1H), 1.25-1.46 (m, 4H)

Example 154

Synthesis of Compound 193

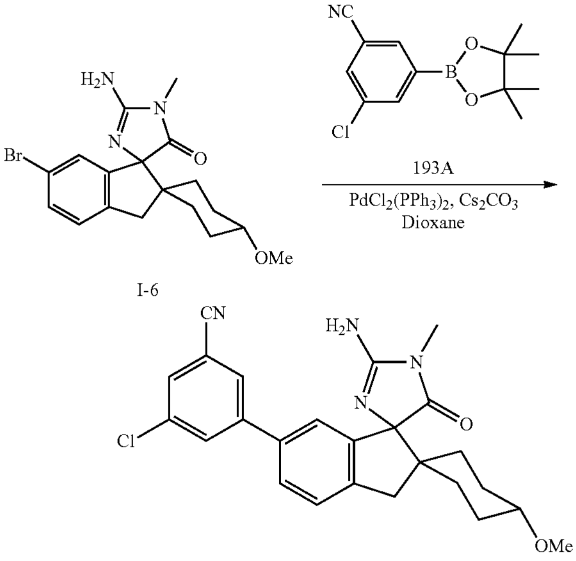

193

According to a similar synthesis of compound 192, compound I-6 (20 mg, 0.051 mmol) was compound with boronic ester 193A (40 mg, 0.153 mmol) to give compound 193 (1.8 mg, yield 8%) as a white solid. LC-MS $t_R$=0.999 min in 2 min chromatography, MS (ESI) m/z 449.0 $[M+H]^+$; $^1$H NMR ($CDCl_3$ 400 MHz): δ 7.66 (d, J=14.4 Hz, 2H), 7.51 (s, 1H), 7.37 (m, 2H), 7.12 (s, 1H), 3.28 (s, 3H), 3.21-3.01 (m, 6H), 1.95 (m, 3H), 1.48 (m, 1H), 1.36 (m, 2H), 1.24 (m, 2H).

Example 155

Synthesis of Compound 194

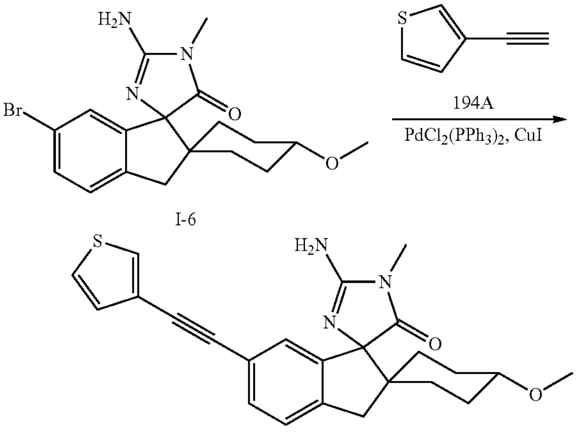

194

Compound I-6 (16 mg, 0.041 mmol) was dissolved in $Et_3N$ (5 ml) and $Et_2NH$ (1 ml), the resulting mixture was degassed and purged with nitrogen for three times. $Pd(PPh_3)_2Cl_2$ (2 mg, 0.003 mmol) and CuI (0.57 mg, 0.003 mmol) were added under a nitrogen atmosphere and the system was degassed again. 3-ethynylthiophene (194A) (11 mg, 0.10 mmol) was added by syringe. The system was degassed one more time, then was heated at 50~60° C. for 12 h. LCMS showed that the reaction was completed and the solvent was removed under reduced pressure. The residue was purified by preparative TLC (petroleum ether:ethyl acetate=5:1) and preparative RP-HPLC to afford compound 194 (1.9 mg, 11%) as a white solid. LC-MS $t_R$=0.995 min in 2 min chromatography, MS (ESI) m/z 420.0 $[M+H]^+$. $^1$H NMR ($CD_3OD$ 400 MHz): δ 7.60 (s, 1H), 7.40-7.46 (m, J=7.6 Hz, 2H), 7.31-7.33 (d, J=8.0 Hz, 1H), 7.17-7.18 (d, J=4.8 Hz, 1H), 7.10 (s, 1H), 3.36 (s, 3H), 3.11-3.17 (m, 3H), 3.06 (s, 3H), 1.93-2.04 (m, 2H), 1.82-1.88 (m, 1H), 1.60-1.63 (m, 1H), 1.30-1.38 (m, 2H), 1.24-1.29 (m, 2H).

Example 156

Synthesis of Compound 195

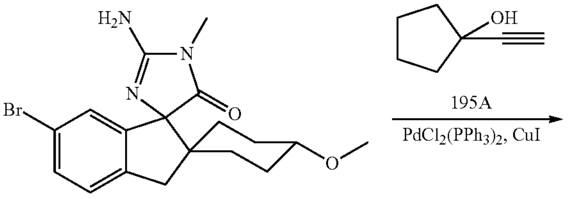

I-6

-continued

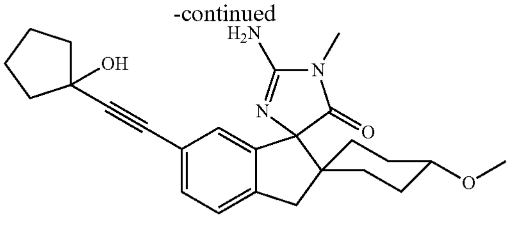

195

According to a similar synthesis of compound 194, compound I-6 (16 mg, 0.041 mmol) was coupled with 1-ethynylcyclopentanol (195A) (23 mg, 0.204 mmol) to afford compound 195 (3.7 mg, 22%) as a white solid. LC-MS $t_R$=1.057 min in 2 min chromatography, MS (ESI) m/z 422.2 $[M+H]^+$. $^1H$ NMR ($CD_3OD$ 400 MHz): δ 7.29-7.30 (m, 2H), 7.02 (s, 1H), 3.33 (s, 3H), 3.14-3.27 (m, 1H), 3.07-3.11 (m, 2H), 3.06 (s, 3H), 1.94-2.03 (m, 6H), 1.78-1.86 (m, 5H), 1.55-1.65 (m, 1H), 1.27-1.43 (m, 4H).

Example 157

Synthesis of Compound 196

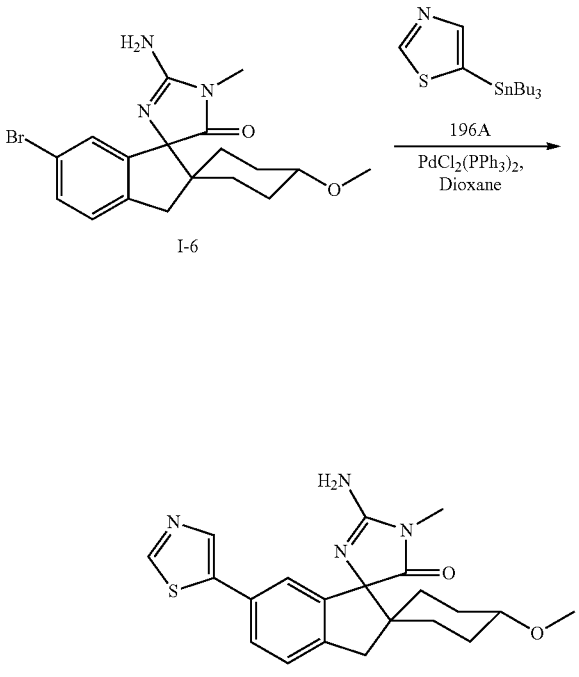

I-6

196

To a solution of compound I-6 (50 mg, 0.127 mmol) in 1,4-dioxane (2 mL) was added compound 196A (120 mg, 0.314 mmol), $PdCl_2(PPh_3)_2$ (10 mg, 0.014 mmol). The reaction mixture was heated at 125° C. in a CEM microwave reactor for 45 min. The solvents were removed under reduced pressure, and the residue was purified by preparative HPLC to give compound 196 (3.4 mg, 6.7%). LC-MS: $t_R$=0.894 min in 2 min chromatography, MS (ESI) m/z 397.1 $[M+H]^+$. $^1H$ NMR ($CD_3OD$ 400 MHz): δ 8.87 (s, 1H), 8.08 (s, 1H), 7.56-7.58 (dd, J=1.6, 7.6 Hz, 1H), 7.49-7.50 (s, 1H), 7.34-7.36 (d, J=8.0 Hz, 1H), 3.21 (s, 3H), 3.13 (s, 3H), 3.09-3.11 (m, 1H), 3.02-3.06 (m, 1H), 1.89-1.99 (m, 2H), 1.75-1.78 (m, 1H), 1.16-1.36 (m, 6H).

Example 158

Synthesis of Compound 197

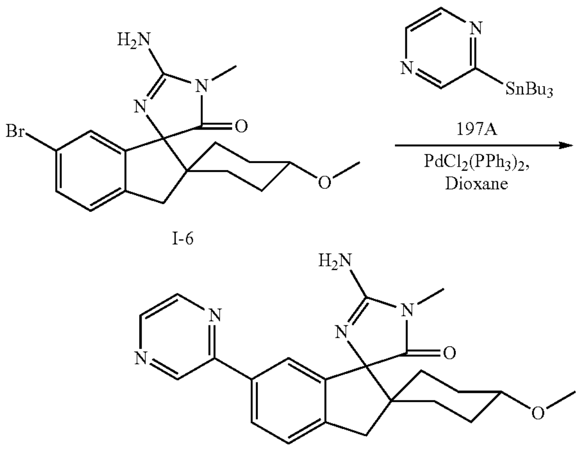

197

According to a similar synthesis of compound 196, compound I-6 (25 mg, 0.064 mmol) was coupled with compound 197A (59 mg, 0.16 mmol) to give compound 197 (1.3 mg, 5%) as a white solid. LC-MS $t_R$=0.948 min in 2 min chromatography, MS (ESI) m/z 392.2 $[M+H]^+$. $^1H$ NMR ($CD_3OD$ 400 MHz): δ 9.03 (s, 1H), 8.56 (s, 1H), 8.44 (s, 1H), 8.02 (d, J=8.0 Hz, 1H), 7.86 (s, 1H), 7.45 (d, J=8.0 Hz, 1H), 7.23 (m, 1H), 3.25 (s, 3H), 3.17-3.03 (m, 6H), 1.97 (m, 2H), 1.78 (m, 1H), 1.38-1.19 (m, 5H).

Example 159

Synthesis of Compounds 198 and 199

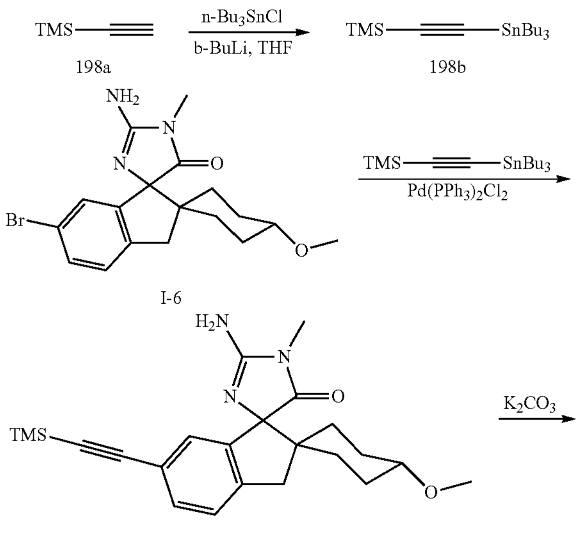

198c

-continued

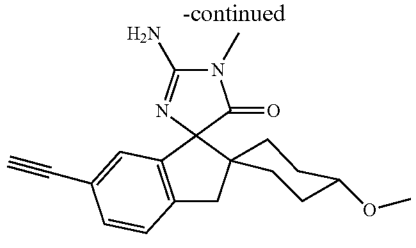

198

+

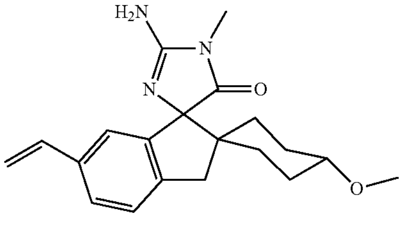

199

Procedure for Preparation of Compound 198b

To a solution of compound 198a (2.65 g, 27 mmol) in THF (80 mL) was added n-BuLi (2.5 M in hexanes, 11.88 mL, 29.7 mmol) at −78° C., and the reaction mixture was stirred at −78° C. for 30 min and at 0° C. 30 min. After being cooled to −78° C., the reaction mixture was treated with n-$Bu_3SnCl$ (9.67 g, 8 mL, 29.7 mmol), and allowed to warm to room temperature over 5 h. The solvent was removed under vacuum, and the residue was partitioned between diethyl ether (100 mL) and $H_2O$ (80 mL). The diethyl ether layer was washed with brine (80 mL), dried over anhydrous $Na_2SO_4$, and concentrated. Flash chromatography of the crude ($Al_2O_3$, petroleum) afforded compound 198b as a colorless oil (9.4 g, 90%).

Procedure for Preparation of Compound 198c

A solution containing compound I-6 (50 mg, 0.13 mmol) and compound 198b (246 mg, 0.635 mmol) in toluene (4 mL) was deoxygenated by bubbling a stream of nitrogen through the reaction mixture for 5 min. Then, $PdCl_2(PPh_3)_2$ (5 mg) was added. The reaction vial was sealed and placed into CEM microwave reactor and irradiated at 130° C. for 30 min. After being cooled to room temperature, the mixture was partitioned between EtOAc (10 mL) and aqueous of CsF (4M, 8 mL), and the aqueous layer was extracted with EtOAc (3×10 mL). The combined organic layers were washed with brine (10 mL), dried over anhydrous $Na_2SO_4$, filtered, and concentrated in vacuo. The residue was purified by preparative TLC (petroleum/ethyl acetate=1:1) to give compound 198c (30 mg, 58%) as a white solid.

Procedure for Preparation of Compounds 198 and 199

Anhydrous $K_2CO_3$ (100 mg, 0.7 mmol) and compound 198c (30 mg, 0.07 mmol) were suspended in MeOH (2 mL) and stirred at room temperature for 1 h. LCMS showed that the reaction was completed. The solvent was removed under reduced pressure and the residue was dissolved in $CH_2Cl_2$ (10 mL), washed with brine (2×10 mL) and the organic layer was dried over anhydrous $Na_2SO_4$ and concentrated to dryness. Purification of this residue by preparative HPLC (basic) afforded compound 198 (6.80 mg, 29%), LC-MS $t_R$=0.890 min in 2 min chromatography, MS (ESI) m/z 338.1 $[M+H]^+$.

$^1H$ NMR ($CD_3OD$, 400 MHz): δ 7.38-7.40 (d, J=8.0 Hz, 1H), 7.29-7.31 (d, J=8.0 Hz, 1H), 7.09 (s, 1H), 3.44 (s, 1H), 3.36 (s, 3H), 3.10-3.18 (m, 3H), 3.06 (s, 3H), 1.96-2.03 (m, 2H), 1.80-1.85 (m, 1H), 1.57-1.65 (m, 1H). 1.23-1.44 (m, 4H); and by-product compound 199 (8.20 mg, 35%) as a white solid, LC-MS $t_R$=0.815 min in 2 min chromatography, MS (ESI) m/z 340.1 $[M+H]^+$. $^1H$ NMR ($CD_3OD$, 400 MHz): δ 7.21-7.23 (d, J=8.0 Hz, 1H), 7.14-7.16 (d, J=8.0 Hz, 1H), 6.96 (s, 1H), 6.56-6.63 (q, 1H), 5.58-5.62 (d, J=17.6 Hz, 1H), 5.05-6.07 (d, J=11.2 Hz, 1H), 3.24 (s, 3H), 2.88-3.07 (m, 6H), 1.84-1.94 (m, 2H), 1.72-1.75 (m, 1H), 1.47-1.54 (m, 1H). 1.12-1.35 (m, 4H).

Example 160

Synthesis of Compound 200

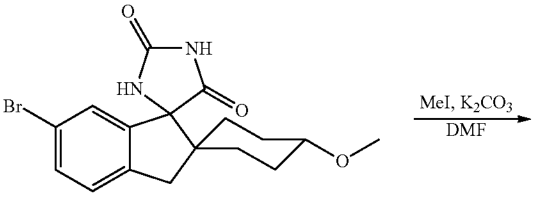

200a

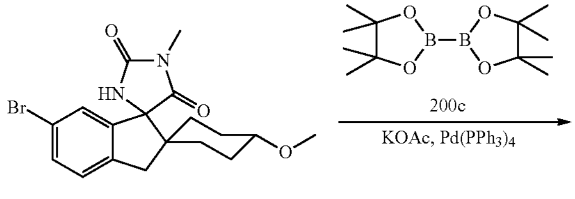

200b

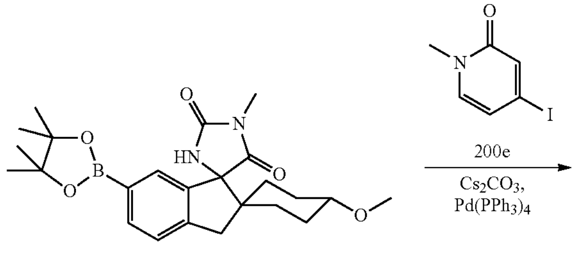

200d

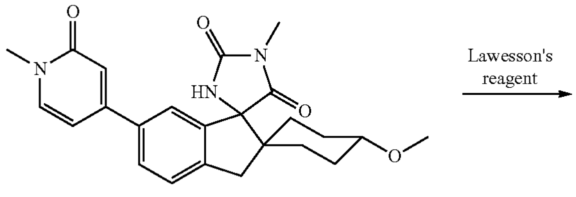

200f

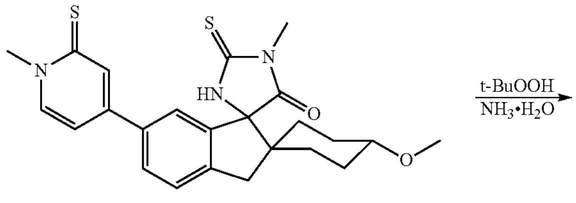

200g

-continued

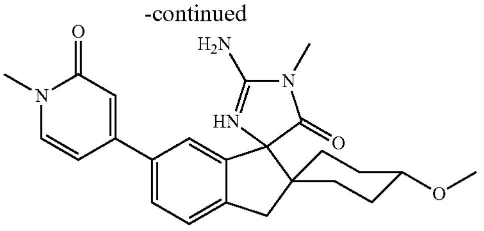

200

Procedure for Preparation of Compound 200b

To a solution of compound 200a (200 mg, 0.53 mmol) in DMF (2 mL), $K_2CO_3$ (116 mg, 1.06 mmol) and MeI (60 mg, 0.53 mmol) was added subsequently. After stirring for 3 h, the reaction mixture was diluted with water (3 mL), the precipitate was collected by filtration, washed with water, dried in vacuo to give compound 200b (160 mg, 77% crude yield) as a white solid, which was used directly in next step.

Procedure for Preparation of Compound 200d

The crude product of compound 200b (160 mg 0.41 mmol), compound 200c (155 mg, 0.6 mmol), KOAc (120 mg, 1.2 mmol) and $Pd(PPh_3)_4$ (94 mg, 0.08 mmol) were suspended in anhydrous dioxane (2 mL) under a nitrogen atmosphere and then was heated at 90° C. for 4 h. The mixture was diluted with water (5 mL), extracted with EtOAc (3×5 mL). The combined organic layers were dried over $Na_2SO_4$, filtered and concentrated to give the crude product 200d, which was used for next step without further purification.

Procedure for Preparation of Compound 200f

The crude product of compound 200d was dissolved in dioxane (2 mL) under a nitrogen atmosphere. Compound 200e (96 mg, 0.41 mmol), $Pd(PPh_3)_4$ (90 mg, 0.08 mmol) and $Cs_2CO_3$ (2.0 M aq. 0.5 mL) were added subsequently under a nitrogen atmosphere. The reaction mixture was heated at 90° C. overnight. The solvent was evaporated and the residue was purified on preparative TLC eluting with EtOAc to give compound 200f (50 mg, 30% yield for two steps) as a white solid.

Procedure for Preparation of Compound 200g

A solution of compound 200f (28 mg, 0.066 mmol) and Lawesson's Reagent (67 mg, 0.166 mmol) in anhydrous toluene (2 mL) was stirred at 140° C. for 30 min in a microwave reactor. LCMS showed that the reaction was completed, the mixture was concentrated under reduced pressure, and the residue was purified by preparative TLC (petroleum ether: ethyl acetate=2:1) to give compound 200g (20 mg, 66%) as a white solid.

Procedure for Preparation of Compound 200

A mixture of compound 200g (20 mg, 0.044 mmol) and t-butyl hydroperoxide (122 mg, ca. 65% solution in water, 0.88 mmol) in ammonia (1 mL) and MeOH (5 mL) was stirred at room temperature overnight, LCMS showed that the reaction was completed. The reaction mixture was concentrated under reduced pressure to dryness, which was purified by preparative TLC ($CH_2Cl_2$:MeOH=10:1) and preparative RP-HPLC to give compound 200 (5.6 mg, 25%) as a white solid.

LC-MS $t_R$=0.826 min in 2 min chromatography, MS (ESI) m/z 421.1 $[M+H]^+$. $^1H$ NMR ($CD_3OD$ 400 MHz): δ 7.69-7.71 (d, J=7.2 Hz, 1H), 7.60-7.62 (d, J=7.6 Hz, 1H), 7.43-7.45 (d, J=7.6 Hz, 1H), 7.30 (s, 1H), 6.75 (s, 1H), 6.68-6.70 (d, J=7.2 Hz, 1H), 3.60 (s, 3H), 3.33 (s, 3H), 3.11-3.21 (q, 3H), 3.07 (s, 3H), 1.93-2.05 (m, 2H), 1.85-1.88 (m, 1H), 1.61-1.65 (m, 1H), 1.36-1.45 (m, 2H), 1.30-1.33 (m, 2H).

Example 161

Synthesis of Compound 201

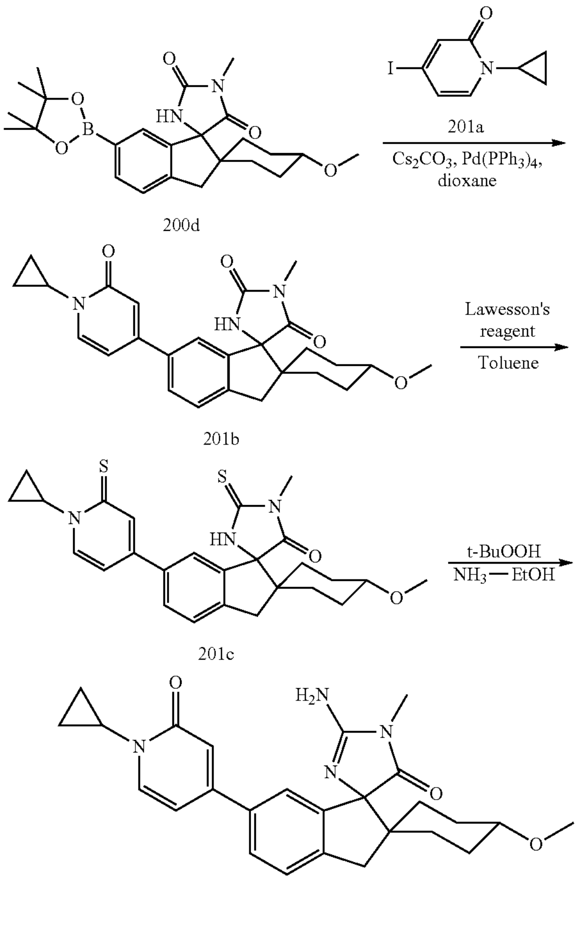

201

According to a similar synthesis of compound 200, compound 200d was coupled with compound 201a (99 mg, 0.38 mmol) to give compound 201b (70 mg, 59% yield). Compound 201b (70 mg, 0.16 mmol) was reacted with Lawesson's reagent (64 mg, 0.16 mmol) to give compound 201c (20 mg, 26%), which was converted to final product compound 201 (3.5 mg, 18%) as a white solid. LC-MS $t_R$=0.887 min in 2 min chromatography, MS (ESI) m/z 447.3 $[M+H]^+$. $^1H$ NMR (methanol-$d_4$ 400 MHz TMS): δ 7.70-7.73 (m, 2H), 7.60 (s, 1H), 7.52 (d, J=8.0 Hz, 1H), 6.79 (s, 1H), 6.72 (d, J=7.2 Hz, 1H), 3.38 (s, 3H), 3.28-3.14 (m, 7H), 2.11-2.04 (m, 2H), 1.91-1.88 (m, 1H), 1.48-1.31 (m, 5H), 1.20-1.15 (m, 2H), 0.97-0.95 (m, 2H).

Example 162

Synthesis of Compound 202

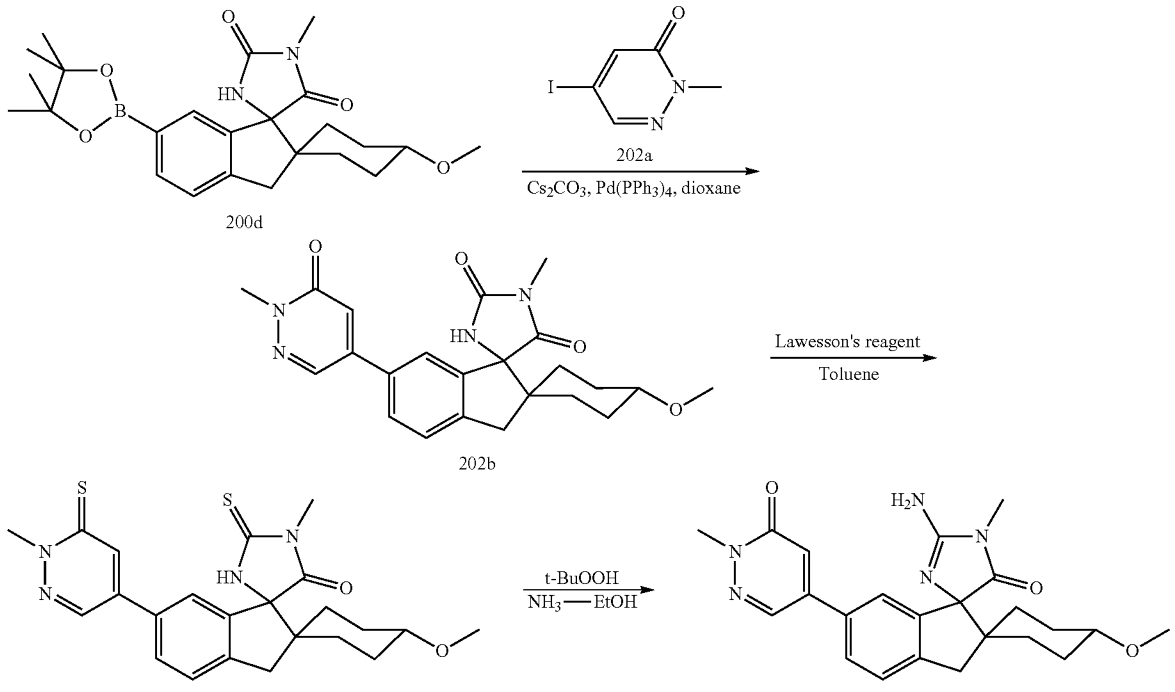

200d

202b

202c

202

According to a similar synthesis of compound 200, compound 200d was coupled with compound 202a (89 mg, 0.38 mmol) to give compound 202b (70 mg, 65% yield). Compound 202b (70 mg, 0.17 mmol) was then reacted with Lawesson's reagent (67 mg, 0.17 mmol) to give compound 202c (25 mg, 33%), which was converted to the final product compound 202 (3.5 mg, 14.5%). LC-MS $t_R$=0.828 min in 2 min chromatography, MS (ESI) m/z 422.1 $[M+H]^+$. $^1H$ NMR (methanol-$d_4$ 400 MHz TMS): δ 8.32 (s, 1H), 7.81-7.79 (m, 1H), 7.68 (s, 1H), 7.58-7.56 (m, 1H), 7.18 (s, 1H), 3.82 (s, 3H), 3.38 (s, 3H), 3.26-3.19 (m, 6H), 2.12-2.05 (m, 2H), 1.91-1.88 (m, 1H), 1.52-1.43 (m, 3H), 1.36-1.25 (m, 2H).

Example 163

Synthesis of Compound 203

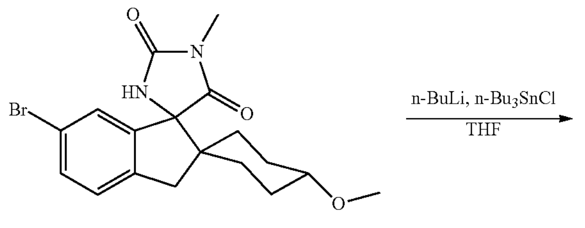

200b

-continued

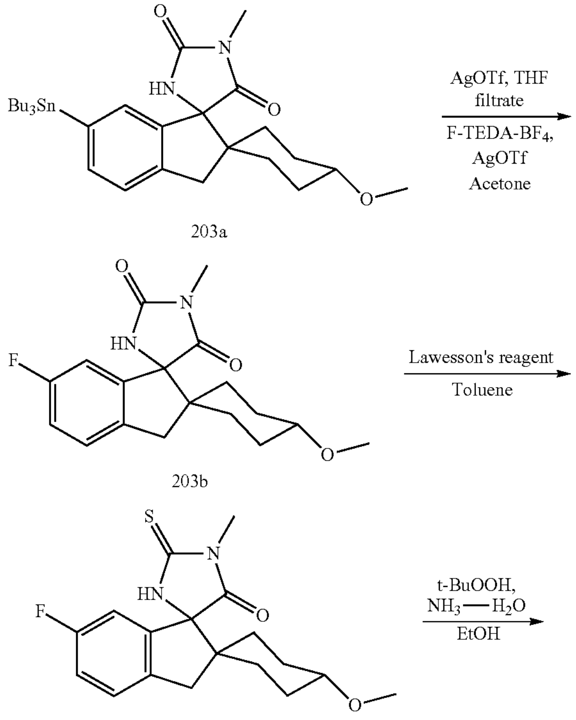

203a

203b

203c

-continued

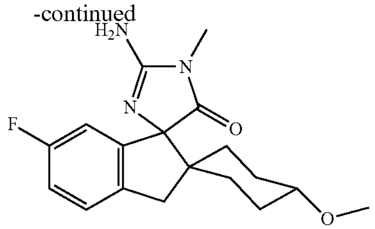

203

Procedure for Preparation of Compound 203a

To a solution of compound 200b (150 mg, 0.38 mmol) in THF (5 mL) at −78° C. was added n-BuLi (2.5 M, 0.48 mL). The reaction mixture was stirred at −78° C. for 2 h. Then, $Bu_3SnCl$ (150 mg, 0.45 mmol) was added and stirred at −78° C. for 2 h more. The mixture was warmed up to 10° C. and quenched by addition with saturated $NH_4Cl$ (5 mL). The mixture was extracted with ethyl acetate (2×30 mL). The organic fractions were concentrated to give crude compound 203a (230 mg, 100% crude) as a yellow oil, which was used directly in the next step without further purification.

Procedure for Preparation of Compound 203b

A suspension of compound 203a (230 mg, 0.4 mmol), F-TEDA-$BF_4$ (170 mg, 0.48 mmol) and AgOTf (200 mg, 0.8 mmol) in anhydrous acetone (5 mL) was stirred at 15° C. for 20 min. The mixture was concentrated in vacuo, the residue was purified by preparative TLC eluting with petroleum ether:ethyl acetate (1:1) to give compound 203b (62 mg, 50%) as a white solid.

Procedure for Preparation of Compound 203c

A suspension of compound 203c (60 mg, 0.18 mmol) and Lawesson's Reagent (77 mg, 0.19 mmol) in anhydrous toluene (2 mL) was heated at 130° C. for 40 min in a CEM microwave reactor. The mixture was concentrated in vacuo, the residue was purified by preparative preparative HPLC to give compound 203d (33 mg, 45%) as a white solid.

Procedure for Preparation of Compound 203

A solution of compound 203c (30 mg, 0.085 mmol), t-BuOOH (0.5 mL), $NH_3$—$H_2O$ (0.5 mL) in EtOH (2 mL) was stirred at 10° C. for 10 h. The mixture was concentrated in vacuo to give the residue, which was purified by preparative HPLC to give compound 203 (22 mg, 50%) as a white solid. LCMS: $t_R$=1.243 min in 3 min chromatography, MS ESI m/z 332.2 $[M+H]^+$. $^1H$ NMR ($CD_3OD$ 300 MHz): δ 7.20-7.30 (m, 1H), 6.90-7.00 (m, 1H), 6.65-6.75 (d, J=8.4 Hz, 1H), 3.35-3.40 (s, 3H), 2.90-3.15 (m, 6H), 1.90-2.10 (m, 2H), 1.75-1.85 (m, 1H), 1.50-1.65 (m, 1H), 1.20-1.45 (m, 4H). $^{19}F$ NMR ($CD_3OD$ 19F 400 MHz): δ −118.00.

Example 164

Synthesis of Compound 204

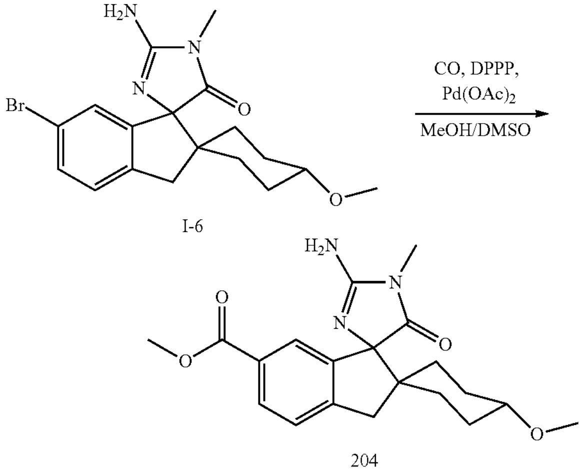

I-6

204

To a solution of compound I-6 (100 mg, 0.255 mmol) in MeOH (2 mL) and DMSO (6 mL) was added DPPP (52 mg, 0.127), $Pd(OAc)_2$ (31 mg, 0.127 mmol) and $Et_3N$ (2 mL). The reaction was heated at 80° C. under CO at 40 psi for 24 h. The mixture was filtered and the filtrated was concentrated to give the residue, which was purified by preparative TLC ($CH_2Cl_2$:MeOH=10:1) and acidic preparative HPLC to give compound 204 (5.0 mg, 5%) as a white solid. LC-MS $t_R$=0.859 min in 2 min chromatography, MS (ESI) m/z 372 $[M+H]^+$. $^1H$ NMR ($CD_3OD$ 400 MHz): δ 8.07 (d, J=7.6 Hz, 1H), 7.89 (s, 1H), 7.52 (d, J=8.0 Hz, 1H), 3.90 (s, 3H), 3.37 (s, 3H), 3.29-3.18 (m, 6H), 2.07 (m, 2H), 1.87 (m, 1H), 1.46 (m, 4H), 1.34 (m, 1H).

Example 165

Synthesis of Compound 205

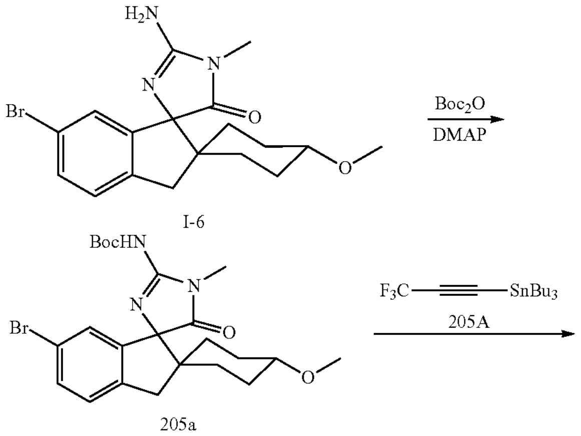

I-6

205a

-continued

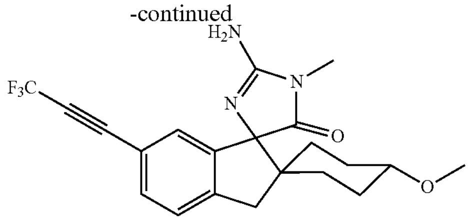

205

Procedure for Preparation of Compound 205a

Compound I-6 (50 mg, 0.127 mmol) and $Boc_2O$ (42 mg, 0.19 mmol) was dissolved in THF (5 mL), this solution was added DMAP (23 mg, 0.19 mmol) and $Et_3N$ (0.04 mL, 0.25 mmol), the reaction mixture was stirred at room temperature overnight. LCMS showed that the reaction was completed. The reaction mixture was concentrated in vacuo to give the residue, which was purified by preparative TLC (petroleum ether:ethyl acetate=5:1) to give 205a (30 mg, 48%) as a white solid.

Procedure for Preparation of Compound 205

A solution containing compound 205a (47 mg, 0.122 mmol) and compound 205A (40 mg, 0.081 mmol) in toluene (5 mL) was deoxygenated by bubbling a stream of nitrogen through the reaction mixture for 5 min. Then, $PdCl_2(PPh_3)_2$ (4 mg) was added. The reaction vial was sealed and placed into CEM microwave reactor and irradiated at 125° C. for 45 min. After being cooled to room temperature, the mixture was partitioned between EtOAc (10 mL) and aqueous CsF (4 M, 10 mL), and the aqueous layer was extracted with EtOAc (3×10 mL). The combined organic layers were washed with brine (15 mL), dried over anhydrous $Na_2SO_4$, filtered, and concentrated in vacuo. The residue was purified by preparative TLC ($CH_2Cl_2$:MeOH=10:1) and preparative HPLC to afford product compound 205 (0.6 mg, 1%) as a white solid. LC-MS $t_R$=1.130 min in 2 min chromatography, MS (ESI) m/z 406.2 $[M+H]^+$; $^1H$ NMR ($CD_3OD$ 400 MHz): δ 7.57-7.60 (d, J=10.4 Hz, 1H), 7.44-7.47 (d, J=10.4 Hz, 1H), 7.36 (s, 1H), 3.36 (s, 3H), 3.18-3.32 (m, 3H), 3.11 (s, 3H), 1.96-2.07 (m, 2H), 1.83-1.89 (m, 1H), 1.52-1.59 (m, 1H), 1.26-1.40 (m, 4H).

Example 166

Synthesis of Compound 206

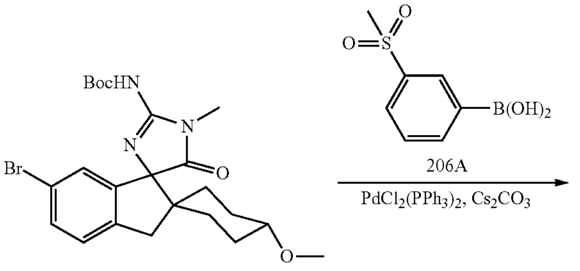

205a

-continued

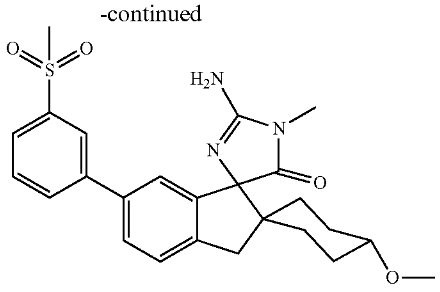

206

$Pd(PPh_3)_2Cl_2$ (4 mg) was treated sequentially with compound 205a (30 mg, 0.06 mmol) in 1,4-dioxane (2 mL), $Cs_2CO_3$ (2 M in water, 0.15 mL, 0.3 mmol)) and compound 206A (24 mg, 0.12 mmol) under $N_2$ atmosphere. The mixture was stirred at 120° C. for 15 min in microwave. LCMS showed that the reaction was completed. The reaction mixture was concentrated under reduced pressure to give the residue, which was purified by preparative TLC ($CH_2Cl_2$/MeOH=5:1) and preparative HPLC to give compound 206 (15.0 mg, 54%) as a white solid. LC-MS $t_R$=0.942 min in 2 min chromatography, MS (ESI) m/z 468.2 $[M+H]^+$. $^1H$ NMR ($CD_3OD$ 400 MHz): δ 8.12 (s, 1H), 7.90-7.95 (t, J=8.4, 9.2 Hz, 2H), 7.67-7.71 (t, J=8.0 Hz, 1H), 7.59-7.61 (d, J=8.0 Hz, 1H), 7.43-7.45 (d, J=7.6 Hz, 1H), 7.28 (s, 1H), 3.36 (s, 3H), 3.08-3.21 (m, 6H), 3.05 (s, 3H), 1.96-2.04 (m, 2H), 1.85-1.87 (m, 1H), 1.63-1.67 (t, J=14.0 Hz, 1H), 1.36-1.42 (m, 2H), 1.29-1.33 (m, 2H).

Example 167

Synthesis of Compound 207

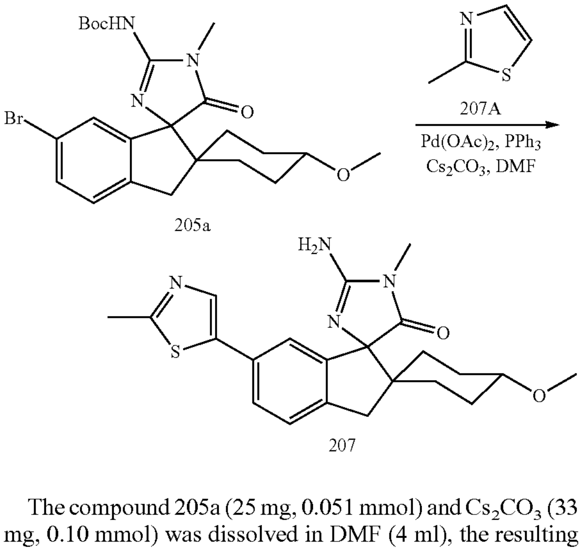

205a

207

The compound 205a (25 mg, 0.051 mmol) and $Cs_2CO_3$ (33 mg, 0.10 mmol) was dissolved in DMF (4 ml), the resulting mixture was degassed and purged with nitrogen for three times. $Pd(OAc)_2$ (2 mg, 0.008 mmol) and $PPh_3$ (2 mg, 0.005 mmol) were added under a nitrogen atmosphere and the system was degassed again. 2-methyl-thiazole (207A) (100 mg, 1.0 mmol) was added by syringe. The system was degassed one more time. The reaction was heated to 168° C. for 45 min in a microwave reactor. LCMS showed that the reaction was completed, and the solvent was removed by evaporation under reduced pressure. The residue was purified by preparative TLC (petroleum ether:ethyl acetate=5:1) and preparative RP-HPLC to afford compound 207 (1.9 mg, 8%) as a white solid. LC-MS $t_R$=1.009 min in 2 min chromatography, MS (ESI) m/z 411.2 $[M+H]^+$. $^1H$ NMR ($CD_3OD$ 400 MHz): δ 7.84 (s, 1H), 7.51-7.53 (d, J=8.0 Hz, 1H), 7.36-7.38 (d, J=7.6 Hz, 1H), 7.22 (s, 1H), 3.36 (s, 3H), 3.11-3.18 (m, 3H), 3.07 (s, 3H), 2.71 (s, 3H), 1.96-2.04 (m, 2H), 1.84-1.91 (m, 1H), 1.60-1.64 (m, 1H), 127-1.41 (m, 4H).

Example 168

Synthesis of Compound 208

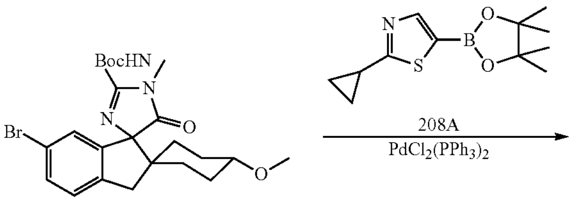

205a

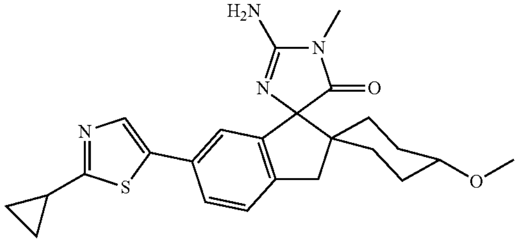

208

According to a similar synthesis of compound 206, compound 205a (20 mg, 0.051 mmol) was coupled with compound 208A (20 mg, 0.077 mmol) to give compound 208 (4.3 mg, 15%) as a white solid. LC-MS $t_R$=0.951 min in 2 min chromatography, MS (ESI) m/z 437 $[M+H]^+$; $^1H$ NMR ($CDCl_3$ 400 MHz): δ 7.58 (s, 1H), 7.32 (d, J=7.6 Hz, 1H), 7.22 (s, 1H), 7.05 (s, 1H), 3.27 (s, 3H), 3.11 (d, J=15.2 Hz, 1H), 3.04 (m, 1H), 2.99 (s, 3H), 2.95 (d, J=15.2 Hz, 1H), 2.22 (m, 2H), 1.9 (m, 2H), 1.38 (m, 5H), 1.0 (m, 4H).

Example 169

Synthesis of Compound 209

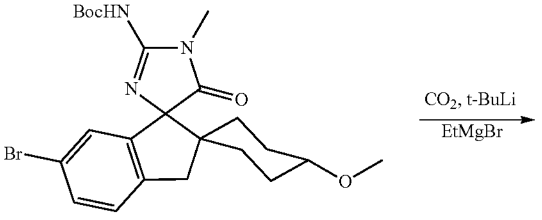

205a

-continued

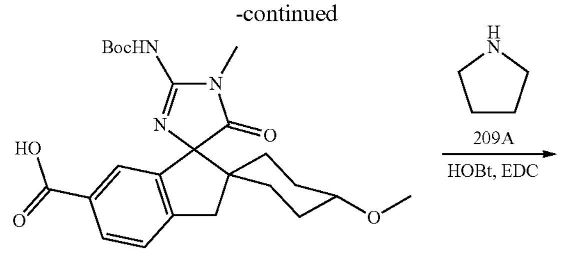

209a

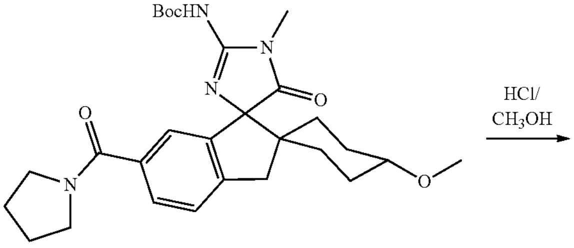

209b

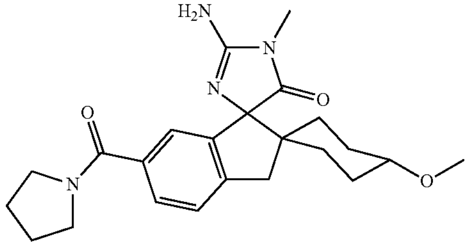

209

Procedure for Preparation of Compound 209a

A solution of compound 205a (100 mg, 0.203 mmol) in dry THF (5 mL) was added dropwise EtMgBr (0.3 mL, 1.0 mmol) at −78° C. under a $N_2$ atmosphere. After stirring for 15 min, t-BuLi (0.8 mL, 1.1 mmol) was added dropwise and stirred for 20 min. $CO_2$ was bubbled through the reaction mixture for 25 min. the reaction was quenched with saturated aqueous $NH_4Cl$ solution and extracted with ethyl acetate (3×20 mL). The combined organic layers were dried over $Na_2SO_4$, and concentrated under reduced pressure to give compound 209a (0.1 g, 85%) as a brown oil.

Procedure for Preparation of Compound 209b

A mixture of compound 209a (50 mg, 6 mmol), 209A (5 mg, 60 mmol), HOBt (2.7 mg, 18 mmol) and EDC-HCl (4 mg, 18 mmol) in $Et_3N$ (2 mg, 18 mmol) and $CH_2Cl_2$ was stirred at room temperature overnight. The solvent was removed by evaporation to give the residue, which was purified by preparative TLC (petroleum:ethyl acetate=1:1) to give compound 209b (18 mg, 50%) as a yellow solid.

Procedure for Preparation of Compound 209

A solution of compound 209b (18 mg, 0.035 mmol) in HCl/dioxane (5 mL, 4 N) was stirred at room temperature for 15 min. The solvent was removed to give the residue and which was purified by preparative HPLC (acidic) to afford compound 209 (3.1 mg, 10%) as a white solid. LC-MS $t_R$=1.316 min in 2 min chromatography, MS (ESI) m/z 410.23 $[M+H]^+$. $^1H$ NMR ($CD_3OD$ 300 MHz): δ 7.54-7.36 (m, 3H), 3.60 (m, 2H), 3.45 (m, 2H), 3.36 (s, 3H), 3.2 (s, 3H), 3.07 (s, 1H), 1.9-1.8 (m, 7H), 1.5-1.3 (m, 5H).

Example 170

Synthesis of Compound 210

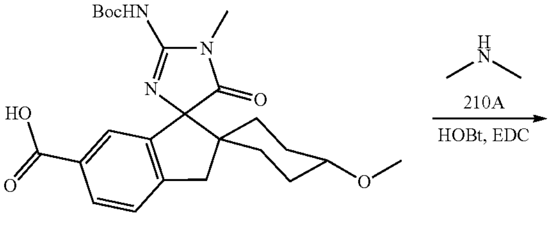

209a

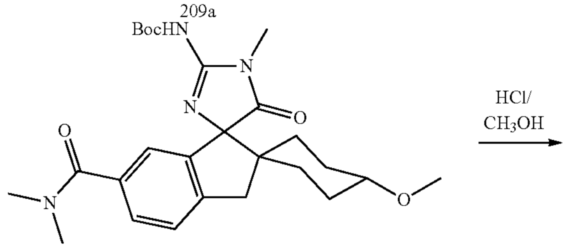

210a

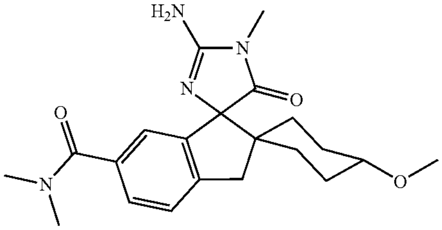

210

According to a similar synthesis of compound 210, compound 209a (30 mg, 6 mmol) was coupled with compound 210A (5 mg, 60 mmol) to give crude compound 210a (22 mg, 70%) as a yellow solid, which was removed the protecting group in HCl/dioxane (5 mL, 4N) to afford compound 210 (trifluoroacetic salt) (1.7 mg, 10%) as a white solid. LC-MS $t_R$=0.807 min in 2 min chromatography, MS (ESI) m/z 384.22 $[M+H]^+$. $^1$H NMR ($CD_3OD$ 400 MHz): δ 7.35 (q, 2H), 7.18 (s, 1H), 3.25 (s, 3H), 3.09 (m, 3H), 3.12 (s, 1H), 2.9 (s, 3H), 2.8 (s, 3H), 1.9-1.7 (m, 3H), 1.3-1.2 (m, 5H).

Example 171

Synthesis of Compound 211

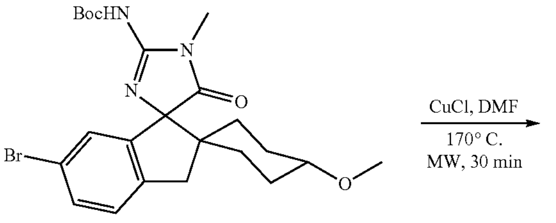

205a

-continued

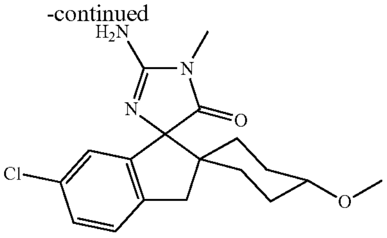

211

Compound 205a (25 mg, 0.051 mmol) and CuCl (60 mg, 0.61 mmol) was dissolved in DMF (3 mL), the resulting mixture was degassed and purged with $N_2$ for three times. The reaction was heated at 170° C. for 30 min in microwave. LCMS showed that the reaction was completed and solvent was removed under reduced pressure. The residue was purified by preparative TLC ($CH_2Cl_2$:MeOH=5:1) and preparative HPLC to afford compound 211 (14.1 mg, 80%) as a white solid. LC-MS $t_R$=1.014 min in 2 min chromatography, MS (ESI) m/z 348.1 $[M+H]^+$. $^1$H NMR ($CD_3OD$ 400 MHz): δ 7.26-7.32 (m, 2H), 7.01 (s, 1H), 3.33 (s, 3H), 3.12-3.18 (m, 1H), 3.02-3.09 (m, 5H), 1.96-2.07 (m, 2H), 1.82-1.84 (m, 1H), 1.59-1.67 (m, 1H), 1.32-1.44 (m, 2H), 1.27-1.30 (m, 2H)

Example 172

Synthesis of Compounds 212 and 213

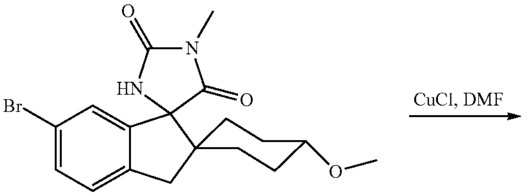

211a

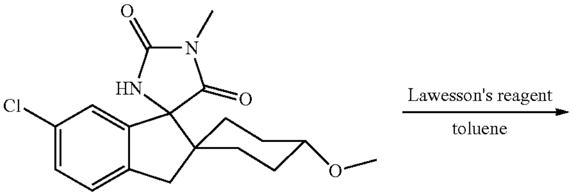

211b

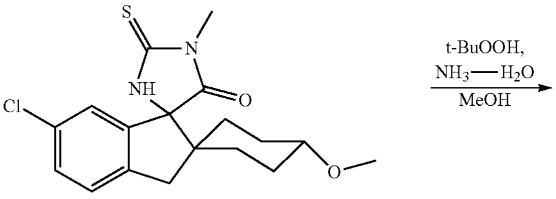

211c

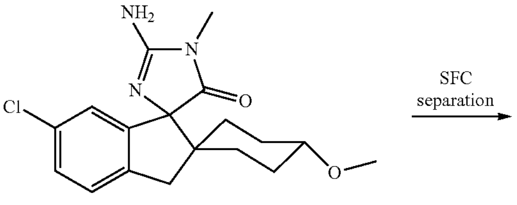

211

-continued

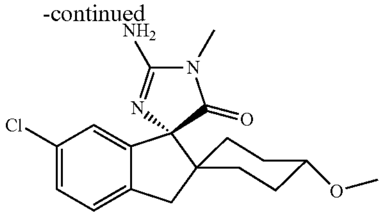

212

+

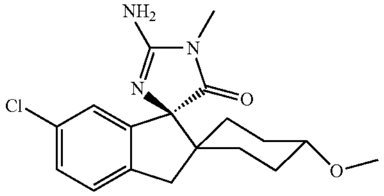

213

Procedure for Preparation of Compound 211b

A suspension of compound 211a (600 mg, 1.5 mmol), CuCl (600 mg, 6.1 mmol) in anhydrous DMF (15 mL) was heated at 180° C. for 45 min in a CEM microwave reactor. The mixture was concentrated in vacuo, the residue was purified by preparative TLC on silica gel eluting with petroleum ether: ethyl acetate=1:1 to give compound 211b (510 mg, 90%) as a yellow solid.

Procedure for Preparation of Compound 211c

A suspension of compound 211b (510 mg, 1.47 mmol) and Lawesson's Reagent (650 mg, 1.6 mmol) in anhydrous toluene (15 mL) was heated at 130° C. for 40 min in a CEM microwave reactor. The mixture was concentrated in vacuo, the residue was purified by prep HPLC to give compound 211c (316 mg, 60%) as a white solid.

Procedure for Preparation of Compound 211, 212 and 213

A solution of compound 211c (310 mg, 0.85 mmol), t-BuOOH (3 mL), $NH_3$—$H_2O$ (3 mL) in EtOH (10 mL) was stirred at 10° C. for 10 h. The mixture was concentrated in vacuo to give the residue, which was purified by preparative HPLC to give compound 211 (150 mg, 50%) as a white solid. LCMS: 728-054-1B, $t_R$=1.310 min in 3 min chromatography, MS (ESI) m/z=348.1 $[M+H]^+$. $^1H$ NMR ($CD_3OD$ 300 MHz): δ 7.20-7.35 (m, 2H), 6.90-7.00 (s, 1H), 3.35-3.40 (s, 3H), 3.00-3.20 (m, 6H), 1.90-2.10 (m, 1H), 1.75-1.85 (s, 1H), 1.55-1.70 (m, 1H), 1.20-1.45 (m, 4H).

Compound 211 (40 mg, 0.12 mmol) was separated by preparative SFC to give compound 212 (8.2 mg, 20%), LCMS: $t_R$=0.899 min in 2 min chromatography, MS (ESI) m/z=348.1 $[M+H]^+$. SFC: $t_R$=6.29 min in 15 min chromatography, ee=99.6%. $^1H$ NMR ($CD_3OD$ 300 MHz): δ 7.20-7.35 (m, 2H), 6.90-7.00 (s, 1H), 3.35-3.40 (s, 3H), 3.00-3.20 (m, 6H), 1.90-2.10 (m, 1H), 1.75-1.85 (s, 1H), 1.55-1.70 (m, 1H), 1.20-1.45 (m, 4H); and compound 212 (8.3 mg, 21%). LCMS: $t_R$=0.893 min in 2 min chromatography, MS (ESI) m/z=348.1 $[M+H]^+$. SFC: $t_R$=8.39 min in 15 min chromatography, ee=99.8%. $^1H$ NMR ($CD_3OD$ 300 MHz): δ 7.20-7.35 (m, 2H), 6.90-7.00 (s, 1H), 3.35-3.40 (s, 3H), 3.00-3.20 (m, 6H), 1.90-2.10 (m, 1H), 1.75-1.85 (s, 1H), 1.55-1.70 (m, 1H), 1.20-1.45 (m, 4H).

Example 173

Synthesis of Compound 214

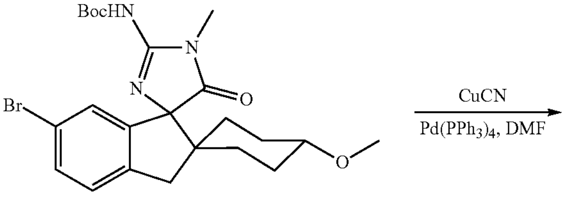

205a

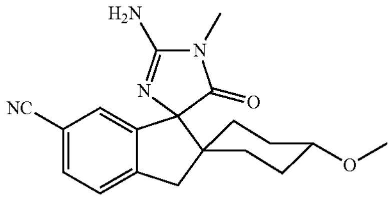

214

To a suspension of compound 205a (40 mg, 0.08 mmol) and cyanocopper (18 mg, 0.2 mmol) in DMF (5 mL) was added $Pd(PPh_3)_4$ (5.5 mg, 0.0048 mmol) at room temperature under a nitrogen atmosphere. After addition, the resulting mixture was heated at 120° C. in a sealed tube for 30 h. After cooling to room temperature, the mixture was diluted with ethyl acetate (30 mL) and washed with brine (10 mL). The separated organic layer was dried over $Na_2SO_4$, filtered and concentrated under reduced pressure. The residue was purified by basic preparative HPLC (basic) to give compound 214 (8.4 mg, 30%) as a white solid. LC-MS $t_R$=0.820 min in 2 min chromatography, MS (ESI) m/z 338.9 $[M+H]^+$. $^1H$ NMR ($CD_3OD$ variant 400): δ 7.62 (d, J=7.6 Hz, 1H), 7.45 (d, J=7.6 Hz, 1H), 7.29 (s, 1H), 3.32 (s, 3H), 3.29-3.10 (m, 2H), 3.11 (m, 1H), 2.99 (s, 3H), 2.0-1.93 (m, 2H), 1.80 (m, 1H), 1.64 (m, 1H), 1.40 (m, 1H), 1.30-1.23 (m, 3H).

Example 174

Synthesis of Compounds 215 and 216

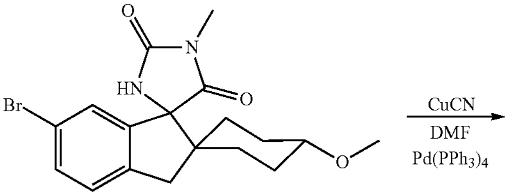

211a

-continued

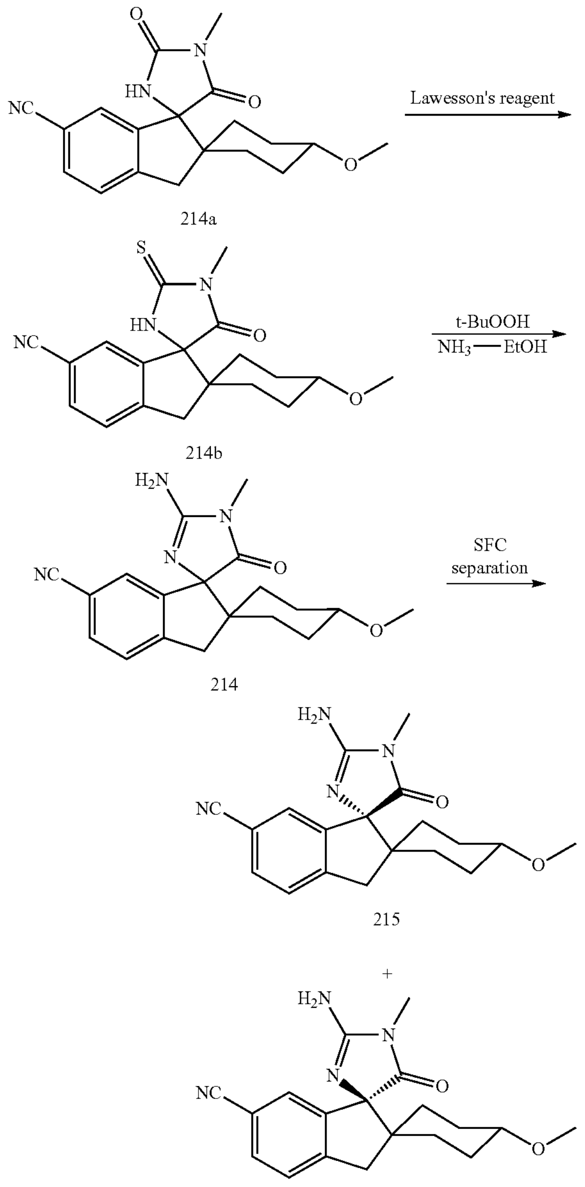

214a

214b

214

215

+

216

Procedure for Preparation of Compound 214a

To a solution of compound 211a (1.5 g, 3.3 mmol) in DMF (15 mL) was added CuCN (682.5 mg, 6.6 mmol), and $Pd(PPh_3)_4$ (205.5 mg, 0.17 mmol) under nitrogen, the mixture was stirred at 180° C. in a CEM microwave reactor for 30 min. The reaction mixture was diluted with $H_2O$ (20 mL) and extracted with EtOAc (3×10 mL). The combined organic layers were washed with brine (30 mL), dried over $Na_2SO_4$ and concentrated to give the crude product which was purified by column chromatography on silica gel eluting with hexane: EtOAc (20:1 to 5:1) to give compound 214a (0.75 g, 58%) as a white solid. $^1$H NMR ($CDCl_3$ 400 MHz): δ 7.55 (s, 1H), 7.44 (d, J=7.2 Hz, 2H), 6.05 (s, 1H), 3.41 (s, 3H), 3.38-3.41 (m, 1H), 3.15-3.21 (d, J=14 Hz, 2H), 2.94-2.97 (s, 3H), 1.89-2.10 (m, 3H), 1.18-1.47 (m, 5H).

Procedure for Preparation of Compounds 214, 215 and 216

According to a similar synthesis of compound 211 described in Example 172, compound 214a (750 mg, 2.21 mmol) was reacted with Lawesson's Reagent (893.6 mg, 2.21 mmol) under a nitrogen atmosphere to give compound 214b (500 mg, 63%) as a white solid. $^1$H NMR ($CDCl_3$ 300 MHz): δ 7.57 (d, J=8.4 Hz, 1H), 7.35-7.44 (d, J=8.4 Hz, 1H), 7.31 (s, 1H), 3.41 (s, 3H), 3.28-3.37 (m, 1H), 3.19 (s, 3H), 3.09-3.23 (m, 2H), 1.87-2.12 (m, 3H), 1.18-1.37 (m, 5H).

Compound 214b (500 mg, 1.40 mmol) was converted to compound 214, which was separated by preparative SFC to give compound 215 (85.6 mg), LCMS: $t_R$=0.937 min in 2 min chromatography, MS (ESI) m/z 339.1 $[M+H]^+$. SFC: $t_R$=5.26 min in 16 min chromatography, ee %=99.7%. $^1$H NMR ($CD_3OD$ 400 MHz): δ 7.65-7.63 (d, J=8.0 Hz, 1H), 7.51 (d, J=8.0 Hz, 1H), 7.36 (s, 1H), 3.34 (s, 3H), 3.23-3.32 (m, 1H), 3.13-3.19 (m, 2H), 3.06 (s, 3H), 1.98-2.03 (m, 2H), 1.84-1.98 (m, 1H), 1.62-1.69 (m, 1H), 1.38-1.42 (m, 2H), 1.29-1.38 (m, 2H); and compound 216 (100 mg, totally 38%) as white solid, LCMS: $t_R$=0.943 min in 2 min chromatography, MS (ESI) m/z 339.1 $[M+H]^+$. SFC: $t_R$=5.92 min in 16 min chromatography, ee %=100%. $^1$H NMR ($CD_3OD$ 400 MHz): δ 7.53 (d, J=8.0 Hz, 1H), 7.44 (d, J=8.8 Hz, 1H), 7.21 (s, 1H), 3.40 (s, 3H), 3.26-3.38 (m, 1H), 2.95-3.07 (m, 2H), 3.06 (s, 3H), 1.86-1.94 (m, 2H), 1.82-1.86 (m, 1H), 1.54-1.67 (m, 1H), 1.29-1.44 (m, 2H), 1.10-1.27 (m, 2H).

Example 175

Synthesis of Compound 217

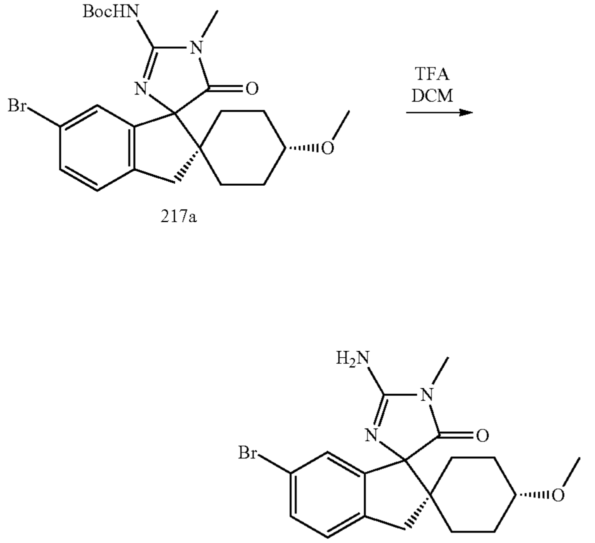

217a

217

To a solution of compound 217a (8.0 mg, 0.016 mmol) in DCM there was added TFA (10 drops), and the solution was stirred at room temperature for 1 hour, solvent was removed in vacuum, and the residue was purified by HPLC to give compound 217 (6.7 mg, 81%) as a TFA salt. LC-MS $t_R$=1.17 min in 3 min chromatography, MS (ESI) m/z 393.0 $[M+H]^+$ $^1H$ NMR ($CD_3OD$, 400 MHz): δ 7.48 (dd, J=1.2, 7.8 Hz, 1H), 7.42 (d, J=1.2 Hz, 1H), 7.26 (d, J=7.8 Hz, 1H), 3.34 (s, 3H), 3.18 (s, 3H), 3.16-3.04 (m, 3H), 2.02 (m, 2H), 1.84 (m, 1H), 1.44-1.24 (m, 5H).

Example 176

Synthesis of Compound 218

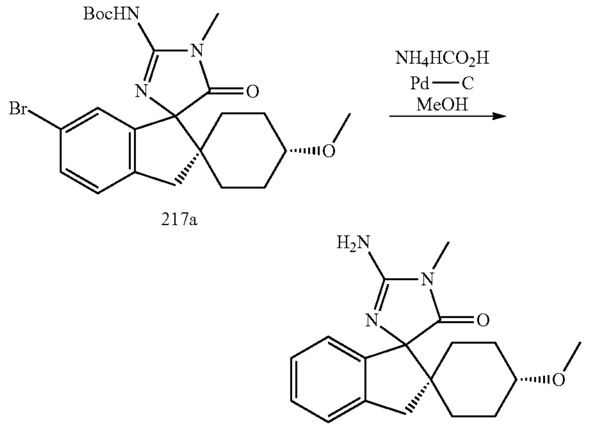

217a

218

To a solution of compound 217a (7.5 mg, 0.015 mmol) in MeOH (0.2 mL) was added ammonium formate (2.8 mg, 0.045 mmol) followed by Pd—C (1 mg). The resulting mixture was heated at 120° C. in a CEM microwave reactor for 10 min. The reaction mixture was filtered and the filtrate was purified by revised phase HPLC to give compound 218 (3.8 mg, 59%) as a TFA salt. LC-MS $t_R$=1.07 min in 3 min chromatography, MS (ESI) m/z 314.0 $[M+H]^+$; $^1H$ NMR ($CD_3OD$, 400 MHz): δ 7.38 (m, 2H), 7.24 (m, 1H), 7.18 (m, 1H), 3.34 (s, 3H), 3.18 (s, 3H), 3.14 (m, 3H), 2.02 (m, 2H), 1.84 (m, 1H), 1.44-1.24 (m, 5H).

Alternatively, compound 218 can be prepared according to the following scheme:

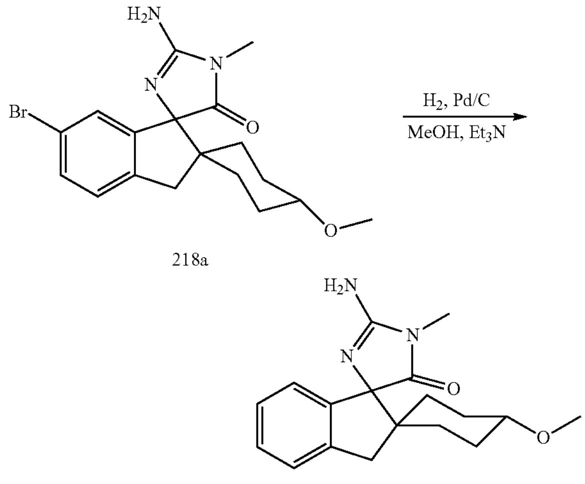

218a

218

To a solution of compound 218a (20 mg, 0.051 mmol) in MeOH (3 mL) was added $Et_3N$ (0.1 mL) and Pd/C (10 mg, 10 wt %). The resulting mixture was stirred at room temperature for 15 h under $H_2$ (15 psi), LC-MS showed that the reaction was completed. The reaction mixture was filtered and the filtrate was concentrated under reduced pressure. The residue was purified by pre-TLC ($CH_2Cl_2$:MeOH=10:1) and pre-HPLC to give compound 218 (5.2 mg, 33%) as a white solid. LC-MS $t_R$=0.940 min in 2 min chromatography, MS (ESI) m/z 314.1 $[M+H]^+$; $^1H$ NMR ($CD_3OD$ 400 MHz): δ 7.25-7.31 (m, 2H), 7.16-7.20 (t, J=7.2 Hz, 1H), 6.99-7.00 (d, J=7.6 Hz, 1H), 3.36 (s, 3H), 3.08-3.18 (m, 3H), 3.04 (s, 3H), 1.96-2.03 (m, 2H), 1.84-1.87 (m, 1H), 1.57-1.65 (m, 1H), 1.32-1.45 (m, 2H), 1.28-1.32 (m, 2H).

Example 177

Synthesis of Compound 219

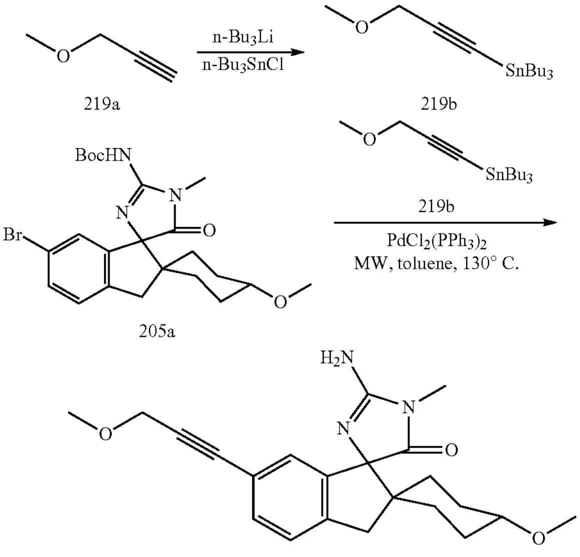

219a

219b

205a

219

Procedure for Preparation of Compound 219b n-BuLi (2.5 M in hexane, 10.8 mL, 27 mmol) was added to a solution of compound 219a (1.7 g, 2 mL, 24 mmol) in THF (50 mL) at −78° C., and the reaction mixture was stirred at −78° C. for 30 min and at 0° C. for 30 min. After cooled to −78° C., the reaction mixture was treated with n-$Bu_3$SnCl (8.68 g, 7.3 mL, 27 mmol), and allowed to warm to room temperature over 5 h. The solvent was removed under vacuum, and the residue was partitioned between diethyl ether (50 mL) and $H_2O$ (30 mL). The diethyl ether layer was washed with brine (2×30 mL), dried over anhydrous $Na_2SO_4$, and concentrated. Flash chromatography of the crude ($Al_2O_3$, PE) afforded compound 219b as colorless oil (6.5 g, 75%).

Procedure for Preparation of Compound 219

To a solution of compound 205a (50 mg, 0.1 mmol) and compound 219b (73 mg, 0.2 mmol) in toluene (4 mL) was added $Pd(PPh_3)_2Cl_2$ (4 mg) under $N_2$ atmosphere. The mixture was stirred at 135° C. for 45 min in microwave. LCMS showed that the reaction was completed. The reaction mixture was concentrated in vacuo to give the residue. The residue was partitioned by EtOAc (10 mL) and aqueous of CsF (4 M, 8 mL). The aqueous layer was extracted with EtOAc (2×10 mL), the combined organic layers were washed with brine (2×10 mL), dried over anhydrous $Na_2SO_4$ and concentrated to dryness. Purification of this residue by preparative TLC ($CH_2Cl_2$:MeOH=10:1) afforded compound 219 (25 mg, 66%), LC-MS $t_R$=0.926 min in 2 min chromatography, MS (ESI) m/z 382.2 $[M+H]^+$. $^1H$ NMR ($CD_3OD$, 400 MHz): δ 7.34-7.36 (d, J=8.8 Hz, 1H), 7.28-7.30 (d, J=8.0 Hz, 1H), 7.03 (s, 1H), 4.31 (s, 2H), 3.42 (s, 3H), 3.37 (s, 3H), 3.09-3.16 (m, 3H), 3.04 (s, 3H), 1.96-2.03 (m, 2H), 1.83-1.85 (m, 1H), 1.26-1.39 (m, 5H).

Example 178

Synthesis of Compound 220

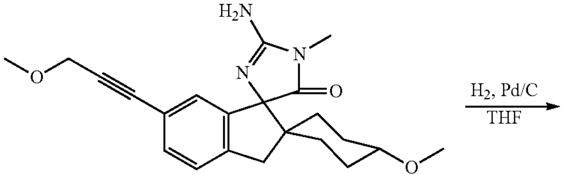

219

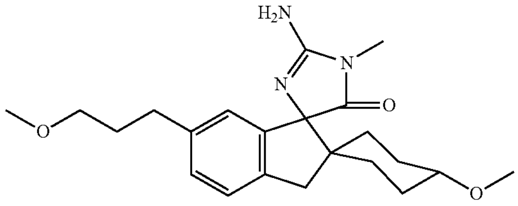

220

To a solution of compound 219 (30 mg, 0.079 mmol) in THF (5 mL) was added Pd/C (3 mg, 10 wt %). The resulting mixture was stirred under $H_2$ atmosphere at room temperature for 1 h, LC-MS showed that the reaction was completed. The reaction mixture was filtered through a pad of celite, and the filtrate was concentrated to give the residue, which was purified by preparative HPLC to afford compound 220 (3.6 mg, 12%) as a white solid. LC-MS $t_R$=0.893 min in 2 min chromatography, MS (ESI) m/z 386.0 $[M+H]^+$. $^1H$ NMR ($CD_3OD$, 400 MHz): δ 7.17-7.19 (d, J=8.0 Hz, 1H), 7.06-7.08 (d, J=7.6 Hz, 1H), 6.80 (s, 1H), 3.34-3.36 (m, 5H), 3.32 (s, 3H), 3.07-3.12 (m, 1H), 2.97-3.03 (m, 5H), 2.58-2.60 (t, J=7.6 Hz, 2H), 1.90-2.00 (m, 2H), 1.74-1.82 (m, 3H), 1.52-1.56 (m, 1H), 1.23-1.37 (m, 4H).

Example 179

Synthesis of Compound 221

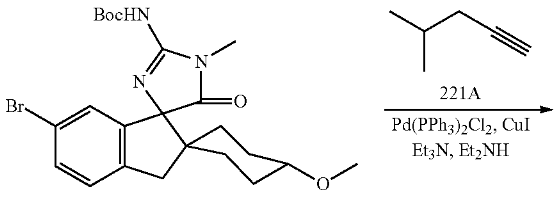

205a

-continued

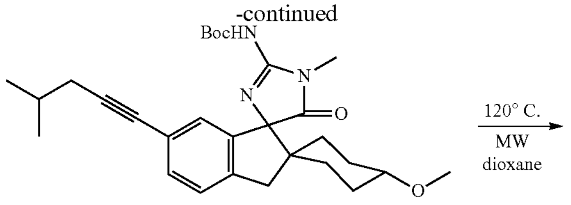

221a

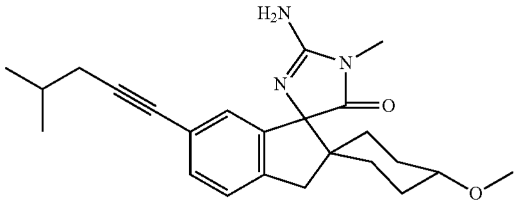

221

Procedure for Preparation of Compound 221a

A dry three-necked round bottom flask equipped with a condenser was charged with compound 205a (50 mg, 0.1 mmol), $Et_3N$ (5 mL) and DEA (1 mL) under $N_2$ atmosphere. To this solution was added CuI (1 mg, 0.005 mmol), and $PdCl_2(PPh_3)_2$ (3.5 mg, 0.005 mmol). After being degassed once again, compound 221A (0.057 mL, 0.5 mmol) was added, and the mixture was heated at 50° C. (oil bath) with stirring for 12 h. LCMS showed that the reaction was completed. After evaporation, the residue was partitioned with EtOAc (15 mL) and water (10 mL), and the aqueous layer was extracted with EtOAc (2×10 mL). The combined organic layers were washed with brine (10 mL), dried over $Na_2SO_4$, and concentrated under reduced pressure, and the crude product was purified by preparative TLC (petroleum ether:ethyl acetate=5:1) to give compound 221a (40 mg, 80%) as a white solid.

Procedure for Preparation of Compound 221

Compound 221a (20 mg, 0.04 mmol) was dissolved in 1,4-dioxane (3 mL). The mixture was stirred at 125° C. for 20 min in microwave. LCMS showed that the reaction was completed. The reaction mixture was concentrated under reduced pressure and the residue was purified by preparative HPLC (basic) to afford compound 221 (5.1 mg, 32%) as a white solid. LC-MS $t_R$=1.195 min in 2 min chromatography, MS (ESI) m/z 394.2 $[M+H]^+$; $^1H$ NMR ($CD_3OD$, 400 MHz): δ 7.21-7.28 (q, 2H), 6.96 (s, 1H), 3.35 (s, 3H), 3.04-3.17 (m, 3H), 3.01 (s, 3H), 2.27-2.34 (d, J=8.8 Hz, 2H), 1.93-2.02 (m, 2H), 1.82-1.91 (m, 1H), 1.56-1.61 (m, 1H), 1.35-1.43 (m, 2H), 1.25-1.33 (m, 2H), 1.02-1.05 (d, J=8.8 Hz, 6H).

Example 180

Synthesis of Compound 222

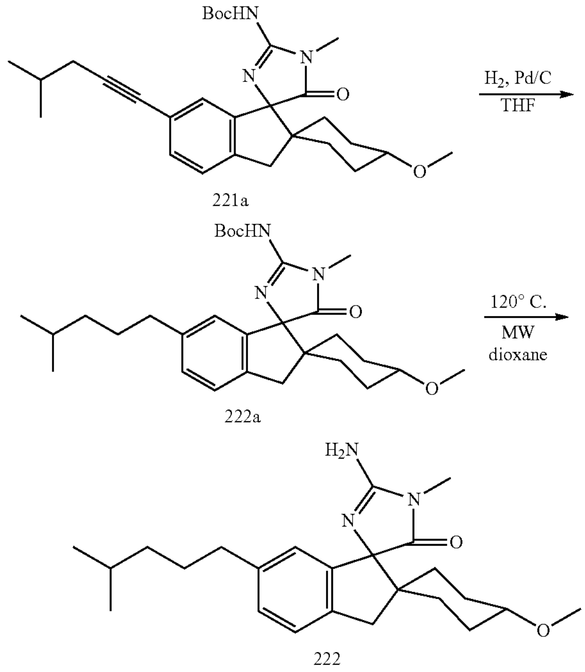

Procedure for Preparation of Compound 222a

To a solution of compound 221a (20 mg, 0.04 mmol) in THF (3 mL) was added Pd/C (10 mg, 10 wt %). The reaction mixture was stirred at room temperature under $H_2$ atmosphere for 1 h, LC-MS showed that the reaction was completed. The reaction mixture was filtered though a pad of celite, and the filtrate was concentrated to the residue, which was purified by preparative TLC (petroleum ether:ethyl acetate=5:1) to afford compound 222a (18 mg, 91%) as a white solid.

Procedure for Preparation of Compound 222

Compound 222a (18 mg, 0.036 mmol) was dissolved in 1,4-dioxane (3 mL). The mixture was stirred at 125° C. for 20 min in microwave. LCMS showed that the reaction was completed. The reaction mixture was concentrated under reduced pressure and the residue was purified by preparative HPLC (basic) to afford compound 222 (3.1 mg, 22%) as a white solid. LC-MS $t_R$=1.243 min in 2 min chromatography, MS (ESI) m/z 398.3 $[M+H]^+$. $^1H$ NMR ($CD_3OD$, 400 MHz): δ 7.16-7.18 (d, J=7.6 Hz, 1H), 7.06-7.08 (d, J=7.6 Hz, 1H), 6.81 (s, 1H), 3.32 (s, 3H), 3.08-3.13 (m, 1H), 3.03 (s, 3H), 2.97-3.02 (m, 2H), 2.50-2.54 (t, J=7.6 Hz, 2H), 1.92-2.03 (m, 2H), 1.78-1.82 (m, 1H), 1.50-1.57 (m, 4H), 1.32-1.39 (m, 2H), 1.22-1.27 (m, 2H), 1.12-1.19 (m, 2H), 0.84-0.85 (d, J=6.4 Hz, 6H).

Example 181

Synthesis of Compound 223

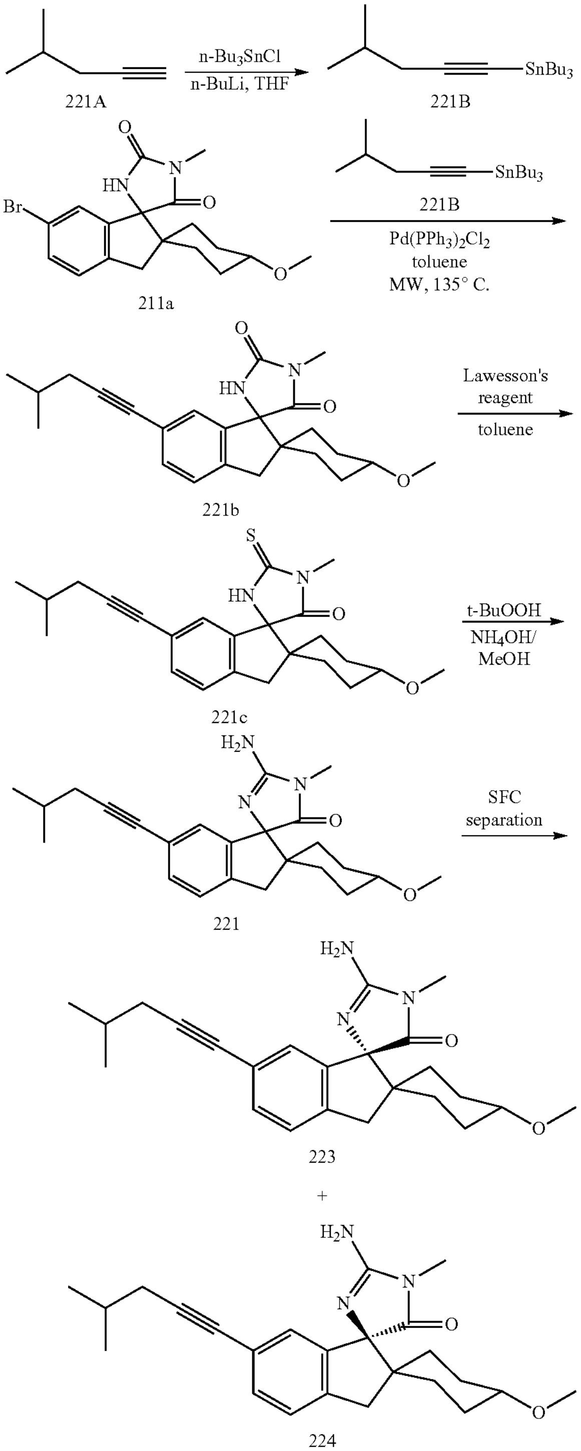

Procedure for Preparation of Compound 221B n-BuLi (2.5 M in hexane, 11.88 mL, 29.7 mmol) was added to a solution of compound 221A (2.216 g, 3.175 mL, 27 mmol) in THF (80 mL) at −78° C., and the reaction mixture was stirred at −78° C. for 30 min and at 0° C. for 30 min. After cooled to −78° C., the reaction mixture was treated with n-$Bu_3SnCl$ (9.67 g, 8 mL, 29.7 mmol), and allowed to warm to room temperature over 5 h. The solvent was removed under reduced pressure, and the residue was partitioned between diethyl ether (100 mL) and $H_2O$ (3×80 mL). The diethyl ether layer was washed with brine (80 mL), dried over anhydrous $Na_2SO_4$, and concentrated. Flash chromatography of the crude product on $Al_2O_3$ eluting with petroleum ether afforded compound 221B (9 g, 90%) as a colorless oil.

Procedure for Preparation of Compound 221b

To a solution of compound 211a (800 mg, 2.04 mmol) and compound 221B (3.79 mg, 10.18 mmol) in toluene (25 mL) was added $Pd(PPh_3)_2Cl_2$ (72 mg) under $N_2$ atmosphere. The mixture was stirred at 135° C. for 45 min in microwave. LCMS showed that the reaction was completed. The reaction mixture was concentrated under reduced pressure to give the residue. The residue was partitioned by EtOAc (100 mL) and aqueous of CsF (4M, 80 mL). The aqueous layer was extracted by EtOAc (2×100 mL), the combined organic layers were washed with brine (2×100 mL), dried over anhydrous $Na_2SO_4$ and concentrated to dryness. Purification of this residue by preparative TLC (petroleum:ethyl acetate=2:1) afforded compound 221b (600 mg, 75%) as a white solid.

Procedure for Preparation of Compound 221c

A solution of compound 221b (600 mg, 1.52 mmol) and Lawesson's Reagent (677 mg, 1.68 mmol) in dry toluene (50 mL) was refluxed for 5 h. LCMS showed that the reaction was completed, the mixture was concentrated under reduced pressure, and the residue was purified by preparative TLC (petroleum ether:ethyl acetate=2:1) to give compound 221c (500 mg, 81%) as a white solid.

Procedure for Preparation of Compounds 221, 223 and 224

A mixture of compound 221c (0.5 g, 1.23 mmol) and t-butyl hydroperoxide (3.4 g, ca. 65% solution in water, 24.6 mmol) in $NH_4OH$/MeOH (10/50 mL) was stirred overnight at room temperature, LCMS showed that the reaction was completed, the reaction mixture was concentrated under reduced pressure to dryness. Purification of this residue by preparative TLC ($CH_2Cl_2$:MeOH=10:1) and preparative HPLC (basic) afforded compound 221 (60 mg, 12%, 18.50 mg delivered) and then further separated by SFC to afford compound compound 223 (12.5 mg), LC-MS $t_R$=1.069 min in 2 min chromatography, MS (ESI) m/z 394.2 $[M+H]^+$. ee: 98%; $^1H$ NMR ($CD_3OD$, 400 MHz): δ 7.23-7.28 (q, J=7.6 Hz, 2H), 6.95 (s, 1H), 3.35 (s, 3H), 3.02-3.14 (m, 6H), 2.28-2.29 (d, J=6.4 Hz, 2H), 1.83-2.08 (m, 4H), 1.58-1.66 (m, 1H), 1.26-1.42 (m, 4H), 1.03-1.06 (d, J=6.8 Hz, 6H); and compound 224 (11.50 mg) as a white solid; LC-MS $t_R$=1.064 min in 2 min chromatography, MS (ESI) m/z 394.2 $[M+H]^+$; ee: 98%; $^1H$ NMR ($CD_3OD$, 400 MHz): δ 7.12-7.17 (m, 2H), 6.85 (s, 1H), 3.23 (s, 3H), 2.87-3.06 (m, 6H), 2.16-2.17 (d, J=6.4 Hz, 2H), 1.71-1.90 (m, 4H), 1.45-1.49 (m, 1H), 1.14-1.30 (m, 4H), 0.87-0.93 (d, J=6.4 Hz, 6H).

Example 182

Synthesis of Compound 225

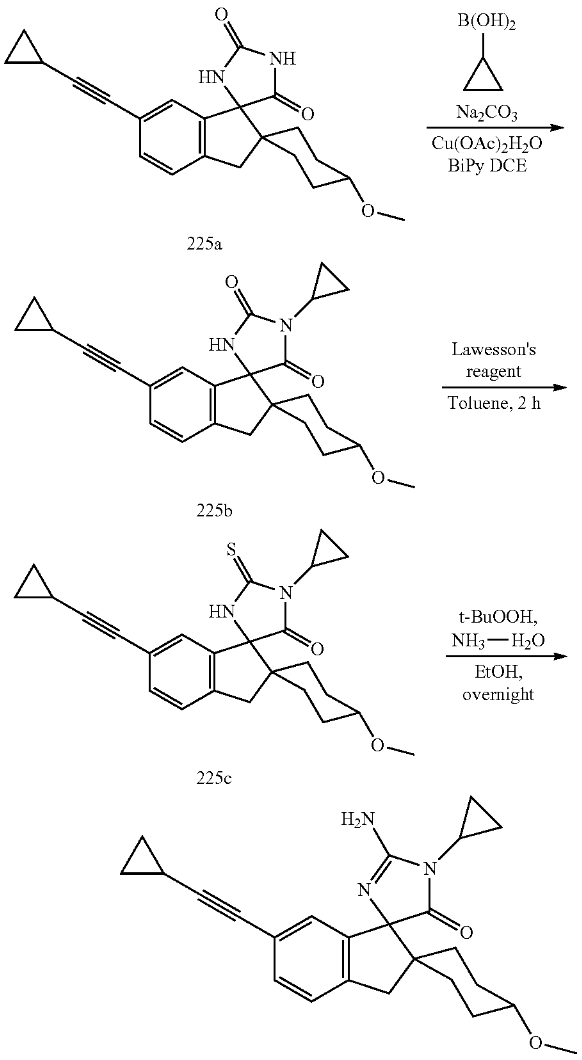

225a

225b

225c

225

Procedure for Preparation of Compound 225b

To a solution of compound 225a (80 mg, 0.22 mmol) in $ClCH_2CH_2Cl$ (8 mL) was added $Cu(OAc)_2.H_2O$ (90 mg, 0.45 mmol), BiPy (70 mg, 0.45 mmol), $Na_2CO_3$ (60 mg, 0.45 mmol) and cyclopropylboronic (20 mg, 0.23 mmol). The reaction mixture was stirred at 70° C. in the open air for 6 h. The mixture was quenched by saturated $NH_4Cl$ (3 mL). The mixture was partitioned with $CH_2Cl_2$ (20 mL) and water (10 mL). The aqueous layer was extracted with $CH_2Cl_2$ (2×10 mL). The combined organic layers were washed with brine (10 mL), dried over $Na_2SO_4$, and concentrated under reduced pressure to anhydrousness. The residue was purified by preparative TLC on silica gel (eluent:petroleum ether:ethyl acetate=2:1) to give compound 225b (31 mg, 31%) as a white solid.

Procedure for Preparation of Compound 225c

A suspension of compound 225b (28 mg, 0.07 mmol) and Lawesson's Reagent (35 mg, 0.08 mol) in anhydrous toluene (10 mL) was heated at reflux for 2 h. The mixture was concentrated in vacuo and the residue was purified by preparative TLC on silica gel (eluent:petroleum ether:ethyl acetate=2:1) to give compound 225c (13 mg, 45%) as a white solid.

Procedure for Preparation of Compound 225

A solution of compound 225c (13 mg, 0.03 mmol), t-BuOOH (60 mg, 0.6 mmol), $NH_3$—$H_2O$ (0.5 mL) in EtOH (2 mL) was stirred at 20° C. for 10 h. The mixture was concentrated in vacuo to give the residue, which was purified by preparative TLC on silica gel (eluent:$CH_2Cl_2$:$CH_3OH$=15:1) to give compound 225 (4.2 mg, 30%) as a white solid. LCMS: $t_R$=1.06 min in 2 min chromatography, MS (ESI) m/z 404 $[M+H]^+$. $^1H$ NMR ($CD_3OD$ 400 MHz): δ 7.05-7.11 (m, 2H), 6.76 (s, 1H), 3.20 (s, 3H), 2.86-3.09 (m, 3H), 2.42-2.46 (m, 1H), 1.80-1.96 (m, 2H), 1.65-1.67 (m, 1H), 1.47-1.54 (m, 1H), 1.30-1.36 (m, 1H), 1.02-1.28 (m, 4H), 0.85-0.95 (m, 2H), 0.70-0.80 (m, 3H), 0.61-0.68 (m, 3H).

Example 183

Synthesis of Compound 226

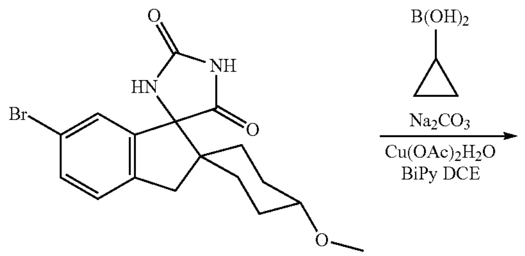

226a

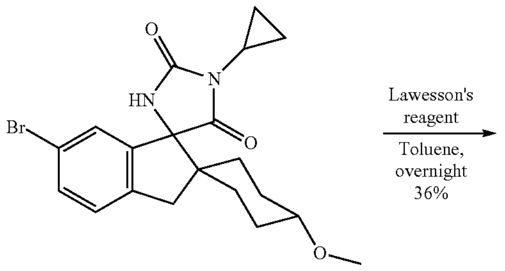

226b

-continued

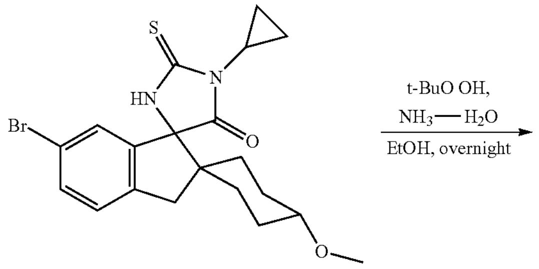

226c

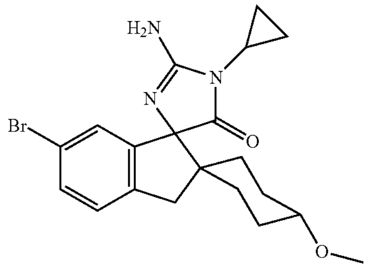

226

According to a similar synthesis of compound 225, compound 226a (100 mg, 0.28 mmol) was coupled with cyclopropylboronic (25 mg, 0.3 mmol) to give compound 226b (57 mg, 50%) as a white solid.

Compound 226b (55 mg, 0.13 mmol) wad then reacted with Lawesson's Reagent (65 mg, 0.716 mol) to give compound 226c (26 mg, 36%) as a yellow solid, which was converted to compound 226 as a white solid (16 mg, 62%). LCMS: $t_R$=1.55 min in 3 min chromatography, MS (ESI) m/z 420 $[M+H]^+$. $^1H$ NMR ($CD_3OD$ 400 MHz): δ 7.37-7.40 (m, 1H), 7.21-7.23 (d, J=8.0 Hz, 1H), 7.07 (s, 1H), 3.34 (s 3H), 2.95-3.15 (m, 3H), 2.54-2.58 (m, 1H), 1.92-2.02 (m, 2H), 1.72-1.80 (d, 1H), 1.58-1.70 (m, 1H), 1.15-1.40 (m, 4H), 0.98-2.05 (m, 2H), 0.84-0.91 (m, 2H), 0.85-0.92 (m, 1H), 0.75-0.81 (m, 1H).

Example 184

Synthesis of Compound 227

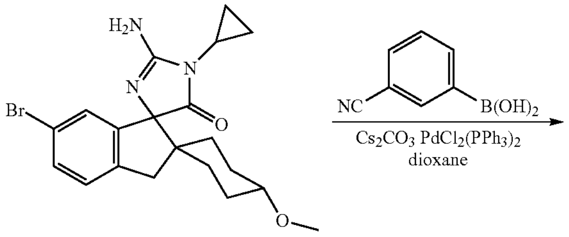

226

-continued

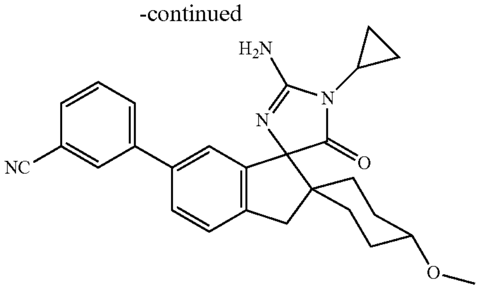

227

A suspension of compound 226 (13 mg, 0.03 mmol), 3-cyanophenylboronic acid (5 mg, 0.03 mmol), $Pd(PPh_3)_2Cl_2$ (1 mg, 0.003 mmol) and $Cs_2CO_3$ (0.1 mL, 2 N in water) in 1,4-dioxane (2 mL) was heated at 120° C. for 15 min in a CEM microwave reactor. The mixture was concentrated in vacuo and the residue was purified by preparative HPLC to give compound 227 (0.7 mg, 5%) as a white solid. LCMS: $t_R$=1.82 min in 3 min chromatography, MS (ESI) m/z 439 $[M+H]^+$. $^1$H NMR ($CD_3OD$ 400 MHz): δ 7.89-7.95 (m, 2H), 7.56-7.69 (m, 3H), 7.41-7.43 (m, 1H), 7.23 (s, 1H), 3.36 (s, 3H), 3.07-3.18 (m, 3H), 2.57-2.62 (m, 1H), 1.96-2.04 (m, 2H), 1.80-1.83 (m, 1H), 1.60-1.75 (m, 1H), 1.21-1.41 (m, 5H), 1.00-1.10 (m, 2H), 0.75-0.96 (m, 2H)

Example 185

Synthesis of Compound 228

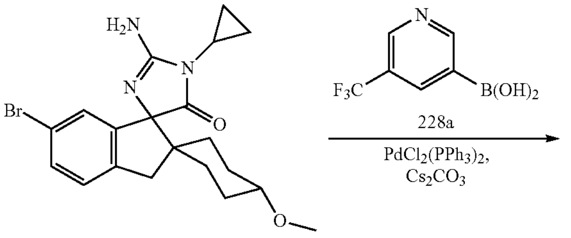

226

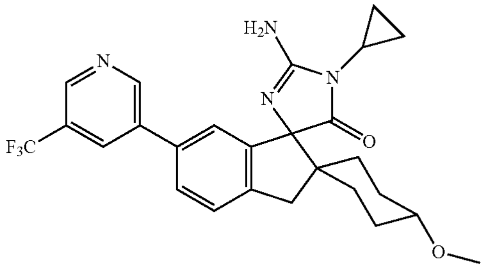

228

According to a similar synthesis of compound 227, compound 226 (7 mg, 0.017 mmol) was coupled with compound 228a (3.8 mg, 0.02 mmol) to give compound 228 (8.7 mg, 30%) as a white trifluoroacetic salt solid. LC-MS $t_R$=0.973 min in 2 min chromatography, MS (ESI) m/z 485.1 $[M+H]^+$. $^1$H NMR: ($CD_3OD$ 400 MHz): δ 8.98 (s, 1H), 8.76 (s, 1H), 8.26 (s, 1H), 7.66-7.64 (d, J=8.0 Hz, 1H), 7.55 (s, 1H), 7.45-7.43 (d, J=8.0 Hz, 1H), 3.15-3.04 (d, J=15.6 Hz, 2H), 2.63 (s, 1H), 1.925 (m, 2H), 1.71 (m, 1H), 1.32 (s, 3H), 1.28-1.25 (m, 3H), 1.03 (m, 2H), 0.91 (m, 1H), 0.81 (s, 1H).

Example 186

Synthesis of Compound 229

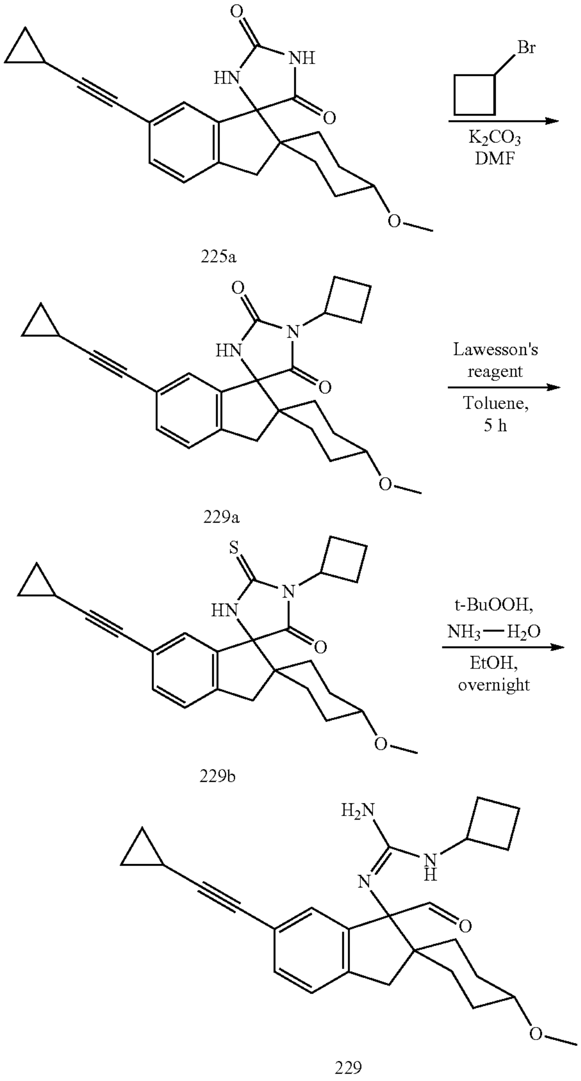

Procedure for Preparation of Compound 229a

To a solution of compound 225a (100 mg, 0.27 mmol) in DMF (5 mL) was added $K_2CO_3$ (120 mg, 0.8 mmol) and bromo-cyclobutane (75 mg, 0.55 mmol). The reaction mixture was stirred at 20° C. for 20 h. The mixture was filtered and the filtrate was concentrated in vacuo to give the residue, which was purified by preparative TLC (eluent:petroleum ether:ethyl acetate=2:1) to give compound 229a (81 mg, 73%) as a white solid.

Procedure for Preparation of Compound 229

According to a similar synthesis of compound 225, compound 229a (80 mg, 0.19 mmol) was reacted with Lawesson's Reagent (82 mg, 0.2 mol) to give compound 229b (33 mg, 40%) as a white solid. Compound 229b (30 mg, 0.07 mmol) was then converted to compound 229 (3.5 mg, 10%) as a white solid. LCMS: $t_R$=2.00 min in 3 min chromatography, MS (ESI) m/z 418 $[M+H]^+$. $^1H$ NMR ($CD_3OD$ 400 MHz): δ 7.42-7.48 (m, 2H), 7.25-7.29 (d, J=8.4 Hz, 1H), 3.45 (s, 3H), 3.20-3.32 (m, 3H), 2.54-2.56 (m, 1H), 2.02-2.19 (m, 3H), 1.30-1.60 (m, 7H), 0.99-1.02 (m, 2H), 0.82-0.84 (m, 2H), 0.50-0.73 (m, 3H).

Example 187

Synthesis of Compound 230

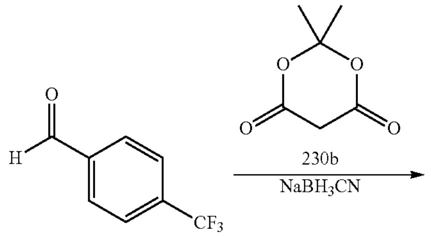

230a

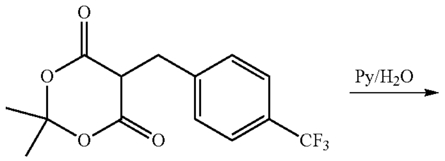

230c

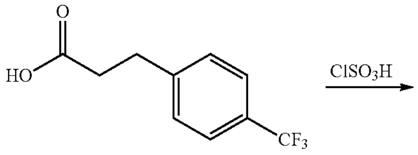

230d

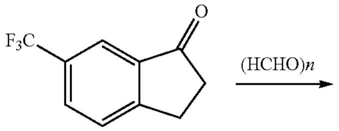

230e

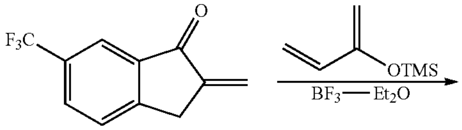

230f

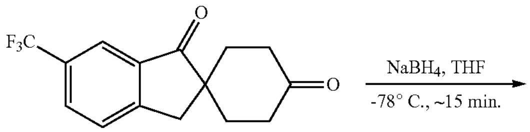

230g

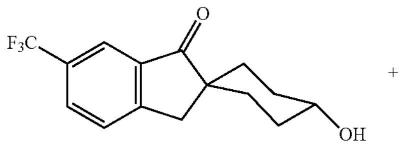

230h

-continued

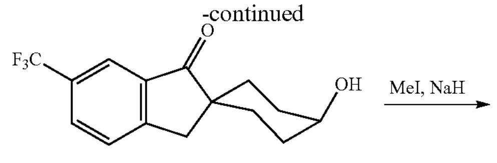

230i

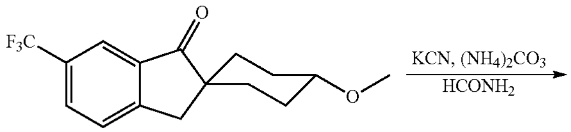

230j

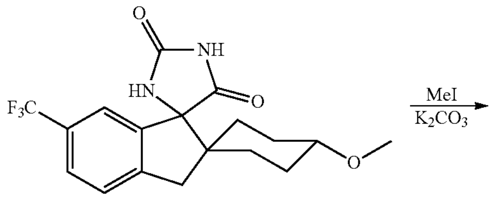

230k

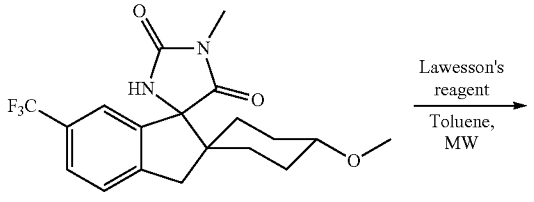

230l

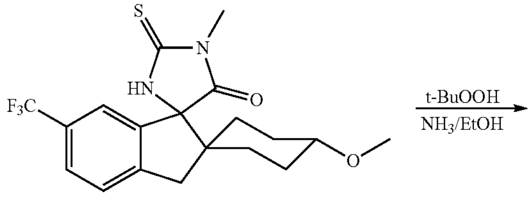

230m

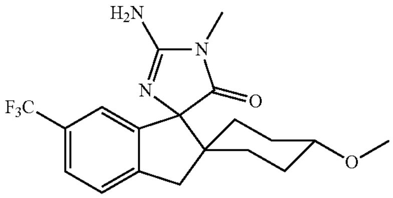

230

Procedure for Preparation of Compound 230c

To a solution of compound 230a (17 g, 0.1 mol) and compound 230b (14.4 g, 0.1 mol) in EtOH (100 mL), piperidium acetate (1.45 g, 0.01 mol) was added. After addition, the reaction mixture was stirred at room temperature for 30 min and then cooled to 0° C., $NaBH_3CN$ (9.45 g, 0.15 mol) was added portionwise upon cooling. After addition, the mixture was allowed to warm to room temperature and stirred for 2 h. The reaction mixture was cooled to 0° C. and quenched with 1 M HCl till gas evolution ceased. The mixture was extracted with EtOAc (3×100 mL), the combined organic layers were evaporated and the residue was recrystallized from MeOH to give a white solid 230c, which was used in the next step directly. $^1H$ NMR ($CDCl_3$ 400 MHz TMS): δ 7.48 (d, J=8.0

Hz, 2H), 7.40 (d, J=8.4 Hz, 2H), 3.71 (t, J=5.2 Hz, 1H), 3.47 (d, J=3.2 Hz, 2H), 1.70 (s, 3H), 1.55 (s, 3H).

Procedure for Preparation of Compound 230d

The crude product of compound 230c was dissolved in pyridine (45 mL) and water (15 mL). The mixture was heated at reflux for 2 h and then diluted with water (100 mL), acidified with conc. HCl till pH=2. The mixture was extracted with EtOAc (3×100 mL), the combined organic layers were dried over anhydrous $Na_2SO_4$, filtered and evaporated to give of compound 230d (11 g, 50% yield for two steps) as a white solid. $^1H$ NMR ($CDCl_3$ 400 MHz TMS): δ 7.48 (d, J=8.0 Hz, 2H), 7.26 (d, J=8.0 Hz, 2H), 2.95 (t, J=7.6 Hz, 2H), 2.64 (d, J=8.0 Hz, 2H).

Procedure for Preparation of Compound 230e

Compound 230d (9 g, 0.04 mol) was added portionwise to $ClSO_3H$ (100 mL) while cooling with ice-water bath. After addition, the reaction mixture was stirred at 0° C. for 1.5 h and then poured into ice water carefully. The mixture was extracted with EtOAc (3×200 mL), the combined organic layers were evaporated and the residue was purified by column chromatography on silica gel (petroleum ether: EtOAc=10:1) to give compound 230e (4.44 g, 55% yield) as a clear oil. $^1H$ NMR ($CDCl_3$ 400 MHz TMS): δ 7.95 (s, 1H), 7.77-7.75 (m, 1H), 7.55 (d, J=8.0 Hz, 1H), 3.17-3.14 (m, 2H), 2.72-2.68 (m, 2H).

Procedure for Preparation of Compound 230f

Compound 230e (4.44 g, 22 mmol), $(CH_2O)_n$ (3 g, 0.1 mol) and N-methyl-aniline trifluoroacetate (7.15 g, 35 mmol) were dissolved in anhydrous THF (50 mL) under a nitrogen atmosphere. The mixture was heated at reflux overnight and then diluted with water (~100 mL), extracted with EtOAc (3×100 mL), the combined organic layers were evaporated and the residue was purified by column chromatography on silica gel (petroleum ether:EtOAc=10:1) to give compound 230f (2.5 g, 54%) as a yellow liquid. $^1H$ NMR ($CDCl_3$ 400 MHz TMS): δ 8.16 (s, 1H), 7.87 (d, J=7.6 Hz, 1H), 7.65 (d, J=8.0 Hz, 1H), 6.47-6.46 (m, 1H), 5.76 (s, 1H), 3.85 (s, 2H).

Procedure for Preparation of Compound 230g

Compound 230f (2.5 g, 11 mmol) was dissolved in anhydrous $CH_2Cl_2$ (20 mL), the solution was cooled in acetone/dry ice bath. Trimethyl-(1-methylene-allyloxy)-silane (1.85 g, 12 mmol) and $BF_3.Et_2O$ (0.84 g, 5 mmol) were added subsequently. The reaction mixture was stirred at −78° C. for 20 min and then diluted with MeOH (20 mL), after warmed to room temperature, the mixture was diluted with water (50 mL) and extracted with EtOAc (3×50 mL), the combined organic layers were dried over anhydrous $Na_2SO_4$, filtered and evaporated, the residue was purified by column chromatography on silica gel (petroleum ether:EtOAc=3:1) to give compound 230g (400 mg, 13%) as a white solid.

Procedure for Preparation of Compound 230h and 230i

Compound 230g (400 mg, 1.4 mmol) was dissolved in anhydrous THF (4 mL) under a nitrogen atmosphere, cooled in acetone-dry ice bath, $NaBH_4$ (32 mg, 0.84 mmol) was added in one portion. The reaction mixture was stirred at −78° C. for 5 min and then quenched with MeOH, after warmed to 0° C., the mixture was diluted with EtOAc, washed with water, the aqueous layer was extracted with EtOAc, the combined organic layers were dried over $Na_2SO_4$, filtered and evaporated, the crude product containing compound 230h and compound 230i was used in the next step without further purification.

Procedure for Preparation of Compound 230j

The crude product containing compound 230h and compound 230i was dissolved in anhydrous THF (5 mL) under a nitrogen atmosphere and cooled to 0° C., NaH (168 mg, 2.1 mmol) was added in one portion, after 10 min MeI (986 mg, 7 mmol) was added in one portion. After addition, the reaction mixture was allowed to warm to room temperature and stirred overnight. The mixture was quenched by addition of water at 0° C. and extracted with EtOAc, the combined organic layers were dried over anhydrous $Na_2SO_4$, filtered and evaporated, and the residue was purified by prep. TLC (petroleum ether: EtOAc=4:1) to give compound 230j (100 mg, 24% yield for 2 steps) as a white solid.

Procedure for Preparation of Compound 230k

Compound 230j (50 mg, 0.17 mmol), KCN (33 mg, 0.51 mmol) and $(NH_4)_2CO_3$ (121 mg, 1.26 mmol) was suspended in $HCONH_2$ (1.5 mL) and the mixture was heated at 90° C. in a steel autoclave for 3 days. After cooling to room temperature, the mixture was poured onto crashed ice and stirred for 20 min, and then acidified with conc. HCl till pH=2. The solid precipitated out was collected by filtration and washed with water, and then the solid was dissolved in EtOAc and washed with water, dried over $Na_2SO_4$, filtered and evaporated to give compound 230k (35 mg, 59%) as a yellow solid.

Procedure for Preparation of Compound 230

According to a similar synthesis of compound 229, compound 230k (35 mg, 0.1 mmol) was methylated with MeI (14 mg, 0.1 mmol) to give compound 2301 (27 mg, 70%) as a yellow solid.

Compound 2301 (27 mg, 0.07 mmol) was reacted with Lawesson's reagent (40 mg, 0.1 mmol) to give compound 230m (15 mg, 57%), which was converted to compound 230 (1.8 mg, 12%) as a white solid. LC-MS $t_R$=0.925 min in 2 min chromatography, MS (ESI) m/z 382.1 $[M+H]^+$. $^1H$ NMR ($CD_3OD$, 400 MHz): δ 7.59 (d, J=8.0 Hz, 1H), 7.54 (s, 1H), 7.47 (d, J=8.0 Hz, 1H), 3.25 (s, 3H), 3.10-3.03 (m, 6H), 2.00-1.89 (m, 2H), 1.79-1.74 (m, 1H), 1.38-1.28 (m, 5H). $^{19}F$ NMR (690-190-1C7 $CD_3OD$ 19F): δ −63.57

Example 188
Synthesis of Compound 231
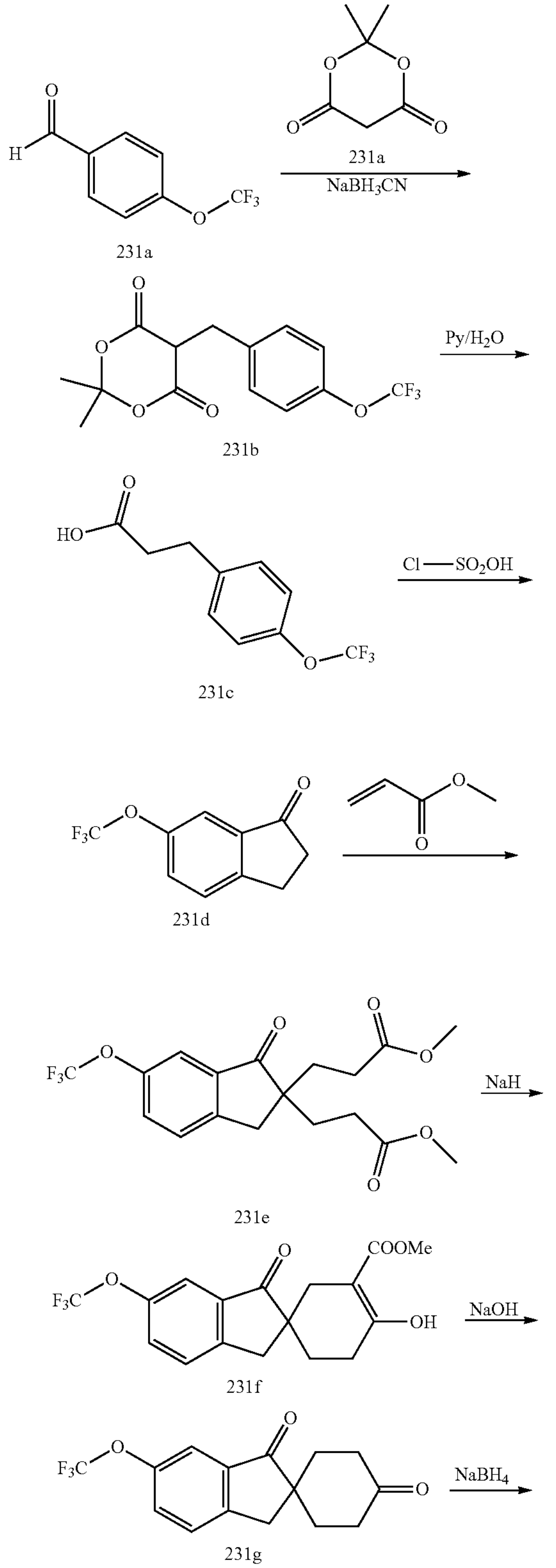
231a
231b
231c
231d
231e
231f
231g
-continued
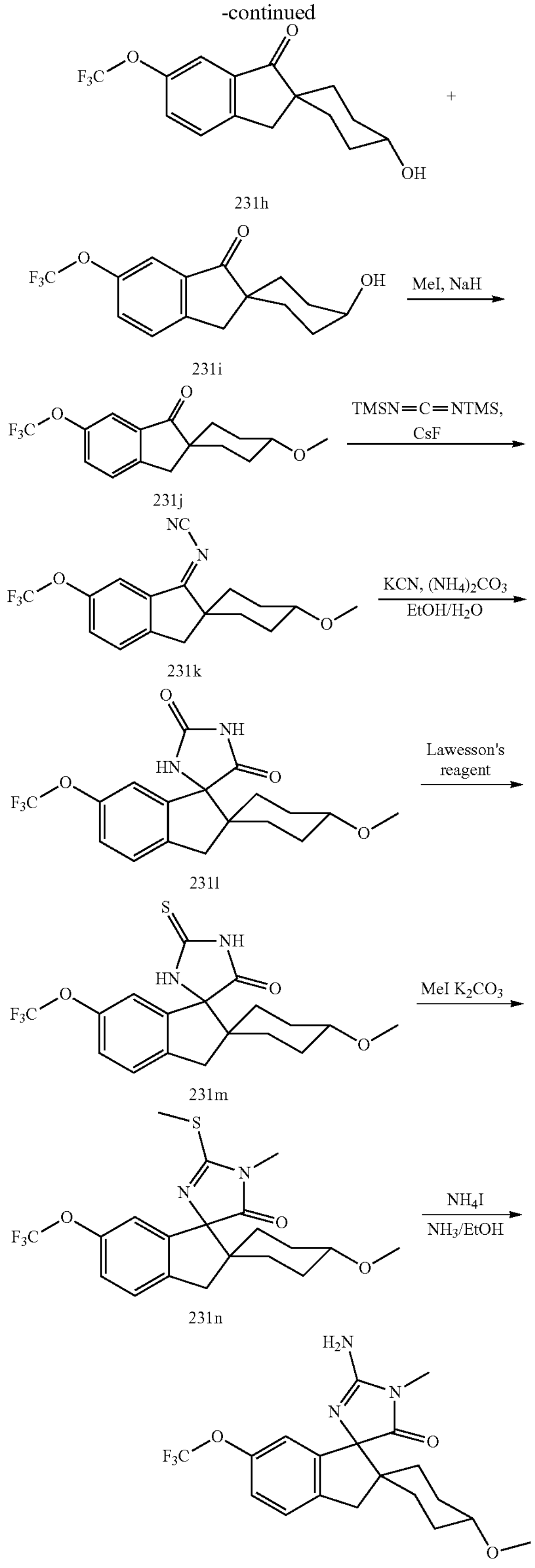
231h
231i
231j
231k
231l
231m
231n
231

Procedure for Preparation of Compound 231d

According to a similar synthesis of compound 230e in compound 230, compound 231a (1.0 g, 5.26 mmol) was reacted compound 231A (75 mg, 0.53 mmol) to give compound 231b (0.8 g, 47%) as a white solid, which was used directly in next step without purification.

Compound 231b (5.0 g, 15.72 mmol) was heated in pyridine/$H_2O$ (15 mL/5 mL) to give compound 231c (3.0 g, 82%) as a colorless oil. $^1$H NMR ($CDCl_3$ 300 MHz): δ 7.17 (m, 2H), 7.07 (m, 2H), 2.89 (m, 2H), 2.61 (m, 2H).

Compound 231c (4.0 g, 17.09 mmol) was converted to compound 231d (1.1 g, 30%) as a white solid. $^1$H NMR ($CDCl_3$ 400 MHz): δ 7.49 (s, 1H), 7.43 (m, 1H), 7.33 (m, 1H), 3.07 (m, 2H), 2.67 (m, 2H).

Procedure for Preparation of Compound 231e

To a refluxed solution of compound 231d (4.7 g, 21.76 mmol) in anhydrous toluene (40 mL) was added Triton B (2.45 mL, 13.49 mmol) under a nitrogen atmosphere. The reflux solution was kept stirring for 30 min, then methyl acrylate (25 mL, 281.7 mmol) was added and the resulting solution was stirred at reflux overnight. The reaction solution was poured into water and extracted with EtOAc (2×100 mL). The combined organic layer was dried over anhydrous $Na_2SO_4$, evaporated under reduced pressure. The residue was purified by column chromatograph on silica gel to give compound 231e (4.0 g, 48%) as a colorless oil.

Procedure for Preparation of Compound 231f

To a solution of compound 231e (2.6 g, 6.70 mmol) in 50 mL of anhydrous toluene was added NaH (1.07 g, 26.80 mmol) portionwise under a nitrogen atmosphere. The mixture was heated to reflux overnight. Brine (10 mL) was added to quench the reaction, and the mixture was extracted with EtOAc (2×25 mL). The combined organic layers were dried over $Na_2SO_4$, evaporated under reduced pressure. The residue was purified by column chromatograph on silica gel to give compound 231f (1.2 g, 52%) as a colorless oil.

Procedure for Preparation of Compound 231g

To a solution of compound 231f (1.2 g, 3.37 mmol) in MeOH/$H_2O$ (2.4 mL/7.6 mL) was added NaOH (0.92 g, 23.02 mmol). The mixture was heated at reflux for 1 h. Then the reaction solution was cooled to room temperature and extracted with EtOAc (2×50 mL). The combined organic layer was dried, evaporated under reduced pressure to give crude compound 231g (0.6 g, crude), which was used in next step without further purification.

Procedure for Preparation of Compound 231h and 231i

To a solution of compound 231g (0.6 g, 2.01 mmol) in 10 mL of anhydrous THF was added $NaBH_4$ (22.8 mg, 0.60 mmol) at −78° C. The mixture was stirred at −78° C. for 5 min, and MeOH (5 mL) and EtOAc (5 mL) were added. The resulting mixture was allowed to warm to room temperature. Water (5 mL) was added, and the organic layer was separated, dried and evaporated under reduced pressure to give the crude procut containing compound 231h and compound 231i (0.3 g, crude), which was used for next step without further purification.

Procedure for Preparation of Compound 231j

A crude mixture containing compound 231h and compound 231i (0.3 g, 1.00 mmol) in anhydrous THF (10 mL) was added NaH (160 mg, 4.0 mmol) at 0° C. under a nitrogen atmosphere. The mixture was stirred for 30 min at room temperature, and then MeI (1.54 g, 10.0 mmol) was added. The resulting solution was stirred at room temperature for 2 h. The reaction was quenched by addition of brine (5 mL) and extracted with EtOAc (2×10 mL). The combined organic layer was dried over anhydrous sodium sulfate and evaporated under reduced pressure to give crude compound 231j (0.3 g, 96%) as a white solid.

Procedure for Preparation of Compound 231k

To a solution of compound 231j (0.3 g, 0.96 mmol) in 10 mL of acetonitrile was added CsF (580 mg, 3.83 mmol) under a nitrogen atmosphere. The mixture was stirred at 50° C. for 30 min, then bis-trimethylsilylcarbodiimide (712 mg, 3.827 mmol) was added. The resulting mixture was stirred at 50° C. for 1 h. 5 mL of water was added to quench the reaction and extracted with EtOAc (2×10 mL). The combined organic layer was dried over anhydrous sodium sulfate and evaporated under reduced pressure to give the crude compound 231k (0.28 g, crude), which was used for the next step without further purification.

Procedure for Preparation of Compound 231l

To a solution of compound 231k (0.28 g, 0.85 mmol) in EtOH/$H_2O$ (10 mL/10 mL) was added KCN (0.22 g, 3.42 mmol), $(NH_4)_2CO_3$ (1.2 g, 11.95 mmol). The mixture was heated to 75° C. overnight in a sealed tube. Then the reaction was cooled to room temperature, water (10 mL) and EtOAc (10 mL) were added. The organic layer was separated, dried over anhydrous sodium sulfate and evaporated under reduced pressure. The residue was purified by preparative TLC to give compound 231l (0.1 g, 30%) as a white solid.

Procedure for Preparation of Compound 231m

To a solution of compound 231l (40 mg, 0.10 mmol) in anhydrous toluene was added Lawesson's reagent (46 mg, 0.12 mmol). The mixture was heated to 120° C. in a microwave reactor for 30 min. Then the solvent was evaporated under reduced pressure and the residue was purified by preparative TLC to give compound 231m (30 mg, 70%) as a white solid.

Procedure for Preparation of Compound 231n

To a solution of compound 231m (50 mg, 0.13 mmol) in 3 mL of DMF was added $K_2CO_3$ (86 mg, 0.63 mmol). The mixture was stirred for 10 min at room temperature, then MeI (48 mg, 0.31 mmol) was added. The final mixture was stirred at room temperature and monitored by preparative TLC. When compound 231m was consumed, brine (50 mL) was added and the mixture was extracted with EtOAc (2×10 mL). The combined organic layers were washed with brine (5 mL), dried over anhydrous sodium sulfate, evaporated under reduced pressure. The residue was purified by preparative TLC to give compound 231n (36 mg, 67%) as a white solid.

Procedure for Preparation of Compound 231

To a solution of compound 231n (16 mg, 0.037 mmol) in $NH_3$/EtOH (3 mL) was added $NH_4I$ (59 mg, 0.37 mmol). The mixture was heated to 120° C. for 2.5 h in a microwave reactor. The solvent was evaporated under reduced pressure and the residue was purified by preparative RP-HPLC to give compound 231 (13 mg, 87%) as a gray solid. LC-MS $t_R$=1.579 min in 3 min chromatography, MS (ESI) m/z 398 $[M+H]^+$. $^1$H NMR ($CD_3OD$): δ 7.45 (d, J=8.0 Hz, 1H), 7.26 (m, 2H), 3.34 (s, 3H), 3.12-3.21 (m, 6H), 1.97-2.10 (m, 2H), 1.82 (m, 1H), 1.39-1.50 (m, 4H), 1.28-1.35 (m, 1H). $^{19}$F NMR ($CD_3OD$): 5-59.57.

Example 189

Synthesis of Compound 232

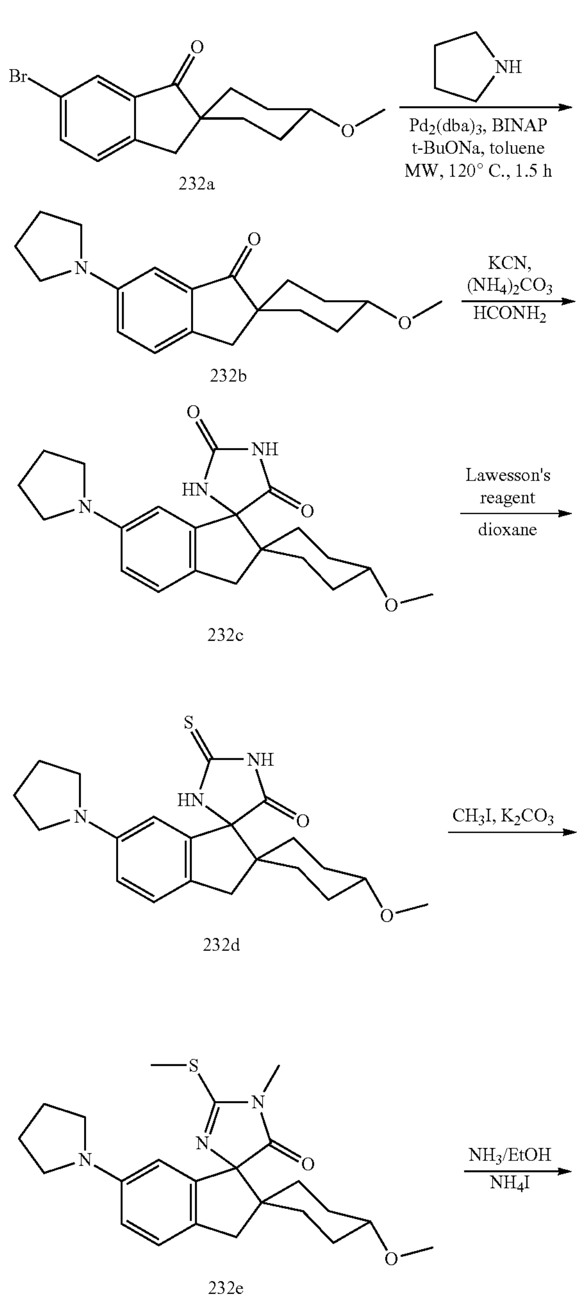

232a

232b

232c

232d

232e

-continued

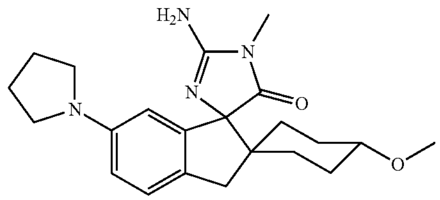

232

Procedure for Preparation of Compound 232b

To a solution of pyrrolidine (138 mg, 1.94 mmol) in toluene (15 mL) was added t-BuONa (186 mg, 1.94 mmol). After stirring at room temperature for 5 min under a $N_2$ atmosphere, compound 232a (400 mg, 1.29 mmol), $Pd_2(dba)_3$ (135 mg, 0.13 mmol) and BINAP (121 mg, 0.19 mmol) was added under a nitrogen atmosphere, the mixture was heated at 120° C. with stirring for 1.5 h in a microwave reactor. LCMS showed that the reaction was completed. The reaction mixture was concentrated under reduced pressure to give the residue, which was purified by preparative TLC (petroleum/ethyl acetate=3:1) to give compound 232b (370 mg, 91%) as a yellow solid.

Procedure for Preparation of Compound 232

According to a similar synthesis for I-6 described in Example I-2, compound 232b (300 mg, 1.00 mmol) was condensed to form hydantoin 232c (100 mg, 27%) as a white solid.

Compound 232c (100 mg, 0.27 mmol) was reacted with Lawesson's Reagent (109 mg, 0.27 mmol) to give compound 232d (50 mg, 48%) as a white solid.

Then compound 232d (20 mg, 0.052 mmol) was dimethylated with MeI (30 mg, 0.21 mmol) to give compound 232e (15 mg, 72%) as a white solid, which was converted to compound 232 (2.1 mg, 14%) as a white solid. LC-MS $t_R$=0.882 min in 2 min chromatography, MS (ESI) m/z 383 $[M+H]^+$. $^1$H NMR ($CD_3OD$ 400 MHz): δ 7.09-7.11 (d, J=8.4 Hz, 1H), 6.50-6.52 (d, J=8.0 Hz, 1H), 6.21 (s, 1H), 3.36 (s, 3H), 3.27 (s, 1H), 3.21 (s, 3H), 3.15 (m, 1H), 3.05 (s, 3H), 2.91-3.02 (m, 2H), 1.92-2.00 (m, 5H), 1.83 (m, 1H), 1.53-1.59 (m, 1H), 1.35-1.42 (m, 2H), 1.22-1.35 (m, 3H).

Example 190

Synthesis of Compound 233

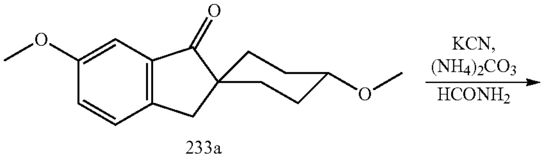

233a

-continued

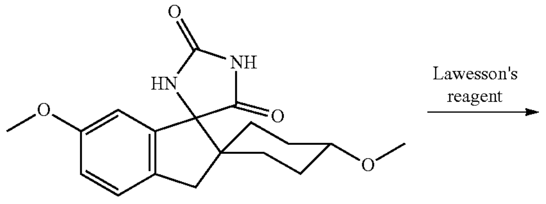

233b

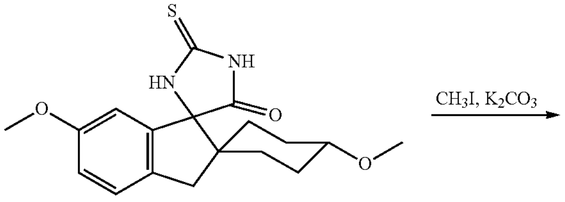

233c

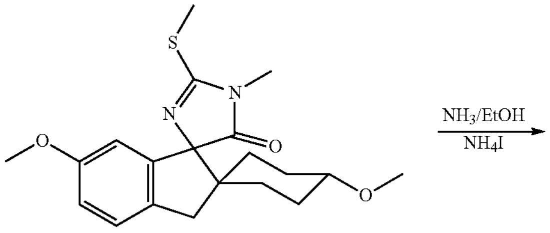

233d

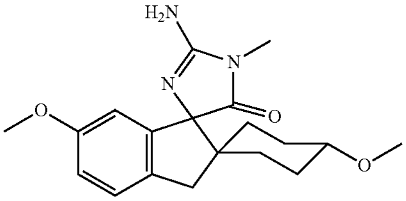

233

According to a similar synthesis for I-4 described in Example I-2, compound 233a (300 mg, 1.15 mmol) was condensed to give compound 233b (150 mg, 39%) as a white solid.

Compound 233b (50 mg, 0.152 mmol) was reacted with Lawessons reagent (73.5 mg, 0.182 mmol) to give compound 233c (30 mg, 58%) as a white solid.

Compound 233c (30 mg, 0.0867 mmol) was dimethylated with iodomethane (18.5 mg, 0.130 mmol) in DMF (1 mL) to give crude compound 233d (26 mg, 80%) as a white solid, which was converted to compound 233 (2.8 mg, 15%) as a white solid. LC-MS $t_R$=0.884 min in 2 min chromatography, MS (ESI) m/z 344.2 $[M+H]^+$; $^1$H NMR ($CD_3OD$ 400 MHz): δ 7.25 (d, J=8.4 Hz, 1H), 6.93 (dd, J=2.4, 8.4 Hz, 1H), 6.75 (d, J=2.4 Hz, 1H), 3.77 (s, 3H), 3.35 (s, 3H), 3.19 (s, 3H), 3.15 (m, 1H), 3.01-3.08 (m, 2H), 1.96-2.10 (m, 2H), 1.84 (d, 1H), 1.27-1.49 (m, 5H).

Example I-3

Synthesis of (1r,4r)-6'-hydroxy-4-methoxyspiro[cyclohexane-1,2'-inden]-1'(3'H)-one (I-9)

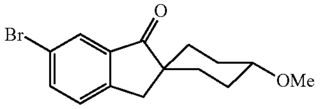

I-7

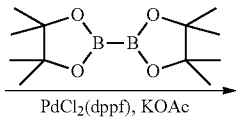

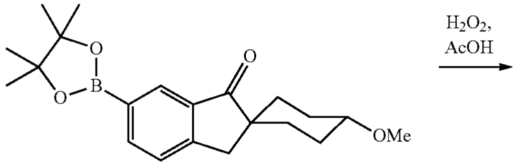

I-8

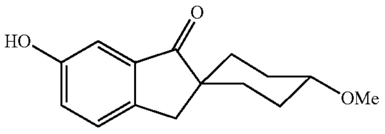

I-9

Procedure for Preparation of Compound I-8

To a solution of compound I-7 (500 mg, 1.61 mmol) in 1,4-dioxane (10 mL), was added KOAc (0.46 g, 4.69 mmol), 4,4,5,5-tetramethyl-2-(4,4,5,5-tetramethyl-1,3,2-dioxaborolan-2-yl)-1,3,2-dioxaborolane (450 mg, 1.77 mmol) and $PdCl_2$(dppf) (150 mg, 0.18 mmol) under a nitrogen atmosphere, the mixture was stirred at 100° C. in a CEM microwave reactor for 1 h. LCMS showed the complete consumption of compound I-7. Water (5 mL) was added to the mixture, and the precipitate was filtered off through a pad of celite, and then was washed with EtOAc (3×10 mL). The combined organic fractions were washed with brine (20 mL), dried over $Na_2SO_4$ and concentrated to give compound I-8 (284 mg, 50%) as a black solid which was used in the next step without further purification. $^1$H NMR ($CDCl_3$ 400 MHz): δ 8.20 (s, 1H), 7.97 (d, J=8.0 Hz, 2H), 3.41 (s, 3H), 3.21 (m, 1H), 2.96 (s, 2H), 2.06 (m, 2H), 1.64 (m, 2H), 1.56 (m, 2H), 1.44 (m, 2H), 1.31 (s, 12H).

Procedure for Preparation of Compound I-9

To a solution of compound I-8 (100 mg, 0.28 mmol) in THF (10 mL) was added HOAc (0.2 mL) and $H_2O_2$ (1 mL) under a nitrogen atmosphere, the mixture was stirred at room temperature overnight. The mixture was quenched by addition of $NaHSO_3$ solution (10 mL), and then was extracted with EtOAc (3×10 mL). The combined organic layers were washed with brine (30 mL), dried over $Na_2SO_4$ and concentrated to afford the crude product which was purified by column chromatography on silica gel eluting with hexane: EtOAc (100:10 to 30:10) to afford (1r,4r)-6'-hydroxy-4-methoxyspiro[cyclohexane-1,2'-inden]-1'(3'H)-one (I-9) (50 mg, 72%) as a yellow oil. $^1$H NMR ($CDCl_3$ 400 MHz): δ 7.24

(s, 1H), 7.10 (d, J=8.0 Hz, 2H), 3.33 (s, 3H), 3.26 (m, 1H), 2.86 (s, 2H), 2.20-2.21 (m, 2H), 1.68-1.69 (m, 2H), 1.44-1.65 (m, 2H), 1.20-1.40 (m, 2H).

Example 191

Synthesis of Compound 134

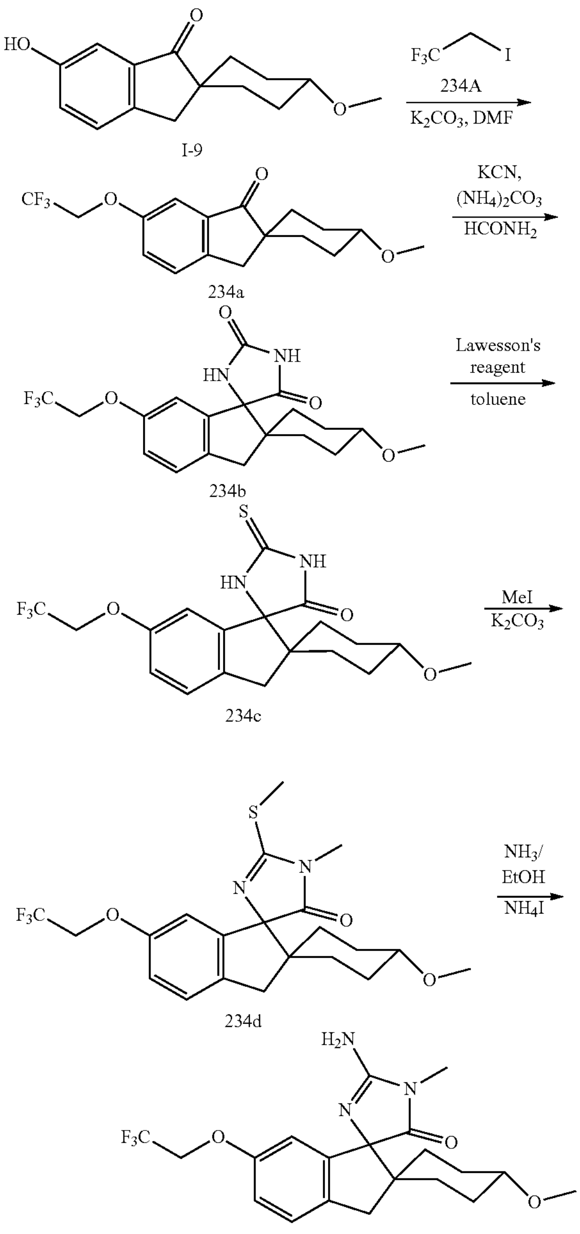

I-9
234a
234b
234c
234d
234

Procedure for Preparation of Compound 234a

To a solution of compound I-9 (360 mg, 1.46 mmol) in DMF (2 mL) was added $K_2CO_3$ (403.5 mg, 2.92 mmol), and compound 234A (373.6 mg, 1.60 mmol), the mixture was stirred at ambient temperature overnight. The reaction was added with $H_2O$ (5 mL), and the aqueous layer was extracted with EtOAc (3×10 mL). The combined organic layers were washed with brine (30 mL), dried over $Na_2SO_4$ and concentrated to give compound 234a (320 mg, 66%) as a white solid, which was used in the next step without further purification. $^1$H NMR ($CDCl_3$ 300 MHz): δ 7.35 (d, J=8.4 Hz, 1H), 7.28 (d, J=8.0 Hz, 1H), 7.17 (s, 1H), 4.26 (dd, J=8.1, 16.2 Hz, 2H), 3.41 (s, 3H), 3.25-3.29 (m, 1H), 2.91 (s, 2H), 1.97-2.28 (m, 2H), 1.66-1.89 (m, 2H), 1.32-1.45 (m, 2H), 1.23-1.35 (m, 2H).

Procedure for Preparation of Compound 234b

A steel autoclave was charged with a mixture of compound 234a (320 mg, 0.97 mmol), KCN (126.8 mg, 1.95 mmol), $(NH_4)_2CO_3$ (702.4 mg, 7.31 mmol) and formamide (20 mL). The mixture was heated at 100° C. for 72 h. The reaction mixture was cooled and poured into ice. The mixture was filtrated to collect the solid, which was dissolved in ethyl acetate (100 mL), and was washed with water (2×50 mL). The combined organic layers were dried over $Na_2SO_4$ and concentrated to give the crude product, which was purified by preparative TLC eluting with hexane:EtOAc=1:1 to afford compound 234b (90 mg, 23%) as a white solid. LCMS: $t_R$=1.080 min in 2 min chromatography, MS (ESI) m/z 399.1 $[M+H]^+$.

Procedure for Preparation of Compound 234c

To a solution of compound 234b (70 mg, 0.17 mmol) in anhydrous toluene (2 mL) was added Lawesson's Reagent (71 mg, 0.17 mmol) under a nitrogen atmosphere, the mixture was stirred at 110° C. for 3 h. The solvent was removed in vacuo to give the crude product which was purified by preparative TLC eluting with hexane:EtOAc=3:1 to afford compound 234c (40 mg, 57%) as a white solid. LCMS: $t_R$=1.165 min in 2 min chromatography, MS (ESI) m/z 415.1$[M+H]^+$.

Procedure for Preparation of Compound 234d

To a solution of compound 234c (40 mg, 0.096 mmol) in $CH_3CN$ (2 mL) was added $K_2CO_3$ (53.2 mg, 0.39 mmol). After being stirred for 5 min, MeI (56.8 mg, 0.39 mmol) was added, and the reaction mixture was heated at 60° C. for 10 min and at 100° C. for another 10 min in a CEM microwave reactor. The mixture was filtered through pad of celite, and the filtrate was concentrated in vacuo, the residue was purified by preparative TLC eluting with hexane:EtOAc=3:1 to give compound 234d (30 mg, 70%) as a white solid. LCMS: $t_R$=1.397 min in 2 min chromatography, MS (ESI) m/z 443.1 $[M+H]^+$.

Procedure for Preparation of Compound 234

A solution of compound 234d (30 mg, 0.067 mmol), $NH_4I$ (97.3 mg, 0.67 mmol) in $NH_3$-EtOH (2 mL, 5 N) was heated at 120° C. in a CEM microwave reactor for 3 h. After being cooled, the mixture was concentrated in vacuo, and the residue was purified by preparative TLC eluting with dichloromethane:methanol=10:1 and by preparative RP-HPLC to give compound 234 (2.4 mg, 8%) as a white solid. LCMS: $t_R$=1.406 min in 2 min chromatography, MS (ESI) m/z 412.2 $[M+H]^+$. $^1$H NMR ($CD_3OD$ 400 MHz): δ 7.39 (d, J=8.0 Hz, 1H), 6.92 (d, J=6.4 Hz, 1H), 6.90 (s, 1H), 4.50 (dd, J=8.4, 15.6

Hz, 2H), 3.40 (s, 3H), 3.35 (m, 1H), 3.14-3.27 (m, 2H), 3.03 (s, 3H), 1.97-2.16 (m, 2H), 1.62-1.84 (m, 2H), 1.36-1.42 (m, 2H), 1.27-1.36 (m, 2H).

Example 192

Synthesis of Compound 235

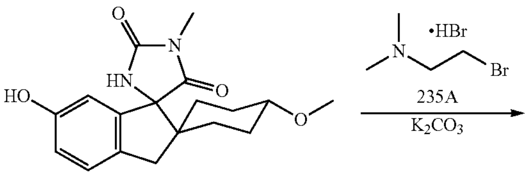

235a

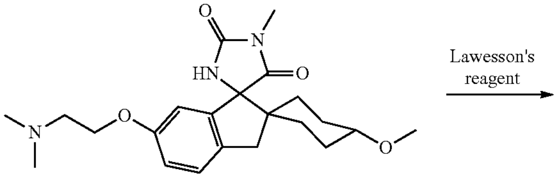

235b

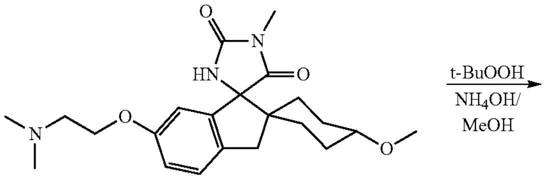

235c

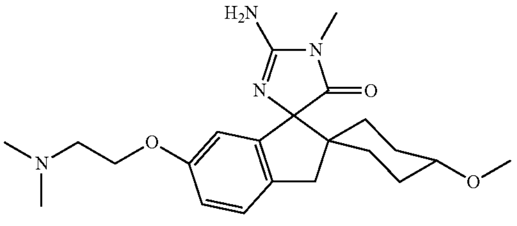

235

Procedure for Preparation of Compound 235b

To a solution of compound 235a (100 mg, 0.3 mmol) in DMF (5 mL) were added compound 235A (104.8 mg, 0.45 mmol) and $K_2CO_3$ (117 mg, 0.45 mol). After addition, the mixture was stirred at ambient temperature overnight. The mixture was concentrated in vacuo and the residue was purified by preparative TLC (petroleum ether:EtOAc=1:1) to give compound 235b with 49% purity (10.0 mg, 28%) as a white solid. LC-MS $t_R$=0.80 min in 2 min chromatography, MS (ESI) m/z 402.2 $[M+H]^+$

Procedure for Preparation of Compound 235c

To a mixture of compound 235b (30.0 mg, 0.07 mmol) in toluene (2 mL) was added Lawesson's reagent (30.0 mg, 0.07 mmol). The mixture was heated to 130° C. in a CEM microwave reactor for 1 h. After cooling down, the precipitate was filtered off and washed with ethyl acetate (40 mL×2). The filtrate and the washing were concentrated in vacuo and the residue was purified by preparative TLC ($CH_2Cl_2$: MeOH=10:1) to give compound 235c with 80% purity (10.0 mg, 33%) as a pale yellow solid. LC-MS $t_R$=0.888 min in 2 min chromatography, MS (ESI) m/z 418.2 $[M+H]^+$

Procedure for Preparation of Compound 235

To a solution of compound 235c (10 mg, 0.023 mmol) in EtOH (4 mL) was added $NH_3H_2O$ (1 mL) and tert-butyl hydroperoxide (0.20 g, 2.22 mol). After addition, the mixture was stirred at ambient temperature overnight. The mixture was concentrated in vacuo and the residue was purified by preparative HPLC to give compound 235 with 93% purity (8.0 mg, 74%) as a white solid. LC-MS $t_R$=0.823 min in 2 min chromatography, MS (ESI) m/z 401.2 $[M+H]^+$; $^1H$ NMR: ($CDCl_3$ 400 MHz): δ 7.35-7.33 (d, J=8.0 Hz, 1H), 7.07-7.04 (m, 1H), 6.909-6.904 (d, J=2.4 Hz, 1H), 4.35-4.31 (m, 2H), 3.60-3.58 (m, 2H), 3.36 (s, 3H), 3.21 (s, 3H), 3.18-3.08 (m, 3H), 2.98 (s, 6H), 2.09-2.03 (m, 2H), 1.89-1.83 (m, 1H), 1.47-1.26 (m, 5H).

Example 193

Synthesis of Compound 236

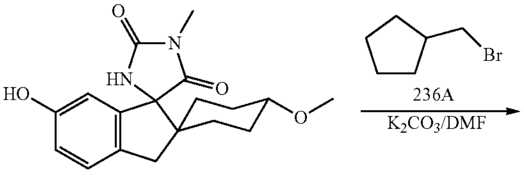

235a

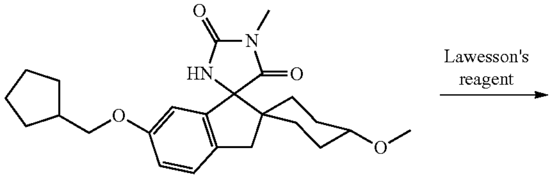

236a

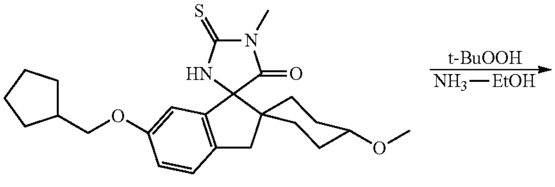

236b

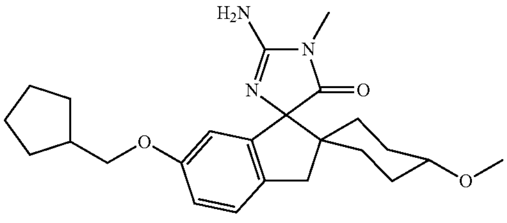

236

According to a similar synthesis of compound 235, compound 235a (50 mg, 0.15 mmol) was alkylated with compound 236A (33.5 mg, 0.225 mmol) to give compound 236a with 84% purity (60.0 mg, 94%) as a white solid. LC-MS $t_R$=1.113 min in 2 min chromatography, MS (ESI) m/z 399.2 $[M+H]^+$ Compound 236a (60 mg, 0.15 mmol) was then reacted with Lawesson's reagent (60.0 g, 0.15 mmol) to give compound 236b with 80% purity (38.0 mg, 62%) as a pale yellow solid. LC-MS $t_R$=1.416 min in 2 min chromatography, MS (ESI) m/z 415.1 $[M+H]^+$.

Compound 236b (38 mg, 0.09 mmol) was finally converted to compound 236 (6.3 mg, 16%) as a white solid. LC-MS $t_R$=1.117 min in 2 min chromatography, MS (ESI) m/z 398.2 $[M+H]^+$; $^1H$ NMR: ($CD_3OD$ 400 MHz): δ 7.16-7.14 (d, J=8.0 Hz, 1H), 7.071-7.045 (m, 1H), 6.90 (m, 1H), 4.73 (s, 1H), 3.34 (s, 3H), 3.14 (m, 1H), 3.02 (s, 3H), 2.97 (m, 2H), 2.03-1.80 (m, 5H), 1.61 (m, 3H), 1.39-1.23 (m, 4H).

Example 194

Synthesis of Compound 237

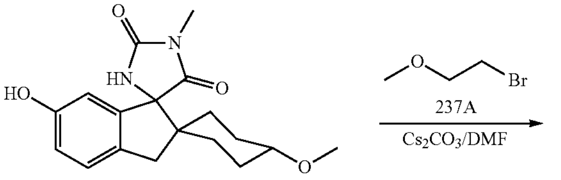

235a

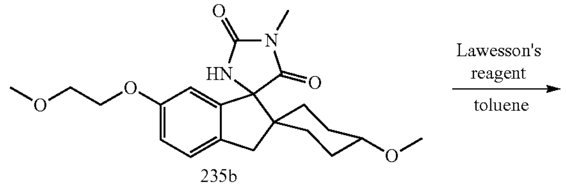

235b

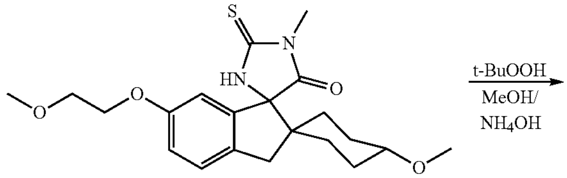

25c

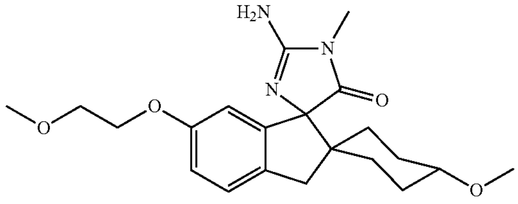

235

According to a similar synthesis of compound 235, compound 235a (57 mg, 0.172 mmol) was alkylated with compound 237A (34 mg, 0.258 mmol) in $Cs_2CO_3$ (84 mg, 0.258 mmol) to afford compound 235b (32 mg, 48%).

And compound 235b (32 mg, 0.082 mmol) was reacted with Lawesson's reagent (50 mg, 0.124 mmol) to give compound 235c (32 mg, 94%), which was converted to compound 235 (2.9 mg, 10%) as a white solid. LC-MS $t_R$=0.994 min in 2 min chromatography, MS (ESI) m/z 388 $[M+H]^+$; $^1H$ NMR ($CD_3OD$, 300 MHz): δ 7.28 (d, J=9.0 Hz, 1H), 6.94 (d, J=9.0 Hz, 1H), 6.80 (s, 1H), 4.09 (s, 2H), 3.73 (m, 2H), 3.41 (s, 3H), 3.31-3.35 (m 3H), 3.19 (s, 4H), 3.01-3.13 (m, 2H), 2.01-2.03 (m, 2H), 1.86 (m, 2H), 1.27-1.44 (m, 5H).

Example 195

Synthesis of Compound 238

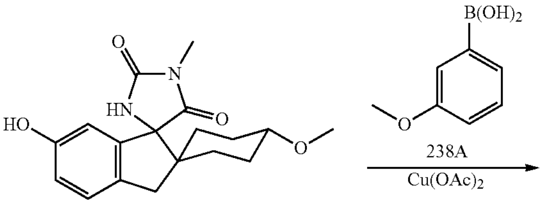

235a

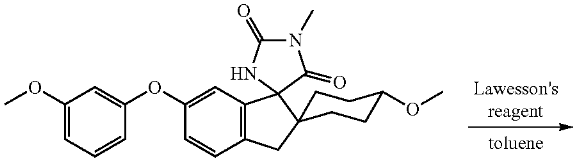

238a

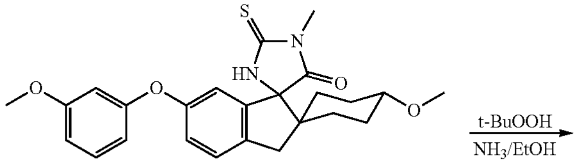

238b

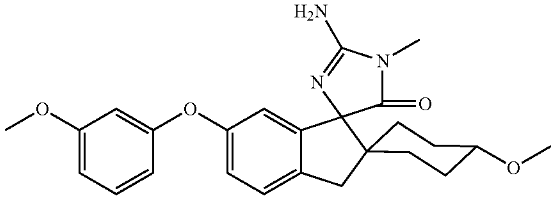

238

Procedure for Preparation of Compound 238a

To a mixture of compound 235a (40 mg, 0.12 mmol), compound 238A (40 mg, 0.24 mmol), $Et_3N$ (0.1 mL, 0.6 mmol) in anhydrous $CH_2Cl_2$ (10 mL) was added molecular sieves (40 mg) and $Cu(OAc)_2$ (44 mg, 0.24 mmol) at room temperature. The resulting suspension was stirred at room temperature under $O_2$ atmosphere overnight. The mixture was diluted with EtOAc (20 mL) and filtered through a pad of Celite. The filtrate was concentrated under reduced pressure to afford the residue, which was purified by preparative TLC with petroleum ether: ethyl acetate (3:1) to give compound 238a (20 mg, 45%) as a white solid. LC-MS $t_R$=1.321 min in 2 min chromatography, MS (ESI) m/z 437 $[M+H]^+$.

Procedure for Preparation of Compound 238

A suspension of compound 238a (30 mg, 0.068 mmol) and Lawesson's Reagent (31 mg, 0.075 mmol) in dry toluene (3 mL) was heated under 120° C. for 45 min in a CEM microwave reactor. The mixture was concentrated under reduced pressure and the residue was purified by preparative TLC (petroleum:ethyl acetate=5:1) to give compound 238b (15 mg, 50% purity) as a yellow solid. LC-MS $t_R$=1.435 min in 2 min chromatography, MS (ESI) m/z 453.1 $[M+H]^+$.

The mixture of compound 238b (15 mg, 0.033 mmol), t-BuOOH (80 mg, 0.887 mmol) in ammonia (3 mL) and methanol (1 mL) was stirred at room temperature overnight. The mixture was concentrated under reduced pressure to the residue, which was purified by acidic preparative HPLC to give compound 238 (3.5 mg, 30%) as a white solid. LC-MS $t_R$=1.000 min in 2 min chromatography, MS (ESI) m/z 436 $[M+H]^+$. $^1$H NMR ($CD_3OD$ 400 MHz): δ 7.28 (d, J=8.0 Hz, 1H), 7.20 (t, J=8.6 Hz, 1H), 6.92 (dd, J=8.4 Hz, 2.8, 1H), 6.66 (d, J=7.2 Hz, 1H), 6.59 (s, 1H), 6.50 (s, 1H), 6.48 (s, 1H), 3.75 (s, 3H), 3.36 (s, 3H), 3.14 (d, J=9.6 Hz, 1H), 3.08 (s, 1H), 3.05 (s, 1H), 3.01 (s, 1H), 2.01 (m, 2H), 1.85 (m, 1H), 1.62 (m, 1H), 1.39 (m, 4H).

Example 196

Synthesis of Compound 239

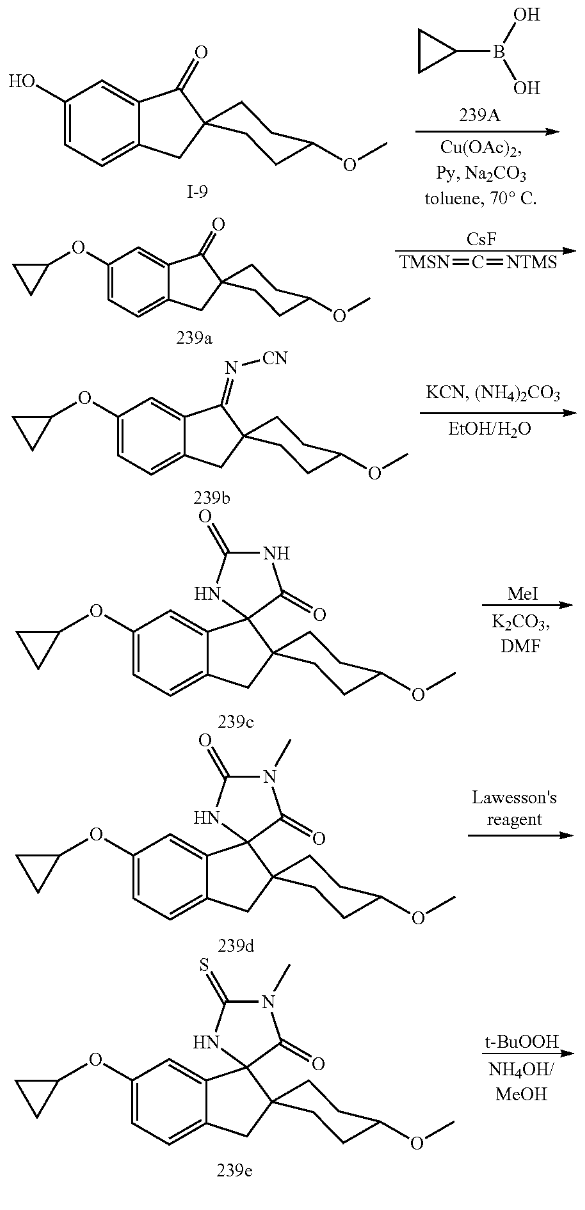

I-9

239a

239b

239c

239d

239e

-continued

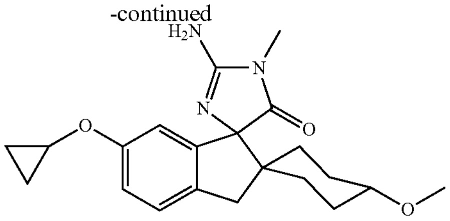

239

Procedure for Preparation of Compound 239a

To a suspension of compound 239A (70 mg, 0.816 mmol), compound I-9 (100 mg, 0.408 mmol), and $Na_2CO_3$ (71 mg, 0.816 mmol) in toluene (2 mL) was added a suspension of $Cu(OAc)_2$ (74 mg, 0.408 mmol) and pyridine (33 mg, 0.408 mmol) in hot toluene (4 mL). The reaction mixture was warmed to 70° C. and stirred overnight under air. The result mixture was cooled to room temperature, and a saturated aqueous $NH_4Cl$ solution was added, followed by water. The organic layer was separated, and the aqueous layer was extracted with $CH_2Cl_2$. The combine organic layers were washed with brine, dried over $Na_2SO_4$ and concentrated to give the residue, which was purified by preparative TLC (petroleum:EtOAc=3:1) to afford compound 239a (15 mg, 13%) as a white solid. $^1$H NMR ($CDCl_3$ 400 MHz): δ 7.38 (s, 1H), 7.26 (d, J=8.8 Hz 1H), 7.14 (m, 1H), 3.69 (m, 1H), 3.33 (s, 3H), 3.21 (m, 1H), 2.89 (s, 2H), 2.09 (m, 2H), 1.70 (m, 2H), 1.44 (m, 2H), 1.28 (m, 3H), 0.73 (m, 2H), 0.68 (m, 2H).

Procedure for Preparation of Compound 239b

To a solution of compound 239a (150 mg, 0.524 mmol) in dry $CH_3CN$ (2 mL) was added CsF (239 mg, 1.573 mmol) under $N_2$. The reaction mixture was heated at 50° C. for 15 min, and bis-trimethylsilylcarbodiimide (0.59 mL, 2.62 mmol) was added. The final reaction mixture was stirred at 50° C. overnight. The reaction was cooled to room temperature and quenched with water (10 mL), extracted with EtOAc (10 mLx3). The organic layer was washed with brine, dried over $Na_2SO_4$ and concentrated to give compound 239b (120 mg, crude), which was used for the next step.

Procedure for Preparation of Compound 239c

In a 30 mL sealed tube was added compound 239b (120 mg, 0.387 mmol), KCN (101 mg, 1.548 mmol) and $(NH_4)_2CO_3$ (376 mg, 3.87 mmol). To this solid was added $H_2O$ (2 mL) and EtOH (2 mL). The sealed tube was capped and heated in an oil bath at 75° C. overnight. The reaction was cooled to room temperature and water was added. The mixture was extracted with EtOAc (20 mLx3). The organic layer was washed with water, brine, dried over $Na_2SO_4$ and concentrated to give compound 239c (138 mg, 100%) as a yellow solid.

Procedure for Preparation of Compound 239

According to a similar synthesis of compound 229, compound 239c (138 mg, 0.387 mmol) was methylated with MeI (55 mg, 0.387 mmol) to give compound 239d (100 mg, 70%) as a white solid.

Compound 239d (100 mg, 0.27 mmol) in dry toluene (3 mL) was reacted with Lawesson's reagent (164 mg, 0.405 mmol) to give compound 239e (60 mg, 58%) as a white solid, which was converted to compound 239 (8.5 mg, 15%) as a white solid. LC-MS $t_R$=1.040 min in 2 min chromatography, MS (ESI) m/z 370 $[M+H]^+$; $^1H$ NMR ($CD_3OD$ 300 MHz): δ 7.25 (d, J=8.1 Hz, 1H), 7.05 (d, J=8.4 Hz, 1H), 6.85 (s, 1H), 3.74 (m, 1H), 3.33 (s, 1H), 3.11 (m, 4H), 3.04 (m, 3H), 2.04 (m, 2H), 1.83 (m, 1H), 1.42-1.25 (m, 3H), 0.75-0.58 (m, 4H).

Example 197

Synthesis of Compound 240

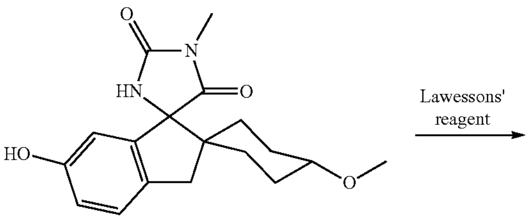

235a

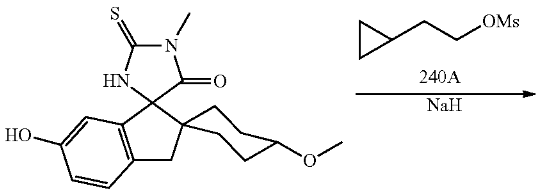

240b

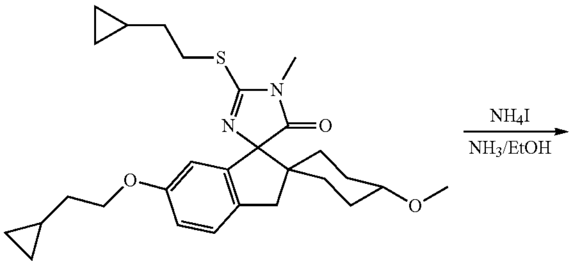

240c

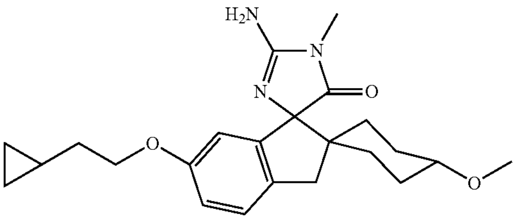

240

Procedure for Preparation of Compound 240b

To a solution of compound 235a (80 mg, 0.242 mmol) in dry toluene (2 mL) was added Lawesson's reagent (118 mg, 0.291 mmol) under $N_2$. The reaction mixture was heated in a CEM microwave reactor at 130° C. for 60 min. The solvent was removed under reduced pressure, and the residue was purified by preparative TLC ($CH_2Cl_2$:MeOH=10:1) to give compound 240b (20 mg, 24%) as a white solid.

Procedure for Preparation of Compound 240c

To a solution of compound 240b (30 mg, 0.0865 mmol) in DMF (2 mL) was added NaH (13 mg, 0.346 mmol) at 0° C.

After stirring for 1 h, compound 240A (43 mg, 0.259 mmol) was added and the reaction was stirred at room temperature overnight. The reaction was quenched with water (15 mL), extracted with EtOAc (10 mL×3). The organic layer was washed with brine, dried over $Na_2SO_4$ and concentrated to give the residue, which was purified by preparative TLC (petroleum ether:EtOAc=3:1) to afford compound 240c (30 mg, impure) as an oil.

Procedure for Preparation of Compound 240

To a solution of compound 240c (15 mg, 0.031 mmol) in $NH_3$/EtOH (2 mL) was added $NH_4I$ (46 mg, 0.31 mmol). The reaction mixture was heated in a CEM microwave reactor at 120° C. for 2 h. The solvent was removed under reduced pressure, and the residue was purified by preparative HPLC to give compound 240 (2.0 mg, 17%) as a white solid. LC-MS $t_R$=1.017 min in 2 min chromatography, MS (ESI) m/z 498 $[M+H]^+$; $^1H$ NMR ($CD_3OD$ 400 MHz): δ 7.15 (d, J=8.0 Hz, 1H), 6.82 (d, J=6.0 Hz, 1H), 6.68 (s, 1H), 3.92 (m, 2H), 3.23 (s, 3H), 3.09 (s, 3H), 2.97 (m, 3H), 1.95 (m, 2H), 1.73 (m, 1H), 1.54 (m, 2H), 1.38-1.23 (m, 4H), 1.27 (m, 1H), 0.75 (m, 1H), 0.36 (m, 2H), 0.05 (m, 2H).

Example 198

Synthesis of Compounds 241, 242 and 243

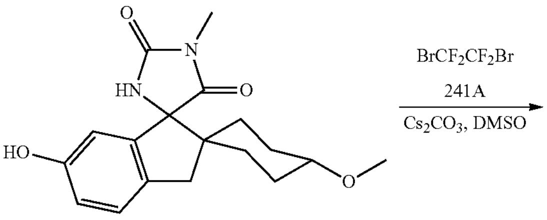

235a

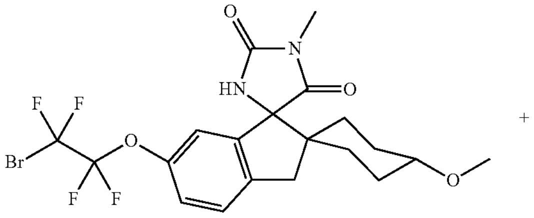

241a

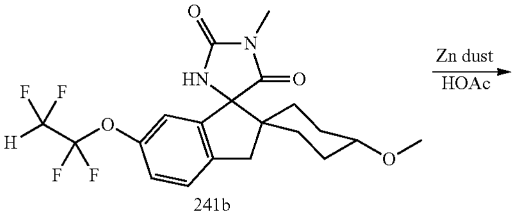

241b

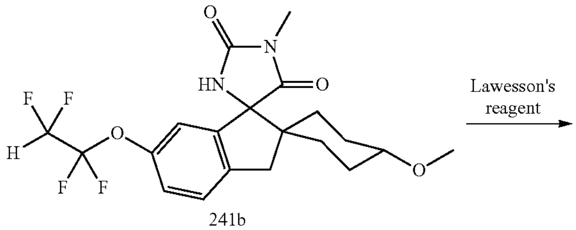

241b

-continued

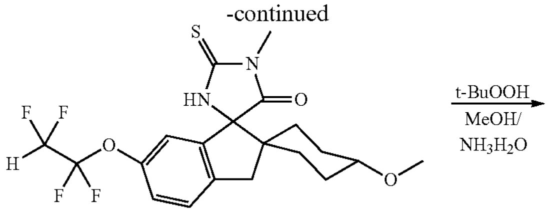

241c

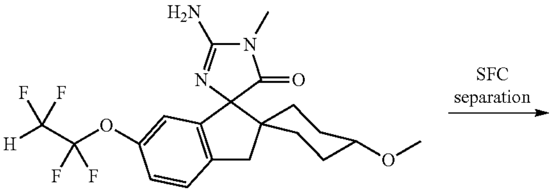

241

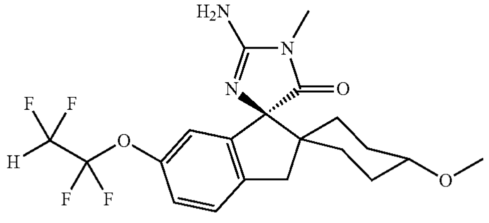

+

242

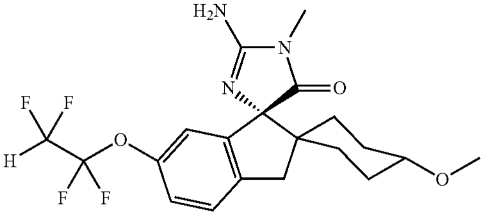

243

Procedure for Preparation of Compounds 241a and 241b

A mixture of compound 235a (80 mg, 0.19 mmol), compound 241A (98 mg, 0.38 mmol), and $Cs_2CO_3$ (93 mg, 0.29 mmol) in dry DMSO (1.5 mL) was heated at 50° C. overnight. LCMS showed the reaction was completed. After cooling to room temperature, water (10 mL) and $CH_2Cl_2$ (10 mL) were added and the mixture was stirred for 15 min. The organic layer was separated and the aqueous phase was extracted with $CH_2Cl_2$ (10 mLx3). The combined organic layers were washed with water, brine, dried over $Na_2SO_4$ and concentrated to give the residue, which was purified by preparative TLC (petroleum ether:EtOAc=3:1) to afford a mixture of compounds 241a and 241b (70 mg, 60%) as a white solid.

Procedure for Preparation of Compound 241b

A solution of compounds 241a and 241b (70 mg, 0.157 mmol) in HOAc (2 mL) was heated to 50° C. To the solution was added Zn dust (31 mg, 0.0.471 mmol) under $N_2$ in portions. After stirring at 70° C. overnight, water (10 mL) and $CH_2Cl_2$ (10 mL) were added and the mixture was stirred for 30 min. The organic layer was separated and the aqueous phase was extracted with $CH_2Cl_2$ (10 mL*3). The combined organic layers were washed with water, brine, dried over $Na_2SO_4$ and concentrated to give the residue, which was purified by preparative TLC (petroleum ether:EtOAc=1:1) to afford compound 241b (20 mg, 29%) as a white solid. $^1H$ NMR ($CDCl_3$ 400 MHz): δ 7.24 (d, J=8.4 Hz, 1H), 7.08 (d, J=8.4 Hz, 1H), 6.88 (s, 1H), 5.96-5.68 (m, 1H), 5.51 (d, 1H), 3.29 (s, 3H), 3.12 (m, 3H), 2.96 (s, 3H), 2.04 (m, 1H), 1.93 (m, 2H), 1.38 (m, 1H), 1.27 (m, 4H), 1.19 (m, 1H).

Procedure for Preparation of Compound 241c

To a solution of compound 241b (40 mg, 0.093 mmol) in dry toluene (2.5 mL) was added Lawesson's reagent (56 mg, 0.140 mmol) under $N_2$. The reaction mixture was heated in a CEM microwave reactor at 130° C. for 1 h. The solvent was removed under reduced pressure, and the residue was purified by preparative TLC (petroleum ether:EtOAc=3:1) to give compound 241c (30 mg, 71%) as a white solid.

Procedure for Preparation of Compound 241

To a solution of compound 241c (30 mg, 0.067 mmol) in MeOH (3 mL) and $NH_3.H_2O$ (0.6 mL) was added t-BuOOH (197 mg, 13.5 mmol). The reaction mixture was stirred at room temperature overnight. The solvent was removed and the residue was purified by preparative HPLC to give compound 241 (9 mg, 31%) as a white solid. LC-MS $t_R$=1.063 min in 2 min chromatography, MS (ESI) m/z 430 $[M+H]^+$; $^1H$ NMR ($CD_3OD$ 400 MHz): δ 7.43 (d, J=8.0 Hz, 1H), 7.25 (d, J=8.0 Hz, 1H), 7.19 (s, 1H), 6.42-6.06 (tt, 1H), 3.43 (s, 3H), 3.22-3.13 (m, 6H), 2.15 (m, 2H), 1.84 (m, 1H), 1.48 (m, 3H), 1.41-1.22 (m, 2H). $^{19}F$ NMR ($CD_3OD$ 19F 400 MHz): δ −89.826, −139.278

Procedure for Preparation of Compounds 242 and 243

Compound 241 (80 mg, 0.186 mmol) was separated by SFC to give compound 243 (15 mg, 19%), LC-MS $t_{RA}$=0.899 min in 2 min chromatography, MS (ESI) m/z 430 $[M+H]^+$; $^1H$ NMR ($CD_3OD$ 400 MHz): δ 7.36 (d, J=8.0 Hz, 1H), 7.13 (d, J=8.0 Hz, 1H), 6.85 (s, 1H), 6.41-6.15 (t, J=52.8 Hz 1H), 3.36 (s, 3H), 3.15-3.13 (m, 3H), 3.06 (s, 3H), 2.02 (m, 2H), 1.86 (m, 1H), 1.66 (m, 1H), 1.41 (m, 2H), 1.29 (m, 2H). $^{19}F$ NMR ($CD_3OD$ 19F 400 MHz): δ −89.925, −139.348; ee %:100%; and compound 242 (30 mg, 38%) as white solids. LC-MS $t_{RB}$=0.893 min in 2 min chromatography, MS (ESI) m/z 430 $[M+H]^+$; $^1H$ NMR ($CD_3OD$ 400 MHz): δ 7.25 (d, J=8.4 Hz, 1H), 7.02 (d, J=8.0 Hz, 1H), 6.75 (s, 1H), 6.17-6.03 (t, J=52.8 Hz, 1H), 3.27 (s, 3H), 3.05-3.98 (m, 3H), 2.95 (s, 3H), 1.89 (m, 2H), 1.71 (m, 1H), 1.51 (m, 1H), 1.27 (m, 2H), 1.16 (m, 2H). $^{19}F$ NMR ($CD_3OD$ 19F 400 MHz): δ −89.918, −139.343; ee %:100%.

Example 199

Synthesis of Compounds 244, 245 and 246

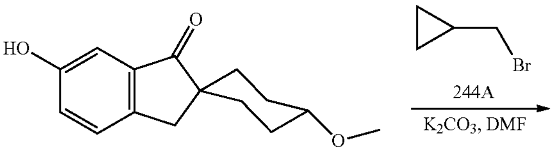

I-9

-continued

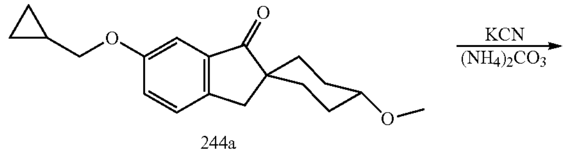

244a

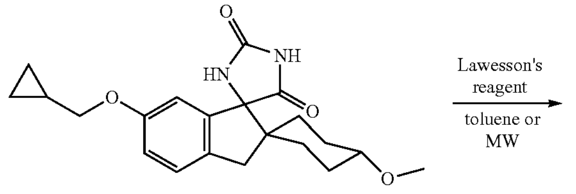

244b

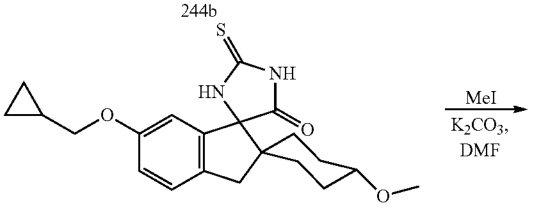

244c

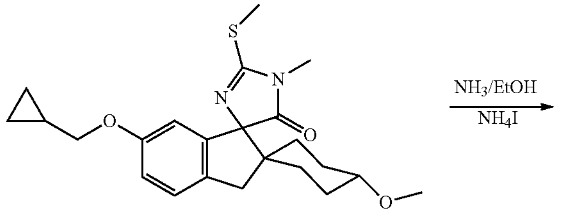

244d

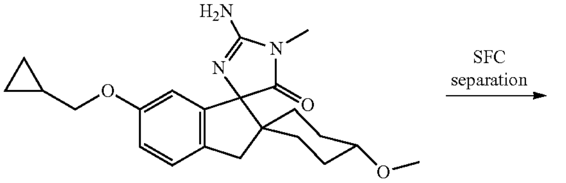

244

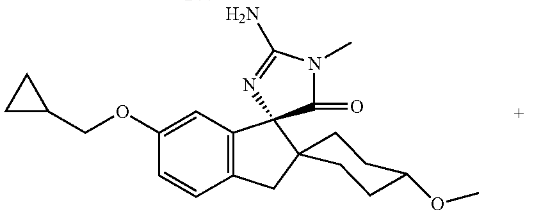

245

+

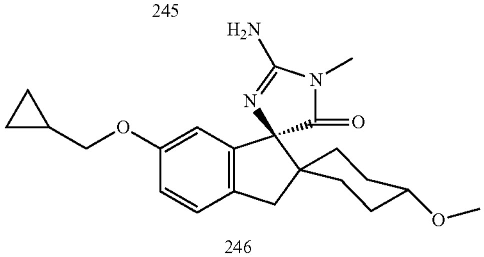

246

Procedure for Preparation of Compound 244a

To a solution of compound I-9 (380 mg, 1.53 mmol in DMF (5 mL) was added $K_2CO_3$ (422.2 mg, 3.06 mmol), and compound 244A (249.2 mg, 1.84 mmol), the mixture was stirred at ambient temperature overnight. The reaction was added with $H_2O$ (10 mL), and the aqueous layer was extracted with EtOAc (10 mL×3). The combined organic layers were washed with brine (30 mL), dried over $Na_2SO_4$ and concentrated to give compound 244a (380 mg, 67%) as a white solid which was used in the next step without further purification. $^1$H NMR ($CDCl_3$ 400 MHz): δ 7.27 (d, J=8.4 Hz, 1H), 7.23 (d, J=7.6 Hz, 1H), 7.19 (s, 1H), 3.69 (d, J=6.8 Hz, 2H), 3.42 (s, 3H), 3.27-3.37 (m, 1H), 2.90 (s, 2H), 1.97-2.09 (m, 2H), 1.65-1.72 (m, 2H), 1.48-1.55 (m, 2H), 1.34-1.43 (m, 2H), 1.27-1.34 (m, 1H), 0.79-0.80 (m, 2H), 0.28-0.32 (m, 2H).

Procedure for Preparation of Compound 244

According to a similar synthesis for I-6 described in Example I-2, compound 244a (380 mg, 1.26 mmol) was condensed to hydantoin 244b (70 mg, 18%) as white solid. LCMS: $t_R$=1.191 min in 2 min chromatography, MS (ESI) m/z=371.2 [M+H]$^+$.

Compound 244b (50 mg, 0.13 mmol) was reacted with Lawesson's Reagent (60 mg, 0.14 mmol) under $N_2$ to afford compound 244c (30 mg, 57%) as a white solid, which was methylated with MeI (45.6 mg, 0.31 mmol) to give compound 244d (20 mg, 65%) as a white solid. LCMS: $t_R$=1.412 min in 2 min chromatography, MS (ESI) m/z=415.2 [M+H]$^+$.

Finally, compound 244d (20 mg, 0.046 mmol) was converted to compound 244 (2.4 mg, 5%) as a white solid. LCMS: $t_R$=1.678 min in 3 min chromatography, MS (ESI) m/z=384.2 [M+H]$^+$. $^1$H NMR ($CD_3OD$ 400 MHz): δ 7.18 (d, J=8.0 Hz, 1H), 6.83 (d, J=8.4 Hz, 1H), 6.51 (s, 1H), 3.77 (d, J=6.8 Hz, 2H), 3.35 (s, 3H), 3.27 (m, 1H), 3.27-3.15 (m, 2H), 3.06 (s, 3H), 2.01-1.94 (m, 2H), 1.94-1.84 (m, 2H), 1.59-1.50 (m, 1H), 1.50-1.39 (m, 2H), 1.39-1.29 (m, 2H), 0.61-0.60 (m, 2H), 0.34-0.31 (m, 2H).

Compound 244 (~400 mg) was purified by SFC to give compound 245 (133.7 mg, 27%), LCMS: $t_R$=0.833 min in 2 min chromatography, MS (ESI) m/z=384.1 [M+H]$^+$. SFC: $t_R$=5.82 min in 16 min chromatography, ee %=100%. $^1$H NMR ($CD_3OD$ 400 MHz): δ 7.17-7.15 (d, J=8.0 Hz, 1H), 6.81-6.79 (dd, J=2.4, 8.0 Hz, 1H), 6.50 (s, 1H), 3.78 (d, J=8.0 Hz, 2H), 3.34 (s, 3H), 3.27-3.12 (m, 1H), 3.04 (m, 4H), 2.97-2.93 (d, J=15.6 Hz, 1H), 2.01-1.96 (m, 2H), 1.93-1.82 (m, 1H), 1.70-1.50 (m, 1H), 1.35-1.31 (m, 2H), 1.31-1.28 (m, 3H), 0.61-0.60 (m, 2H), 0.36-0.35 (m, 2H).

& compound 246 (144 mg, 29%) as white solids; LCMS: $t_R$=1.080 min in 2 min chromatography, MS (ESI) m/z=384.3 [M+H]$^+$. SFC: $t_R$=9.28 min in 16 min chromatography, ee %=99%. $^1$H NMR ($CD_3OD$ 400 MHz): δ 7.17-7.15 (d, J=8.0 Hz, 1H), 6.81-6.79 (dd, J=2.4, 8.0 Hz, 1H), 6.50 (s, 1H), 3.78 (d, J=8.0 Hz, 2H), 3.34 (s, 3H), 3.27-3.12 (m, 1H), 3.04 (m, 4H), 2.97-2.93 (d, J=15.6 Hz, 1H), 2.01-1.96 (m, 2H), 1.93-1.82 (m, 1H), 1.70-1.50 (m, 1H), 1.35-1.31 (m, 2H), 1.31-1.28 (m, 3H), 0.61-0.60 (m, 2H), 0.36-0.35 (m, 2H).

Example 200

Synthesis of Compound 247

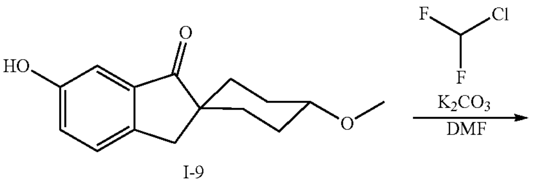

I-9

-continued

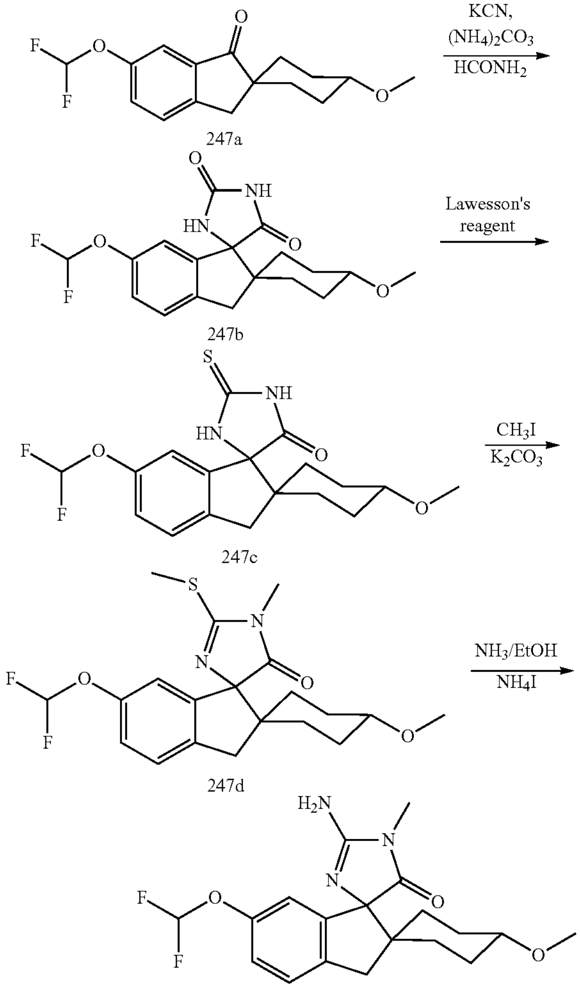

247a

247b

247c

247d

247

Procedure for Preparation of Compound 247a

To a solution of compound I-9 (1.0 g, 4.06 mmol) in DMF (15 mL) was added $K_2CO_3$ (0.62 g, 4.47 mol). The mixture was bubbled with a flow of chloro-difluoro-methane at 85° C. for 6 h. Water (10 mL) was added and extracted with EtOAc (2×15 mL). The combined organic layers were washed with al. sat. $NH_4Cl$ (2×10 mL), dried over $Na_2SO_4$ and evaporated under vacuum to give the crude. The crude was purified by preparative TLC (hexane:EtOAc=5:1) to afford compound 247a (420 mg, 35%) as a white solid.

Procedure for Preparation of Compound 247

According to a similar synthesis for compound I-6 described in Example I-2, compound 247a (420 mg, 1.42 mmol) was condensed to hydantoin 247b (45 mg, 8%) as a white solid. And compound 247b (40 mg, 0.11 mmol) was reacted with Lawesson's reagent (53 mg, 0.13 mmol) to give compound 247c (36 mg, 85%) as a whit solid.

Compound 247c (36 mg, 0.094 mmol) was then dimethylated with iodomethane (20 mg, 0.14 mmol) in DMF (1 mL) to afford compound 247d (21 mg, 54%) as a white solid, which was converted to compound 247 (6.1 mg, 31%) as a white solid. LC-MS $t_R$=1.008 min in 2 min chromatography, MS (ESI) m/z 380 [M+H]$^+$. $^1$H NMR ($CD_3OD$ 1H): δ 7.32 (d, J=8.4 Hz, 1H), 7.08 (dd, J=2.4, 8.0 Hz, 1H), 6.98 (d, J=2.4 Hz, 1H), 6.52-6.89 (m, 1H), 3.28 (s, 3H), 3.12 (s, 3H), 3.09 (m, 1H), 3.00-3.07 (m, 2H), 1.92-2.01 (m, 2H), 1.77 (m, 1H), 1.20-1.42 (m, 5H). $^{19}$F NMR ($CD_3OD$ 19F): δ −83.426

Example 201

Synthesis of Compound 248

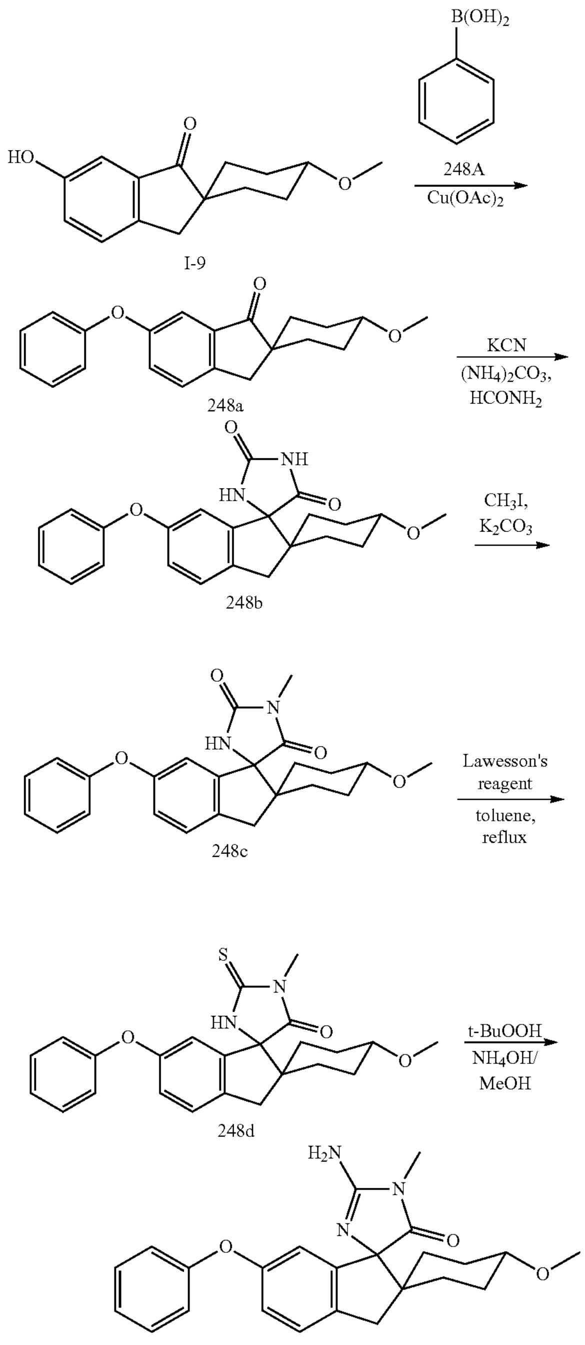

I-9

248a

248b

248c

248d

248

Procedure for Preparation of Compound 248a

A suspension of compound I-9 (247 mg, 2.03 mmol), 248A (500 mg, 2.03 mmol), $Cu(OAc)_2$ (737 mg, 4.06 mmol), $Et_3N$ (1.42 mL, 10.05 mmol) and molecular sieves (200 mg) in anhydrous $CH_2Cl_2$ (20 mL) was stirred under open air at room temperature overnight. The mixture was filtered and the filtrate was concentrated. The residue was purified by column chromatography on silica gel (petroleum ether:ethyl acetate=10:1) to give compound 248a (0.45 g, 85%) as a brown oil.

Procedure for Preparation of Compound 248b

A steel autoclave were charged with a mixture of compound 248a (450 mg, 1.4 mmol), KCN (180 mg, 2.8 mmol), $(NH_4)_2CO_3$ (1.1 g, 11.3 mmol) and formamide (15 mL). The mixture was heated at 120° C. for 72 h. The reaction mixture was then cooled and poured into ice. After acidification with concentrated HCl (20 mL), the mixture was filtrated to give the solid, which was dissolved in ethyl acetate (600 mL) and washed with water (2×150 mL). The combined organic layers were dried over $Na_2SO_4$, and concentrated under reduced pressure to dryness. The crude product was purified by re-crystallization from ethyl acetate to afford compound 248b (0.18 g, 33%) as a black solid.

Procedure for Preparation of Compound 248c

To a solution of compound 248b (180 mg, 0.46 mmol) in $CH_3CN$ (3.0 mL) was added $K_2CO_3$ (100 mg, 0.69 mmol). After stirring for 5 min, MeI (98 mg, 0.60 mmol) was added and the reaction mixture was heated at 80° C. for 35 min in a microwave reactor. The mixture was filtered and the filtrate was concentrated under reduced pressure to give compound 248c (120 mg, 87%) as a yellow solid, which was used for the next step directly without purification.

Procedure for Preparation of Compound 248d

A suspension of compound 248c (120 mg, 0.29 mmol) and Lawesson's Reagent (143 mg, 0.35 mmol) in anhydrous toluene (3 mL) was heated at 120° C. for 45 min in a CEM microwave reactor. The mixture was concentrated under reduced pressure and the residue was purified by preparative TLC (petroleum ether:ethyl acetate=3:1) to give compound 248d (60 mg, 90%) as a yellow solid.

Procedure for Preparation of Compound 248

A solution of compound 248d (60 mg, 0.14 mmol), t-BuOOH (255 mg, 2.84 mmol) in a solution of $NH_4OH$/MeOH (2 mL/5 mL) was stirred at room temperature overnight. The solvent was removed by evaporation to give the residue, which was purified by preparative RP-HPLC (acid) to give compound 248 (17.2 mg, 30%) (TFA salt) as a white solid. LC-MS $t_R$=0.967 min in 2 min chromatography, MS (ESI) m/z 406.0 $[M+H]^+$. $^1H$ NMR ($CD_3OD$ 300 MHz): δ 7.37-7.30 (t, J=5.7 Hz, 3H), 7.14-7.09 (t, J=6.3 Hz, 1H), 7.01-6.91 (m, 4H), 3.42 (s, 3H), 3.19 (s, 4H), 3.15-3.12 (d, J=6.3 Hz, 2H), 2.09-2.04 (m, 2H), 1.88-1.84 (m, 1H), 1.51-1.29 (m, 5H).

Example 202

Synthesis of Compound 249

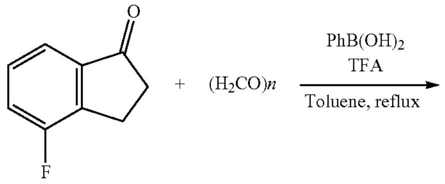

249a

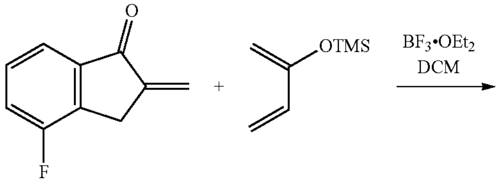

249b

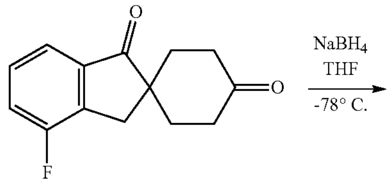

249c

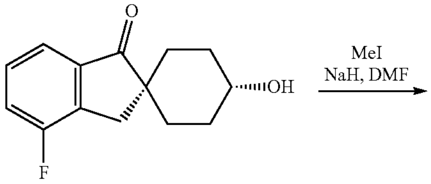

249d

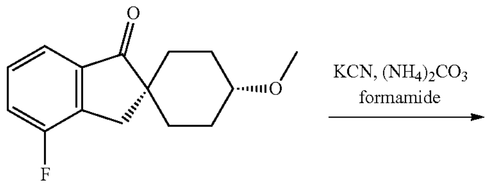

249e

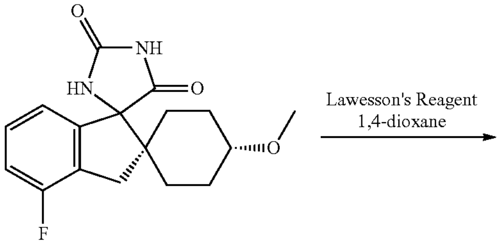

249f

-continued

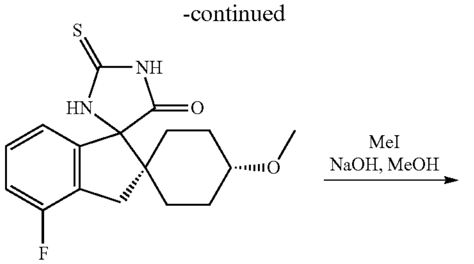

249g

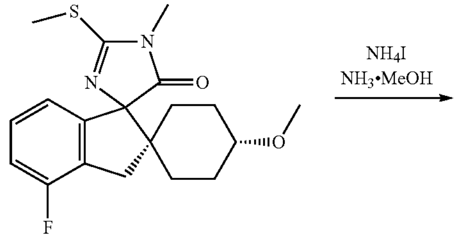

249h

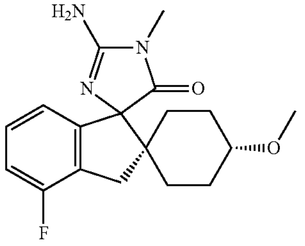

249

Procedure for Preparation of Compound 249b

To a 1000 mL round bottle flask were charged 4-fluoro-2,3-dihydro-1H-inden-1-one (249a) (5.04 g, 33.6 mmol), paraformaldehyde (10.08 g, 336 mmol), phenylboronic acid (4.92 g, 40.3 mmol) followed by toluene (235 mL), to the suspension was added TFA 2.6 mL, 33.6 mmol), and the resulting suspension was refluxed for 4 hrs, which resulted a clear yellowish solution. The solution was cooled to room temperature, and the pH was adjusted to 7-8 by adding saturated $NaHCO_3$. After extracting with ethyl acetate, the organic layers were combined, and evaporated. The residue was purified by flash chromatography (0 to 30% EtOAc/Hexane) to give 4-fluoro-2-methylene-2,3-dihydro-1H-inden-1-one (249b) (3.91 g, 72%). LC-MS $t_R$=1.49 min in 3 min chromatography, MS (ESI) m/z 163 $[M+H]^+$ Procedure for Preparation of Compound 249c To a solution of 4-fluoro-2-methylene-2,3-dihydro-1H-inden-1-one (249b) (3.71 g, 22.9 mmol) and (buta-1,3-dien-2-yloxy)trimethylsilane (5.2 mL, 29.8 mmol) in DCM (200 mL) at 0° C., there was added $BF_3.Et_2O$ (0.5 mL dropwise. The resulting solution was stirred at 0° C. for another 30 min, quenched with MeOH (0.3 mL), warmed to room temperature, acidified with 2N HCl aqueous solution (15 mL) and extracted with DCM (10 mL×4). The combined organic layers were dried over $Na_2SO_4$, filtered and evaporated, and the residue was purified by flash chromatography (0 to 50% EtOAc/Hexane) to give 4'-fluorospiro[cyclohexane-1,2'-indene]-1',4(3'H)-dione (249c) (2.77 g, 49%). LC-MS $t_R$=1.41 min in 3 min chromatography, MS (ESI) m/z 233 $[M+H]^+$.

Procedure for Preparation of Compound 249d

To a solution of 4'-fluorospiro[cyclohexane-1,2'-indene]-1',4(3'H)-dione (249c) (2.77 g, 11.9 mmol) in THF (40 mL) at −78° C., there was added $NaBH_4$ (0.45 g, 11.9 mmol) portion by portion (control the temperature below −70° C.). The resulting solution was stirred at −78° C. for another 30 min, and −78° C. acetone was added to quench the extra $NaBH_4$. The reaction mixture was then allowed to warm to room temperature, water (10 mL) was added, and the mixture was extracted with EtOAc (10 mL×4), combined organic layers were washed with brine (10 mL), dried over $Na_2SO_4$, and evaporated to dryness. The residue was purified by flash chromatography (0 to 60% EtOAc/Hexane) to give (1r,4r)-4'-fluoro-4-hydroxyspiro[cyclohexane-1,2'-inden]-1'(3'H)-one (249d) and its isomer as a 3:1 mixture (2.35 g, 84%), which could not be separated by normal phase chromatography. LC-MS $t_R$=1.29 min in 3 min chromatography, MS (ESI) m/z 235 $[M+H]^+$. For its isomer, LC-MS $t_R$=1.37 min in 3 min chromatography, MS (ESI) m/z 235 $[M+H]^+$.

Procedure for Preparation of Compound 249e

To a solution of (1r,4r)-4'-fluoro-4-hydroxyspiro[cyclohexane-1,2'-inden]-1'(3'H)-one (249d) (2.11 g, 9.0 mmol) in anhydrous DMF (30 mL) there was added NaH (60% in mineral oil, 1.80 g, 27.0 mmol) slurry in DMF (5 mL) dropwise. The resulting mixture was stirred at room temperature for 30 min, the completion of reaction was confirmed by LC-MS. The reaction was quenched by adding MeOH slowly followed by water, after extraction with DCM, the organic layer was evaporated, and the residue was purified by flash chromatography (20% EtOAc/Hexane) to give (1r,4r)-4'-fluoro-4-methoxyspiro[cyclohexane-1,2'-inden]-1'(3'H)-one (5) (1.50 g, 67%), the two isomer still could not be separated. The product was recrystallized with Hexane to give pure isomer 249e (0.94 g, 63%).

Procedure for Preparation of Compound 249f

According to a similar synthesis of compound I-6 described in Example I-2, (1r,4r)-4'-fluoro-4-methoxyspiro[cyclohexane-1,2'-inden]-1'(3'H)-one (249e) (0.22 g, 0.89 mmol) was condensed to hydantoin 249f (100 mg, 64% corrected yield, 99 mg of starting material 249e was recovered). LC-MS $t_R$=0.23 min in 3 min chromatography, MS (ESI) m/z 319 $[M+H]^+$.

Hydantoin 249f (100 mg, 0.31 mmol) was reacted with Lawesson's Reagent (125 mg, 0.31 mmol) to afford thiohydantoin 249g (91.3 mg, 88%). LC-MS $t_R$=1.37 min in 3 min chromatography, MS (ESI) m/z 335 $[M+H]^+$. This thiohydantoin 7 (91.3 mg, 0.27 mmol) was further dimethylated MeI (0.2 mL, excess) to give thioether 249h (79.7 mg, 80%). LC-MS $t_R$=1.74 min in 3 min chromatography, MS (ESI) m/z 363 $[M+H]^+$.

Finally, thioether 249h (40 mg, 0.11 mmol) was converted to compound 249 as a TFA salt (25.6 mg, 70%). LC-MS $t_R$=1.09 min in 3 min chromatography, MS (ESI) m/z 332 $[M+H]^+$; $^1H$ NMR ($CD_3OD$, 400 MHz): δ 7.26 (m, 1H), 7.14-7.00 (m, 2H), 3.36 (s, 3H), 3.22 (m, 2H), 3.18 (s, 3H), 3.04 (m, 1H), 2.08-1.94 (m, 2H), 1.82 (m, 1H), 1.44-1.22 (m, 5H).

Example 203

Synthesis of Compound 250

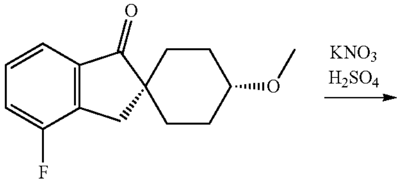

249e

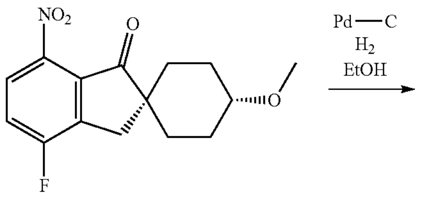

250a

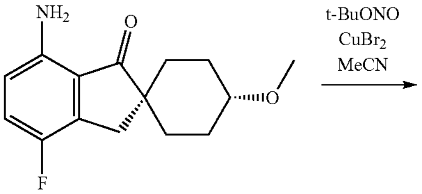

250b

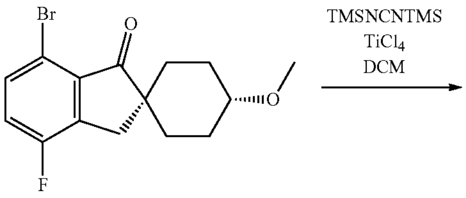

250c

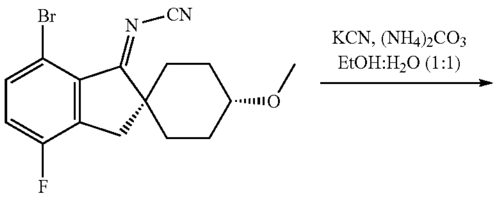

250d

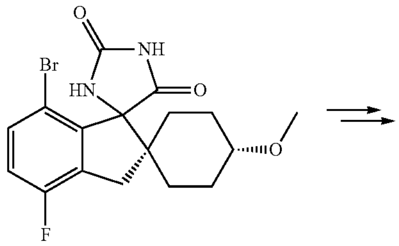

250e

-continued

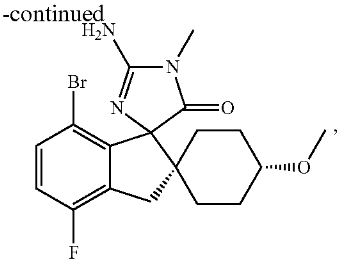

250

Procedure for Preparation of Compound 250a

To a solution of (1r,4r)-4'-fluoro-4-methoxyspiro[cyclohexane-1,2'-inden]-1'(3'H)-one (249e) (1.17 g, 4.7 mmol) in concentrate $H_2SO_4$ (6.0 mL) at 0° C., there was added $KNO_3$ (0.48 g, 4.7 mmol) in concentrate $H_2SO_4$ (1.5 mL) dropwise, the resulting solution was stirred at 0° C. for 2 hours, ice was added to stop the reaction, and the mixture was extracted with EtOAc (10 mL×4), combined organics were washed with sat. $NaHCO_3$ (10 mL), brine (10 mL) dried over $Na_2SO_4$, and the solvent was removed in vacuum to give (1r,4r)-4'-fluoro-4-methoxy-7'-nitrospiro[cyclohexane-1,2'-inden]-1'(3'H)-one (250a) (1.31 g, 95%), which was used for the next step without purification. LC-MS $t_R$=1.68 min in 3 min chromatography, MS (ESI) m/z 294 $[M+H]^+$.

Procedure for Preparation of Compound 250b

A solution of 1r,4r)-4'-fluoro-4-methoxy-7'-nitrospiro[cyclohexane-1,2'-inden]-1'(3'H)-one (250a) (1.31 g, 4.5 mmol) and Pd—C (100 mg) in EtOH (60 mL) was stirred with the connection of a $H_2$ balloon at room temperature for 5 hours. Reaction completion was confirmed by LC-MS, and the solution was filtered, and removed in vacuum to give (1r,4r)-7'-amino-4'-fluoro-4-methoxyspiro[cyclohexane-1,2'-inden]-1'(3'H)-one (250b) (1.18 g, 100%), which was used for the next step without purification. LC-MS $t_R$=1.58 min in 3 min chromatography, MS (ESI) m/z 264 $[M+H]^+$.

Procedure for Preparation of Compound 250c

To a solution of $CuBr_2$ (1.25 g, 5.55 mmol) and tert-butyl nitrite (1.48 mL, 11.1 mmol) in anhydrous MeCN (15 mL) at 0° C. there was added 1r,4r)-7'-amino-4'-fluoro-4-methoxyspiro[cyclohexane-1,2'-inden]-1'(3'H)-one (250b) (1.17 g, 4.44 mmol) in anhydrous MeCN (5 mL) dropwise to keep the temperature lower than 5° C. After adding, the resulting solution was warmed up slowly to room temperature, and stirred for another 1 hour, quenched with 1N HCl, and extracted with EtOAc (10 mL×4). The combined organic layers were washed with brine (10 mL), dried over $Na_2SO_4$. The solvent was removed in vacuum, and the residue was purified by flash chromatography (0 to 50% EtOAc/Hexane) to give (1r,4r)-7'-bromo-4'-fluoro-4-methoxyspiro[cyclohexane-1,2'-inden]-1'(3'H)-one (250c) (1.15 g, 79%). LC-MS $t_R$=1.84 min in 3 min chromatography, MS (ESI) m/z 327 $[M+H]^+$.

Procedure for Preparation of Compound 250d

To a solution of 1r,4r)-7'-bromo-4'-fluoro-4-methoxyspiro[cyclohexane-1,2'-inden]-1'(3'H)-one (250c) (1.14 g, 3.48 mmol) in anhydrous DCM (35 mL) there was added $TiCl_4$ (1 M in DCM, 7.0 mL, 7.0 mmol), the resulting solution was stirred at room temperature, then N,N'-methanediylidenebis (1,1,1-trimethylsilanamine) (1.74 mL, 7.6 mmol) was added dropwise. The solution was stirred at room temperature overnight. Water was added, and the mixture was extracted with DCM (10 mL×4). The combined organic layers were washed with water (10 mL), brine (10 mL), and dried over $Na_2SO_4$. The solvent was removed in vacuum to give crude (E)-N-((1r, 4r)-4'-bromo-7'-fluoro-4-methoxyspiro[cyclohexane-1,2'-indene]-3'(1'H)-ylidene)cyanamide (250d) (1.22 g, 100%), which was used for the next step without purification. LC-MS $t_R$=1.82 min in 3 min chromatography, MS (ESI) m/z 351 $[M+H]^+$.

Procedure for Preparation of Compound 250e

To a 50 mL sealed tube there was charged (E)-N-((1r,4r)-4'-bromo-7'-fluoro-4-methoxyspiro[cyclohexane-1,2'-indene]-3'(1'H)-ylidene)cyanamide (250d) (1.22 g, 3.48 mmol), KCN (0.47 g, 7.0 mmol), $(NH_4)_2CO_3$ (2.34 g, 24.4 mmol), and EtOH (10 mL) and water (10 mL). The tube was sealed, and heated at 75° C. overnight. The solution was cooled to room temperature, and water (15 mL) was added, filtered to give solid product 6 (0.70 g), the filtration was extracted with DCM, after removal of solvent, the residue was purified by flash chromatography to give another 0.24 product 250e (total 68%).

Procedure for Synthesis of Compound 250

Using the similar synthesis of compound 249, compound 250 was synthesized as a TFA salt. LC-MS $t_R$=1.21 min in 3 min chromatography, MS (ESI) m/z 410 $[M+H]^+$. $^1H$ NMR ($CD_3OD$, 400 MHz): δ 7.48 (m, 1H), 7.14 (m, 1H), 3.38 (s, 3H), 3.26 (m, 1H), 3.24 (s, 3H), 3.20 (m, 1H), 3.00 (m, 1H), 2.06 (m, 2H), 1.82 (m, 1H), 1.56-1.26 (m, 5H); $^{19}F$ NMR ($CD_3OD$, 376 MHz): δ −77.8, −121.0.

Example 204

Synthesis of Compound 251

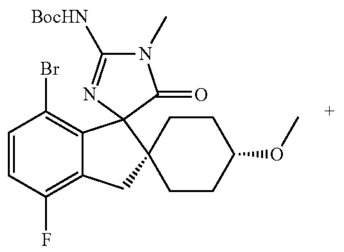

251a

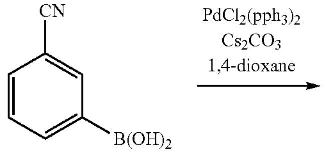

-continued

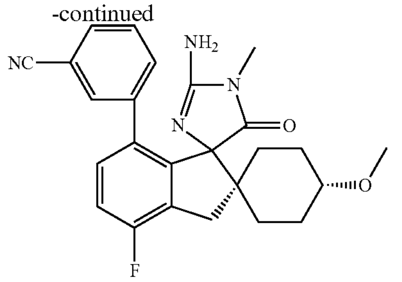

251

To a 10 mL CEM tube there was charged compound 251a (102 mg, 0.2 mmol), $PdCl_2(pph_3)_2$ (7.0 mg), $Cs_2CO_3$ (130 mg. 0.4 mmol), 1,4-dioxane (1 mL) and water (0.2 mL). The tube was heated in a CEM microwave reactor at 120° C. for 30 min. The solution was filtered, solvent was removed in vacuum, and the residue was purified with HPLC to give compound compound 251 (5.5 mg, 6%). LC-MS $t_R$=1.31 min in 3 min chromatography, MS (ESI) m/z 433 $[M+H]^+$. $^1H$ NMR ($CD_3OD$, 400 MHz): δ 7.80 (m, 1H), 7.62 (m, 1H), 7.60-7.24 (m, 2H), 7.22 (m, 1H), 7.14 (m, 1H), 3.36 (s, 3H), 3.30 (m, 1H), 3.20-3.02 (m, 5H), 2.04 (m, 2H), 1.80 (m, 1H), 1.52-1.24 (m, 5H); $^{19}F$ NMR ($CD_3OD$, 376 MHz): δ −77, −120.

Example 205

Synthesis of Compound 252

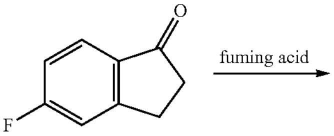

252a

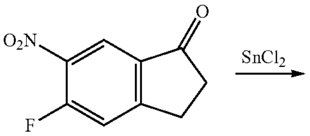

252b

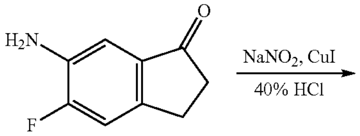

252c

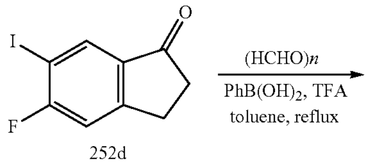

252d

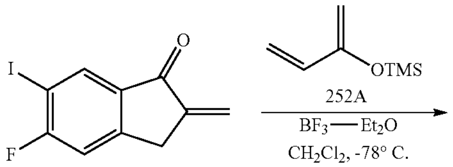

252e

-continued

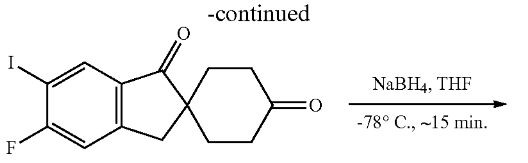

252f

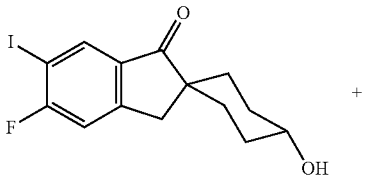

252g

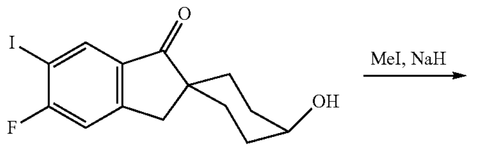

252h

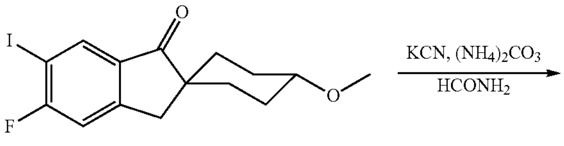

252i

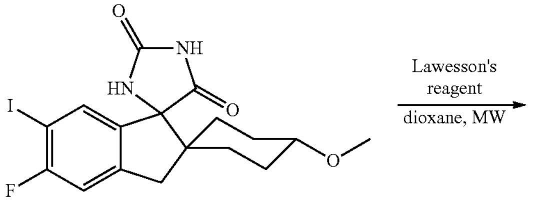

252j

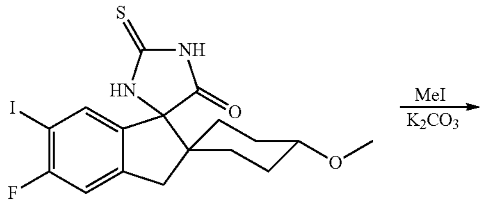

252k

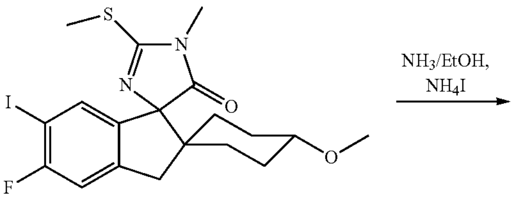

252l

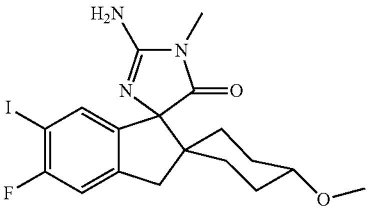

252

Procedure for Preparation of Compound 252b

To a well-stirred solution of fuming nitric acid (92 mL) was added compound 252a (20 g, 133 mmol) at 0° C. slowly. The resulting mixture was stirred at 0° C. for 3 h. TLC showed the reaction was completed, and the reaction mixture was poured into ice (100 g) to give the yellow solid. The resulting mixture was filtered, and the filter cake was dissolved in ethyl acetate (200 mL) and washed with water (2×500 mL). The organic layer was dried over $Na_2SO_4$ and concentrated under vacuum to give compound 252b (8.5 g, 33%) as a yellow solid. $^1$H NMR ($CDCl_3$ 400 MHz): δ 8.36-8.44 (m, 1H), 7.33-7.42 (m, 1H), 3.18-3.30 (m, 2H), 2.73-2.81 (m, 2H).

Procedure for Preparation of Compound 252c

To a solution of $SnCl_2$ (39.35 g, 174 mmol) in concentrated aqueous HCl (33 mL) was added a solution of compound 252b (8.5 g, 43.6 mmol) in 95% ethanol (16 mL). The resulting mixture was stirred at room temperature for 2 h. TLC showed the reaction was completed, and the mixture was treated with 50% aqueous NaOH solution (100 mL) to give the yellow solid. The resulting mixture was filtered, and the filter cake was dissolved in $CH_2Cl_2$ (200 mL). The mixture was filtered, and the filtrate was dried over $Na_2SO_4$ and concentrated in vacuo to give compound 252c (5.5 g, 77%) as a yellow solid. $^1$H NMR ($CDCl_3$ 400 MHz): δ 6.99-7.20 (m, 2H), 3.79 (s, 2H), 2.93-2.96 (m, 2H), 2.58-2.60 (m, 2H).

Procedure for Preparation of Compound 252d

A mixture of compound 252c (5.5 g, 33.3 mmol) in concentrated HCl (19 mL) was stirred at room temperature. Then to the mixture was added ice (10 g) and stirred for a few min. Then to the above mixture was added a solution of $NaNO_2$ (2.59 g, 36.7 mmol) in $H_2O$ (13 mL) slowly while keeping temperature between −5° C.-0° C., and stirred for 30 min. Then to the mixture was added a solution of KI (55.24 g, 333 mmol) in $H_2O$ (70 mL) slowly and stirred for another 3 h. The resulting mixture was filtered, and the filtrate was extracted with ethyl acetate (2×100 mL). The combined organic layers were dried over $Na_2SO_4$ and concentrated in vacuo to give compound 252d (5 g, 54%) as a yellow solid. $^1$H NMR ($CDCl_3$ 400 MHz): δ 8.10 (d, J=6.0 Hz, 1H), 7.12 (d, J=9.2 Hz, 1H), 3.02-3.05 (m, 2H), 2.65-2.68 (m, 2H).

Procedure for Preparation of Compound 252e

A solution of compound 252d (10 g, 36.2 mmol), paraformaldehyde (5.1 g, 163 mol), N-methylaniline TFA salt (12 g, 54.3 mmol) in anhydrous THF (120 mL) was refluxed for 8 h. When starting material was totally consumed, the crude mixture was cooled to room temperature, concentrated to give the residue, extracted with ethyl acetate (2×200 mL). The combined organic layers were washed with brine (100 mL), dried over $Na_2SO_4$ and concentrated under reduced pressure. The residue was purified by column chromatography on silica gel (petroleum ether:ethyl acetate=10:1) to give compound 252e (6.7 g, 65%) as a yellow solid. $^1$H NMR ($CDCl_3$ 400 MHz): δ 8.22 (d, J=6.0 Hz, 1H), 7.11 (d, J=7.6 Hz, 1H), 6.30 (s, 1H), 5.60 (s, 1H), 3.66 (s, 2H).

Procedure for Preparation of Compound 252f

To a solution of compound 252e (1.6 g, 5.56 mmol, 1 equivalent) in dichloromethane (20 mL) was added 2-trimethylsilyloxy-1,3-butadiene (1.05 mL, 6.11 mmol, 1.1 equivalents) and the reaction was cooled down to −78° C. After stirring for 15 min at −78° C., BF$_3$.Et$_2$O (0.36 mL, 2.78 mmol, 0.5 equivalents) was slowly added and the reaction was allowed to stir at −78° C. During the addition, the color of the solution changed from colorless to light yellow. After 25 min of the BF$_3$.Et$_2$O addition, the TLC indicated total consumption of the dienophile, formation of the silyl enol ether Diels Alders adduct and the desired ketone. The reaction was rapidly quenched with MeOH (3.5 mL), allowed to stir 5 min at −78° C. and warmed up to room temperature. Once at room temperature, an aqueous diluted HCl solution (2 M, 25 mL) was added and the biphasic solution was allowed to stir no more than 5 min. The two phases were separated and the aqueous phase was back-extracted with CH$_2$Cl$_2$ (2×100 mL). The combined organic phases were dried over MgSO$_4$ and concentrated under reduced pressure. At this point, the TLC indicated mostly the desired ketone along with other minor side products. The crude material was purified by column chromatography on silica gel (petroleum ether:ethyl acetate=10:1). The corresponding fractions were combined and concentrated under reduced pressure yielding compound 252f (0.72 g, 37%) as a white solid. $^1$H NMR (CDCl$_3$ 400 MHz): δ 8.14 (d, J=6.0 Hz, 1H), 7.12 (d, J=7.2 Hz, 1H), 3.10 (s, 2H), 2.61-2.65 (m, 2H), 2.32-2.37 (m, 2H), 2.09-2.13 (m, 2H), 1.77-1.83 (m, 2H).

Procedure for Preparation of Compounds 252 g and 252h

To a solution of compound 252f (720 mg, 2.01 mmol) in THF (8 mL) was cooled down to −78° C. After 5 min, NaBH$_4$ (76 mgs, 2.01 mmol) was added, and the reaction mixture was stirred at −78° C. no more than 5 min. When TLC indicated the consumption of the diketone, the reaction was quenched by addition of MeOH (2 mL). The mixture was diluted with ethyl acetate (50 mL). Water was added (25 mL), and the aqueous layer was extracted with ethyl acetate (2×20 mL). The combined organic layers were dried over Na$_2$SO$_4$, filtered, concentrated under reduced pressure to afford the mixture containing compound 252 g and compound 252h (750 mg, 90% crude yield) as a yellow oil.

Procedure for Preparation of Compound 252i

To a solution of compound 252 g (800 mg, 2.22 mmol) in THF (12 mL) was added NaH (267 mg, 6.66 mmol) and the mixture was stirred at 0° C. for 15 min. Then to the above mixture was added methyl iodide (1.39 mL, 22.2 mmol). The reaction was stirred at room temperature overnight, and TLC showed the reaction was completed. The reaction mixture was filtered through a pad of celite, and washed with ethyl acetate (40 mL). The filtrate was concentrated under reduced pressure, and purified by column chromatography on silica gel (petroleum ether:ethyl acetate=40:1) to afford compound 252i (200 mg, 23%) as a white solid. $^1$H NMR (CDCl$_3$ 400 MHz): δ 8.10 (d, J=5.6 Hz, 1H), 7.08 (d, J=7.6 Hz, 1H), 3.30 (s, 3H), 3.16-3.22 (m, 1H), 2.82 (s, 2H), 1.90-2.10 (m, 2H), 1.66-1.73 (m, 2H), 1.42-1.50 (m, 2H), 1.30-1.41 (m, 2H).

Procedure for Preparation of Compound 252

According to a similar synthesis of compound I-6 described in Example I-2, compound 252i (617 mg, 2.0 mmol) was condensed to hydantoin 252j (50 mg, 6%) as a white solid. Hydantoin 252j (20 mg, 0.045 mmol) was then reacted with Lawesson's Reagent (18 mg, 0.045 mmol) to give compound 252k (10 mg, 50%) as a yellow solid.

Compound 252k (15 mg, 0.033 mmol) was then dimethylated with MeI (9 mg, 0.063 mmol) to give compound 252l (8 mg, 50% crude yield) as a yellow solid, which was converted to compound 252 (1 mg, 15%). LC-MS t$_R$=0.937 min in 2 min chromatography, MS (ESI) m/z 458 [M+H]$^+$. $^1$H NMR (CD$_3$OD 400 MHz): δ 7.70 (s, 1H), 7.21 (d, J=8.0 Hz, 1H), 3.23-3.33 (s, 3H), 3.15-3.18 (m, 3H), 3.05 (m, 1H), 2.67-2.70 (m, 1H), 2.08-2.17 (m, 1H), 1.95-2.05 (m, 2H), 1.83-1.86 (m, 1H); 1.34-1.45 (m, 3H), 1.20-1.28 (m, 2H)

Example 206

Synthesis of Compound 253

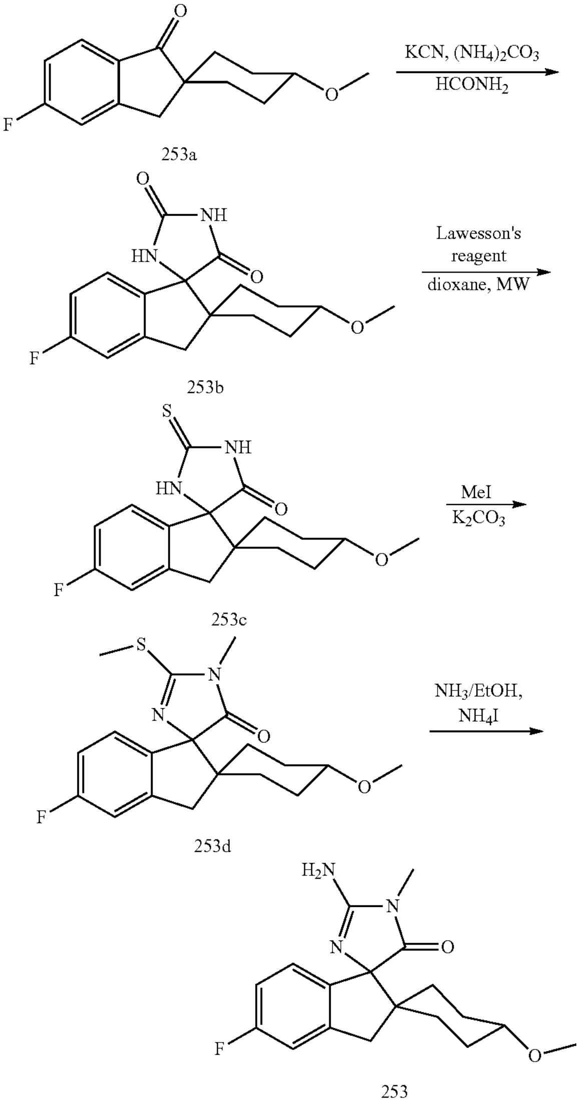

According to a similar synthesis of compound I-6 described in Example I-2, compound 253a (800 mg, 2.45 mmol) was condensed to hydantoin 253b (500 mg, 49%) as a white solid. Then compound 253b (200 mg, 0.47 mmol) was reacted with Lawesson's Reagent (254 mg, 0.47 mmol) in anhydrous toluene (6 mL) to give compound 253c (70 mg, 33%) as a yellow solid, which was dimethylated with MeI (118 mg, 0.42 mmol) and K$_2$CO$_3$ (116 mg, 0.84 mmol to give compound 253d (70 mg, 90%) as a yellow solid, which was used directly in next step without purification.

Finally, compound 253d (75 mg, 0.21 mmol) was converted to compound 253 (6.0 mg, 8%). LC-MS $t_R$=0.854 min in 2 min chromatography, MS (ESI) m/z 432 $[M+H]^+$; $^1H$ NMR ($CD_3OD$ 400 MHz): δ 7.10-7.15 (m, 1H), 7.02 (d, J=9.2 Hz, 1H), 6.93 (t, J=12.0 Hz, 1H), 3.23-3.33 (s, 3H), 3.15-3.18 (s, 3H), 3.05 (m, 1H), 2.97-3.04 (m, 2H), 1.91-2.05 (m, 2H), 1.73-1.77 (m, 1H), 1.26-1.34 (m, 3H), 1.14-1.22 (m, 2H)

Example I-4

Synthesis of hydantoin I-14

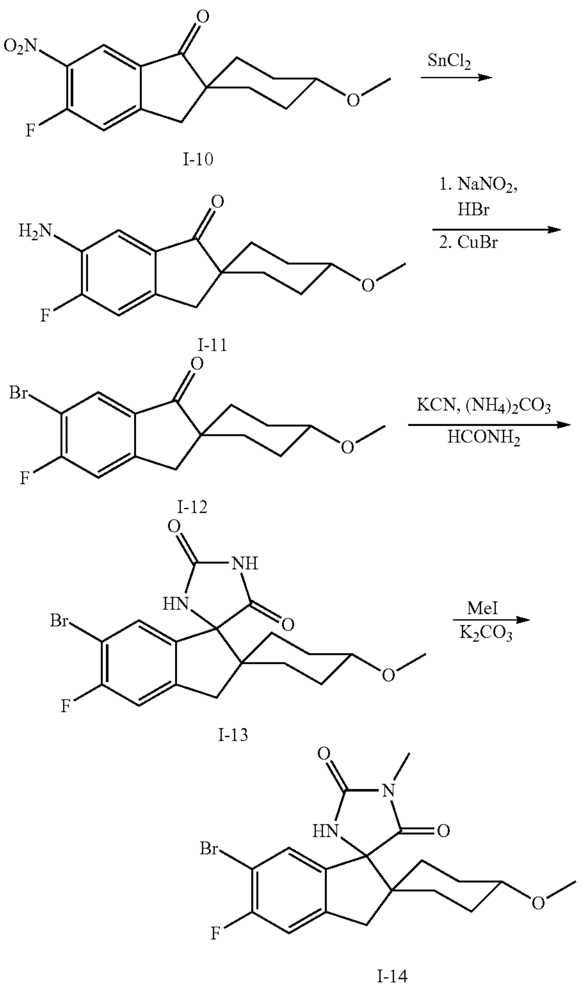

Procedure for Preparation of Compound I-11

To a solution of $SnCl_2$ (9.25 g, 41 mmol) in concentrated HCl (7.5 mL) was added a solution of compound I-10 (3 g, 10.24 mmol) in 95% ethanol (3.6 mL). The resulting mixture was stirred at room temperature for 2 h. TLC showed the reaction was completed; the mixture was treated with 50% aqueous NaOH solution (50 mL) to give the yellow solid. The resulting mixture was filtered, and the filtered cake was dissolved in $CH_2Cl_2$ (100 mL). The mixture was filtered, and the filtrate was dried over $Na_2SO_4$ and concentrated in vacuo to give compound I-11 (2 g, 67%) as a yellow solid.

Procedure for Preparation of Compound I-12

A mixture of compound I-11 (2 g, 7.60 mmol) in concentrated HBr (13.3 mL) was stirred at room temperature. Then to the mixture was added ice (10 g) and stirred for a few min. Then to the above mixture was added a solution of $NaNO_2$ (585 mg, 8.36 mmol) in $H_2O$ (2.28 mL) slowly while keeping temperature between −5° C.-0° C., and stirred for 30 min. Then to the mixture was added a solution of CuBr (1.21 g, 8.36 mmol) in concentrated HBr (13.3 mL) slowly and stirred for another 30 min. The resulting mixture was filtered, and the filtrate was extracted with ethyl acetate (2×100 mL). The combined organic layer was dried over $Na_2SO_4$ and concentrated to give compound I-12 (0.85 g, 41%) as a yellow solid.

Procedure for Preparation of Compound I-13

A steel autoclave was charged with a mixture of compound I-12 (850 mg, 2.60 mmol), KCN (338 mg, 5.20 mmol) and $(NH_4)_2CO_3$ (1.87 g, 19.5 mmol) in formamide (25 mL). The mixture was stirred at 110° C. for 72 h, cooled to room temperature, and poured into ice (10 g). After acidification with conc. HCl solution (10 mL), the resulting mixture was filtered, and the filter cake was dissolved in ethyl acetate (100 mL) and washed with water (2×200 mL). The organic layer was dried over $Na_2SO_4$ and concentrated under reduced pressure to give compound I-13 (650 mg, 63%) as a white solid, which was used in the next step without purification.

Procedure for Preparation of Compound I-14

To a solution of compound I-13 (140 mg, 0.354 mmol) in $CH_3CN$ (7 mL) was added MeI (77 mg, 0.53 mmol) and $K_2CO_3$ (77 mg, 0.53 mmol). After being stirred at 80° C. for 15 min in microware, the mixture was filtrated and the filtrate was concentrated in vacuo to give the residue, which was dissolved in $CH_2Cl_2$, filtered and the filtrate was concentrated under vacuum to give the crude product, which was purified by preparative TLC (petroleum ether:ethyl acetate=2:1) to give compound I-14 (70 mg, 50%) as a yellow solid.

Example 207

Synthesis of Compound 254

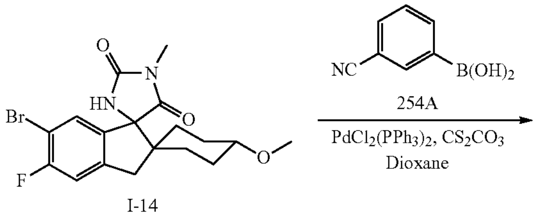

-continued

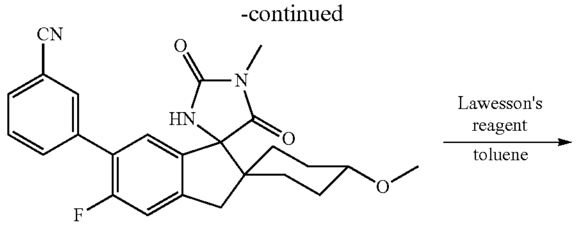

254a

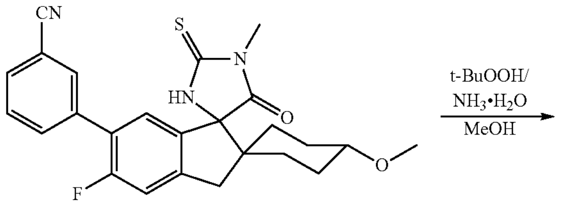

254b

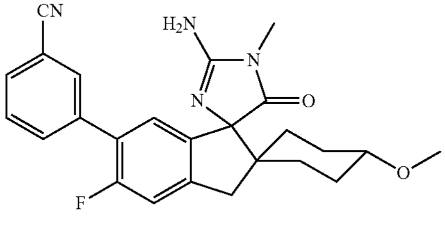

254

Procedure for Preparation of Compound 254a

A solution containing compound 254A (48 mg, 0.329 mmol) and compound I-14 (90 mg, 0.220 mmol) in dioxane (6 mL), and aqueous $Cs_2CO_3$ (2 M, 1.56 mL) was deoxygenated by bubbling a stream of nitrogen through the reaction mixture for 5 min. Then, $PdCl_2(PPh_3)_2$ (15.6 mg) was added. The reaction vial was sealed and placed into CEM microwave reactor and irradiated at 120° C. for 15 min. After being cooled to room temperature, the mixture was diluted with EtOAc and filtered through a short Celite pad. The solution was concentrated in vacuo and the residue was purified by preparative TLC ($CH_2Cl_2$:MeOH=15:1) to give compound 254a (65 mg, 73%).

Procedure for Preparation of Compound 254b

A suspension of compound 254a (65 mg, 0.15 mmol) and Lawesson's Reagent (61 mg, 0.15 mmol) in anhydrous toluene (4 mL) was heated at reflux overnight. The mixture was concentrated in vacuo, and the residue was purified by prep-TLC (petroleum ether:ethyl acetate=3:1) to give compound 254b (26 mg, 40%) as a yellow solid.

Procedure for Preparation of Compound 254

A solution of compound 254b (26 mg, 0.058 mmol) and t-BuOOH (104 mg, 1.158 mmol) in $NH_4OH$ (0.8 mL) and MeOH (1.5 mL) was stirred at room temperature overnight. The reaction mixture was concentrated under reduced pressure and purified by HPLC to give compound 254 (3.2 mg, 12%). LC-MS $t_R$=0.970 min in 2 min chromatography, MS (ESI) m/z 433 $[M+H]^+$. $^1H$ NMR ($CD_3OD$ 400 MHz): δ7.70-7.81 (m, 2H), 7.65-7.70 (m, 1H), 7.51-7.60 (m, 1H), 7.20-7.27 (m, 1H), 7.20 (d, J=14.4 Hz, 4H), 3.23-3.33 (s, 3H), 3.05-3.10 (m, 1H), 3.05 (s, 2H), 3.01 (s, 3H), 1.85-2.00 (m, 2H), 1.71-1.78 (m, 1H), 1.35-1.42 (m, 2H), 1.21-1.32 (m, 1H), 1.18-1.25 (m, 2H)

Example 208

Synthesis of Compound 255

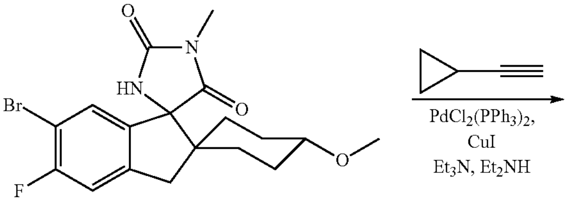

I-14

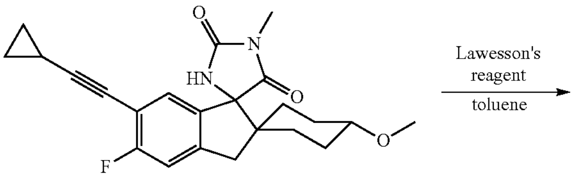

255a

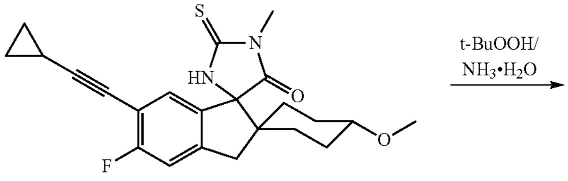

255b

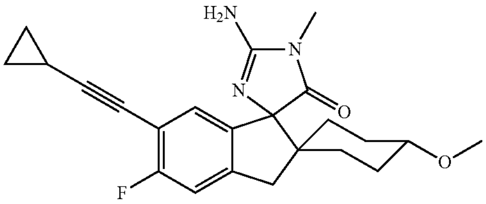

255

According to a similar synthesis of compound 254, compound I-14 (20 mg, 0.049 mmol) was coupled with cyclopropyl acetylene (0.2 mL, excess) in the present of CuI (0.5 mg, 0.00245 mmol) and $PdCl_2(PPh_3)_2$ (1.7 mg, 0.00245 mmol) to give compound 255a (18 mg, 96%) as white solid.

Compound 255a (20 mg, 0.051 mmol) was then reacted with Lawesson's Reagent (20.4 mg, 0.051 mmol) to give compound 255b (7 mg, 34%) as a yellow solid, which was converted to compound 255 (2.2 mg, 31%). LC-MS $t_R$=1.001 min in 2 min chromatography, MS (ESI) m/z 396 $[M+H]^+$. $^1H$ NMR ($CD_3OD$ 400 MHz): δ 6.95-7.01 (m, 1H), 6.88-6.93 (m, 1H), 3.23-3.33 (s, 3H), 3.05-3.10 (m, 1H), 3.05 (s, 2H), 3.01 (s, 3H), 1.80-1.92 (m, 2H), 1.71-1.74 (m, 1H), 1.42-1.45

(m, 1H), 1.34-1.39 (m, 1H), 1.20-1.28 (m, 2H), 1.10-1.18 (m, 2H), 0.75-0.85 (m, 2H), 0.60-0.66 (m, 2H).

Example 209

Synthesis of Compound 256

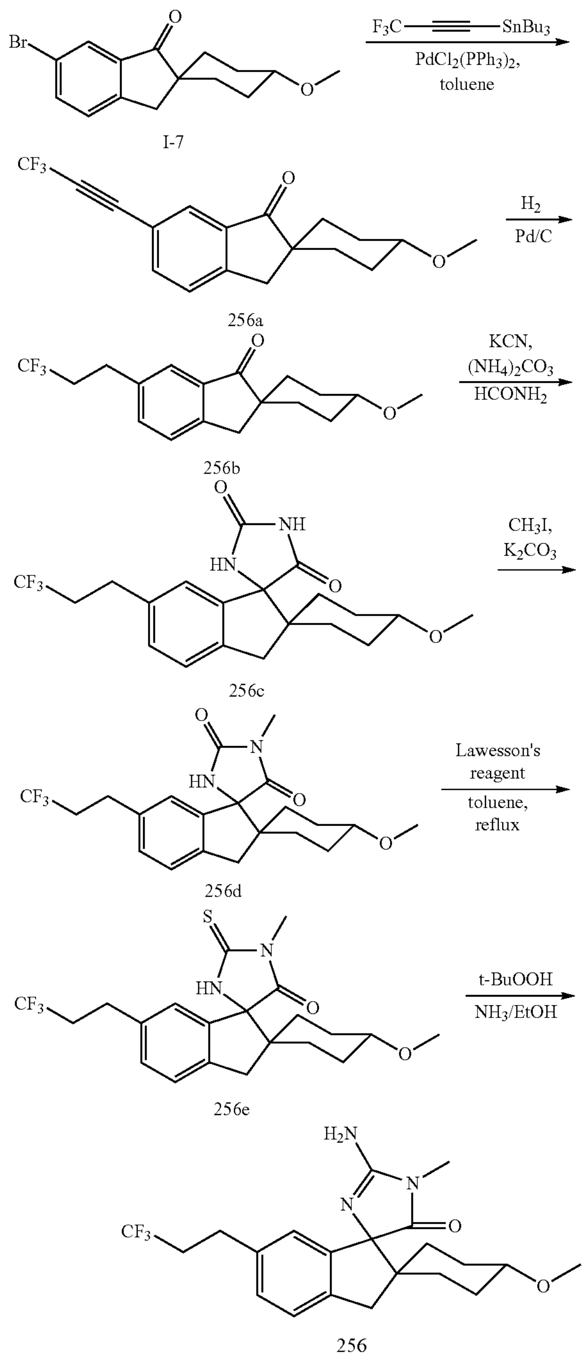

I-7

256a

256b

256c

256d

256e

256

Procedure for Preparation of Compound 256a

A solution containing the tributyl (3,3,3-trifluoroprop-1-ynyl)stannane (1.166 g, 2.91 mmol) and compound I-7 (600 mg, 1.94 mmol) in toluene (10 mL) was deoxygenated by bubbling a stream of nitrogen through the reaction mixture for 5 min. Then $PdCl_2(PPh_3)_2$ (68 mg, 0.097 mmol) was added. The reaction vial was sealed and placed into CEM microwave reactor and irradiated at 125° C. for 45 min. After being cooled to room temperature, the mixture was partitioned between EtOAc (10 mL) and aqueous CsF (4 M, 10 mL), and the aqueous layer was extracted with EtOAc (3×10 mL). The combined organic layers were washed with brine (15 mL), dried over anhydrous $Na_2SO_4$, filtered, and concentrated in vacuo to give the residue, which was purified preparative TLC (petroleum/ethyl acetate=3:1) to give compound 256a (400 mg, 64%) as a white solid.

Procedure for Preparation of Compound 256b

To a solution of compound 256a (5 mg, 0.016 mmol) in THF (5 mL) was added Pd/C (2 mg, 10% in w.t.). The reaction mixture was stirred at room temperature for 1 h under $H_2$ atmosphere (1 atm), LCMS showed that the reaction was completed. The reaction mixture was filtered and the filtrate was concentrated to give compound 256b (4 mg, crude, 80%) as a white solid, which was used directly for next step without further purification.

Procedure for Preparation of Compound 256c

A steel autoclave was charged with a mixture of compound 256b (100 mg, 0.307 mmol), KCN (40 mg, 0.614 mmol), and $(NH_4)_2CO_3$ (221 mg, 2.3 mmol). Formamide (25 mL) was added. The mixture was heated at 100° C. for 72 h, and the reaction mixture was cooled, and poured into ice. After acidification with concentrated aqueous HCl solution (3 mL), the mixture was filtrated to give the solid, which was dissolved in ethyl acetate (100 mL) and washed with water (2×25 mL). The organic phase was dried over $Na_2SO_4$ and concentrated to give the crude compound 256c, which was purified by preparative TLC (petroleum:ethyl acetate=1:1) to give compound 4 (68 mg, 56%) as a white solid.

Procedure for Preparation of Compound 256d

To a solution of compound 256c (50 mg, 0.126 mmol) in $CH_3CN$ (4 mL) was added $K_2CO_3$ (52 mg, 0.378 mmol). After being stirred for 5 min, MeI (20 mg, 0.139 mmol) was added, and the reaction mixture was heated at 60° C. for 10 min in microwave, and at 100° C. for another 10 min. The mixture was filtered, and the filtrate was concentrated under reduced pressure to give compound 256d (30 mg, 55%) as a white solid, which was used for the next step directly without purification.

Procedure for Preparation of Compound 256e

A solution of compound 256d (16 mg, 0.039 mmol) and Lawesson's Reagent (16 mg, 0.039 mmol) in dry toluene (1.5 mL) was heated at 140° C. for 30 min in a CEM microwave reactor. LCMS showed that the reaction was completed, the mixture was concentrated under reduced pressure, and the residue was purified by preparative TLC (petroleum:ethyl acetate=2:1) to give compound 256e (14 mg, 84%) as a white solid.

Procedure for Preparation of Compound 256

A mixture of compound 256e (30 mg, 0.07 mmol) and t-butyl hydroperoxide (127 mg of a 65% solution in water, 1.41 mmol) in $NH_3$/EtOH (10 mL, 5 N) was stirred at room temperature overnight, LCMS showed that the reaction was completed, then reaction mixture was concentrated under reduced pressure to dryness. Purification of this residue by preparative TLC ($CH_2Cl_2$:MeOH=5:1) and preparative HPLC gave compound 256 (5.7 mg, 22%) as a white solid. LC-MS $t_R$=1.097 min in 2 min chromatography, MS (ESI) m/z 410.2 $[M+H]^+$. $^1H$ NMR ($CD_3OD$ 400 MHz): δ 7.23-7.26 (d, J=7.6 Hz, 1H), 7.15-7.18 (d, J=8.0 Hz, 1H), 6.87 (s, 1H), 3.36 (s, 3H), 3.08-3.18 (m, 2H), 3.04-3.06 (m, 1H), 3.03 (s, 3H), 2.81-2.85 (t, J=9.6 Hz, 2H), 2.36-2.49 (m, 2H), 1.95-2.02 (m, 2H), 1.83-1.85 (m, 1H), 1.57-1.65 (t, J=14.0 Hz, 1H), 1.34-1.44 (m, 2H), 1.25-1.32 (m, 2H). $^{19}F$ NMR ($CD_3OD$): δ −58.90, −64.78, −68.17.

Example I-5

Synthesis of Intermediate I-20

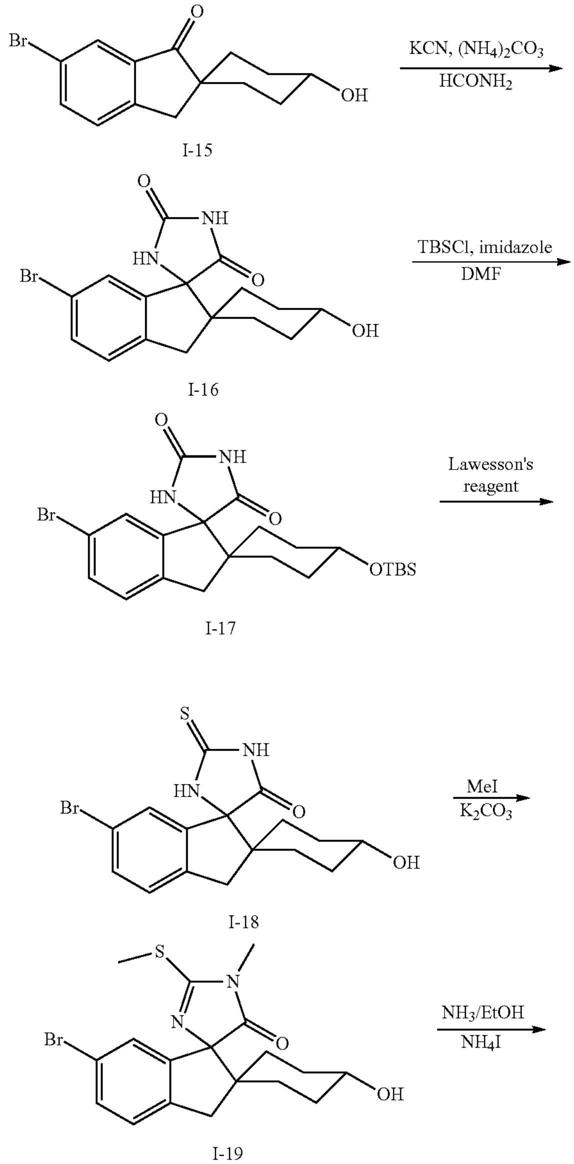

I-15

I-16

I-17

I-18

I-19

-continued

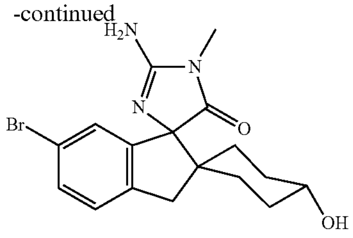

I-20

Procedure for Preparation of Compound I-16

A steel autoclave was charged with a mixture of compound I-15 (4.33 g, 14.67 mmol), KCN (1.9 g, 29.36 mmol) and $(NH_4)_2CO_3$ (10.57 g, 110.03 mmol) in formamide (80 mL). The mixture was stirred at 110° C. for 72 h, cooled to room temperature, and poured into ice (20 g). After acidification with conc. HCl solution (25 mL), the resulting mixture was filtered, and the filter cake was dissolved in ethyl acetate (100 mL) and washed with water (2×500 mL). The organic layer was dried over $Na_2SO_4$ and concentrated in vacuo to give compound I-16 (2.78 g, 52%) as a brown solid.

Procedure for Preparation of Compound I-17

A solution of compound I-16 (1.8 g, 4.95 mmol), TBSCl (0.89 g, 5.93 mmol) and imidazole (674 mg, 9.9 mmol) in DMF (18 mL) was stirred at room temperature overnight. Water (15 mL) and EtOAc (3×10 mL) were added, and the organic layer was dried over $Na_2SO_4$ and concentrated in vacuo to give compound I-17 (1.3 g, 60%) as a white solid.

Procedure for Preparation of Compound I-18

A suspension of compound I-17 (1.3 g, 2.73 mmol) and Lawesson's Reagent (1.1 g, 2.73 mmol) in anhydrous toluene (52 mL) was heated at reflux overnight. The mixture was concentrated in vacuo, and the residue was purified by column chromatography on silica gel ($CH_2Cl_2$:MeOH=10:1) to give compound I-18 (750 mg, 71%) as a yellow solid.

Procedure for Preparation of Compound I-19

To a solution of compound I-18 (50 mg, 0.132 mmol) in $CH_3CN$ (4 mL) was added MeI (37 mg, 0.263 mmol) and $K_2CO_3$ (73 mg, 0.53 mmol). After being stirred at 60° C. for 10 min in microware, additional MeI (37 mg, 0.263 mmol) was added. The reaction mixture was stirred at 100° C. for another 10 min in microware, concentrated in vacuo to give compound I-19 (40 mg, 80%) as a yellow solid.

Procedure for Preparation of Compound I-20

A solution of compound I-19 (80 mg, 0.196 mmol) and $NH_4I$ (284 mg, 1.96 mmol) in $NH_3$/EtOH (5.0 N, 3.5 mL) was irradiated at 120° C. in a microwave reactor for 3 h. The reaction mixture was concentrated under reduced pressure. The residue was added $CH_2Cl_2$ (15 mL), and stirred for 30 min. The mixture was filtered, concentrated in vacuo to give compound I-20 (30 mg, 38%) as a yellow solid.

Example 210

Synthesis of Compound 257

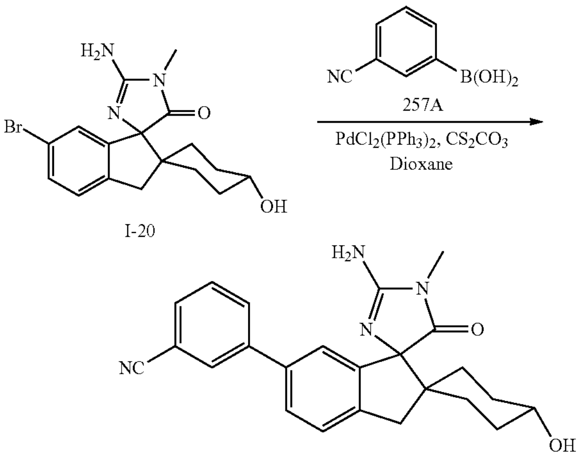

I-20

257

A solution containing compound I-20 (30 mg, 0.080 mmol) and compound 257A (17.5 mg, 0.119 mmol) in dioxane (2 mL), and aqueous $Cs_2CO_3$ (2 M, 0.56 mL) was deoxygenated by bubbling a stream of nitrogen through the reaction mixture for 5 min. Then, $PdCl_2(PPh_3)_2$ (5.6 mg, 0.008 mmol) was added. The reaction vial was sealed and placed into CEM microwave reactor and irradiated at 120° C. for 15 min. After being cooled to room temperature, the mixture was diluted with EtOAc and filtered through a short Celite pad. The solution was concentrated in vacuo and the residue was purified by preparative HPLC to afford compound 257 (2.4 mg, 7%) as a white solid. LC-MS $t_R$=0.846 min in 2 min chromatography, MS (ESI) m/z 401 $[M+H]^+$. $^1H$ NMR ($CD_3OD$ 400 MHz): δ 8.96 (s, 1H), 7.92 (d, J=8.0 Hz, 1H), 7.70 (d, J=8.0 Hz, 1H), 7.58-7.68 (m, 2H), 7.45 (d, J=7.6 Hz, 1H), 7.29 (s, 1H), 3.47-3.52 (m, 1H), 3.18 (m, 2H), 3.10 (s, 3H), 1.83-1.95 (m, 3H), 1.66 (m, 1H), 1.40-1.51 (m, 1H), 1.30-1.48 (m, 3H).

Example 211

Synthesis of Compound 258

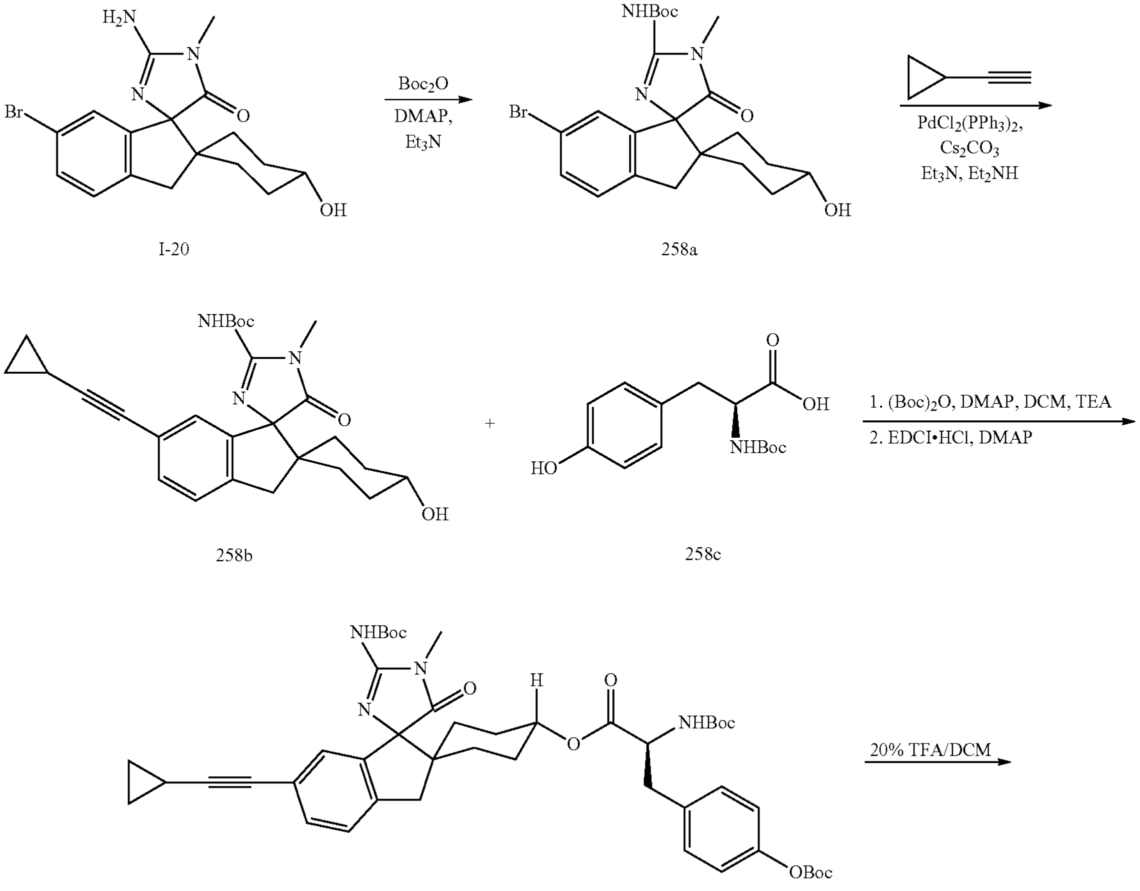

I-20

258a

258b

258c

258d

-continued

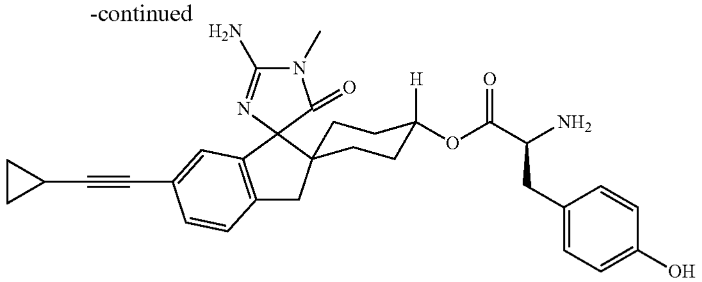

258

Procedure for Preparation of Compound 258a

To a solution of compound I-20 (400 mg, 1.06 mmol) in anhydrous THF (16 mL) was added DMAP (194 mg, 1.59 mmol), $Boc_2O$ (347 mg, 1.59 mmol) and $Et_3N$ (214 mg, 2.12 mmol), the reaction mixture was stirred at ambient temperature overnight. The solvent was removed by evaporation in vacuo to yield the crude compound 258a, which was purified by preparative TLC (petroleum ether:ethyl acetate=1:1) to give compound 258a (100 mg, 25%) as a white solid.

Procedure for Preparation of Compound 258b

An oven dried three-necked round bottom flask equipped with condenser was charged with compound 258a (80 mg, 0.17 mmol), $Et_3N$ (5 mL) and $Et_2NH$ (1 mL) under a nitrogen atmosphere. To this solution was added CuI (3.2 mg, 0.017 mmol) and $PdCl_2(PPh_3)_2$ (11.8 mg, 0.017 mmol). The system was degassed once again, then cyclopropyl acetylene (0.7 mL, excess) was added and the mixture was stirred at 60° C. in an oil bath for 15 h. The solvent was evaporated in vacuo and the residue was partitioned between ethyl acetate (20 mL) and water (10 mL). The aqueous layer was extracted with ethyl acetate (2×30 mL). The combined organic layers were washed with brine (30 mL), dried over $Na_2SO_4$ and concentrated under reduced pressure to dryness. The crude product was purified by preparative TLC eluting with petroleum ether:ethyl acetate (1:1) to give compound 258b (54 mg, 70%) as a white solid.

Procedure for Preparation of Compound 258d

To a solution of compound 258c (44 mg, 0.16 mmol), DMAP (0.2 mg, 0.0016 mmol) and $Et_3N$ (0.02 mL, 0.16 mmol) in anhydrous dichloromethane (3 mL) was added $Boc_2O$ (44 mg, 0.202 mmol) at room temperature. After being stirred for 3 h, the reaction mixture was added compound 258b (60 mg, 0.13 mmol), DMAP (4 mg, 0.032 mmol) and EDCl.HCl (38 mg, 0.20 mmol). Then the mixture was stirred at room temperature for 24 h. The reaction mixture was purified by preparative TLC (petroleum ether:EtOAc=2:1) to give compound 258d (32 mg, 25%) as a white solid. $^1H$ NMR: ($CDCl_3$ 400 MHz): δ 8.65 (s, 1H), 7.24 (d, J=6.8 Hz, 1H), 7.13 (d, J=6.4 Hz, 1H), 7.06 (d, J=8.4 Hz, 2H), 7.02 (m, 3H), 4.90 (m, 1H), 4.59 (m, 1H), 4.43 (m, 1H), 3.13-3.09 (d, J=16.4 Hz, 1H), 3.00 (s, 3H), 3.01-2.93 (m, 3H), 1.87-1.79 (m, 2H), 1.78-1.68 (m, 1H), 1.51 (s, 9H), 1.48 (s, 9H), 1.35 (s, 9H), 1.49-1.15 (m, 6H), 0.83-0.74 (m, 2H), 0.72-0.67 (m, 2H).

Procedure for Preparation of Compound 258

To a solution of compound 258d (15 mg, 0.018 mmol) in dichloromethane (0.5 mL) was added a solution of TFA in dichloromethane (20%, 2 mL) at ~0° C. and then stirred for 1 h. The reaction mixture was concentrated under reduced pressure to dryness. The residue was purified by preparative RP-HPLC (neutral) to give compound 258 (4.5 mg, 47%) as a white solid. LC-MS: $t_R$=0.85 min in 2 min chromatography, MS (ESI) m/z 527.2 $[M+H]^+$. $^1H$ NMR: ($CDCl_3$ 400 MHz): δ 7.22 (d, J=7.6 Hz, 1H), 7.11 (d, J=8 Hz, 1H), 7.00 (s, 1H), 6.96-6.93 (dd, J=8.4 Hz, 2H), 6.68-6.64 (dd, J=8.4 Hz, 2H), 4.62-4.52 (m, 1H), 3.60-3.56 (m, 1H), 3.10 (d, J=15.6 Hz, 1H), 2.97 (s, 3H), 2.93 (d, J=16 Hz, 1H), 2.89-2.84 (m, 1H), 2.80-2.74 (m, 1H), 1.89-1.75 (m, 3H), 1.75-1.67 (m, 1H), 1.49-1.41 (m, 2H), 1.40-1.24 (m, 4H), 0.81-0.72 (m, 2H), 0.71-0.68 (m, 2H).

Example 212

Synthesis of Compound 259

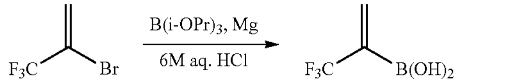

1 2

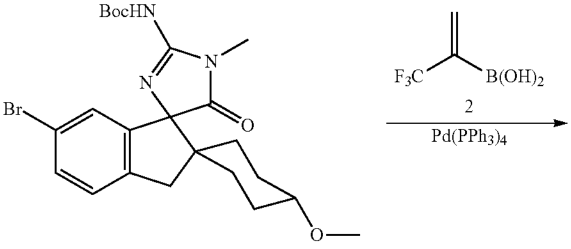

3

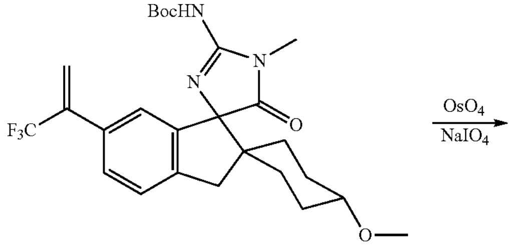

4

-continued

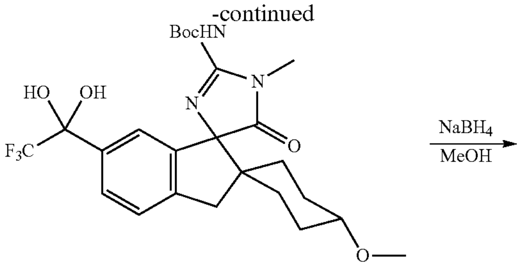

5

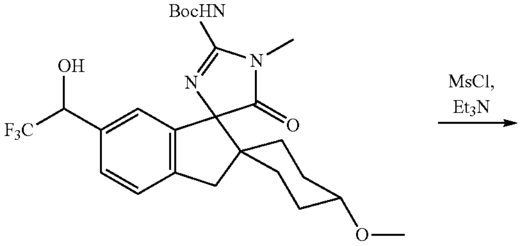

6

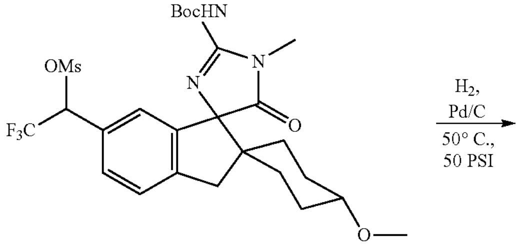

7

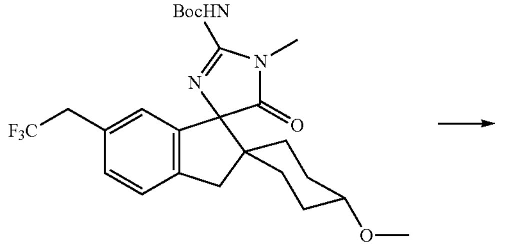

8

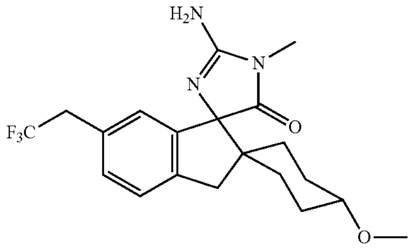

259

Procedure for Preparation of Compound 2

To a solution of magnesium turning (0.7 g, 24 mmol) and trimethoxyborane (8.1 mL, 72.5 mmol) in anhydrous THF (50 mL) was added 2-bromo-3,3,3-trifluoropropene (2.5 mL, 29 mmol) in THF (5 mL) over 20 min at 0° C. under a nitrogen atmosphere. The reaction mixture was stirred at 0° C. for 3 h. Most of magnesium turning was disappeared. The reaction was quenched by addition of aq. HCl solution (30 mL, 6 M), extracted with $Et_2O$ (3×50 mL), washed with brine (30 mL), dried over anhydrous $Na_2SO_4$. The solvent was removed under reduced pressure to give the crude product (200 mg) as a gray solid, which was used for next step directly without purification without purification. $^1H$ NMR (DMSO-$d_6$ 400 MHz): δ 8.33 (br, 2H), 6.32 (s, 2H)

Procedure for Preparation of Compound 4

To a solution of compound 3 (100 mg, 0.2 mmol) in toluene/methanol (3 mL, 5:1) was added compound 2, aq. $Na_2CO_3$ solution (0.5 mL, 1.0 M), and $Pd(PPh_3)_4$ (10 mg, 0.01 mmol) successively under a nitrogen atmosphere. The reaction mixture was heated at 70° C. for 12 h. The mixture was separated between EtOAc and water. The aqueous layer was extracted with EtOAc (3×25 mL), washed with brine (30 mL), dried over anhydrous $Na_2SO_4$, concentrated under reduced pressure to the crude product, which was purified by preparative TLC (petroleum ether:EtOAc=3:1) to give compound 4 (45 mg, 45%) as a white solid. $^1H$ NMR ($CDCl_3$ 400 MHz): δ 8.69 (s, 1H), 7.32 (m, 1H), 7.25 (m, 1H), 6.91 (s, 1H), 5.87 (s, 1H), 5.64 (s, 1H), 3.24 (m, 1H), 3.05 (m, 5H), 1.97 (m, 3H), 1.85 (m, 1H), 1.50 (m, 10H), 1.34 (m, 5H), 1.25 (m, 5H)

Procedure for Preparation of Compound 5

To a solution of compound 4 (25 mg, 0.05 mmol) in t-BuOH/$H_2O$ (2 mL, 4:1) was added $OsO_4$ (1.0 mg) and $NaIO_4$ (30 mg, 0.15 mmol). The reaction mixture was stirred at room temperature overnight, then quenched by saturate aqueous $Na_2S_2O_3$ solution, extracted with EtOAc (3×35 mL), washed with brine (20 mL), dried over $Na_2SO_4$, concentrated in vacuo to give the crude product (50 mg), which was purified by preparative TLC (petroleum ether:EtOAc=3:1) to give crude compound 5 (25 mg, 100% crude yield) as a white solid, which was used for next step without purification.

Procedure for Preparation of Compound 6

To a solution of compound 5 (30 mg, 0.057 mmol) in MeOH (0.5 mL) was added $NaBH_4$ (11 mg, 0.285 mmol), the reaction mixture was stirred at room temperature for 2 h. The reaction mixture was quenched by water, precipitate was filtered off, and redissolved in EtOAc (10 mL), extracted with EtOAc (3×20 mL), washed with brine, dried over $Na_2SO_4$, concentrated in vacuo to give the crude product (30 mg, 100% crude yield) as a light yellow oil, which was used for next step without purification.

Procedure for Preparation of Compound 7

To a solution of compound 6 (30 mg, 0.06 mmol) in $CH_2Cl_2$ (1 mL) was added $Et_3N$ (25 uL, 0.18 mmol) followed by MsCl (9 mg, 0.072 mmol). The reaction mixture was stirred at room temperature for 1 h. Water (10 mL) was added, the aqueous layer was extracted with EtOAc (3×15 mL), washed with brine (10 mL), dried over $Na_2SO_4$, concentrated in vacuo to give the crude product (30 mg, 100% crude yield) as a light yellow oil, which was used for next step without purification.

Procedure for Preparation of Compound 8

To a solution of compound 7 (10 mg, 0.017 mmol) in EtOH (3 mL) was added Pd/C (5 mg), the reaction mixture was hydrogenated at 50° C. under 50 PSI overnight. The catalyst was filtered, and the filtrate was concentrated under reduced pressure to give the crude product (10 mg), which was used for next step without purification.

Procedure for Preparation of Compound 259

To a solution of compound 8 (8 mg, 0.016 mmol) in dioxane was heated at 120° C. in a microwave reactor for 30 min. The solvent was removed under reduced pressure to give the residue, which was purified by preparative RP-HPLC to give compound 259 (0.5 mg, 8%) as a white solid. LC-MS $t_R$=1.068 min in 2 min chromatography, MS (ESI) m/z 396 $[M+H]^+$. $^1$H NMR ($CD_3OD$ 300 MHz): δ 7.44-7.25 (m, 2H), 7.02 (s, 1H), 3.50 (m, 5H), 3.11 (m, 6H), 2.04 (m, 2H), 1.83 (m, 1H), 1.58 (m, 1H), 1.43-1.27 (m, 4H); $^{19}$F NMR ($CD_3OD$ 400 MHz) δ −62.3

Example 213

Synthesis of Compound 260

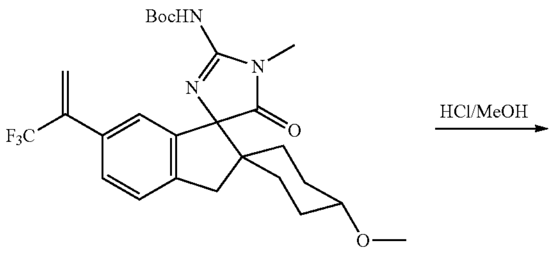

4

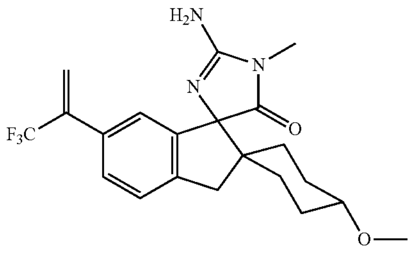

260

Compound 4 in Example 212 (14 mg, 0.076 mmol) was dissolved in 4 M HCl/MeOH solution, the reaction mixture was stirred at room temperature for 3 h. After completion, the solvent was removed under reduced pressure, and the residue was purified by acidic preparative RP-HPLC to give compound 260 (3.1 mg, 28%) as a white solid. LC-MS $t_R$=1.089 min in 2 min chromatography, MS (ESI) m/z 408 $[M+H]^+$. $^1$H NMR ($CD_3OD$ 400 MHz): δ 7.51-7.44 (m, 2H), 7.36 (s, 1H), 6.03 (s, 1H), 5.91 (s, 1H), 3.50 (m, 4H), 3.18 (m, 5H), 2.08 (m, 2H), 1.86 (m, 1H), 1.38 (m, 5H)

Example 214

Synthesis of Compound 261

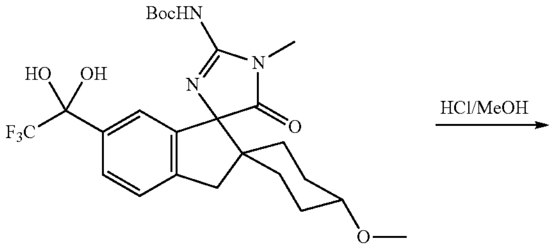

5

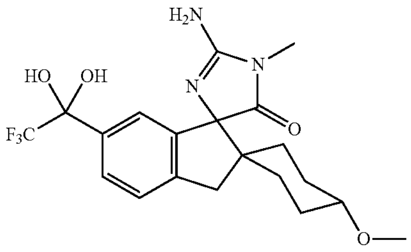

VT_B040909_02B

Compound 5 in Example 212 was dissolved in 2 M HCl/MeOH (1 mL), and the resulting mixture was stirred at room temperature overnight. The solvent was removed under reduced pressure to the residue, which was purified by preparative RP-HPLC to afford compound 261 (7.0 mg, 35%) as a white solid. LC-MS $t_R$=0.964 min in 2 min chromatography, MS (ESI) m/z 428 $[M+H]^+$. $^1$H NMR ($CD_3OD$ 300 MHz): δ 7.62 (m, 1H), 7.45 (m, 2H), 3.55 (s, 3H), 3.22 (m, 6H), 2.10 (m, 2H), 1.86 (m, 1H), 1.45-1.27 (m, 5H); $^{19}$F NMR δ −84.4

Example 215

Synthesis of Compound 262

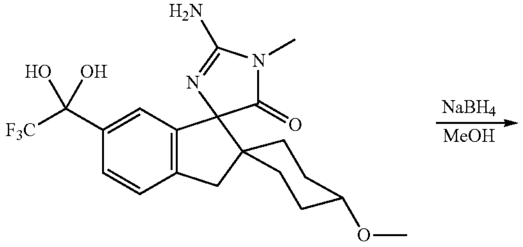

VT_B040909_02B

-continued

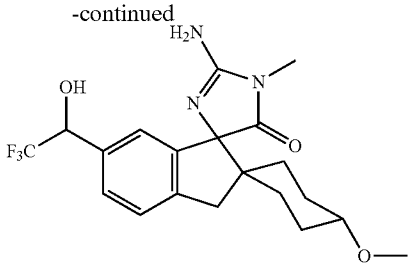

VT_B040909_02

To a solution of compound 261 (5 mg, 0.012 mmol) in MeOH (0.5 mL) was added $NaBH_4$ (2 mg, 0.06 mmol), the reaction mixture was stirred at room temperature for 2 h. The solvent was removed and the residue was purified by preparative RP-HPLC to give compound 262 (1.9 mg, 40%) as a white solid. LC-MS $t_R$=0.993 min in 2 min chromatography, MS (ESI) m/z 412 $[M+H]^+$; $^1H$ NMR ($CDCl_3$ 400 MHz): δ 7.53-7.33 (m, 3H), 5.04 (m, 1H), 3.34 (s, 3H), 3.19 (m, 6H), 2.04 (m, 2H), 1.85 (m, 1H), 1.43-1.29 (m, 5H); $^{19}F$ NMR ($CDCl_3$ 400 MHz) δ −71.3.

Example 216

Synthesis of Compound 263

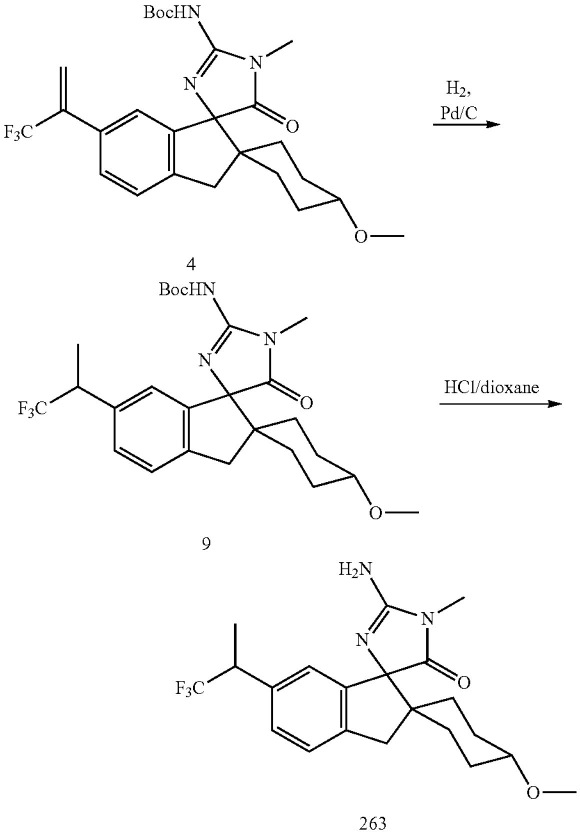

4

9

263

To a solution of compound 4 described in Example 212 (15 mg, 0.03 mmol) in MeOH (2 mL) was added Pd/C (10 mg), the reaction mixture was stirred at room temperature with $H_2$ balloon for overnight. The catalyst was filtered, and the filtrate was concentrated under reduced pressure to give the crude product (10 mg, 66%) compound 9 as a colorless oil, which was used for next step without purification.

To a solution of compound 9 (10 mg, 0.02 mmol) was added 4 M HCl/dioxane solution (1 mL), the reaction mixture was stirred at room temperature overnight, the solvent was removed under reduced pressure to give the residue, which was purified by preparative RP-HPLC to give compound 263 (1.5 mg, 18%) as a white solid. LC-MS $t_R$=1.108 min in 2 min chromatography, MS (ESI) m/z 410 $[M+H]^+$. $^1H$ NMR ($CD_3OD$ 400 MHz): δ 7.30 (m, 2H), 6.99 (s, 1H), 3.56 (m, 1H), 3.31 (s, 3H), 3.17-3.04 (m, 6H), 2.00 (m, 2H), 1.84 (m, 1H), 1.63 (m, 1H), 1.46 (m, 3H), 1.40-1.29 (m, 4H); $^{19}F$ NMR ($CD_3OD$ 400 MHz): δ −62.3.

Example 217

Synthesis of Compound 264

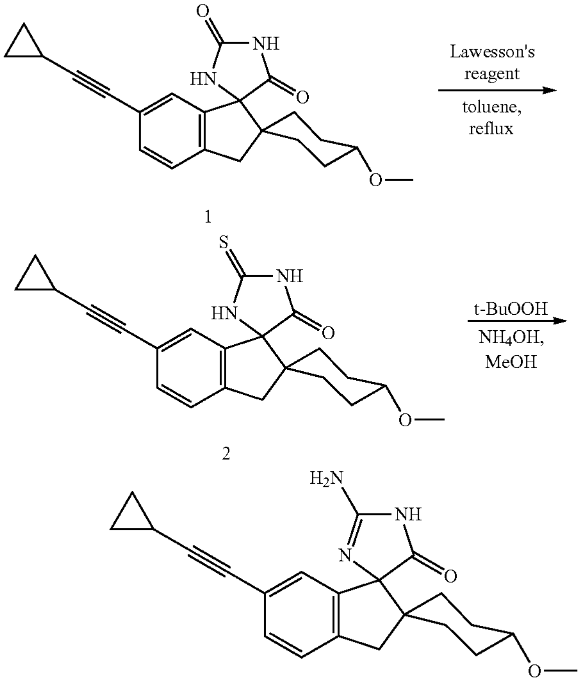

1

2

264

Procedure for Preparation of Compound 2

A suspension of compound 1 (70 mg, 0.192 mmol) and Lawesson's Reagent (85 mg, 0.212 mmol) in anhydrous toluene (10 mL) was heated to reflux overnight. LCMS showed that the reaction was completed. The mixture was concentrated under reduced pressure, and the residue was purified by preparative TLC (petroleum ether:ethyl acetate=1:1) to give compound 2 as a white solid (30 mg, 41%).

Procedure for Preparation of Compound 264

A mixture of compound 2 (15 mg, 0.04 mmol) and t-butyl hydroperoxide (0.11 g of a 65% solution in water, 0.8 mmol) in methanol (5 mL) was added aqueous ammonium hydroxide (1 mL), the mixture was stirred at room temperature overnight. The mixture was concentrated under reduced pressure to dryness. The residue was purified by preparative TLC ($CH_2Cl_2$: MeOH=5:1) and preparative RP-HPLC to give compound 264 (5.8 mg, 40%) as a white solid. LC-MS $t_R$=1.068 min in 2 min chromatography, MS (ESI) m/z 364.2 $[M+H]^+$. $^1H$ NMR ($CD_3OD$ 400 MHz): δ 7.23 (s, 2H), 6.95 (s, 1H), 3.36 (s, 3H), 3.11-3.15 (d, J=15.6 Hz, 2H), 3.01-3.05 (d, J=15.2 Hz, 1H), 1.96-2.07 (m, 3H), 1.24-1.48 (m, 6H), 0.85-0.89 (m, 2H), 0.69-0.73 (m, 2H).

Example 218

Synthesis of Compound 265

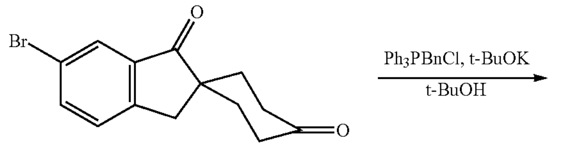

1

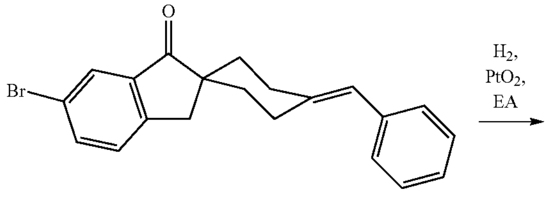

2

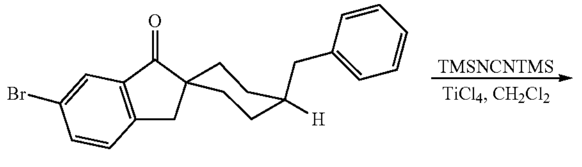

3

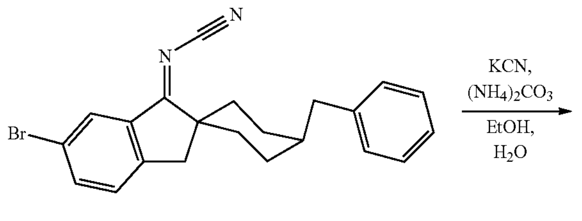

4

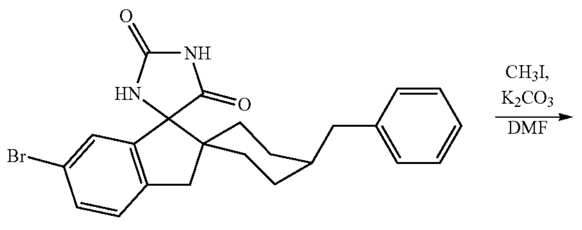

5

-continued

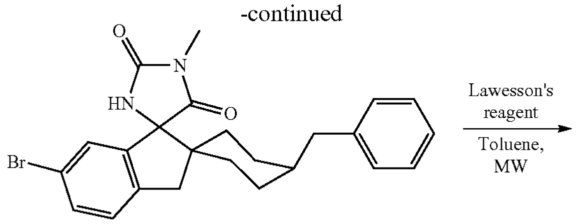

6

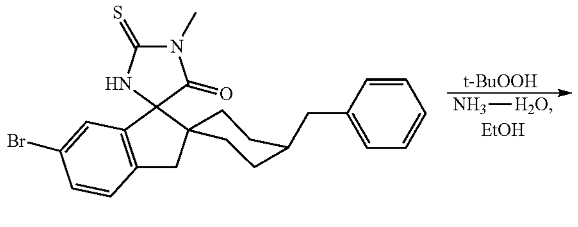

7

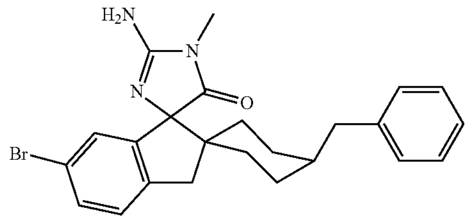

265

Procedure for Preparation of Compound 2

To a solution of potassium tert-butoxide (1.8 g, 15.5 mmol) in tert-butyl alcohol (60 mL) was added benzyl triphenyl phosphonium chloride (4.8 g, 12.2 mmol). The mixture was stirred at ambient temperature for 1 h. Compound 1 (3.0 g, 10.2 mmol) was added under nitrogen. The reaction mixture was stirred at ambient temperature for 5 h. The solvent was removed by evaporation in vacuo. The residue was added $H_2O$ (100 mL) and then was extracted with ethyl acetate (50 mL×3), the combined organic layers were washed with saturated brine (50 mL×2). The separated organic phase was dried over $Na_2SO_4$ and concentrated in vacuo to yield crude product, which was purified by column chromatography on silica gel eluting with petroleum ether:ethyl acetate=100:1 to 10:1 to give compound 2 (2.8 g, 75%) as a white solid.

Procedure for Preparation of Compound 3

A mixture of compound 2 (2.8 g, 7.6 mmol), ethyl acetate (150 mL) and $PtO_2$ (0.20 g, 0.88 mmol) was stirred at ambient temperature under 1 atm hydrogen atmosphere overnight. The precipitate was filtered off and washed with ethyl acetate (50 mL×2). The filtrate and the washings were concentrated by evaporation in vacuo. The residue was purified by column chromatography on silica gel eluting with petroleum ether: ethyl acetate=100:1 to 10:1 and then by preparative TLC on silica gel eluting with petroleum ether:ethyl acetate=10:1 to give compound 3 (0.70 g, 24%) as a white solid. LC-MS: $t_R$=2.41 min in 3 min chromatography, MS (ESI) m/z=369.0 $[M+H]^+$. $^1H$ NMR: ($CD_3OD$ 400 MHz): δ 7.60-7.70 (m, 2H), 7.30-7.35 (d, 1H, J=8.0 Hz), 7.10-7.20 (m, 2H), 7.00-7.10 (m, 3H), 2.80-2.90 (s, 2H), 2.50-2.60 (d, 2H, J=7.2 Hz), 1.75-1.85 (m, 2H), 1.65-1.75 (m, 1H), 1.55-1.65 (m, 2H), 1.35-1.45 (m, 2H).

Procedure for Preparation of Compound 4

A flask was charged with compound 3 (0.30 g, 0.81 mmol), anhydrous dichloromethane (6 mL) and $TiCl_4$ (3.2 mL, 3.2 mmol, 1 M in $CH_2Cl_2$). The tube was stirred at ambient temperature for 1 h. N,N'-methanediylidene bis-(1,1,1-trimethylsilianamine) (0.45 g, 2.4 mmol) was added. The reaction mixture was stirred at ambient temperature overnight. The mixture was quenched with ice-water (10 mL) carefully with stirring. Brine (10 mL) was added, and the mixture was extracted with dichloromethane (10 mL×3). The combined organic layers were washed with saturated brine (10 mL×2). The separated organic phase was dried over $Na_2SO_4$, filtered and concentrated in vacuo to give crude compound 4 (0.31 g, 97% crude yield) as a pale yellow solid, which was used in the next step without further purification.

Procedure for Preparation of Compound 5

A steel clave was charged with a mixture of compound 4 (0.31 g, 0.79 mmol), KCN (0.20 g, 3.16 mmol), $(NH_4)_2CO_3$ (0.80 g, 8.32 mmol), Ethanol (3 mL) and $H_2O$ (3 mL) carefully. The mixture was heated at 80° C. overnight. The reaction mixture was cooled, and poured into ice-water (40 mL). The mixture was extracted with ethyl acetate (contained 10% iso-propanol) (50 mL×3), and the combined organic layers were washed with brine (50 mL×3). The separated organic phase was dried over $Na_2SO_4$ and concentrated in vacuo to give the crude compound 5 (0.36 g, 102% crude yield) as a white solid, which was used in next step without further purification. LC-MS: $t_R$=1.85 min in 3 min chromatography, MS (ESI) m/z=439.0 $[M+H]^+$.

Procedure for Preparation of Compound 6

A flask was charged with a mixture of compound 5 (0.25 g, 0.57 mmol, crude), $K_2CO_3$ (0.30 g, 0.22 mmol) and DMF (5 mL). The mixture was stirred at ambient temperature for 1 h, and then iodomethane (90 mg, 0.63 mmol) in DMF (0.5 mL) was added dropwise via a syringe with stirring. The mixture was stirred at ambient temperature overnight. The reaction mixture was poured into brine (100 mL). The mixture was extracted with ethyl acetate (contained with 10% methanol) (20 mL×3). The combined organic layers were washed with brine (20 mL×2). The separated organic phase was dried over $Na_2SO_4$ and concentrated in vacuo to give crude product, which was purified by preparative TLC on silica gel eluting with petroleum ether:ethyl acetate=1:1 to give compound 6 (0.14 g, 54%) as a white solid. LC-MS: $t_R$=2.29 min in 3 min chromatography, MS (ESI) m/z=453.3 $[M+H]^+$.

Procedure for Preparation of Compound 7

A sealed tube was charged with a mixture of compound 6 (0.13 g, 0.29 mmol), Lawesson's reagent (0.14 g, 0.35 mmol) in anhydrous toluene (3 mL) under nitrogen. The mixture was heated at 130° C. in a CEM microwave reactor for 1 h. After cooling down, the solvent was removed by evaporation in vacuo and the residue was purified by column chromatography on silica gel eluting with petroleum ether:ethyl acetate=2:1 to give compound 7 (60 mg, 44%) as a white solid.

Procedure for Preparation of Compound 265

To a solution of compound 7 (60 mg, 0.13 mmol) in EtOH (4 mL) was added $NH_3$—$H_2O$ (1 mL) and tert-butyl hydroperoxide (0.20 g, 2.2 mol). After addition, the mixture was stirred at ambient temperature for 24 h. The mixture was concentrated in vacuo and the residue was purified by preparative HPLC to give compound 265 (30 mg, 51%) as a white solid. LC-MS:

$t_R$=1.88 min in 3 min chromatography, MS (ESI) m/z=452.2 $[M+H]^+$. $^1H$ NMR: ($CD_3OD$, 300 MHz): δ 7.35-7.45 (m, 1H), 7.20-7.30 (m, 3H), 7.10-7.20 (m, 4H), 3.05-3.15 (d, J=16.8 Hz, 1H), 3.00-3.10 (s, 3H), 2.85-2.95 (d, J=20.4 Hz, 1H), 2.55-2.65 (m, 2H), 1.80-2.00 (m, 2H), 1.45-1.80 (m, 5H), 1.25-1.35 (m, 1H), 1.05-1.15 (m, 1H).

Example 219

Synthesis of Compound 266

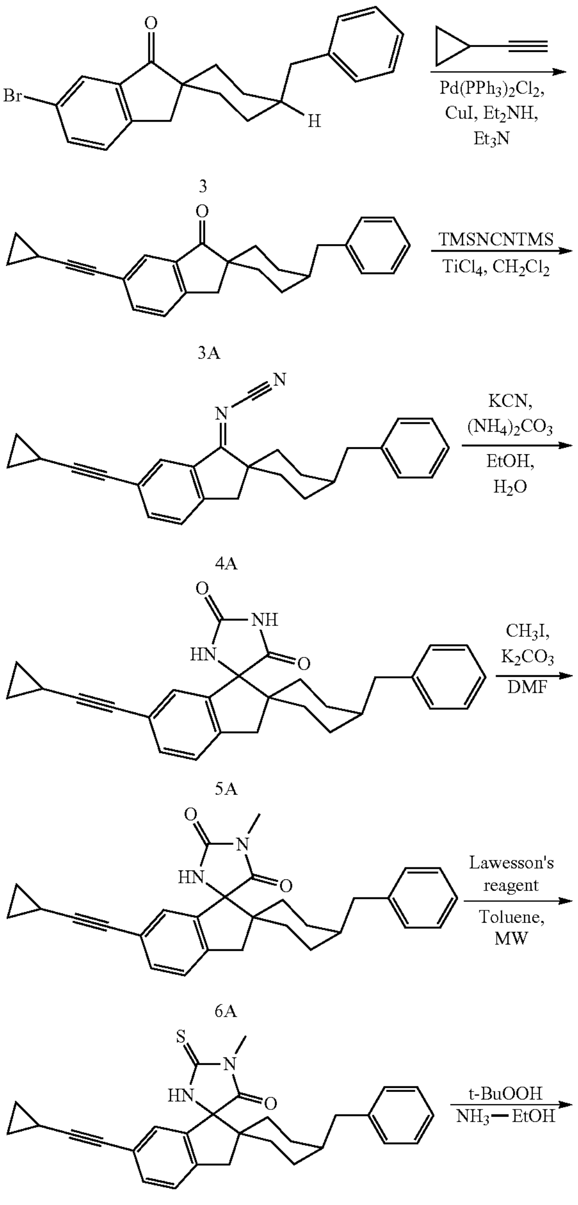

3

3A

4A

5A

6A

7A

-continued

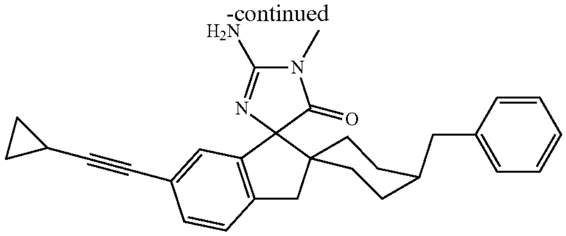

266

4. Procedure for Preparation of Compound 3A

A flask was charged with compound 3 described in Example 218 (0.30 g, 0.81 mmol), $Et_3N$ (10 mL), $Et_2N$ (2 mL), $Pd(PPh_3)_2Cl_2$ (0.034 g, 0.48 mmol), CuI (0.009 g, 0.047 mmol) and ethynyl cyclopropane (3 mL) under nitrogen at ambient temperature in turn. The reaction mixture was stirred at 60° C. for 48 h. After cooling down, the solvent was removed by evaporation in vacuo. The residue was dissolved in ethyl acetate (100 mL), and the resulting organic mixture was washed with 1 N HCl aqueous solution (30 mL), $H_2O$ (30 mL) and brine (30 mL×2) successively. The separated organic layer was dried over $Na_2SO_4$, filtered off the solid and concentrated in vacuo to give the crude product as red oil, which was purified by column chromatography on silica gel eluting with petroleum ether:ethyl acetate=100:1 to 5:1 to give compound 3A (0.28 g, 97%) as a yellow oil. LC-MS: $t_R$=2.51 min in 3 min chromatography, MS (ESI) m/z=355.1 $[M+H]^+$.

Procedure for Preparation of Compound 4A

A flask was charged with compound 3A (0.15 g, 0.42 mmol), dried dichloromethane (3 mL) and $TiCl_4$ (1.7 mL, 1.7 mmol, 1 M in $CH_2Cl_2$). The tube was stirred at ambient temperature for 1 h. After cooling down, N,N'-methanediylidene bis-(1,1,1-trimethylsilianamine) (0.24 g, 1.3 mmol) was added. The reaction mixture was stirred at ambient temperature overnight. The mixture was quenched with ice-water (10 mL) carefully with stirring. Saturated brine (10 mL) was added, and the mixture was extracted with dichloromethane (10 mL×3). The combined organic layers were washed with saturated brine (10 mL×2). The separated organic phase was dried over $Na_2SO_4$, filtered and concentrated in vacuo to give crude compound 4A (0.16 g, 100% crude yield) as a pale yellow solid, which was used directly in next step.

Procedure for Preparation of Compound 5A

A steel clave was charged with a mixture of compound 4A (0.31 g, 0.79 mmol), KCN (0.20 g, 3.16 mmol), $(NH_4)_2CO_3$ (0.80 g, 8.32 mmol), ethanol (3 mL) and $H_2O$ (3 mL) carefully. The mixture was heated at 80° C. overnight, and the reaction mixture was cooled, and poured into ice-water (40 mL). The mixture was extracted with ethyl acetate (contained 10% iso-propanol) (50 mL×3), and the combined organic layers were washed with saturated brine (50 mL×3). The separated organic phase was dried over $Na_2SO_4$ and concentrated in vacuo to give the crude product, which was purified by column chromatography on silica gel eluting with petroleum ether:ethyl acetate=50:1 to 2:1 to give compound 5A (0.40 g, 22%) as a pale yellow solid. LC-MS: $t_R$=2.50 min in 3 min chromatography, MS (ESI) m/z=425.2 $[M+H]^+$.

Procedure for Preparation of Compound 6A

A flask was charged with a mixture of compound 5A (40 mg, 0.094 mmol), $K_2CO_3$ (50 mg, 0.36 mmol) and DMF (3 mL). The mixture was stirred at ambient temperature for 1 h, and then a solution of iodomethane (14 mg, 0.099 mmol) in DMF (0.5 mL) was added dropwise via a syringe with stirring. The mixture was stirred at ambient temperature overnight. The reaction mixture was poured into saturated brine (50 mL). The mixture was extracted with ethyl acetate (20 mL×2). The combined organic layers were washed with saturated brine (20 mL×2). The separated organic phase was dried over $Na_2SO_4$ and concentrated in vacuo to give crude compound 6A (40 mg, 97% crude yield) as a white solid, which was used directly in next step. LC-MS: $t_R$=2.50 min in 3 min chromatography, MS (ESI) m/z=425.2 $[M+H]^+$.

Procedure for Preparation of Compound 7A

A sealed tube was charged with a mixture of compound 6A (40 mg, 0.091 mmol), Lawesson's reagent (40 mg, 0.099 mmol) in anhydrous toluene (1 mL) under nitrogen. The mixture was heated at 130° C. in a CEM microwave reactor for 40 min. After cooling down, the solvent was removed by evaporation in vacuo and the residue was purified by column chromatography on silica gel eluting with petroleum ether: ethyl acetate=2:1 to give compound 7A (10 mg, 24%) as a white solid. LC-MS: $t_R$=2.65 min in 3 min chromatography, MS (ESI) m/z=455.2 $[M+H]^+$.

Procedure for Preparation of Compound 266

To a solution of compound 7A (10 mg, 0.022 mmol) in EtOH (1 mL) was added $NH_3$—$H_2O$ (0.5 mL) and tert-butyl hydroperoxide (50 mg, 0.56 mol). After addition, the mixture was stirred at ambient temperature for 24 h. The mixture was concentrated in vacuo and the residue was purified by preparative HPLC to give compound 266 (9.1 mg, 94%) as a white solid. LC-MS: $t_R$=1.97 min in 3 min chromatography, MS (ESI) m/z=438.2 $[M+H]^+$. $^1H$ NMR: ($CD_3OD$, 400 MHz): δ 7.15-7.25 (m, 1H), 7.10-7.15 (m, 3H), 7.00-7.10 (m, 4H), 3.05-3.15 (s, 3H), 2.97-3.05 (d, J=16.0 Hz, 1H), 2.90-2.97 (d, J=15.6 Hz, 1H), 2.50-2.60 (d, J=7.6 Hz, 2H), 1.75-1.85 (m, 1H), 1.40-1.75 (m, 4H), 1.30-1.40 (m, 2H), 1.20-1.30 (m, 2H), 1.05-1.15 (m, 1H), 0.70-0.80 (m, 2H), 0.50-0.60 (m, 2H).

Example 220

Synthesis of Compound 267

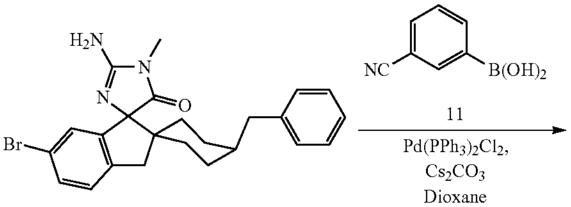

265

-continued

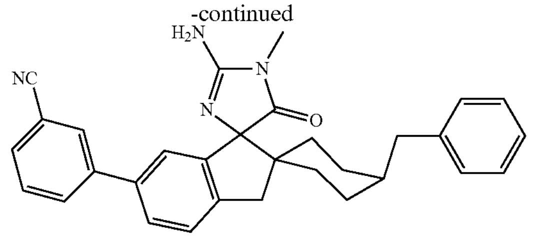

267

A mixture of compound 265 (10 mg, 0.022 mmol), 3-cyanophenylboronic acid (5 mg, 0.034 mmol), $Cs_2CO_3$ (0.2 mL, 0.40 mmol, 2M in water) and $Pd(PPh_3)_2Cl_2$ (1 mg, 0.0014 mmol) in 1,4-dioxane (0.5 mL) under nitrogen was stirred at 120° C. in a CEM microwave reactor for 20 min. After cooling down, saturated brine (10 mL) was added and the mixture was extracted with ethyl acetate (10 mL×3). The combined organic layers were washed with saturated brine (10 mL×2), dried over $Na_2SO_4$, filtered and concentrated in vacuo, the resulting crude product was purified by preparative HPLC to give compound 267 (7.7 mg, 74%) with 98% purity based on LC-MS as a pale yellow solid. LC-MS: $t_R$=1.93 min in 3 min chromatography, MS (ESI) m/z=475.2 $[M+H]^+$. $^1H$ NMR: ($CD_3OD$ 400 MHz): δ 7.95-8.00 (s, 1H), 7.85-7.95 (m, 1H), 7.60-7.70 (m, 2H), 7.55-7.60 (m, 1H), 7.45-7.55 (s, 1H), 7.40-7.45 (m, 1H), 7.20-7.30 (m, 2H), 7.05-7.15 (m, 3H), 3.17-3.25 (s, 3H), 3.05-3.17 (m, 2H), 2.55-2.65 (m, 2H), 1.85-1.95 (m, 1H), 1.55-1.85 (m, 5H), 1.20-1.45 (m, 3H).

Example 221

Synthesis of Compounds 268 and 269

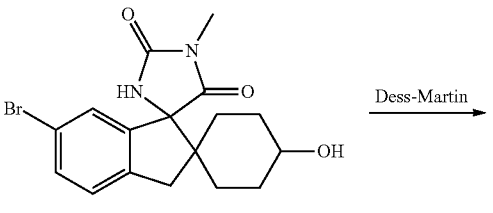

1

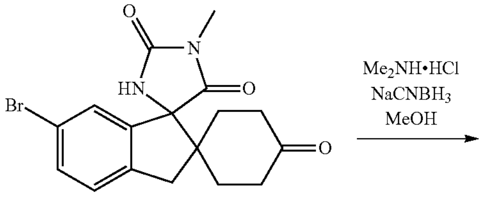

2

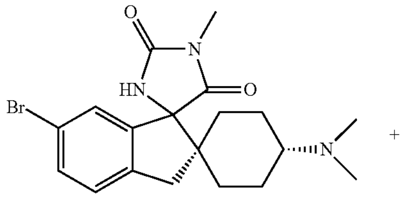

+

3A

-continued

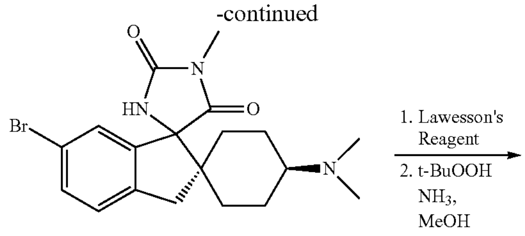

3B

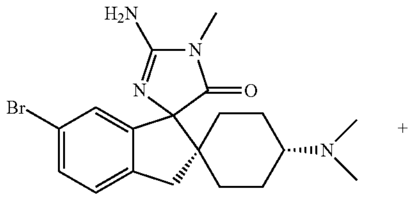

+

268

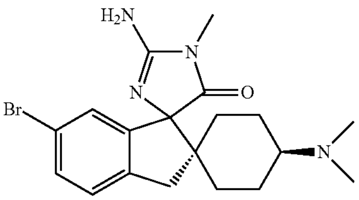

269

Procedure for Preparation of Compound 2

To a solution of compound 1 (0.2 g, 0.53 mmol) in 1,2-dichloroethane (1.5 mL) in a 10 mL CEM microwave tube, there was added Dess-Martin periodinane (247 mg, 0.58 mmol). The resulting mixture was heated with a CEM microwave reactor at 70° C. for 5 min, washed with 1N NaOH aqueous solution, brine, and dried over $Na_2SO_4$. The solvent was removed to give compound 2 (156.0 mg, 77%), which was used for the next step without purification.

Procedure for Preparation of Compound 3A and 3B

To a solution of compound 2 (156.0 mg, 0.41 mmol) in MeOH (3 mL), there was added dimethylamine hydrochloride (6.1 mg, 0.82 mmol), KOH (23 mg, 0.41 mmol) followed by $NaCNBH_3$ (52 mg, 0.82 mmol). The resulting solution was stirred at room temperature overweekend, and purified by HPLC to give compound 3A (82.8 mg, 39%), LC-MS $t_R$=3.65 min in 16 min chromatography, MS (ESI) m/z 406 $[M+H]^+$. And compound 3B (60.5 mg, 32%), LC-MS $t_R$=3.47 min in 16 min chromatography, MS (ESI) m/z 406 $[M+H]^+$.

Procedure for Preparation of Compounds 268 and 269

According to the similar synthesis of compound 291, compound 3A (50 mg, 0.12 mmol) afforded compound 268 (3.2 mg, 5%) as a TFA salt. LC-MS $t_R$=0.93 min in 3 min chromatography, MS (ESI) m/z 405 $[M+H]^+$. $^1H$ NMR ($CD_3OD$, 400 MHz): δ 7.54 (d, J=7.6 Hz, 1H), 7.48 (s, 1H), 7.28 (d, J=7.6 Hz, 1H), 3.22 (m, 1H), 3.20 (s, 3H), 3.18 (m, 2H), 2.84 (s, 6H), 2.10-1.94 (m, 3H), 1.84-1.46 (m, 5H). And compound 3B (30 mg, 0.07 mmol) afforded compound 269 (1.90 mg, 5%) as a TFA salt. LC-MS $t_R$=1.09 min in 3 min chromatography, MS (ESI) m/z 405 $[M+H]^+$. $^1H$ NMR ($CD_3OD$, 400 MHz): δ 7.54 (d, J=7.6 Hz, 1H), 7.46 (s, 1H), 7.28 (d, J=7.6 Hz, 1H), 3.22 (m, 1H), 3.20 (s, 3H), 3.12 (m, 2H), 2.86 (s, 3H), 2.68 (s, 3H), 2.10-1.80 (m, 4H), 1.76 (m, 2H).

Example 222

Synthesis of Compound 270

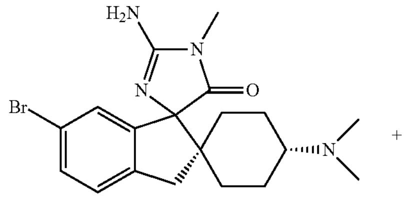

1

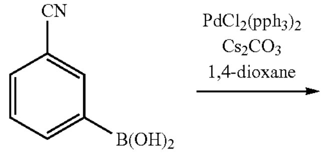

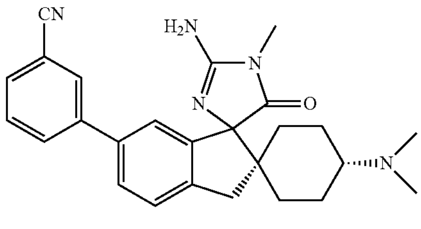

VTP-000034615

According to a similar synthesis of compound 251, compound 1 (10.0 mg, 0.02 mmol) was reacted with 3-cyanophenylboronic acid to gave final product compound 270 (0.91 mg, 8%) as a TFA salt. LC-MS $t_R$=1.08 min in 3 min chromatography, MS (ESI) m/z 428[M+H]$^+$. $^1$H NMR ($CD_3OD$, 400 MHz): δ 8.00 (s, 1H), 7.94 (m, 1H), 7.68 (m, 2H), 7.62 (m, 2H), 7.52 (m, 1H), 3.24 (m, 3H), 3.22 (s, 3H), 2.86 (s, 6H), 2.16-2.00 (m, 3H), 1.88-1.52 (m, 5H).

Example 223

Synthesis of Compound 271

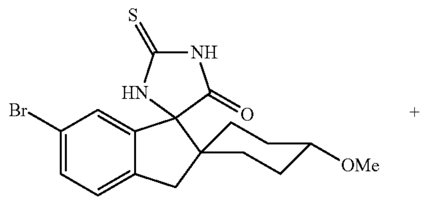

1

-continued

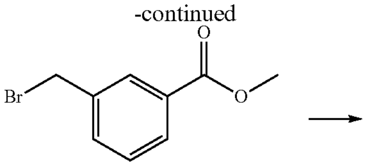

2

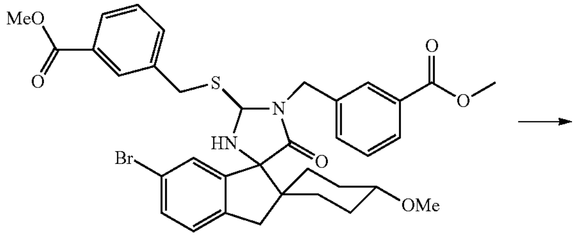

3

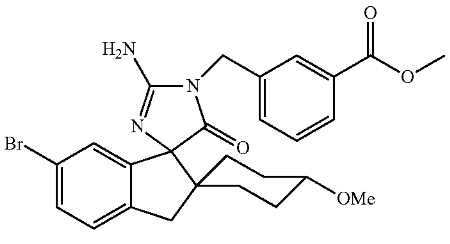

4

Step 1

A flask containing 1 (67 mg, 0.17 mmol), cesium carbonate (130 mg, 0.4 mmol), and methyl 3-(bromomethyl)benzoate (86 mg, 0.37 mmol) in DMF (2 mL) was stirred overnight at room temperature. The reaction was diluted with water and the aqueous layer was extracted with EtOAc 3×. The combined organic layers were washed with brine, dried over $Na_2SO_4$, filtered, and the solvent evaporated to afford a crude mixture of 3. The product was used as is in the next step. LC/MS ret=2.3 min ES+=691 (M+1).

Step 2

A mixture of 3 (~0.17 mmol), ammonia (7M in MeOH, 1 mL), ammonium iodide (123 mg, 0.85 mmol) in MeOH (6 mL) was heated using microwave at 100° C. for 40 min. The solvent was evaporated and the crude mixture purified via Gilson to afford compound 271 (7 mg). LC/MS $t_R$=1.64 min, ES+=526 (M+1). $^1$HNMR (MeOD) δ 8.01 (ap d, 1H, J=7.6 Hz), 7.93 (s, 1H), 7.61 (d, 1H, J=7.9 Hz), 7.54 (t, 2H, J=8.2 Hz), 7.43 (d, 1H, J=1.8 Hz), 7.31 (d, 1H, J=7.9 Hz), 5.04 (d, 1H, J=16.7 Hz), 4.92 (d, 1H, J=16.4 Hz), 3.92 (s, 3H), 3.34 (s, 3H), 3.17 (m, 1H), 3.16 (d, 1H, J=16 Hz), 3.07 (d, 1H, J=16 Hz), 1.99 (m, 2H), 1.79 (ap d, 1H, J=13.5 Hz), 1.48-1.22 (m, 5H).

Example 224

Synthesis of Compound 272

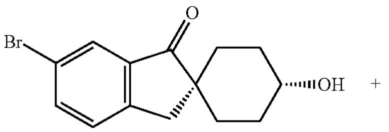

1

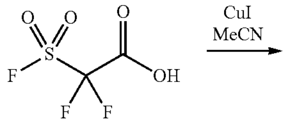

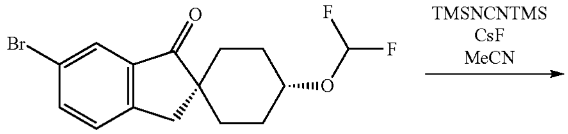

2

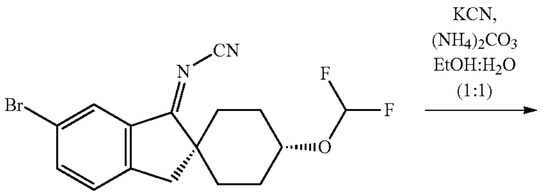

3

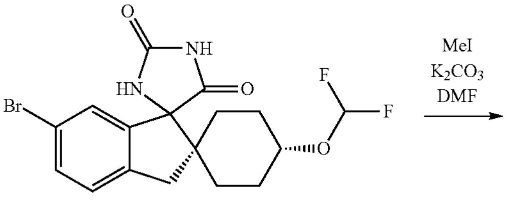

4

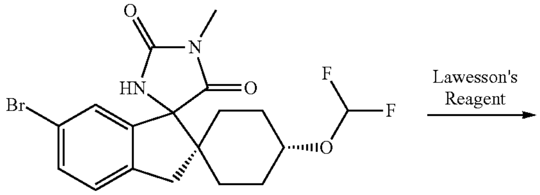

5

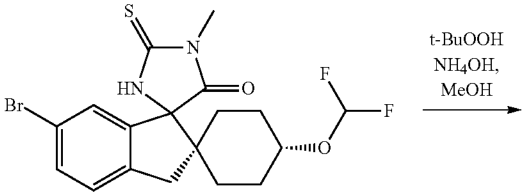

6

-continued

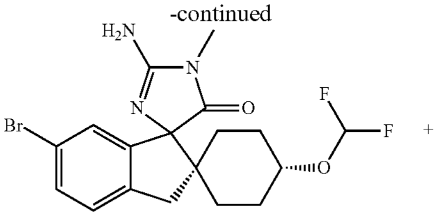

272

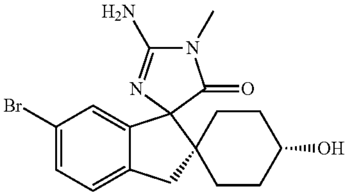

273

Procedure for Preparation of Compound 2

A solution of (1r,4r)-6'-bromo-4-hydroxyspiro[cyclohexane-1,2'-inden]-1'(3'H)-one (1) (0.87 g, 2.95 mmol) and CuI (57.1 mg, 0.30 mmol) in anhydrous MeCN (9 mL) was heated at 60° C. under $N_2$ for 10 minutes to give a clear solution. 2,2-difluoro-2-(fluorosulfonyl)acetic acid (0.55 g, 0.32 mL, 3.10 mmol) was added to the solution dropwise, and the resulting solution was stirred at the same temperature for 5 min, cooled down to room temperature, quenched with water (15 mL), extracted with DCM (10 mL×4). Combined organic layers were washed with brine, dried over $Na_2SO_4$, concentrated in vacuum. The residue was purified by flash chromatography (0 to 40% EtOAc/Hexane) to afford (1r,4r)-6'-bromo-4-(difluoromethoxy)spiro[cyclohexane-1,2'-inden]-1'(3'H)-one (2) (0.55 g, 54%). LC-MS $t_R$=2.06 min in 3 min chromatography, MS (ESI) m/z 345 $[M+H]^+$.

Procedure for Preparation of Compound 3

To a solution of (1r,4r)-6'-bromo-4-(difluoromethoxy)spiro[cyclohexane-1,2'-inden]-1'(3'H)-one (2) (364 mg, 1.05 mmol) and CsF (0.64 g, 4.2 mmol) in anhydrous MeCN (10 mL) there was added N,N'-methanediylidenebis(1,1,1-trimethylsilanamine) (0.95 mL, 4.2 mmol). The resulting solution was stirred at room temperature overnight. The reaction was added water (10 mL), extracted with DCM (10 mL×4), combined organic layers were washed with brine (10 mL), dried over $Na_2SO_4$, and the solvent was removed in vacuum to give (E)-N-((1r,4r)-5'-bromo-4-(difluoromethoxy)spiro[cyclohexane-1,2'-indene]-3'(1'H)-ylidene)cyanamide (3) (0.39 g, 100%), which was used for next step without purification. LC-MS $t_R$=2.04 min in 3 min chromatography, MS (ESI) m/z 369 $[M+H]^+$.

Procedure for Preparation of Compound 4

To a 50 mL sealed tube there was charged (E)-N-((1r,4r)-5'-bromo-4-(difluoromethoxy)spiro[cyclohexane-1,2'-indene]-3'(1'H)-ylidene)cyanamide (3) (0.39 g, 1.05 mmol), KCN (141 mg, 2.1 mmol), $(NH_4)_2CO_3$ (0.71 g, 7.3 mmol), and EtOH (3 mL) and water (3 mL). The tube was sealed, and heated at 75° C. overnight. The solution was cooled to room temperature, diluted with water (10 mL), extracted with EtOAc (5 mL×4). Combined organic layers were washed with brine (10 mL), dried over $Na_2SO_4$, and the solvent was removed in vacuum to give hydantoin 4 (423.3 mg), which was used for the next step without purification. LC-MS $t_R$=1.62 min in 3 min chromatography, MS (ESI) m/z 415 $[M+H]^+$.

Procedure for Preparation of Compound 5

To a solution of above crude hydantoin 4 (158.9 mg, 0.38 mmol) in DMF (1 mL) there was added $K_2CO_3$ (0.42 g, 3.04 mmol) followed by MeI (59.7 mg, 0.42 mmol), the resulting mixture was stirred at room temperature for 45 min, reaction completion was confirmed by LC-MS. The mixture was then diluted with water (5 mL), extracted with DCM (5 mL×4).

Combined organics were washed with brine (5 mL), dried over $Na_2SO_4$, and the solvent was removed in vacuum to give compound 5 (170.1 mg), which was used for the next step without purification. LC-MS $t_R$=1.76 min in 3 min chromatography, MS (ESI) m/z 429 $[M+H]^+$.

Procedure for Preparation of Compound 6

The above crude 5 (0.38 mmol) was dissolved in 1,4-dioxane (3 mL) and transferred to a 10 mL CEM tube. Lawesson's reagent (154 mg, 0.38 mmol) was added to the tube, and the resulting mixture was heated in a CEM microwave reactor at 120° C. for 130 min. Solvent was removed and the residue was purified with flash chromatography (0 to 60% EtOAc/Hexane) to give thio-hydantoin 6 (113.7 mg, 67%). LC-MS $t_R$=1.94 min in 3 min chromatography, MS (ESI) m/z 445 $[M+H]^+$.

Procedure for Preparation of Compounds 272 and 273

To a solution of thio-hydantoin 6 (113.7 mg, 0.26 mmol) in MeOH (10 mL) there was added ammonium hydroxide (7 mL) followed by t-butyl hydroperoxide (~5.5 m in nonane, 0.8 mL). the resulting mixture was stirred at room temperature over weekend. Upon removal of solvent, the residue was purified by HPLC to give compound 273 (1.10 mg, 1%). LC-MS $t_R$=1.52 min in 3 min chromatography, MS (ESI) m/z 428 $[M+H]^+$. $^1$H NMR ($CD_3OD$, 400 MHz): δ 7.54 (dd, J=1.2, 7.8 Hz, 1H), 7.44 (d, J=1.2 Hz, 1H), 7.32 (d, J=7.8 Hz, 1H), 6.38 (t, J=76 Hz, 1H), 4.04 (m, 1H), 3.20 (s, 3H), 3.18 (m, 1H), 3.08 (m, 1H), 1.98 (m, 2H), 1.84 (m, 1H), 1.74-1.40 (m, 5H). $^{19}$F NMR ($CD_3OD$, 376 MHz): δ −77.4, −82.3 (d, J=76 Hz). and compound 272 (1.54 mg, 1.6%), LC-MS $t_R$=1.05 min in 3 min chromatography, MS (ESI) m/z 378 $[M+H]^+$. $^1$H NMR ($CD_3OD$, 400 MHz): δ 7.54 (dd, J=1.2, 7.8 Hz, 1H), 7.44 (d, J=1.2 Hz, 1H), 7.28 (d, J=7.8 Hz, 1H), 6.38 (t, J=76 Hz, 1H), 3.46 (m, 1H), 3.18 (s, 3H), 3.20-3.04 (m, 2H), 1.94-78 (m, 3H), 1.54-1.26 (m, 5H).

Example 225

Synthesis of Compound 274

Method 1

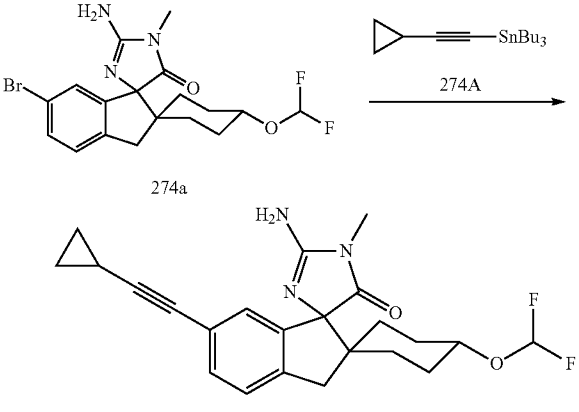

274a

274

A mixture containing compound 274a (0.2 g, 0.468 mmol), compound 274A (0.5 g, 1.41 mmol) in dry toluene (15 mL) was deoxygenated by bubbling a stream of nitrogen through the reaction mixture for 5 min. Then $PdCl_2$(dppf) (20 mg, 0.023 mmol) was added. The reaction vial was sealed and placed into CEM microwave reactor and irradiated at 130° C. for 45 min. After being cooled to room temperature, the mixture was diluted with EtOAc (10 mL), and filtered through a short Celite pad. The solution was concentrated in vacuo and the residue was purified by acidic preparative HPLC to give compound 274 (30 mg, 15%) as a white solid. LC-MS $t_R$=3.282 min in 7 min chromatography, MS (ESI) m/z 414.2 $[M+H]^+$. $^1$H NMR ($CD_3OD$ 400 MHz): δ 7.34 (m, 2H), 7.23 (s, 1H), 6.22-6.60 (m, 1H), 4.06 (m, 1H), 3.11-3.21 (m, 5H), 2.01 (m, 2H), 1.87 (d, J=12.4 Hz, 1H), 1.68-1.77 (m, 1H), 1.40-1.60 (m, 5H), 0.8 (m, 2H), 0.71 (m, 2H). $^{19}$F NMR ($CD_3OD$ 376 MHz): δ −81.91

Method 2

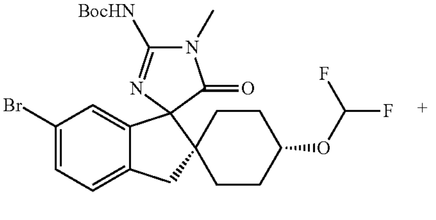

274b

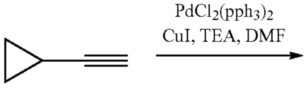

-continued

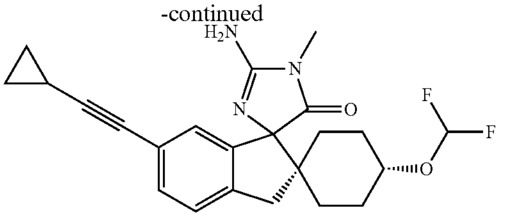

274

A 10 mL CEM microwave tube was charged with compound 274b (48.2 mg, 0.11 mmol), PdCl2(pph3)2 (cat. amount), CuI (cat. amount), triethylamine (0.3 mL) and DMF (0.3 mL). The mixture was degassed then protected with $N_2$. In a separated tube, ethynylcyclopropane in Toluene was degassed at −78° C., then warmed to room temperature. After degassing, excess ethynylcyclopropane in Toluene was added to the microwave tube with other reagents, and the resulting mixture was heated in a CEM microwave reactor at 120° C. for 60 min. The mixture was filtered, and purified by HPLC to give compound 274 (5 mg, 11%) as a TFA salt. LC-MS $t_R$=1.64 min in 3 min chromatography, MS (ESI) m/z 414 $[M+H]^+$. $^1$H NMR ($CD_3OD$, 400 MHz): δ 7.34 (m, 2H), 7.20 (s, 1H), 6.40 (t, J=76 Hz, 1H), 4.04 (m, 1H), 3.20 (s, 3H), 3.16 (m, 2H), 1.98 (m, 2H), 1.84 (m, 1H), 1.76-1.40 (m, 6H), 0.86 (m, 2H), 0.66 (m, 2H). $^{19}$F NMR ($CD_3OD$, 376 MHz): δ −77.1, −82.3 (d, J=76 Hz).

Example 226

Synthesis of Compound 275

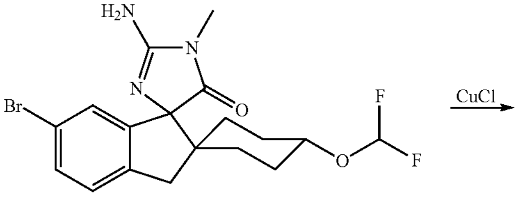

275a

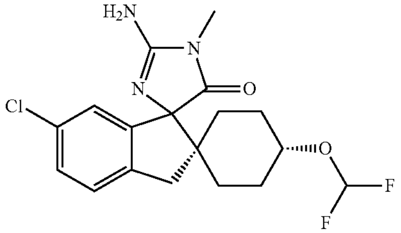

275

In an 8 mL vial was charged with compound 275a (20 mg, 0.047 mmol) and CuCl (23 mg, 0.234 mmol). DMF (3 mL) was added, and the vial was sealed and placed into CEM microwave reactor and irradiated at 170° C. for 1 h. After cooling down, the solid was filtered and the filtrate was removed by evaporation in vacuo and the resulting residue was purified by acidic preparative HPLC to give compound 275 (2.5 mg, 37%) as a whit solid, LC-MS $t_R$=1.454 min in 3 min chromatography, MS (ESI) m/z 384.2 $[M+H]^+$. $^1$H NMR ($CD_3OD$ 400 MHz): δ 7.39 (d, J=1.2 Hz, 2H), 7.34 (s, 1H), 6.23-6.61 (m, 1H), 4.06 (m, 1H), 3.11-3.24 (m, 5H), 1.96-2.07 (m, 2H), 1.84-1.97 (m, 1H), 1.67-1.75 (m, 1H), 1.54-1.62 (m, 5H), 1.45-1.54 (m, 1H). $^{19}$F NMR ($CD_3OD$ 376 MHz): δ −81.95.

Example 227

Synthesis of Compound 276

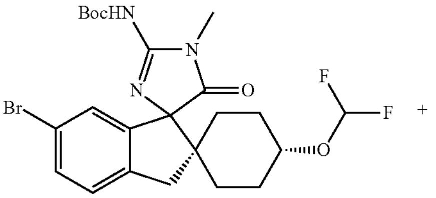

1

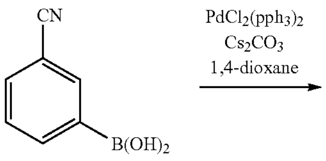

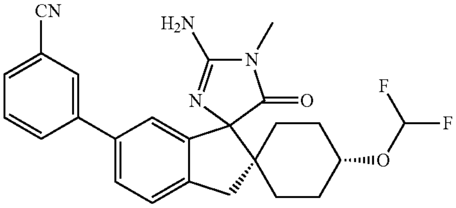

276

According to a similar synthesis of compound 251, compound 1 (16.0 mg, 0.03 mmol) was reacted with 3-cyanophenylboronic acid to gave final product compound 276 (10.1 mg, 74%) as a TFA salt. LC-MS $t_R$=1.52 min in 3 min chromatography, MS (ESI) m/z 428 $[M+H]^+$. $^1$H NMR ($CD_3OD$, 400 MHz): δ 8.02 (s, 1H), 7.94 (m, 1H), 7.68 (m, 2H), 7.60 (m, 2H), 7.52 (m, 1H), 6.40 (t, J=76 Hz, 1H), 4.06 (m, 1H), 3.20 (sm, 5H), 2.02 (m, 2H), 1.88 (m, 1H), 1.80-1.44 (m, 5H). $^{19}$F NMR ($CD_3OD$, 376 MHz): δ −77.4, −82.2 (d, J=76 Hz).

Example 228

Synthesis of Compound 277

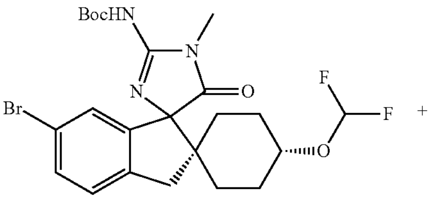

1

-continued

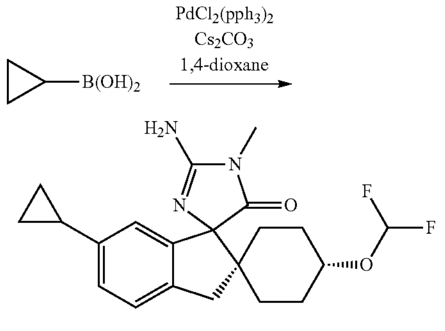

277

According to a similar synthesis of compound 251, compound 1 (19.3 mg, 0.036 mmol) was reacted with cyclopropylboronic acid to gave final product compound 277 (2.9 mg, 20%) as a TFA salt. LC-MS $t_R$=1.51 min in 3 min chromatography, MS (ESI) m/z 390 $[M+H]^+$. $^1H$ NMR ($CD_3OD$, 400 MHz): δ 7.24 (d, J=7.8 Hz, 1H), 7.08 (d, J=7.8 Hz, 1H), 6.90 (s, 1H), 6.38 (t, J=76 Hz, 1H), 4.02 (m, 1H), 3.20 (s, 3H), 3.14 (m, 2H), 2.02-1.82 (m, 4H), 1.76-1.40 (m, 5H), 0.94 (m, 2H), 0.84 (m, 2H). $^{19}F$ NMR ($CD_3OD$, 376 MHz): δ −77.4, −82.2 (d, J=76 Hz).

Example 229

Synthesis of Compound 278

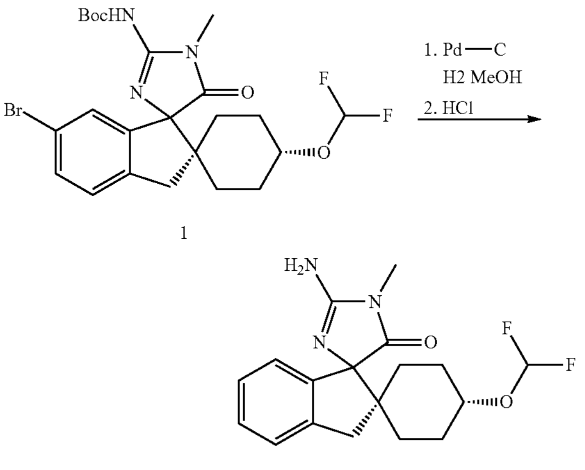

1

278

A solution of compound 1 (10 mg, 0.019 mmol) and Pd—C (cat. amount) in MeOH (1 mL) was degassed and charged $H_2$ with a balloon, and stirred at room temperature for 1 hour. Upon filtration, the filtrate was concentrated and retreated with 4N HCl in 1,4-dioxane (2 mL) for overnight. Solvent was removed in vacuum and the residue was purified with HPLC to give compound 278 (1.09 mg, 12%) as a TFA salt. LC-MS $t_R$=1.36 min in 3 min chromatography, MS (ESI) m/z 350 $[M+H]^+$. $^1H$ NMR ($CD_3OD$, 400 MHz): δ 7.38 (m, 2H), 7.26 (m, 1H), 7.18 (m, 1H), 6.40 (t, J=76 Hz, 1H), 4.04 (m, 1H), 3.18 (s, 3H), 3.16 (m, 2H), 2.04-1.40 (m, 8H); $^{19}F$ NMR ($CD_3OD$, 376 MHz): δ −77.5, −82.3 (d, J=76 Hz).

Example 230

Synthesis of Compound 279

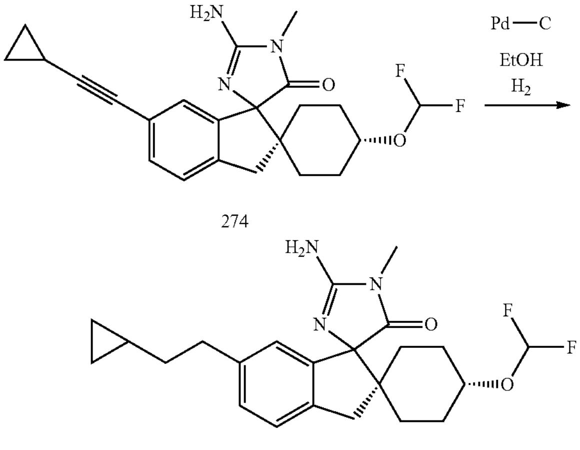

274

279

A solution of compound 274 (3 mg, 0.007 mmol) and Pd—C (cat. amount) in EtOH (1 mL) was degassed and charged with a $H_2$ balloon, and stirred at room temperature for 3 hours. Upon filtration, the filtrate was purified with HPLC to give compound 279 (1.54 mg, 41%) as a TFA salt. LC-MS $t_R$=1.70 min in 3 min chromatography, MS (ESI) m/z 418 $[M+H]^+$. $^1H$ NMR ($CD_3OD$, 400 MHz): δ 7.26 (d, J=7.6 Hz, 1H), 7.20 (d, J=7.6 Hz, 1H), 7.02 (s, 1H), 6.38 (t, J=76 Hz, 1H), 4.04 (m, 1H), 3.20 (s, 3H), 3.16 (m, 2H), 2.68 (t, J=7.2 Hz, 2H), 2.04-1.40 (m, 10H), 0.66 (m, 1H), 0.40 (m, 2H), 0.02 (m, 2H). $^{19}F$ NMR ($CD_3OD$, 376 MHz): δ −77.4, −82.3 (d, J=76 Hz).

Example 231

Synthesis of Compound 280

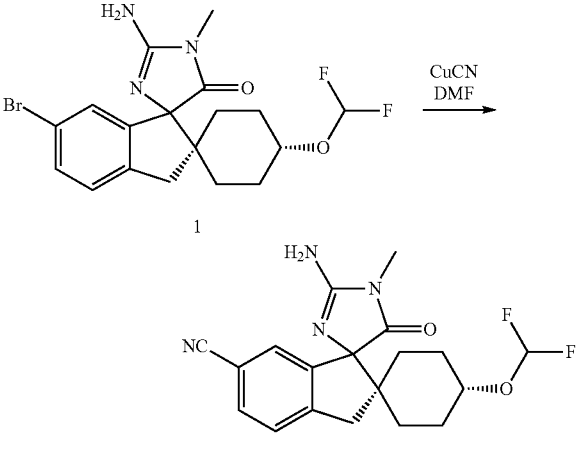

1

280

In a 10 mL CEM microwave tube there was added compound 1 (5 mg, 0.012 mmol), CuCN (excess) followed by DMF (0.2 mL). The mixture was heated with a CEM microwave reactor at 150° C. for 90 min. The resulting mixture was carefully added 1 N HCl (0.3 mL) in a hood, filtered and purified with HPLC to give compound 280 (3.0 mg, 51%) as a TFA salt. LC-MS $t_R$=1.29 min in 3 min chromatography, MS (ESI) m/z 375 $[M+H]^+$. $^1H$ NMR ($CD_3OD$, 400 MHz): δ 7.76 (d, J=7.6 Hz, 1H), 7.70 (s, 1H), 7.58 (d, J=7.6 Hz, 1H), 6.40 (t, J=76 Hz, 1H), 4.04 (m, 1H), 3.26 (m, 2H), 3.20 (s, 3H), 2.02 (m, 2H), 1.86 (m, 1H), 1.78-1.40 (m, 5H). $^{19}F$ NMR ($CD_3OD$, 376 MHz): δ −77.4, −82.3 (d, J=76 Hz).

Example 232

Synthesis of Compounds 281 and 282

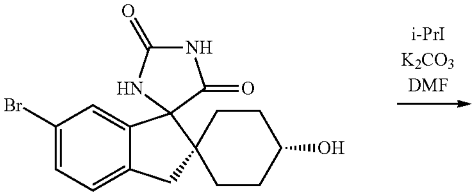

1

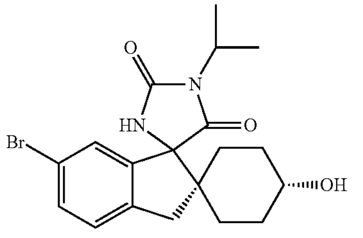

+

2

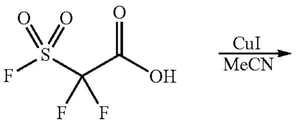

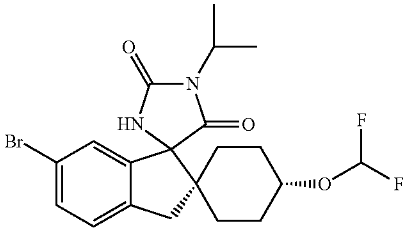

+

3

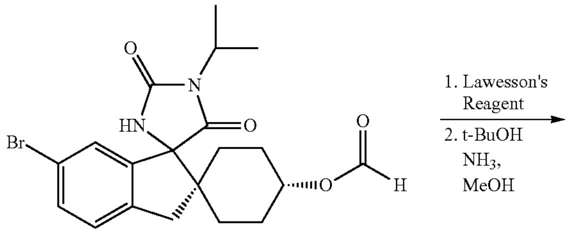

4

-continued

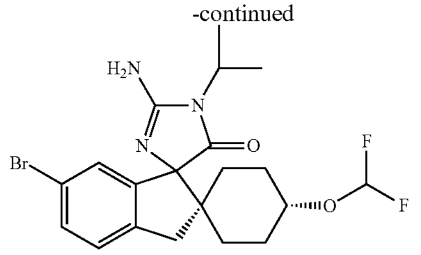

+

281

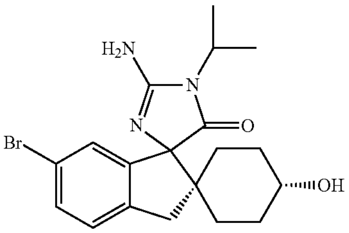

282

Procedure for Preparation of Compound 2

To a solution of compound 1 (0.29 g, 0.80 mmol) in DMF (1 mL) there was added $K_2CO_3$ (0.33 g, 2.4 mmol), followed by 2-iodopropane (52.6 mg, 0.88 mmol). The resulting mixture was stirred at room temperature over weekend, diluted with water (5 mL), extracted with DCM (5 mL×4). Combined organic layers were washed with brine (5 mL), the solvent was removed in vacuum, and the residue was purified by a flash chromatography (0-70% EtOAx/Hexane) to afford compound 2 (219.5 mg, 67%). LC-MS $t_R$=1.49 min in 3 min chromatography, MS (ESI) m/z 407 $[M+H]^+$.

Procedure for Preparation of Compound 3& 4

A solution of compound 1 (217.0 mg, 0.53 mmol) and CuI (10.0 mg, 0.05 mmol) in anhydrous MeCN (5 mL) was heated at 60° C. under $N_2$ for 10 minutes to give a clear solution. 2,2-difluoro-2-(fluorosulfonyl)acetic acid (99.1 mg, 0.56 mmol) was added to the solution dropwise, and the resulting solution was stirred at the same temperature for 5 min, cooled down to room temperature, quenched with water (10 mL), extracted with DCM (10 mL×4). Combined organic layers were washed with brine, dried over $Na_2SO_4$, concentrated in vacuum to afford compound 3 and 4 as a 2:1 mixture (223.2 mg), which was used for the next step without purification. Compound 3: LC-MS $t_R$=1.96 min in 3 min chromatography, MS (ESI) m/z 457 $[M+H]^+$; Compound 4: LC-MS $t_R$=1.83 min in 3 min chromatography, MS (ESI) m/z 435 $[M+H]^+$.

Procedure for Preparation of Compounds 281 and 282

According to a similar synthesis of compound 291, mixture of 3 and 4 (221.7 mg, 0.48 mmol) afforded compound 281 (60.0 mg, 22%) as a TFA salt. LC-MS $t_R$=1.56 min in 3 min chromatography, MS (ESI) m/z 456$[M+H]^+$. $^1H$ NMR ($CD_3OD$, 400 MHz): δ 7.54 (dd, J=0.8, 7.6 Hz, 1H), 7.44 (d, J=0.8 Hz, 1H), 7.32 (d, J=7.6 Hz, 1H), 6.38 (t, J=76 Hz, 1H), 4.28 (m, 1H), 4.04 (m, 1H), 3.12 (m, 2H), 2.06-1.88 (m, 3H), 1.78-1.40 (m, 11H). $^{19}F$ NMR ($CD_3OD$, 376 MHz): δ −77.4, −82.24 (d, J=76 Hz). Compound 282 (6.95 mg) as a TFA salt. LC-MS $t_R$=1.42 min in 3 min chromatography, MS (ESI) m/z 456[M+H]$^+$. $^1$H NMR ($CD_3OD$, 400 MHz): δ 7.54 (m, 1H), 7.40 (s, 1H), 7.28 (m, 1H), 4.28 (m, 1H), 3.48 (m, 1H), 3.10 (m, 2H), 1.90 (m, 3H), 1.70-1.28 (m, 11H).

Example 233

Synthesis of Compound 283

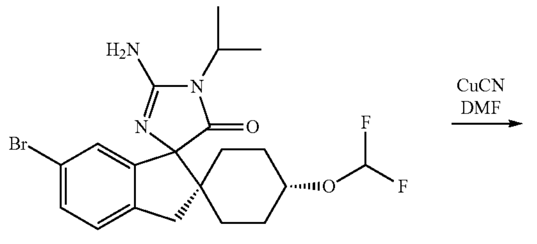

1

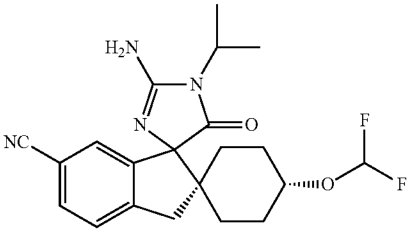

283

According to a similar synthesis of compound 280, compound 1 (5 mg, 0.01 mmol) was heat in a CEM microwave reactor at 150° C. for 130 min to afford compound 283 (1.75 mg, 34%) as a TFA salt. LC-MS $t_R$=1.43 min in 3 min chromatography, MS (ESI) m/z 403[M+H]$^+$. $^1$H NMR ($CD_3OD$, 400 MHz): δ 7.76 (m, 2H), 7.58 (m, 1H), 6.40 (t, J=76 Hz, 1H), 4.28 (m, 1H), 4.04 (m, 1H), 3.20 (m, 2H), 2.06-1.94 (m, 3H), 1.78-1.30 (m, 11H). $^{19}$F NMR ($CD_3OD$, 376 MHz): δ −75.8, −82.34 (d, J=76 Hz).

Example 234

Synthesis of Compound 284

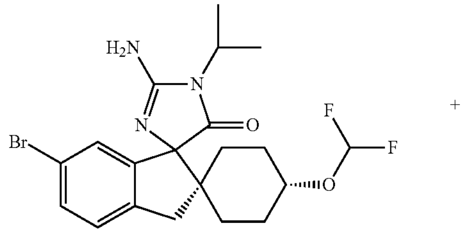

1

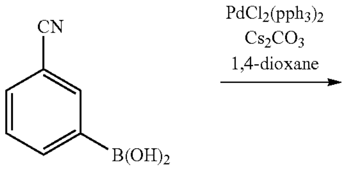

-continued

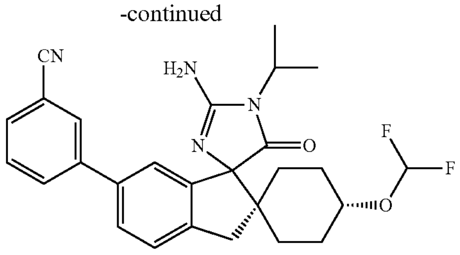

284

According to a similar synthesis of compound 251, compound 1 (5.0 mg, 0.01 mmol) was reacted with 3-cyanophenylboronic acid to gave final product compound 284 (1.42 mg, 24%) as a TFA salt. LC-MS $t_R$=1.70 min in 3 min chromatography, MS (ESI) m/z 479[M+H]$^+$. $^1$H NMR ($CD_3OD$, 400 MHz): δ 8.00 (s, 1H), 7.94 (m, 1H), 7.68 (m, 2H), 7.62 (m, 1H), 7.56 (s, 1H), 7.52 (m, 1H), 6.40 (t, J=76 Hz, 1H), 4.28 (m, 1H), 4.06 (m, 1H), 3.20 (m, 2H), 2.06-1.94 (m, 3H), 1.80-1.40 (m, 11H). $^{19}$F NMR ($CD_3OD$, 376 MHz): δ −77.6, −82.28 (d, J=76 Hz).

Example 235

Synthesis of Compound 285

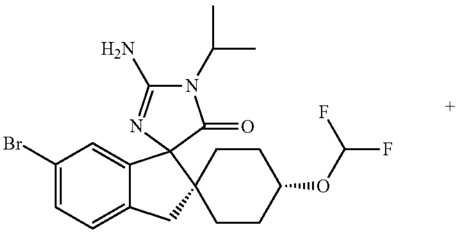

1

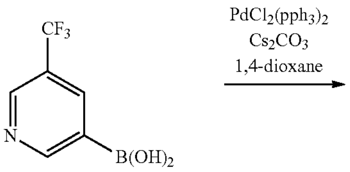

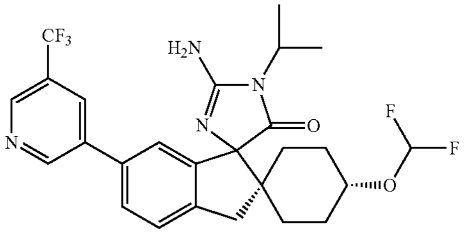

285

According to a similar synthesis of compound 251, compound 1 (13.6 mg, 0.03 mmol) was reacted with (5-(trifluoromethyl)pyridin-3-yl)boronic acid to gave final product compound 285 (1.80 mg, 9%) as a TFA salt. LC-MS $t_R$=1.68 min in 3 min chromatography, MS (ESI) m/z 523[M+H]$^+$. $^1$H NMR ($CD_3OD$, 400 MHz): δ 9.04 (s, 1H), 8.84 (s, 1H), 8.38 (s, 1H), 7.78 (m, 1H), 7.66 (s, 1H), 7.56 (m, 1H), 6.40 (t, J=76 Hz, 1H), 4.28 (m, 1H), 4.06 (m, 1H), 3.22 (m, 2H), 2.08-1.90

(m, 3H), 1.80-1.42 (m, 11H). $^{19}F$ NMR ($CD_3OD$, 376 MHz): δ −64.34, −77.6, −82.28 (d, J=76 Hz).

Example 236

Synthesis of Compound 286

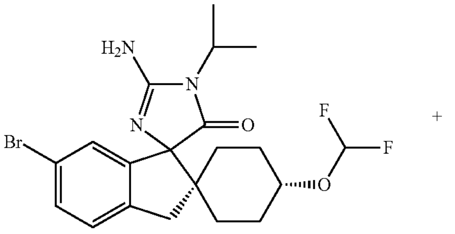

1

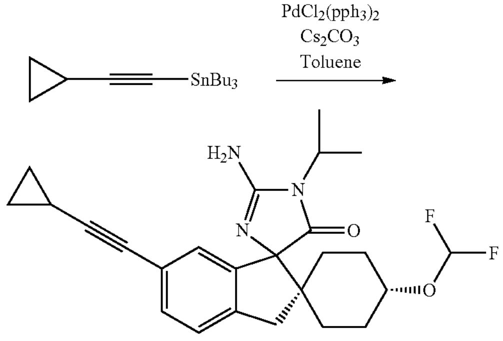

286

A 10 mL CEM microwave tube was charged with compound 1 (13.0 mg, 0.028 mmol), PdCl2(pph3)2, Cs2CO3 and Toluene (0.5 mL), and degassed for 2-3 minutes, then flushed with N2. Tributyl(cyclopropylethynyl)stannane (0.1 mL, excess) was added, and the resulting mixture was heated with a CEM microwave reactor at 120° C. for 30 min. Upon filtration, the solvent was removed, and the residue was purified by HPLC to afford compound 286 (4.29 mg, 28%) as a TFA salt. LC-MS $t_R$=1.80 min in 3 min chromatography, MS (ESI) m/z 442 $[M+H]^+$. $^1H$ NMR ($CD_3OD$, 400 MHz): δ 7.34 (m, 2H), 7.18 (s, 1H), 6.40 (t, J=76 Hz, 1H), 4.28 (m, 1H), 4.04 (m, 1H), 3.16 (m, 2H), 2.04-1.84 (m, 3H), 1.76-1.40 (m, 12H), 0.86 (m, 2H), 0.68 (m, 2H). $^{19}F$ NMR ($CD_3OD$, 376 MHz): δ −77.1, −82.3 (d, J=76 Hz).

Example 237

Synthesis of Compound 287

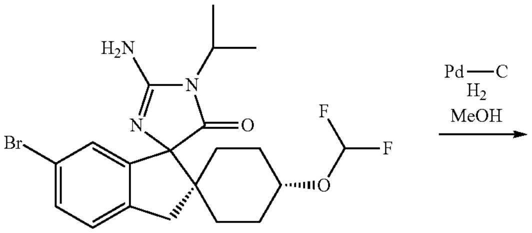

1

-continued

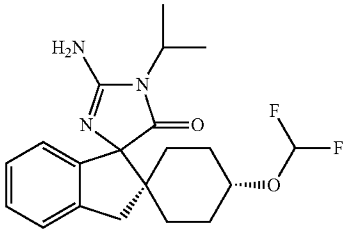

287

A solution of compound 1 (15 mg, 0.03 mmol) and Pd—C (cat. amount) in MeOH (2 mL) was degassed and charged $H_2$ with a balloon. The resulting mixture was stirred at room temperature for 45 min. Upon filtration, the filtrate was concentrated and purified with HPLC to give compound 287 (5.26 mg, 36%) as a TFA salt. LC-MS $t_R$=1.43 min in 3 min chromatography, MS (ESI) m/z 378 $[M+H]^+$. $^1H$ NMR ($CD_3OD$, 400 MHz): δ 7.38 (m, 2H), 7.26 (m, 1H), 7.16 (m, 1H), 6.40 (t, J=76 Hz, 1H), 4.28 (m, 1H), 4.06 (m, 1H), 3.18 (m, 2H), 2.04-1.92 (m, 3H), 1.78-1.40 (m, 11H). $^{19}F$ NMR ($CD_3OD$, 376 MHz): δ −77.4, −82.20 (d, J=76 Hz).

Example 238

Synthesis of Compound 288

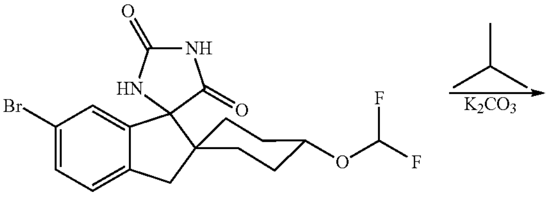

1

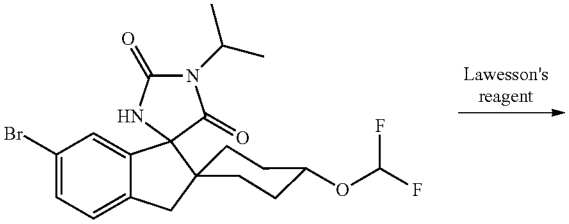

2

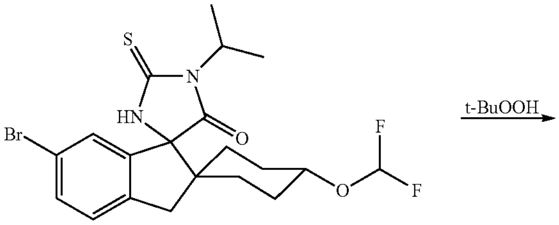

3

-continued

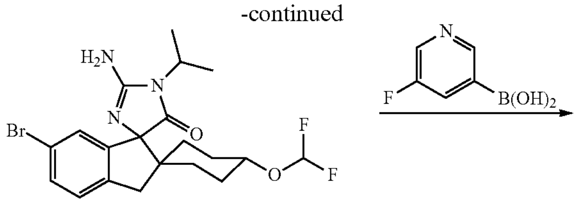

4

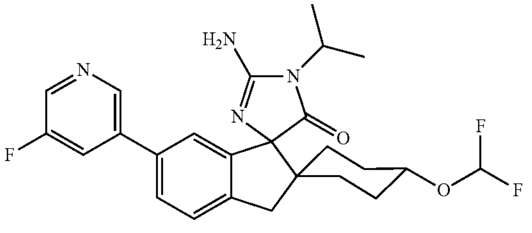

288

1. Procedure for Preparation of Compound 2

To a solution of compound 1 (0.23 g, 0.558 mmol) in DMF (3 mL) was added $K_2CO_3$ (0.15 g, 1.116 mmol). After addition, the resulting mixture was stirred at room temperature for 10 min. Then iodomethane (95 mg, 0.558 mmol) in DMF (1 mL) was added dropwise via a syringe with stirring. The mixture was stirred at room temperature overnight. The reaction mixture was partitioned between $H_2O$ (25 mL) and ethyl acetate (25 mL). The separated organic phase was washed with saturated brine (3×20 mL), dried over anhydrous $Na_2SO_4$ and concentrated in vacuo to give the crude. The crude was purified by preparative TLC (hexane/EtOAc=3/1) to give compound 2 (0.18 g, 71%) as a white solid.

2. Procedure for Preparation of Compound 3

A 35 mL vial was charged with compound 2 (0.18 g, 0.395 mmol), Lawessons reagent (0.19 g, 0.474 mmol). Toluene (5 mL) was added, and the vial was sealed and placed into CEM microwave reactor and irradiated at 130° C. for 1 h. After cooling down, the solvent was removed by evaporation in vacuo and the resulting residue was purified by preparative TLC (hexane/EtOAc=3/1) to give compound 6 (56 mg, 30%) as a white solid.

3. Procedure for Preparation of Compound 4

To a solution of compound 3 (56 mg, 0.118 mmol) in MeOH (4 mL) was added $NH_3$—$H_2O$ (0.8 mL) and tert-butyl hydroperoxide (0.37 g, 2.36 mmol). After addition, the mixture was stirred at room temperature overnight. The solvent was removed by evaporation in vacuo. The residue was partitioned between EtOAc (contained 10% methanol) (5 mL) and $H_2O$ (2 mL). The organic layer was separated and washed with brine (5 mL), dried over anhydrous $Na_2SO_4$, filtered and concentrated in vacuo. The residue was purified by preparative TLC (EtOAc) to give compound 4 (15 mg, 28%) as a white solid.

4. Procedure for Preparation of Compound 288

A solution containing compound 4 (15 mg, 0.033 mmol), compound 4A (7 mg, 0.049 mmol) in dioxane (2 mL) and aqueous $Cs_2CO_3$ (2 M, 0.6 mL) was deoxygenated by bubbling a stream of nitrogen through the reaction mixture for 5 min. Then, $PdCl_2(dppf)$ (1.5 mg, 0.002 mmol) was added. The reaction was heated to reflux overnight. The organic layer was separated and washed with water (2×10 mL), dried over anhydrous $Na_2SO_4$, and evaporated under vacuum to give the crude. The crude was purified by acidic preparative HPLC to give compound 288 (6.6 mg, 42%) as a white solid. LC-MS $t_R$=3.016 min in 7 min chromatography, MS (ESI) m/z 473.4 $[M+H]^+$. $^1H$ NMR ($CD_3OD$ 400 MHz): δ 9.59 (s, 1H), 9.36 (d, J=2.4 Hz, 1H), 8.84 (m, 1H), 8.64 (dd, J=7.6, 1.6 Hz, 1H), 8.51 (s, 1H), 8.44 (d, J=8.0 Hz, 2H), 7.1-7.5 (m, 1H), 5.20 (m, 1H), 4.97 (m, 1H), 4.15 (m, 2H), 2.83-3.00 (m, 3H), 2.58-2.70 (m, 1H), 2.32-2.57 (m, 10H). $^{19}F$ NMR ($CD_3OD$ 376 MHz): δ −81.88, −128.26.

Example 239

Synthesis of Compound 289

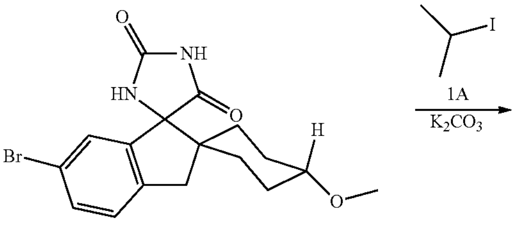

1

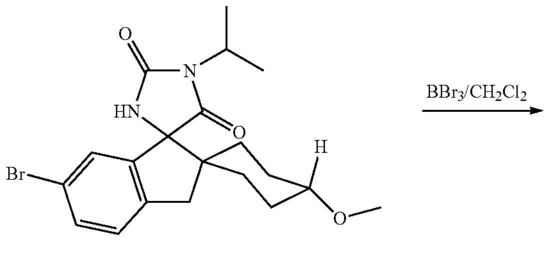

2

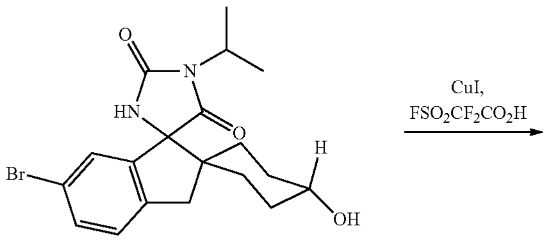

3

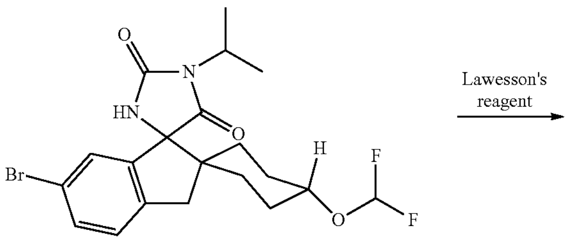

4

-continued

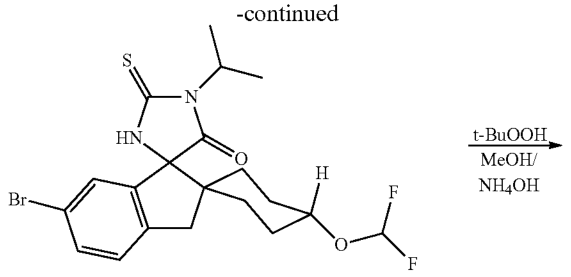

5

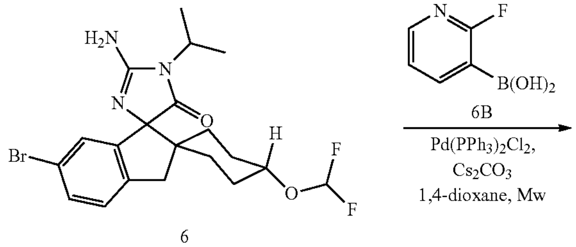

6

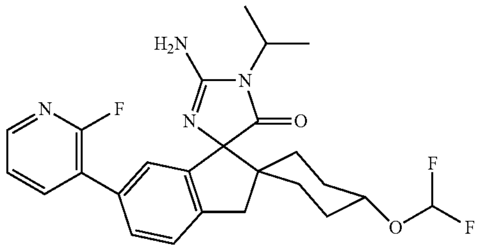

289

Procedure for Preparation of Compound 2

To a solution of compound 1 (500 mg, 2.32 mmol) in DMF (15 mL) was added $K_2CO_3$ (355 mg, 2.55 mmol) and compound 1A (0.26 mL, 2.55 mmol). The reaction mixture was stirred at room temperature overnight. Water (20 mL) was added and the mixture was extracted with EtOAc (15 mL×4). The organic layer was washed with water, brine, dried over $Na_2SO_4$ and concentrated to give the residue, which was purified by preparative TLC (petroleum ether: EtOAc=3:1) to afford compound 2 (366 mg, 66%) as a white solid.

Procedure for Preparation of Compound 3

To a solution of compound 2 (80 mg, 0.19 mmol) in $CH_2Cl_2$ (1 mL) was added $BBr_3$ (0.4 mL, 1 M in $CH_2Cl_2$, 0.4 mmol) under $N_2$ at −78° C. The reaction mixture was allowed to warm to room temperature and stirred for 1 h. TLC showed compound 2 was completely consumed. The reaction was cooled to 0° C. and quenched with 1 N HCl, extracted with EtOAc (10 mL×3). The organic layer was washed with brine, dried over $Na_2SO_4$ and concentrated the residue, which was purified by preparative TLC (petroleum ether:EtOAc=1:1) to afford compound 3 (30 mg, 39%) as a white solid. $^1H$ NMR ($CDCl_3$ 400 MHz): δ 7.48 (m, 1H), 7.25 (m, 2H), 5.43 (s, 1H), 4.22 (m, 1H), 3.51 (s, mH), 3.09-2.91 (m, 2H), 1.88 (m, 3H), 1.46 (m, 1H), 1.43 (m, 8H), 1.24 (m, 2H).

Procedure for Preparation of Compound 4

A solution of compound 3 (30 mg, 0.074 mmol) and CuI (3 mg, 0.015 mmol) in $CH_3CN$ (1.5 mL) was stirred at 70° C. for 30 min. $FSO_2CFCOOH$ (14 mg, 0.078 mmol) in $CH_3CN$ (0.2 mL) was added dropwise. The reaction mixture was continued stirring at 70° C. for 15 min and the solvent was removed. $H_2O$ (10 mL) was added and the mixture extracted with EtOAc (10 mL×3). The organic layer was washed with brine, dried over $Na_2SO_4$ and concentrated to give the residue, which was purified by preparative TLC (petroleum ether: EtOAc=3:1) to afford compound 4 (10 mg, 29%) as a white solid.

Procedure for Preparation of Compound 5

To a solution of compound 4 (25 mg, 0.055 mmol) in dry toluene (2 mL) was added Lawesson's reagent (33 mg, 0.082 mmol) under $N_2$. The reaction mixture was heated in a CEM microwave reactor at 130° C. for 1 h. The solvent was removed under reduced pressure, and the residue was purified by preparative TLC (petroleum ether:EtOAc=3:1) to give compound 5 (12 mg, 46%) as a white solid.

Procedure for Preparation of Compound 6

To a solution of compound 5 (12 mg, 0.021 mmol) in MeOH (3 mL) and $NH_3.H_2O$ (0.6 mL) was added t-BuOOH (65 mg, 0.424 mmol). The reaction mixture was stirred at room temperature for 4 h. The solvent was removed and the residue was purified by preparative HPLC to give compound 6 (8 mg, 60%) as a white solid.

Procedure for Preparation of Compound 289

To a solution of compound 6 (8 mg, 0.0175 mmol) in 1,4-dioxane (1 mL) was added compound 6B (5 mg, 0.035 mmol), $PdCl_2(PPh_3)_2$ (5 mg) and $Cs_2CO_3$ solution (0.05 mL, 2M in $H_2O$, 0.1 mmol). The reaction mixture was heated in a CEM microwave reactor at 120° C. for 15 min. The solvent was removed under reduced pressure, and the residue was purified by preparative HPLC to give compound 289 (2 mg, 24%) as a white solid. LC-MS $t_R$=1.089 min in 2 min chromatography, MS (ESI) m/z 473 $[M+H]^+$, $^1H$ NMR ($CD_3OD$ 400 MHz): δ 8.11 (m, 1H), 7.94 (t, J=15.6, 8.0 Hz, 1H), 7.51 (dd, J=10.0, 8.0 Hz, 34.4, 2H), 7.43 (m, 2H), 6.50-6.13 (t, J=151.6, 67.6 Hz, 1H), 4.19 (m, 0.3H), 3.98. (m, 0.5H), 3.38 (m, 1H), 3.08 (m, 2H), 2.01 (m, 1H), 1.48 (m, 2H), 1.65 (m, 0.4; H), 1.53 (m, 5H), 1.43 (m, 3H). $^{19}F$ NMR ($CD_3OD$ 19F 400 MHz): δ −74.081, −81.921

Example 240

Synthesis of Compound 290

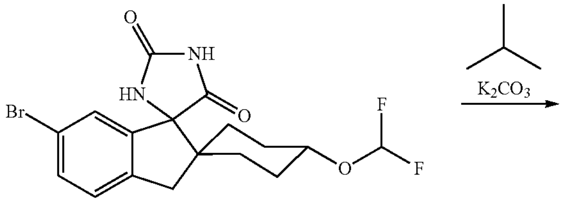

4

-continued

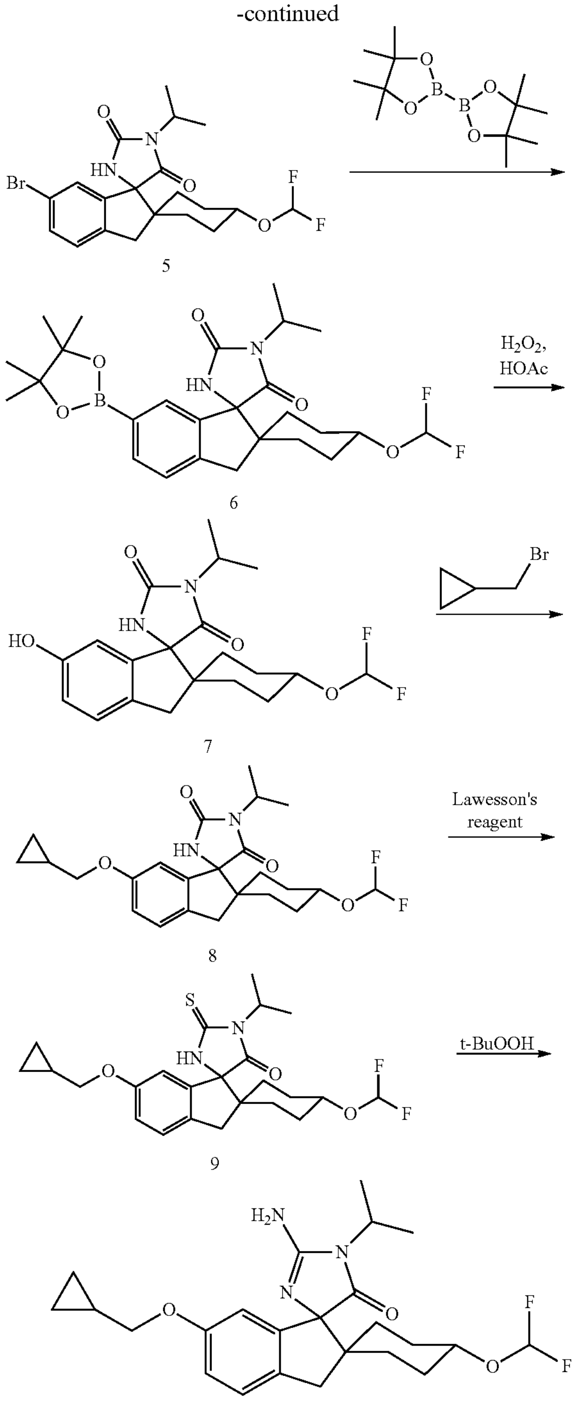

5

6

7

8

9

290

1. Procedure for Preparation of Compound 5

To a solution of compound 4 (0.28 g, 0.676 mmol) in DMF (10 mL) was added $K_2CO_3$ (280 mg, 2.029 mmol) and 2-iodo-propane (0.172, 1.014 mmol). The mixture was stirred for 3 h at room temperature. Then brine (15 mL) was added and extracted with of EtOAc (2×10 mL). The combined organic layers were separated, dried over $Na_2SO_4$, and evaporated to give crude compound 5 (280 mg, crude) as a white solid.

2. Procedure for Preparation of Compound 6

To a solution of compound 5 (280 mg, 0.614 mmol) in dry 1,4-dioxane (5 mL) was added compound 5A (172 mg, 0.675 mmol), KOAc (174 mg, 1.781 mmol) and $PdCl_2$(dppf) (21 mg, 0.0307 mmol) in a $N_2$ atmosphere. The mixture was heated to reflux overnight. Brine (5 mL) was added to quench the reaction and extracted with EtOAc (2×10 mL). The combined organic layers were dried over anhydrous $Na_2SO_4$, evaporated to give crude compound 6 (300 mg, crude) as a white solid, which was used for the next step without further purification.

3. Procedure for Preparation of Compound 7

To a solution of compound 6 (300 mg, 0.595 mmol) in THF (20 mL) was added HOAc (30 mL) and $H_2O_2$ (10 mL). The solution was stirred at room temperature overnight. Sat. $NaHSO_3$ (20 mL) was added to quench the reaction. Then the reaction mixture was neutralized with sat. $Na_2CO_3$ and the solution was extracted with EtOAc (2×150 mL). The combined organic layers were dried over anhydrous $Na_2SO_4$ and evaporated. The residue was purified by acidic preparative HPLC to give compound 7 (100 mg, 43%) as a white solid.

4. Procedure for Preparation of Compound 8

To a solution of compound 7 (50 mg, 0.127 mmol) in DMF (3 mL) was added bromomethyl-cyclopropane (22 mg, 0.165 mmol) and $K_2CO_3$ (53 mg, 0.381 mmol). The reaction mixture was stirred at room temperature overnight. Sat. $NH_4Cl$ (5 mL) solution was added to quench the reaction, and then extracted with EtOAc (3×10 mL). The combined organic layers were washed with brine and dried over $Na_2SO_4$, evaporated under vacuum. The residue was purified by acidic preparative HPLC to give compound 8 (10 mg, 18%) as a white solid.

5. Procedure for Preparation of Compound 9

An 8 mL vial was charged with compound 8 (20 mg, 0.0446 mmol), Lawesson's reagent (22 mg, 0.0536 mmol). Toluene (2 mL) was added, and the vial was sealed and placed into CEM microwave reactor and irradiated at 130° C. for 1 h. After cooling down, the solvent was removed by evaporation in vacuo and the resulting residue was purified by column chromatography on silica gel (petroleum ether:EtOAc, 50:1 to 10:1) to give compound 9 (20 mg, 95%) as a white solid.

6. Procedure for Preparation of Compound 290

To a solution of compound 9 (20 mg, 0.0431 mmol) in MeOH (3 mL) was added $NH_3$—$H_2O$ (0.6 mL) and t-butyl hydroperoxide (135 mg, 0.862 mmol). After addition, the mixture was stirred at room temperature for 24 h. The solvent was removed by evaporation in vacuo. The residue was partitioned between EtOAc (contained 10% methanol) (50 mL) and $H_2O$ (20 mL). The organic layer was separated and washed with brine (20 mL), dried over $Na_2SO_4$, filtered and concentrated in vacuo. The residue was purified by preparative HPLC to give compound 290 (9.0 mg, 50%) as a white solid. LC-MS $t_R$=1.161 min in 2 min chromatography, MS (ESI) m/z 448 $[M+H]^+$. $^1H$ NMR ($CD_3OD$ 300 MHz): δ 7.02 (d, J=8.1 Hz, 1H), 6.68 (dd, J=2.4, 7.4 Hz, 1H), 6.47 (d, J=2.1 Hz, 1H), 5.90-6.40 (m, 1H), 4.05 (m, 1H), 3.80 (m, 1H), 3.54 (d, J=6.9 Hz, 2H), 2.83 (m, 2H), 1.54-1.84 (m, 3H), 1.32-1.51

(m, 2H), 1.23 (m, 9H), 1.47 (m, 1H), 0.35 (m, 2H), 0.08 (m, 2H). $^{19}F$ NMR ($CD_3OD$ 376 MHz): δ −74.61

Example 241

Synthesis of Compound 291

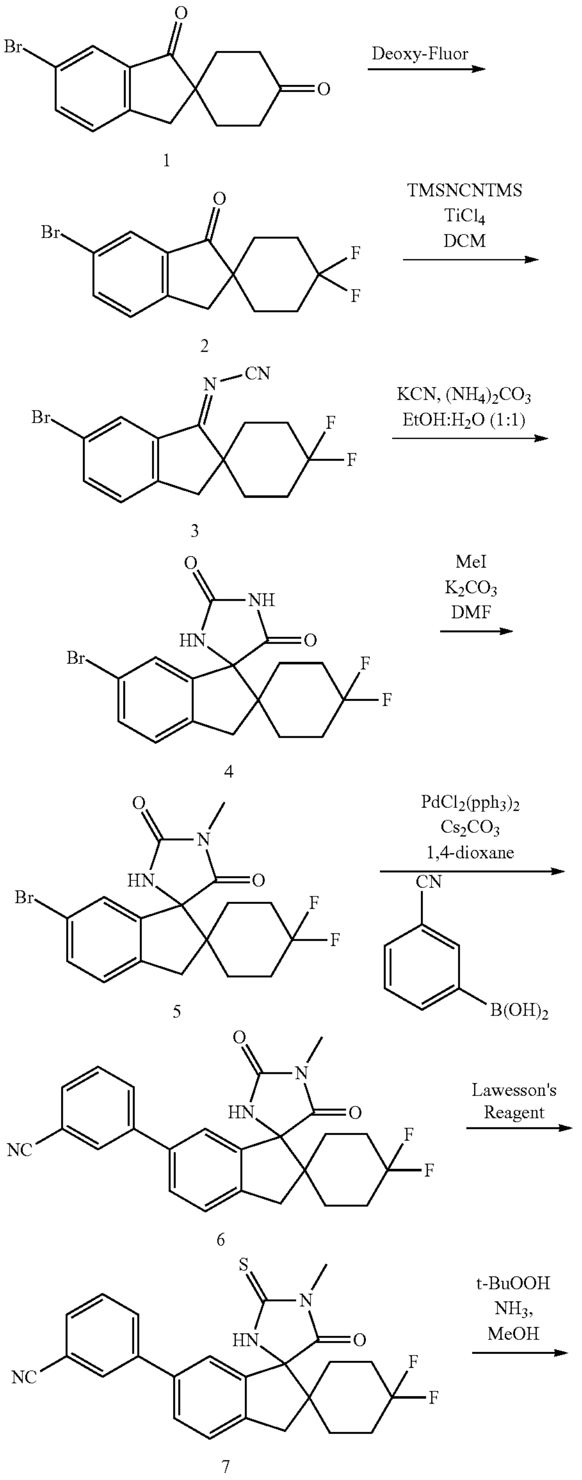

-continued

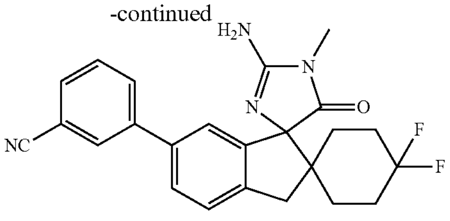

291

Procedure for Preparation of Compound 2

To a mixture of 6'-bromospiro[cyclohexane-1,2'-indene]-1',4(3'H)-dione (1) (1.04 g, 3.55 mmol) and silica gel (500 mg) in a 50 mL plastic tube there was added Deoxy-Fluor (20 mL, 50% in Toluene) slowly. Heat was generated at the beginning, and the addition of Deoxy-Fluor was stopped for 5 min before the rest of the reagent was added. The tube was capped, and the mixture was stirred at room temperature for 4 hours. Water was added slowly, the solution was cooled to room temperature. Upon removal of Toluene, the residue was purified by flash chromatography to give 6'-bromo-4,4-difluorospiro[cyclohexane-1,2'-inden]-1'(3'H)-one (2) (120.0 mg, 11%). LC-MS $t_R$=2.00 min in 3 min chromatography, MS (ESI) m/z 315 $[M+H]^+$.

Procedure for Preparation of Compound 5

According to similar synthesis for compound 250, 6'-bromo-4,4-difluorospiro[cyclohexane-1,2'-inden]-1'(3'H)-one (2) (120.0 mg, 0.38 mmol) was converted to compound 5 (88.0 mg, 58% 3 steps). Compound 3: LC-MS $t_R$=1.96 min in 3 min chromatography, MS (ESI) m/z 339 $[M+H]^+$; Compound 4: LC-MS $t_R$=1.49 min in 3 min chromatography, MS (ESI) m/z 385 $[M+H]^+$; Compound 5: LC-MS $t_R$=1.78 min in 3 min chromatography, MS (ESI) m/z 399 $[M+H]^+$.

Procedure for Preparation of Compound 6

To a 10 mL CEM tube there was charged compound 5 (35.8 mg, 0.09 mmol), $PdCl_2(pph_3)_2$ (3.0 mg), $Cs_2CO_3$ (87 mg. 0.27 mmol), 1,4-dioxane (1 mL) and water (0.2 mL). The tube was heated in a CEM microwave reactor at 120° C. for 60 min. The solution was filtered, solvent was removed in vacuum, and the residue was purified with HPLC to give compound 6 (30.7 mg, 81%). LC-MS $t_R$=1.76 min in 3 min chromatography, MS (ESI) m/z 422 $[M+H]^+$.

Procedure for Preparation of Compound 291

The above compound 6 (30.7 mg, 0.07 mmol) was dissolved in 1,4-dioxane (1 mL) and transferred to a 10 mL CEM tube. Lawesson's reagent (29.5 mg, 0.07 mmol) was added to the tube, and the resulting mixture was heated in a CEM microwave reactor at 120° C. for 90 min, then 130° C. for 60 min. Solvent was removed and the residue was purified with flash chromatography (0 to 60% EtOAc/Hexane) to give thio-hydantoin 7 (24.0 mg, 78%). LC-MS $t_R$=1.92 min in 3 min chromatography, MS (ESI) m/z 438 $[M+H]^+$.

To a solution of thio-hydantoin 7 (24.0 mg, 0.05 mmol) in $NH_3$-MeOH (7 N in MeOH, 3 mL) there was added t-butyl hydroperoxide (~5.5 N in nonane, 0.5 mL). The resulting mixture was stirred at room temperature overnight. Upon removal of solvent, the residue was purified by HPLC to give compound 291 (5.7 mg, 21%). LC-MS $t_R$=1.43 min in 3 min chromatography, MS (ESI) m/z 421 $[M+H]^+$. $^1H$ NMR ($CD_3OD$, 400 MHz): δ 8.02 (s, 1H), 7.96 (m, 1H), 7.72 (m, 2H), 7.62 (m, 2H), 7.52 (m, 1H), 3.24 (m, 2H), 3.20 (s, 3H), 2.20-1.84 (m, 5H), 1.72 (m, 2H), 1.54 (m, 1H). $^{19}F$ NMR ($CD_3OD$, 376 MHz): δ −77.4, −93.78 (d, J=237 Hz), −105.68 (d, J=237 Hz).

Example 242

Synthesis of Compound 292

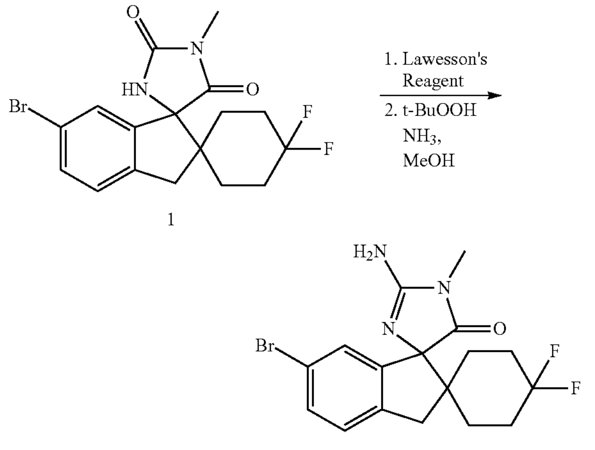

1

292

According to the similar synthesis of compound 291, compound 1 (14 mg, 0.035 mmol) afforded compound 292 (3.8 mg, 21%) as a TFA salt. LC-MS $t_R$=1.33 min in 3 min chromatography, MS (ESI) m/z 398 $[M+H]^+$. $^1H$ NMR ($CD_3OD$, 400 MHz): δ 7.54 (dd, J=0.8, 7.6 Hz, 1H), 7.48 (d, J=0.8 Hz, 1H), 7.34 (d, J=7.6 Hz, 1H), 3.22 (m, 2H), 3.20 (s, 3H), 2.20-1.80 (m, 5H), 1.64 (m, 2H), 1.48 (m, 1H). $^{19}F$ NMR ($CD_3OD$, 376 MHz): δ −77.4, −94.35 (d, J=237 Hz), −105.68 (d, J=237 Hz).

Example 243

Synthesis of Compound 293

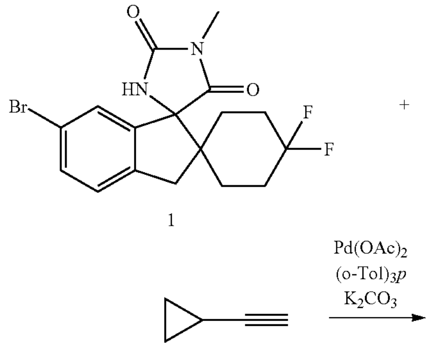

1

-continued

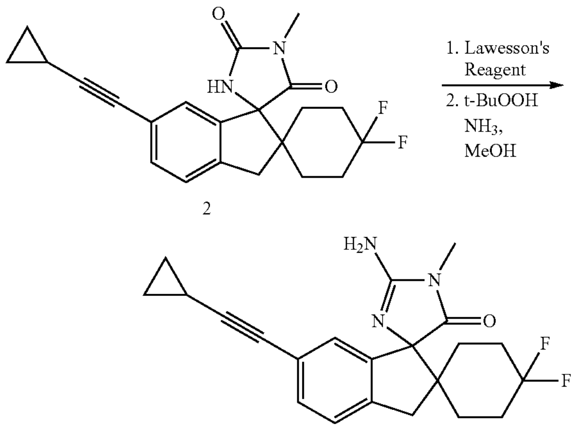

2

293

Procedure for Preparation of Compound 2

A 10 mL CEM microwave tube was charged with compound 1 (107 mg, 0.27 mmol), $Pd(OAc)_2$ (6.1 mg, 10 mol %), $(o\text{-}Tol)_3p$ (16.4 mg, 20 mol %) and $K_2CO_3$ (75 mg, 0.54 mmol). The mixture was degassed then protected with $N_2$. In a separated tube, ethynylcyclopropane in Toluene was degassed at −78° C., then warmed to room temperature. After degassing, excess ethynylcyclopropane in Toluene was added to the microwave tube with other reagents, and the resulting mixture was heated in a CEM microwave reactor at 120° C. for 180 min. The mixture was filtered, and purified by flash chromatography (0 to 60% EtOAx/Hexane) to give compound 2 (28.9 mg, 11%). LC-MS $t_R$=1.82 min in 3 min chromatography, MS (ESI) m/z 385 $[M+H]^+$.

Procedure for Preparation of Compound 293

According to the similar synthesis of compound 291, compound 2 (28.9 mg, 0.075 mmol) afforded compound 293 (9.0 mg, 75%) as a TFA salt. LC-MS $t_R$=1.49 min in 3 min chromatography, MS (ESI) m/z 384 $[M+H]^+$. $^1H$ NMR ($CD_3OD$, 400 MHz): δ 7.34 (m, 2H), 7.22 (s, 1H), 3.20 (m, 2H), 3.20 (s, 3H), 2.16-1.80 (m, 5H), 1.64 (m, 2H), 1.42 (m, 2H), 0.84 (m, 2H), 0.64 (m, 2H). $^{19}F$ NMR ($CD_3OD$, 376 MHz): δ −77.4, −94.29 (d, J=237 Hz), −105.69 (d, J=237 Hz).

Example 244

Synthesis of Compounds 294 and 295

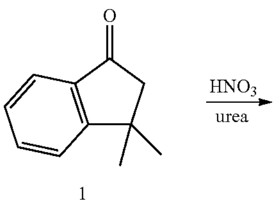

1

-continued
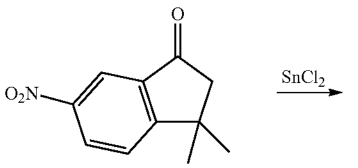
2
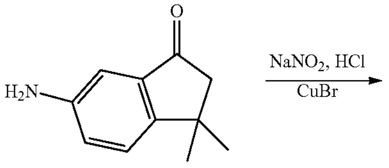
3
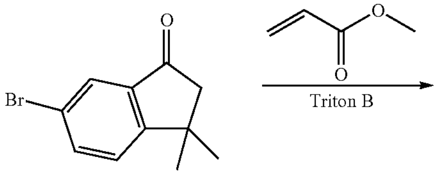
4
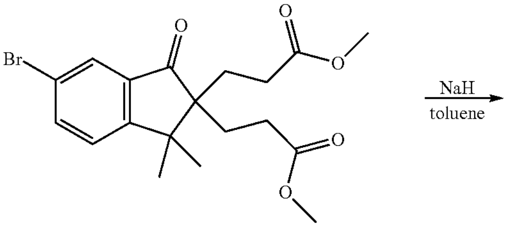
5
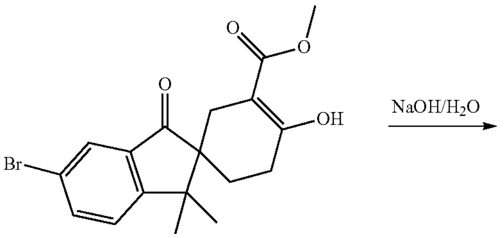
6
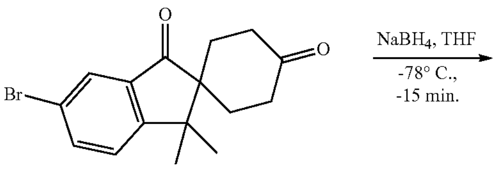
7
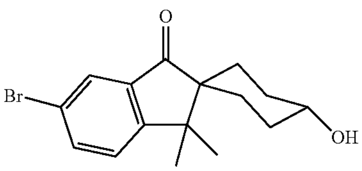
8A
+
-continued
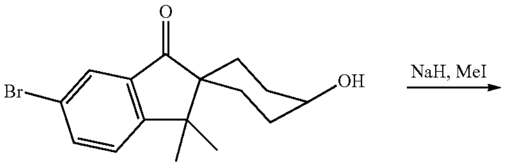
8B
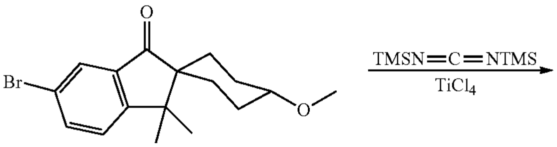
9
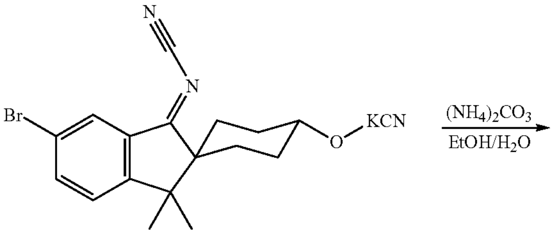
10
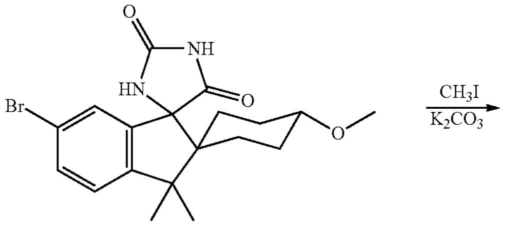
11
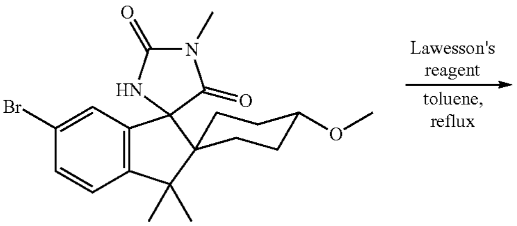
12
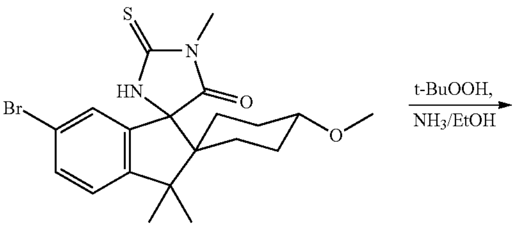
13
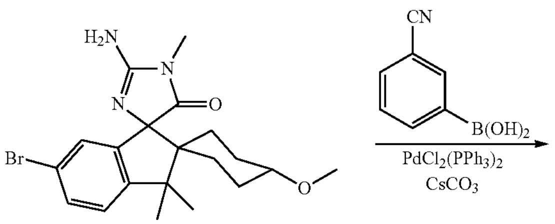
294

-continued

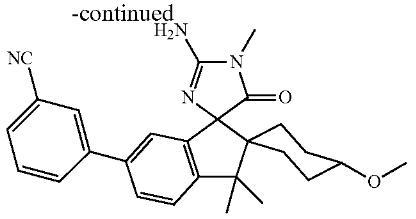

295

Procedure for Preparation of Compound 2

To a well-stirred solution of fuming nitric acid (40 mL) was added urea (0.2 g, 3.3 mmol) at room temperature. The solution was cooled to −15° C. and was stirred for 30 min. Compound 1 (10.0 g, 62.5 mmol) was added to the above solution slowly. The resulting mixture was stirred at −15° C. for 30 min. The reaction mixture was poured into ice (50.0 g) and filtered to collect the solid and dried in vacuo to give compound 2 (10.2 g, 80%) as a white solid. $^1$H-NMR ($CDCl_3$ 400 MHz): δ 8.51 (d, J=2.0 Hz, 1H), 8.47 (dd, J=2.4, 8.4 Hz, 1H), 7.67 (d, J=8.4 Hz, 1H), 2.71 (s, 2H), 1.48 (s, 6H).

Procedure for Preparation of Compound 3

To a solution of $SnCl_2$ (44.9 g, 199 mmol) in concentrated HCl (30 mL) was added a solution of compound 2 (10.2 g, 49.8 mmol) in 95% ethanol (10 mL). The resulting mixture was stirred at room temperature overnight. The mixture was treated with 50% aqueous NaOH (100 mL) to form yellow solid. The resulting mixture was filtered, and the filter cake was dissolved in $CH_2Cl_2$ (200 mL) and then was filtered, and the filtrate was dried over $Na_2SO_4$ and concentrated to give compound 3 (8.0 g, 92%) as a white solid.

Procedure for Preparation of Compound 4

A mixture of compound 3 (4.5 g, 25.7 mmol) in ethanol (20 mL) and 40% HBr (10 mL) was cooled to −5° C.~0° C. Then to the above mixture was added a solution of $NaNO_2$ (2.13 g, 30.9 mmol) in $H_2O$ (10 mL) slowly while keeping temperature between −5° C.~0° C. After addition, the mixture was stirred at −5° C.~0° C. for 1 h. Then the resulting diazonium salt solution was added at 0° C. via a pipette to a mixture of CuBr (4.38 g, 30.9 mmol) in 40% aqueous HBr solution (20 mL) at 95° C. and the mixture was heated to reflux and was stirred for 15 min. After cooling down, the resulting mixture was extracted with ethyl acetate (100 mL×3). The combined organic layers were dried over $Na_2SO_4$ and concentrated to give the crude compound 4, which was purified by column chromatography on silica gel (petroleum ether:ethyl acetate=100:1) to give compound 4 (3.3 g, 54%) as a white solid.

Procedure for Preparation of Compound 5

Compound 4 (3.0 g, 12.6 mol) was dissolved in dry toluene (400 mL) and was heated at 100° C. under $N_2$. Benzyltrimethylammoniumhydroxide (3 mL, 0.92 g/mL) was added dropwise to the reaction mixture at 100° C. and was stirred at 100° C. for 30 min. Methylacrylate (40 mL, 0.954 g/mL) was added dropwise to the reaction mixture. The reaction mixture was refluxed at 100° C. overnight. TLC (petroleum ether: ethyl acetate=5:1) showed compound 4 was consumed. The reaction mixture was poured into water (600 mL) and extracted with $CH_2Cl_2$ (200 mL×3). The combined organic layer was dried over $Na_2SO_4$ and concentrated in vacuo to give the crude compound 5 (4.0 g), which was purified by column chromatography (petroleum ether:ethyl acetate=10:1) to give pure compound 5 (1.7 g, 33%) as a red oil.

Procedure for Preparation of Compound 6

A mixture of compound 5 (1.7 g, 4.24 mmol) in dry toluene (100 mL) was added NaH (0.7 g, 16.97 mmol) slowly under $N_2$. The resulting mixture was heated at reflux overnight. The reaction mixture was added dropwise to water (200 mL) and extracted with EtOAc (100 mL×3). The combined organic layer was dried over $Na_2SO_4$ and concentrated in vacuo to give the crude compound 6 (1.1 g, crude), which was used in next step directly.

Procedure for Preparation of Compound 7

Compound 6 (1.1 g, 2.94 mmol) was dissolved in $CH_3OH$ (20 mL) and NaOH/$H_2O$ (26 mL, 0.77 mol/L). The resulting mixture was heated at reflux for 4 h. TLC (petroleum ether: ethyl acetate=5:1) showed compound 6 was consumed. $CH_2Cl_2$ (50 mL) was added. The separated organic layer was dried over $Na_2SO_4$ and concentrated in vacuo to give compound 7 (970 mg, 92%). $^1$H NMR ($CDCl_3$ 400 MHz): δ 7.78 (s, 1H), 7.65 (dd, J=1.2 Hz, 8.0 Hz, 1H), 7.28 (d, J=8.0 Hz, 1H), 2.92 (m, 2H), 2.26 (m, 2H), 1.87 (m, 4H), 1.18 (s, 6H).

Procedure for Preparation of Compound 8

Compound 7 (700 mg, 2.18 mmol) was dissolved in anhydrous THF (70 mL) and was cooled to −78° C. $NaBH_4$ (24.8 mg, 0.66 mmol) was added dropwise to the reaction mixture at −78° C. No more than 5 min, TLC (petroleum ether:ethyl acetate=1:1) showed compound 7 was consumed. $CH_3OH$ (10 mL) and EtOAc (20 mL) was added and allowed to warm to room temperature. Water (50 mL) was added and concentrated in vacuo to remove THF and $CH_3OH$. EtOAc (30 mL×3) was added again to dissolve the residue. The organic layer was separated, dried over $Na_2SO_4$ and concentrated in vacuo to give the crude compound 8 (650 mg, 90% crude yield), which was used in next step without purification.

Procedure for Preparation of Compound 9

Compound 8 (650 mg, 1.89 mmol) was dissolved in anhydrous THF (30 mL) and was cooled to 0° C. NaH (379 mg, 9.47 mmol) was added to the reaction mixture at 0° C. slowly. After being stirred for 15 min, MeI (7.27 g, 37.89 mmol) was added dropwise to the reaction mixture at 0° C. The reaction mixture was stirred at 0° C. for 1 h and stirred at room temperature overnight. TLC (petroleum ether:ethyl acetate=5:1) showed compound 8 was consumed. Ethyl acetate (150 mL) and water (100 mL) was added. The separated organic layer was dried over $Na_2SO_4$ and concentrated in vacuo, which was purified by column chromatography on silica gel (petroleum ether:ethyl acetate=5:1) to give pure compound 9 (300 mg, 44% for the two steps) as a yellow solid. $^1$H NMR ($CDCl_3$ 400 MHz): δ 7.72 (s, 1H), 7.59 (d, J=8.0 Hz, 1H), 7.22 (d, J=8.4 Hz 1H), 3.29 (s, 3H), 3.08 (m, 1H), 1.83 (m, 4H), 1.62 (m, 2H), 1.42 (m, 2H), 1.13 (s, 6H).

Procedure for Preparation of Compound 10

To a solution of compound 9 (100 mg, 0.3 mmol) in anhydrous $CH_2Cl_2$ (5 mL) was added $TiCl_4$ (0.6 mL, 0.6 mmol, 1M in $CH_2Cl_2$). The mixture was stirred at room temperature for 1 h. To the resulting mixture was added bis-trimethylsilylcarbodiimide (122 mg, 0.65 mmol). The resulting mixture was stirred at room temperature overnight. The reaction mixture was poured into ice-water, extracted with $CH_2Cl_2$ (30 mL). The combined organic layers were dried over anhydrous $Na_2SO_4$, concentrated in vacuo to give compound 10 (140 mg, 80%).

Procedure for Preparation of Compound 11

In a 30 mL steel autoclave was added compound 10 (140 mg, 0.39 mmol), KCN (100 mg, 1.56 mmol) and $(NH_4)_2CO_3$ (373 mg, 3.93 mmol). To this solid mixture was added EtOH (5 mL) and $H_2O$ (5 mL). The steel autoclave was heated and stirred at 70° C. overnight. The reaction mixture was poured into ice-water, filtered to collect the solid and dried in vacuo to give compound 11 (44 mg, 29%) as a white solid.

Procedure for Preparation of Compound 12

To a solution of compound 11 (44 mg, 0.073 mmol) in DMF (3 mL) was added $K_2CO_3$ (20 mg, 0.146 mmol) and MeI (9 mg, 0.066 mmol). The mixture was stirred at room temperature for 3 h. The solution was filtered, and the filtrate was concentrated in vacuo. The residue was purified by preparative TLC on silica gel (petroleum ether:ethyl acetate=3:1) to give compound 12 (17 mg, 40%) as a white solid.

Procedure for Preparation of Compound 13

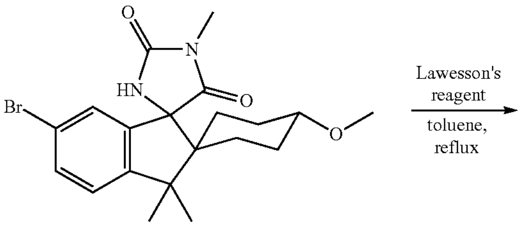

12

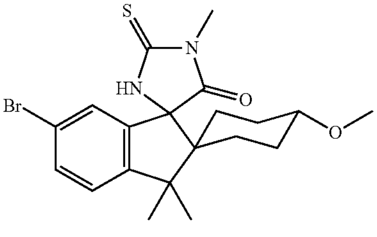

13

A mixture of compound 12 (17 mg, 0.04 mmol) and Lawesson'reagent (16 mg, 0.04 mmol) in toluene (2 mL) was heated at 130° C. for 30 min in a CEM microwave reactor. The mixture was cooled, and concentrated in vacuo. The residue was purified by column chromatography on silica gel (petroleum ether:ethyl acetate=3:1) to give the compound 13 (8 mg, 45%).

Procedure for Preparation of Compound 294

To a solution of compound 13 (8 mg, 0.02 mmol) in a mixture of MeOH (2 mL) and $NH_4OH$ (4 mL) was added t-BuOOH (0.3 mL, 0.37 mmol, 65% in water). The mixture was stirred at room temperature overnight, and concentrated. Water (15 mL) and was added and the mixture was extracted with EtOAc (10 mL×3), and the combined organic layer was dried over $Na_2SO_4$ and concentrated to give the residue which was purified by HPLC to give the compound 294 (1.8 mg, 23%) as a white solid. LC-MS: $t_R$=0.977 min in 2 min chromatography, MS (ESI) m/z=419 $[M+H]^+$. $^1H$ NMR ($CD_3OD$ 400 MHz): δ 7.58 (dd, J=2.0, 8.1 Hz, 1H), 7.47 (d, J=1.6 Hz, 1H), 7.30 (d, J=8.0 Hz, 1H), 3.35 (s, 3H), 3.32 (s, 3H), 3.29 (m, 1H), 2.05 (m, 2H), 1.76 (m, 2H), 1.45 (m, 2H), 1.45 (s, 3H), 1.36 (s, 3H), 0.91 (m, 1H).

Procedure for Preparation of Compound 295

$Pd(PPh_3)_2Cl_2$ (8 mg) in a 10 mL of flask under $N_2$ was treated sequentially with compound compound 294 (40 mg, 0.06 mmol), in 1,4-dioxane (3 mL), and compound 1A (20 mg, 0.12 mmol), $Cs_2CO_3$ (2 N, 0.84 mL). The mixture was stirred at 120° C. 15 min under $N_2$ in CEM microwave reactor. The reaction mixture was concentrated in vacuo to give the residue, which was purified by preparative TLC on silica gel ($CH_2Cl_2$:MeOH=10:1) and by HPLC (0.1% TFA as additive) to give compound 295 (8 mg, 24%) as a white solid. LC-MS: $t_R$=1.076 min in 2 min chromatography, MS (ESI) m/z=442, 443 $[M+H]^+$. $^1H$ NMR ($CD_3OD$ 400 MHz): δ 8.02 (d, 1H), 7.92 (dd, 1H), 7.72 (m, 1H), 7.68 (m, 1H), 7.60 (t, 1H), 7.55 (d, 1H), 7.45 (d, 1H), 3.33 (s, 3H), 3.28 (m, 2H), 3.25 (m, 1H), 2.02 (m, 3H), 1.78 (m, 2H), 1.58 (m, 2H), 1.45 (s, 3H), 1.36 (s, 3H), 0.96 (m, 1H).

Example 245

Synthesis of Compound 296

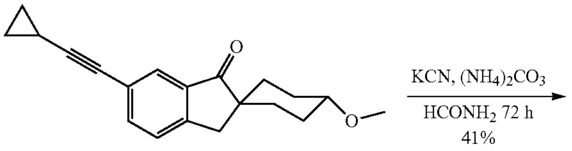

1

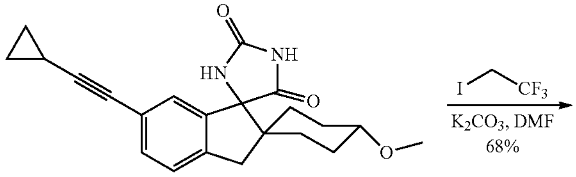

2

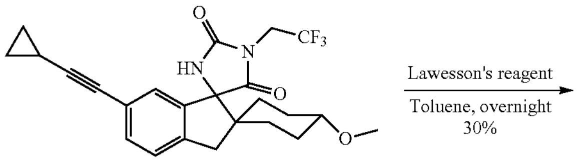

3

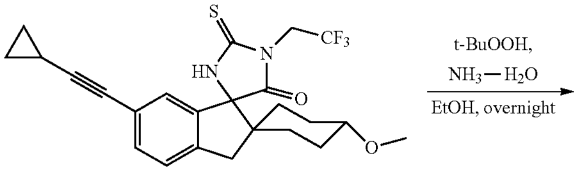

4

-continued

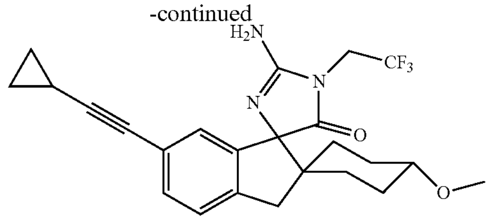

296

Procedure for Preparation of Compound 2

A steel autoclave was charged with a mixture of compound 1 (1.5 g, 5.1 mmol), KCN (0.7 g, 10.7 mmol), and $(NH_4)_2CO_3$ (4.0 g, 41.7 mmol). Formamide (60 mL) was added to the tube. The mixture was heated at 120° C. for 72 h, and the reaction mixture was cooled, and poured into ice-water (200 ml). After acidification with concentrated aqueous HCl solution (10 mL), the mixture was extracted with ethyl acetate (4×100 mL), and the combined organic layers were washed with brine (2×100 mL). The separated organic phase was dried over $Na_2SO_4$ and concentrated in vacuo. The residue was purified by column chromatography over silica gel (petroleum ether:EtOAc=5:1 to 1:1) to give compound 2 (0.78 g, 41%) as pale yellow solid. LC-MS: $t_R$=1.83 min in 3 min chromatography, MS (ESI) m/z 365.1 $[M+H]^+$. $^1H$ NMR ($CDCl_3$ 400 MHz): δ 8.27 (s, 1H), 7.20-7.25 (dd, J=1.2, 5.2 Hz, 1H), 7.15-7.20 (d, 1H, J=1.2 Hz), 7.05-7.15 (d, 1H, J=5.2 Hz), 6.05 (s, 1H), 3.35-3.40 (s, 3H), 3.00-3.10 (m, 2H), 2.90-3.00 (m, 1H), 1.95-2.05 (m, 2H), 1.15-1.45 (m, 6H), 0.75-0.85 (m, 2H), 0.65-0.75 (m, 2H).

Procedure for Preparation of Compound 3

A steel autoclave was charged with a mixture of compound 2 (0.15 g, 0.41 mmol), 1,1,1-trifluoro-2-iodo-ethane (0.30 g, 1.4 mmol) and $K_2CO_3$ (0.30 g, 5.2 mmol) in DMF (2 mL). The mixture was heated at 80° C. for 2 h in a CEM microwave reactor. The reaction mixture was then cooled and poured into brine (40 ml). The mixture was extracted with ethyl acetate (3×20 mL). The combined organic layers were washed with brine (2×20 mL). The separated organic phase was dried over $Na_2SO_4$ and concentrated in vacuo, the resulting residue was purified by column chromatography on silica gel (petroleum ether:EtOAc=50:1 to 2:1) to give compound 3 (0.12 g, 68%) as a white solid. LC-MS: $t_R$=2.11 min in 3 min chromatography, MS (ESI) m/z 447.1 $[M+H]^+$.

Procedure for Preparation of Compound 4

A flask equipped with a condenser and a nitrogen balloon was charged with a mixture of compound 3 (0.12 g, 0.22 mmol), Lawesson's reagent (0.48 g, 1.2 mmol) in toluene (30 mL). The reaction mixture was heated to 130° C. for 4 h. After cooling down, the precipitate was filtered off and washed with ethyl acetate (2×40 mL). The filtrate and the washing were concentrated in vacuo and the residue was purified by column chromatography on silica gel (petroleum ether:EtOAc, 50:1 to 2:1) to give compound 4 with 80% purity (30 mg, 30%) as a white solid.

Procedure for Preparation of Compound 296

To a solution of compound 4 (15 mg, 0.032 mmol) in EtOH (2 mL) was added $NH_3$—$H_2O$ (0.5 ml) and tert-butyl hydroperoxide (0.10 g, 1.1 mol). After addition, the mixture was stirred at ambient temperature for 3 h. The mixture was concentrated in vacuo and the residue was purified by preparative RP-HPLC to give compound 296 (6.4 mg, 31%) as a white solid. LC-MS: $t_R$=1.75 min in 3 min chromatography, MS (ESI) m/z 446.2 $[M+H]^+$. $^1H$ NMR: ($CD_3OD$, 400 MHz): δ 7.35-7.40 (d, J=8.0 Hz, 1H), 7.30-7.35 (d, J=7.6 Hz, 1H), 7.18-7.22 (s, 1H), 4.58-4.70 (m, 1H), 4.45-4.55 (m, 1H), 3.35-3.40 (s, 3H), 3.15-3.25 (m, 2H), 3.05-3.15 (m, 1H), 1.95-2.15 (m, 2H), 1.80-1.90 (m, 1H), 1.40-1.50 (m, 4H), 1.25-1.40 (m, 2H), 0.85-0.95 (m, 2H), 0.65-0.75 (m, 2H).

Example 246

Synthesis of Compound 297

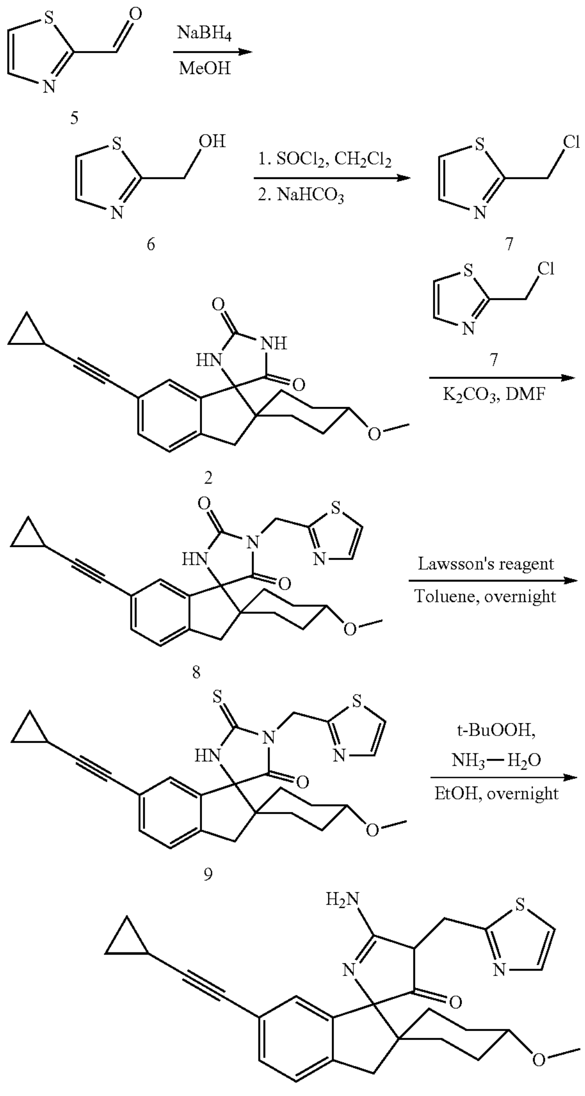

297

Procedure for Preparation of Compound 2

To a mixture of 2-formylthiazole (0.30 g, 2.65 mmol) and methanol (30 mL) was added sodium borohydride (0.20 g, 5.30 mmol) at 0° C., the resulting mixture was stirred at ambient temperature for 1 h. Water (1 mL) was added to this reaction mixture to quench the reaction. The solvent was removed by evaporation in vacuo. $H_2O$ (30 mL) was added and the mixture was adjusted to pH=7-8 by addition of 1 N HCl. The mixture was extracted with ethyl acetate (contained 10% ethanol) (3×30 mL). The combined organic layers were washed with brine (2×30 mL), dried over $Na_2SO_4$, filtered and concentrated in vacuo to give compound 6 (0.30 g, 100% crude yield) as a yellow oil. $^1$H NMR ($CDCl_3$, 400 MHz): δ 7.65-7.70 (d, J=3.2 Hz, 1H), 7.20-7.30 (d, J=3.2 Hz, 1H), 4.89-4.96 (s, 2H).

Procedure for Preparation of Compound 7

To a solution of compound 6 in $CH_2Cl_2$ (30 mL) was added $SOCl_2$ (0.34 g, 2.86 mmol) via a syringe at 0° C. under a nitrogen atmosphere. The reaction mixture was stirred at 0° C. for 1 h and then allowed to warm to ambient temperature overnight. Saturated $NaHCO_3$ (15 mL) was added and the mixture was stirred at ambient temperature for another 10 min. After stirring, the mixture was separated and the aqueous layer was extracted with $CH_2Cl_2$ (2×10 mL). The combined organic layers were washed with brine (2×10 mL), dried over $Na_2SO_4$, filtered and concentrated in vacuo to give crude compound 7 (0.26 g, 74% crude yield) as a red oil, which was used for the next step without purification. $^1$H NMR: ($CDCl_3$ 400 MHz): δ 7.75-7.85 (d, J=3.2 Hz, 1H), 7.40-7.45 (d, J=3.2 Hz, 1H), 4.90-4.95 (s, 2H).

Procedure for Preparation of Compound 297

According to a similar synthesis of compound 296, compound 2 described in Example 245 (0.10 g, 0.23 mmol) was alkylated with compound 7 (50 mg, 0.37 mmol) in the presence of $K_2CO_3$ (0.10 g, 0.72 mmol) in DMF (2 mL) to give compound 8 (0.12 g, 95%) as a yellow solid. LC-MS: $t_R$=1.99 min in 3 min chromatography, MS (ESI) m/z 462.1 $[M+H]^+$. $^1$H NMR: ($CDCl_3$, 400 MHz): δ 7.55-7.85 (d, J=3.2 Hz, 1H), 7.32-7.40 (m, 2H,), 7.20-7.30 (m, 2H), 5.70-5.75 (s, 1H), 5.00-5.10 (s, 2H), 3.35-3.45 (s, 3H), 3.18-3.22 (m, 1H), 3.10-3.18 (m, 1H), 3.05-3.10 (m, 1H). 2.05-2.15 (m. 1H), 1.95-2.05 (m, 2H), 1.35-1.50 (m, 6H), 0.85-0.95 (m, 2H), 0.75-0.85 (m, 2H).

Compound 8 (0.12 g, 0.26 mmol) was then reacted with Lawesson's reagent (0.25 g, 0.62 mmol) to give compound 9 with 74% purity (30 mg, 25%) as a yellow solid, which was used for the next step directly without purification. LC-MS: $t_R$=1.23 min in 3 min chromatography, MS (ESI) m/z 478 $[M+H]^+$.

Finally, compound 9 (30 mg, 0.063 mmol) was converted to compound 297 (12 mg, 34%) as a white solid. LC-MS: $t_R$=1.70 min in 3 min chromatography, MS (ESI) m/z 461.2 $[M+H]^+$. $^1$H NMR ($CD_3OD$, 400 MHz): δ 7.78-7.82 (d, J=3.2 Hz, 1H), 7.60-7.70 (d, J=3.2 Hz, 1H), 7.35-7.40 (d, J=7.6 Hz, 1H), 7.28-7.35 (d, J=7.6 Hz, 1H), 7.20-7.25 (s. 1H), 5.27-5.35 (d, J=17.2 Hz, 1H), 5.20-5.27 (d, J=17.6 Hz, 1H), 3.35-3.40 (s, 3H), 3.15-3.25 (m, 2H), 3.05-3.15 (m, 1H), 3.05-3.10 (m, 1H). 2.00-2.10 (m. 2H), 1.75-1.85 (m, 1H), 1.40-1.55 (m, 5H), 1.25-1.35 (m, 1H), 0.85-0.95 (m, 2H), 0.65-0.75 (m, 2H).

Example 247

Synthesis of Compound 298

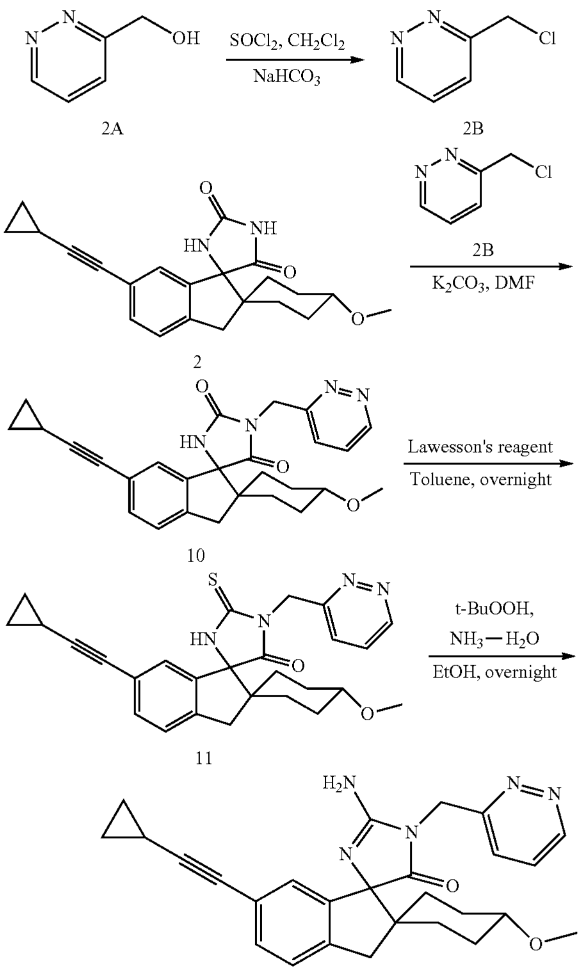

2A 2B 2B 2 10 11 298

Procedure for Preparation of Compound 2B

To a solution of 2A (200 mg, 1.8 mmol) in anhydrous $CH_2Cl_2$ (10 mL) was added $SOCl_2$ (428 mg, 3.6 mmol) at 0° C., the mixture was stirred at 0° C. for 10 min, then was allowed to warm to room temperature overnight. The reaction was quenched by addition of aq. sat. $NaHCO_3$ (10 mL), then was extracted with $CH_2Cl_2$ (2×10 mL). The combined organic layers were washed with brine (20 mL), dried over $Na_2SO_4$ and concentrated to give compound 2B (100 mg, 43%) as a yellow solid, which was used in the next step without further purification. $^1$H NMR: (DMSO-$d_6$ 400 MHz): 9.21 (d, J=4.8 Hz, 1H), 7.94 (d, J=8.0 Hz, 1H), 7.73 (m, 1H), 5.05 (s, 2H).

Procedure for Preparation of Compound 298

According to a similar synthesis of compound 296, compound 2 described in Example 245 (200 mg, 0.54 mmol) was alkylated with compound 2B (77.3 mg, 0.60 mmol) to give compound 10 (100 mg, 40%) as a yellow solid. which was used in the next step without further purification; LCMS: $t_R$=1.239 min in 2 min chromatography, MS (ESI) m/z 457.2 [M+H]

Compound 10 (15 mg, 0.032 mmol) was reacted with Lawesson's reagent (13.2 mg, 0.032 mmol) under a nitrogen atmosphere to afford compound 11 (10 mg, 64%) as a white solid. LCMS: $t_R$=1.313 min in 2 min chromatography, MS (ESI) m/z 473.1 [M+H]

Finally, compound 11 (10 mg, 0.02 mmol) in EtOH (1 mL) was converted to compound 298 (1 mg, 10%) as a white solid. LCMS: $t_R$=1.750 min in 2 min chromatography, MS (ESI) m/z 456.2 $[M+H]^+$. $^1$H NMR ($CD_3OD$ 400 MHz): δ 9.16 (d, J=4.8 Hz, 1H), 7.77 (d, J=4.8 Hz, 2H), 7.29 (d, J=6.8 Hz, 2H), 7.24 (s, 1H), 5.18 (d, J=16.8 Hz, 2H), 3.36 (s, 3H), 3.15-3.21 (m, 1H), 3.09 (s, 2H), 2.05-1.98 (m, 2H), 1.79-1.76 (m, 1H), 1.76-1.64 (m, 1H), 1.64-1.49 (m, 4H), 1.36-1.28 (m, 1H), 0.91 (m, 2H), 0.7 (m, 2H).

Example 248

Synthesis of Compound 299

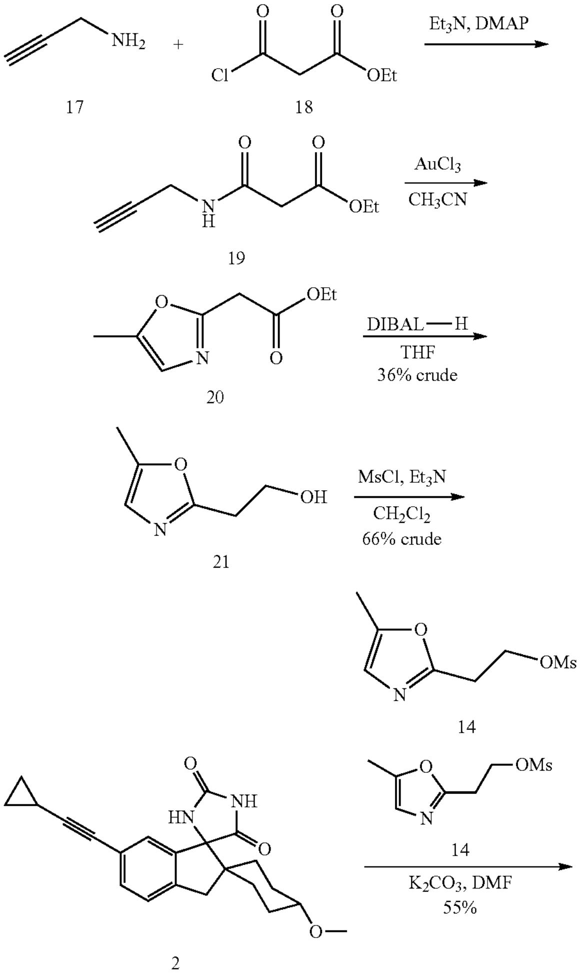

-continued

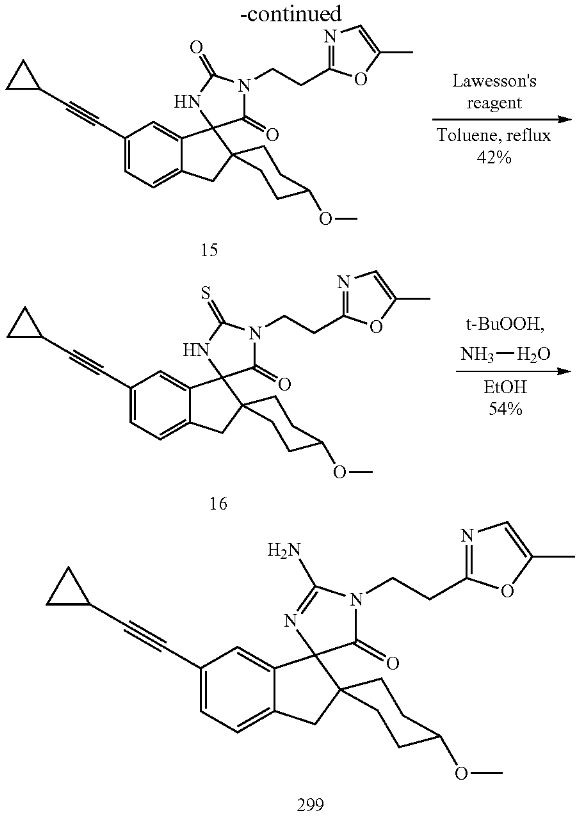

299

Procedure for Preparation of Compound 19

To a stirred 0° C. solution of compound 17 (2.00 g, 36.30 mmol), $Et_3N$ (3.70 g, 36.30 mmol) and DMAP (85 mg, 7.80 mmol) in $CH_2Cl_2$ (2 mL) under Argon was added dropwise slowly a solution of compound 18 (5.50 g, 36.30 mmol) in $CH_2Cl_2$ (12 mL). The reaction was stirred at 0° C. for 1 h. The temperature was allowed to rise to room temperature. The reaction was stirred at room temperature overnight. The solvent was removed in vacuo to give crude product, which was purified by silica gel with hexane:ethyl acetate (4:1) to give compound 19 (4.10 g, 67%) as a yellow oil. $^1$H NMR ($CDCl_3$, 400 MHz): δ 8.02 (s, 1H), 4.27 (s, 1H), 4.48 (s, 1H), 4.06 (s, 2H), 3.56-3.51 (m, 1H), 3.40-3.25 (m, 3H), 3.07-3.00 (m, 1H).

Procedure for Preparation of Compound 20

To a stirred solution of compound 19 (2.40 g, 14.2 mmol) in $CH_3CN$ (40 mL) under Argon was added $AuCl_3$ (432 mg, 1.42 mmol) at room temperature. The reaction was heated to reflux overnight. The solvent was removed in vacuo to give crude product, which was purified by silica gel with hexane/ethyl acetate (10:1 to 5:1) to give compound 20 (1.00 g, 42%) as a yellow oil. $^1$H NMR ($CDCl_3$, 400 MHz): δ 6.65 (s, 1H), 4.20-4.15 (m, 2H), 3.76 (s, 3H), 1.25-1.20 (t, J=7.2 Hz, 3H).

Procedure for Preparation of Compound 21

To a solution of compound 20 (0.60 g, 3.72 mmol) in anhydrous THF (30 mL) was added DIBAL-H (4.5 mL, 4.5 mmol, 1 M in toluene) at 0° C. under nitrogen. The mixture was stirred at 0° C. for 4 h, and then was warmed to ambient temperature overnight. The mixture was cooled to 0° C. again, and then was quenched by adding $H_2O$ (0.18 mL), 15% NaOH aq. (0.18 mL) and $H_2O$ (0.45 mL). The mixture was warmed to ambient temperature, then $MgSO_4$ (5 g) and EtOAc (30 mL) were added with stirring. After stirring at ambient temperature for 15 min, the precipitate was filtered off and was washed with EtOAc (20 mL). The combined organic fractions were concentrated in vacuo to give crude compound 21 (0.17 g, 36% crude yield) as a yellow oil, which was used directly in next step without purification.

Procedure for Preparation of Compound 14

To a solution of compound 21 (0.16 g, 1.26 mmol, crude) and $Et_3N$ (0.30 g, 2.96 mmol) in anhydrous THF (10 mL) was added MsCl (0.22 g, 1.89 mmol) at 0° C. under nitrogen with stirring. The mixture was stirred at 0° C. for 1 h, and then was warmed to ambient temperature overnight. The mixture was cooled to 0° C. again, and then $H_2O$ (20 mL) and EtOAc (20 mL) were added with stirring. The mixture was separated and the aqueous layer was extracted with EtOAc (2×10 mL). The combined organic layers were washed with brine (2×10 mL), dried over $Na_2SO_4$, filtered and concentrated in vacuo to give crude compound 14 (0.17 g, 66% crude yield) as a yellow oil, which was used directly in next step without purification.

Procedure for Preparation of Compound 299

According to a similar synthesis of compound 296, compound 2 described in Example 245 (100 mg, 0.27 mmol) was alkylated with compound 14 to give compound 15 (70 mg, 55%) as a white solid. LC-MS: $t_R$=1.897 min in 3 min chromatography, MS (ESI) m/z=474 $[M+H]^+$. $^1H$ NMR ($CDCl_3$ 400 MHz): δ 7.24 (d, J=6.4 Hz, 1H), 7.12 (d, J=7.6, 1H), 6.52 (s, 1H), 5.23 (m, 1H), 3.80 (t, J=6.8 Hz, 1H), 3.28 (s, 3H), 2.98-3.05 (m, 5H), 2.14 (s, 3H), 1.85-2.03 (m, 2H), 1.78 (m, 1H), 1.15-1.35 (m, 6H), 0.80 (m, 2H), 0.71 (m, 2H).

Compound 15 (70 mg, 0.15 mmol) was then reacted with Lawesson's reagent to give compound 16 (22 mg, 30%, 42% purity) as a white solid. LC-MS: $t_R$=1.434 min in 2 min chromatography, MS (ESI) m/z=490 $[M+H]^+$.

Finally, compound 16 (22 mg, 0.018 mmol, 42% purity) was converted to compound 299 (4.6 mg, 54%) as a white solid. LC-MS: $t_R$=1.563 min in 3 min chromatography, MS (ESI) m/z=473 $[M+H]^+$. $^1H$ NMR ($CD_3OD$ 400 MHz): δ 7.13 (dd, J=1.6, 8.0 Hz, 1H), 7.09 (d, J=7.6 Hz, 1H), 6.83 (s, 1H), 6.53 (d, J=1.2 Hz, 1H), 3.81 (t, J=6.4 Hz, 2H), 3.29 (s, 3H), 3.01 (m, 3H), 2.98 (s, 2H), 2.09 (s, 3H), 1.89 (m, 2H), 1.59 (m, 1H), 1.05-1.50 (m, 6H), 0.75 (m, 2H), 0.60 (m, 2H).

Example 249

Synthesis of Compound 300

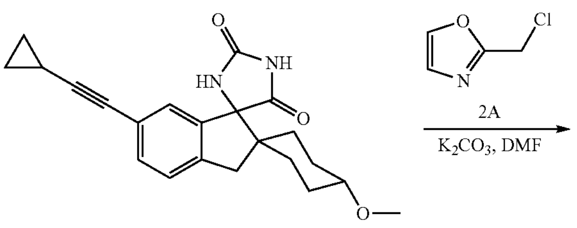

2

-continued

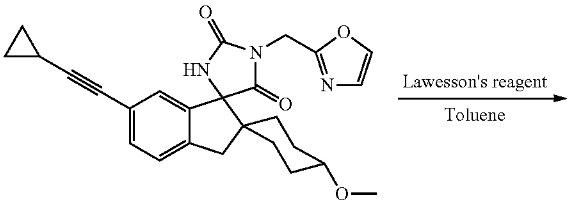

3

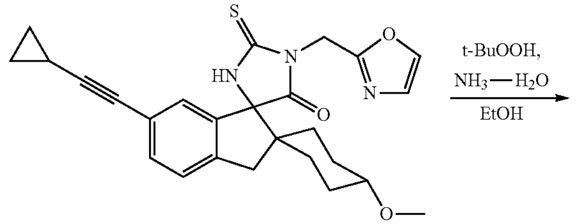

4

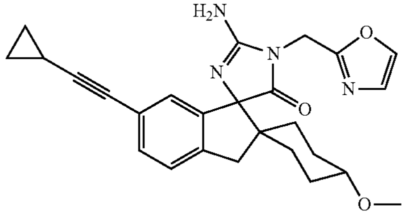

300

According to a similar synthesis of compound 296, compound 2 described in Example 245 (0.10 g, 0.27 mmol) was alkylated with 2-chloromethyl-oxazole (2A) (0.032 g, 0.27 mmol) to give compound 3 (0.056 g, 69%) as a pale yellow solid. LC-MS $t_R$=1.770 min in 3 min chromatography, MS (ESI) m/z 446 $[M+H]^+$. $^1H$ NMR ($CDCl_3$ 400 MHz): δ7.51 (s, 1H), 7.24 (dt, J=7.6, 1.2 Hz, 1H), 7.16 (m, 2H), 6.97 (s, 1H), 6.37 (s, 1H), 4.73 (s, 2H), 3.28 (s, 3H), 3.10 (m, 2H), 2.97 (d, J=15.6, 1H), 2.01 (m, 1H), 1.88 (m, 2H), 1.15-1.60 (m, 6H), 0.80 (m, 2H), 0.68 (m, 2H).

Compound 3 (65 mg, 0.15 mmol) was then reacted with Lawesson's reagent (70 mg, 0.17 mmol) to give compound 4 (30 mg, 43%) as a pale yellow solid, which was converted compound 300 (9.9 mg, 34%) as a white solid. LC-MS: $t_R$=1.509 min in 3 min chromatography, MS (ESI) m/z 445 $[M+H]^+$. $^1H$ NMR ($CD_3OD$ 400 MHz): δ 7.89 (s, 1H), 7.26 (d, J=1.6 Hz, 1H), 7.24 (d, J=1.2 Hz, 1H), 7.15 (s, 1H), 7.02 (s, 1H), 4.89 (s, 2H), 3.35 (s, 3H), 3.15 (m, 1H), 3.11 (d, J=16.8 Hz, 1H), 3.06 (d, J=15.6 Hz, 1H), 2.03 (m, 2H), 1.84 (m, 1H), 1.65 (m, 1H), 1.20-1.50 (m, 5H), 0.89 (m, 2H), 0.71 (m, 2H).

Example 250

Synthesis of Compound 301

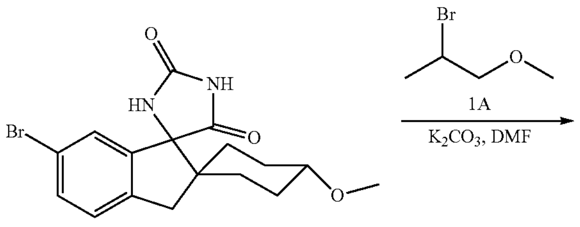

1

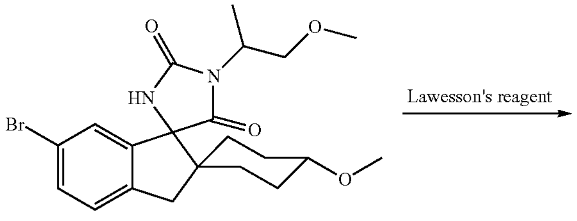

2

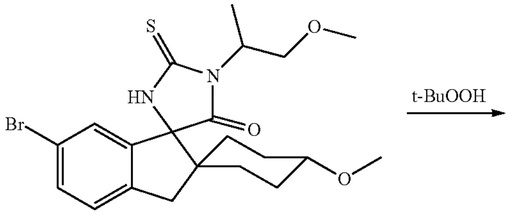

3

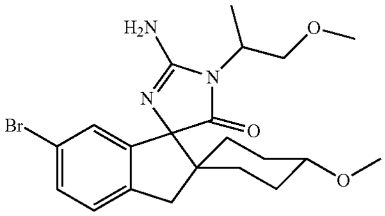

301

Procedure for Preparation of Compound 2

To a solution of compound 1 (350 mg, 0.923 mmol) in DMF (15 mL) was added $K_2CO_3$ (382 mg, 2.77 mmol). After being stirred for 5 min, compound 1A (169 mg, 1.1 mmol) was added, and the reaction mixture was stirred at room temperature for 5 h, LCMS showed that the reaction was completed. The reaction mixture was poured into water (20 mL), extracted with EtOAc (2×20 mL). The combined organic phases were dried over anhydrous $Na_2SO_4$ and filtered. The filtrate was concentrated and purified by preparative TLC (petroleum/ethyl acetate=1:1) to give compound 2 (233 mg, 56%) as a white solid.

Procedure for Preparation of Compound 3

A solution of compound 2 (200 mg, 0.44 mmol) and Lawesson's Reagent (197 mg, 0.487 mmol) in dry toluene (20 mL) was heated to reflux for 5 h under $N_2$ atmosphere. LCMS showed that the reaction was completed, the mixture was concentrated under reduced pressure, and the residue was purified by preparative TLC (petroleum/ethyl acetate=2:1) to give compound 3 (180 mg, 87%) as a white solid.

Preparation of Compound 301

A mixture of compound 3 (180 mg, 0.385 mmol) and t-butyl hydroperoxide (1.07 g of a 65% solution in water, 7.7 mmol) in $NH_4OH$/MeOH (4/20 mL) was stirred overnight at room temperature, LCMS showed that the reaction was completed. The solvent was concentrated under reduced pressure to dryness. Purification of this residue by preparative TLC (petroleum/ethyl acetate=1:1) afforded compound compound 301 (130 mg, 75%) and one part was further purified by preparative HPLC to give compound compound 301 (5.5 mg delivered) as a white solid. LC-MS $t_R$=1.002 min in 2 min chromatography, MS (ESI) m/z 450.1 & 452.1 $[M+H]^+$. $^1H$ NMR ($CD_3OD$, 400 MHz): δ 7.40-7.43 (d, J=8.0 Hz, 1H), 7.23-7.25 (d, J=8.0 Hz, 1H), 7.11-7.15 (d, J=15.2 Hz, 1H), 4.27-4.32 (m, 1H), 3.77-3.90 (tt, 1H), 3.46-3.53 (m, 1H), 3.38-3.40 (d, J=8.4 Hz, 6H), 3.12-3.18 (m, 1H), 3.05 (s, 2H), 1.96-2.06 (m, 2H), 1.86-1.92 (m, 1H), 1.59-1.65 (m, 1H), 1.24-1.44 (m, 7H).

Example 251

Synthesis of Compound 302

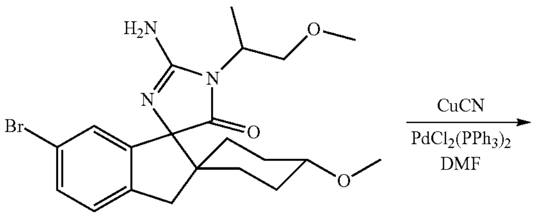

301

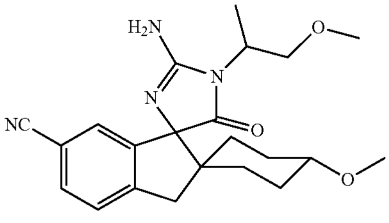

302

To a solution of compound 301 (30 mg, 0.067 mmol) in DMF (5 mL) was added $PdCl_2(PPh_3)_2$ (3 mg) and CuCN (60 mg, 0.67 mmol) under $N_2$ atmosphere, the resulting mixture was degassed and purged with $N_2$ for three times. The reaction was heated to 180° C. for 30 min in microwave. LCMS showed that the reaction was completed, and the solvent was removed under reduced pressure. The residue was purified by preparative TLC ($CH_2Cl_2$/MeOH=15:1) and preparative HPLC to give compound 302 (3.0 mg, 11%) as a white solid. LC-MS $t_R$=0.932 min in 2 min chromatography, MS (ESI) m/z 397.2 $[M+H]^+$. $^1H$ NMR ($CD_3OD$, 400 MHz): δ 7.64-7.66 (d, J=8.0 Hz, 1H), 7.49-7.51 (d, J=8.0 Hz, 1H), 7.30-7.35 (d, J=20.4 Hz, 1H), 4.27-4.32 (m, 1H), 3.78-3.90 (tt, 1H), 3.46-3.53 (m, 1H), 3.36-3.38 (d, J=8.4 Hz, 6H), 3.13-3.17 (m, 3H), 1.96-2.06 (m, 2H), 1.87-1.92 (m, 1H), 1.62-1.66 (m, 1H), 1.28-1.40 (m, 7H).

Example 252

Synthesis of Compound 303

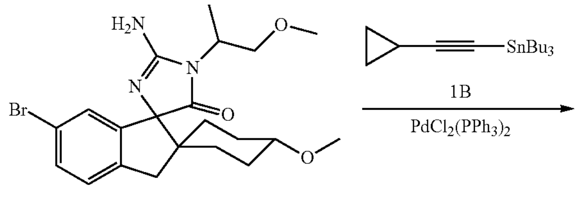

301

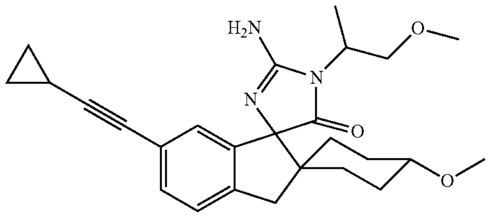

303

A solution containing compound 301 (30 mg, 0.067 mmol) and compound 1B (47 mg, 0.133 mmol) in toluene (4 mL) was deoxygenated by bubbling a stream of nitrogen through the reaction mixture for 5 min. Then, $PdCl_2(PPh_3)_2$ (3 mg) was added. The reaction vial was sealed and placed into CEM microwave reactor and irradiated at 130° C. for 30 min. After being cooled to room temperature, the mixture was partitioned between EtOAc (10 mL) and aqueous CsF (4 M, 10 mL), and the aqueous layer was extracted with EtOAc (3×10 mL). The combined organic layers were washed with brine (10 mL), dried over anhydrous $Na_2SO_4$, filtered, and concentrated in vacuo. The residue was purified by preparative TLC (petroleum/ethyl acetate=1:1) and preparative HPLC to give compound 303 (1.7 mg, 5.8%) as a white solid. LC-MS $t_R$=0.947 min in 2 min chromatography, MS (ESI) m/z 436.3 $[M+H]^+$. $^1H$ NMR ($CD_3OD$, 400 MHz): δ 7.19-7.27 (q, 2H), 6.94 (s, 1H), 4.27-4.34 (m, 1H), 3.78-3.91 (tt, 1H), 3.46-3.53 (m, 1H), 3.36-3.38 (d, J=7.2 Hz, 6H), 3.13-3.19 (m, 3H), 1.83-2.09 (m, 3H), 1.54-1.65 (m, 1H), 1.22-1.49 (m, 8H), 0.84-0.93 (m, 2H), 0.65-0.78 (m, 2H).

Example 253

Synthesis of Compound 304

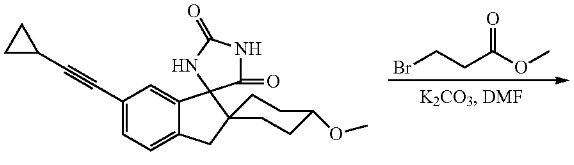

2

-continued

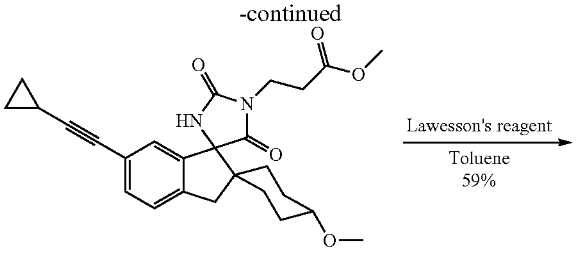

11

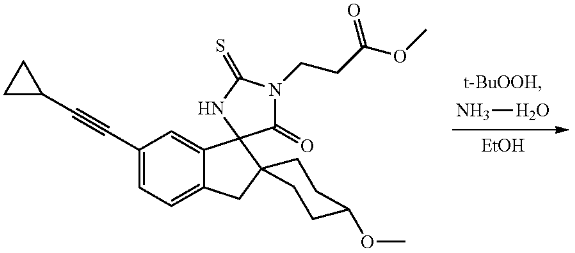

12

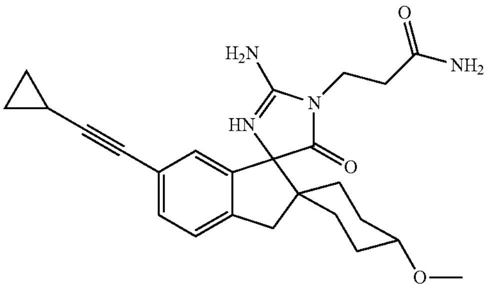

304

According to a similar synthesis of compound 296, compound 2 described in Example 245 (65 mg, 0.18 mmol) was alkylated with 3-Bromo-propionic acid methyl ester (36 mg, 0.22 mmol) to give compound 11 (56 mg, 69%) as a white solid. LC-MS: $t_R$=1.809 min in 3 min chromatography, MS (ESI) m/z=451 $[M+H]^+$. $^1H$ NMR ($CDCl_3$ 400 MHz): δ 7.27 (m, 2H), 7.13 (d, J=10.4 Hz, 1H), 7.04 (s, 1H), 6.31 (s, 1H), 3.71 (t, J=9.6 Hz, 2H), 3.56 (s, 3H), 3.28 (s, 3H), 3.10 (m, 2H), 2.97 (d, J=21.2 Hz, 1H), 2.58 (t, J=9.2 Hz, 2H), 1.70-2.10 (m, 3H), 1.15-1.40 (m, 6H), 0.80 (m, 2H), 0.70 (m, 2H).

Compound 11 (56 mg, 0.11 mmol) was then reacted with Lawesson's reagent (60 mg, 0.15 mmol) in anhydrous toluene (1 mL) under nitrogen to give compound 12 (25 mg, 59%) as a white solid. LC-MS: $t_R$=1.931 min in 3 min chromatography, MS (ESI) m/z=467 $[M+H]^+$.

Finally, compound 12 (25 mg, 0.054 mmol) was converted to compound 304 (10.4 mg, 44%) as a white solid. LC-MS: $t_R$=1.421 min in 3 min chromatography, MS (ESI) m/z=435 $[M+H]^+$. $^1H$ NMR ($CD_3OD$ 400 MHz): δ 7.24 (s, 2H), 6.90 (s, 1H), 3.80 (t, J=6.8 Hz, 2H), 3.33 (s, 3H), 3.15 (m, 2H), 2.97

(d, J=15.6 Hz, 1H), 2.54 (t, J=8.4 Hz, 2H), 1.90-2.10 (m, 2H), 1.84 (m, 1H), 1.65 (m, 1H), 1.25-1.50 (m, 5H), 0.88 (m, 2H), 0.68 (m, 2H).

Example 254

Synthesis of Compound 305

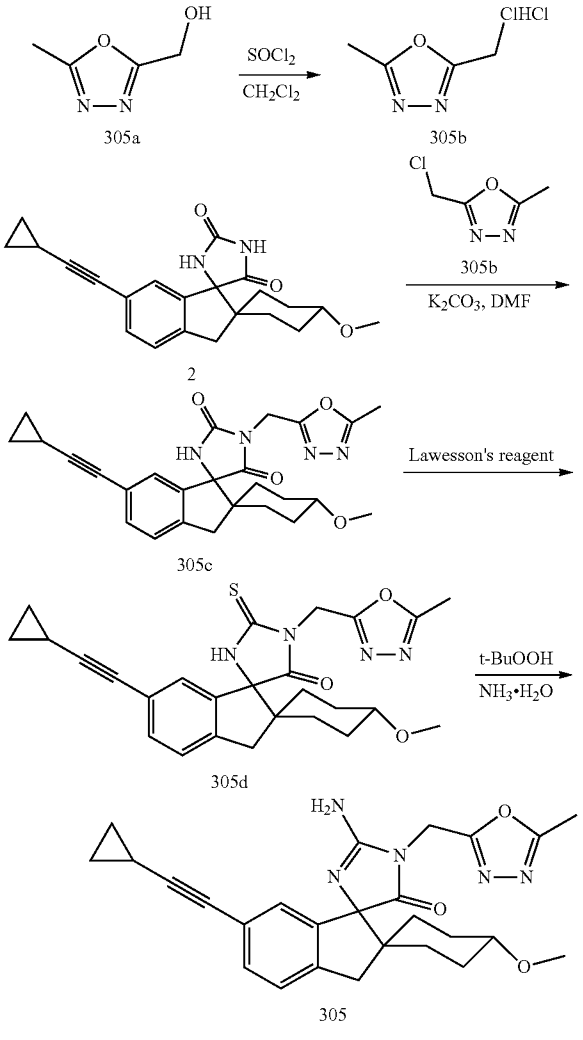

305a, 305b, 2, 305c, 305d, 305

Procedure for Preparation of Compound 305b

To a solution of compound 305a (100 mg, 0.88 mol) in anhydrous $CH_2Cl_2$ (50 mL) was added $SOCl_2$ (130 mg, 1.2 mol). The resulting suspension was stirred at 15° C. for 12 h. The mixture was concentrated to afford the crude compound 305b (95 mg, 80%) as a yellow oil, which was used in next step without purification.

Procedure for Preparation of Compound 305

According to a similar synthesis of compound 296, compound 2 described in Example 245 (70 mg, 0.19 mmol) was alkylated with compound 38 (28 mg, 0.2 mmol) to give compound 39 (70 mg, 80%) as a white solid.

Compound 39 (40 mg, 0.9 mmol) was reacted with Lawesson's Reagent (40 mg, 1.0 mmol) to give compound 39A (18 mg, 45%) as a white solid, which was converted to compound 305 (2.20 mg, yield 15%) as a white solid. LCMS: $t_R$=1.005 min in 2 min chromatography, MS (ESI) m/z=460.2 [M+H]$^+$. $^1$H NMR ($CD_3OD$ 400 MHz): δ 7.20-7.30 (m, 2H), 7.00-7.10 (s, 1H), 5.00-5.05 (s, 2H), 3.30-3.40 (s, 3H), 3.25-3.30 (m, 1H), 3.05-3.10 (m, 2H), 2.55-2.60 (s, 3H), 1.95-2.10 (m, 1H), 1.85-1.90 (m, 1H), 1.55-1.75 (m, 1H), 1.20-1.50 (m, 5H), 0.85-0.95 (m, 2H), 0.65-0.75 (m, 2H).

Example 255

Synthesis of Compound 306

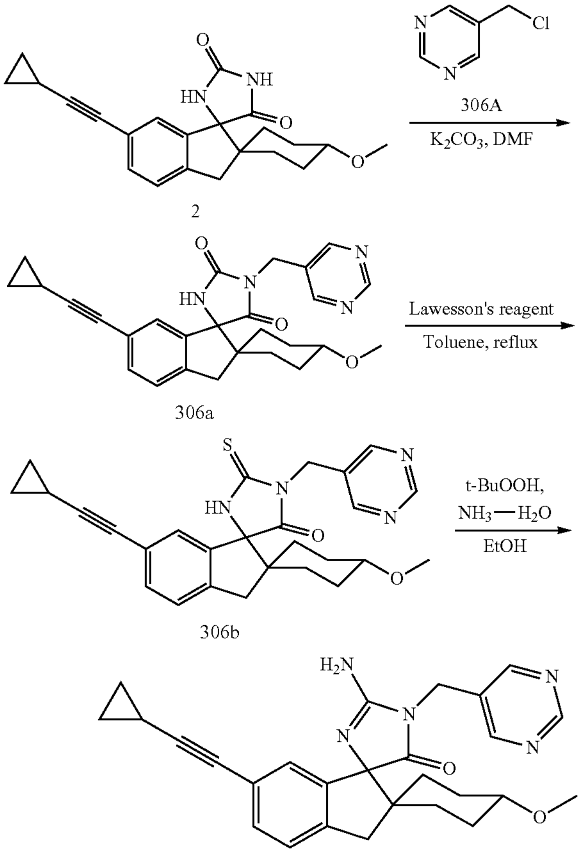

2, 306a, 306b, 306

According to a similar synthesis of compound 296, compound 2 described in Example 245 (100 mg, 0.27 mmol) was alkylated with 5-Chloromethylpyrimidine (306A) (38 mg, 0.30 mmol) to give compound 306a (95 mg, 77%) as a white solid. LC-MS: $t_R$=2.130 min in 3 min chromatography, MS (ESI) m/z 457 [M+H]$^+$.

Compound 306a (90 mg, 0.20 mmol) was then reacted with Lawesson's reagent (120 mg, 0.30 mmol) to give compound 306b (24 mg, 25%) as a white solid, which was converted to compound 306 (6.0 mg, 26%) as a white solid. LC-MS: $t_R$=1.639 min in 3 min chromatography, MS (ESI) m/z 456 [M+H]$^+$. $^1$H NMR: ($CD_3OD$, 300 MHz): δ 9.09 (s, 1H), 8.74 (s, 2H), 7.21 (m, 2H), 6.90 (s, 1H), 4.78 (s, 2H), 3.31 (s, 3H), 3.14 (m, 3H), 1.85-2.10 (m, 2H), 1.75 (m, 1H), 1.25-1.60 (m, 6H), 0.85 (m, 2H), 0.70 (m, 2H).

Example 256

Synthesis of Compound 307

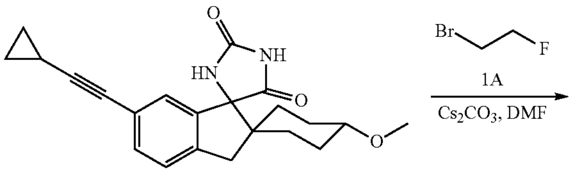

2

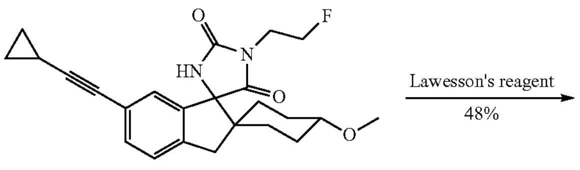

2A

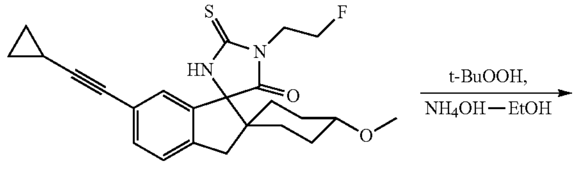

3

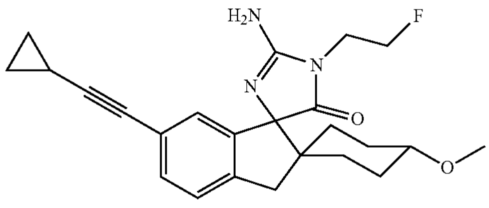

307

According to a similar synthesis of compound 296, compound 2 described in Example 245 (120 mg, 0.33 mmol) was alkylated with compound 1A (50 mg, 0.40 mmol) to give compound 2A (70 mg, 51%) as a white solid.

Compound 2A (30 mg, 0.073 mmol) was then reacted with Lawesson's Reagent (33 mg, 0.080 mmol) to give compound 3 (15 mg, 48%), which was converted to compound 307 (7.9 mg, 38%) as a white solid. LC-MS $t_R$=1.014 min in 2 min chromatography, MS (ESI) m/z 410.2 $[M+H]^+$. $^1H$ NMR ($CD_3OD$ 400 MHz): δ 7.37 (m, 2H), 7.19 (s, 1H), 4.67 (m, 1H), 4.55 (m, 1H), 4.07 (m, 2H), 3.37 (s, 3H), 3.19 (m, 3H), 2.07 (m, 2H), 1.90 (d, J=12.0 Hz, 1H), 1.40 (m, 6H), 0.91 (m, 2H), 0.73 (m, 2H). $^{19}F$ NMR ($CD_3OD$, 400 MHz): δ −76.97.

Example 267

Synthesis of Compound 308

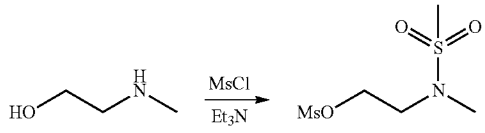

308A 308a

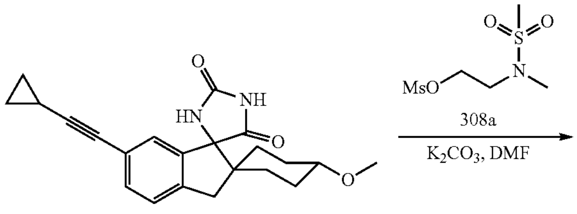

2

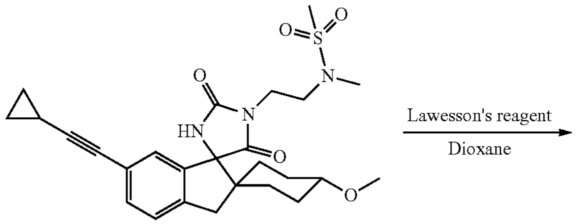

308b

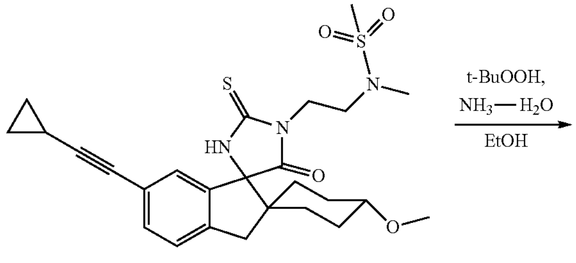

38c

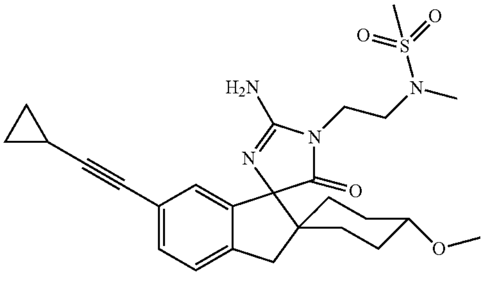

308

Procedure for Preparation of Compound 308a

To a solution of compound 308A (1.0 g, 13.3 mmol) and $Et_3N$ (4.0 g, 40 mmol) in $CH_2Cl_2$ (30 mL) was added MsCl (3.2 g, 28 mmol) slowly. The reaction mixture was stirred at 25° C. for 10 h. $H_2O$ (100 mL) was added and the mixture was extracted with $CH_2Cl_2$ (2×50 mL). The organic layers were concentrated in vacuo to give the crude compound 308a (2.0 g, 60%) as a yellow oil, which was used directly in next step.

Procedure for Preparation of Compound 308

According to a similar synthesis of compound 296, compound 2 described in Example 245 (70 mg, 0.19 mmol) was alkylated with compound 308a (46 mg, 0.19 mmol) to give compound 308b (93 mg, 80%) as a colorless oil.

Compound 308b (90 mg, 0.17 mmol) was reacted with Lawesson's Reagent (75 mg, 0.18 mmol) in dry toluene (4 mL) to give compound 19 (31 mg, 30%) as a colorless oil, which was converted compound 308 (15 mg, 50%) as a white solid. LCMS: $t_R$=1.00 in 2 min chromatography, MS (ESI) m/z=499.2 $[M+H]^+$. $^1H$ NMR ($CD_3OD$ 300 MHz): δ 7.15-7.30 (m, 2H), 7.00-7.05 (s, 1H), 3.80-3.90 (m, 1H), 3.65-3.75 (m, 1H), 3.45-3.55 (m, 1H), 3.35-3.40 (s, 3H), 3.00-3.30 (m, 4H), 2.80-2.90 (s, 6H), 2.00-2.10 (m, 1H), 1.90-2.00 (m, 1H), 1.80-1.90 (m, 1H), 1.20-1.55 (m, 6H), 0.80-0.90 (m, 2H), 0.65-0.75 (m, 2H).

Example 258

Synthesis of Compound 309

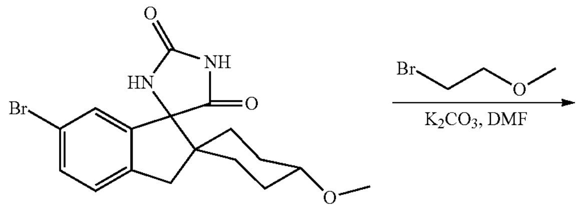

1

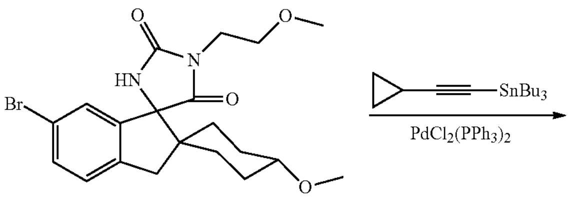

2

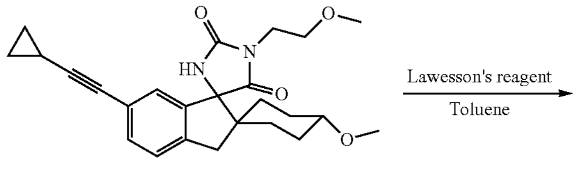

3

-continued

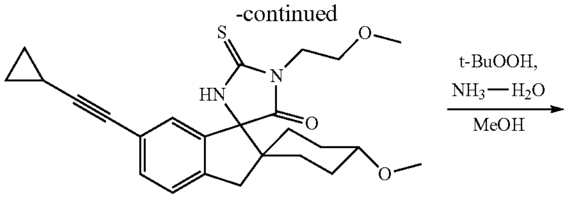

4

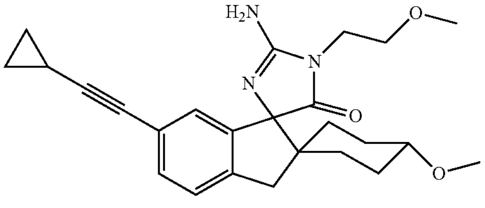

309

Procedure for Preparation of Compound 2

To a solution of compound 1 (500 mg, 1.3 mmol) in DMF (10 mL) was added $K_2CO_3$ (550 mg, 4 mmol). After stirring for 5 min, 1-bromo-2-methoxy-ethane (185 mg, 1.3 mmol) was added and the reaction mixture was stirred at 25° C. for 10 h. The precipitate was filtered off, the filtrate was concentrated in vacuo to give the residue, which was purified by preparative HPLC to give compound 2 (400 mg, 80%) as a white solid.

Procedure for Preparation of Compound 3

A suspension of compound 2 (100 mg, 0.23 mmol), tributyl-cyclopropylethynyl-stannane (420 mg, 1.2 mmol) and $PdCl_2(PPh_3)_2$ (16 mg, 0.03 mmol) in dry toluene (2.5 mL) was heated at 130° C. for 30 min in a CEM microwave reactor. The mixture was concentrated in vacuo and the residue was purified by preparative TLC on silica gel (petroleum ether: ethyl acetate=1:1) to give compound 3 (50 mg, 50%) as a yellow oil.

Procedure for Preparation of Compound 4

A suspension of compound 3 (50 mg, 0.12 mmol) and Lawesson's Reagent (50 mg, 0.13 mmol) in dry toluene (2 mL) was heated at 130° C. for 35 min in a CEM microwave reactor. The mixture was concentrated in vacuo and the residue was purified by preparative TLC on silica gel (eluent: petroleum ether/ethyl acetate=1/1) to give compound 4 (20 mg, 40%) as a colorless oil.

Procedure for Preparation of Compound 309

A solution of compound 4 (20 mg, 0.045 mmol), t-BuOOH (0.5 mL), $NH_3.H_2O$ (0.5 mL) in MeOH (2 mL) was stirred at 20° C. for 10 h. Then, the mixture was concentrated in vacuo to give the residue, which was purified by preparative HPLC to give compound 309 (16 mg, 80%) as a white solid. LC-MS $t_R$=1.020 min in 2 min chromatography, MS (ESI) m/z=422.2 $[M+H]^+$. $^1H$ NMR ($CD_3OD$ 300 MHz): δ 7.15-7.30 (m, 2H), 6.95-7.00 (s, 1H), 3.70-3.80 (m, 2H), 3.45-3.55 (m, 2H), 3.35-3.40 (s, 3H), 3.00-3.30 (m, 3H), 2.00-2.10 (m, 2H), 1.80-1.90 (m, 1H), 1.55-1.70 (m, 1H), 1.20-1.55 (m, 5H), 0.80-0.90 (m, 2H), 0.65-0.75 (m, 2H).

Example 259

Synthesis of Compound 310

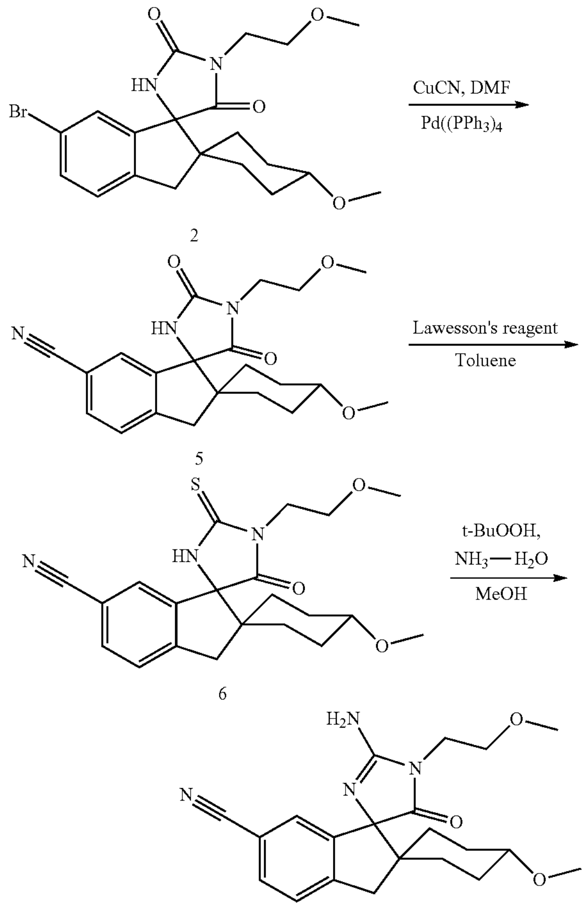

310

Procedure for Preparation of Compound 5

A suspension of compound 2 (100 mg, 0.23 mmol), CuCN (41 mg, 0.46 mmol) and $Pd(PPh_3)_4$ (25 mg, 0.03 mmol) in dry DMF (2 mL) was heated under 180° C. for 45 min in a CEM microwave reactor. The mixture was concentrated in vacuo and the residue was purified by preparative TLC on silica gel (petroleum ether:ethyl acetate=1:1) to give compound 5 (56 mg, 60%) as a white solid.

Procedure for Preparation of Compound 6

A suspension of compound 5 (55 mg, 0.14 mmol) and Lawesson's Reagent (60 mg, 0.15 mmol) in dry toluene (2 mL) was heated under 130° C. for 35 min in a CEM microwave reactor. The mixture was concentrated in vacuo and the residue was purified by column (eluent: petroleum ether/ethyl acetate=2/1) to give compound 6 (33 mg, 60%) as a colorless oil.

Procedure for Preparation of Compound 310

A solution of compound 6 (33 mg, 0.08 mmol), t-BuOOH (0.5 mL), $NH_3.H_2O$ (0.5 mL) in EtOH (2 mL) was stirred at 20° C. for 10 h. Then, the mixture was concentrated in vacuo to give the residue, which was purified by preparative HPLC to give compound 310 as a white solid (24 mg, 60%). LC-MS $t_R$=1.450 min in 2 min chromatography, MS (ESI) m/z=383.2 $[M+H]^+$. $^1H$ NMR ($CD_3OD$ 300 MHz): δ 7.60-7.65 (d, J=7.8 Hz, 1H), 7.45-7.50 (d, J=7.8 Hz, 1H), 7.25-7.30 (s, 1H), 3.70-3.80 (m, 2H), 3.50-3.60 (m, 2H), 3.35-3.40 (s, 3H), 3.10-3.30 (m, 3H), 2.00-2.10 (m, 2H), 1.80-1.90 (m, 1H), 1.55-1.70 (m, 1H), 1.20-1.45 (m, 4H).

Example 260

Synthesis of Compound 311

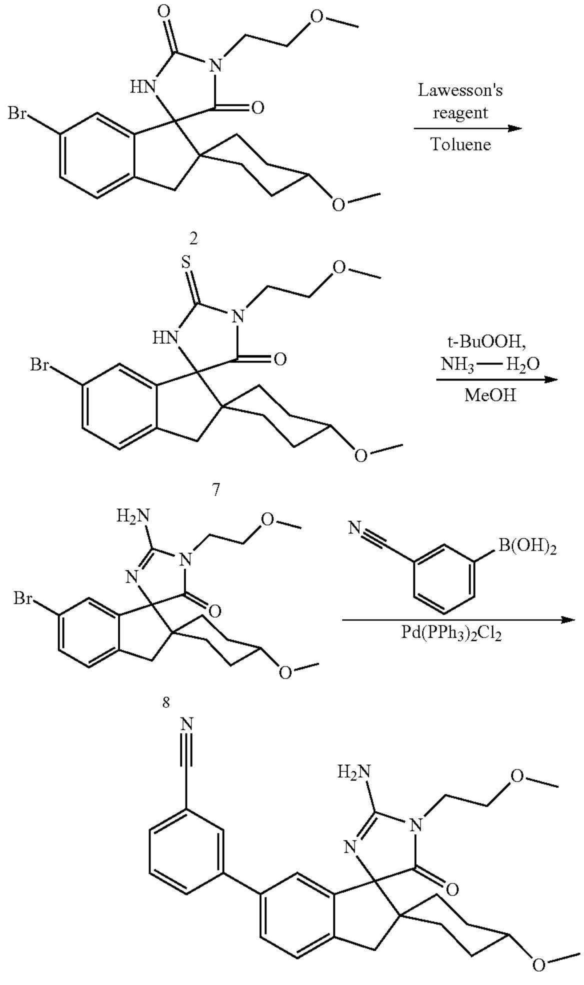

311

Procedure for Preparation of Compound 7

A suspension of compound 2 (60 mg, 0.14 mmol) and Lawesson's Reagent (60 mg, 0.15 mmol) in dry toluene (2 mL) was heated under 130° C. for 35 min in a CEM microwave reactor. The mixture was concentrated in vacuo and the residue was purified by preparative TLC on silica gel (eluent: petroleum ether:ethyl acetate=2:1) to give compound 7 (24 mg, 40%) as a colorless oil.

Procedure for Preparation of Compound 8

A solution of compound 7 (24 mg, 0.05 mmol), t-BuOOH (0.5 mL), $NH_3.H_2O$ (0.5 mL) in EtOH (2 mL) was stirred at 20° C. for 10 h. Then, the mixture was concentrated in vacuo to give the residue, which was purified by preparative HPLC to give compound 8 (17 mg, 55%) as white a solid.

Procedure for Preparation of Compound 311

A suspension of compound 8 (17 mg, 0.04 mmol), 3-cyanophenylboronic acid (4 mg, 0.05 mmol), $PdCl_2(PPh_3)$ (3 mg, 0.004 mmol) and $Cs_2CO_3$ (0.1 mL, 2 N in water) in 1,4-dioxane (1 mL) was heated under 120° C. for 15 min in CEM microwave reactor. The mixture was concentrated in vacuo and the residue was purified by preparative HPLC to give compound 311 (15 mg, 80%) as a white solid. LC-MS $t_R$=1.010 min in 2 min chromatography, MS (ESI) m/z=459.2 $[M+H]^+$. $^1$H NMR ($CD_3OD$ 300 MHz): δ 7.90-8.05 (m, 2H), 7.55-7.70 (m, 3H), 7.45-7.55 (m, 2H), 3.85-4.05 (m, 2H), 3.50-3.60 (m, 2H), 3.35-3.40 (m, 6H), 3.10-3.30 (m, 3H), 2.00-2.15 (m, 2H), 1.90-2.00 (m, 1H), 1.55-1.70 (m, 1H), 1.20-1.45 (m, 4H).

Example 261

Synthesis of Compound 312

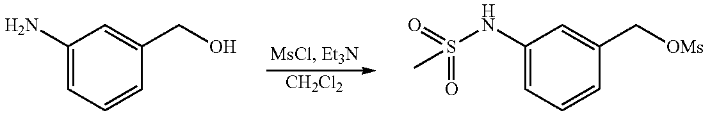

312a

312b

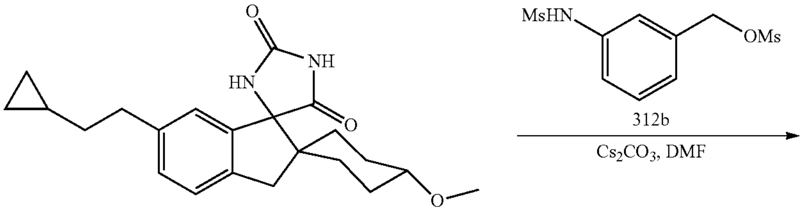

312b

312c

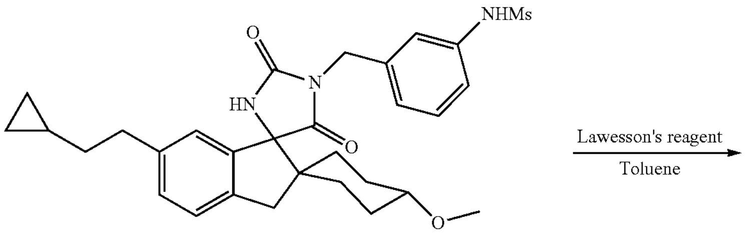

312d

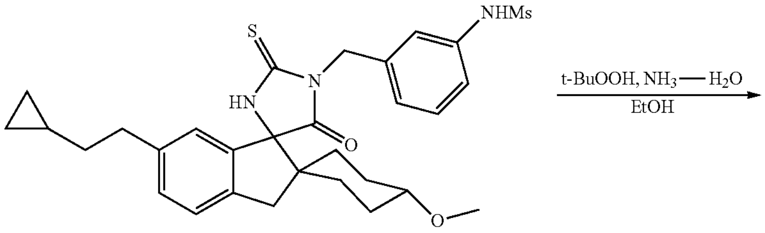

312c

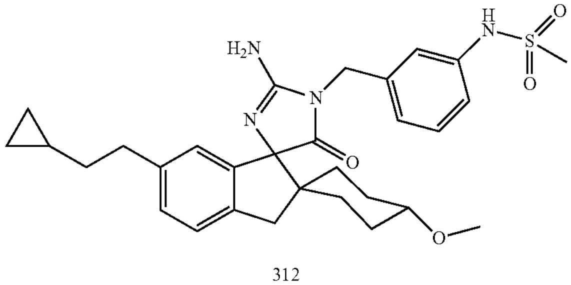

312

Procedure for Preparation of Compound 312b

To a solution of (3-amino-phenyl)-methanol (0.20 g, 1.414 mmol) and $Et_3N$ (0.50 g, 4.94 mmol) in $CH_2Cl_2$ (20 mL) was added Methane sulfonyl chloride (0.50 g, 4.36 mmol) via a syringe slowly with stirring. After addition, the reaction mixture was stirred at ambient temperature overnight. The reaction was quenched by addition 20 mL saturated $NaHCO_3$ with stirring. The mixture was separated and the aqueous layer was extracted with $CH_2Cl_2$ (3×20 mL). The combined organic layers were washed with saturated brine (2×10 mL), dried over $Na_2SO_4$, filtered and concentrated in vacuo to give the crude compound 312b (0.40 g, 100%) as a brown oil, which was used directly in next step.

Procedure for Preparation of Compound 312

According to a similar synthesis of compound 296, compound 312c (50 mg, 0.14 mmol) was alkylated with methanesulfonic acid 3-methanesulfonylamino-benzyl ester (58 mg, 0.21 mmol) at the presence of $Cs_2CO_3$ (0.10 g, 0.31 mmol) to give compound 312d (40 mg, 52%) as a white solid. LC-MS: $t_R$=1.894 min in 3 min chromatography, MS (ESI) m/z 520 $[M-31]^+$, 552 $[M+H]^+$, 574 $[M+23]^+$. $^1H$ NMR ($CDCl_3$ 400 MHz): δ 8.77 (s, 1H), 7.40, (d, J=8.0 Hz, 1H), 7.33 (d, J=5.2 Hz, 1H), 7.30 (d, J=8.0 Hz, 1H), 7.19 (t, J=8.0 Hz, 2H), 7.14 (d, J=7.6 Hz, 1H), 6.83 (s, 1H), 6.65 (s, 1H), 4.66 (s, 2H), 3.36 (s, 3H), 3.16 (d, J=15.2 Hz, 1H), 3.09 (m, 5H), 2.66 (t, J=7.6 Hz, 2H), 1.85-2.10 (m, 3H), 1.20-1.50 (m, 7H), 0.65 (m, 1H), 0.40 (m, 2H), 0.01 (m, 2H).

Compound 312d (40 mg, 0.073 mmol) was then reacted with Lawesson's reagent (40 mg, 0.099 mmol) in anhydrous Toluene (1 mL) to give compound 312e (19 mg, 42%) as a white solid. LC-MS: $t_R$=1.230 min in 2 min chromatography, MS (ESI) m/z 568 $[M+H]^+$.

Finally, compound 312e (19 mg, 0.030 mmol) was reacted with $NH_3$-EtOH (1 mL) and tert-butyl hydroperoxide (100 mg, 1.11 mmol) to give compound 312 (16.7 mg, 92%) as a white solid. LC-MS: $t_R$=1.424 min in 3 min chromatography, MS (ESI) m/z 551 $[M+H]^+$. $^1H$ NMR ($CD_3OD$ 400 MHz): δ 7.33, (m, 2H), 7.20 (d, J=7.6 Hz, 1H), 7.15 (m, 3H), 6.87 (s, 1H), 4.78 (s, 2H), 3.32 (s, 3H), 3.15 (m, 1H), 3.10 (d, J=15.6 Hz, 1H), 3.04 (d, J=15.2 Hz, 1H), 2.93 (s, 3H), 2.69 (t, J=7.6 Hz, 2H), 1.90-2.10 (m, 2H), 1.85 (m, 1H), 1.65 (m, 1H), 1.20-1.50 (m, 6H), 0.65 (m, 1H), 0.40 (m, 2H), 0.03 (m, 2H).

Example 262

Synthesis of Compound 313

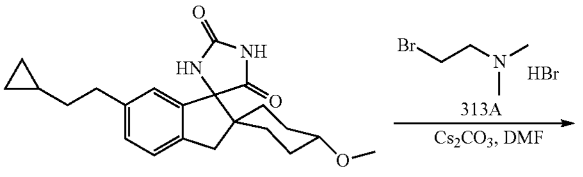

313a

-continued

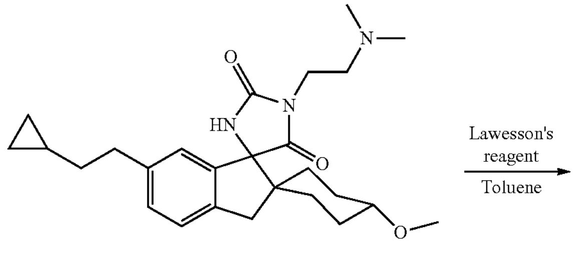

313b

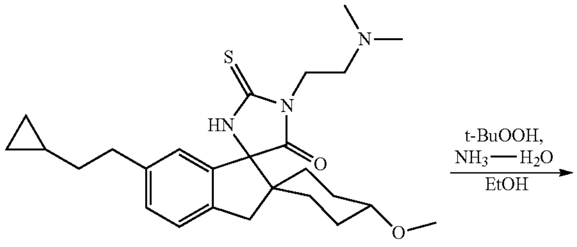

313c

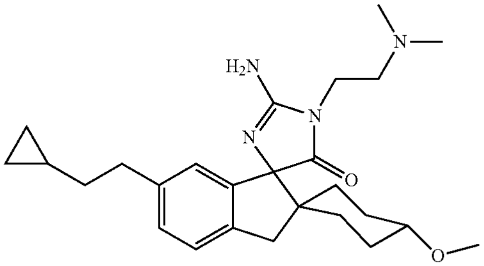

313

According to a similar synthesis of compound 296, compound 313a (50 mg, 0.14 mmol) was alkylated with compound 1A (35 mg, 0.15 mmol) to give compound 313b (28 mg, 47%), which was reacted with Lawesson's Reagent (30.9 mg, 0.077 mmol) in anhydrous toluene (2.5 mL) to give compound 313c (21 mg, 70%).

Compound 313c (21 mg, 0.046 mmol) was then reacted with t-BuOOH (127.9 mg, 0.92 mmol) in $NH_4OH$ (1 mL) and EtOH (2.5 mL) to give compound 313 (2.8 mg, 14%) as a white solid. LC-MS: $t_R$=1.018 min in 2 min chromatography, MS (ESI) m/z 439.4 $[M+H]^+$. $^1H$ NMR ($CD_3OD$ 400 MHz): δ 7.259 (d, J=11.6 Hz, 2H), 7.087 (s, 1H), 4.130 (d, J=5.6 Hz, 2H), 3.352 (m, 5H), 3.173 (m, 3H), 2.940 (s, 6H), 2.711 (d, J=14.8 Hz, 2H), 2.083 (m, 2H), 1.874 (d, J=9.6 Hz, 1H), 1.447 (s, 6H), 1.32 (m, 1H), 0.68 (s, 1H), 0.42 (s, 2H), 0.02 (s, 2H).

Example 263

Synthesis of Compound 314

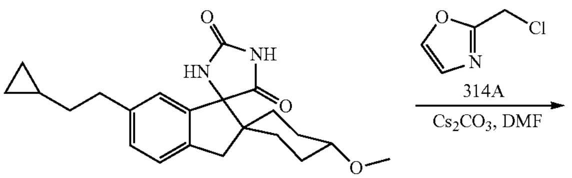

314a

-continued

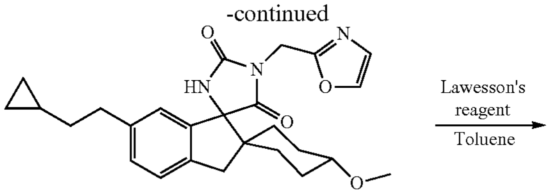

314b

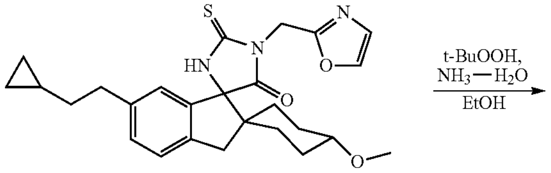

314c

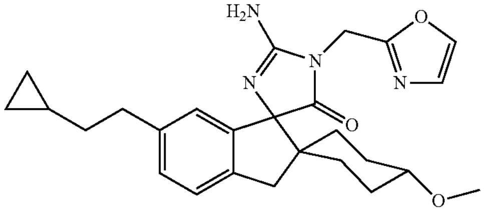

314

According to a similar synthesis of compound 296, compound 314a (50 mg, 0.14 mmol) was alkylated with 2-chloromethyl oxazole (25 mg, 0.21 mmol) to give compound 314b (40 mg, 63%) as a white solid. LC-MS: $t_R$=2.038 min in 3 min chromatography, MS (ESI) m/z=450 $[M+H]^+$.

Compound 314b (50 mg, 0.11 mmol) was then reacted with Lawesson's reagent (60 mg, 0.15 mmol) to give compound 314c (30 mg, 59%) as a white solid. LC-MS: $t_R$=1.214 min in 2 min chromatography, MS (ESI) m/z=466 $[M+H]^+$.

Compound 314c (30 mg, 0.064 mmol) was then reacted with $NH_3$-EtOH (1 mL) and tert-butyl hydroperoxide (200 mg, 2.22 mmol) to give compound 314 (20.6 mg, 72%) as a white solid. LC-MS: $t_R$=1.383 min in 3 min chromatography, MS (ESI) m/z=449 $[M+H]^+$. $^1$H NMR ($CD_3OD$ 400 MHz): δ 7.88 (s, 1H), 7.19 (d, J=7.6 Hz, 1H), 7.13 (s, 1H), 7.11 (d, J=8.0 Hz, 1H), 4.89 (m, 2H), 3.36 (s, 3H), 3.18 (m, 1H), 3.09 (d, J=15.6 Hz, 1H), 3.05 (d, J=15.6 Hz, 1H), 2.68 (t, J=7.6 Hz, 2H), 1.90-2.10 (m, 2H), 1.85 (m, 1H), 1.65 (m, 1H), 1.20-1.50 (m, 5H), 0.65 (m, 1H), 0.40 (m, 2H), 0.00 (m, 2H).

Example 264

Synthesis of Compound 315

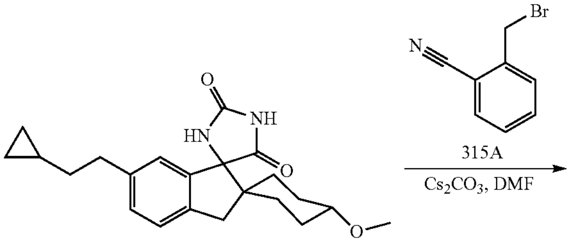

1

-continued

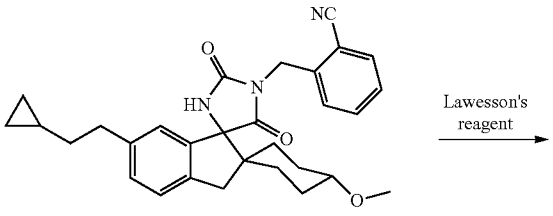

315a

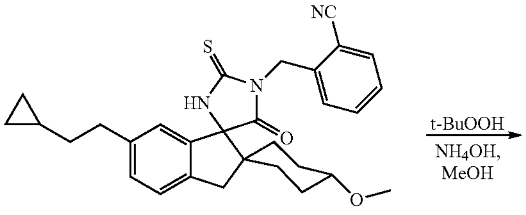

315b

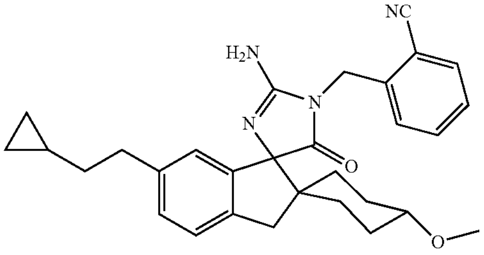

315

According to a similar synthesis of compound 296, compound 1 (50 mg, 0.14 mmol) was alkylated with compound 315A (26.5 mg, 0.14 mmol) to give compound 315a (26 mg, 41%).

Compound 315a (26 mg, 0.038 mmol) was then reacted with Lawesson'reagent (18.3 mg, 0.045 mmol) to give compound 315b (20 mg, 75%), which was converted to compound 315 (11.2 mg, 58%) as a white solid. LC-MS: $t_R$=1.223 min in 2 min chromatography, MS (ESI) m/z=483 $[M+H]^+$. $^1$H NMR ($CD_3OD$ 400 MHz): δ 7.80 (d, J=7.6 Hz, 1H), 7.70 (t, J=7.2 Hz, 1H), 7.53 (t, J=7.2 Hz, 1H), 7.38 (d, J=7.6 Hz, 1H), 7.23 (m, 2H), 7.14 (s, 1H), 5.13 (s, 2H), 3.35 (s, 3H), 3.20 (m, 1H), 3.06 (m, 2H), 2.73 (t, J=7.6 Hz, 2H), 2.01 (m, 2H), 1.75 (m, 1H), 1.50 (m, 6H), 1.33 (m, 1H), 0.69 (m, 1H), 0.39 (m, 2H), 0.01 (m, 2H).

Example 265

Synthesis of Compound 316

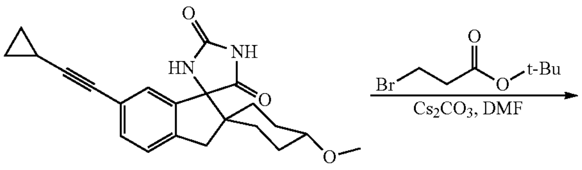

2

-continued

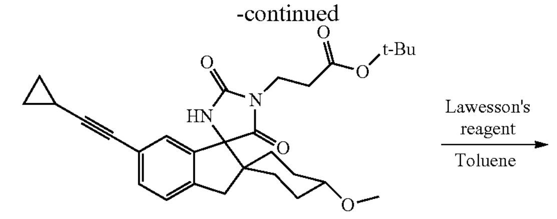

316a

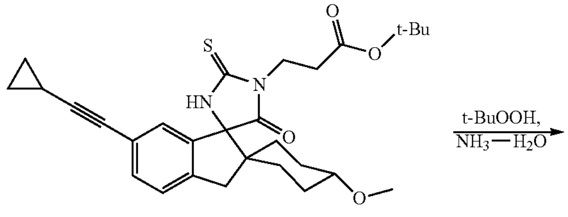

316b

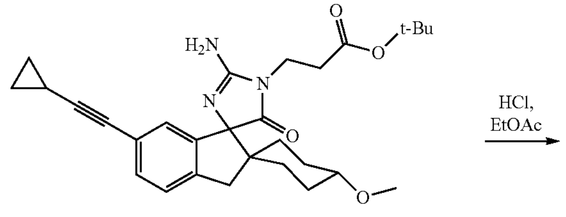

316c

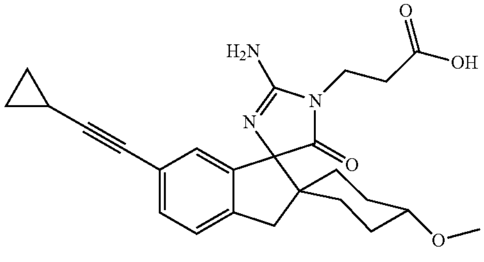

316

Procedure for Preparation of Compound 316a

According to a similar synthesis of compound 296, compound 2 (0.20 g, 0.55 mmol) was alkylated with tert-butyl 3-bromopropanoate to give compound 316a (0.20 g, 72%) as a white solid. $^1$H NMR ($CDCl_3$ 300 MHz): δ 7.29 (d, J=7.8 Hz, 1H), 7.18 (d, J=7.8 Hz, 1H), 7.08 (s, 1H), 5.45 (s, 1H), 3.73 (t, J=7.2 Hz, 2H), 3.55 (s, 3H), 3.16 (d, J=16.2 Hz, 1H), 3.07 (m, 1H), 3.01 (d, J=15.3 Hz, 1H), 2.58 (t, J=6.9 Hz, 2H), 1.70-2.10 (m, 3H), 1.40 (s, 9H), 1.20-1.35 (m, 6H), 0.85 (m, 2H), 0.75 (m, 2H).

Compound 316a (0.19 g, 0.39 mmol) was then reacted with Lawesson's Reagent to give compound 316b (60 mg, 30%) as a white solid. LC-MS: $t_R$=1.346 min in 2 min chromatography, MS (ESI) m/z=453 $[M-56]^+$, 531 $[M+Na]^+$.

Compound 316b (60 g, 0.12 mmol) was then converted to compound 316c (20 mg, 34%) as a white solid. LC-MS: $t_R$=1.716 min in 3 min chromatography, MS (ESI) m/z=492 $[M+H]^+$.

Procedure for Preparation of Compound 316

A flask was charged with EtOAc (5 mL), the flask was immersed into ice-water for 5 min, and then dried HCl gas was bubbled into the flask at 0° C. for 5 min. After that, compound 316c (18 mg, 0.037 mmol) was added and the resulting mixture was stirred at ambient temperature overnight. The solvent was removed by evaporation in vacuo and the residue was purified by preparative HPLC (TFA as buffer) to give the product as a white solid with 90% purity, which was re-purified by preparative HPLC (TFA as buffer) to give pure compound 316 (4.5 mg, 23%) as a white solid. LC-MS: $t_R$=1.475 min in 3 min chromatography, MS (ESI) m/z=436 $[M+H]^+$. $^1$H NMR ($CD_3OD$ 300 MHz): δ 7.33 (d, J=8.1 Hz, 1H), 7.28 (d, J=8.1 Hz, 1H), 7.25 (s, 1H), 3.94 (t, J=5.7 Hz, 2H), 3.33 (s, 3H), 3.15 (m, 3H), 2.70 (m, 2H), 1.90-2.10 (m, 2H), 1.84 (m, 1H), 1.25-1.50 (m, 6H), 0.85 (m, 2H), 0.65 (m, 2H).

Example 266

Synthesis of Compound 317

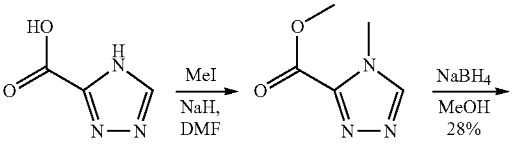

317a 317b

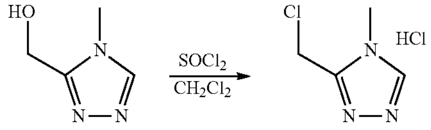

317c 317b

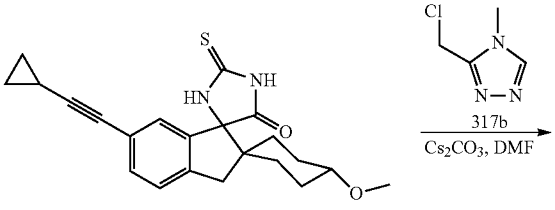

1

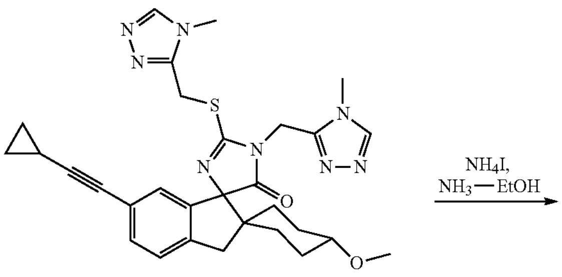

317d

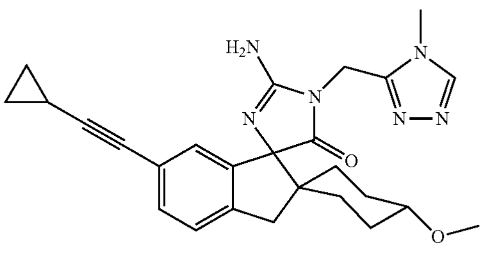

317

Procedure for Preparation of Compound 317b

To a solution of compound 317a (500 mg, 4.4 mmol) in anhydrous DMF (10 mL) was added NaH (318.5 mg, 13.2 mmol) and MeI (1.29 g, 8.8 mmol). The resulting suspension was stirred at 50° C. for 1 h in a CEM microwave reactor. Water (10 mL) was added and the mixture was extracted with EtOAc (10 mL×3). The combined organic layers were washed with brine (30 mL), dried over $Na_2SO_4$ and concentrated to give compound 317b (200 mg, 32%) as a yellow liquid which was used in the next step without further purification. $^1$H NMR ($CDCl_3$ 400 MHz): δ 7.97 (s, 1H), 2.92 (s, 3H), 2.84 (s, 3H).

Procedure for Preparation of Compound 317c

To a solution of compound 317b (200 mg, 1.41 mmol) in MeOH (5 mL) was added $NaBH_4$ (214 mg, 5.67 mmol) under nitrogen, the reaction mixture was heated at reflux overnight. After cooling, water (2 mL) was added and the mixture was extracted with EtOAc (10 mL×3). The combined organic layers were washed with brine (30 mL), dried over $Na_2SO_4$ and concentrated to give compound 317c (50 mg, 28%) as a white solid which was used in the next step without further purification. H NMR ($CD_3OD$ 400 MHz): δ 8.30 (s, 1H), 4.57 (s, 2H), 3.85 (s, 3H).

Procedure for Preparation of Compound 317d

To a solution of compound 317c (50 mg, 0.44 mmol) in $CH_2Cl_2$ (2 mL) was added $SOCl_2$ (58 mg, 0.48 mmol) at 0° C. After addition, the mixture was warmed to ambient temperature and was stirred at room temperature overnight. The reaction was quenched with $NaHCO_3$ (5 mL), extracted with $CH_2Cl_2$ (5 mL×3), washed with brine (30 mL), dried over $Na_2SO_4$ and concentrated to give compound 317d (46 mg, 80%) as a yellow oil which was used in the next step without further purification.

Procedure for Preparation of Compound 317e

To a solution of compound 1 (20 mg, 0.052 mmol) in DMF (2 mL) was added $Cs_2CO_3$ (68 mg, 0.21 mmol) and compound 317d (27.6 mg, 0.21 mmol), the reaction mixture was stirred at room temperature overnight. The mixture was filtered, and the filtrate was extracted with EA (10 mL×3), washed with brine (30 mL), dried over $Na_2SO_4$, concentrated to give the crude product which was purified by preparative TLC on silica gel eluting with hexane:EtOAc=1:1 to give compound 317e (10 mg, 33%) as a white solid. LC-MS: $t_R$=1.153 min in 2 min chromatography, MS (ESI) m/z=571.3 $[M+H]^+$.

Procedure for Preparation of Compound 317

A solution of compound 317e (10 mg, 0.017 mmol), $NH_4I$ (25 mg, 0.17 mmol) in $NH_3$-EtOH (2 mL, 5 N) was heated at 120° C. in a CEM microwave reactor for 3 h. After being cooled, the mixture was concentrated in vacuo, and the residue was purified by preparative TLC on silica gel eluting with dichloromethane:methanol=10:1 and by preparative HPLC to give compound 317 (3.0 mg, 37%) as a white solid. LC-MS: $t_R$=1.004 min in 2 min chromatography, MS (ESI) m/z=459.2 $[M+H]^+$. $^1$H NMR ($CD_3OD$ 400 MHz): δ 8.32 (s, 1H), 7.31 (d, J=8.0, Hz, 2H), 7.20 (s, 1H), 4.80 (s, 2H), 3.91-3.88 (s, 3H), 3.36 (s, 3H), 3.19-3.12 (m, 1H), 3.12 (s, 2H), 2.03-1.90 (m, 2H), 1.90-1.82 (m, 1H), 1.70-1.51 (m, 1H), 1.50-1.32 (m, 3H), 1.30-1.12 (m, 2H), 0.91-0.80 (m, 2H), 0.71-0.60 (m, 2H).

Example 267

Synthesis of Compound 318

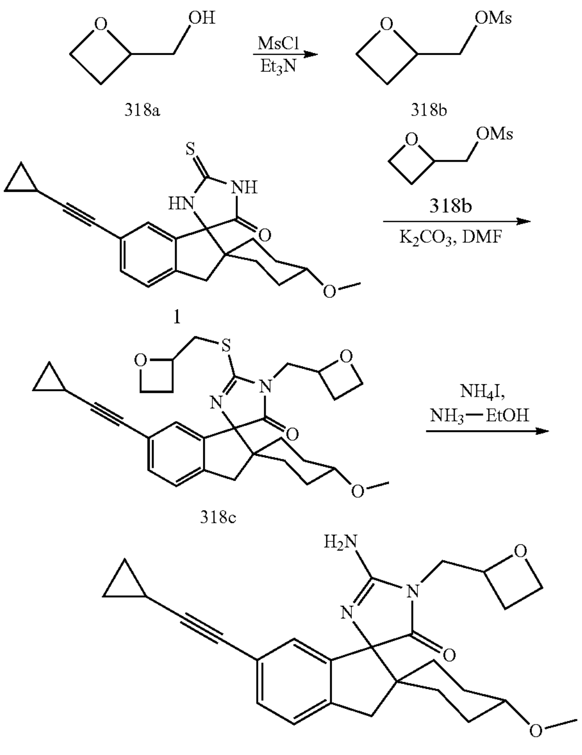

318a

318b

1

318c

318

Procedure for Preparation of Compound 318b

To a solution of compound 318a (200 mg, 2.27 mmol) in $CH_2Cl_2$ (10 mL) was added MsCl (286 mg, 2.50 mmol) and $Et_3N$ (689 mg, 6.81 mmol) at 0° C., the mixture was stirred at 0° C. for 1 h. Then $H_2O$ (20 mL) was added and extracted with $CH_2Cl_2$ (3×20 mL), the organic layer was dried over $Na_2SO_4$ and concentrated to give compound 318b as a yellow oil (160 mg, 42%), which was used for the next step without further purification.

Procedure for Preparation of Compound 318

According to a similar synthesis of compound 317, compound 1 (200 mg, 0.53 mmol) was alkylated with compound 318b (262 mg, 1.29 mmol) in the presence of $Cs_2CO_3$ (511 mg, 1.59 mmol) to give compound 318c (200 mg, 73%) as a white solid.

Compound 318c (200 mg, 0.38 mmol) was then converted to compound 318 (50 mg, 30%) as a white solid. LC-MS $t_R$=0.959 min in 2 min chromatography, MS (ESI) m/z 434 $[M+H]^+$. $^1$H NMR ($CD_3OD$ 400 MHz): δ 7.23 (m, 2H), 7.08 (m, 1H), 4.90 (m, 1H), 4.61 (m, 1H), 4.45 (m, 1H), 3.86 (m, 2H), 3.24 (s, 3H), 3.10 (m, 2H), 3.02 (m, 2H), 2.63 (m, 1H), 2.36 (m, 1H), 1.83 (m, 3H), 1.33 (m, 5H), 1.22 (m, 1H), 0.76 (m, 2H), 0.57 (m, 2H).

Example 268

Synthesis of Compound 319

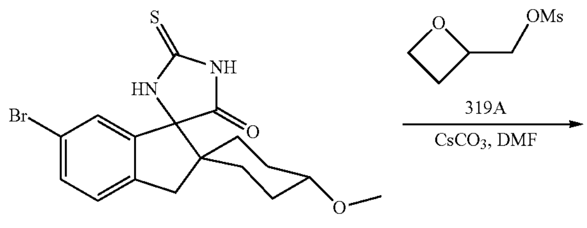

1

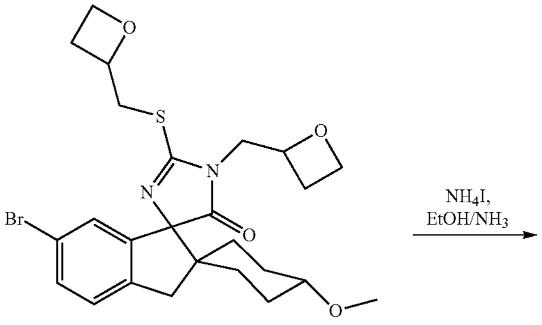

319a

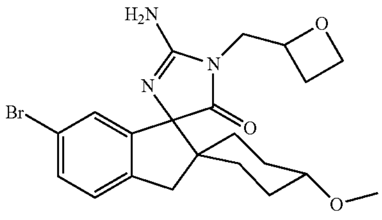

319b

According to a similar synthesis of compound 317, compound 1 (150 mg, 0.38 mmol) was alkylated with compound 319A (190 mg, 1.14 mmol) to give compound 319a (151 mg, 74%) as a white solid. Compound 319a (100 mg, 0.18 mmol) was reacted with $NH_4I$ (217 mg, 1.49 mmol) in a solution of $NH_3$/EtOH (3 mL, 0.5 N) to give compound 319b (50 mg, 59%) as a white solid.

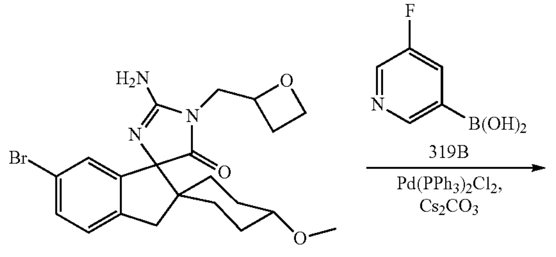

319b

-continued

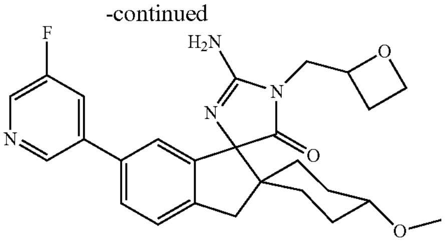

319

Compound 319b (20 mg, 0.04 mmol) in a 10 mL of flask under $N_2$ was treated sequentially with compound 319B (12.6 mg, 0.08 mmol) in 1,4-dioxane (1 mL), $Cs_2CO_3$ (2 N, 0.06 mL, 0.12 mmol) and $Pd(PPh_3)_2Cl_2$ (5 mg). The mixture was heated at 120° C. at $N_2$ under microwave for 15 min. The reaction mixture was concentrated in vacuo to give the residue, which was purified by preparative TLC ($CH_2Cl_2$:MeOH=10:1) and HPLC (TFA buffer) to give compound 319 (3.0 mg, 15%) as a white solid. LC-MS $t_R$=0.930 min in 2 min chromatography, MS (ESI) m/z 465 $[M+H]^+$. $^1H$ NMR ($CD_3OD$ 400 MHz): δ 8.57 (m, 1H), 8.35 (m, 1H), 7.84 (m, 1H), 7.65 (m, 1H), 7.50 (m, 1H), 7.45 (m, 1H), 4.92 (m, 1H), 4.60 (m, 1H), 4.46 (m, 1H), 3.92 (m, 2H), 3.26 (s, 3H), 3.15 (m, 1H), 3.12 (m, 2H), 2.55 (m, 1H), 2.39 (m, 1H), 1.98 (m, 3H), 1.39 (m, 4H), 1.23 (m, 1H). $^{19}F$ NMR ($CD_3OD$ 19F): δ −128.25.

Example 269

Synthesis of Compound 320

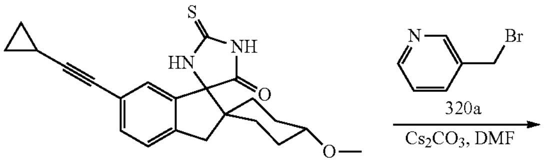

1

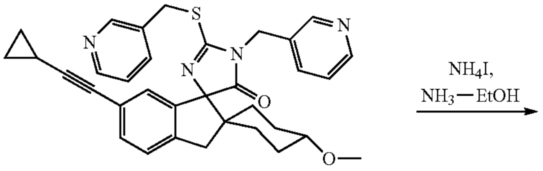

320b

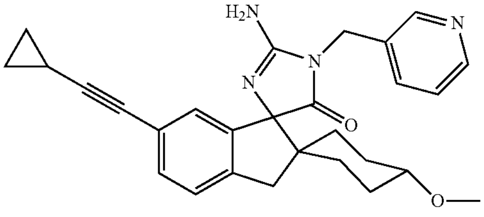

320

According to a similar synthesis of compound 317, compound 1 (30 mg, 0.076 mmol) was dialkylated with compound 320a (79.8 mg, 0.315 mmol) to give compound 320b (20 mg, 45%) as a yellow solid. LC-MS $t_R$=1.003 min in 2 min chromatography, MS (ESI) m/z=563.2 $[M+H]^+$.

Compound 320b (20 mg, 0.035 mmol) was then converted to compound 320 (2.0 mg, 13%) as a white solid. LC-MS $t_R$=0.918 min in 2 min chromatography, MS (ESI) m/z=455.1 $[M+H]^+$. $^1$H NMR ($CD_3OD$, 400 MHz): δ 8.54 (s, 1H), 8.50-8.49 (d, J=3.6 Hz, 1H), 7.85-7.75 (d, J=7.2 Hz, 1H), 7.46-7.44 (m, 1H), 7.26-7.15 (m, 2H), 7.01-6.80 (s, 1H), 4.79 (s, 2H), 3.34 (s, 3H), 3.19-3.05 (m, 3H), 2.10-1.91 (m, 2H), 1.85-1.70 (m, 1H), 1.65-1.51 (m, 1H), 1.50-1.41 (m, 1H), 1.41-1.20 (m, 4H), 0.92-0.82 (m, 2H), 0.75-0.65 (m, 2H).

Example 270

Synthesis of Compound 321

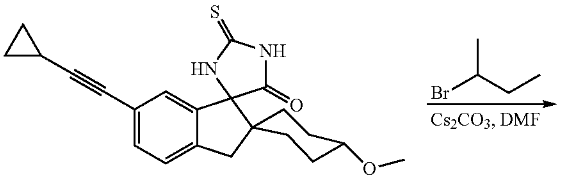

1

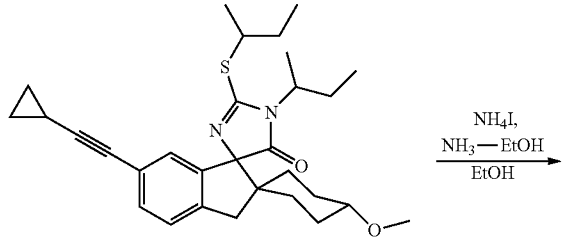

321a

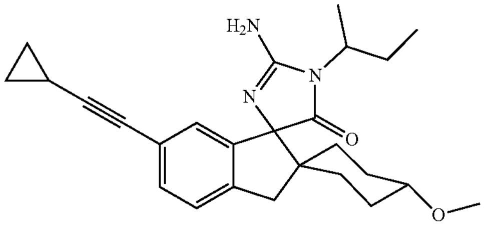

321

According to a similar synthesis of compound 317, compound 1 (30 mg, 0.079 mmol) was dialkylated with 2-bromobutane (60 mg, 0.44 mmol) in DMF (2 mL) to give compound 321a (38 mg, 97%) as a white solid, which was used directly in next step. LC-MS: $t_R$=2.002 min in 3 min chromatography, MS (ESI) m/z=493 $[M+H]^+$.

Compound 321a (38 mg, 0.077 mmol) was then reacted with $NH_4I$ (100 mg, 0.69 mmol) and $NH_3$-EtOH (2 mL) to give compound 321 (3.7 mg, 12%) as a white solid. LC-MS: $t_R$=1.621 min in 3 min chromatography, MS (ESI) m/z=420 $[M+H]^+$. $^1$H NMR ($CD_3OD$ 400 MHz): δ 7.13 (m, 2H), 6.79 (s, 1H), 3.85 (m, 1H), 3.23 (s, 3H), 3.03 (m, 1H), 2.99 (d, J=16.0 Hz, 1H), 2.95 (d, J=15.6 Hz, 1H), 1.93 (m, 2H), 1.88 (m, 2H), 1.67 (m, 2H), 1.15-1.45 (m, 8H), 0.82 (m, 5H), 0.61 (m, 2H).

Example 271

Synthesis of Compound 322

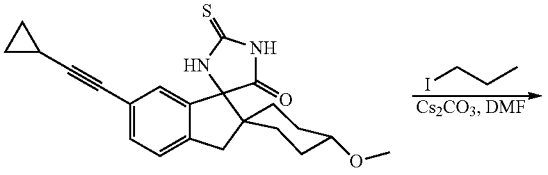

1

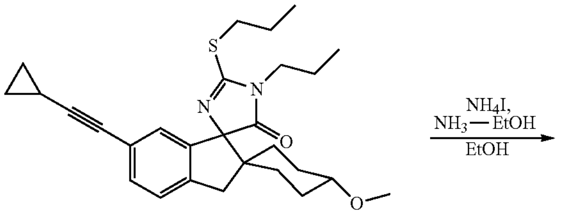

322a

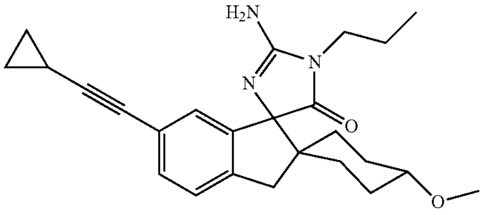

322

According to a similar synthesis of compound 317, compound 1 (30 mg, 0.079 mmol) was dialkylated to give compound 322a (33 mg, 89%) as a pale yellow solid, which was used directly in next step. LC-MS: $t_R$=1.862 min in 3 min chromatography, MS (ESI) m/z=465 $[M+H]^+$.

Compound 322a (33 mg, 0.071 mmol) was then converted to compound 322 (14.3 mg, 50%) as a white solid. LC-MS: $t_R$=1.561 min in 3 min chromatography, MS (ESI) m/z=406 $[M+H]^+$. $^1$H NMR ($CD_3OD$ 400 MHz): δ 7.26 (m, 2H), 6.93 (s, 1H), 3.52 (t, J=7.2 Hz, 2H), 3.35 (s, 3H), 3.17 (m, 2H), 3.07 (d, J=15.6 Hz, 1H), 2.03 (m, 2H), 1.87 (m, 1H), 1.67 (m, 3H), 1.25-1.50 (m, 5H), 0.95 (t, J=7.2 Hz, 3H), 0.87 (m, 2H), 0.73 (m, 2H).

Example 272

Synthesis of Compound 323

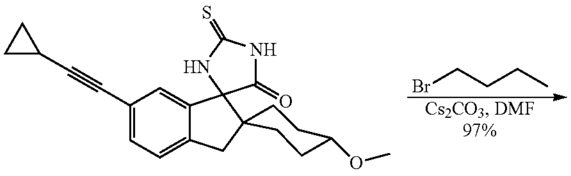

1

-continued

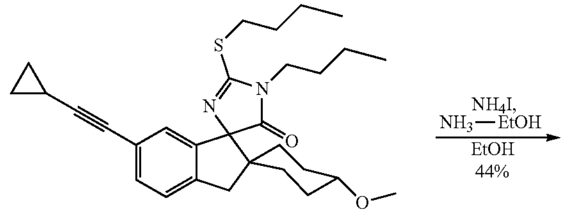

323a

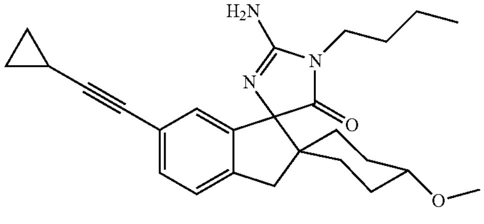

323

According to a similar synthesis of compound 317, compound 1 (30 mg, 0.079 mmol) was dialkylated to give compound 323a (38 mg, 97%) as a white solid, which was used directly in next step. LC-MS: $t_R$=2.010 min in 3 min chromatography, MS (ESI) m/z=493 $[M+H]^+$.

Compound 323a (38 mg, 0.077 mmol) was converted to compound 323 (14.3 mg, 44%) as a white solid. LC-MS: $t_R$=1.620 min in 3 min chromatography, MS (ESI) m/z=420 $[M+H]^+$.

$^1$H NMR ($CD_3OD$ 400 MHz): δ 7.16 (m, 2H), 6.82 (s, 1H), 3.45 (t, J=7.2 Hz, 2H), 3.39 (s, 3H), 3.08 (m, 2H), 2.97 (d, J=15.6 Hz, 1H), 1.93 (m, 1H), 1.88 (m, 1H), 1.78 (m, 1H), 1.55 (m, 3H), 1.25-1.40 (m, 7H), 0.88 (t, J=7.2 Hz, 3H), 0.79 (m, 2H), 0.63 (m, 2H).

Example 273

Synthesis of Compound 324

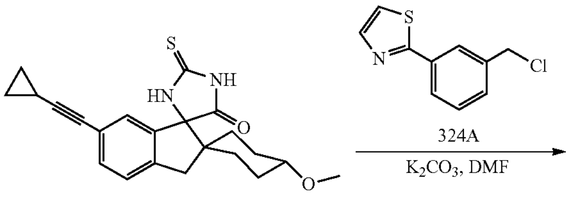

1

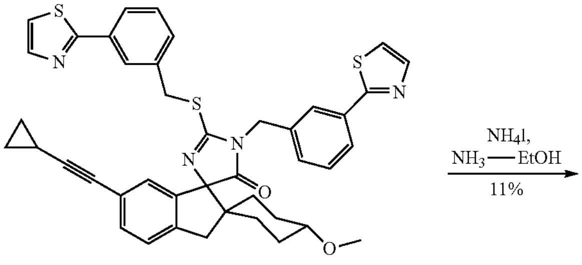

324a

-continued

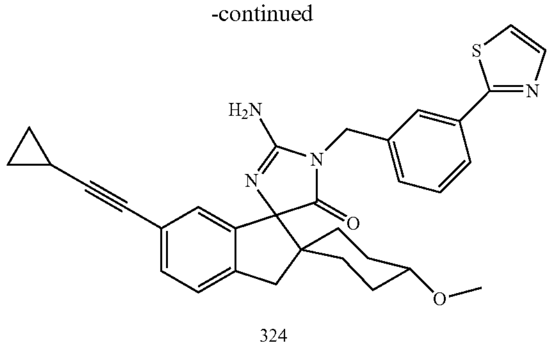

324

According to a similar synthesis of compound 317, compound 1 (30 mg, 0.080 mmol) was dialkylated with compound 324A (35 mg, 0.17 mmol) in the presence of $K_2CO_3$ (54 mg, 0.40 mmol), to give compound 324a (42 mg, 74%) as a white solid.

Compound 324a (42 mg, 0.058 mmol) was then reacted with $NH_4I$ (84 mg, 0.58 mmol) in $NH_3$-EtOH (2.5 mL) to give compound 324 (3.3 mg, 11%) as a white solid. LC-MS: $t_R$=1.127 min in 2 min chromatography, MS (ESI) m/z 537.2 $[M+H]^+$. $^1$H NMR ($CD_3OD$ 400 MHz): δ 7.94 (m, 2H), 7.88 (s, 1H), 7.67 (m, 1H), 7.55 (m, 2H), 7.35 (m, 2H), 7.24 (s, 1H), 4.90 (m, 2H), 3.32 (m, 3H), 3.16 (m, 3H), 2.02 (m, 2H), 1.82 (m, 1H), 1.47 (m, 5H), 1.32 (m, 1H), 0.90 (m, 2H), 0.072 (m, 2H).

Example 274

Synthesis of Compound 325

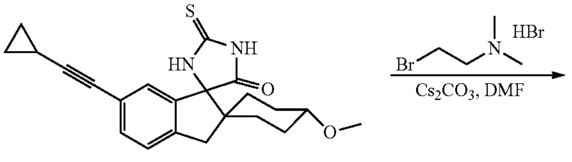

1

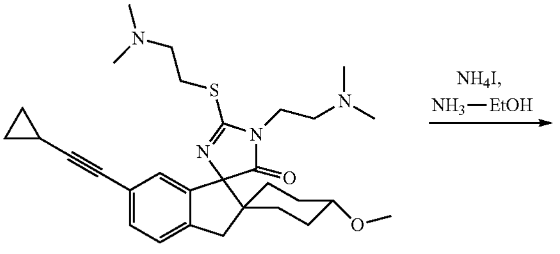

325a

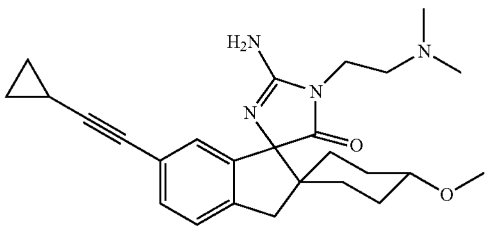

325

According to a similar synthesis of compound 317, compound 1 (0.030 g, 0.079 mmol) was dialkylated with (2-Bromo-ethyl)-dimethyl-amine hydrobromide salt (0.25 g, 1.07 mmol) to give compound 325a (15 mg, 10%) as a yellow oil.

Compound 325a (15 mg, 0.029 mmol) was then reacted with $NH_4I$ (50 mg, 0.35 mmol) and $NH_3$-EtOH (1 mL) to give compound 325 (5.0 mg, 40%) as a white solid. LC-MS: $t_R$=1.275 min in 3 min chromatography, MS (ESI) MS (ESI) m/z=435 $[M+H]^+$. $^1H$ NMR ($CD_3OD$ 400 MHz): δ 7.18 (dd, J=1.2, 7.6 Hz, 1H), 7.15 (d, J=7.6 Hz, 1H), 6.92 (s, 1H), 3.64 (t, J=6.0 Hz, 2H), 3.26 (s, 3H), 3.08 (m, 1H), 2.95 (m, 2H), 2.55 (t, J=6.0 Hz, 2H), 2.28 (s, 6H), 1.95 (m, 2H), 1.87 (m, 1H), 1.52 (m, 1H), 1.15-1.40 (m, 5H), 0.80 (m, 2H), 0.63 (m, 2H).

Example 275

Synthesis of Compound 326

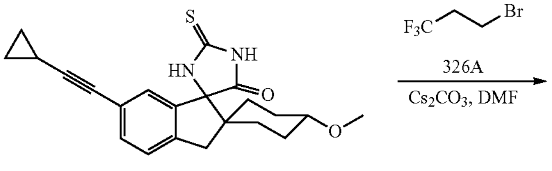

1

-continued

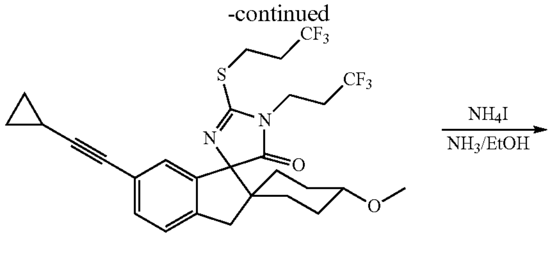

326a

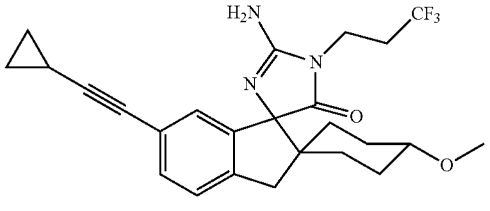

326

According to a similar synthesis of compound 317, compound 1 (50 mg, 0.13 mmol) was dialkylated compound 326A (70 mg, 0.13 mmol) to give compound 326a (34 mg, 45%) as a white solid.

Compound 326a (54 mg, 0.09 mmol) was then reacted with $NH_4I$ (137 mg, 0.94 mmol) in $NH_3$/EtOH (2.5 mL) to give compound 326 (3.3 mg, 8%) as a white solid. LC-MS $t_R$=1.061 min in 2 min chromatography, MS (ESI) m/z 460.2 $[M-41]^+$. $^1H$ NMR ($CD_3OD$ 400 MHz): δ 7.37 (m, 2H), 7.19 (s, 1H), 4.01 (m, 2H), 3.37 (s, 3H), 3.17 (m, 3H), 2.68 (m, 2H), 2.02 (m, 3H), 1.42 (m, 6H), 0.89 (m, 2H), 0.71 (m, 2H). $^{19}F$ NMR ($CD_3OD$ 400 MHz): δ −77.05, −66.31.

Example 276

Synthesis of Compound 327

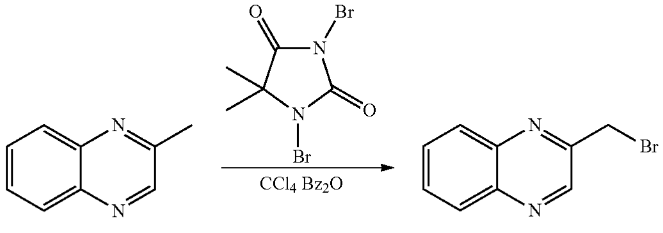

327a

327b

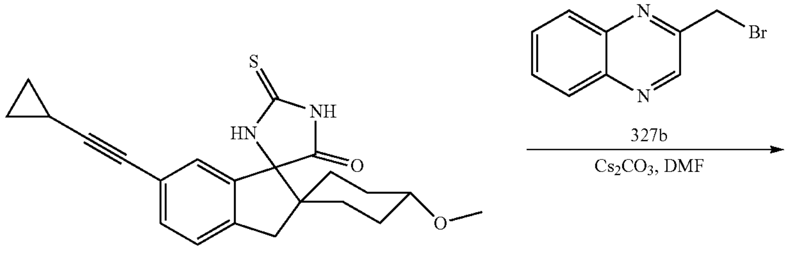

1

-continued

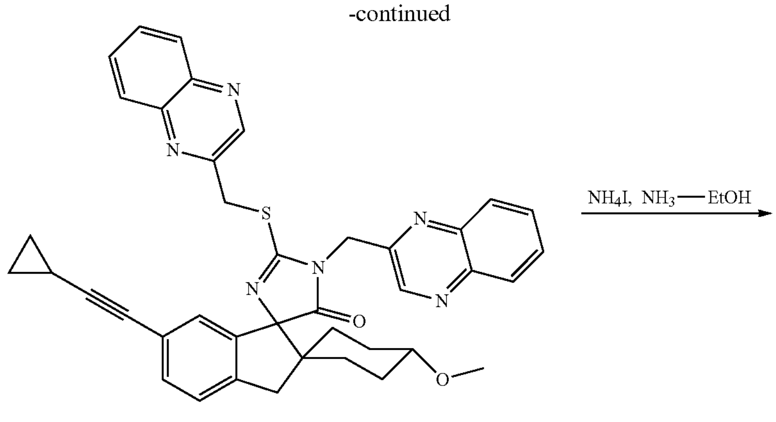

327c

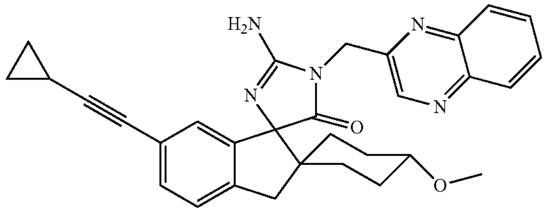

327

Procedure for Preparation of Compound 9

To a solution of compound 327a (500 mg, 3.47 mmol) in anhydrous $CCl_4$ (10 mL) was added 1,3-dibromo-5,5-dimethyl-imidazolidine-2,4-dione (694 mg, 2.42 mmol) and $Bz_2O$ (92 mg, 0.38 mmol). The resulting suspension was heated at reflux for 12 h. The mixture was filtered through a pad of celite and the filtrate was concentrated under reduced pressure to give the crude product which was purified by preparative TLC on silica gel eluting with hexane: EtOAc=3:1 to give compound 327b (50 mg, 6%) as a yellow liquid. $^1$H NMR ($CDCl_3$ 300 MHz): δ 8.93 (s, 1H), 8.07-8.01 (m, 2H), 7.74-7.71 (m, 2H), 4.72 (s, 2H).

Procedure for Preparation of Compound 327

According to a similar synthesis of compound 317, compound 1 (30 mg, 0.076 mmol) was dialkylated with 2-(bromomethyl)quinoxaline (327b) to give compound 327c (20 mg, 38%) as a yellow solid. LC-MS: $t_R$=1.418 min in 2 min chromatography, MS (ESI) m/z 665.2 $[M+H]^+$.

Compound 327c (20 mg, 0.03 mmol) was then converted to compound 327 (2.20 mg, 14%) as a white solid. LC-MS: $t_R$=0.935 min in 2 min chromatography, MS (ESI) m/z 506.1 $[M+H]^+$. $^1$H NMR ($CD_3OD$ 400 MHz): δ 8.85-8.80 (s, 1H), 8.10-8.01 (m, 2H), 7.90-7.70 (m, 2H), 7.45-7.41 (s, 1H), 7.29-7.25 (dd, J=1.6, 8.0 Hz, 1H), 7.25-7.20 (d, J=8.0 Hz, 1H), 5.40-5.30 (d, J=19.6 Hz, 1H), 5.40-5.30 (d, J=19.6 Hz, 1H), 3.28 (s, 3H), 3.20-3.10 (m, 2H), 3.05-2.95 (d, J=19.6 Hz, 1H), 2.10-1.90 (m, 2H), 1.90-1.80 (m, 1H), 1.70-1.50 (m, 1H), 1.50-1.30 (m, 4H), 1.30-1.10 (m, 1H), 0.91-0.81 (m, 2H), 0.72-0.61 (m, 2H).

Example 277

Synthesis of Compound 328

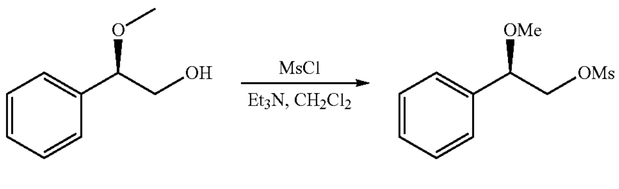

328a 328b

-continued

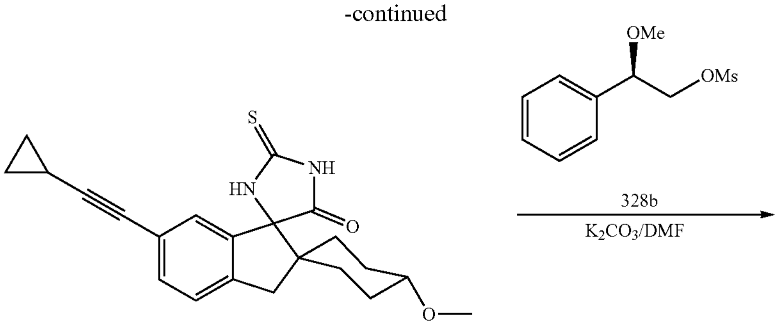

1

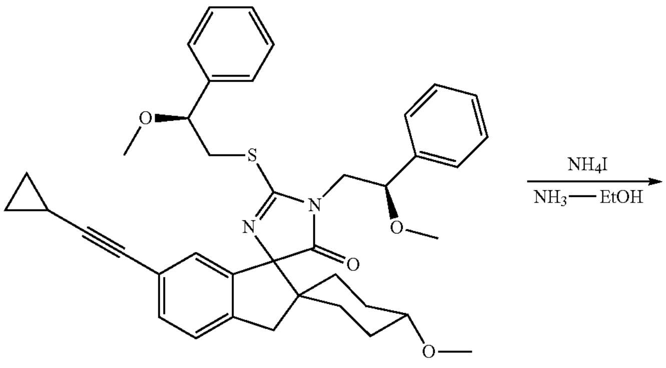

328c

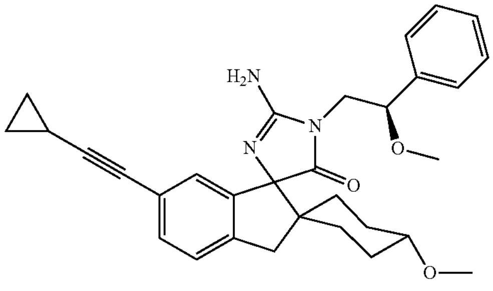

328

Procedure for Preparation of Compound 328b

To a solution of compound 328a (200 mg, 1.32 mmol) in $CH_2Cl_2$ (10 mL) was added MsCl (226 mg, 1.97 mmol) and $Et_3N$ (266 mg, 2.63 mmol) at 0° C., the mixture was stirred at 0° C. for 1 h. Then $H_2O$ (20 mL) was added and extracted with EtOAc (3×20 mL), the organic layer was dried over $Na_2SO_4$ and concentrated to give compound 328b (350 mg, crude) as a yellow oil, which was used for the next step without further purification.

Procedure for Preparation of Compound 328

According to a similar synthesis of compound 317, compound 1 (60 mg, 0.16 mmol) was dialkylated with compound 328b (181 mg, 0.79 mmol), to give compound 328c (100 mg, 98%).

Compound 328c (125 mg, 0.19 mmol) was then reacted with $NH_4I$ (280 mg, 1.93 mmol) in $NH_3$-EtOH (3 mL) to give compound 328 (15.0 mg, 16%) as a white solid. LC-MS: $t_R$=1.128 min in 2 min chromatography, MS (ESI) m/z=498.2 $[M+H]^+$. $^1H$ NMR ($CD_3OD$ 400 MHz): δ 7.40 (m, 6H), 7.31 (m, 1H), 7.08 (s, 1H), 4.53 (m, 1H), 3.99 (m, 1H), 3.87 (m, 1H), 3.33 (s, 3H), 3.27 (d, J=8.4 Hz, 3H), 3.18 (m, 2H), 3.09 (m, 1H), 2.03 (s, 2H), 1.68 (m, 1H), 1.34 (m, 6H), 0.90 (m, 2H), 0.72 (m, 2H).

Example 278

Synthesis of Compound 329

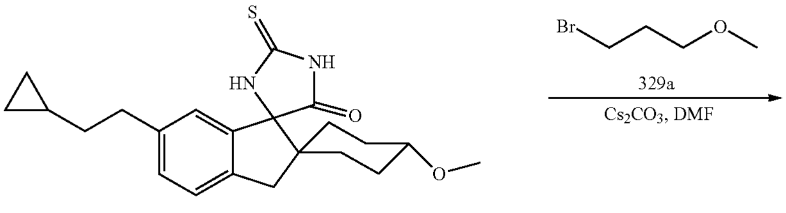

1

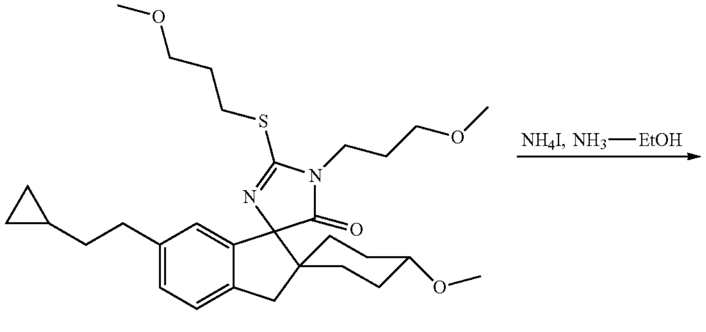

329b

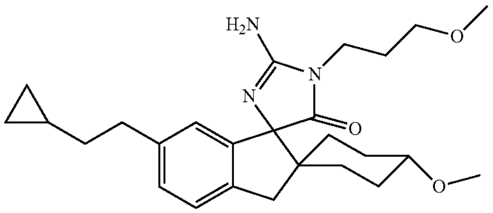

329

According to a similar synthesis of compound 317, compound 1 (30 mg, 0.078 mmol) was dialkylated with 1-bromo-3-methoxy-propane (329a) (35 mg, 0.23 mmol) to give compound 329b (25 mg, 61%) as a white solid.

Compound 329b (25 mg, 0.048 mmol) was then reacted with $NH_4I$ (100 mg, 0.69 mmol) and $NH_3$-EtOH (2 mL) to give compound 329 (18.3 mg, 87%) as a white solid. LC-MS: $t_R$=1.604 min in 3 min chromatography, MS (ESI) m/z=440 $[M+H]^+$. $^1H$ NMR ($CD_3OD$, 400 MHz): δ 7.18 (d, J=7.6 Hz, 1H), 7.09 (d, J=7.6 Hz, 1H), 6.78 (s, 1H), 3.59 (t, J=6.8 Hz, 2H), 3.39 (t, J=6.4 Hz, 2H), 3.33 (s, 3H), 3.15 (m, 1H), 3.09 (d, J=15.6 Hz, 1H), 3.01 (d, J=15.2 Hz, 1H), 2.91 (s, 3H), 2.67 (t, J=7.6 Hz, 2H), 1.80-2.10 (m, 5H), 1.61 (m, 1H), 1.25-1.50 (m, 6H), 0.65 (m, 1H), 0.40 (m, 2H), 0.00 (m, 2H).

Example 279

Synthesis of Compound 330

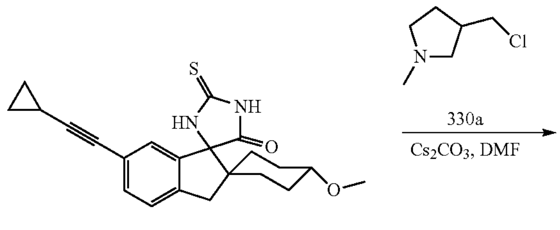

1

-continued

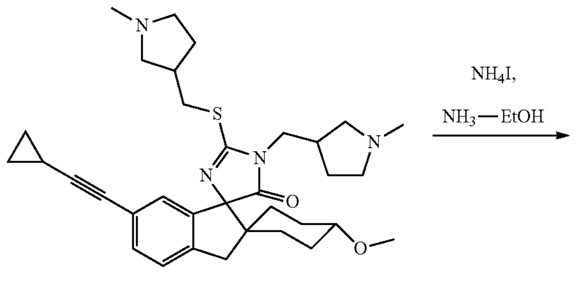

330b

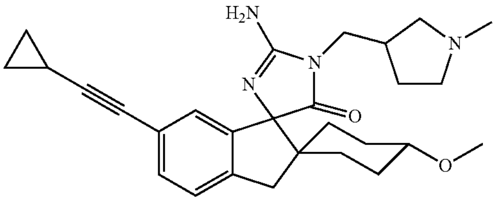

330

According to a similar synthesis of compound 317, compound 1 (50 mg, 0.13 mmol) was dialkylated with 3-chloromethyl-1-methyl-pyrrolidine (330a) (52 mg, 0.39 mmol) to give compound 330b (40 mg, 53%) as a pale yellow sticky oil. LC-MS: $t_R$=1.166 min in 3 min chromatography, MS (ESI) m/z 575 $[M+H]^+$.

Compound 330b (40 mg, 0.070 mmol) was then converted to compound 330 (10.0 mg, 31%) as a white solid. LC-MS: $t_R$=1.298 min in 3 min chromatography, MS (ESI) m/z 461 $[M+H]^+$. $^1$H NMR: ($CD_3OD$, 400 MHz): δ 7.21 (m, 2H), 6.88 (s, 1H), 3.52 (d, J=6.8 Hz, 2H), 3.35 (s, 3H), 3.16 (m, 2H), 3.07 (d, J=12.8 Hz, 1H), 2.68 (m, 4H), 2.35 (m, 4H), 1.75-2.10 (m, 4H), 1.50-1.70 (m, 2H), 1.25-1.50 (m, 5H), 0.85-1.05 (m, 6H), 0.87 (m, 2H), 0.69 (m, 2H).

Example 280

Synthesis of Compound 331

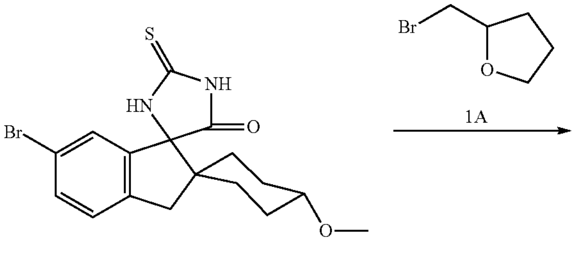

1

-continued

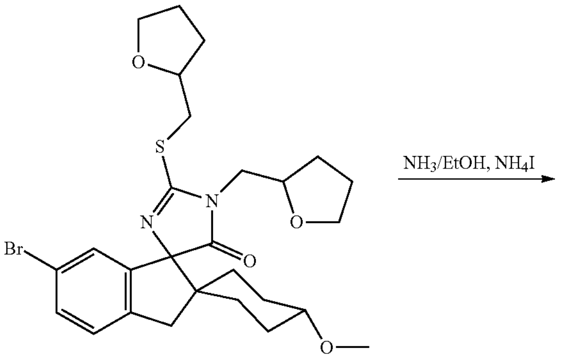

2

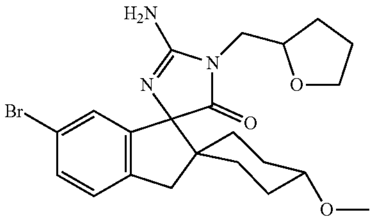

331

According to a similar synthesis of compound 317, compound 1 (100 mg, 0.25 mmol) was dialkylated with compound 1A (166 mg, 1.02 mmol) to give compound 2 (100 mg, 70%).

Compound 2 (100 mg, 0.18 mmol) was then reacted with $NH_4I$ (257.5 mg, 1.78 mmol) in $NH_3$/EtOH (5.0 N, 2 mL) to give compound 331 (25.1 mg, 31%) as a white solid. LC-MS: $t_R$=0.953 min in 2 min chromatography, MS (ESI) m/z 462 $[M+H]^+$. $^1$H NMR ($CD_3OD$ 400 MHz): δ 7.54 (d, J=8.0 Hz, 1H), 7.42 (dd, J=1.6, 8.0 Hz, 1H), 7.32 (d, J=8.0 Hz, 1H), 4.12 (m, 1H), 3.70-3.90 (m, 4H), 3.36 (s, 3H), 3.15 (m, 3H), 2.11-1.86 (m, 6H), 1.62 (m, 1H), 1.45 (m, 4H), 1.32 (m, 1H).

Example 281

Synthesis of Compound 332

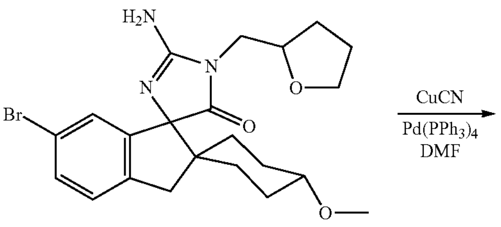

331

-continued

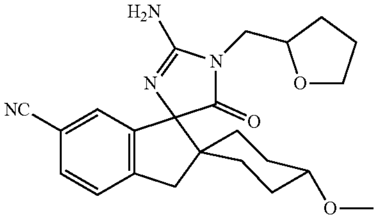

332

To a solution of compound 331 (25 mg, 0.054 mmol) in DMF (2 mL) was added CuCN (10 mg, 0.108 mmol) and $Pd(PPh_3)_4$ (6 mg, 0.005 mmol) under $N_2$. The reaction mixture was heated at 180° C. for 40 min in a CEM microwave reactor. The reaction mixture was added water (20 mL) and extracted with EtOAc (30 mL), the combined organic layers were concentrated under reduced pressure and purified by HPLC (0.1% TFA as buffer) to give compound 332 (5.7 mg, 41%) as a white solid. LC-MS: $t_R$=0.892 min in 2 min chromatography, MS (ESI) m/z=409 $[M+H]^+$. $^1H$ NMR ($CD_3OD$ 400 MHz): δ 7.77 (d, J=8.0 Hz, 1H), 7.68 (d, J=10.4 Hz, 1H), 7.59 (d, J=8.0 Hz, 1H), 4.12 (m, 1H), 3.70-3.90 (m, 4H), 3.36 (s, 3H), 3.15 (m, 3H), 2.11-1.86 (m, 6H), 1.62 (m, 1H), 1.45 (m, 4H), 1.32 (m, 1H).

Example 282

Synthesis of Compounds 333, 334, 335, 336 and 337

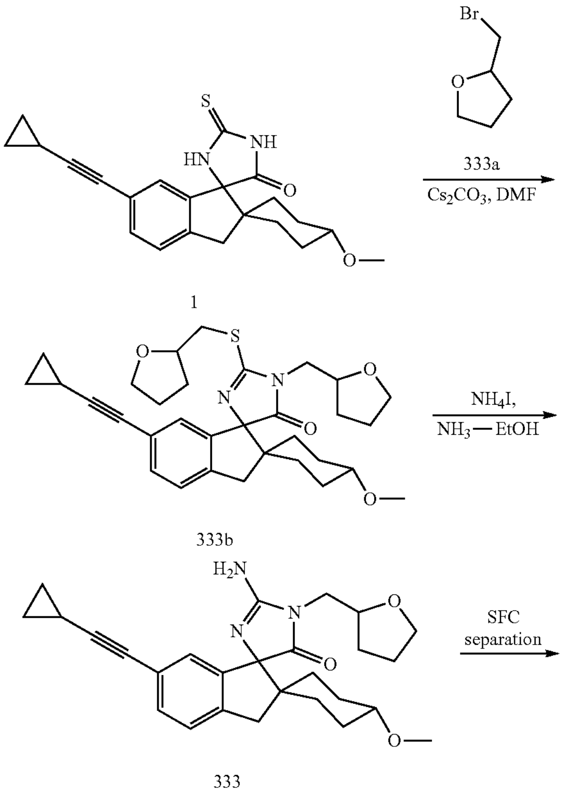

1

333b

333

-continued

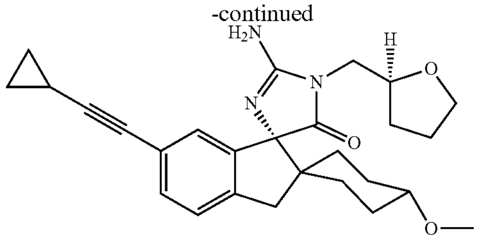

334

+

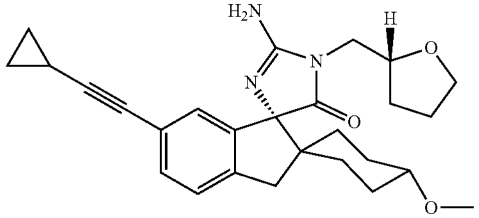

335

+

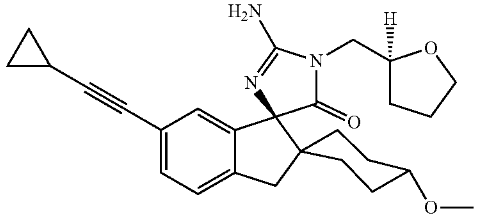

336

+

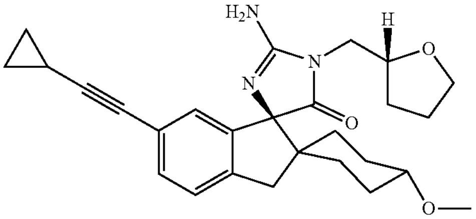

337

According to a similar synthesis of compound 317, compound 1 (130 mg, 0.34 mmol) was alkylated with compound 333a (225.7 mg, 1.36 mmol) to give compound 333b (77 mg, 41%) as a white solid. LC-MS $t_R$=1.408 min in 2 min chromatography, MS (ESI) m/z=549.3 $[M+H]^+$.

Compound 333b (20 mg, 0.036 mmol) was reacted with $NH_4I$ (52.3 mg, 0.36 mmol) in $NH_3$-EtOH (2 mL, 5 N) to give compound 333 (2.00 mg, 12%) as a white solid. LC-MS $t_R$=1.162 min in 2 min chromatography, MS (ESI) m/z 448.4 $[M+H]^+$. $^1H$ NMR ($CD_3OD$ 400 MHz): δ 7.36 (d, J=7.6 Hz, 2H), 7.20 (s, 1H), 4.21-4.10 (m, 1H), 4.01-3.91 (m, 2H), 3.81-3.62 (m, 2H), 3.36 (s, 3H), 3.18-3.12 (m, 1H), 3.09-2.97 (d, J=6.4 Hz, 2H), 2.20-2.01 (m, 2H), 2.00-1.80 (m, 3H), 1.70-1.51 (m, 1H), 1.50-1.30 (m, 5H), 1.30-1.20 (m, 2H), 0.95-0.82 (m, 2H), 0.82-0.62 (m, 2H).

Another portion of compound 333b (70 mg, 0.127 mmol) was reacted with $NH_4I$ (183.3 mg, 1.27 mmol) in $NH_3$/EtOH and purified by preparative SFC to give compound 334 (3.20 mg, 6%) LC-MS $t_R$=1.060 min in 2 min chromatography, MS (ESI) m/z=448.2 $[M+H]^+$. SFC: $t_R$=6.22 min in 15 min chromatography, ee=86%. $^1H$ NMR ($CD_3OD$, 400 MHz): δ 7.37 (d, J=7.6 Hz, 2H), 7.18 (s, 1H), 4.21-4.11 (m, 1H), 4.11-3.92 (m, 1H), 3.81-3.71 (m, 3H), 3.36 (s, 3H), 3.16-3.10 (m, 1H), 3.09-3.01 (d, J=6.4 Hz, 2H), 2.20-1.85 (m, 6H), 1.72-1.51 (m, 1H), 1.50-1.30 (m, 5H), 1.31-1.21 (m, 1H), 0.93-0.82 (m, 2H), 0.82-0.61 (m, 2H).

& compound 335 (3.50 mg, 6%) LC-MS $t_R$=1.022 min in 2 min chromatography, MS (ESI) m/z=448.1 $[M+H]^+$. SFC: $t_R$=6.49 min in 15 min chromatography, ee=98%. $^1$H NMR ($CD_3OD$, 400 MHz): δ 7.30 (d, J=7.6 Hz, 2H), 6.90 (s, 1H), 4.10-3.90 (m, 1H), 3.91-3.71 (m, 1H), 3.71-3.62 (m, 1H), 3.61-3.40 (m, 2H), 3.34 (s, 3H), 3.14-3.10 (m, 1H), 3.00-2.80 (d, J=6.8 Hz, 2H), 2.01-1.70 (m, 6H), 1.60-1.40 (m, 2H), 1.40-1.10 (m, 5H), 0.80-0.71 (m, 2H), 0.70-0.51 (m, 2H).

& compound 336 (2.50 mg, 4%) LC-MS $t_R$=1.053 min in 2 min chromatography, MS (ESI) m/z=448.2 [M+H]SFC: $t_R$=6.95 min in 15 min chromatography, ee=100%. $^1$H NMR ($CD_3OD$, 400 MHz): δ 7.33 (d, J=8.0 Hz, 2H), 7.10 (s, 1H), 4.10-3.90 (m, 1H), 3.90-3.71 (m, 2H), 3.71-3.62 (m, 1H), 3.62-3.50 (m, 1H), 3.34 (s, 3H), 3.16-3.14 (m, 1H), 3.08-2.96 (d, J=8.4 Hz, 2H), 2.02-1.71 (m, 6H), 1.60-1.40 (m, 1H), 1.40-1.31 (m, 5H), 1.30-1.10 (m, 1H), 0.82-0.72 (m, 2H), 0.71-0.52 (m, 2H).

& compound 337 (2.80 mg, 5%) as white solid. LC-MS $t_R$=1.054 min in 2 min chromatography, MS (ESI) m/z=448.2 [M+H]SFC: $t_R$=7.44 min in 15 min chromatography, ee=92%. $^1$H NMR ($CD_3OD$, 400 MHz): δ 7.32 (d, J=7.6 Hz, 2H), 7.15 (s, 1H), 4.10-3.91 (m, 1H), 3.90-3.81 (m, 1H), 3.80-3.60 (m, 3H), 3.35 (s, 3H), 3.18-3.10 (m, 1H), 3.08-2.98 (d, J=7.6 Hz, 2H), 2.10-1.71 (m, 6H), 1.60-1.40 (m, 1H), 1.40-1.21 (m, 5H), 1.20-1.10 (m, 1H), 0.82-0.72 (m, 2H), 0.72-0.62 (m, 2H).

Example 283

Synthesis of Compound 338

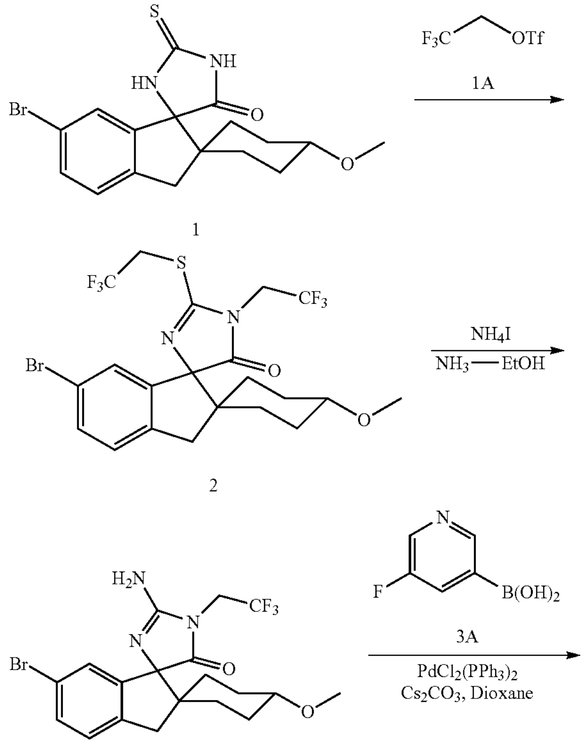

1

2

3

-continued

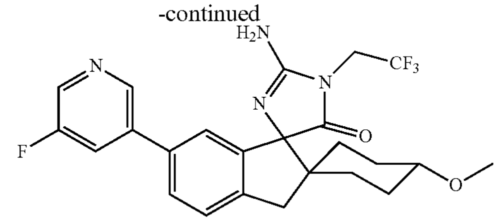

338

According to a similar synthesis of compound 317, compound 1 (40 mg, 0.10 mmol) was dialkylated with compound 1A (47 mg, 0.2 mmol) to give compound 2 (43 mg, 76%) as a white solid.

Compound 2 (43 mg, 0.08 mmol) was reacted with $NH_4I$ (112 mg, 0.77 mmol) in $NH_3$/EtOH (2.5 mL) to give compound 3 (13 mg, 37%) as a white solid.

Procedure for Preparation of 338

A suspension of compound 3 (13 mg, 0.03 mmol), compound 3A (6 mg, 0.04 mmol), $PdCl_2(PPh_3)_2$ (2 mg) and $Cs_2CO_3$ (0.2 mL, 2 N in water) in 1,4-dioxane (0.72 mL) was heated under 120° C. for 15 min in a CEM microwave reactor. The mixture was concentrated in vacuo and the residue was purified by acid preparative HPLC to give compound 338 (3.0 mg, 22%) as a white solid. LC-MS $t_R$=0.841 min in 2 min chromatography, MS (ESI) m/z 477.2 $[M+H]^+$. $^1$H NMR ($CD_3OD$ 400 MHz): δ 8.71 (s, 1H), 8.49 (s, 1H), 7.95 (d, J=8.8 Hz, 1H), 7.75 (m, 1H), 7.64 (m, 1H), 7.56 (d, J=6.8 Hz, 1H), 4.31 (m, 2H), 3.39 (s, 3H), 3.25 (m, 3H), 2.14 (m, 3H), 1.47 (m, 5H). $^{19}$F NMR ($CD_3OD$ 400 MHz): δ −73.34, −77.21, −128.26.

Example 284

Synthesis of Compound

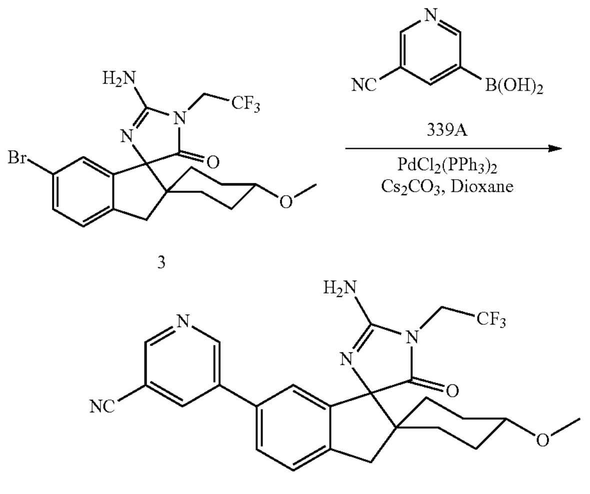

3

339

A suspension of compound 3 described in Example 283 (30 mg, 0.07 mmol), compound 339A (15 mg, 0.10 mmol), $PdCl_2(PPh_3)_2$ (5 mg) and $Cs_2CO_3$ (0.5 mL, 2 N in water) in 1,4-dioxane (1.7 mL) was heated under 120° C. for 15 min in a CEM microwave reactor. The mixture was concentrated in vacuo and the residue was purified by acid preparative HPLC to give compound 339 (7.4 mg, 23%) as a white solid. LC-MS $t_R$=2.686 min in 2 min chromatography, MS (ESI) m/z 484.2 $[M+H]^+$. $^1$H NMR ($CD_3OD$ 400 MHz): δ 9.09 (s, 1H), 8.91 (s, 1H), 8.47 (s, 1H), 7.79 (d, J=8.0 Hz, 1H), 7.65 (s, 1H), 7.58 (d, J=8.0 Hz, 1H), 4.68 (m, 1H), 4.54 (m, 1H), 3.38 (m, 3H), 3.33 (m, 3H), 2.07 (m, 3H), 1.48 (m, 5H). $^{19}$F NMR ($CD_3OD$ 400 MHz): δ −77.14, −71.99.

Example 285

Synthesis of Compound 340

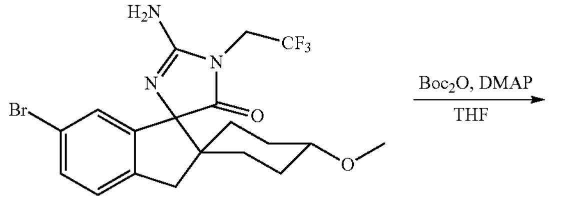

3

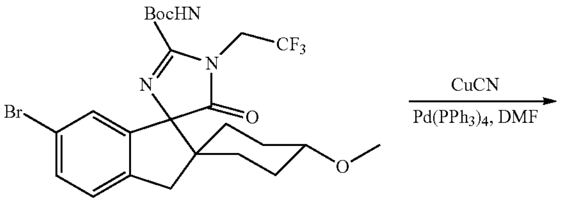

340a

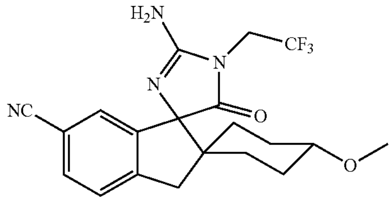

340

Procedure for Preparation of Compound 340a

A mixture of compound 3 described in Example 283 (15 mg, 0.033 mmol, crude), $Boc_2O$ (14 mg, 0.066 mmol) and DMAP (0.008 g, 0.066 mmol) in THF (3 mL) was stirred at ambient temperature overnight. The solvent was removed by evaporation to yield the crude product which was purified by preparative TLC on silica gel eluting with petroleum ether: ethyl acetate=3:1 to afford compound 340a (17 mg, 71%) as a white solid. LC-MS: $t_R$=1.609 min in 2 min chromatography, MS (ESI) m/z 504, 506 $[M-56]^+$ Procedure for Preparation of Compound 340

A sealed tube was charged with compound 340a (17 mg, 0.03 mmol), CuCN (30 mg, 0.33 mmol), $Pd(PPh_3)_4$ (2 mg, 0.0017 mmol) and DMF (1 mL) in turn under nitrogen. The tube was heated at 180° C. in a CEM microwave reactor for 1.5 h. Ethyl acetate (10 mL) and methanol (1 mL) were added with stirring, and the resulting precipitate was filtered off and washed with ethyl acetate (10 mL). The filtrate and washings were combined and washed with brine (10 mL×2), dried over $Na_2SO_4$, filtered and concentrated in vacuo. The residue was purified by preparative HPLC to give pure compound 340 (6.2 mg, 51%) as a white solid. LC-MS: $t_R$=1.527 min in 3 min chromatography, MS (ESI) m/z 407, $[M+H]^+$. $^1$H NMR ($CD_3OD$ 400 MHz): δ 7.66 (d, J=8.0 Hz, 1H), 7.52 (d, J=7.6, Hz, 2H), 7.32 (s, 1H), 4.37 (d, J=8.8 Hz, 1H), 4.32 (d, J=8.8 Hz, 1H), 3.38 (s, 3H), 3.22 (m, 3H), 1.99 (m, 2H), 1.85 (m, 1H), 1.65 (m, 1H), 1.45 (m, 1H), 1.35 (m, 3H). $^{19}$F NMR ($CD_3OD$, 400 MHz) δ −71.96

Example 286

Synthesis of Compound 341

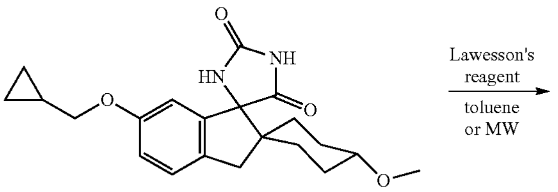

341a

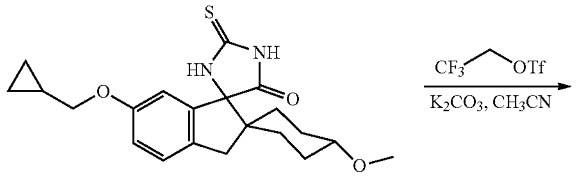

341b

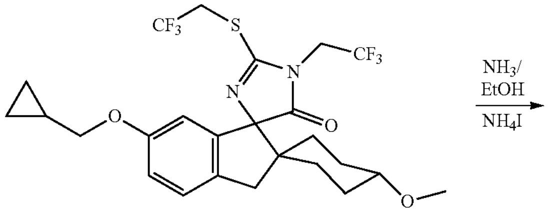

341c

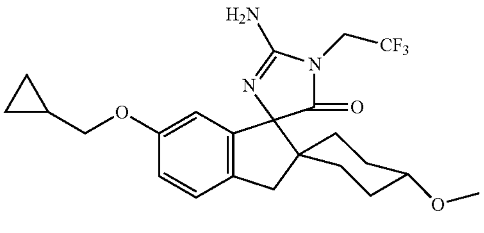

341

Procedure for Preparation of Compound 341b

To a solution of compound 341a (80 mg, 0.21 mmol) in anhydrous toluene (2 mL) was added Lawesson's Reagent (84.8 mg, 0.21 mmol) under $N_2$, the mixture was stirred at 110° C. for 3 h. The solvent was removed in vacuo to give the crude product which was purified by preparative TLC on silica gel eluting with hexane:EtOAc=3:1 to afford compound 341b (50 mg, 60%) as a white solid. LCMS: $t_R$=1.258 min in 2 min chromatography, MS (ESI) m/z=387.2 $(M+H)^{30}$.

Procedure for Preparation of Compound 341c

To a solution of compound 341b (20 mg, 0.05 mmol) in $CH_3CN$ (2 mL) was added $K_2CO_3$ (27.6 mg, 0.20 mmol). After stirring for 5 min, compound 341b (48 mg, 0.20 mmol) was added. The reaction mixture was heated at 60° C. for 4 h. The precipitate was filtered off and the filtrate was concentrated in vacuo. The residue was purified by preparative TLC on silica gel eluting with hexane:EtOAc=3:1 to give compound 341c (20 mg, 70%) as a white solid. LCMS: $t_R$=1.622 min in 2 min chromatography, MS (ESI) m/z=551.2 $(M+H)^{30}$.

Procedure for Preparation of Compound 341

A solution of compound 341c (20 mg, 0.036 mmol), $NH_4I$ (50 mg, 0.36 mmol) in $NH_3$-EtOH (2 mL, 5 N) was heated at 120° C. in a CEM microwave reactor for 3 h. After being cooled, the mixture was concentrated in vacuo, and the residue was purified by preparative TLC on silica gel eluting with dichloromethane:methanol=10:1 and preparative HPLC to give compound 341 (2.0 mg, 20%) as a white solid. LCMS: $t_R$=1.968 min in 3 min chromatography, MS (ESI) m/z=452.2 $(M+H)^{30}$. $^1$H-NMR ($CD_3OD$ 400 MHz): δ 7.20 (d, J=8.0 Hz, 1H), 6.90 (d, J=8.4 Hz, 1H), 6.54 (s, 1H), 4.36 (m, 2H), 3.77 (d, J=8.0 Hz, 2H), 3.36 (s, 3H), 3.27-3.17 (m, 1H), 3.05-2.97 (s, 2H), 2.10-1.98 (m, 2H), 1.97-1.86 (m, 1H), 1.60-1.57 (m, 1H), 1.57-1.44 (m, 2H), 1.34-1.20 (m, 3H), 0.7-0.50 (m, 2H), 0.40-0.20 (m, 2H). $^{19}$F NMR ($CD_3OD$): δ: −66.52

Example 287

Synthesis of Compound 342

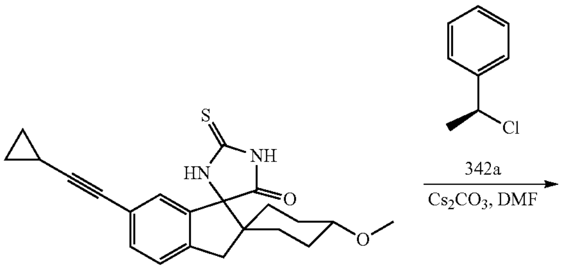

1

-continued

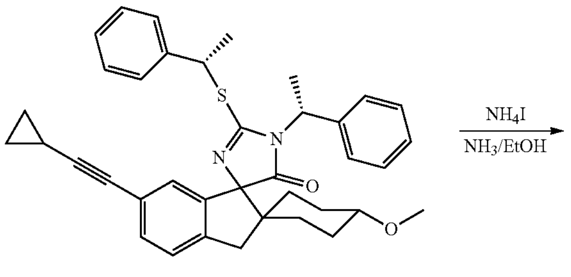

342b

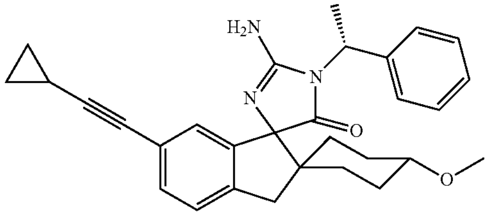

342

According to a similar synthesis of compound 317, compound 1 (40 mg, 0.10 mmol) was dialkylated with (S)-(1-chloroethyl)benzene (342a) to give compound 342b (15 mg, 24%) as a white solid. LC-MS: $t_R$=1.812 min in 2 min chromatography, MS (ESI) m/z=589.3 $[M+H]^+$.

Compound 342b (15 mg, 0.025 mmol) was then converted to compound 342 (2.00 mg, 16%) as a white solid. LC-MS: $t_R$=0.988 min in 2 min chromatography, MS (ESI) m/z=468.1 $[M+H]^+$. $^1$H NMR ($CD_3OD$ 400 MHz): δ 7.48-6.95 (m, 8H), 5.38-5.32 (m, 1H), 3.31 (s, 3H), 3.09-3.01 (m, 1H), 3.00-2.93 (m, 2H), 2.10-1.89 (m, 1H), 1.88-1.70 (m, 3H), 1.60-1.20 (m, 5H), 1.20-0.9 (m, 3H), 0.90-0.80 (m, 2H), 0.7-0.6 (m, 2H).

Example 288

Synthesis of Compound 343

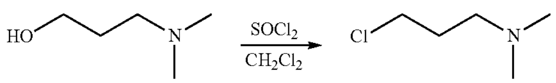

343a

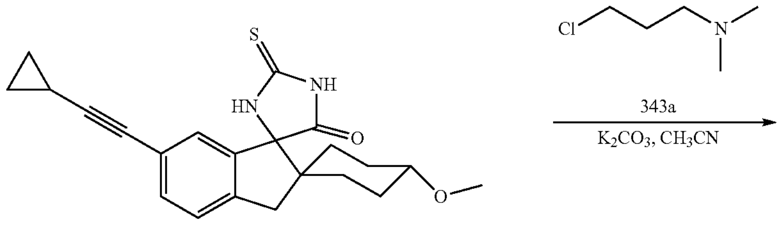

1

-continued

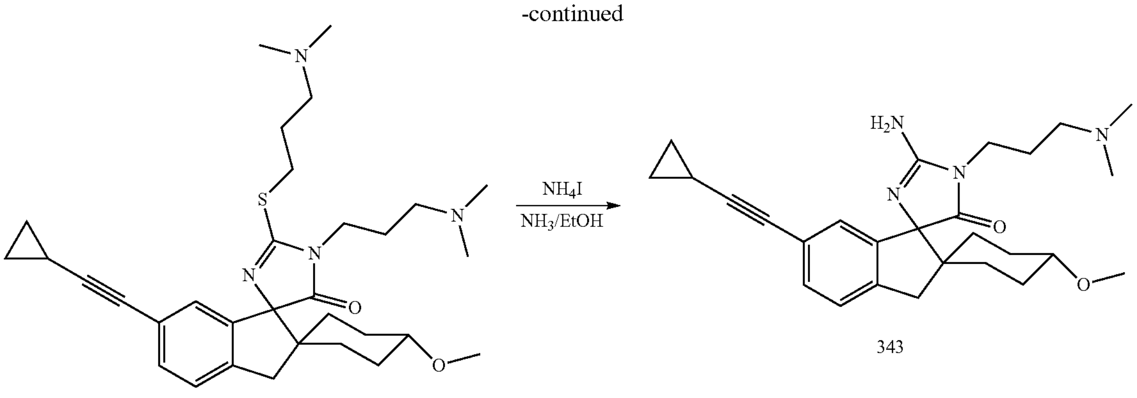

343b

343

Procedure for Preparation of Compound 20

To a solution of 3-dimethylamino-propan-1-ol (1.0 g, 9.7 mmol) in anhydrous $CH_2Cl_2$ (10 mL) was added $SOCl_2$ (1.26 g, 10.6 mmol) at 0° C. under $N_2$. After addition, the mixture was warmed to room temperature and was stirred at room temperature overnight. The solvent was removed in vacuo to give compound 343a (0.94 g, 80%) as a white solid, which was used for the next step without further purification. $^1H$ NMR ($CDCl_3$ 300 MHz): δ 3.84-3.5 (t, J=6.3 Hz, 2H), 3.40-3.10 (m, 2H), 3.0-2.60 (d, J=5.1 Hz, 6H), 2.50-2.20 (m, 2H).

Procedure for Preparation of Compound 343

According to a similar synthesis of compound 317, compound 1 (30 mg, 0.078 mmol) was dialkylated with compound 343a (38 mg, 0.32 mmol) to give compound 343b (0.021 g, 50%) as a white solid. LC-MS: $t_R$=0.782 min in 2 min chromatography, MS (ESI) m/z=551.4 $[M+H]^+$.

Compound 343b (20 mg, 0.036 mmol) was then reacted with $NH_4I$ (52.1 mg, 0.36 mmol) and $NH_3$-EtOH (2 mL) to give compound 343 (2.50 mg, 15%) as a white solid. LC-MS: $t_R$=1.863 min in 3 min chromatography, MS (ESI) m/z=449.3 $[M+H]^+$. $^1H$ NMR ($CD_3OD$ 400 MHz): δ 7.27 (s, 2H), 6.90-6.80 (s, 1H), 3.50-3.41 (m, 2H), 3.36 (s, 3H), 3.16 (m, 2H), 3.09-2.91 (d, 15.6 Hz, 1H), 2.60-2.40 (m, 2H), 2.40-2.30 (s, 3H), 2.30-2.20 (s, 3H), 2.00-1.85 (m, 3H), 1.85-1.75 (m, 2H), 1.40-1.30 (m, 4H), 1.30-1.20 (m, 2H), 0.85-0.75 (m, 2H), 0.65-0.55 (m, 2H).

Example I-6

Synthesis of Thiohydantoin Intermediate

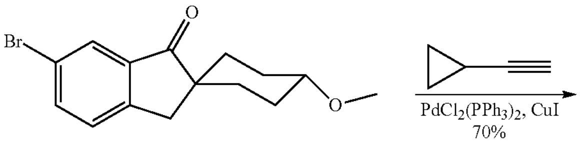

1

-continued

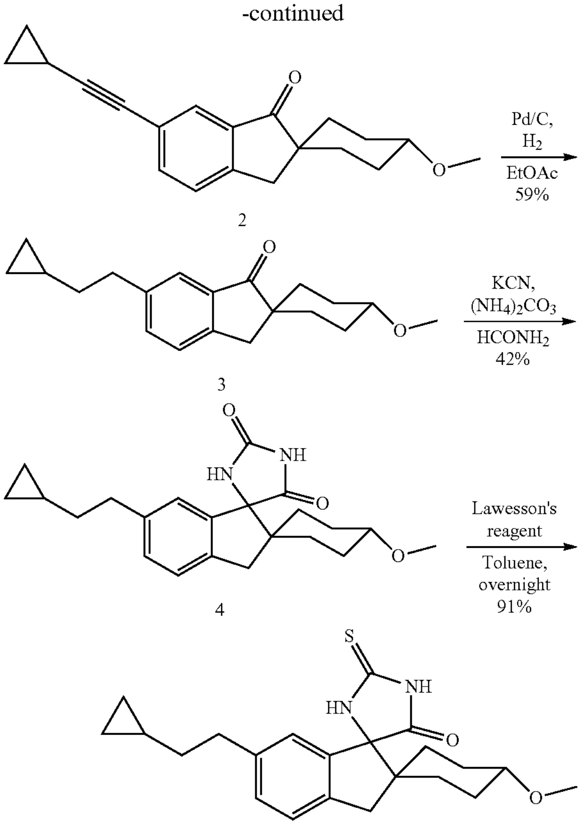

2

3

4

5

Procedure for Preparation of Compound 2

A flask equipped with a condenser and a nitrogen balloon was charged with compound 1 (7.5 g, 24.3 mmol), $Et_2NH$ (20 mL), $Et_3N$ (100 mL), $Pd(PPh_3)_2Cl_2$ (1.0 g, 1.5 mmol), CuI (0.29 g, 1.5 mmol) and Ethynyl cyclopropane (15 mL) in turn under nitrogen. The reaction mixture was stirred at 60° C. overnight. After cooling down, the solvent was removed by evaporation in vacuo. The residue was added ethyl acetate (150 mL), and then the mixture was filtered through a pad of silica gel and washed with ethyl acetate (50 mL×2). The combined organic filtrates were washed with brine (100 mL×2), dried over $Na_2SO_4$, filtered and concentrated in vacuo. The resulting residue was purified by column chromatography on silica gel eluting with petroleum ether:ethyl acetate (100:1 to 10:1) to give compound 2 (5.0 g, 70%) as a red-brown solid. $^1$H NMR: ($CDCl_3$ 300 MHz): δ 7.75 (s, 1H), 7.55 (d, J=8.0 Hz, 1H), 7.35 (d, J=8.1 Hz, 1H), 3.42 (s, 3H), 3.25 (m, 1H), 3.00 (s, 2H), 2.15 (m, 2H), 1.85 (m, 2H), 1.35-1.55 (m, 5H), 0.75-0.95 (m, 4H).

Procedure for Preparation of Compound 3

A mixture of compound 2 (4.0 g, 13.6 mmol), Pd/C (1.0 g), ethyl acetate (200 mL) and MeOH (20 mL) was stirred at temperature under 1 atm hydrogen atmosphere for 24 h. The precipitate was filtered off and washed with ethyl acetate (100 mL×2). The filtrate was concentrated by evaporation in vacuo. The residue was purified by preparative HPLC to give compound 3 (2.4 g, 59%) as a pale yellow oil. LC-MS: $t_R$=2.371 min in 3 min chromatography, MS (ESI) m/z=299 $[M+H]^+$. $^1$H NMR: ($CDCl_3$ 300 MHz): δ 7.65 (s, 1H), 7.42 (d, J=7.8 Hz, 1H), 7.32 (d, J=7.8 Hz, 1H), 3.36 (s, 3H), 3.27 (m, 1H), 2.95 (s, 2H), 2.72 (t, J=7.2 Hz, 2H), 2.15 (m, 2H), 1.75 (m, 2H), 1.25-1.55 (m, 6H), 0.65 (m, 1H), 0.40 (m, 2H), 0.00 (m, 2H).

Procedure for Preparation of Compound 4

A steel autoclave was charged with a mixture of compound 3 (2.1 g, 7.0 mmol), $(NH_4)_2CO_3$ (4.0 g, 41.7 mmol), formamide (60 mL) and KCN (1.2 g, 18.5 mmol), carefully. The mixture was heated at 120-130° C. for 72 h. After cooling down, the reaction mixture was poured into ice-water (300 mL). The mixture was extracted with ethyl acetate (contained 20% iso-propanol) (200 mL×3), and the combined organic layers were washed with brine (200 mL x 3). The separated organic phase was dried over $Na_2SO_4$ and concentrated in vacuo to give the crude compound as a yellow oil, which was purified by preparative HPLC to give pure compound 4 (1.1 g, 42%) as a pale yellow oil. LC-MS: $t_R$=1.747 min in 3 min chromatography, MS (ESI) m/z=369 $[M+H]^+$. $^1$H NMR: ($CDCl_3$ 400 MHz): δ 8.45, (s, 1H), 7.17 (d, J=8.0 Hz, 1H), 7.11 (d, J=7.8 Hz, 1H), 6.95 (s, 1H), 6.10 (s, 1H), 3.35 (s, 3H), 3.10 (m, 2H), 2.90 (d, J=15.2, 1H), 2.60 (t, J=7.6 Hz, 2H), 1.90-2.10 (m, 3H), 1.40-1.50 (m, 4H), 1.30-1.40 (m, 3H), 0.65 (m, 1H), 0.40 (m, 2H), 0.00 (m, 2H).

Procedure for Preparation of Compound 5

A flask equipped with a condenser and a nitrogen balloon was charged with a mixture of compound 4 (1.1 g, 2.98 mmol), Lawesson's reagent (1.3 g, 3.21 mmol) in anhydrous toluene (15 mL) under nitrogen. The mixture was heated at 130° C. for 2 h. After cooling down, the solvent was removed by evaporation in vacuo and the residue was purified by column chromatography on silica gel eluting with petroleum ether:ethyl acetate (50:1 to 5:1) to give compound 5 (1.0 g, 91%) as a white solid. LC-MS: $t_R$=2.037 min in 3 min chromatography, MS (ESI) m/z=385 $[M+H]^+$.

Example 289

Synthesis of Compound 344

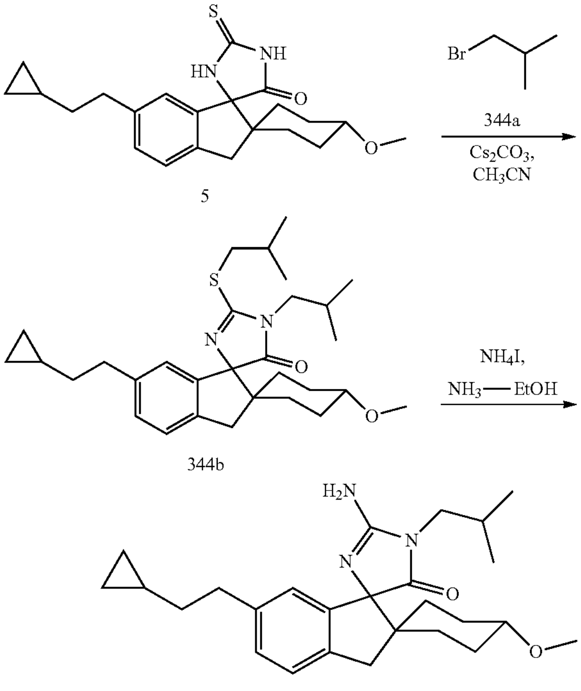

5
344b
344

Procedure for Preparation of Compound 344a

A sealed tube was charged with a mixture of compound 5 described in Example I-6 (30 mg, 0.078 mmol), DMF (2 mL), $Cs_2CO_3$ (0.10 g, 0.31 mmol) and 1-bromo-2-methyl-propane (50 mg, 0.36 mmol). The mixture was heated at 80° C. for 2.5 h. After cooling down, $H_2O$ (30 mL) was added and the mixture was extracted with ethyl acetate (10 mL×2). The combined organic layers were washed with brine (10 mL×2). The separated organic phase was dried over $Na_2SO_4$ and concentrated in vacuo. The residue was purified by preparative TLC on silica gel eluting with petroleum ether:ethyl acetate (4:1) to give compound 344b (28 mg, 72%) as a pale yellow solid. LC-MS: $t_R$=2.695 min in 3 min chromatography, MS (ESI) m/z=497 $[M+H]^+$.

Procedure for Preparation of Compound 344

A sealed tube was charged with a mixture of compound 344b (28 mg, 0.056 mmol), $NH_4I$ (100 mg, 0.69 mmol) and $NH_3$-EtOH (1 mL). The mixture was heated at 120° C. in a CEM microwave reactor for 2 h. After cooling down, Ethyl acetate (30 mL) was added and the mixture was washed brine (10 mL×2), dried over $Na_2SO_4$, filtered and concentrated in vacuo and the residue was purified by preparative HPLC to give compound 344 (10.2 mg, 42%) as a white solid; LC-MS: $t_R$=4.207 min in 7 min chromatography, MS (ESI) m/z=424 $[M+H]^+$. $^1$H NMR: ($CD_3OD$, 300 MHz): δ 7.19 (d, J=7.6 Hz, 1H), 7.09 (d, J=7.6 Hz, 1H), 7.80 (s, 1H), 3.34 (s, 3H), 3.10 (m, 2H), 3.02 (d, J=15.2 Hz, 1H), 2.67 (t, J=7.6 Hz, 2H), 1.75-2.20 (m, 5H), 1.50-1.70 (m, 2H), 1.25-1.50 (m, 6H), 0.85-1.05 (m, 6H), 0.65 (m, 1H), 0.40 (m, 2H), 0.00 (m, 2H).

Example 290

Synthesis of Compound 345

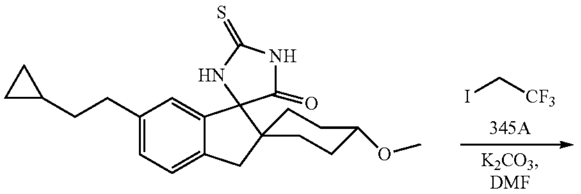

5

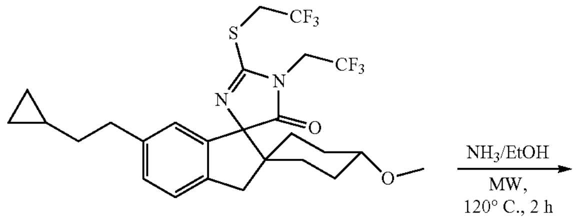

345a

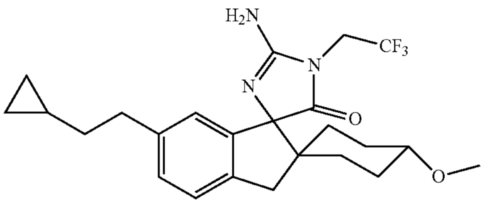

345

According to a similar synthesis of compound 344, compound 5 describe in Example I-6 (50 mg, 0.13 mmol) was dialkylated with compound 345A (109 mg, 0.52 mmol) to give compound 345a (29 mg, 41%) as a white solid.

Compound 345a (29 mg, 0.053 mmol) was then reacted with $NH_4I$ (77 mg, 0.53 mmol) in saturated $NH_3$/EtOH (2 mL) to give compound 345 (3.20 mg, 13%) as a white solid. LC-MS $t_R$=1.095 min in 2 min chromatography, MS (ESI) m/z 450.2 $[M+H]^+$. $^1H$ NMR ($CD_3OD$ 400 MHz): δ 7.18-7.20 (d, J=7.6 Hz, 1H), 7.09-7.11 (d, J=7.6 Hz, 1H), 6.82 (s, 1H), 4.28-4.35 (m, 2H), 3.36 (s, 3H), 3.09-3.15 (m, 1H), 3.04-3.05 (d, J=5.2 Hz, 2H), 2.64-2.68 (t, J=7.6 Hz, 2H), 1.95-2.02 (m, 2H), 1.84-1.86 (m, 1H), 1.56-1.59 (t, J=14.0

Hz, 1H), 1.35-1.47 (m, 4H), 1.28-1.31 (d, 2H), 0.64-0.68 (m, 1H), 0.38-0.41 (m, 2H), 0.02 (m, 2H). $^{19}F$ NMR ($CD_3OD$ 19F): δ −71.87.

Example 291

Synthesis of Compound 346

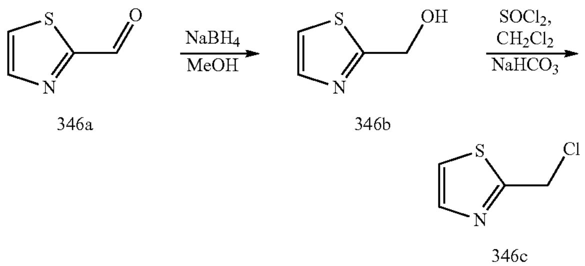

346a

346b

346c

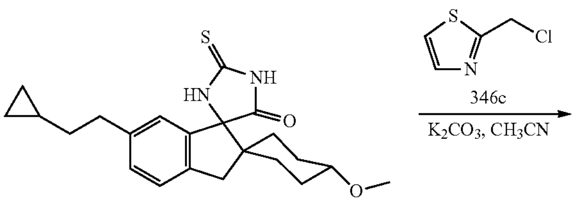

5

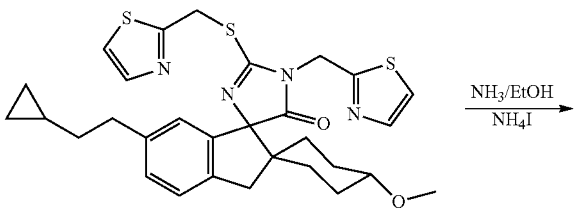

346d

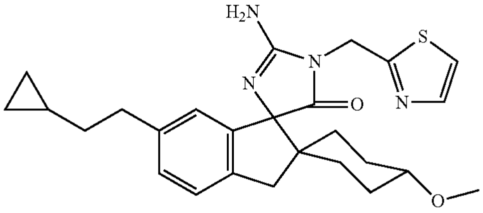

346

Procedure for Preparation of Compound 346b

To a solution of compound 346a (300 mg, 2.65 mmol) in MeOH (30 mL) was added $NaBH_4$ (0.2 g, 5.26 mmol) at 0° C. After addition, the mixture was warmed to room temperature and was stirred at room temperature for 1 h. The reaction was quenched with $H_2O$ (10 mL) and the solvent was removed in vacuo. The residue was extracted with EtOAc (10 mL×3). The combined organic layers were washed with brine (30 mL), dried over $Na_2SO_4$ and concentrated to give compound 346b (200 mg, 66%) as a yellow solid which was used in the next step without further purification. $^1H$ NMR (DMSO-$d_6$ 300 MHz): δ 7.81 (d, J=3.3 Hz, 1H), 7.71 (d, J=3.0 Hz, 1H), 4.82-4.80 (d, J=6.0 Hz, 2H).

Procedure for Preparation of Compound 346c

To a solution of compound 346b (70 mg, 0.60 mmol) in $CH_2Cl_2$ (2 mL) was added $SOCl_2$ (79.6 mg, 0.66 mmol) at 0°

C., After addition, the mixture was warmed to room temperature and was stirred at room temperature overnight. The reaction was quenched with aqueous $NaHCO_3$ (5 mL) and extracted with $CH_2Cl_2$ (5 mL×3). The combined organic layers were washed with brine (30 mL), dried over $Na_2SO_4$ and concentrated to give compound 346c (56.9 mg, 70%) as a yellow oil which was used in the next step without further purification.

Procedure for Preparation of Compound 346

According to a similar synthesis of compound 344, compound 5 (20 mg, 0.05 mmol) was alkylated with compound 346c (27.6 mg, 0.20 mmol) to give compound 346d (20 mg, 66%) as a white solid. LCMS: $t_R$=1.555 min in 2 min chromatography, MS (ESI) m/z=579.2 $[M+H]^+$.

Compound 346d (20 mg, 0.034 mmol) was then reacted with $NH_4I$ (49.6 mg, 0.34 mmol) in $NH_3$-EtOH (2 mL, 5 N) to give compound 346 (3.00 mg, 19%) as a white solid. LCMS: $t_R$=1.204 min in 2 min chromatography, MS (ESI) m/z=465.2 $[M+H]^+$. $^1H$ NMR ($CD_3OD$ 400 MHz): δ 7.77 (d, J=6.4 Hz, 1H), 7.76 (d, J=3.2 Hz, 1H), 7.26 (d, J=7.6 Hz, 1H), 7.21 (d, J=8.0 Hz, 1H), 7.19 (s, 1H), 5.27 (s, 2H), 3.34 (s, 3H), 3.24-3.20 (m, 1H), 3.11-3.04 (d, J=10.4 Hz, 2H), 2.72 (t, J=7.6 Hz, 2H), 2.10-2.01 (m, 2H), 1.81-1.78 (m, 1H), 1.54-1.41 (m, 5H), 1.45-1.27 (m, 2H), 0.69-0.64 (m, 1H), 0.40-0.37 (m, 2H), 0.11-0.05 (m, 2H).

Example 292

Synthesis of Compound 347

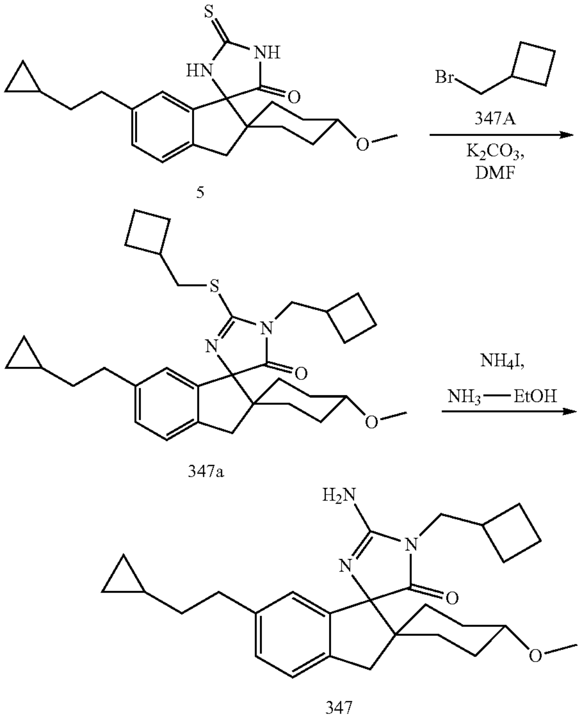

5

347a

347

According to a similar synthesis of compound 344, compound 5 (50 mg, 0.13 mmol) was alkylated with compound 347A (77 mg, 0.52 mmol) to afford the crude product 347a (40 mg, 80%), which was used directly for the next step without further purification.

Compound 347a (40 mg, 0.076 mmol) was then reacted with $NH_4I$ (111 mg, 0.76 mmol) in a solution of $NH_3$/EtOH (5 mL, 5 N) to give compound 347 (21 mg, 38%) as a white solid. LC-MS $t_R$=1.146 min in 2 min chromatography, MS (ESI) m/z 436.2 $[M+H]^+$; $^1H$ NMR ($CDCl_3$ 400 MHz): δ 11.4 (m, 1H), 10.89 (s, 1H), 8.52 (s, 1H), 7.21 (dd, J=26, 18.4 Hz, 1H), 6.81 (s, 1H), 3.72 (m, 2H), 3.35 (s, 3H), 3.1 (m, 3H), 2.66 (m, 3H), 2.04 (m, 1H), 1.90 (m, 6H), 1.49 (m, 7H), 0.65 (m, 1H), 0.39 (m, 2H), 0.01 (m, 2H).

Example 293

Synthesis of Compound 348

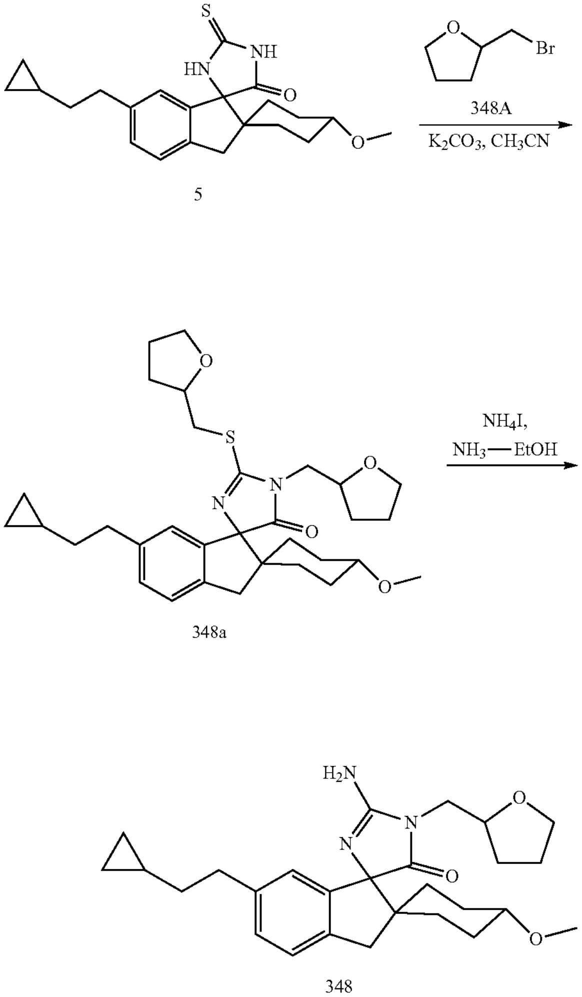

5

348a

348

According to a similar synthesis of compound 344, compound 5 (30 mg, 0.078 mmol) was alkylated with compound 348A (32 mg, 0.20 mmol) to give compound 348a (22 mg, 51%).

Compound 348a (22 mg, 0.040 mmol) was then reacted with $NH_4I$ (58 mg, 0.40 mmol) in $NH_3$-EtOH (2.5 mL) to give compound 348 (2.2 mg, 12%). LC-MS: $t_R$=1.110 min in 2 min chromatography, MS (ESI) m/z=452.3 $[M+H]^+$. $^1H$ NMR ($CD_3OD$ 400 MHz): δ7.15 (m, 1H), 7.05 (m, 1H), 6.75 (m, 1H), 4.05 (m, 1H), 3.83 (m, 1H), 3.60 (m, 1H), 3.59 (m, 2H), 3.28 (m, 3H), 3.10 (m, 1H), 3.02 (m, 2H), 2.63 (m, 2H), 1.87 (m, 6H), 1.41 (m, 8H), 0.60 (m, 1H), 0.36 (m, 2H), 0.049 (m, 2H).

Example 294

Synthesis of Compound 349

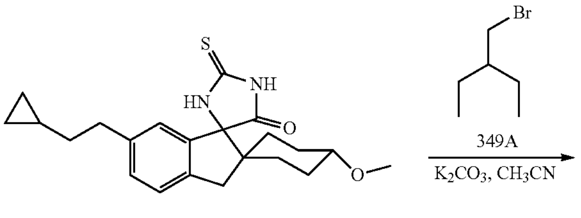

5

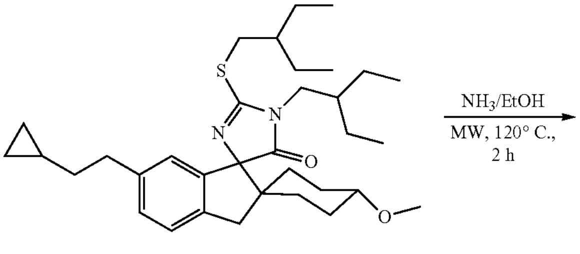

349a

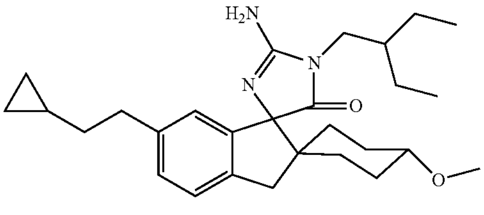

349

According to a similar synthesis of compound 344, compound 5 (30 mg, 0.078 mmol) was alkylated with compound 349A (32 mg, 0.20 mmol) to give compound 349a (44 mg, 44%) as a white solid.

Compound 349a (44 mg, 0.080 mmol) was then reacted with $NH_4I$ (116 mg, 0.80 mmol) in $NH_3$-EtOH (2.5 mL) to give compound 349 (11.8 mg, 33%). LC-MS: $t_R$=1.195 min in 2 min chromatography, MS (ESI) m/z=452.3 [M+H]$^+$. $^1$H NMR ($CD_3OD$ 400 MHz): δ 7.28 (d, J=7.6 Hz, 1H), 7.22 (d, J=7.6 Hz, 1H), 6.95 (s, 1H), 3.59 (m, 2H), 3.31 (m, 3H), 3.12 (m, 3H), 2.69 (m, 2H), 2.02 (m, 2H), 1.98 (m, 1H), 1.74 (m, 1H), 1.41 (m, 11H), 0.93 (m, 6H), 0.65 (m, 1H), 0.40 (m, 2H), 0.01 (m, 2H).

Example 295

Synthesis of Compounds 350 and 351

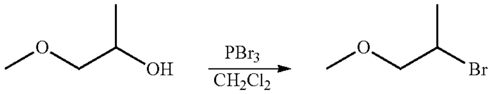

1 2

-continued

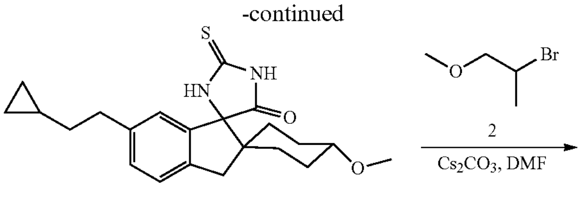

5

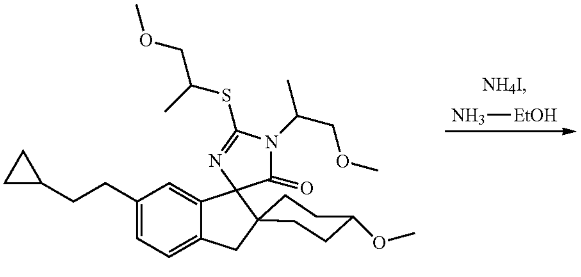

4

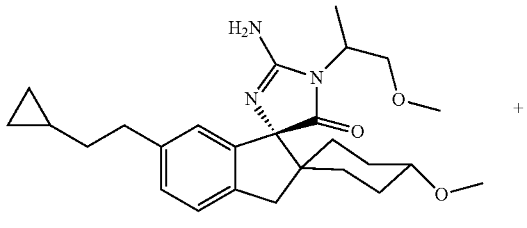

350

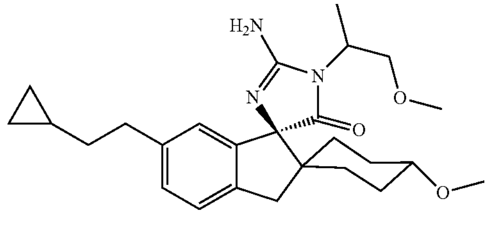

351

Procedure for Preparation of Compound 2

To a solution of compound 1 (3.68 g, 0.04 mol) in $CH_2Cl_2$ (40 mL) was added phosphorus tribromide (5.4 g, 1.9 mL, 0.02 mol). The mixture was heated to reflux for 18 h. The mixture was quenched with 5% aqueous $NaHCO_3$, and was extracted with $CH_2Cl_2$ (3×40 mL). The combined organic layers were washed with brine (2×40 mL), dried over $Na_2SO_4$, concentrated under reduced pressure to give compound 2 (3.1 g, 51%) as a yellow oil, which was used for the next step without purification.

Procedure for Preparation of Compounds 350 and 351

According to a similar synthesis of compound 344, compound 5 (100 mg, 0.26 mmol) was alkylated with compound 2 (159 mg, 1.04 mmol) in the presence of $Cs_2CO_3$ (339 mg, 1.04 mmol) to give compound 4 (73 mg, 53%).

Compound 4 (79 mg, 0.15 mmol) was then reacted with $NH_4I$ (217 mg, 1.5 mmol) in a solution of $NH_3$/EtOH (2 mL) to give compound 350 (2.8 mg, 5%) LC-MS $t_R$=1.052 min in 2 min chromatography, MS (ESI) m/z 440.2 [M+H]$^+$, $^1$H NMR ($CD_3OD$ 400 MHz): δ 7.18-7.25 (m, 2H), 6.98-7.02 (d, J=7.6, Hz, 1H), 4.15 (s, 1H), 3.61 (s, 1H), 3.49-3.58 (m, 1H), 3.30-3.43 (m, 6H), 3.01-3.12 (m, 4H), 2.68-2.72 (t, J=7.8 Hz, 2H), 2.00-2.08 (m, 3H), 1.32-1.48 (m, 10H), 0.67 (m, 1H), 0.38-0.40 (d, J=7.2 Hz, 2H), 0.01 (s, 2H).

and compound 351 (7.8 mg, 15%) as a white solid. LC-MS $t_R$=1.096 min in 2 min chromatography, MS (ESI) m/z 440.3 $[M+H]^+$. $^1H$ NMR ($CD_3OD$ 400 MHz): δ 7.20-7.28 (dd, J=7.6 Hz, 2H), 6.91-7.00 (d, J=38.4 Hz, 1H), 4.52 (m, 1H), 3.73-3.87 (m, 1H), 3.52-3.56 (m, 1H), 3.30-3.31 (m, 6H), 3.01-3.18 (m, 3H), 2.69-2.72 (t, J=7.6 Hz, 2H), 2.00-2.09 (m, 3H), 1.36-1.51 (m, 10H), 0.65-0.70 (m, 1H), 0.38-0.42 (m, 2H), 0.00 (m, 2H).

Example 296

Synthesis of Compound 352

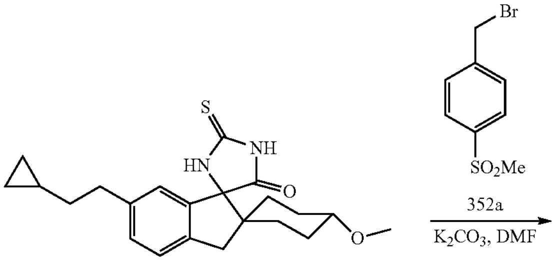

5

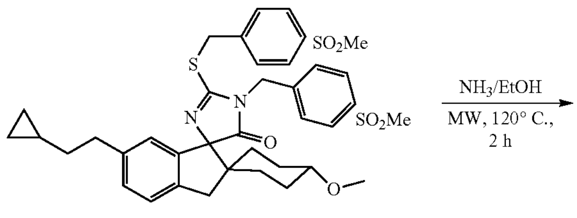

352b

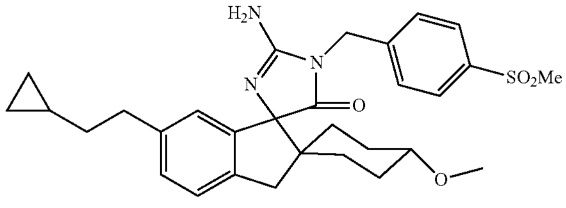

352

According to a similar synthesis of compound 344, compound 5 (30 mg, 0.078 mmol) was alkylated with compound 352a (38.9 mg, 0.156 mmol) to give compound 352b (30 mg, 53%) as a white solid. LCMS: $t_R$=1.165 min in 2 min chromatography, MS (ESI) m/z=415.1$[M+H]^+$.

Compound 352b (30 mg, 0.041 mmol) was then heated with $NH_4I$ (59 mg, 0.41 mmol) in $NH_3$-EtOH (2 mL, 5 N) to give compound 352 (11.0 mg, 57%) as a white solid. LCMS $t_R$=1.196 min in 2 min chromatography, MS (ESI) m/z=536.2 $(M+H)^{30}$. $^1H$ NMR ($CD_3OD$ 400 MHz): δ 7.99-7.97 (d, J=8.4 Hz, 2H), 7.56-7.54 (d, J=8.4 Hz, 2H), 7.30-7.26 (d, J=7.6 Hz, 1H), 7.25-7.20 (d, J=7.6 Hz, 1H), 7.02 (m, 1H), 5.03 (s, 2H), 3.34 (s, 3H), 3.20-3.00 (m, 6H), 2.71-2.69 (t, J=7.6 Hz, 2H), 2.10-1.90 (m, 2H), 1.85-1.75 (m, 1H), 1.50-1.20 (m, 7H), 0.71-0.60 (m, 1H), 0.40-0.30 (m, 2H), 0.10-0.01 (m, 2H).

Example 297

Synthesis of Compound 353

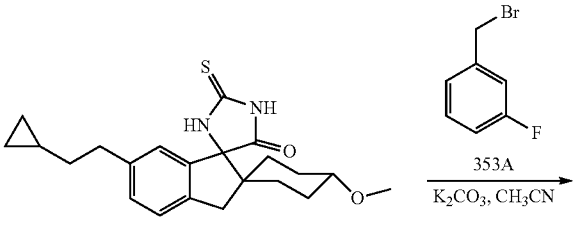

5

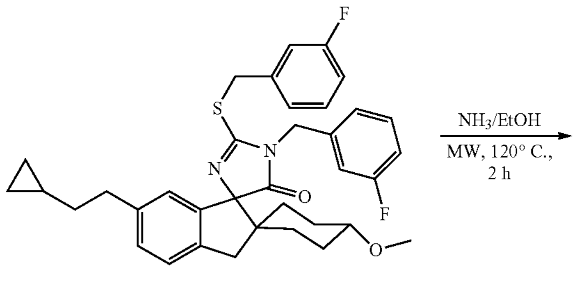

353a

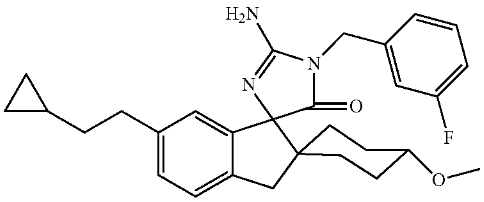

353

According to a similar synthesis of compound 344, compound 5 (50 mg, 0.13 mmol) was dialkylated with compound 353A (98 mg, 0.52 mmol) to give compound 353a (45 mg, 56%) as a white solid.

Compound 353a (45 mg, 0.075 mmol) was then heated with $NH_4I$ (109 mg, 0.75 mmol) in a solution of $NH_3$/EtOH (2 mL, 5 N) to give compound 353 (9.2 mg, 26%) as a white solid. LC-MS $t_R$=1.152 min in 2 min chromatography, MS (ESI) m/z 476.2 $[M+H]^+$; $^1H$ NMR ($CD_3OD$ 400 MHz): δ 7.39-7.44 (dd, J=8.0 Hz, 1H), 7.26-7.28 (d, J=7.6 Hz, 1H), 7.20-7.22 (d, J=8.0 Hz, 1H), 7.04-7.14 (m, 3H), 6.97 (s, 1H), 5.00 (s, 2H), 3.35 (s, 3H), 3.11-3.14 (m, 3H), 2.68-2.72 (t, J=8.0 Hz, 2H), 2.01 (s, 2H), 1.81-1.83 (d, J=10.4 Hz, 1H), 1.41-1.49 (m, 5H), 1.27-1.35 (m, 2H), 0.60-0.68 (m, 1H), 0.37-0.40 (m, 2H), 0.03 (m, 2H). $^{19}$F NMR ($CD_3OD$ 19F 400 MHz): δ −113.92

Example 298

Synthesis of Compound 354

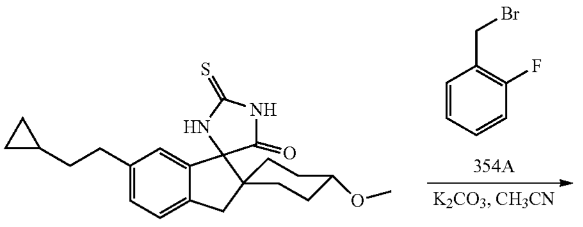

5

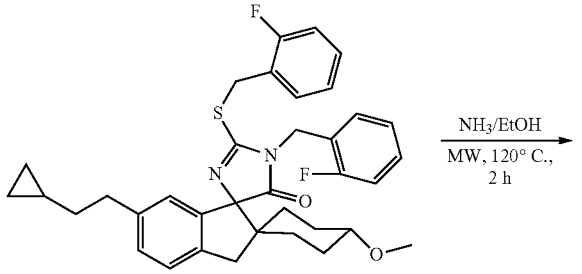

354a

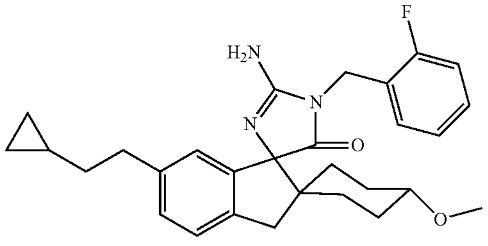

354

According to a similar synthesis of compound 344, compound 5 (50 mg, 0.13 mmol) was dialkylated with compound 354A (98 mg, 0.52 mmol) to give compound 354a (45 mg, 58%) as a white solid.

Compound 354a (45 mg, 0.075 mmol) was then heated with $NH_4I$ (109 mg, 0.75 mmol) in $NH_3$/EtOH (2 mL, saturated) to give compound 354 (5.00 mg, 14%) as a white solid. LC-MS $t_R$=1.127 min in 2 min chromatography, MS (ESI) m/z 476.3 $[M+H]^+$. $^1$H NMR ($CD_3OD$ 400 MHz): δ 7.40-7.43 (m, 1H), 7.32-7.38 (t, J=7.2 Hz, 1H), 7.15-7.26 (m, 4H), 7.00 (s, 1H), 5.04 (s, 2H), 3.35 (s, 3H), 3.00-3.17 (m, 3H), 2.69-2.73 (t, J=7.6 Hz, 2H), 1.94-2.01 (m, 2H), 1.65-1.68 (m, 1H), 1.42-1.53 (m, 5H), 1.23-1.35 (m, 2H), 0.63-0.69 (m, 1H), 0.36-0.43 (m, 2H), 0.02 (m, 2H). $^{19}$F NMR ($CD_3OD$ 400 MHz): δ −118.84

Example 299

Synthesis of Compound 355

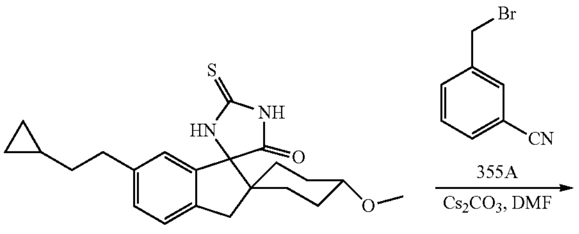

5

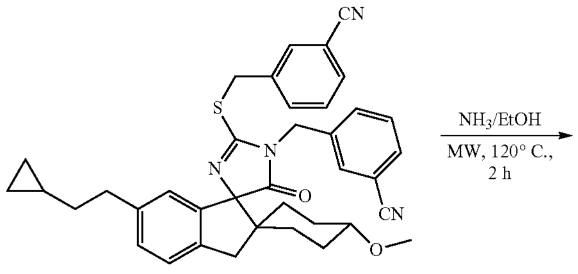

355a

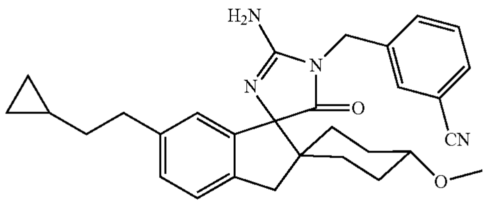

355

According to a similar synthesis of compound 344, compound 5 (50 mg, 0.13 mmol) was dialkylated with compound 355A (95 mg, 0.52 mmol) to give compound 355a (45 mg, 56%) as a white solid.

Compound 355a (45 mg, 0.07 mmol) was then heated with $NH_4I$ (107 mg, 0.7 mmol) in a solution of $NH_3$/EtOH (2 mL, 5 N) to give compound 355 (2.7 mg, 8%) as a white solid. LC-MS $t_R$=1.120 min in 2 min chromatography, MS (ESI) m/z 483.2 $[M+H]^+$; $^1$H NMR ($CD_3OD$ 400 MHz): δ 7.73-7.75 (d, J=7.2 Hz, 1H), 7.57-7.73 (m, 3H), 7.26-7.28 (d, J=7.6 Hz, 1H), 7.21-7.23 (d, J=8.0 Hz, 1H), 7.28-6.99 (s, 1H), 4.99 (s, 2H), 3.24 (s, 3H), 3.05-3.19 (m, 3H), 2.69-2.72 (t, J=7.6

Hz, 2H), 1.99 (s, 2H), 1.77-1.80 (m, 1H), 1.41-1.48 (m, 4H), 1.28-1.35 (m, 3H), 0.62-0.67 (m, 1H), 0.36-0.39 (m, 2H), −0.01-0.00 (m, 2H).

Example 300

Synthesis of Compound 356

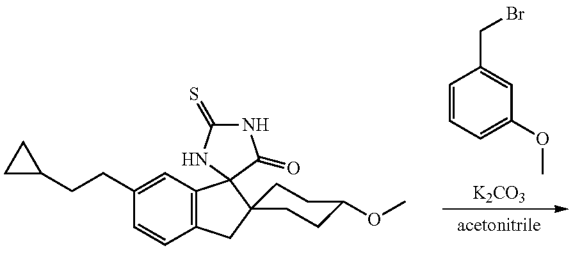

5

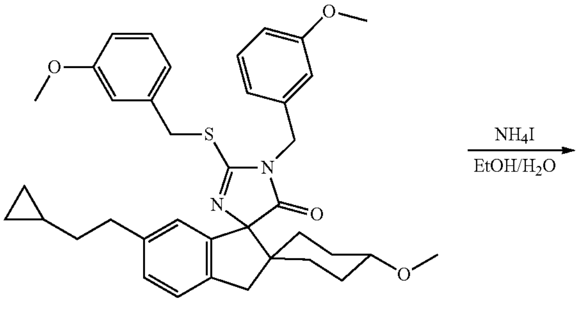

356a

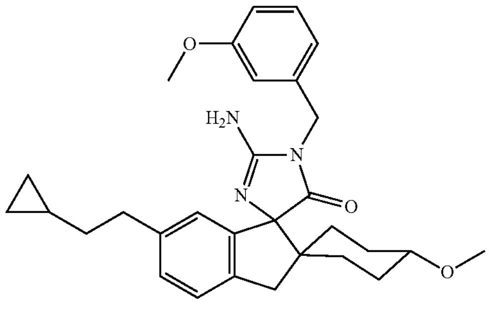

356

According to a similar synthesis of compound 344, compound 5 (50 mg, 0.13 mmol) was dialkylated with 1-bromomethyl-3-methoxy-benzene (65 mg, 0.326 mmol) to give compound 356a (30 mg, 38%) as a white solid.

Compound 356a (30 mg, 0.049 mmol) was then heated with $NH_4I$ (77 mg, 0.492 mmol) and $NH_3$-EtOH (2 mL, 5 N) to give compound 356 (8.0 mg, 33%) as a white solid. LC-MS $t_R$=1.257 min in 2 min chromatography, MS (ESI) m/z 488 $[M+H]^+$; $^1H$ NMR ($CD_3OD$ 400 MHz): δ 7.21 (m, 2H), 7.10 (d, J=7.6 Hz, 1H), 6.84 (m, 4H), 4.60-4.70 (m, 2H), 3.73 (s, 3H), 3.31 (m, 3H), 3.00-3.15 (m, 3H), 1.81-2.02 (m, 3H), 1.58 (m, 1H), 1.22-1.48 (m, 6H), 0.65 (m, 1H), 0.38 (d, J=8.4 Hz, 2H), 0.01 (d, J=5.2 Hz, 2H).

Example 301

Synthesis of Compound 357

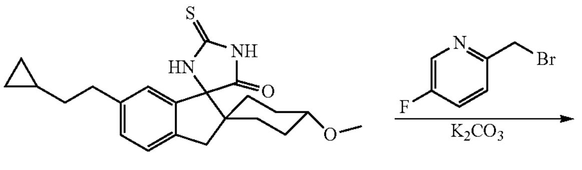

5

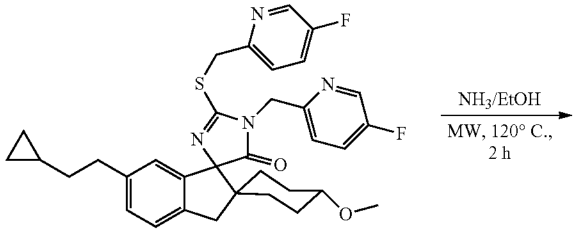

357a

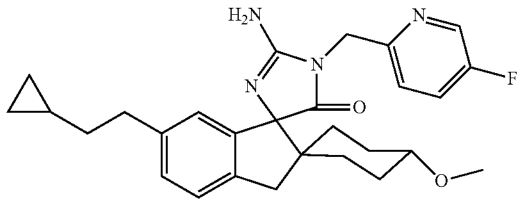

357

According to a similar synthesis of compound 344, compound 5 (50 mg, 0.13 mmol) was dialkylated with 2-(bromomethyl)-5-fluoropyridine to give compound 357a (20 mg, 0.033 mmol), which was heated with $NH_4I$ (47.6 mg, 0.33 mmol) in $NH_3$/EtOH (2 mL, 5 N) to give compound 357 (9.10 mg, 57%) as a white solid. LCMS: $t_R$=2.128 min in 3 min chromatography, MS (ESI) m/z=477.2 $[M+H]^+$. $^1H$ NMR ($CD_3OD$ 400 MHz): δ 8.41-8.40 (d, J=2.8 Hz, 1H), 7.60-7.55 (td, J=2.8, 8.8 Hz, 1H), 7.38-7.30 (dd, J=4.4, 8.8 Hz, 1H), 7.18-7.10 (d, J=7.6 Hz, 1H), 7.10-7.01 (d, J=7.6 Hz, 1H), 6.90-6.80 (m, 1H), 4.70 (s, 2H), 3.35 (s, 3H), 3.2-3.10 (m, 1H), 3.09-3.05 (d, J=15.8 Hz, 1H), 3.05-2.95 (d, J=15.8 Hz, 1H), 2.69-2.60 (m, 2H), 2.10-1.90 (m, 2H), 1.90-1.80 (m, 1H), 1.70-1.51 (m, 1H), 1.51-1.21 (m, 6H), 0.70-0.60 (m, 1H), 0.50-0.30 (m, 2H), 0.10-0.01 (m, 2H).

Example 302

Synthesis of Compound 358

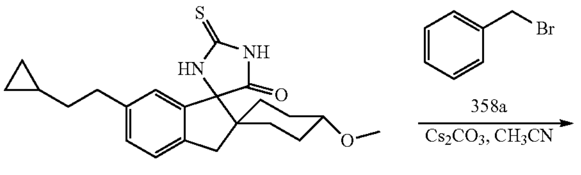

5

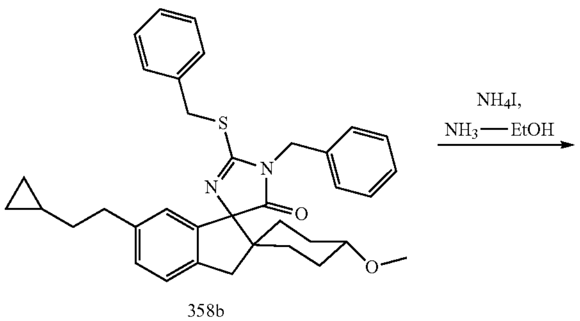

358b

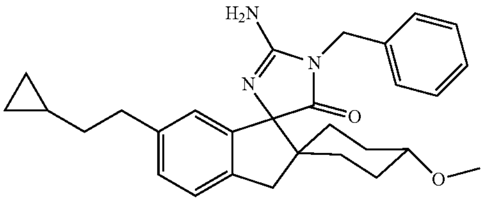

358

According to a similar synthesis of compound 344, compound 5 (30 mg, 0.078 mmol) was dialkylated with bromomethylbenzene (50 mg, 0.29 mmol) to give compound 358b (34 mg, 77%) as a pale yellow solid. LC-MS: $t_R$=2.500 min in 3 min chromatography, MS (ESI) m/z 565 $[M+H]^+$.

Compound 358b (34 mg, 0.060 mmol) was heated with $NH_4I$ (100 mg, 0.69 mmol) and $NH_3$-EtOH (1 mL) to give compound 358 (14.4 mg, 59%) as a white solid. LC-MS: $t_R$=4.202 min in 7 min chromatography, MS (ESI) m/z 458 $[M+H]^+$. $^1$H NMR: ($CD_3OD$, 400 MHz): δ 7.29 (m, 5H), 7.18 (d, J=7.6 Hz, 3H), 7.10 (d, J=7.6 Hz, 3H), 6.78 (s, 1H), 4.76 (d, J=15.6 Hz, 1H), 4.69 (d, J=15.6 Hz, 1H), 3.33 (s, 3H), 3.13 (m, 2H), 3.13 (d, J=14.4 Hz, 1H), 2.67 (t, J=8.0 Hz, 1H), 1.96 (m, 2H), 1.83 (m, 1H), 1.64 (m, 1H), 1.30-1.50 (m, 4H), 1.38 (m, 2H), 0.65 (m, 1H), 0.40 (m, 2H), 0.00 (m, 2H).

Example 303

Synthesis of Compound 359

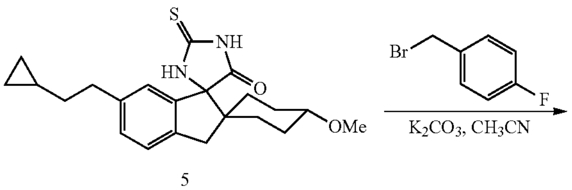

5

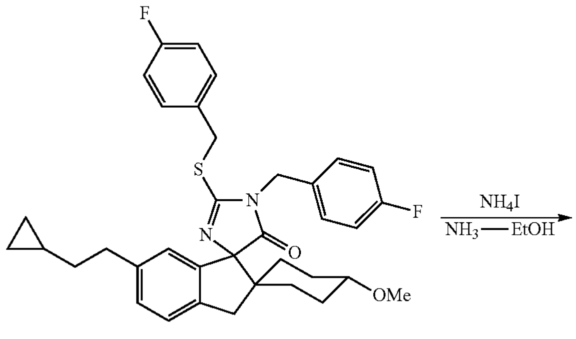

359a

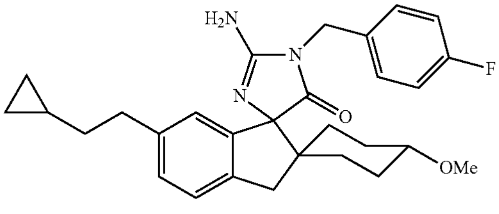

359

According to a similar synthesis of compound 344, compound 5 (50 mg, 0.13 mmol) was alkylated with 1-bromomethyl-4-fluoro-benzene (55 mg, 0.3 mmol) to give compound 359a (54 mg, 80%) as a white solid.

Compound 359a (50 mg, 0.08 mmol) was heated with $NH_4I$ (60 mg, 0.4 mmol) in a solution of $NH_3$-EtOH (3 mL, 5 N) to give compound 359 (17 mg, 45%) as a white solid. LC-MS: $t_R$=1.92 min in 3 min chromatography, MS (ESI) m/z 476.2 $[M+H]^+$. $^1$H NMR ($CD_3OD$ 400 MHz): δ 7.30-7.40 (m, 2H), 7.20-7.25 (d, 1H, J=8.4 Hz), 7.15-7.20 (d, 1H, J=8.4 Hz), 7.00-7.10 (m, 2H), 6.80-6.85 (s, 1H), 3.35-3.40 (s, 3H), 3.00-3.20 (m, 3H), 2.60-2.70 (m, 2H), 1.90-2.10 (m, 2H), 1.70-1.80 (m, 1H), 1.30-1.50 (m, 5H), 1.20-1.30 (m, 2H), 0.60-

0.70 (m, 1H), 0.35-0.45 (m, 2H), 0.05-0.10 (m, 2H). $^{19}F$ NMR: ($CD_3OD$ 400 MHz): δ −115.20.

Example 304

Synthesis of Compounds 360 and 361

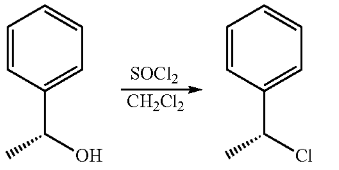

360a

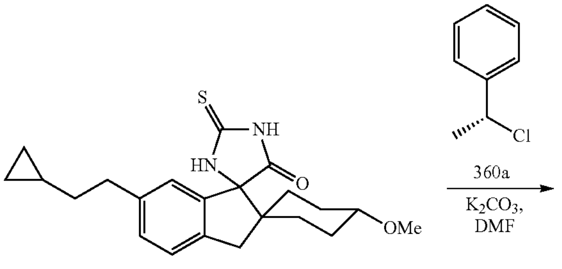

5

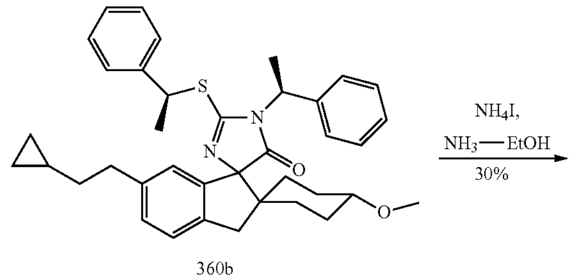

360b

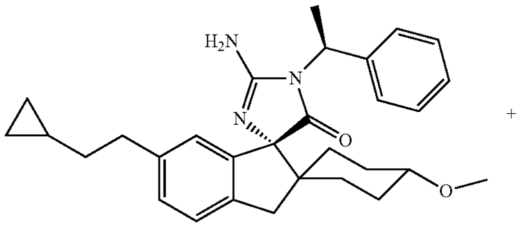

360

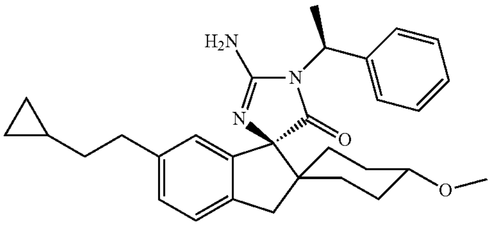

361

Procedure for Preparation of Compound 360a

To a solution of 1-phenyl-ethanol (100 mg, 0.81 mmol) in anhydrous $CH_2Cl_2$ (2 mL) was added $SOCl_2$ (107 mg, 0.90 mmol) at 0° C. under $N_2$, the mixture was stirred at room temperature on night. The solvent was removed in vacuo to give compound 360a (90 mg, 80%) as a yellow oil which was used in the next step without further purification. $^1H$ NMR (DMSO-$d_6$ 400 MHz): δ 7.41-7.39 (m, 2H), 7.31-7.29 (m, 3H), 5.28-5.26 (m, 1H), 1.72-1.71 (d, J=6.8 Hz, 3H)

Procedure for Preparation of Compounds 360 and 361

According to a similar synthesis of compound 344, compound 5 (30 mg, 0.077 mmol) was dialkylated with compound 360a (21.9 mg, 0.15 mmol) to give compound 360b (20 mg, 43%) as a white solid. LC-MS: $t_R$=1.678 min in 2 min chromatography, MS (ESI) m/z=593.3 $[M+H]^+$.

Compound 360b (20 mg, 0.033 mmol) was then heated with $NH_4I$ (48.4 mg, 0.33 mmol) in $NH_3$-EtOH (2 mL, 5 N) was heated at 120° C. in a CEM microwave reactor for 3 h. After being cooled, the mixture was concentrated under vacuum and the residue was purified by preparative TLC (dichloromethane:methanol=10:1) and preparative HPLC to give compound 360 (3.00 mg, 19%), LC-MS: $t_R$=2.091 min in 3 min chromatography, MS (ESI) m/z=472.3 $[M+H]^+$. $^1H$ NMR ($CDCl_3$ 400 MHz): δ 7.47-7.45 (m, 3H), 7.44-7.28 (dd, J=1.6, 8.0 Hz, 2H), 7.28-7.19 (d, J=7.8 Hz, 1H), 7.19-7.7.10 (dd, J=1.2, 7.6 Hz, 1H), 6.79 (s, 1H), 5.59-5.57 (q, J=7.2 Hz, 1H), 3.32 (s, 3H), 3.31-3.14 (m, 1H), 3.08-3.03 (m, 2H), 2.67-2.62 (m, 2H), 2.10-1.99 (m, 2H), 1.90-1.80 (m, 1H), 1.75-1.67 (d, J=6.8 Hz, 3H), 1.56-1.10 (m, 7H), 0.70-0.60 (m, 1H), 0.40-0.30 (m, 2H), 0.10-0.05 (m, 2H).

& compound 361 (1.80 mg, 11%) as white solid. LC-MS: $t_R$=2.330 min in 3 min chromatography, MS (ESI) m/z=472.3 $[M+H]^+$. $^1H$ NMR ($CD_3OD$ 400 MHz): δ 7.38-7.33 (m, 5H), 7.30-7.20 (d, J=7.6 Hz, 1H), 7.20-7.10 (dd, J=1.2, 7.6 Hz, 1H), 6.84 (s, 1H), 5.50-5.40 (q, J=7.2 Hz, 1H), 3.39 (s, 3H), 3.31-3.20 (m, 1H), 3.18-3.10 (d, J=17.2 Hz, 0.2H), 3.10-3.00 (d, J=17.2 Hz, 0.2H), 2.71-2.67 (t, J=7.6 Hz, 2H), 2.20-2.10 (m, 1H), 2.10-1.95 (m, 2H), 1.95-1.90 (d, J=7.2 Hz, 3H), 1.58-1.30 (m, 7H), 0.71-0.61 (m, 1H), 0.50-0.30 (m, 2H), 0.10-0.03 (m, 2H).

Example 305

Synthesis of Compound 362

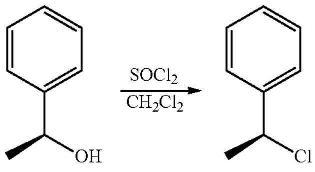

362a 362b

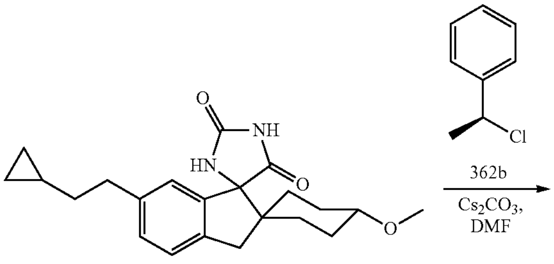

5

-continued

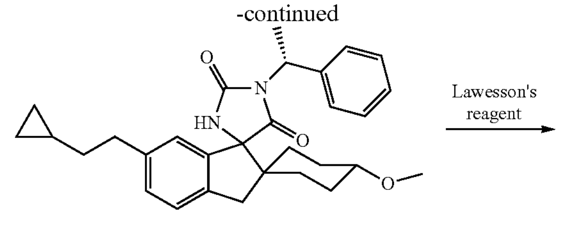

362c

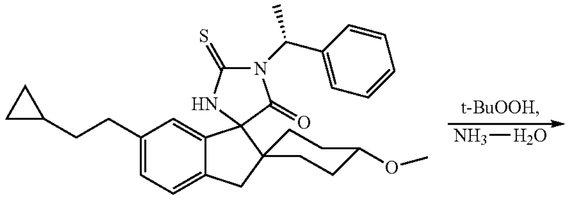

362d

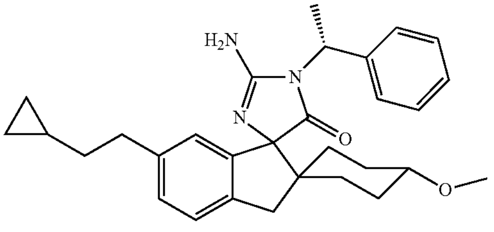

362

Procedure for Preparation of Compound 362b

Synthesized by a route analogously to compound 360a described in Example 304, reaction of compound 362a (100 mg, 0.81 mmol) with $SOCl_2$ gave compound 362b (90 mg, 80%) as a yellow oil which was used in the next step without further purification. $^1$H NMR (DMSO-$d_6$ 400 MHz): δ 7.41-7.39 (m, 2H), 7.31-7.23 (m, 3H), 5.34-5.20 (m, 1H), 1.72-1.71 (d, J=6.8 Hz, 3H).

Procedure for Preparation of Compound 362c

Synthesized by a route analogously to compound 360b described in Example 304, reaction compound 5 (50 mg, 0.14 mmol) and compound 362b gave compound 362c (35 mg, 54%) as a white solid after purification by preparative TLC on silica gel eluted with hexane:

EtOAc=3:1 to give. LC-MS: $t_R$=1.515 min in 2 min chromatography, MS (ESI) m/z=473.2 [M+H]$^+$.

Procedure for Preparation of Compound 362d

To a solution of compound 362c (35 mg, 0.077 mmol) in anhydrous toluene (2 mL) was added Lawesson's Reagent (32.9 mg, 0.081 mmol) under $N_2$, the mixture was stirred at 130° C. in a CEM microwave reactor for 40 min. The solvent was removed in vacuo to give the crude product which was purified by preparative TLC on silica gel eluting with hexane: EtOAc=3:1 to give compound 362d (15 mg, 41%) as a white solid. LC-MS: $t_R$=1.628 min in 2 min chromatography, MS (ESI) m/z=489.2 [M+H]$^+$.

Procedure for Preparation of Compound 362

To a solution of compound 362d (15 mg, 0.03 mmol) in EtOH (10 mL) was added t-BuOOH (1.0 mL) and $NH_3.H_2O$ (3.0 mL), the mixture was stirred at room temperature overnight, LCMS analysis showed the complete consumption of compound 362d, the mixture was concentrated in vacuum, and the residue was purified by preparative TLC on silica gel eluting with dichloromethane:methanol=10:1 and by prep-HPLC to give compound 362 (1.80 mg, 12.5%) as a white solid. LC-MS: $t_R$=1.017 min in 2 min chromatography, MS (ESI) m/z=472.2 [M+H]$^+$. $^1$H NMR ($CD_3OD$ 400 MHz): δ 7.48-7.24 (m, 5H), 7.25-7.11 (d, J=7.6 Hz, 1H), 7.11-7.06 (d, J=7.6 Hz, 1H), 6.84-6.62 (s, 1H), 5.46-5.34 (m, 1H), 3.36 (s, 3H), 3.21-3.14 (m, 1H), 3.10-2.98 (m, 2H), 2.66-2.62 (t, J=7.6 Hz, 2H), 2.08-2.05 (m, 1H), 1.99-1.81 (m, 2H), 1.80-1.76 (d, J=7.2 Hz, 3H), 1.56-1.20 (m, 7H), 0.68-0.61 (m, 1H), 0.41-0.30 (m, 2H), 0.10-0.03 (m, 2H).

Example 306

Synthesis of Compound 363

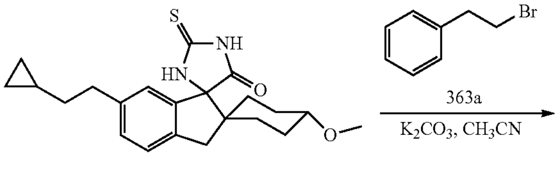

5

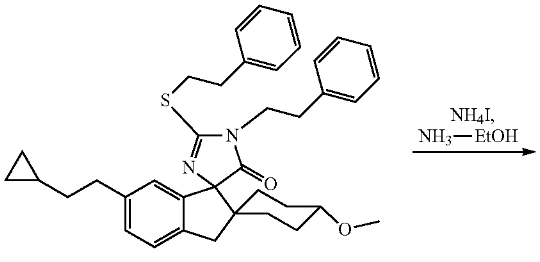

363b

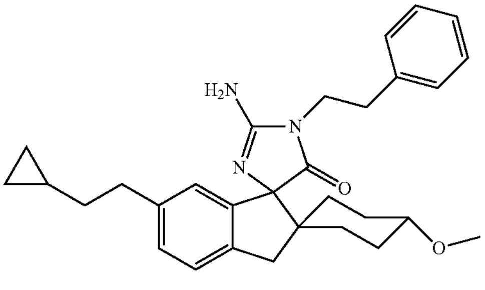

363

According to a similar synthesis of compound 344, compound 5 (50 mg, 0.13 mmol) was dialkylated with 2-bromo-ethyl-benzene (363a) (0.10 g, 0.54 mmol) to give compound 363b (56 mg, 72%) as a pale yellow solid. LC-MS: $t_R$=2.649 min in 3 min chromatography, MS (ESI) m/z=593 [M+H]$^+$.

Compound 363b (56 mg, 0.084 mmol) was then heated with $NH_4I$ (100 mg, 0.69 mmol) and $NH_3$-EtOH (1 mL) to give compound 363 (15.2 mg, 38%) as a white solid. LC-MS: $t_R$=1.887 min in 3 min chromatography, MS (ESI) m/z=472, [M+H]$^+$. $^1$H NMR: ($CD_3OD$, 400 MHz): δ 7.25 (m, 4H), 7.20 (m, 1H), 7.16 (d, J=7.6 Hz, 1H), 7.06 (d, J=7.6 Hz, 1H), 6.72 (s, 1H), 3.70-3.85 (m, 2H), 3.32 (s, 3H), 3.03 (m, 1H), 2.95 (m, 4H), 2.66 (t, J=8.0 Hz, 2H), 1.90 (m, 2H), 1.58 (m, 2H), 1.45 (m, 2H), 1.30 (m, 2H), 1.20 (m, 1H), 1.05 (m, 1H), 0.65 (m, 1H), 0.40 (m, 2H), 0.00 (m, 2H).

Example 307

Synthesis of Compound 364

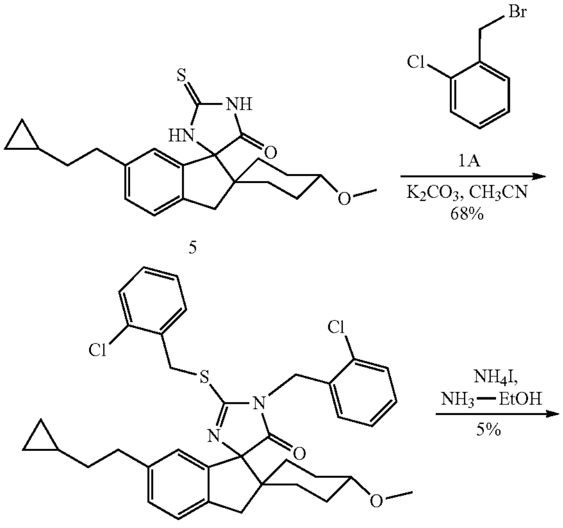

5

2

-continued

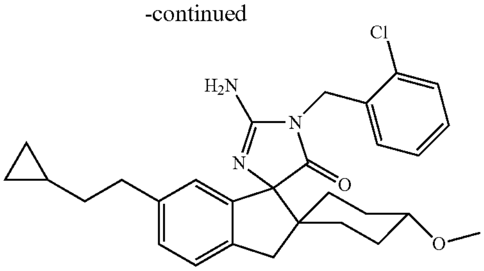

364

According to a similar synthesis of compound 344, compound 5 (50 mg, 0.13 mmol) was dialkylated with compound 1A (66 mg, 0.33 mmol) to give the crude compound 2 (56 mg, 68%), which was used for the next step directly.

Compound 2 (56 mg, 0.089 mmol) was then heated with $NH_4I$ (128.5 mg, 0.89 mmol) in $NH_3$-EtOH (2.5 mL) to give compound 364 (2 mg, 5%). LC-MS: $t_R$=1.295 min in 2 min chromatography, MS (ESI) m/z=492.4 $[M+H]^+$. $^1H$ NMR ($CD_3OD$ 400 MHz): δ 7.49 (m, 1H), 7.36 (m, 2H), 7.33 (m, 1H), 7.26 (m, 2H), 7.09 (s, 1H), 5.00 (s, 2H), 3.31 (m, 3H), 3.30 (m, 1H), 3.05 (m, 2H), 2.73 (t, J=7.6 Hz, 2H), 2.01 (m, 2H), 1.75 (m, 1H), 1.51 (m, 1H), 1.48 (m, 4H), 1.35 (m, 1H), 0.66 (m, 1H), 0.40 (m, 2H), 0.00 (m, 2H).

Example 308

Synthesis of Compound 365

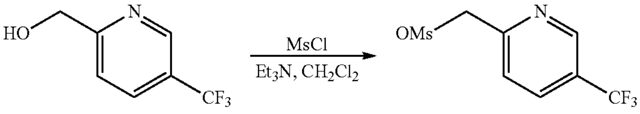

9

5A

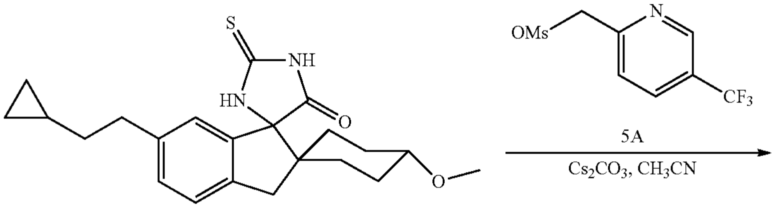

5

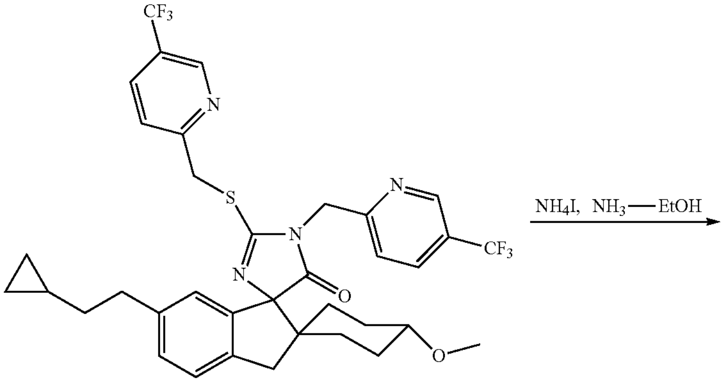

6

-continued

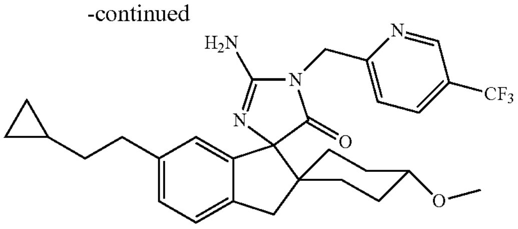

365

Procedure for Preparation of Compound 5A

To a solution of compound 9 (100 mg, 0.56 mmol) in $CH_2Cl_2$ (2 mL) was added $Et_3N$ (114 mg, 1.12 mmol) and MsCl (71 mg, 0.61 mmol) under nitrogen, the mixture was stirred at room temperature for 4 h. The reaction was quenched with $H_2O$ (10 mL) and extracted with $CH_2Cl_2$ (5 mL×3). The combined organic layers were washed with brine (20 mL), dried over $Na_2SO_4$ and concentrated to give compound 5A (86 mg, 60%) as yellow oil, which was used in the next step without further purification. $^1$H NMR ($CDCl_3$ 400 MHz): δ 8.90 (s, 1H), 8.06 (d, J=7.2 Hz, 1H), 7.53 (d, J=8.0 Hz, 1H), 5.26 (s, 2H), 3.10 (s, 3H).

Procedure for Preparation of Compound 365

According to a similar synthesis of compound 344, compound 5 (30 mg, 0.078 mmol) was dialkylated with compound 5A (39.8 mg, 0.156 mmol) to afford compound 6 (30 mg, 55%) as a white solid. LCMS: $t_R$=1.561 min in 2 min chromatography, MS (ESI) m/z=703.2 [M+H]$^+$.

Compound 6 (30 mg, 0.042 mmol) was then heated with $NH_4I$ (61.3 mg, 0.42 mmol) in $NH_3$-EtOH (2 mL, 5 N) to give compound 365 (4.90 mg, 26%) as a white solid. LCMS: $t_R$=1.149 min in 2 min chromatography, MS (ESI) m/z=527.2 [M+H]$^+$. $^1$H NMR ($CD_3OD$ 400 MHz): δ 8.80 (s, 1H), 8.08 (d, J=8.0 Hz, 1H), 7.53 (d, J=8.0 Hz, 1H), 7.28 (d, J=8.4 Hz, 1H), 7.18 (d, J=7.8 Hz, 1H), 7.01 (s, 1H), 4.91 (s, 2H), 3.37 (s, 3H), 3.21-3.15 (m, 1H), 3.15-2.91 (d, J=6.4 Hz, 2H), 2.76 (t, J=7.6 Hz, 2H), 2.17-1.94 (m, 2H), 1.94-1.85 (m, 1H), 1.70-1.62 (m, 1H), 1.51-1.30 (m, 5H), 1.30-1.27 (m, 1H), 0.71-0.69 (m, 1H), 0.43-0.35 (m, 2H), 0.1-0.05 (m, 2H). $^{19}$F NMR ($CD_3OD$ 19F 400 MHz): δ -63.844.

Example 309

Synthesis of Compound 366

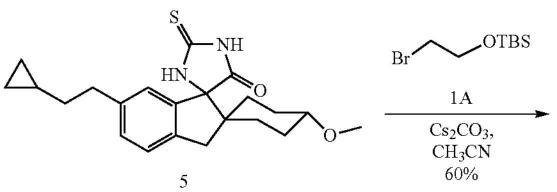

5

-continued

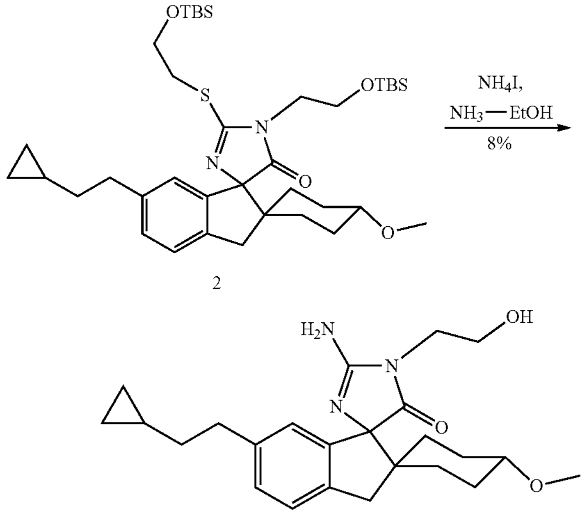

2

366

According to a similar synthesis of compound 344, compound 5 (45 mg, 0.12 mmol) was dialkylated with compound 1A (84 mg, 0.35 mmol) in the presence of $Cs_2CO_3$ (191 mg, 0.59 mmol) to give compound 2 (41 mg, 60%).

Compound 2 (41 mg, 0.070 mmol) was then heated $NH_4I$ (101 mg, 0.70 mmol) in $NH_3$-EtOH (2.5 mL) to give compound 366 (2.4 mg, 8%) as a white solid. LC-MS: $t_R$=1.137 min in 2 min chromatography, MS (ESI) m/z=412.2 [M+H]$^+$. $^1$H NMR ($CD_3OD$ 400 MHz): δ 7.29 (m, 1H), 7.20 (m, 1H), 7.00 (s, 1H), 3.82 (m, 2H), 3.70 (m, 2H), 3.30 (m, 3H), 3.10 (m, 3H), 2.60 (m, 2H), 2.05 (m, 2H), 1.89 (m, 1H), 1.45 (m, 5H), 1.32 (m, 1H), 0.69 (m, 1H), 0.40 (m, 2H), 0.00 (m, 2H).

Example 310

Synthesis of Compound 367

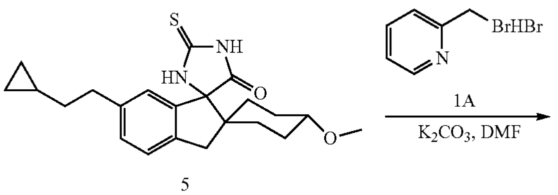

5

-continued

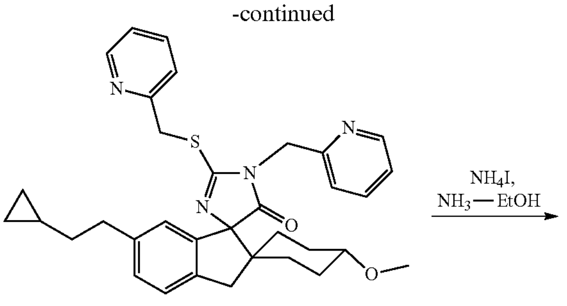

2

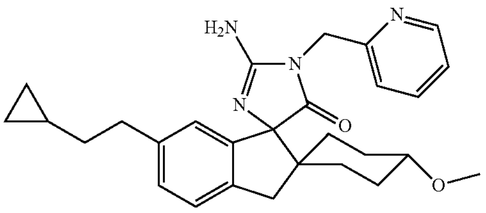

367

According to a similar synthesis of compound 344, compound 5 (50 mg, 0.13 mmol) was dialkylated with compound 1A (134 mg, 0.52 mmol) at the presence of $Cs_2CO_3$ (170 mg, 0.52 mmol) to give compound 2 (45 mg, 56%) as a white solid.

Compound 2 (49 mg, 0.086 mmol) was heated with $NH_4I$ (125 mg, 0.86 mmol) in a solution of $NH_3$/EtOH (2 mL, 5 N) to give compound 367 (3.4 mg, 12%) as a white solid. LC-MS $t_R$=1.085 min in 2 min chromatography, MS (ESI) m/z 459.2 $[M+H]^+$. $^1H$ NMR ($CD_3OD$ 400 MHz): δ 8.51-8.52 (d, J=4.4 Hz, 1H), 7.79-7.83 (t, J=7.6 Hz, 1H), 7.11-7.42 (m, 5H), 4.97-5.06 (m, 2H), 3.24-325 (m, 3H), 3.03-3.24 (m, 3H), 2.70-2.74 (t, J=7.6 Hz, 2H), 2.02-2.03 (m, 2H), 1.79-1.82 (m, 1H), 1.28-1.52 (m, 7H), 0.65-0.69 (m, 1H), 0.37-0.39 (m, 2H), 0.00 (m, 2H).

Example 311

Synthesis of Compound 368

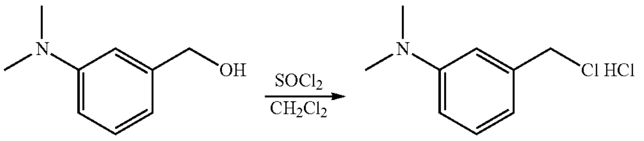

368a 368b

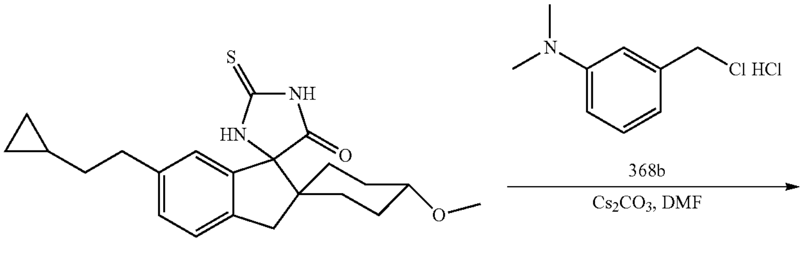

5

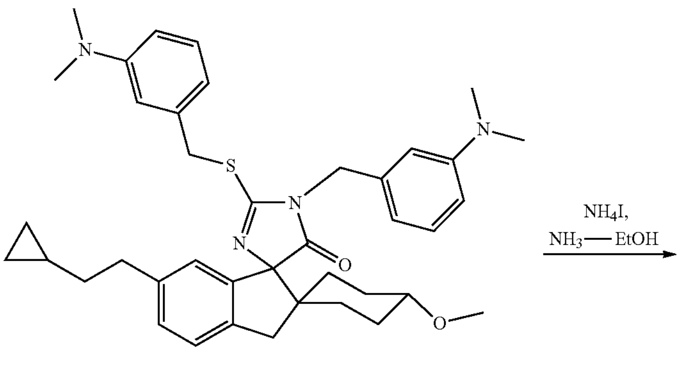

368c

-continued

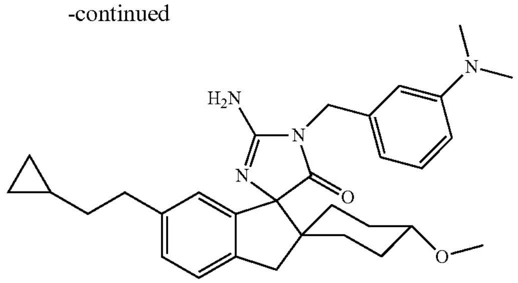

368

Procedure for Preparation of Compound 368b

To a solution of (3-dimethylamino-phenyl)-methanol (0.20 g, 1.32 mmol) in $CH_2Cl_2$ (20 mL) was added $SOCl_2$ (0.3 mL) via a syringe slowly with stirring. After addition, the reaction mixture was stirred at ambient temperature overnight. The mixture was concentrated in vacuo to give the crude compound 368b (0.31 g, 100% crude) as a red solid, which was used directly in next step.

Procedure for Preparation of Compound 368

According to a similar synthesis of compound 344, compound 5 (30 mg, 0.078 mmol) was dialkylated with compound 368b (60 mg, 0.29 mmol) to give compound 368c (13 mg, 26%) as a yellow oil. LC-MS: $t_R$=2.323 min in 3 min chromatography, MS (ESI) m/z 651 $[M+H]^+$. Compound 386c (13 mg, 0.060 mmol) was then heated with $NH_4I$ (100 mg, 0.69 mmol) and $NH_3$-EtOH (2 mL) to give compound 386 (5.4 mg, 54%) as a white solid. LC-MS: $t_R$=1.622 min in 3 min chromatography, MS (ESI) m/z 501 $[M+H]^+$. $^1$H NMR ($CD_3OD$, 400 MHz): δ 7.21 (d, J=7.6 Hz, 1H), 7.15 (t, J=8.0 Hz, 1H), 7.11 (d, J=8.0 Hz, 1H), 6.80 (s, 1H), 6.71 (d, J=11.2 Hz, 2H), 6.64 (d, J=7.6 Hz, 1H), 4.68 (d, J=6.8 Hz, 2H), 3.35 (s, 3H), 3.13 (m, 2H), 3.04 (d, J=15.2 Hz, 1H), 2.91 (s, 3H), 2.67 (t, J=7.6 Hz, 2H), 1.85-2.05 (m, 3H), 1.61 (m, 1H), 1.35-1.50 (m, 4H), 1.25-1.35 (m, 2H), 0.65 (m, 1H), 0.40 (m, 2H), 0.00 (m, 2H).

Example 312

Synthesis of Compound 369

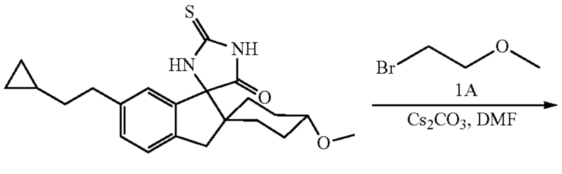

5

-continued

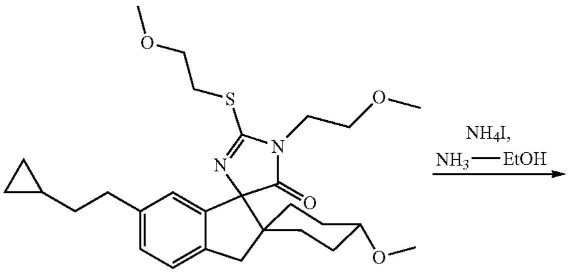

2

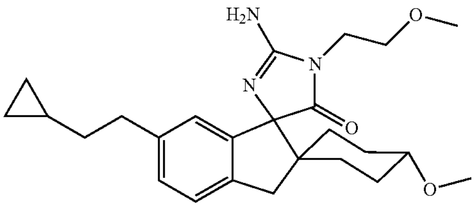

369

According to a similar synthesis of compound 344, compound 5 (45 mg, 0.12 mmol) was dialkylated with compound 1A (40 mg, 0.29 mmol) to give compound 2 (28 mg, 47%), which was heated with $NH_4I$ (80.8 mg, 0.56 mmol) in $NH_3$-EtOH (5.0 N, 3 mL) to give compound 369 (10 mg, 42%) as a white solid. LC-MS: $t_R$=1.053 min in 2 min chromatography, MS (ESI) m/z=426 $[M+H]^+$. $^1$H NMR ($CD_3OD$ 400 MHz): δ 7.25 (d, J=7.6 Hz, 1H), 7.20 (d, J=7.6 Hz, 1H), 6.97 (s, 1H), 3.91 (m, 2H), 3.55 (m, 2H), 3.34 (s, 6H), 3.15 (m, 1H), 3.10 (m, 2H), 2.70 (t, J=7.6 Hz, 2H), 2.01 (m, 2H), 1.87 (m, 1H), 1.46 (m, 7H), 0.66 (m, 1H), 0.40 (m, 2H), 0.01 (m, 2H).

Example 313

Synthesis of Compound 370

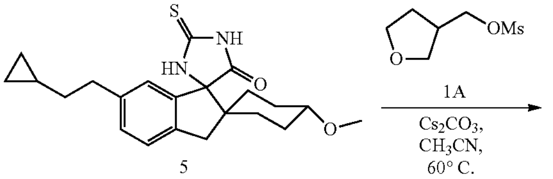

5

-continued

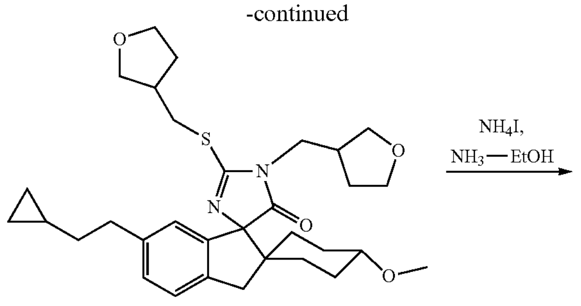

2

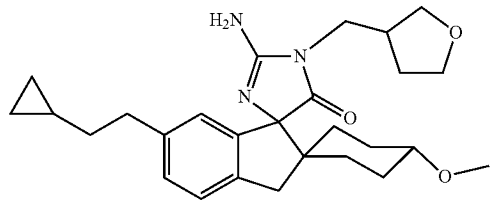

370

According to a similar synthesis of compound 344, compound 5 (30 mg, 0.078 mmol) was dialkylated with compound 1A (17.0 mg, 0.166 mmol) to give compound 2 (31 mg, 72%), which was heated with $NH_4I$ (81.4 mg, 0.56 mmol) in $NH_3$-EtOH (5.0 N, 3 mL) to give compound 370 (5.7 mg, 30%) as a white solid. LC-MS $t_R$=1.077 min in 2 min chromatography, MS (ESI) m/z=452 $[M+H]^+$. $^1H$ NMR ($CD_3OD$ 400 MHz): δ 7.25 (d, J=7.6 Hz, 1H), 7.20 (d, J=7.6 Hz, 1H), 7.00 (s, 1H), 3.89 (m, 2H), 3.72 (m, 4H), 3.45 (m, 1H), 3.34 (s, 3H), 3.12 (m, 3H), 2.01 (m, 3H), 1.89 (m, 1H), 1.64 (m, 1H), 1.45 (m, 6H), 1.30 (m, 1H), 0.65 (m, 1H), 0.38 (m, 2H), 0.01 (m, 2H).

Example 314

Synthesis of Compound 371

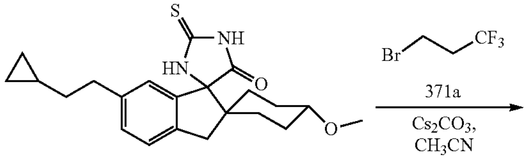

5

-continued

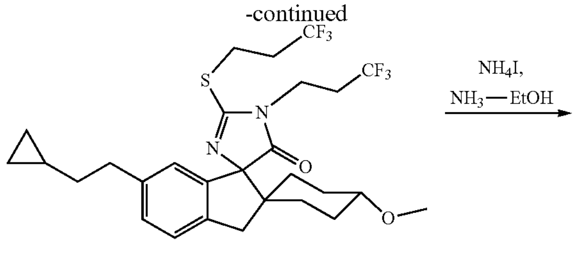

371b

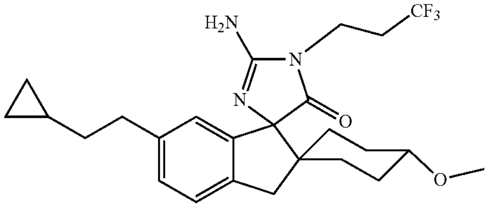

371

According to a similar synthesis of compound 344, compound 5 (30 mg, 0.078 mmol) was dialkylated with 3-bromo-1,1,1-trifluoro-propane (50 mg, 0.28 mmol) to give compound 371b (36 mg, 80%) as a white solid. LC-MS: $t_R$=2.581 min in 3 min chromatography, MS (ESI) m/z=424 $[M+H]^+$.

Compound 371b (36 mg, 0.062 mmol) was then heated with $NH_4I$ (100 mg, 0.69 mmol) and $NH_3$-EtOH (2 mL) to give compound 371 (7.7 mg, 27%) as a white solid. LC-MS: $t_R$=1.658 min in 3 min chromatography, MS (ESI) m/z=464 $[M+H]^+$. $^1H$ NMR: ($CD_3OD$, 400 MHz): δ 7.19 (d, J=7.6 Hz, 1H), 7.09 (d, J=7.6 Hz, 1H), 7.80 (s, 1H), 3.83 (m, 2H), 3.34 (s, 3H), 3.14 (m, 1H), 3.05 (d, J=15.2 Hz, 1H), 3.02 (d, J=15.2 Hz, 1H), 2.68 (t, J=7.6 Hz, 2H), 2.56 (m, 2H), 1.75-2.10 (m, 3H), 1.50-1.60 (m, 1H), 1.25-1.50 (m, 6H), 0.85-1.05 (m, 6H), 0.65 (m, 1H), 0.40 (m, 2H), 0.00 (m, 2H). $^{19}F$ NMR: ($CD_3OD$ 400 MHz): δ −66.676

Example 315

Synthesis of Compound 372

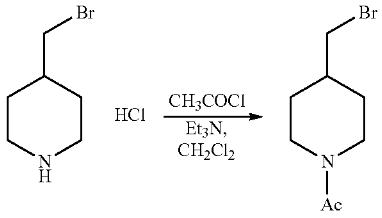

372a

372b

-continued

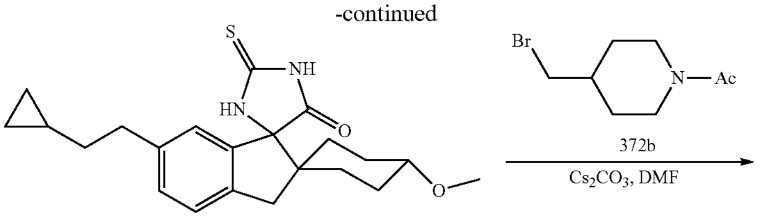

5

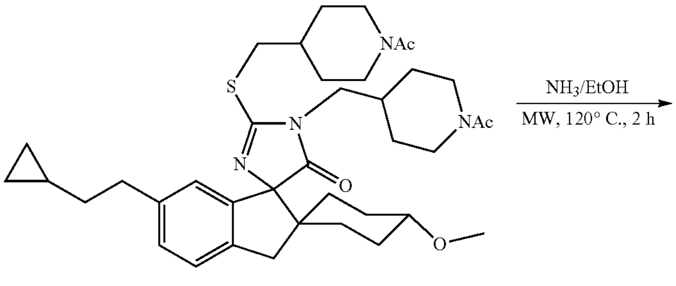

372c

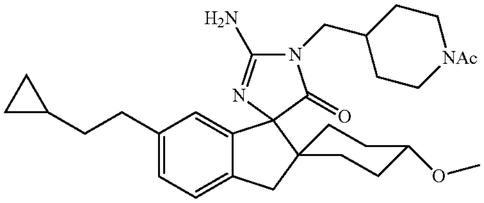

372

Procedure for Preparation of Compound 372b

To a solution of 4-bromomethyl-piperidine hydrochloride salt (0.10 g, 0.47 mmol) anhydrous dichloromethane (10 mL) were added acetyl chloride (75 mg, 0.94 mmol) and triethylamine (0.10 g, 0.99 mmol) in turn. The reaction mixture was stirred at ambient temperature overnight. The reaction was quenched by adding brine (10 mL) with stirring. The mixture was separated and the aqueous layer was extracted with dichloromethane (10 mL×2). The combined organic layers were washed with brine (10 mL×2). The separated organic phase was dried over $Na_2SO_4$ and concentrated in vacuo to give crude compound 372b (0.12 g, crude) as a red oil, which was used directly in next step without purification. $^1H$ NMR ($CDCl_3$, 400 MHz): δ 4.68 (m, 1H), 3.78 (m, 1H), 3.24 (d, J=5.2 Hz, 2H), 2.96 (m, 1H), 2.62 (m, 1H), 2.04 (s, 3H), 1.87 (m, 2H), 1.16 (m, 2H).

Procedure for Preparation of Compound 372

According to a similar synthesis of compound 344, compound 5 (30 mg, 0.078 mmol) was dialkylated with compound 372b (60 mg, 0.078 mmol) to give compound 372c (44 mg, 85%) as a yellow oil. LC-MS: $t_R$=1.944 min in 3 min chromatography, MS (ESI) m/z=663 $[M+H]^+$.

Compound 372c (40 mg, 0.060 mmol) was then heated with $NH_4I$ (100 mg, 0.69 mmol) and $NH_3$-EtOH (2 mL) to give compound 372 (9.0 mg, 30%) as a white solid. LC-MS: $t_R$=1.557 min in 3 min chromatography, MS (ESI) m/z=507 $[M+H]^+$. $^1H$ NMR ($CD_3OD$, 400 MHz): δ 7.18 (d, J=7.6 Hz, 1H), 7.09 (d, J=7.6 Hz, 1H), 6.81 (s, 1H), 4.46 (m, 1H), 3.83 (m, 1H), 3.42 (d, J=7.2 Hz, 2H), 3.33 (s, 3H), 3.13 (m, 1H), 3.09 (m, 2H), 3.01 (d, J=15.2 Hz, 1H), 3.02 (d, J=15.2 Hz, 1H), 2.67 (t, J=7.2 Hz, 2H), 2.56 (m, 1H), 2.05 (d, J=7.2 Hz, 3H), 1.85-2.05 (m, 3H), 1.50-1.80 (m, 3H), 1.25-1.50 (m, 6H), 1.00-1.25 (m, 2H), 0.65 (m, 1H), 0.40 (m, 2H), 0.00 (m, 2H).

Example 316

Synthesis of Compound 373

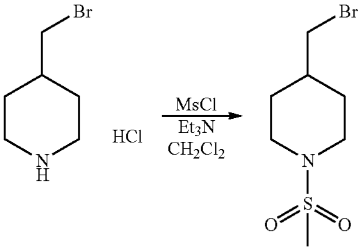

373a

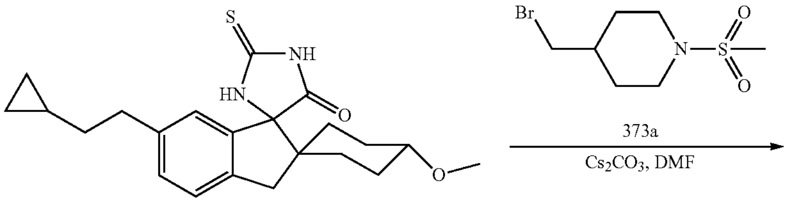

5

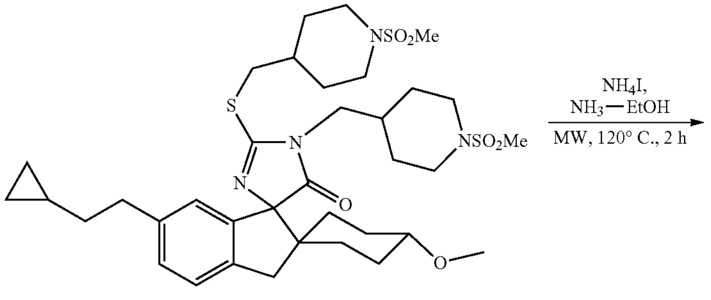

373b

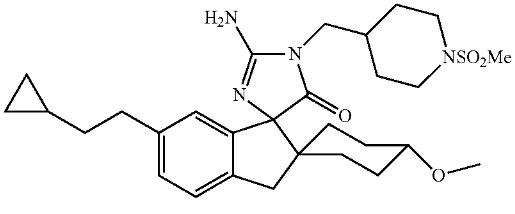

373

Procedure for Preparation of Compound 373a

Synthesized by a route analogously to compound 372b, reaction of 4-bromomethyl-piperidine hydrochloride salt with MsCl gave crude compound 373a (0.11 g, crude) as a pale yellow oil, which was used directly in next step without purification. $^1$H NMR ($CDCl_3$, 400 MHz): δ 3.80 (d, J=12.0 Hz, 2H), 3.26 (d, J=6.4 Hz, 2H), 2.72 (s, 3H), 2.63 (m, 2H), 1.92 (d, J=12.8 Hz, 2H), 1.74 (m, 1H), 1.16 (dt, J=4.0, 12.4 Hz, 2H).

Procedure for Preparation of Compound 373

According to a similar synthesis of compound 344, compound 5 (30 mg, 0.078 mmol) was alkylated with compound compound 373a to give compound 373b (47 mg, 82%) as a white solid. LC-MS: $t_R$=2.082 min in 3 min chromatography, MS (ESI) m/z=735 $[M+H]^+$.

Compound 373b (40 mg, 0.054 mmol) was then converted to compound 373 (10.7 mg, 36%) as a white solid. LC-MS: $t_R$=1.610 min in 3 min chromatography, MS (ESI) m/z=543 $[M+H]^+$. $^1$H NMR ($CD_3OD$, 400 MHz): δ 7.18 (d, J=7.6 Hz, 1H), 7.09 (d, J=7.6 Hz, 1H), 6.81 (s, 1H), 3.71 (m, 2H), 3.44 (d, J=6.8 Hz, 2H), 3.31 (s, 3H), 3.13 (m, 1H), 3.09 (d, J=15.6 Hz, 1H), 3.02 (d, J=15.2 Hz, 1H), 3.02 (d, J=15.2 Hz, 1H), 2.81 (s, 3H), 2.73 (m, 1H), 2.67 (t, J=7.6 Hz, 2H), 1.85-2.05 (m, 4H), 1.50-1.80 (m, 3H), 1.20-1.50 (m, 8H), 0.65 (m, 1H), 0.40 (m, 2H), 0.00 (m, 2H).

Example 317

Synthesis of Compound 374

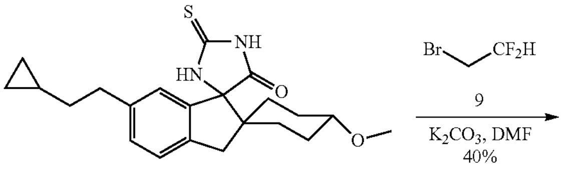

5

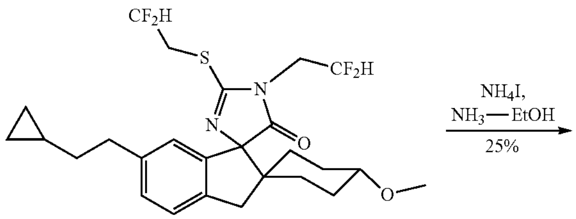

10

-continued

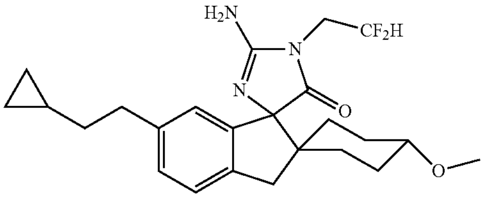

374

According to a similar synthesis of compound 344, compound 5 (50 mg, 0.13 mmol) was dialkylated with 2-bromo-1,1-difluoro-ethane (9) (33 mg, 0.3 mmol) to give compound 10 (24 mg, yield 40%) as a white solid.

Compound 10 (20 mg, 0.04 mmol) was then heated with $NH_4I$ (60 mg, 0.4 mmol) in a solution of $NH_3$-EtOH (3 mL, 5 N) to give compound 374 (5 mg, 25%) as a white solid. LCMS:

$t_R$=1.58 min in 3 min chromatography, MS (ESI) m/z=432.2 $[M+H]^+$. $^1H$ NMR ($CD_3OD$ 400 MHz): δ 7.00-7.20 (m, 2H), 6.75-6.85 (s, 1H), 5.80-6.30 (m, 1H), 3.85-4.00 (m, 2H), 3.35-3.40 (s, 3H), 3.00-3.20 (m, 3H), 2.60-2.70 (m, 2H), 1.90-2.10 (m, 3H), 1.30-1.70 (m, 7H), 0.60-0.70 (m, 1H), 0.35-0.45 (m, 2H), 0.05-0.10 (m, 2H). $^{19}F$ NMR: ($CD_3OD$ 400 MHz): δ -124.396

Example 318

Synthesis of Compound 375

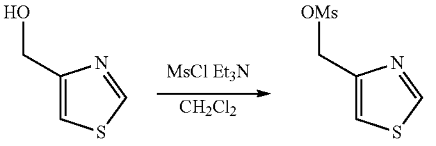

375a

375b

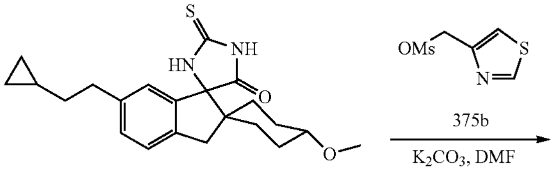

5

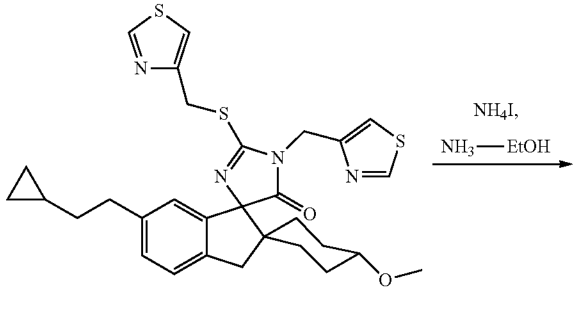

375c

-continued

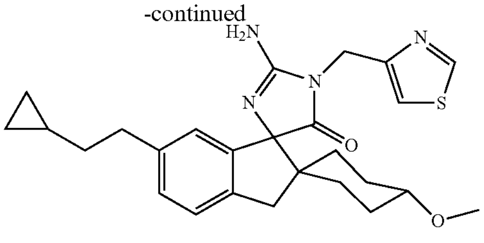

375

Procedure for Preparation of Compound 27

To a solution of compound 375a (100 mg, 0.86 mmol) in $CH_2Cl_2$ (2 mL) was added $Et_3N$ (175.4 mg, 1.73 mmol) and MsCl (109.3 mg, 0.95 mmol) under nitrogen, the mixture was stirred at room temperature for 4 h. The reaction was quenched with $H_2O$ (10 mL) and extracted with $CH_2Cl_2$ (5 mL×3). The combined organic layers were washed with brine (20 mL), dried over $Na_2SO_4$ and concentrated to give compound 375b (72.8 mg, 75%) as a yellow oil which was used in the next step without further purification. $^1H$ NMR ($CDCl_3$ 400 MHz): δ 8.79-8.78 (d, J=2.0 Hz, 1H), 7.35-7.34 (d, J=2.0 Hz, 1H), 4.73 (s, 2H), 3.65 (s, 3H).

Procedure for Preparation of Compound 375

According to a similar synthesis of compound 344, compound 5 (30 mg, 0.077 mmol) was dialkylated with compound 27 (28.9 mg, 0.156 mmol) to afford compound 375c (30 mg, 55%) as a white solid. LCMS: $t_R$=1.626 min in 2 min chromatography, MS (ESI) m/z=579.3 $[M+H]^+$.

Compound 375c (20 mg, 0.034 mmol) was then heated with $NH_4I$ (49.6 mg, 0.34 mmol) in $NH_3$-EtOH (2 mL, 5 N) to give compound 375 (8.10 mg, 51%) as a white solid. LCMS: $t_R$=1.075 min in 2 min chromatography, MS (ESI) m/z=465.2 $(M+H)^{30}$. $^1H$ NMR ($CD_3OD$ 400 MHz): δ 8.98-8.97 (d, J=2.0 Hz, 1H), 7.54-7.52 (d, J=7.6 Hz, 1H), 7.25-7.19 (d, J=7.6 Hz, 1H), 7.19-7.15 (d, J=7.6 Hz, 1H), 7.10-7.04 (s, 1H), 5.10-5.01 (s, 2H) 3.33 (s, 3H), 3.20-3.10 (m, 2H), 3.10-3.05 (d, J=15.2 Hz, 2H), 2.70-2.66 (t, J=15.2 Hz, 2H), 2.10-1.98 (m, 2H), 1.80-1.70 (m, 1H), 1.60-1.35 (m, 5H), 1.35-1.20 (m, 2H), 0.67-0.64 (m, 1H), 0.41-0.38 (m, 2H), 0.10-0.07 (m, 2H).

Example 319

Synthesis of Compound 376

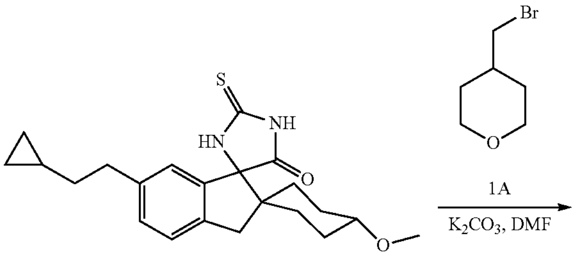

5

-continued

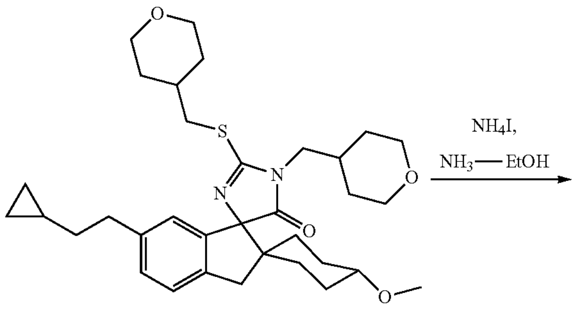

2

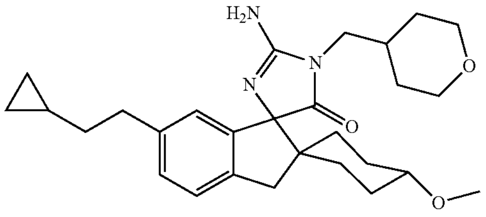

376

According to a similar synthesis of compound 344, compound 5 (50 mg, 0.13 mmol) was dialkylated with compound 1A (77 mg, 0.52 mmol) to afford the crude product 2 (45 mg, 80%), which was heated $NH_4I$ (98 mg, 0.68 mmol) in a solution of $NH_3$/EtOH (5 mL, 5 N) to give compound 376 (15 mg, 42%) as a white solid. LC-MS $t_R$=1.057 min in 2 min chromatography, MS (ESI) m/z 466.2 $[M+H]^+$; $^1H$ NMR ($CDCl_3$ 400 MHz): δ 7.13 (dd, J=32.8, 7.6 Hz, 2H), 6.83 (s, 1H), 3.95 (t, J=11.2 Hz, 2H), 3.4 (d, J=7.2 Hz, 2H), 3.44 (s, 1H), 3.35 (m, 3H), 3.15 (d, J=15.2 Hz, 1H), 3.0 (d, J=15.2 Hz, 1H), 2.6 (t, J=15.6 Hz, 2H), 2.0 (m, 5H), 1.6 (m, 2H), 1.4 (m, 8H), 0.6 (m, 1H), 0.39 (d, J=7.6 Hz, 2H), 0.68 (d, J=12.4 Hz, 2H).

Example 320

Synthesis of Compound 377

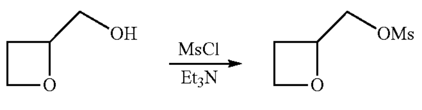

7A 7

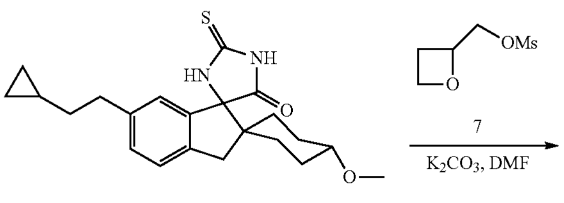

5

-continued

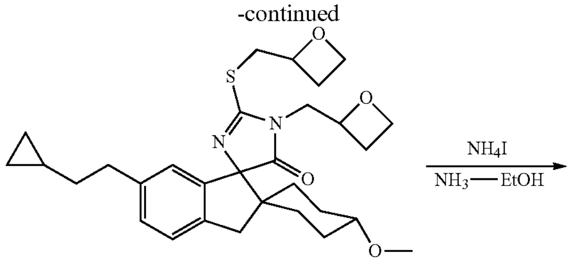

8

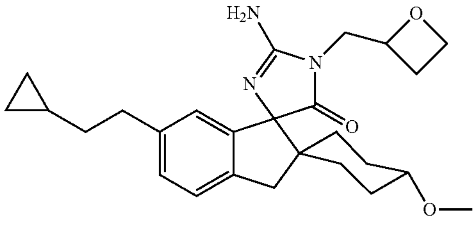

377

Procedure for Preparation of Compound 7

To a solution of compound 7A (200 mg, 2.27 mmol) in $CH_2Cl_2$ (10 mL) was added MsCl (286 mg, 2.50 mmol) and $Et_3N$ (689 mg, 6.81 mmol) at 0° C., the mixture was stirred at 0° C. for 1 h. Then $H_2O$ (20 mL) was added and extracted with $CH_2Cl_2$ (3×20 mL), the organic layer was dried over $Na_2SO_4$ and concentrated to give compound 7 (160 mg, 42%) as a yellow oil, which was used for the next step without further purification.

Procedure for Preparation of Compound 377

According to a similar synthesis of compound 344, compound 5 (30 mg, 0.078 mmol) was dialkylated with compound 7 (38.9 mg, 0.234 mmol) to give compound 8 (16 mg, 39%) as a white solid.

Compound 8 (20 mg, 0.038 mmol) was then heated with $NH_4I$ (44.2 mg, 0.305 mmol) in a solution of $NH_3$/EtOH (2 mL, 0.5 N) to give compound 377 (4.3 mg, 26%) as a white solid. LC-MS $t_R$=0.920 min in 2 min chromatography, MS (ESI) m/z 438 $[M+H]^+$. $^1H$ NMR ($CD_3OD$ variant 400 MHz): δ 7.21 (d, J=7.6 Hz, 2H), 7.11 (d, J=7.6 Hz, 2H), 6.84 (d, J=14.8 Hz, 1H), 5.01 (s, 1H), 4.67 (m, 1H), 4.54 (m, 1H), 3.76 (m, 2H), 3.36 (s, 3H), 3.12 (m, 3H), 2.69 (m, 3H), 2.52 (m, 1H), 2.00 (m, 3H), 1.85 (m, 1H), 1.40 (m, 6H), 0.71 (m, 1H), 0.40 (m, 2H), 0.01 (m, 2H).

Example 321

Synthesis of Compound 378

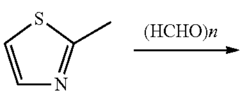

15A

-continued

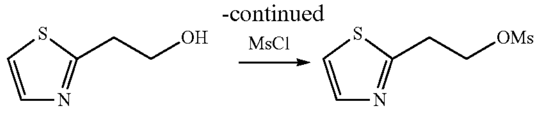

15B 15

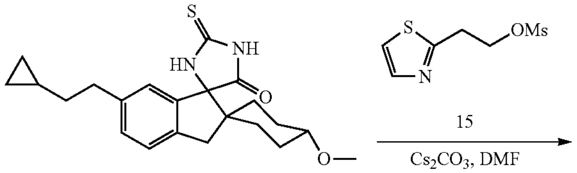

5

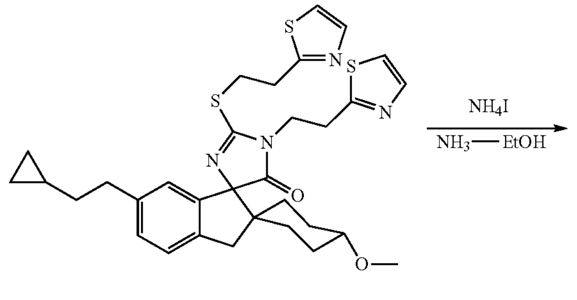

16

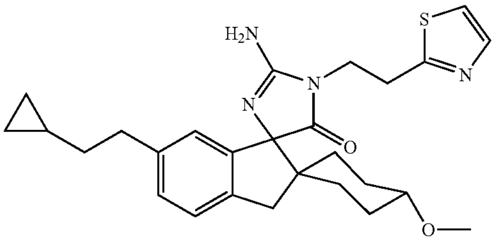

378

Procedure for Preparation of Compound 15B

Compound 15A (6 g, 60.5 mmol) and $(HCHO)_n$ (2.76 g, 30.25 mmol) were heated together in a sealed tube at 165° C. for 3 h. After cooling, the reaction mixture was removed carefully and purified by column chromatography ($CH_2Cl_2$: EtOAc=1:1) to give compound 15B (1.6 g, 20%) as a yellow oil.

Procedure for Preparation of Compound 15

To a solution of compound 15B (200 mg, 1.55 mmol) in $CH_2Cl_2$ (5 mL) was added MsCl (195 mg, 1.70 mmol) and $Et_3N$ (470 mg, 4.65 mmol) at 0° C., the mixture was stirred at 0° C. for 1 h. Then $H_2O$ (20 mL) was added and extracted with $CH_2Cl_2$ (3×20 mL), the organic layer was dried over $Na_2SO_4$ and concentrated to give compound 15 (150 mg, 47%) as a yellow oil, which was used for the next step without further purification.

Procedure for Preparation of Compound 378

According to a similar synthesis of compound 344, compound 5 (30 mg, 0.078 mmol) was dialkylated with compound 15 (48.5 mg, 0.234 mmol) to give compound 16 (40 mg, 85%) as a white solid.

Compound 16 (45 mg, 0.074 mmol) was then heated with $NH_4I$ (86 mg, 0.593 mmol) in a solution of $NH_3$/EtOH (2 mL, 5 N) to give compound 378 (2.5 mg, 7%) as a white solid. LC-MS $t_R$=1.081 min in 2 min chromatography, MS (ESI) m/z 479 $[M+H]^+$. $^1H$ NMR ($CD_3OD$ 400 MHz): δ 7.68 (d, J=3.2 Hz, 1H), 7.50 (d, J=3.2 Hz, 1H), 7.20 (m, 2H), 7.01 (s, 1H), 4.15 (m, 2H), 3.42 (m, 2H), 3.22 (s, 3H), 3.00 (m, 1H), 2.97 (m, 2H), 2.69 (m, 2H), 1.97 (m, 2H), 1.63 (m, 1H), 1.47 (m, 5H), 1.31 (m, 2H), 0.69 (m, 1H), 0.40 (m, 2H), 0.01 (m, 2H).

Example 323

Synthesis of Compounds 379 and 380

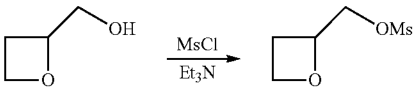

7A 7

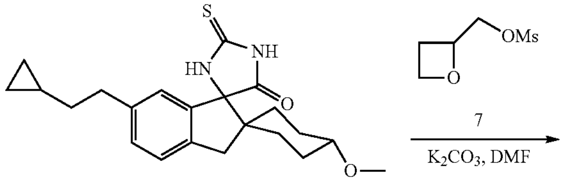

5

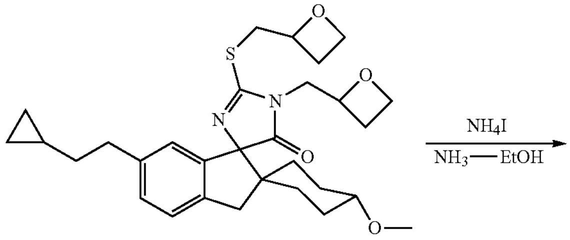

8

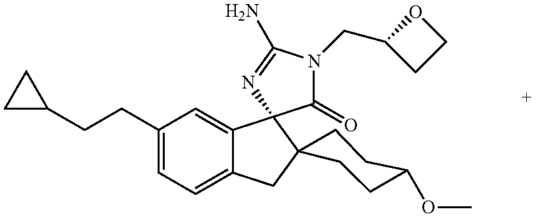

379

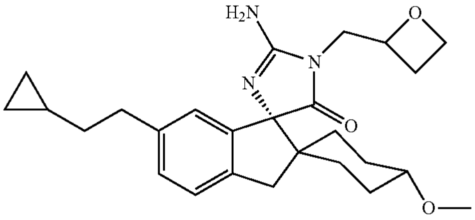

380

Procedure for Preparation of Compound 7

To a solution of compound 7A (200 mg, 2.27 mmol) in $CH_2Cl_2$ (10 mL) was added MsCl (286 mg, 2.50 mmol) and $Et_3N$ (689 mg, 6.81 mmol) at 0° C., the mixture was stirred at 0° C. for 1 h. Then $H_2O$ (20 mL) was added and extracted with $CH_2Cl_2$ (3×20 mL), the organic layer was dried over $Na_2SO_4$ and concentrated to give compound 7 as a yellow oil (160 mg, 42%), which was used for the next step without further purification.

Procedure for Preparation of Compounds 379 and 380

According to a similar synthesis of compound 344, compound 5 (30 mg, 0.078 mmol) was dialkylated with compound 7 (38.9 mg, 0.234 mmol) to give compound 8 (16 mg, 39%) as a white solid.

Compound 8 (20 mg, 0.038 mmol) was then heated with $NH_4I$ (44.2 mg, 0.305 mmol) in a solution of $NH_3$/EtOH (2 mL, 0.5 N) and purified by preparative TLC ($CH_2Cl_2$:MeOH=10:1) and HPLC and SFC to give compound 379 (3.0 mg, 37%), SFC: $t_R$=6.15 min in 16 min chromatography, ee=98%, LC-MS $t_R$=1.025 min in 2 min chromatography, MS (ESI) m/z 438 $[M+H]^+$. $^1H$ NMR ($CD_3OD$ 400 MHz): δ 7.22 (m, 2H), 7.06 (m, 1H), 4.30 (m, 1H), 4.11 (m, 1H), 3.90 (m, 2H), 3.63 (m, 1H), 3.33 (s, 3H), 3.13 (m, 1H), 3.11 (m, 2H), 2.70 (m, 2H), 2.42 (m, 1H), 2.00 (m, 3H), 1.85 (m, 1H), 1.40 (m, 6H), 1.38 (m, 1H), 0.65 (m, 1H), 0.40 (m, 2H), 0.01 (m, 2H).

and compound 380 (3.2 mg, 38%) as a white solid. SFC: $t_R$=6.84 min in 16 min chromatography, ee=98%, LC-MS $t_R$=1.030 min in 2 min chromatography, MS (ESI) m/z 438 $[M+H]^+$. $^1H$ NMR ($CD_3OD$ 400 MHz): δ 7.21 (d, J=3.6 Hz, 1H), 7.11 (d, J=3.6 Hz, 1H), 7.06 (d, J=14.4 Hz, 1H), 5.01 (m, 1H), 4.67 (m, 1H), 4.54 (m, 1H), 3.86 (m, 2H), 3.33 (s, 3H), 3.15 (m, 1H), 3.09 (m, 2H), 2.71 (m, 3H), 2.65 (m, 1H), 2.00 (m, 3H), 1.66 (m, 1H), 1.40 (m, 6H), 0.65 (m, 1H), 0.40 (m, 2H), 0.01 (m, 2H).

Example 323

Synthesis of Compound 381

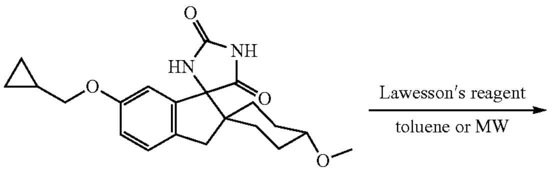

381a

-continued

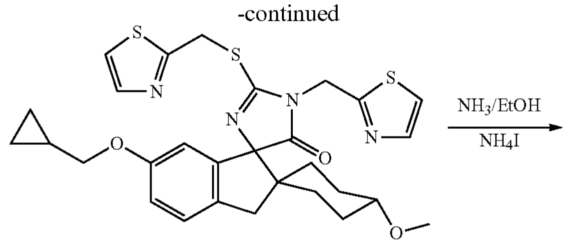

381d

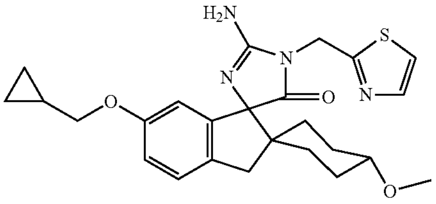

381

Procedure for Preparation of Compound 381b

To a solution of compound 381a (80 mg, 0.21 mmol) in anhydrous toluene (2 mL) was added Lawesson's Reagent (84.8 mg, 0.21 mmol) under $N_2$, the mixture was stirred at 110° C. for 3 h. The solvent was removed in vacuo to give the crude product which was purified by preparative TLC on silica gel eluting with hexane:EtOAc=3:1 to afford compound 381b (50 mg, 60%) as a white solid. LCMS: $t_R$=1.258 min in 2 min chromatography, MS (ESI) m/z=387.2 $[M+H]^+$.

Procedure for Preparation of Compound 381

According to a similar synthesis of compound 344, compound 381b (20 mg, 0.05 mmol) was dialkylated compound 381c (26.7 mg, 0.20 mmol) to give compound 381d (20 mg, 66%) as a white solid. LCMS: $t_R$=1.427 min in 2 min chromatography, MS (ESI) m/z=387.2 $[M+H]^+$.

Compound 381d (20 mg, 0.034 mmol) was then heated with $NH_4I$ (49.4 mg, 0.34 mmol) in $NH_3$-EtOH (2 mL, 5 N) to give compound 381 (1.20 mg, 8%) as a white solid. LCMS: $t_R$=1.827 min in 3 min chromatography, MS (ESI) m/z=467.2 $[M+H]^+$. $^1H$ NMR ($CD_3OD$ 400 MHz): δ 7.80 (s, 1H), 7.60 (s, 1H), 7.30 (d, J=8.0 Hz, 1H), 6.90 (d, J=8.0 Hz, 1H), 6.60 (s, 1H), 5.20 (s, 2H), 3.77 (d, J=6.8 Hz, 2H), 3.35-3.33 (s, 3H), 3.20-3.15 (m, 1H), 3.14-2.93 (m, 2H), 2.10-1.90 (m, 2H), 1.90-1.80 (m, 1H), 1.70-1.50 (m, 1H), 1.50-1.10 (m, 5H), 0.63-0.59 (m, 2H), 0.38-0.32 (m, 2H).

Example 324

Synthesis of Compound 382

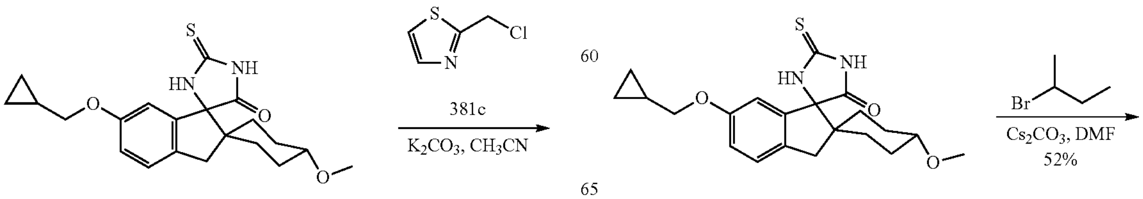

381b

1

-continued

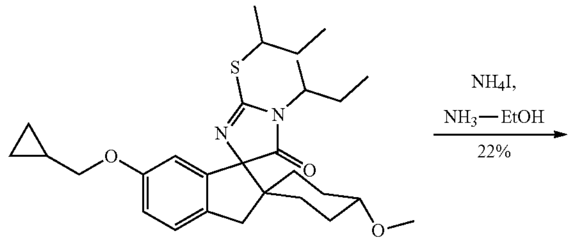

2

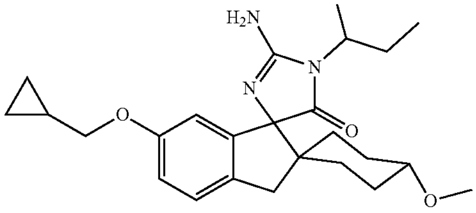

382

According to a similar synthesis of compound 344, compound 1 (30 mg, 0.077 mmol) was dialkylated with 2-bromobutane (42.4 mg, 0.31 mmol) to give compound 2 (20 mg, 52%) as a white solid. LC-MS $t_R$=1.488 min in 2 min chromatography, MS (ESI) m/z=499.3 $[M+H]^+$.

Compound 2 (20 mg, 0.045 mmol) was then heated with $NH_4I$ (57 mg, 0.40 mmol) in $NH_3$-EtOH (2 mL, 5 N) to give compound 382 (3.80 mg, 22%) as a white solid. LC-MS $t_R$=1.05 min in 2 min chromatography, MS (ESI) MS (ESI) m/z=426.3 $[M+H]^+$. $^1H$ NMR ($CD_3OD$ 400 MHz): δ 7.07-7.05 (d, J=8.0 Hz, 1H), 6.80-6.69 (dd, J=1.6, 8.0 Hz, 1H), 6.40 (d, J=2.4 Hz, 1H), 4.01-3.82 (m, 1H), 3.73-3.64 (d, J=6.8 Hz, 2H), 3.34 (s, 3H), 3.10-3.01 (m, 1H), 2.95-2.89 (d, J=14.8 Hz, 1H), 2.87-2.82 (d, J=15.2 Hz, 1H), 2.01-1.70 (m, 4H), 1.60-1.40 (m, 2H), 1.40-1.26 (m, 2H), 1.31-1.22 (m, 3H), 1.22-1.05 (m, 3H), 0.90-0.71 (m, 3H), 0.60-0.40 (m, 2H), 0.31-0.21 (m, 2H).

Example 325

Synthesis of Compound 383

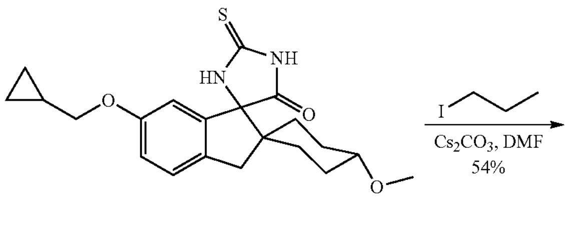

1

-continued

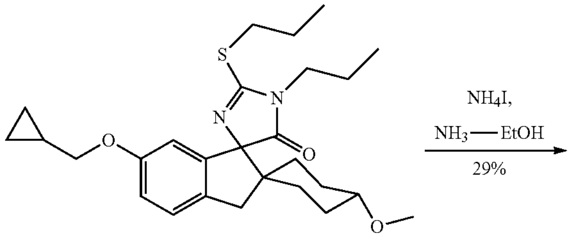

3

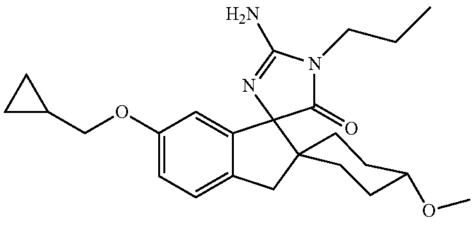

383

According to a similar synthesis of compound 344, compound 1 (30 mg, 0.077 mmol) was dialkylated with 1-Iodopropane (52.6 mg, 0.31 mmol) to give compound 3 (20 mg, 54%) as a white solid. LC-MS $t_R$=1.37 min in 2 min chromatography, MS (ESI) MS (ESI) m/z=471.2 $[M+H]^+$.

Compound 3 (20 mg, 0.042 mmol) was then heated with $NH_4I$ (61 mg, 0.42 mmol) in $NH_3$-EtOH (2 mL, 5 N) to give compound 383 (5.10 mg, 29%) as a white solid. LC-MS $t_R$=1.02 in 2 min chromatography, MS (ESI) MS (ESI) m/z=412.2 $[M+H]^+$. $^1H$ NMR ($CD_3OD$ 400 MHz): δ 7.08-7.06 (d, J=8.0 Hz, 1H), 6.80-6.65 (dd, J=2.4, 8.4 Hz, 1H), 6.40 (d, J=2.4 Hz, 1H), 3.79-3.71 (m, 2H), 3.41-3.35 (t, J=7.2 Hz, 2H), 3.38 (s, 3H), 3.10-3.01 (m, 1H), 2.95-2.90 (d, J=14.8 Hz, 1H), 2.95-2.85 (d, J=14.4 Hz, 1H), 2.01-1.80 (m, 2H), 1.80-1.70 (m, 1H), 1.64-1.40 (m, 3H), 1.41-1.22 (m, 2H), 1.22-1.05 (m, 3H), 0.85-0.71 (t, J=7.6 Hz, 3H), 0.60-0.40 (m, 2H), 0.31-0.12 (m, 2H).

Example 326

Synthesis of Compound 384

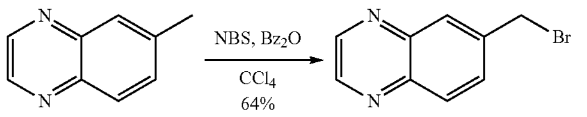

8

6

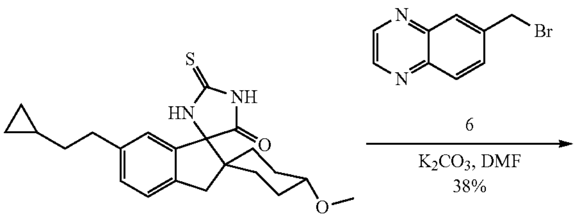

5

-continued

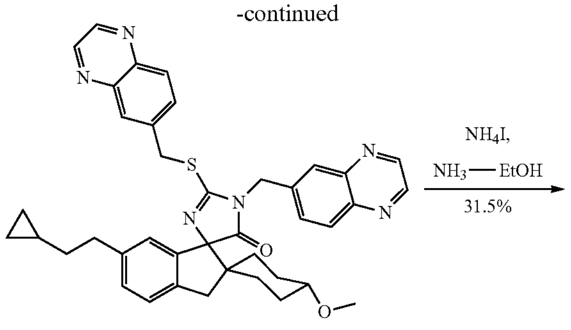

7

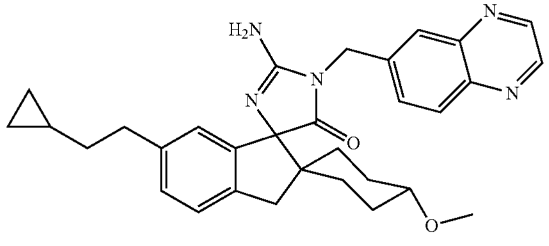

384

Procedure for Preparation of Compound 6

To a solution of compound 8 (100 mg, 0.69 mmol) in anhydrous $CCl_4$ (2 mL) was added NBS (135.9 mg, 0.76 mmol) and $Bz_2O$ (3.80 mg, 0.015 mmol). The resulting suspension was heated at reflux for 12 h. The mixture was filtered through a pad of celite and the filtrate was concentrated under reduced pressure to give the crude product which was purified by preparative TLC on silica gel eluting with hexane: EtOAc=3:1 to give compound 6 (100 mg, 64%) as a yellow liquid. $^1$H NMR ($CDCl_3$ 400 MHz): δ 8.4-8.25 (m, 2H), 8.12-8.05 (m, 2H), 7.82-7.74 (dd, J=2.0, 8.8 Hz, 1H), 4.62 (s, 2H), Procedure for Preparation of Compound 384

According to a similar synthesis of compound 344, compound 5 (30 mg, 0.078 mmol) was heated with compound 6 (69.1 mg, 0.31 mmol) to give compound 7 (20 mg, 38%) as a white solid, LC-MS: $t_R$=1.436 min in 2 min chromatography, MS (ESI) m/z 669.3 $[M+H]^+$.

Compound 7 (20 mg, 0.029 mmol) was then heated with $NH_4I$ (42.9 mg, 0.29 mmol) in $NH_3$-EtOH (2 mL, 5 N) to give compound 384 (4.80 mg 31%) as a white solid. LC-MS: $t_R$=0.940 min in 2 min chromatography, MS (ESI) m/z 510.2 $[M+H]^+$. $^1$H NMR ($CD_3OD$ 300 MHz): δ 9.03-8.97 (s, 2H), 8.25-8.17 (d, J=8.7 Hz, 1H), 8.05-7.95 (s, 1H), 7.90-7.80 (dd, J=1.8, 6.0 Hz, 1H), 7.35-7.30 (d, J=7.8 Hz, 1H), 7.30-7.20 (dd, J=1.2, 7.5 Hz, 1H), 7.09-7.01 (s, 1H), 5.23 (s, 2H) 3.38 (s, 3H), 3.25-3.10 (m, 3H), 2.80-2.68 (t, J=7.5 Hz, 2H), 2.20-

2.02 (m, 2H), 2.03-1.81 (m, 1H), 1.70-1.20 (m, 7H), 0.75-0.60 (m, 1H), 0.50-0.30 (m, 2H), 0.30-0.01 (m, 2H).

Example 327

Synthesis of Compound 385

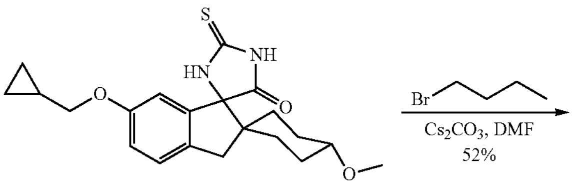

1

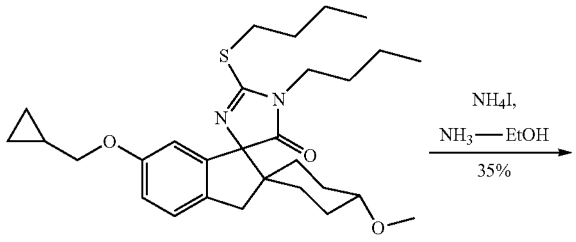

4

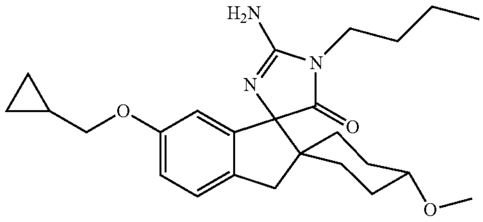

385

According to a similar synthesis of compound 344, compound 1 (30 mg, 0.077 mmol) was dialkylated 2-Bromobutane (42.4 mg, 0.31 mmol) to give compound 4 (20 mg, 52%) as a white solid. LC-MS $t_R$=1.47 min in 2 min chromatography, MS (ESI) MS (ESI) m/z=499.3 $[M+H]^+$.

Compound 4 (20 mg, 0.045 mmol) was then heated with $NH_4I$ (57 mg, 0.40 mmol) in $NH_3$-EtOH (2 mL, 5 N) to give compound 385 (9.20 mg, 35%) as a white solid. LC-MS $t_R$=1.056 min in 2 min chromatography, MS (ESI) m/z=426.2 $[M+H]^+$. $^1$H NMR ($CD_3OD$ 400 MHz): δ 7.20-7.01 (d, J=8.4 Hz, 1H), 6.80-6.60 (dd, J=2.4, 8.4 Hz, 1H), 6.40 (d, J=2.4 Hz, 1H), 3.75-3.60 (m, 2H), 3.45-3.35 (t, J=7.2 Hz, 2H), 3.38 (s, 3H), 3.10-3.01 (m, 1H), 2.95-2.90 (d, J=14.8 Hz, 1H), 2.90-2.81 (d, J=14.8 Hz, 2H), 2.01-1.80 (m, 2H), 1.81-1.70 (m, 1H), 1.64-1.46 (m, 3H), 1.41-1.05 (m, 7H), 0.90-0.80 (t, J=7.2 Hz, 3H), 0.60-0.40 (m, 2H), 0.31-0.12 (m, 2H).

Example 328

Synthesis of Compound 386

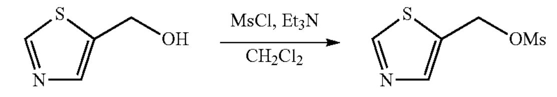

26

24

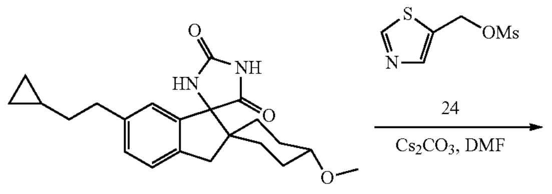

1A

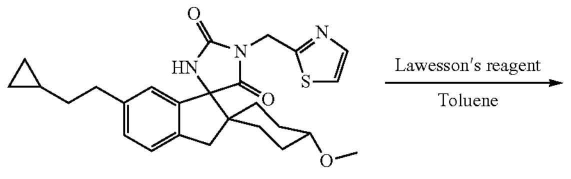

25A

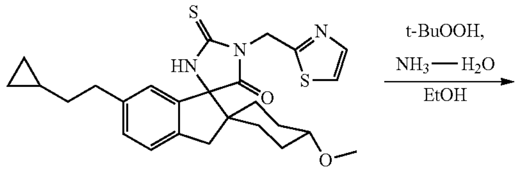

25B

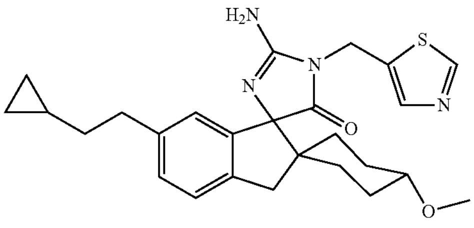

386

Procedure for Preparation of Compound 24

To a solution of thiazol-5-yl-methanol (0.20 g, 1.74 mmol) and $Et_3N$ (0.40 g, 3.95 mmol) in $CH_2Cl_2$ (10 mL) was added methane sulfonyl chloride (0.40 g, 3.49 mmol) via a syringe slowly with stirring. After addition, the reaction mixture was stirred at ambient temperature for 7 h. The reaction was quenched by addition 10 mL brine with stirring. The mixture was separated and the aqueous layer was extracted with $CH_2Cl_2$ (10 mL×2). The combined organic layers were washed with brine (10 mL×2), dried over $Na_2SO_4$, filtered and concentrated in vacuo to give the crude compound 24 (0.40 g, crude) as a brown oil, which was used directly in next step.

Procedure for Preparation of Compound 386

According to a similar synthesis of compound 296, compound 1A (50 mg, 0.14 mmol) was alkylated with compound 24 to give compound 25A (31 mg, 48%) as a white solid. $^1$H NMR ($CDCl_3$ variant 400 MHz): δ 8.73 (s, 1H), 7.86, (s, 1H), 7.21 (d, J=7.6 Hz, 1H), 7.14 (d, J=8.0 Hz, 1H), 6.83 (s, 1H), 6.18 (m, 1H), 4.87 (s, 2H), 3.36 (s, 3H), 3.15 (d, J=14.4 Hz, 1H), 3.09 (m, 1H), 2.66 (t, J=7.2 Hz, 2H), 1.85-2.10 (m, 3H), 1.15-1.50 (m, 7H), 0.65 (m, 1H), 0.40 (m, 2H), 0.01 (m, 2H).

Compound 25A (31 mg, 0.069 mmol) was then reacted with Lawesson's reagent to give compound 25B (13 mg, 41%) as a white solid. LC-MS: $t_R$=1.214 min in 2 min chromatography, MS (ESI) m/z=482 $[M+H]^+$.

Finally, compound 25B (13 mg, 0.027 mmol) was converted to compound 386 (9.7 mg, 78%) as a white solid. LC-MS: $t_R$=1.382 min in 3 min chromatography, MS (ESI) m/z=465 $[M+H]^+$. $^1$H NMR ($CD_3OD$ 400 MHz): δ 8.95 (s, 1H), 7.90, (s, 1H), 7.20 (d, J=7.6 Hz, 1H), 7.11 (d, J=7.6 Hz, 1H), 6.74 (s, 1H), 4.98 (s, 2H), 3.33 (s, 3H), 3.11 (m, 2H), 3.03 (d, J=15.2 Hz, 1H), 2.66 (t, J=7.2 Hz, 2H), 1.80-2.00 (m, 3H), 1.15-1.50 (m, 7H), 0.65 (m, 1H), 0.40 (m, 2H), 0.01 (m, 2H).

Example 329

Synthesis of Compound 387

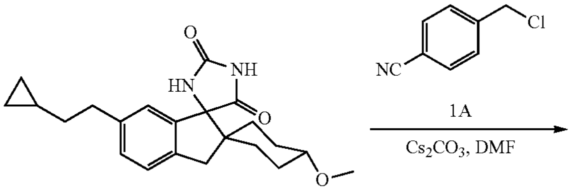

1

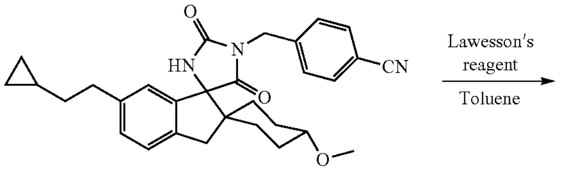

2

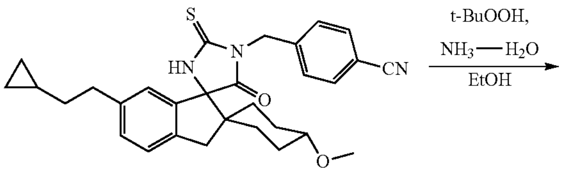

3

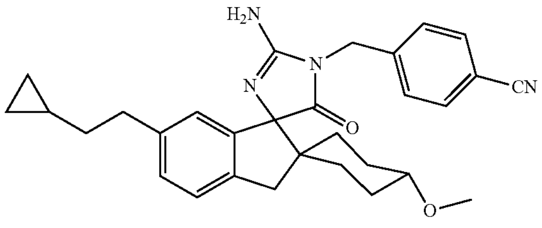

387

According to a similar synthesis of compound 296, compound 1 (50 mg, 0.14 mmol) was alkylated with compound 1A (23 mg, 0.149 mmol) to give compound 2 (20 mg, 31%) as a white solid.

Compound 2 (20 mg, 0.041 mmol) was then reacted with Lawesson's Reagent (18 mg, 0.046 mmol) in anhydrous toluene (2.5 mL) to give the crude product 3 (25 mg), which was converted to compound 387 (2.5 mg, 10%) as a white solid. LC-MS: $t_R$=1.008 min in 2 min chromatography, MS (ESI) m/z 483.2[M+H]$^+$. $^1$H NMR ($CD_3OD$ 400 MHz): δ 7.77 (d, J=6.4 Hz, 2H), 7.49 (d, J=6.4 Hz, 2H), 7.27 (d, J=7.6 Hz, 1H), 7.22 (d, J=7.6 Hz, 1H), 7.00 (s, 1H), 4.92 (m, 2H), 3.34 (s, 3H), 3.16 (m, 3H), 2.72 (t, J=7.6 Hz, 2H), 2.00 (m, 2H), 1.74 (m, 1H), 1.48 (m, 7H), 0.62 (m, 1H), 0.39 (m, 2H), 0.00 (m, 2H).

Example 330

Synthesis of Compound 388

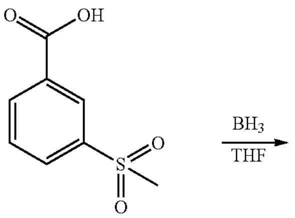

50

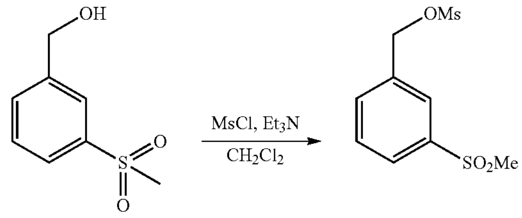

51

52

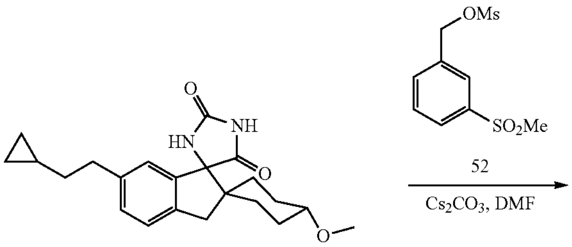

1a

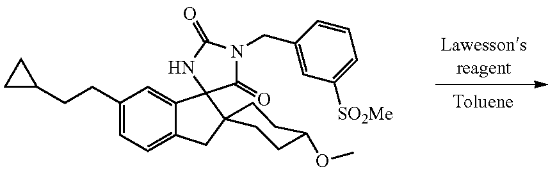

53

-continued

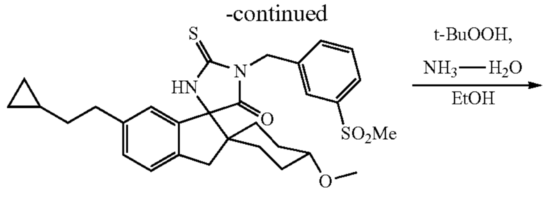

53A

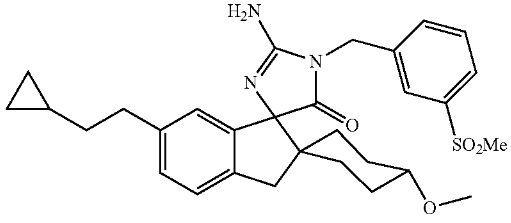

388

Procedure for Preparation of Compound 51

A flask equipped with a nitrogen balloon was charged with 3-methanesulfonyl-benzoic acid (0.50 g, 2.5 mmol) and anhydrous THF (10 mL). The mixture was cooled down to 0° C. with an ice water bath. A complex of $BH_3$-THF (3.0 mL, 3.0 mmol, 1 M in THF) was added with stirring at 0° C. slowly and the mixture was warmed to ambient temperature, then stirred at ambient temperature overnight. The mixture was quenched by additing methanol (10 mL) carefully. The solvent was removed by evaporation in vacuo, the residue was dissolved in ethyl acetate (100 mL). The mixture was washed with 1N NaOH aqueous solution (30 mL), brine (30 mL×2) in turn. The separated organic layer was dried over $Na_2SO_4$, filtered and concentrated to give crude compound 51 (0.25 g, 50% crude yield) as a colorless oil, which was used directly in next step without purification.

Procedure for Preparation of Compound 52

To a solution of crude compound 51 (25 mg, 1.30 mmol) and $Et_3N$ (0.40 g, 3.95 mmol) in $CH_2Cl_2$ (10 mL) was added Methane sulfonyl chloride (400 mg, 3.49 mmol) via a syringe slowly with stirring. After addition, the reaction mixture was stirred at ambient temperature overnight. The reaction was quenched by addition 30 mL brine with stirring. The mixture was separated and the aqueous layer was extracted with $CH_2Cl_2$ (10 mL×2). The combined organic layers were washed with brine (10 mL×2), dried over $Na_2SO_4$, filtered and concentrated in vacuo to give the crude product, which was purified by preparative TLC on silica gel eluting with petroleum ether: ethyl acetate=2:1 to give compound 52 (100 mg, 29%) as a pale yellow oil.

Procedure for Preparation of Compound 388

According to a similar synthesis of compound 296, compound 1A (50 mg, 0.14 mmol) was alkylated with compound 52 give compound 53 (34 mg, 45%) as a white solid. $^1$H NMR ($CDCl_3$ variant 400): δ 7.89 (s, 1H), 7.87 (dd, J=1.2, 7.6 Hz, 1H), 7.61 (d, J=8.0 Hz, 1H), 7.14 (dd, J=1.6, 7.6 Hz, 1H), 7.20 (d, J=7.6 Hz, 1H), 6.89 (s, 1H), 6.06 (m, 1H), 4.73 (s, 2H), 3.36 (s, 3H), 3.14 (m, 2H), 3.03 (m, 4H), 2.65 (td, J=2.8, 7.4 Hz, 2H), 1.80-2.10 (m, 3H), 1.20-1.50 (m, 7H), 0.65 (m, 1H), 0.40 (m, 2H), 0.01 (m, 2H).

Compound 53 (31 mg, 0.069 mmol) was then reacted with Lawesson's reagent to give compound 53A (27 mg, 77%) as a white solid. LC-MS: $t_R$=1.245 min in 2 min chromatography, MS (ESI) m/z=521 (M-31), 575 (M+23).

Finally, compound 53A (27 mg, 0.027 mmol) was converted to compound 388 (14.9 mg, 57%) as a white solid. LC-MS: $t_R$=1.382 min in 3 min chromatography, MS (ESI) m/z=465 $[M+H]^+$. $^1$H NMR ($CD_3OD$ 400 MHz): δ 7.91 (d, J=8.0 Hz, 1H), 7.87, (s, 1H), 7.60-7.70 (m, 2H), 7.22 (d, J=8.0 Hz, 1H), 7.14 (d, J=7.6 Hz, 1H), 6.90 (s, 1H), 4.89 (m, 2H), 3.37 (s, 3H), 3.20-3.30 (m, 4H), 3.071 (m, 2H), 2.74 (m, 2H), 1.95-2.10 (m, 2H), 1.70-1.80 (m, 1H), 1.20-1.60 (m, 7H), 0.65 (m, 1H), 0.40 (m, 2H), 0.01 (m, 2H).

Example 331

Synthesis of Compound 389

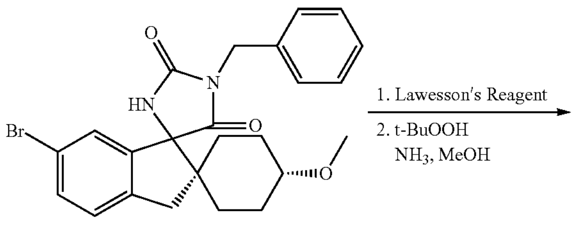

1

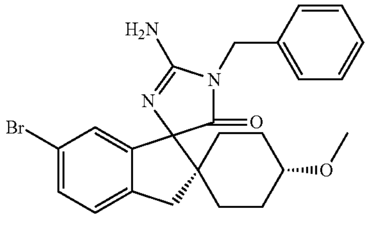

389

According to a similar synthesis of compound 291, compound 1 afforded compound 389 (25 mg) as a TFA salt. LC-MS $t_R$=1.45 min in 3 min chromatography, MS (ESI) m/z 468 $[M+H]^+$. $^1$H NMR ($CD_3OD$, 400 MHz): δ 7.76 (m, 1H), 7.74-7.28 (m, 7H), 4.90 (m, 2H), 3.28 (s, 3H), 3.20-3.04 (m, 3H), 2.04-1.92 (m, 2H), 1.76 (m, 1H), 1.42 (m, 3H), 1.24 (m, 2H).

Example 332

Synthesis of Compounds 390 and 391

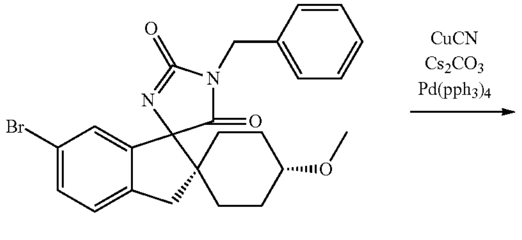

1

-continued

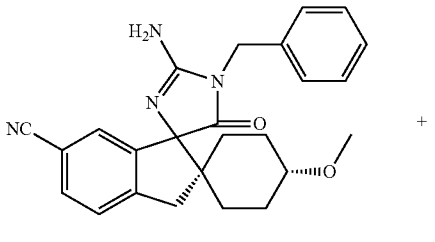

390

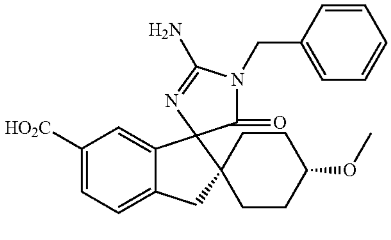

391

To a solution of compound 1 (10 mg, 0.021 mmol) in DMF (0.5 mL) in a 10 mL CEM microwave tube, there was add CuCN (excess), $Cs_2CO_3$ (2 eq), and $Pd(pph_3)_4$ (cat. amount). The resulting mixture was heated in a CEM microwave reactor at 160° C. for 180 min. The mixture was filtered, and the filtration was loaded directly to a HPLC to afford compound 390 (5.9 mg, 52%) as a TFA salt. LC-MS $t_R$=1.35 min in 3 min chromatography, MS (ESI) m/z 415 $[M+H]^+$. $^1$H NMR ($CD_3OD$, 400 MHz): δ 7.76 (m, 1H), 7.66 (m, 1H), 7.56 (m, 1H), 7.42-7.32 (m, 5H), 4.90 (m, 2H), 3.28 (s, 3H), 3.24-3.06 (m, 3H), 1.98 (m, 2H), 1.76 (m, 1H), 1.46-1.20 (m, 5H); and compound 391 (2.9 mg, 25%) as a by-product, also a TFA salt. LC-MS $t_R$=1.19 min in 3 min chromatography, MS (ESI) m/z 433 $[M]^+$. $^1$H NMR ($CD_3OD$, 400 MHz): δ 7.90 (m, 1H), 7.72 (m, 1H), 7.48 (m, 1H), 7.42-7.30 (m, 5H), 4.90 (m, 2H), 3.32 (s, 3H), 3.20 (m, 3H), 1.98 (m, 2H), 1.78 (m, 1H), 1.42-1.24 (m, 5H).

Example 333

Synthesis of Compound 392

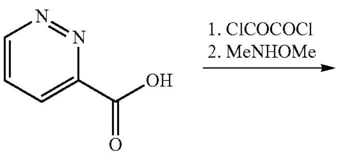

1

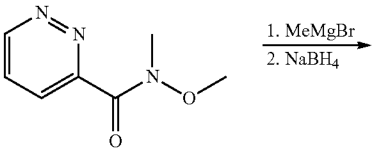

2

-continued

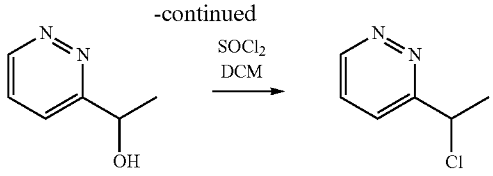

3 4

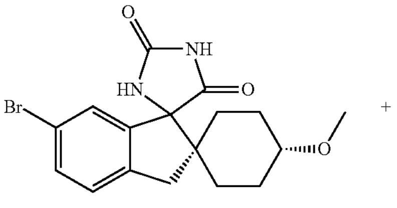

5

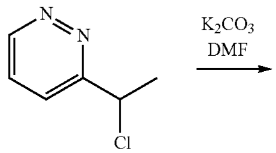

4

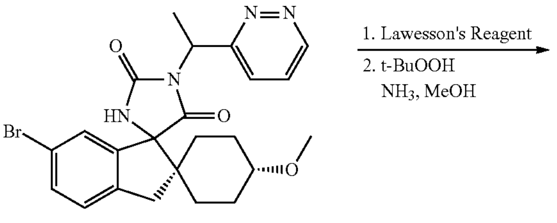

6

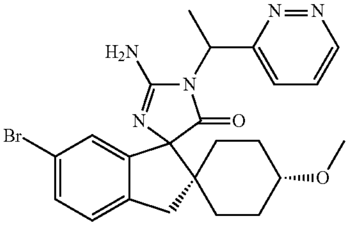

392

Step 1. Synthesis of N-methoxy-N-methylpyridazine-3-carboxamide (2)

To a solution of pyridazine-3-carboxylic acid (1) (0.44 g, 3.47 mmol) in DCM (10 mL), there was added oxalyl chloride (0.67 g, 5.2 mmol) followed by 2 drops of DMF. The reaction was stirred at room temperature for 1 hr, and the solvent was removed in vacuum to give acid chloride, which was used for the next step without purification.

To the above product there was added $K_2CO_3$ (1.44 g, 10.4 mmol) and N,O-dimethylhydroxylamine hydrochloride (0.69 g, 5.2 mmol), followed by MeCN (10 mL). The resulting mixture was stirred at room temperature overnight, filtered through a cotton ball, and the filtration was concentrated to give N-methoxy-N-methylpyridazine-3-carboxamide (2) (0.41 g, 71% for two steps).

Step 2. Synthesis of 1-(pyridazin-3-yl)ethanol (3)

To a solution of N-methoxy-N-methylpyridazine-3-carboxamide (2) (0.41 g, 2.45 mmol) in anhydrous THF (8 mL)

at −78° C., there was added methyl Grignard reagent (1.4 N in Toluene/THF (75:25), 3.5 mL). After finishing addition, the reaction was stirred at the same temperature for another 1 hr, quenched with MeOH, and warmed up to 0° C.

To the above solution there was added $NaBH_4$ (excess), and resulting mixture was stirred at 0° C. for 30 min, warmed to room temperature, quenched with acetone. After adding silica gel (5 g), the solvent was removed, and the residue was solid loaded to column for purification. The column was eluented with 0 to 10% MeOH in DCM to give 1-(pyridazin-3-yl) ethanol (3) (0.19 g, 63% for 2 steps).

Step 3. Synthesis of 3-(1-chloroethyl)pyridazine (4)

To a solution of 1-(pyridazin-3-yl)ethanol (3) (50 mg, 0.40 mmol) in DCM (1 mL), there was added sulfurous dichloride (0.2 mL). The resulting solution was stirred at room temperature for 3 hrs. Solvent was removed to give 3-(1-chloroethyl) pyridazine (4), which was used for the next step without purification.

Step 4. Synthesis of compound 6

To a solution of hydantoin 5 (53.0 mg, 0.14 mmol) in DMF (0.2 mL0, there was added $K_2CO_3$ (excess) followed by 3-(1-chloroethyl)pyridazine (4) (0.2 mmol) in DMF (0.25 mL), the resulting mixture was heated at 70° C. for 4 hrs, cooled to room temperature, added water (5 mL), and extracted with DCM (5 mL×4). The combined organic layers were washed with brine, dried over $Na_2SO_4$, and the solvent was removed to give compound 6 (60.7 mg, 89%), LC-MS $t_R$=1.45 min in 3 min chromatography, MS (ESI) m/z 4875 $[M]^+$.

Step 5. Synthesis of Compound 392

According to a similar synthesis of compound 291, compound 6 (30.4 mg, 0.06 mmol) afforded compound 392 (11.0 mg, 36%) as a TFA salt. LC-MS $t_R$=1.21 min in 3 min chromatography, MS (ESI) m/z 484 $[M]^+$. $^1H$ NMR ($CD_3OD$, 400 MHz): δ 9.18 (m, 1H), 7.90 (m, H), 7.78 (m, 1H), 7.46 (m, 2H), 7.24 (m, 1H), 5.78 (m, 1H), 3.34 (s, 3H), 3.24-2.86 (m, 3H), 2.10-1.80 (m, 5H), 1.60 (m, 1H), 1.42-1.24 (m, 5H).

Example 334

Synthesis of Compound 393

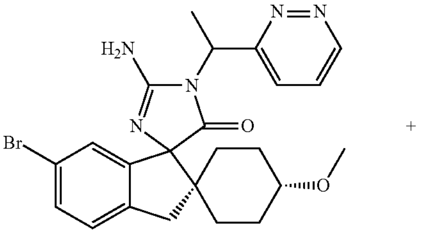

392

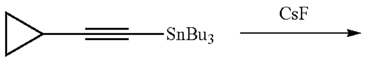

-continued

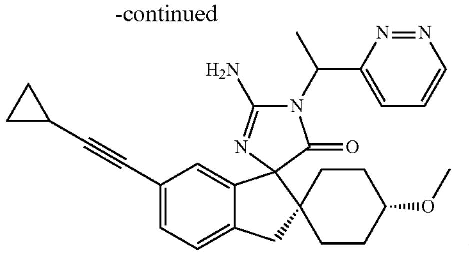

393

To a 10 mL CEM microwave there was added compound 392 (7 mg, 0.01 mmol), PdCl2(pph3)2 (cat.) and CsF (3 eq), there solid was degassed followed by blowing $N_2$ through the tube. Toluene (0.5 mL) was added, and the system was degassed again before tributyl(cyclopropylethynyl)stannane (exaee) was added. The resulting mixture was heated in a CEM microwave reactor at 120° C. for 30 min, filtered, solvent was removed, and the residuea was purified on HPLC to afford compound 393 (3.4 mg, 52%) as a TFA salt. LC-MS $t_R$=1.39 min in 3 min chromatography, MS (ESI) m/z 470 $[M+H]^+$. $^1$H NMR ($CD_3OD$, 400 MHz): δ 9.16 (m, 1H), 7.90 (m, H), 7.78 (m, 1H), 7.32-7.20 (m, 3H), 5.78 (m, 1H), 3.36 (s, 3H), 3.22-2.94 (m, 3H), 2.08-1.80 (m, 6H), 1.60-1.20 (m, 6H), 0.86 (d, 2H), 0.72 (m, 2H).

Example I-7

Synthesis of 6'-bromo-5,6,8,9-tetrahydrospiro[benzo[7]annulene-7,2'-inden]-1'(3'H)-one (4)

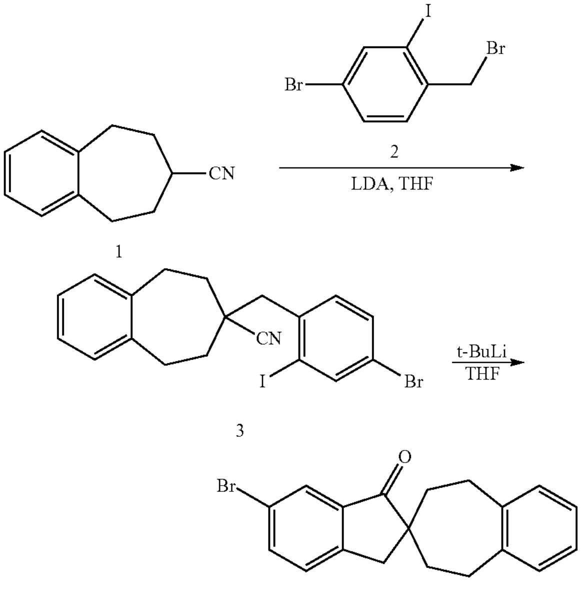

Procedure for Preparation of Compound 3

To a solution of LDA (23.4 mL, 42.1 mmol, 1.8 M in THF) in THF (150 mL) was added slowly a solution of compound 1 (3.6 g, 21.05 mmol) in THF (77 mL) at −60° C. under a $N_2$ atmosphere. After being stirred at −60° C. for 1 h, a solution of compound 2 (7.05 g, 18.9 mmol)) in THF (23 mL) was added slowly to the above solution. The resulting mixture was stirred at −60° C. for 2 h. The reaction mixture was quenched with water (15 mL). The aqueous layer was extracted with EtOAc (3×40 mL). The combined organic layers were washed with brine (20 mL), dried over $Na_2SO_4$ and concentrated under reduced pressure to dryness. The residue was purified by column chromatography on silica gel (petroleum: ethyl acetate, 10:1) to give compound 3 (2.5 g, yield 26%) as a yellow solid.

Procedure for Preparation of Compound 4

A flame dried 100 mL RBF was charged with compound 3 (2.11 g, 4.5 mmol) and anhydrous THF (80 mL) under $N_2$ atmosphere. The resulting solution was stirred and chilled to −70° C., and t-BuLi (1.3 M, in hexane 6.95 mL, 9 mmol, 2 eq.) was added dropwise. Deep red was observed during the addition. The reaction was stirred another 1 h after the addition. The reaction was quenched with MeOH (0.4 mL), and followed by aq. HCl solution (2 M, 8 mL). The resulting solution was concentrated to remove organic solvent. The residue was stirred in 0.5 M aq. HCl solution (40 mL). The suspension was heated to reflux (oil bath 105° C.). The reaction was cooled down to room temperature and filter. The cake was washed with $H_2O$. The light yellow solid was collected and co-evaporated with MeOH two times to remove water to give crude product, which was purified by chromatography to give 6'-bromo-5,6,8,9-tetrahydrospiro[benzo[7]annulene-7,2'-inden]-1'(3'H)-one (4) (450 mg, yield 35%) as a white solid. $^1$H NMR ($CDCl_3$ 400 MHz): δ 7.80-8.01 (m, 1H), 7.63-7.66 (m, 1H), 7.30-7.32 (m, 1H), 7.00-7.18 (m, 4H), 3.10 (s, 2H), 2.91-2.97 (m, 2H), 2.81 (brs, 2H), 1.78-1.85 (m, 2H), 1.57-1.62 (m, 2H).

Example I-8

Synthesis of hydantoin 5-Method 1

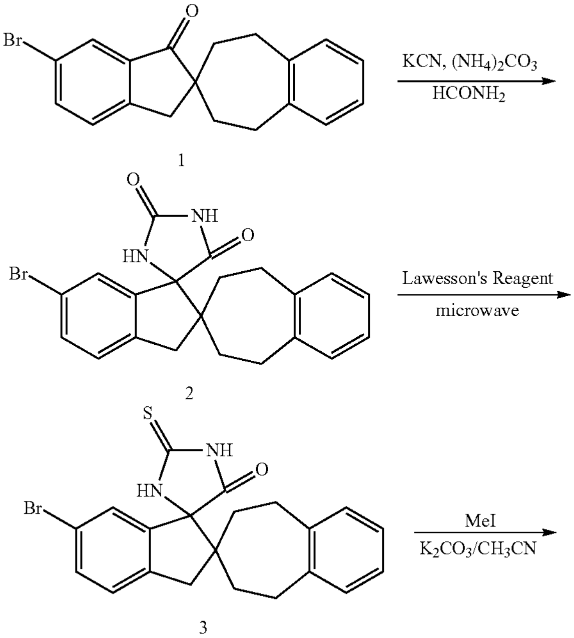

-continued

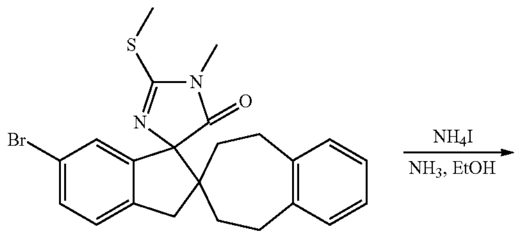

4

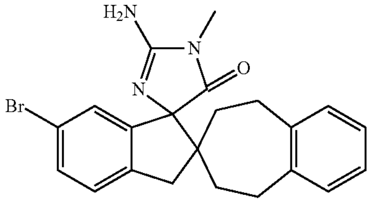

5

Procedure for Preparation of Compound 2

A steel autoclave was charged with a mixture of compound 1 (1 g, 2.94 mmol), KCN (573 mg, 8.82 mmol) and $(NH_4)_2CO_3$ (2.82 g, 29.4 mmol) in formamide (30 mL). The mixture was stirred at 110° C. for 72 h, cooled to room temperature, and poured into ice (20 g). After acidification with conc. HCl solution (10 mL), the resulting mixture was filtered, and the filter cake was dissolved in ethyl acetate (100 mL) and washed with water (2×50 mL). The organic layer was dried over $Na_2SO_4$ and concentrated in vacuo to give compound 2 (80 mg, yield 8%) as a yellow solid.

Procedure for Preparation of Compound 3

A suspension of compound 2 (20 mg, 0.049 mmol) and Lawesson's Reagent (20 mg, 0.049 mmol) in anhydrous dioxane (1 mL) was stirred at 150° C. for 35 min in a CEM microware reactor. The mixture was concentrated in vacuo, and the residue was purified by prep-TLC to give compound 3 (20 mg, 96%) as a yellow solid.

Procedure for Preparation of Compound 4

To a solution of compound 3 (20 mg, 0.047 mmol) in $CH_3CN$ (2 mL) was added MeI (13.3 mg, 0.094 mmol) and $K_2CO_3$ (26 mg, 0.188 mmol). After being stirred at 60° C. for 10 min in microware, additional MeI (13.3 mg, 0.094 mmol) was added. The reaction mixture was stirred at 80° C. for 10 min in microware, concentrated in vacuo to give compound 4 (25 mg, 100%) as a yellow solid.

Procedure for Preparation of Compound 5

A solution of compound 4 (40 mg, 0.088 mmol) and $NH_4I$ (127 mg, 0.088 mmol) in $NH_3$/EtOH (5.0 N, 2 mL) was stirred at 120° C. in a microwave reactor for 3 h. The reaction mixture was concentrated under reduced pressure. The residue was added $CH_2Cl_2$ (15 mL), and stirred for 30 min. The mixture was filtered, and the filtrate was concentrated in vacuo to give compound 5 (35 mg, yield 92%) as a yellow solid.

Example I-9

Synthesis of Hydantoin 5-Method 2

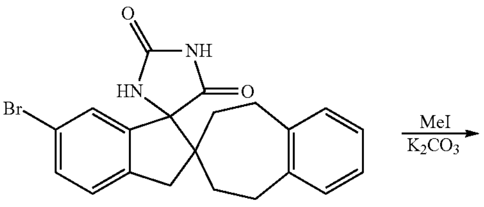

2

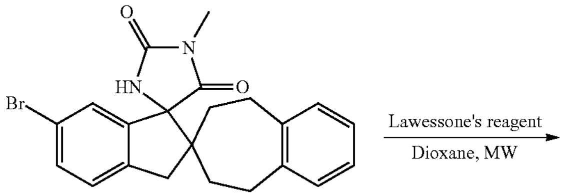

3

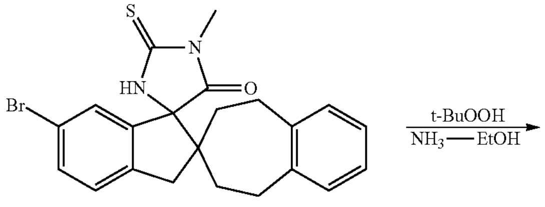

4

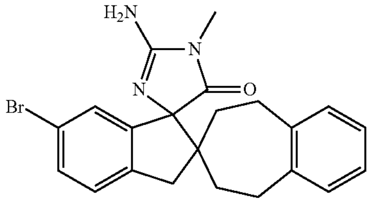

5

Procedure for Preparation of Compound 3

To a solution of compound 2 (500 mg, 0.86 mmol) in DMF (10 mL) was added $K_2CO_3$ (510 mg, 3.72 mmol) and MeI (350 mg, 0.86 mmol). The mixture was stirred at room temperature for 2 h. The mixture was added water (50 mL), the precipitate was collected by filtration to collected the solid, which was dried in vacuo a crude compound 3 (300 mg, 58%) as a white solid, which was used directly in next step without purification.

Procedure for Preparation of Compound 4

A mixture of compound 3 (300 mg, 0.42 mmol) and Lawesson'reagent (186 mg, 0.46 mmol) in dioxane (10 mL) was heated at 150° C. for 30 min in a CEM microwave reactor. The mixture was cooled, and concentrated in vacuo. The residue was purified by preparative TLC (petroleum ether: ethyl acetate=3:1) to give compound 4 (180 mg, 58%).

Procedure for Preparation of Compound 5

To a solution of compound 4 (500 mg, 1.14 mmol) in a mixture of MeOH (30 mL) and $NH_3$-EtOH (6 mL) was added t-BuOOH (2 mL, 22.8 mmol, 65% in water). The mixture was stirred at room temperature overnight, and concentrated. Water (25 mL) was added, the mixture was extracted with EtOAc (3×20 mL). The combined organic layers were dried over $Na_2SO_4$ and concentrated to give the residue which was purified by RP-HPLC to give compound 5 (250 mg, 52%) as a white solid.

Example 335

Synthesis of Compound 394

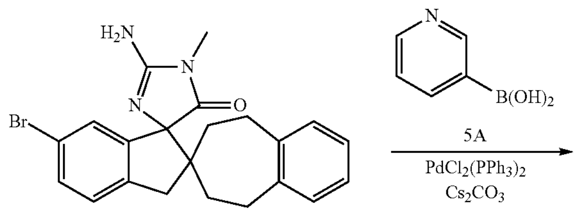

5

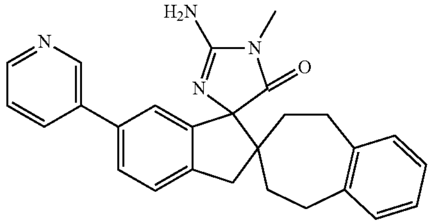

394

A solution containing hydantoin 5 (25 mg, 0.057 mmol) and compound 5A (11 mg, 0.089 mmol) in dioxane (1.5 mL), and aqueous $Cs_2CO_3$ (2 M, 0.4 mL) was deoxygenated by bubbling a stream of nitrogen through the reaction mixture for 5 min. Then, $PdCl_2(PPh_3)_2$ (4 mg) was added. The reaction vial was sealed and placed into CEM microwave reactor and irradiated at 120° C. for 15 min. After being cooled to room temperature, the mixture was diluted with EtOAc and filtered through a short Celite pad. The solution was concentrated in vacuo and the residue was purified by preparative TLC ($CH_2Cl_2$:MeOH, 10:1) and HPLC to give compound 394 (2.8 mg, yield 11%) as a white solid. LC-MS $t_R$=0.863 min in 2 min chromatography, MS (ESI) m/z 423 $[M+H]^+$; $^1$H NMR ($CD_3OD$ 400 MHz): δ 8.77 (s, 1H), 8.50 (d, J=1.2 Hz, 1H), 8.08 (d, J=8.4 Hz, 1H), 7.60-7.63 (m, 1H), 7.50-7.52 (m, 2H), 7.50 (s, 1H), 7.07-7.08 (m, 4H), 3.23-3.33 (m, 2H), 3.07-3.11

(m, 1H), 3.05 (s, 3H), 3.95-3.04 (m, 1H), 2.69-2.73 (m, 1H), 2.55-2.67 (m, 1H), 2.14-2.19 (m, 1H); 1.68 (s, 2H), 1.29-1.35 (m, 1H).

Example 336

Synthesis of Compounds 395, 396 and 397

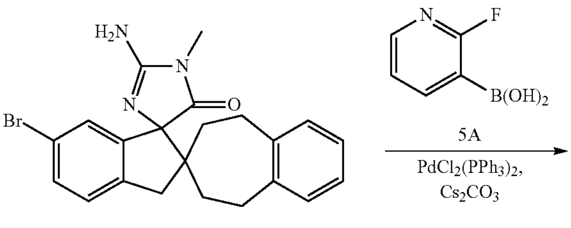

5

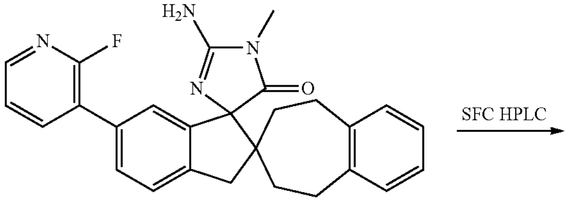

395

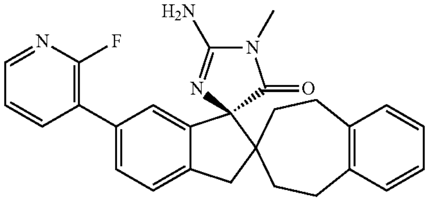

+

396

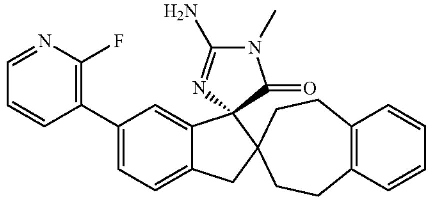

397

Procedure for Preparation of Compound 395

According to a similar synthesis of compound 394, hydantoin 5 (350 mg, 0.62 mmol), 1,4-dioxane (12 mL) was reacted with compound 5A (175 mg, 1.24 mmol) to give compound 395 (80 mg, 31%) as a white solid. LC-MS $t_R$=0.921 min in 2 min chromatography, MS (ESI) m/z 441 $[M+H]^+$. $^1$H NMR ($CD_3OD$ 400 MHz): δ 8.22 (d, J=4.8 Hz, 1H), 8.06 (m, 1H), 7.66 (d, J=8.0 Hz, 1H), 7.59 (d, J=8.0 Hz, 1H), 7.48 (s, 1H), 7.41 (m, 1H), 7.11 (m, 4H), 3.60 (m, 1H), 3.40 (m, 1H), 3.19 (s, 3H), 3.14 (m, 1H), 2.77 (m, 1H), 2.76 (m, 1H), 2.64 (m, 1H), 2.22 (m, 1H), 1.78 (m, 1H), 1.47 (m, 2H).

Procedure for Preparation of Compounds 396 and 397

Compound 395 (43 mg) was purified by preparative SFC to give two enantiomers of compound 396 (16 mg, 38%), LC- MS $t_R$=1.033 min in 2 min chromatography, MS (ESI) m/z 441 $[M+H]^+$. SFC: $t_R$=2.630 min in 4 min chromatography, ee=100%. $^1$H NMR ($CD_3OD$ 400 MHz): δ 8.20 (d, J=4.8 Hz, 1H), 8.07 (m, 1H), 7.66 (d, J=8.0 Hz, 1H), 7.59 (d, J=8.0 Hz, 1H), 7.48 (s, 1H), 7.41 (m, 1H), 7.11 (m, 4H), 3.60 (m, 1H), 3.40 (m, 1H), 3.19 (s, 3H), 3.14 (m, 1H), 2.77 (m, 1H), 2.76 (m, 1H), 2.64 (m, 1H), 2.22 (m, 1H), 1.78 (m, 1H), 1.48 (m, 2H); and compound 397 (19 mg, 44%) as a white solid. LC-MS $t_R$=1.028 min in 2 min chromatography, MS (ESI) m/z 441 $[M+H]^+$. SFC: $t_R$=3.1580 min in 4 min chromatography, ee=98.7%. $^1$H NMR ($CD_3OD$ 400 MHz): δ 8.20 (d, J=4.4 Hz, 1H), 8.07 (m, 1H), 7.66 (d, J=8.0 Hz, 1H), 7.59 (d, J=8.0 Hz, 1H), 7.48 (s, 1H), 7.41 (m, 1H), 7.11 (m, 4H), 3.60 (m, 1H), 3.40 (m, 1H), 3.19 (s, 3H), 3.14 (m, 1H), 2.77 (m, 1H), 2.76 (m, 1H), 2.64 (m, 1H), 2.22 (m, 1H), 1.78 (m, 1H), 1.48 (m, 2H).

Example 337

Synthesis of Compound 398

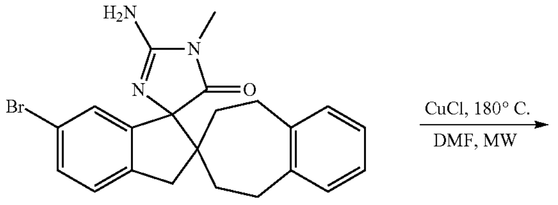

5

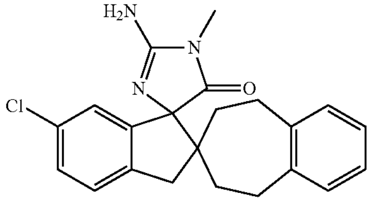

398

To a solution of compound 5 (20 mg, 0.047 mmol) in DMF (4 mL) was added CuCl (64 mg, 0.85 mmol), the resulting mixture was heated at 180° C. in a CEM tube under microwave reactor for 0.5 h. After cooling, the mixture was concentrated under vacuum to give the residue, which was purified by preparative-basic HPLC to give compound 398 (8.4 mg, 31%) as a white solid. LC-MS $t_R$=1.062 min in 2 min chromatography, MS (ESI) m/z 380.1 $[M+H]^+$. $^1$H NMR ($CD_3OD$ 400 MHz): δ 7.28-7.33 (m, 2H), 7.19 (s, 1H), 6.98-6.70 (m, 4H), 3.38-3.42 (d, J=15.6 Hz, 1H), 3.14-3.21 (m, 1H), 2.98-3.07 (m, 3H), 2.81-2.88 (t, J=14.0 Hz, 1H), 2.61-2.65 (m, 1H), 2.56 (s, 1H), 2.47-2.52 (m, 1H), 2.02-2.08 (m, 1H), 1.58-1.63 (m, 1H), 1.19-1.37 (m, 2H).

Example 338

Synthesis of Compound 399

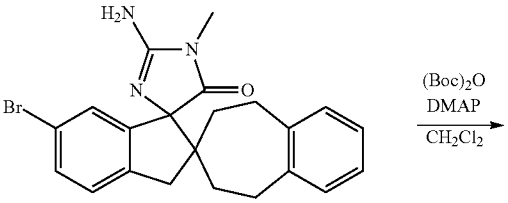

7

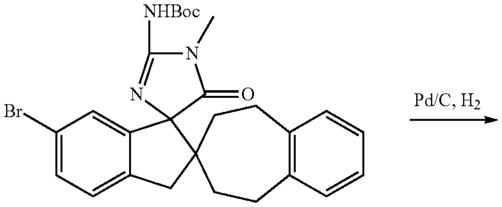

8

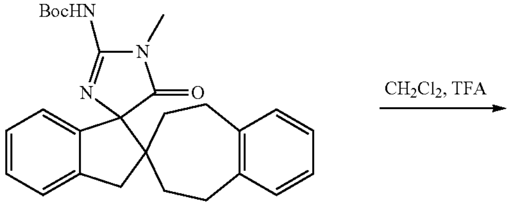

9

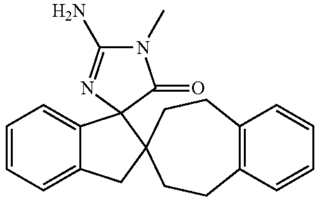

399

Procedure for Preparation of Compound 8

To a solution of compound 7 (45 mg, 0.1 mmol) and DMAP (25 mg, 0.2 mmol) in $CH_2Cl_2$ (8 mL) was added $(Boc)_2O$ (45 mg, 0.2 mmol). The reaction mixture was stirred at 25° C. for 2 h. The mixture was concentrated in vacuo to give the residue, which was purified by preparative TLC (eluent:petroleum ether:ethyl acetate=4:1) to give compound 8 (50 mg, 95%) as a white solid.

Procedure for Preparation of Compound 9

A solution of compound 8 (20 mg, 0.038 mmol) and Pd/C (4 mg) in MeOH (5 mL) was stirred under $H_2$ atmosphere (10 Psi) at 25° C. for 2 h. The mixture was filtered and the filtrate was concentrated in vacuo to give crude compound 9 (18 mg, crude yield 100%), which was used directly to next step.

Procedure for Preparation of Compound 399

To a solution of compound 9 (18 mg, 0.046 mmol) in $CH_2Cl_2$ (8 mL) was added TFA (1 mL) dropwise. The reaction mixture was stirred at 25° C. for 2 h. The mixture was concentrated in vacuo to give the residue, which was purified by preparative RP-HPLC to give compound 399 (8.8 mg, 50%) as a white solid. LCMS: $t_R$=1.69 min in 3 min chromatography, MS (ESI) m/z 346.2 $[M+H]^+$. $^1H$ NMR ($CD_3OD$ 400 MHz): δ 7.34-7.46 (m, 2H), 7.28-7.32 (m, 1H), 7.18-7.21 (d, J=7.2 Hz, 1H), 7.04 (m, 4H), 3.50-3.55 (d, J=15.6 Hz, 1H), 3.29-3.31 (m, 1H), 3.18 (s, 3H), 3.11-3.14 (m, 1H), 2.95-3.02 (m, 1H), 2.71-2.77 (m, 1H), 2.57-2.63 (m, 1H), 2.18-2.22 (m, 1H), 1.71-1.76 (m, 1H), 1.38-1.48 (m, 2H).

Example 339

Synthesis of Compound 400

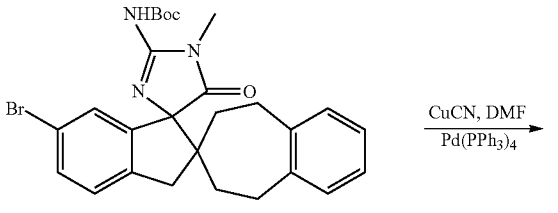

8

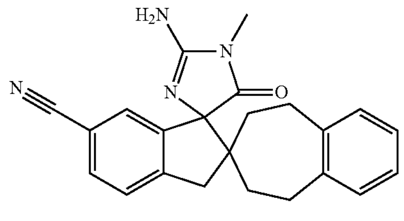

400

A steel autoclave was charged with a mixture of compound 8 (30 mg, 0.057 mmol), CuCN (14 mg, 0.16 mmol), $Pd(PPh_3)_4$ (6 mg, 0.0052 mmol) and DMF (3 mL). The mixture was heated at 120° C. for 10 h. The mixture was filtered, the filtrate was concentrated in vacuo to give the residue, which was purified by preparative RP-HPLC to afford compound 400 (5.8 mg, 15%) as a white solid; LCMS: $t_R$=1.65 min in 3 min chromatography, MS (ESI) m/z 371.2 $[M+H]^+$; $^1H$ NMR ($CD_3OD$ 400 MHz): δ 7.79-7.81 (d, J=7.6 Hz, 1H), 7.69 (s, 1H), 7.64-7.66 (d, J=8.0 Hz, 1H), 7.11 (s, 4H), 3.61-3.65 (d, J=12.4, Hz, 1H), 3.40 (m, 1H), 3.19 (s, 3H), 3.09-3.16 (m, 1H), 2.94-3.01 (m, 1H), 2.73-2.78 (m, 1H), 2.58-2.64 (m, 1H), 1.64-1.69 (m, 1H), 1.40-1.50 (m, 1H).

Example 340

Synthesis of Compound 401

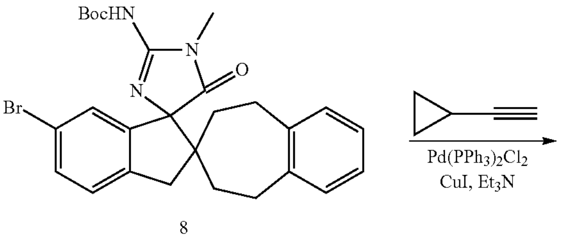

8

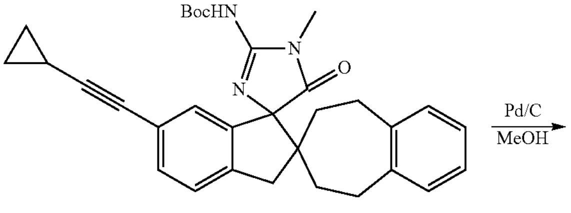

8A

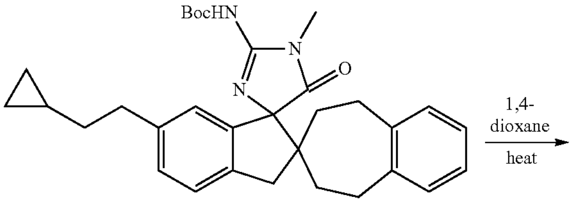

8B

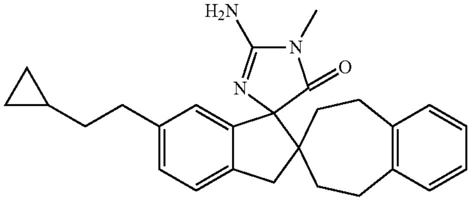

401

Procedure for Preparation of Compound 8A

An oven dried three-necked round bottom flask equipped with condenser was charged with compound 8 (66 mg, 0.126 mmol), $Et_3N$ (4 mL) and $Et_2NH$ (0.8 mL) under $N_2$ atmosphere. To this solution was added CuI (1.2 mg, 0.0063 mmol) and $PdCl_2(PPh_3)_2$ (4.4 mg, 0.0063 mmol). The system was degassed once again, then cyclopropyl acetylene (0.8 mL, excess) was added and the mixture was stirred at 60° C. (oil bath) overnight. The solvent was evaporated in vacuo and the residue was partitioned with ethyl acetate (20 mL) and water (10 mL). The aqueous layer was extracted with ethyl acetate (2×30 mL), the combined organic layers were washed with brine (30 mL), dried over $Na_2SO_4$, and concentrated under reduced pressure to dryness. The crude product was purified by preparative TLC (petroleum:ethyl acetate=3:1) to give compound 8A (50 mg, 78%) as a yellow solid.

Procedure for Preparation of Compound 8B

To a solution of compound 8A (25 mg, 0.049 mmol) in MeOH (3 mL) was added Pd/C (5 mg), the mixture was stirred at room temperature under $H_2$ atmosphere (1 atm) for 2 h The reaction mixture was filtered through a Celite pad, the filtrate was concentrated in vacuo to give the residue, which was purified by preparative TLC (petroleum:ethyl acetate=3:1) to give compound 8A (8 mg, 32%) as a white solid.

Procedure for Preparation of Compound 401

A solution of compound 4 (8 mg, 0.002 mmol) in 1,4-dioxane (1 mL) was heated at 120° C. in a microwave reactor for 15 min. The solvent was removed by evaporation in vacuo to yield the crude compound, which was purified by HPLC to give compound 401 (4.5 mg, 52%) as a white solid. LC-MS $t_R$=1.193 min in 2 min chromatography, MS (ESI) m/z 414 $[M+H]^+$; $^1$H-NMR ($CD_3OD$ 400 MHz): δ 7.30 (d, J=7.6 Hz, 1H), 7.22 (d, J=7.6 Hz, 1H), 7.06 (s, 4H), 6.99 (s, 1H), 3.45-3.50 (m, 1H), 3.23-3.32 (m, 1H), 3.33 (s, 3H), 2.86-3.10 (m, 2H), 2.67-2.71 (m, 3H), 2.54-2.59 (m, 1H), 2.11-2.16 (m, 1H), 1.68-1.71 (m, 1H), 1.27-1.48 (m, 4H); 0.67-0.68 (m, 1H), 0.38-0.40 (m, 2H), 0.01-0.03 (m, 2H).

Example 341

Synthesis of Compound 402

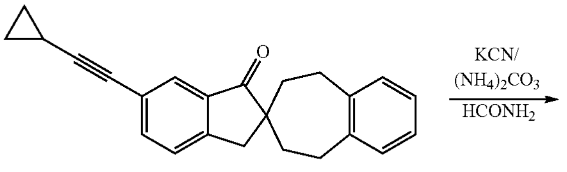

13

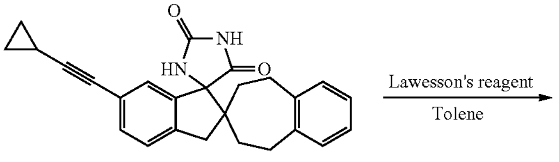

14

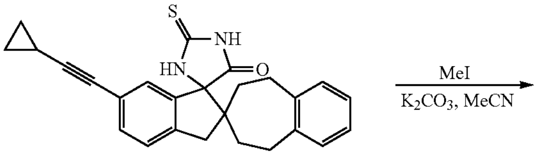

15

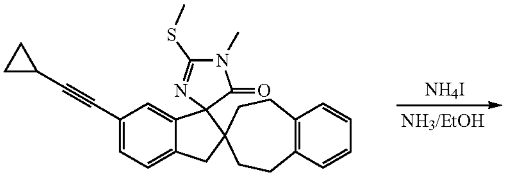

16

-continued

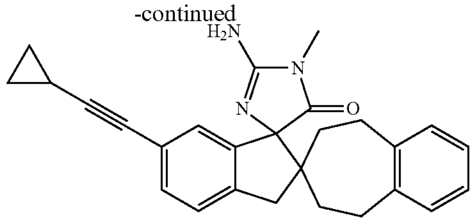

402

Procedure for Preparation of Compound 14

A steel autoclave was charged with a mixture of compound 13 (0.40 g, 1.2 mmol), KCN (0.15 g, 2.4 mmol) and $(NH_4)_2CO_3$ (1.0 g, 11.0 mmol) in Formamide (20 mL). The mixture was heated at 120° C. for 72 h. The reaction mixture was then cooled and poured into ice-water (200 mL). The mixture was extracted with ethyl acetate (3×100 mL), and the combined organic layers were washed with brine (2×100 mL). The separated organic phase was dried over $Na_2SO_4$ and concentrated in vacuo. The resulting residue was purified by preparative TLC eluting with petroleum ether:ethyl acetate=2:1 to give compound 14 (70 mg, 18%) as a yellow solid. LC-MS: $t_R$=1.40 min in 2 min chromatography, MS (ESI) m/z 397.1 $[M+H]^+$.

Procedure for Preparation of Compound 15

A sealed tube was charged with a mixture of compound 14 (55 mg, 14 mmol), Lawessons reagent (0.15 g, 0.37 mmol) in toluene (30 mL) was heated at 120° C. for 6 h. After cooling down, the precipitate was filtered off and washed with ethyl acetate (2×40 mL). The filtrate was concentrated in vacuo and the resulting residue was purified by preparative TLC eluting with petroleum ether:ethyl acetate (2:1) to give compound 15 (25 mg, 43%) as a yellow solid. LC-MS: $t_R$=2.21 min in 3 min chromatography, MS (ESI) m/z 413.1 $[M+H]^+$.

Procedure for Preparation of Compound 16

A mixture of compound 15 (25 mg, 0.061 mmol), iodomethane (20 mg, 0.14 mmol) and $K_2CO_3$ (50 mg, 0.36 mmol) in DMF (2 mL) was stirred at ambient temperature overnight. The reaction mixture was poured into brine (30 mL). The mixture was extracted with ethyl acetate (3×10 mL). The combined organic layers were washed with brine (2×10 mL). The separated organic phase was dried over $Na_2SO_4$ and concentrated in vacuo, the resulting residue was purified by preparative TLC eluting with petroleum ether:ethyl acetate (10:1) to give compound 16 (15 mg, 55%) as a yellow solid. LC-MS: $t_R$=2.25 min in 3 min chromatography, MS (ESI) m/z 441.1 $[M+H]^+$.

Procedure for Preparation of Compound 402

A sealed tube was charged with a mixture of compound 16 (15 mg, 0.034 mmol), $NH_4I$ (30 mg, 0.21 mmol) and a solution of $NH_3$ in ethanol (2 mL). The mixture was heated at 120° C. in a CEM microwave reactor for 3 h. After cooling down, the solvent was removed by evaporation in vacuo and the residue was purified by preparative RP-HPLC to give compound 402 (3.0 mg, 21%) with 99% purity as a white solid. LC-MS: $t_R$=1.89 min in 3 min chromatography, MS (ESI) m/z 410.2 $[M+H]^+$. $^1$H NMR: ($CD_3OD$ 400 MHz): δ 7.30-7.40 (s, 2H), 7.10-7.15 (s, 1H), 7.00-7.10 (s, 4H), 3.05-3.15 (s, 3H), 3.00-3.05 (m, 1H), 2.85-2.95 (m, 2H), 2.60-2.70 (m, 1H), 2.50-2.60 (m, 1H), 2.05-2.15 (m, 1H), 1.60-1.70 (m, 1H), 1.30-1.45 (m, 2H), 1.20-1.30 (m, 2H), 0.75-0.85 (m, 2H), 0.60-0.70 (m, 2H).

Example I-10

Synthesis of Intermediate Hydantoin 4

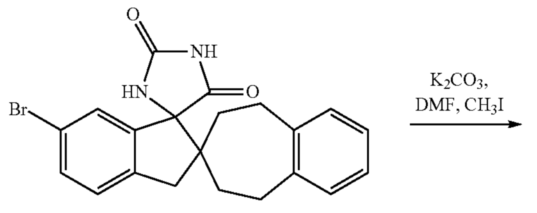

1

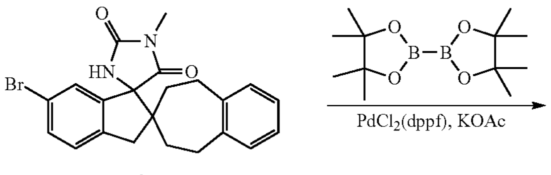

2

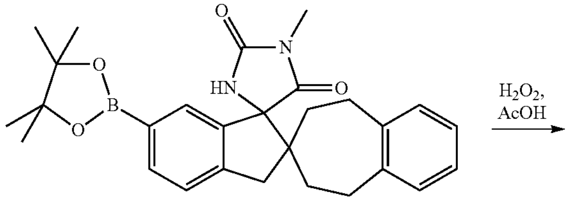

3

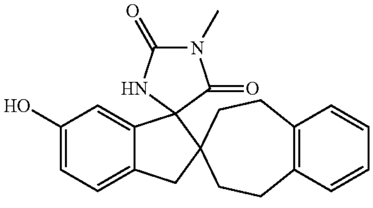

4

Procedure for Preparation of Compound 2

To a solution of compound 1 (200 mg, 0.49 mmol) in DMF (5 mL) was added $K_2CO_3$ (200 mg, 1.46 mmol) and $CH_3I$ (76 mg, 0.51 mmol). The reaction mixture was stirred at 30° C. for 10 h. The mixture was filtered and filtrate was concentrated in vacuo to give the residue, which was purified by preparative TLC (eluent:petroleum ether:ethyl acetate=2:1) to give compound 2 (175 mg, 85%) as a white solid.

Procedure for Preparation of Compound 3

A suspension of compound 2 (170 mg, 0.4 mmol), compound 2A (112 mg, 0.44 mmol), $PdCl_2(dppf)_2$ (50 mg, 0.08 mmol) and KOAc (118 mg, 1.2 mmol) in anhydrous 1,4-dioxane (6 mL) was heated at 100° C. for 60 min in a CEM microwave reactor. The mixture was concentrated in vacuo and the residue was purified by preparative TLC (eluent: petroleum ether:ethyl acetate=3:1) to give compound 3 (140 mg, 70%, 67% purity) as a yellow solid.

Procedure for Preparation of Compound 4

To a solution of compound 3 (140 mg, 0.39 mmol) in THF (8 mL) was added AcOH (1 mL) and $H_2O_2$ (3 mL). The reaction mixture was stirred at 30° C. for 10 h. The mixture was quenched by addition of saturated $NaHCO_3$ (6 mL) and then partitioned between EtOAc (2×20 mL) and water (10 mL). The organic layers were collected and concentrated in vacuo to give the residue, which was purified by preparative TLC (eluent:petroleum ether:ethyl acetate=1:1) to give hydantoin 4 (89 mg, 70%) as a colorless oil.

Example 342

Synthesis of Compound 403

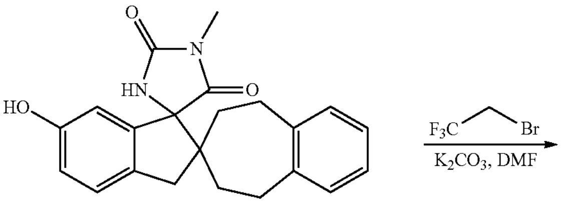

4

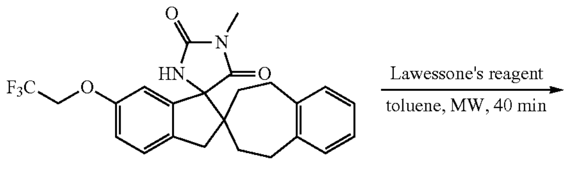

5

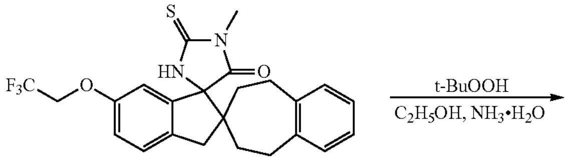

6

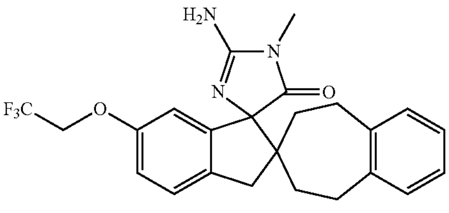

403

Procedure for Preparation of Compound 5

To a solution of compound 4 (45 mg, 0.12 mmol) in DMF (4 mL) was added $K_2CO_3$ (35 mg, 0.25 mmol). After stirring for 5 min, 2-bromo-1,1,1-trifluoro-ethane (30 mg, 0.18 mmol) was added and the reaction mixture was stirred at 25° C. for 10 h. The mixture was filtered, the filtrate was concentrated in vacuo to give the residue, which was purified by preparative TLC (eluent:petroleum ether:ethyl acetate=2:1) to give compound 5 (31 mg, 78%) as a white solid.

Procedure for Preparation of Compound 6

A suspension of compound 5 (27 mg, 0.06 mmol) and Lawesson's Reagent (24 mg, 0.06 mmol) in anhydrous toluene (1 mL) was heated at 130° C. for 40 min in a CEM microwave reactor. The mixture was concentrated in vacuo and the residue was purified by prep. TLC (eluent:petroleum ether:ethyl acetate=3:1) to give compound 6 (21 mg, 65%, 73% purity) as a white solid.

Procedure for Preparation of Compound 403

A solution of compound 6 (21 mg, 0.046 mmol), t-BuOOH (90 mg, 0.9 mmol), $NH_3.H_2O$ (1 mL) in EtOH (3 mL) was stirred at 30° C. for 10 h. The mixture was concentrated in vacuo to give the residue, which was purified by preparative RP-HPLC to give compound 403 (5.0 mg, 25%) as a white solid. LCMS: $t_R$=1.79 min in 3 min chromatography, MS (ESI) m/z 444.2 $[M+H]^+$. $^1H$ NMR ($CD_3OD$ 400 MHz): δ 7.40-7.47 (d, 1H), 7.05-7.38 (m, 5H), 6.92 (s, 1H), 4.49-4.59 (m, 2H), 3.50-3.55 (m, 2H), 3.17 (s, 3H), 3.08-3.13 (m, 1H), 2.92-3.01 (m, 1H), 2.60-2.80 (m, 2H), 2.13-2.20 (m, 1H), 1.70-1.77 (m, 1H), 1.35-1.50 (m, 2H).

Example 343

Synthesis of Compound 404

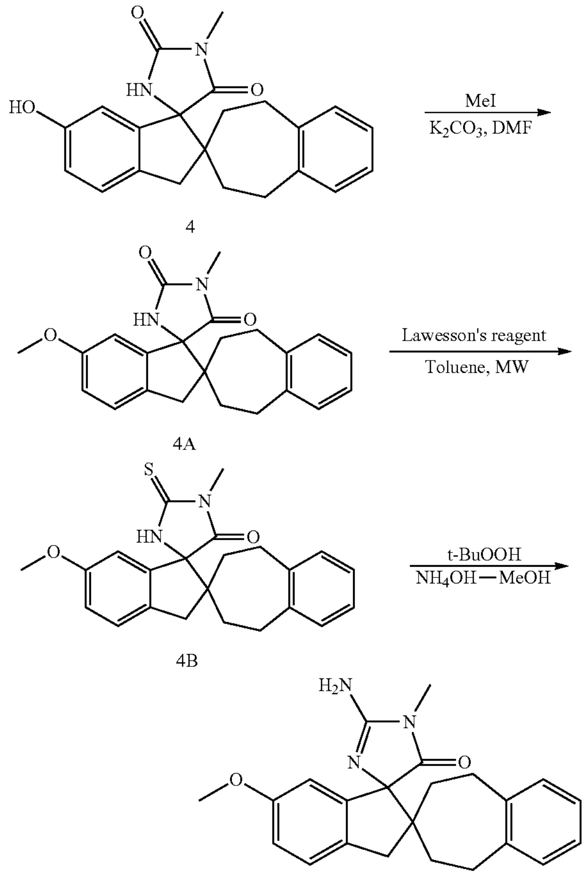

4

4A

4B

404

According to a similar synthesis of compound 403, hydantoin 4 (30 mg, 0.08 mmol) was methylated with $CH_3I$ (13 mg, 0.09 mmol) to give compound 4A (15 mg, 50%) as a white solid. Compound 4A (15 mg, 0.04 mmol) was then reacted with Lawesson's Reagent (18 mg, 0.04 mmol) to give compound 4B (11 mg, 70%) as a white solid. Finally, compound 4B (11 mg, 0.03 mmol) was converted to compound 404 (4.60 mg, 40%) as a white solid. LC-MS: $t_R$=1.73 min in 3 min chromatography, MS (ESI) m/z 376.1 $[M+H]^+$. $^1H$ NMR ($CD_3OD$ 400 MHz): δ 7.15-7.20 (d, J=8.0 Hz, 1H), 6.90-7.00 (m, 4H), 6.70-6.75 (dd, J=2.4, 8.4 Hz, 1H), 6.45-6.55 (d, J=1.6 Hz, 1H), 3.60-3.65 (s, 3H), 3.10-3.20 (m, 2H,), 2.90-3.00 (m, 4H), 2.75-2.90 (m 1H), 2.55-2.65 (m, 1H), 2.50-2.60 (m, 1H), 1.95-2.05 (m, 1H), 1.50-1.60 (s, 2H), 1.10-1.20 (m, 1H).

Example 344

Synthesis of Compound 405, 406 and 407

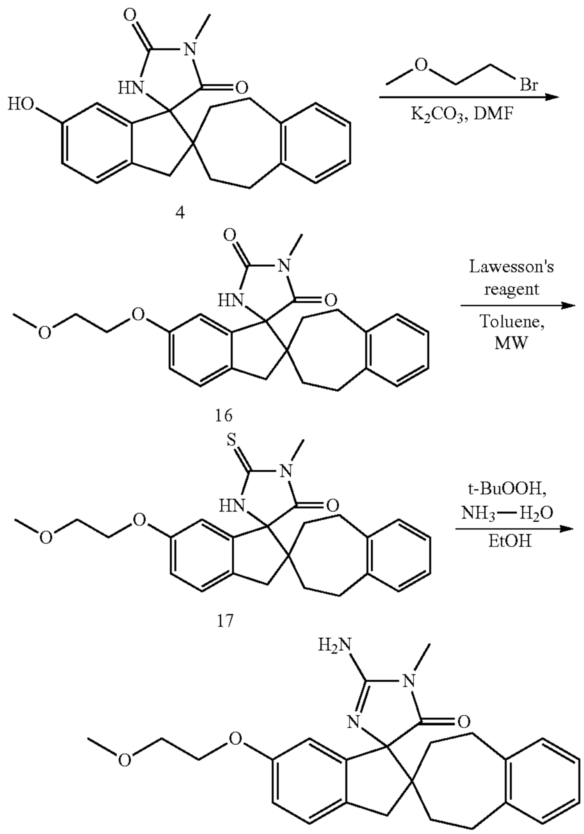

4

16

17

VT_B100609_01

According to a similar synthesis of compound 403, hydantoin 4 (800 mg, 2.2 mmol) was alkylated with 1-bromo-2-methoxy-ethane (350 mg, 2.4 mmol) to give compound 16 (430 mg, 50%) as a white solid. Compound 16 (420 mg, 1 mmol) was converted to thiohydantoin 17 (300 mg, 50%) as a white solid by a Lawesson's Reagent (420 mg, 1.05 mmol); Finally, compound 17 (300 mg, 0.69 mmol) afforded compound 405 (170 mg, 55%) as a white solid. LCMS: $t_R$=1.553 min in 3 min chromatography, MS ESI m/z 420.1 $[M+H]^+$. $^1H$ NMR ($CD_3OD$ 300 MHz): δ 7.25-7.35 (d, J=8.4 Hz, 1H,), 7.05-7.10 (m, 4H), 6.90-7.00 (d, J=8.1 Hz, 1H,), 6.75-6.80 (s, 1H), 4.00-4.10 (s, 2H), 3.55-3.65 (m, 2H), 3.35-3.45 (m, 4H), 3.10-3.25 (m, 4H), 3.05-3.10 (m, 1H), 2.85-3.00 (m, 1H), 2.50-2.75 (m, 2H), 2.05-2.15 (m, 1H), 1.65-1.80 (m, 1H), 1.35-1.40 (m, 2H).

Procedure for Preparation of Compounds 406 and 407

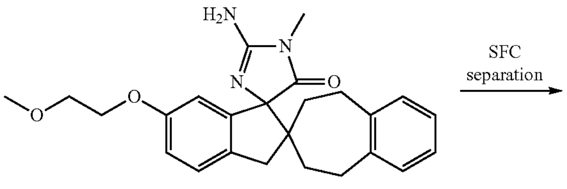

405

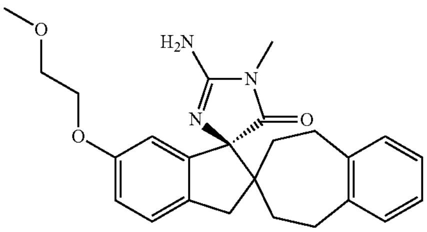

406

+

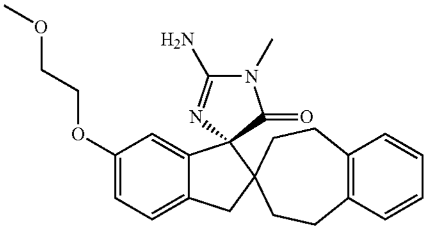

407

Compound 405 (50 mg, 0.12 mmol) was re-purified by preparative SFC to give compound 406 (13.40 mg, 30%) as a white solid, LCMS: $t_R$=1.565 min in 3 min chromatography, MS ESI m/z 420.1 $[M+H]^+$. SFC: $t_R$=1.434 min in 8 min chromatography, ee=100%. $^1H$ NMR ($CD_3OD$ 400 MHz): δ 7.25-7.35 (d, J=8.4 Hz, 1H,), 7.05-7.10 (s, 4H), 6.90-7.00 (d, J=8.1 Hz, 1H,), 6.75-6.80 (s, 1H), 4.00-4.10 (s, 2H), 3.55-3.65 (m, 2H), 3.35-3.45 (m, 4H), 3.10-3.25 (m, 4H), 3.05-3.10 (m, 1H), 2.85-3.00 (m, 1H), 2.50-2.75 (m, 2H), 2.05-2.15 (m, 1H), 1.65-1.80 (m, 1H), 1.35-1.40 (m, 2H); and compound 407 (18.10 mg, 32%) as the white solid, LCMS: $t_R$=1.561 min in 3 min chromatography, MS (ESI) m/z 420.1 $[M+H]^+$. SFC: $t_R$=3.338 min in 8 min chromatography, ee=100%. $^1H$ NMR ($CD_3OD$ 400 MHz): δ 7.25-7.35 (d, J=8.4 Hz, 1H,), 7.05-7.10 (s, 4H), 6.90-7.00 (d, J=8.1 Hz, 1H,), 6.75-6.80 (s, 1H), 4.00-4.10 (s, 2H), 3.55-3.65 (m, 2H), 3.35-3.45 (m, 4H), 3.10-3.25 (m, 4H), 3.05-3.10 (m, 1H), 2.85-3.00 (m, 1H), 2.50-2.75 (m, 2H), 2.05-2.15 (m, 1H), 1.65-1.80 (m, 1H), 1.35-1.40 (m, 2H).

Example 345

Synthesis of Compound 408

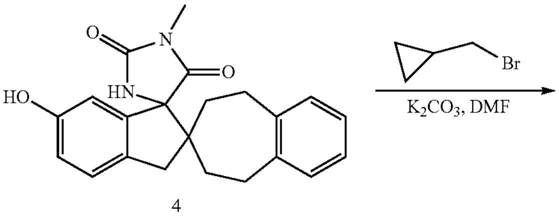

4

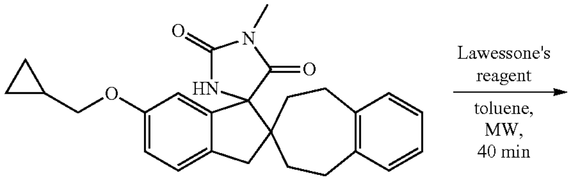

2

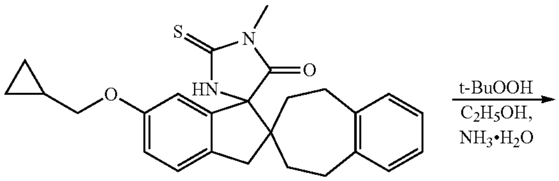

3

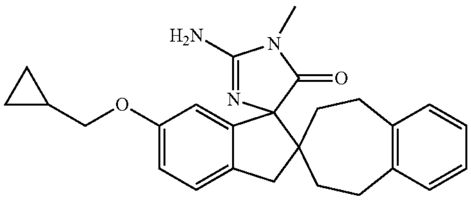

408

According to a similar synthesis of compound 403, hydantoin 4 (44 mg, 0.12 mmol) reacted with bromomethylcyclopropane (24 mg, 0.18 mmol) to give compound 2 (29 mg, 61%) as a white solid. Compound 2 (22 mg, 0.05 mmol) was then converted to thio-hydantoin 3 (19 mg, 85%, 90% purity) with a Lawesson's Reagent (23 mg, 0.06 mmol) in anhydrous toluene (2 mL). And compound 3 was further reacted with ammonia under oxidation conditions to give compound 408 as a white solid (7.20 mg, 40%). LCMS: $t_R$=1.81 min in 3 min chromatography, MS (ESI) m/z 416.2 $[M+H]^+$. $^1H$ NMR ($CD_3OD$, 400 MHz): δ 7.31-7.33 (d, J=7.2 Hz, 1H), 7.09-7.12 (m, 4H), 6.94-6.97 (dd, J=2.4, 8.4 Hz, 1H), 6.76 (s, 1H), 3.81 (s, 2H), 3.41-3.45 (d, J=19.2 Hz, 1H), 3.20-3.24 (d, J=19.2 Hz, 1H), 3.16 (s, 3H), 3.09-3.13 (m, 1H), 2.93-3.00 (m, 1H), 2.63-2.68 (m, 1H), 2.58-2.61 (m, 1H), 2.14-2.17 (m, 1H), 1.73-1.77 (m, 1H), 1.31-1.44 (m, 2H), 1.19-1.27 (m, 1H), 0.56-0.64 (m, 2H), 0.28-0.39 (m, 2H).

Example 406

Synthesis of Compound 409

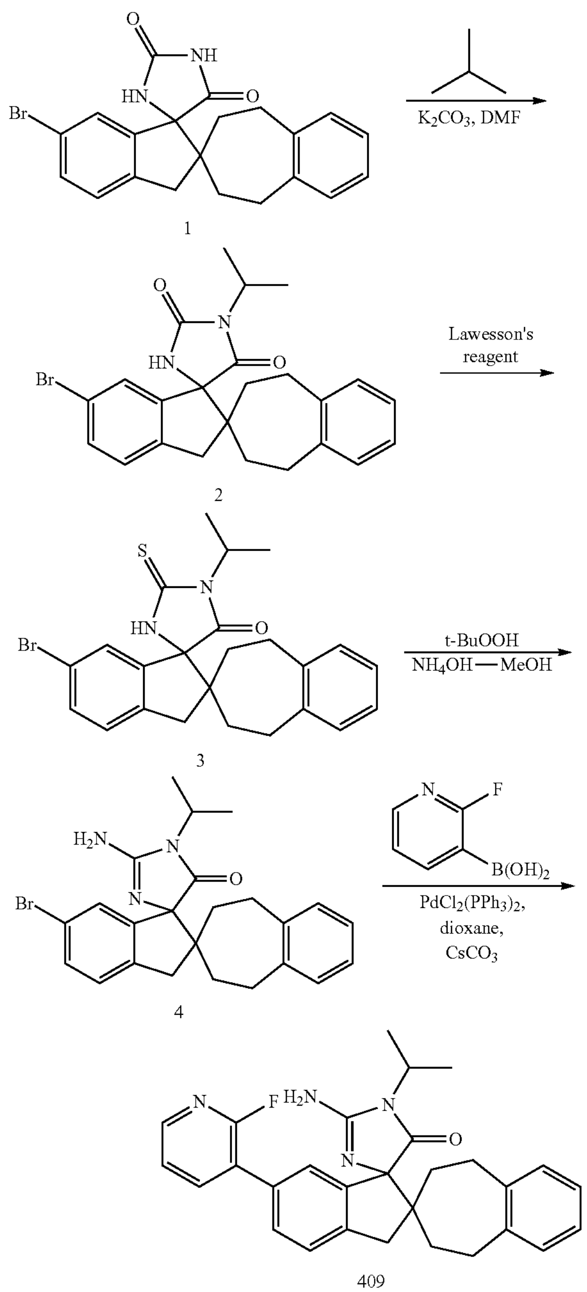

1

2

3

4

409

Procedure for Preparation of Compound 2

To a solution of compound 1 (700 mg, 1.7 mmol) in DMF (15 mL) was added $K_2CO_3$ (700 mg, 5.2 mmol). After stirring for 5 min, 2-iodo-propane (300 mg, 1.8 mmol) was added and the reaction mixture was stirred at 25° C. for 10 h. The precipitate was filtered off and washed with ethyl acetate (2×40 mL), the filtrate was concentrated in vacuo to give the residue, which was purified by preparative TLC (eluent:petroleum ether:ethyl acetate=2:1) to give compound 2 (410 mg, 52%) as a white solid.

Procedure for Preparation of Compound 3

A suspension of compound 2 (180 mg, 0.4 mmol) and Lawesson's Reagent (180 mg, 0.44 mmol) in dry toluene (4 mL) was heated under 130° C. for 35 min in a CEM microwave reactor. The mixture was concentrated in vacuo and the residue was purified by column (eluent:petroleum ether:ethyl acetate=5:1) to give compound 3 as a white solid (96 mg, 50%) as a white solid.

Procedure for Preparation of Compound 4

A solution of compound 3 (95 mg, 0.2 mmol), t-BuOOH (1.5 mL), $NH_3.H_2O$ (1.5 mL) in MeOH (8 mL) was stirred at 25° C. for 10 h. Then, the mixture was concentrated in vacuo to give the residue, which was purified by preparative TLC (eluent:dichloromethane:MeOH=12:1) to give compound 4 (47 mg, 50%) as a white solid. LC-MS: $t_R$=1.26 min, in 3 min chromatography; MS (ESI) m/z 452.2 $[M+H]^+$. $^1$H NMR ($CD_3OD$ 400 MHz): δ 7.30-7.35 (d, J=11.2 Hz, 1H), 7.15-7.20 (d, J=8.0 Hz, 1H), 6.90-7.00 (m, 5H), 4.05-4.15 (m, 1H), 3.20-3.25 (m, 1H), 3.05-3.15 (d, J=15.2 Hz, 1H), 2.95-3.05 (m, 1H), 2.75-2.85 (m, 1H), 2.55-2.65 (m, 1H), 2.40-2.50 (m, 1H), 2.05-2.10 (m, 1H), 1.40-1.50 (m, 2H), 1.25-1.35 (m, 6H), 1.15-1.20 (m, 1H).

Procedure for Preparation of Compound 409

A suspension of compound 4 (14 mg, 0.03 mmol), 2-fluoro-3-pyridine boronic acid (5.5 mg, 0.03 mmol), $PdCl_2(PPh_3)_2$ (2 mg, $2.8\times10^{-3}$ mmol) and $Cs_2CO_3$ (0.1 mL, 2 N in water) in 1,4-dioxane (3 mL) was heated at 120° C. for 15 min in a CEM microwave reactor. The mixture was concentrated in vacuo, the residue was purified by prep. HPLC to give compound 409 (3.1 mg, 28%) as a white solid. LCMS: $t_R$=1.85 min in 3 min chromatography, MS (ESI) m/z=469.2 $[M+H]^+$. $^1$H NMR ($CD_3OD$ 400 MHz): δ 8.16-8.17 (d, J=4.8 Hz, 1H), 8.03-8.05 (m, 1H), 7.61-7.63 (d, J=8.0 Hz, 1H), 7.54-7.56 (d, J=8.0 Hz, 1H), 7.38-7.40 (m, 2H), 7.07-7.10 (m, 4H), 4.21-4.26 (m, 1H), 3.53-3.57 (d, J=16.0 Hz, 1H), 3.28-3.34 (d, J=15.2 Hz, 1H), 3.09-3.16 (m, 1H), 2.93-3.00 (m, 1H), 2.72-2.77 (m, 1H), 2.57-2.62 (m, 1H), 2.21-2.26 (m, 1H), 1.70-1.75 (m, 1H), 1.40-1.50 (m, 8H).

Example 347

Synthesis of Compound 410

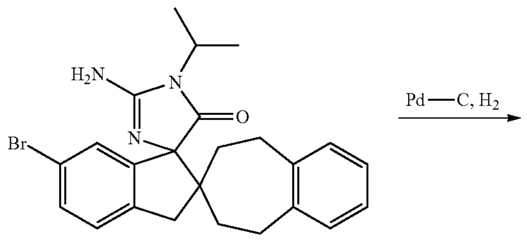

4

-continued

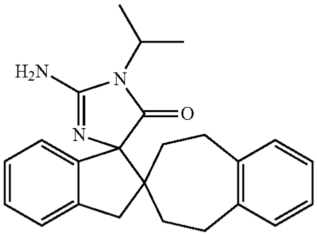

410

A solution of compound 4 described in Example 346 (10 mg, 0.022 mmol) and Pd/C (2 mg) in MeOH (4 mL) was stirred at 25° C. under $H_2$ (10 psi) for 2 h. The mixture was filtered and filtrate was concentrated in vacuo to give the residue which was purified by preparative TLC on silica gel (Dichloromethane:MeOH=12:1) to give compound 410 (4.3 mg, 55%) as a white solid. LC-MS: $t_R$=1.82 min in 2 min chromatography, MS (ESI) m/z 374.2 $[M+H]^+$. $^1H$ NMR ($CD_3OD$ 300 MHz): δ 7.20-7.35 (m, 2H), 7.10-7.20 (m, 1H), 6.90-7.05 (m, 5H), 4.05-4.15 (m, 1H), 3.20-3.25 (m, 1H), 3.05-3.15 (d, J=15.2 Hz, 1H), 2.95-3.05 (m, 1H), 2.75-2.85 (m, 1H), 2.55-2.65 (m, 1H), 2.40-2.50 (m, 1H), 2.05-2.10 (m, 1H), 1.40-1.50 (m, 2H), 1.25-1.35 (m, 6H), 1.15-1.20 (m, 1H).

Example 348

Synthesis of Compound 411

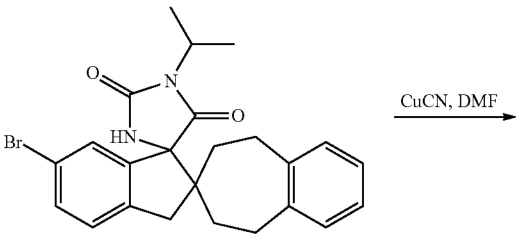

2

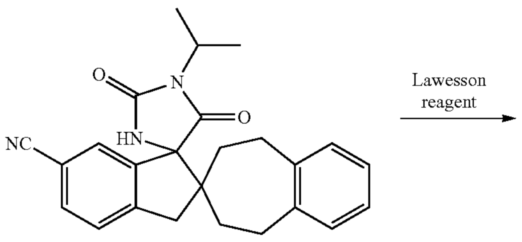

3

-continued

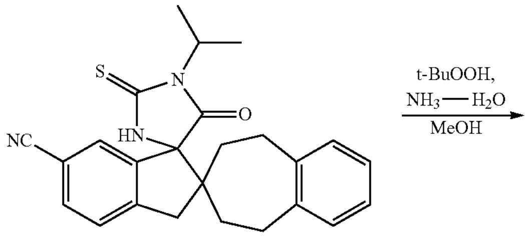

4

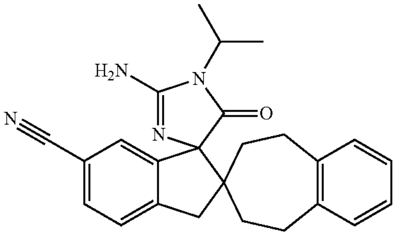

411

Procedure for Preparation of Compound 3

To a solution of compound 2 (100 mg, 0.22 mmol) in DMF (10 mL) was added CuCN (40 mg, 0.44 mmol), $Pd(PPh_3)_4$ (12 mg, 0.01 mmol) under $N_2$ at room temperature. The resulting mixture was stirred 30 min at 180° C. in a microwave reactor. Water (15 mL) was added and the mixture was extracted with EtOAc (3×20 mL), and the combined organic layers were dried over $Na_2SO_4$ and concentrated to give the residue which was purified by preparative TLC on silica gel (petroleum ether:ethyl acetate=5:1) to give compound 3 (46 mg, 52%) as a white solid.

Procedure for Preparation of Compound 4

A mixture of compound 3 (46 mg, 0.115 mmol) and Lawesson'reagent (70 mg, 0.175 mmol) in toluene (2 mL) was heated at 130° C. for 30 min in a microwave reactor under $N_2$. The mixture was cooled, and concentrated in vacuo. The residue was purified by preparative TLC on silica gel (petroleum ether:ethyl acetate=3:1) to give compound 4 (19 mg, 40%) as a white solid.

Procedure for Preparation of Compound 411

To a solution of compound 4 (19 mg, 0.045 mmol) in a mixture of MeOH (10 mL) and $NH_4OH$ (2 mL) was added t-BuOOH (0.5 mL, 65% in water). The mixture was stirred at room temperature overnight, and concentrated. Water (15 mL) and EtOAc (3×10 mL) were added, and the organic layer was dried over $Na_2SO_4$ and concentrated to give the residue which was purified by preparative HPLC to give the compound 411 (8.1 mg, 44%) as a white solid. LC-MS: $t_R$=0.931 min in 2 min chromatography, MS (ESI) m/z 399 $[M+H]^+$. $^1H$ NMR ($CD_3OD$ 400 MHz): δ 7.78 (dd, J=1.6, 8.0 Hz, 1H), 7.70 (d, J=1.2 Hz, 1H), 7.62 (d, J=8.0 Hz, 1H), 7.10 (m, 4H), 4.24 (m, 1H), 3.60 (d, J=16.4 Hz, 1H), 3.38 (m, 1H), 3.28 (m, 1H), 3.11 (m, 1H), 2.96 (m, 1H), 2.74 (m, 1H), 2.57 (m, 1H), 2.20 (m, 1H), 1.61 (m, 1H), 1.48 (d, J=6.8 Hz, 3H), 1.46 (d, J=5.2 Hz, 3H), 1.39 (m, 1H).

Example 349

Synthesis of Compound 412

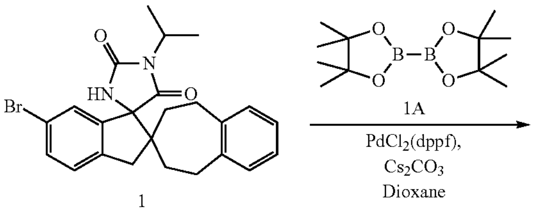

1

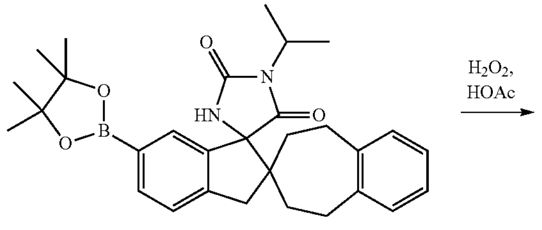

2

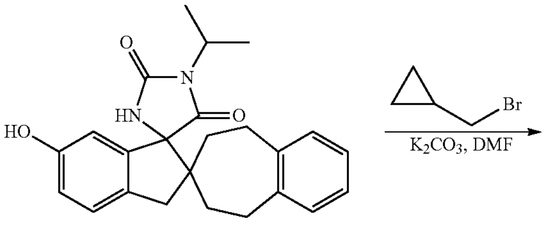

3

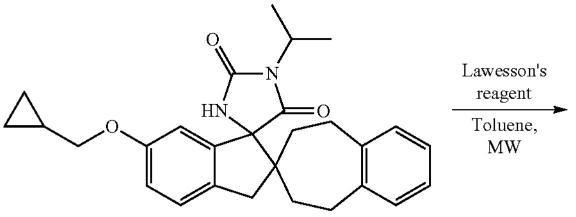

4

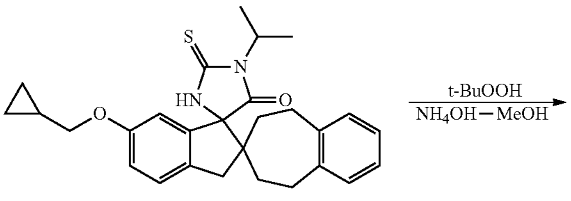

5

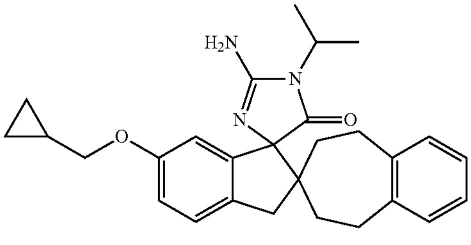

412

Procedure for Preparation of Compound 2

A suspension of compound 1 (220 mg, 0.48 mmol), compound 1A (185 mg, 0.73 mmol), $PdCl_2$(dppf) (70 mg, 0.1 mmol) and KOAc (150 mg, 1.5 mmol) in dry 1,4-dioxane (5 mL) was heated under 100° C. for 60 min in CEM microwave reactor. The mixture was concentrated in vacuo and the residue was purified by column on silica gel (petroleum ether: ethyl acetate=3:1) to give compound 2 (300 mg, crude yield 100%) as a yellow solid.

Procedure for Preparation of Compound 3

To a solution of compound 2 (300 mg, 0.6 mmol) in THF (15 mL) was added AcOH (1 mL) and $H_2O_2$ (3 mL). The reaction mixture was stirred at 30° C. for 10 h. The mixture was quenched with saturated $NaHCO_3$ (6 mL) and then balanced between EtOAc (2×20 mL) and water (10 mL). The organic layers were collected and concentrated in vacuo to give the residue, which was purified by preparative TLC (petroleum ether:ethyl acetate=1:1) to give compound 3 (70 mg, 35%) as a colorless oil.

Procedure for Preparation of Compound 4

To a solution of compound 3 (35 mg, 0.09 mmol) in DMF (4 mL) was added $K_2CO_3$ (40 mg, 0.30 mmol). After stirring for 5 min, bromomethyl-cyclopropane (13 mg, 0.10 mmol) was added and the reaction mixture was stirred at 25° C. for 10 h. The mixture was filtered and filtrate was concentrated in vacuo to give the residue, which was purified by preparative TLC on silica gel (petroleum ether:ethyl acetate=2:1) to give compound 4 (12 mg, 25%) as a white solid.

Procedure for Preparation of Compound 5

A suspension of compound 4 (13 mg, 0.03 mmol) and Lawesson's Reagent (13 mg, 0.03 mmol) in dry toluene (1 mL) was heated under 130° C. for 40 min in CEM microwave reactor. The mixture was concentrated in vacuo and the residue was purified by column (eluent:petroleum ether:ethyl acetate=5:1) to give compound 5 (6 mg, 50%) as a white solid.

Procedure for Preparation of Compound 412

A solution of compound 5 (6 mg, 0.046 mmol), t-BuOOH (0.5 mL), $NH_3.H_2O$ (0.5 mL) in MeOH (2 mL) was stirred at 25° C. for 10 h. Then, the mixture was concentrated in vacuo to give the residue, which was purified by preparative HPLC to give compound 412 (0.8 mg, 15%) as a white solid. LC-MS: $t_R$=1.94 min in 3 min chromatography, MS (ESI) m/z 443.2 $[M+H]^+$. $^1H$ NMR ($CD_3OD$ 400 MHz): δ 7.35-7.45 (d, J=8.0 Hz, 1H), 7.00-7.15 (m, 4H), 6.85-6.90 (d, J=1.6, 8.0 Hz, 1H), 6.50-6.55 (s, 1H), 4.15-4.35 (m, 1H), 3.75-3.80 (d, J=8.4 Hz, 1H), 3.20-3.30 (s, 1H,), 3.15-3.20 (m, 1H), 3.05-3.15 (m 1H), 2.90-3.05 (m, 1H), 2.65-2.75 (m, 1H), 2.50-2.60 (m, 1H), 2.10-2.25 (m, 1H), 1.50-1.70 (m, 5H), 1.30-1.50 (m, 6H), 1.20-1.30 (m, 2H), 0.45-0.55 (m, 2H), 0.30-0.40 (m, 2H).

Example 350

Synthesis of Compound 413

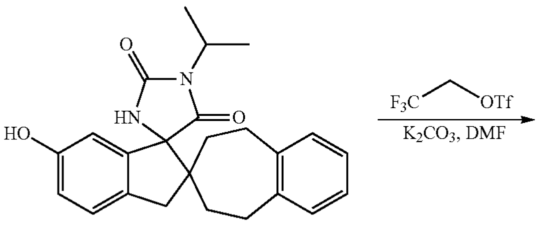

3

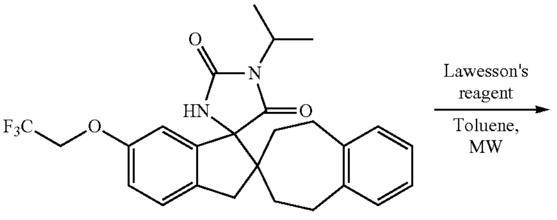

3A

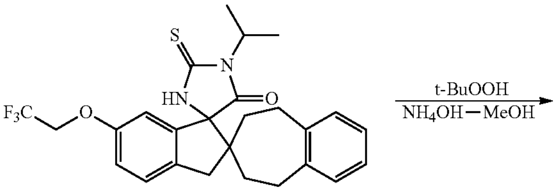

3B

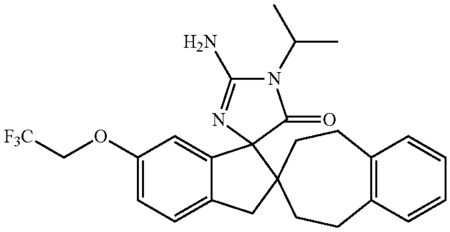

413

According to a similar synthesis of compound 412, compound 3 (35 mg, 0.09 mmol) was alkylated with trifluoro-methanesulfonic acid 2,2,2-trifluoro-ethyl ester (23 mg, 0.10 mmol) to give compound 3a (18 mg, 45%) as a white solid. A suspension of compound 3a (18 mg, 0.04 mmol) was then reacted with Lawesson's Reagent (17 mg, 0.04 mmol) to give compound 3B (8 mg, 45%) as a white solid. Finally, compound 3B (8 mg, 0.016 mmol) was converted to compound 413 (1.90 mg, 25%) as a white solid. LC-MS: $t_R$=1.93 min in 3 min chromatography, MS (ESI) m/z 472.2 $[M+H]^+$. $^1H$ NMR ($CD_3OD$ 400 MHz): δ 7.15-7.20 (m, 1H,), 6.90-7.00 (m, 4H), 6.85-6.90 (dd, J=2.4, 8.0 Hz, 1H), 6.50-6.55 (s, 1H), 4.30-4.40 (m, 2H), 4.15-4.35 (m, 1H), 3.75-3.80 (d, J=8.4 Hz, 1H), 3.20-3.30 (s, 1H,), 3.15-3.20 (m, 1H), 3.05-3.15 (m 1H), 2.90-3.05 (m, 1H), 2.65-2.75 (m, 1H), 2.50-2.60 (m, 1H), 2.10-2.25 (m, 1H), 1.50-1.60 (s, 2H), 1.30-1.50 (m, 6H), 1.20-1.30 (m, 1H).

Example I-11

Synthesis of Hydantoin 4

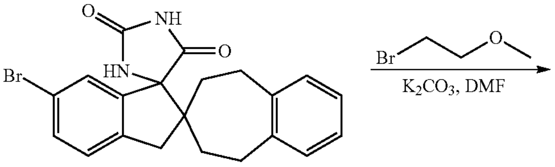

1

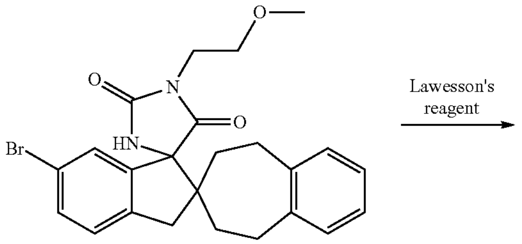

2

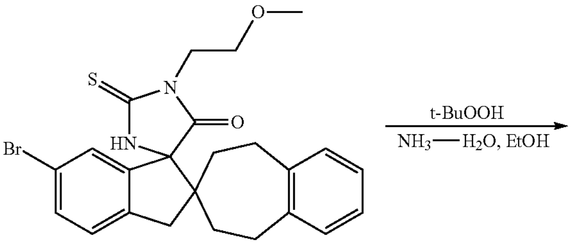

3

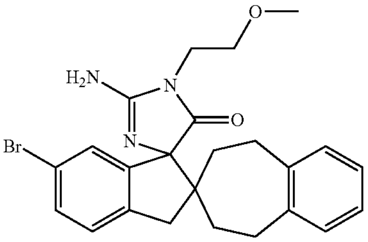

4

According to a similar synthesis of compound 4 described in Example 346, compound 1 (500 mg, 1.17 mmol) was alkylated with 1-Bromo-2-methoxy-ethane (180 mg, 1.3 mmol) to give compound 2 (360 mg, 65%) as a white solid. Compound 2 (200 mg, 0.43 mmol) was reacted with Lawesson's Reagent (190 mg, 0.47 mmol) to give compound 3 (84 mg, 50%) as a white solid. And compound 3 (80 mg, 0.17 mmol) was converted to hydantoin 4 (55 mg, 70%) as a white solid.

Example 351

Synthesis of Compound 414

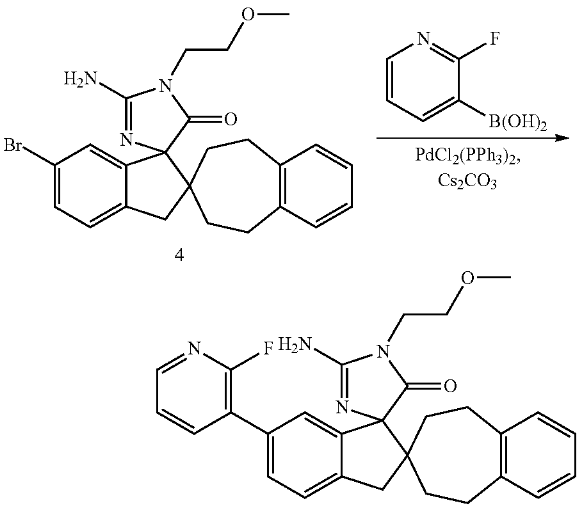

4

414

A suspension of compound 4 (25 mg, 0.05 mmol), 2-fluoro-3-pyridine boronic acid (10 mg, 0.06 mmol), $PdCl_2(PPh_3)_2$ (4 mg, 0.005 mmol) and $Cs_2CO_3$ (0.2 mL, 2 N in water) in 1,4-dioxane (1 mL) was heated at 120° C. for 15 min in CEM microwave reactor. The mixture was concentrated in vacuo, the residue was purified by preparative HPLC to give compound 414 (5.0 mg, 20%) as a white solid. LCMS: $t_R$=1.086 min in 2 min chromatography, MS (ESI) m/z=485.2 $[M+H]^+$. $^1$H NMR ($CD_3OD$ 400 MHz): δ 8.20-8.25 (d, J=3.6 Hz, 1H), 8.05-8.10 (m, 1H), 7.65-7.70 (d, J=4.8 Hz, 1H), 7.55-7.60 (d, J=7.6 Hz, 1H), 7.40-7.45 (m, 2H), 7.05-7.15 (m, 4H), 3.80-4.00 (m, 2H), 3.55-3.60 (m, 3H), 3.35-3.40 (m, 1H), 3.30-3.35 (s, 3H), 3.10-3.20 (m, 1H), 2.95-3.05 (m, 1H), 2.75-2.80 (m, 1H), 2.60-2.70 (m, 1H), 2.20-2.30 (m, 1H), 1.75-1.85 (m, 1H), 1.40-1.55 (m, 2H).

Example 352

Synthesis of Compound 415

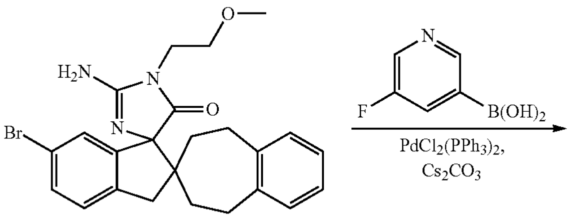

4

-continued

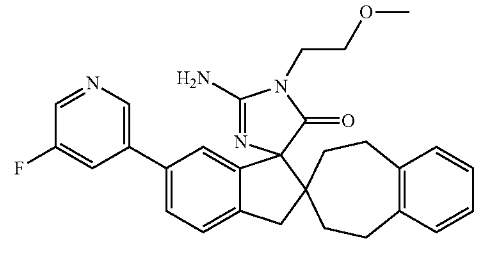

415

Following a similar synthesis of compound 414, compound 4 (25 mg, 0.05 mmol) was reacted with 5-fluoro-3-pyridine boronic acid (10 mg, 0.06 mmol) to give compound 415 (3.7 mg, 20%) as a white solid. LCMS: $t_R$=1.088 min in 2 min chromatography, MS (ESI) m/z=485.2 $[M+H]^+$. $^{19}$F NMR: ($CD_3OD$ 19f): δ −128.50. $^1$H NMR ($CD_3OD$ 400 MHz): δ 8.20-8.25 (s, 1H), 8.50-8.55 (s, 1H), 8.30-8.35 (m, 1H), 7.75-7.80 (d, J=8.4 Hz, 1H), 7.50-7.55 (d, J=8.0 Hz, 1H), 7.45-7.55 (d, J=8.4 Hz, 1H), 7.10-7.15 (s, 1H), 6.90-7.00 (m, 4H), 3.55-3.65 (m, 2H), 3.40-3.45 (m, 2H), 3.25-3.35 (m, 1H), 3.20-3.25 (m, 4H), 2.90-3.00 (m, 1H), 2.80-2.90 (m, 1H), 2.55-2.60 (m, 1H), 2.40-2.50 (m, 1H), 2.00-2.10 (m, 1H), 1.50-1.60 (m, 2H), 1.15-1.25 (m, 1H).

Example 353

Synthesis of Compound 416

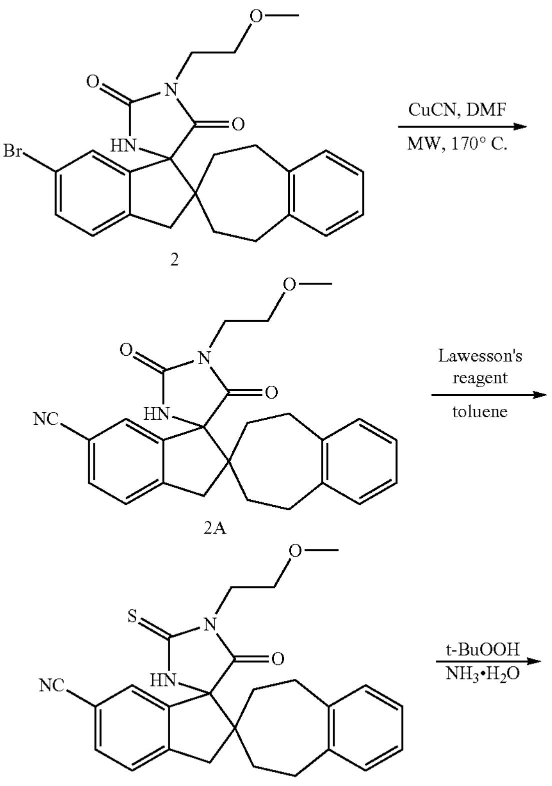

2

2A

2B

-continued

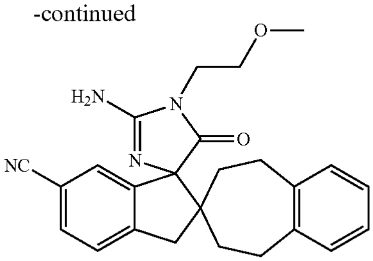

416

Procedure for Preparation of Compound 2A

A suspension of compound 2 (70 mg, 0.15 mmol), CuCN (27 mg, 0.30 mmol) and $Pd(PPh_3)_4$ (17 mg, 0.02 mmol) in anhydrous DMF (2 mL) was heated at 180° C. for 45 min in a CEM microwave reactor. The mixture was concentrated in vacuo, the residue was purified by preparative TLC on silica gel (petroleum ether:ethyl acetate=1:1) to give compound 2A (34 mg, 55%) as a white solid.

Procedure for Preparation of Compound 2B

A suspension of compound 2A (34 mg, 0.08 mmol) and Lawesson's Reagent (35 mg, 0.09 mmol) in anhydrous toluene (2 mL) was heated under 130° C. for 35 min in a CEM microwave reactor. The mixture was concentrated in vacuo and the residue was purified by column on silica gel (eluent: petroleum ether:ethyl acetate=3:1) to give compound 2B (16 mg, 40%) as a white solid.

Procedure for Preparation of Compound 416

A solution of compound 2B (16 mg, 0.04 mmol), t-BuOOH (0.5 mL), $NH_3.H_2O$ (0.5 mL) in EtOH (2 mL) was stirred at 20° C. for 10 h. The mixture was concentrated in vacuo to give the residue, which was purified by preparative HPLC to give compound 416 (1.70 mg, 10%) as a white solid. LCMS: $t_R$=1.028 min in 2 min chromatography, MS (ESI) m/z=415.2 $[M+H]^+$. $^1H$ NMR ($CD_3OD$ 400 MHz): δ 7.50-7.55 (d, J=7.6 Hz, 1H), 7.40-7.45 (d, J=8.0 Hz, 1H,), 7.10-7.15 (s, 1H), 6.90-7.00 (m, 4H), 3.55-3.65 (m, 2H), 3.40-3.45 (m, 2H), 3.25-3.35 (m, 4H), 2.90-3.00 (m, 1H), 2.80-2.90 (m, 1H), 2.55-2.60 (m, 1H), 2.40-2.50 (m, 1H), 2.00-2.10 (m, 1H), 1.50-1.60 (m, 2H), 1.15-1.25 (m, 2H).

Example 354

Synthesis of Compound 417

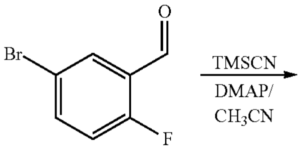

1

-continued

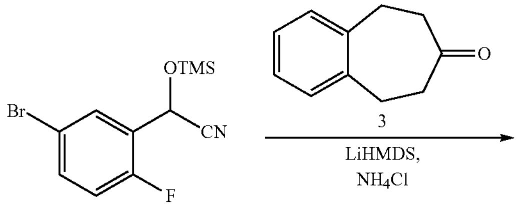

2

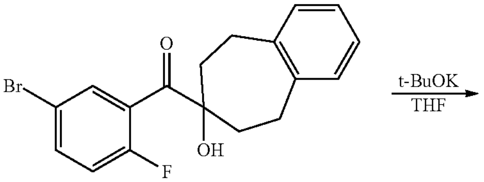

3

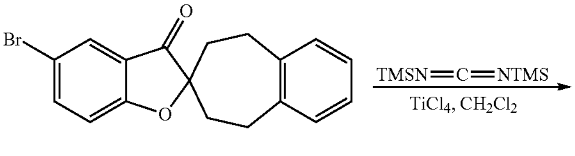

4

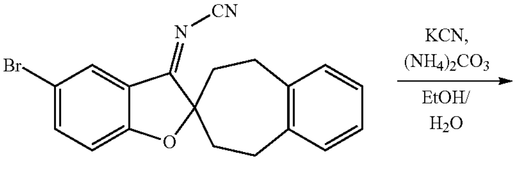

5

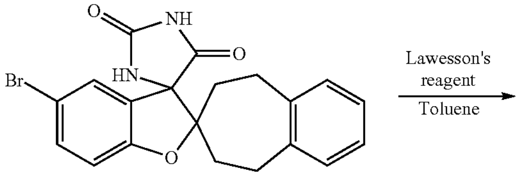

6

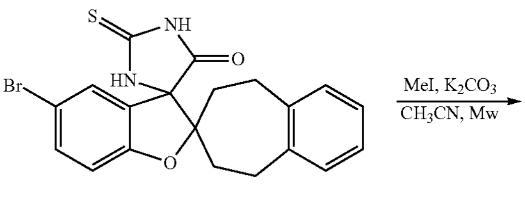

7

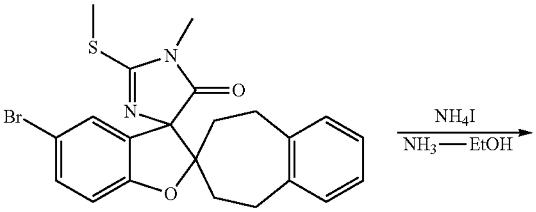

8

-continued

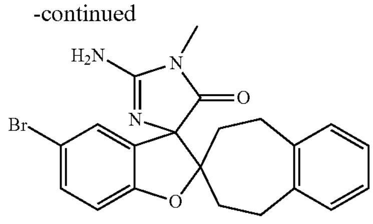

417

Procedure for Preparation of Compound 2

To a solution of compound 1 (4.27 g, 21 mmol) and DMAP (0.029 g, 0.24 mmol) in anhydrous $CH_3CN$ (40 mL) was added TMSCN (2.82 g, 28.4 mmol) via a syringe under a nitrogen atmosphere at room temperature. The reaction mixture was stirred for 4 h at room temperature, and the solvent was removed under reduced pressure to give crude compound 2 (6.35 g, 100%) which was used directly in the next step without further purification.

Procedure for Preparation of Compound 3

To a solution of compound 2 (6.35 g, 21 mmol) in THF (20 mL) was added LiHMDS (1 M in THF, 22 mL, 22 mmol) via a syringe at −78° C. under a nitrogen atmosphere. After 1 h a solution of compound 2A (3.31 g, 20.66 mmol) in THF (32 mL) was added dropwise at −78° C. The mixture was stirred at −78° C. for 1.5 h then quenched by addition of a solution of sat. $NH_4Cl$ (50 mL), the resulting mixture was stirred overnight at room temperature, extracted with ethyl acetate (3×100 mL). The combined organic layers were washed with brine (2×50 mL), dried over sodium sulfate, concentrated in vacuo and the residue was purified by column chromatography on silica gel (petroleum ether:THF=40:1) to give compound 3 (3.21 g, 42%) as a light yellow solid.

Procedure for Preparation of Compound 4

To a solution of compound 3 (3.21 g, 8.8 mmol) in THF (50 mL) was added t-BuOK (1.19 g, 10.6 mmol). The reaction mixture was heated to reflux for 50 min, cooled to room temperature, diluted with water (30 mL), extracted with ethyl acetate (3×50 mL). The combined organic layers were washed with brine (2×30 mL), dried over sodium sulfate, concentrated in vacuo and the residue was purified by column chromatography on silica gel (petroleum ether:EtOAc=40:1) to give compound 4 (1.57 g, 51%) as a yellow solid.

Procedure for Preparation of Compound 5

To a solution of compound 4 (800 mg, 2.34 mmol) in $CH_2Cl_2$ (16 mL) was added $TiCl_4$ (4.10 mL, 1.0 M in dichloromethane, 4.10 mmol) dropwise. After stirring for 1 h at room temperature, bis-trimethylsilylcarbodiimide (1.20 g, 6.45 mmol) was added, and the final mixture was stirred at room temperature overnight. The reaction was quenched by addition of ice-water (30 mL) and stirred for 15 min, extracted with $CH_2Cl_2$ (3×30 mL). The combined organic layers were washed with water, brine, dried over $Na_2SO_4$ and concentrated to give compound 5 (840 mg, crude) which was used for the next step.

Procedure for Preparation of Compound 6

To a solution of compound 5 (840 mg, 2.30 mmol) in EtOH (8 mL) and $H_2O$ (8 mL) was added KCN (596 mg, 9.18 mmol) and $(NH_4)_2CO_3$ (2.23 g, 23 mmol). The reaction was heated at 75° C. overnight. The reaction was cooled to room temperature, and was dissolved in EtOAc (200 mL), washed with water, brine, dried over $Na_2SO_4$ and concentrated to give compound 6 (800 mg, 80% crude) as a white solid. $^1H$ NMR (DMSO-$d_6$ 300 MHz): δ 11.02 (s, 1H), 8.71 (s, 1H), 7.46 (m, 2H), 7.14 (m, 4H), 6.95 (d, J=8.4 Hz, 1H), 3.13 (m, 2H), 2.66 (m, 3H), 2.05 (m, 1H), 1.53 (m, 2H).

Procedure for Preparation of Compound 7

To a solution of compound 6 (600 mg, 1.46 mmol) in toluene (24 mL) was added Lawesson's reagent (647 mg, 1.60 mmol) under a nitrogen atmosphere. The reaction mixture was heated in a CEM microwave reactor at 130° C. for 40 min. The solvent was removed and the residue was purified by chromatography (petroleum ether:EtOAc=20:1) to afford compound 7 (570 mg, 90%) as a white solid.

Procedure for Preparation of Compound 8

To a solution of compound 7 (570 mg, 1.33 mmol) in $CH_3CN$ (45 mL) was added $K_2CO_3$ (554 mg, 3.99 mmol) followed by MeI (1.17 g, 7.97 mmol). The reaction mixture was heated at 60° C. for 10 min and then at 100° C. for 10 min in a CEM microwave reactor. The solution was filtered and the filtrate was concentrated to give the residue, which was purified by chromatography (petroleum ether:EtOAc=30:1) to afford compound 8 (420 mg, 69%) as a white solid. $^1H$ NMR ($CDCl_3$ 400 MHz): δ 7.28 (d, J=8.8 Hz, 1H), 7.06 (s, 4H), 6.82 (m, 2H), 3.24 (m, 2H), 2.94 (s, 3H), 2.62-2.39 (m, 7H), 1.67 (m, 1H), 1.36 (m, 1H).

Procedure for Preparation of Compound 417

To a solution of compound 8 (20 mg, 0.044 mmol) in $NH_3$-EtOH (2 mL) was added $NH_4I$ (52 mg, 0.35 mmol). The reaction mixture was heated at 120° C. in a CEM microwave reactor for 2 h. The solvent was removed and the residue was purified by preparative RP-HPLC to afford compound 417 (4.2 mg, 22%) as a white solid. LC-MS $t_R$=1.199 min in 2 min chromatography, m/z 428.1 $[M+H]^+$. $^1H$ NMR ($CD_3OD$ 300 MHz): δ 7.58 (m, 2H), 7.19 (s, 4H), 6.98 (d, J=8.1 Hz, 1H), 3.17 (s, 3H), 2.73-2.55 (m, 4H), 2.23 (m, 1H), 1.71-1.52 (m, 2H).

Example 355

Synthesis of Compound 418

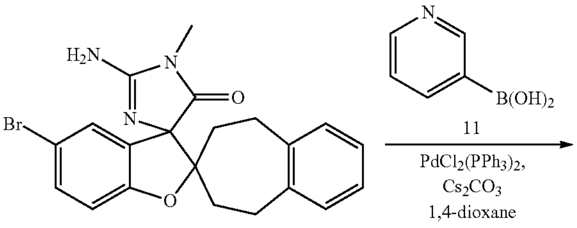

417

-continued

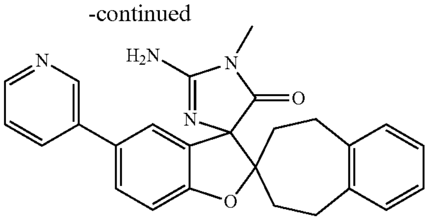

418

To a solution of compound compound 417 (40 mg, 0.094 mmol) in 1,4-dioxane (1 mL) was added compound 11 (23 mg, 0.19 mmol), $PdCl_2(PPh_3)_2$ (10 mg) and aq. $Cs_2CO_3$ (0.1 mL, 2M in $H_2O$). The reaction mixture was heated at 120° C. in a CEM microwave reactor for 15 min under a nitrogen atmosphere. The solvent was removed under reduced pressure, and the residue was purified by preparative RP-HPLC to give compound 418 (8 mg, 20%) as a white solid. LC-MS $t_R$=1.016 min in 2 min chromatography, m/z 425.2 $[M+H]^+$; $^1H$ NMR ($CD_3OD$ 300 MHz): δ 8.93 (m, 1H), 8.66 (m, 1H), 8.45 (m, 1H), 7.83 (m, 3H), 7.22-7.11 (m, 5H), 3.46 (m, 2H), 3.23 (s, 3H), 2.74-2.61 (m, 3H), 2.35 (m, 1H), 1.78-1.57 (m, 2H).

Example 356

Synthesis of Compound 419

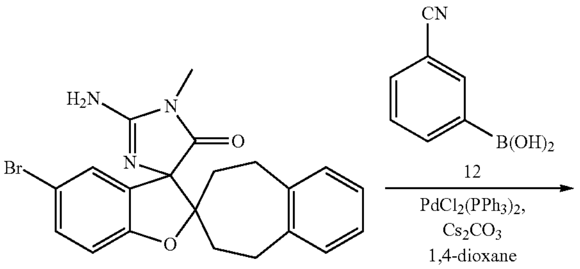

417

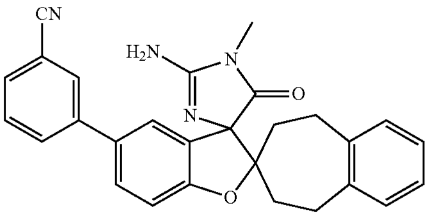

419

According to a similar synthesis of compound 418, compound 417 (20 mg, 0.047 mmol) was reacted with compound 12 (14 mg, 0.094 mmol) to give compound 419 (7.5 mg, 36%) as a white solid. LC-MS $t_R$=1.237 min in 2 min chromatography, MS (ESI) m/z 449.2 $[M+H]^+$. $^1H$ NMR ($CD_3OD$ 300

MHz): δ 7.96 (m, 2H), 7.77-7.59 (m, 4H), 7.14 (m, 5H), 3.46 (m, 2H), 3.21 (s, 3H), 2.69 (m, 3H), 2.33 (m, 1H), 1.74-1.53 (m, 2).

Example 357

Synthesis of Compound 420

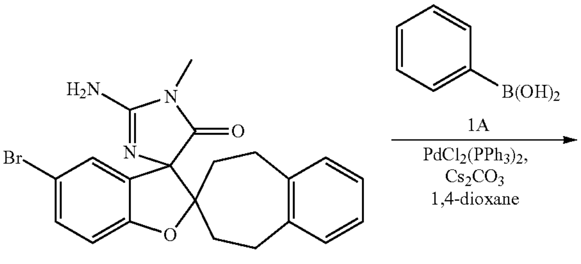

VT_B050409_01

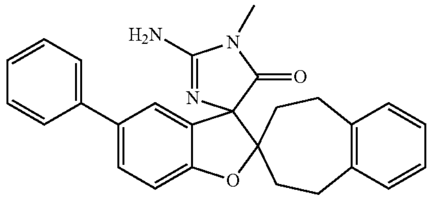

VT_B072209_06

According to a similar synthesis of compound 418, compound 417 (20 mg, 0.047 mmol) was coupled with compound 1A (12 mg, 0.094 mmol) to give compound 420 (6.1 mg, 30%) as a white solid. LC-MS $t_R$=1.265 min in 2 min chromatography, MS (ESI) m/z 424.1 $[M+H]^+$; $^1H$ NMR ($CD_3OD$ 300 MHz): δ 7.38-7.43 (m, 3H), 7.23-7.29 (m, 2H), 7.12-7.17 (m, 1H), 7.06-7.07 (s, 1H), 6.97 (s, 4H), 6.87-6.89 (d, J=8.1 Hz, 1H).

Example 358

Synthesis of Compound 421

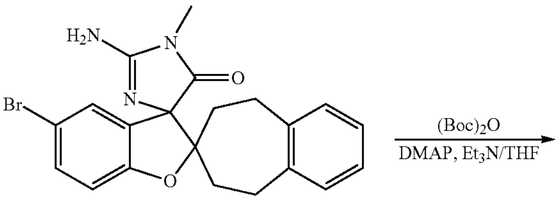

417

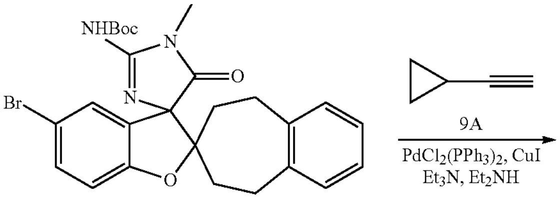

9

-continued

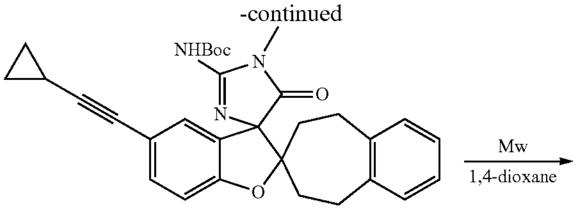

10

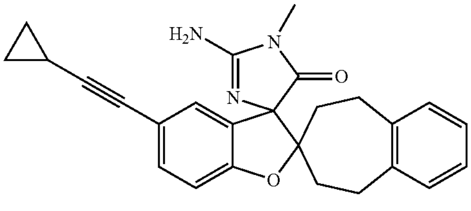

421

Procedure for Preparation of Compound 9

To a solution of compound 417 (50 mg, 0.12 mmol) in THF (3 mL) was added $(Boc)_2O$ (32 mg, 0.14 mmol), $Et_3N$ (14 mg, 0.14 mmol) and DMAP (5 mg, 0.04 mmol). The reaction mixture was stirred at room temperature overnight. The solvent was removed under reduced pressure, and the residue was purified by preparative TLC (petroleum ether:EtOAc=5:1) to give compound 9 (60 mg, 99%) as a white solid.

Procedure for Preparation of Compound 10

To a solution of compound 9 (60 mg, 0.11 mmol) in $Et_3N$ (5 mL) and $Et_2NH$ (1 mL) was added CuI (22 mg, 0.11 mmol) and $PdCl_2(PPh_3)_2$ (32 mg, 0.046 mmol) under a nitrogen atmosphere. The reaction mixture was sealed and 9A (75 mg, 0.11 mmol) was added and the reaction mixture was heated at 50° C. overnight. The solvent was removed under reduced pressure, and the residue was purified by preparative TLC (petroleum ether:EtOAc=4:1) to give compound 10 (38 mg, 65%) as a yellow solid. $^1$H NMR ($CDCl_3$ 300 MHz): δ 8.72 (s, 1H), 7.63 (s, 1H), 7.28 (m, 3H), 7.07 (m, 4H), 7.03 (s, 1), 6.82 (d, J=8.7 Hz, 1H), 3.79 (m, 2H), 3.02 (s, 3H), 2.58 (m, 3H), 2.14 (m, 1H) 1.63 (m, 2H), 1.48 (s, 9H), 1.32 (m, 1H), 0.37 (m, 2H), 0.71 (m, 2H).

Procedure for Preparation of Compound 421

Compound 10 (38 mg, 0.074 mmol) was dissolved in 1,4-dioxane (1 mL) and heated in a CEM microwave reactor at 120° C. for 15 min. The solvent was removed and the residue was purified by preparative RP-HPLC to afford compound 421 (12 mg, 40%) as a white solid. LC-MS $t_R$=1.257 min in 2 min chromatography, MS (ESI) m/z 412.1 $[M+H]^+$. $^1$H NMR ($CD_3OD$ 300 MHz): δ 7.38 (d, J=8.7 Hz, 2H), 7.13 (s, 4H), 6.96 (d, J=8.4 Hz, 1H), 3.46 (m, 2H), 3.20 (s, 3H), 2.65 (m, 3H), 2.23 (m, 1H), 1.66 (m, 2H), 1.48 (m, 1H), 0.88 (m, 2H), 0.71 (m, 2H).

Example 329

Synthesis of Compound 422

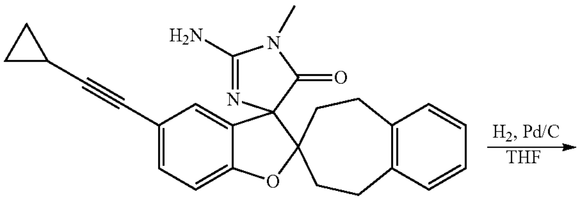

421

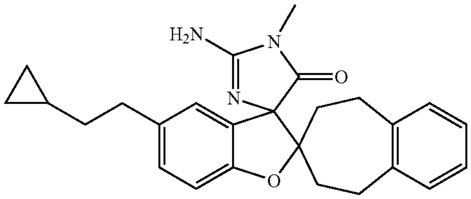

422

To a solution of compound 421 (10 mg, 0.0243 mmol) in THF (3 mL) was added Pd/C (10 mg). The reaction mixture was stirred under $H_2$ atmosphere at room temperature for 3 h. The solution was filtered and the filtrate was concentrated to give the residue, which was purified by preparative HPLC to afford compound 422 (3 mg, 30%) as a white solid. LC-MS $t_R$=1.305 min in 2 min chromatography, MS (ESI) m/z 416.2 $[M+H]^+$; $^1$H NMR ($CD_3OD$ 400 MHz): δ 7.22 (d, J=9.2 Hz, 1H), 7.13 (s, 5H), 6.91 (d, J=8.4 Hz, 1H), 3.33 (m, 2H), 3.17 (s, 3H), 2.63 (m, 5H), 2.26 (m, 1H), 1.63-1.42 (m, 4H), 0.66 (m, 1H), 0.49 (m, 2H), 0.01 (m, 2H).

Example 330

Synthesis of Compound 423

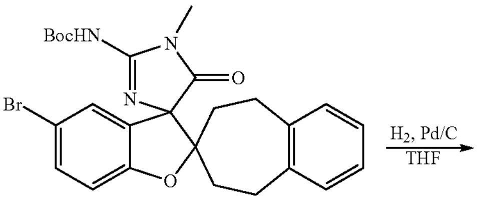

9

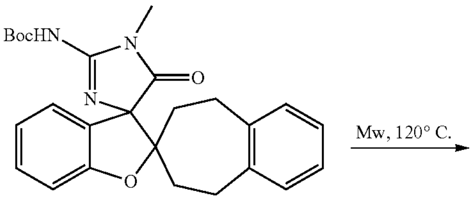

9A

-continued

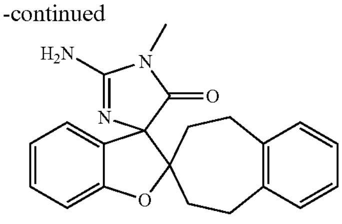

423

Procedure for Preparation of Compound 9A

To a solution of compound 9 (22 mg, 0.043 mmol) in MeOH (3 mL) was added Pd/C (10 mg). The reaction mixture was stirred under $H_2$ atmosphere at room temperature for 3 h. The solution was filtered and the filtrate was concentrated to give compound 9A (11 mg, 60%).

Procedure for Preparation of Compound 423

Compound 9A (11 mg, 0.024 mmol) was dissolved in 1,4-dioxane (1 mL) and heated in a CEM microwave reactor at 120° C. for 15 min. The solvent was removed and the residue was purified by preparative HPLC to afford compound 423 (3 mg, 19%) as a white solid. LC-MS $t_R$=1.145 min in 2 min chromatography, MS (ESI) m/z 348.1 $[M+H]^+$; $^1$H NMR ($CD_3OD$ 400 MHz): δ 7.31 (m, 1H), 7.17 (d, J=8.0 Hz, 1H), 7.07 (m, 4H), 6.92 (m, 2H), 3.22 (m, 2H), 3.09 (s, 3H), 2.56 (m, 3H), 2.18 (m, 1H), 1.53 (m, 2H).

Example 361

Synthesis of Compound 424

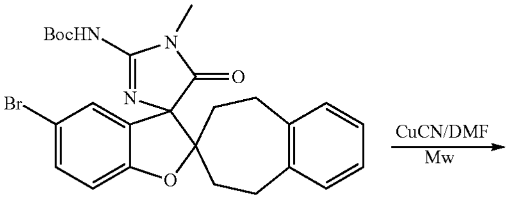

9

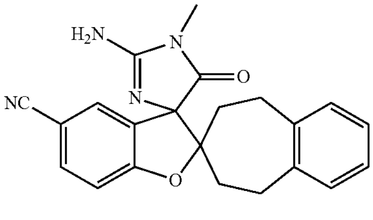

424

To a solution of compound 9 (30 mg, 0.057 mmol) in DMF (2 mL) was added CuCN (25 mg, 0.29 mmol) and $Pd(PPh_3)_2Cl_2$ (3 mg) under $N_2$. The reaction mixture was heated in a CEM microwave reactor at 150° C. for 1 h. Water (10 mL) was added and the mixture was extracted with EtOAc (10 mL×3). The organic layer was washed with water, brine, dried over $Na_2SO_4$ and concentrated. The residue was purified by preparative TLC to give compound 424 (3 mg, 14%) as a white solid. LC-MS $t_R$=1.148 min in 2 min chromatography, MS (ESI) m/z 373.1 $[M+H]^+$; $^1$H NMR ($CD_3OD$ 400 MHz): δ 7.83 (m, 2H), 7.16 (m, 5H), 3.43 (m, 2H), 3.28 (s, 3H), 2.74-2.58 (m, 3H), 2.29 (m, 1H), 1.27-1.56 (m, 2H).

Example I-12

Synthesis of hydantoin 6C

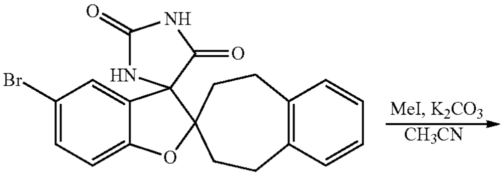

6

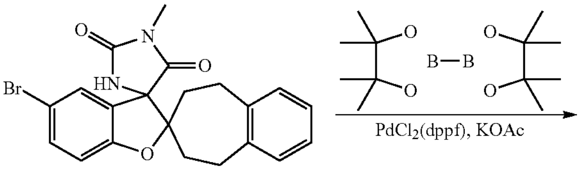

6A

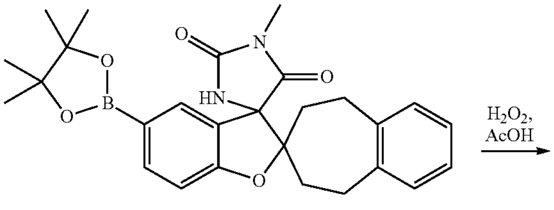

6B

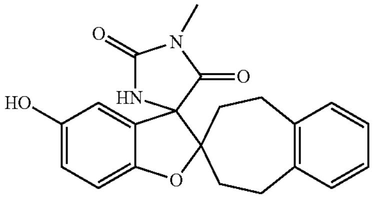

6C

Procedure for Preparation of Compound 6A

To a solution of compound 6 (820 mg, 1.99 mmol) in DMF (10 mL) and $CH_3CN$ (10 mL) was added compound $K_2CO_3$ (332 mg, 2.39 mmol) and MeI (0.18 mL, 2.99 mmol). The reaction mixture was stirred at room temperature for 2 h. $CH_3CN$ was removed and water (80 mL) was added, extracted with EtOAc (50 mL×3). The organic layer was washed with water, brine, dried over $Na_2SO_4$ and concentrated to give the residue, which was purified by chromatography (petroleum ether:EtOAc=10:1) to give compound 6A (650 mg, 77%).

Procedure for Preparation of Compound 6B

To a solution of compound 6A (560 mg, 1.526 mmol) in 1,4-dioxane (15 mL) was added 4,4,4',4',5,5,5',5'-octamethyl-2,2'-bi(1,3,2-dioxaborolane) (465 mg, 1.831 mmol), KOAc (449 mg, 4.578 mmol) and $PdCl_2(dppf)$ under $N_2$. The reaction mixture was heated at 100° C. in a CEM microwave reactor for 1 h. The solution was filtered and the filtrate was concentrated to give compound 6B (1 g, crude), which was used for the next step.

Procedure for Preparation of Compound 6C

To a solution of compound 6B (1 g, crude) in THF (80 mL) was added $H_2O_2$ (1.5 mL) and HOAc (5 mL). The reaction mixture was stirred at room temperature overnight. The reaction was quenched with $NaHSO_3$ solution (50 mL). After stirring for 30 min, the mixture was extracted with EtOAc (50 mL×3). The organic layer was washed with brine, dried over $Na_2SO_4$ and concentrated to give the residue which was purified by preparative TLC (petroleum ether: EtOAc=1:1) to afford compound 6C (400 mg with 50% purity).

Example 362

Synthesis of Compound 425

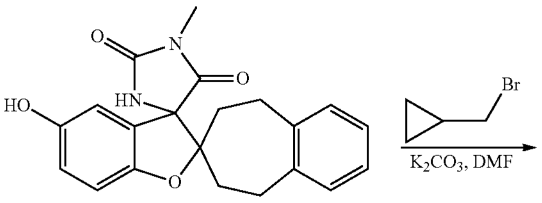

6C

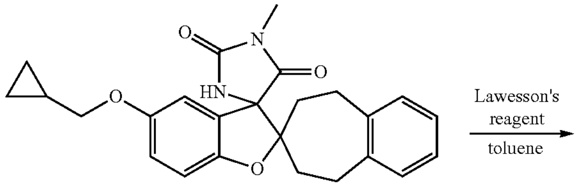

7

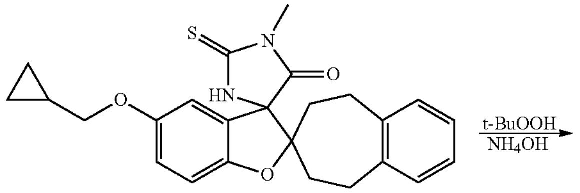

8

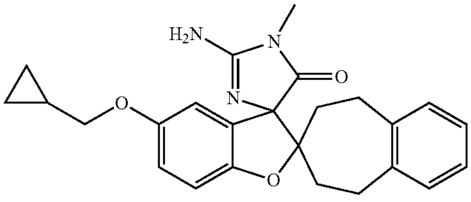

425

Procedure for Preparation of Compound 7

To a solution of compound 6C (150 mg, 0.206 mmol) in DMF (5 mL) was added $K_2CO_3$ (34 mg, 0.24 mmol) followed by (bromomethyl)cyclopropane (42 mg, 0.309 mmol). The reaction mixture was stirred at room temperature for 2 days. Water was added and the mixture was extracted with EtOAc (20 mL×2). The organic layer was washed with water, brine, dried over $Na_2SO_4$ and concentrated to give the residue which was purified by preparative TLC (petroleum ether:EtOAc=3:1) to afford compound 7 (40 mg, 47%) as a white solid. $^1H$ NMR ($CDCl_3$ 300 MHz): δ 7.18 (s, 4H), 6.81 (s, 2H), 6.51 (s, 1H), 5.07 (s, 1H), 3.64 (d, J=6.9 Hz, 2H), 3.40 (m, 2H), 2.96 (s, 3H), 2.57 (m, 3H), 2.08 (m, 1H), 1.53 (m, 1H), 1.48 (m, 1H), 1.15 (m, 1H), 0.53 (m, 2H), 0.25 (m, 2H).

Procedure for Preparation of Compound 8

To a solution of compound 7 (40 mg, 0.0957 mmol) in dry toluene (1 mL) was added Lawesson's reagent (58 mg, 0.143 mmol) under $N_2$. The reaction mixture was heated in a CEM microwave reactor at 130° C. for 60 min. The solvent was removed under reduced pressure, and the residue was purified by preparative TLC (petroleum ether:EtOAc=3:1) to give compound 8 (24 mg, 57%) as a white solid.

Procedure for Preparation of Compound 425

To a solution of compound 8 (24 mg, 0.055 mmol) in MeOH (3 mL) and $NH_3.H_2O$ (0.6 mL) was added t-BuOOH (162 mg, 1.11 mmol). The reaction mixture was stirred at room temperature overnight. LCMS showed the reaction was completed. The solvent was removed and the residue was purified by preparative HPLC to give compound 425 (9.0 mg, 39%) as a white solid; LC-MS $t_R$=1.231 min in 2 min chromatography, MS (ESI) m/z 418.1 $[M+H]^+$; $^1H$ NMR ($CD_3OD$ 400 MHz): δ 7.13 (m, 4H), 6.98 (m, 3H), 3.79 (d, J=6.8 Hz, 2H), 3.38 (m, 2H), 3.18 (s, 3H), 2.63 (m, 3H), 2.27 (m, 1H), 1.67-1.48 (m, 2H), 1.22 (m, 1H), 0.61 (m, 2H), 0.32 (m, 2H).

Example 363

Synthesis of Compound 426

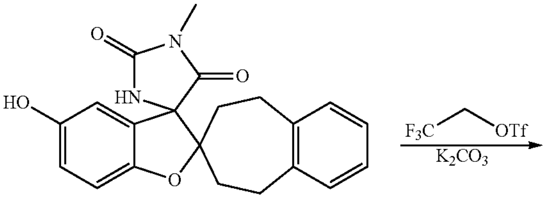

6C

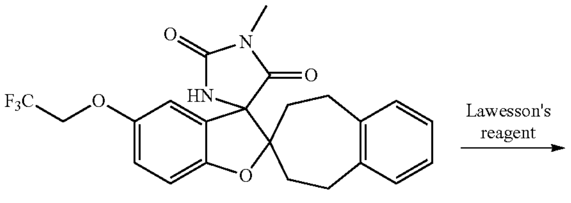

9

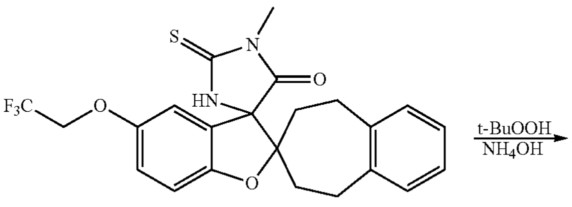

10

-continued

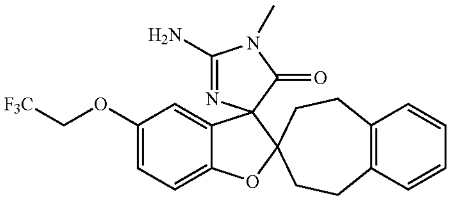

426

According to a similar synthesis of compound 425, compound 6C (100 mg, 0.137 mmol) was alkylated with 2,2,2-trifluoroethyl trifluoromethanesulfonate (96 mg, 0.412 mmol) to give compound 9 (35 mg, 81%) as a white solid. $^1$H NMR ($CDCl_3$ 400 MHz): δ 7.19 (s, 4H), 6.87 (s, 2H), 6.61 (s, 1H), 4.21 (m, 1H), 3.27 (m, 1H), 2.96 (s, 3H), 2.64-2.47 (m, 3H), 2.06 (m, 1H), 1.61 (m, 1H), 1.42 (m, 1H). Compound 9 (35 mg, 0.0783 mmol) was then reacted with Lawesson's reagent (47 mg, 0.117 mmol) under $N_2$ to give compound 10 (29 mg, 81%) as a white solid. Finally, compound 10 (29 mg, 0.063 mmol) was converted to compound 426 (8.0 mg, 29%) as a white solid. LC-MS $t_R$=1.241 min in 2 min chromatography, MS (ESI) m/z 446.2 [M+H]$^+$; $^1$H NMR ($CDCl_3$ 400 MHz): δ 7.05 (m, 6H), 6.94 (m, 1H), 4.39 (m, 1H), 3.31 (m, 2H), 3.12 (s, 3H), 2.62-2.47 (m, 3H), 2.21 (m, 1H), 1.62-1.41 (m, 2H). $^{19}$F NMR ($CD_3OD$ 19F 400 MHz): δ −70.293, −71.342

Example 364

Synthesis of Compound 427

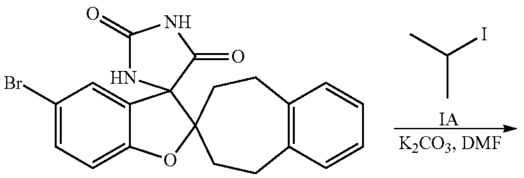

1

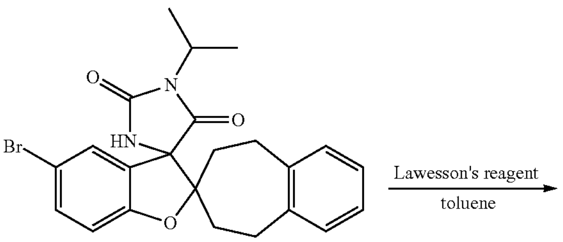

2

-continued

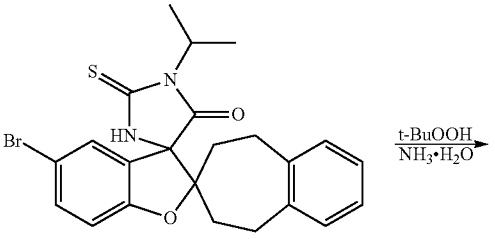

3

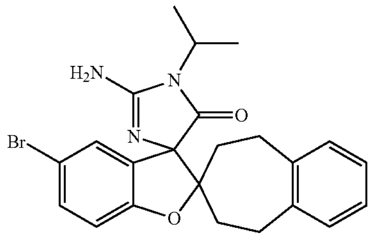

427

Procedure for Preparation of Compound 2

To a solution of compound 1 (100 mg, 0.243 mmol) in DMF (5 mL) was added $K_2CO_3$ (41 mg, 0.292 mmol) and 2-iodopropane (1A) (45 mg, 0.267 mmol). The reaction mixture was stirred at room temperature for 3 h. Water (15 mL) was added, and the mixture was extracted with EtOAc (10 mL×3). The organic layer was washed with water, brine, dried over $Na_2SO_4$ and concentrated to give the residue, which was purified by preparative TLC (petroleum ether: EtOAc=3:1) to give compound 2 (68 mg, 62%) as a white solid. $^1$H NMR ($CDCl_3$ 400 MHz): δ 7.35 (d, J=8.8 Hz, 1H), 7.06 (m, 5H), 6.79 (d, J=8.4 Hz, 1H), 4.23 (m, 1H), 3.25 (m, 2H), 2.66 (m, 2H), 2.48 (m, 1H), 2.06 (m, 1H), 1.59 (m, 1H), 1.43 (m, 1H), 1.32 (m, 6H).

Procedure for Preparation of Compound 3

To a solution of compound 2 (68 mg, 0.149 mmol) in dry toluene (2 mL) was added Lawesson's reagent (91 mg, 0.224 mmol) under $N_2$. The reaction mixture was heated in a CEM microwave reactor at 130° C. for 1 h. The solvent was removed under reduced pressure, and the residue was purified by preparative TLC (petroleum ether:EtOAc=3:1) to give compound 3 (46 mg, 66%) as a white solid.

Procedure for Preparation of Compound 427

To a solution of compound 3 (46 mg, 0.0977 mmol) in MeOH (3 mL) and $NH_3.H_2O$ (0.6 mL) was added t-BuOOH (286 mg, 1.95 mmol). The reaction mixture was stirred at room temperature overnight. LCMS showed the reaction was completed. The solvent was removed and the residue was purified by preparative HPLC to give compound 427 (13 mg, 30%) as a white solid. LC-MS $t_R$=1.278 min in 2 min chromatography, MS (ESI) m/z 454.0 [M+H]$^+$; $^1$H NMR ($CD_3OD$ 300 MHz): δ 7.55 (m, 2H), 7.14 (m, 4H), 6.98 (d, J=8.7 Hz, 1H), 4.26 (m, 1H), 3.39 (m, 1H), 3.28 (m, 1H), 2.77-2.53 (m, 3H), 2.24 (m, 1H), 1.63 (m, 2H), 1.49 (m, 6H).

Example 365

Synthesis of Compound 428

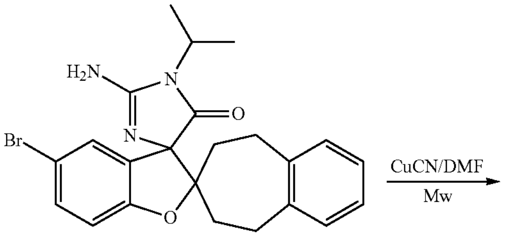

427

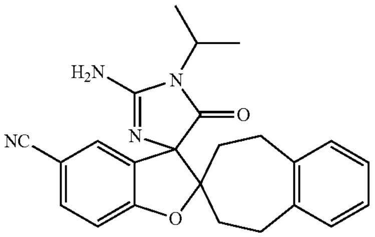

428

To a solution of compound 427 (30 mg, 0.066 mmol) in DMF (2 mL) was added CuCN (40 mg, excess) under $N_2$. The reaction mixture was heated in a CEM microwave reactor at 150° C. for 1 h. Water (10 mL) was added and the mixture was extracted with EtOAc (10 mL×3). The organic layer was washed with water, brine, dried over $Na_2SO_4$ and concentrated. The residue was purified by preparative TLC to give compound 428 (2.1 mg, 8%). LC-MS $t_R$=1.223 min in 2 min chromatography, MS (ESI) m/z 401.2 $[M+H]^+$; $^1H$ NMR ($CD_3OD$ 300 MHz): δ 7.81 (m, 2H), 7.18 (m, 5H), 4.26 (m, 1H), 3.45 (m, 2H), 2.78-2.57 (m, 3H), 2.26 (m, 1H), 1.74-1.53 (m, 2H), 1.49 (m, 6H).

Example I-13

Synthesis of (1s,4s)-ethyl 1'-amino-6'-bromo-4-methoxy-1',3'-dihydrospiro[cyclohexane-1,2'-indene]-1'-carboxylate (7)—Method 1

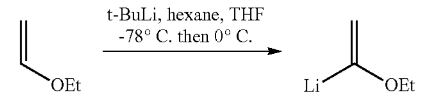

1 2

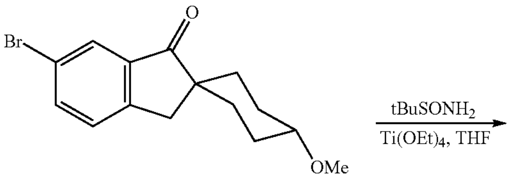

3

-continued

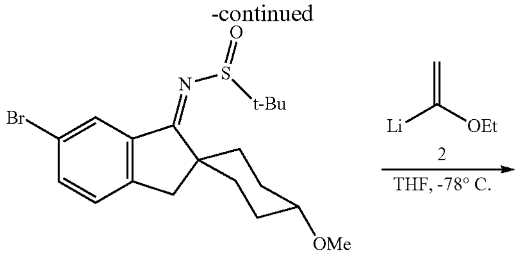

4

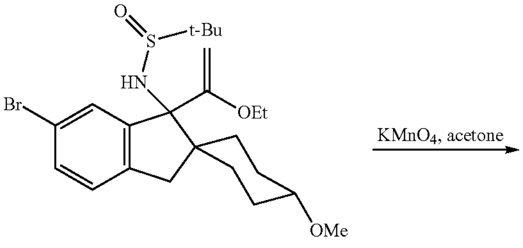

5

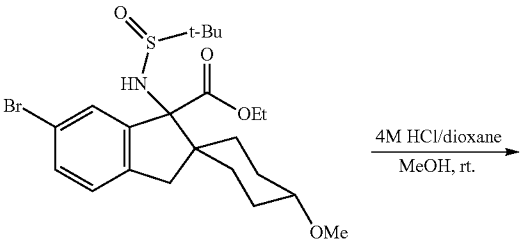

6

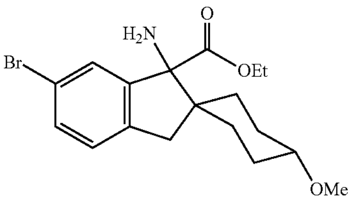

7

Step 1: Preparation of N-(5'-bromo-4-methoxyspiro[cyclohexane-1,2'-indene]-3'(1'H)-ylidene)-2-methylpropane-2-sulfinamide (4)

To a solution of 6'-bromo-4-methoxyspiro[cyclohexane-1,2'-inden]-1'(3'H)-one (3) (923 mg, 2.99 mmol) and 2-methylpropane-2-sulfinamide (1.450 g, 11.96 mmol, 4 eq.) in anhydrous THF (75 mL) was added $Ti(OEt)_4$ (5.46 g, 4.96 mL, 23.92 mmol, 8.0 eq). The resulting mixture was heated to reflux overnight. LC-MS showed ca. 45% conversion. After another 8 h, no further improvement. To the refluxing mixture was added 2-methylpropane-2-sulfinamide (0.725 g, 5.98 mmol, 2 eq.) and $Ti(OEt)_4$ (2.73 g, 2.5 mL, 11.96 mmol, 4.0 eq) and followed by another equal portions of 2-methylpropane-2-sulfinamide and $Ti(OEt)_4$ after 14 hours. The reaction mixture was refluxed for another 2 days, 93% conversion achieved at this point. The reaction was quenched with brine (3 mL) after cooled down to room temperature. The mixture was stirred for another 30 min before filtered through a short pad of Celite®. The filter cake was washed with EA, and the filtrate was concentrated to dryness. The residue was purified by silica gel chromatography. The fraction of desired product with 2-methylpropane-2-sulfinamide was dissolved in EA (100 mL) and washed with saturated aqueous $NaHCO_3$ (45 mL), 1 M NaOH (40 mL) and brine successively. Solvent was removed under reduced pressure after dried over $Na_2SO_4$ and filtered to afford 0.968 g of the desired product 4 as a light yellow solid. MS ESI+ve m/z 412 $(M+H)^{30}$.

Step 2: Preparation of N-(6'-bromo-1'-(1-ethoxyvinyl)-4-methoxy-1',3'-dihydrospiro[cyclohexane-1,2'-indene]-1'-yl)-2-methylpropane-2-sulfinamide (5)

To solution of ethyl vinyl ether (1) (269 mg, 357 μL, 3.73 mmol, 5 eq.) in dry THF (10 mL) chilled to −78° C. under $N_2$ was added 1.7 M t-BuLi in heptanes (1.75 mL, 2.98 mmol, 4 eq.) dropwise within 10 min. The temperature of the resulting yellow clear solution[1] was allowed to warm to 0° C. slowly within 30 min. By removing dry ice and adding water to dry ice-acetone bath, finally the cooling bath was replaced with a ice water bath. The color changed from yellow to nearly colorless after being stirred ca 5 min at 0° C. Then the lithium regent solution (2) was cooled to −78° C. again and cannulated to a solution of starting material 4 (307.5 mg, 0.746 mmol) in dry THF (5 mL) at −78° C. with positive pressure. The resulting mixture was stirred at this temperature for another 30 min. The reaction was quenched with saturated aqueous $NH_4Cl$ and extracted with ether and EA, the combined organic phases were washed with water and brine, dried, and filtered. The solvent was removed under reduced pressure to generate off-white foam, which was purified by flash chromatography on silica gel 9:1 eluted with EA in hexane (0-40%) to produce the desired product 5 and its diastereomers in a ratio (321 mg, yield 89%). MS ESI+ve m/z 484 $(M+H)^{30}$.

Step 3: Preparation of ethyl 6'-bromo-1'-(1,1-dimethylethylsulfinamido)-4-methoxy-1',3'-dihydrospiro[cyclohexane-1,2'-indene]-1'-carboxylate (6)

To a solution of N-(6'-bromo-1'-(1-ethoxyvinyl)-4-methoxy-1',3'-dihydrospiro[cyclohexane-1,2'-indene]-1'-yl)-2-methylpropane-2-sulfinamide (5) (200 mg, 0.48 mmol) in acetone (15 mL) at room temperature (23° C.) was added a $KMnO_4$ solution (5.8 mL, prepared by dissolving 9.5 g of $KMnO_4$ in 100 mL of $H_2O$). The mixture was stirred room temperature for 16 h. Another portion of $KMnO_4$ solution (2.2 mL) was added and stirred another 12 h. The reaction was quenched with 5% $NaHSO_3$, stirring until colorless clear solution achieved before combined. The combined organic phases were extracted with EA 2 times, washed with brine, dried over $Na_2SO_4$, evaporated after filtration. The residue was purified by flash chromatography on silica gel eluted with EA in hexane (0-60%) to afford the desired amino ester (6) (62.8 mg, 31%). MS ESI+ve m/z 486 $(M+H)^{30}$.

Step 4: Preparation of ethyl 1'-amino-6'-bromo-4-methoxy-1',3'-dihydrospiro[cyclohexane-1,2'-indene]-1'-carboxylate (7)

To a solution of ethyl 6'-bromo-1'-(1,1-dimethylethylsulfinamido)-4-methoxy-1',3'-dihydrospiro[cyclohexane-1,2'-indene]-1'-carboxylate (6) (62.8 mg, 0.129 mmol) in MeOH (5 mL) was added a 4 M HCl solution in dioxane (2 mL). The resulting mixture was stirred for 30 min. Solvent was removed under reduced pressure, and the residue 7 was used for next step without further purification. MS ESI+ve m/z 382 $(M+H)^{30}$.

Example I-14

Synthesis of (1s,4s)-ethyl 1'-amino-6'-bromo-4-methoxy-1',3'-dihydrospiro[cyclohexane-1,2'-indene]-1'-carboxylate (7)—Method 2

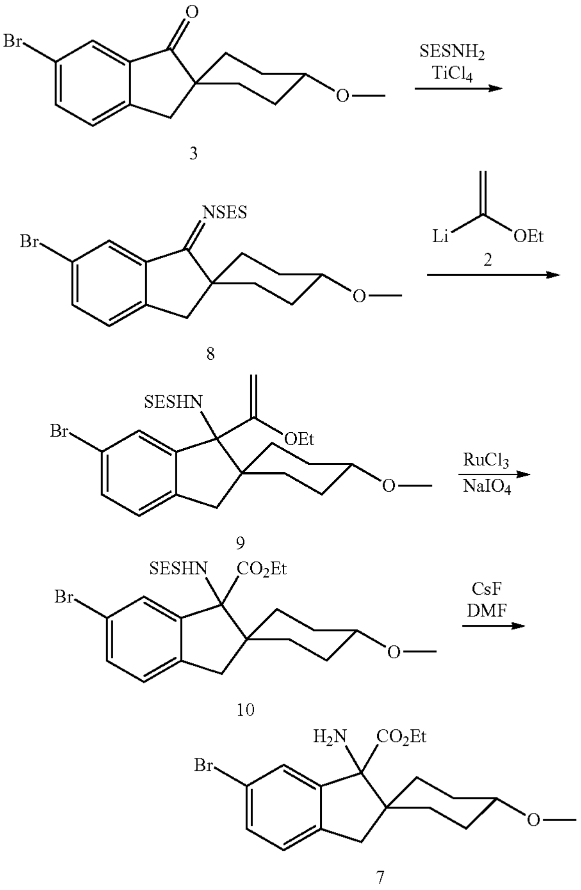

Step 1. N-(5'-bromo-4-methoxyspiro[cyclohexane-1,2'-indene]-3'(1'H)-ylidene)-2-(trimethylsilyl)ethanesulfonamide (8)

To a mixture of 6'-bromo-4-methoxyspiro[cyclohexane-1,2'-inden]-1'(3'H)-one (3) (0.9822 g, 3.18 mmol, 1.0 equiv) and 2-(trimethylsilyl)ethanesulfonamide) ($SESNH_2$) (0.6338 g, 3.50 mmol, 1.1 equiv) in $ClCH_2CH_2Cl$ (10 mL), cooled to 0° C., were successively added $Et_3N$ (0.9 mL, 6.46 mmol, 2.0 equiv) and $TiCl_4$ (1.0 M in $CH_2Cl_2$, 3.4 mL, 3.4 mmol, 1.1 equiv). After 10 min, the ice bath was removed. The reaction mixture was stirred at room temperature for 3 h and then heated at 110° C. for 42 h. The reaction mixture was cooled to room temperature, quenched with water, and extracted with $CH_2Cl_2$. The combined organic phase was dried ($Na_2SO_4$) and evaporated. The residue was purified by chromatography on silica gel eluted with hexanes/ethyl acetate to afford 1.3685 g (91%) of N-(5'-bromo-4-methoxyspiro[cyclohexane-1,2'-indene]-3'(1'H)-ylidene)-2-(trimethylsilyl)ethanesulfonamide (8) as a solid. LC-MS $t_R$=2.31 min in 3 min chromatography, m/z 472, 474 ($MH^+$); $^1H$ NMR (400 MHz, $CDCl_3$) δ 8.78 (br s, 1H), 7.67 (dd, J=8.2, 1.8 Hz, 1H), 7.29 (d, J=8.2 Hz, 1H), 3.39 (s, 3H), 3.29-3.21 (m, 3H), 2.98 (s, 2H), 2.16-2.12 (m, 2H), 1.80-1.76 (m, 2H), 1.62-1.57 (m, 2H), 1.42-1.33 (m, 2H), 1.21-1.17 (m, 2H), 0.10 (s, 9H); $^{13}C$ NMR (100 MHz, $CDCl_3$) δ 189.97, 151.30, 137.91, 133.35, 127.50, 121.43, 78.10, 55.80, 51.79, 51.39, 39.55, 33.97, 28.60, 9.98, −1.93.

Step 2. N-(6'-bromo-1'-(1-ethoxyvinyl)-4-methoxy-1',3'-dihydrospiro[cyclohexane-1,2'-indene]-1'-yl)-2-(trimethylsilyl)ethanesulfonamide (9)

To a solution of ethyl vinyl ether (7 mL, 73 mmol) in THF (10 mL) was added dropwise a solution of 1.7 M t-BuLi in pentane (26 mL, 44 mmol) at −78° C. under nitrogen. After 10 min, the reaction mixture was cooled in an ice bath and stirred for 45 min. To a solution of N-(5'-bromo-4-methoxyspiro[cyclohexane-1,2'-indene]-3'(1'H)-ylidene)-2-(trimethylsilyl)ethanesulfonamide (2) (1.3508 g, 2.86 mmol) in THF (20 mL) was added a solution of -ethoxyvinyllithium, obtained as described above, at −78° C. under nitrogen via a cannula. After 2 h, LC-MS indicated the disappearance of starting material. The reaction mixture was quenched with saturated $NaHCO_3$ (5 mL) and saturated brine (20 mL) and then vigorously stirred at room temperature for 1 h. The mixture was extracted three times with EtOAc. The combined organic layers were dried over $Na_2SO_4$, filtered and evaporated. The crude product 9 (1.7654 g) was directly used in the next step without further purification. LC-MS $t_R$=2.43 min in 3 min chromatography, m/z 544, 546 ($MH^+$), 480, 482.

Step 3. ethyl 6'-bromo-4-methoxy-1'-(2-(trimethylsilyl)ethylsulfonamido)-1',3'-dihydrospiro[cyclohexane-1,2'-indene]-1'-carboxylate (10)

To a solution of $NaIO_4$ (5.9503 g, 27.82 mmol) in water (40 mL) was added $RuCl_3$ hydrate (0.0526 g, 0.25 mmol) followed by a solution of crude N-(6'-bromo-β-(1-ethoxyvinyl)-4-methoxy-1',3'-dihydrospiro[cyclohexane-1,2'-indene]-1'-yl)-2-(trimethylsilyl)ethanesulfonamide (9) (1.0894 g), obtained as described above, in EtOAc (60 mL). The resulting mixture was vigorously stirred at room temperature for 30 min and LC-MS indicated the disappearance of starting material. The organic layer was separated and the aqueous layer was extracted twice with EtOAc. The combined organic layers was dried over $Na_2SO_4$, filtered and evaporated. The residue was purified by chromatography on silica gel eluted with hexanes/ethyl acetate to afford ethyl 6'-bromo-4-methoxy-1'-(2-(trimethylsilyl)ethylsulfonamido)-1',3'-dihydrospiro[cyclohexane-1,2'-indene]-1'-carboxylate (10) (0.5329 g, 50% in two steps). LC-MS $t_R$=2.27 min in 3 min chromatography, m/z 568, 570 ($MNa^+$), 333, 335; $^1H$ NMR (400 MHz, $CDCl_3$) δ 7.90 (s, 1H), 7.41 (d, J=7.9 Hz, 1H), 7.12 (d, J=8.2 Hz, 1H), 4.41-4.25 (m, 2H), 3.32 (s, 3H), 3.08-3.02 (m, 2H), 2.80 (d, J=15.8 Hz, 1H), 2.16-2.04 (m, 3H), 1.91-1.87 (m, 2H), 1.80-1.72 (m, 1H), 1.40-1.22 (m, 7H), 0.95-0.88 (m, 1H), 0.80-0.72 (m, 1H), 0.65-0.57 (m, 1H), −0.17 (s, 9H); $^{13}C$ NMR (100 MHz, $CDCl_3$) δ 170.13, 142.21, 140.91, 132.97, 132.25, 126.52, 119.45, 78.49, 75.10, 61.87, 55.79, 53.06, 50.92, 38.15, 28.64, 28.38, 28.33, 27.82, 14.18, 9.98, −2.28.

Step 4. ethyl 1'-amino-6'-bromo-4-methoxy-1',3'-dihydrospiro[cyclohexane-1,2'-indene]-1'-carboxylate (7)

A mixture of ethyl 6'-bromo-4-methoxy-1'-(2-(trimethylsilyl)ethylsulfonamido)-1',3'-dihydrospiro[cyclohexane-1,2'-indene]-1'-carboxylate (10) (0.2229 g, 0.41 mmol) and CsF (0.7893 g, 5.20 mmol) in DMF (2 mL) was heated at 110° C. for 24 h. The mixture was diluted with MeOH, and concentrated in vacuo. The residue was extracted with $Et_2O$, filtered through Celite® 545, and evaporated. The crude product was purified by reversed-phase HPLC (SunFire™ Prep $C_{18}$ OBD™ 5 μm 19×50 mm column, 10%→90% MeOH/$H_2O$, 0.1% $CF_3COOH$ over 8 min and then 90% MeOH/$H_2O$, 0.1% $CF_3COOH$ over 2 min, flow rate 20 mL/min) to afford ethyl 1'-amino-6'-bromo-4-methoxy-1',3'-dihydrospiro[cyclohexane-1,2'-indene]-1'-carboxylate (6) (165.8 mg, 82%) as a TFA salt; LC-MS $t_R$=1.17 min in 3 min chromatography, m/z 382, 384 (MH), 365, 367, 333, 335; $^1H$ NMR (400 MHz, $CD_3OD$) δ 7.47-7.45 (m, 2H), 7.22 (d, J=8.8 Hz, 1H), 4.18 (q, J=7.1 Hz, 2H), 3.27 (s, 3H), 3.14-3.07 (m, 2H), 2.96 (d, J=16.4 Hz, 1H), 2.00-1.97 (m, 2H), 1.55-1.52 (m, 2H), 1.46-1.21 (m, 4H), 1.14 (t, J=7.1 Hz, 3H); $^{13}C$ NMR (100 MHz, $CD_3OD$) δ 169.72, 143.43, 140.85, 134.40, 128.80, 128.11, 121.64, 79.44, 75.09, 64.34, 56.10, 52.49, 40.03, 31.05, 29.50, 29.44, 28.87, 14.24.

Example I-15

Chiral Synthesis of (1r,1'S,4S)-ethyl 1'-amino-6'-bromo-4-methoxy-1',3'-dihydrospiro[cyclohexane-1,2'-indene]-1'-carboxylate (14)

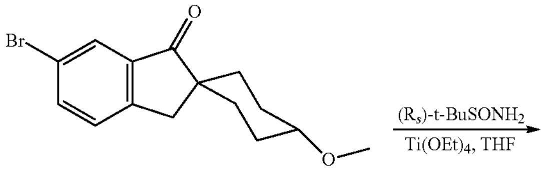

3

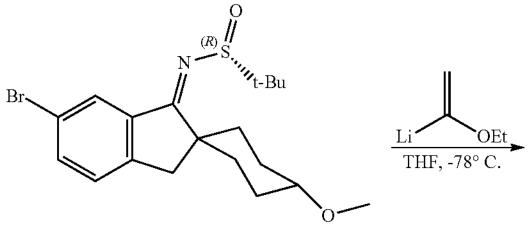

11

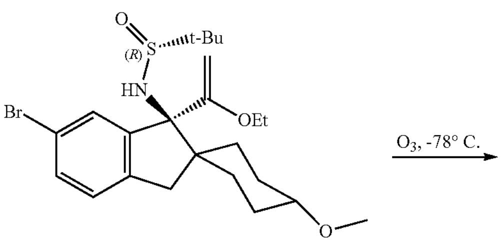

12

-continued

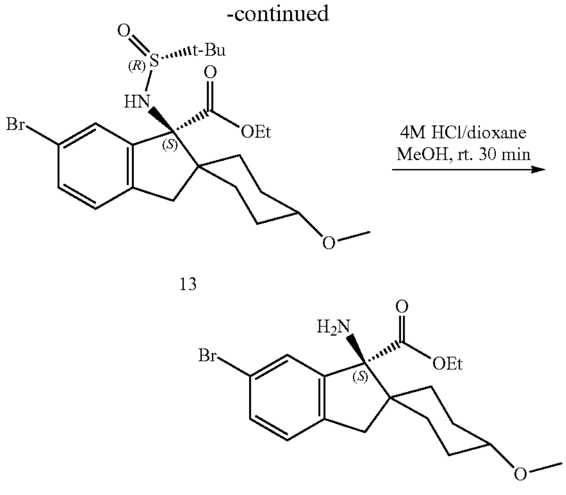

13

14

Procedure for Preparation of Compound 11

The titled compound was synthesized according to the method described in Example I-13 step 1, compound 11 in similar yield starting from compound 3 and ($R_S$)-tert-butylsulfinamide.

Procedure for Preparation of Compound 12

To a solution of compound ethoxy-ethene (7.25 g, 0.101 mol) in anhydrous THF (100 mL) at −78° C. under a $N_2$ atmosphere was added dropwise of t-BuLi (63 mL, 0.10 mol, 1.6 M in hexane) and stirred for 20 min. The resulting mixture was then stirred at 0° C. for another 45 min. To the solution obtained formerly at −78° C. was added dropwise of compound 11 (8.24 g, 0.02 mol) in anhydrous THF (300 mL) and stirred for 2.5 h. The reaction was quenched with sat. $NH_4Cl$ (50 mL) and extracted with ethyl acetate (3×50 mL). The organic phase was concentrated to give the residue which was purified by column on silica gel (petroleum/ethyl acetate=10/1) and further purified by preparative HPLC (basic) to give compound 12 (5.2 g, 65%) as a white solid. LC-MS $t_R$=1.351 min in 2 min chromatography, MS (ESI) m/z 484.1, 486.1 $[M+H]^+$. SFC: $t_R$=3.76 min in 15 min chromatography, ee=100%. $^1$H NMR ($CDCl_3$ 400 MHz): δ 7.82 (s, 1H), 7.37-7.39 (d, J=8.0 Hz, 1H), 7.07-7.09 (d, J=8.0 Hz, 1H), 4.33 (s, 1H), 4.31-4.32 (d, J=2.8 Hz, 1H), 4.22-4.23 (d, J=2.8 Hz, 1H), 3.80-3.87 (m, 2H), 3.35 (s, 3H), 3.04-3.09 (m, 1H), 2.96-2.99 (d, J=15.6 Hz, 1H), 2.56-2.60 (d, J=15.6 Hz, 1H), 2.04 (s, 1H), 1.86-1.94 (m, 2H), 1.73-1.81 (m, 2H), 1.34-1.37 (t, J=7.0 Hz, 3H), 1.27-1.16 (m, 3H), 1.00 (s, 9H).

Procedure for Preparation of Compound 13

Compound 12 (5.0 g, 10.33 mmol) was dissolved in $CH_2Cl_2$:MeOH=5:1 (100 mL) and pyridine (20 mL) was added, the mixture was chilled to −78° C. and ozone was bubbled through the mixture for 20 min, the mixture changed from colorless to blue, TLC showed that the reaction was completed. The mixture was purged with $N_2$ and treated with $Me_2S$ at −78° C., then allowed to warm to room temperature and stirred for 3 h. The solvent was removed in vacuo, the residue was purified by preparative TLC (petroleum/ethyl acetate=3/1) to give compound 13 (4.5 g, 90%) as a white solid and one portion of the crude product was further purified by preparative HPLC (basic) to give compound 3 (43.30 mg) as a white solid. LC-MS $t_R$=1.316 min in 2 min chromatography, MS (ESI) m/z 486.1, 488.1 $[M+H]^+$.SFC: $t_R$=4.37 min in 15 min chromatography, ee=100%. $^1$H NMR ($CD_3OD$ 400 MHz): δ 7.77-7.78 (d, J=1.6 Hz, 1H), 7.48-7.51 (dd, J=2.0, 8.0 Hz, 1H), 7.23-7.25 (d, J=8.0 Hz, 1H), 4.24-4.39 (m, 1H), 3.36 (s, 3H), 3.07-3.14 (d, J=27.2 Hz, 2H), 2.72-2.76 (d, J=15.6 Hz, 1H), 2.11-2.14 (m, 1H), 1.94-2.00 (m, 2H), 1.78-1.86 (m, 1H), 1.25-1.44 (m, 6H), 1.17 (s, 9H), 0.98-1.09 (m, 1H).

Procedure for Preparation of Compound 14

To a solution of compound 13 (4.5 g, 9.26 mmol) in MeOH (25 mL) was added a 4 M HCl solution in dioxane (10 mL). The resulting mixture was stirred for 30 min. LC-MS shown no starting material left and product was about 70% purity. Solvent was removed under reduced pressure to give crude product 14 (3.0 g, 85%) as a colorless oil; the residue was used for next step without further purification and one portion of the crude product was further purified by preparative HPLC (basic) to give 14 (39.70 mg) as a colorless oil. LC-MS $t_R$=0.894 min in 2 min chromatography, MS (ESI) m/z 404.1, 406.1 [M+Na]SFC: $t_R$=6.25 min in 15 min chromatography, ee=100%. $^1$H NMR ($CD_3OD$ 400 MHz): δ 7.48 (d, J=2.0 Hz, 1H), 7.37-7.40 (dd, J=2.0, 8.0 Hz, 1H), 7.16-7.18 (d, J=8.0 Hz, 1H), 4.12-4.19 (m, 1H), 3.37 (s, 3H), 3.14-3.22 (m, 1H), 2.92-3.03 (q, J=15.6 Hz, 14.0 Hz, 2H), 2.02-2.06 (m, 2H), 1.58-1.66 (m, 1H), 1.30-1.51 (m, 5H), 1.20-1.23 (t, J=7.2 Hz, 3H).

Example I-16

Chiral Synthesis of (1r,1'R,4R)-ethyl 1'-amino-6'-bromo-4-methoxy-1',3'-dihydrospiro[cyclohexane-1,2'-indene]-1'-carboxylate (18)

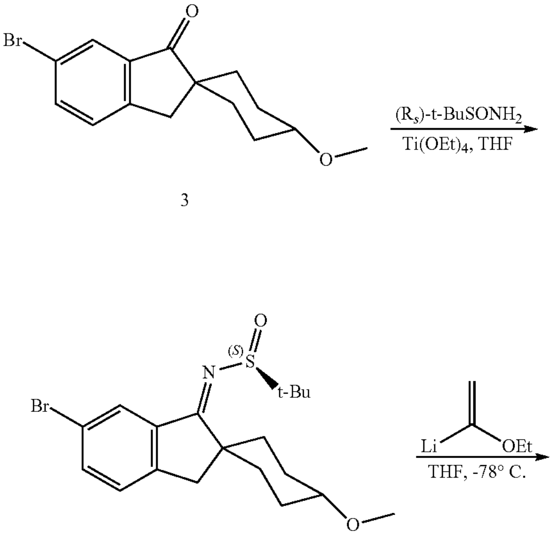

3

15

-continued

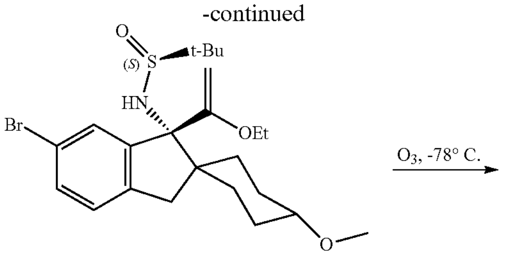

16

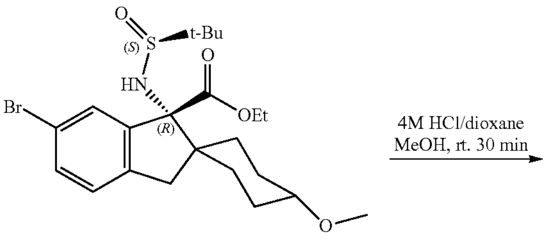

17

-continued

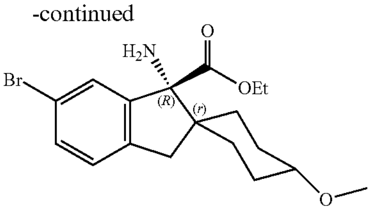

18

The titled compound was synthesized as described in Example I-15. LC-MS $t_R$=0.894 min in 2 min chromatography, MS (ESI) m/z 404.1, 406.1 $[M+Na]^+$. SFC: $t_R$=6.25 min in 15 min chromatography, ee=100%. $^1H$ NMR ($CD_3OD$ 400 MHz): δ 7.48 (d, J=2.0 Hz, 1H), 7.37-7.40 (dd, J=2.0, 8.0 Hz, 1H), 7.16-7.18 (d, J=8.0 Hz, 1H), 4.12-4.19 (m, 1H), 3.37 (s, 3H), 3.14-3.22 (m, 1H), 2.92-3.03 (q, J=15.6 Hz, 14.0 Hz, 2H), 2.02-2.06 (m, 2H), 1.58-1.66 (m, 1H), 1.30-1.51 (m, 5H), 1.20-1.23 (t, J=7.2 Hz, 3H).

Example I-17

Synthesis of Methyl 1'-amino-6'-bromo-4-methoxy-1',3'-dihydrospiro[cyclohexane-1,2'-indene]-1'-carboxylate

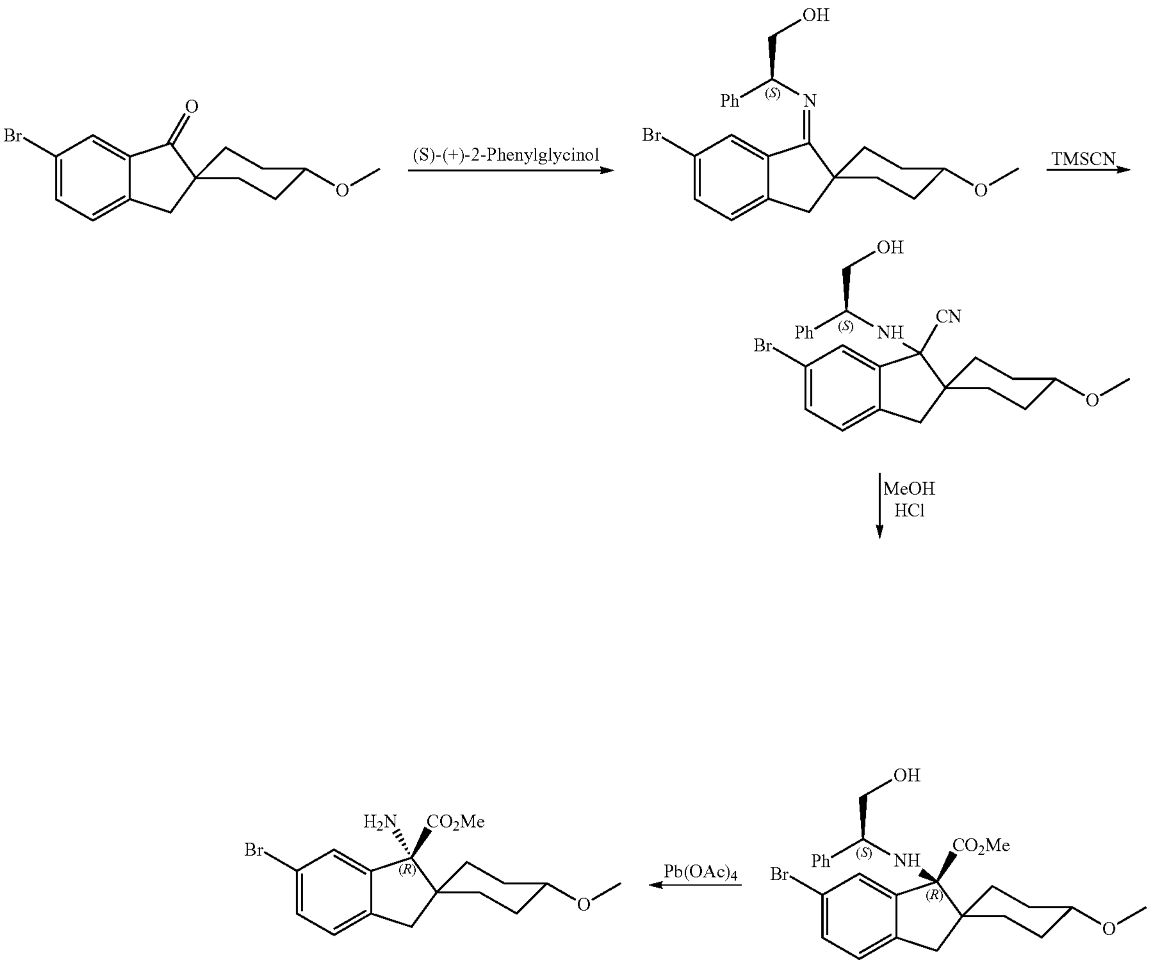

Step 1. Preparation of (S)-2-((5'-bromo-4-methoxyspiro[cyclohexane-1,2'-inden]-3'(1'H)-ylidene)amino)-2-phenylethanol A mixture of cis-6'-bromo-4-methoxyspiro[cyclohexane-1,2'-inden]-1'(3'H)-one (2.0105 g, 6.50 mmol), (S)-(+)-2-phenylglycinol (0.9290 g, 6.77 mmol), and p-TsOH monohydrate (0.0640 g, 0.34 mmol) in toluene was refluxed with a Dean-Stark trap for 2 d and LC-MS indicated about 70% conversion of starting material. After removal of the solvent at reduced pressure, the crude product was directly used in the next step without further purification. LC-MS $t_R$=1.27 min in 3 min chromatography, m/z 428, 430 ($MH^+$).

Step 2. Preparation of 6'-bromo-1'-(((S)-2-hydroxy-1-phenylethyl)amino)-4-methoxy-1',3'-dihydrospiro[cyclohexane-1,2'-indene]-1'-carbonitrile A solution of (S)-2-((5'-bromo-4-methoxyspiro[cyclohexane-1,2'-inden]-3'(1'1H)-ylidene)amino)-2-phenylethanol, obtained as described above, in dry $CH_2Cl_2$ (8 mL) was cooled with ice-water, and then TMSCN (1.8 mL, 13.5 mmol) and dry MeOH (3.6 mL) were added. The cooling bath was removed, and the reaction mixture was stirred at room temperature for 24 h. After removal of the solvent at reduced pressure, the crude product was directly used in the next step without further purification. LC-MS $t_R$=2.02 min in 3 min chromatography, m/z 455, 457 ($MH^+$)

Step 3. Preparation of methyl 6'-bromo-1'-(((S)-2-hydroxy-1-phenylethyl)amino)-4-methoxy-1',3'-dihydrospiro[cyclohexane-1,2'-indene]-1'-carboxylate The 6'-bromo-1'-(((S)-2-hydroxy-1-phenylethyl)amino)-4-methoxy-1',3'-dihydrospiro[cyclohexane-1,2'-indene]-1'-carbonitrile, obtained as described above, was dissolved in 40 mL of saturated methanolic HCl. The resulting mixture was heated at 100° C. for 18 h. The methanol was evaporated and the residue was diluted with ethyl acetate. The organic layer was washed with saturated $NaHCO_3$, water, and brine, respectively, and dried over $Na_2SO_4$. After removal of the solvent, the residue was purified by chromatography on silica gel eluted with hexanes/ethyl acetate to afford 0.2166 g (7%) of amino esters as a mixture of diastereomers, and recovered 1.5226 g (75%) of cis-6'-bromo-4-methoxyspiro[cyclohexane-1,2'-inden]-1'(3'H)-one.

The amino esters was further purified by reversed-phase HPLC (SunFire™ Prep $C_{18}$ OBD™ 5 μm 19×50 mm column, 10%→90% MeOH/$H_2O$, 0.1% $CF_3COOH$ over 8 min and then 90% MeOH/$H_2O$, 0.1% $CF_3COOH$ over 2 min, flow rate 20 mL/min) to afford methyl 6'-bromo-1'-(((S)-2-hydroxy-1-phenylethyl)amino)-4-methoxy-1',3'-dihydrospiro[cyclohexane-1,2'-indene]-1'-carboxylate as a TFA salt. LC-MS $t_R$=1.96 min in 3 min chromatography, $t_R$=9.49 (major), 9.99 (minor) min in 16 min chromatography as a ratio of (93:7), m/z 488, 490 ($MH^+$); $^1H$ NMR (400 MHz, $CD_3OD$) δ 7.21-6.95 (m, 8H), 4.17 (dd, J=10, 4 Hz, 1H), 3.94 (s, 3H), 3.65 (dd, J=11, 4 Hz, 1H), 3.45 (t, J=10 Hz, 1H), 3.34 (s, 3H), 3.18-3.01 (m, 3H), 2.29-2.15 (m, 2H), 1.93-1.85 (m, 2H), 1.39-1.27 (m, 3H), 0.99-0.93 (m, 1H).

Step 4. methyl 1'-amino-6'-bromo-4-methoxy-1',3'-dihydrospiro[cyclohexane-1,2'-indene]-1'-carboxylate To a solution of methyl 6'-bromo-1'-(((S)-2-hydroxy-1-phenylethyl)amino)-4-methoxy-1',3'-dihydrospiro[cyclohexane-1,2'-indene]-1'-carboxylate (0.0180 g, 0.03 mmol) in $CH_2Cl_2$ (3 mL) and MeOH (1.5 mL) was added $Pb(OAc)_4$ (0.0500 g, 0.11 mmol) at 0° C. The mixture was stirred for 2 h. After the solvents were evaporated under reduced pressure, the residue was purified by reversed-phase HPLC (SunFire™ Prep $C_{18}$ OBD™ 5 μm 19×50 mm column, 10%→90% MeOH/$H_2O$, 0.1% $CF_3COOH$ over 8 min and then 90% MeOH/$H_2O$, 0.1% $CF_3COOH$ over 2 min, flow rate 20 mL/min) to afford 0.0136 g (94%) of methyl 1'-amino-6'-bromo-4-methoxy-1',3'-dihydrospiro[cyclohexane-1,2'-indene]-1'-carboxylate as a TFA salt. LC-MS $t_R$=1.11 min in 3 min chromatography, m/z 368, 370 (MH), 351, 353, 319, 321; $^1H$ NMR (400 MHz, $CD_3OD$) δ 7.57-7.54 (m, 2H), 7.31 (d, J=8 Hz, 1H), 3.79 (s, 3H), 3.35 (s, 3H), 3.25-3.15 (m, 2H), 3.04 (d, J=16 Hz, 1H), 2.09-2.06 (m, 2H), 1.61-1.29 (m, 6H); $^{13}C$ NMR (100 MHz, $CD_3OD$) δ 170.36, 143.46, 140.64, 134.50, 128.89, 128.09, 121.70, 79.44, 75.22, 56.11, 54.06, 52.58, 39.97, 31.11, 29.52, 29.44, 28.88.

Example 366

Synthesis of Compound 429

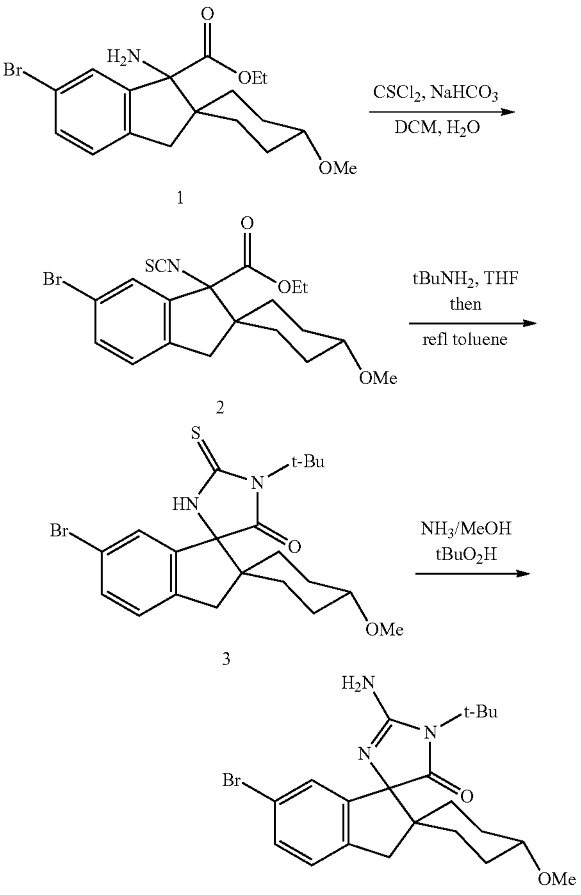

1

2

3

429

Step 1: Preparation of Isothiocyanide 2

Crude compound 1 (0.13 mmol) was added to a solution of $NaHCO_3$ (714 mg, 8.5 mmol) in $H_2O$ (10 mL) and DCM (1 mL) which was chilled at 0° C., to this stirred mixture was added thiophosgene (12 μL, 18.4 mg, 0.16 mmol) and stirred for 30 h at ° C., then another portion of thiophosgene (8 μL, 0.11 mmol). The reaction was diluted with DCM and the separated organic phase was washed with saturated brine and dried over anhydrous $Na_2SO_4$, and filtered, and concentrated to produce the desired product (1s,4s)-ethyl 6'-bromo-1'-isothiocyanato-4-methoxy-1',3'-dihydrospiro[cyclohexane-1,2'-indene]-1'-carboxylate (2) as an oil.

Step 2: Preparation of Thiohydantoin 3

To a solution of (1s,4s)-ethyl 6'-bromo-1'-isothiocyanato-4-methoxy-1',3'-dihydrospiro[cyclohexane-1,2'-indene]-1'-carboxylate (2) obtained in previous step in THF (3 mL) was added tert-butylamine (0.2 mL), and stirred for 12 h. The reaction was diluted with EA washed with 1 M HCl, brine, and dried over anhydrous $Na_2SO_4$, and filtered, and concentrated. The residue was dissolved in toluene (3 mL) and refluxed 2.5 h. The reaction mixture was concentrated to dryness. The residue was used for next step without further purification. The solvent was removed under reduced pressure and the residue was dissolved in DCM (2 mL) and hexane (2 mL) and evaporated to afford 209 mg of 6-bromo-β-methyl-2-phenyl-2'-thioxo-2',3'-dihydro-1'H-spiro [chroma N-4,4'-pyrimidin]-6'(5'H)-one (3) as a white foam. This product was used for next without further purification. MS ESI+ve m/z 451 $(M+H)^{30}$.

Step 3: Preparation of Acylguanidine 4

To the solution of above crude product in 7 M $NH_3$ solution in MeOH (8 mL) was added $tBuO_2H$ solution (5 M in nonane, 1 mL). The resulting mixture was stirred overnight before diluted with EA, then washed with 5% $NaHSO_3$, and brine successively, and dried over $Na_2SO_4$. Solvent was removed under reduced pressure, the residue was purified by preparative HPLC to afford the desired product 2.51 mg as TFA salt. MS ESI+ve m/z 434 $(M+H)^{30}$. $t_R$: 1.60 min. $^1H$ NMR (400 MHz, $CD_3OD$) δ: 7.51 (dd, J=8.4, 2.0, 1H), 7.41 (d, J=2.0 Hz, 1H), 7.28 (d, J=8.0 Hz, 1H), 3.35 (s, 3H), 3.18 (m, 1H), 3.12 (d, J=15.6 Hz, 1H), 3.05 (d, J=15.6 Hz, 1H), 2.08 (m, 1H), 2.00 (m, 1H), 1.68 (s, 9H), 1.48-1.27 (m, 5H).

Example 367

Synthesis of Compound 430

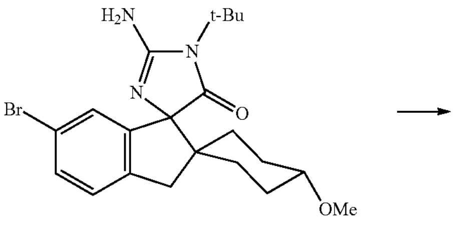

429

-continued

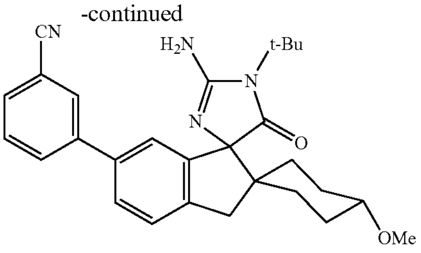

430

The title compound was made by the method described in example 27. MS ESI+ve m/z 457 $(M+H)^{30}$. $^1H$ NMR (400 MHz, $CD_3OD$) δ: 8.00 (s, 1H), 7.94 (d, J=8.0 Hz, 1H), 7.71-7.68 (m, 2H), 7.62 (t, J=8.0 Hz, 1H), 7.54 (d, J=1.6 Hz, 1H), 7.49 (d, J=8.0 Hz, 1H), 3.36 (s, 3H), 3.21 (d, J=15.6 Hz, 1H), 3.19 (m, 1H), 3.13 (d, J=15.6 Hz, 1H), 2.11 (m, 1H), 2.01 (m, 1H), 1.92 (m, 1H), 1.69 (s, 9H), 1.48-1.42 (m, 3H), 1.37-1.29 (m, 2H).

Example 368

Synthesis of Compound 431

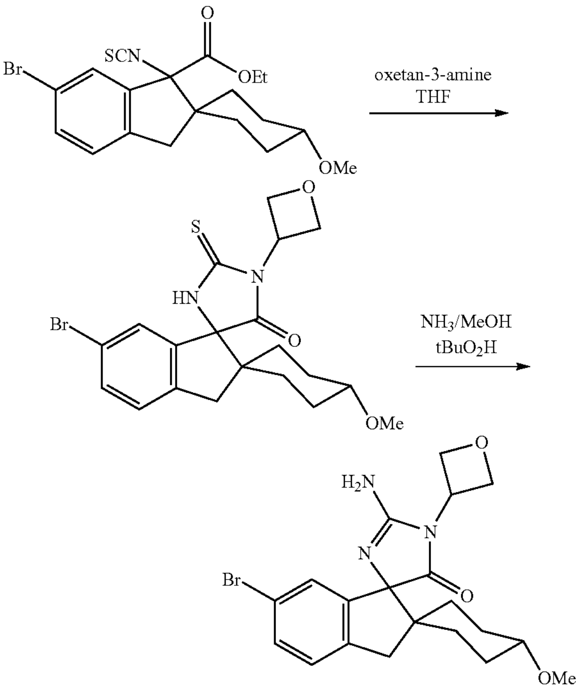

431

Step 1

A mixture of (1s,4s)-ethyl 6'-bromo-1'-isothiocyanato-4-methoxy-1',3'-dihydrospiro[cyclohexane-1,2'-indene]-1'-carboxylate (110 mg, 0.26 mmol) and oxetaN-3-amine (80 mg, 1.09 mmol) was stirred at room temperature for 2 h and concentrated to dry give the desired product. MS ESI+ve m/z 451 $(M+H)^{30}$.

Step 2

To the solution of above crude product (35 mg, 0.078 mmol) in 7 M $NH_3$ solution in MeOH (3 mL) was added $tBuO_2H$ solution (5 M in nonane, 0.6 mL). The resulting mixture was stirred overnight before diluted with EA, then washed with 5% $NaHSO_3$, and brine successively, and dried over $Na_2SO_4$. Solvent was removed under reduced pressure, the residue was purified by preparative HPLC to afford the desired product 6.3 mg as TFA salt. MS ESI+ve m/z 434 $(M+H)^{30}$. $t_R$: 1.24 min. $^1H$ NMR (400 MHz, $CD_3OD$) δ: 7.53 (d, J=8.0 Hz, 1H), 7.50 (s, 1H), 7.31 (d, J=8.0 Hz, 1H), 5.26 (m, 1H), 5.14 (m, 2H), 4.86 (m, 2H), 3.34 (s, 3H), 3.17 (d, J=16.0 Hz, 1H), 3.16 (m, 1H), 3.08 (d, J=16.0 Hz, 1H), 2.08 (m, 1H), 2.01 (m, 1H), 1.92 (m, 1H), 1.69 (s, 9H), 1.52 (dd, J=13.6, 3.6 Hz, 1H), 1.47-1.41 (m, 2H), 1.36-1.28 (m, 2H).

Example 369

Synthesis of Compound 432

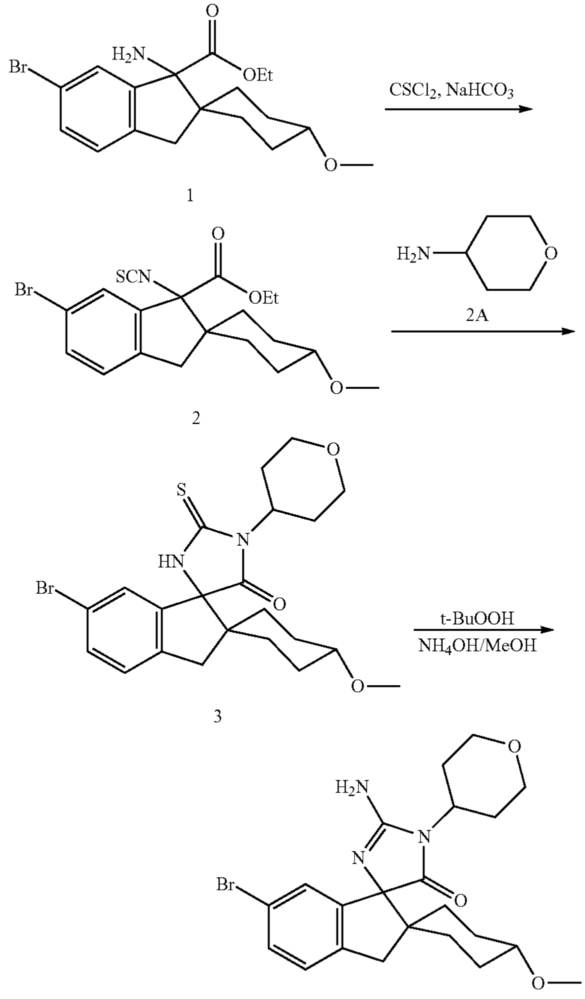

1, 2, 3, 432

General Procedure for Preparation of Compound 2

To compound 1 (200 mg, 0.523 mmol) was added $CH_2Cl_2$ (10 mL), $H_2O$ (10 mL) and $NaHCO_3$ (439 mg, 5.23 mmol). To this stirred mixture was added thiophosgene (144 mg, 1.26 mmol.) was added. The mixture was stirred for 50 min, LC-MS shown no starting material left. After extracted with $CH_2Cl_2$ (3×10 mL), washed with brine (2×10 mL), dried and solvent was removed under reduced pressure to give crude compound 2 (200 mg, 90%) as a yellow oil, which was used for next step without further purification.

General Procedure for Preparation of Compound 3

To a solution of compound 2 (50 mg, 0.118 mmol) in THF (5 mL) was added compound 2A (24 mg, 0.236 mmol). The mixture was stirred overnight at r.t., LC-MS showed the reaction was completed. The reaction was diluted with EtOAc (20 mL) and washed with 1 M HCl (2×5 mL) to remove excess amine, followed by saturated aqueous $NaHCO_3$ (2×10 mL) and brine (2×10 mL) washing. Solvent was removed after dried over $Na_2SO_4$ to give crude compound 3 (50 mg, 88%) as a yellow oil. The residue was used for next step without further purification.

Procedure for Preparation of Compound 432

To a solution of compound 3 (50 mg, 0.104 mmol) in MeOH (5 ml) and $NH_4OH$ (1 ml) was added a solution of $t\text{-}BuO_2H$ (289 mg, 2.09 mmol, 65% in water). The mixture was stirred overnight and evaporated to remove solvent. The residue was purified by preparative HPLC (basic) to give compound 432 (7.0 mg, 15%) as a white solid. LC-MS $t_R$=0.962 min in 2 min chromatography, MS (ESI) MS (ESI) m/z 462.1, 464.1 $[M+H]^+$. $^1H$ NMR ($CD_3OD$ 400 MHz): δ 7.41-7.43 (dd, J=1.6, 8.0 Hz, 1H), 7.23-7.25 (d, J=8.0 Hz, 1H), 7.13 (s, 1H), 3.99-4.08 (m, 3H), 3.43-3.49 (t, J=7.6 Hz, 2H), 3.36 (s, 3H), 3.14-3.17 (m, 1H), 3.00-3.08 (m, 2H), 2.38-2.58 (m, 2H), 1.89-2.05 (m, 3H), 1.56-1.63 (m, 3H), 1.29-1.43 (m, 4H).

Example 370

Synthesis of Compound 433

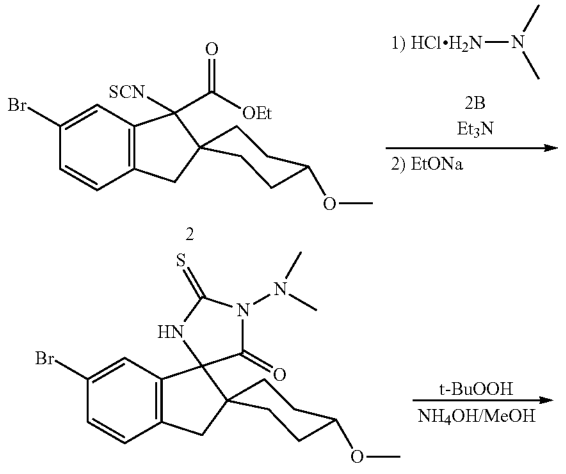

2, 4

-continued

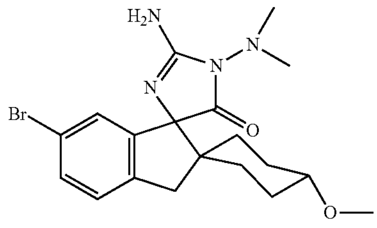

433

1. Procedure for Preparation of Compound 4

To a solution of compound 2 (50 mg, 0.118 mmol) in THF (5 mL) was added compound 2B (31 mg, 0.236 mmol) and $Et_3N$ (24 mg, 0.236 mmol). The mixture was stirred overnight at r.t., LC-MS showed only have intermediate, EtONa (16 mg, 0.236 mmol) was added, the mixture was stirred overnight at r.t., LC-MS showed the reaction completed, the reaction was diluted with EtOAc (20 mL) and washed with 1 M HCl (2×5 mL) to remove excess amine, followed by saturated aqueous $NaHCO_3$ (2×10 mL) and brine (2×10 mL) washing. Solvent was removed after dried over $Na_2SO_4$ to give crude compound 4 (50 mg, 97%) as a yellow oil. The residue was used for next step without further purification.

2. Procedure for Preparation of Compound 433

To a solution of compound 4 (50 mg, 0.114 mmol) in MeOH (5 ml) and $NH_4OH$ (1 ml) was added a solution of t-$BuO_2H$ (317 mg, 2.28 mmol, 65% in water). The mixture was stirred overnight and evaporated to remove solvent. The residue was purified by preparative HPLC (basic) to give compound 433 (10.0 mg, 22%) as a white solid. LC-MS $t_R$=0.971 min in 2 min chromatography, MS (ESI) m/z 421.1, 423.1 $[M+H]^+$. $^1H$ NMR ($CD_3OD$ 400 MHz): δ 7.40-7.42 (dd, J=1.6, 8.0 Hz, 1H), 7.23-7.25 (d, J=8.0 Hz, 1H), 7.10 (d, J=1.6 Hz, 1H), 3.35 (s, 3H), 3.11-3.20 (m, 1H), 2.98-3.09 (m, 2H), 2.87-2.91 (d, J=16.0 Hz, 6H), 1.92-2.06 (m, 3H), 1.64-1.71 (m, 1H), 1.28-1.42 (m, 4H).

Example 371

Synthesis of Compound 434

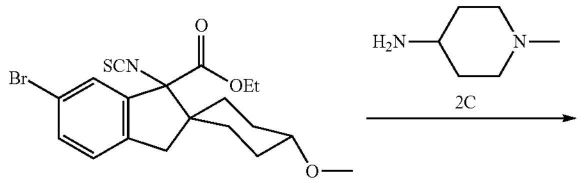

2

-continued

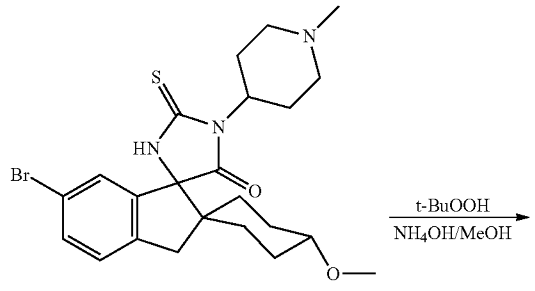

5

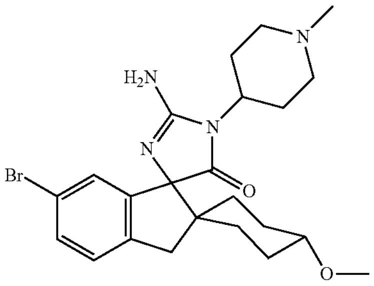

434

The titled compound as a white solid was synthesized as described in Example 369, starting from compound 2 and 1-methylpiperidin-4-amine. LC-MS $t_R$=0.717 min in 2 min chromatography, MS (ESI) m/z 475.2, 477.2 $[M+H]^+$. $^1H$ NMR ($CD_3OD$ 400 MHz): δ 7.40-7.42 (dd, J=2.0, 8.0 Hz, 1H), 7.22-7.24 (d, J=8.0 Hz, 1H), 7.10 (s, 1H), 3.87 (m, 1H), 3.35 (s, 3H), 3.14 (m, 1H), 3.02-3.04 (d, J=8.0 Hz, 2H), 2.96-2.98 (m, 2H), 2.43-2.61 (m, 2H), 2.29 (s, 3H), 1.89-2.16 (m, 6H), 1.56-1.70 (m, 3H), 1.26-1.42 (m, 3H).

Example 372

Synthesis of Compound 435

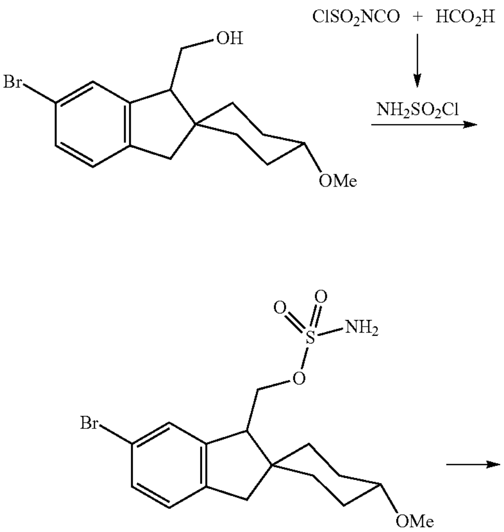

-continued

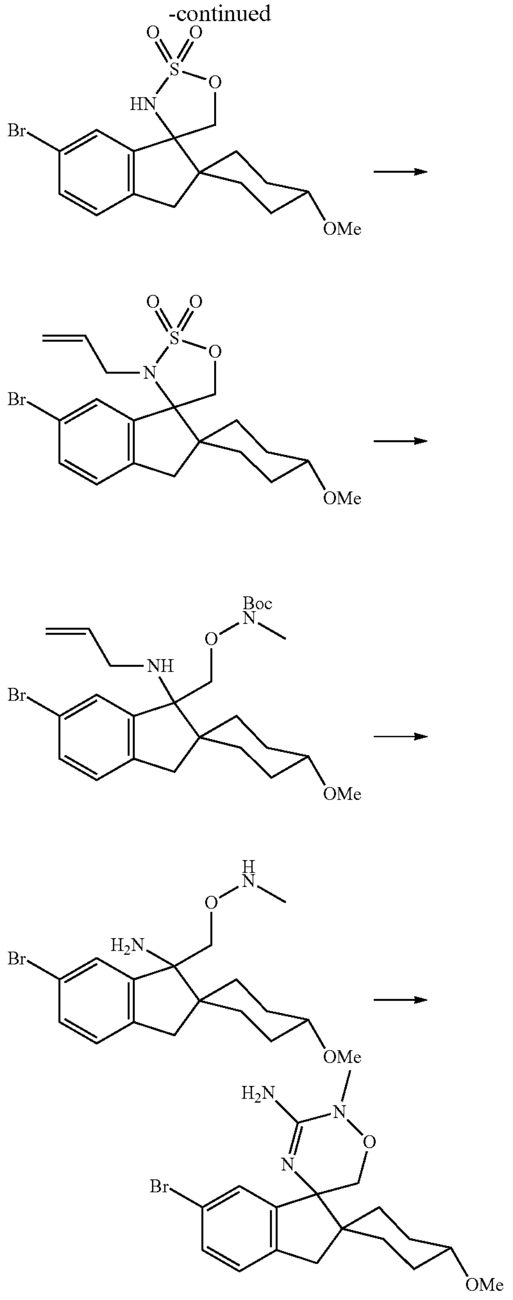

435

Step 1

To chlorosulfonyl isocyanate (1.6 mL, 2.60 g, 18.38 mmol) in toluene (8 mL) was added formic acid (0.69 mL, 846 mg, 18.38 mmol) dropwise. The mixture was stirred for 10 min at room temperature and concentrated to dry to afford sulfamoyl chloride, which was used without purification.

To a solution of alcohol (226 mg, 0.69 mmol) in N,N-dimethylacetamide (3 mL) at 0° C. under $N_2$ atmosphere was added sulfamoyl chloride (241 mg, 2.08 mmol, 3 eq.). The resulting mixture was stirred at room temperature overnight. The reaction was diluted with EA and washed with $H_2O$, and brine successively, and dried over $Na_2SO_4$, and filtered, and evaporated under reduced pressure to afford the crude product, which was used for next step without future purification.

Step 2

To a solution of above crude product in dry DCM (10 mL) under $N_2$ atmosphere was added MgO (64 mg, 1.59 mmol, 2.3 eq.), $Rh_2(OAc)_4$ (11 mg, 3.6 mmol %) and $PhI(OAc)_2$ (244 mg, 0.76 mmol, 1.1 eq.). The resulting mixture was stirred for 3 h at room temperature, then filtered through a short pad of $MgSO_4$ and washed with DCM. The filtrate was evaporated and residue was purified by silica gel column and eluted with EA/hexane (0-60%) to afford the desired product 168 mg as white solid.

Step 3

To a solution of above product (138 mg, 0.34 mmol) in DCM (8 mL) at room temperature was added allyl iodide (0.4 mL), $Bu_4NCl$ (16 mg, 0.058 mmol) and 40% NaOH (3 mL). The reaction mixture was extracted with DCM after stirred overnight. The organic phase was washed with $H_2O$, brine successively, and dried over anhydrous $Na_2SO_4$, and filtered, and concentrated to dryness to produce the desired product.

Step 4

To a solution of tert-butyl hydroxy(methyl)carbamate (600 mg, 4.08 mmol, prepared according the procedure described in *Org. Lett* 2007, 9, 4009) in anhydrous DMF (2.5 mL) at room temperature under $N_2$ atmosphere was added NaH (60%, 163 mg, 4.08 mmol). The mixture was stirred for 15 min, then a solution of above crude product in anhydrous DMF (1.5 mL) was added. The resulting mixture was stirred 16 h. The reaction was quenched with saturated aqueous $NH_4Cl$ and extracted with EA, the separated organic phase was washed with $H_2O$, brine successively, and dried over anhydrous $Na_2SO_4$, and filtered, and concentrated to dryness. The residue was used for next step without further purification. MS ESI+ve m/z 509 $(M+H)^{30}$.

Step 5

A solution of above product and $RhCl_3$ $nH_2O$ in EtOH (5 mL) was refluxed for 3 h and concentrated. The residue was dissolved in 20% TFA in DCM and stirred for 30 min. The reaction was concentrated and purified by preparative HPLC to afford the desire product as TFA salt. It was dissolved in DCM and washed with aqueous $NaHCO_3$ and bring, and dried over anhydrous $Na_2SO_4$, and filtered, and concentrated to dryness to afford 4.5 mg of the desire product as free amine. MS ESI+ve m/z 369 $(M+H)^{30}$.

Step 6

To a solution of above product (4.5 mg, 0.012 mmol) in EtOH (3 mL) was added a solution of cyanogen bromide (0.2 M in THF, 0.2 mL, 0.04 mmol). The resulting mixture was stirred overnight. The solvent was removed under reduced pressure. The residue was purified by preparative HPLC to afford the desire product as TFA salt. MS ESI+ve m/z 394 $(M+H)^{30}$. $t_R$: 1.31 min. $^1H$ NMR (400 MHz, $CD_3OD$) δ: 7.52 (d, J=1.6 Hz, 1H), 7.47 (dd, J=7.6, J=1.6 Hz, 1H), 7.22 (d, J=7.6 Hz, 1H), 4.56 (d, J=12.4 Hz, 1H), 4.09 (d, J=12.4 Hz, 1H), 3.43 (s, 3H), 3.35 (s, 3H), 3.17 (m, 1H), 3.06 (d, J=16.4

Hz, 1H), 2.85 (d, J=16.4 Hz, 1H), 2.04 (m, 2H), 1.70 (dd, J=13.6, 2.8 Hz, 1H), 1.61 (td, J=13.6, 4.0 Hz, 1H), 1.51-1.29 (m, 4H).

Example 373

Synthesis of Compound 436

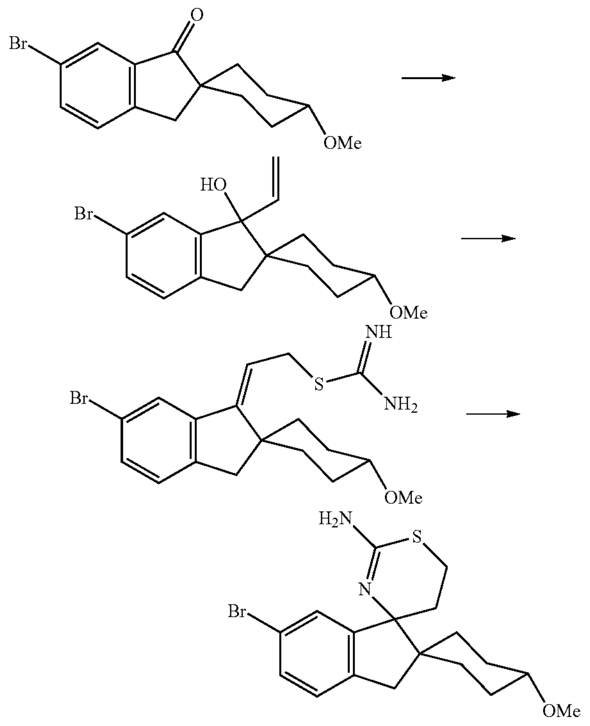

436

Step 1

To a solution of (1s,4s)-6'-bromo-4-methoxyspiro[cyclohexane-1,2'-inden]-1'(3'H)-one (353 mg, 1.14 mmol) in anhydrous THF (8 mL) at −78° C. was added a solution of vinylmagnesiun bromide in THF (1 M, 5.7 mL, 5.7 mmol) dropwise. The reaction temperature was allowed to warm to room temperature and stirred for another 1 h. The reaction was chilled to 0° C. and quenched with sat. aq. $NH_4Cl$ and extracted with ethyl ether (2×20 mL). The combined organic phases were washed with $H_2O$, brine, and dried over $Na_2SO_4$, and filtered. The filtrate was concentrated and the residue was purified through flash chromatography on silica gel to afford 320 mg of (1r,4r)-6'-bromo-4-methoxy-1'-vinyl-1',3'-dihydrospiro[cyclohexane-1,2'-inden]-1'-ol. MS ESI+ve m/z 319 (M+H—$H_2O$)'.

Step 2

The mixture of (1r,4r)-6'-bromo-4-methoxy-1'-vinyl-1',3'-dihydrospiro[cyclohexane-1,2'-inden]-1'-ol (162 mg, 0.48 mmol) and thiourea (55 mg, 0.72 mmol) in HOAc (3 mL) and 1 M HCl (1.2 mL) was stirred at room temperature for 20 min then 40° C. for 12 h. The solvents was removed under reduced pressure to give 252 mg of a mixture of 2-((1r,4r)-5'-bromo-4-methoxyspiro[cyclohexane-1,2'-inden]-3'(1'H)-ylidene)ethyl carbamimidothioate HCl salt and thiourea. It was used for next step without purification. MS ESI+ve m/z 395 (M+H)[30].

Step 3

Above mixture of 2-((1r,4r)-5'-bromo-4-methoxyspiro[cyclohexane-1,2'-inden]-3'(1'H)-ylidene)ethyl carbamimidothioate HCl salt and thiourea (98 mg, ca. 0.187 mmol) was dissolved in TFA (1.5 mL) contain $MeSO_3H$ (0.15 mL) and stirred at room temperature for 1 h. The solvent was removed under reduced pressure. The residue was dissolved in ethyl acetate and washed with sat $NaHCO_3$. The separated aqueous phase was extracted with ethyl acetate once and the combined organic phases were washed with brine, and dried over $Na_2SO_4$, and filtered. The filtrate was concentrated and the residue was purified by preparative HPLC to afford 69 mg of the desired product as TFA salt. MS ESI+ve m/z 395 (M+H)[30]. $t_R$: 1.25 min. $^1$H NMR (400 MHz, $CD_3OD$): 7.50-7.46 (m, 2H), 7.25 (d, J=7.2 Hz, 1H), 3.39-3.18 (m, 3H), 3.36 (s, 3H), 3.03 (d, J=16.4 Hz, 1H), 2.96 (d, J=16.4 Hz, 1H), 2.48 (m, 1H), 2.34 (m, 1H), 2.07 (m, 2H), 1.65-1.51 (m, 4H), 1.43-1.32 (m, 2H).

Example 374

Synthesis of Compound 437

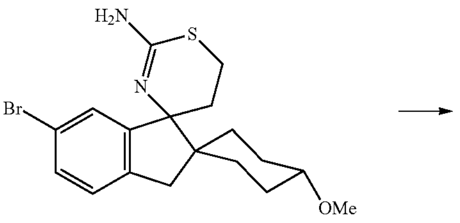

436

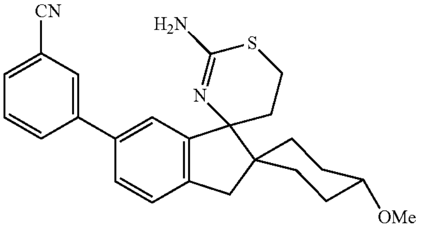

437

A mixture of compound 436 (15.9 mg, 0.03 mmol), 3-cyanophenylboronic acid (20 mg, 0.14 mmol), $Cs_2CO_3$ (60 mg, 0.18 mmol) and a catalytic amount of $PdCl_2(PPh_3)_2$ in 1,4-dioxane (3 mL) and $H_2O$ (0.2 mL) was heated at 110° C. in microwave oven for 15 min and 130° C. in microwave oven for another 10 min. 10 mL of water was added and extracted with EA, the separated organic phase was washed with brine, and dried over $Na_2SO_4$, and filtered. The filtrate was concentrated and the residue was purified through preparative HPLC to give the desired product. MS ESI+ve m/z 418 (M+H)[30]. $t_R$: 1.37 min. $^1$H NMR (400 MHz, $CD_3OD$): 8.00 (s, 1H), 7.94 (d, J=8.4 Hz, 1H), 7.10 (d, J=8.4 Hz, 1H), 7.67-7.58 (m, 2H), 7.57 (s, 1H), 7.46 (d, J=8.0 Hz, 1H), 3.38 (s, 3H), 3.36 (m, 1H), 3.23 (m, 2H), 2.5-2.44 (m, 2H), 2.10 (m, 2H), 2.07 (m, 2H), 1.66-1.56 (m, 4H), 1.45-1.39 (m, 2H).

Example 375

Synthesis of Compound 438

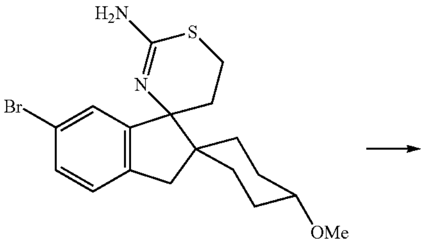

436

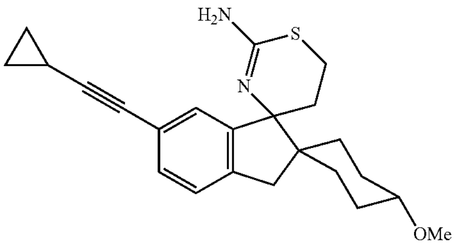

438

A mixture of compound 436 (41 mg, 0.08 mmol), $Cs_2CO_3$ (72 mg, 0.22 mmol) and a catalytic amount of $PdCl_2(PPh_3)_2$ in toluene (3 mL) was de-gased and purged with $N_2$ 3 times, then, followed by adding tributyl(cyclopropylethynyl)stannane (43 mg, 0.12 mmol). The resulting mixture was heated at 130° C. in microwave oven for 10 min. The reaction was diluted with EA, washed with aqueous CsF solution, and brine successively, and dried over $Na_2SO_4$, and filtered. The filtrate was concentrated and the residue was purified through preparative HPLC to give the desired product. MS ESI+ve m/z 381 $(M+H)^{30}$. $t_R$: 1.47 min. $^1H$ NMR (400 MHz, $CD_3OD$): 7.32 (d, J=8.4 Hz, 1H), 7.30-7.24 (m, 2H), 3.36 (s, 3H), 3.35-3.18 (m, 3H), 3.05 (d, J=16.4 Hz, 1H), 2.98 (d, J=16.4 Hz, 1H), 2.46 (m, 1H), 2.33 (m, 1H), 2.07 (m, 2H), 1.65-1.34 (m, 7H), 0.88 (m, 2H), 0.71 (m, 2H).

Example 376

Synthesis of Compound 439

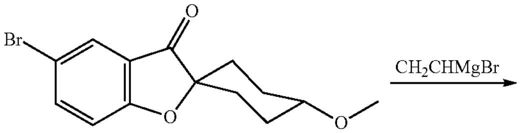

1

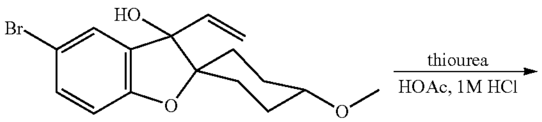

2

-continued

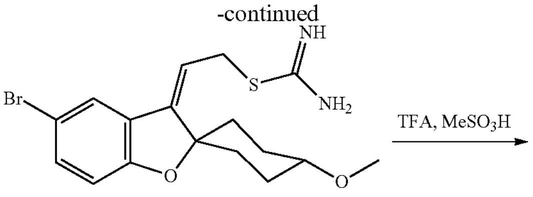

3

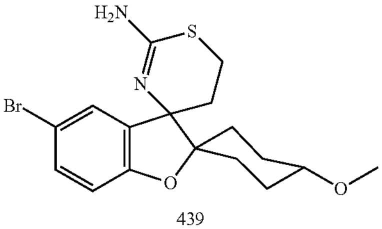

439

The titled compound was synthesized as described in Example 373 starting from compound 1. LC-MS $t_R$=0.772 min in 2 min chromatography, MS (ESI) m/z 397, 399 $[M+H]^+$. $^1H$ NMR ($CD_3OD$ 400 MHz): δ 7.53 (d, J=2.0 Hz, 1H), 7.42 (dd, J=2.0, 8.4 Hz, 1H), 6.83 (d, J=8.4 Hz, 1H), 3.27-3.37 (m, 6H), 2.49-2.60 (m, 2H), 2.00-2.10 (m, 2H), 1.40-1.47 (m, 1H), 1.52-1.69 (m, 5H).

Example 377

Synthesis of Compound 440

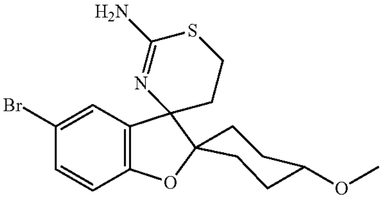

+

1

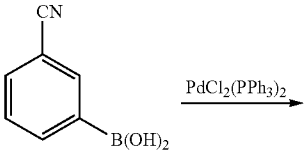

1A

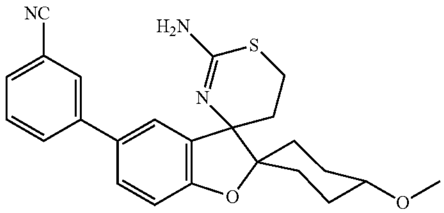

440

A solution containing compound 1A (19 mg, 0.126 mmol) and compound 1 (50 mg, 0.126 mmol) in 1,4-dioxane (3.2 mL), and aqueous $Cs_2CO_3$ (2 M, 1.5 mL) was deoxygenated by bubbling a stream of nitrogen through the reaction mixture for 5 min. Then, $PdCl_2(PPh_3)_2$ (5 mg, 0.006 mmol) was added. The reaction vial was sealed and placed into CEM microwave reactor and irradiated at 120° C. for 35 min. TLC showed that the reaction was completed. The reaction mixture was concentrated in vacuo and the residue was purified by preparative TLC (hexane: EtOAc=5:1) and preparative HPLC to give product compound 440 (1.0 mg, 2%) as a white solid. LC-MS $t_R$=0.965 min in 2 min chromatography, MS (ESI) m/z 420 $[M+H]^+$. $^1H$ NMR ($CDCl_3$ 400 MHz): δ 7.69 (m, 2H), 7.52 (d, J=7.6 Hz, 1H), 7.45 (m, 1H), 7.35 (d, J=7.6 Hz, 1H), 7.24 (s, 1H), 6.86 (d, J=8.4 Hz, 1H), 3.32 (s, 3H), 3.10-3.20 (m, 2H), 2.98-3.10 (m, 1H), 1.94-2.03 (m, 4H), 1.59-1.77 (m, 5H), 1.18 (m, 1H).

Example 378

Synthesis of Compound 441

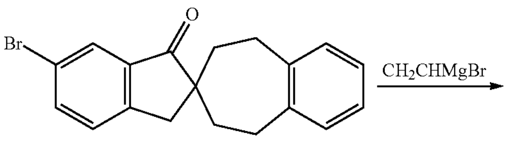

1

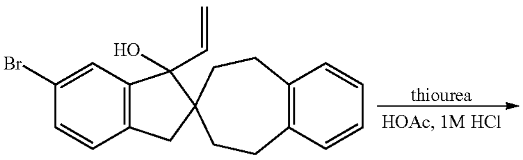

2

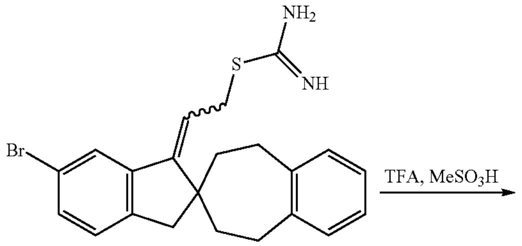

3

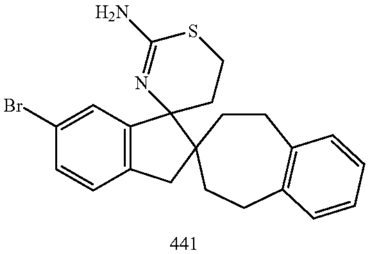

441

The titled compound was synthesized as described in Example 373 starting from compound 1. LC-MS $t_R$=0.923 min in 2 min chromatography, MS (ESI) m/z 427, 429 $[M+H]^+$. $^1H$ NMR ($CD_3OD$ 400 MHz): δ 7.46 (dd, J=1.6, 8.0 Hz, 1H), 7.41 (d, J=1.2 Hz, 1H), 7.25 (d, J=8.0 Hz, 1H), 7.03 (m, 4H), 3.18 (m, 2H), 3.11 (m, 2H), 2.92-3.02 (m, 2H), 2.63 (m, 2H), 2.42 (m, 1H), 2.27 (m, 1H), 1.77 (m, 2H), 1.40-1.50 (m, 2H).

Example 379

Synthesis of Compound 442

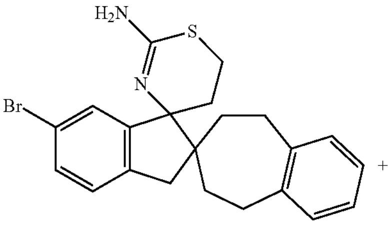

1

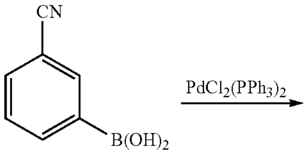

1A

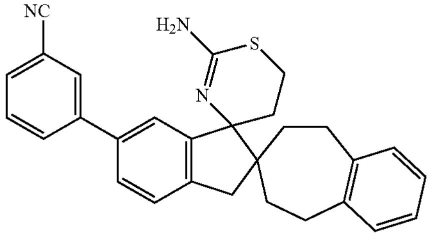

442

The titled compound was synthesized as described in Example 377, in 26% yield starting from compound 1 and 1A. LC-MS $t_R$=1.121 min in 2 min chromatography, MS (ESI) m/z 450 $[M+H]^+$. $^1H$ NMR ($CD_3OD$ 400 MHz): δ 8.04 (s, 1H), 7.98 (d, J=8.0 Hz, 1H), 7.74 (t, J=8.0 Hz, 2H), 7.66 (t, J=8.0 Hz, 1H), 7.62 (s, 1H), 7.55 (d, J=8.0 Hz, 1H), 7.15 (m, 4H), 3.41 (m, 2H), 3.27 (m, 2H), 3.06-3.16 (m, 2H), 3.74 (m, 2H), 3.48-3.61 (m, 2H), 1.94 (m, 2H), 1.55-1.66 (m, 2H).

Example 380

Synthesis of Compounds 443 and 444

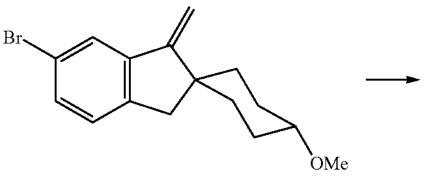

-continued

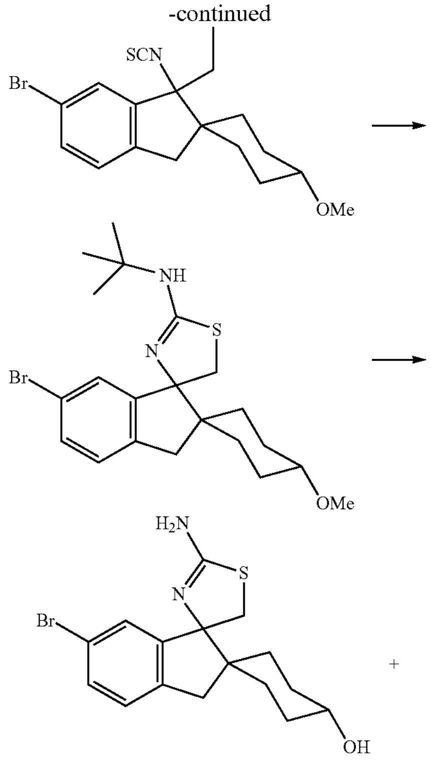

443

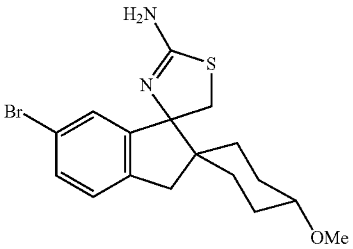

444

Step 1

To a solution of (1s,4s)-6'-bromo-4-methoxy-1'-methylene-1',3'-dihydrospiro[cyclohexane-1,2'-indene] (10.3 mg, 0.034 mmol), $I_2$ (20 mg, 0.104 mmol) in DCM (2 mL) was added KSCN (16.5 mg, 0.17 mmol), catalytic amount of tetrabutylammonium chloride and $H_2O$ (0.1 mL). The mixture was stirred at room temperature overnight and quenched with 10% $NaHSO_3$ and extracted with DCM once. The separated organic phase was washed with brine, and dried over $Na_2SO_4$, and filtered. The filtrate was concentrated to generate the crude product (1r,4r)-6'-bromo-1'-(iodomethyl)-1'-isothiocyanato-4-methoxy-1',3'-dihydrospiro[cyclohexane-1,2'-indene], which was used for next step without further purification.

Step 2

To a solution of above crude product in THF (3 mL) was added tert-butylamine (5 mg, 7 μL, 0.068 mmol). The mixture was stirred overnight at room temperature and concentrated. The residue was purified by preparative HPLC to give 8 mg of the desired product. MS ESI+ve m/z 437 $(M+H)^{30}$.

Step 3

Above product in concentrated HCl (2 mL) was refluxed for 60-90 min. The reaction was cool to room temperature and diluted with EA, neutralized with $K_2CO_3$, washed with brine, and dried over $Na_2SO_4$, and filtered. The filtrate was concentrated and the residue was purified by preparative HPLC to give 1.7 mg of compound 443 and 3 mg of compound 444. Compound 443: MS ESI+ve m/z 367 $(M+H)^{30}$. $t_R$: 1.07 min. $^1H$ NMR (400 MHz, $CD_3OD$): 7.70 (d, J=2.0 Hz, 1H), 7.50 (dd, J=8.0, 2.0 Hz, 1H), 7.25 (d, J=8.0 Hz, 1H), 4.05 (d, J=12.4 Hz, 1H), 3.64 (d, J=12.4 Hz, 1H), 3.54 (m, 1H), 3.03 (d, J=16.4 Hz, 1H), 2.97 (d, J=16.4 Hz, 1H), 1.92 (m, 2H), 1.64 (m, 2H), 1.54-1.42 (m, 4H).

Compound 444

MS ESI+ve m/z 381 $(M+H)^{30}$. $t_R$: 1.27 min. $^1H$ NMR (400 MHz, $CD_3OD$): 7.70 (d, J=2.0 Hz, 1H), 7.50 (dd, J=8.0, 2.0 Hz, 1H), 7.25 (d, J=8.0 Hz, 1H), 4.05 (d, J=12.4 Hz, 1H), 3.65 (d, J=12.4 Hz, 1H), 3.36 (s, 3H), 3.20 (m, 1H), 3.02 (d, J=16.4 Hz, 1H), 2.97 (d, J=16.4 Hz, 1H), 2.06 (m, 2H), 1.67-1.62 (m, 2H), 1.54-1.52 (m, 2H), 1.40-1.33 (m, 2H).

Example 381

Synthesis of Compound 445

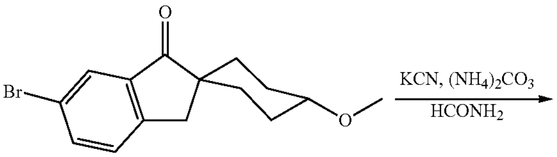

1A

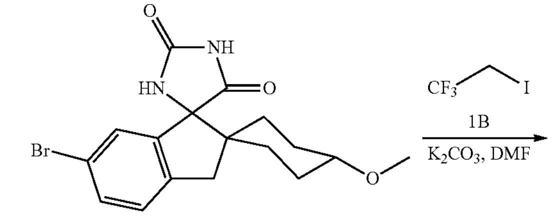

1

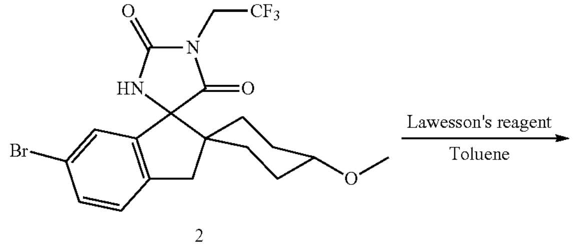

2

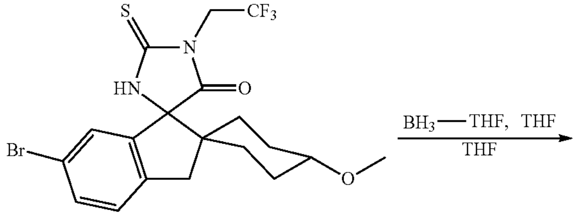

3

-continued

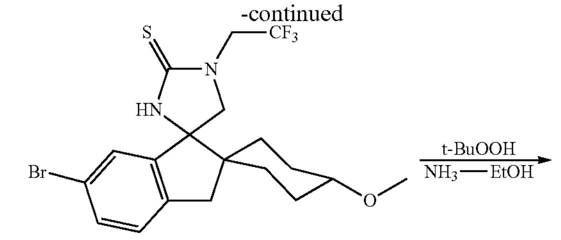

4

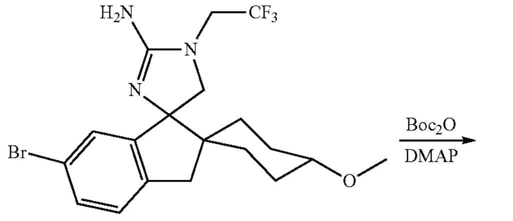

5

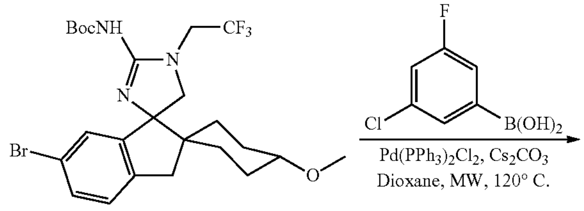

6

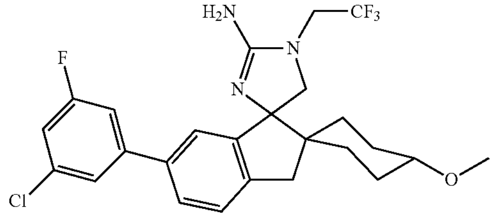

445

Procedure for Preparation of Compound 1

A steel autoclave was charged with a mixture of compound 1A (3.0 g, 9.7 mmol), KCN (1.4 g, 21.5 mmol) and $(NH_4)_2CO_3$ (9.5 g, 98.9 mmol) in formamide (60 mL). The mixture was heated at 120° C. for 72 h. The reaction mixture was then cooled and poured onto ice, then was extracted with ethyl acetate:isopropanol=3:1 (200 mL×3). The combined organic fractions were washed with brine (200 mL×2). The separated organic phase was dried over $Na_2SO_4$ and concentrated in vacuo. The residue was washed with a mixed solvent of petroleum ether:ethyl acetate=10:1 (50 mL×2) to give compound 1 (2.4 g, 68%) as a yellow solid with 70% purity on LC-MS, which was used for the next step without purification. LC-MS: $t_R$=1.69 min in 3 min chromatography, MS (ESI) m/z=379.25 $[M+H]^+$.

Procedure for Preparation of Compound 2

A steel autoclave was charged with a mixture of compound 1 (0.8 g, 1.41 mmol), 1,1,1-trifluoro-2-iodo-ethane (1.5 g, 7.14 mmol) and $K_2CO_3$ (1.0 g, 7.24 mmol) in DMF (30 mL). The mixture was heated at 80° C. in a CEM microwave reactor for 2 h. The reaction mixture was then cooled and poured into brine (100 mL). The mixture was extracted with ethyl acetate (50 mL×3). The combined organic layers were washed with brine (50 mL×3). The separated organic phase was dried over $Na_2SO_4$ and concentrated in vacuo, the resulting residue was purified by column chromatography on silica gel eluting with petroleum ether:ethyl acetate=20:1 to 3:1 to give compound 2 (0.60 g, 92%) as a pale yellow solid.

LC-MS: $t_R$=2.02 min in 3 min chromatography, MS (ESI) m/z=461.5 $[M+H]^+$.

Procedure for Preparation of Compound 3

A sealed tube was charged with a mixture of compound 2 (0.20 g, 0.43 mmol), Lawessons's reagent (0.20 g, 0.48 mmol) in dioxane (2 mL) was heated to 150° C. in a CEM microwave reactor for 1 h. After cooling down, the precipitate was filtered off and washed with Ethyl acetate (20 mL×2). The filtrate and the washing were concentrated in vacuo and the residue was purified by preparative TLC on silica gel eluting with petroleum ether:ethyl acetate=2:1 to give compound 3 (0.15 g, 73%) as a white solid.

Procedure for Preparation of Compound 4

To a solution of compound 3 (0.15 g, 0.31 mmol) in anhydrous THF (2 mL) was added $BH_3$.THF (1 M in THF, 20 mL, 20 mmol) at room temperature. After addition, the mixture was stirred at reflux for 72 h. After cooling down, the mixture was quenched with methanol (20 mL) carefully, then was concentrated under vacuum and the residue was dissolved in $CH_2Cl_2$ (50 mL). The mixture was washed with 1 N NaOH (10 mL) and brine (20 mL×2) in turn. The separated organic layer was dried over $Na_2SO_4$ and concentrated in vacuo. The residue was purified by preparative TLC on silica gel eluting with petroleum ether:ethyl acetate=5:1 to give compound 4 (60 mg, 42%) as a white solid with 59% purity on LC-MS, which was used directly in next step directly. LC-MS: $t_R$=2.15 min in 3 min chromatography, MS (ESI) m/z=463.4 $[M+H]^+$.

Procedure for Preparation of Compound 5

To a solution of compound 4 (60 mg, 0.13 mmol) in EtOH (4 mL) was added $NH_3$—$H_2O$ (1 mL) and tert-butyl hydroperoxide (0.20 g, 2.22 mol). After addition, the mixture was stirred at ambient temperature overnight. The mixture was concentrated in vacuo. $H_2O$ (20 mL) was added to the residue, and the resulting mixture was extracted with ethyl acetate (contained 10% methanol) (20 mL×3). The combined organic layers were washed with brine (20 mL×2), dried over $Na_2SO_4$, filtered off the solid and concentrated in vacuo to give the crude product, which was purified by preparative TLC on silica gel eluting with petroleum ether:ethyl acetate=1:1 to give compound 5 with 76% purity (50 mg, 86%) as a white solid, which was used directly in next step. LC-MS: $t_R$=1.62 min in 3 min chromatography, MS (ESI) m/z=446.0 $[M+H]^+$.

Procedure for Preparation of Compound 6

A mixture of compound 5 (50 mg, 0.11 mmol, 76% purity), tert-Butyl dicarbonate (48 mg, 0.22 mmol) and DMAP (27 mg, 0.22 mmol) in THF (5 mL) was stirred at ambient temperature overnight. The solvent was removed by evaporation in vacuo, the residue was purified by preparative TLC on silica gel eluting with petroleum ether:ethyl acetate=2:1 to give compound 6 (30 mg, 50%) as a white solid. LC-MS: 699-091-1B, $t_R$=2.06 min in 3 min chromatography, MS (ESI) m/z=546.2 $[M+H]^+$.

Procedure for Preparation of Compound 445

A mixture of compound 6 (10 mg, 0.018 mmol), 3-chloro-5-fluoro benzeneboronic acid (6 mg, 0.034 mmol), $Cs_2CO_3$ (2 M, 0.2 mL) and $Pd(PPh_3)_2Cl_2$ (1 mg) in 1,4-dioxane (0.5 mL) under nitrogen was stirred at 120° C. in a CEM microwave reactor for 30 min. The reaction mixture was concentrated in vacuo, and the residue was purified preparative TLC and then preparative HPLC to give compound 445 with 98% purity (3.4 mg, 38%). $^1H$ NMR: ($CD_3OD$, 400 MHz): δ 7.55-7.65 (dd, J=2.0, 6.0 Hz, 1H), 7.50-7.55 (s, 1H), 7.40-7.45 (s, 1H), 7.35-7.40 (d, J=7.6 Hz, 1H), 7.25-7.30 (m, 1H), 7.10-7.20 (m, 1H), 4.25-4.30 (d, J=8.8 Hz, 1H), 4.20-4.25 (d, J=9.2 Hz, 1H) 4.10-4.20 (d, J=10.4 Hz, 1H), 3.80-3.90 (d, J=10.0 Hz, 1H), 3.20-3.25 (s, 3H), 3.10-3.15 (m, 1H), 2.95-3.05 (s, 2H), 1.95-2.10 (m, 2H), 1.45-1.60 (m, 3H), 1.20-1.40 (m, 3H). LC-MS $t_R$=1.85 min in 3 min chromatography, MS (ESI) m/z=496.1 $[M+H]^+$.

HRMS: MS (ESI) m/z=496.1764 $[M+H]^+$.

Example 382

Synthesis of Compound 446

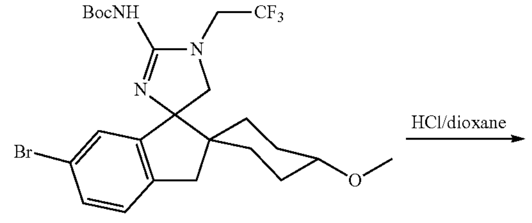

6

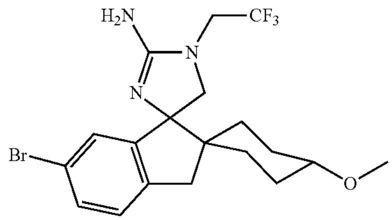

446

A mixture of compound 6 (10 mg, 0.018 mmol) in HCl/dioxane (2 mL, 4 M in dioxane) was stirred at ambient temperature for 1 h. The reaction mixture was concentrated in vacuo, and the residue was purified preparative HPLC to give compound 446 with 93% purity (1.1 mg, 14%). $^1H$ NMR: (300 MHz): δ 7.45-7.55 (m, 2H), 7.20-7.30 (m, 1H), 4.25-4.30 (d, J=11.6 Hz, 1H), 4.20-4.25 (d, J=12.0 Hz, 1H) 4.10-4.20 (d, J=13.6 Hz, 1H), 3.75-3.85 (d, J=14.0 Hz, 1H), 3.35-3.40 (s, 3H), 3.10-3.25 (m, 1H), 2.85-3.00 (s, 2H), 1.95-2.10 (m, 2H), 1.45-1.60 (m, 3H), 1.25-1.45 (m, 3H). LC-MS: $t_R$=1.65 min in 3 min chromatography, MS (ESI) m/z=466.1 $[M+H]^+$.

Example 383

Synthesis of Compounds 447 and 448

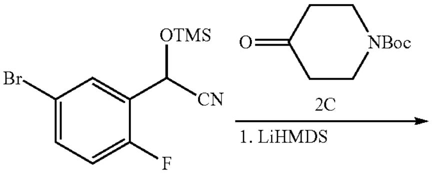

10A

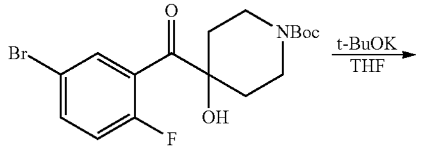

10B

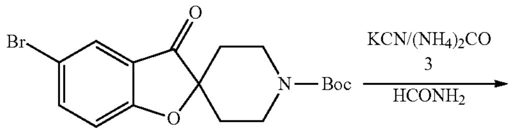

10

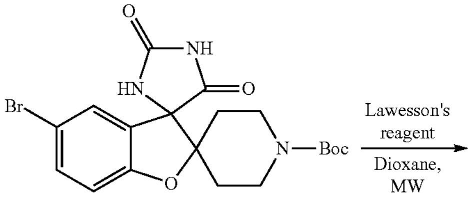

13

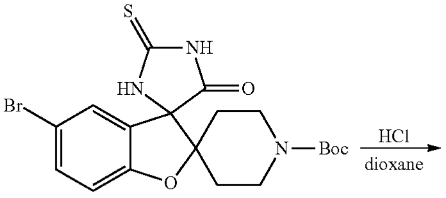

14

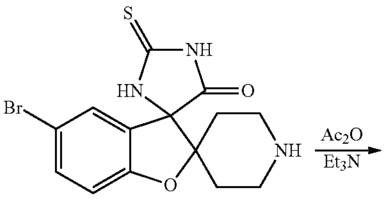

15

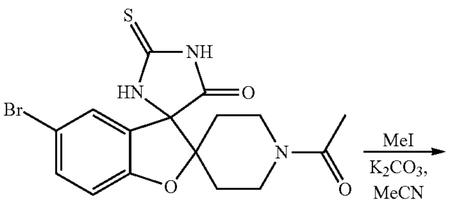

16

-continued

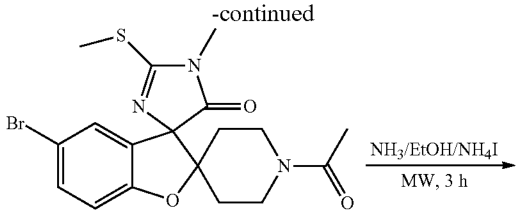

17

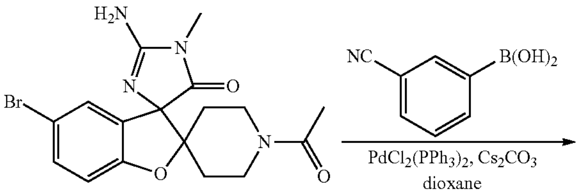

447

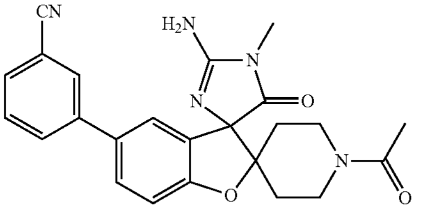

448

Procedure for Preparation of Compound 10B

To a solution of 2-(5-bromo-2-fluorophenyl)-2-(trimethylsilyloxy)acetonitril (25.0 g, 82.7 mmol) in anhydrous THF (150 mL) was added LiHMDS (1.0 M in THF, 91.0 mL, 91.0 mmol) dropwise via an addition funnel at −78° C. under nitrogen. After 1.5 h, a solution of 4-oxopiperidine-1-carboxylic acid tert-butyl ester (18.1 g, 91.0 mmol) in anhydrous THF was added dropwise via an addition funnel at −78° C. under nitrogen. After addition, the reaction mixture was stirred at −78° C. for 3 h. 1 N HCl (200 mL) was added via an addition funnel at −78° C. carefully. After that, the reaction mixture was allowed to warm to ambient temperature and kept at this temperature overnight. The mixture was separated and the aqueous layer was extracted with EtOAc (3×150 mL). The combined organic layers were washed with brine (2×200 mL), dried over $Na_2SO_4$ and concentrated in vacuo. The residue was purified by column chromatography on silica gel (eluent:petroleum ether:EtOAc=50:1 to 10:1) to give pure compound 10B (32.0 g, 77% yield) as a white solid.

Procedure for Preparation of Compound 10

10 Sealed tubes were charged with compound 10B (3.2 g, 6.59 mmol), THF (10 mL) and t-BuOK (0.81 g, 7.25 mmol) in each of them. These tubes were heated at 70° C. for 30 min in a CEM microwave reactor parallelly. After cooling down, all the reactions were quenched by addition of 10 mL $H_2O$ in each of them and combined and separated, the aqueous layer was extracted with EtOAc (3×100 mL). The combined organic layers were washed with brine (2×100 mL), dried over $Na_2SO_4$, filtered and concentrated in vacuo. The residue was purified by column chromatography on silica gel eluting with petroleum ether:ethyl acetate=100:1 to 10:1 to give compound 10 (15.0 g, 60%) as a white solid.

Procedure for Preparation of Compound 13

A steel autoclave was charged with a mixture of compound 10 (3 g, 7.8 mmol), KCN (1.02 g, 15 mmol), $(NH_4)_2CO_3$ (5.65 g, 58 mmol) and formamide (30 mL) and the mixture was heated at 100° C. for 72 h. The reaction mixture was cooled and poured into ice, then was filtrated to collect the solid, which was dissolved in ethyl acetate (100 mL) and was washed with water (2×50 mL), dried over $Na_2SO_4$ and concentrated to give the crude product which was purified by column chromatography on silica gel eluting with hexane:EtOAc (10:1 to 3:1) to give compound 13 (0.7 g, 20%) as a yellow solid. $^1H$ NMR ($CDCl_3$ 300 MHz): δ 8.20 (s, 1H), 7.31 (d, J=7.6 Hz, 2H), 1.40-1.97 (m, 8H), 1.24-1.29 (s, 9H).

Procedure for Preparation of Compound 14

To a solution of compound 13 (400 mg, 0.88 mmol) in anhydrous 1,4-dioxane (10 mL) was added Lawesson's Reagent (393.2 mg, 0.97 mmol) under a nitrogen atmosphere, the mixture was stirred at 120° C. for 30 min in a CEM microwave reactor. The solvent was removed in vacuo to give the crude product which was purified by preparative TLC on silica gel eluting with hexane:EtOAc=3:1 to afford compound 14 (100 mg, 24%) as a white solid. LCMS: $t_R$=1.335 min in 2 min chromatography, MS (ESI) m/z 490 $[M+Na]^+$.

Procedure for Preparation of Compound 15

To a solution of compound 14 (50 mg, 0.11 mmol) was added HCl/dioxane (4.0 M, 2 mL) under a nitrogen atmosphere, the mixture was stirred at room temperature for 2 h, the solvent was removed in vacuo to give compound 15 (30 mg, 76%), which was used in the next step without further purification. LCMS: $t_R$=0.872 min in 2 min chromatography, MS (ESI) m/z 368 $[M+H]^+$.

Procedure for Preparation of Compound 16

To a solution of compound 15 (30 mg, 0.08 mmol) in $CH_2Cl_2$ (2 mL) was added $Ac_2O$ (8.3 mg, 0.08 mmol), $Et_3N$ (16.4 mg, 0.16 mmol) and DMAP (0.09 mg, 0.008 mmol) under nitrogen at 0° C. After stirring at 0° C. for 2 h, water (5 mL) was added and the mixture was extracted with $CH_2Cl_2$ (3×10 mL). The combined organic layers were washed with brine (10 mL), dried over $Na_2SO_4$ and concentrated to give compound 16 (25 mg, 75%), which was used in the next step without further purification. LCMS: $t_R$=1.097 min in 2 min chromatography, MS (ESI) m/z 410 $[M+H]^+$.

Procedure for Preparation of Compound 17

To a solution of compound 16 (25 mg, 0.06 mmol) in $CH_3CN$ (2 mL) was added $K_2CO_3$ (16.5 mg, 0.12 mmol), and MeI (17.6 mg, 0.12 mmol) under nitrogen, the mixture was heated at 60° C. for 10 min and at 100° C. for another 10 min in a CEM microwave reactor. The mixture was filtered off, and the filtrate was concentrated in vacuo. The residue was purified by preparative TLC on silica gel eluting with hexane:EtOAc=3:1 to give compound 17 (20 mg, 76%) as a white solid. LCMS: $t_R$=1.097 min in 2 min chromatography, MS (ESI) m/z 410 $[M+H]^+$.

Procedure for Preparation of Compound 447

A solution of compound 17 (20 mg, 0.046 mmol), $NH_4I$ (68 mg, 0.46 mmol) in $NH_3$-EtOH (2 mL, 5 N) was heated at 120° C. in a CEM microwave reactor for 3 h. After being cooled, the mixture was concentrated in vacuo, and the residue was purified by preparative TLC on silica gel eluting with dichloromethane:methanol=10:1 and preparative HPLC to give compound 447 (8 mg, 43%) as a white solid. $^1H$ NMR ($CD_3OD$ 400 MHz): δ 7.41 (d, J=8.8 Hz, 1H), 7.15 (s, 1H), 6.86 (d, J=8.4 Hz, 1H), 3.88 (m, 2H), 3.54 (m, 2H), 3.10 (s, 3H), 2.17 (s, 3H), 1.89-1.92 (m, 2H), 1.62-1.79 (m, 2H). LCMS: $t_R$=1.410 min in 2 min chromatography, MS (ESI) m/z 407 $[M+H]^+$.

Procedure for Preparation of Compound 448

To a solution of compound 447 (7 mg, 0.017 mmol) in 1,4-dioxane (2 mL) were added 3-cyanophenylboronic acid (3.78 mg, 0.025 mmol), $Cs_2CO_3$ (2 N, 0.2 mL) and $Pd(PPh_3)_2Cl_2$ (0.1 mg, 0.00017 mmol) under nitrogen, the mixture was heated at 120° C. in a CEM microwave reactor for 15 min, LCMS analysis showed the complete consumption of compound compound 447. Water (2 mL) was added and the mixture was filtered through a pad of celite, then was washed with EtOAc (3×10 mL). The combined organic layers were washed with brine (20 mL), dried over $Na_2SO_4$ and concentrated to give the crude product which was purified by preparative TLC on silica gel eluting with dichloromethane: methanol=10:1 followed by preparative HPLC to afford compound 448 (1.2 mg, 16%) as a white solid. $^1H$ NMR ($CD_3OD$ 400 MHz): δ 7.81 (s, 1H), 7.55 (d, J=7.6 Hz, 1H), 7.51 (d, J=8.8 Hz, 3H), 7.23 (s, 1H), 6.93 (d, J=8.4 Hz, 1H), 3.75-3.80 (m, 2H), 3.38-3.47 (m, 2H), 3.01 (s, 3H), 2.0 (s, 3H), 1.72-1.85 (m, 2H), 1.42-1.56 (m, 2H). LCMS: $t_R$=1.558 min in 2 min chromatography, MS (ESI) m/z 430.2 $[M+H]^+$.

Example 384

Synthesis of Compound 449

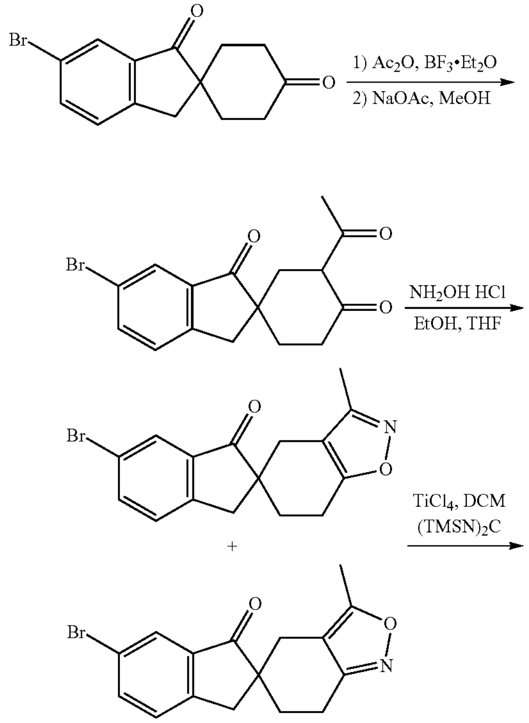

-continued

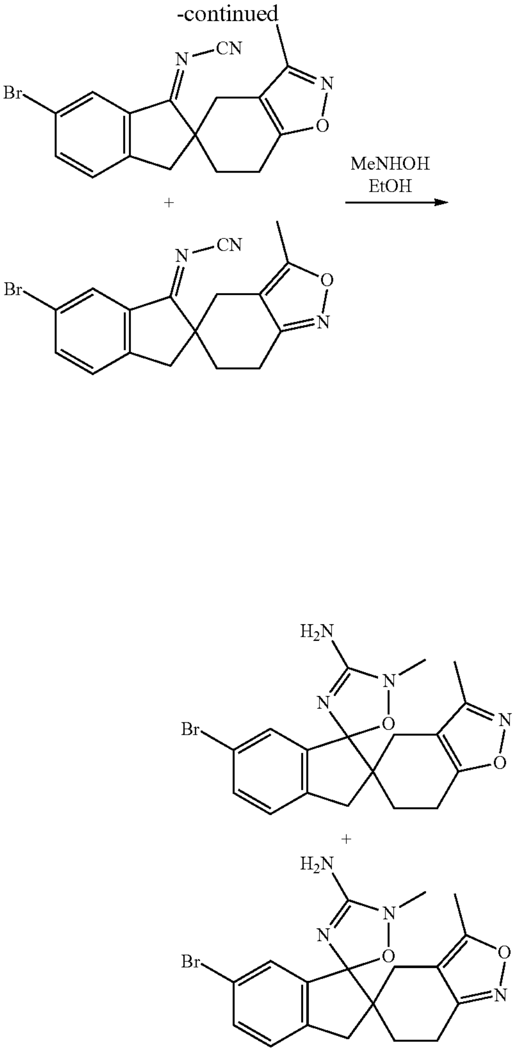

449

Step 1: Preparation of 3-acetyl-6'-bromospiro[cyclohexane-1,2'-indene]-1',4(3'H)-dione To a suspension of 6'-bromospiro[cyclohexane-1,2'-indene]-1',4(3'H)-dione (545.6 mg, 1.86 mmol) and $Ac_2O$ (3 mL) which was stirred at room temperature was added $BF_3.Et_2O$ (1 mL) was added dropwise. The mixture color turned dark brown within several minutes. The reaction mixture was quenched with ice-water after being stirred overnight, and stirred another 1 h before diluted with EA. It was washed with saturated aqueous $NaHCO_3$ and brine successively, and dried over anhydrous $Na_2SO_4$, and filtered, and evaporated to produce 580 mg of brown foam. The brown foam was dissolved in MeOH (6 mL). To this solution was added a solution of NaOAc (610 mg, 7.44 mmol) in $H_2O$ (1 mL). The mixture was heated to reflux for 3 h. Organic solvent was removed under reduced pressure before re-dissolved in EA (60 mL). The resulting solution was washed with $H_2O$ and brine successively, and dried over anhydrous $Na_2SO_4$, and filtered, and evaporated to produce dark oil, which was purified by flash chromatography on silica gel to afford 294.5 mg of the desired product as light yellow solid. MS ESI+ve m/z 335 $(M+H)^{30}$. $t_R$: 1.86 min.

Step 2: Preparation of 6'-bromo-3-methyl-6,7-dihydro-4H-spiro[benzo[d]isoxazole-5,2'-inden]-1'(3'H)-one and 6'-bromo-3-methyl-6,7-dihydro-4H-spiro[benzo[c]isoxazole-5,2'-inden]-1'(3'H)-one A mixture of 3-acetyl-6'-bromospiro[cyclohexane-1,2'-indene]-1',4(3'H)-dione (41.5 mg, 0.124 mmol) and $NH_2OH.HCl$ (26 mg, 0.374 mmol) and EtOH/THF (2/0.5 mL) charged in a 10-mL CEM microwave test tube was heated in a CEM microwave reactor at 100° C. for 10 min. To this mixture was added 3-acetyl-6'-bromospiro[cyclohexane-1,2'-indene]-1',4(3'H)-dione (41.5 mg, 0.124 mmol) solution in THF (0.5 mL) and $NH_2OH.HCl$ (45 mg, 0.647 mmol). The mixture was heated to 110° C. for another 10 min in the CEM microwave reactor. $NaHCO_3$ (158 mg, 1.88 mmol) was added and stirred for 5 min before filtered and evaporated. The residue was purified by flash chromatography on silica gel to afford 70 mg of the desired product as a mixture with the ratio close 1:1. MS ESI+ve m/z 332 $(M+H)^{30}$. $t_R$: 1.80 min.

Step 3: Preparation of N-(5'-bromo-3-methyl-6,7-dihydro-4H-spiro[benzo[c]isoxazole-5,2'-indene]-3'(1'H)-ylidene)cyanamide and N-(5'-bromo-3-methyl-6,7-dihydro-4H-spiro[benzo[d]isoxazole-5,2'-indene]-3'(1'H)-ylidene)cyanamide To a solution of 6'-bromo-3-methyl-6,7-dihydro-4H-spiro[benzo[d]isoxazole-5,2'-inden]-1'(3'H)-one and 6'-bromo-3-methyl-6,7-dihydro-4H-spiro[benzo[c]isoxazole-5,2'-inden]-1'(3'H)-one (ca 1:1 ration) (70 mg, 0.021 mmol) in anhydrous DCM (5 mL) under N2 atmosphere at room temperature was added $TiCl_4$ (1.0 M solution in DCM, 0.42 mL, 0.42 mmol) dropwise. The resulting yellow suspension was stirred for 1 h before bis-trimethylsilylcarbodiimide (86 mg, 105 μL, 0.46 mmol) was added. The resulting mixture was stirred overnight. $TiCl_4$ (1.0 M solution in DCM, 0.42 mL, 0.42 mmol) was added followed by bis-trimethylsilylcarbodiimide (86 mg, 105 μL, 0.46 mmol). The mixture was stirred for another 16 h before quenched by ice-water. The mixture was stirred another 30 min and extracted with DCM 3 times, the combined organic layers were dried over anhydrous $Na_2SO_4$, and filtered, and evaporated to produce 76 mg of crude product, which was used for next step without further purification. MS ESI+ve m/z 356 $(M+H)^{30}$. $t_R$: 1.80 min.

Step 4: Preparation of Compound 449

To a suspension of above crude product in EtOH (3 mL) was added a solution of N-methylhydroxylamine (1.5 mL, prepared by adding 25 wt % NaOMe in MeOH (72 μL, 1.26 mmol) to a solution of MeNHOH.HCl (117 mg, 1.4 mmol) in EtOH (10 mL) being stirred for 5 min). After being stirred overnight, another portion of N-methylhydroxylamine (1.5 mL) was added followed by another same portion of N-methylhydroxylamine after 10 min. The mixture was stirred overnight and evaporated to dryness and purified by preparative HPLC to afford 80 mg of the desired product as TFA salt. MS ESI+ve m/z 403 $(M+H)^{30}$. $t_R$: 1.27 min. $^1H$ NMR (400 MHz, $CD_3OD$) δ: 7.72 (m, 1H), 7.60 (dd, J=8.4 Hz, 1.6 Hz, 1H), 7.24 (d, J=8.4 Hz, 1H), 3.37, 3.36, 3.35, 3.34 (four s, total 3H), 3.01-2.39 (m, 6H), 2.29, 2.25, 2.17, 2.13 (four s, total 3H), 2.30-1.87 (m, 2H).

Example 385

Synthesis of Compound 450

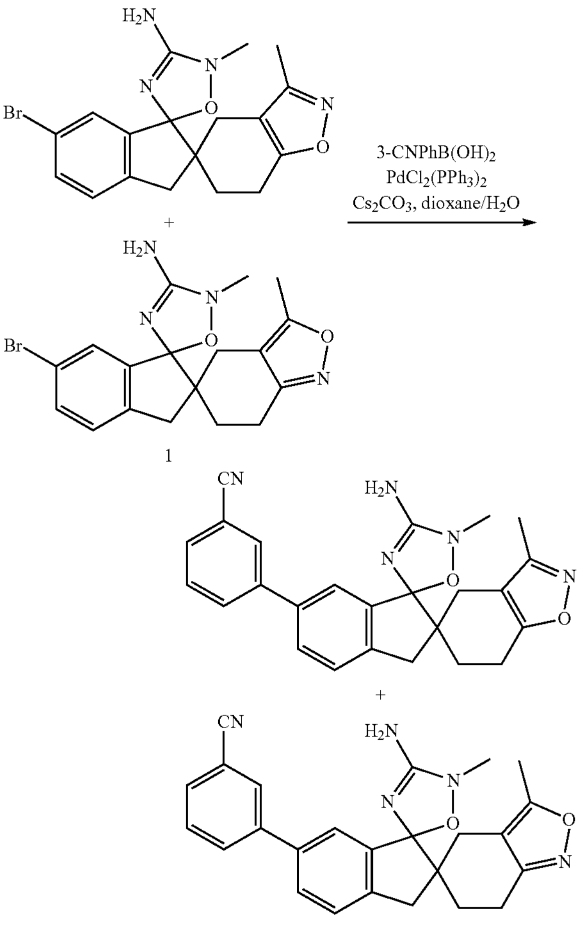

1

450

To a solution of compound 1 TFA salt (10 mg, 0.019 mmol), 3-cyanophenylboronic acid (6 mg, 0.041 mmol) and $Cs_2CO_3$ (40 mg, 0.12 mmol) in 1,4-dioxane (2 mL) and $H_2O$ (0.1 mL) charged in a 10 mL CEM microwave test tube was added $PdCl_2(PPh_3)_2$ (2 mg, 0.0028 mmol), then the system was degassed by sweeping $N_2$. The tube was sealed and heated to 110° C. for 10 min in a CEM microwave reactor. Due to low conversion $PdCl_2(PPh_3)_2$ (2 mg, 0.0028 mmol), and 3-cyanophenylboronic acid (6 mg, 0.041 mmol) was added and heated at 110° C. for another 10 min in microwave reactor. Solvent was removed in vacuum and the residue was purified by preparative HPLC to yield 5.7 mg of the desired product as a TFA salt. MS ESI+ve m/z 426 $(M+H)^{30}$. $t_R$: 1.45 min. $^1H$ NMR (400 MHz, $CD_3OD$) δ: 8.04 and 8.01 (tow s, total 1H), 7.98 and 7.93 (two d, J=8.0 Hz, total 1H), 7.85 and 7.84 (two s, total 1H), 7.81-7.63 (m, 3H), 7.44 (d, J=7.6 Hz, 1H), 3.39, 3.38, 3.36 and 3.35 (four s, 3H), 3.10-2.45 (m, 6H), 2.31, 2.26, 2.19 and 2.14 (four s, 3H), 2.32-1.91 (m, 2H).

Example 386

Synthesis of Compound 451

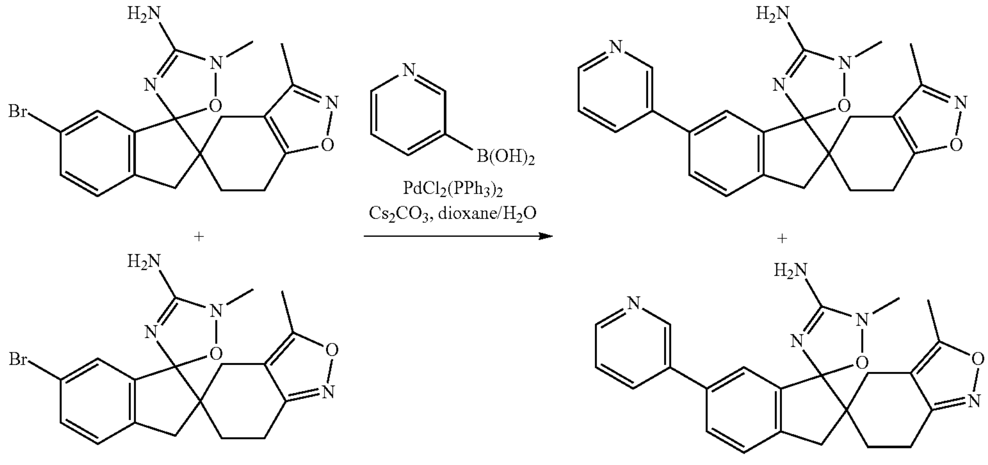

451

The title compound was made by the method described in example 385. MS ESI+ve m/z 402 (M+H)[30]. $t_R$: 1.07 min. $^1H$ NMR (400 MHz, $CD_3OD$) δ: 9.20 (s, 1H), 8.88-8.83 (m, 2H), 8.12 (m, 1H), 8.03 (s, 1H), 7.92 (d, J=8.0 Hz, 1H), 7.55 (d, J=7.2 Hz, 1H), 3.39, 3.38, 3.37 and 3.36 (four s, 3H), 3.13-2.44 (m, 6H), 2.30, 2.26, 2.19 and 2.14 (four s, 3H), 2.34-1.93 (m, 2H).

Example 387

Synthesis of Compound 452

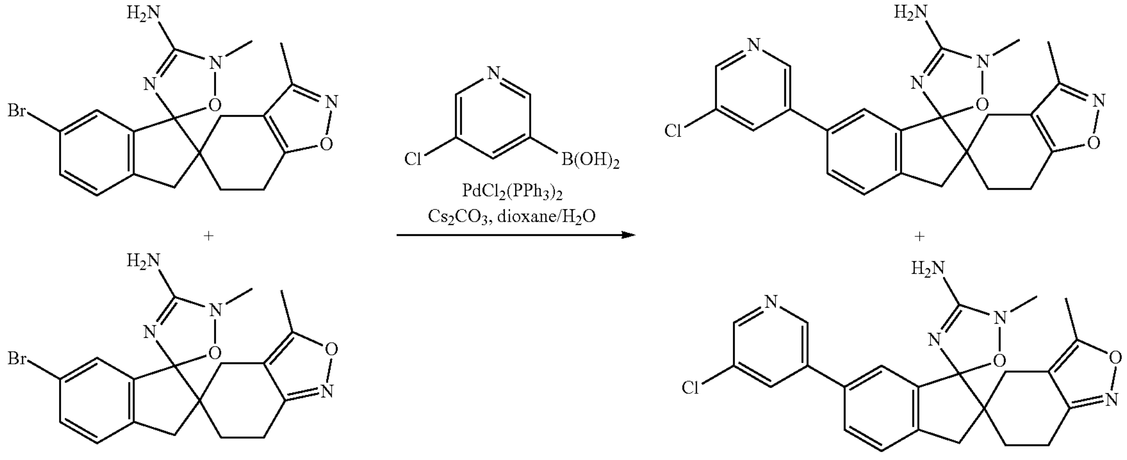

452

The title compound was made by the method described in example 385. MS ESI+ve m/z 436 (M+H)[30]. $t_R$: 1.37 min. $^1H$ NMR (400 MHz, $CD_3OD$) δ: 8.80 (s, 1H), 8.60 (s, 1H), 8.23 (s, 1H), 7.91 (s, 1H), 7.82 (d, J=8.0 Hz, 1H), 7.48 (d, J=8.0 Hz, 1H), 3.39, 3.38, 3.36 and 3.35 (four s, 3H), 3.11-2.45 (m, 6H), 2.31, 2.26, 2.19 and 2.14 (four s, 3H), 2.32-1.91 (m, 2H).

Example 388

Synthesis of Compound 453

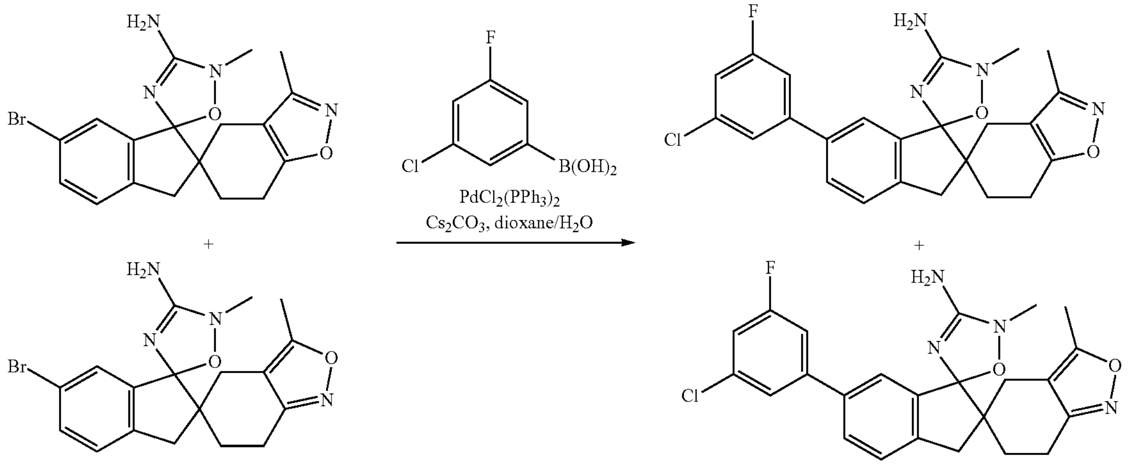

453

The title compound was made by the method described in example 385. MS ESI+ve m/z 453 (M+H)$^{30}$. $t_R$: 1.74 min. $^1$H NMR (400 MHz, $CD_3OD$) δ: 7.82 (s, 1H), 7.75 (d, J=8.0 Hz, 1H), 7.53 (s, 1H), 7.44-7.38 (m, 2H), 7.22 (d, J=8.4 Hz, 1H), 3.39, 3.38, 3.36 and 3.35 (four s, 3H), 3.09-2.45 (m, 6H), 2.30, 2.26, 2.19 and 2.14 (four s, 3H), 2.32-1.90 (m, 2H); $^{19}$F NMR (376 MHz, $CD_3OD$) δ: −112.29, −112.83, −112.85, −112.88.

Example 389

Synthesis of Compound 454

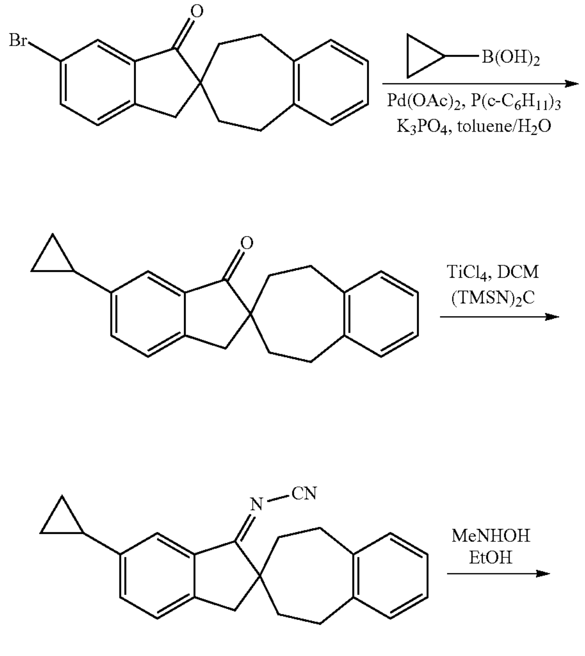

-continued

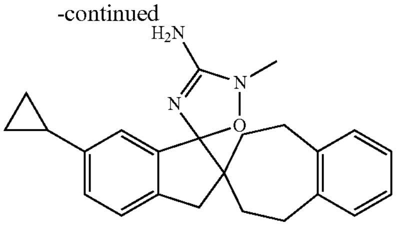

454

Step 1

A mixture of 6'-bromo-5,6,8,9-tetrahydrospiro[benzo[7]annulene-7,2'-inden]-1'(3'H)-one (50 mg, 0.147 mmol), $K_3PO_4$ (125 mg, 0.588 mmol), cyclopropylboronic acid (19 mg, 0.220 mmol), tricyclohexylphosphine (4.2 mg, 0.015 mmol, 10 mol %), toluene (3 mL), $H_2O$ (0.15 mL) and $Pd(OAc)_2$ (3.4 mmol, 0.0147 mmol) charged in a 10-mL CEM microwave reactor was charged $N_2$. The mixture was heated at 110° C. for 70 min. The reaction mixture was diluted with EA and washed with $H_2O$ and brine, and dried over anhydrous $Na_2SO_4$, and filtered, and evaporated to produce the crude product, which was used for next step without further purification; MS ESI+ve m/z 303 (M+H)$^{30}$. $t_R$: 2.30 min.

Step 2

To a solution of above crude product in anhydrous DCM (5 mL) under $N_2$ atmosphere at room temperature was added $TiCl_4$ (1.0 M solution in DCM, 0.42 mL, 0.42 mmol) drop-wise. The resulting yellow suspension was stirred for 1 h before bis-trimethylsilylcarbodiimide (86 mg, 105 μL, 0.46 mmol) was added. The resulting mixture was stirred overnight. $TiCl_4$ (1.0 M solution in DCM, 0.65 mL, 0.65 mmol) was added followed by bis-trimethylsilylcarbodiimide (137 mg, 167 μL, 0.735 mmol). The mixture was stirred for another 16 h before quenched by ice-water. The mixture was stirred another 30 min and extracted with DCM 3 times, the combined organic layers were dried over anhydrous $Na_2SO_4$, and filtered, and evaporated to produce the desired crude product, which was used for next step without further purification. MS ESI+ve m/z 327 $(M+H)^{30}$. $t_R$: 2.29 min.

Step 3

To a suspension of above crude product in EtOH (3 mL) was added a solution of N-methylhydroxylamine (4.15 mL, prepared by adding 25 wt % NaOMe in MeOH (72 mL, 1.26 mmol) to a solution of MeNHOH.HCl (117 mg, 1.4 mmol) in EtOH (10 mL) being stirred for 5 min). After being stirred overnight, the reaction mixture was evaporated to dryness and purified by preparative HPLC to afford 54 mg of the desired product as TFA salt. MS ESI+ve m/z 374 $(M+H)^{30}$. $t_R$: 1.78 min. $^1H$ NMR (400 MHz, $CD_3OD$) δ: 7.52 (d, J=8.0 Hz, 1H), 7.41 (d, J=8.0 Hz, 1H), 7.23 (d, J=8.4 Hz, 1H), 7.18-7.07 (m, 4H), 3.22 (s, 3H), 3.34-2.94 (m, 4H), 2.81-2.64 (m, 2H), 2.06-1.49 (m, 5H), 1.05-0.95 (m, 2H), 0.68 (m, 2H).

Example 390

Synthesis of Compound 455

HPLC (SunFire™ Prep $C_{18}$ OBD™ 5 μm 19×50 mm column, 10%→90% MeOH/$H_2O$, 0.1% $CF_3COOH$ over 8 min and then 90% MeOH/$H_2O$, 0.1% $CF_3COOH$ over 2 min, flow rate 20 mL/min) to afford 0.0657 g (18%) of 6'-bromo-5,7-dihydrospiro[cyclopenta[d]pyridazine-6,2'-inden]-1'(3'H)-one, 0.0083 g (2%) of 6'-bromo-2,4a,5,7-tetrahydrospiro[cyclopenta[d]pyridazine-6,2'-inden]-1'(3'H)-one, and recover 0.0550 g (18%) of 6'-bromospiro[cyclopent[3]ene-1,2'-inden]-1'(3'H)-one.

For 6'-bromo-5,7-dihydrospiro[cyclopenta[d]pyridazine-6,2'-inden]-1'(3'H)-one, LC-MS $t_R$=1.35 min in 3 min chromatography, m/z 315, 317 $(MH^+)$; $^1H$ NMR (400 MHz, $CD_3OD$) δ 9.17 (s, 2H), 7.59-7.55 (m, 2H), 7.24 (d, J=8.2 Hz, 1H), 3.36 (d, J=17.9 Hz, 2H), 3.13 (d, J=17.9 Hz, 2H), 3.08 (s, 2H); $^{13}C$ NMR (100 MHz, $CD_3OD$) δ 207.41, 152.76, 152.37, 148.80, 139.59, 137.86, 129.84, 128.04, 122.99, 57.87, 43.33, 42.33.

For 6'-bromo-2,4a,5,7-tetrahydrospiro[cyclopenta[d]pyridazine-6,2'-inden]-1'(3'H)-one, LC-MS $t_R$=1.41 min in 3 min chromatography, m/z 317, 319 $(MH^+)$; $^1H$ NMR (400 MHz, $CD_3OD$) δ 9.22 (m, 1H), 9.14 (m, 1H), 7.86-7.85 (m, 1H), 7.74-7.71 (m, 1H), 7.43 (d, J=7.9 Hz, 1H), 3.37-3.30 (m, 1H), 2.95-2.71 (m, 4H), 2.22-2.16 (m, 1H), 1.90-1.84 (m, 1H).

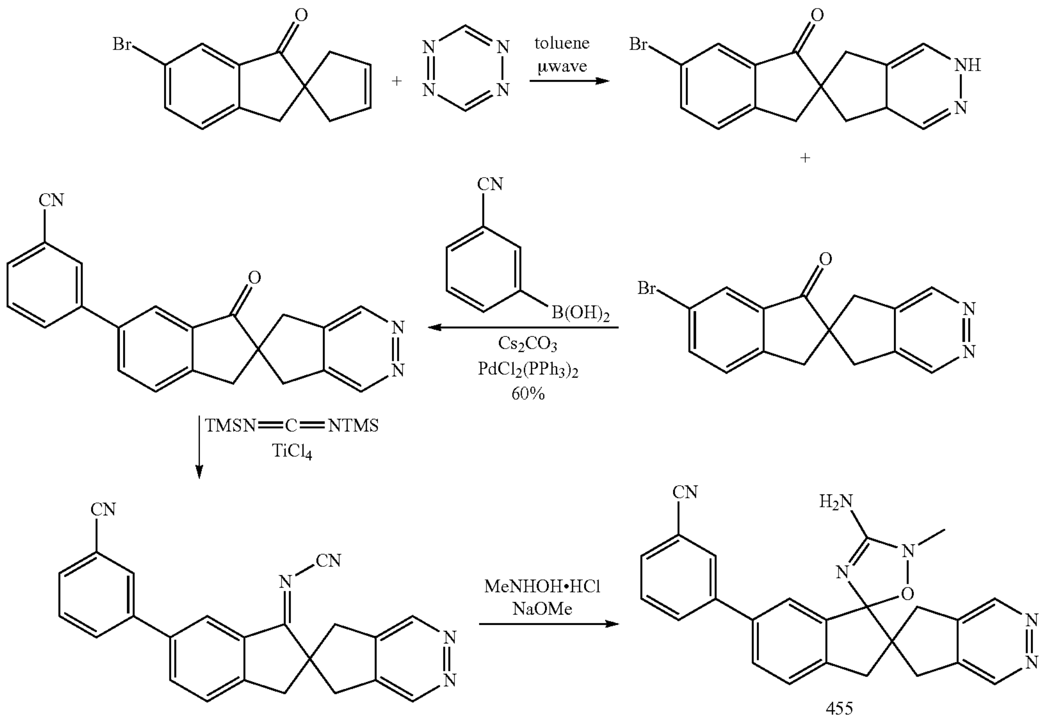

455

Step 1. 6'-bromo-5,7-dihydrospiro[cyclopenta[d]pyridazine-6,2'-inden]-1'(3'H)-one and 6'-bromo-2,4a,5,7-tetrahydrospiro[cyclopenta[d]pyridazine-6,2'-inden]-1'(3'H)-one A 10 mL microwave tube was charged with 6'-bromospiro[cyclopent[3]ene-1,2'-inden]-1'(3'H)-one (0.3045 g, 1.16 mmol), 1,2,4,5-tetrazine (0.1120 g, 1.36 mmol), and toluene (5 mL). The tube was heated in a CEM microwave reactor at 150° C. for 1 h. After the solvent was evaporated under reduced pressure, the residue was purified by reversed-phase Step 2. 3-(1'-oxo-1',3',5,7-tetrahydrospiro[cyclopenta[d]pyridazine-6,2'-inden]-6'-yl)benzonitrile A 10 mL microwave tube was charged with 6'-bromo-5,7-dihydrospiro[cyclopenta[d]pyridazine-6,2'-inden]-1'(3'H)-one (0.0600 g, 0.19 mmol), 3-cyanophenylboronic acid (0.1221 g, 0.83 mmol), $Cs_2CO_3$ (0.2822 g, 0.87 mmol), 1,4-dioxane (4 mL), water (1 mL), and $PdCl_2(PPh_3)_2$ (0.0360 g, 0.05 mmol). The tube was heated in a CEM microwave reactor at 110° C. for 30 min. The reaction mixture was diluted with $CH_2Cl_2$ and dried over $Na_2SO_4$. After the solvent was evaporated under reduced pressure, the residue was purified by reversed-phase HPLC (SunFire™ Prep $C_{18}$ OBD™ μm 19×50 mm column, 10%→90% MeOH/$H_2O$, 0.1% $CF_3COOH$ over 8 min and then 90% MeOH/$H_2O$, 0.1% $CF_3COOH$ over 2 min, flow rate 20 mL/min) to afford 0.0386 g (60%) of 3-(1'-oxo-1',3',5,7-tetrahydrospiro[cyclopenta[d]pyridazine-6,2'-inden]-6'-yl)benzonitrile. LC-MS $t_R$=1.43 min in 3 min chromatography, m/z 338 ($MH^+$).

Step 3. N-(5'-(3-cyanophenyl)-5,7-dihydrospiro[cyclopenta[d]pyridazine-6,2'-inden]-3'(1'H)-ylidene) cyanamide To a solution of 3-(1'-oxo-1',3',5,7-tetrahydrospiro[cyclopenta[d]pyridazine-6,2'-inden]-6'-yl)benzonitrile (0.0386 g, 0.11 mmol) in $CH_2Cl_2$ (5 mL) was added 0.5 mL of 1.0 M $TiCl_4$ in $CH_2Cl_2$ at room temperature. After 1.5 h, 0.4 mL of bis(trimethylsilyl)carbodiimide was added to the yellow solution. The resulting mixture was then stirred at room temperature for 20 h. The mixture was quenched with ice, diluted with $CH_2Cl_2$, and dried over $Na_2SO_4$. After the solvent was removed under reduced pressure, the crude product was directly used in the next step without further purification. LC-MS $t_R$=1.43 min in 3 min chromatography, m/z 362 ($MH^+$).

Step 4. Compound 455

A 50 mL flask was charged with 32 mL of EtOH, 0.8452 g of sodium methoxide (25 wt. % solution in MeOH), and 0.3707 g of N-methylhydroxylamine hydrochloride. The suspension was filtered through HPLC filter and 10 mL of the filtrate was added to N-(5'-(3-cyanophenyl)-5,7-dihydrospiro[cyclopenta[d]pyridazine-6,2'-inden]-3'(1'H)-ylidene)cyanamide, obtained as described above. The resulting mixture was stirred at room temperature overnight. The mixture was purified by reversed-phase HPLC (SunFire™ Prep $C_{18}$ OBD™ μm 19×50 mm column, 10%→90% MeOH/$H_2O$, 0.1% $CF_3COOH$ over 8 min and then 90% MeOH/$H_2O$, 0.1% $CF_3COOH$ over 2 min, flow rate 20 mL/min) to afford compound 455 as a TFA salt. LC-MS $t_R$=1.23 min in 3 min chromatography, m/z 409 ($MH^+$); $^1$H NMR (400 MHz, $CD_3OD$) δ 9.36 (m, 2H), 8.03-7.48 (m, 7H), 3.78 (d, J=16 Hz, 1H), 3.48 (d, J=16 Hz, 1H), 3.35-3.17 (m, 7H).

Example 391

Synthesis of Compounds 456 and 457

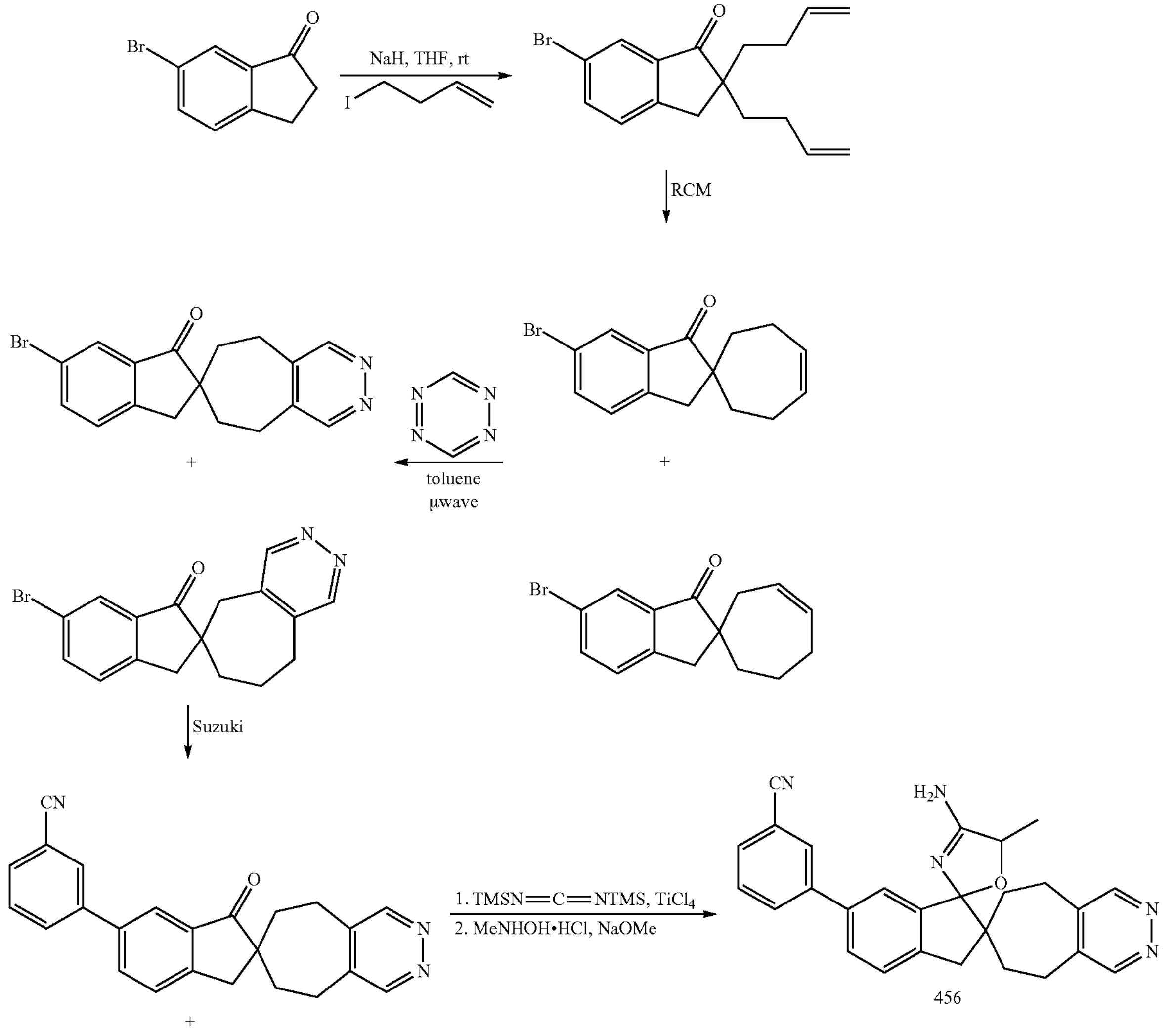

456

-continued

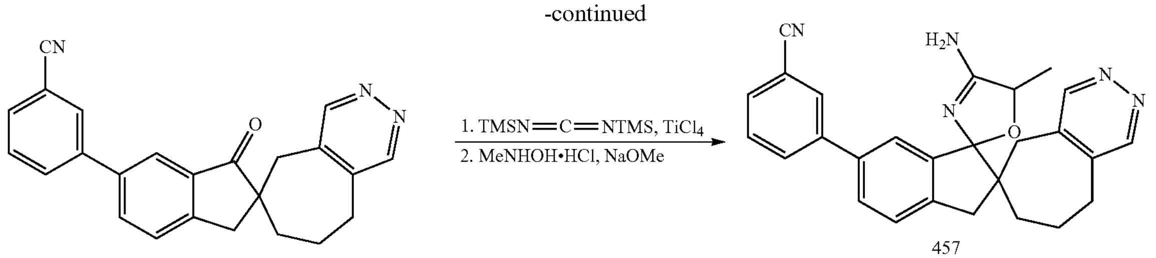

457

Step 1. 6-bromo-2,2-di(but-3-en-1-yl)-2,3-dihydro-1H-inden-1-one

To a stirred solution of 6-bromo-1-indanone (0.5330 g, 2.52 mmol) in dry THF (10 mL) was added NaH (0.3380 g, 60% in a mineral oil, 8.45 mmol) at 0° C. under nitrogen. After being stirred for 10 min, 4-iodobut-1-ene (1.3450 g, 7.39 mmol) was added and then the mixture was stirred at ambient temperature for 20 h. The reaction mixture was cooled to 0° C., quenched with 1 N HCl, extracted with ethyl acetate, and dried over $Na_2SO_4$. After the solvents were evaporated, the residue was purified by chromatography on silica gel eluted with hexanes/ethyl acetate to afford 0.1304 g of 6-bromo-2,2-di(but-3-en-1-yl)-2,3-dihydro-1H-inden-1-one. LC-MS $t_R$=2.33 min in 3 min chromatography, m/z 319, 321 ($MH^1$); $^1H$ NMR (400 MHz, $CDCl_3$) δ 7.84 (s, 1H), 7.67 (d, J=8 Hz, 1H), 7.33 (d, J=8 Hz, 1H), 5.76-5.66 (m, 2H), 4.94-4.87 (m, 4H), 2.98 (s, 2H), 1.98-1.63 (m, 8H); $^{13}C$ NMR (100 MHz, $CDCl_3$) δ 209.23, 151.43, 138.85, 137.85, 137.54, 127.94, 126.75, 121.55, 114.81, 52.87, 37.28, 36.58, 28.54.

Step 2. 6'-bromospiro[cyclohept[4]ene-1,2'-inden]-1'(3'H)-one and 6'-bromospiro[cyclohept[3]ene-1,2'-inden]-1'(3'H)-one To a solution of 6-bromo-2,2-di(but-3-en-1-yl)-2,3-dihydro-1H-inden-1-one (0.1300 g, 0.41 mmol) in toluene (40 mL) was added Hoveyda-Grubbs catalyst 2nd generation [301224-40-8] (0.0308 g, 0.049 mmol). The resulting mixture was heated at 120° C. under nitrogen for 20 h. After the solvent was evaporated, the residue was purified by chromatography on silica gel eluted with hexanes/ethyl acetate to afford 0.1204 g (100%) of a mixture of 6'-bromospiro[cyclohept[4]ene-1,2'-inden]-1'(3'H)-one and 6'-bromospiro[cyclohept[3]ene-1,2'-inden]-1'(3'H)-one as observed by $^1H$ NMR. LC-MS $t_R$=2.25 min in 3 min chromatography, m/z 291, 293 ($MH^+$).

Step 3. 6'-bromo-5,6,8,9-tetrahydrospiro[cyclohepta[d]pyridazine-7,2'-inden]-1'(3'H)-one and 6'-bromo-5,7,8,9-tetrahydrospiro[cyclohepta[d]pyridazine-6,2'-inden]-1'(3'H)-one A 10 mL microwave tube was charged with a mixture of 6'-bromospiro[cyclohept[4]ene-1,2'-inden]-1'(3'H)-one and 6'-bromospiro[cyclohept[3]ene-1,2'-inden]-1'(3'H)-one (0.1204 g), obtained as described above, 1,2,4,5-tetrazine (0.0767 g, 0.93 mmol), and toluene (5 mL). The tube was heated in a CEM microwave reactor at 150° C. for 1 h. After the solvent was evaporated under reduced pressure, the residue was purified by reversed-phase HPLC (SunFire™ Prep $C_{18}$ OBD™ 5 μm 19×50 mm column, 10%→90% MeOH/$H_2O$, 0.1% $CF_3COOH$ over 8 min and then 90% MeOH/$H_2O$, 0.1% $CF_3COOH$ over 2 min, flow rate 20 mL/min) to afford 0.1646 g of a mixture of 6'-bromo-5,6,8,9-tetrahydrospiro[cyclohepta[d]pyridazine-7,2'-inden]-1'(3'H)-one and 6'-bromo-5,7,8,9-tetrahydrospiro[cyclohepta[d]pyridazine-6,2'-inden]-1'(3'H)-one. LC-MS $t_R$=6.21, 6.35 min in 16 min chromatography, $t_R$=1.49 min in 3 min chromatography, m/z 343, 345 ($MH^+$).

Step 4. 3-(1'-oxo-1',3',5,6,8,9-hexahydrospiro[cyclohepta[d]pyridazine-7,2'-inden]-6'-yl)benzonitrile and 3-(1'-oxo-1',3',5,7,8,9-hexahydrospiro[cyclohepta[d]pyridazine-6,2'-inden]-6'-yl)benzonitrile A 10 mL microwave tube was charged with a mixture of 6'-bromo-5,6,8,9-tetrahydrospiro[cyclohepta[d]pyridazine-7,2'-inden]-1'(374)-one and 6'-bromo-5,7,8,9-tetrahydrospiro[cyclohepta[d]pyridazine-6,2'-inden]-1'(374)-one (0.1646 g), obtained as described above, 3-cyanophenylboronic acid (0.2530 g, 1.7 mmol), $Cs_2CO_3$ (0.6177 g, 1.9 mmol), 1,4-dioxane (4 mL), water (1 mL), and $PdCl_2(PPh_3)_2$ (0.0360 g, 0.05 mmol). The tube was heated in a CEM microwave reactor at 110° C. for 30 min. The reaction mixture was diluted with $CH_2Cl_2$ and dried over $Na_2SO_4$. After the solvent was evaporated under reduced pressure, the residue was purified by reversed-phase HPLC (SunFire™ Prep $C_{18}$ OBD™ 5 μm 19×50 mm column, 10%→90% MeOH/$H_2O$, 0.1% $CF_3COOH$ over 8 min and then 90% MeOH/$H_2O$, 0.1% $CF_3COOH$ over 2 min, flow rate 20 mL/min) to afford 0.0281 g of 3-(1'-oxo-1',3',5,6,8,9-hexahydrospiro[cyclohepta[d]pyridazine-7,2'-inden]-6'-yl)benzonitrile and 0.0925 g of 3-(1'-oxo-1',3',5,7,8,9-hexahydrospiro[cyclohepta[d]pyridazine-6,2'-inden]-6'-yl)benzonitrile.

For 3-(1'-oxo-1',3',5,6,8,9-hexahydrospiro[cyclohepta[d]pyridazine-7,2'-inden]-6'-yl)benzonitrile, LC-MS $t_R$=1.51 min in 3 min chromatography, m/z 366 ($MH^+$); $^1H$ NMR (400 MHz, $CD_3OD$) δ 9.35 (m, 2H), 8.03-7.97 (m, 4H), 7.75-7.63 (m, 3H), 3.40-3.23 (m, 6H), 2.01-1.85 (m, 4H).

For 3-(1'-oxo-1',3',5,7,8,9-hexahydrospiro[cyclohepta[d]pyridazine-6,2'-inden]-6'-yl)benzonitrile, LC-MS $t_R$=1.54 min in 3 min chromatography, m/z 366 ($MH^+$); $^1H$ NMR (400 MHz, $CD_3OD$) δ 9.36 (m, 2H), 7.99-7.89 (m, 3H), 7.74-7.56 (m, 4H), 3.45-2.89 (m, 6H), 2.15-1.72 (m, 4H).

Step 5. Preparation of Compound 456

To a solution of 3-(1'-oxo-1',3',5,6,8,9-hexahydrospiro[cyclohepta[d]pyridazine-7,2'-inden]-6'-yl)benzonitrile (0.0281 g) in $CH_2Cl_2$ (5 mL) was added 0.5 mL of 1.0 M $TiCl_4$ in $CH_2Cl_2$ at room temperature. After 1.5 h, 0.4 mL of bis(trimethylsilyl)carbodiimide was added to the yellow solution. The resulting mixture was then stirred at room temperature for 18 h. The mixture was quenched with ice, diluted with $CH_2Cl_2$, and dried over $Na_2SO_4$. After the solvent was removed under reduced pressure, the crude product (0.0830 g) was directly used in the next step without further purification. LC-MS $t_R$=1.51 min in 3 min chromatography, m/z 390 ($MH^+$)

A 50 mL flask was charged with 33 mL of EtOH, 1.5833 g of sodium methoxide (25 wt. % solution in MeOH), and 0.6517 g of N-methylhydroxylamine hydrochloride. The suspension was filtered through HPLC filter and 12 mL of the filtrate was added to N-(5'-(3-cyanophenyl)-5,6,8,9-tetrahydrospiro[cyclohepta[d]pyridazine-7,2'-inden]-3'(1'H)-ylidene)cyanamide, obtained as described above. The resulting mixture was stirred at room temperature for 16 h. The mixture was purified by reversed-phase HPLC (SunFire™ Prep $C_{18}$ OBD™ 5 μm 19×50 mm column, 10%→90% MeOH/$H_2O$, 0.1% $CF_3COOH$ over 8 min and then 90% MeOH/$H_2O$, 0.1% $CF_3COOH$ over 2 min, flow rate 20 mL/min) to afford compound 456 as a TFA salt. LC-MS $t_R$=1.09, 1.23 min in 3 min chromatography, m/z 437 ($MH^+$); $^1H$ NMR (400 MHz, $CD_3OD$) δ 9.25 (m, 2H), 8.04-7.50 (m, 7H), 3.51-3.03 (m, 9H), 2.25-1.75 (m, 4H).

Step 6. Preparation of Compound 457

To a solution of 3-(1'-oxo-1',3',5,7,8,9-hexahydrospiro[cyclohepta[d]pyridazine-6,2'-inden]-6'-yl)benzonitrile (0.0925 g) in $CH_2Cl_2$ (10 mL) was added 1.0 mL of 1.0 M $TiCl_4$ in $CH_2Cl_2$ at room temperature. After 1.5 h, 0.8 mL of bis(trimethylsilyl)carbodiimide was added to the yellow solution. The resulting mixture was then stirred at room temperature for 18 h. The mixture was quenched with ice, diluted with $CH_2Cl_2$, and dried over $Na_2SO_4$. After the solvent was removed under reduced pressure, the crude product (0.1630 g) was directly used in the next step without further purification. LC-MS $t_R$=1.58 min in 3 min chromatography, m/z 390 ($MH^+$)

A 50 mL flask was charged with 33 mL of EtOH, 1.5833 g of sodium methoxide (25 wt. % solution in MeOH), and 0.6517 g of N-methylhydroxylamine hydrochloride. The suspension was filtered through HPLC filter and 23 mL of the filtrate was added to N-(5'-(3-cyanophenyl)-5,7,8,9-tetrahydrospiro[cyclohepta[d]pyridazine-6,2'-inden]-3'(1'H)-ylidene)cyanamide, obtained as described above. The resulting mixture was stirred at room temperature for 16 h. The mixture was purified by reversed-phase HPLC (SunFire™ Prep $C_{18}$ OBD™ 5 μm 19×50 mm column, 10%→90% MeOH/$H_2O$, 0.1% $CF_3COOH$ over 8 min and then 90% MeOH/$H_2O$, 0.1% $CF_3COOH$ over 2 min, flow rate 20 mL/min) to afford compound 457 as a TFA salt. LC-MS $t_R$=1.19, 1.25 min in 3 min chromatography, m/z 437 ($MH^+$); $^1H$ NMR (400 MHz, $CD_3OD$) δ 9.25 (m, 2H), 8.16-7.35 (m, 7H), 3.63-1.62 (m, 13H).

Example 392

Synthesis of Compound 458

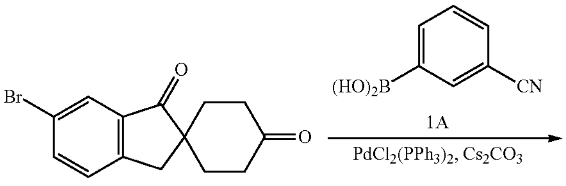

1

-continued

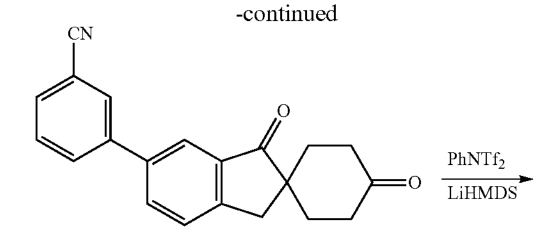

2

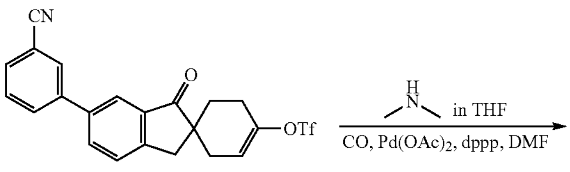

3

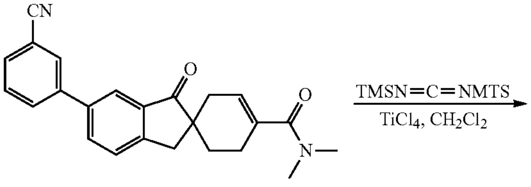

4

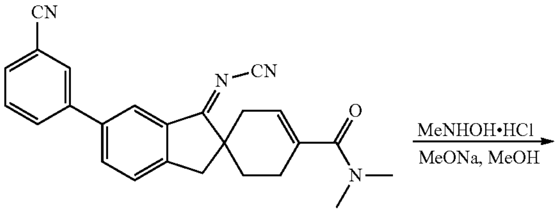

5

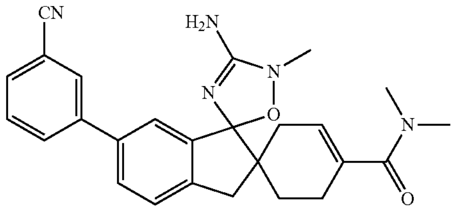

458

Step 1: Preparation of Compound 2

A mixture of compound 1 (1.5 g, 5.1 mmol), 3-cyanophenylboronic acid (1.2 g, 7.7 mmol), aq. $Cs_2CO_3$ (2 M, 20 mL) and $Pd(PPh_3)_2Cl_2$ (0.15 g, 0.21 mmol) in 1,4-dioxane (20 mL) under a nitrogen atmosphere was stirred at 80° C. for 1 h. After cooling down, $H_2O$ (50 mL) was added with stirring. The mixture was separated and the aqueous layer was extracted with ethyl acetate (100 mL×2). The combined organic fractions were washed with brine (50 mL×2), dried over $Na_2SO_4$, filtered and concentrated in vacuo. The resulting residue was purified by column chromatography on silica gel eluting with petroleum ether:ethyl acetate=50:1 to 20:1 to give compound 2 (1.4 g, 87.5% yield) as a pale yellow solid. $^1H$ NMR: ($CDCl_3$ 400 MHz): δ 7.95-8.05 (d, 1H, J=5.2 Hz), 7.88-7.95 (s, 1H), 7.80-7.88 (m, 2H), 7.68-7.73 (d, 1H, J=7.6 Hz), 7.55-7.68 (m, 2H), 3.30-3.35 (s, 2H), 2.70-2.80 (m, 2H), 2.45-2.55 (m, 2H), 2.25-2.35 (m, 2H), 1.90-2.00 (m, 2H). LC-MS: $t_R$=1.96 min in 3 min chromatography, MS (ESI) m/z 316.1 $[M+H]^+$.

Step 2: Preparation of Compound 3

To a solution of compound 2 in THF (60 mL) was added LiHMDS (10 mL, 10 mmol, 1.0 M in THF) dropwise at −78° C. under a nitrogen atmosphere. The mixture was stirred at this temperature for 1 h and a solution of $PhNTf_2$ (3.2 g, 8.88 mmol) in THF (20 mL) was added. The reaction mixture was stirred at −78° C. for another 2 h and then allowed to warm to ambient temperature for 4 h. The reaction mixture was quenched with brine (50 mL) and extracted with ethyl acetate (100 mL×3). The combined organic layers were washed with brine (100 mL), dried over $Na_2SO_4$, filtered and concentrated in vacuo. The resulting residue was purified by column chromatography on silica gel eluting with petroleum ether:ethyl acetate=50:1 to 20:1 to give compound 3 (1.5 g, 78.9% yield) as a pale yellow solid. $^1H$ NMR ($CDCl_3$ 400 MHz): δ 7.85-7.95 (d, 1H, J=5.2 Hz), 7.80-7.85 (s, 1H), 7.75-7.80 (m, 2H), 7.60-7.65 (m, 1H), 7.45-7.55 (m, 2H), 7.20-7.35 (m, 1H), 5.80-5.85 (m, 1H), 3.05-3.15 (d, 1H, J=14.0 Hz), 2.90-3.00 (d, 1H, J=14.0 Hz), 2.60-2.70 (m, 1H), 2.45-2.55 (m, 2H), 1.95-2.10 (m, 2H), 1.60-1.70 (m, 1H). LC-MS: $t_R$=2.30 min in 3 min chromatography, MS (ESI) m/z 448.1 $[M+H]^+$.

Step 3: Preparation of Compound 4

A mixture of compound 3 (0.70 g, 1.6 mmol), dimethylamine in THF (40 mL, 80 mmol, 1 M in THF), $Pd(OAc)_2$ (0.011 g, 0.048 mmol) and dppp (20 mg, 0.048 mmol) was stirred at 70° C. under CO (10 PSI) atmosphere for 24 h. The precipitate was filtered off and the filtrate was concentrated in vacuo and then the residue was purified by column chromatography on silica gel eluting with dichloromethane:methanol=100:1 to 50:1 to give compound 4 (0.43 g, yield: 72.9%) as a brown solid. $^1H$ NMR (DMSO-$d_6$ 400 MHz): δ 8.20-8.25 (s, 1H), 8.05-8.15 (m, 2H), 7.95-8.00 (s, 1H), 7.70-8.00 (d, 1H, J=7.6 Hz), 7.55-7.65 (m, 2H), 5.75-5.85 (m, 1H), 3.82 (m, 1H), 3.10-3.20 (d, 1H, J=17.6 Hz), 2.90-3.00 (d, 1H, J=17.6 Hz), 2.70-2.80 (m, 6H), 2.25-2.40 (m, 2H), 1.95-2.05 (m, 1H), 1.65-1.75 (m, 1H), 1.50-1.60 (m, 1H).

LC-MS: $t_R$=1.90 min in 3 min chromatography, MS (ESI) m/z 371.1 $[M+H]^+$.

Step 4: Preparation of Compound 5

To a solution of compound 4 (50 mg, 0.13 mmol) in anhydrous $CH_2Cl_2$ (3 mL) was added $TiCl_4$ (0.26 mL, 0.26 mmol, 1 M in $CH_2Cl_2$) under a nitrogen atmosphere, the mixture was stirred in microwave at 50° C. for 15 min, then bis(trimethylsilyl)carbodiimide (50 mg, 0.26 mmol) was added. The mixture was stirred at 60° C. in microwave for 15 min. The mixture was poured into ice-water (5 mL). The aqueous layer was extracted with $CH_2Cl_2$ (20 mL×2), the combined organic layers were washed with brine (50 mL), dried over $Na_2SO_4$ and concentrated to give crude compound 5 (60 mg, crude) as a pale yellow solid which was used directly for the next step without purification.

Step 5: Preparation of Compound 458

To a solution of N-methylhydroxylamine hydrochloride (13 mg, 0.15 mmol) in MeOH (5 mL) was added MeONa (75 mg, 0.15 mmol, 25% (Wt.) in MeOH), followed by compound 5 (60 mg, 0.15 mmol). After stirred at ambient temperature overnight, the reaction was completed detecting by LC-Ms, and the solvent was removed in vacuo to give the crude product which was purified by preparative HPLC to afford compound 458 (15 mg, 22.7% yield for 2 steps) as a white solid. $^1H$ NMR ($CD_3OD$ 400 MHz): δ 7.95-8.00 (s, 1H), 7.90-7.95 (d, 1H, J=8.0 Hz), 7.70-7.75 (d, 1H, J=7.6 Hz), 7.60-7.70 (m, 2H), 7.55-7.60 (dd, 1H, J=4.0, 8.0 Hz), 5.80-5.90 (m, 1H), 3.10-3.20 (m, 3H), 3.05-3.10 (m, 3H), 2.95-3.05 (m, 3H), 2.75-2.85 (d, 1H, J=15.6 Hz), 2.45-2.55 (m, 1H), 2.30-2.40 (m, 2H), 1.95-2.10 (m, 1H), 1.65-1.80 (m, 2H).

LC-Ms: $t_R$=1.55 min in 3 min chromatography, MS (ESI) m/z 442.2 $[M+H]^+$.

Example 393

Synthesis of Compound 459

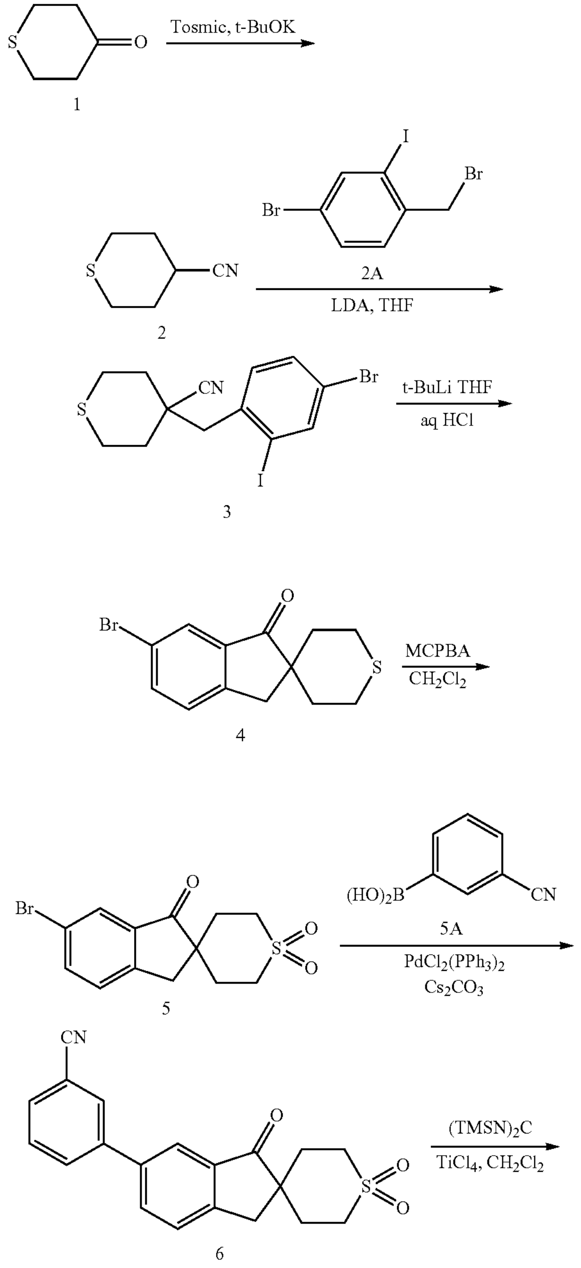

-continued

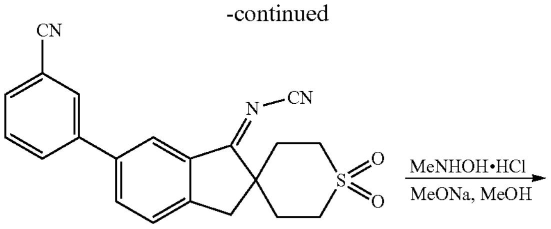

7

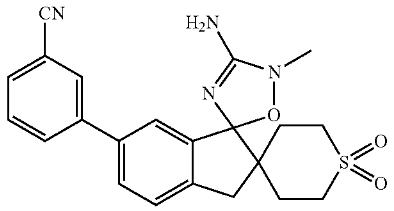

459

Step 1: Preparation of Compound 2

To a stirred solution of t-BuOK (9.66 g, 86 mmol) in THF (500 mL) was added Tosmic (16.8 g, 86 mmol) and compound 1 (10 g, 86 mmol) at −10° C. and the mixture was stirred at 0° C. for 1 h. The reaction mixture was evaporated and the residue was extracted with ether, the extracts were washed with water and dried over $Na_2SO_4$. The solvent was removed under reduced pressure and the residue was dissolved in MeOH (125 mL). To this solution was added a solution of sodium (3.9 g, 172 mmol) in MeOH (250 mL), and then the mixture was refluxed for 1 h. The reaction mixture was evaporated and the residue was purified by column chromatography on a silica gel (hexanes:EtOAc=20:1) to afford compound 2 (2 g, yield 23%). $^1H$ NMR ($CDCl_3$ 400 MH): δ 2.73-2.82 (m, 3H), 2.48-2.52 (m, 2H), 1.97-2.10 (m, 4H).

Step 2: Preparation of Compound 3

To a solution of LDA (6 mL, 10.8 mmol, 1.8 M in THF) in THF (15 mL) was added the solution of compound 2 (690 mg, 5.4 mmol) in THF (5 mL) slowly at −60° C., and the reaction mixture was stirred at −60° C. for 1 h. To the resulting mixture was added the solution of compound 2A (1.83 g, 4.9 mmol)) in THF (5 mL). The resulting mixture was stirred at −60° C. for 2 h, and then quenched with water (15 mL). The aqueous layer was extracted with EtOAc (3×40 mL). The combined organic layers were washed with brine (20 mL), dried over $Na_2SO_4$ and concentrated to dryness. The crude product was purified by chromatography on silica gel to give compound 3 (372 mg, yield 24%) as a yellow solid.

Step 3: Preparation of Compound 4

A flame dried 50 mL RBF was charged with compound 3 (372 mg, 0.88 mmol) and anhydrous THF (15 mL) under $N_2$ atmosphere. The resulting solution was stirred and cooled to −70° C., and 1.3 M t-BuLi solution in hexane (1.36 mL, 1.76 mmol, 2 eq.) was added dropwise. Deep red color was observed during the addition. The reaction was stirred another 1 h after the addition. The reaction was quenched with MeOH (0.1 mL), and followed by 2 M aq. HCl solution (2 mL). The resulting solution was concentrated to remove organic solvent. The residue was stirred in 0.5 M aq. HCl solution (10 mL). The suspension was heated to reflux (oil bath 105° C.). The reaction was cooled down to room temperature and filter. The cake was washed with $H_2O$. The light yellow solid was collected and co-evaporated with MeOH two times to remove water to give crude product, which was purified by chromatography on silica gel to give compound 4 (150 mg, yield 56%) as a white solid.

Step 4: Preparation of Compound 5

To a solution of compound 4 (80 mg, 0.27 mmol) in $CH_2Cl_2$ (10 mL) and was dropwise m-CPBA (186 mg, 1.08 mmol) kept below 20° C. The solution was stirred at room temperature for 2 h. The solid was filtered off, and the filtrate washed with $NaHCO_3$, extracted with $CH_2Cl_2$, dried over $Na_2SO_4$ and concentrated in vacuo to give crude compound 5 (80 mg, 95%). $^1H$ NMR ($CDCl_3$ 400 MHz): δ 7.92 (m, 1H), 7.66 (m, 1H), 7.36 (m, 1H), 3.65-3.70 (m, 1H), 3.35 (m, 1H), 3.11 (m, 2H), 2.97-3.01 (m, 2H), 2.30 (m, 4H).

Step 5: Preparation of Compound 6

A mixture of compound 5 (100 mg, 0.3 mmol), compound 5A (89 mg, 0.6 mmol), $Cs_2CO_3$ (2 M, 0.45 mL) and $Pd(PPh_3)_2Cl_2$ (10 mg) in 1,4-dioxane (5 mL) under a nitrogen atmosphere was stirred in microwave at 120° C. for 15 min. The reaction mixture was concentrated in vacuo to give the residue, which was purified pre-TLC to give compound 6 (40 mg, yield 30%) as a white solid. $^1H$ NMR ($CDCl_3$ 400 MHz): δ 8.05 (m, 1H), 7.87 (m, 3H), 7.72 (m, 3H), 7.60 (m, 1H), 3.69-3.75 (m, 2H), 3.17 (m, 2H), 3.01 (m, 2H), 2.30 (m, 4H).

Step 6: Preparation of Compound 7

To a solution of compound 6 (40 mg, 0.11 mmol) in DCM (3 mL) was added $TiCl_4$ (0.22 mL, 0.22 mmol) and the mixture was stirred in microwave at 50° C. for 10 min. After the reaction, bis-trimehtlysilylcarbodiimide (62 mg, 0.33 mmol) was added and the mixture was stirred in microwave at 60° C. for 10 min. The reaction was quenched with ice water and extracted with $CH_2Cl_2$, the organic layer was washed with water, brine, dried and concentrated to give the product 7 (20 mg, 57%).

Step 7: Preparation of Compound 459

To a solution of N-methylhydroxylamine hydrochloride (4.4 mg, 0.05 mmol) in MeOH (1 mL) was added NaOMe (10% in MeOH, 24.3 mg, 0.045 mmol) and the mixture was stirred for 5 min. Then a solution of compound 7 (20 mg, 0.05 mmol) in MeOH (2 mL) was added to above solution. Then reaction mixture was stirred at room temperature for 5 min. Then the solution was concentrated in vacuo and the residue was purified pre-TLC and HPLC to give compound 459 (2 mg, yield 10%) as a white solid. $^1H$ NMR ($CD_3OD$ 400 MHz): δ 7.93 (m, 2H), 7.70 (m, 4H), 7.39 (d, J=7.6 Hz, 1H), 3.38 (m, 1H), 3.20 (s, 3H), 3.18 (m, 5H), 2.56 (m, 1H), 2.30

(m, 2H), 1.72-1.77 (m, 1H). LC-MS $t_R$=0.989 min in 2 min chromatography, MS (ESI) m/z 423 $[M+H]^+$ Example 394

Synthesis of Compound 460

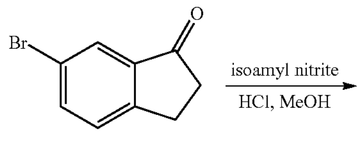

1

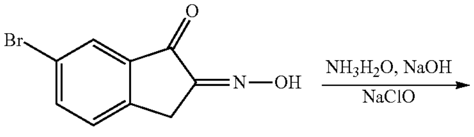

2

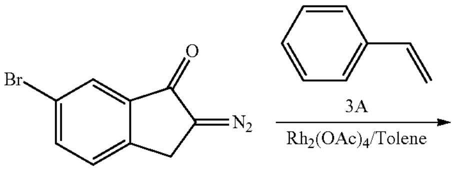

3

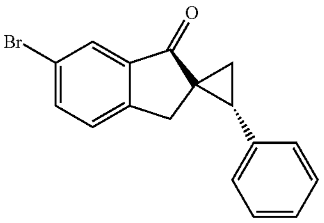

+

4

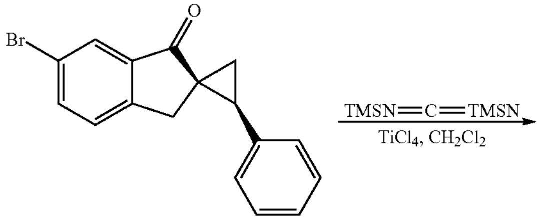

5

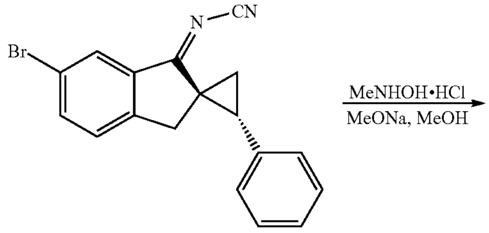

6

-continued

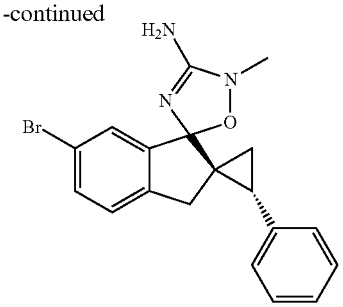

460

Procedure for Preparation of Compound 2

A solution of compound 1 (6.3 g, 0.03 mmol) in methanol (60 mL) was warmed to 40° C., then 3 mL of concentrated HCl was added dropwise, followed by isoamyl nitrite (4.38 mL, 0.033 mmol). The reaction mixture was stirred at 40° C. for 1 h. The formed precipitate was collected by filtration, washed with methanol (2×25 mL), dried in the vacuo to dryness to give compound 2 (4.0 g, 56%) as a yellow solid. $^1H$ NMR (DMSO-$d_6$ 400 MHz): δ 12.75 (s, 1H), 7.87-7.89 (dd, J=2.0, 8.0 Hz, 1H), 7.83-7.85 (m, 1H), 7.57-7.59 (d, J=8.8 Hz, 1H), 3.71 (s, 2H).

Procedure for Preparation of Compound 3

A solution of compound 2 (2.5 g, 10.4 mmol) in 1.2 N aq. NaOH solution (10 mL) and water (250 mL) was cooled to 4° C., then ammonia (3 mL) was added, followed by 5% aq. NaClO solution (40 mL). After addition, the mixture was warmed to ambient temperature and stirred for 3 h, then was extracted with $CH_2Cl_2$ (3×125 mL). The combined organic phases were dried over $Na_2SO_4$, filtered and concentrated in vacuo to give compound 3 (1.1 g, 46%) as a yellow solid. $^1H$ NMR ($CDCl_3$ 400 MHz): δ 7.87 (s, 1H), 7.61-7.63 (d, J=8.0 Hz, 1H), 7.25-7.27 (d, J=8.0 Hz, 1H), 3.96 (s, 2H).

Procedure for Preparation of Compounds 4 and 5

To a suspension of $Rh_2(OAc)_4$ (26 mg, 0.059 mmol) in anhydrous toluene (10 mL) was added compound 3A (4.41 g, 42.3 mmol) at 2025° C., then a solution of compound 3 (1.0 g, 4.23 mmol) in toluene (10 mL) was added dropwise to the mixture over 30 min and stirred for one more hour. The mixture was filtered, and the filtrate was concentrated in vacuo, the residue was purified by column chromatography on silica gel (petroleum ether:EtOAc=50:1 to 30:1) to give two isomers: compound 4 (250 mg, 30%) and compound 5 (600 mg, 64%). $^1H$ NMR compound 4 ($CDCl_3$ 400 MHz): δ 7.78 (d, J=1.6 Hz, 1H), 7.68-7.71 (dd, J=2.0, 8.4 Hz, 1H), 7.39-7.42 (d, J=8.4 Hz, 1H), 7.21-7.31 (m, 5H), 3.35-3.36 (d, J=2.8 Hz, 2H), 2.93-2.98 (t, J=8.0 Hz, 1H), 2.19-2.22 (m, 1H), 1.76-1.80 (m, 1H). LC-MS: $t_R$=1.43 min in 2 min chromatography, MS (ESI) m/z 312.9 $[M+H]^+$. $^1H$ NMR compound 5 ($CDCl_3$ 400 MHz) δ 7.94 (d, J=1.2 Hz, 1H), 7.65-7.67 (dd, J=2.0, 8.0 Hz, 1H), 7.33-7.37 (t, J=7.2, 14.8 Hz, 2H), 7.26-7.29 (m, 2H), 7.14-7.16 (d, J=7.2 Hz, 2H), 2.94-3.00 (m, 2H), 2.73-2.77 (d, J=18.0 Hz, 1H), 2.02-2.07 (m, 1H), 1.74-1.77 (m, 1H).

LC-MS: $t_R$=1.36 min in 2 min chromatography, MS (ESI) m/z 312.9 $[M+H]^+$.

Procedure for Preparation of Compound 6

To a solution of compound 4 (60 mg, 0.19 mmol) in anhydrous $CH_2Cl_2$ (1 mL) was added a solution of $TiCl_4$ (0.387 mL, 0.38 mmol in $CH_2Cl_2$) at ambient temperature. After stirring for 1 h, bis(trimethylsilyl)carbodiimid (70 mg, 0.38 mmol) was added, then the final mixture was stirred at ambient temperature for 20 h. The reaction mixture was quenched by addition of ice (5 g), extracted with $CH_2Cl_2$ (10 mL). The separated organic layer was dried over $Na_2SO_4$, filtered, and the filtrate was concentrated in vacuo to give compound 6 (70 mg, 42%) with 39% purity, which was used in next step directly without purification. LC-MS: $t_R$=1.505 min in 2 min chromatography, MS (ESI) m/z 336.9 $[M+H]^+$.

Procedure for Preparation of Compound 460

To a solution of MeNHOH.HCl (17.4 mg, 0.208 mmol) in methanol (1 mL) was added MeONa (10.3 mg, 0.187 mmol). The mixture was stirred at ambient temperature for 10 min, then a solution of compound 6 (60 mg, 0.19 mmol) in methanol (3 mL) was added dropwise at ambient temperature and stirred for 10 min. The reaction mixture was concentrated in vacuo and the residue was purified by preparative RP-HPLC to give compound 460 (2.7 mg, 34%) as a white solid. $^1H$ NMR ($CD_3OD$ 400 MHz): δ 7.35-7.44 (m, 2H), 7.21-7.31 (m, 2H), 7.12-7.19 (m, 2H), 7.05-7.07 (m, 1H), 7.00-7.02 (m, 1H), 2.99-3.33 (m, 3H), 2.38-2.78 (m, 3H), 1.45-1.51 (m, 1H), 1.21-1.30 (m, 1H). LC-MS: $t_R$=1.15 min in 2 min chromatography, MS (ESI) m/z 384.0 $[M+H]^+$.

Example 395

Synthesis of Compound 461

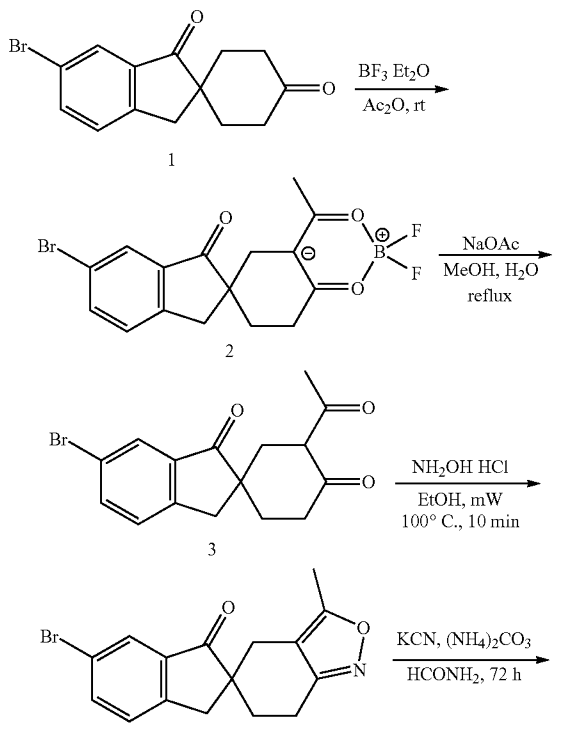

1

2

3

4

-continued

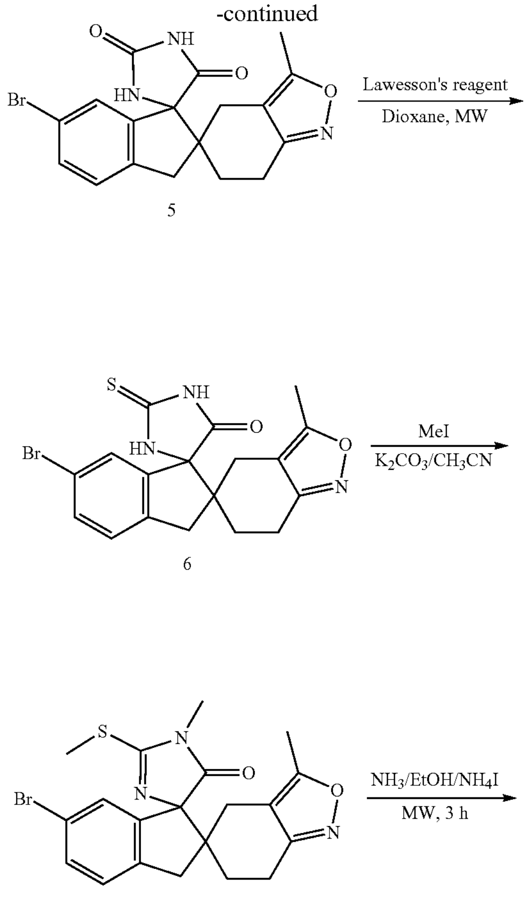

5

6

7

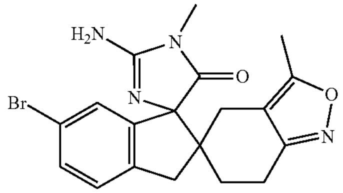

461

Procedure for Preparation of Compound 2

To a suspension of compound 1 (545.6 mg, 1.86 mmol) in $Ac_2O$ (3 mL) was added $BF_3$ $Et_2O$ (1 mL) dropwise at room temperature. The mixture was stirred overnight and quenched with ice water. The mixture was stirred another 1 h and extracted with ethyl acetate (25 mL) washed with $H_2O$ (20 mL), saturated aqueous $NaHCO_3$ (20 mL) and brine (20 mL) successively, then was dried over anhydrous $Na_2SO_4$, filtered and concentrated to give the crude compound 2 (600 mg, 84%) as a light brown foam, which was used in next step without further purification.

Procedure for Preparation of Compound 3

To a solution of crude compound 2 (300 mg, 0.78 mmol) in MeOH (3 mL) was added a solution of NaOAc (305 mg, 3.72 mmol) in $H_2O$ (0.5 mL). The mixture was heated at reflux for 3 h. MeOH was removed under reduced pressure. The residue was dissolved in EtOAc (10 mL), washed with $H_2O$ (10 mL) and brine (10 mL) successively, dried over anhydrous $Na_2SO_4$, filtered and concentrated to dryness. The oil was purified by column chromatography on silica gel (hexanes: EtOAc=20:1) to give compound 3 (153 mg, 69%); $^1$H NMR ($CDCl_3$ 400 MHz): δ 7.85 (s, 1H), 7.65 (s, 1H), 7.27-7.29 (d, J=8.0 Hz, 1H), 2.87 (m, 2H), 2.65 (m, 1H), 2.48 (m, 2H), 2.12 (m, 2H), 2.10 (s, 3H), 1.51 (m, 2H).

Procedure for Preparation of Compound 4

To a solution of compound 3 (153 mg, 0.46 mmol) in a mixture of EtOH (10 mL) and THF (2.5 mL) was added $NH_2OH$ HCl (95 mg, 1.37 mmol). The mixture was heated at reflux for 3 h. The solvent was removed under reduced pressure. The residue was purified by column chromatography on silica gel (hexanes:EtOAc=10:1) to give compound 4 (100 mg, 66%) as a light yellow solid.

Procedure for Preparation of Compound 5

A steel autoclave was charged with a mixture of compound 4 (1.8 g, 5.4 mmol), KCN (706 mg, 10.8 mmol) and $(NH_4)_2CO_3$ (3.9 g, 40.5 mmol) in formamide (50 mL). The mixture was stirred at 80° C. for 72 h, cooled to room temperature and poured into ice (50 g). After acidification with conc. HCl solution (20 mL), the resulting mixture was filtered and the filter cake was dissolved in ethyl acetate (100 mL) and washed with water (5×20 mL). The organic layer was dried over $Na_2SO_4$ and concentrated to give compound 5 (1 g, 47%). as a brown solid, which was used in next step without purification.

Procedure for Preparation of Compound 6

A suspension of compound 5 (400 mg, 0.99 mmol) and Lawesson's Reagent (402 mg, 0.99 mmol) in anhydrous 1,4-dioxane (15 mL) was stirred at 150° C. for 30 min in a CEM microware reactor. The mixture was concentrated in vacuo, and the residue was purified by prep-TLC to give compound 6 (140 mg, 34%) as a white solid.

Procedure for Preparation of Compound 7

To a solution of compound 6 (230 mg, 0.55 mmol) in $CH_3CN$ (15 mL) was added $K_2CO_3$ (304 mg, 2.2 mmol). After being stirred for 5 min, MeI (155 mg, 1.1 mmol) was added. The reaction mixture was stirred at 60° C. for 15 min in a CEM microwave reactor. The mixture was concentrated in vacuo, the residue was purified by prep-TLC to give compound 7 (120 mg, 50%) as a white solid.

Procedure for Preparation of Compound 461

A solution of compound 7 (140 mg, 0.31 mmol) and $NH_4I$ (362 mg, 2.5 mmol) in $NH_3$/EtOH (5.0 N, 5 mL) was stirred at 120° C. in a microwave reactor for 3 h. The reaction mixture was concentrated under reduced pressure. The residue was added $CH_2Cl_2$ (15 mL) and stirred for 30 min. The mixture was filtered, concentrated and purified by prep-HPLC (basic) to give compound 461 (80 mg, 57%) as a white solid. LC-MS $t_R$=0.882 min in 2 min chromatography, MS (ESI) m/z 414, 417 $[M+H]^+$. $^1$H NMR ($CD_3OD$ 400 MHz): δ 7.52-7.53 (d, J=7.2 Hz, 2H), 7.26 (d, J=8.4 Hz, 1H), 3.38 (m, 1H), 3.29 (s, 3H), 2.81 (m, 3H), 2.53 (m, 1H), 2.34 (m, 1H), 2.22 (m, 2H), 2.17 (m, 2H), 1.78 (m, 1H).

Example 396

Synthesis of Compound 462

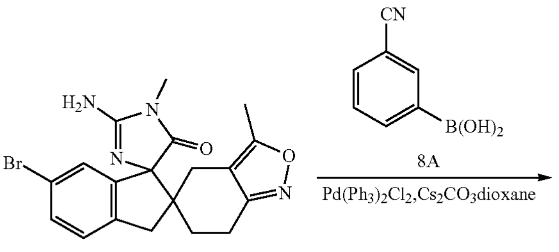

461

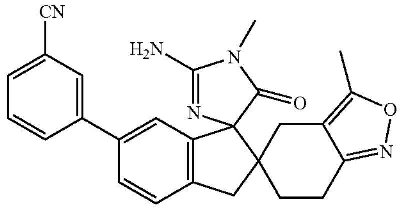

462

To a solution of compound 461 (20 mg, 0.047 mmol) in 1,4-dioxane (1 mL) was added compound 8A (15 mg, 0.10 mmol) and aq.$Cs_2CO_3$ (2M, 0.072 mL, 0.14 mmol), and deoxygenated by bubbling a stream of nitrogen. Then $PdCl_2(PPh_3)_2$ (50 mg, 0.071 mmol) was added The reaction mixture was heated at 120° C. in a CEM microwave reactor for 30 min. The solvents were removed under reduced pressure, and the residue was purified by preparative HPLC to give compound 462 (4.1 mg, 19%). LC-MS: $t_R$=1.08 min in 2 min chromatography, MS (ESI) m/z 438.2 $[M+H]^+$. $^1$H NMR ($CD_3OD$ 400 MHz): δ 7.934 (s, 1H), 7.85-7.87 (d, J=8.0 Hz, 1H), 7.61-7.63 (d, J=8.0 Hz, 2H), 7.51-7.54 (t, J=8.0, Hz, 2H), 7.35-7.40 (t, J=8.0, 10.6 Hz, 1H), 3.21-3.29 (m, 1H), 3.12-3.15 (s, 3H), 2.67-2.80 (m, 3H), 2.46-2.50 (d, J=13.2, 1H), 2.23-2.31 (t, J=18.4, 15.6 Hz, 1H), 2.10-2.18 (t, J=15.6, 18.8 Hz, 2H), 1.91-2.07 (m, 2H), 1.73-1.91 (m, 1H).

Example 397

Synthesis of Compound 463

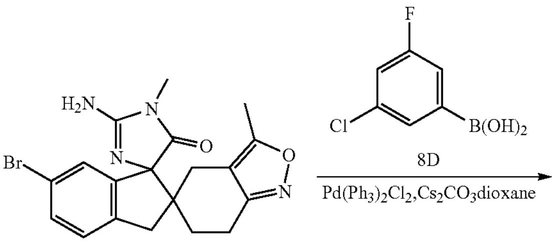

461

-continued

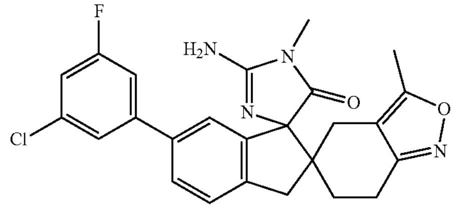

463

According to a similar synthesis of compound 462, compound 461 (20 mg, 0.05 mmol) was coupled with compound 8D (16.8 mg, 0.097 mmol) to give compound 463 (2.5 mg, 11%) as a white solid. LC-MS $t_R$=1.036 min in 2 min chromatography, MS (ESI) m/z 464 [MH+]. $^1$H NMR ($CD_3OD$ 400 MHz): δ 7.61-7.64 (m, 1H), 7.54 (s, 1H), 7.45 (s, 1H), 7.38 (d, J=8.0 Hz, 1H), 7.38 (d, J=10.0 Hz, 1H), 7.11-7.15 (m, 1H), 3.30 (m, 1H), 3.12-3.15 (s, 3H), 2.71-2.76 (m, 3H), 2.45-2.50 (m, 1H), 2.30 (m, 1H), 2.15 (m, 2H), 2.05 (m, 2H), 1.85 (m, 1H).

Example 398

Synthesis of Compound 464

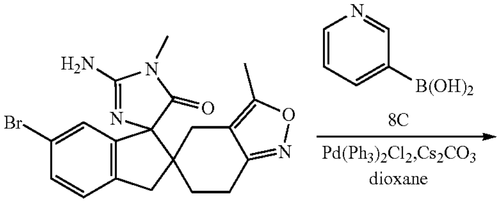

461

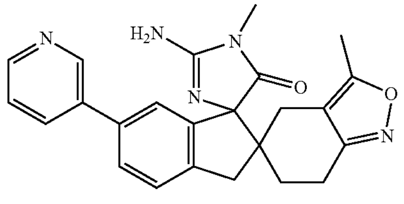

464

According to a similar synthesis of compound 462, compound 461 (20 mg, 0.048 mmol) was coupled with compound 8C (12 mg, 0.096 mmol) to give compound 464 (2.8 mg, 14%) as a white solid. LC-MS $t_R$=0.757 min in 2 min chromatography, MS (ESI) m/z 414 $[M+H]^+$. $^1$H NMR ($CD_3OD$ 400 MHz): δ 8.66 (d, J=1.2 Hz, 1H), 8.40 (d, J=4.4 Hz, 1H), 7.97 (d, J=8.0 Hz, 1H), 7.47 (m, 1H), 7.40 (m, 1H), 7.32 (m, 1H), 7.19 (m, 1H), 3.29 (m, 1H), 2.99 (s, 3H), 2.66 (m, 4H), 2.18 (m, 3H), 1.98 (m, 2H), 1.67 (m, 1H).

Example 399

Synthesis of Compound 465

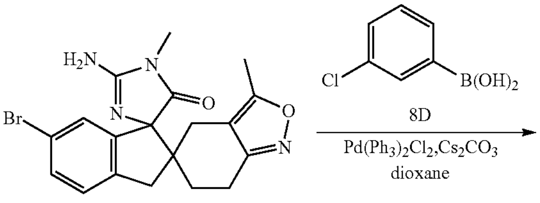

461

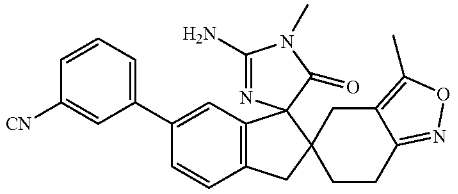

465

According to a similar synthesis of compound 462, compound 461 (20 mg, 0.048 mmol) was coupled with compound 8D (11.3 mg, 0.072 mmol) to give compound 465 (11 mg, 50%.); LC-MS $t_R$=1.021 min in 2 min chromatography, MS (ESI) m/z 447 $[M+H]^+$. $^1$HNMR ($CD_3OD$, 400 MHz): δ 7.65-7.63 (m, 2H), 7.57-7.54 (m, 2H), 7.45-7.38 (m, 2H), 7.34 (d, J=8.0 Hz, 1H), 3.36-3.32 (m, 1H), 3.23 (s, 3H), 2.88-2.75 (m, 3H), 2.54 (m, 1H), 2.41 (m, 1H), 2.23 (m, 2H), 2.14-2.09 (m, 2H), 1.98-1.83 (m, 1H).

Example 400

Synthesis of Compound 466

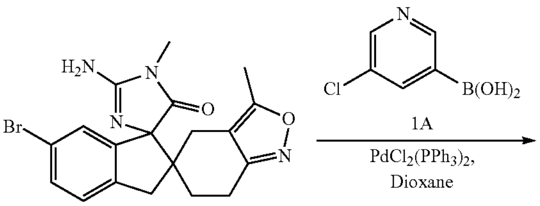

461

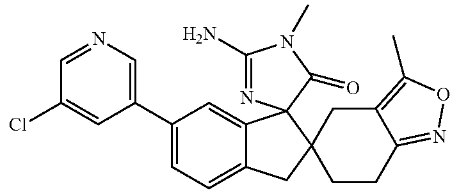

466

According to a similar synthesis of compound 462, compound 461 (30 mg, 0.072 mmol) was coupled with compound 1A (23 mg, 0.144 mmol) to give compound 466 (1.5 mg, 6%) as white solid. LC-MS $t_R$=0.921 min in 2 min chromatography, MS (ESI) m/z 448.0 $[M+H]^+$. $^1H$ NMR ($CD_3OD$ 400 MHz): δ 8.50 (s, 1H), 8.33 (s, 1H), 7.92 (s, 1H), 7.43 (s, 1H), 7.25 (m, 1H), 7.12 (m, 1H), 2.89 (m, 3H), 2.58 (m, 1H), 2.15-2.38 (m, 1H), 1.88-2.03 (m, 4H), 1.59 (m, 1H).

Example 401

Synthesis of Compound 467

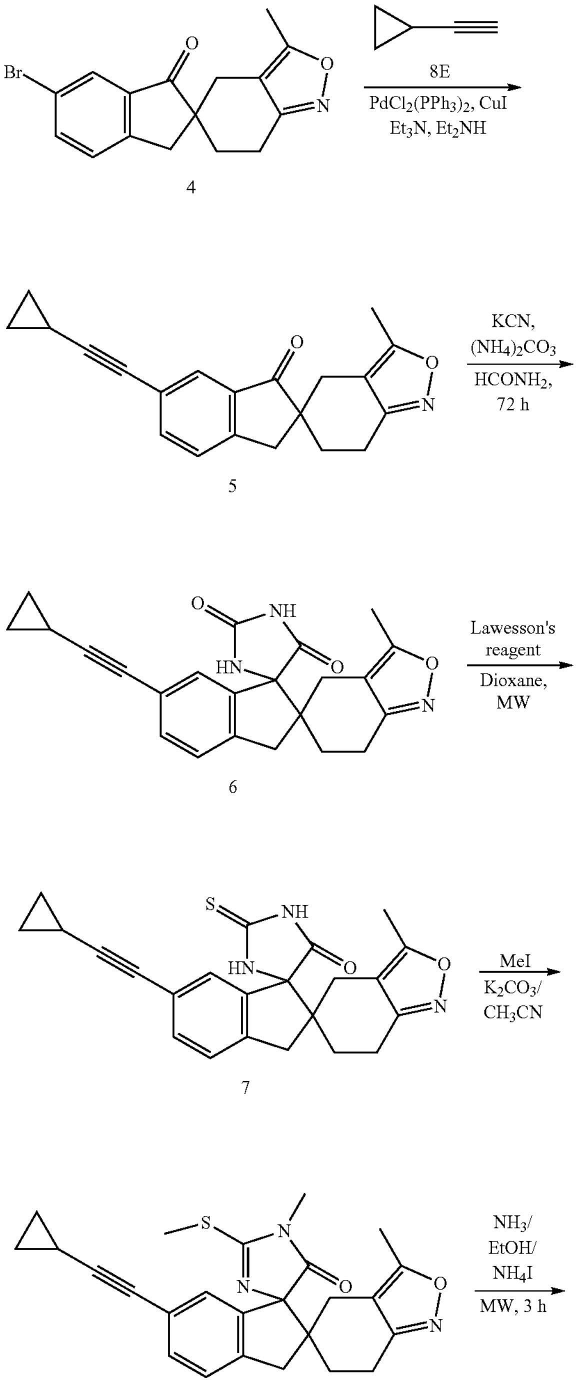

4

5

6

7

8

-continued

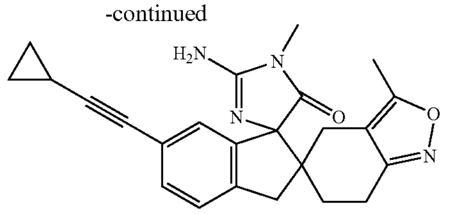

467

Procedure for Preparation of Compound 5

Compound 4 (500 mg, 1.5 mmol) was dissolved in $Et_3N$ (10 mL) and $Et_2NH$ (2 mL) was added $Pd(PPh_3)_2Cl_2$ (150 mg) and CuI (142.5 mg) under a nitrogen atmosphere. Compound 8E (1 mL) was added by syringe. The system was degassed purged $N_2$ one more time, the reaction was heated at 50° C. for 12 h, LCMS indicated that the reaction was completed. The reaction mixture was concentrated in vacuo to give the residue, which was purified preparative TLC (hexanes:EtOAc=2:1) to give compound 5 (262 mg, 55%) as a yellow solid.

Procedure for Preparation of Compound 6

A steel autoclave was charged with a mixture of compound 5 (262 mg, 0.83 mmol), KCN (107 mg, 1.65 mmol), $(NH_4)_2CO_3$ (594 mg, 6.19 mmol) and formamide (20 mL). The mixture was heated at 80° C. for 72 h, then was cooled and poured into ice. After acidification with concentrated HCl solution to pH=1, the mixture was filtered, and the solid was dissolved in $CH_2Cl_2$ (500 mL). The organic layer was washed with water (2×200 mL), dried over $Na_2SO_4$, filtered, and concentrated in vacuo. The residue was purified by column chromatography on silica gel ($CH_2Cl_2$:MeOH=50:1) to give compound 5 (178 mg, 55%) as an orange solid.

Procedure for Preparation of Compound 7

To solution of compound 5 (100 mg, 0.26 mmol) and Lawesson'reagent (104 mg, 0.26 mmol) in dioxane (3 mL) was heated at 150° C. for 30 min in a microwave reactor. The mixture was cooled, and concentrated in vacuo. The residue was purified by column chromatography on silica gel (hexanes:EtOAc=20:1) to give compound 7 (30 mg, 38%) as a light orange solid.

Procedure for Preparation of Compound 8

To a solution of compound 7 (70 mg, 0.17 mmol) in $CH_3CN$ (2 mL) was added $K_2CO_3$ (96 mg, 0.69 mmol) and MeI (48 mg, 0.34 mmol). The mixture was stirred at room temperature for 3 h. The mixture was filtered, and the filtrate was concentrated in vacuo. The residue was purified by preparative TLC (hexanes:EtOAc=3:1) to give compound 8 (38 mg, 51%) as a white solid.

Procedure for Preparation of Compound 467

A solution of compound 7 (38 mg, 0.088 mmol) and $NH_4I$ (102 mg, 0.70 mmol) in a solution of $NH_3$/EtOH (2 mL, 0.5 N) was heated at 120° C. in a CEM microwave reactor for 3 h. The mixture was concentrated in vacuo and the residue was added $CH_2Cl_2$ (20 mL) and filtered. The filtrate was concentrated in vacuo and the residue was purified by preparative TLC ($CH_2Cl_2$:MeOH=10:1) and preparative HPLC to give compound 467 (3.1 mg, 8.8%) as a white solid. LC-MS $t_R$=0.979 min in 2 min chromatography, MS (ESI) m/z 401 $[M+H]^+$. $^1H$ NMR ($CD_3OD$ 400 MHz): δ 7.24 (m, 3H), 3.20 (m, 3H), 2.94 (m, 1H), 2.74 (m, 3H), 2.63 (m, 1H), 2.44 (m, 1H), 2.25 (m, 2H), 2.00 (m, 1H), 1.70 (m, 1H), 1.40 (m, 1H), 1.18 (m, 1H), 0.74 (m, 2H), 0.63 (m, 2H).

Example 402

Synthesis of Compound 468

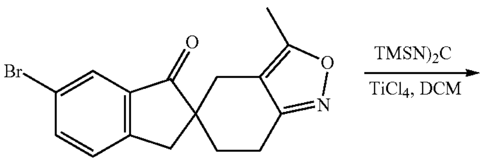

4

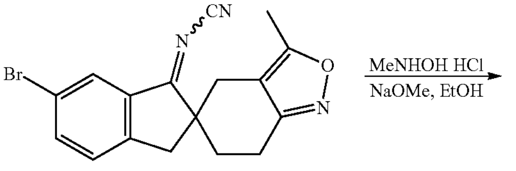

5

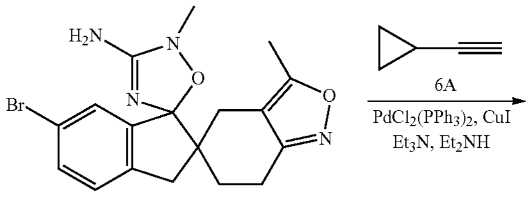

6

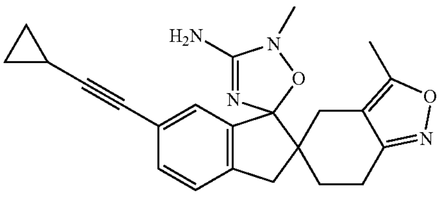

468

Procedure for Preparation of Compound 5

To a solution of compound 4 (100 mg, 0.3 mmol) in dichloromethane (5 mL) was added $TiCl_4$ (0.6 mL, 1.0 M in $CH_2Cl_2$, 0.6 mmol) and the mixture was reacted in microwave at 50° C. for 10 min. After the reaction, bis-trimehtlysilylcarbodiimide (168 mg, 0.9 mmol) was added and the mixture was reacted in microwave at 60° C. for 10 min. The reaction was quenched by addition of ice water and extracted with $CH_2Cl_2$, the organic layer was washed with water, brine, dried and concentrated to give the product 5 (104 mg, 97%) as a yellow oil, which was used in next step without purification.

Procedure for Preparation of Compound 6

To a solution of MeNHOH.HCl (24.4 mg, 0.29 mmol) in MeOH (5 mL) was added NaOMe (10 wt % in MeOH, 141 mg, 0.26 mmol) and the mixture was stirred for 5 min. Then to a solution of compound 5 (104 mg, 0.29 mmol) in MeOH (8 mL) was added to above solution. Then final reaction mixture was stirred at room temperature for 45 min. Then the solution was concentrated and the residue was purified, which was purified preparative TLC to give compound 6 (80 mg, 68%) as a white solid.

Procedure for Preparation of Compound 468

The compound 6 (40 mg, 0.1 mmol) was dissolved in $Et_3N$ (3 mL) and $Et_2NH$ (1 mL) under a nitrogen atmosphere was added $Pd(PPh_3)_2Cl_2$ (5 mg) and CuI (5 mg). Compound 6A (0.5 mL) was added by syringe. The system was degassed purged $N_2$ one more time, the reaction was heated 50° C. for 12 h, LCMS indicated that the reaction was completed. The reaction mixture was concentrated in vacuo to give the residue, which was purified preparative TLC and preparative HPLC to give compound 468 (1.9 mg, 5%) as a white solid. LC-MS $t_R$=0.994 min in 2 min chromatography, MS (ESI) m/z 389 $[M+H]^+$. $^1H$ NMR ($CD_3OD$ 400 MHz): δ 7.15-7.17 (d, J=5.6 Hz, 2H), 7.00-7.02 (d, J=8.0 Hz, 1H), 2.92 (s, 3H), 2.73 (m, 2H), 2.55 (m, 3H), 2.20 (m, 5H), 1.74 (m, 1H), 1.37 (m, 1H), 0.82 (m, 2H), 0.64 (m, 2H).

Example 403

Synthesis of Compound 469

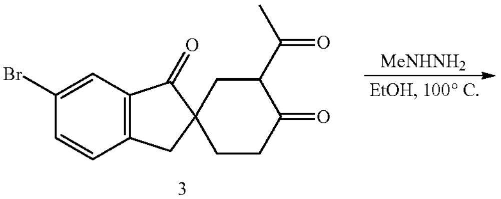

3

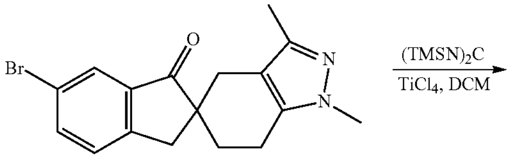

4

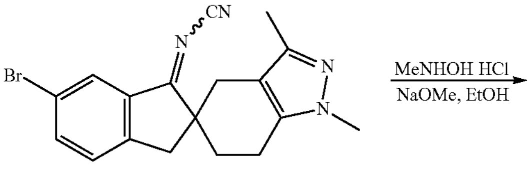

5

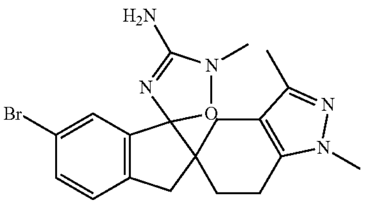

469

Procedure for Preparation of Compound 4

To a solution of compound 3 (140 mg, 0.42 mmol) in anhydrous EtOH (5 mL) was added $CH_3NHNH_2$ (95 mg, 2.09 mmol). The reaction mixture was heated at reflux overnight. The solvent was removed under reduced pressure and the residue was purified by preparative TLC (EtOAc) to give compound 4 (42 mg, 29%) as a white solid.

Procedure for Preparation of Compound 5

To a solution of compound 4 (42 mg, 0.12 mmol) in anhydrous dichloromethane (2 mL) was added $TiCl_4$ (115 mg, 0.61 mmol). The mixture was heated at 50° C. for 10 min in a microwave reactor, then N,N'-methanediylidene bis(1,1,1-trimethylsilianamine) (168 mg, 0.36 mmol) was added. The reaction mixture was heated at 60° C. for 40 min in a microwave reactor. The reaction mixture was poured into ice (20 g) and extracted with dichloromethane (3×30 mL). The combined organic layers were washed with brine (2×30 mL), dried over sodium sulfate, concentrated under reduced pressure and the residue was purified by preparative TLC (EtOAc) to give compound 5 (10 mg, 24%) as a white solid.

Procedure for Preparation of Compound 469

To a solution of compound 5 (10 mg, 0.027 mmol) in MeOH (2 mL) was added MeNHOHHCl (2.3 mg, 0.027 mmol) and MeONa solution (10 wt % in MeOH, 13.5 mg, 0.025 mmol). The reaction mixture was stirred at room temperature overnight, concentrated in vacuo and the residue was purified by preparative HPLC to give compound 469 (10 mg, 88%) as a white solid. LC-MS $t_R$=0.851 min in 2 min chromatography, MS (ESI) m/z 418 $[M+H]^+$. $^1$HNMR ($CD_3OD$, 400 MHz): δ 7.60-7.48 (m, 2H), 7.16 (d, J=7.6 Hz, 1H), 3.73 (m, 3H), 2.20-3.15 (m, 3H), 2.88-2.63 (m, 3H), 2.60-2.56 (m, 3H), 2.18-1.94 (m, 4H), 1.81-1.80 (m, 1H).

Example 404

Synthesis of Compound 470

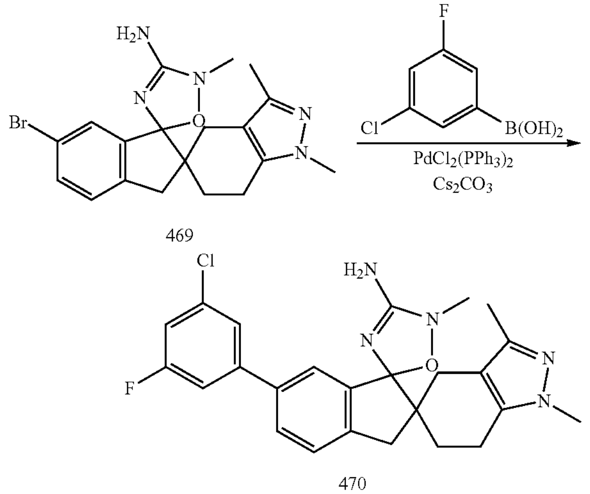

469

470

To a solution of compound 469 (20 mg, 0.048 mmol) and 3-chloro-5-fluoro-phenyl bromic acid (12.6 mg, 0.072 mmol) in dioxane (3 mL) was added $PdCl_2(PPh_3)_2$ (6.7 mg, 0.009 mmol) and $Cs_2CO_3$ (2N, 0.048 mL, 0.096 mmol). The reaction mixture was heated at 110° C. for 15 min in a microwave reactor under nitrogen, then diluted with ethyl acetate (80 mL), washed with brine (2×50 mL), dried over sodium sulfate, concentrated under reduced pressure and the residue was purified by preparative HPLC to give compound 470 (11 mg, 50%) as a white solid. LC-MS $t_R$=0.983 min in 2 min chromatography, MS (ESI) m/z 466 $[M+H]^+$. $^1$HNMR ($CD_3OD$, 400 MHz): δ 7.61-7.58 (m, 2H), 7.47 (s, 1H), 7.35-7.29 (m, 2H), 7.19 (d, J=7.2 Hz, 1H), 3.74-3.66 (m, 3H), 3.14-3.06 (m, 3H), 2.92-2.73 (m, 2H), 2.69-2.59 (m, 3H), 2.16-2.03 (m, 4H), 1.84-1.81 (m, 1H), 1.27-1.25 (m, 1H).

Example 405

Synthesis of Compound 471

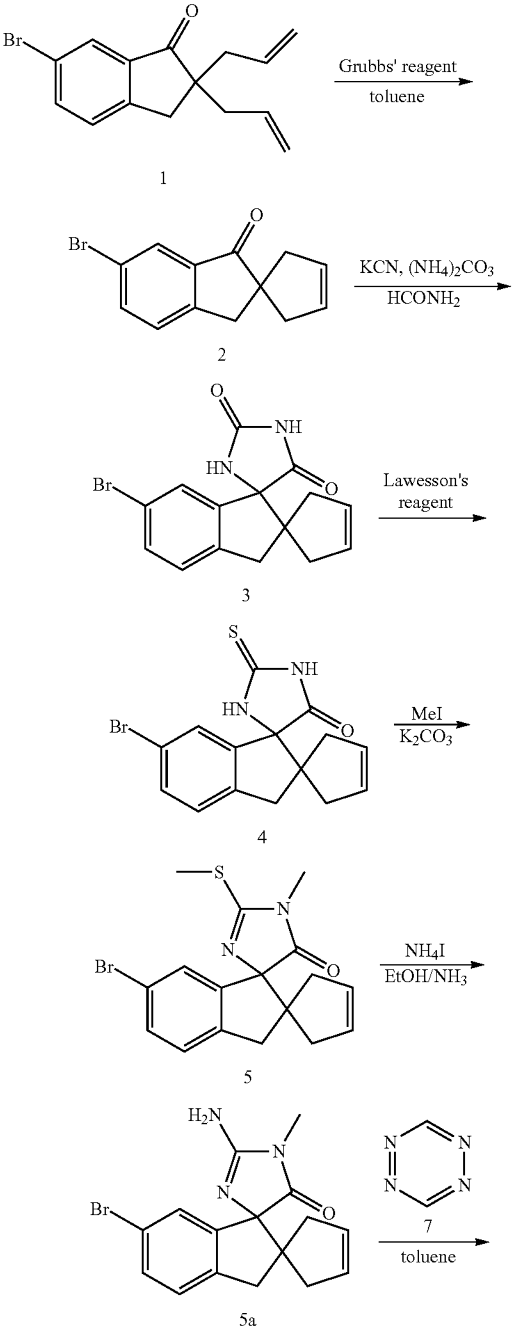

1

2

3

4

5

5a

7

-continued

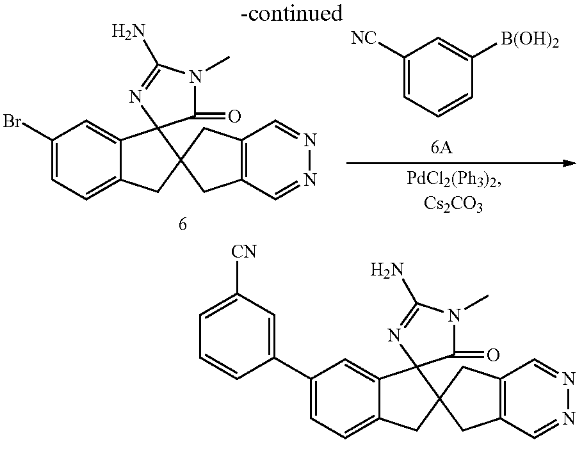

6

471

Procedure for Preparation of Compound 2

To a solution of compound 1 (7.0 g, 24.1 mmol) in toluene (600 mL) was added Grubbs Catalyst 1$^{st}$ generation (2.98 g, 3.62 mmol), and the reaction mixture was refluxed overnight. The mixture was concentrated in vacuo to give the residue, which was purified by chromatography (petroleum ether:EtOAc=100:1) to give compound 2 (5.21 g, 82%) as a white solid. LC-MS $t_R$=1.464 min in 2 min chromatography, MS (ESI) m/z 263.0 $[M+H]^+$; $^1$H NMR ($CDCl_3$ 400 MHz): δ 7.83 (s, 1H), 7.62 (m, 1H), 7.28 (m, 1H), 5.66 (s, 2H), 3.06 (s, 2H), 2.84 (d, J=14.8 Hz, 2H), 2.29 (d, J=14.8 Hz, 2H).

Procedure for Preparation of Compound 3

A steel autoclave was charged with a mixture of compound 2 (2 g, 7.6 mmol), KCN (988 mg, 15.2 mmol), and $(NH_4)_2CO_3$ (5.8 g, 60.8 mmol), formamide (60 mL) was added. The mixture was heated at 80° C. for 72 h. The reaction mixture was then cooled and poured into ice. After acidification with concentrated HCl (50 mL), the mixture was filtrated to give the solid, which was dissolved in ethyl acetate (600 mL) and washed with water (2×150 mL). The combined organic phase was dried and concentrated to give compound 3 (2.2 g, 87%) as a white solid, which was used in the next step without purification.

Procedure for Preparation of Compound 4

To a solution of compound 3 (600 mg, 1.8 mmol) in 1,4-dioxane (45 mL) was added Lawesson's reagent (800 mg, 2.97 mmol) under a nitrogen atmosphere. The reaction mixture was heated in a CEM microwave reactor at 120° C. for 60 min. The solvent was removed under reduced pressure, and the residue was purified by chromatography (petroleum ether:EtOAc=5:1) to give compound 4 (410 mg, 65%) as a white solid.

Procedure for Preparation of Compound 5

To a solution of compound 4 (300 mg, 0.86 mmol) in $CH_3CN$ (15 mL) was added compound $K_2CO_3$ (478 mg, 3.44 mmol) and MeI (488 mg, 3.44 mmol). The reaction mixture was heated at 60° C. for 10 min and then at 100° C. for 10 min in a CEM microwave reactor. The solution was filtered and the filtrate was concentrated to give the residue, which was purified by preparative TLC (petroleum ether:EtOAc=15:1) to afford compound 5 (240 mg, 71%).

Procedure for Preparation of Compound 5a

To a solution of compound 5 (420 mg, 1.11 mmol) in $NH_3$/EtOH (10 mL) was added $NH_4I$ (1.13 g, 7.80 mmol). The reaction mixture was heated at 120° C. in a CEM microwave reactor for 3 h. The solution was concentrated to give the residue, which was purified by preparative TLC ($CH_2Cl_2$:MeOH=10:1) to afford compound 5a (399 mg, 90%) as a white solid. LC-MS $t_R$=1.054 min in 2 min chromatography, MS (ESI) m/z 346.0 $[M+H]^+$. $^1$H NMR ($CDCl_3$ 400 MHz): δ 7.43 (m, 1H), 7.12 (s, 1H), 7.08 (m, 1H), 5.09 (m, 2H), 3.31 (d, J=15.2 Hz, 1H), 3.07 (s, 3H), 2.82 (d, J=12.0 Hz, 1H), 2.53-2.36 (m, 2H), 2.27 (m, 1H), 1.91 (m, 1H).

Procedure for Preparation of Compound 6

To a solution of compound 5a (100 mg, 0.29 mmol) in anhydrous toluene (3 mL) was added compound 7 (52 mg, 0.636 mmol) under a nitrogen atmosphere. The reaction mixture was heated at 150° C. in a CEM microwave reactor for 1 h. The solution was concentrated to give the residue, which was purified by preparative TLC ($CH_2Cl_2$:MeOH=8:1) to afford compound 6 (30 mg, 26%) as a red solid.

Procedure for Preparation of Compound 471

$Pd(PPh_3)_2Cl_2$ (10 mg, 0.14 mmol) in a 10 mL of flask under a nitrogen atmosphere was treated sequentially with compound 6 (30 mg, 0.075 mmol), 1,4-dioxane (1 mL), $Cs_2CO_3$ (2 N, 0.1 mL) and compound 6A (22 mg, 0.15 mmol). The mixture was heated at 120° C. under a nitrogen atmosphere in a microwave reactor for 15 min. The reaction mixture was concentrated in vacuo to give the residue, which was purified by preparative HPLC to afford compound 471 (3.1 mg, 10%). LC-MS $t_R$=0.978 min in 2 min chromatography, MS (ESI) m/z 421.0 $[M+H]^+$. $^1$H NMR ($CD_3OD$ 400 MHz): δ 9.10 (d, J=15.6 Hz, 2H), 7.98 (s, 1H), 7.88 (m, 1H), 7.67 (m, 2H), 7.56 (m, 2H), 7.43 (d, J=8.0 Hz, 1H), 3.43 (m, 1H), 3.26 (m, 2H), 3.16 (s, 3H), 3.02 (m, 1H), 2.92 (m, 1H), 2.58 (m, 1H).

Example 406

Synthesis of Compound 472

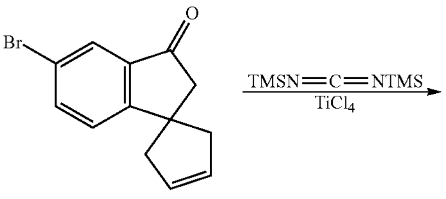

4

-continued

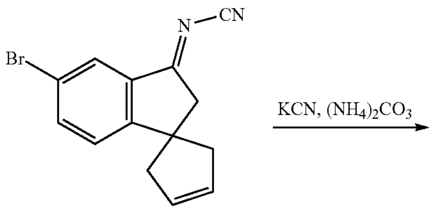

5

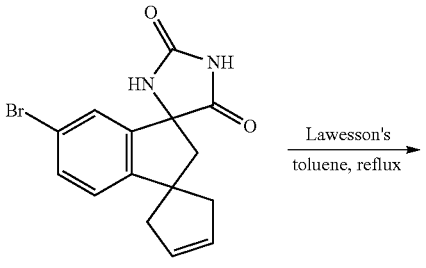

6

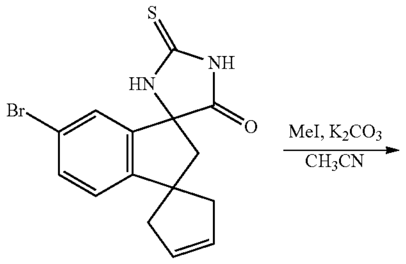

7A

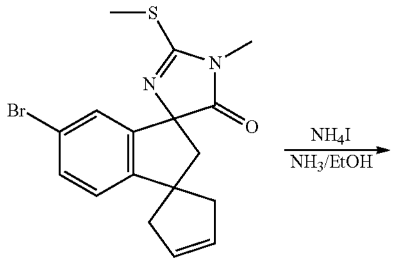

8B

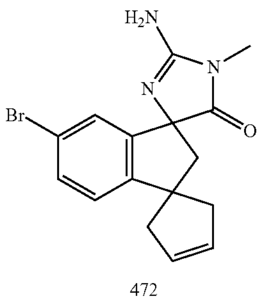

472

Procedure for Preparation of Compound 5

To a solution of compound 4 (477 mg, 1.8 mmol) in anhydrous $CH_2Cl_2$ (10 mL) was added $TiCl_4$ (1 M in $CH_2Cl_2$, 3.6 mL, 3.6 mmol) at room temperature. After the mixture was stirred in microwave at 50° C. for 15 min., bis-trimethylsilyl-carbodiimide (1.17 mL, 5.4 mmol) was added, and the mixture was stirred in microwave at 60° C. for 25 min. TLC showed the reaction was completed, and the mixture was poured into ice-water (10 mL), and extracted with $CH_2Cl_2$ (15 mL×3). The combined organic layers were washed with brine (15 mL), dried over $Na_2SO_4$, concentrated to give compound 5 (400 mg, 90%) as a yellow solid, which was used for the next step without purification.

Procedure for Preparation of 6

A steel clabe was charged with a mixture of compound 5 (400 mg, 1.39 mmol), KCN (362 mg, 5.57 mmol) in EtOH (4 mL) and $H_2O$ (4 mL). The mixture was heated at 80° C. for 24 h. The reaction mixture was cooled to room temperature and poured into ice (10 g) and filtered. The filter cake was washed with water (10 mL×2) and $CH_2Cl_2$ (10 mL×2), dried under reduced pressure to give compound 6 (440 mg, 78%) as a white solid. LC-MS $t_R$=1.219 min in 2 min chromatography, MS (ESI) m/z 333, 335 $[M+H]^+$; $^1H$ NMR (DMSO 400 MHz): δ 10.82 (m, 1H), 8.52 (d, J=27.2 Hz, 1H), 7.53 (m, 1H), 7.34 (m, 2H), 5.78 (d, J=6.4 Hz, 2H), 2.61 (m, 4H), 2.23 (m, 2H).

Procedure for Preparation of Compound 7A

A suspension of compound 6 (100 mg, 0.3 mmol) and Lawesson's reagent (121 mg, 0.3 mmol) in anhydrous toluene (4 mL) was heated at 130° C. for 35 min in a CEM microwave reactor. The reaction mixture was concentrated under reduced pressure, and the residue was purified by prep-TLC (petroleum ether:EtOAc=3:1) to give compound 7A (70 mg, 67%) as a white solid.

Procedure for Preparation of Compound 8B

To a solution of compound 7A (70 mg, 0.2 mmol) in $CH_3CN$ (2 mL) was added $K_2CO_3$ (110 mg, 0.8 mmol). After being stirred for 5 min., MeI (56.5 mg, 0.4 mmol) was added, and the reaction mixture was heated at 60° C. for 15 min in a CEM microwave reactor. The reaction mixture was concentrated under reduced pressure, and there residue was purified by prep-TLC (petroleum ether:EtOAc=5:1) to give compound 8B (60 mg, 79%).

Procedure for Preparation of Compound 472

A solution of compound 8B (30 mg, 0.08 mmol) and $NH_4I$ (92 mg, 0.64 mmol) in $NH_3$/EtOH (5.0 N, 2 mL) was heated at 120° C. in a microwave reactor for 3 h. The reaction mixture was concentrated, and the residue was purified by prep-HPLC (acidic) to give compound 472 (1.8 mg, 7%) as a white solid. LC-MS $t_R$=1.077 min in 2 min chromatography, MS (ESI) m/z 348, 350 $[M+H]^+$; $^1H$ NMR ($CD_3OD$ 400 MHz): δ 7.51 (dd, J=1.6 Hz, 4 Hz, 1H), 7.33 (d, J=8.4 Hz, 1H), 7.06 (d, J=1.6 Hz, 1H), 5.81 (s, 2H), 2.91 (m, 2H), 2.87 (s, 3H), 2.61 (m, 2H), 2.44 (m, 1H), 2.40 (m, 1H).

Example 407

Synthesis of Compound 473

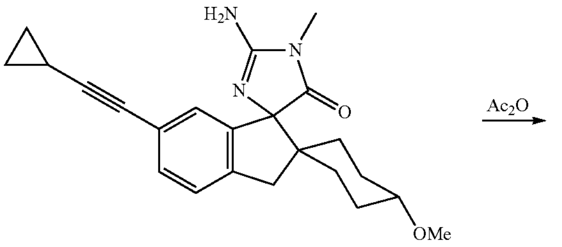

76

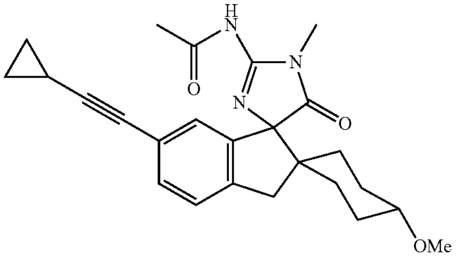

474

To a solution of compound 76 (7.38 mg, 0.02 mmol) in pyridine was added acetic anhydride (5 drops). The resulting solution was stirred at room temperature for 30 min, quenched with MeOH, and purified with a revised phase HPLC to give compound 474 (8.3 mg, 80%) as a TFA salt. LC-MS: $t_R$=1.84 min, 3 min method, MS (ESI) m/z 420 $[M+H]^+$; $^1$H NMR ($CD_3OD$ 400 MHz): δ 7.28 (m, 2H), 7.10 (s, 1H), 3.32 (s, 3H), 3.20-3.08 (m, 6H), 2.28 (s, 3H), 2.04-1.98 (m, 2H), 1.84 (m, 1H), 1.56-1.20 (m, 6H), 0.84 (m, 2H), 0.64 (m, 2H).

Example 408

Synthesis of Compound 476

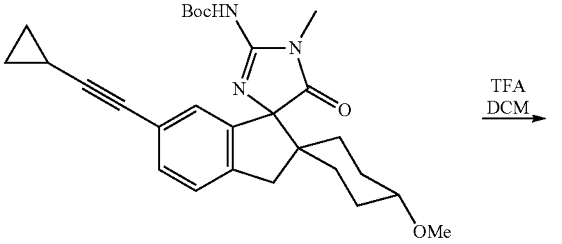

1

-continued

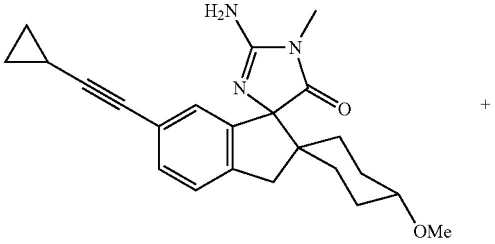

+

76

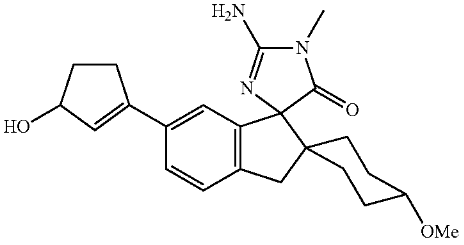

476

Compound 1 was dissolved in DCM (1 mL) and treated with TFA (1 mL) at room temperature for 30 min, and purified by a HPLC to give compound 76 (5.7 mg) as TFA salt, along with compound 476 (5.0 mg, TFA salt) as a by-product. LC-MS: $t_R$=1.17 min, 3 min method, MS (ESI) m/z 396 $[M+H]^+$; $^1$H NMR ($CD_3OD$ 400 MHz): δ 7.28 (m, 2H), 7.04 (s, 1H), 6.38 (s, 1H), 4.78 (m, 1H), 3.32 (s, 3H), 3.20-3.04 (m, 6H), 2.76-2.38 (m, 2H), 2.10-1.80 (m, 4H), 1.48-1.24 (m, 6H).

Example 409

Synthesis of Compounds 477 and 478

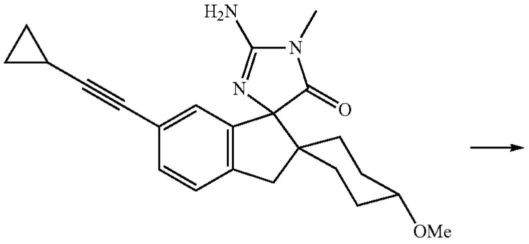

76

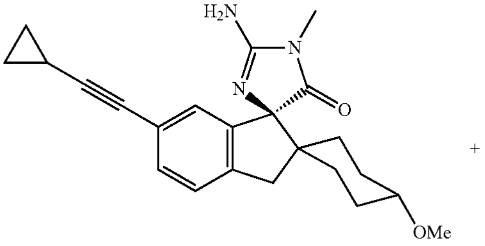

+

477

-continued

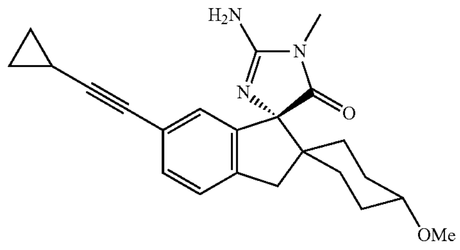

478

Compound 76 (5 mg, was purified on a chiral HPLC followed by a revised phase HPLC to give compound 478 (1.53 mg) as a TFA salt, $t_R$=37.86 min (ADH column, eluented with 80% Hexane/EtOH with 0.1% diethylamine, flow rate 4 mL/min); LC-MS: MS (ESI) m/z 378 $[M+H]^+$; $^1H$ NMR ($CD_3OD$ 400 MHz): δ 7.32 (m, 2H), 7.18 (s, 1H), 3.34 (s, 3H), 3.20-3.12 (m, 6H), 2.06-1.96 (m, 2H), 1.82 (m, 1H), 1.44-1.24 (m, 6H), 0.84 (m, 2H), 0.68 (m, 2H); and compound 477 (1.64 mg) as a TFA salt, $t_R$=42.76 min (ADH column, eluented with 80% Hexane/EtOH with 0.1% diethylamine, flow rate 4 mL/min); LC-MS: MS (ESI) m/z 378 $[M+H]^+$; $^1H$ NMR ($CD_3OD$ 400 MHz): δ 7.34 (m, 2H), 7.18 (s, 1H), 3.34 (s, 3H), 3.20-3.10 (m, 6H), 2.06-1.96 (m, 2H), 1.82 (m, 1H), 1.44-1.24 (m, 6H), 0.84 (m, 2H), 0.66 (m, 2H).

Example 410

Synthesis of Compounds 488-518 and 592-604

| | | | | |
|---|---|---|---|---|
| Microsorb 1s: | Column: Varian Microsorb 100 C18, 30 × 4.6 mm | | | |
| | UV-Detection: 210-380 nm | | | |
| | Eluent A: Water (0.15% TFA), Eluent B: Acetonitrile | | | |
| | | Time (min) | % Eluent B | Flow mL/min |
| | Gradient: | 0.00 | 5 | 3.5 |
| | | 0.18 | 5 | 3.5 |
| | | 2.00 | 98 | 3.5 |
| | | 2.20 | 98 | 3.5 |
| | | 2.30 | 5 | 3.5 |
| | | 2.50 | 5 | 3.5 |

| | | | | |
|---|---|---|---|---|
| Microsorb 4s MeOH: | Column: Varian Microsorb 100 C18, 30 × 4.6 mm | | | |
| | UV-Detection: 210-380 nm | | | |
| | Eluent A: Water (0.13% TFA), Eluent B: Methanol | | | |
| | | Time (min) | % Eluent B | Flow mL/min |
| | Gradient: | 0.00 | 5 | 2.4 |
| | | 0.35 | 5 | 2.4 |
| | | 3.95 | 100 | 2.4 |
| | | 4.45 | 100 | 2.4 |
| | | 4.55 | 5 | 2.4 |
| | | 4.90 | 5 | 2.4 |

| | | | | |
|---|---|---|---|---|
| Microsorb 7s MeOH: | Column: Varian Microsorb C18, 20 × 4.6 mm | | | |
| | UV-Detection: 210-380 nm | | | |
| | Eluent A: Water (0.13% TFA), Eluent B: Methanol | | | |
| | | Time (min) | % Eluent B | Flow mL/min |
| | Gradient: | 0.00 | 5 | 5.2 |
| | | 0.25 | 5 | 5.2 |
| | | 1.90 | 100 | 5.2 |
| | | 2.05 | 100 | 5.2 |
| | | 2.15 | 5 | 5.2 |
| | | 2.25 | 5 | 5.2 |

A. Compound 504

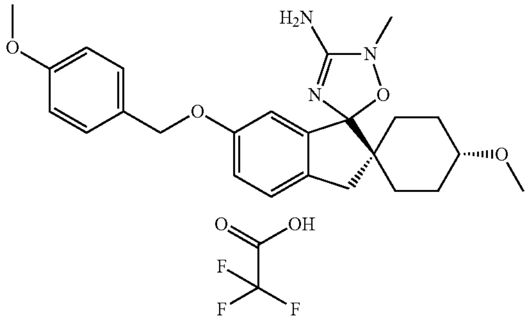

Step 1. 6-(4-Methoxy-benzyloxy)-indan-1-one

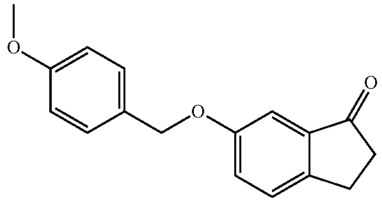 [SMILES: COc1ccc(COc2ccc3c(c2)C(=O)CC3)cc1]

4-methoxybenzylchloride (9.19 mL, 67.5 mmol) was added to a mixture of 6-hydroxy-1-indanone (10 g, 67.5 mmol) and potassium carbonate (14 g, 101 mmol) in 15 mL DMF. The mixture was reacted at RT for 14 h. The reaction mixture was diluted with water and extracted with DCM. The organic layer was separated and the solvents were removed by evaporation. The residue was dissolved in DCM and filtered through a plug of activated basic alumina. 6-(4-Methoxy-benzyloxy)-indan-1-one (18 g, 99%) was obtained after evaporation of the filtrate. The material was taken to the next step without further purification.

HPLC (Method: Microsorb 1s),

Rt: 1.46 min; Mass: $(M+H)^+$=269

By using the same synthetic strategy as for compound 504 step 1 the following compound was obtained:

| No. | Starting material 1 | Starting material 2 | Product | MS m/z [M + H]+ | HPLC Method | Rt min |
|---|---|---|---|---|---|---|
| 1.1.1 | compound 505 Step1 | 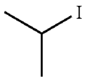 | 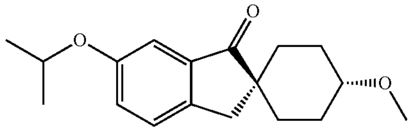 | 289 | Microsorb 1s | 1.55 |
| 1.1.2 | compound 4.1.1 | 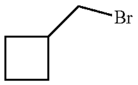 | 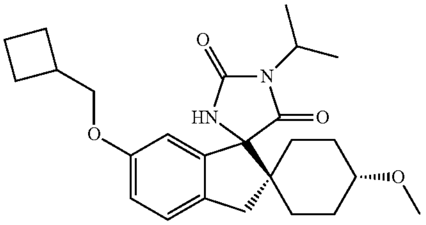 | 427 | Microsorb 1s | 1.75 |
| 1.1.3 | 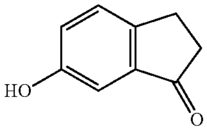 [SMILES: O=C1CCc2ccc(O)cc21] | 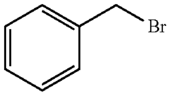 | 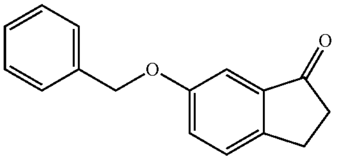 [SMILES: O=C1CCc2ccc(OCc3ccccc3)cc21] | 239 | Microsorb 1s | 1.52 |

Compound 504 Step 2

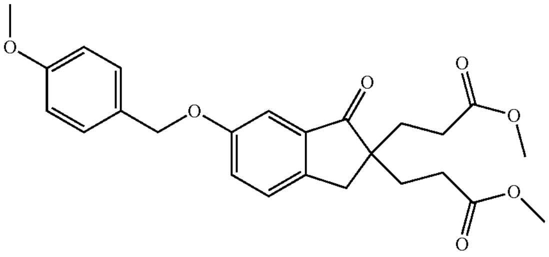 [SMILES: COC(=O)CCC1(CCC(=O)OC)Cc2ccc(OCc3ccc(OC)cc3)cc2C1=O]

6-(4-Methoxy-benzyloxy)-indan-1-one (13.5 g 95%, 47.8 mmol) was mixed with methyl acrylate (17.33 mL, 191 mmol) and heated to 60° C. Potassium fluoride (60% on alumina, Aldrich, 22.2 g, 382 mmol) was added in portions. The mixture was cooled to RT and Celite was added. The mixture was washed with DCM (200 mL). Evaporation yielded the crude product Compound 504 Step 2 (14.8 g, 70%). The material was taken to the next step without further purification.

HPLC (Method: Microsorb 1s)

Rt: 1.55 min; Mass: $(M+H)^+=441$

By using the same synthetic strategy as for compound 504 step 2 the following compound was obtained:

| No. | Starting material | Product | MS m/z [M + H]+ | HPLC Method | Rt min |
|---|---|---|---|---|---|
| 1.2.1 | compound 518 Step1 | 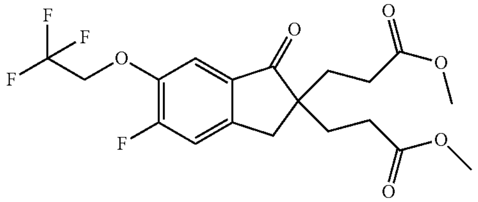 [SMILES: COC(=O)CCC1(CCC(=O)OC)Cc2cc(F)c(OCC(F)(F)F)cc2C1=O] | 421 | Microsorb 1s | 1.46 |

Compound 504 Step 3

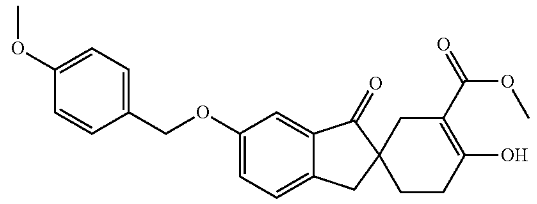 [SMILES: COC(=O)C1=C(O)CCC2(C1)Cc1ccc(OCc3ccc(OC)cc3)cc1C2=O]

Potassium-3,7-dimethyl-octan-3-olate (14.4 g, 36.7 mmol, 50% in heptane, BASF) in toluene (50 mL) was heated to reflux under nitrogen. Compound 504 Step 2 (14.7 g, 33.4 mmol) was added in toluene (50 mL). The mixture was refluxed for 12 h. The solvents were evaporated and the crude product Compound 504 Step 3 was taken to the next step without further purification.

HPLC (Method: Microsorb 1s)

Rt: 1.69 min; Mass: $(M+H)^+$=409

By using the same synthetic strategy as for compound 504 step 3 the following compound was obtained:

| No. | Starting material | Product | MS m/z [M + H]+ | HPLC Method | Rt min |
|---|---|---|---|---|---|
| 1.3.1 | 1.2.1 | 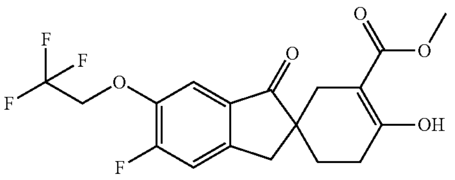 [SMILES: COC(=O)C1=C(O)CCC2(C1)Cc1cc(F)c(OCC(F)(F)F)cc1C2=O] | 389 | Microsorb 1s | 1.58 |

Compound 504 Step 4

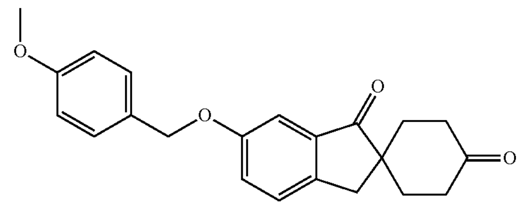 [SMILES: COc1ccc(COc2ccc3c(c2)C(=O)C2(CCC(=O)CC2)C3)cc1]

To Compound 504 Step 3 (2.78 g) in MeOH (20 mL) was added 4 M aqueous NaOH (7.0 mL, 28.0 mmol). The mixture was stirred for 2 h at 70° C. The mixture was cooled to RT. The precipitate was filtered, washed with water and dried to give Compound 504 Step 4 (1.2 g, 50%).

HPLC (Method: Microsorb 1s)

Rt: 1.49 min; Mass: $(M+H)^+$=351

Compound 504 Step 5

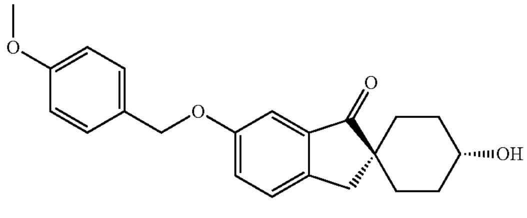 [SMILES: COc1ccc(COc2ccc3c(c2)C(=O)[C@]2(CC[C@H](O)CC2)C3)cc1]

Sodium borohydride (1.1 g, 29.2 mmol) was added portionwise over a period of 1 h to Compound 504 Step 4 (10.2 g) in THF (70 mL) at −78° C. After 1 h the mixture was heated to 4° C. and stirred for 12 h. Acetone (13.7 mL) was added. After 15 min the mixture was diluted with water and extracted with EA. The organic layer was separated and the solvents were evaporated to yield Compound 504 Step 5 (8.0 g) that was taken to the next step without further purification. The material contained the diasteromeric alcohol as minor impurity.

HPLC (Method: Microsorb 1s)

Rt: 1.50 min; Mass: $(M+H)^+$=353

By using the same synthetic strategy as for Compound 504 step 5 the following compound was obtained:

| No. | Starting material | Product | MS m/z [M + H ]+ | HPLC Method | Rt min |
|---|---|---|---|---|---|
| 1.5.1 | 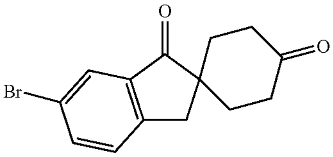 [SMILES: O=C1CCC2(CC1)Cc1ccc(Br)cc1C2=O] | 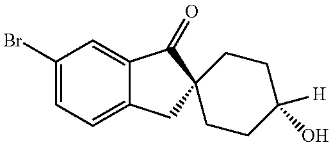 [SMILES: O=C1c2cc(Br)ccc2C[C@]12CC[C@@H](O)CC2] | 295/297 (Br) | Microsorb 1s | 1.31 |
| 1.5.2 | 2.3.1 | 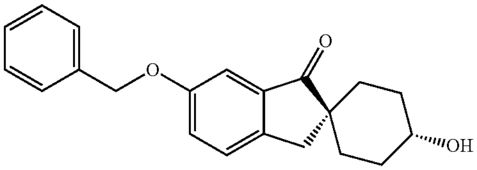 [SMILES: O=C1c2cc(OCc3ccccc3)ccc2C[C@]12CC[C@@H](O)CC2] | 323 | Microsorb 4s MeOH | 3.22 |
| 1.5.3 | 23.1.1 | 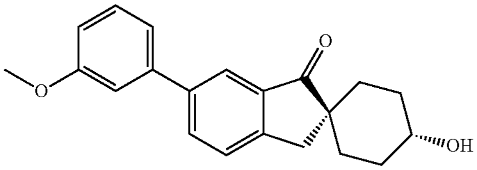 [SMILES: COc1cccc(-c2ccc3c(c2)C(=O)[C@]2(CC[C@H](O)CC2)C3)c1] | 323 | Microsorb 4s MeOH | 3.21 |

Compound 504 Step 6

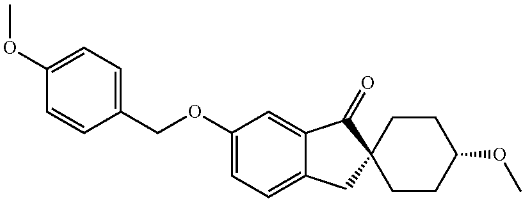 [SMILES: COc1ccc(COc2ccc3c(c2)C(=O)[C@]2(CC[C@H](OC)CC2)C3)cc1]

Methyliodide (5.71 mL, 90.8 mmol) was added to Compound 504 Step 5 (8 g, 22.7 mmol) in DMF (70 mL) followed by portionwise addition of sodium hydride (60% in mineral oil, 4.54 g, 114 mmol). The mixture was stirred for 2 h at RT and 2 h at 40° C. Methanol was added (1 mL). The reaction was diluted with water and extracted with DCM. The organic layer was separated and the solvents were evaporated. The crude product was purified by HPLC (eluent A:water+0.13% TFA, eluent B:methanol) to give Compound 504 Step 6 (4.5 g) as a white solid.

HPLC (Method: Microsorb 1s)

Rt: 1.77 min; Mass: $(M+H)^+$=367

By using the same synthetic strategy as for Compound 504 step 6 the following compound was obtained:

| No. | Starting materials | Product | MS m /z [M + H]+ | HPLC Method | Rt min |
|---|---|---|---|---|---|
| 1.6.1 | 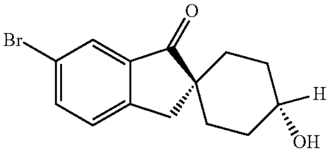 [SMILES: O=C1c2cc(Br)ccc2C[C@]12CC[C@@H](O)CC2] | 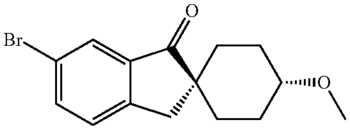 [SMILES: CO[C@H]1CC[C@]2(CC1)Cc1ccc(Br)cc1C2=O] | 309/311 (Br) | Microsorb 1s | 1.55 |
| 1.6.2 | 1.5.2 | 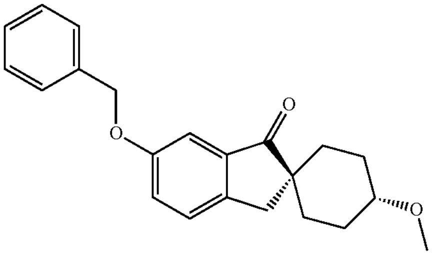 [SMILES: CO[C@H]1CC[C@]2(CC1)Cc1ccc(OCc3ccccc3)cc1C2=O] | 337 | Microsorb 4s MeOH | 3.45 |

Compound 504 Step 7

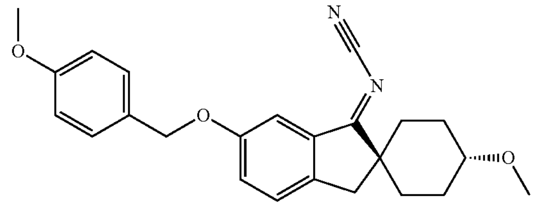 [SMILES: COc1ccc(COc2ccc3c(c2)/C(=N\C#N)[C@]2(CC[C@H](OC)CC2)C3)cc1]

Compound 504 Step 6 (96 mg, 0.26 mmol) was dissolved in anhydrous acetonitrile (2 mL) and evaporated to dryness. The residue was dissolved in acetonitrile (6 mL) and cesium fluoride (160 mg, 1.05 mmol) and 1,3-bis(trimethylsilyl)carbodimide (0.24 mL, 1.05 mmol) were added. The mixture was stirred at 50° C. for 13 h. The reaction mixture was quenched with water and extracted with EA. The organic layer was separated. Evaporation yielded Compound 504 Step 7. Toluene was added (2 mL) and evaporated to dryness to remove traces of water. The residual material was taken to the next step without further purification.

HPLC (Method: Microsorb 1s)

Rt: 1.70 min; Mass: $(M+H)^+=391$

By using the same synthetic strategy as for Compound 504 step 7 the following compound was obtained:

Compound 504 Step 8

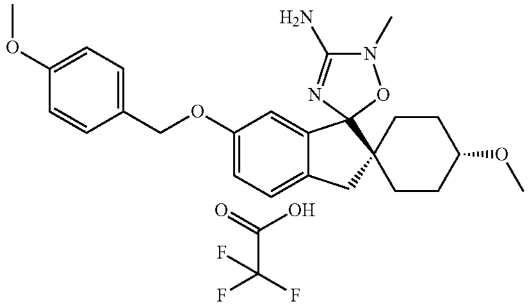

A mixture of N-methylhydroxylamine hydrochloride (43 mg, 0.51 mmol) in anhydrous EtOH (2 mL) was treated with sodium hydride (60% in mineral oil, 18 mg, 0.46 mmol) and added to a mixture of Compound 504 Step 7 (100 mg, 0.26 mmol) in anhydrous EtOH (2 mL). The mixture was stirred for 45 min at RT. Water was added and the mixture was extracted with EA. The solvents were evaporated and the residue was purified by HPLC (eluent A:water+0.13% TFA, eluent B:methanol) to give the desired product Compound 504 (21 mg, 12%).

HPLC (Method: Microsorb 1s):

Rt: 1.33/1.39 min; Mass: $(M+H)^+=438$

| No. | Starting material | Product | MS m/z $[M+H]^+$ | HPLC Method | Rt min |
|---|---|---|---|---|---|
| 1.7.1 | 1.1.1 | 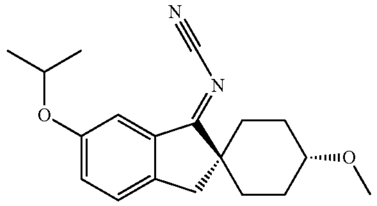 [SMILES: CO[C@H]1CC[C@]2(CC1)Cc1ccc(OC(C)C)cc1/C2=N\C#N] | 313 | Microsorb 1s | 1.59 |
| 1.7.2 | 1.1.3 | 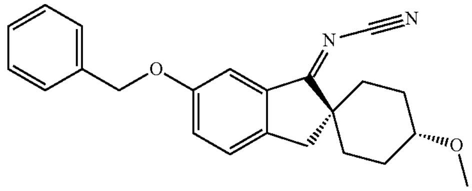 [SMILES: CO[C@H]1CC[C@]2(CC1)Cc1ccc(OCc3ccccc3)cc1/C2=N/C#N] | 361 | Microsorb 4s MeOH | 3.51 |

By using the same synthetic strategy as for Compound 504 step 8 the following compounds were obtained:
| No. | Starting material | Product | MS m/z [M + H]+ | HPLC Method | Rt min |
|---|---|---|---|---|---|
| Compound 516 | 1.7.2 | 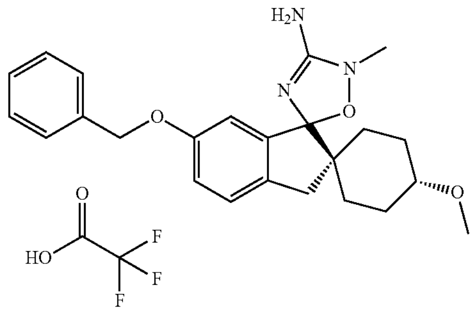 | 408 | Microsorb 4s MeOH | 2.82/ 3.08 |
| Compound 594 | 32.3.2 | 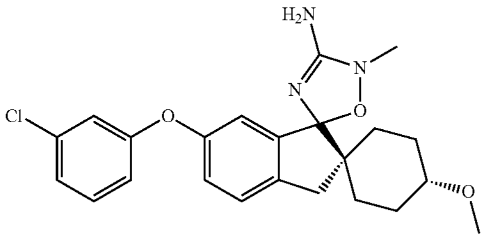 | 428 | Microsorb 4s MeOH | 3.20 |
| Compound 595 | 32.3.3 | 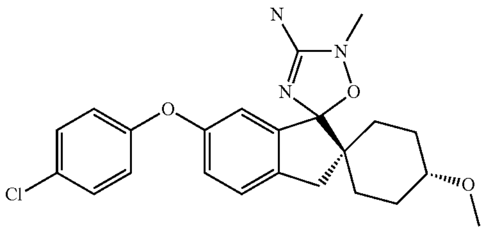 | 428 | Microsorb 4s MeOH | 2.88/ 3.19 |
| Compound 596 | 32.3.4 | 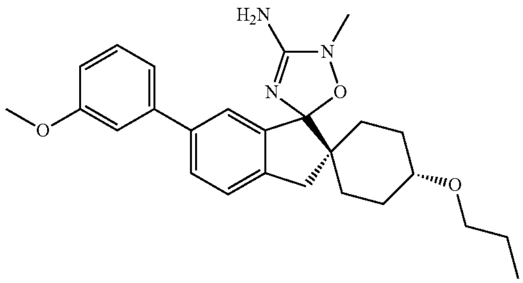 | 436 | Microsorb 4s MeOH | 3.05/ 3.29 |
| Compound 597 | 32.3.5 | 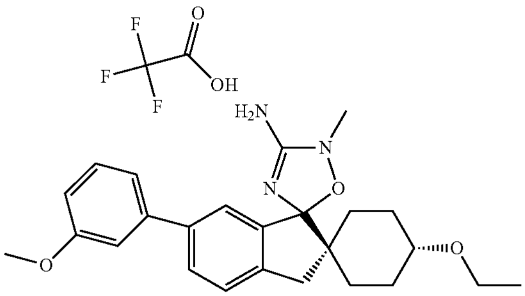 | 422 | Microsorb 1s MeOH | 1.42/ 1.50 |

B. Compound 488

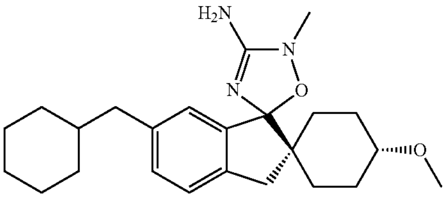

Compound 488 Step 1. 3-[6-Bromo-2-(2-methoxy-carbonyl-ethyl)-1-oxo-indan-2-yl]-propionic acid methyl ester

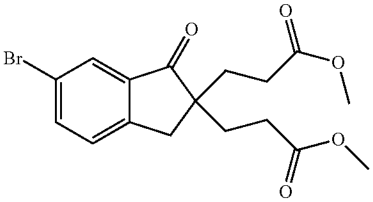 [SMILES: COC(=O)CCC1(CCC(=O)OC)Cc2ccc(Br)cc2C1=O]

To 6-bromo-1-indanone (25 g, 0.12 mol) in dioxane (150 mL) was added Triton B (2.48 mL, 6.3 mmol) and hydroquinone (5 mg, 0.05 mmol). After stirring the mixture for 10 min at 50° C. methylacrylate (21.5 mL, 0.24 mol) in 50 mL dioxane was added. The mixture was stirred for 4 h at 50° C. and 14 h at RT. Then 2 mL methylacrylate was added and the reaction was stirred for 1 h at 50° C. The reaction mixture was poured onto water, extracted with EA and the solvents were evaporated. The residue was purified by MPLC (340 g silica-gel, gradient:CH/EA 100:0 to 50:50) to give 3-[6-Bromo-2-(2-methoxycarbonyl-ethyl)-1-oxo-indan-2-yl]-propionic acid methyl ester (38 g, 84%).

HPLC (Method: Microsorb 4s MeOH),

Rt: 3.18 min; Mass: $(M+H)^+$=383/385 (Br)

By using the same synthetic strategy as for compound 488 step 1 the following compounds were obtained:

Compound 488 Step 2

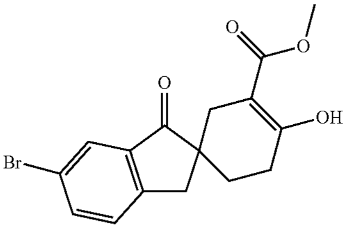

200 mL toluene which contained 2.5 g (108 mmol) of sodium were heated to reflux. Under an atmosphere of nitrogen 3-[6-Bromo-2-(2-methoxycarbonyl-ethyl)-1-oxo-indan-2-yl]-propionic acid methyl ester (compound 504 Step 1) (38 g, 99.3 mmol) in 200 mLToluol were added. The reaction was RF for 14 h and 0.5 g sodium was added. After 2.5 h under reflux the mixture was cooled to RT and 0.5 M aqueous HCl (400 mL) was added. The aqueous layer was extracted with EA and the organic layer was evaporated. The residue was purified by MPLC (340 g silicagel, gradient CH/EA 100:0 to 70:30) to give Compound 488 Step 2 (17 g, 49%).

HPLC (Method: Microsorb 4s MeOH),

Rt: 3.54 min; Mass: $(M+H)^+$=351/353 (Br)

By using the same synthetic strategy as for Compound 488 step 2 the following compounds were obtained:

| No. | Starting material | Product | MS m/z $[M+H]^+$ | HPLC Method | Rt min |
|---|---|---|---|---|---|
| 2.1.1 | 1.1.3 | 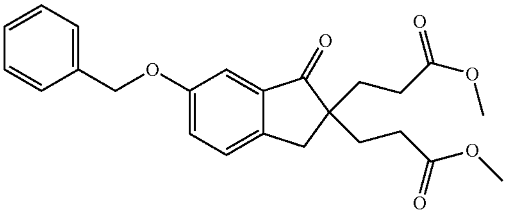 [SMILES: COC(=O)CCC1(CCC(=O)OC)Cc2ccc(OCc3ccccc3)cc2C1=O] | 411 | Microsorb 4s MeOH | 3.36 |

| No. | Starting material | Product | MS m/z $[M+H]^+$ | HPLC Method | Rt min |
|---|---|---|---|---|---|
| 2.2.1 | 2.1.1 | 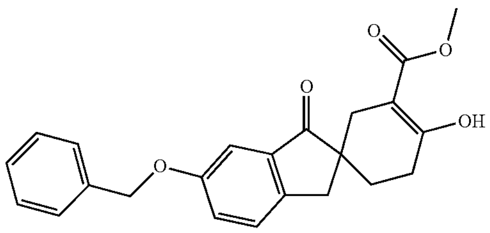 [SMILES: COC(=O)C1=C(O)CCC2(C1)Cc1ccc(OCc3ccccc3)cc1C2=O] | 379 | Microsorb 4s MeOH | 3.66 |

Compound 488 Step 3

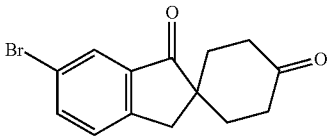 [SMILES: O=C1CCC2(CC1)Cc1ccc(Br)cc1C2=O]

To Compound 488 Step 2 (17.1 g, 48.7 mmol) in MeOH (170 mL) was added 1 M aqueous NaOH (200 mL, 200 mmol). The mixture was stirred for 2 h at 120° C. The reaction was cooled and the precipitate was filtered off, washed with water and MeOH and dried to give Compound 488 Step 3 (12.6 g, 81%).

HPLC (Method: Microsorb 4s MeOH),

Rt: 2.98 min; Mass: $(M+H)^+$=293/395 (Br)

By using the same synthetic strategy as for compound 488 step 3 the following compounds were obtained:

| No. | Starting material | Product | MS m/z $[M+H]^+$ | HPLC Method | Rt min |
|---|---|---|---|---|---|
| 2.3.1 | 2.2.1 | 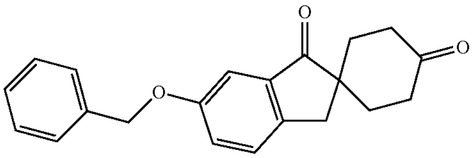 [SMILES: O=C1CCC2(CC1)Cc1ccc(OCc3ccccc3)cc1C2=O] | 321 | Microsorb 4s MeOH | 3.23 |

Compound 488 Step 4

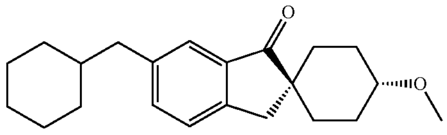 [SMILES: CO[C@H]1CC[C@]2(CC1)Cc1ccc(CC3CCCCC3)cc1C2=O]

To compound 1.6.1 (300 mg, 0.97 mmol) in dioxane (12 mL) was added $PdCl_2dppf$ (72 mg, 0.1 mmol) and (cyclohexyl)methyl zinc-bromide (9.6 mL, 4.8 mmol) under argon atmosphere. The mixture was stirred for 1.5 h at 50° C. Then the reaction was diluted with DCM and water was added. The layers was separated and the organic layer was washed with brine and aqueous ammonium chloride solution. The organic layer was evaporated. The residue was purified by MPLC (50 g silicagel, gradient petrol PE/EA 100:0 to 70:30) to give Compound 488 Step 4 (213 mg, 67%).

HPLC (Method: Microsorb 1s),

Rt: 1.99 min; Mass: $(M+H)^+$=327

By using the same synthetic strategy as for Compound 488 step 4 the following compounds were obtained:

| No. | Starting material | Product | MS m/z [M + H]+ | HPLC Method | Rt min |
|---|---|---|---|---|---|
| 2.4.1 | | | 272 | Microsorb 1s | 1.65 |
| 2.4.2 | | | 287 | Microsorb 1s | 1.74 |
| 2.4.3 | | | 335 | Microsorb 1s | 1.75 |
| 2.4.4 | | | 301 | Microsorb 1s | 1.88 |
| 2.4.5 | | | 273 | Microsorb 1s | 1.78/ 1.81 |
| 2.4.6 | | | 301 | Microsorb 1s | 1.84 |
| 2.4.7 | | | 287 | Microsorb 1s | 1.91 |
| 2.4.8 | | | 299 | Microsorb 1s | 1.93 |
| 2.4.9 | | | 325 | Microsorb 1s | 1.97 |

-continued

| No. | Starting material | Product | MS m/z [M + H]+ | HPLC Method | Rt min |
|---|---|---|---|---|---|
| 2.4.10 | 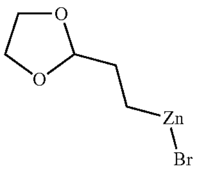 | 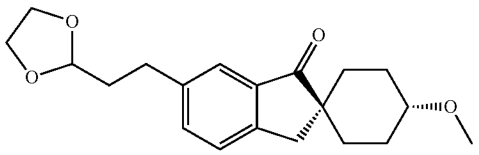 [SMILES: CO[C@H]1CC[C@]2(CC1)Cc1ccc(CCC3OCCO3)cc1C2=O] | 331 | Microsorb 7s | 1.38 |

Compound 488 Step 5

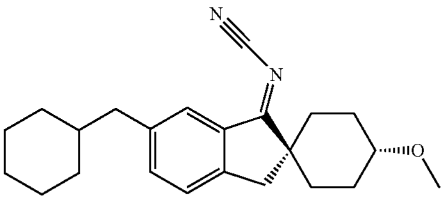 [SMILES: CO[C@H]1CC[C@]2(CC1)Cc1ccc(CC3CCCCC3)cc1/C2=N\C#N]

A mixture of Compound 488 Step 4 (210 mg, 0.64 mmol) and titanium-(IV)chloride (1N in DCM) (1.29 mL, 1.29 mmol) was stirred for 1 h at RT. Then 1,3-bis(trimethylsiyl) carbodiimide (0.48 mL, 2.07 mmol) was added. The reaction was stirred for 2 h at RT. The reaction was quenched with water and extracted with DCM. The organic layer was evaporated and the crude product Compound 488 Step 5 was taken to the next step.

HPLC (Method: Microsorb 1s)

Rt: 1.99 min; Mass: $(M+H)^+$=351

By using the same synthetic strategy as for Compound 488 step 5 the following compounds were obtained:

| No. | Starting material | Product | MS m/z [M + H]+ | HPLC Method | Rt min |
|---|---|---|---|---|---|
| 2.5.1 | 2.4.1 | 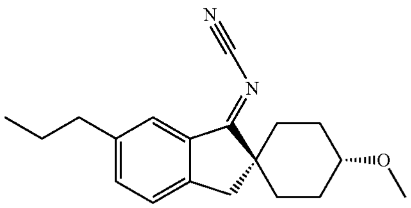 [SMILES: CCCc1ccc2c(c1)/C(=N\C#N)[C@]1(CC[C@H](OC)CC1)C2] | 297 | Microsorb 1s | 1.70 |
| 2.5.2 | 2.4.2 | 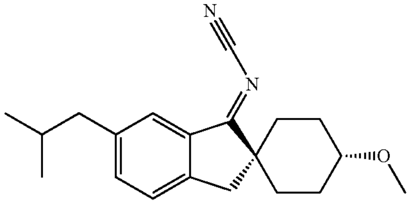 [SMILES: CO[C@H]1CC[C@]2(CC1)Cc1ccc(CC(C)C)cc1/C2=N\C#N] | 311 | Microsorb 1s | 1.77 |
| 2.5.3 | 2.4.3 | 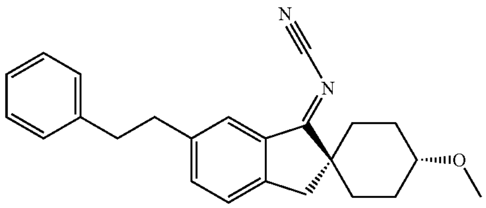 [SMILES: CO[C@H]1CC[C@]2(CC1)Cc1ccc(CCc3ccccc3)cc1/C2=N\C#N] | 359 | Microsorb 1s | 1.78 |
| 2.5.4 | 2.4.4 | 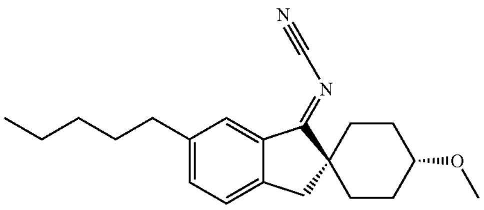 [SMILES: CCCCCc1ccc2c(c1)/C(=N\C#N)[C@]1(CC[C@H](OC)CC1)C2] | 325 | Microsorb 1s | 1.89 |

-continued
| No. | Starting material | Product | MS m/z [M + H]+ | HPLC Method | Rt min |
|---|---|---|---|---|---|
| 2.5.5 | 2.4.5 | 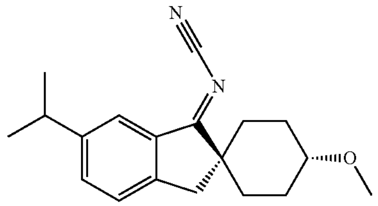 [SMILES: CO[C@H]1CC[C@]2(CC1)Cc1ccc(C(C)C)cc1/C2=N\C#N] | 297 | Microsorb 1s | 1.81/ 1.83 |
| 2.5.6 | 2.4.6 | 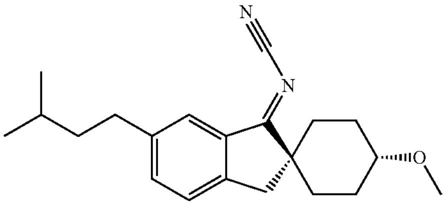 [SMILES: CO[C@H]1CC[C@]2(CC1)Cc1ccc(CCC(C)C)cc1/C2=N\C#N] | 325 | Microsorb 1s | 1.87 |
| 2.5.7 | Compound 502 step1 | 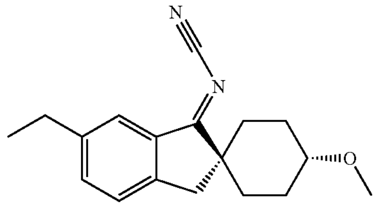 [SMILES: CCc1ccc2c(c1)/C(=N\C#N)[C@]1(CC[C@H](OC)CC1)C2] | 283 | Microsorb 1s | 1.72 |
| 2.5.8 | 2.4.7 | 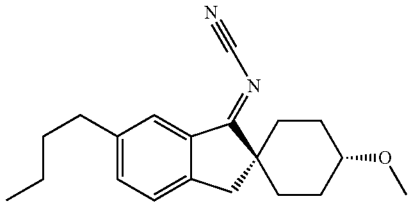 [SMILES: CCCCc1ccc2c(c1)/C(=N\C#N)[C@]1(CC[C@H](OC)CC1)C2] | 311 | Microsorb 1s | 1.92 |
| 2.5.9 | 2.4.8 | 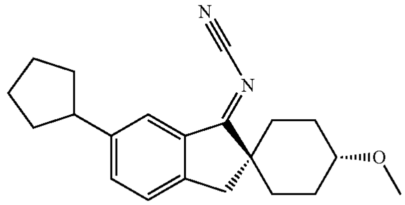 [SMILES: CO[C@H]1CC[C@]2(CC1)Cc1ccc(C3CCCC3)cc1/C2=N\C#N] | 323 | Microsorb 1s | 1.97 |
| 2.5.10 | 2.4.9 | 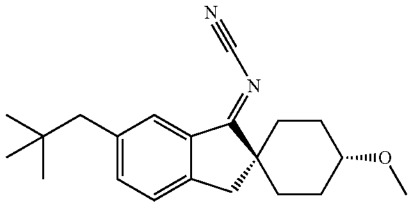 [SMILES: CO[C@H]1CC[C@]2(CC1)Cc1ccc(CC(C)(C)C)cc1/C2=N\C#N] | 325 | Microsorb 1s | 1.97 |
| 2.5.11 | Compound 517 Step2 | 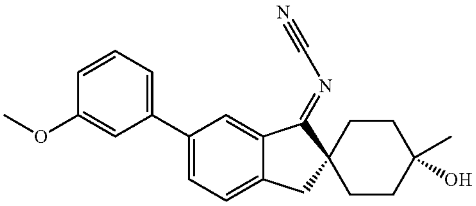 | 361 | Microsorb 1s | 1.54 |

-continued

| No. | Starting material | Product | MS m/z [M + H]+ | HPLC Method | Rt min |
|---|---|---|---|---|---|
| 2.5.12 | Compound 518 Step3 | 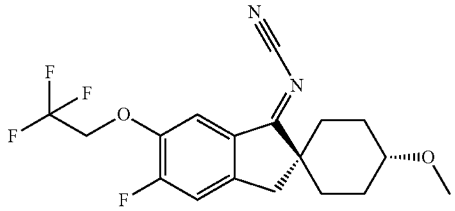 [SMILES: CO[C@H]1CC[C@]2(CC1)Cc1cc(F)c(OCC(F)(F)F)cc1/C2=N\C#N] | 371 | Microsorb 1s | 1.66 |
| 20.5.13 | Compound 602 Step1 | 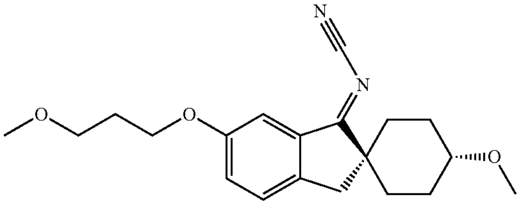 | 343 | Microsorb 1s | 1.60 |
| 2.5.14 | Compound 603 Step2 | 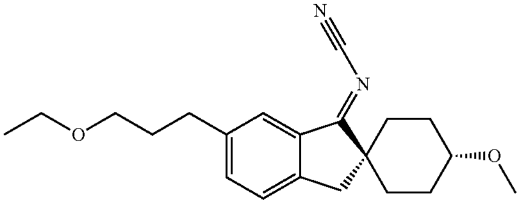 [SMILES: CCOCCCc1ccc2c(c1)/C(=N\C#N)[C@]1(CC[C@H](OC)CC1)C2] | 341 | Microsorb 1s | 1.68 |
| 2.5.15 | Compound 602 Step2 | 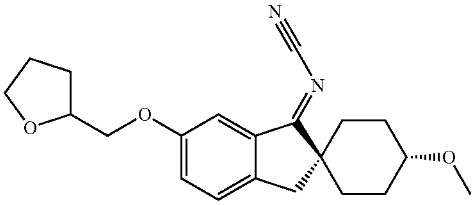 [SMILES: CO[C@H]1CC[C@]2(CC1)Cc1ccc(OCC3CCCO3)cc1/C2=N\C#N] | 355 | Microsorb 1s | 1.55 |
| 2.5.16 | Compound 504 Step6 | 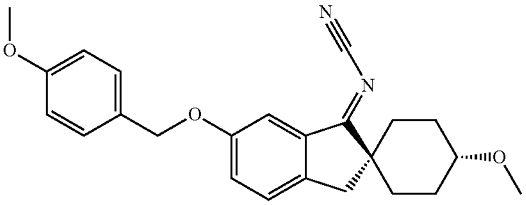 [SMILES: COc1ccc(COc2ccc3c(c2)/C(=N\C#N)[C@]2(CC[C@H](OC)CC2)C3)cc1] | 391 | Microsorb 1s | 1.67 |

Compound 488 step 6

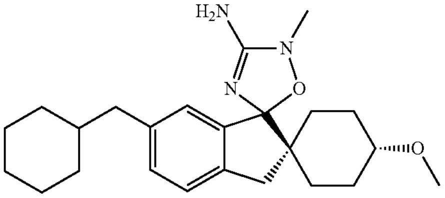

A mixture of N-methylhydroxylamine (35 mg, 0.42 mmol) in EtOH (2 mL) was treated with sodium hydride (60% in Mineral Oil) (16.8 mg, 0.42 mmol) and added to a mixture of Compound 488 Step 5 (73 mg, 0.21 mmol) in EtOH (2 mL). The reaction was stirred for 1 h at RT. Water was added and the mixture was extracted with EA. The solvents were evaporated and the residue was purified by MPLC (10 g Silicagel, CH/EE 100:0 to 50:50) to give the desired product compound 488 (43 mg, 52%). (Method: Microsorb 7s MeOH)

Rt: 1.52/1.65 min; Mass: $(M+H)^+=398$

By using the same synthetic strategy as for compound 488 step 6 the following compounds were obtained:

| No. | Starting material | Product | MS m/z [M + H]+ | HPLC Method | Rt min |
|---|---|---|---|---|---|
| Compound 489 | 2.5.1 | 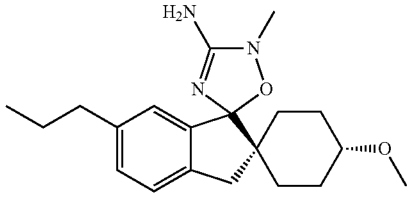 | 297 | Microsorb 1s | 1.27/ 1.36 |
| Compound 490 | 2.5.2 | 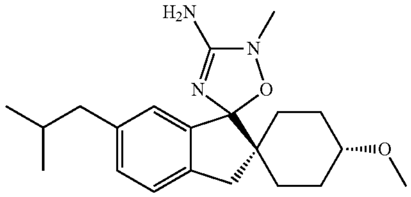 | 297 | Microsorb 1s | 1.34/ 1.44 |

C. Compound 491

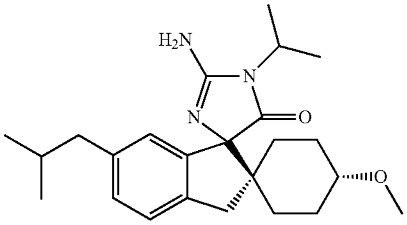

Compound 491 Step 1

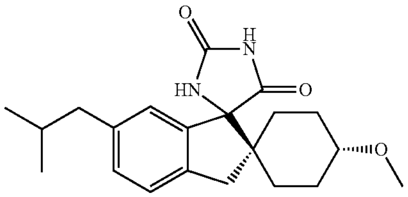

Compound 2.5.2 (155 mg, 0.5 mmol), potassium cyanide (65 mg, 1 mmol) and ammonium carbonate (336 mg, 3.5 mmol) in EtOH (1.5 mL) and water (1.5 mL) were stirred for 14 h at 75° C. in a sealed tube. The mixture was cooled, diluted with water and extracted with EA. The organic layer was washed with brine and evaporated. The crude product Compound 491 Step 1 was taken to the next step.

HPLC (Method: Microsorb 1s),

Rt: 1.38 min; Mass: $(M+H)^+$=357

By using the same synthetic strategy as for Compound 491 step 1 the following compounds were obtained:

| No. | Starting material | Product | MS m/z [M + H]+ | HPLC Method | Rt min |
|---|---|---|---|---|---|
| 3.1.1 | Compound 504 Step7 | 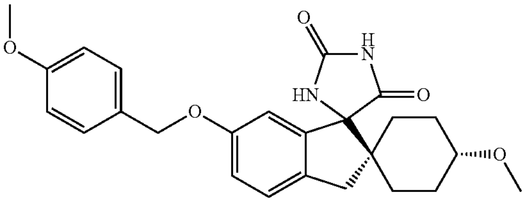 | 437 | Microsorb 1s | 1.33 |
| 3.1.2 | Compound 488 Step5 | 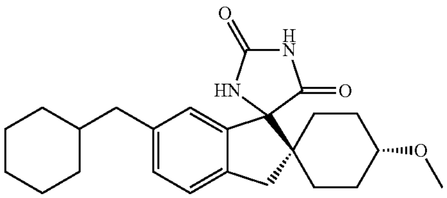 | 397 | Microsorb 1s | 1.66 |

-continued
| No. | Starting material | Product | MS m/z [M + H]+ | HPLC Method | Rt min |
|---|---|---|---|---|---|
| 3.1.3 | 2.5.1 | 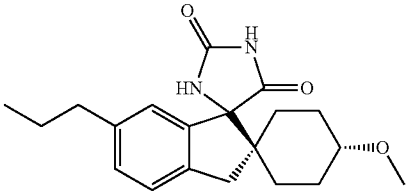 | 343 | Microsorb 1s | 1.30 |
| 3.1.4 | 2.5.3 | 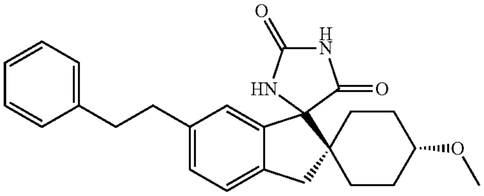 | 405 | Microsorb 1s | 1.44 |
| 3.1.5 | 2.5.4 | 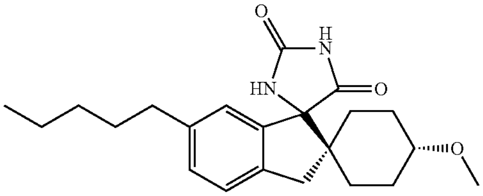 | 371 | Microsorb 1s | 1.58 |
| 3.1.6 | 2.5.5 | 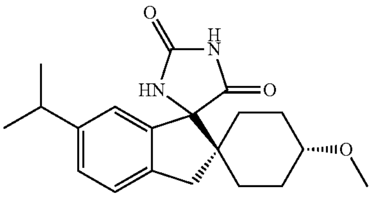 | 343 | Microsorb 1s | 1.34/ 1.37 |
| 3.1.7 | 2.5.6 | 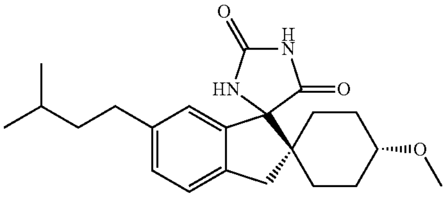 | 371 | Microsorb 1s | 1.55 |
| 3.1.8 | 2.5.7 | 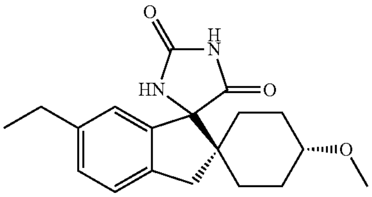 | 329 | Microsorb 1s | 1.27 |
| 3.1.9 | 2.5.8 | 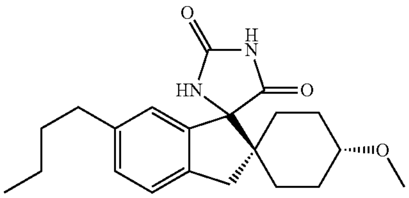 | 357 | Microsorb 1s | 1.47 |

-continued
| No. | Starting material | Product | MS m/z [M + H]+ | HPLC Method | Rt min |
|---|---|---|---|---|---|
| 3.1.10 | 2.5.9 | 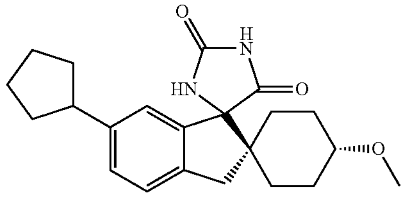 | 410 | Microsorb 1s | 1.47 |
| 3.1.11 | 2.5.10 | 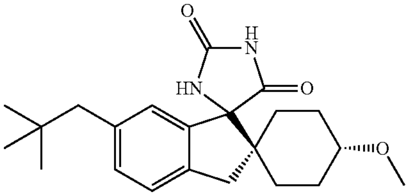 | 371 | Microsorb 1s | 1.51 |
| 3.1.12 | 2.5.13 | 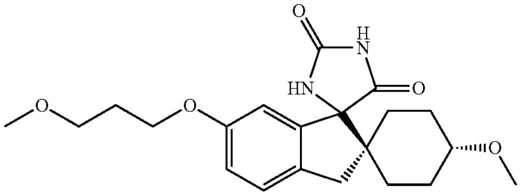 | 389 | Microsorb 1s | 1.19 |
| 3.1.13 | 2.5.14 | 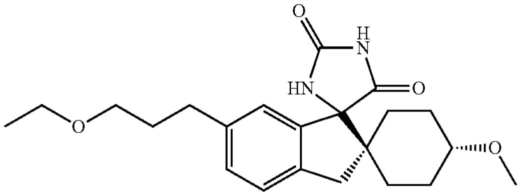 | 387 | Microsorb 1s | 1.28 |
| 3.1.14 | 2.5.15 | 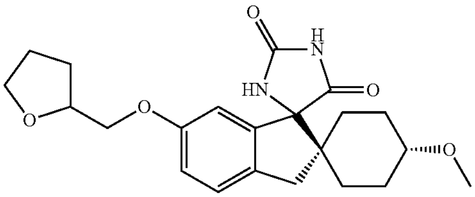 | 401 | Microsorb 1s | 1.15 |
| 3.1.15 | 2.5.16 | 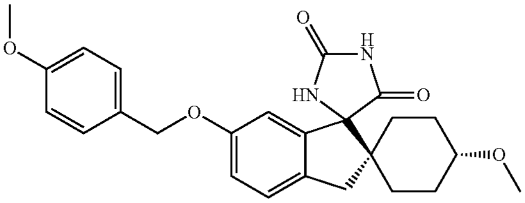 | 437 | Microsorb 1s | 1.42 |

Compound 491 Step 2

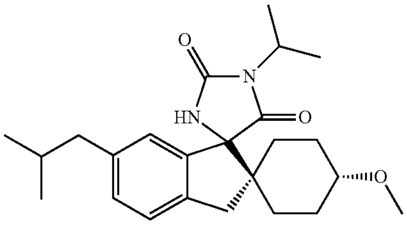

Compound 491 Step 1 (155 mg, 0.3 mmol, purity: 72%), 2-iodopropane (35 μl, 0.35 mmol) and $K_2CO_3$ (49 mg, 0.35 mmol) in DMF (3 mL) were stirred for 14 h at RT. Then 0.02 mL2-iodopropane was added and the mixture was stirred for 3 h. The reaction was diluted with DCM and extracted with water. The organic layer was evaporated. The residue was purified by MPLC (10 g silicagel, gradient CH/EA 100:0 to 70:30) to give Compound 491 Step 2 (89 mg, 71%).

HPLC (Method: Microsorb 1s),

Rt: 1.64 min; Mass: $(M+H)^+=399$

By using the same synthetic strategy as for Compound 491 step 2 the following compounds were obtained:

| No. | Starting material | Product | MS m/z [M + H]+ | HPLC Method | Rt min |
|---|---|---|---|---|---|
| 3.2.1 | 3.1.1 | 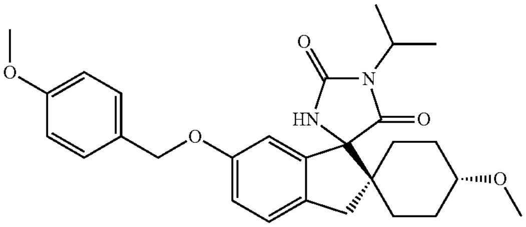 | 479 | Microsorb 1s | 1.54 |
| 3.2.2 | 3.1.2 | 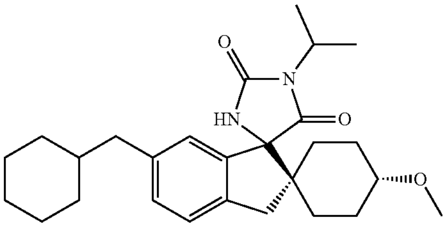 | 439 | Microsorb 1s | 1.99 |
| 3.2.3 | 3.1.3 | 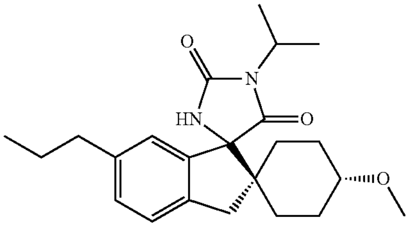 | 385 | Microsorb 1s | 1.57 |
| 3.2.4 | 3.1.4 | 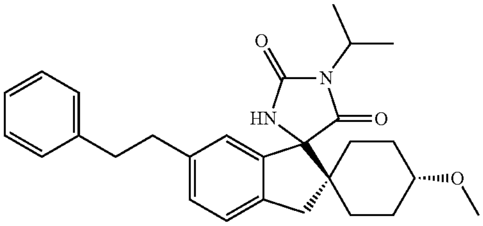 | 447 | Microsorb 1s | 1.80 |
| 3.2.5 | 3.1.5 | 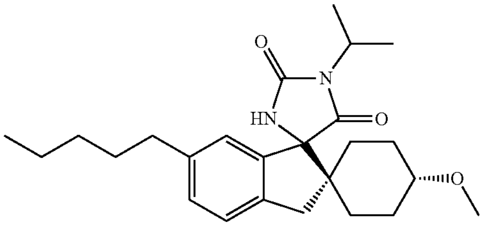 | 413 | Microsorb 1s | 1.88 |

-continued
| No. | Starting material | Product | MS m /z [M + H]+ | HPLC Method | Rt min |
|---|---|---|---|---|---|
| 3.2.6 | 3.1.6 | 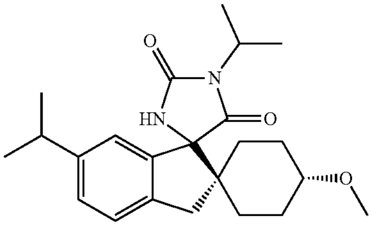 | 385 | Microsorb 1s | 1.66/ 1.68 |
| 3.2.7 | 3.1.7 | 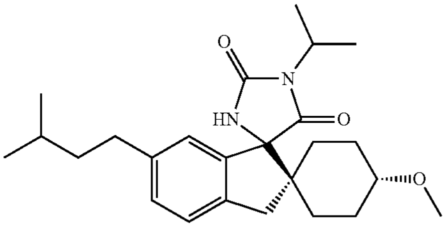 | 429 | Microsorb 1s | 2.03 |
| 3.2.8 | 3.1.8 | 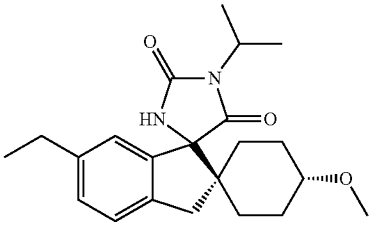 | 371 | Microsorb 1s | 1.59 |
| 3.2.9 | 3.1.9 | 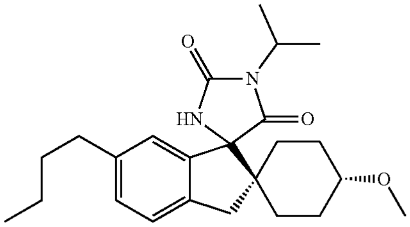 | 399 | Microsorb 1s | 1.77 |
| 3.2.10 | 3.1.10 | 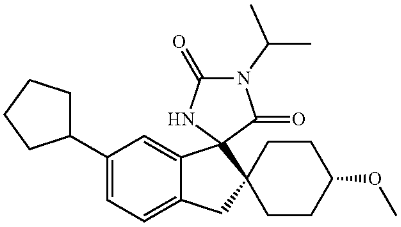 | 411 | Microsorb 1s | 1.77 |
| 3.2.11 | 3.1.11 | 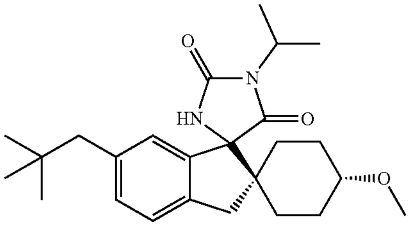 | 413 | Microsorb 1s | 1.79 |

-continued
| No. | | Starting material | Product | MS m/z [M + H]+ | HPLC Method | Rt min |
|---|---|---|---|---|---|---|
| 3.2.12 | 3.3.15 | 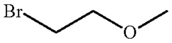 | 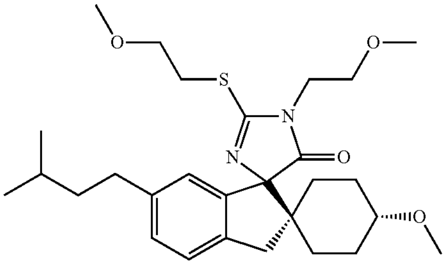 | 503 | Microsorb 1s | 1.93 |
| 3.2.13 | 3.3.15 | 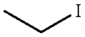 | 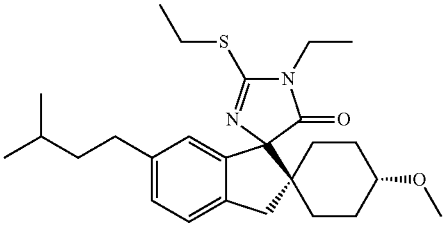 | 443 | Microsorb 1s | 2.08 |
| 3.2.14 | 3.3.15 | 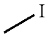 | 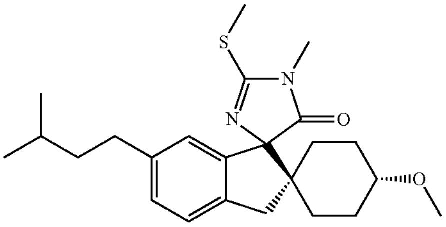 | 443 | Microsorb 1s | 1.72/ 1.83 |
| 3.2.15 | 32.4.1 | 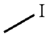 | 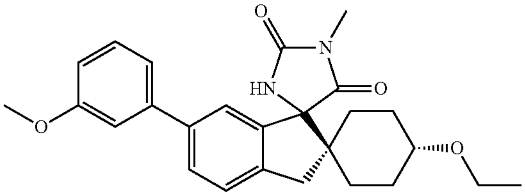 | 435 | Microsorb 1s | 1.56 |
| 3.2.16 | 3.1.12 | 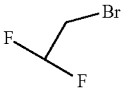 | 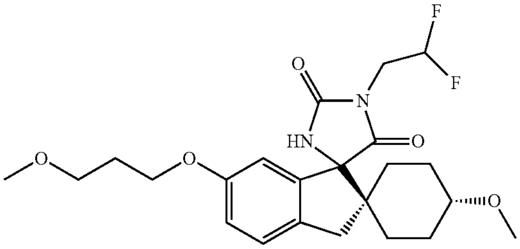 | 453 | Microsorb 7s | 1.30 |
| 3.2.17 | 3.1.13 | 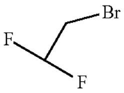 | 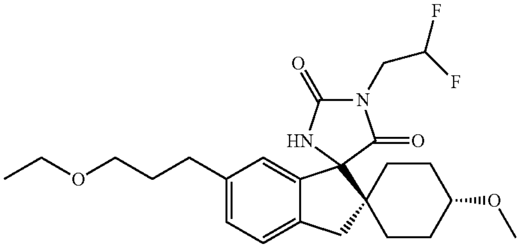 | 451 | Microsorb 1s | 1.50 |

-continued

| No. | Starting material | Product | MS m/z [M + H]+ | HPLC Method | Rt min |
|---|---|---|---|---|---|
| 3.2.18 | 3.1.14 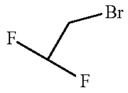 | 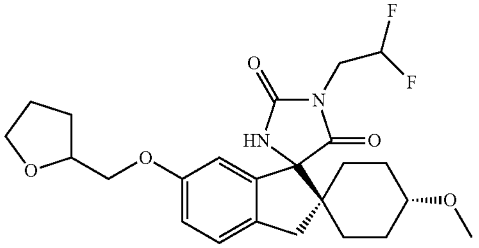 | 465 | Microsorb 7s | 1.28 |

Compound 491 Step 3

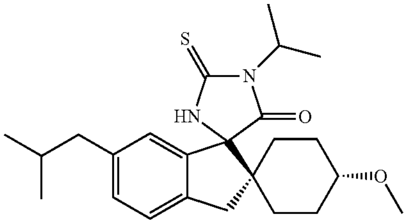

Compound 491 Step 2 (88 mg, 0.22 mmol) and 2,4-bis-(4-methoxy-phenyl)-[1,3,2,4]dithiadiphosphetane 2,4-disulfide (178.6 mg, 0.44 mmol) in dioxane (4 mL) were stirred for 1 h at 130° C. in the microwave. Then additional (178.6 mg, 0.44 mmol) 2,4-bis-(4-methoxy-phenyl)-[1,3,2,4]dithiadiphosphetane 2,4-disulfide was added and the mixture was stirred for 1 h under the same conditions. The solvent was evaporated. The residue purified by MPLC (25 g silicagel, gradient: CH/EA 100:0 to 60:40 to give Compound 491 Step 3 (66 mg, 72%).

HPLC (Method: Microsorb 1s),

Rt: 1.81 min; Mass: $(M+H)^+=415$

By using the same synthetic strategy as for compound 491 step 3 the following compounds were obtained:

| No. | Starting material | Product | MS m/z [M + H]+ | HPLC Method | Rt min |
|---|---|---|---|---|---|
| 3.3.1 | 1.1.2 | 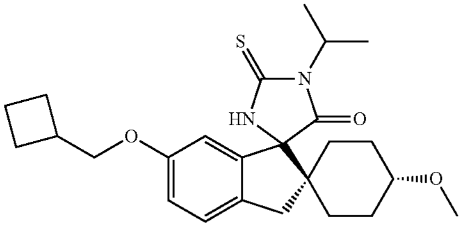 | 443 | Microsorb 1s | 1.94 |
| 3.3.2 | 3.2.2 | 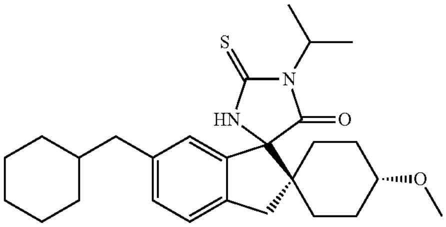 | 445 | Microsorb 1s | 2.13 |
| 3.3.3 | 3.2.3 | 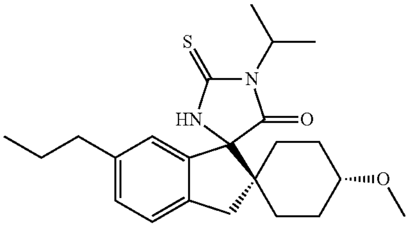 | 401 | Microsorb 1s | 1.74 |

-continued
| No. | Starting material | Product | MS m/z [M + H]+ | HPLC Method | Rt min |
|---|---|---|---|---|---|
| 3.3.4 | 3.2.4 | 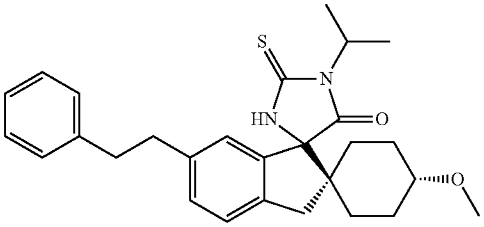 | 463 | Microsorb 1s | 1.96 |
| 3.3.5 | 3.2.5 | 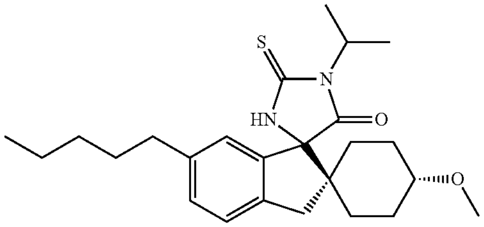 | 429 | Microsorb 1s | 2.05 |
| 3.3.6 | 3.2.6 | 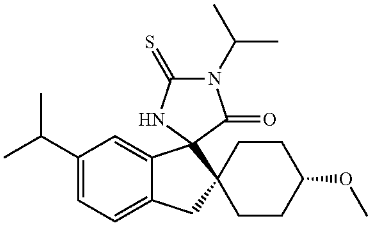 | 401 | Microsorb 1s | 1.85/ 1.88 |
| 3.3.7 | 3.2.7 | 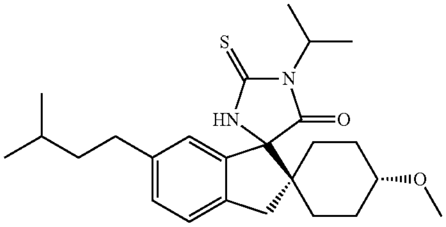 | 412 | Microsorb 1s | 1.59 |
| 3.3.8 | 3.2.8 | 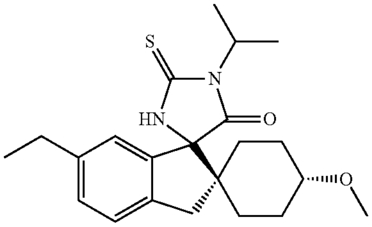 | 387 | Microsorb 1s | 1.78 |
| 3.3.9 | 3.2.9 | 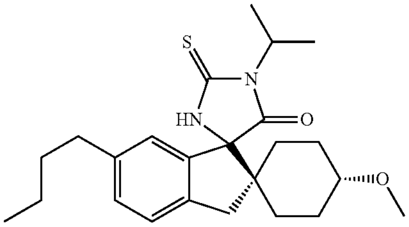 | 415 | Microsorb 1s | 1.92 |

-continued
| No. | Starting material | Product | MS m/z [M + H]+ | HPLC Method | Rt min |
| --- | --- | --- | --- | --- | --- |
| 3.3.10 | 3.2.10 | 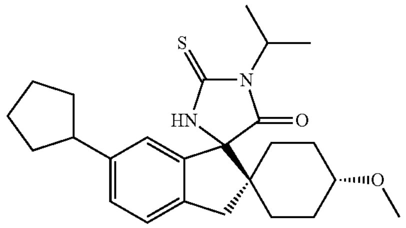 | 427 | Microsorb 1s | 1.93 |
| 3.3.11 | 3.2.11 | 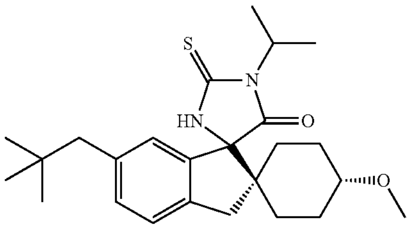 | 429 | Microsorb 1s | 1.97 |
| 3.3.12 | Compound 510 Step5 | 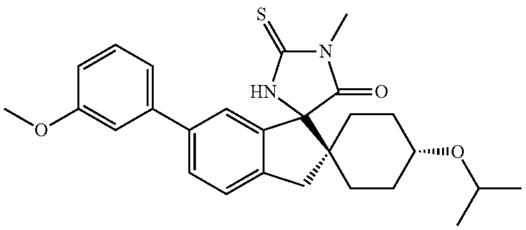 | 465 | Microsorb 1s | 1.80 |
| 3.3.13 | Compound 511 Step1 | 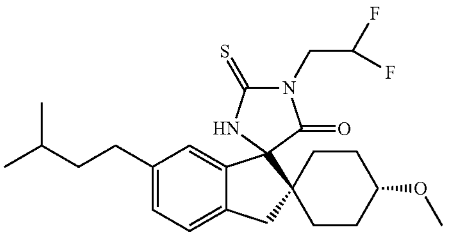 | 451 | Microsorb 1s | 1.87 |
| 3.3.14 | Compound 512 Step1 | 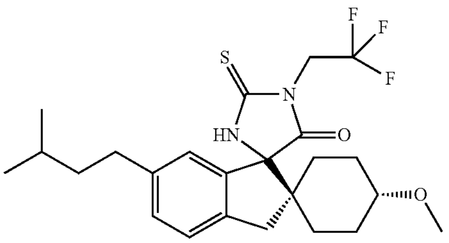 | 469 | Microsorb 1s | 1.91 |
| 3.3.15 | 3.1.7 | 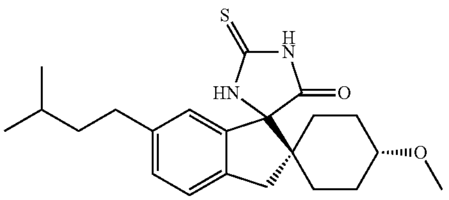 | 387 | Microsorb 7s MeOH | 1.51 |

-continued
| No. | Starting material | Product | MS m/z [M + H]+ | HPLC Method | Rt min |
|---|---|---|---|---|---|
| Compound 599 | Compound 599 Step2 | 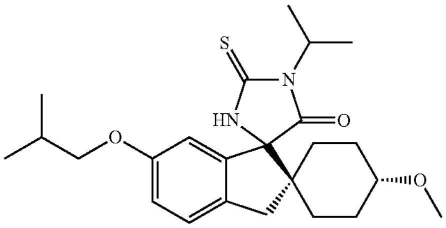 | 431 | Microsorb 1s | 1.88 |
| Compound 600 | 39.2.1 | 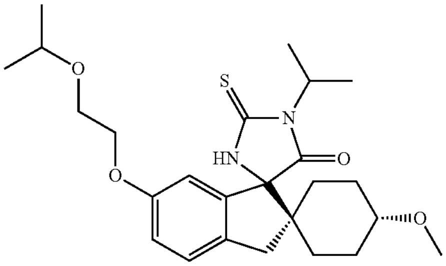 | 461 | Microsorb 1s | 1.76 |
| Compound 602 | 3.2.16 | 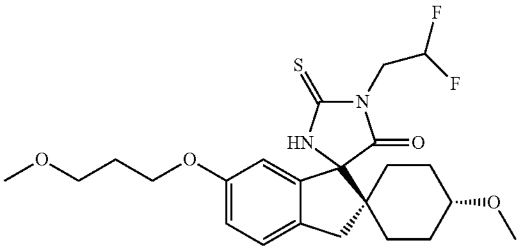 | 469 | Microsorb 1s | 1.56 |
| Compound 603 | 3.2.17 | 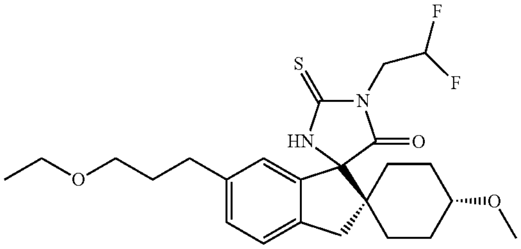 | 467 | Microsorb 1s | 1.64 |
| Compound 604 | 3.2.18 | 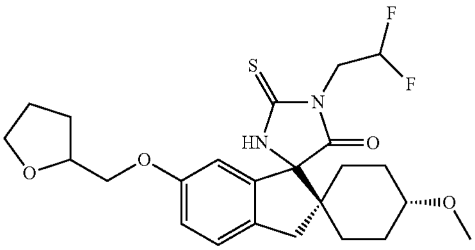 | 481 | Microsorb 1s | 1.55 |

Compound 491 Step 4

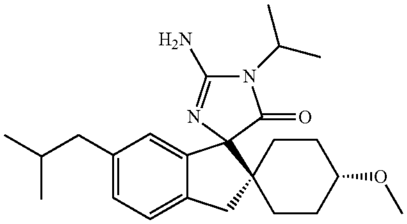

Compound 491 Step 3 (65 mg, 0.16 mmol) and tert-butyl hydroperoxide (6 M in decane, 0.55 mL, 3.30 mmol) and 5 mL ammonia in methanol (7 M) were stirred for 3 d. The solvent was evaporated and the residue purified by MPLC (10 g silicagel, gradient:DCM/MeOH 100:0 to 90:10) to give Compound 491 Step 4 (22 mg, 35%).

HPLC (Method: Microsorb 7s MeOH)

Rt: 1.55 min; Mass: $(M+H)^+=398$

By using the same synthetic strategy as for Compound 491 step 4 the following compound was obtained:

Compound 505 Step 1

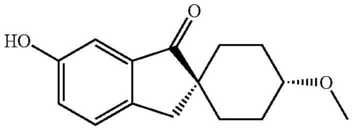

Compound 504 Step 6 (900 mg, 2.46 mmol) was added to a mixture of DCM (5 mL), TFA (5 mL), water (0.050 mL), and triisopropylsilane (1 mL). The mixture was stirred at RT for 5 min. The solvents were evaporated and the residue was purified by HPLC (eluent A:water+0.13% TFA, eluent B:methanol) to yield the desired product Compound 505 Step 1 (300 mg, 50%) as an oil.

HPLC (Method: Microsorb 1s):

Rt: 1.12 min; Mass: $(M+H)^+=247$

By using the same synthetic strategy as for compound 505 step 1 the following compound was obtained:

| No. | Starting material | Product | MS m/z $[M+H]^+$ | HPLC Method | Rt min |
|---|---|---|---|---|---|
| Compound 598 | 32.5.2 | 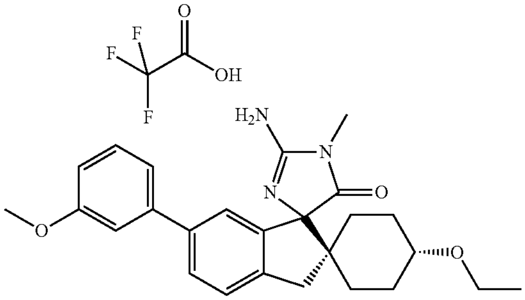 | 434 | Microsorb 1s | 1.41 |

D. Compound 505

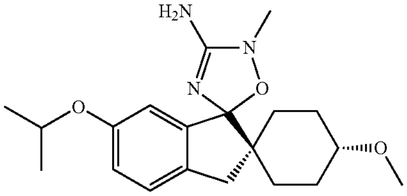

| No. | Starting material | Product | MS m/z $[M+H]^+$ | HPLC Method | Rt min |
|---|---|---|---|---|---|
| 4.1.1 | 3.2.1 | 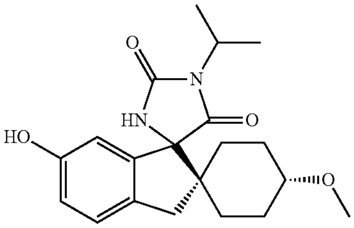 | 359 | Microsorb 1s | 1.25 |

Compound 505 Step 2

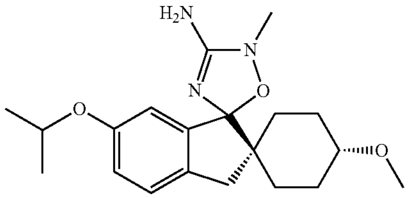

A mixture of N-methylhydroxylamin hydrochloride (77 mg, 0.92 mmol) in anhydrous EtOH (3 mL) was treated with sodium hydride (60% in mineral oil, 34 mg, 0.86 mmol) and added to a mixture of compound 1.7.1 (120 mg) in anhydrous EtOH (3 mL). The mixture was stirred for 3 h min at RT. Water was added and the mixture was extracted with EA. The solvents were evaporated and the residue was purified by HPLC (eluent A:water+0.13% TFA, eluent B:methanol). The base was liberated by dissolution in DCM and extraction with aqueous potassium carbonate solution. Separation of the organic layer and evaporation of the solvents yields the desired product Compound 505 (5 mg, 5%) as a white solid.

HPLC (Method: Microsorb 1s):

Rt: 1.27/1.34 min; Mass: $(M+H)^+$=360

E. Compound 506

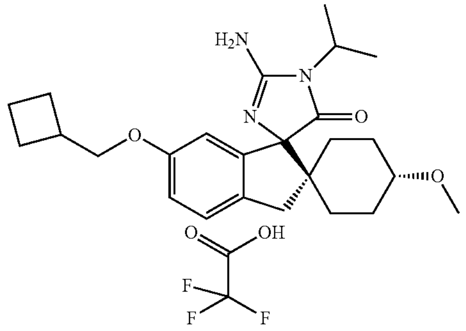

Compound 506 Step 1

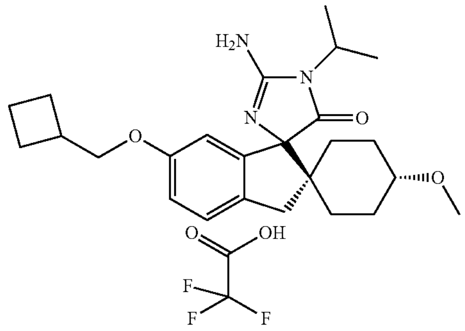

Compound 3.3.1 (260 mg) was mixed with ammonia (7 M in MeOH, 2 mL) and tert.-butylhydroperoxide (5.5 M in nonane, 0.49 mL, 2.70 mmol) and stirred for 48 h at RT. DCM and $Na_2S_2O_3$ (10% in water) were added. The organic layer was separated and the solvents were evaporated. The residue was purified by HPLC (eluent A:water+0.13% TFA, eluent B: methanol) to yield the desired product Compound 506 (25 mg) as a white solid.

HPLC (Method: Microsorb 1s)

Rt: 1.56 min; Mass: $(M+H)^+$=426

F. Compound 492

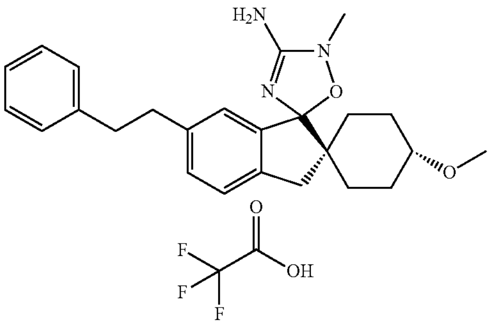

Compound 492 Step 1

The product was obtained in analogy to compound 505 step 2 from compound 2.5.3. The crude product was purified by HPLC (eluent A:water+0.13% TFA, eluent B:methanol) to yield the product as TFA salt compound 492 as a white solid (101 mg, 80%).

HPLC (Method: Microsorb 1s)

Rt: 1.38/1.47 min, Mass: $(M+H)^+$=406

By using the same synthetic strategy as for compound 492 step 1 the following compounds were obtained:
| No. | Starting material | Product | MS m/z $[M + H]^+$ | HPLC Method | Rt min |
|---|---|---|---|---|---|
| Compound 493 | 2.5.4 | 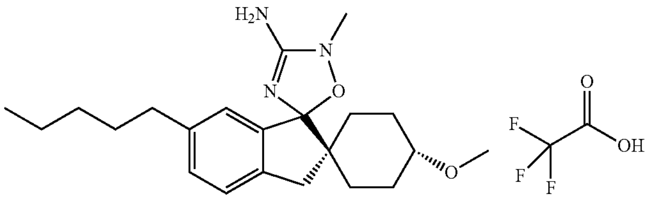 | 372 | Microsorb 1 s | 1.43/1.54 |
| Compound 497 | 2.5.5 | 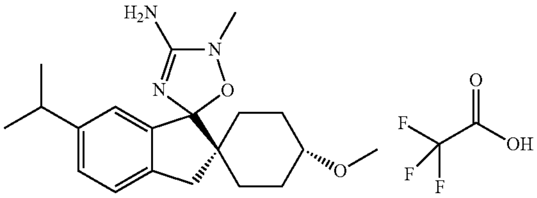 | 344 | Microsorb 1 s | 1.31/1.39 |
| Compound 501 | 2.5.6 | 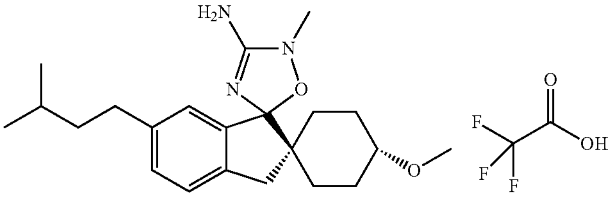 | 372 | Microsorb 1 s | 1.40/1.51 |
| Compound 502 | 2.5.7 | 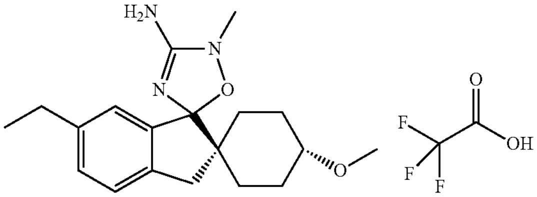 | 330 | Microsorb 1 s | 1.23/1.32 |
| Compound 517 | 2.5.11 | 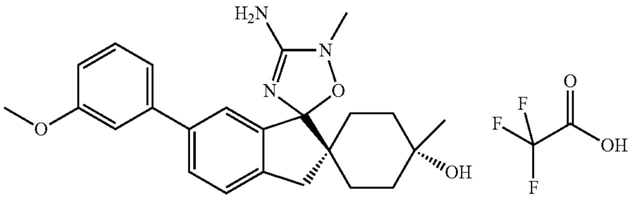 | 408 | Microsorb 1 s | 1.18/1.26 |
| Compound 518 | 2.5.12 | 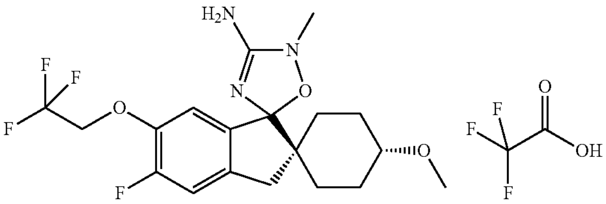 | 418 | Microsorb 1 s | 1.28 |

Compound 502 step 1

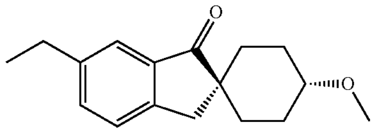 [SMILES: CCc1ccc2c(c1)C(=O)[C@]1(CC[C@H](OC)CC1)C2]

To compound 1.6.1 (300 mg, 0.97 mmol) and $PdCl_2$dppf (70 mg, 0.096 mmol) in dioxane (10 mL) at 0° C. diethyl-zinc in hexane (1 M, 2.00 mL, 2.00 mmol) was added under argon atmosphere. The mixture was allowed to warm to RT and stirred for 14 h. The mixture was purified by MPLC (25 g silicagel, gradient CH/EA 100:0 to 60:40) to give Compound 502 Step 1 (197 mg, 79%).

HPLC (Method: Microsorb 1s),

Rt: 1.69 min; Mass: $(M+H)^+$=259

G. Compound 495

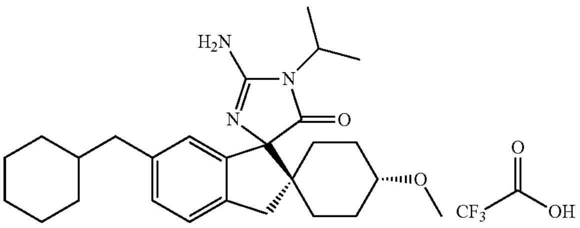

Compound 495 Step 1

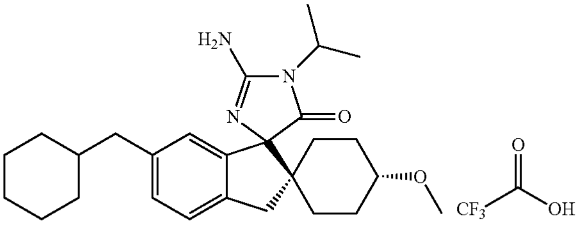

Compound 3.3.2 (50 mg, 0.11 mmol) was mixed with ammonia (7 M in MeOH, 3 mL) and tert.-butylhydroperoxide (6 M in decane, 0.38 mL, 2.28 mmol). The mixture was stirred for 3 d at RT. The solvents were evaporated. The residue was purified by HPLC (eluent A:water+0.13% TFA, eluent B:methanol) to yield the desired product compound 495 (30 mg, 50%) as a white solid.

HPLC (Method: Microsorb 1s)

Rt: 1.71 min; Mass: $(M+H)^+$=438

By using the same synthetic strategy as for compound 495 step 1 the following compounds were obtained:

| No. | Starting material | Product | MS m/z $[M+H]^+$ | HPLC Method | Rt min |
|---|---|---|---|---|---|
| Compound 494 | 3.3.3 | 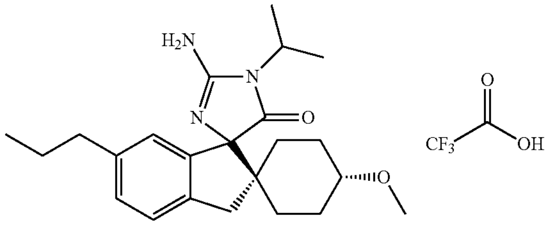 | 384 | Microsorb 1 s | 1.43 |
| Compound 496 | 3.3.4 | 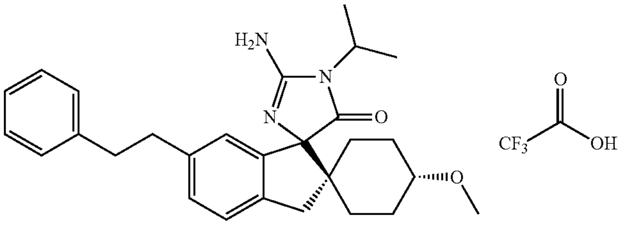 | 446 | Microsorb 1 s | 1.58 |
| Compound 503 | 3.3.5 | 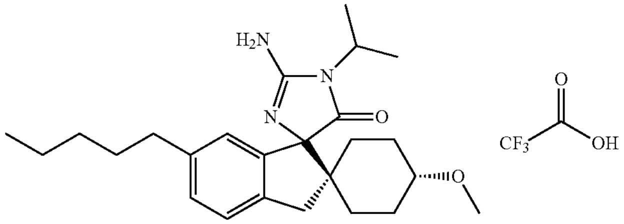 | 412 | Microsorb 1 s | 1.62 |

-continued
| No. | Starting material | Product | MS m/z [M + H]+ | HPLC Method | Rt min |
|---|---|---|---|---|---|
| Compound 499 | 3.3.6 | 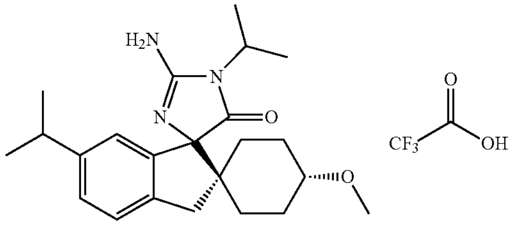 | 384 | Microsorb 7 s | 1.47 |
| Compound 498 | 3.3.7 | 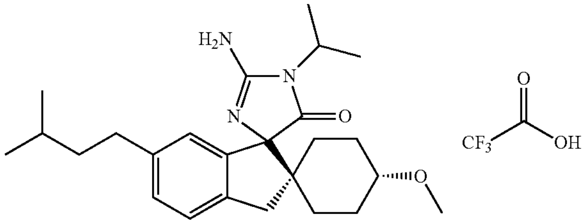 | 412 | Microsorb 1 s | 1.59 |
| Compound 500 | 3.3.8 | 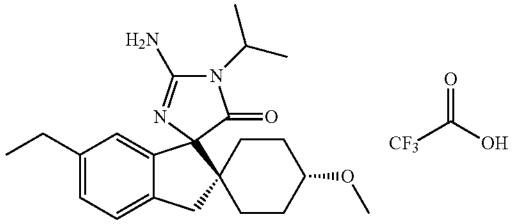 | 370 | Microsorb 1 s | 1.37 |
| Compound 508 | 3.3.9 | 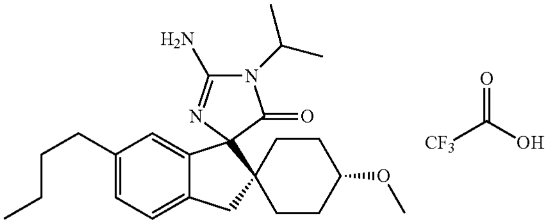 | 398 | Microsorb 7 s | 1.52 |
| Compound 507 | 3.3.10 | 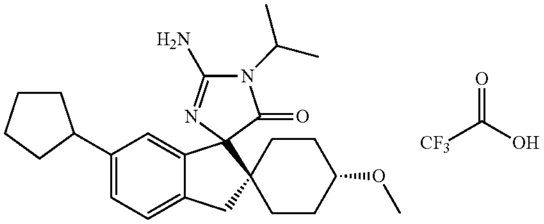 | 410 | Microsorb 1 s | 1.54 |
| Compound 509 | 3.3.11 | 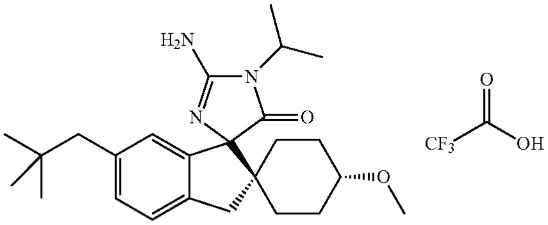 | 412 | Microsorb 7 s | 1.53 |

-continued

| No. | Starting material | Product | MS m/z [M + H]+ | HPLC Method | Rt min |
|---|---|---|---|---|---|
| Compound 510 | 3.3.12 | 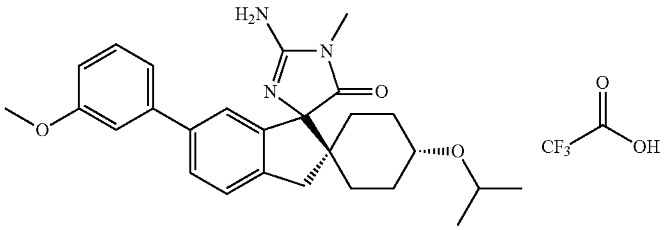 | 448 | Microsorb 1 s | 1.43 |
| Compound 511 | 3.3.13 | 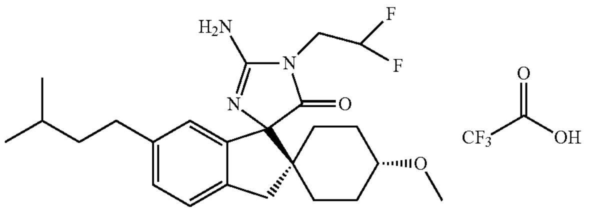 | 434 | Microsorb 7 s | 1.48 |
| Compound 512 | 3.3.14 | 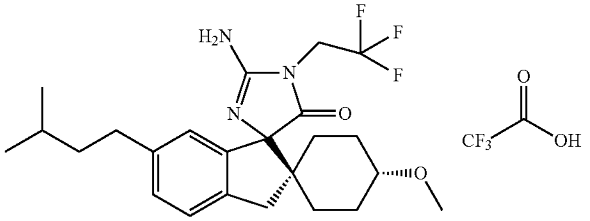 | 452 | Microsorb 7 s | 1.53 |

Compound 510 Step 1

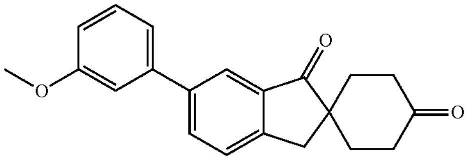 [SMILES: COc1cccc(-c2ccc3c(c2)C(=O)C2(CCC(=O)CC2)C3)c1]

The reaction was split between 7 microwave vials (20 mL). To Compound 488 Step 3 (4.99 g, 16.7 mmol) in 61 mL dioxane was added 3-methoxyphenyl boronic acid (3.05 g, 20.0 mmol), Na2CO3 solution (2 M in water, 25 mL, 51.8 mmol) and 1,1'-bis(diphenylphosphino)-ferrocene-dichloro-palladium-(II). Argon was bubbled through the mixture for 1 min and the vials with the mixture were heated in the microwave to 140° C. for 30 min. The content of the vials was pooled and the mixture concentrated. The residue was mixed with DCM, filtered over silica and the filtrate washed with aqueous saturated ammonium chloride solution and brine. The organic phase was dried and evaporated. The crude product was purified by MPLC (340 g silicagel, gradient:CH/EA 1:0 to 1:1, 90 min). The product was dissolved in DCM and washed with aqueous NaOH solution. The organic layer was evaporated to yield the product Compound 510 Step 1 (3.25 g, 61%)

HPLC (Method: Microsorb 1s),

Rt: 1.51 min; Mass: $(M+H)^+$=321

By using the same synthetic strategy as for Compound 510 step 1 the following compounds were obtained:

| No. | Starting material | Product | MS m/z [M + H]+ | HPLC Method | Rt min |
|---|---|---|---|---|---|
| 23.1.1 | Compound 488 step 3 | 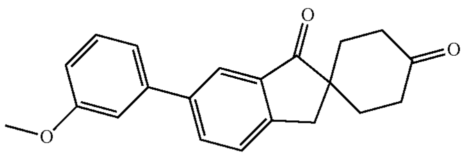 [SMILES: COc1cccc(-c2ccc3c(c2)C(=O)C2(CCC(=O)CC2)C3)c1] | 321 | Microsorb 4 s MeOH | 3.21 |

Compound 510 Step 2

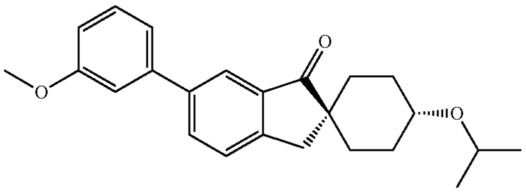 [SMILES: COc1cccc(-c2ccc3c(c2)C(=O)[C@]2(CC[C@H](OC(C)C)CC2)C3)c1]

To a mixture of anhydrous iron-(III) chloride 15.2 mg (0.094 mmol) and Compound 510 Step 1 (600 mg, 1.87 mmol) in ACN (20 mL) isopropoxy-trimethylsilane (1.66 mL, 9.36 mmol) and triethylsilane (1.05 mL, 6.56 mmol) were added successively at RT under an argon atmosphere. The mixture was stirred 14 h. 50 mg of iron-(III) chloride were added and the mixture was stirred for 24 h at RT. The mixture was diluted with phosphate buffer (pH 7) and extracted with DCM. The mixture was evaporated and the crude product purified by HPLC (C18, eluent A:water+0.13% TFA, eluent B:ACN). The first eluting diastereomer was collected. Freeze drying gave the product Compound 510 Step 2 as a white powder.

HPLC (Method: Microsorb 1s),

Rt: 1.95 min; Mass: $(M+H)^+=365$

By using the same synthetic strategy as for Compound 510 step 2 the following compounds were obtained:

| No. | Starting material | Product | MS m/z [M + H]$^+$ | HPLC Method | Rt min |
|---|---|---|---|---|---|
| 23.2.1 | 23.1.1 | 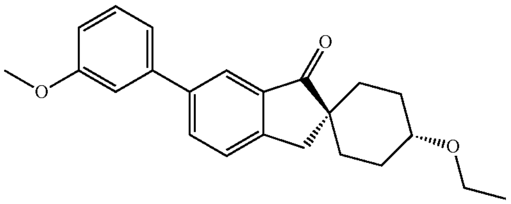 [SMILES: CCO[C@H]1CC[C@]2(CC1)Cc1ccc(-c3cccc(OC)c3)cc1C2=O] | 351 | Microsorb 1 s MeOH | 1.88 |

Compound 510 Step 3

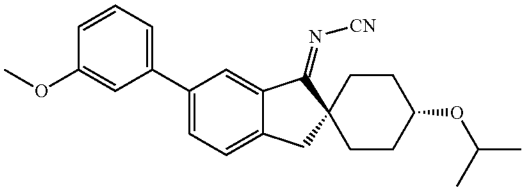 [SMILES: COc1cccc(-c2ccc3c(c2)/C(=N/C#N)[C@]2(CC[C@H](OC(C)C)CC2)C3)c1]

To Compound 510 Step 2 (300 mg, 0.82 mmol) in dry DCM (3 mL) titanium-(IV) chloride (1 N in DCM, 1.73 mL, 1.73 mmol) was added. The mixture was stirred for 45 min at RT. 1,3-bis(trimethylsilyl)carbodimid (0.67 mL, 2.88 mmol) was added and the mixture stirred for 2 h at RT. The mixture was diluted with water and extracted with DCM. The organic layer was evaporated to yield the product Compound 510 Step 3 as white solid (310 mg, 97%.)

HPLC (Method: Microsorb 1s),

Rt: 1.96 min; Mass: $(M+H)^+=389$

Compound 510 Step 4

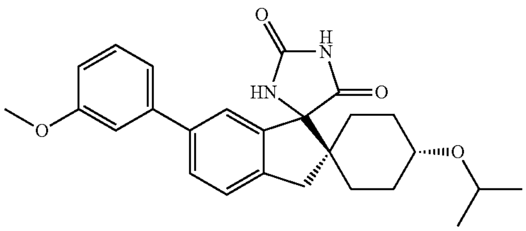

Compound 510 Step 3 (247 mg, 0.64 mmol), potassium cyanide (82.7 mg, 1.27 mmol) and ammonium carbonate (428 mg, 4.45 mmol) in EtOH (1.0 mL) and water (1.0 mL) were stirred for 14 h at 75° C. in a sealed tube. The mixture was cooled, diluted with water and extracted with EA. The organic layer was evaporated. The crude product was evaporated and purified by MPLC (25 g silicagel, gradient:DCM/MeOH 100:0 to 93:3). The product Compound 510 Step 4 was obtained as white solid (150 mg, 54%).

HPLC (Method: Microsorb 1s),

Rt: 1.51 min; Mass: $(M+H)^+=335$

Compound 510 Step 5

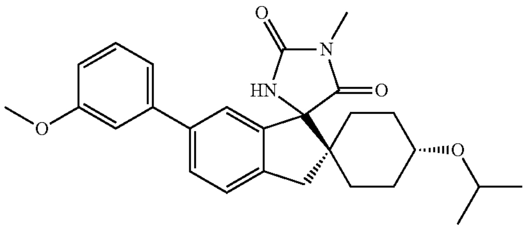

Compound 510 Step 4 (150 mg, 0.35 mmol), methyliodide (24 µA, 0.38 mmol) and $K_2CO_3$ (105 mg, 0.76 mmol) in ACN (5 mL) were mixed and stirred in the microwave for 20 min at 100° C. The reaction was diluted with DCM and water and the mixture extracted with DCM. The organic layer was evaporated. The was residue purified by HPLC (eluent A:water+

0.13% TFA, eluent B:methanol) to yield the desired product Compound 510 Step 5 (150 mg, 97%).

HPLC (Method: Microsorb 1s),

Rt: 1.63 min; Mass: $(M+H)^+$=449

Compound 511 Step 1

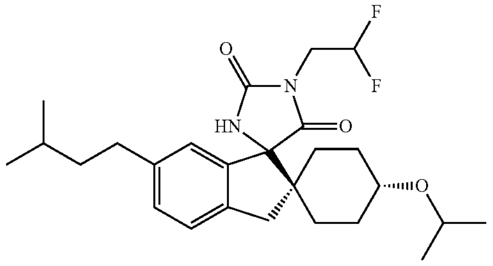

Compound 511 Step 1 was prepared from 3.1.7 (87%, 167 mg, 0.40 mmol) in analogy to Compound 510 Step 2. Instead of 2-iodopropane 2-bromo-1,1-difluoroethane (63 mg, 0.44 mmol) was used to obtain 173 mg (95%) Compound 511 Step 1 as a colorless resin.

HPLC (Method: Microsorb 7s),

Rt: 1.57 min; Mass: $(M+H)^+$=435

Compound 512 Step 1

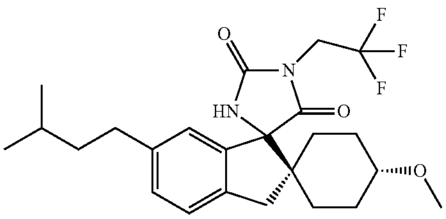

Compound 512 Step 1 was prepared from 3.1.7 (87% 167 mg, 0.40 mmol) in analogy to Compound 491 Step 2. Instead of 2-iodopropane 2,2,2-trifluoroethyltrifluoromethylsulfonate (63 μl, 0.44 mmol) was used to obtain 165 mg (93%) Compound 512 Step 1 as a colorless resin.

HPLC (Method: Microsorb 7s),

Rt: 1.61 min; Mass: $(M+H)^+$=453.

H. Compound 513

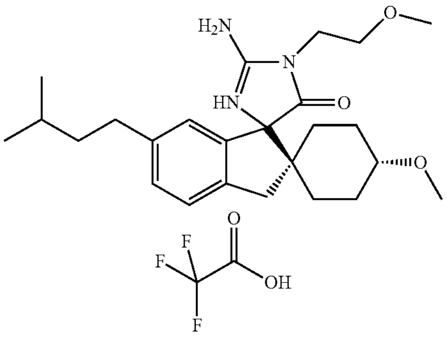

Compound 513 Step 1

Product 3.2.12 (152 mg, 0.3 mmol) and ammonium iodide (350 mg, 2.41 mmol) in ammonia (2 M in EtOH, 6.0 mL, 17.3 mmol) were stirred for 2 h at 120° C. in the microwave. The solvents were evaporated. The residue was purified by HPLC (eluent A:water+0.13% TFA, eluent B:methanol) to yield the product as TFA salt compound 513 as a white solid (98.8 mg, 60%).

HPLC (Method: Microsorb 1s)

Rt: 1.52 min, Mass: $(M+H)^+$=428

By using the same synthetic strategy as for compound 513 step 1 the following compounds were obtained:

| No. | Starting material | Product | MS m/z $[M+H]^+$ | HPLC Method | Rt min |
|---|---|---|---|---|---|
| Compound 514 | 3.2.13 | 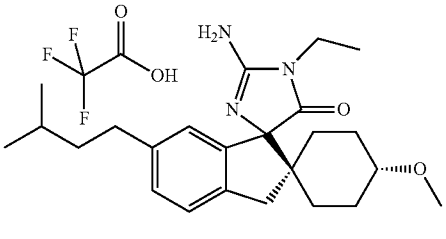 | 398 | Microsorb 7 s MeOH | 1.50 |
| Compound 515 | 3.2.14 | 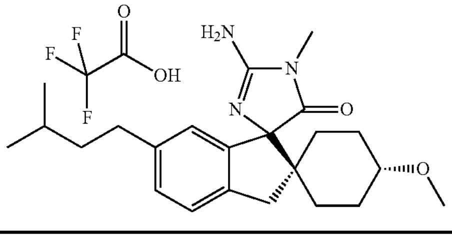 | 384 | Microsorb 7 s MeOH | 1.48 |

I. Compound 517

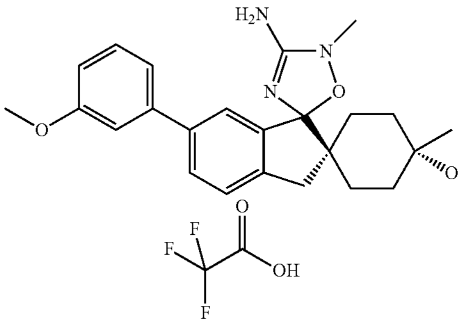

Compound 517 Step 1

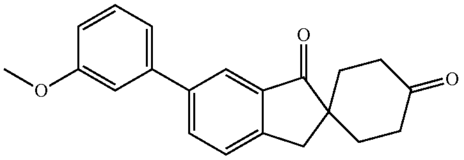 [SMILES: COc1cccc(-c2ccc3c(c2)C(=O)C2(CCC(=O)CC2)C3)c1]

To Compound 488 Step 3 (1.5 g, 5.12 mmol), 3-methoxyphenylboronic acid (930 mg, 6.12 mmol), $PdCl_2$dppf (200 mg, 0.27 mmol) and potassium carbonate (2M in water, 7.65 mL, 15.3 mmol) in dioxane (18 mL) and MeOH (6 mL) were stirred for 30 min at 140° C. in the microwave. The solvents were evaporated. To the residue was added DCM. The organic layer was washed with ammonium chloride solution and with brine. The DCM was evaporated. The crude product was purified by MPLC (100 g silicagel, gradient:CH/EA 100:0 to 50:50). The product Compound 517 Step 1 was obtained as a solid (1.39 g, 85%).

HPLC (Method: Microsorb 1s),

Rt: 1.53 min; Mass: $(M+H)^+$=321

Compound 517 Step 2

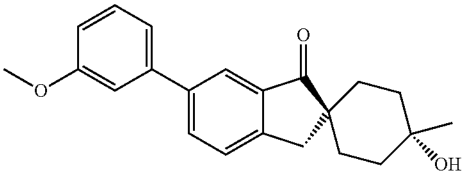

To Compound 517 Step 1 (1.39 g, 4.34 mmol) in THF at −78° C. was added methylmagnesium chloride (3 M, 1.6 mL, 4.8 mmol) in THF. After stirring for 1.5 h at −78° C. the mixture was warmed to RT. The reaction was cooled down to 0° C. and methylmagnesium chloride (1 mL) was added. The reaction was quenched with ammonium chloride solution and extracted with DCM. The organic layer was washed with brine and the solvent was evaporated. The crude product was purified by MPLC (120 g silicagel, gradient:DCM/MeOH 100:0 to 95:5) and then by MPLC (120 g silicagel, gradient: CH/EA 100:0 to 50:50). The first eluting stereoisomer was collected. The product Compound 517 Step 2 was obtained as a solid (1.39 g, 85%).

HPLC (Method: Microsorb 1s),

Rt: 1.48 min; Mass: $(M+H)^+$=337

J. Compound 518

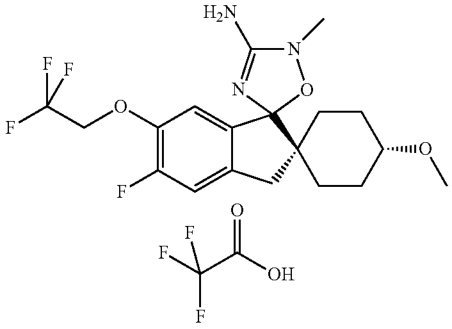

Compound 518 Step 1

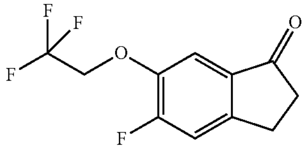 [SMILES: O=C1CCc2cc(F)c(OCC(F)(F)F)cc21]

5-Fluoro-6-hydroxy-indan-1-one (7.50 g, 45.1 mmol) and $K_2CO_3$ (17.0 g, 123 mmol) in DMF (50 mL) were stirred for 10 min at 80° C. Then 2,2,2-trifluoroethyl-trifluoro-methanesulphonate (10.7 g, 46.1 mmol) was added and the mixture was stirred for 2 min at 80° C. Water was added and the mixture was extracted with EA. The organic layer separated and the solvents were evaporated to give Compound 518 Step 1 (10.4 g, 93%).

HPLC (Method: Microsorb 1s),

Rt: 1.34 min; Mass: $(M+H)^+$=249

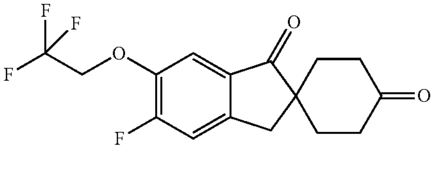 [SMILES: O=C1CCC2(CC1)Cc1cc(F)c(OCC(F)(F)F)cc1C2=O]

Compound 518 Step 2

To compound 1.3.1 (28.5 g) in dioxane (80 mL) was added 4 M aqueous HCl (50 mL). The mixture was stirred for 14 h at 120° C. The solvents were evaporated. The was residue purified by HPLC (eluent A:water+0.13% TFA, eluent B:methanol) to yield the desired product Compound 518 Step 2 (4.8 g).

HPLC (Method: Microsorb 1s)

Rt: 1.49 min; Mass: $(M+H)^+$=331

Compound 518 Step 3

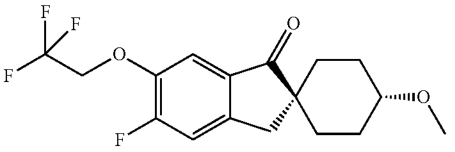 [SMILES: CO[C@H]1CC[C@]2(CC1)Cc1cc(F)c(OCC(F)(F)F)cc1C2=O]

To compound 518 Step 2 (1.30 g, 3.94 mmol) and ferric chloride (31.9 mg, 0.20 mmol) in anhydrous acetonitrile (50 mL) was added methoxytrimethylsilane (5.43 mL, 39.4 mmol) and triethylsilane (6.29 mL, 39.4 mmol). The mixture was stirred 10 min at RT. The solvents were evaporated. The residue was purified by HPLC (eluent A:water+0.13% TFA, eluent B: acetonitrile) to yield the desired product Compound 518 Step 3 (610 mg, 45%) as the earlier eluting diastereomer.

HPLC (Method: Microsorb 1s)

Rt: 1.64 min; Mass: $(M+H)^+=347$

K. Compound 592

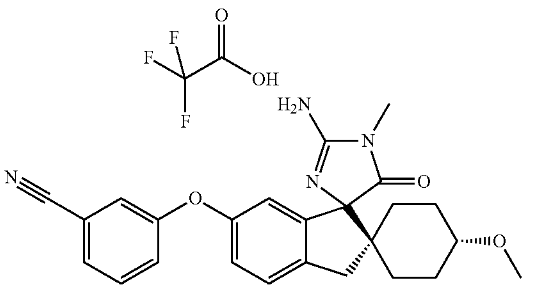

Compound 592 Step 1

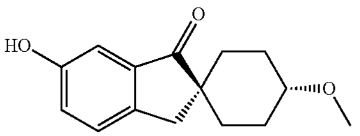 [SMILES: CO[C@H]1CC[C@]2(CC1)Cc1ccc(O)cc1C2=O]

To 6'-bromo-4-methoxyspiro[cyclohexane-1,2'-inden]-1'(3'H)-one (1.00 g, 3.23 mmol) in dioxane/water (1:1, 10 mL) was added potassium hydroxide (1.05 g, 18.7 mmol), tris(dibenzylideneacetone)dipalladium(0) (150 mg, 0.16 mmol) and di-tert-butyl-(2',4',6'-triisopropyl-3,4,5,6-tetramethyl-biphenyl-2-yl)-phosphane (280 mg, 0.58 mmol). The mixture was stirred in the microwave for 10 min at 140° C. The mixture was diluted with EA and 1 M HCl and extracted with EA. The organic layer was washed with brine, dried and evaporated. The residue was purified by MPLC (100 g siliciagel, gradient:CH/EA 100:0 to 40:60 over 70 min). The product compound 592 Step 1 was obtained as a yellow resin (660 mg, 83%).

HPLC (Method: Microsorb 7s MeOH),

Rt: 1.16 min; Mass $(M+H)^+$ 247

Compound 592 Step 2

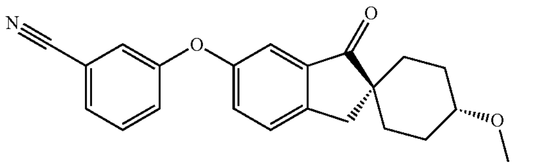 [SMILES: CO[C@H]1CC[C@]2(CC1)Cc1ccc(Oc3cccc(C#N)c3)cc1C2=O]

Compound 592 Step 1 (275 mg, 1.12 mmol), 3-cyanophenylboronic acid (330 mg, 2.25 mmol, copper(II)-acetate (17.3 mg, 0.095 mmol) and molecular sieves (4 A, 1.0 g) in DCM (7 mL) were mixed, than pyridine (442 µA, 5.58 mmol) was added and argon was bubbled through the mixture. The mixture was stirred in a sealed tube for 14 h at RT. The tube was opened and 17 mg copper(II)-acetate was added. The vial was closed again and stirred 14 h at RT. Then it was opened again and stirred with a drying tube over night at RT. 270 mg 3-cyanophenyl boronic acid, 17 mg copper(II)-acetate and 440 µL pyridine were added and the mixture stirred at RT for 3 days. The precipitate was separated, the filtrate was diluted with DCM, saturated $NaHCO_3$-solution and brine. The organic layer was separated and the solvent was evaporated. The crude product was purified by MPLC (25 g siliciagel, gradient:CH/EA 100:0 to 50:50 over 50 min) to give Compound 592 Step 2 (197 mg, 51%) as a white solid.

HPLC (Method: Microsorb 1s),

Rt: 1.65 min; Mass $(M+H)^+$ 348

By using the same synthetic strategy as for Compound 592 step 2 the following compounds were obtained:

| No. | Starting material 1 | Starting material 2 | Product | MS m/z $[M+H]^+$ | HPLC Method | Rt min |
|---|---|---|---|---|---|---|
| 32.2.1 | Compound 592 Step 1 | 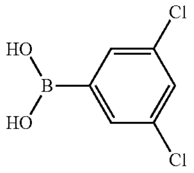 [SMILES: OB(O)c1cc(Cl)cc(Cl)c1] | 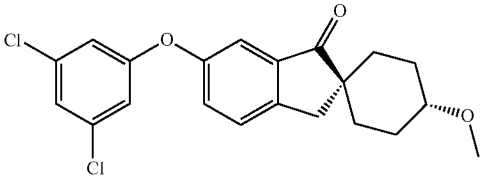 [SMILES: CO[C@H]1CC[C@]2(CC1)Cc1ccc(Oc3cc(Cl)cc(Cl)c3)cc1C2=O] | 391 | Microsorb 1 s | 2.04 |

-continued

| No. | Starting material 1 | Starting material 2 | Product | MS m/z [M + H]+ | HPLC Method | Rt min |
|---|---|---|---|---|---|---|
| 32.2.2 | Compound 594 Step 1 | 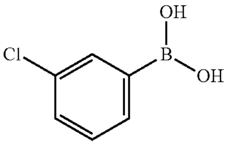 | 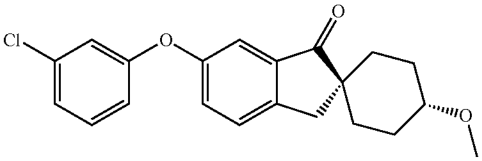 [SMILES: CO[C@H]1CC[C@]2(CC1)Cc1ccc(Oc3cccc(Cl)c3)cc1C2=O] | 357 | Microsorb 4 s MeOH | 3.56 |
| 32.2.3 | Compound 595 Step 1 | 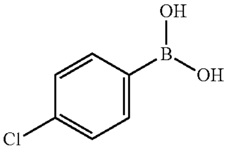 | 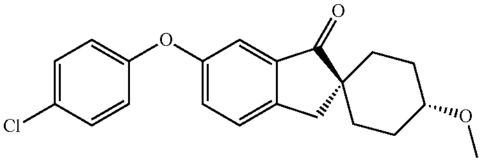 [SMILES: CO[C@H]1CC[C@]2(CC1)Cc1ccc(Oc3ccc(Cl)cc3)cc1C2=O] | 357 | Microsorb 4 s MeOH | 3.53 |

Compound 592 Step 3

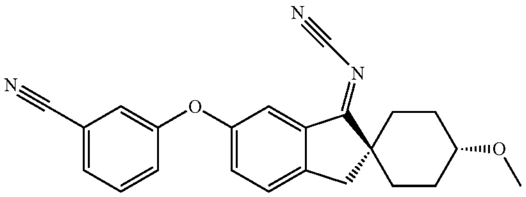 [SMILES: CO[C@H]1CC[C@]2(CC1)Cc1ccc(Oc3cccc(C#N)c3)cc1/C2=N\C#N]

To compound 592 Step 2 (195 mg, 0.561 mmol) in DCM (anhydrous, 12 mL) titanium(IV)-chloride (1 N in dioxane, 1.11 mL, 1.11 mmol) was added and the mixture stirred at RT for 1 h. Then 1,3-bis(trimethylsilyl)carbodiimde (418 μl, 1.80 mmol) was added and mixture stirred at RT for 3 h. The reaction mixture was quenched with water and extracted with DCM. The organic layer was separated and the solvent was evaporated to give compound 592 Step 3 (239 mg, purity 85%, 97%) as a resin.

HPLC (Method: Microsorb 1s),

Rt: 1.67 min; Mass $(M+H)^+$ 372

By using the same synthetic strategy as for compound 592 step 3 the following compounds were obtained:

| No. | Starting material 1 | Product | MS m/z [M + H]+ | HPLC Method | Rt min |
|---|---|---|---|---|---|
| 32.3.1 | 32.2.1 | 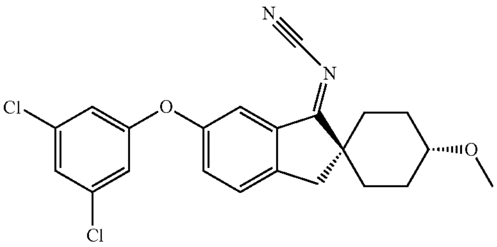 [SMILES: CO[C@H]1CC[C@]2(CC1)Cc1ccc(Oc3cc(Cl)cc(Cl)c3)cc1/C2=N\C#N] | 415/417 | Microsorb 1 s | 2.01 |
| 32.3.2 | 32.2.2 | 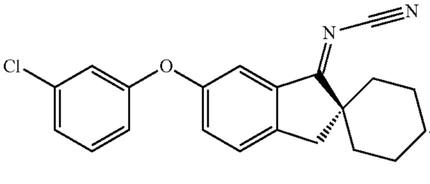 | 381 | Microsorb 4 s MeOH | 3.56 |
| 32.3.3 | 32.2.3 | 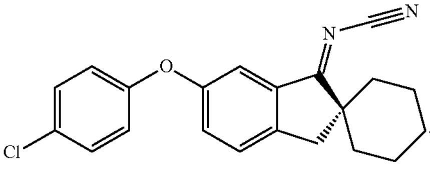 | 381 | Microsorb 4 s MeOH | 3.52/3.67 |

-continued

| No. | Starting material 1 | Product | MS m/z [M + H]+ | HPLC Method | Rt min |
|---|---|---|---|---|---|
| 32.3.4 | Compound 597 step 1 | 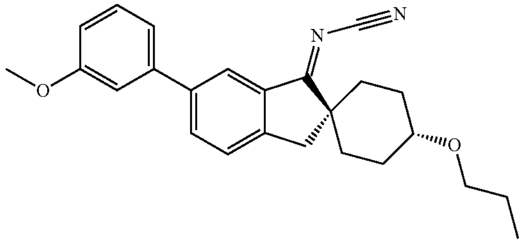 [SMILES: CCCO[C@H]1CC[C@]2(CC1)Cc1ccc(-c3cccc(OC)c3)cc1/C2=N/C#N] | 389 | Microsorb 4 s MeOH | 3.71 |
| 32.3.5 | 23.2.1 | 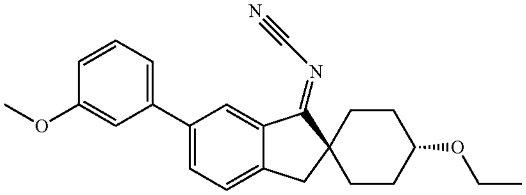 [SMILES: CCO[C@H]1CC[C@]2(CC1)Cc1ccc(-c3cccc(OC)c3)cc1/C2=N\C#N] | 375 | Microsorb 1 s MeOH | 1.88 |
| 32.3.6 | 36.1.1 | 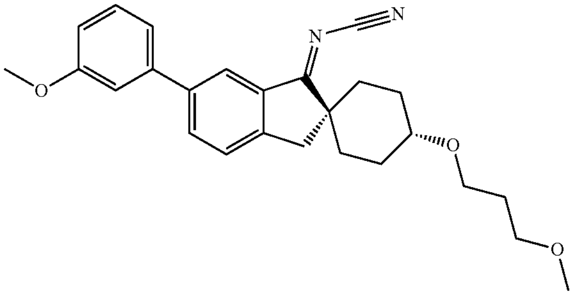 | 419 | Microsorb 1 s MeOH | 3.58 |

Compound 592 Step 4

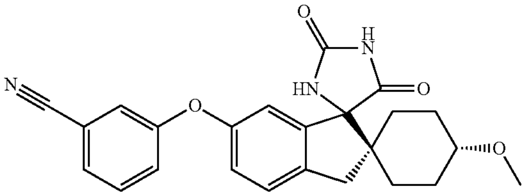

Compound 592 Step 3 (188 mg, 0.506 mmol), potassium cyanide (66 mg, 1.01 mmol) and ammonium carbonate (500 mg, 5.20 mmol) in EtOH (1.5 mL) and water (1.5 mL) were mixed and stirred for 14 h at 75° C. The mixture was cooled, diluted with water and EA. The mixture extracted with EA. The organic layer was washed with brine, dried and evaporated to give compound 592 Step 4 as a with solid of 90% purity (164 mg, 70%).

HPLC (Method: Microsorb 1s),

Rt: 1.34 min; Mass: $(M+H)^+$=418

By using the same synthetic strategy as for compound 592 step 4 the following compound was obtained:

| No. | Starting material | Product | MS m/z [M + H]+ | HPLC Method | Rt min |
|---|---|---|---|---|---|
| 32.4.1 | 32.3.5 | 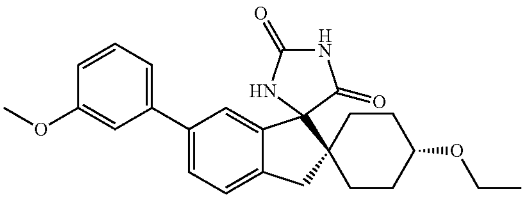 | 421 | Microsorb 1 s | 1.45 |

Compound 592 Step 5

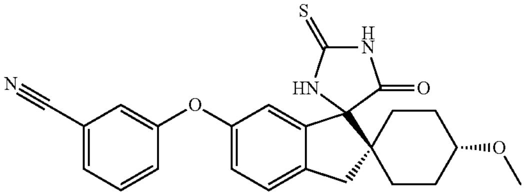

To compound 592-Step 4 (164 mg, purity 90%, 0.35 mmol) in toluene (anhydrous, 10 mL) 2,4-bis-(4-methoxy-phenyl)-[1,3,2,4]dithiadiphosphetane 2,4-disulfide (145 mg, 0.36 mmol) was added and nitrogen was bubbled trough the mixture. Then the reaction was stirred for 14 h at 125° C. The solvent was evaporated. The residue was purified by MPLC (25 g silicagel, gradient: CH/EA 100:0 to 50:50 over 50 min) to give compound 592-Step 5 (107 mg, 71%) as a yellow resin.

HPLC (Method: Microsorb 1s),

Rt: 1.45 min; Mass: $(M+H)^+=434$

By using the same synthetic strategy as for compound 592 step 5 the following compounds were obtained:

Compound 592 Step 6

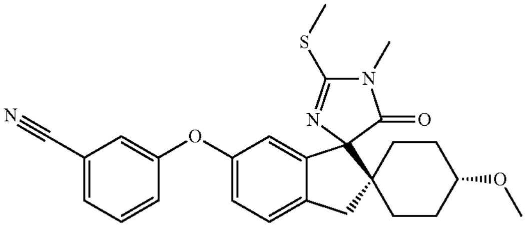

Compound 592 Step 5 (107 mg, 0.25 mmol), methyliodide (62 μA, 1.0 mmol) and $K_2CO_3$ (160 mg, 1.16 mmol) in ACN (anhydrous, 3 mL) were mixed and stirred in the microwave first for 20 min at 60° C. then 20 min at 100° C. The reaction was diluted with DCM and water and the mixture extracted with DCM. The organic layer was evaporated to yield the desired product compound 592 Step 6 (100 mg, purity 88%, 77%) as a colorless resin.

HPLC (Method: Microsorb 1s),

Rt: 1.61 min; Mass: $(M+H)^+=462$

By using the same synthetic strategy as for compound 592 step 6 the following compound was obtained:

| No. | Starting material | Product | MS m/z $[M + H]^+$ | HPLC Method | Rt min |
|---|---|---|---|---|---|
| 32.5.1 | Compound 593 Step 1 | 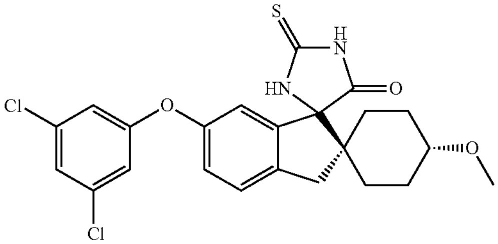 | 477/479 | Microsorb 1 s | 1.70 |
| 32.5.2 | 3.2.15 | 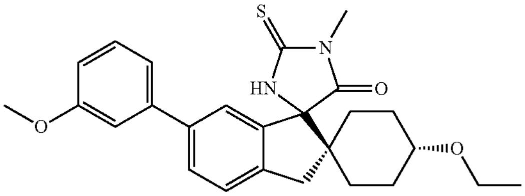 | 451 | Microsorb 1 s | 1.73 |

| No. | Starting material | Product | MS m/z [M + H]+ | HPLC Method | Rt min |
| --- | --- | --- | --- | --- | --- |
| 32.6.1 | 32.5.1 | 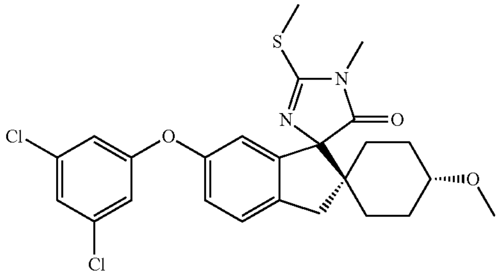 | 505/507 | Microsorb 1 s | 1.98 |

Compound 592 Step 7

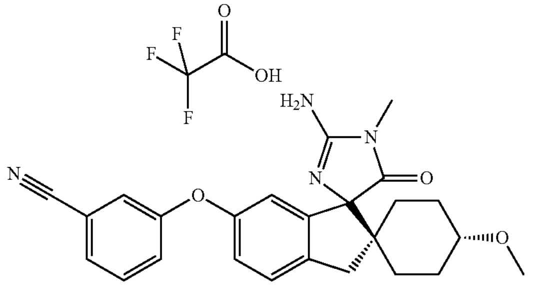

Compound 592 Step 6 (100 mg, 0.19 mmol) and ammonium iodide (221 mg, 1.53 mmol) in ammonia (2 M in EtOH, 4.0 mL, 8 mmol) were stirred for 3 h at 120° C. in the microwave. The solvents were evaporated. The residue was purified by HPLC (eluent A:water+0.13% TFA, eluent B:methanol) to yield the product as TFA salt compound 592 as a white solid (69 mg, 67%).

HPLC (Method: Microsorb 1s)

Rt: 1.30 min, Mass: $(M+H)^+=431$

By using the same synthetic strategy as for compound 592 step 7 the following compound was obtained:

| No. | Starting material | Product | MS m/z [M + H]+ | HPLC Method | Rt min |
| --- | --- | --- | --- | --- | --- |
| Compound 593 | 32.6.1 | 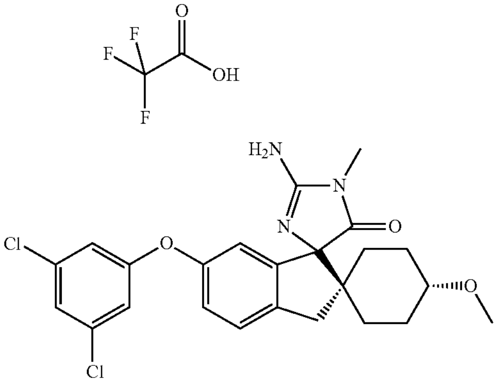 | 474/476 | Microsorb 1 s MeOH | 1.54 |

L. Compound 593

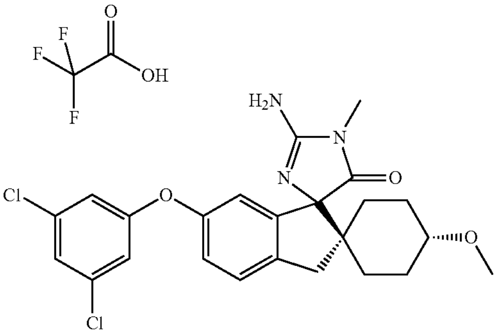

Compound 593 Step 1

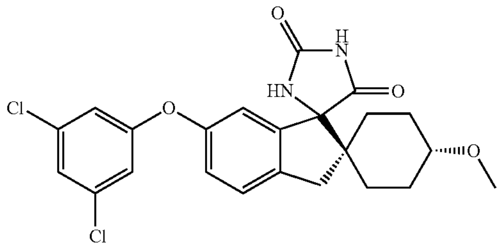

Product 32.3.1 (166 mg, 0.40 mmol), potassium cyanide (52 mg, 0.80 mmol) and ammonium carbonate (270 mg, 2.81 mmol) in EtOH (1.5 mL) and water (1.5 mL) were mixed and stirred for 14 h at 75° C. The mixture was cooled, diluted with water and EA. The mixture extracted with EA. The organic layer was washed with brine, dried and evaporated to give compound 593 Step 1 as a with solid of 80% purity (176 mg, 76%).

HPLC (Method: Microsorb 1s),

Rt: 1.60 min; Mass: $(M+H)^+$=461/46

M. Compound 596

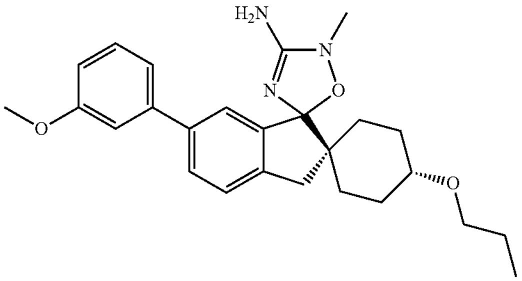

Compound 596-Step 1

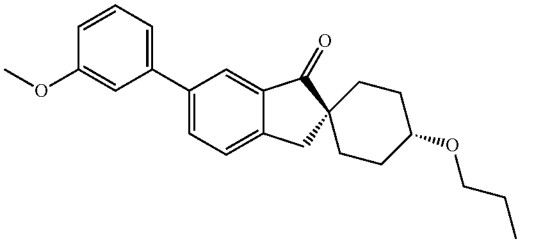 [SMILES: CCCO[C@H]1CC[C@]2(CC1)Cc1ccc(-c3cccc(OC)c3)cc1C2=O]

To product 1.5.3 (200 mg, 0.62 mmol) in THF was added NaH (112 mg, 2.79 mmol) and the mixture was stirred for 30 min at RT. Then 1-iodopropane (131.7 mg, 0.78 mmol) was added slowly at 0° C. and the mixture was allowed to warm up and stirred for 14 h at RT. The mixture was quenched with water and the organic layer was evaporated. The residue was extracted with DCM. The organic layer was washed with brine, dried and evaporated. The crude product was purified by HPLC (eluent A:water+0.13% TFA, eluent B:methanol) to yield the product compound 596 step 1 as a white solid (100 mg, 44%).

HPLC (Method: Microsorb 4s)

Rt: 3.66 min, Mass: $(M+H)^+$=365

By using the same synthetic strategy as for compound 596 step 1 the following compound was obtained:

| No. | Starting material 1 | Starting material 2 | Product | MS m/z $[M+H]^+$ | HPLC Method | Rt min |
|---|---|---|---|---|---|---|
| 36.1.1 | 1.5.3 | 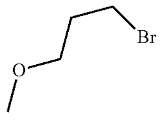 | 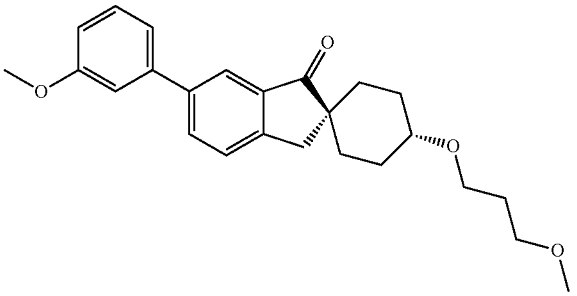 | 395 | Microsorb 4 s | 3.51 |

N. Compound 599

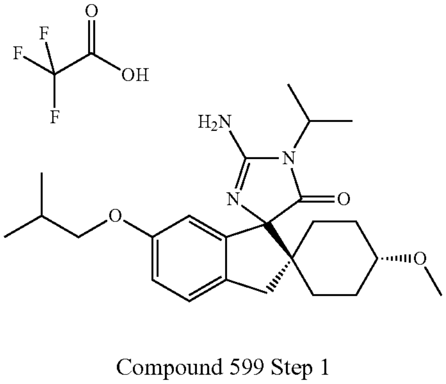

Compound 599 Step 1

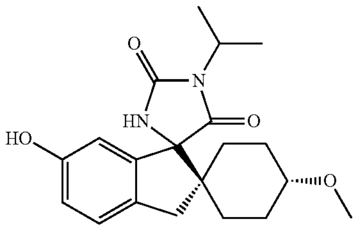

Product 3.2.1 (2.6 g, 5.43 mmol) and trifluoroacetic acid containing 5% water (5.0 mL) in DCM (5.0 mL) were mixed and stirred for 5 min at RT. The solvents were evaporated, the residue was stirred in MeOH, the precipitate was filtered off and the filtrate was evaporated to give compound 599 Step 1 as an orange oil (2.3 g, 80% purity, 95% yield).

HPLC (Method: Microsorb 1s)

Rt: 1.25 min, Mass: $(M+H)^+=359$

Compound 599 Step 2

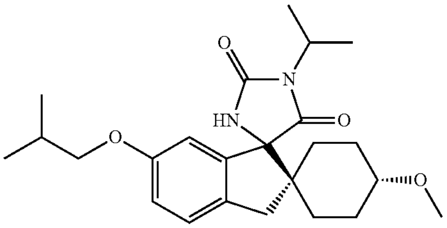

To compound 599 Step 1 (300 mg, 0.67 mmol) in DMF (anhydrous, 1.0 mL), 1-iodo-2-methylpropane (0.95 mL, 8.04 mmol) and sodium hydride (320 mg, 60%, 8.035 mmol) were mixed together and stirred for 20 h at 35° C. The mixture was diluted with 2 M HCl and extracted with DCM. The organic layer was separated and evaporated. The crude product was purified by MPLC (gradient DCM/MeOH 100:0 to 98:2 over 30 min) to give compound 599 Step 2 as an oil (300 mg, 85% purity, 92% yield).

HPLC (Method: Microsorb 1s)

Rt: 1.69 min, Mass: $(M+H)^+=415$

By using the same synthetic strategy as for compound 599 step 2 the following compound was obtained:

| No. | Starting material 1 | Starting material 2 | Product | MS m/z $[M + H]^+$ | HPLC Method | Rt min |
|---|---|---|---|---|---|---|
| 39.2.1 | Compound 599 Step 1 | 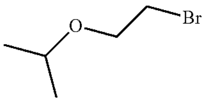 | 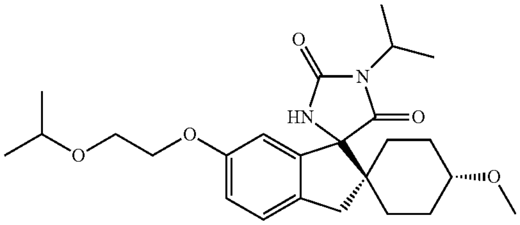 | 445 | Microsorb 1 s | 1.56 |

O. Compound 602

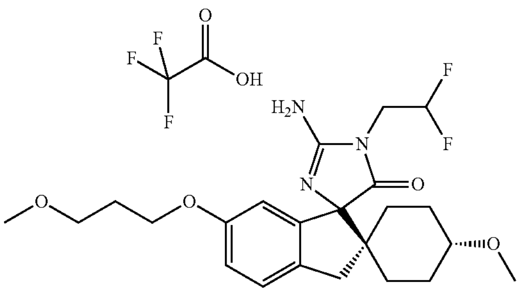

Compound 602 Step 1

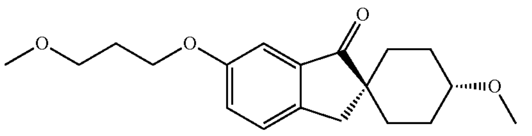

Product compound 592 step 1 (200 mg, 0.812 mmol), 1-bromo-3-methoxypropane (130 mg, 0.850 mmol) and potassium carbonate (340 mg, 2.46 mmol) in DMF (3 mL) were mixed and stirred for 14 h at 100° C. The mixture was diluted with EA and extracted with water. The organic layer was separated and the solvent was evaporated to give compound 602 Step 1 as a yellow resin (234 mg, 91%).

HPLC (Method: Microsorb 1s)

Rt: 1.52 min, Mass: $(M+H)^+=319$

By using the same synthetic strategy as for compound 602 step 1 the following compound was obtained:

| No. | Starting material 1 | Starting material 2 | Product | MS m/z [M + H]$^+$ | HPLC Method | Rt min |
|---|---|---|---|---|---|---|
| 42.1.1 | Compound 592 step 1 | 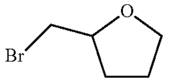 | 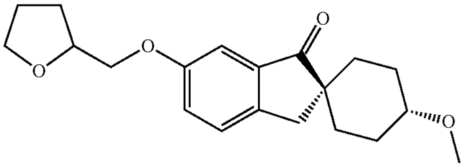 [SMILES: CO[C@H]1CC[C@]2(CC1)Cc1ccc(OCC3CCCO3)cc1C2=O] | 331 | Microsorb 1 s | 1.49 |

Compound 603 Step 1

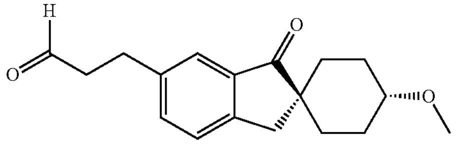

Product 2.4.10 (395 mg, 1.20 mmol), trifluoroacetic acid (4.0 mL) and water (50 μL, 2.78 mmol) in DCM (4.0 mL) were mixed and stirred for 14 h at RT. The mixture was diluted with DCM and quenched with saturated $NaHCO_3$ and NaOH (1 M). The organic layer was washed with water, dried and evaporated to give compound 603 Step 1 as a yellow solid (285 mg, 83%).

HPLC (Method: Microsorb 1s)

Rt: 1.31 min, Mass: $(M+H)^+=287$

P. Compound 603

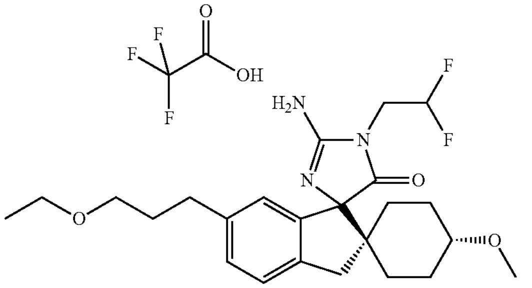

Compound 603 Step 2

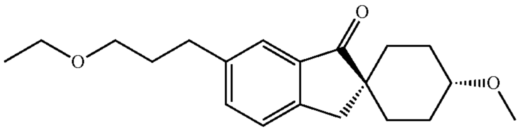 [SMILES: CCOCCCc1ccc2c(c1)C(=O)[C@]1(CC[C@H](OC)CC1)C2]

To compound 603 Step 1 (200 mg, 0.698 mmol) in ACN (anhydrous, 5 mL) ferric chloride (5.7 mg, 0.035 mmol) was added. Then trimethylethoxysilane (328 μL, 2.108 mmol) and triethylsilane (343 μL, 2.153 mmol) were added successively at RT under an argon atmosphere. The mixture was stirred for 14 h at RT. The mixture was diluted with phosphate buffer (pH7) and extracted with DCM. The organic layer was separated and evaporated. The crude product was purified by MPLC (25 g silicagel, gradient:CH/EA 100:0 to 70:30 over 45 min) to give compound 603 Step 2 as a resin (134 mg, 61%).

HPLC (Method: Microsorb 1s)

Rt: 1.63 min, Mass: $(M+H)^+=317$

Example 411

Synthesis of Compound 519

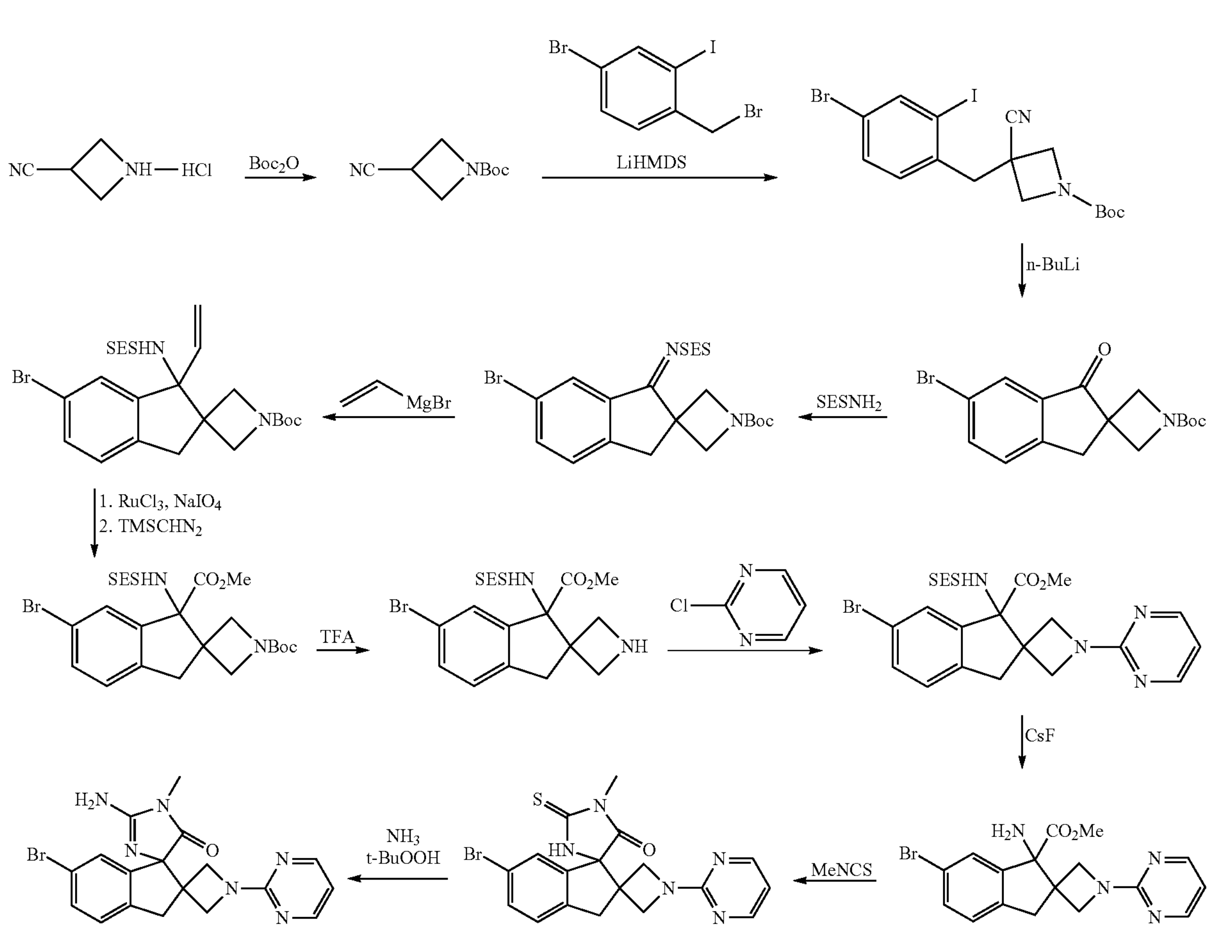

519

Step 1. tert-butyl 3-cyanoazetidine-1-carboxylate

A mixture of azetidine-3-carbonitrile hydrochloride (5.03 g, 42 mmol), $Boc_2O$ (10.75 g, 49 mmol), and $NaHCO_3$ (10.1 g, 120 mmol) in $CH_2Cl_2$ (50 mL) and $H_2O$ (20 mL) was vigorously stirred at room temperature for 15 h. The organic phase was separated and aqueous phase was extracted with $CH_2Cl_2$. The combined organic layers were dried over $Na_2SO_4$. After the solvent was evaporated under reduced pressure, the residue was purified by chromatography on silica gel eluted with hexanes/ethyl acetate to afford 7.3143 g (95%) of tert-butyl 3-cyanoazetidine-1-carboxylate as a solid. LC-MS $t_R$=1.27 min in 3 min chromatography, m/z 183 ($MH^+$), 168 ($MH^+$-15), 127 ($MH^+$-56); $^1H$ NMR (400 MHz, $CDCl_3$) δ 4.23-4.15 (m, 4H), 3.43-3.35 (m, 1H), 1.44 (s, 9H); $^{13}C$ NMR (100 MHz, $CDCl_3$) δ 155.40, 119.43, 80.68, 52.37, 28.21, 16.99.

Step 2. tert-butyl 3-(4-bromo-2-iodobenzyl)-3-cyanoazetidine-1-carboxylate

To a solution of tert-butyl 3-cyanoazetidine-1-carboxylate (2.1774 g, 11.95 mmol) and 4-bromo-1-(bromomethyl)-2-iodobenzene (5.0227 g, 13.36 mmol) in THF (30 mL) was added LiHMDS (1.0 M in THF, 15 mL, 15 mmol) at −78° C. The mixture was allowed to slowly warm to room temperature over 20 h. The reaction mixture was then quenched with saturated $NH_4Cl$, extracted with EtOAc, and dried over $Na_2SO_4$. After the solvent was evaporated under reduced pressure, the residue was purified by chromatography on silica gel eluted with hexanes/ethyl acetate to afford 4.2959 g (75%) of tert-butyl 3-(4-bromo-2-iodobenzyl)-3-cyanoazetidine-1-carboxylate as foam. LC-MS $t_R$=2.17 min in 3 min chromatography, m/z 477, 479 ($MH^+$), 462, 464 ($MH^+$-15), 421, 423 ($MH^+$-56).

Step 3. tert-butyl 6'-bromo-β-oxo-1',3'-dihydrospiro [azetidine-3,2'-indene]-1-carboxylate To a solution of tert-butyl 3-(4-bromo-2-iodobenzyl)-3-cyanoazetidine-1-carboxylate (4.2876 g, 8.99 mmol) in THF (120 mL) was added n-BuLi (2.5 Min hexane, 3.8 mL, 9.5 mmol) at −78° C. dropwise over 10 min under nitrogen. After 1 h, the reaction mixture was quenched with saturated $NH_4Cl$, diluted with $CH_2Cl_2$, and dried over $Na_2SO_4$. After the solvent was evaporated under reduced pressure, the residue was purified by chromatography on silica gel eluted with hexanes/ethyl acetate to afford 1.7020 g (54%) of tert-butyl 6'-bromo-1'-oxo-1',3'-dihydrospiro[azetidine-3,2'-indene]-1-carboxylate as a solid. LC-MS $t_R$=1.90 min in 3 min chromatography, m/z 352, 354 ($MH^+$), 337, 339 ($MH^+$-15), 296, 298 ($MH^+$-56); $^1H$ NMR (400 MHz, $CDCl_3$) δ 7.91 (m, 1H), 7.74-7.71

(m, 1H), 7.35 (d, J=7.9 Hz, 1H), 4.23 (d, J=8.2 Hz, 2H), 3.88 (d, J=8.2 Hz, 2H), 3.40 (s, 2H), 1.46 (s, 9H); $^{13}C$ NMR (100 MHz, $CDCl_3$) δ 204.38, 156.03, 150.44, 138.17, 137.24, 127.88, 127.29, 122.19, 80.05, 57.88, 44.70, 39.67, 28.35.

Step 4. tert-butyl 6'-bromo-1'-(((2-(trimethylsilyl)ethyl)sulfonyl)imino)-1',3'-dihydrospiro[azetidine-3,2'-indene]-1-carboxylate A mixture of tert-butyl 6'-bromo-1'-oxo-1',3'-dihydrospiro[azetidine-3,2'-indene]-1-carboxylate (0.2863 g, 0.8 mmol), 2-(trimethylsilyl)ethanesulfonamide (0.2000 g, 1.1 mmol), and $Ti(OEt)_4$ (0.6900 g, 3.0 mmol) in 1,2-dichloroethane (3 mL) was heated at 110° C. for 20 h. The reaction mixture was then quenched with ice, extracted with $CH_2Cl_2$, and dried over $Na_2SO_4$. After the solvent was evaporated under reduced pressure, the residue was purified by chromatography on silica gel eluted with hexanes/ethyl acetate to afford 0.4031 g (96%) of tert-butyl 6'-bromo-1'-(((2-(trimethylsilyl)ethyl)sulfonyl)imino)-1',3'-dihydrospiro[azetidine-3,2'-indene]-1-carboxylate. LC-MS $t_R$=2.31 min in 3 min chromatography, m/z 515, 517 (MH), 459, 461 ($MH^+$-56).

Step 5. tert-butyl 6'-bromo-1'-(2-(trimethylsilyl)ethylsulfonamido)-1'-vinyl-1',3'-dihydrospiro[azetidine-3,2'-indene]-1-carboxylate To a solution of tert-butyl 6'-bromo-1'-(((2-(trimethylsilyl)ethyl)sulfonyl)imino)-1',3'-dihydrospiro[azetidine-3,2'-indene]-1-carboxylate (0.4031 g, 0.78 mmol) in THF (3 mL) was added vinylmagnesium bromide (1.0 M in THF, 3 mL, 3.0 mmol) at 0° C. under nitrogen. The mixture was allowed to slowly warm to room temperature over 18 h. The reaction mixture was then quenched with saturated $NH_4Cl$, extracted with EtOAc, and dried over $Na_2SO_4$. After the solvent was evaporated under reduced pressure, the crude product was directly used in the next step without further purification. LC-MS $t_R$=2.31 min in 3 min chromatography, m/z 543, 545 (MH), 487, 489 ($MH^+$-56).

Step 6. 6'-bromo-1-(tert-butoxycarbonyl)-1'-(2-(trimethylsilyl)ethylsulfonamido)-1',3'-dihydrospiro[azetidine-3,2'-indene]-1'-carboxylic acid A mixture of tert-butyl 6'-bromo-1'-(2-(trimethylsilyl)ethylsulfonamido)-1'-vinyl-1',3'-dihydrospiro[azetidine-3,2'-indene]-1-carboxylate, obtained as described above, and $NaIO_4$ (1.3800 g, 6.45 mmol), and $RuCl_3$ hydrate (0.0180 g, 0.0867 mmol) in $CH_3CN$ (4 mL), $CH_2Cl_2$ (3 mL), and $H_2O$ (3 mL) was vigorously stirred at room temperature for 18 h. The reaction mixture was then diluted with $CH_2Cl_2$, dried over $Na_2SO_4$. After the solvent was evaporated under reduced pressure, the crude product was directly used in the next step without further purification. LC-MS $t_R$=1.98 min in 3 min chromatography, m/z 533, 535 ($MH^+$-28), 505, 507 ($MH^+$-56).

Step 7. 1-tert-butyl 1'-methyl 6'-bromo-1'-(2-(trimethylsilyl)ethylsulfonamido)-1',3'-dihydrospiro[azetidine-3,2'-indene]-1,1'-dicarboxylate A mixture of 6'-bromo-1-(tert-butoxycarbonyl)-1'-(2-(trimethylsilyl)ethylsulfonamido)-1',3'-dihydrospiro[azetidine-3,2'-indene]-1'-carboxylic acid, obtained as described above, and $TMSCHN_2$ (2.0 M in hexane, 1 mL) in $CH_2Cl_2$ (6 mL) and MeOH (3 mL) was stirred at room temperature for 19 h. After the solvent was evaporated under reduced pressure, the residue was purified by chromatography on silica gel eluted with hexanes/ethyl acetate to afford 0.3263 g (72% in three steps) of 1-tert-butyl 1'-methyl 6'-bromo-1'-(2-(trimethylsilyl)ethylsulfonamido)-1',3'-dihydrospiro[azetidine-3,2'-indene]-1,1'-dicarboxylate as foam. LC-MS $t_R$=2.20 min in 3 min chromatography, m/z 575, 577 ($MH^+$), 547, 549 ($MH^+$-28), 519, 521 ($MH^+$-56).

Step 8. methyl 6'-bromo-1'-(2-(trimethylsilyl)ethylsulfonamido)-1',3'-dihydrospiro[azetidine-3,2'-indene]-1'-carboxylate A mixture of 1-tert-butyl 1'-methyl 6'-bromo-1'-(2-(trimethylsilyl)ethylsulfonamido)-1',3'-dihydrospiro[azetidine-3,2'-indene]-1,1'-dicarboxylate (0.3010 g, 0.52 mmol) and TFA (1 mL) in $CH_2Cl_2$ (5 mL) was stirred at room temperature for 2 h. After the solvent was evaporated under reduced pressure, the residue was purified by reversed-phase HPLC (SunFire™ Prep $C_{18}$ OBD™ 5 μm 19×50 mm column, 10%→90% MeOH/$H_2O$, 0.1% $CF_3COOH$ over 8 min and then 90% MeOH/$H_2O$, 0.1% $CF_3COOH$ over 2 min, flow rate 20 mL/min) to afford 0.2346 g (76%) of TFA salt of methyl 6'-bromo-1'-(2-(trimethylsilyl)ethylsulfonamido)-1',3'-dihydrospiro[azetidine-3,2'-indene]-1'-carboxylate. LC-MS $t_R$=1.50 min in 3 min chromatography, m/z 475, 477 ($MH^+$).

Step 9. methyl 6'-bromo-1-(pyrimidin-2-yl)-1'-(2-(trimethylsilyl)ethylsulfonamido)-1',3'-dihydrospiro[azetidine-3,2'-indene]-1'-carboxylate To a solution of methyl 6'-bromo-1'-(2-(trimethylsilyl)ethylsulfonamido)-1',3'-dihydrospiro[azetidine-3,2'-indene]-1'-carboxylate trifluoroacetate (0.2196 g, 0.37 mmol) and 2-chloropyrimidine (0.1080 g, 0.94 mmol) in MeOH (4 mL) was added $Et_3N$ (0.5 mL) at room temperature. The mixture was stirred at 80° C. for 18 h and then concentrated under reduced pressure. The residue was purified by reversed-phase HPLC (SunFire™ Prep $C_{18}$ OBD™ 5 μm 19×50 mm column, 10%→90% MeOH/$H_2O$, 0.1% $CF_3COOH$ over 8 min and then 90% MeOH/$H_2O$, 0.1% $CF_3COOH$ over 2 min, flow rate 20 mL/min) to afford 0.0803 g (39%) of methyl 6'-bromo-1-(pyrimidin-2-yl)-1'-(2-(trimethylsilyl)ethylsulfonamido)-1',3'-dihydrospiro[azetidine-3,2'-indene]-1'-carboxylate. LC-MS $t_R$=1.87 min in 3 min chromatography, m/z 553, 555 ($MH^+$).

Step 10. methyl 1'-amino-6'-bromo-1-(pyrimidin-2-yl)-1',3'-dihydrospiro[azetidine-3,2'-indene]-1'-carboxylate A mixture of methyl 6'-bromo-1-(pyrimidin-2-yl)-1'-(2-(trimethylsilyl)ethylsulfonamido)-1',3'-dihydrospiro[azetidine-3,2'-indene]-1'-carboxylate (0.0803 g, 0.145 mmol) and CsF (0.6400 g, 4.2 mmol) in DMF (1.5 mL) was heated at 110° C. for 18 h. The mixture was diluted with MeOH, filtered through HPLC filter, and then purified by reversed-phase HPLC (SunFire™ Prep $C_{18}$ OBD™ 5 μm 19×50 mm column, 10%→90% MeOH/$H_2O$, 0.1% $CF_3COOH$ over 8 min and then 90% MeOH/$H_2O$, 0.1% $CF_3COOH$ over 2 min, flow rate 20 mL/min) to afford 0.0249 g (34%) of TFA salt of methyl 1'-amino-6'-bromo-1-(pyrimidin-2-yl)-1',3'-dihydrospiro[azetidine-3,2'-indene]-1'-carboxylate. LC-MS $t_R$=1.05 min in 3 min chromatography, m/z 389, 391 ($MH^+$).

Step 11

To a solution of methyl 1'-amino-6'-bromo-1-(pyrimidin-2-yl)-1',3'-dihydrospiro[azetidine-3,2'-indene]-1'-carboxylate trifluoroacetate (0.0249 g, 0.0494 mmol) in $CH_2Cl_2$ (1.5 mL) was added $Et_3N$ (0.15 mL) followed by methylisothiocyanate (0.0615 g, 0.84 mmol). The reaction mixture was heated at 110° C. for 15 h and then concentrated under reduced pressure. The crude product was directly used in the next step without further purification. LC-MS $t_R$=1.54 min in 3 min chromatography, m/z 430, 432 (MH).

Step 12. Compound 519

A mixture of 3-methyl-2-thioxo-imidazolidin-4-one, obtained as described above, ammonia (ca. 7 N solution in MeOH, 2 mL), and TBHP (~5.5 M solution in nonane, 0.5 mL) was stirred at room temperature for 19 h. After the solvent was evaporated under reduced pressure, the residue was purified by reversed-phase HPLC (SunFire™ Prep $C_{18}$ OBD™ 5 μm 19×50 mm column, 10%→90% MeOH/$H_2O$, 0.1% $CF_3COOH$ over 8 min and then 90% MeOH/$H_2O$, 0.1% $CF_3COOH$ over 2 min, flow rate 20 mL/min) to afford compound 519 as a TFA salt. LC-MS $t_R$=1.09 min in 3 min chromatography, m/z 413, 415 (MH); $^1H$ NMR (400 MHz, $CD_3OD$) δ 8.36 (d, J=5.0 Hz, 2H), 7.58-7.54 (m, 2H), 7.34 (d, J=8.5 Hz, 1H), 6.74 (t, J=5.0 Hz, 1H), 4.25 (d, J=9.1 Hz, 1H), 4.17 (d, J=9.8 Hz, 1H), 4.12 (d, J=9.8 Hz, 1H), 3.92 (d, J=9.1 Hz, 1H), 3.66 (d, J=16.4 Hz, 1H), 3.42 (d, J=16.1 Hz, 1H), 3.23 (s, 3H).

Example 412

Synthesis of Compound 591

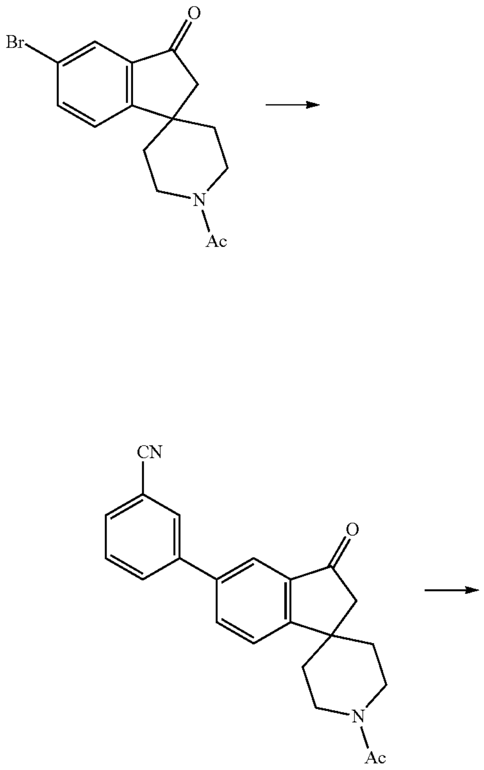

-continued

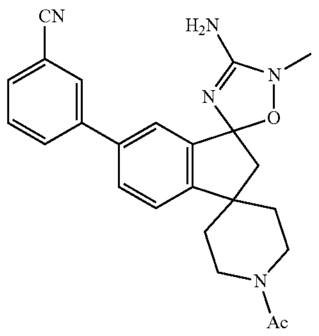

The title compound was made by the method described in example 389. MS ESI+ve m/z 416 $(M+H)^+$. $t_R$: 1.15 min. $^1H$ NMR (400 MHz, $CD_3OD$) δ: 8.06-7.98 (m, 2H), 7.88 (m, 2H), 7.78 (m, 1H), 7.69 (m, 2H), 7.56 (d, J=6.8 Hz, 1H), 3.43 (m, 7H), 3.14 (m, 1H), 2.84 (m, 1H), 2.39-1.68 (m, 4H).

Example 413

Synthesis of Compound 527

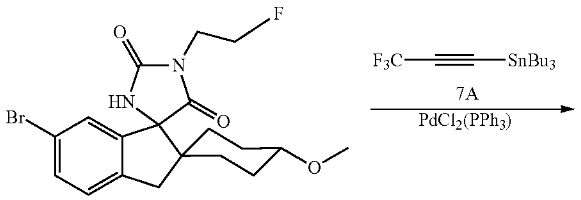

7

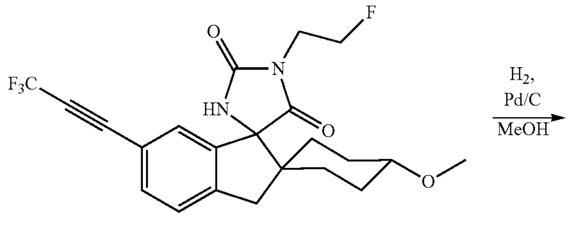

8

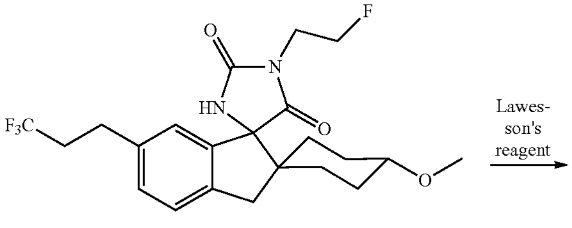

9

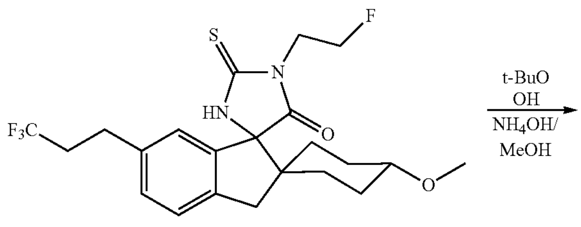

10

-continued

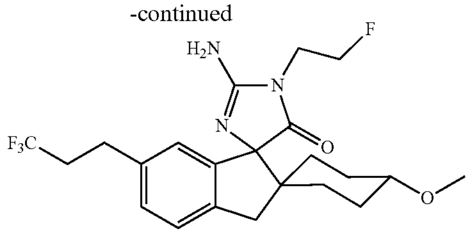

527

Procedure for Preparation of Compound 8

A solution containing 7A (0.216 g, 0.56 mmol) and compound 7 (0.2 g, 0.47 mmol) in toluene (5 mL) was deoxygenated by bubbling a stream of nitrogen through the reaction mixture for 5 min. Then, $PdCl_2(PPh_3)_2$ (20 mg, 0.047 mmol) was added. The reaction vial was sealed and placed into CEM microwave reactor and irradiated at 130° C. for 40 min. After being cooled to room temperature, the mixture was partitioned between EtOAc (5 mL) and aqueous CsF (4 M, 5 mL), and the aqueous layer was extracted with EtOAc (3×5 mL). The combined organic layers were washed with brine (20 mL), dried over anhydrous $Na_2SO_4$, filtered, and concentrated in vacuo. The residue was purified by preparative TLC over silica gel eluted with petroleum ether:EtOAc=3:1 to give compound 8 (80 mg, 38%) as a yellow solid. LC-MS: $t_R$=1.173 min in 2 min chromatography MS (ESI) m/z 439.1 $[M+H]^+$.

Procedure for Preparation of Compound 9

A Parr flask was charged with compound 8 (80 mg, 0.182 mmol) and methanol (5 mL), 10% Pd/C (10 mg) was added. The suspension was degassed under vacuum and flushed several times with hydrogen and then pressurized with hydrogen (50 Psi) at 60° C. with vigorous stirring for 24 h. The precipitate was filtered off and washed with methanol (2×50 mL). The filtrate and washings were concentrated by evaporation in vacuo. The residue was purified by preparative TLC over silica gel eluting with petroleum ether:EtOAc=3:1 to give compound 9 (40 mg, 49%) as a yellow solid. LC-MS: $t_R$=1.335 min in 2 min chromatography, MS (ESI) m/z 443.2 $[M+H]^+$.

Procedure for Preparation of Compound 10

To a solution of compound 9 (40 mg, 0.090 mmol) in anhydrous toluene (5 mL) was added Lawesson's reagent (40 mg, 0.099 mmol) under a nitrogen atmosphere, the mixture was heated at reflux for 12 h. After cooling down, the solvent was removed by evaporation in vacuo and the resulting residue was purified by column chromatography on silica gel (petroleum ether: EtOAc=3:1) to give compound 10 (30 mg, 73%) as a white solid. LC-MS $t_R$=1.420 min in 2 min chromatography, MS (ESI) m/z 459.1 $[M+H]^+$.

Procedure for Preparation of Compound 527

To a solution of compound 10 (30 mg, 0.065 mmol) in MeOH (10 mL) was added $NH_4OH$ (3 mL) and tert-butyl hydroperoxide (1 mL). After addition, the mixture was stirred at room temperature for 24 h. The solvent was removed by evaporation in vacuo. The residue was partitioned between EtOAc (contained 10% methanol) (20 mL) and $H_2O$ (20 mL). The organic layer was separated and washed with brine (20 mL), dried over $Na_2SO_4$, filtered and concentrated in vacuo. The residue was purified by preparative HPLC to give VT_B011010_03 (5 mg, 17%) as a white solid. LC-MS $t_R$=1.118 min in 2 min chromatography, MS (ESI) m/z 442.2 $[M+H]^+$. $^1$H-NMR ($CD_3OD$ 400 MHz): δ 7.26 (d, J=7.6 Hz, 1H), 7.17 (d, J=7.2 Hz, 1H), 6.89 (s, 1H), 4.61-4.70 (m, 1H), 4.40-4.49 (m, 1H), 3.70-3.94 (m, 2H), 3.36 (s, 3H), 3.12-3.22 (m, 1H), 3.02-3.12 (m, 2H), 2.71-2.89 (m, 2H), 2.36-2.53 (m, 2H), 1.95-2.08 (m, 2H), 1.83-1.95 (m, 1H), 1.58-1.66 (m, 1H), 1.35-1.51 (m, 2H), 1.20-1.33 (m, 2H); $^{19}$F NMR ($CD_3OD$ 400 MHz): δ -76.92, -68.15.

Example 414

Synthesis of Compound 533

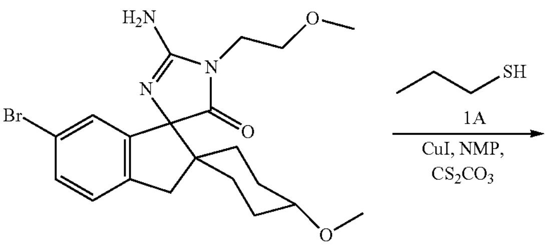

1

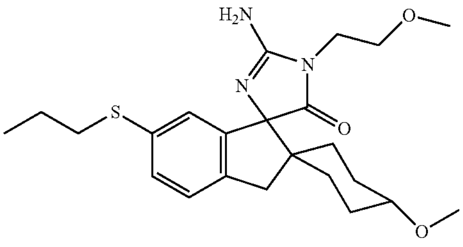

533

A mixture of compound 1 (50 mg, 0.115 mmol), compound 1A (8.6 mg, 0.115 mmol), CuI (21.8 mg, 0.115 mmol) and $Cs_2CO_3$ (75 mg, 0.23 mmol) in NMP (1 mL) was placed into CEM microwave reactor and irradiated at 195° C. for 1 h. After being cooled to room temperature, the mixture was partitioned between $H_2O$ (10 mL) and EtOAc (20 mL). The aqueous layer was extracted with EtOAc (3×20 mL). The combined organic layers were washed with brine (10 mL), dried over $Na_2SO_4$ and concentrated in vacuo to dryness. The residue was purified by RP-HPLC (acidic) to give compound 533 (5.3 mg, 12%) as a white solid. LC-MS $t_R$=1.152 min in 2 min chromatography, MS (ESI) m/z 432.1 $[M+H]^+$; $^1$H-NMR (MeOD 400 MHz): δ 7.32-7.38 (m, 2H), 7.15 (s, 1H), 3.90-3.97 (m, 2H), 3.56-3.59 (m, 2H), 3.33 (s, 6H), 3.07

(m, 1H), 2.98-3.03 (m, 2H), 2.90-2.94 (m, 2H), 2.02-2.10 (m, 2H), 1.89 (m, 1H), 1.61-1.67 (m, 2H), 1.32-1.46 (m, 5H), 1.01-1.04 (m, 3H).

Example 415

Synthesis of Compounds 521a and 521b

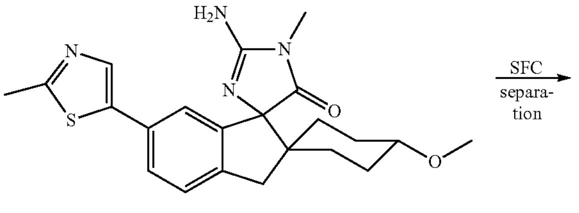

207

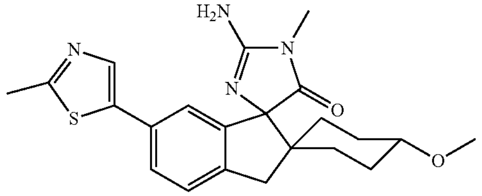

+

521b

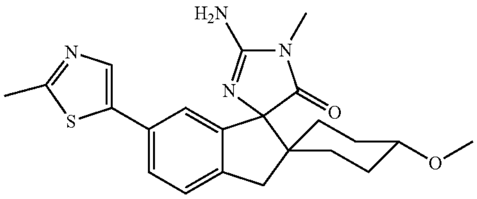

521a 40 mg of compound 207 was purified by preparative SFC HPLC to give compound 521b (11.3 mg, 28%), LC-MS: $t_R$=1.009 min in 2 min chromatography, MS (ESI) m/z=411.1 $[M+H]^+$; CHIRAL SFC-MS: $t_R$=4.362 min in 8 min chromatography (OD-H_S_4_5_40_3 ML_8 min), MS (ESI) m/z=411.1 $[M+H]^+$; $^1$H NMR ($CD_3OD$ 400 MHz): δ7.71 (s, 1H), 7.38-7.40 (d, J=8.0 Hz, 1H), 7.23-7.25 (d, J=8.0 Hz, 1H), 7.07 (s, 1H), 3.24 (s, 3H), 2.98-3.05 (m, 3H), 2.94 (s, 3H), 2.59 (s, 3H), 1.83-1.91 (m, 2H), 1.72 (m, 1H), 1.52 (m, 1H), 1.26-1.28 (m, 2H), 1.16-1.18 (m, 2H).

and compound 521a (8.6 mg, 21%), LC-MS: $t_R$=1.017 min in 2 min chromatography, MS (ESI) m/z=411.1 $[M+H]^+$; CHIRAL SFC-MS: $t_R$=5.544 min in 8 min chromatography (OD-H_S_4_5_40_3 ML_8 min), MS (ESI) m/z=411.1 $[M+H]^+$; $^1$H NMR ($CD_3OD$ 400 MHz): δ7.71 (s, 1H), 7.38-7.40 (d, J=8.0 Hz, 1H), 7.24-7.26 (d, J=8.0 Hz, 1H), 7.08 (s, 1H), 3.24 (s, 3H), 2.98-3.05 (m, 3H), 2.94 (s, 3H), 2.59 (s, 3H), 1.84-1.92 (m, 2H), 1.72 (m, 1H), 1.48-1.55 (m, 1H), 1.16-1.28 (m, 4H).

Example 416

Synthesis of Compound 473

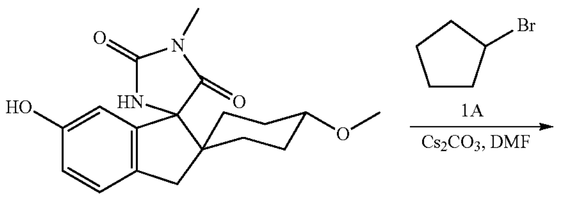

1

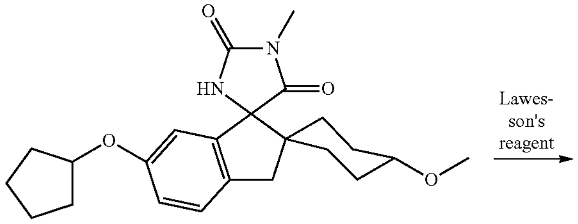

2

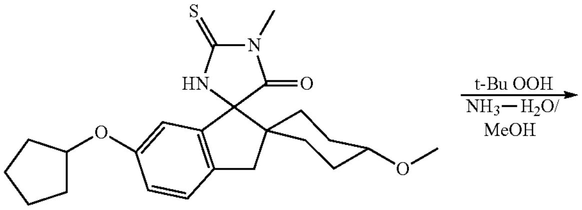

3

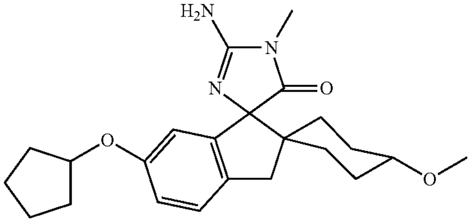

473

Procedure for Preparation of Compound 2

To a solution of compound 1 (50 mg, 0.15 mmol) in DMF (5 mL) was added compound 1A (33.5 mg, 0.225 mmol) and $Cs_2CO_3$ (58 mg, 0.17 mmol). After addition, the mixture was stirred at ambient temperature overnight. The mixture was concentrated in vacuo to give the residue, which was purified by preparative TLC (petroleum ether:EtOAc=1:1) to give compound 2 with 84% purity (60 mg, 94%) as a white solid. LC-MS $t_R$=1.113 min in 2 min chromatography, MS (ESI) m/z=399.2 $[M+H]^+$ Procedure for Preparation of Compound 3

To a mixture of compound 2 (60 mg, 0.15 mmol) was added Lawesson's reagent (60 mg, 0.15 mmol) in toluene (4 mL). The reaction was heated at 130° C. in a CEM microwave reactor for 1 h. After cooling down, the precipitate was filtered off and washed with ethyl acetate (40 mL×2). The filtrate and the washing were concentrated in vacuo and the residue was purified by preparative TLC (petroleum ether: EtOAc=1:1) to give compound 3 with 80% purity (38 mg, 62%) as a pale yellow solid. LC-MS $t_R$=1.416 min in 2 min chromatography, MS (ESI) m/z 415.1 $[M+H]^+$ Procedure for Preparation of Compound 473

To a solution of compound 3 (38 mg, 0.09 mmol) in MeOH (4 mL) was added $NH_3$—$H_2O$ (1 mL) and tert-butyl hydroperoxide (263 mg, 1.8 mmol). After addition, the mixture was stirred at ambient temperature overnight. The mixture was concentrated in vacuo and the residue was purified by preparative HPLC to give compound 473 (6.3 mg, 16%) as a white solid. LC-MS $t_R$=1.000 min in 2 min chromatography, MS (ESI) m/z 398.2 $[M+H]^+$; $^1$H NMR: ($CD_3OD$ 400M Hz): δ 7.16 (d, J=8.0 Hz, 1H), 6.78 (d, J=8.0 Hz, 1H), 6.47 (s, 1H), 4.73 (m, 1H), 3.34 (s, 3H), 3.14 (m, 1H), 2.93-3.02 (m, 5H), 1.76-2.03 (m, 9H), 1.62 (m, 3H), 1.24-1.39 (m, 4H).

Example 417

Synthesis of Compounds 483 and 484

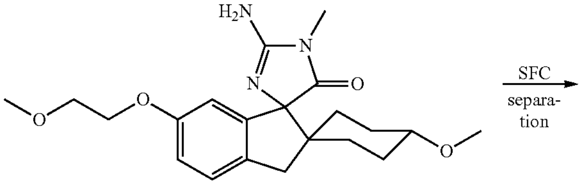

237

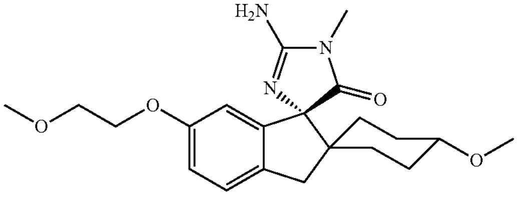

+

484

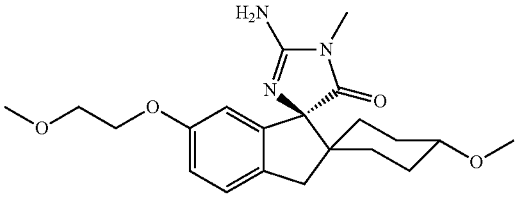

483

40 mg of compound 237 was purified by preparative SFC HPLC to give compound 484 (10.3 mg, 28%), LC-MS: $t_R$=0.844 min in 2 min chromatography, MS (ESI) m/z=388.0 $[M+H]^+$. CHIRAL SFC-MS: $t_R$=5.87 min in 15 min chromatography, Column: OJ-H, Method: 5-40_2.5 mL, Co-solvent: MeOH (0.05% DEA); $^1$H NMR (MeOD 300 MHz): δ 7.25 (d, J=5.1 Hz, 1H), 6.93 (d, J=5.4 Hz, 1H), 6.78 (s, 1H), 4.07 (d, J=2.4 Hz, 2H), 3.69 (d, J=2.1 Hz, 2H), 3.56 (s, 3H), 3.52 (s, 3H), 3.38 (s, 3H), 3.29 (m, 3H), 2.04 (m, 2H), 1.83 (m, 1H), 1.24-1.42 (m, 5H); and compound 483 (8.0 mg, 20%), LC-MS: $t_R$=0.852 min in 2 min chromatography, MS (ESI) m/z=388.1 $[M+H]^+$; CHIRAL SFC-MS: $t_R$=7.92 min in 16 min chromatography, Column: OJ-H, Method: 5-40_2.5 mL, Co-solvent: MeOH (0.05% DEA); $^1$H NMR (MeOD 300 MHz): δ 7.25 (d, J=5.4 Hz, 1H), 6.93 (d, J=5.4 Hz, 1H), 6.78 (s, 1H), 4.07 (d, J=2.4 Hz, 2H), 3.69 (d, J=2.1 Hz, 2H), 3.56 (s, 3H), 3.52 (s, 3H), 3.38 (s, 3H), 3.29 (m, 3H), 2.04 (m, 2H), 1.83 (m, 1H), 1.25-1.42 (m, 5H).

Example 418

Synthesis of Compound 569

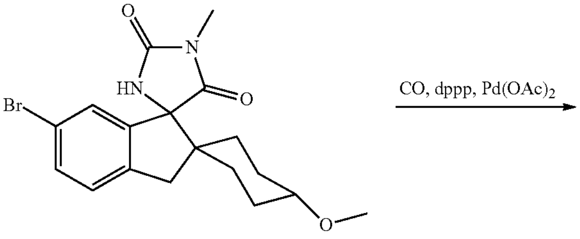

20

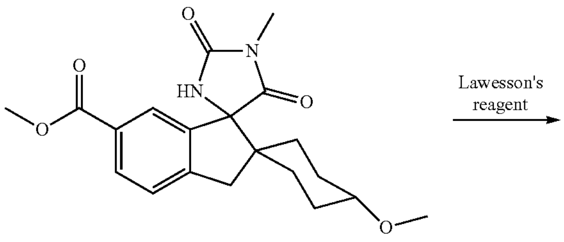

21

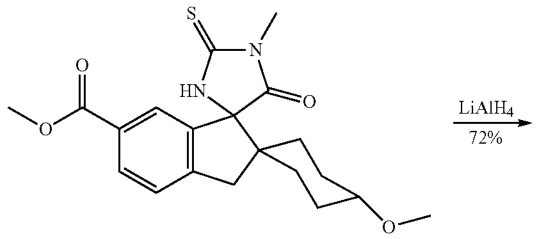

22

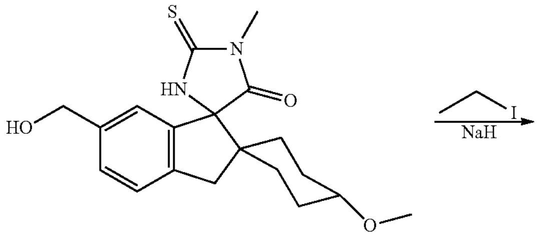

23

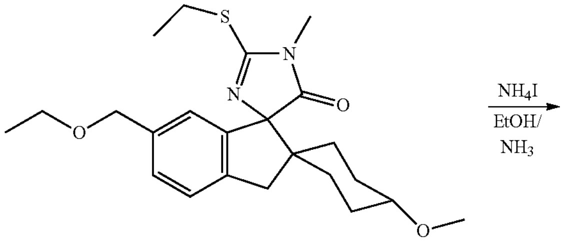

24

-continued

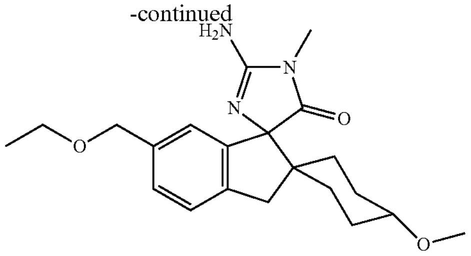

569

Procedure for Preparation of Compound 21

To a solution of compound 20 (600 mg, 1.53 mmol) in MeOH (10 mL) and DMSO (30 mL) was added dppp (314 mg, 0.76 mmol), $Pd(OAc)_2$ (171 mg, 0.76 mmol) and $Et_3N$ (6 mL). The reaction was heated at 80° C. under CO atmosphere (40 psi) for 16 h. The mixture was filtered and the filtrate was concentrated under reduced pressure to give the residue, which was purified by preparative TLC ($CH_2Cl_2$:MeOH, 10:1) to afford compound 21 (270 mg, 47%) as a white solid.

Procedure for Preparation of Compound 22

To a solution of compound 21 (50 mg, 0.134 mmol) in dry toluene (2 mL) was added Lawesson's reagent (55 mg, 0.161 mmol) under nitrogen. The reaction mixture was heated at 120° C. for 2 h. After cooling down, the solvent was removed under reduced pressure, and the residue was purified by preparative TLC (petroleum ether:EtOAc, 1:1) to give compound 22 (45 mg, 86%) as a white solid.

Procedure for Preparation of Compound 23

A solution of $LiAlH_4$ (13 mg, 0.348 mmol) in THF (2 mL) was stirred at 0° C. and a mixture of compound 22 (45 mg, 0.116 mmol) in THF (1 mL) was added dropwise. After addition, the reaction mixture was stirred at 0° C. for 2 h. The reaction was quenched by addition of 5 drops of water and 3 M of NaOH aqueous solution. After stirring for 10 min, the mixture was filtered and the filtrated was concentrated to give crude compound 23 (30 mg, 72%), which was used for the next step without purification.

Procedure for Preparation of Compound 24

To a solution of compound 23 (30 mg, 0.083 mmol) in DMF (3 mL) was added NaH (33 mg, 0.83 mmol) at 0° C. After stirring for 30 min, iodo-ethanethe (104 mg, 0.667 mmol) was added dropwise, and the reaction mixture was stirred at room temperature overnight. The reaction was quenched by addition of water (10 mL). The mixture was extracted with EtOAc (3×10 mL). The organic layer was washed with water, brine, dried over $Na_2SO_4$ and concentrated to give the residue, which was purified by preparative TLC (petroleum ether:EtOAc, 3:1) to afford compound 24 (23 mg, 67%) as a white solid.

Procedure for Preparation of Compound 569

A sealed tube was charged with compound 24 (23 mg, 0.055 mmol), $NH_4I$ (81 mg, 0.55 mmol). $NH_3$-EtOH (2 mL, 5 N) was added, and the vial was sealed and placed into CEM microwave reactor and irradiated at 120° C. for 2 h. After cooling down, the solvent was removed and the residue was purified by preparative TLC ($CH_2Cl_2$:MeOH, 10:1) and acidic RP-HPLC to give compound 569 (5.5 mg, 27%) as a white solid. LC-MS $t_R$=0.893 min in 2 min chromatography, MS (ESI) m/z 372.2 $[M+H]^+$; $^1H$ NMR ($CD_3OD$ 400 MHz): δ 7.25 (s, 2H), 7.09 (s, 1H), 4.37 (s, 2H), 3.45 (m, 2H), 3.25 (s, 3H), 3.09 (s, 3H), 3.03-3.06 (m, 3H), 1.89-2.01 (m, 2H), 1.77 (m, 1H), 1.22-1.34 (m, 5H), 1.11 (t, J=7.6 Hz, 3H).

Example 419

Synthesis of Compound 559 and 560

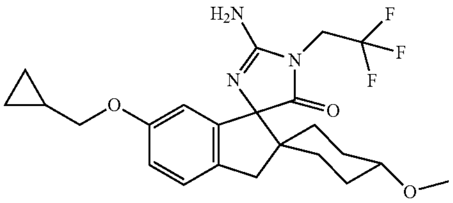

341

SFC separation

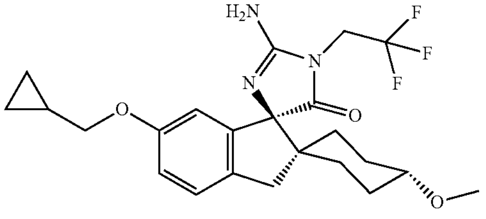

560

+

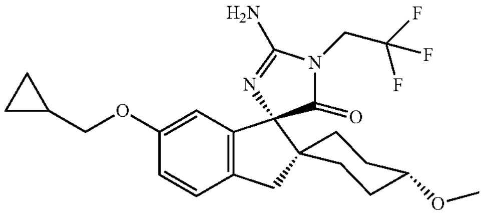

559

Compound 341 (40 mg, 0.088 mmole) was purified by preparative SFC to give compound 560 (12.60 mg, 31%), LCMS: $t_R$=0.975 min in 2 min chromatography, MS (ESI) m/z 452.0 $[M+H]^+$; SFC: $t_R$=4.49 min in 15 min chromatography (OJ-H_5_5_40%_2, 35 ML), ee=100%; $^1H$-NMR ($CD_3OD$ 400 MHz): 7.07 (d, J=8.4 Hz, 1H), 6.71 (d, J=6.8 Hz, 1H), 6.40 (s, 1H), 4.23 (m, 2H), 3.67 (d, J=6.4 Hz, 2H), 3.23 (s, 3H), 2.93-3.06 (m, 1H), 2.84-2.93 (m, 2H), 1.83-1.98 (m, 2H), 1.72-1.83 (m, 1H), 1.39-1.72 (m, 1H), 1.31-1.39 (m, 2H), 1.22-1.28 (m, 2H), 1.05-1.10 (m, 1H), 0.40-0.50 (m, 2H), 0.20-0.30 (m, 2H); $^{19}F$ NMR ($CD_3OD$ 400 MHz): δ −72.07.

and compound 559 (10.90 mg, 27%) as a white solid, LCMS: $t_R$=0.958 min in 2 min chromatography, MS (ESI) m/z 452.1 $[M+H]^+$; SFC: $t_R$=6.76 min in 15 min chromatography (OJ-H_5_5_40%_2, 35 ML), ee=98%; $^1H$-NMR ($CD_3OD$ 400 MHz): 7.07 (d, J=8.0 Hz, 1H), 6.81 (d, J=7.2 Hz, 1H), 6.39 (s, 1H), 4.23 (m, 2H), 3.72 (d, J=6.8 Hz, 2H), 3.24 (s, 3H), 2.93-3.03 (m, 1H), 2.85-2.93 (m, 2H), 1.83-1.98 (m, 2H), 1.73-1.83 (m, 1H), 1.45-1.68 (m, 1H), 1.22-1.32 (m, 2H), 1.10-1.18 (m, 2H), 1.01-1.10 (m, 1H), 0.39-0.50 (m, 2H), 0.22-0.29 (m, 2H); $^{19}$F NMR ($CD_3OD$ 400 MHz): δ −72.07.

Example 420

Synthesis of Compounds 522 and 523

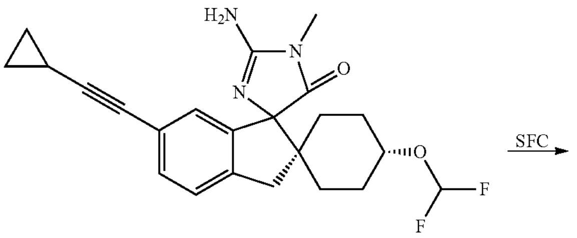

274

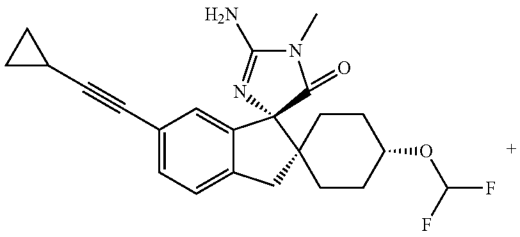

+

523

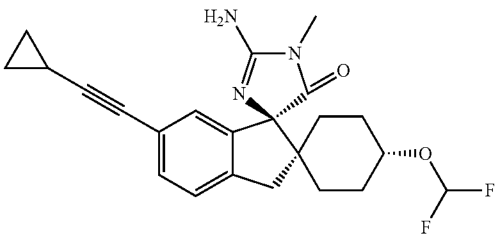

522

Compound 274 (50 mg, 0.121 mmol) was re-purified by preparative SFC to give compound 523 (20 mg), LC-MS $t_R$=3.070 min in 7 min chromatography, MS (ESI) m/z 414.5 [M+H]SFC $t_R$=3.652 min in 8 min chromatography (OD-H_S_3_5_40_3 ML_8MIN.M), ee=100%; $^1$H NMR ($CD_3OD$ 400 MHz): 7.12 (s, 2H), 6.80 (s, 1H), 6.08-6.46 (t, J=76.0 Hz, 1H), 3.86 (m, 1H), 2.95-3.05 (m, 2H), 2.92 (s, 3H), 1.70-1.90 (m, 3H), 1.40-1.54 (m, 3H), 1.17-1.34 (m, 3H), 0.75 (m, 2H), 0.58 (m, 2H). $^{19}$F NMR ($CD_3OD$ 400 MHz 19F): δ −81.48.

And compound 522 (24 mg) as a white solid, LC-MS $t_R$=3.061 min in 7 min chromatography, MS (ESI) m/z 414.5 [M+H]$^+$; SFC $t_R$=4.179 min in 8 min chromatography (OD-H_S_3_5_40_3 ML_8MIN.M), ee=96%; $^1$H NMR ($CD_3OD$ 400 MHz): δ 7.11 (s, 2H), 6.81 (s, 1H), 6.08-6.46 (m, J=76.0 Hz, 1H), 3.86 (m, 1H), 2.95-3.05 (m, 2H), 2.92 (s, 3H), 1.70-1.90 (m, 3H), 1.40-1.54 (m, 3H), 1.17-1.34 (m, 3H), 0.75 (m, 2H), 0.58 (m, 2H); $^{19}$F NMR ($CD_3OD$ 400 MHz 19F): δ −81.47.

Example 421

Synthesis of Compounds 580 and 581

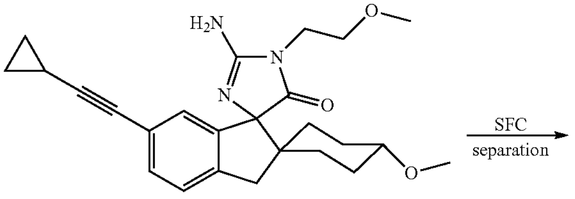

309

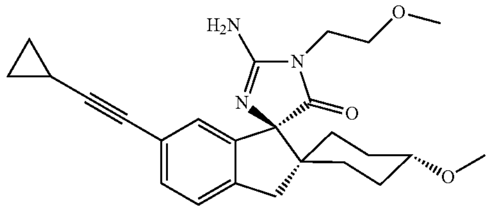

+

581

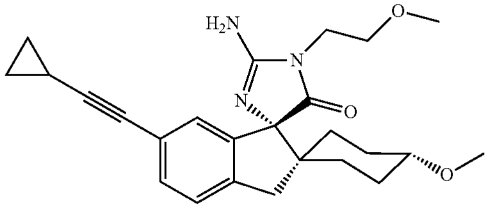

580

Compound 309 (40 mg) was purified by preparative SFC column to give compound 581, LC-MS: $t_R$=0.969 min in 2 min chromatography, MS (ESI) m/z 422.1 [M+H]$^+$; SFC: $t_R$=5.77 min in 15 min chromatography ee=96%, Column: OJ-H, Method: 5-40_2.5 mL, Co-solvent: IPA (0.05% DEA); $^1$H NMR ($CD_3OD$ 400 MHz): δ 7.30-7.36 (m, 2H), 7.15 (s, 1H), 3.85-3.99 (m, 2H), 3.55-3.59 (m, 2H), 3.36 (m, 6H), 3.09-3.20 (m, 3H), 2.02-2.09 (m, 2H), 1.89 (m, 1H), 1.31-1.44 (m, 6H), 0.86-0.90 (m, 2H), 070-0.72 (m, 2H).

And compound 580, LC-MS: $t_R$=0.967 min in 2 min chromatography, MS (ESI) m/z 422.1 [M+H]$^+$; SFC: $t_R$=6.39 min in 15 min chromatography, ee=96.5%, Column: OJ-H, Method: 5-40_2.5 mL, Co-solvent: IPA (0.05% DEA); $^1$H NMR ($CD_3OD$ 400 MHz): δ 7.35 (dd, J=1.2, 7.6 Hz, 1H), 7.31 (d, J=8.0 Hz 1H), 7.14 (s, 1H), 3.87-3.98 (m, 2H), 3.55-3.58 (m, 2H), 3.36 (m, 6H), 3.09-3.20 (m, 3H), 2.02-2.09 (m, 2H), 1.89 (m, 1H), 1.30-1.46 (m, 6H), 0.86-0.90 (m, 2H), 069-0.72 (m, 2H).

Example 422

Synthesis of Compound 557

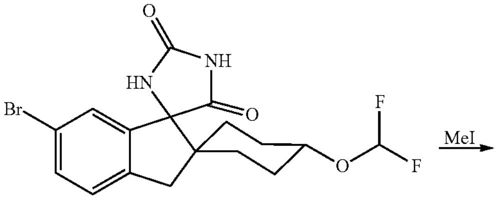

1

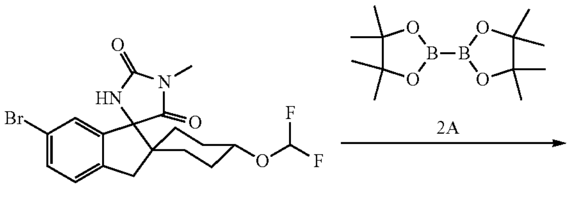

2

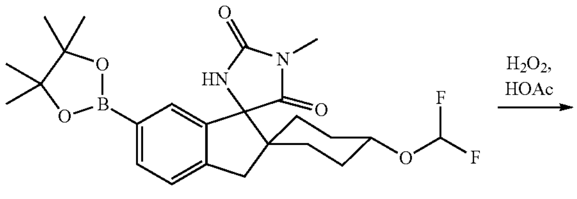

3

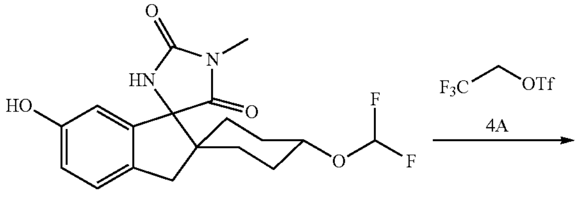

4

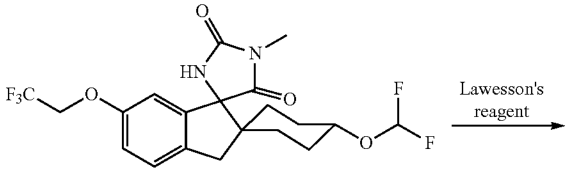

5

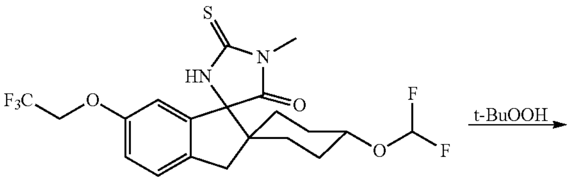

6

-continued

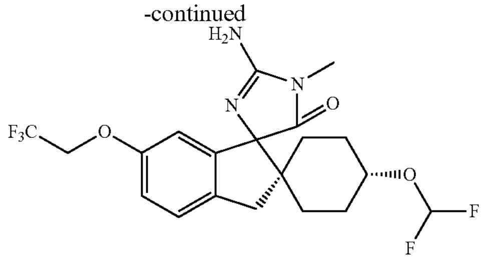

557

Procedure for Preparation of Compound 2

To a solution of compound 1 (0.20 g, 0.483 mmol) in DMF (4 mL) was added $K_2CO_3$ (0.166 g, 0.208 mmol). After addition, the resulting mixture was stirred at room temperature for 10 min. Then iodomethane (74 mg, 0.531 mmol) in DMF (2 mL) was added dropwise via a syringe with stirring. The mixture was stirred at room temperature overnight. The reaction mixture was partitioned between $H_2O$ (25 mL) and ethyl acetate (25 mL). The separated organic phase was washed with saturated brine (3×20 mL), dried over anhydrous $Na_2SO_4$ and concentrated in vacuo to give the crude product. The crude was purified by preparative TLC (hexane: EtOAc=3:1) to give compound 2 (0.15 g, 73%) as a white solid.

Procedure for Preparation of Compound 3

To a solution of compound 2 (0.2 g, 0.467 mmol) in dioxane (5 mL) was added compound 2A (0.131 g, 0.514 mmol), KOAc (0.132 g, 1.4 mmol). The mixture was deoxygenated by bubbling a stream of nitrogen through the reaction mixture for 5 min. Then, $PdCl_2$(dppf) (1.6 mg, 0.002 mmol) was added. The mixture was heated to reflux overnight in a $N_2$ atmosphere. The reaction mixture was cooled to room temperature and the solid was filtered off. The filtrate was concentrated in vacuo to give the crude compound 3 (0.2 g, crude). It can be used for the next step without further purification.

Procedure for Preparation of Compound 4

To a solution of compound 3 (0.2 g, crude) in dioxane (10 mL) was added $H_2O_2$ (10 mL) and HOAc (30 mL). The final solution was stirred at room temperature overnight. Then the solvent was evaporated in vacuo and the residue was purified by preparative TLC (hexane; EtOAc=1:1) to give the compound 4 (0.1 g, 65%) as a white solid.

Procedure for Preparation of Compound 5

To a solution of compound 4 (0.1 g, 0.273 mmol) in DMF (3 mL) was added $K_2CO_3$ (83 mg, 0.501 mmol) and compound 4A (70 mg, 0.306 mmol). The mixture was stirred at room temperature and monitored by TLC. When the compound 4 was consumed, Sat.$NH_4Cl$ (5 mL) was added to quench the reaction. The mixture was extracted with EtOAc (2×5 mL). The combined organic layers were separated, dried over $Na_2SO_4$, and evaporated in vacuo to give the crude. The crude was purified by preparative TLC (hexane:EtOAc=3:1) to give the compound 5 (20 mg, 16%) as a white solid.

Procedure for Preparation of Compound 6

An 8 mL vial was charged with compound 5 (20 mg, 0.0446 mmol), Lawesson's reagent (19.9 mg, 0.0491 mmol). Toluene (3 mL) was added, and the vial was sealed and placed into CEM microwave reactor and irradiated at 130° C. for 1 h. After cooling down, the solvent was removed by evaporation in vacuo and the resulting residue was purified by preparative TLC (hexane:EtOAc=2:1) to give compound 6 (10 mg, 47%) as a white solid.

Procedure for Preparation of Compound 557

To a solution of compound 6 (10 mg, 0.022 mmol) in MeOH (2.5 mL) was added $NH_3$—$H_2O$ (0.5 mL) and tert-butyl hydroperoxide (66 mg, 0.447 mmol). After addition, the mixture was stirred at room temperature for 24 h. The solvent was removed by evaporation in vacuo. The residue was partitioned between EtOAc (contained 10% methanol) (50 mL) and $H_2O$ (20 mL). The organic layer was separated and washed with brine (20 mL), dried over $Na_2SO_4$, filtered and concentrated in vacuo. The residue was purified by preparative HPLC to give compound 557 (2.8 mg, 28%) as a white solid; LC-MS $t_R$=1.015 min in 2 min chromatography, MS (ESI) m/z 448.1 $[M+H]^+$; $^1H$ NMR ($CD_3OD$ 400 MHz): δ 7.44 (d, J=8.0 Hz, 1H), 7.13 (d, J=8.4 Hz, 1H), 7.04 (s, 1H), 6.32-6.69 (m, 1H), 4.61 (m, 1H), 4.15 (m, 1H), 3.16-3.34 (m, 5H), 2.13 (m, 2H), 1.94 (m, 1H), 1.77-1.87 (m, 1H), 1.52-1.72 (m, 4H); $^{19}F$ NMR ($CD_3OD$ 400 MHz 19F): δ −77.00, −81.94.

Example 423

Synthesis of Compound 487

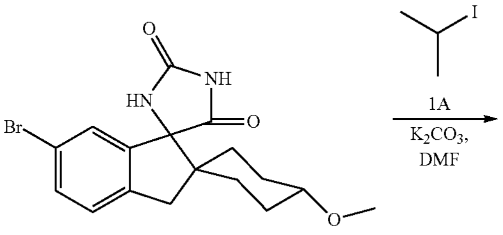

1

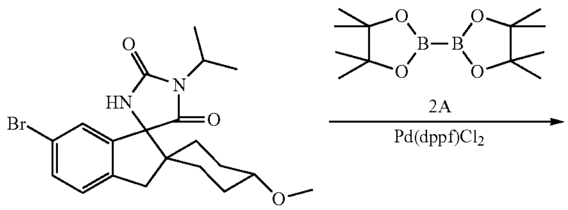

2

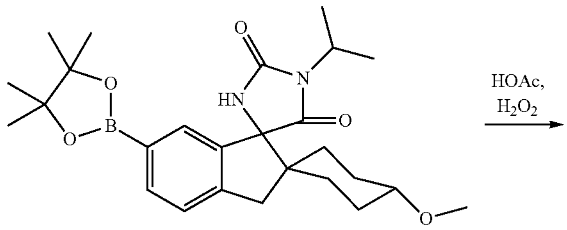

3

-continued

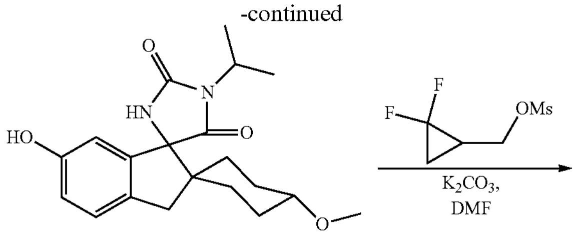

4

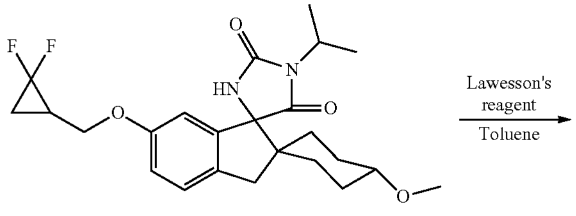

5

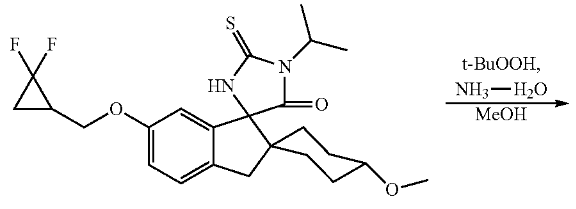

6

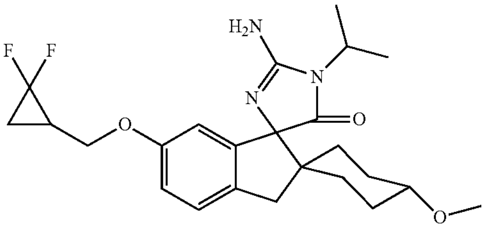

487

Procedure for Preparation of Compound 2

To a solution of compound 1 (1.2 g, 3.17 mmol) in DMF (20 mL) was added $K_2CO_3$ (530 mg, 3.81 mmol) and compound 1A (0.38 mL, 3.81 mmol). The reaction mixture was stirred at room temperature overnight. Water (20 mL) was added and the mixture was extracted with EtOAc (3×30 mL). The organic layer was washed with water, brine, dried over $Na_2SO_4$ and concentrated to give the residue, which was purified by chromatography (petroleum ether: EtOAc=5:1) to afford compound 2 (1.07 g, 80%) as a white solid.

Procedure for Preparation of Compound 3

To a solution of compound 2 (405 mg, 0.964 mmol) in 1,4-dioxane (10 mL) was added compound 2A (294 mg, 1.157 mmol), KOAc (280 mg, 2.892 mmol) and $Pd(dppf)Cl_2$ (120 mg) under $N_2$. The reaction mixture was refluxed overnight. The solution was filtered and the filtrate was concentrated to give the residue, which was purified by chromatography (petroleum ether: EtOAc=8:1) to afford compound 3 (450 mg, 98%) as a white solid.

Procedure for Preparation of Compound 4

To a solution of compound 3 (450 mg, 0.96 mmol) in THF (10 mL) was added HOAc (1.2 mL) and $H_2O_2$ (3.6 mL). The reaction was stirred at room temperature overnight. The reaction was quenched with $Na_2S_2O_3$ solution (15 mL), and stirred for 15 min. The mixture was extracted with EtOAc (3×30 mL). The organic layer was washed with brine, dried over $Na_2SO_4$ and concentrated to give compound 4 (315 mg, 90%) as a white solid.

Procedure for Preparation of Compound 5

To a solution of compound 4 (80 mg, 0.223 mmol) in DMF (3 mL) was added $K_2CO_3$ (62 mg, 0.446 mmol) and compound 4A (62 mg, 0.335 mmol). The reaction mixture was heated at 50° C. overnight. LCMS showed the reaction was completed. Water (10 mL) was added and the mixture was extracted with EtOAc (3×20 mL). The organic layer was washed with water, brine, dried over $Na_2SO_4$ and concentrated to give the residue, which was purified by preparative TLC (petroleum ether:EtOAc=1:1) to afford compound 5 (80 mg, 80%) as a white solid. $^1$H NMR ($CDCl_3$ 400 MHz): δ 7.12 (d, J=8.4 Hz, 1H), 6.75 (d, J=8.4 Hz, 1H), 6.54 (s, 1H), 5.31 (s, 1H), 4.23 (m, 3H), 3.91 (m, 2H), 3.28 (s, 3H), 3.06-2.88 (m, 6H), 2.03 (m, 1H), 1.91 (m, 2H), 1.57 (m, 1H), 1.33 (m, 6H), 1.25 (m, 4H).

Procedure for Preparation of Compound 6

To a solution of compound 5 (77 mg, 0.172 mmol) in dry toluene (2.5 mL) was added Lawesson's reagent (104 mg, 0.258 mmol) under nitrogen. The reaction mixture was heated in a CEM microwave reactor at 130° C. for 60 min. The solvent was removed under reduced pressure, and the residue was purified by preparative TLC (petroleum ether:EtOAc=3:1) to give compound 6 (67 mg, 84%) as a white solid.

Procedure for Preparation of Compound 487

To a solution of compound 6 (67 mg, 0.144 mmol) in MeOH (3 mL) and $NH_3$—$H_2O$ (0.6 mL) was added t-BuOOH (422 mg, 2.89 mmol). The reaction mixture was stirred at room temperature overnight. The solvent was removed and the residue was purified by preparative HPLC to give compound 487 (19.5 mg, 30%) as a white solid, LC-MS $t_R$=1.032 min in 2 min chromatography, MS (ESI) m/z 488 [M+H]$^+$; $^1$H NMR ($CDCl_3$ 400 MHz): δ 8.02 (s, 1H), 7.28 (d, J=8.4 Hz, 1H), 6.79 (m, 1H), 6.51 (s, 1H), 4.19 (m, 1H), 3.95 (m, 2H), 3.38. (s, 3H), 3.12-2.95 (m, 3H), 2.03 (m, 3H), 1.88 (m, 1H), 1.52 (m, 2H), 1.46 (m, 6H), 1.32 (m, 2H), 1.21 (m, 3H); $^{19}$F NMR ($CD_3OD$ 400 MHz): δ −130.560, −145.261

Example 424

Synthesis of Compounds 479 and 480

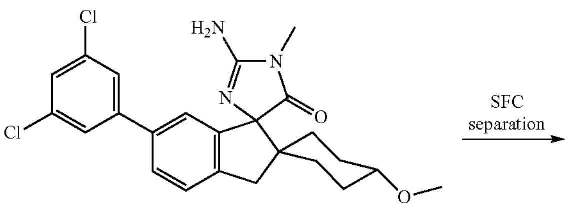

182

-continued

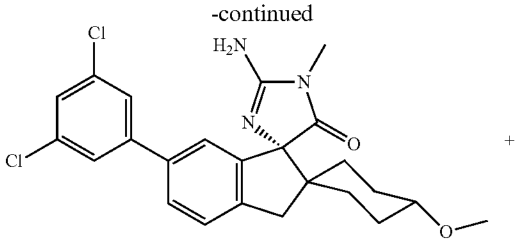

480

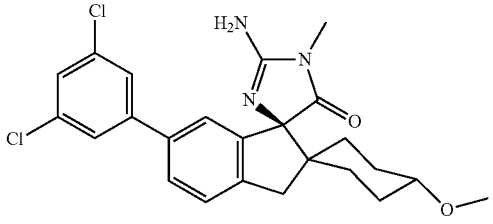

479

Compound 182 (53 mg) was purified by SFC to give compound 480 (15.2 mg), LC-MS $t_R$=0.978 min in 2 min chromatography, MS (ESI) m/z 458.2 [M+H]$^+$; SFC: $t_R$=1.63 min in 10 min chromatography, ee=100%, Column: OD-3, Method: 40_2.5 ml, Co-Solvent: IPA (0.05% DEA); $^1$H NMR ($CD_3OD$ 400 MHz): δ 7.63-7.68 (t, J=7.6 Hz, 3H), 7.57 (s, 1H), 7.44-7.52 (t, J=8.0 Hz, 2H), 3.38 (s, 3H), 3.16-3.27 (m, 6H), 2.05-2.12 (m, 2H), 1.88-1.91 (m, 1H), 1.33-1.49 (m, 5H).

And compound 479 (20.6 mg) as a white solid, LC-MS $t_R$=1.101 min in 2 min chromatography, MS (ESI) m/z 458.1 [M+H]$^+$; SFC: $t_R$=5.87 min in 10 min chromatography, ee=100%, Column: OD-3; Method: 40_2.5 ml, Co-Solvent: IPA (0.05% DEA); $^1$H NMR (DMSO-$d_6$ 400 MHz): δ 7.54-7.70 (m, 4H), 7.36-7.38 (d, J=7.6 Hz, 1H), 7.07 (s, 1H), 6.52-6.81 (brs, 1H), 3.22 (s, 3H), 2.95-3.09 (q, 3H), 2.90 (s, 3H), 1.64-1.97 (m, 3H), 1.09-1.36 (m, 5H).

Example 425

Synthesis of Compound 590

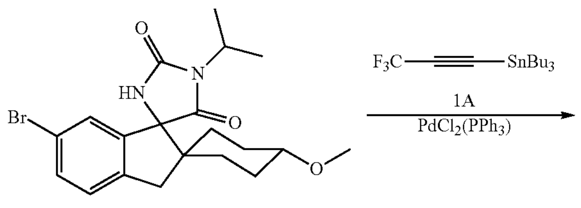

1

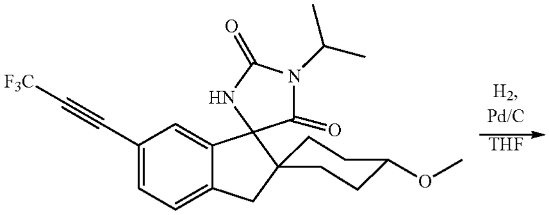

2

-continued

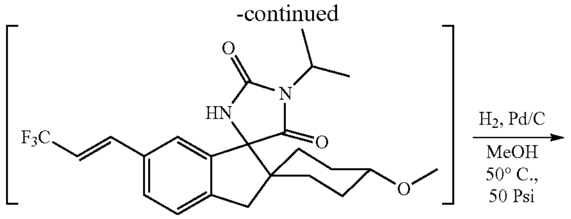

by-product

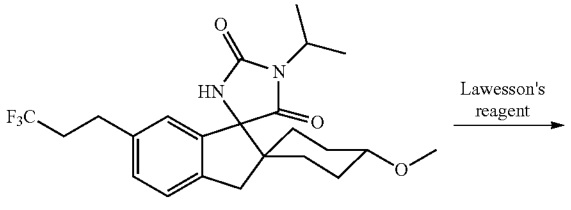

3

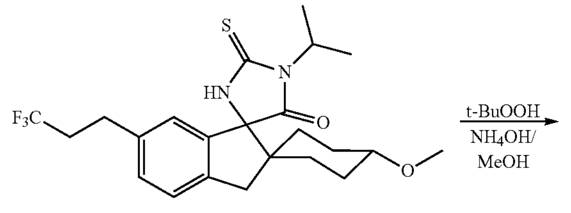

4

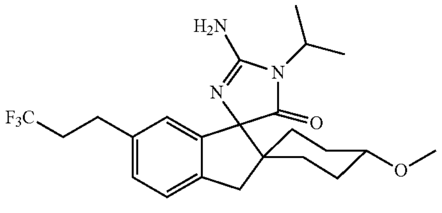

590

Procedure for Preparation of Compound 2

A solution containing the compound 1A (164 mg, 0.427 mmol) and compound 1 (150 mg, 0.356 mmol) in toluene (8 mL) was deoxygenated by bubbling a stream of nitrogen through the reaction mixture for 5 min. Then, $PdCl_2(PPh_3)_2$ (13 mg, 0.018 mmol) was added. The reaction vial was sealed and placed into CEM microwave reactor and irradiated at 125° C. for 45 min. After being cooled to room temperature, the mixture was partitioned between EtOAc (10 mL) and aqueous CsF (4 M, 10 mL), and the aqueous layer was extracted with EtOAc (3×10 mL). The combined organic layers were washed with brine (3×10 mL), dried over anhydrous $Na_2SO_4$, filtered, and concentrated in vacuo to give the residue, which was purified preparative TLC (petroleum/ethyl acetate=3:1) to give compound 2 (100 mg, 65%) as a white solid.

Procedure for Preparation of Compound 3

To a solution of compound 2 (100 mg, 0.23 mmol) in THF (10 mL) was added Pd/C (10 mg, 10 wt %). The reaction mixture was stirred at room temperature for overnight under $H_2$ atmosphere, LCMS showed only by-product was formed, the reaction mixture was filtered and the filtrate was concentrated, the residue was dissolved in MeOH (10 mL) was added dry Pd/C (10 mg, 10 wt %). The reaction mixture was stirred at 50° C. for overnight under $H_2$ (50 Psi) atmosphere, LCMS showed that the reaction was completed. The reaction mixture was filtered and the filtrate was concentrated to give compound 3 (80 mg, crude, 80%) as a white solid, which was used directly for next step without further purification.

Procedure for Preparation of Compound 4

A solution of compound 3 (80 mg, 0.18 mmol) and Lawesson's Reagent (89 mg, 0.219 mmol) in dry toluene (10 mL) was heated at reflux for 5 h under a nitrogen atmosphere. LCMS showed that the reaction was completed, the mixture was concentrated under reduced pressure, and the residue was purified by preparative TLC ($CH_2Cl_2$/MeOH=15:1) to give compound 4 (50 mg, 61%) as a white solid.

Procedure for Preparation of Compound 590

A mixture of compound 4 (50 mg, 0.11 mmol) and t-butyl hydroperoxide (305 mg of a 65% solution in water, 2.2 mmol) in $NH_4OH$/MeOH (2 mL/10 mL) was stirred overnight at room temperature, LCMS showed that the reaction was completed, which was concentrated under reduced pressure to dryness. Purification of this residue by preparative TLC ($CH_2Cl_2$/MeOH=10:1) and preparative HPLC to gave compound 590 (6.7 mg, 14%) as a white solid, LC-MS $t_R$=1.055 min in 2 min chromatography, MS (ESI) m/z 438.2 $[M+H]^+$; $^1H$ NMR ($CD_3OD$ 400 MHz): δ 7.11-7.13 (d, J=7.6 Hz, 1H), 7.03-7.05 (d, J=8.0 Hz, 1H), 6.76 (s, 1H), 4.07-4.14 (m, 1H), 3.26 (s, 3H), 2.97-3.05 (m, 1H), 2.87-2.93 (m, 2H), 2.70-2.77 (m, 2H), 2.24-2.36 (m, 2H), 1.91-1.97 (m, 1H), 1.75-1.85 (m, 2H), 1.42-1.48 (m, 1H), 1.25-1.35 (m, 7H), 1.15-1.21 (m, 3H); $^{19}F$ NMR ($CD_3OD$ 400 MHz 19F): δ -68.09

Example 426

Synthesis of Compound 551

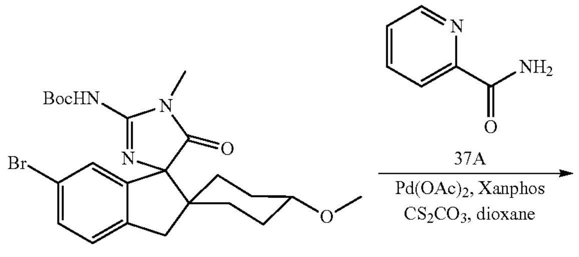

37

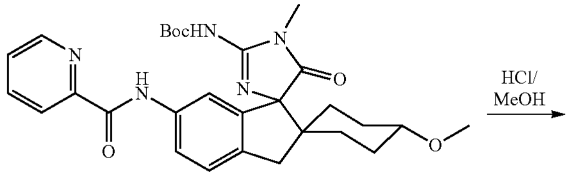

37A

-continued

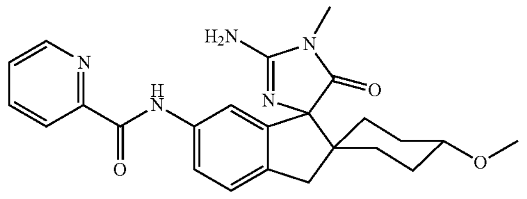

551

Procedure for Preparation of Compound 37A

To a solution of compound 37 (50 mg, 0.102 mmol) in t-BuOH (2 mL) was added compound 37A (19 mg, 0.152 mmol), $K_3PO_4$ (32 mg, 0.152 mmol), $Pd_2(dba)_3$ (5 mg) and 2-di-t-butylphosphino-3,4,5,6-tetramethyl-2',4',6'-tri-1-propylbiphenyl (5 mg,). The reaction mixture was heated at 80~100° C. under a nitrogen atmosphere for 16 h. The mixture was filtered and the filtrate was concentrated by evaporation in vacuo to give the residue, which was purified by preparative TLC (petroleum:EtOAc, 1:1) to afford compound 37A (40 mg, 74%) as a white solid.

Procedure for Preparation of Compound 551

A solution of compound 37A (50 mg, 0.093 mmol) in HCl/MeOH (10 mL, 5 M) was stirring at room temperature overnight. LCMS showed the reaction was completed and 3 N aqueous NaOH was added until pH=9. MeOH was removed and the aqueous phase was extracted with EtOAc (3x20 mL). the organic layer was washed with brine, dried over $Na_2SO_4$ and concentrated to give the residue, which was purified by acidic RP-HPLC to give compound VT_B111609_07 (10 mg, 25%) as a white solid, LC-MS $t_R$=0.900 min in 2 min chromatography, MS (ESI) m/z 434.1 $[M+H]^+$; $^1H$ NMR ($CD_3OD$ 400 MHz): δ 7.72 (s, 1H), 8.22 (d, J=8.0 Hz, 1H), 8.04 (t, J=7.6 Hz, 1H), 7.85 (s, 1H), 7.64 (m, 2H), 7.42 (d, J=8.0 Hz, 1H), 3.38 (s, 3H), 3.16-3.23 (m, 6H), 2.04-2.11 (m, 2H), 1.91 (m, 1H), 1.49-1.53 (m, 4H), 1.35-1.47 (m, 1H).

Example 427

Synthesis of Compound 541

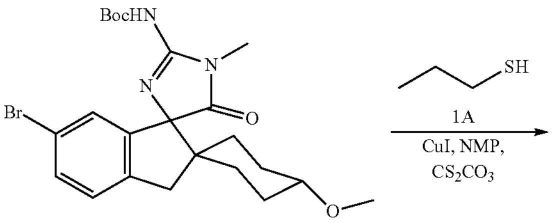

1

-continued

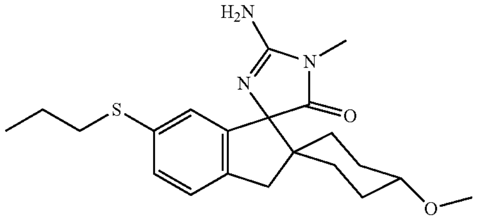

541

A mixture of compound 1 (50 mg, 0.1 mmol), compound 1A (7.6 mg, 0.1 mmol), CuI (19 mg, 0.1 mmol) and $Cs_2CO_3$ (66 mg, 0.2 mmol) in NMP (1 mL) was placed into CEM microwave reactor and irradiated at 195° C. for 1 h. After being cooled to room temperature, the mixture was partitioned between $H_2O$ (10 mL) and EtOAc (20 mL). The aqueous layer was extracted with EtOAc (3x20 mL). The combined organic layers were washed with brine (10 mL), dried over $Na_2SO_4$ and concentrated in vacuo to dryness. The residue was purified by RP-HPLC (acidic) to give the compound 541 (3.5 mg, 9%) as a white solid, LC-MS $t_R$=0.971 min in 2 min chromatography, MS (ESI) m/z 388.1 $[M+H]^+$; $^1H$-NMR ($CD_3OD$ 400 MHz): δ 7.31-7.38 (m, 2H), 7.22 (s, 1H), 3.33 (s, 3H), 3.13 (s, 3H), 3.07 (m, 1H), 2.98-3.03 (m, 2H), 2.88-2.94 (m, 2H), 2.02-2.09 (m, 2H), 1.84 (m, 1H), 1.61-1.67 (m, 2H), 1.30-1.45 (m, 5H), 1.01-1.04 (m, 3H)

Example 428

Synthesis of Compound 528

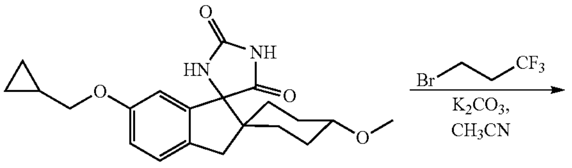

8

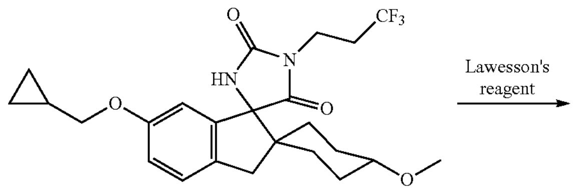

9

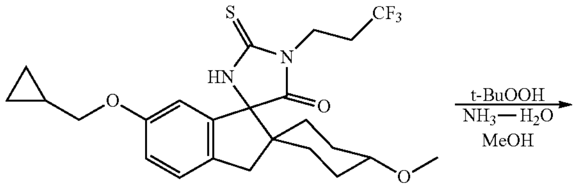

10

-continued

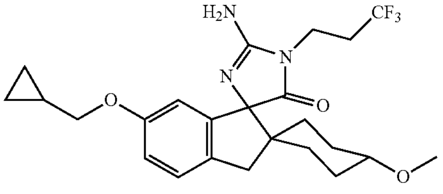

528

Procedure for Preparation of Compound 9

To a solution of compound 8 (100 mg, 0.27 mmol) in $CH_3CN$ (5 mL) was added $K_2CO_3$ (74 mg, 0.54 mmol). After addition, the resulting mixture was stirred at room temperature for 10 min. Then 3-bromo-1,1,1-trifluoro-propane (47.8 mg, 0.27 mmol) in $CH_3CN$ (5 mL) was added dropwise via a syringe with stirring. The mixture was stirred at 60° C. overnight, and then the mixture was filtered off, the filtrate was concentrated to give compound 9 (97 mg, 80%) as a white solid, which was used for the next step directly without purification. LC-MS $t_R$=1.392 min in 2 min chromatography, MS (ESI) m/z 467.2 $[M+H]^+$.

Procedure for Preparation of Compound 10

To a solution of compound 9 (90 mg, 0.19 mmol) in anhydrous toluene (10 mL) was added Lawesson's reagent (84 mg, 0.20 mmol) under a nitrogen atmosphere, the mixture was heated to reflux for 12 h. After cooling down, the solvent was removed by evaporation in vacuo and the resulting residue was purified by column chromatography on silica gel eluting with petroleum ether:EtOAc (3:1) to give compound 10 (65 mg, 70%) as a white solid. LC-MS $t_R$=1.503 min in 2 min chromatography, MS (ESI) m/z 483.1 $[M+H]^+$.

Procedure for Preparation of Compound 528

To a solution of compound 10 (65 mg, 0.135 mmol) in MeOH (10 mL) was added $NH_3$—$H_2O$ (3 mL) and tert-butyl hydroperoxide (1 mL). After addition, the mixture was stirred at room temperature for 24 h. The solvent was removed by evaporation in vacuo. The residue was partitioned between EtOAc (contained 10% methanol) (50 mL) and $H_2O$ (20 mL). The organic layer was separated and washed with brine (20 mL), dried over $Na_2SO_4$, filtered and concentrated in vacuo. The residue was purified by basic RP-HPLC to give compound 528 (28.10 mg, 44%) as a white solid. LC-MS: $t_R$=1.150 min in 2 min chromatography, MS (ESI) m/z 466.2 $[M+H]^+$; $^1H$ NMR ($CD_3OD$ 400 MHz): δ 7.19 (d, J=8.0 Hz, 1H), 6.84 (d, J=8.0 Hz, 1H), 6.52 (s, 1H), 3.80-3.86 (t, J=9.6 Hz, 2H), 3.75-3.76 (d, J=6.8 Hz, 2H), 3.35 (s, 3H), 3.06-3.17 (m, 1H), 2.96-3.06 (m, 2H), 2.49-2.60 (m, 2H), 1.95-2.10 (m, 2H), 1.85-1.95 (m, 1H), 1.53-1.60 (m, 1H), 1.30-1.53 (m, 2H), 1.10-1.35 (m, 3H), 0.5-0.7 (m, 2H), 0.2-0.4 (m, 2H); $^{19}F$ NMR ($CD_3OD$ 400 MHz): δ −66.67.

Example 429

Synthesis of Compound 572

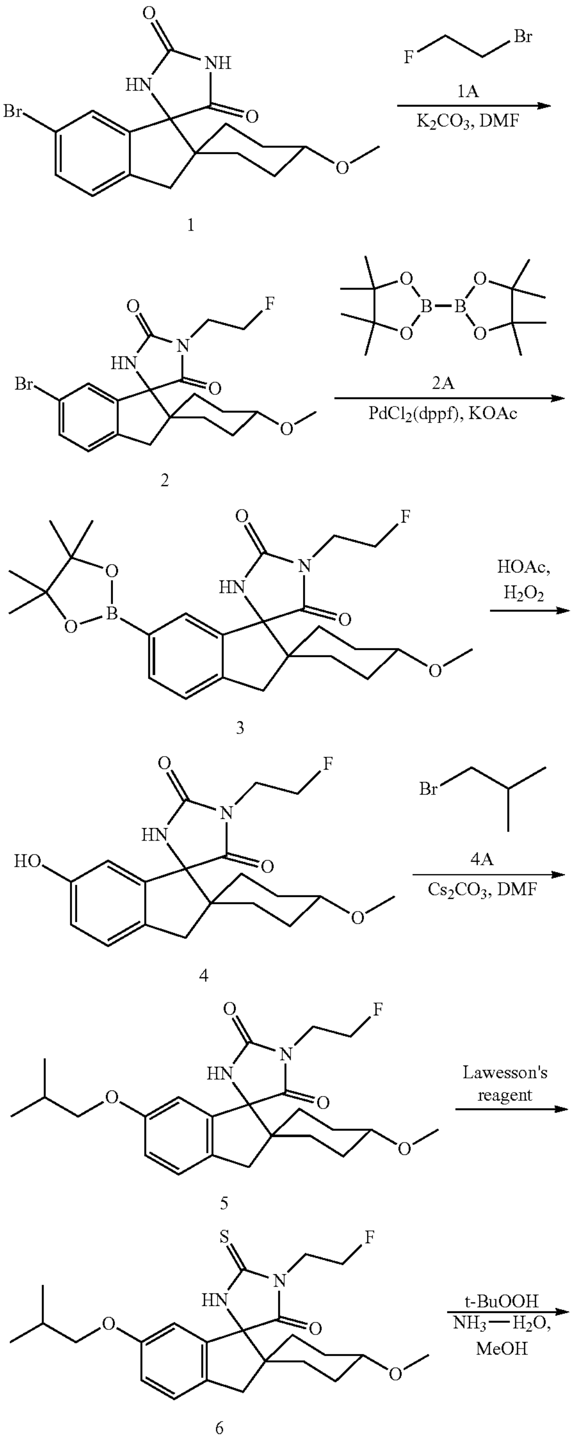

-continued

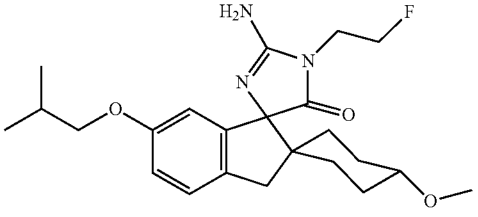

572

Procedure for Preparation of Compound 2

To a solution of compound 1 (300 mg, 0.79 mmol) in DMF (5 mL) was added $K_2CO_3$ (328 mg, 2.37 mmol). After addition, the resulting mixture was stirred at room temperature for 10 min. Then compound 1A (96 mg, 0.79 mmol) in DMF (2 mL) was added dropwise via a syringe with stirring. The mixture was stirred at 40° C. for 1 h. The reaction mixture was partitioned between $H_2O$ (50 mL) and ethyl acetate (50 mL). The separated organic phase was washed with brine (3×20 mL), dried over $Na_2SO_4$ and concentrated in vacuo to give crude compound 2 (335 mg, 100%) as a white solid, which was used for the next step directly without purification. LC-MS $t_R$=1.094 min in 2 min chromatography, MS (ESI) m/z=425.0 $[M+H]^+$.

Procedure for Preparation of Compound 3

To a solution of compound 2 (340 mg, 0.8 mmol) in 1,4-dioxane (20 mL) was added compound 2A (243 mg, 0.96 mmol), $PdCl_2$(dppf) (100 mg), and KOAc (235 mg, 2.4 mmol). The mixture was refluxed for 4 h under nitrogen. After cooling down, the mixture was filtered and the filtrate was concentrated to give compound 3 (370 mg, crude), which was used for the next step directly without purification. LC-MS $t_R$=1.182 min in 2 min chromatography, MS (ESI) m/z=473.2 $[M+H]^+$.

Procedure for Preparation of Compound 4

To a solution of compound 3 (370 mg, 0.8 mmol) in THF (8 mL) was added HOAc (3 mL) and $H_2O_2$ (5 mL), the mixture was stirred at room temperature overnight. Then quenched with aqueous $NaHSO_3$ (10 mL), extracted with EtOAc (3×20 mL). The combined organic layers were dried over $Na_2SO_4$, filtered and concentrated to give the residue, which was purified by preparative TLC (petroleum ether:EtOAc=1:1) to give compound 4 (200 mg, 70%) as a white solid. LC-MS $t_R$=0.924 min in 2 min chromatography, MS (ESI) m/z=363.1 $[M+H]^+$.

Procedure for Preparation of Compound 5

To a solution of compound 4 (95 mg, 0.26 mmol) in DMF (5 mL) was added compound 4A (40 mg, 0.26 mmol) and $Cs_2CO_3$ (325 mg, 1.0 mmol), the mixture was stirred at 40° C. for 4 h. Then quenched with $H_2O$ (10 mL), extracted with EtOAc (3×15 mL), the combined organic layer was dried over $Na_2SO_4$, filtered and concentrated to give the residue, which was purified by preparative TLC (petroleum ether:EtOAc=3:1) to give compound 5 (100 mg, 91%) as a white solid. LC-MS $t_R$=1.163 min in 2 min chromatography, MS (ESI) m/z=419.2 $[M+H]^+$.

Procedure for Preparation of Compound 6

A 8 mL vial was charged with compound 5 (130 mg, 0.316 mmol) and Lawesson's reagent (138 mg, 0.342 mmol). Toluene (2 mL) was added, and the vial was sealed and placed into CEM microwave reactor and irradiated at 140° C. for 1 h. After cooling down, the solvent was removed by evaporation in vacuo and the resulting residue was purified by column chromatography over silica gel (petroleum ether:EtOAc, 50:1 to 10:1) to give compound 6 (35 mg, 25%) as a whit solid. LC-MS $t_R$=1.244 min in 2 min chromatography, MS (ESI) m/z=435.2 $[M+H]^+$.

Procedure for Preparation of Compound 572

To a solution of compound 6 (35 mg, 0.080 mmol) in MeOH (10 mL) was added $NH_3$—$H_2O$ (3 mL) and tert-butyl hydroperoxide (117 mg, 0.8 mmol). After addition, the mixture was stirred at room temperature for 24 h. The solvent was removed by evaporation. The residue was purified by preparative HPLC to give compound 572 (4.8 mg, 14%) as a white solid. LC-MS $t_R$=1.011 min in 2 min chromatography, MS (ESI) m/z=418.2 $[M+H]^+$; $^1H$ NMR: ($CD_3OD$ 400 MHz): δ 7.14-7.16 (d, J=8.4 Hz, 1H), 6.81-6.84 (d, J=8.4 Hz, 1H), 6.64 (s, 1H), 4.43-4.57 (m, 2H), 3.89-4.03 (m, 2H), 3.59-3.61 (d, J=6.4 Hz, 1H), 3.25 (s, 1H), 2.91-3.09 (m, 3H), 1.76-1.97 (m, 4H), 1.22-1.41 (m, 5H), 1.18-1.21 (m, 6H); $^{19}F$ NMR ($CD_3OD$ 19F 400 MHz): δ −75.932

Example 430

Synthesis of Compound 526

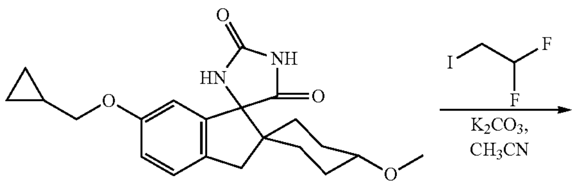

9

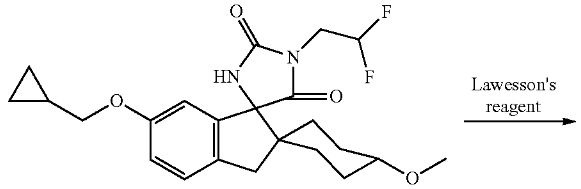

10

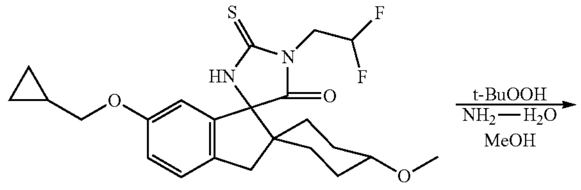

11

-continued

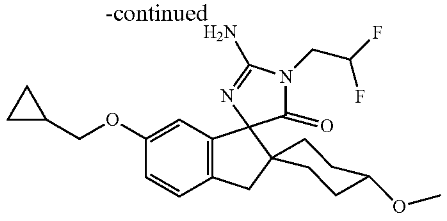

526

Procedure for Preparation of Compound 10

To a solution of compound 9 (100 mg, 0.27 mmol) in $CH_3CN$ (5 mL) was added $K_2CO_3$ (74 mg, 0.54 mmol). After addition, the resulting mixture was stirred at room temperature for 10 min. Then 1,1-difluoro-2-iodo-ethane (51.8 mg, 0.27 mmol) in $CH_3CN$ (5 mL) was added dropwise via a syringe with stirring. The mixture was stirred at 60° C. overnight. Then the mixture was filtered off, the filtrate was concentrated to give compound 10 (90 mg, 77%) as a white solid, which was used for the next step directly without purification. LC-MS $t_R$=1.337 min in 2 min chromatography, MS (ESI) m/z 435.2 $[M+H]^+$.

Procedure for Preparation of Compound 11

To a solution of compound 10 (90 mg, 0.20 mmol) in anhydrous toluene (10 mL) was added Lawesson's reagent (92 mg, 0.22 mmol) under a nitrogen atmosphere, the mixture was heated at reflux for 12 h. After cooling down, the solvent was removed by evaporation in vacuo and the resulting residue was purified by column chromatography over silica gel petroleum ether:EtOAc=3:1 to give compound 11 (65 mg, 70%) as a white solid. LC-MS $t_R$=1.439 min in 2 min chromatography, MS (ESI) m/z 451.1 $[M+H]^+$.

Procedure for Preparation of Compound 526

To a solution of compound 11 (65 mg, 0.14 mmol) in MeOH (10 mL) was added $NH_3$—$H_2O$ (3 mL) and tert-butyl hydroperoxide (1 mL). After addition, the mixture was stirred at room temperature for 24 h. The solvent was removed by evaporation in vacuo. The residue was partitioned between EtOAc (contained 10% methanol) (20 mL) and $H_2O$ (10 mL). The organic layer was separated and washed with brine (20 mL), dried over $Na_2SO_4$, filtered and concentrated in vacuo. The residue was purified by basic preparative HPLC to give compound 526 (25.20 mg, 40%) as a white solid. LC-MS: $t_R$=1.109 min in 2 min chromatography, MS (ESI) m/z 434.2 $[M+H]^+$; $^1H$ NMR ($CD_3OD$ 400 MHz): δ 7.19 (d, J=8.4 Hz, 1H), 6.84 (d, J=8.4 Hz, 1H), 6.54 (s, 1H), 5.92-6.22 (t, J=55.6 Hz, 1H), 3.92-4.04 (d, J=12.4 Hz, 2H), 3.75-3.77 (d, J=6.8 Hz, 2H), 3.35 (s, 3H), 3.05-3.17 (m, 1H), 2.96-3.01 (m, 2H), 1.95-2.10 (m, 2H), 1.81-1.95 (m, 1H), 1.56-1.63 (m, 1H), 1.30-1.56 (m, 2H), 1.17-1.30 (m, 3H), 0.5-0.7 (m, 2H), 0.2-0.4 (m, 2H); $^{19}F$ NMR ($CD_3OD$ 400 MHz): δ −124.36

Example 431

Synthesis of Compound 525

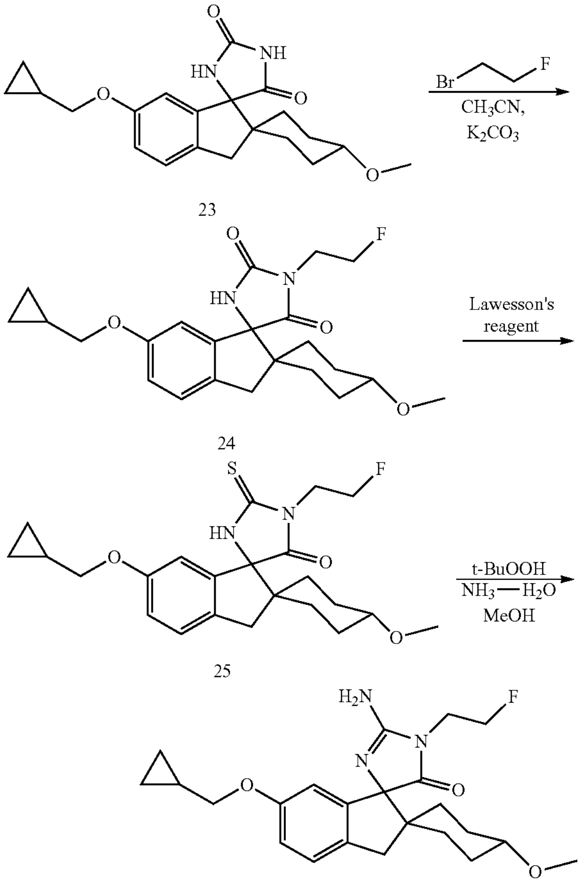

23

24

25

525

Procedure for Preparation of Compound 24

To a solution of compound 23 (100 mg, 0.27 mmol) in $CH_3CN$ (5 mL) was added $K_2CO_3$ (74 mg, 0.54 mmol). After addition, the resulting mixture was stirred at room temperature for 10 min. Then 1-bromo-2-fluoro-ethane (41 mg, 0.27 mmol) in $CH_3CN$ (5 mL) was added dropwise via a syringe with stirring. The mixture was stirred at 60° C. overnight. Then the mixture was filtered off, the filtrate was concentrated to give compound 24 (87 mg, 77%) as a white solid which was used for the next step directly without purification. LC-MS $t_R$=1.303 min in 2 min chromatography, MS (ESI) m/z 417.2 $[M+H]^+$.

Procedure for Preparation of Compound 25

To a solution of compound 24 (87 mg, 0.209 mmol) in anhydrous toluene (10 mL) was added lawsson's reagent (93 mg, 0.23 mmol) under a nitrogen atmosphere, the mixture was heated at reflux for 12 h. After cooling down, the solvent was removed by evaporation in vacuo and the resulting residue was purified by column chromatography on silica gel eluting with petroleum ether:EtOAc (3:1) to give compound 25 (63 mg, 70%) as a white solid. LC-MS $t_R$=1.406 min in 2 min chromatography, MS (ESI) m/z 433.2 $[M+H]^+$.

Procedure for Preparation of Compound 525

To a solution of compound 25 (63 mg, 0.145 mmol) in MeOH (10 mL) was added $NH_3$—$H_2O$ (3 mL) and tert-butyl hydroperoxide (1 mL). After addition, the mixture was stirred at room temperature for 24 h. The solvent was removed by evaporation in vacuo. The residue was partitioned between EtOAc (contained 10% methanol) (20 mL) and $H_2O$ (10 mL). The organic layer was separated and washed with brine (30 mL), dried over $Na_2SO_4$, filtered and concentrated in vacuo. The residue was purified by basic RP-HPLC to give compound 525 (39.60 mg, 65%) as a white solid. LC-MS: $t_R$=1.083 min in 2 min chromatography, MS (ESI) m/z 416.2 $[M+H]^+$; $^1H$ NMR ($CD_3OD$ 400 MHz): δ 7.19 (d, J=8.4 Hz, 1H), 6.83 (d, J=8.0 Hz, 1H), 6.53 (s, 1H), 4.59-4.70 (m, 1H), 4.49-4.59 (m, 1H), 3.82-3.95 (m, 2H), 3.75 (d, J=6.8 Hz, 2H), 3.35 (s, 3H), 3.05-3.17 (m, 1H), 2.90-3.05 (m, 2H), 1.95-2.03 (m, 2H), 1.82-1.92 (m, 1H), 1.52-1.64 (m, 1H), 1.30-1.52 (m, 2H), 1.10-1.30 (m, 3H), 0.50-0.70 (m, 2H), 0.20-0.40 (m, 2H); $^{19}F$ NMR ($CD_3OD$ 400 MHz): δ −76.90.

Example 432

Synthesis of Compound 535

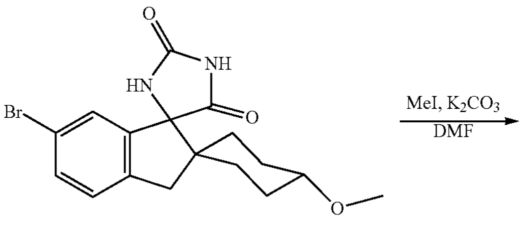

1

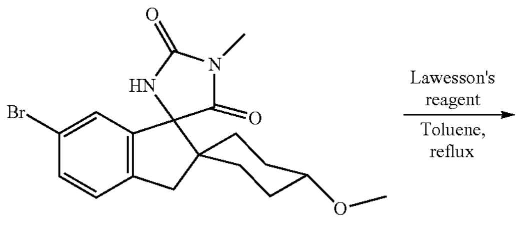

2

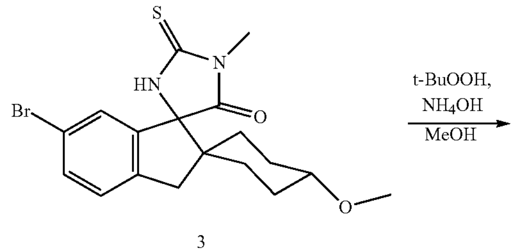

3

-continued

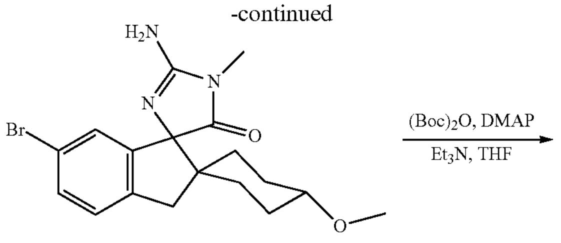

4

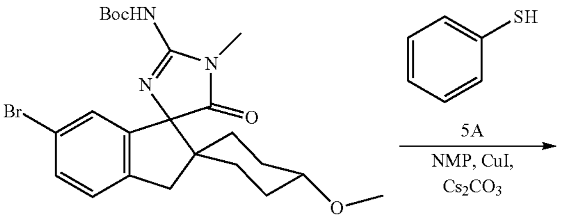

5

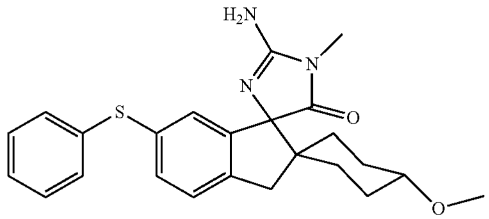

535

Procedure for Preparation of Compound 2

To a solution of compound 1 (6.0 g, 15.9 mmol, crude) in DMF (80 mL) was added $K_2CO_3$ (3.3 g, 23.8 mmol). After addition, the resulting mixture was stirred at room temperature for 10 min. Then iodomethane (2.1 g, 15.9 mmol) in DMF (2 mL) was added dropwise via a syringe with stirring. The mixture was stirred at room temperature overnight. The reaction mixture was partitioned between $H_2O$ (200 mL) and ethyl acetate (600 mL). The separated organic phase was washed with saturated brine (3×50 mL), dried over $Na_2SO_4$ and concentrated in vacuo to give crude compound 5 (6.13 g, 90%) as a white solid, which was used for the next step directly without purification.

Procedure for Preparation of Compound 3

To a solution of compound 2 (4.0 g, 10.2 mmol) in toluene (100 mL) was added Lawesson's reagent (4.53 g, 11.2 mmol). The resulting mixture was heated at reflux overnight. After cooling down, the solvent was removed by evaporation in vacuo and the resulting residue was purified by column chromatography over silica gel (petroleum ether:EtOAc=10:1) to give compound 3 (4.7 g, 68%) as a whit solid.

Procedure for Preparation of Compound 4

To a solution of compound 3 (4.7 g, 11.5 mmol) in MeOH (450 mL) was added $NH_3$—$H_2O$ (90 mL) and tert-butyl hydroperoxide (31.9 g, 230.4 mmol). After addition, the mixture was stirred at 40° C. for 24 h. The solvent was removed by evaporation in vacuo. The residue was partitioned between EtOAc (contained 10% methanol) (600 mL) and $H_2O$ (100 mL). The organic layer was separated and washed with brine (50 mL), dried over $Na_2SO_4$, filtered and concentrated in vacuo to give crude compound 4 (3.8 g, 60% purity, 72%) as a white solid, which was used for the next step directly without purification.

Procedure for Preparation of Compound 5

To a solution of compound 4 (3.8 g, 60% purity, 9.7 mmol) in THF (40 mL) was added $Boc_2O$ (8.5 g, 38.9 mmol), DMAP (2.4 g, 19.4 mmol) and $Et_3N$ (2 mL, 19.4 mmol). After addition, the mixture was stirred at 40° C. for 24 h. The solvent was removed by evaporation in vacuo. The resulting residue was purified by column chromatography over silica gel (petroleum ether:EtOAc=10:1) to give compound 5 (1.7 g, 61%) as a whit solid.

Procedure for Preparation of Compound 535

A mixture of compound 5 (50 mg, 0.1 mmol), compound 5A (11.2 mg, 0.1 mmol), CuI (19 mg, 0.1 mmol), and $Cs_2CO_3$ (66 mg, 0.2 mmol) in NMP (1 mL) was placed into CEM microwave reactor and irradiated at 195° C. for 1 h under nitrogen atmosphere. After being cooled to room temperature, the mixture was added brine (20 mL) and extracted with EtOAc (3x30 mL). The combined organic layers were dried over $Na_2SO_4$ and concentrated in vacuo to dryness. The residue was purified by RP-HPLC to give compound compound 535 (15 mg, 36%) as a white solid. LC-MS: $t_R$=0.987 min in 2 min chromatography, MS (ESI) m/z 422.0 $[M+H]^+$; $^1H$ NMR ($CD_3OD$ 400 MHz): δ 7.26-7.38 (m, 8H), 3.36 (s, 3H), 3.10-3.21 (m, 6H), 2.02-2.09 (m, 2H), 1.84-1.87 (m, 1H), 1.30-1.45 (m, 5H).

Example 433

Synthesis of Compound 554

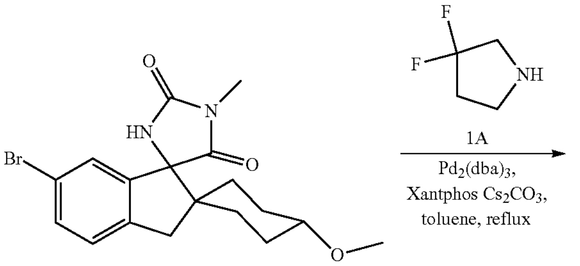

1

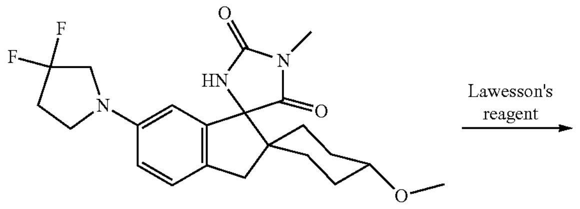

2

-continued

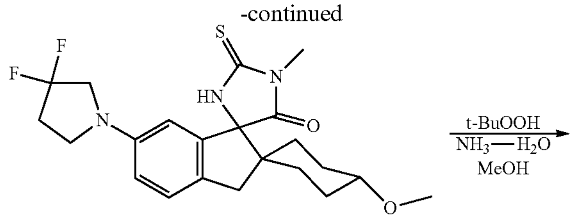

3

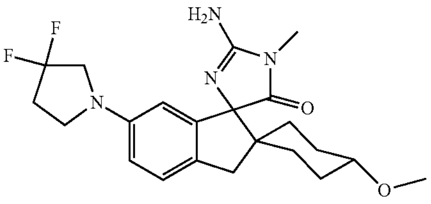

554

Procedure for Preparation of Compound 2

To a solution of compound 1 (150 mg, 0.38 mmol) in toluene (5 mL) was added compound 1A (82 mg, 0.57 mmol), $Cs_2CO_3$ (371 mg, 1.14 mmol), $Pd_2(dba)_3$ (7.5 mg), and Xantphos (30 mg) under a nitrogen atmosphere. The reaction mixture was refluxed overnight, then quenched with $H_2O$ (10 mL), the reaction was extracted with EtOAc (3x20 mL), the combined organic layer was washed with brine (30 mL), dried over anhydrous $Na_2SO_4$ and concentrated to give the residue, which was purified by preparative TLC (petroleum ether: EtOAc=1:1) to afford compound 2 (108 mg, 68%) as a white solid.

Procedure for Preparation of Compound 3

An 8 mL vial was charged with compound 2 (116 mg, 0.27 mmol) and Lawesson's reagent (112 mg, 0.27 mmol). Toluene (5 mL) was added, and the vial was refluxed overnight. After cooling down, the solvent was removed by evaporation in vacuo and the resulting residue was purified by preparative TLC (petroleum ether:EtOAc=1:1) to give compound 3 (70 mg, 58%) as a whit solid.

Procedure for Preparation of Compound 554

To a solution of compound 3 (100 mg, 0.23 mmol) in MeOH (5 mL) was added $NH_3$—$H_2O$ (1 mL) and tert-butyl hydroperoxide (219 mg, 4.6 mmol). After addition, the mixture was stirred at room temperature for 24 h. The solvent was removed by evaporation in vacuo. The residue was partitioned between EtOAc (contained 10% methanol) (10 mL) and $H_2O$ (10 mL). The organic layer was separated and washed with brine (10 mL), dried over $Na_2SO_4$, filtered and concentrated in vacuo. The residue was purified by preparative HPLC to give compound 554 (6.6 mg, 7%) as a white solid. LC-MS $t_R$=0.915 min in 2 min chromatography, MS (ESI) m/z=419 $[M+H]^+$; $^1H$ NMR ($CD_3OD$ 400 MHz): δ 7.23 (d, J=8.0 Hz, 1H), 6.84 (dd, J=4.0, 2.4 Hz, 1H), 6.46 (s, 1H), 3.67 (m, 2H), 3.52 (m, 2H), 3.48 (m, 2H), 3.21 (s, 3H), 3.09 (m, 1H), 3.04 (m, 2H), 2.50 (m, 2H), 2.05 (m, 2H), 1.83 (m, 1H), 1.49-1.29 (m, 5H); $^{19}F$ NMR (19F $CD_3OD$): δ −96.71.

Example 434

Biological Data

A. BACE Enzyme Assay

Inhibitory activity of compounds was assessed by a fluorescence quench assay of BACE activity using commercially available substrate HiLyte Fluor™488-Glu-Val-Asn-Leu-Asp-Ala-Glu-Phe-Lys-(QXLT™ 520)-OH (AnaSpec, San Jose, Calif.) and truncated human beta-secretase (residues 1-458, $His_6$-tagged at the C-terminus) expressed in insect cells *D. melanogaster* S2 using a baculovirus expression system (Mallender et al., Characterization of recombinant, soluble beta-secretase from an insect cell expression system., Mol Pharmacol 59:619-26, 2001). The assay was performed at room temperature in 96-well white opaque Optiplates aque Optiplates (PerkinElmer, Waltham, Mass.) in a total volume of 200 μl of the incubation mixture containing 50 mM sodium acetate buffer, pH 4.5, 0.4 μM FRET substrate, 2.4 nM enzyme, 5% DMSO, and 0.05% Brij-35. The tested compounds were serially diluted in DMSO and pre-incubated with the substrate. The reaction was started by addition of enzyme, and the progress of the reaction was followed by measuring fluorescence with an excitation wavelength of 480 nm and an emission wavelength of 520 nm. Ten measurements were taken every 5-10 min, and the intensity of fluorescence was regressed against time in order to derive velocities of reaction in all 96 wells. These velocities were used for calculating percent inhibition using an uninhibited control containing 5% DMSO and a fully inhibited control incubations performed in the absence of enzyme. $IC_{50}$ values were calculated by fitting percent inhibition vs inhibitor concentration into a four-parametric logistic model using XLFit software (IDBS, Guildford, UK).

B. BACE Cell Assay

H4 neuroglioma cell line that stably expresses Amyloid Precursor Protein (APP) containing the KM-NL Swedish mutation (H4-APPsw) was generated. For the assay, cells are treated overnight in the presence of inhibitor and the culture media are subjected to ELISA analysis of soluble Amyloid Beta 1-40 (Aβ 1-40).

Materials

H4 neuroglioma cell line: ATCC, Cat #HTB-148

Dulbecco's Minimal Essential Medium (DMEM): Invitrogen, Cat #11995

Fetal bovine serum (FBS): Hyclone, Cat #SH30070.03)

Penicillin/streptomycin: Invitrogen, Cat#15140-122

Zeocin: Invitrogen, Cat #R25001

0.5% Trypsin/EDTA: Invitrogen, Cat #25300

96-well plate for compound serial dilution in DMSO 96-well deep well plate 96-well Black Polymer BTM P-D-L plate: Nunc, Cat #152037

96-well White polystyrene ½ area optiplate: Corning, Cat #3642

DMSO: Sigma, Cat #494429

Aβ 1-40 ELISA kit: Covance, Cat #sig38940

CellTiter Glo Viability Assay: Promega, Cat #G7571

Aβ 1-40 AlphaLISA kit: PerkinElmer, Cat #AL202F

Microscope

Wallac Victor$^2$ Multilabel HTS counter

PerkinElmer Fusion-Alpha FP-HT Multiplate reader

SpectraMax 384 plus plate reader

Generation and Maintenance of H4-APPsw Cell Line

H4 neuroglioma cell line was cultured in DMEM with 10% FBS and 1% penicillin/streptomycin (Culture Medium) at 37° C., 5% $CO_2$. The culture plate (150 mm) with 50% confluence of H4 cells was transfected with 15 ug plasmid pcDNA3.1/Neo(+) containing a 2310-bp insert of APPsw at Hind3/XbaI sites. 24 hrs after transfection, the cells were replaced into three new plates (150 mm) in fresh Culture Medium with 250 ug/mL Zeocin. The stably transfected cell colonies were isolated in about 2-3 weeks. The levels of APPsw expression were analyzed by immunoblotting and the production of Aβ 1-40 was detected by ELISA of culture supernatants. The selected clones are maintained in Culture Medium with 250 μg/mL Zeocin and routinely split in 3-4 days to maintain 20-80% confluence.

Assay Protocol

Final Assay Conditions (96-Well Plate)

| | |
|---|---|
| H4-APPsw cells | 6 × $10^3$cells/well |
| DMEM | 200 μL |
| DMSO | 0.2% |

Day 1

Split Cells.

Split H4-APPsw cells in Culture Medium and culture overnight such that cells will be ~80% confluent next morning.

Day 2

Create Compound Dilution Plate.

After determining the desired final concentration of compound to be tested, create a 500× dilution plate. Add DMSO, but not inhibitor, to each well of Column 1. Use Column 2 for Control Compound (BACE inhibitor IV, EMD Bioscience, Cat #565788) serial dilution starting at 5 mM (final concentration of 2.5 μM). Add compounds of interest at 500× desired final concentration to wells A3-A10. Add DMSO, but not inhibitor, to each well of Columns 11 and 12. Dilute contents of Row A 1:3 in Row B, then continue through Rows C-H.

Create Media Plate.

To create a 2× solution of compound in media, add 996 μL Culture Medium to each well of a 96-well 2 mL deep well plate (Media Plate) in biosafety hood. Add 4 μL 5 mM control compound to Media Plate wells A1-D1 for determination of full inhibition. Add 4 μL from Compound Dilution Plate to corresponding wells of Medium Plate (do not add additional DMSO to wells A1-D1).

Add Media to Cell Plate.

With a multichannel pipettor, mix each well of Media Plate several times to insure homogeneity. Add 1004 of mixture to Black polymer bottom β-D-L plates. Next, place Medium Plate and Cell Plate in the incubator.

Add cells to Cell Plate.

Trypsinize and count H4-APPsw cells. Dilute cells 6×$10^5$ cells/mL in Culture Medium and remove Cell Plate from incubator. Vortex cells to homogeneity, then using a multichannel repeating pipettor, add 100 μL cell suspension to Cell Plate, adding cells from Row H to Row A. Place Cell Plate in incubator.

Change Media in Cell Plate.

After 5 h, check Cell Plate by microscope to insure cells are attached. In culture hood, remove media from Cell Plate using multichannel repeating pipettor. Add 100 μl Culture Medium to each well. Remove Media Plate from incubator and mix with pipettor as previous. Add 100 μl from each well of Media Plate to corresponding well in Cell Plate. Place Cell Plate in incubator overnight.

Day 3

Perform ELISA to Determine Levels of Secreted Aβ 1-40.

After 16 h incubation, spin Cell Plate for 8 min at 1200 rpm. The primary reading of Aβ 1-40 levels is done using PerkinElmer AlphaLISA technology. Follow the manufacturer's protocol for performing AlphaLISA in a white ½ area Optiwell plate using Row 12 for peptide standard (1:2 dilutions, starting at 15 ng/ml). Data are acquired using PerkinElmer Fusion-Alpha FP-HT, Alpha protocol (Count Time 0.6s, Count Time Ratio 30%:70%). To validate IC50 determinations, a second Aβ 1-40 ELISA was performed using a kit from Covance that uses different antibodies to Aβ 1-40 and a different detection method (absorbance at 490 nM) than the PerkinElmer kit.

Perform Viability Assay to Determine Compound Toxicity.

Remove remaining media from Cell Plate and add 100 μL CellTiter Glo reagent to cells. Incubate 9 min at room temperature and read luminescence counts on Wallac Victor$^2$ Multilabel HTS counter.

Data Reduction

Export data from Fusion using Columnar Report format into a separate file for each plate. Upload data into Activity Base using RIA-DOSE-RESPONSE protocol (Version 1). Data from at least eight doses were fitted to a four parameter logistical model using XLfit software to determine potency.

Results

The in vitro cell activity studies were carried out for compounds of the invention and the data is shown below:

| COMPOUND NO. | $IC_{50}$ |
|---|---|
| 1-4 | ***** |
| 5-7 | **** |
| 8 | ***** |
| 9 | **** |
| 10 | ** |
| 11-12 | ***** |
| 13 | **** |
| 14 | ***** |
| 15 | ** |
| 16 | ***** |
| 17 | *** |
| 18 | ***** |
| 19-20 | **** |
| 21-23 | ** |
| 25 | ***** |
| 26 | ** |
| 27 | * |
| 28-29 | **** |
| 30-31 | ** |
| 34-35 | *** |
| 36 | * |
| 38 | # |
| 39 | * |
| 40-41 | ** |
| 42 | ***** |
| 43-45 | ** |
| 46-47 | * |
| 49-50 | *** |
| 52 | ** |
| 53 | # |
| 54 | ** |

-continued

| COMPOUND NO. | $IC_{50}$ |
|---|---|
| 56-57 | ** |
| 58 | ***** |
| 59 | **** |

# represents $IC_{50}$ less than 50 μM;
* represents $IC_{50}$ less than 10 μM;
** represents $IC_{50}$ less than 5 μM;
*** represents $IC_{50}$ less than 1 μM;
**** represents $IC_{50}$ less than 500 nM;
***** represents $IC_{50}$ less than 100 nM.

Example 435

BACE Assay

For each compound being tested, the BACE activity was monitored in a fluorescence quenching assay (FRET) using the ectodomain of BACE (aa 1-454) fused to a myc-his tag and secreted from HEK293/$BACE_{ect}$. cells into OptiMEM™ (Invitrogen) as enzyme source and a substrate peptide derived from the APP-Swedish mutation which possesses a Cy3-fluorophore at the N-terminus and a Cy5Q-quencher at the C-terminus (Cy3-SEVNLDAEFK-Cy5Q-NH2; Amersham). The substrate was dissolved at 1 mg/mL in DMSO.

The assay was performed in the presence of 5 μl OptiMEM (supernatant collected over 24 hours and cleared from cellular debris by centrifugation) containing the ectodomain of BACE, 25 μl water containing the desired concentration of test compound and 1% DMSO, substrate peptide, 20 mM NaOAc, pH 4.4 and 0.04% Triton-X100 in a total assay volume of 50 μl in a 384 well plate. In general, 25 μl of compound dilution were given to the plate followed by the addition of 10 μl of BACE containing OptiMEM™ diluted 1:2 in water with 0.2% Triton X-100. The reaction was started with the addition of 15 μl substrate in NaOAc buffer. The reaction was incubated at 30° C. in a fluorimeter and the cleavage of the substrate was recorded as kinetic for 60 min. at ex: 530 nm, em: 590 nm. Blank wells containing either no inhibitor or no enzyme were included on each plate.

The intensity of fluorescence was regressed against time in order to derive velocities of reaction in all 384 wells. These velocities were used for calculating percent inhibition using an uninhibited control containing 1% DMSO and a fully inhibited control incubations performed in the absence of enzyme. $IC_{50}$ values were calculated by fitting percent inhibition vs inhibitor concentration using standard software like GraphPadPrism.

Using this assay protocol, compound dilutions were either done using a Tecan Freedom EV0 (assay format A) or manually using multichannel pipettes (assay format B).

The BACE inhibitor activities of compounds of the invention were tested according to protocols described in Example 434A or Example 435, and are shown below:

| Compound No. | Structure/Ex. No. | $IC_{50}$ (nM) |
|---|---|---|
| 1 | 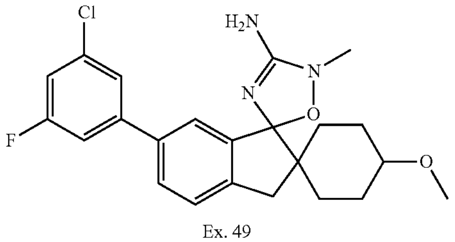 [SMILES: COC1CCC2(CC1)Cc1ccc(-c3cc(F)cc(Cl)c3)cc1C21N=C(N)N(C)O1] Ex. 49 | 2.6[a] |

-continued
| Compound No. | Structure/Ex. No. | $IC_{50}$ (nM) |
|---|---|---|
| 2 | 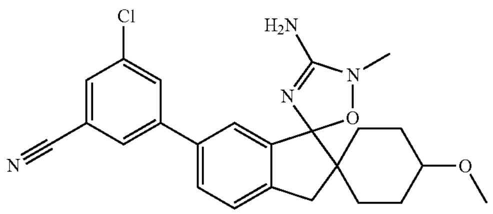 Ex. 50 | 3.5[a] |
| 3 | 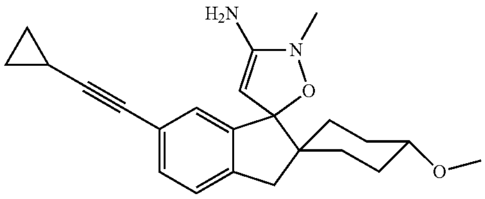 Ex. 54 | 4.5[a] |
| 4 | 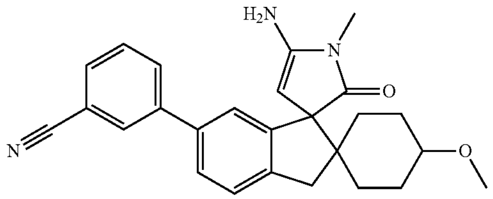 Ex. 27 | 4.0[a] |
| 5 | 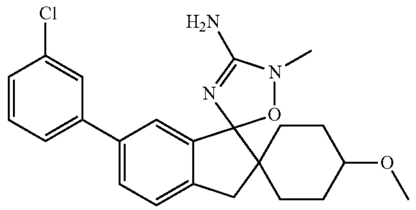 Ex. 33 | 4.5[a] |
| 6 | 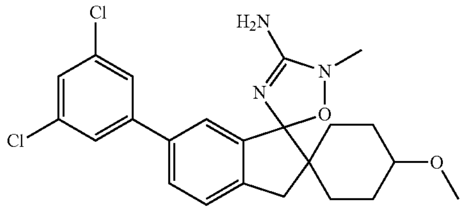 Ex. 35 | 4.8[a] |
| 7 | 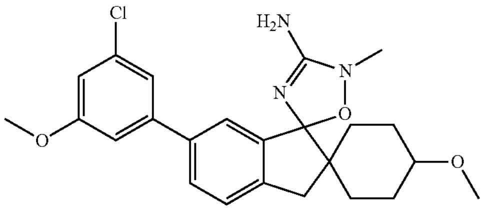 Ex. 51 | 5.9[a] |

-continued
| Compound No. | Structure/Ex. No. | $IC_{50}$ (nM) |
|---|---|---|
| 8 | 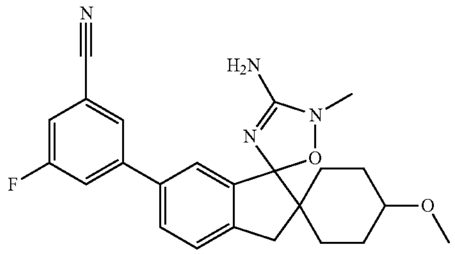 Ex. 38 | 5.9[a] |
| 9 | 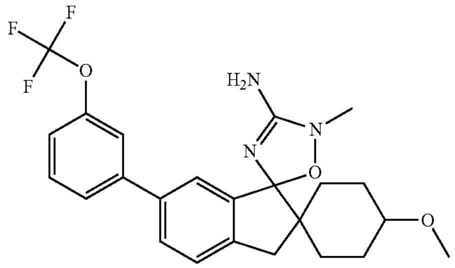 Ex. 37 | 7.0[a] |
| 10 | 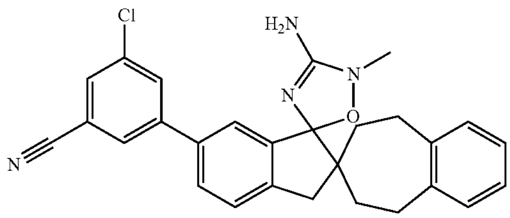 Ex. 47 | 7.4[a] |
| 11 | 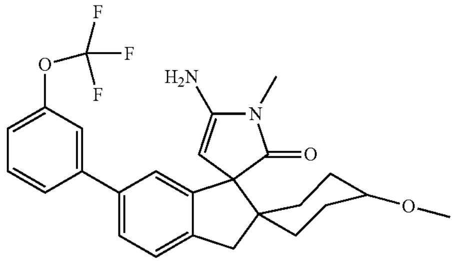 Ex. 29 | 7.8[a] |
| 12 | 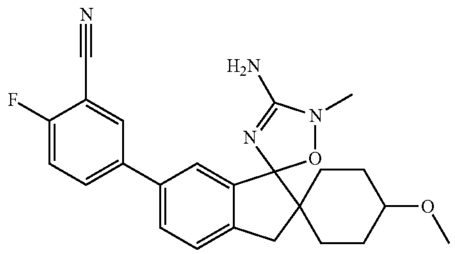 Ex. 39 | 7.9[a] |

-continued
| Compound No. | Structure/Ex. No. | $IC_{50}$ (nM) |
|---|---|---|
| 13 | 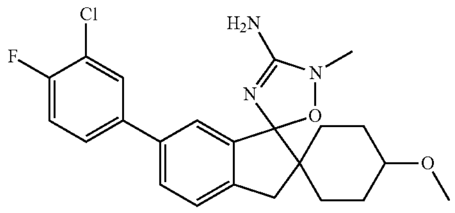 Ex. 32 | 8.8[a] |
| 14 | 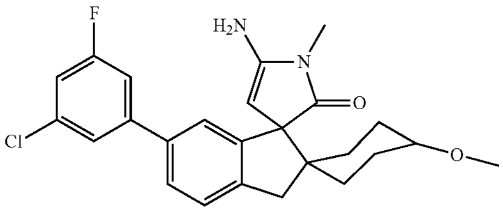 Ex. 30 | 11.1[a] |
| 15 | 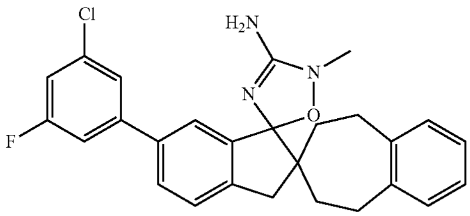 Ex. 45 | 11.2[a] |
| 16 | 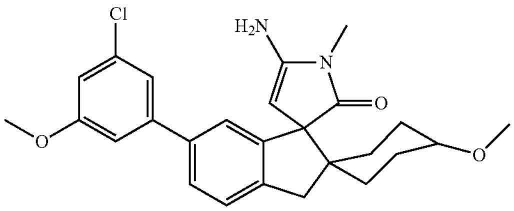 Ex. 55 | 11.5[a] |
| 17 | 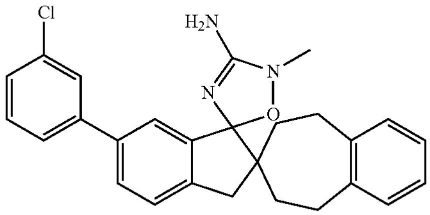 Ex. 43 | 12.1[a] |
| 18 | 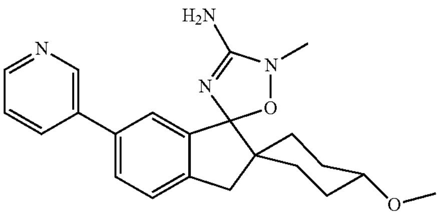 Ex. 59 | 16.8[a] |

-continued
| Compound No. | Structure/Ex. No. | IC50 (nM) |
|---|---|---|
| 19 | 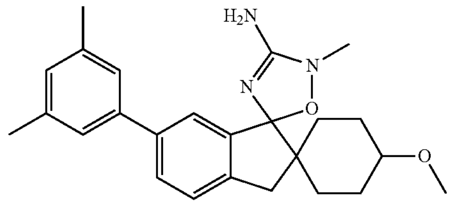 Ex. 34 | 14.6[a] |
| 20 | 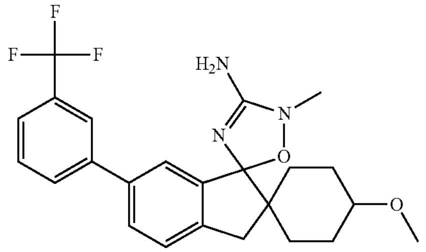 Ex. 36 | 18.7[a] |
| 21 | 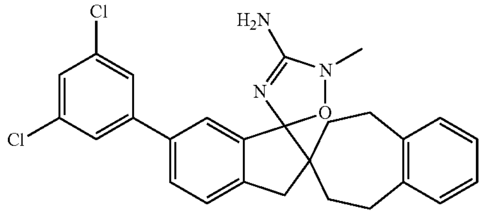 Ex. 46 | 18.9[a] |
| 22 | 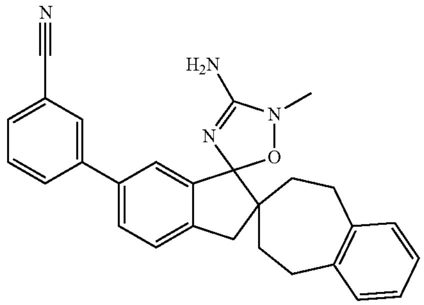 Ex. 20 | 19.3[a] |
| 23 | 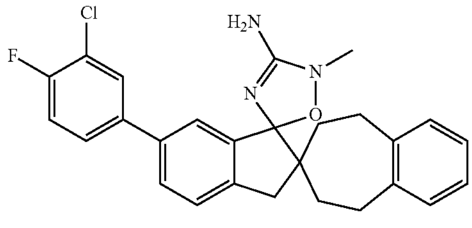 Ex. 44 | 20.7[a] |

-continued
| Compound No. | Structure/Ex. No. | $IC_{50}$ (nM) |
|---|---|---|
| 24 | 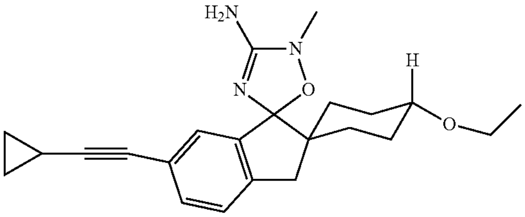 Ex. 14 | 21.0[a] |
| 25 | 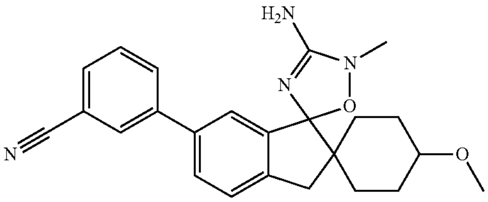 Ex. 17 | 26.2[a] |
| 26 | 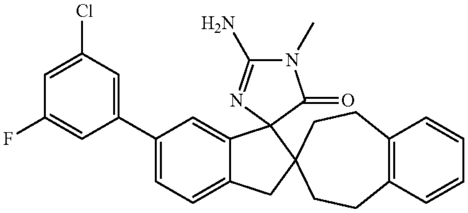 Ex. 15 | |
| 27 | 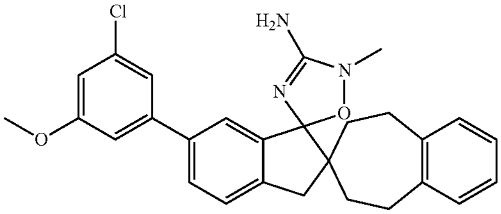 Ex. 48 | 38.3[a] |
| 28 | 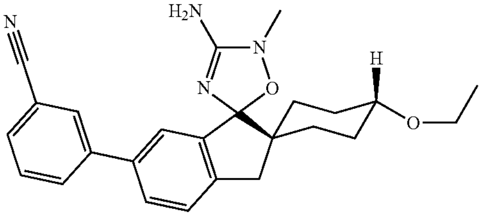 | 41.7[a] |
| 29 | 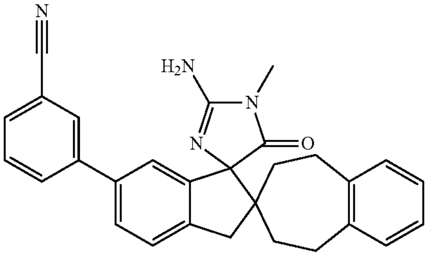 Ex. 15 | 5.3[b] |

-continued
| Compound No. | Structure/Ex. No. | $IC_{50}$ (nM) |
|---|---|---|
| 30 | 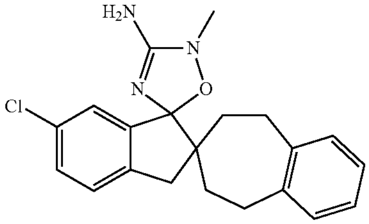 Ex. 21 | 61.6[a] |
| 31 | 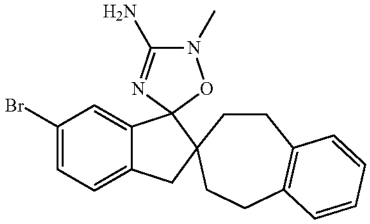 Ex. 57 | 64.0[a] |
| 32 | 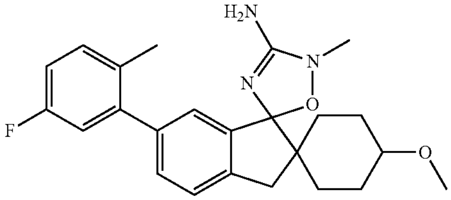 Ex. 36a | 74.1[a] |
| 33 | 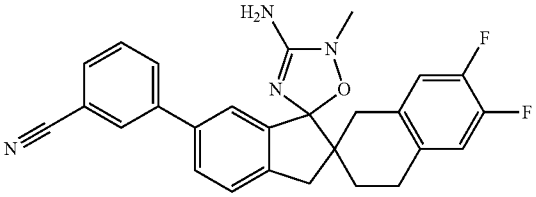 Ex. 26 | 89.0[a] |
| 34 | 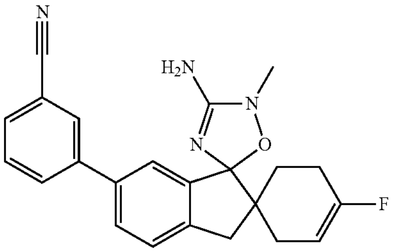 Ex. 14 | 93.3[a] |
| 35 | 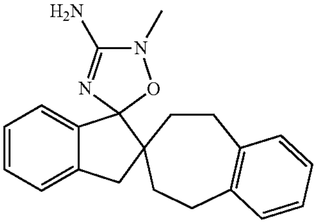 Ex. 58 | 104.6[a] |

-continued
| Compound No. | Structure/Ex. No. | $IC_{50}$ (nM) |
|---|---|---|
| 36 | 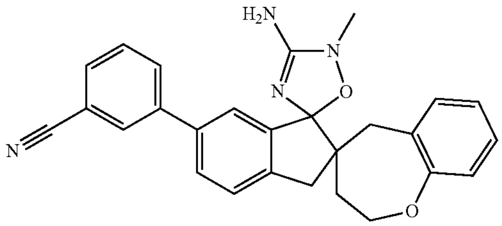 Ex. 52 | 121.7[a] |
| 37 | 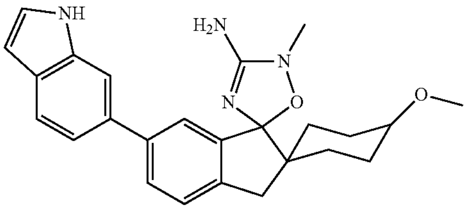 Ex. 60 | 125.6[a] |
| 38 | 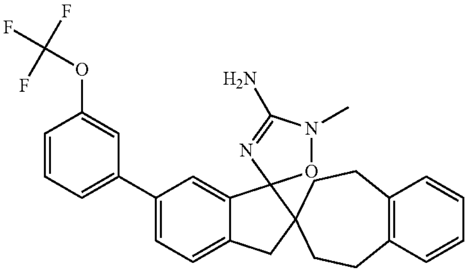 Ex. 41 | 130.4[a] |
| 39 | 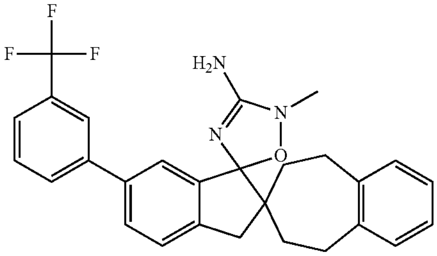 Ex. 42 | 157.6[a] |
| 40 | 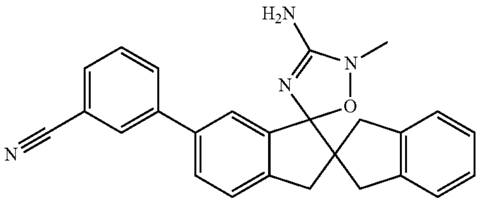 Ex. 23 | 159.6[a] |

-continued
| Compound No. | Structure/Ex. No. | $IC_{50}$ (nM) |
|---|---|---|
| 41 | 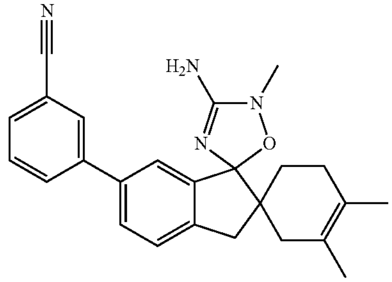 [SMILES: CC1=C(C)CC2(CC1)Cc1ccc(-c3cccc(C#N)c3)cc1C21N=C(N)N(C)O1] | 161.1[a] |
| 42 | 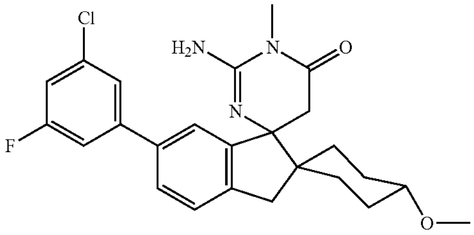 Ex. 7 | 172.7[a] |
| 43 | 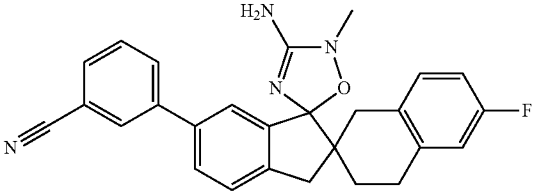 Ex. 25 | 178.4[a] |
| 44 | 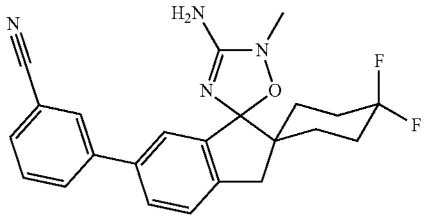 Ex. 14 | 189.1[a] |
| 45 | 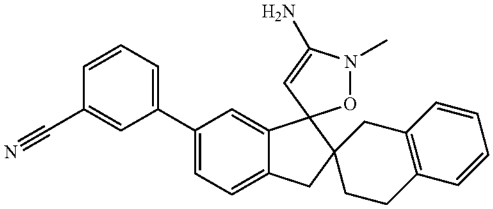 Ex. 1 | 194.7[a] |
| 46 | 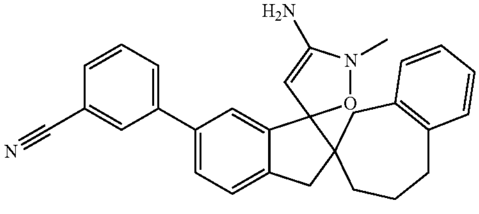 Ex. 18 | 292.9[a] |

-continued
| Compound No. | Structure/Ex. No. | $IC_{50}$ (nM) |
|---|---|---|
| 47 | 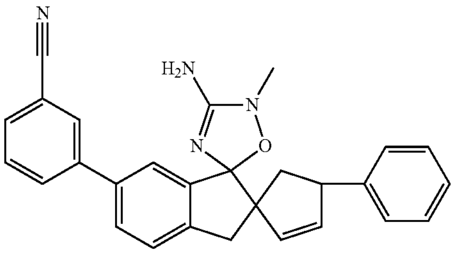 fraction A Ex. 12 | 295.2[a] |
| 48 | 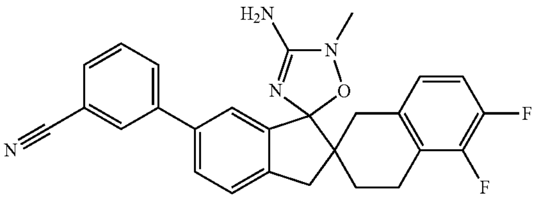 Ex. 19 | 378.3[a] |
| 49 | 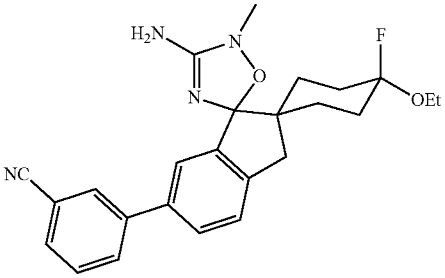 Ex. 11 and 28 | 41.7[a] |
| 50 | 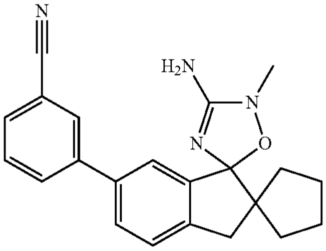 Ex. 9 | 443.2[a] |
| 51 | 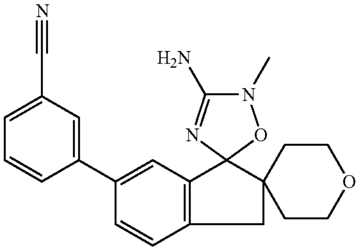 Ex. 2 | 465.8[a] |

-continued
| Compound No. | Structure/Ex. No. | $IC_{50}$ (nM) |
|---|---|---|
| 52 | 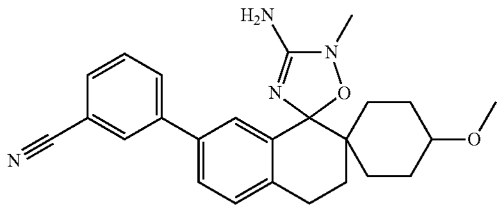<br>Ex. 31 | 505.8[a] |
| 53 | 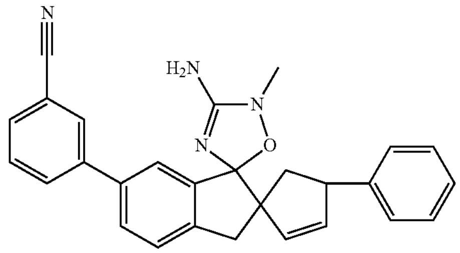<br>FRACTION B<br>Ex. 12 | 514.4[a] |
| 54 | 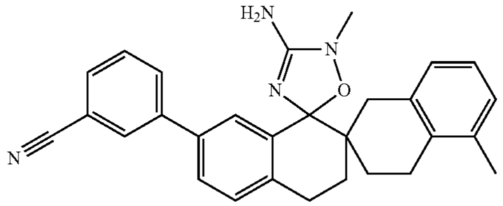<br>Ex. 24 | 617.9[a] |
| 55 | 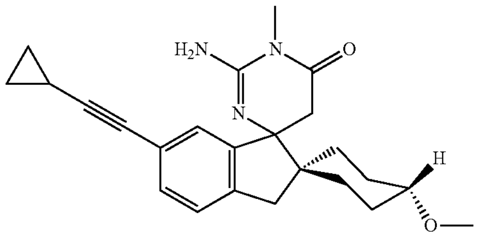<br>Ex. 8 | 670.4[a] |
| 56 | 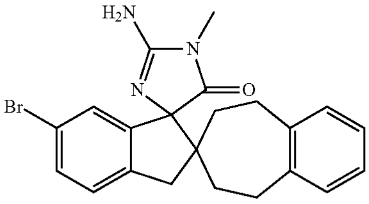<br>Ex. 15 | 204.3[b] |

-continued
| Compound No. | Structure/Ex. No. | $IC_{50}$ (nM) |
|---|---|---|
| 57 | 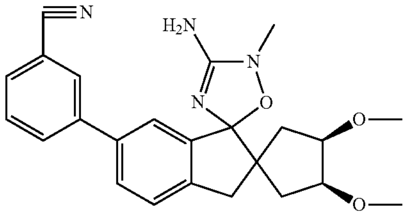 Ex. 10 | 935.52[a] |
| 58 | 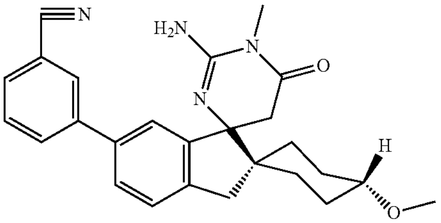 Ex. 5 | 969.7[a] |
| 59 | 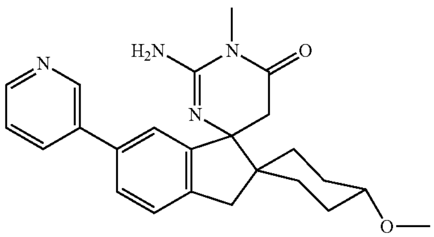 Ex. 6 | 1554.9[a] |
| 60 | 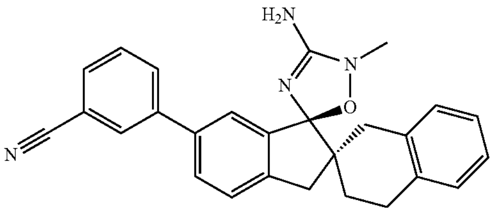 [SMILES: CN1O[C@]2(N=C1N)c1cc(-c3cccc(C#N)c3)ccc1C[C@]21CCc2ccccc2C1] | 1856.1[a] |
| 61 | 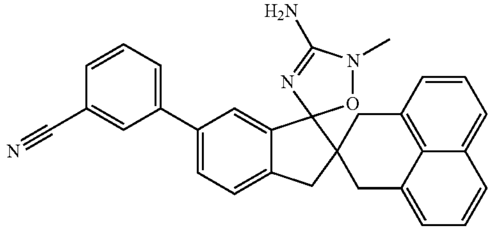 Ex. 22 | 3262.1[a] |
| 62 | 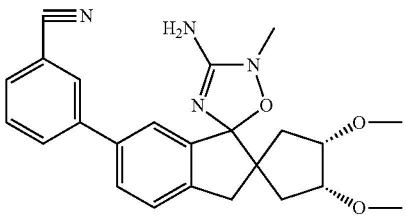 Ex. 10 | 4106.0[a] |

-continued
| Compound No. | Structure/Ex. No. | $IC_{50}$ (nM) |
|---|---|---|
| 63 | 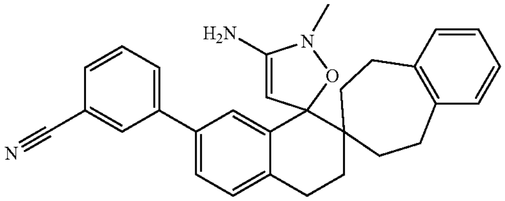 Ex. 53 | 5053.9[a] |
| 64 | 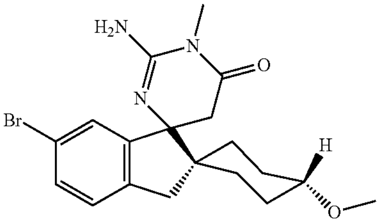 Ex. 4 | 36244.8[a] |
| 65 | 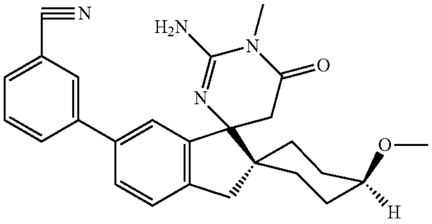 | 50000.0[a] |
| 66 | 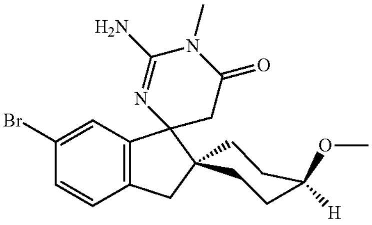 | 200000[a] |
| 67 | 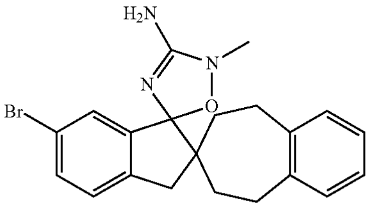 Ex. 16 | 138.5[a] |
| 68 | 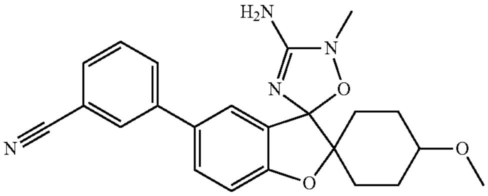 Ex. 40 | 1778.6[a] |

-continued
| Compound No. | Structure/Ex. No. | $IC_{50}$ (nM) |
| --- | --- | --- |
| 69 | 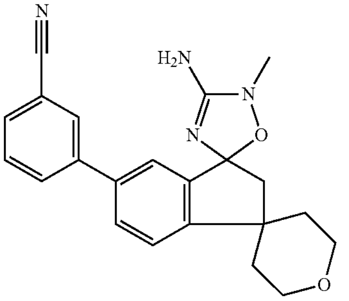 Ex. 3 | 4702.2[a] |
| 70 | 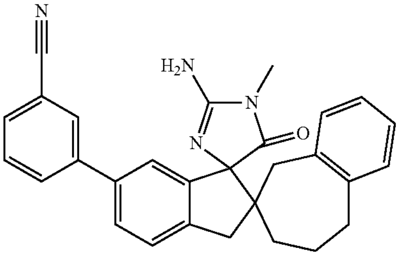 [SMILES: CN1C(=O)C2(N=C1N)c1cc(-c3cccc(C#N)c3)ccc1CC21CCCc2ccccc2C1] | |
| 71 | 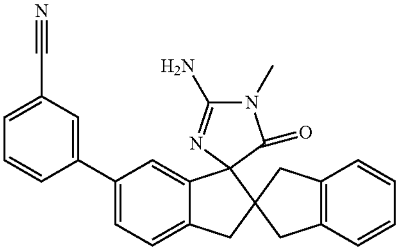 [SMILES: CN1C(=O)C2(N=C1N)c1cc(-c3cccc(C#N)c3)ccc1CC21Cc2ccccc2C1] | |
| 72 | 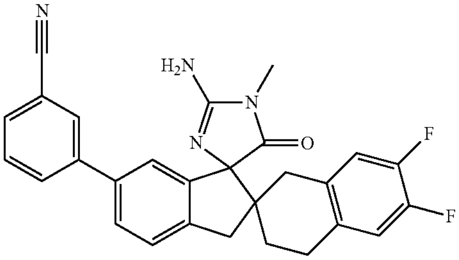 [SMILES: CN1C(=O)C2(N=C1N)c1cc(-c3cccc(C#N)c3)ccc1CC21CCc2cc(F)c(F)cc2C1] | |
| 73 | 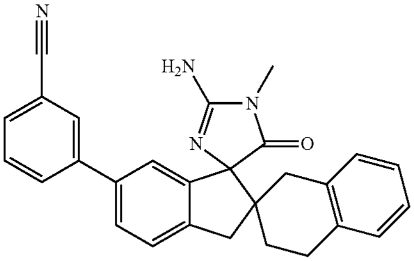 [SMILES: CN1C(=O)C2(N=C1N)c1cc(-c3cccc(C#N)c3)ccc1CC21CCc2ccccc2C1] | |

-continued
| Compound No. | Structure/Ex. No. | $IC_{50}$ (nM) |
|---|---|---|
| 74 | 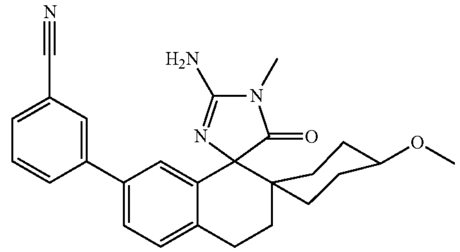 [SMILES: COC1CCC2(CCc3ccc(-c4cccc(C#N)c4)cc3C23N=C(N)N(C)C3=O)CC1] | |
| 75 | 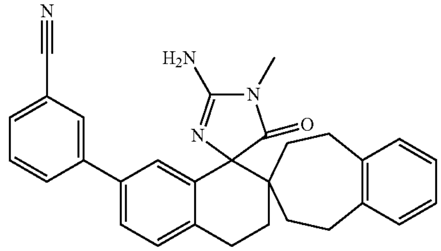 [SMILES: CN1C(=O)C2(N=C1N)c1cc(-c3cccc(C#N)c3)ccc1CCC21CCc2ccccc2CC1] | |
| 76 | 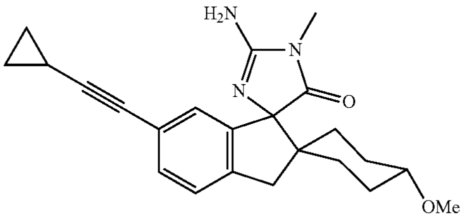 Ex. 56 | 2.1[a] |
| 77 | 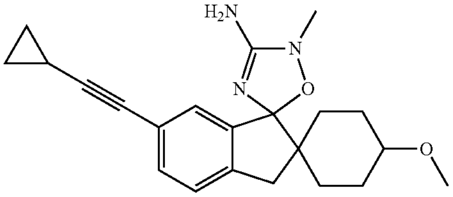 [SMILES: COC1CCC2(CC1)Cc1ccc(C#CC3CC3)cc1C21N=C(N)N(C)O1] | |
| 78 | 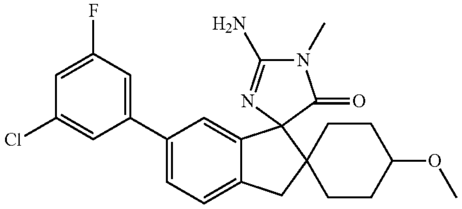 [SMILES: COC1CCC2(CC1)Cc1ccc(-c3cc(F)cc(Cl)c3)cc1C21N=C(N)N(C)C1=O] | |
| 79 | 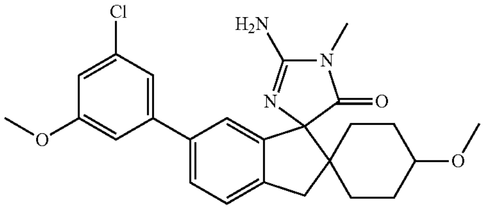 | |

-continued
| Compound No. | Structure/Ex. No. | $IC_{50}$ (nM) |
|---|---|---|
| 80 | 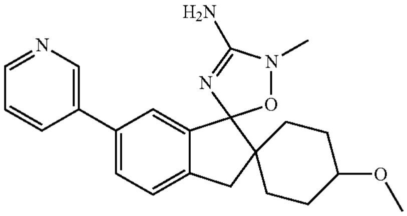 [SMILES: COC1CCC2(CC1)Cc1ccc(-c3cccnc3)cc1C21N=C(N)N(C)O1] | |
| 81 | 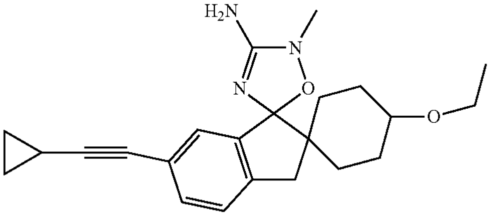 [SMILES: CCOC1CCC2(CC1)Cc1ccc(C#CC3CC3)cc1C21N=C(N)N(C)O1] | |
| 82 | 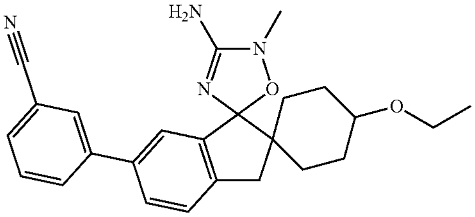 [SMILES: CCOC1CCC2(CC1)Cc1ccc(-c3cccc(C#N)c3)cc1C21N=C(N)N(C)O1] | 432.3[a] |
| 83 | 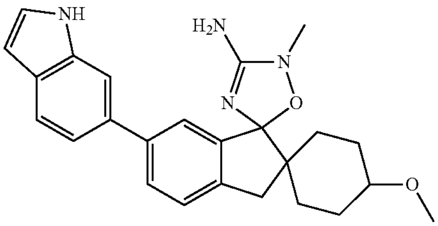 [SMILES: COC1CCC2(CC1)Cc1ccc(-c3ccc4cc[nH]c4c3)cc1C21N=C(N)N(C)O1] | |
| 84 | 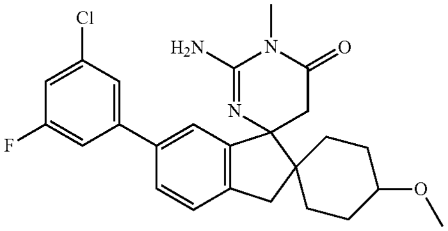 [SMILES: COC1CCC2(CC1)Cc1ccc(-c3cc(F)cc(Cl)c3)cc1C21CC(=O)N(C)C(N)=N1] | |
| 85 | 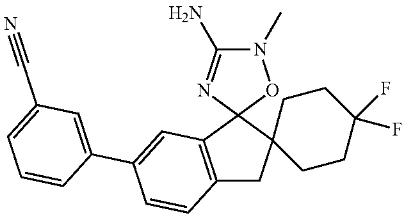 [SMILES: CN1OC2(N=C1N)c1cc(-c3cccc(C#N)c3)ccc1CC21CCC(F)(F)CC1] | |

-continued
| Compound No. | Structure/Ex. No. | $IC_{50}$ (nM) |
|---|---|---|
| 86 | 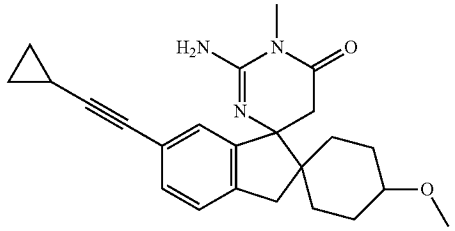 [SMILES: COC1CCC2(CC1)Cc1ccc(C#CC3CC3)cc1C21CC(=O)N(C)C(N)=N1] | |
| 87 | 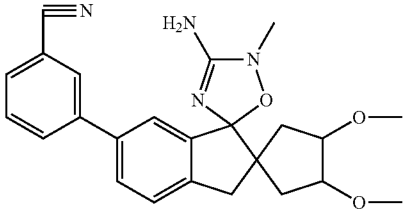 [SMILES: COC1CC2(Cc3ccc(-c4cccc(C#N)c4)cc3C23N=C(N)N(C)O3)CC1OC] | |
| 88 | 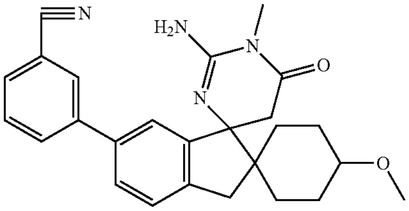 [SMILES: COC1CCC2(CC1)Cc1ccc(-c3cccc(C#N)c3)cc1C21CC(=O)N(C)C(N)=N1] | |
| 89 | 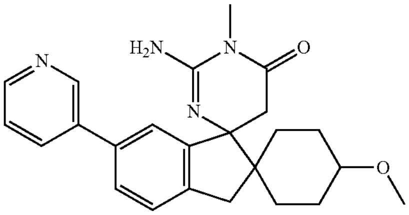 [SMILES: COC1CCC2(CC1)Cc1ccc(-c3cccnc3)cc1C21CC(=O)N(C)C(N)=N1] | |
| 90 | 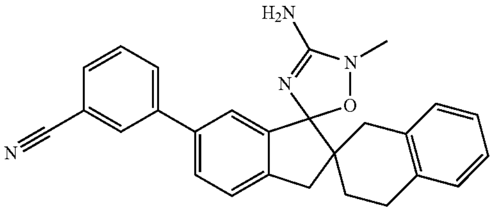 [SMILES: CN1OC2(N=C1N)c1cc(-c3cccc(C#N)c3)ccc1CC21CCc2ccccc2C1] | |
| 91 | 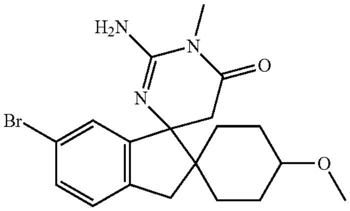 [SMILES: COC1CCC2(CC1)Cc1ccc(Br)cc1C21CC(=O)N(C)C(N)=N1] | |
| 92 | 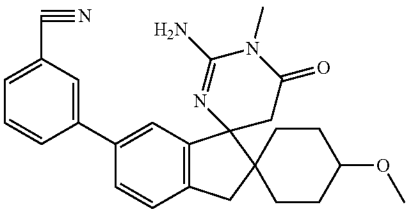 [SMILES: COC1CCC2(CC1)Cc1ccc(-c3cccc(C#N)c3)cc1C21CC(=O)N(C)C(N)=N1] | |

-continued

| Compound No. | Structure/Ex. No. | $IC_{50}$ (nM) |
|---|---|---|
| 93 | 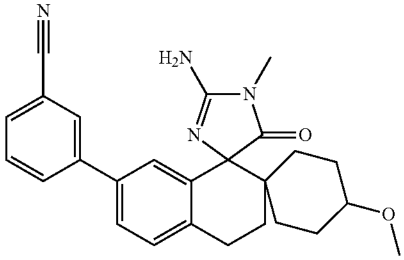 [SMILES: COC1CCC2(CCc3ccc(-c4cccc(C#N)c4)cc3C23N=C(N)N(C)C3=O)CC1] | |
| 94 | Ex. 61 | $222.2^{a}$ |
| 95 | Ex. 62 | $136.8^{a}$ |
| 96 | Ex. 63 | $28.3^{a}$ |
| 97 | Ex. 64 | $3881.1^{a}$ |
| 98 | Ex. 64 | $3322.6^{a}$ |
| 99 | Ex. 65 | $2.4^{a}$ |
| 100 | Ex. 66 | $4.7^{a}$ |
| 101 | Ex. 67 | $56.7^{a}$ |
| 102 | Ex. 68 | $14.7^{a}$ |
| 103 | Ex. 69 | $46.0^{a}$ |
| 104 | Ex. 70 | $255.1^{a}$ |
| 105 | Ex. 71 | $8.4^{a}$ |
| 106 | Ex. 72 | $5.3^{a}$ |
| 107 | Ex. 73 | $228.1^{a}$ |
| 108 | Ex. 74 | $156.3^{a}$ |
| 109 | Ex. 75 | $23.6^{a}$ |
| 110 | Ex. 76 | $14.6^{a}$ |
| 111 | Ex. 77 | $195.7^{a}$ |
| 112 | Ex. 78 | $80.4^{a}$ |
| 113 | Ex. 79 | $24.6^{a}$ |
| 114 | Ex. 80 | $9.7^{a}$ |
| 115 | Ex. 81 | $3.7^{a}$ |
| 116 | Ex. 82 | $76.7^{a}$ |
| 117 | Ex. 83 | $17.4^{a}$ |
| 118 | Ex. 84 | $9.0^{a}$ |
| 119 | Ex. 85 | $2{,}312.0^{b}$ |
| 120 | Ex. 85 | $3{,}505.0^{b}$ |
| 121 | Ex. 86 | $56.2^{a}$ |
| 122 | Ex. 87 | $42.5^{a}$ |
| 123 | Ex. 88 | |
| 124 | Ex. 89 | $21.5^{b}$ |
| 125 | Ex. 90 | $263.5^{b}$ |
| 126 | Ex. 91 | $31.6^{b}$ |
| 127 | Ex. 92 | $14.9^{b}$ |
| 128 | Ex. 93 | $1198.0^{b}$ |
| 129 | Ex. 94 | $28.2^{b}$ |
| 130 | Ex. 95 | $69.1^{b}$ |
| 131 | Ex. 96 | |
| 132 | Ex. 97 | $24.9^{b}$ |
| 133 | Ex. 98 | $38.5^{b}$ |
| 134 | Ex. 99 | $14.4^{a}$ |
| 135 | Ex. 100 | $7.3^{a}$ |
| 136 | Ex. 101 | $8.1^{a}$ |
| 137 | Ex. 102 | $7.8^{b}$ |
| 138 | Ex. 103 | $15.6^{a}$ |
| 139 | Ex. 104 | $13.6^{a}$ |
| 140 | Ex. 105 | $4.5^{b}$ |
| 141 | Ex. 106 | $12.9^{b}$ |
| 142 | Ex. 107 | $2.0^{a}$ |
| 143 | Ex. 108 | $705.8^{b}$ |
| 144 | Ex. 108 | $18.9^{b}$ |
| 145 | Ex. 109 | $16.2^{a}$ |
| 146 | Ex. 110 | $7.9^{a}$ |
| 147 | Ex. 111 | $2.2^{a}$ |
| 148 | Ex. 112 | $5.4^{b}$ |
| 149 | Ex. 113 | $4.8^{a}$ |
| 150 | Ex. 114 | $3.0^{a}$ |
| 151 | Ex. 114 | $207.0^{a}$ |
| 152 | Ex. 115 | $104.2^{b}$ |
| 153 | Ex. 116 | $36.6^{a}$ |
| 154 | Ex. 117 | $30.1^{a}$ |
| 155 | Ex. 118 | $12.2^{a}$ |
| 156 | Ex. 119 | $12.2^{b}$ |
| 157 | Ex. 120 | $342.7^{b}$ |

-continued

| Compound No. | Structure/Ex. No. | $IC_{50}$ (nM) |
|---|---|---|
| 158 | Ex. 121 | 49.3[b] |
| 159 | Ex. 122 | 83.9[b] |
| 160 | Ex. 123 | 53.2[b] |
| 161 | Ex. 124 | 4.8[b] |
| 162 | Ex. 124 | 631.3[b] |
| 163 | Ex. 125 | 8.9 |
| 164 | Ex. 126 | 8.9[b] |
| 165 | Ex. 127 | |
| 166 | Ex. 128 | 11.5[b] |
| 167 | Ex. 129 | 42.5[b] |
| 168 | Ex. 130 | 29.3[b] |
| 169 | Ex. 131 | 20.3[b] |
| 170 | Ex. 132 | 89.7[b] |
| 171 | Ex. 133 | 55.8[b] |
| 172 | Ex. 134 | 7.3[b] |
| 23 | | |
| 173 | Ex. 135 | 16.7[b] |
| 174 | Ex. 136 | 23.5[b] |
| 175 | Ex. 136 | 850.9[b] |
| 176 | Ex. 137 | |
| 177 | Ex. 138 | 1.5[b] |
| 178 | Ex. 139 | 0.6[a] |
| 179 | Ex. 140 | 2.6[a] |
| 180 | Ex. 141 | 1.1[a] |
| 181 | Ex. 142 | 198.3[a] |
| 182 | Ex. 143 | 57.1[a] |
| 183 | Ex. 144 | 1.0[a] |
| 184 | Ex. 145 | 3.3[a] |
| 185 | Ex. 146 | 2.8[a] |
| 186 | Ex. 147 | |
| 187 | Ex. 148 | 2.6[a] |
| 188 | Ex. 149 | 1.9[a] |
| 189 | Ex. 150 | 2.9[a] |
| 190 | Ex. 151 | 10.5[b] |
| 191 | Ex. 152 | 101.7[a] |
| 192 | Ex. 153 | 0.96[a] |
| 193 | Ex. 154 | 0.8[a] |
| 194 | Ex. 155 | 17.4[a] |
| 195 | Ex. 156 | 49.7[a] |
| 196 | Ex. 157 | 11.5[a] |
| 197 | Ex. 158 | 29.6[a] |
| 198 | Ex. 159 | 9.9[b] |
| 199 | Ex. 159 | 110.7[b] |
| 200 | Ex. 160 | 269.2[b] |
| 201 | Ex. 161 | 187.8[b] |
| 202 | Ex. 162 | 32.3[b] |
| 203 | Ex. 163 | 79.8[b] |
| 204 | Ex. 164 | 30.3[b] |
| 205 | Ex. 165 | 4.9[a] |
| 206 | Ex. 166 | 40.8[b] |
| 207 | Ex. 167 | 9.5[b] |
| 208 | Ex. 168 | 39.9[b] |
| 209 | Ex. 169 | 813.7[b] |
| 210 | Ex. 170 | 647.5[b] |
| 211 | Ex. 171 | 28.5[b] |
| 212 | Ex. 172 | 32.4[b] |
| 213 | Ex. 172 | |
| 214 | Ex. 173 | 30.9[a] |
| 215 | Ex. 174 | 24.0[b] |
| 216 | Ex. 174 | 1814.0[b] |
| 217 | Ex. 175 | 32.3[a] |
| 218 | Ex. 176 | 161.0[a] |
| 219 | Ex. 177 | 11.2[b] |
| 220 | Ex. 178 | 23.2[b] |
| 221 | Ex. 179 | 4.0[b] |
| 222 | Ex. 180 | 16.0[b] |
| 223 | Ex. 181 | 5.1[b] |
| 224 | Ex. 181 | 137.9[b] |
| 225 | Ex. 182 | 20.0[a] |
| 226 | Ex. 183 | 350.6[a] |
| 227 | Ex 184 | 12.0[a] |
| 228 | Ex. 185 | 72.4[b] |
| 229 | Ex. 186 | 37.8[a] |
| 230 | Ex. 187 | 321.3[b] |
| 231 | Ex. 188 | 161.3[b] |
| 232 | Ex. 189 | 144.7[b] |
| 233 | Ex. 190 | 144.8[b] |

-continued

| Compound No. | Structure/Ex. No. | $IC_{50}$ (nM) |
|---|---|---|
| 234 | Ex. 191 | |
| 235 | Ex. 192 | 368.5[b] |
| 236 | Ex. 193 | 8.9[b] |
| 237 | Ex. 194 | 10.6[b] |
| 238 | Ex. 195 | 42.8[b] |
| 239 | Ex. 196 | 29.3[b] |
| 240 | Ex. 197 | 10.0[b] |
| 241 | Ex. 198 | 9.6[b] |
| 242 | Ex. 198 | 495.6[b] |
| 243 | Ex. 198 | 6.5[b] |
| 244 | Ex. 199 | 3.5[b] |
| 245 | Ex. 199 | 2.1[b] |
| 246 | Ex. 199 | 423.4[b] |
| 247 | Ex. 200 | 55.4[b] |
| 248 | Ex. 201 | 48.0[b] |
| 249 | Ex. 202 | 493.0[a] |
| 250 | Ex. 203 | 2,010.0[b] |
| 251 | Ex. 204 | 13,500.0[b] |
| 252 | Ex. 205 | |
| 253 | Ex. 206 | 825.3[b] |
| 254 | Ex. 207 | 20.4[b] |
| 255 | Ex. 208 | 618.0[b] |
| 256 | Ex. 209 | 11.6[b] |
| 257 | Ex. 210 | 7.4[b] |
| 258 | Ex. 211 | 639.8[b] |
| 259 | Ex. 212 | |
| 260 | Ex. 213 | 1,071.0[b] |
| 261 | Ex. 214 | 2,543.0[b] |
| 262 | Ex. 215 | 2,226.0[b] |
| 263 | Ex. 216 | 716.1[b] |
| 264 | Ex. 217 | 29.2[a] |
| 265 | Ex. 218 | 634.1[b] |
| 266 | Ex. 219 | |
| 267 | Ex. 220 | |
| 268 | Ex. 221 | |
| 269 | Ex. 221 | 1000.0[b] |
| 270 | Ex. 222 | 13,500.0[b] |
| 271 | Ex. 223 | 10.4[b] |
| 272 | Ex. 224 | 182.5[b] |
| 273 | Ex. 224 | 26.1[b] |
| 274 | Ex. 225 | 8.4[b] |
| 275 | Ex. 226 | 20.0[b] |
| 276 | Ex. 227 | |
| 277 | Ex. 228 | 176.6[b] |
| 278 | Ex. 229 | |
| 279 | Ex. 230 | 13.5[b] |
| 280 | Ex. 231 | |
| 281 | Ex. 232 | 150.8[b] |
| 282 | Ex. 232 | 1580.0[b] |
| 283 | Ex. 233 | 265.3[b] |
| 284 | Ex. 234 | 35.3[b] |
| 285 | Ex. 235 | 18.2[b] |
| 286 | Ex. 236 | 44.9[b] |
| 287 | Ex. 237 | 473.3[b] |
| 288 | Ex. 238 | 14.8[b] |
| 289 | Ex. 239 | 36.1[b] |
| 290 | Ex. 240 | 15.7[b] |
| 291 | Ex. 241 | 125.7[b] |
| 292 | Ex. 242 | 1357.0[b] |
| 293 | Ex. 243 | 91.1[b] |
| 294 | Ex. 244 | 22780.0[b] |
| 295 | Ex. 244 | 3156.5[b] |
| 296 | Ex. 245 | |
| 297 | Ex. 246 | 17.4[b] |
| 298 | Ex. 247 | |
| 299 | Ex. 248 | |
| 300 | Ex. 249 | 14.8[b] |
| 301 | Ex. 250 | 138.6[b] |
| 302 | Ex. 251 | 333.2[b] |
| 303 | Ex. 252 | 18.1[b] |
| 304 | Ex. 253 | 4.7[b] |
| 305 | Ex. 254 | 4.3[b] |
| 306 | Ex. 255 | 15.2[b] |
| 307 | Ex. 256 | 5.3[b] |
| 308 | Ex. 257 | 9.3[b] |
| 309 | Ex. 258 | 9.2[b] |
| 310 | Ex. 259 | 48.9[b] |

-continued

| Compound No. | Structure/Ex. No. | $IC_{50}$ (nM) |
|---|---|---|
| 311 | Ex. 260 | $7.4^b$ |
| 312 | Ex. 261 | $35.2^b$ |
| 313 | Ex. 262 | $12.3^b$ |
| 314 | Ex. 263 | $11.2^b$ |
| 315 | Ex. 264 | $17.3^b$ |
| 316 | Ex. 265 | $15.6^b$ |
| 317 | Ex. 266 | $17.0^b$ |
| 318 | Ex. 267 | $7.3^b$ |
| 319 | Ex. 268 | $13.7^b$ |
| 320 | Ex. 269 | |
| 321 | Ex. 270 | $22.2^b$ |
| 322 | Ex. 271 | $5.2^b$ |
| 323 | Ex. 272 | $7.1^b$ |
| 324 | Ex. 273 | $10.3^b$ |
| 325 | Ex. 274 | $14.0^b$ |
| 326 | Ex. 275 | $16.1^b$ |
| 327 | Ex. 276 | $5.4^b$ |
| 328 | Ex. 277 | $12.0^b$ |
| 329 | Ex. 278 | $7.4^b$ |
| 330 | Ex. 279 | $24.0^b$ |
| 331 | Ex. 280 | $30.9^b$ |
| 332 | Ex. 281 | $34.9^b$ |
| 333 | Ex. 282 | $11.6^b$ |
| 334 | Ex. 282 | $1.7^b$ |
| 335 | Ex. 282 | $2.2^b$ |
| 336 | Ex. 282 | $206.9^b$ |
| 337 | Ex. 282 | $262.2^b$ |
| 338 | Ex. 283 | $19.5^b$ |
| 339 | Ex. 284 | $22.5^b$ |
| 340 | Ex. 285 | $316.1^b$ |
| 341 | Ex. 286 | $13.5^b$ |
| 342 | Ex. 287 | $37.5^b$ |
| 343 | Ex. 288 | $21970.0^b$ |
| 344 | Ex. 289 | |
| 345 | Ex. 290 | $61.5^b$ |
| 346 | Ex. 291 | $16^b$ |
| 347 | Ex. 292 | $20.4^b$ |
| 348 | Ex. 293 | $12.6^b$ |
| 349 | Ex. 294 | $16.3^b$ |
| 350 | Ex. 295 | $481.5^b$ |
| 351 | Ex. 295 | $39.8^b$ |
| 352 | Ex. 296 | $22.9^b$ |
| 353 | Ex. 297 | $15.8^b$ |
| 354 | Ex. 298 | $47.7^b$ |
| 355 | Ex. 299 | $62.3^b$ |
| 356 | Ex. 300 | $192.0^b$ |
| 357 | Ex. 301 | $12.5^b$ |
| 358 | Ex. 302 | |
| 359 | Ex. 303 | $14.1^b$ |
| 360 | Ex. 304 | $97.8^b$ |
| 361 | Ex. 304 | $185.5^b$ |
| 362 | Ex. 305 | $81.1^b$ |
| 363 | Ex. 306 | $17.3^b$ |
| 364 | Ex. 307 | $24.1^b$ |
| 365 | Ex. 308 | $24.3^b$ |
| 366 | Ex. 309 | |
| 367 | Ex. 310 | $15.8^b$ |
| 368 | Ex. 311 | $24.8^b$ |
| 369 | Ex. 312 | $13.2^b$ |
| 370 | Ex. 313 | $3.5^b$ |
| 371 | Ex. 314 | $24.3^b$ |
| 372 | Ex. 315 | $9.7^b$ |
| 373 | Ex. 316 | $13.5^b$ |
| 374 | Ex. 317 | $28.9^b$ |
| 375 | Ex. 318 | $8.8^b$ |
| 376 | Ex. 319 | $11.3^b$ |
| 377 | Ex. 320 | $16.5^b$ |
| 378 | Ex. 321 | $19.6^b$ |
| 379 | Ex. 322 | $886.8^b$ |
| 380 | Ex. 322 | $415.5^b$ |
| 381 | Ex. 323 | |
| 382 | Ex. 324 | $29.2^b$ |
| 383 | Ex. 325 | $6.2^b$ |
| 384 | Ex. 326 | $18.1^b$ |
| 385 | Ex. 327 | $7.0^b$ |
| 386 | Ex. 328 | $7.8^b$ |
| 387 | Ex. 329 | $15.5^b$ |

-continued

| Compound No. | Structure/Ex. No. | $IC_{50}$ (nM) |
|---|---|---|
| 388 | Ex. 330 | $15.4^b$ |
| 389 | Ex. 331 | $17.2^b$ |
| 390 | Ex. 332 | $26.1^b$ |
| 391 | Ex. 332 | $566.5^b$ |
| 392 | Ex. 333 | $353.0^b$ |
| 393 | Ex. 334 | $17.0^b$ |
| 394 | Ex. 335 | $1.4^a$ |
| 395 | Ex. 336 | $6.7^a$ |
| 396 | Ex. 336 | $213.0^b$ |
| 397 | Ex. 336 | $3.4^b$ |
| 398 | Ex. 337 | $33.8^b$ |
| 399 | Ex. 338 | $74.6^b$ |
| 400 | Ex. 339 | $43.0^b$ |
| 401 | Ex. 340 | $25.6^b$ |
| 402 | Ex. 341 | $72.5^b$ |
| 403 | Ex. 342 | |
| 404 | Ex. 343 | $46.8^b$ |
| 405 | Ex. 344 | $11.4^b$ |
| 406 | Ex. 344 | $6.3^b$ |
| 407 | Ex. 344 | $2134.5^b$ |
| 408 | Ex. 345 | $9.7^b$ |
| 409 | Ex. 346 | $19.1^b$ |
| 410 | Ex. 347 | $566^b$ |
| 411 | Ex. 348 | $91.4^b$ |
| 412 | Ex. 349 | $79.3^b$ |
| 413 | Ex. 350 | $48.3^b$ |
| 414 | Ex. 351 | $6.3^b$ |
| 415 | Ex. 352 | $8.1^b$ |
| 416 | Ex. 353 | $16.1^b$ |
| 417 | Ex. 354 | |
| 418 | Ex. 355 | $8.7^b$ |
| 419 | Ex. 356 | $134.9^b$ |
| 420 | Ex. 357 | $23.1^b$ |
| 421 | Ex. 358 | $14.8^b$ |
| 422 | Ex. 359 | $6.8^b$ |
| 423 | Ex. 360 | $186.2^b$ |
| 424 | Ex. 361 | $53.6^b$ |
| 425 | Ex. 362 | $4.1^b$ |
| 426 | Ex. 363 | $7.0^b$ |
| 427 | Ex. 364 | $182.4^b$ |
| 428 | Ex. 365 | $293.2^b$ |
| 429 | Ex. 366 | $1673.5^b$ |
| 430 | Ex. 367 | |
| 431 | Ex. 368 | $55.8^b$ |
| 432 | Ex. 369 | $80.5^b$ |
| 433 | Ex. 370 | $575.2^b$ |
| 434 | Ex. 371 | $532.7^b$ |
| 435 | Ex. 372 | $2336.0^b$ |
| 436 | Ex. 373 | $2357.0^b$ |
| 437 | Ex. 374 | |
| 438 | Ex. 375 | $79.1^b$ |
| 439 | Ex. 376 | $30000.0^b$ |
| 440 | Ex. 377 | $730.2^b$ |
| 441 | Ex. 378 | $19460.0^b$ |
| 442 | Ex. 379 | $1166.5^b$ |
| 443 | Ex. 380 | $6230.5^b$ |
| 444 | Ex. 380 | $1446.0^b$ |
| 445 | Ex. 381 | $339.7^b$ |
| 446 | Ex. 382 | 4327.0 |
| 447 | Ex. 383 | $13,500.0^b$ |
| 448 | Ex. 383 | $1,949.0^b$ |
| 449 | Ex. 384 | $206.8^a$ |
| 450 | Ex. 385 | $8.4^a$ |
| 451 | Ex. 386 | $58.6^a$ |
| 452 | Ex. 387 | $7.0^a$ |
| 453 | Ex. 388 | $6.2^a$ |
| 454 | Ex. 389 | $128.3^a$ |
| 455 | Ex. 390 | $2456.1^a$ |
| 456 | Ex. 391 | $877.2^a$ |
| 457 | Ex. 391 | $1351.28^a$ |
| 458 | Ex. 392 | $3702.8^a$ |
| 459 | Ex. 393 | $693.3^a$ |
| 460 | Ex. 394 | $9805.4^a$ |
| 461 | Ex. 395 | $16.7^a$ |
| 462 | Ex. 396 | $1.4^a$ |
| 463 | Ex. 397 | $1.1^a$ |
| 464 | Ex. 398 | $7.9^a$ |

-continued
| Compound No. | Structure/Ex. No. | $IC_{50}$ (nM) |
|---|---|---|
| 465 | Ex. 399 | 1.2[a] |
| 466 | Ex. 400 | 13.2[a] |
| 467 | Ex. 401 | 2.8[a] |
| 468 | Ex. 402 | 16.7[a] |
| 469 | Ex. 403 | 1519.7[a] |
| 470 | Ex. 404 | 67.0[a] |
| 471 | Ex. 405 | 869.5[a] |
| 472 | Ex. 406 | 13,500.0[b] |
| 473 | Ex. 416 | |
| 474 | Ex. 407 | 26.6[a] |
| 475 | Ex. 76 | 5158.0[a] |
| 476 | Ex. 408 | 33. 1[a] |
| 477 | Ex. 409 | 693.5[a] |
| 478 | Ex. 409 | 2.2[a] |
| 479 | Ex. 424 | 604.1[b] |
| 480 | Ex. 424 | 4.2[b] |
| 481 | 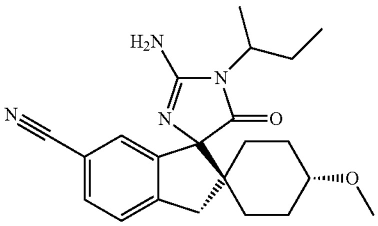 | 273.6[b] |
| 482 | 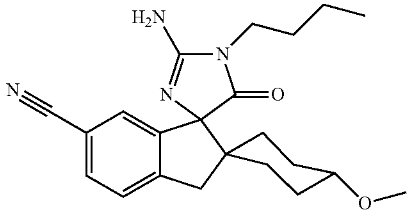 [SMILES: CCCCN1C(=O)C2(N=C1N)c1cc(C#N)ccc1CC21CCC(OC)CC1] | 42.8[b] |
| 483 | Ex. 417 | 960.5[b] |
| 484 | Ex, 417 | 7.2[b] |
| 485 | 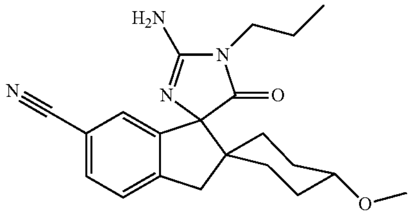 [SMILES: CCCN1C(=O)C2(N=C1N)c1cc(C#N)ccc1CC21CCC(OC)CC1] | 99.1[b] |
| 486 | 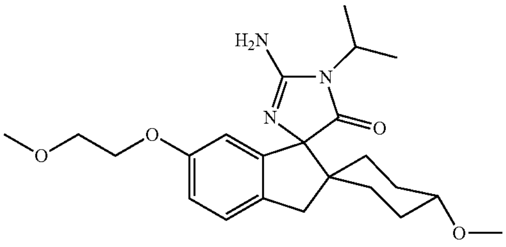 | 87.1[b] |
| 487 | Ex. 423 | 21.2[b] |

-continued
| Compound No. | Structure/Ex. No. | $IC_{50}$ (nM) |
|---|---|---|
| 488 | 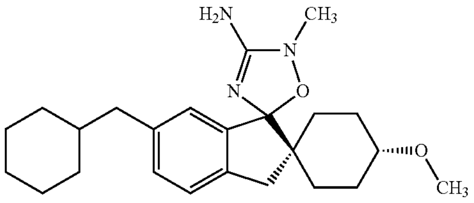 Ex. 410B | $76.3^b$ |
| 489 | 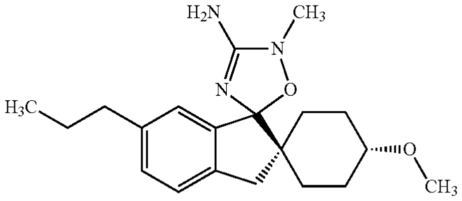 Ex. 410B | $92.8^b$ |
| 490 | 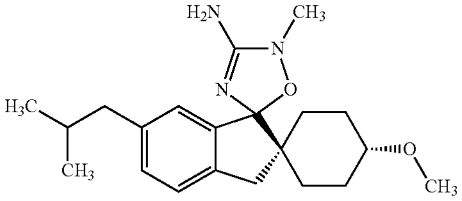 Ex. 410B | $78.2^b$ |
| 491 | 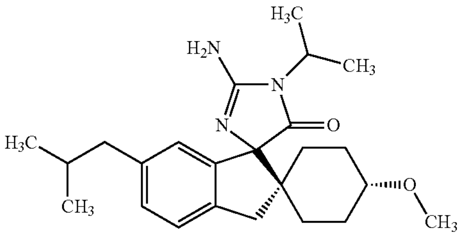 Ex. 410C | $78.2^b$ |
| 492 | 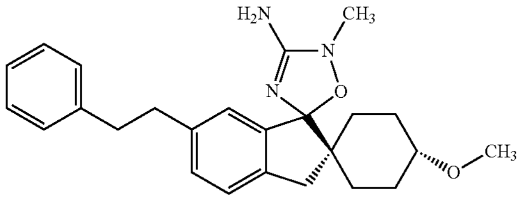 Ex. 410F | $403^b$ |
| 493 | 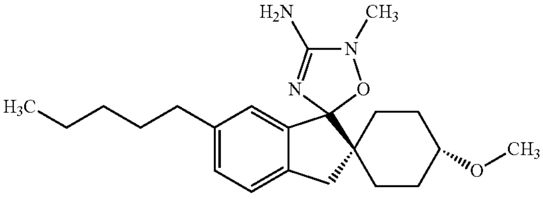 Ex. 410F | $29.8^b$ |

-continued
| Compound No. | Structure/Ex. No. | $IC_{50}$ (nM) |
|---|---|---|
| 494 | 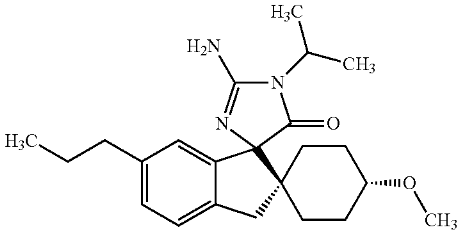 Ex. 410G | 54.3[b] |
| 495 | 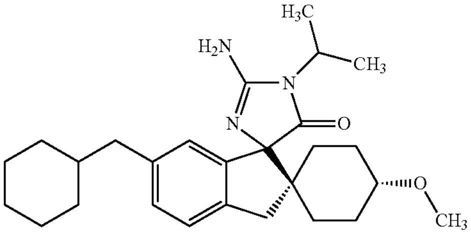 Ex. 410G | 44.3[b] |
| 496 | 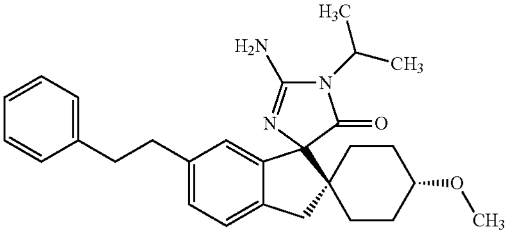 Ex. 410G | 187.8[b] |
| 497 | 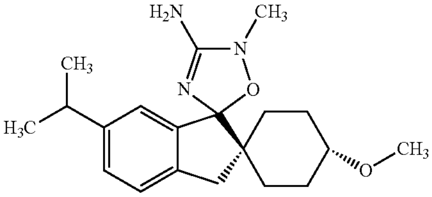 Ex. 410F | 144.3[b] |
| 498 | 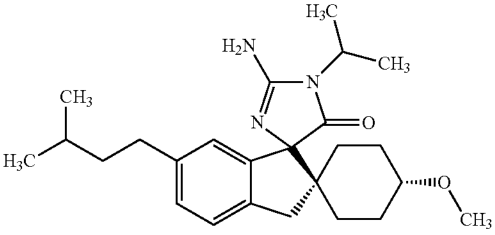 Ex. 410G | 27.1[b] |

-continued
| Compound No. | Structure/Ex. No. | $IC_{50}$ (nM) |
|---|---|---|
| 499 | 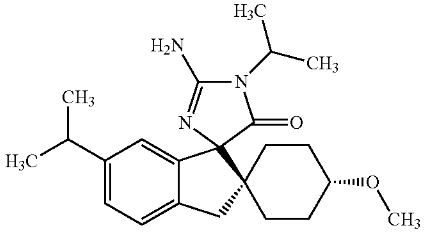<br>Ex. 410G | 148.9[b] |
| 500 | 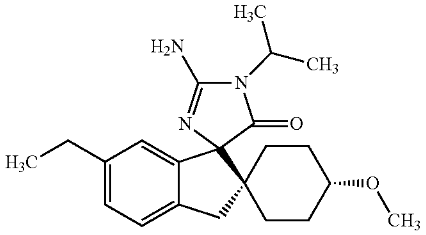<br>Ex. 410G | 199.3[b] |
| 501 | 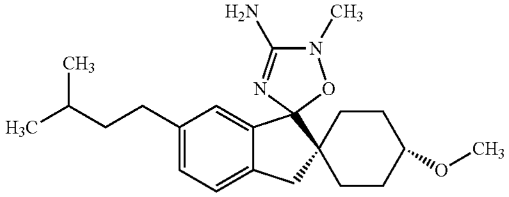<br>Ex. 410F | 15.8[b] |
| 502 | 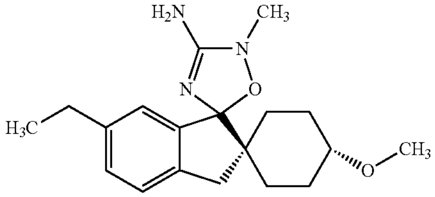<br>Ex. 410F | 521.1[b] |
| 503 | 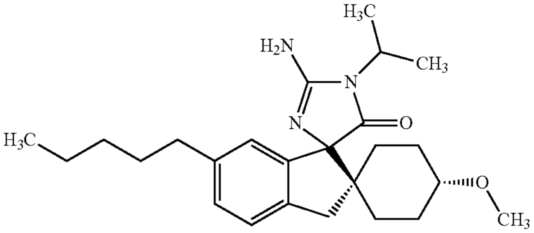<br>Ex. 410G | 39[b] |
| 504 | 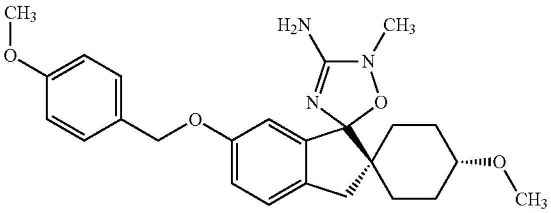<br>Ex. 410A | 807[b] |

-continued
| Compound No. | Structure/Ex. No. | $IC_{50}$ (nM) |
|---|---|---|
| 505 | 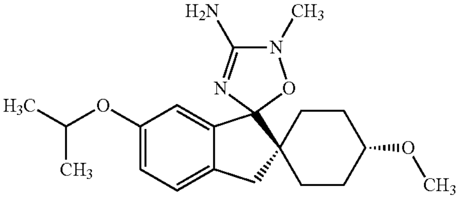<br>Ex. 410D | 170.6[b] |
| 506 | 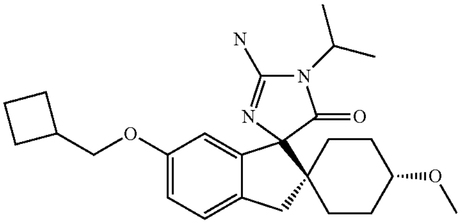<br>Ex. 410E | 34.3[b] |
| 507 | 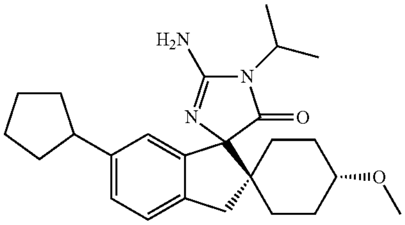<br>Ex. 410G | 128[b] |
| 508 | 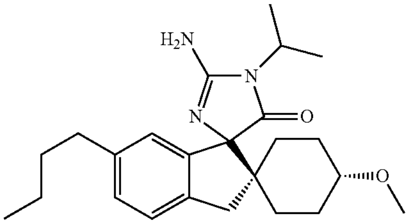<br>Ex. 410G | 48[b] |
| 509 | 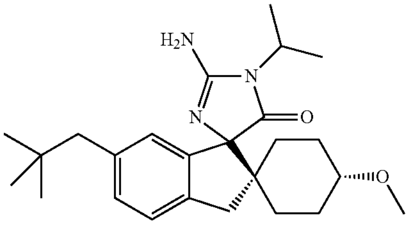<br>Ex. 410G | 267[b] |
| 510 | 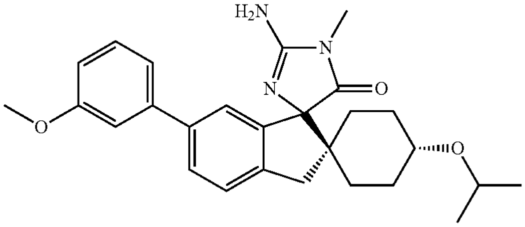<br>Ex. 410G | 61[b] |

-continued
| Compound No. | Structure/Ex. No. | $IC_{50}$ (nM) |
|---|---|---|
| 511 | 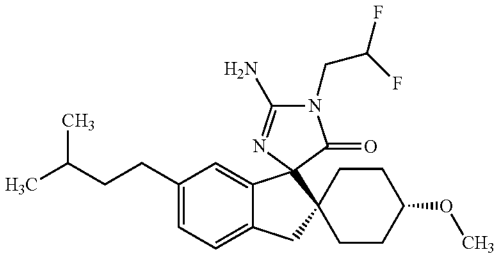 Ex. 410G | $9^b$ |
| 512 | 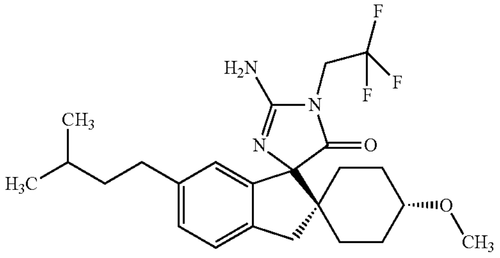 Ex. 410G | $77^b$ |
| 513 | 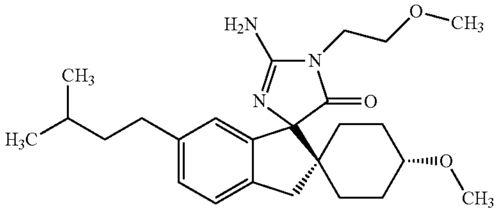 Ex. 410H | $9^b$ |
| 514 | 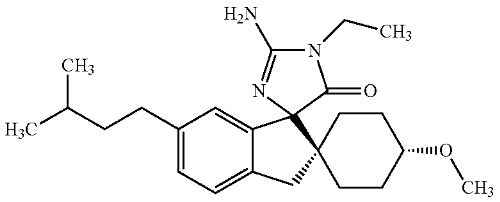 Ex. 410H | $8^b$ |
| 515 | 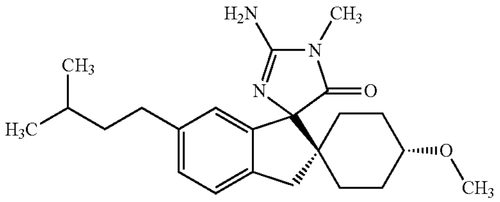 Ex. 410H | $10^b$ |

-continued
| Compound No. | Structure/Ex. No. | $IC_{50}$ (nM) |
|---|---|---|
| 516 | 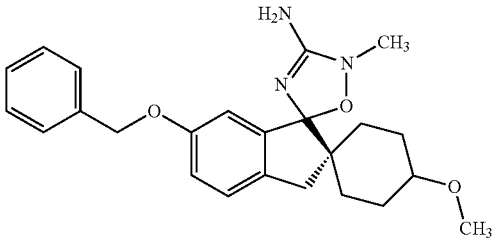 Ex. 410A | 890[b] |
| 517 | 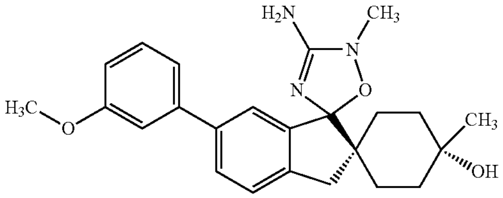 Ex. 410F and 410I | 877.1[b] |
| 518 | 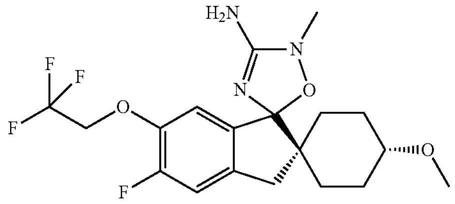 Ex. 410F and 410J | 53[b] |
| 519 | Ex. 411 | |
| 520 | 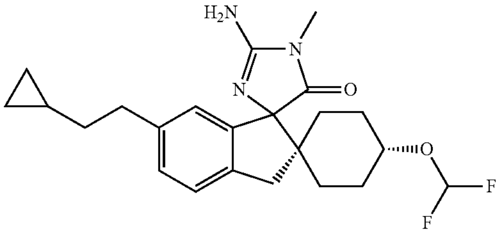 | |
| 521[a] | Ex. 415 | 14[b] |
| 521[b] | Ex. 416 | 691[b] |
| 522 | Ex. 420 | 294[b] |
| 523 | Ex. 420 | 2.4[b] |
| 524 | 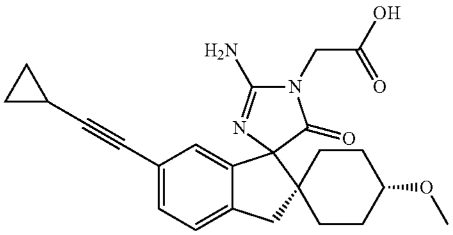 | 5.0[b] |
| 525 | Ex. 431 | 6.8[b] |
| 526 | Ex. 430 | 9.0[b] |
| 527 | Ex. 413 | 16[b] |
| 528 | Ex. 428 | 10[b] |

-continued
| Compound No. | Structure/Ex. No. | $IC_{50}$ (nM) |
|---|---|---|
| 529 | 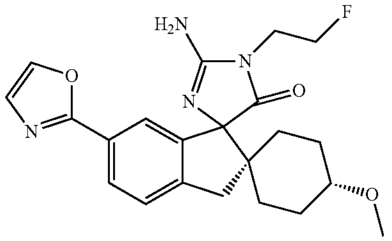 | 128[b] |
| 530 | 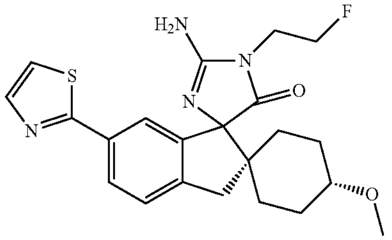 | 115[b] |
| 531 | 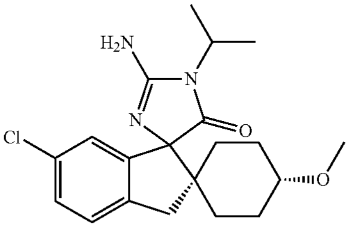 | 169[b] |
| 532 | 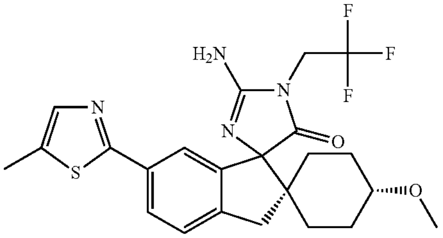 | 320[b] |
| 533 | Ex. 414 | 8.9[b] |
| 534 | 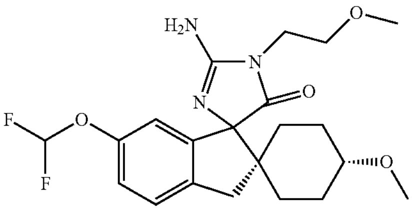 | 128[b] |
| 535 | Ex. 432 | 40[b] |
| 536 | 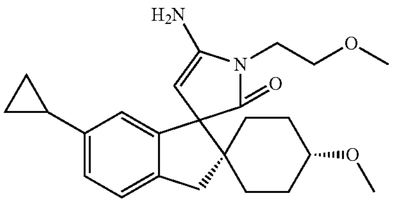 | 172[b] |

-continued
| Compound No. | Structure/Ex. No. | $IC_{50}$ (nM) |
|---|---|---|
| 537 | 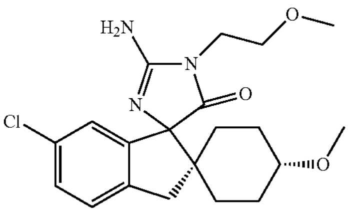 | 88[b] |
| 538 | 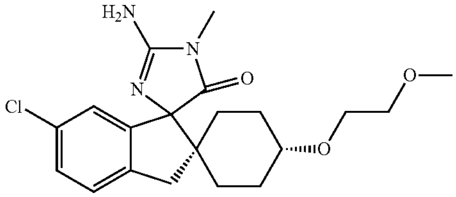 | 614[b] |
| 539 | 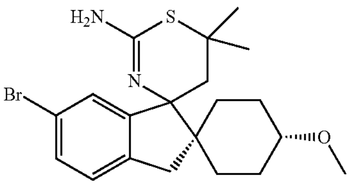 | 2440[b] |
| 540 | 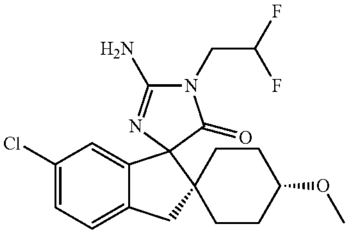 | 138[b] |
| 541 | Ex. 427 | 4.0[b] |
| 542 | 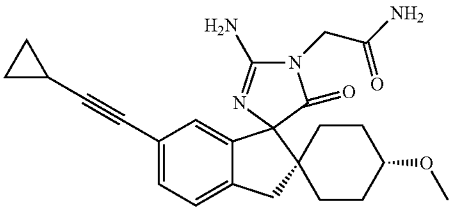 | 11[b] |
| 543 | 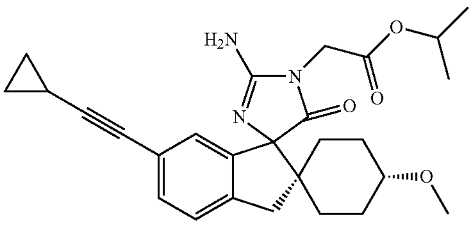 | 4.5[b] |

-continued
| Compound No. | Structure/Ex. No. | $IC_{50}$ (nM) |
| --- | --- | --- |
| 544 | 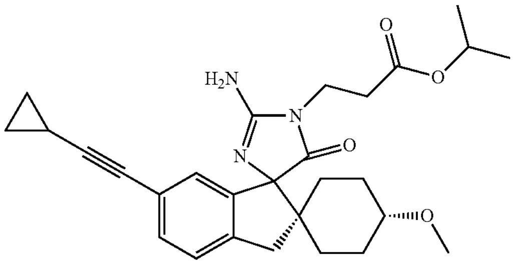 | $21^b$ |
| 545 | 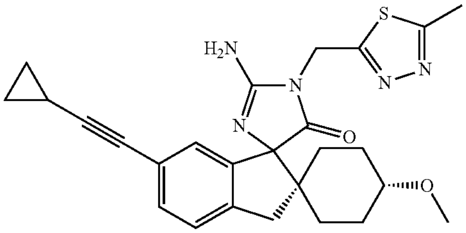 | $9.4^b$ |
| 546 | 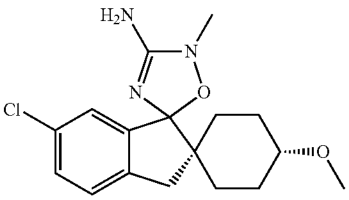 | $212^b$ |
| 547 | 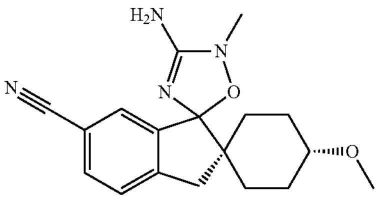 | $157^b$ |
| 548 | 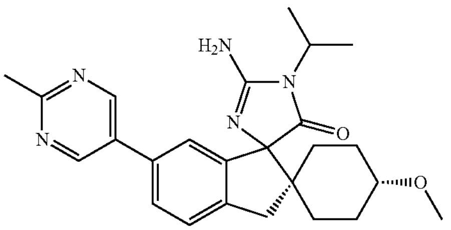 | $23^b$ |
| 549 | 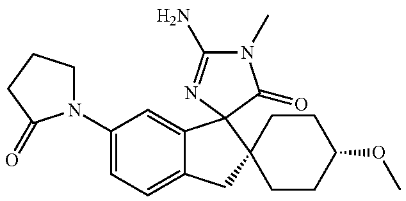 | $110^b$ |

-continued
| Compound No. | Structure/Ex. No. | $IC_{50}$ (nM) |
|---|---|---|
| 550 | 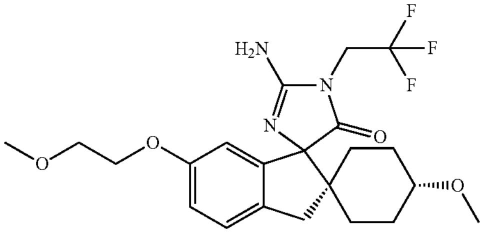 | $77^b$ |
| 551 | Ex. 426 | $12^b$ |
| 552 | 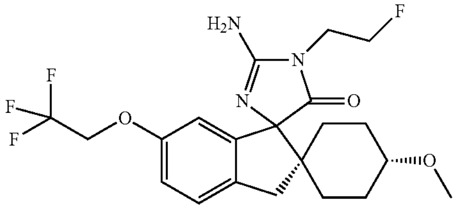 | $25^b$ |
| 553 | 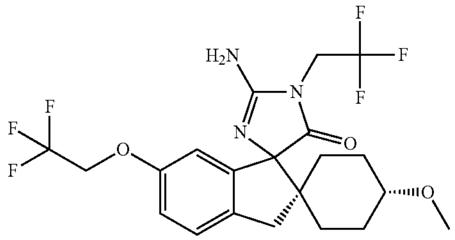 | $34^b$ |
| 554 | Ex. 433 | $30^b$ |
| 555 | 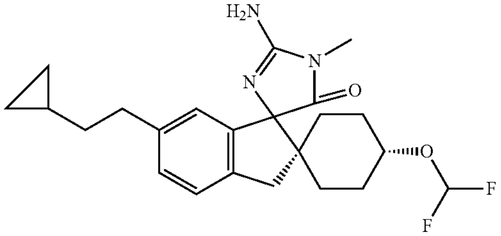 | $149.0^b$ |
| 556 | 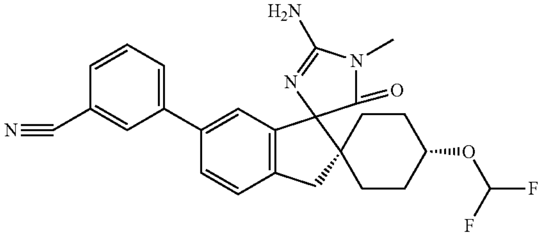 | $176.6^b$ |
| 557 | Ex. 422F | $8^b$ |
| 558 | 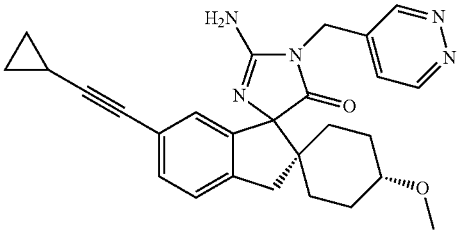 | $4,079.5^b$ |

-continued
| Compound No. | Structure/Ex. No. | $IC_{50}$ (nM) |
|---|---|---|
| 559 | Ex. 419 | $7^b$ |
| 560 | Ex. 419 | $3{,}106.0^b$ |
| 561 | 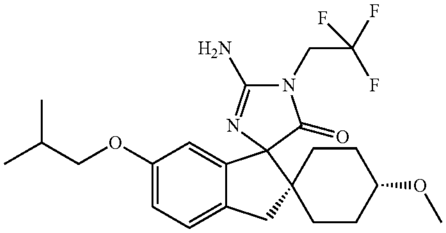 | $11.7^b$ |
| 562 | 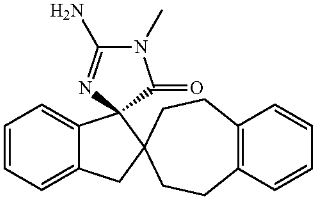 [SMILES: CN1C(=O)[C@@]2(N=C1N)c1ccccc1CC21CCc2ccccc2CC1] | $8{,}052.0^b$ |
| 563 | 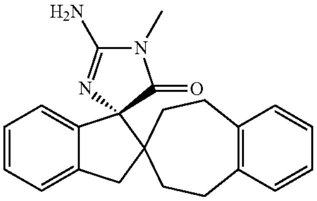 [SMILES: CN1C(=O)[C@]2(N=C1N)c1ccccc1CC21CCc2ccccc2CC1] | $168.7^b$ |
| 564 | 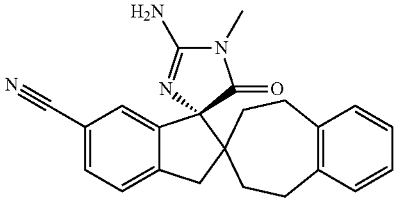 [SMILES: CN1C(=O)[C@]2(N=C1N)c1cc(C#N)ccc1CC21CCc2ccccc2CC1] | $60.0^b$ |
| 565 | 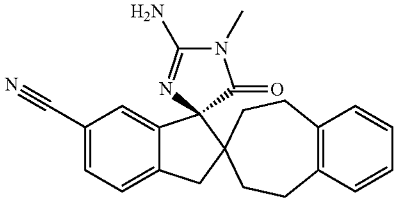 [SMILES: CN1C(=O)[C@@]2(N=C1N)c1cc(C#N)ccc1CC21CCc2ccccc2CC1] | $1{,}452.5^b$ |
| 566 | 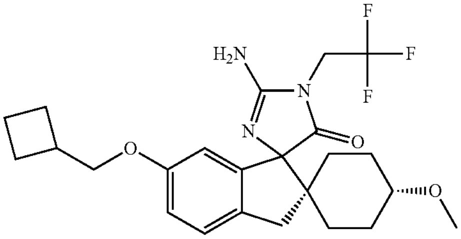 | $134.2^b$ |

-continued
| Compound No. | Structure/Ex. No. | $IC_{50}$ (nM) |
|---|---|---|
| 567 | 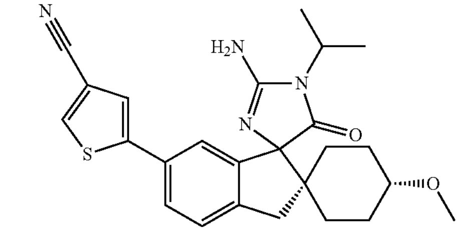 | 250.5[b] |
| 568 | 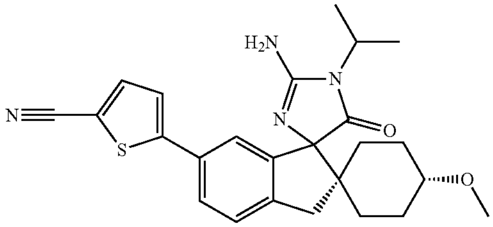 | 546.7[b] |
| 569 | Ex. 418 | 13.2[b] |
| 570 | 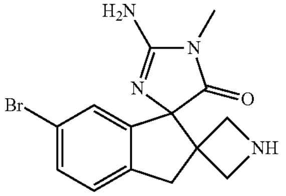 [SMILES: CN1C(=O)C2(N=C1N)c1cc(Br)ccc1CC21CNC1] | 13500[b] |
| 571 | 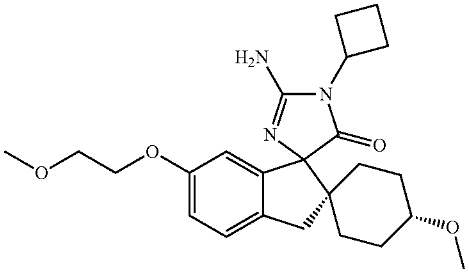 | 111.7[b] |
| 572 | Ex. 429 | 7.0[b] |
| 573 | 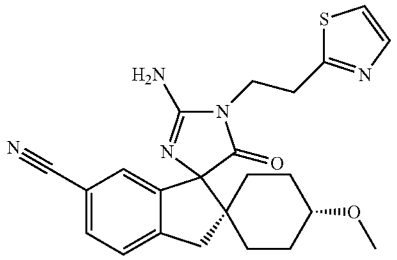 | 57.9[b] |
| 574 | 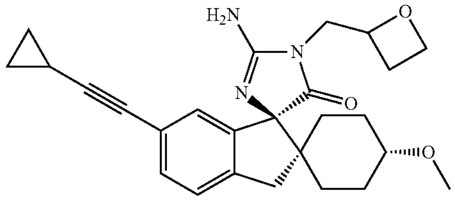 [SMILES: CO[C@H]1CC[C@]2(CC1)Cc1ccc(C#CC3CC3)cc1[C@@]21N=C(N)N(CC2CCO2)C1=O] | 78.6[b] |

-continued
| Compound No. | Structure/Ex. No. | IC$_{50}$ (nM) |
|---|---|---|
| 575 | 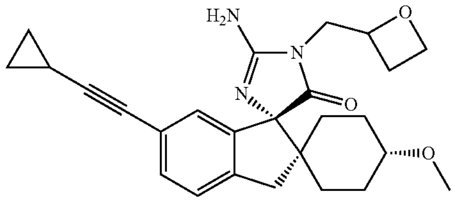 [SMILES: CO[C@H]1CC[C@]2(CC1)Cc1ccc(C#CC3CC3)cc1[C@]21N=C(N)N(CC2CCO2)C1=O] | |
| 576 | 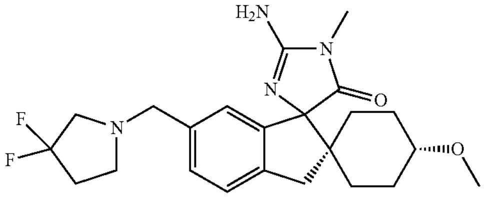 | 108.3[b] |
| 577 | 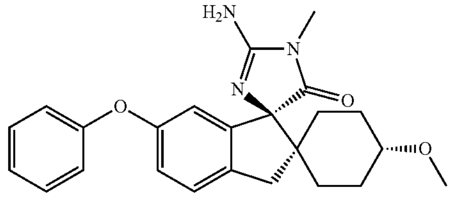 [SMILES: CO[C@H]1CC[C@]2(CC1)Cc1ccc(Oc3ccccc3)cc1[C@@]21N=C(N)N(C)C1=O] | 247.6[b] |
| 578 | 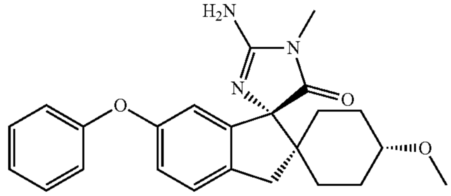 [SMILES: CO[C@H]1CC[C@]2(CC1)Cc1ccc(Oc3ccccc3)cc1[C@]21N=C(N)N(C)C1=O] | 3.9[b] |
| 579 | 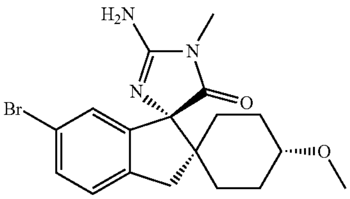 [SMILES: CO[C@H]1CC[C@]2(CC1)Cc1ccc(Br)cc1[C@]21N=C(N)N(C)C1=O] | 15.9[b] |
| 580 | Ex. 421 | 6[b] |
| 581 | Ex. 421 | 181[b] |
| 582 | 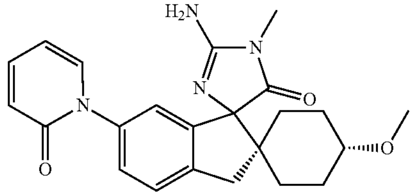 | 457.9[b] |
| 583 | 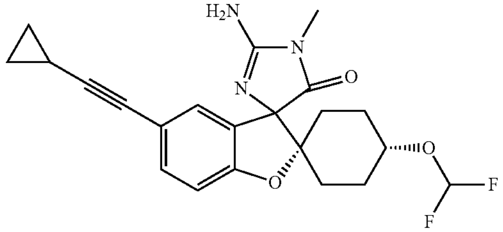 | 267.8[b] |

-continued
| Compound No. | Structure/Ex. No. | $IC_{50}$ (nM) |
|---|---|---|
| 584 | 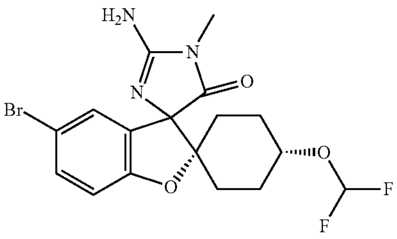 | 423.8[b] |
| 585 | 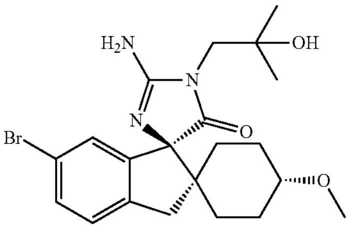 [SMILES: CO[C@H]1CC[C@]2(CC1)Cc1ccc(Br)cc1[C@@]21N=C(N)N(CC(C)(C)O)C1=O] | 4,226.0[b] |
| 586 | 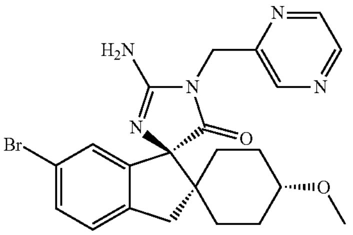 [SMILES: CO[C@H]1CC[C@]2(CC1)Cc1ccc(Br)cc1[C@@]21N=C(N)N(Cc2cnccn2)C1=O] | 2,119.0[b] |
| 587 | 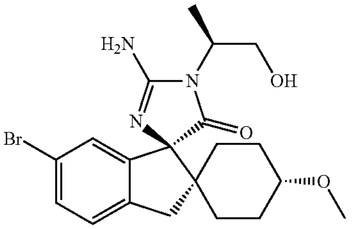 [SMILES: CO[C@H]1CC[C@]2(CC1)Cc1ccc(Br)cc1[C@@]21N=C(N)N([C@@H](C)CO)C1=O] | 13,500.0[b] |
| 588 | 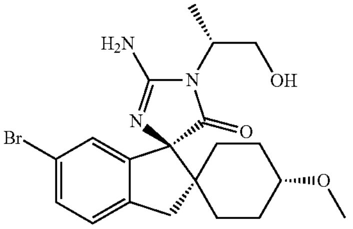 [SMILES: CO[C@H]1CC[C@]2(CC1)Cc1ccc(Br)cc1[C@@]21N=C(N)N([C@H](C)CO)C1=O] | 19,370.0[b] |
| 589 | 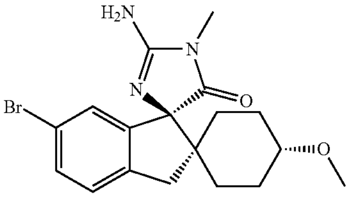 [SMILES: CO[C@H]1CC[C@]2(CC1)Cc1ccc(Br)cc1[C@@]21N=C(N)N(C)C1=O] | 4,509.3[b] |
| 590 | Ex. 425 | |
| 591 | Ex. 412 | |

-continued
| Compound No. | Structure/Ex. No. | $IC_{50}$ (nM) |
|---|---|---|
| 592 | 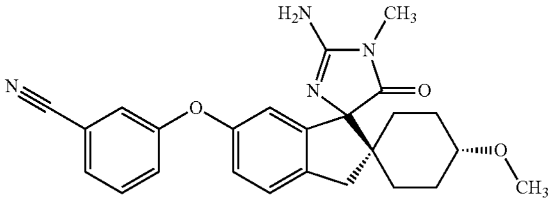 Ex. 410K | $7^b$ |
| 593 | 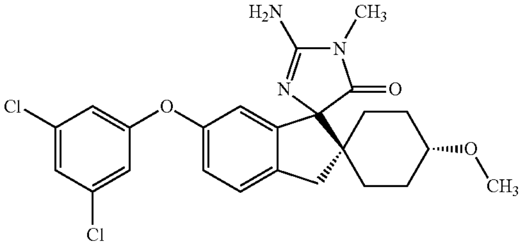 Ex. 410K | $6^b$ |
| 594 | 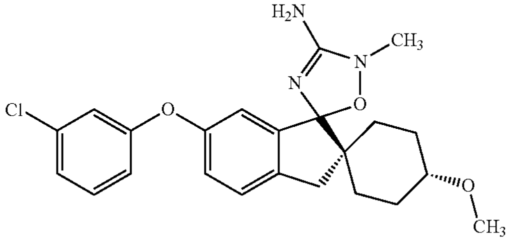 Ex. 410A | $99^b$ |
| 595 | 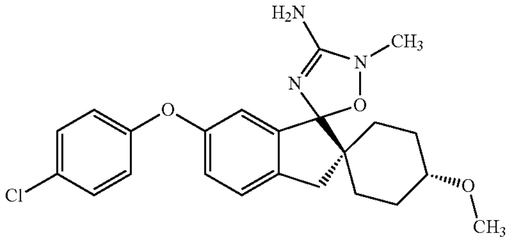 Ex. 410A | $105^b$ |
| 596 | 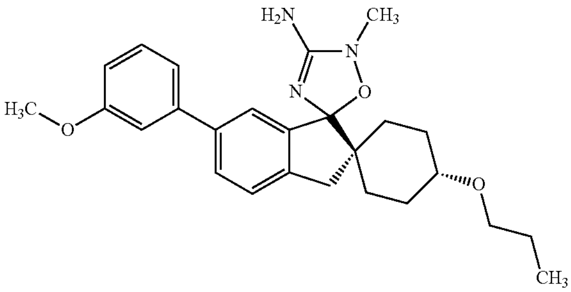 Ex. 410A | $455^b$ |

-continued
| Compound No. | Structure/Ex. No. | $IC_{50}$ (nM) |
| --- | --- | --- |
| 597 | 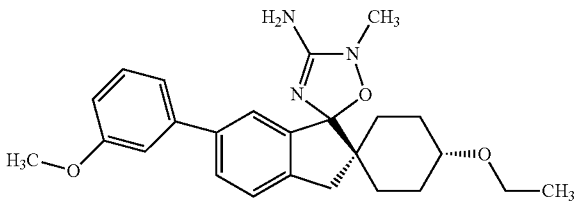 Ex. 410A | $86^b$ |
| 598 | 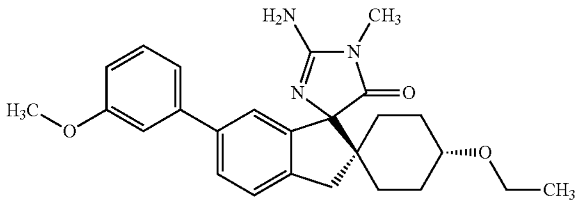 Ex. 410C | $15^b$ |
| 599 | 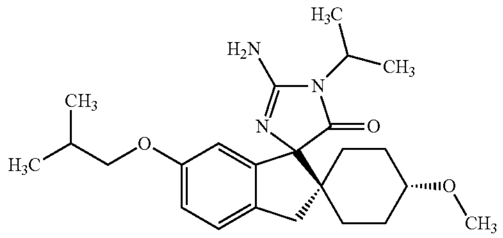 Ex. 410N | $12^b$ |
| 600 | 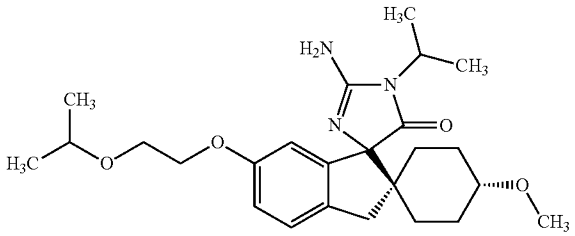 Ex. 410C | $390^b$ |
| 601 | 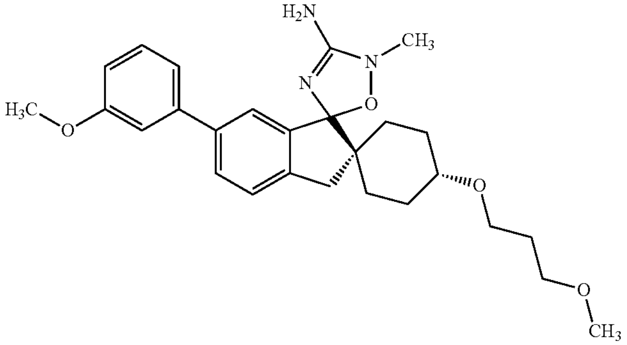 Ex. 410A | $293^b$ |

-continued

| Compound No. | Structure/Ex. No. | $IC_{50}$ (nM) |
|---|---|---|
| 602 | 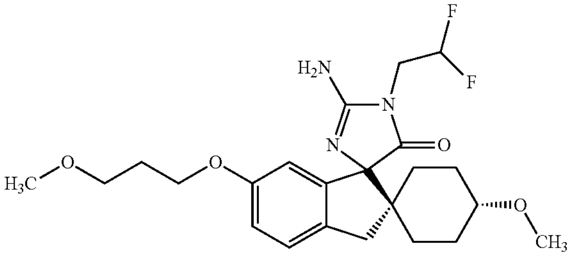<br>Ex. 410C and 410O | 6.2[b] |
| 603 | 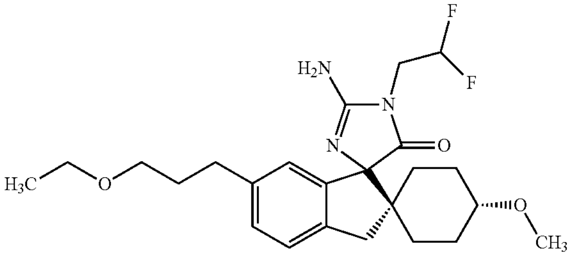<br>Ex. 410B and 410P | 102[b] |
| 604 | 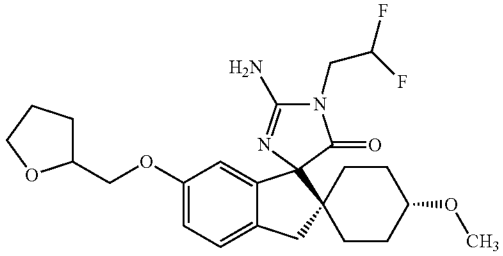<br>Ex. 410C | 31[b] |

[a] $IC_{50}$ values were determined according to protocols described in Example 434A.
[b] $IC_{50}$ values were determined according to protocols described in Example 435.

What is claimed is:

1. A compound represented by the following Structural Formula:

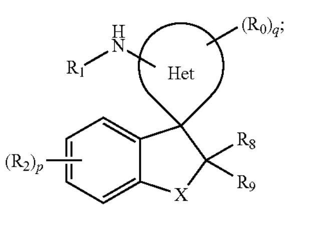

or a pharmaceutically acceptable salt thereof, wherein:

ring Het is a 5 membered monocyclic heterocycle;

X is $—C(R_3R_4)—$;

each $R_0$ is independently selected from —H, =O, =S, $=NR_{15}$, $(C_1-C_6)$alkyl, halo$(C_1-C_6)$alkyl, —CN, $—NO_2$, halogen, $—OR_5$, $—NR_6R_7$, $—S(O)_iR_5$, $—S(O)_iNR_{12}R_{13}$, $—NR_{11}S(O)_iR_5$, $—C(=O)OR_5$, $—OC(=O)OR_5$, $—C(=S)OR_5$, $—O(C=S)R_5$, $—C(=O)NR_{12}R_{13}$, $—NR_{11}C(=O)R_5$, $—C(=S)NR_{12}R_{13}$, $—NR_{11}C(=S)R_5$, $—NR_{11}(C=O)OR_5$, $—O(C=O)NR_{12}R_{13}$, $—NR_{11}(C=S)OR_5$, $—O(C=S)NR_{12}R_{13}$, $—NR_{11}(C=O)NR_{12}R_{13}$, $—C(=S)R_5$, $—C(=O)R_5$, $(C_3-C_8)$cycloalkyl, $(C_3-C_8)$cycloalkyl$(C_1-C_3)$alkyl, $(C_3-C_9)$heterocycloalkyl, $(C_3-C_9)$heterocycloalkyl$(C_1-C_3)$alkyl, aryl, aryl$(C_1-C_6)$alkyl, heteroaryl or heteroaryl$(C_1-C_6)$alkyl, each of the $(C_1-C_6)$alkyl, halo$(C_1-C_6)$alkyl, $(C_3-C_8)$cycloalkyl, $(C_3-C_8)$cycloalkyl$(C_1-C_3)$alkyl, $(C_3-C_9)$heterocycloalkyl, $(C_3-C_9)$heterocycloalkyl$(C_1-C_3)$alkyl, aryl, aryl$(C_1-C_6)$alkyl, heteroaryl or heteroaryl$(C_1-C_6)$alkyl group represented by $R_0$ is optionally substituted with 1 to 5 substituents independently selected from the group consisting of -halogen, —CN, $(C_1-C_6)$alkyl, halo$(C_1-C_6)$alkyl, $(C_1-C_3)$alkoxy, halo$(C_1-C_3)$alkoxy, $(C_1-C_3)$alkoxy$(C_1-C_3)$alkyl, $(C_3-C_8)$cycloalkyl, $(C_3-C_9)$heterocycloalkyl, aryl, heteroaryl, $—NR_6R_7$, $—NR_{11}S(O)_iR_5$, $—C(=O)NR_{12}R_{13}$, $—NR_{11}C(=O)R_5$, $—S(O)_iR_5—$, $—S(O)_iNR_{12}R_{13}$, $—OR_5$, $—C(=O)R_5$, $—C(=S)NR_{12}R_{13}$, $—NR_{11}C(=S)R_5$, $—C(O)OR_5$, $—OC(=O)OR_5$, $—C(=S)OR_5$, $—O(C=S)R_5$, $—O(C=O)NR_{12}R_{13}$, $—NR_{11}(C=O)OR_5$, $—NR_{11}(C=S)OR_5$, $—O(C=S)NR_{12}R_{13}$, $—NR_{11}(C=O)NR_{12}R_{13}$, $—NR_{11}(C=S)NR_{12}R_{13}$ and $—C(=S)R_5$, wherein the cycloalkyl, heterocycloalkyl, aryl and heteroaryl groups in the substituents on the groups represented by $R_0$ are each optionally substituted with 1 to 3 substituents independently selected from halogen, —CN, $(C_1$-$C_6)$alkyl, halo$(C_1$-$C_6)$alkyl, $(C_1$-$C_3)$alkoxy, halo$(C_1$-$C_3)$alkoxy and $(C_1$-$C_3)$alkoxy$(C_1$-$C_6)$alkyl;

$R_1$ is —H, —OH, —$(C_1$-$C_4)$alkoxy, $(C_1$-$C_6)$alkyl, aryl$(C_1$-$C_6)$alkyl, or heteroaryl$(C_1$-$C_6)$alkyl; wherein each alkyl, aryl and heteroaryl is optionally substituted with 1 to 5 substituents independently selected from halogen, —CN, —OH, $(C_1$-$C_4)$alkyl, halo$(C_1$-$C_4)$alkyl, $(C_1$-$C_3)$alkoxy and halo$(C_1$-$C_3)$alkoxy;

each $R_2$ is independently selected from a) —H, -halogen, —CN, —$NO_2$, —$OR_5$, —$NR_6R_7$, —$S(O)_iR_5$, —$NR_{11}S(O)_iR_5$, —$S(O)_iNR_{12}R_{13}$, C(═O)$OR_5$, —OC(═O)$OR_5$, —C(═S)$OR_5$, —O(C═S)$R_5$, —C(═O)$NR_{12}R_{13}$, —$NR_{11}$C(═O)$R_5$, —C(═S)$NR_{12}R_{13}$, —$NR_{11}$C(═S)$R_5$, —$NR_{11}$(C═O)$OR_5$, —O(C═O)$NR_{12}R_{13}$, —$NR_{11}$(C═S)$OR_5$, —O(C═S)$NR_{12}R_{13}$, —$NR_{11}$(C═O)$NR_{12}R_{13}$, —$NR_{11}$(C═S)$NR_{12}R_{13}$, —C(═S)$R_5$, and —C(═O)$R_5$; and b) $(C_1$-$C_6)$alkyl, $(C_2$-$C_6)$alkenyl, $(C_2$-$C_6)$alkynyl, $(C_3$-$C_8)$cycloalkyl, $(C_3$-$C_8)$cycloalkyl$(C_1$-$C_6)$alkyl, $(C_3$-$C_8)$cycloalkyl$(C_2$-$C_6)$alkynyl, $(C_4$-$C_8)$cycloalkenyl, $(C_3$-$C_9)$heterocycloalkyl, $(C_3$-$C_9)$heterocycloalkyl$(C_1$-$C_6)$alkyl, $(C_3$-$C_9)$heterocycloalkyl$(C_2$-$C_6)$alkynyl, aryl, aryl$(C_1$-$C_6)$alkyl, aryl$(C_2$-$C_6)$alkynyl, heteroaryl, heteroaryl$(C_1$-$C_6)$alkyl, and heteroaryl$(C_2$-$C_6)$alkynyl, wherein each of the $(C_1$-$C_6)$alkyl, $(C_2$-$C_6)$alkenyl, $(C_2$-$C_6)$alkynyl, $(C_3$-$C_8)$cycloalkyl, $(C_3$-$C_8)$cycloalkyl$(C_1$-$C_6)$alkyl, $(C_3$-$C_8)$cycloalkyl$(C_2$-$C_6)$alkynyl, $(C_4$-$C_8)$cycloalkenyl, $(C_3$-$C_9)$heterocycloalkyl, $(C_3$-$C_9)$heterocycloalkyl$(C_1$-$C_6)$alkyl, $(C_3$-$C_9)$heterocycloalkyl$(C_2$-$C_6)$alkynyl, aryl, aryl$(C_1$-$C_6)$alkyl, aryl$(C_2$-$C_6)$alkynyl, heteroaryl, heteroaryl$(C_1$-$C_6)$alkyl, and heteroaryl$(C_2$-$C_6)$alkynyl groups represented by $R_2$ is optionally substituted with 1 to 5 substituents independently selected from the group consisting of -halogen, —CN, —$NO_2$, —$OR_5$, —$SR_5$, —$NR_6R_7$, —$S(O)_iR_5$, —$NR_{11}$S(═O)$_iR_5$, —$S(O)_iNR_{12}R_{13}$, —C(═O)$OR_5$, —OC(═O)$R_5$, —C(═S)$OR_5$, —OC(═S)$R_5$, —C(═O)$NR_{12}R_{13}$, —$NR_{11}$C(═O)$R_5$, —C(═S)$NR_{12}R_{13}$, —$NR_{11}$C(═S)$R_5$, —C(═O)$R_5$, —C(═S)$R_5$, —OC(═O)$OR_5$, —O(C═O)$NR_{12}R_{13}$, —$NR_{11}$(C═O)$OR_5$, —$NR_{11}$(C═S)$OR_5$, —O(C═S)$NR_{12}R_{13}$, —$NR_{11}$(C═O)$NR_{12}R_{13}$, —$NR_{11}$(C═S)$NR_{12}R_{13}$, —C(═O)$R_5$, —C(═S)$R_5$, $(C_1$-$C_6)$alkyl, $(C_2$-$C_6)$alkynyl, $(C_3$-$C_8)$cycloalkyl, $(C_4$-$C_8)$cycloalkenyl, $(C_3$-$C_9)$heterocycloalkyl, $(C_2$-$C_6)$alkenyl, halo$(C_1$-$C_6)$alkyl, $(C_1$-$C_3)$alkylsulfonylaminoalkyl, hydroxy$(C_1$-$C_6)$alkyl, cyano$(C_1$-$C_6)$alkyl, $(C_1$-$C_3)$alkylcarbonylamino$(C_1$-$C_6)$alkyl, $(C_1$-$C_3)$alkoxy, halo$(C_1$-$C_3)$alkoxy, $(C_1$-$C_6)$alkoxy$(C_1$-$C_3)$alkyl, aryl and heteroaryl, wherein the cycloalkyl, heterocycloalkyl, aryl and heteroaryl groups in the substituents on the groups represented by $R_2$ are each optionally substituted with 1 to 3 substituents independently selected from halogen, —CN, $(C_1$-$C_6)$alkyl, halo$(C_1$-$C_6)$alkyl, $(C_1$-$C_3)$alkoxy, halo$(C_1$-$C_3)$alkoxy and $(C_1$-$C_3)$alkoxy$(C_1$-$C_6)$alkyl;

$R_3$ and $R_4$ are each independently —H, -halogen, —CN, —$NO_2$, —$OR_5$, —$NR_6R_7$, —$S(O)_iR_5$, —$NR_{11}S(O)_iR_5$, —$S(O)_iNR_{12}R_{13}$, —C(═O)$OR_5$, —OC(═O)$OR_5$, —C(═S)$OR_5$, —O(C═S)$R_5$, —C(═O)$NR_{12}R_{13}$, —$NR_{11}$C(═O)$R_5$, —C(═S)$NR_{12}R_{13}$, —$NR_{11}$C(═S)$R_5$, —$NR_{11}$(C═O)$OR_5$, —O(C═O)$NR_{12}R_{13}$, —$NR_{11}$(C═S)$OR_5$, —O(C═S)$NR_{12}R_{13}$, —$NR_{11}$ (C═O)$NR_{12}R_{13}$, —$NR_{11}$(C═S)$NR_{12}R_{13}$, —C(═S)$R_5$, —C(═O)$R_5$, $(C_1$-$C_6)$alkyl, $(C_2$-$C_6)$alkenyl, $(C_2$-$C_6)$alkynyl, $(C_3$-$C_8)$cycloalkyl, $(C_3$-$C_8)$cycloalkyl$(C_1$-$C_6)$alkyl, $(C_3$-$C_8)$cycloalkyl$(C_2$-$C_6)$alkynyl, $(C_3$-$C_9)$heterocycloalkyl, $(C_3$-$C_9)$heterocycloalkyl$(C_1$-$C_6)$alkyl, $(C_3$-$C_9)$heterocycloalkyl$(C_2$-$C_6)$alkynyl, aryl, aryl$(C_1$-$C_6)$alkyl, aryl$(C_2$-$C_6)$alkynyl, heteroaryl, heteroaryl$(C_1$-$C_6)$alkyl or heteroaryl$(C_1$-$C_6)$alkynyl, wherein each $(C_1$-$C_6)$alkyl, $(C_2$-$C_6)$alkenyl, $(C_2$-$C_6)$alkynyl, $(C_3$-$C_8)$cycloalkyl, $(C_3$-$C_8)$cycloalkyl$(C_1$-$C_6)$alkyl, $(C_3$-$C_8)$cycloalkyl$(C_2$-$C_6)$alkynyl, $(C_3$-$C_9)$heterocycloalkyl, $(C_3$-$C_9)$heterocycloalkyl$(C_1$-$C_6)$alkyl, $(C_3$-$C_9)$heterocycloalkyl$(C_2$-$C_6)$alkynyl, aryl, aryl$(C_1$-$C_6)$alkyl, aryl$(C_2$-$C_6)$alkynyl, heteroaryl, heteroaryl$(C_1$-$C_6)$alkyl or heteroaryl$(C_1$-$C_6)$alkynyl represented by $R_3$ and $R_4$ is optionally substituted with 1 to 5 substituents independently selected from the group consisting of halogen, —$OR_5$, —$NR_6R_7$, —$S(O)_iR_5$, —$NR_{11}S(O)_iR_5$, —$S(O)_iNR_{12}R_{13}$, —C(═O)$OR_5$, —OC(═O)$OR_5$, —C(═S)$OR_5$, —O(C═S)$R_5$, —C(═O)$NR_{12}R_{13}$, —$NR_{11}$C(═O)$R_5$, —C(═S)$NR_{12}R_{13}$, —$NR_{11}$C(═S)$R_5$, —$NR_{11}$(C═O)$OR_5$, —O(C═O)$NR_{12}R_{13}$, —$NR_{11}$(C═S)$OR_5$, —O(C═S)$NR_{12}R_{13}$, —$NR_{11}$(C═O)$NR_{12}R_{13}$, —$NR_{11}$(C═S)$NR_{12}R_{13}$, —C(═S)$R_5$, —C(═O)$R_5$, $(C_1$-$C_6)$alkyl, $(C_2$-$C_6)$alkenyl, halo$(C_1$-$C_6)$alkyl, $(C_1$-$C_3)$alkylsulfonylaminoalkyl, hydroxy$(C_1$-$C_6)$alkyl, cyano$(C_1$-$C_6)$alkyl, $(C_1$-$C_3)$alkylcarbonylamino$(C_1$-$C_6)$alkyl, $(C_1$-$C_3)$alkoxy, halo$(C_1$-$C_3)$alkoxy, $(C_1$-$C_6)$alkoxy$(C_1$-$C_3)$alkyl, $(C_3$-$C_8)$cycloalkyl, $(C_3$-$C_9)$heterocycloalkyl, aryl and heteroaryl, wherein the cycloalkyl, heterocycloalkyl, aryl and heteroaryl groups in the substituents on the groups represented by $R_3$ and $R_4$ are each optionally substituted with 1 to 3 substituents independently selected from halogen, —CN, $(C_1$-$C_6)$alkyl, halo$(C_1$-$C_6)$alkyl, $(C_1$-$C_3)$alkoxy, halo$(C_1$-$C_3)$alkoxy and $(C_1$-$C_3)$alkoxy$(C_1$-$C_6)$alkyl;

$R_5$ is —H, $(C_1$-$C_6)$alkyl, halo$(C_1$-$C_6)$alkyl, $(C_2$-$C_6)$alkenyl, $(C_2$-$C_6)$alkynyl, $(C_1$-$C_3)$alkoxy$(C_1$-$C_6)$alkyl, $(C_3$-$C_8)$cycloalkyl, $(C_3$-$C_8)$cycloalkyl$(C_1$-$C_6)$alkyl, $(C_3$-$C_9)$heterocycloalkyl, $(C_3$-$C_9)$heterocycloalkyl$(C_1$-$C_6)$alkyl, aryl, aryl$(C_1$-$C_6)$alkyl, heteroaryl or heteroaryl$(C_1$-$C_6)$alkyl, each of the alkyl, alkenyl, alkynyl, cycloalkyl, heterocycloalkyl, aryl and heteroaryl in the groups represented by $R_5$ is optionally substituted with 1 to 5 substituents independently selected from the group consisting of halogen, ═O, —$NR_6$C(═NH)$NR_6R_7$, —C(═O)$OR_c$, —$OR_c$, —$SR_c$, —C(═O)$NR_6R_7$, —C(═O)$R_c$, —$S(O)_iR_c$, —$NO_2$, —CN, $(C_1$-$C_6)$alkyl, halo$(C_1$-$C_6)$alkyl, $(C_1$-$C_3)$alkoxy$(C_1$-$C_6)$alkyl, $(C_1$-$C_3)$alkoxy, halo$(C_1$-$C_3)$alkoxy and —$NR_6R_7$;

$R_c$ is —H, $(C_1$-$C_3)$alkyl, halo$(C_1$-$C_3)$alkyl or $(C_1$-$C_3)$alkoxy$(C_1$-$C_3)$alkyl;

$R_6$ and $R_7$ are each independently —H, $(C_1$-$C_6)$alkyl, hydroxy$(C_1$-$C_6)$alkyl, halo$(C_1$-$C_6)$alkyl, $(C_3$-$C_8)$cycloalkyl, $(C_3$-$C_8)$cycloalkyl$(C_1$-$C_6)$alkyl, $(C_3$-$C_9)$heterocycloalkyl, $(C_3$-$C_9)$heterocycloalkyl$(C_1$-$C_6)$alkyl, aryl, aryl$(C_1$-$C_6)$alkyl, heteroaryl, or heteroaryl$(C_1$-$C_6)$alkyl, all of which are optionally substituted with 1 to 3 substituents independently selected from the group consisting of halogen, —CN, $(C_1$-$C_6)$alkyl, halo($C_1$-$C_6$)alkyl, ($C_1$-$C_3$)alkoxy, halo($C_1$-$C_3$)alkoxy and ($C_1$-$C_3$)alkoxy($C_1$-$C_6$)alkyl;

$R_8$ and $R_9$, together with the carbon to which they are attached, form ring A, which is a 3-14 membered monocyclic ring, wherein ring A optionally contains 1 to 3 heteroatoms independently selected from O, N, and S and when the heteroatom is nitrogen, the nitrogen is substituted with —H, ($C_1$-$C_3$)alkyl or halo($C_1$-$C_3$)alkyl, and when the heteroatom is sulfur, the sulfur is optionally mono or di-oxygenated; and ring A is optionally substituted with 1 to 4 substituents independently selected from the group consisting of halogen, —CN, —$OR_5$, —$NR_6R_7$, —$S(O)_iR_5$, —$NR_{11}S(O)_iR_5$, —$S(O)_iNR_{12}R_{13}$, —C(═O)$OR_5$, —OC(═O)$OR_5$, —C(═S)$OR_5$, —O(C═S)$R_5$, —C(═O)$NR_{12}R_{13}$, —$NR_{11}$C(═O)$R_5$, —C(═S)$NR_{12}R_{13}$, —$NR_{11}$C(═S)$R_5$, —$NR_{11}$(C═O)$OR_5$, —O(C═O)$NR_{12}R_{13}$, —$NR_{11}$(C═S)$OR_5$, —O(C═S)$NR_{12}R_{13}$, —$NR_{11}$(C═O)$NR_{12}R_{13}$, —$NR_{11}$(C═S)$NR_{12}R_{13}$, —C(═S)$R_5$, —C(═O)$R_5$, ($C_1$-$C_6$)alkyl, ($C_2$-$C_6$)alkenyl, halo($C_1$-$C_6$)alkyl, ($C_1$-$C_3$)alkylsulfonylamino($C_1$-$C_6$)alkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkynyl, aryl, aryl($C_1$-$C_6$)alkyl, aryl($C_2$-$C_6$)alkynyl, heteroaryl, heteroaryl($C_1$-$C_6$)alkyl, and heteroaryl($C_2$-$C_6$)alkynyl, wherein the cycloalkyl, heterocycloalkyl, aryl and heteroaryl groups in the substituents on ring A are each optionally substituted with 1 to 3 substituents independently selected from halogen, —CN, ($C_1$-$C_6$)alkyl, halo($C_1$-$C_6$)alkyl, ($C_1$-$C_3$)alkoxy, halo($C_1$-$C_3$)alkoxy and ($C_1$-$C_3$)alkoxy($C_1$-$C_6$)alkyl;

$R_{11}$ is —H or ($C_1$-$C_6$)alkyl, wherein ($C_1$-$C_6$)alkyl is optionally substituted with 1 to 5 substituents independently selected from halogen, CN, ($C_1$-$C_6$)alkoxy, ($C_2$-$C_6$)alkynyl, ($C_3$-$C_8$)cycloalkyl, ($C_3$-$C_9$)heterocycloalkyl, aryl and heteroaryl, wherein the ($C_1$-$C_6$)alkoxy, ($C_2$-$C_6$)alkynyl, ($C_3$-$C_8$)cycloalkyl, ($C_3$-$C_9$)heterocycloalkyl, aryl and heteroaryl groups are each optionally substituted with 1 to 3 substituents independently selected from the group consisting of halogen, —CN, ($C_1$-$C_6$)alkyl, halo($C_1$-$C_6$)alkyl, ($C_1$-$C_3$)alkoxy, halo($C_1$-$C_3$)alkoxy and ($C_1$-$C_3$)alkoxy($C_1$-$C_6$)alkyl;

$R_{12}$ and $R_{13}$ are each independently —H, ($C_1$-$C_6$)alkyl, halo($C_1$-$C_6$)alkyl, ($C_1$-$C_3$)alkoxy($C_1$-$C_6$)alkyl, hydroxy($C_1$-$C_6$)alkyl, cyano($C_1$-$C_6$)alkyl, amino($C_1$-$C_6$)alkyl, ($C_1$-$C_3$)alkylamino($C_1$-$C_6$)alkyl, di($C_1$-$C_3$)alkylamino($C_1$-$C_6$)alkyl, ($C_3$-$C_8$)cycloalkyl, ($C_3$-$C_8$)cycloalkyl($C_1$-$C_6$)alkyl, ($C_3$-$C_9$)heterocycloalkyl, ($C_3$-$C_9$)heterocycloalkyl($C_1$-$C_6$)alkyl, aryl, aryl($C_1$-$C_6$)alkyl, heteroaryl or heteroaryl($C_1$-$C_6$)alkyl, wherein the ($C_3$-$C_8$)cycloalkyl, ($C_3$-$C_8$)cycloalkyl($C_1$-$C_6$)alkyl, ($C_3$-$C_9$)heterocycloalkyl, ($C_3$-$C_9$)heterocycloalkyl($C_1$-$C_6$)alkyl, aryl, aryl($C_1$-$C_6$)alkyl, heteroaryl and heteroaryl($C_1$-$C_6$)alkyl group is optionally substituted with 1 to 3 substituents independently selected from the group consisting of -halogen, —CN, ($C_1$-$C_6$)alkyl, halo($C_1$-$C_6$)alkyl, ($C_1$-$C_3$)alkoxy, halo($C_1$-$C_3$)alkoxy and ($C_1$-$C_3$)alkoxy($C_1$-$C_6$)alkyl;

or $R_{12}$ and $R_{13}$, together with the nitrogen to which they are attached, form a 3-8 membered ring optionally substituted with 1 to 3 substituents independently selected from the group consisting of halogen, —CN, —$OR_5$, —$NR_6R_7$, —$S(O)_iR_5$, —$S(O)_iNR_{12}R_{13}$, —$NR_{11}S(O)_iR_5$, —C(═O)$OR_5$, —OC(═O)$OR_5$, —C(═S)$OR_5$, —O(C═S)$R_5$, —C(═O)$NR_6R_7$, —$NR_{11}$C(═O)$R_5$, —C(═S)$NR_6R_7$, —$NR_{11}$C(═S)$R_5$, —NR (C═O)$OR_5$, —O(C═O)$NR_6R_7$, —$NR_{11}$(C═S)$OR_5$, —O(C═S)$NR_6R_7$, —$NR_{11}$(C═O)$NR_6R_7$, —$NR_{11}$(C═S)$NR_6R_7$, —C(═S)$R_5$, —C(═O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy and ($C_1$-$C_6$)alkoxy($C_1$-$C_3$)alkyl, wherein the 3-8 membered ring optionally contains 1 to 3 additional heteroatoms, which are independently selected from O, N and S, wherein when the additional heteroatom is nitrogen, the nitrogen is substituted with —H, ($C_1$-$C_3$)alkyl or halo($C_1$-$C_3$)alkyl, and when the additional heteroatom is sulfur, the sulfur is optionally mono or di-oxygenated;

$R_{15}$ is —H or ($C_1$-$C_6$)alkyl optionally substituted with 1 to 5-F;

i is 0, 1 or 2;

p is 1, 2, 3 or 4; and q is 1, 2 or 3.

2. The compound of claim 1, wherein the compound is represented by the following Structural Formula:

(I)

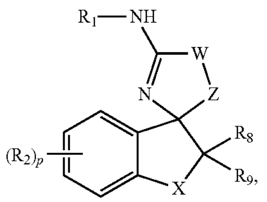

or a pharmaceutically acceptable salt thereof, wherein:

X is —C($R_3R_4$)—;

W is —N($R_{14}$)—, —S—, or —O—;

Z is —C(═O)—, —C(═S)—, —C(═$NR_{15}$)—, —O—, —N($R_{18}$)—, or —$(CR_{16}R_{17})_m$, provided when W is —S— or —O—, Z is not —O—;

$R_1$ is —H, ($C_1$-$C_6$)alkyl, aryl($C_1$-$C_6$)alkyl, or heteroaryl($C_1$-$C_6$)alkyl;

each $R_2$ is independently selected from a) —H, -halogen, —CN, —$NO_2$, —$OR_5$, —$NR_6R_7$, —$S(O)_iR_5$, —C(═O)$OR_5$, —C(═O)$NR_{12}R_{13}$, and —C(═O)$R_5$; and b) ($C_1$-$C_6$)alkyl, ($C_2$-$C_6$)alkenyl, ($C_2$-$C_6$)alkynyl, ($C_3$-$C_8$)cycloalkyl, aryl, heteroaryl, phenoxy, and benzyloxy, each of which is optionally substituted with 1 to 3 substituents selected from the group consisting of —F, —Cl, —Br, —CN, —$OR_5$, —$SR_5$, —$NR_6R_7$, —$S(O)_iR_5$, —$NR_{11}$S(═O)$_iR_5$, —C(═O)$OR_5$, —C(═O)$NR_{12}R_{13}$, —$NR_{11}$C(═O)$R_5$, —C(═S)$NR_{12}R_{13}$, —C(═O)$R_5$, ($C_1$-$C_6$)alkyl, ($C_3$-$C_8$)cycloalkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl;

$R_3$ and $R_4$ are each independently —H, -halogen, —CN, —$NO_2$, —$OR_5$, —$NR_6R_7$, —$S(O)_iR_5$, —C(═O)$OR_5$, —C(═O)$NR_{12}R_{13}$, —C(═O)$R_5$, ($C_1$-$C_6$)alkyl, ($C_2$-$C_6$)alkenyl, ($C_2$-$C_6$)alkynyl, ($C_3$-$C_8$)cycloalkyl, aryl, or heteroaryl, wherein each ($C_1$-$C_6$)alkyl, ($C_2$-$C_6$)alkenyl, ($C_2$-$C_6$)alkynyl, ($C_3$-$C_8$)cycloalkyl, aryl, or heteroaryl is optionally substituted with 1 to 3 substituents independently selected from the group consisting of —F, —Cl, —Br, —CN, —$OR_5$, —$NR_6R_7$, —$S(O)_iR_5$, —$NR_{11}S(═O)_i$ $R_5$, —C(═O)$OR_5$, —C(═O)$NR_{12}R_{13}$, —$NR_{11}C$(═O)$R_5$, —C(═S)$NR_{12}R_{13}$, —C(═O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl;

$R_5$ is —H, ($C_1$-$C_6$)alkyl, halo($C_1$-$C_6$)alkyl, ($C_2$-$C_6$)alkenyl, ($C_2$-$C_6$)alkynyl, ($C_1$-$C_3$)alkoxy($C_1$-$C_6$)alkyl, ($C_3$-$C_8$)cycloalkyl, ($C_3$-$C_8$)cycloalkyl($C_1$-$C_6$)alkyl, ($C_3$-$C_7$) cycloheteroalkyl, aryl, heteroaryl or benzyl, each of which is optionally substituted with 1 to 3 substituents independently selected from the group consisting of —F, —Cl, —Br, —CN, ($C_1$-$C_6$)alkyl, halo($C_1$-$C_6$)alkyl, and ($C_1$-$C_3$)alkoxy($C_1$-$C_6$)alkyl;

$R_6$ and $R_7$ are each independently —H, ($C_1$-$C_6$)alkyl, hydroxy($C_1$-$C_6$)alkyl, halo($C_1$-$C_6$)alkyl, ($C_3$-$C_8$)cycloalkyl, ($C_3$-$C_8$)cycloalkyl($C_1$-$C_6$)alkyl, each of which is optionally substituted with 1 to 3 substituents independently selected from the group consisting of —F, —Cl, —Br, —CN, ($C_1$-$C_6$)alkyl, halo($C_1$-$C_6$)alkyl and ($C_1$-$C_3$)alkoxy($C_1$-$C_6$)alkyl;

$R_8$ and $R_9$, together with the carbon to which they are attached, form ring A, which is a 3-14 membered monocyclic ring, wherein ring A is optionally substituted with 1 to 4 substituents independently selected from the group consisting of —F, —Cl, —Br, —CN, —$OR_5$, —$NR_6R_7$, —$S(O)_iR_5$, —$NR^{11}S(═O)_iR_5$, —C(═O)$OR_5$, —$NR_{11}C$(═O)$NR_{12}R_{13}$, —$NR_{11}C$(═O)$R_5$, —C(═S)$NR_{12}R_{13}$, —C(═O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl;

$R_{11}$ is —H, or ($C_1$-$C_6$)alkyl;

$R_{12}$ and $R_{13}$ are each independently —H, ($C_1$-$C_6$)alkyl, ($C_1$-$C_3$)alkoxy($C_1$-$C_6$)alkyl, hydroxy($C_1$-$C_6$)alkyl, cyano($C_1$-$C_6$)alkyl, amino($C_1$-$C_6$)alkyl, ($C_1$-$C_3$)alkylamino($C_1$-$C_6$)alkyl, or di($C_1$-$C_3$)alkylamino($C_1$-$C_6$)alkyl;

or $R_{12}$ and $R_{13}$, together with the nitrogen to which they are attached, form a 3-8 membered ring optionally substituted with 1 to 3 substituents independently selected from the group consisting of —F, —Cl, —Br, —CN, —$OR_5$, —$NR_6R_7$, —$S(O)_iR_5$, —$NR_{11}S(═O)_iR_5$, —C(═O)$OR_5$, —C(═O)$NR_{12}R_{13}$, —$NR_{11}C$(═O)$R_5$, —C(═S)$NR_{12}R_{13}$, —C(═O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy and ($C_1$-$C_6$)alkoxy($C_1$-$C_3$)alkyl, wherein the 3-8 membered ring optionally contains 1 to 3 additional heteroatoms, which are independently selected from O, N and S, wherein when the additional heteroatom is nitrogen, the nitrogen is substituted with —H, ($C_1$-$C_3$)alkyl or halo($C_1$-$C_3$)alkyl, and when the additional heteroatom is sulfur, the sulfur is optionally mono or di-oxygenated;

$R_{14}$ is —H, ($C_1$-$C_6$)alkyl, halo($C_1$-$C_6$)alkyl, ($C_3$-$C_8$)cycloalkyl, cycloheteroalkyl($C_1$-$C_3$)alkyl, ($C_3$-$C_8$)cycloalkyl($C_1$-$C_3$)alkyl, aryl($C_1$-$C_6$)alkyl, heteroaryl($C_1$-$C_6$)alkyl, each of which is optionally substituted with 1 to 3 substituents independently selected from the group consisting of —F,–Cl, —CN, ($C_1$-$C_6$)alkyl, halo($C_1$-$C_6$)alkyl and ($C_1$-$C_3$)alkoxy;

$R_{15}$ is —H or ($C_1$-$C_6$)alkyl;

$R_{16}$ and $R_{17}$ are each independently —H or ($C_1$-$C_3$)alkyl;

$R_{18}$ is —H or ($C_1$-$C_3$)alkyl;

i is 0, 1 or 2;

p is 1 or 2; and m is 1.

3. The compound of claim 1, wherein the compound is represented by any one of the following Structural Formulas:

(Va)

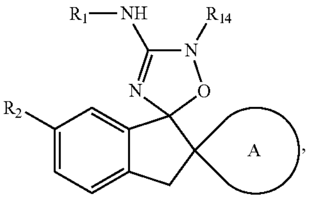

, (VIa)

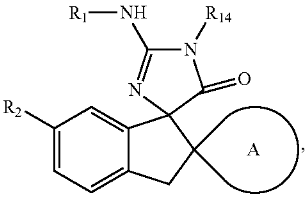

, or (VIIa)

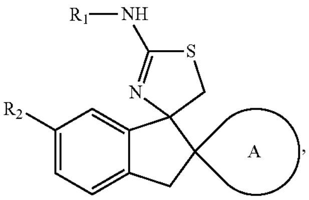

, wherein $R_{14}$ is —H, ($C_1$-$C_6$)alkyl, halo($C_1$-$C_6$)alkyl, ($C_3$-$C_8$)cyclo alkyl, ($C_3$-$C_9$)cycloheteroalkyl($C_1$-$C_3$)alkyl, ($C_3$-$C_8$)cycloalkyl($C_1$-$C_3$)alkyl, aryl($C_1$-$C_6$)alkyl, heteroaryl($C_1$-$C_6$)alkyl, each of which is optionally substituted with 1 to 3 substituents independently selected from the group consisting of —F, —Cl, —CN, ($C_1$-$C_6$)alkyl, halo($C_1$-$C_6$)alkyl and ($C_1$-$C_3$)alkoxy, or a pharmaceutically acceptable salt thereof.

4. The compound of claim 1, wherein the compound is represented by the following Structural Formulas:

(XXIIIa)

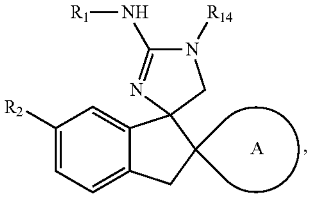

wherein $R_{14}$ is —H, $(C_1\text{-}C_6)$alkyl, halo$(C_1\text{-}C_6)$alkyl, $(C_3\text{-}C_8)$cycloalkyl, $(C_3\text{-}C_9)$cycloheteroalkyl$(C_1\text{-}C_3)$alkyl, $(C_3\text{-}C_8)$cycloalkyl$(C_1\text{-}C_3)$alkyl, aryl$(C_1\text{-}C_6)$alkyl, heteroaryl$(C_1\text{-}C_6)$alkyl, each of which is optionally substituted with 1 to 3 substituents independently selected from the group consisting of —F, —Cl, —CN, $(C_1\text{-}C_6)$alkyl, halo$(C_1\text{-}C_6)$alkyl and $(C_1\text{-}C_3)$alkoxy, or a pharmaceutically acceptable salt thereof.

5. The compound of claim 3, wherein ring A is a 5-7 membered monocyclic ring optionally substituted with 1 to 3 substituents independently selected from the group consisting of —F, —Cl, —Br, —CN, $—OR_5$, $—NR_6R_7$, $—S(O)_iR_5$, $—NR_{11}S({=}O)_iR_5$, $—C({=}O)OR_5$, $—C({=}O)NR_{12}R_{13}$, $—NR_{11}C({=}O)R_5$, $—C({=}S)NR_{12}R_{13}$, $—C({=}O)R_5$, $(C_1\text{-}C_6)$alkyl, $(C_2\text{-}C_6)$alkenyl, halo$(C_1\text{-}C_6)$alkyl, $(C_1\text{-}C_3)$alkylsulfonylaminoalkyl, hydroxy$(C_1\text{-}C_6)$alkyl, cyano$(C_1\text{-}C_6)$alkyl, $(C_1\text{-}C_3)$alkylcarbonylamino$(C_1\text{-}C_6)$alkyl, $(C_1\text{-}C_3)$alkoxy, halo$(C_1\text{-}C_3)$alkoxy, $(C_1\text{-}C_6)$alkoxy$(C_1\text{-}C_3)$alkyl, aryl and heteroaryl, wherein ring A contains 0 to 2 heteroatoms, which are independently selected from O, N and S.

6. The compound of claim 5, wherein ring A is selected from the group consisting of tetrahydrofuran, tetrahydropyran, cyclopentane, cyclohexane, cyclohexene, cycloheptane, oxepane, 1,3-dioxane, and piperidine, each of which is optionally substituted with 1 to 3 substituents independently selected from the group consisting of —F, —Cl, —Br, —CN, $(C_1\text{-}C_6)$alkyl, halo$(C_1\text{-}C_6)$alkyl, hydroxy$(C_1\text{-}C_6)$alkyl, $(C_1\text{-}C_3)$alkoxy, halo$(C_1\text{-}C_3)$alkoxy and phenyl.

7. The compound of claim 6, wherein $R_2$ is a pyridinyl, thiophenyl, pyrrolyl or pyrimidinyl, each of which is optionally substituted with 1 to 3 substituents independently selected from the group consisting of halogen, —CN, $(C_1\text{-}C_6)$alkyl, $(C_3\text{-}C_8)$cycloalkyl, halo$(C_1\text{-}C_6)$alkyl, $(C_1\text{-}C_3)$alkoxy, halo$(C_1\text{-}C_3)$alkoxy and $(C_1\text{-}C_6)$alkoxy$(C_1\text{-}C_3)$alkyl.

8. The compound of claim 3, wherein the compound is represented by any one of the following Structural Formula:

(Vb)

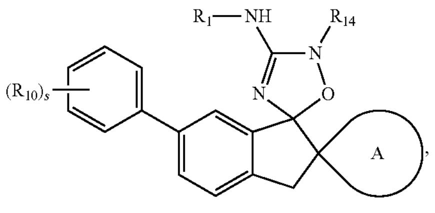

(VIb)

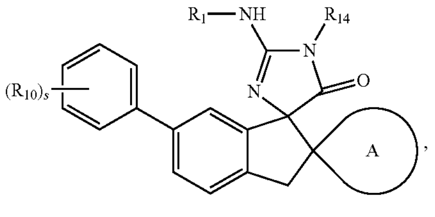

and

-continued (VIIb)

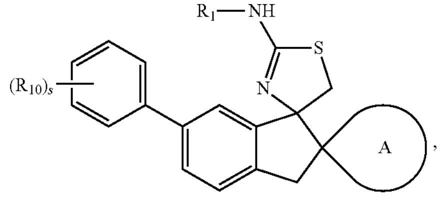

or a pharmaceutically acceptable salt thereof, wherein $R_{10}$ is independently selected from the group consisting of -halogen, —CN, $—NO_2$, $—OR_5$, $—SR_5$, $—NR_6R_7$, $—S(O)_iR_5$, $—NR_{11}S({=}O)_iR_5$, $—S(O)_iNR_{12}R_{13}$, $—C({=}O)OR_5$, $—OC({=}O)R_5$, $—C({=}S)OR_5$, $—OC({=}S)R_5$, $—C({=}O)NR_{12}R_{13}$, $—NR_{11}C({=}O)R_5$, $—C({=}S)NR_{12}R_{13}$, $—NR_{11}C({=}S)R_5$, $—C({=}O)R_5$, $—C({=}S)R_5$, $—OC({=}O)OR_5$, $—O(C{=}O)NR_{12}R_{13}$, $—NR_{11}(C{=}O)OR_5$, $—NR_{11}(C{=}S)OR_5$, $—O(C{=}S)NR_{12}R_{13}$, $—NR_{11}(C{=}O)NR_{12}R_{13}$, $—NR_{11}(C{=}S)NR_{12}R_{13}$, $—C({=}O)R_5$, $—C({=}S)R_5$, $(C_1\text{-}C_6)$alkyl, $(C_2\text{-}C_6)$alkynyl, $(C_3\text{-}C_8)$cycloalkyl, $(C_4\text{-}C_8)$cycloalkenyl, $(C_3\text{-}C_9)$heterocycloalkyl, $(C_2\text{-}C_6)$alkenyl, halo$(C_1\text{-}C_6)$alkyl, $(C_1\text{-}C_3)$alkylsulfonylaminoalkyl, hydroxy$(C_1\text{-}C_6)$alkyl, cyano$(C_1\text{-}C_6)$alkyl, $(C_1\text{-}C_3)$alkylcarbonylamino$(C_1\text{-}C_6)$alkyl, $(C_1\text{-}C_3)$alkoxy, halo$(C_1\text{-}C_3)$alkoxy, $(C_1\text{-}C_6)$alkoxy$(C_1\text{-}C_3)$alkyl, aryl and heteroaryl, wherein the cycloalkyl, heterocycloalkyl, aryl and heteroaryl groups in the groups represented by $R_{10}$ are each optionally substituted with 1 to 3 substituents independently selected from halogen, —CN, $(C_1\text{-}C_6)$alkyl, halo$(C_1\text{-}C_6)$alkyl, $(C_1\text{-}C_3)$alkoxy, halo$(C_1\text{-}C_3)$alkoxy and $(C_1\text{-}C_3)$alkoxy$(C_1\text{-}C_6)$alkyl;

and s is 0, 1, 2 or 3.

9. The compound of claim 4, wherein the compound is represented by the following Structural Formula:

(XXIIIb)

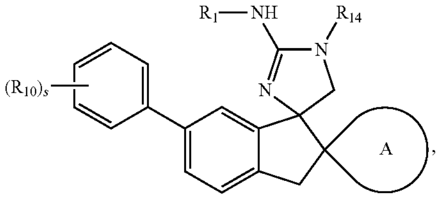

or a pharmaceutically acceptable salt thereof, wherein $R_{10}$ is independently selected from the group consisting of -halogen, —CN, $—NO_2$, $—OR_5$, $—SR_5$, $—NR_6R_7$, $—S(O)_iR_5$, $—NR_{11}S({=}O)_iR_5$, $—S(O)_iNR_{12}R_{13}$, $—C({=}O)OR_5$, $—OC({=}O)R_5$, $—C({=}S)OR_5$, $—OC({=}S)R_5$, $—C({=}O)NR_{12}R_{13}$, $—NR_{11}C({=}O)R_5$, $—C({=}S)NR_{12}R_{13}$, $—NR_{11}C({=}S)R_5$, $—C({=}O)R_5$, $—C({=}S)R_5$, $—OC({=}O)OR_5$, $—O(C{=}O)NR_{12}R_{13}$, $—NR_{11}(C{=}O)OR_5$, $—NR_{11}(C{=}S)OR_5$, $—O(C{=}S)NR_{12}R_{13}$, $—NR_{11}(C{=}O)NR_{12}R_{13}$, $—C({=}O)R_5$, $—C({=}S)R_5$, $(C_1\text{-}C_6)$alkyl, $(C_2\text{-}C_6)$alkynyl, $(C_3\text{-}C_8)$cycloalkyl, $(C_4\text{-}C_8)$cycloalkenyl, $(C_3\text{-}C_9)$heterocycloalkyl, $(C_2\text{-}C_6)$alkenyl, halo$(C_1\text{-}C_6)$alkyl, $(C_1\text{-}C_3)$alkylsulfonylaminoalkyl, hydroxy$(C_1\text{-}C_6)$alkyl, cyano$(C_1\text{-}C_6)$alkyl, $(C_1\text{-}C_3)$alkylcarbonylamino$(C_1\text{-}C_6)$alkyl, $(C_1\text{-}C_3)$alkoxy, halo$(C_1\text{-}C_3)$alkoxy, $(C_1\text{-}C_6)$alkoxy$(C_1\text{-}C_3)$alkyl, aryl and heteroaryl, wherein the cycloalkyl, heterocycloalkyl, aryl and heteroaryl groups in the groups represented by $R_{10}$ are each optionally substituted with 1 to 3 substituents independently selected from halogen, —CN, $(C_1-C_6)$alkyl, halo$(C_1-C_6)$alkyl, $(C_1-C_3)$alkoxy, halo$(C_1-C_3)$alkoxy and $(C_1-C_3)$alkoxy$(C_1-C_6)$alkyl;

and s is 0, 1, 2 or 3.

10. The compound of claim 8, wherein $R_{10}$ is independently selected from the group consisting of —F, —Cl, —CN, $(C_1-C_6)$alkyl, $(C_1-C_6)$alkoxy, halo$(C_1-C_6)$alkyl and halo$(C_1-C_6)$alkoxy.

11. The compound of claim 10, wherein $R_{10}$ is independently selected from the group consisting of —F, —Cl, —CN, —Me, —Et, -OMe, —$CF_3$ and —$OCF_3$.

12. The compound of claim 10, wherein $R_1$ is —H and $R_{14}$, when present, is -Me.

13. The compound of claim 12, wherein ring A is represented by the following structural formula:

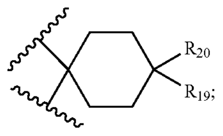

wherein:

$R_{19}$ and $R_{20}$ are each independently selected from —H, halogen, —CN, —$OR_5$, —$NR_6R_7$, —$S(O)_iR_5$, —$NR_{11}S(=O)_iR_5$, —$C(=O)OR_5$, —$C(=O)NR_{12}R_{13}$, —$NR_{11}C(=O)R_5$, —$C(=S)NR_{12}R_{13}$, —$C(=O)R_5$, $(C_1-C_6)$alkyl, $(C_2-C_6)$alkenyl, aryl, aryl$(C_1-C_6)$alkyl, heteroaryl and heteroaryl$(C_1-C_6)$alkyl, wherein each of the $(C_1-C_6)$alkyl, $(C_2-C_6)$alkenyl, aryl, aryl$(C_1-C_6)$alkyl, heteroaryl and heteroaryl$(C_1-C_6)$alkyl groups represented by $R_{19}$ and $R_{20}$ is optionally substituted with 1 to 3 substituents independently selected from the group consisting of halogen, —CN, —$NR_{11}SO_2(C_1-C_3)$alkyl, —$NR_{11}C(=O)$—$(C_1-C_3)$alkyl, $(C_1-C_6)$alkyl, halo$(C_1-C_6)$alkyl, $(C_1-C_3)$alkoxy, halo$(C_1-C_3)$alkoxy and $(C_1-C_3)$alkoxy$(C_1-C_6)$alkyl.

14. The compound of claim 13, wherein:

$R_{20}$ is —H and $R_{19}$ is —OH, $(C_1-C_3)$alkoxy, halo$(C_1-C_3)$alkoxy or $(C_1-C_3)$alkoxy$(C_1-C_3)$alkoxy.

15. The compound of claim 1, wherein:

$R_1$ is —H; and $R_2$ is —H, halogen, —CN, —$OR_5$, —$C(=O)NR_{12}R_{13}$, —$C(=O)OR_5$, —$C(O)R_5$, $(C_1-C_6)$alkyl, $(C_2-C_6)$alkenyl, $(C_2-C_6)$alkynyl, $(C_3-C_6)$cycloalkyl, $(C_3-C_6)$cycloalkyl$(C_1-C_3)$alkyl, $(C_4-C_6)$cycloalkenyl, phenyl, phenyl$(C_1-C_3)$alkyl, heteroaryl, heteroaryl$(C_1-C_3)$alkyl, $(C_5-C_6)$heterocycloalkyl, $(C_5-C_6)$heterocycloalky$(C_1-C_3)$alkyl, wherein the heteroaryl is selected from pyridyl, pyridazinyl, pyridinonyl, pyridazinonyl, thiazolyl, oxazolyl, oxadiazolyl, pyrazinyl, pyrimidyl, indolyl, quinolyl, quinoxalinyl, triazole and thiophenyl, the heterocycloalkyl is selected from oxetanyl, tetrahydrofuran, tetrahydropyran, piperidine, pyrrolidinyl and pyrrolidinonyl, and each of $(C_1-C_6)$alkyl, $(C_2-C_6)$alkenyl, $(C_2-C_6)$alkynyl, $(C_3-C_6)$cycloalkyl, $(C_3-C_6)$cycloalkyl$(C_1-C_3)$alkyl, $(C_4-C_6)$cycloalkenyl, phenyl, phenyl$(C_1-C_3)$alkyl, heteroaryl, heteroaryl$(C_1-C_3)$alkyl, $(C_5-C_6)$heterocycloalkyl and $(C_5-C_6)$heterocycloalky$(C_1-C_3)$alkyl groups represented by $R_2$ is optionally substituted with 1 to 5 substituents independently selected from halogen, —CN, $(C_1-C_3)$alkyl, halo$(C_1-C_3)$alkyl, $(C_2-C_6)$alkynyl, —$NR_6R_7$, —$S(O)_iR_5$, —$C(O)R_5$, —OH, $(C_3-C_6)$cycloalkyl, $(C_1-C_3)$alkoxy and halo$(C_1-C_3)$alkoxy.

16. The compound of claim 15, wherein:

$R_5$ is selected from the group consisting of —H, $(C_1-C_3)$alkyl, halo$(C_1-C_3)$alkyl, $(C_1-C_3)$alkoxy$(C_1-C_3)$alkyl, $(C_3-C_6)$cycloalkyl, $(C_3-C_6)$cycloalkyl$(C_1-C_3)$alkyl, phenyl and phenyl$(C_1-C_3)$alkyl, wherein the phenyl group in the groups represented by $R_5$ is optionally substituted with 1 to 3 substituents independently selected from —F, —Cl, —Br, —CN, =O, —$NR_6R_7$, $(C_1-C_3)$alkyl, halo$(C_1-C_3)$alkyl and $(C_1-C_3)$alkoxy$(C_1-C_3)$alkyl;

$R_6$ is —H or $(C_1-C_3)$alkyl;

$R_7$ is —H, $(C_1-C_3)$alkyl, halo$(C_1-C_3)$alkyl, $(C_3-C_6)$cycloalkyl, $(C_3-C_6)$cycloalkyl$(C_1-C_3)$alkyl or $(C_1-C_3)$alkoxy$(C_1-C_3)$alkyl;

$R_{11}$ is —H or $(C_1-C_3)$alkyl;

$R_{12}$ is —H or $(C_1-C_3)$alkyl; and $R_{13}$ is —H, $(C_1-C_3)$alkyl, halo$(C_1-C_3)$alkyl, $(C_3-C_6)$cycloalkyl$(C_1-C_3)$alkyl or $(C_1-C_3)$alkoxy$(C_1-C_3)$alkyl, or $R_{12}$ and $R_{13}$ together with the nitrogen atom to which they are attached form a pyrrolidine or piperidine ring.

17. A pharmaceutical composition comprising a pharmaceutically acceptable carrier or diluent and a compound of claim 1 or a pharmaceutically acceptable salt thereof.

18. A method for treating Alzheimer's disease in a subject comprising administering to the subject an effective amount of a compound of claim 1 or a pharmaceutically acceptable salt thereof, such that Alzheimer's disease is treated in the subject.

19. A method for treating cognitive impairment or cognitive decline in a subject comprising administering to the subject an effective amount of a compound of claim 1 or a pharmaceutically acceptable salt thereof, such that cognitive impairment or cognitive decline is treated in the subject.

20. A method for treating Down's Syndrome in a subject comprising administering to the subject an effective amount of a compound of claim 1 or a pharmaceutically acceptable salt thereof, such that Down's Syndrome is treated in the subject.

21. A method for treating HCHWA-D in a subject comprising administering to the subject an effective amount of a compound of claim 1 or a pharmaceutically acceptable salt thereof, such that HCHWA-D is treated in the subject.

22. A method for treating glaucoma in a subject comprising administering to the subject an effective amount of a compound of claim 1 or a pharmaceutically acceptable salt thereof, such that glaucoma is treated in the subject.

23. A compound represented by any one of the following structural formulas:

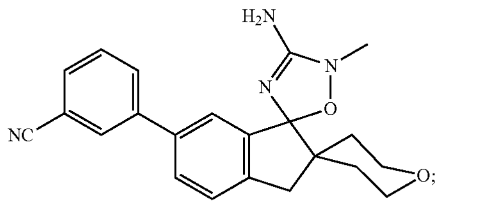

-continued
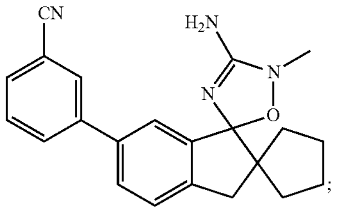
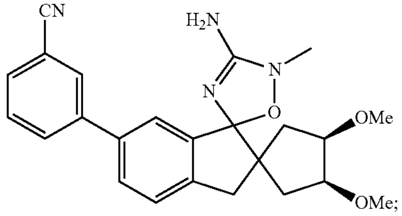
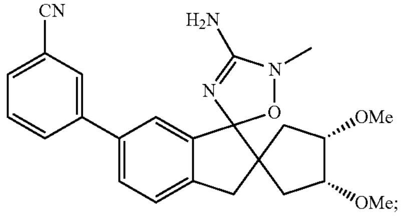
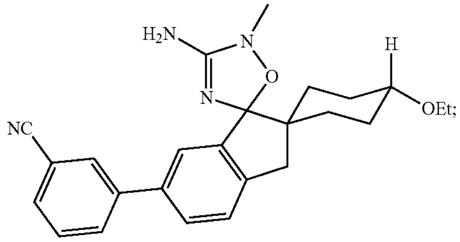
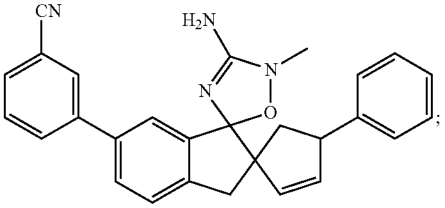
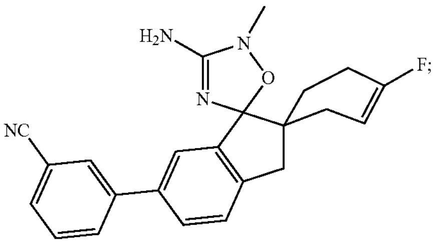
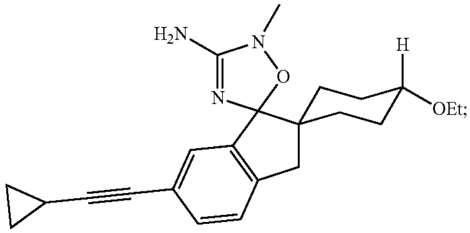
-continued
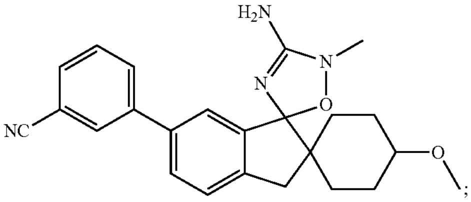
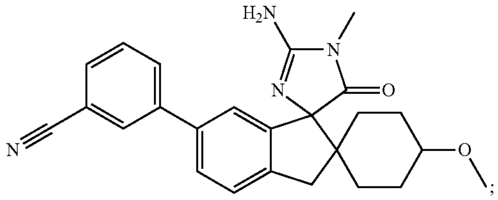
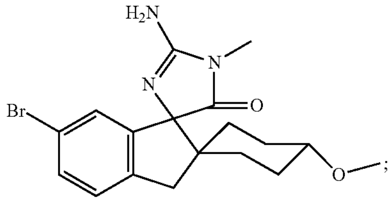
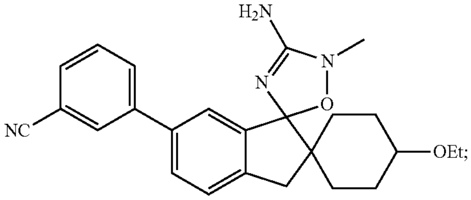
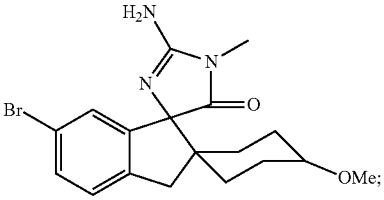
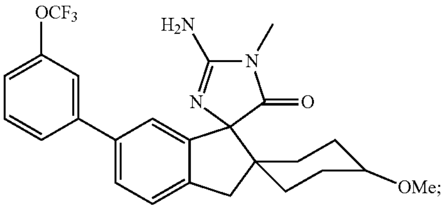
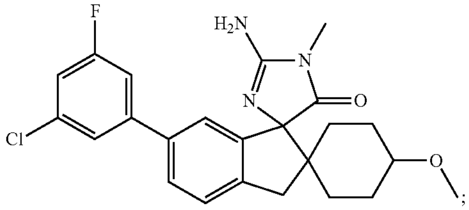
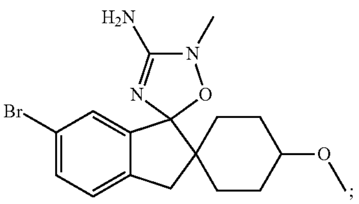

-continued
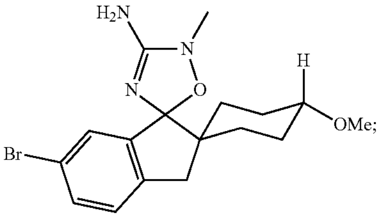
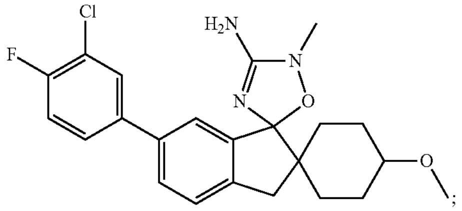
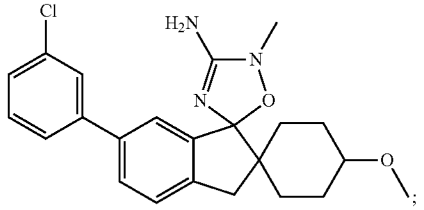
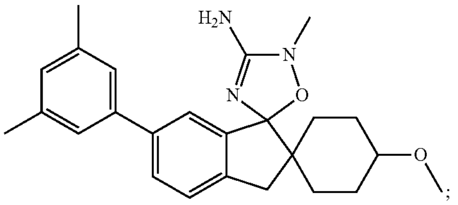
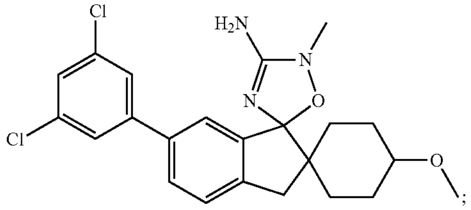
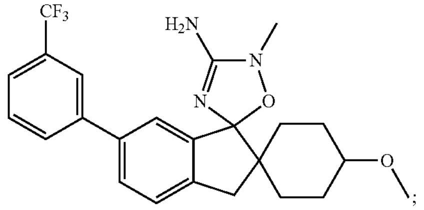
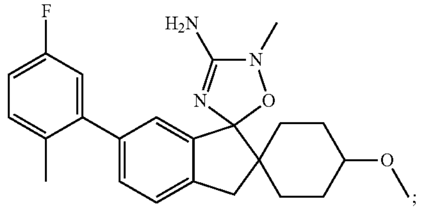
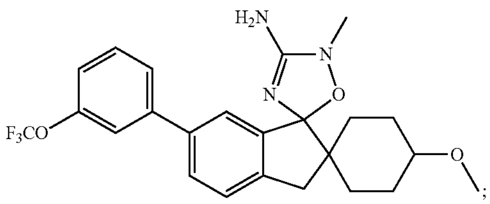
-continued
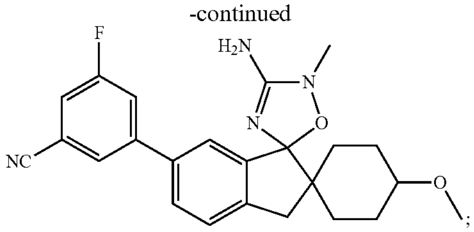
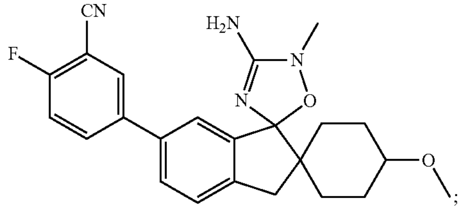
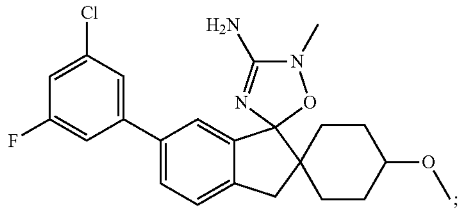
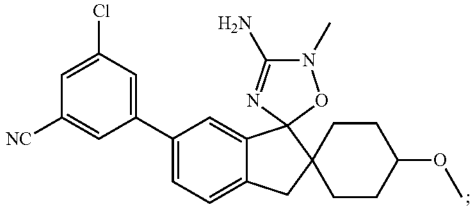
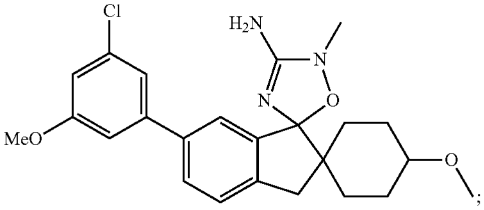
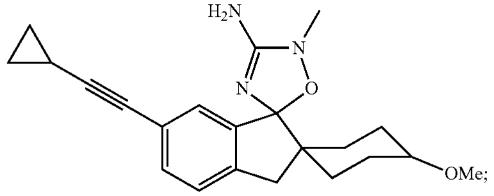
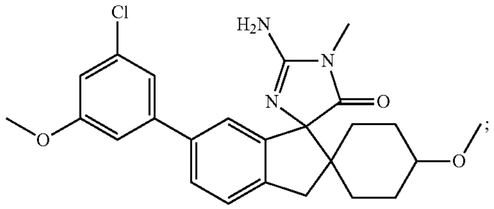
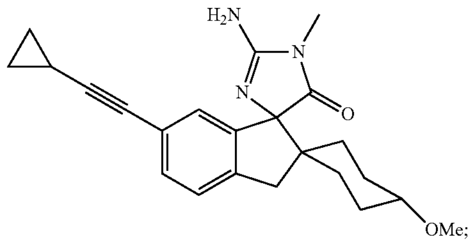

-continued
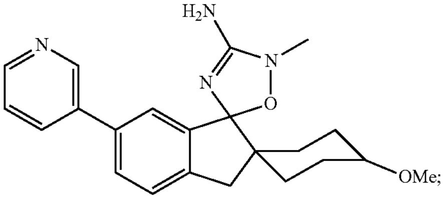
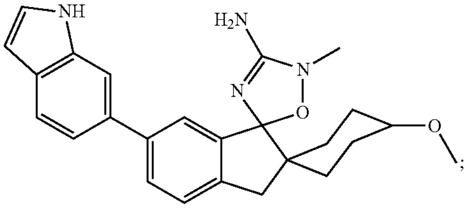
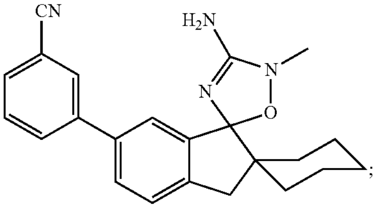
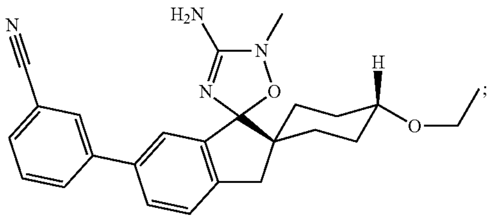
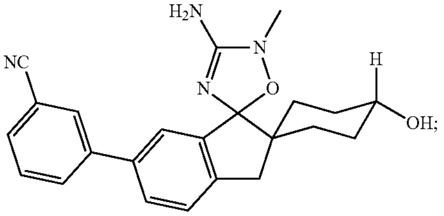
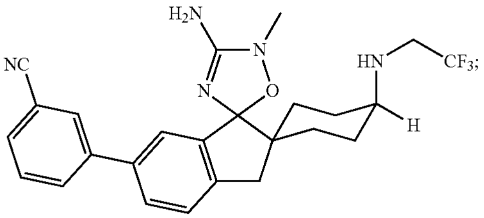
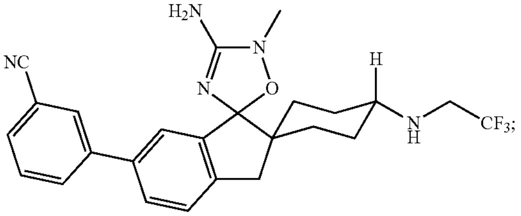
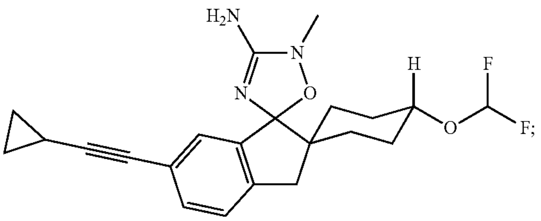
-continued
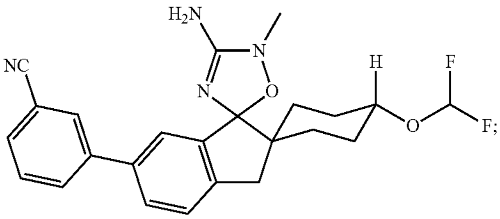
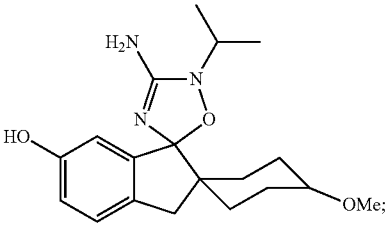
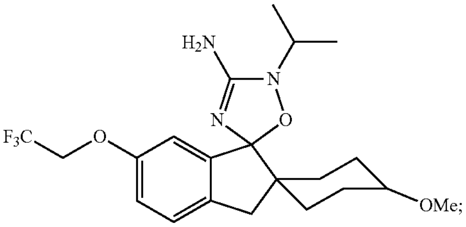
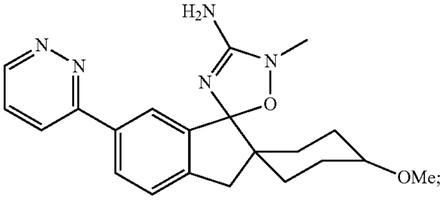
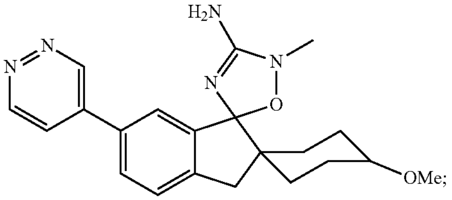
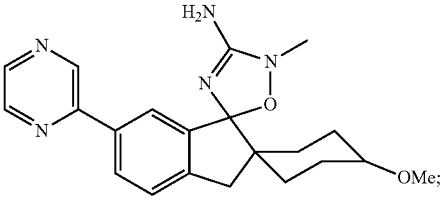
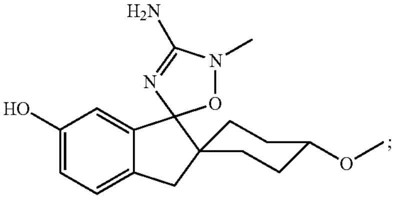
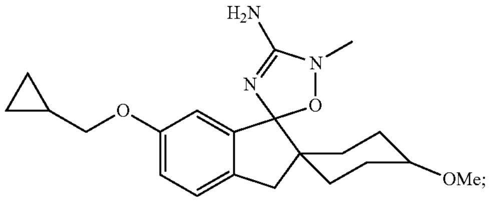

-continued
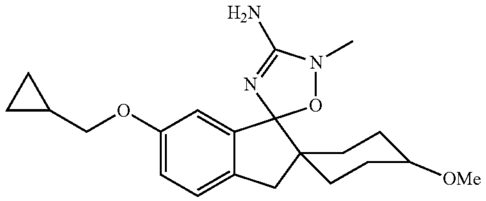
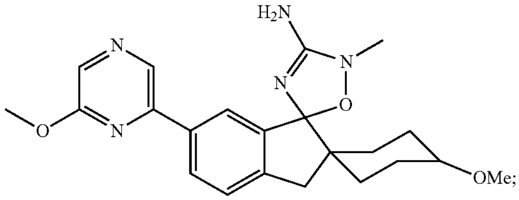
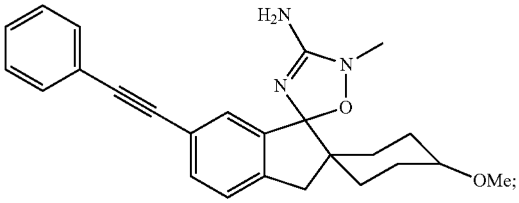
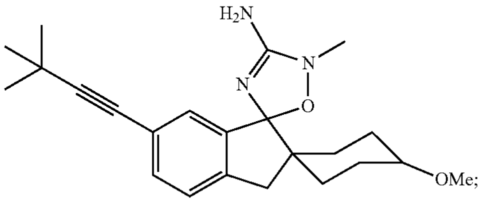
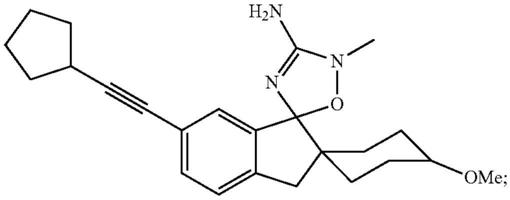
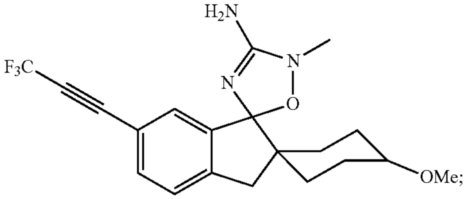
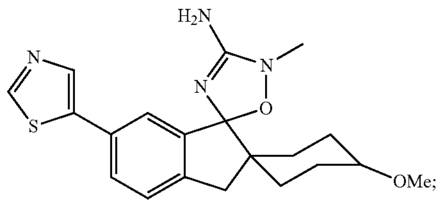
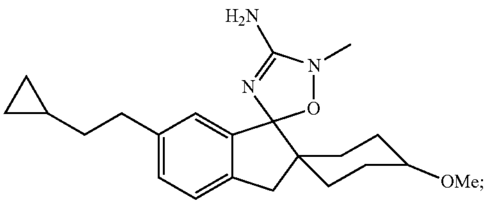
-continued
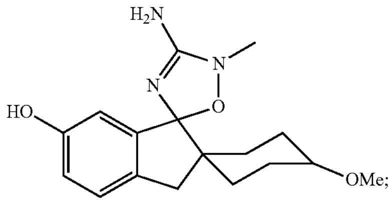
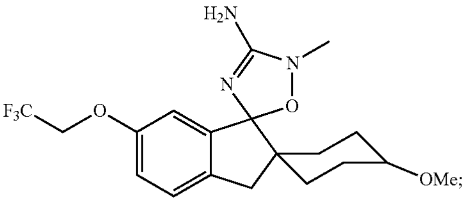
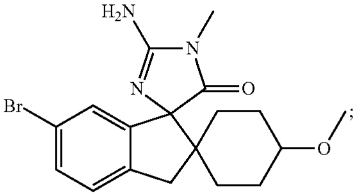
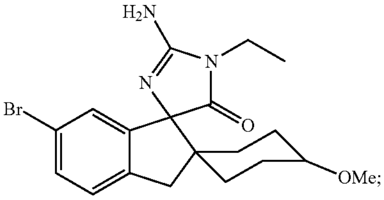
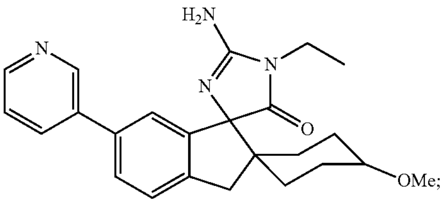
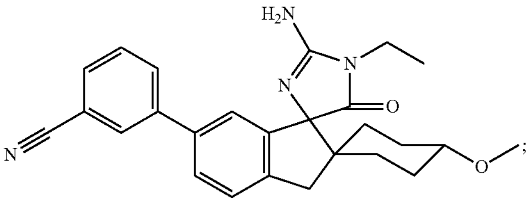
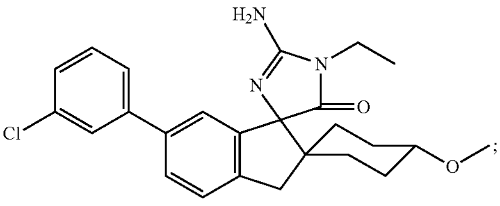
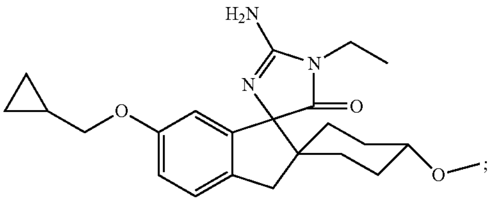

-continued
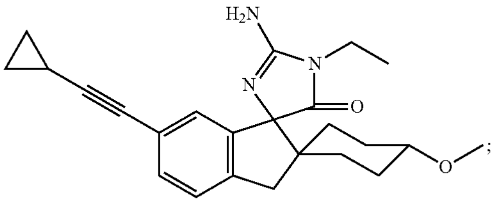
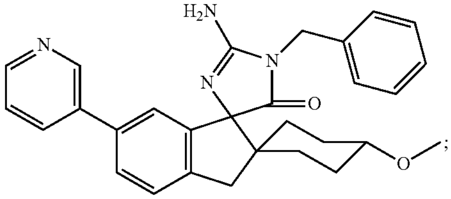
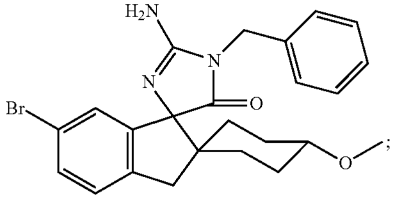
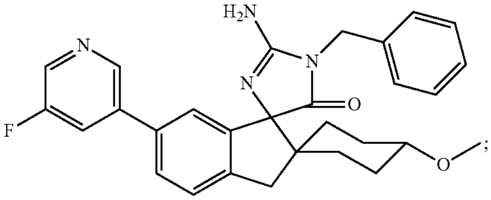
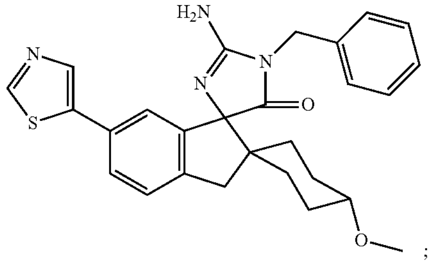
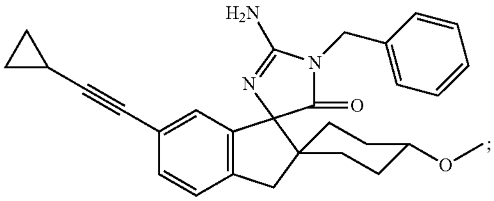
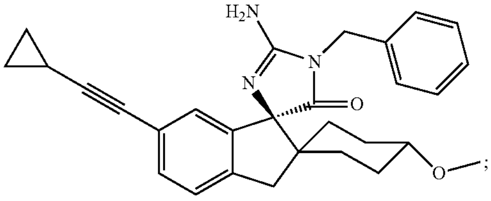
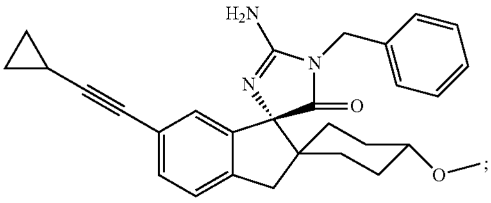
-continued
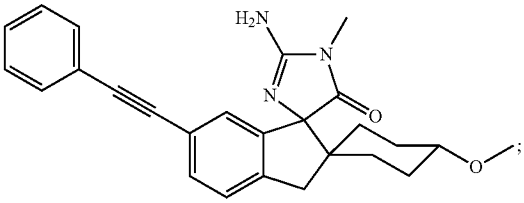
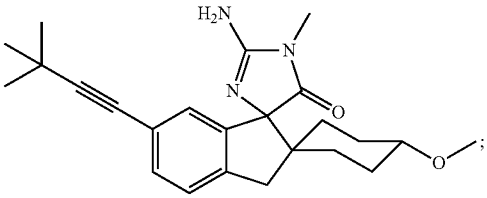
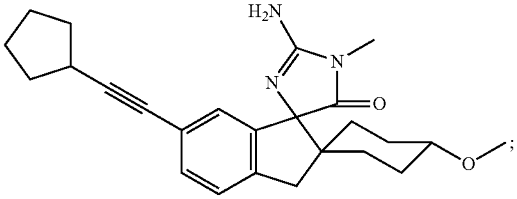
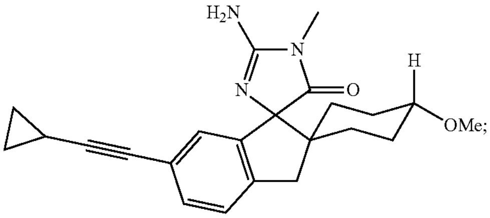
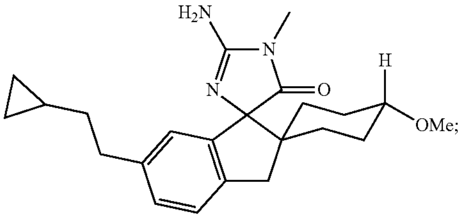
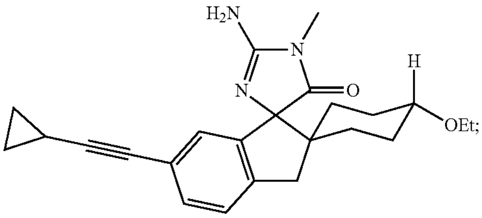
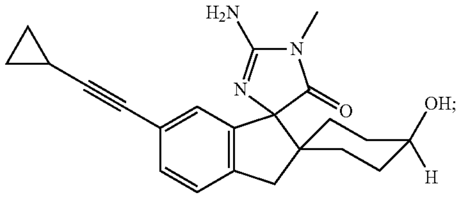
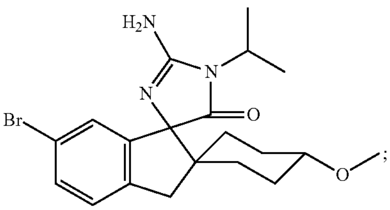

-continued
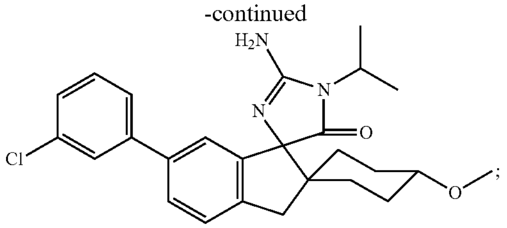
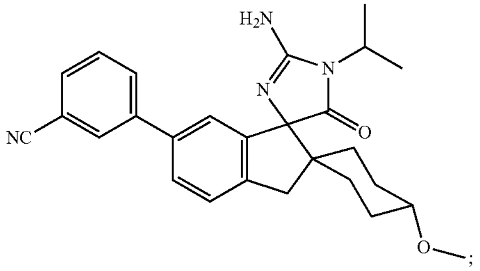
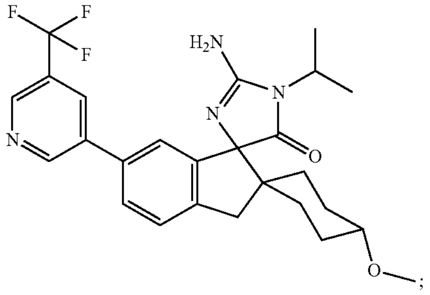
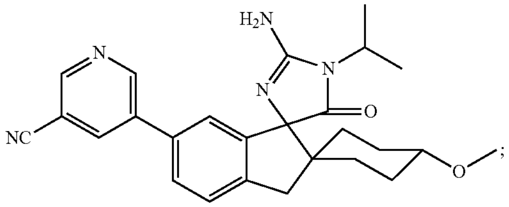
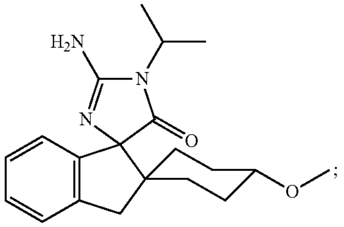
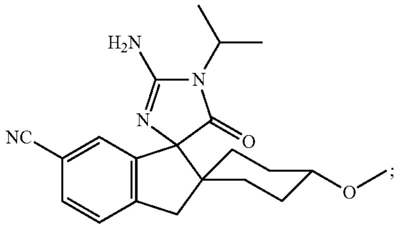
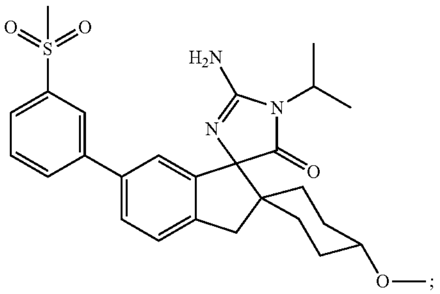
-continued
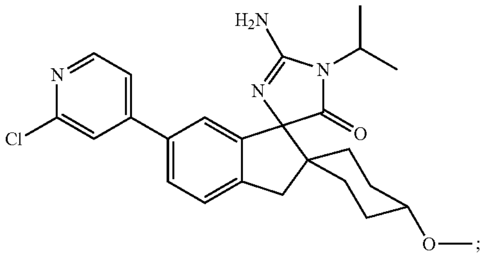
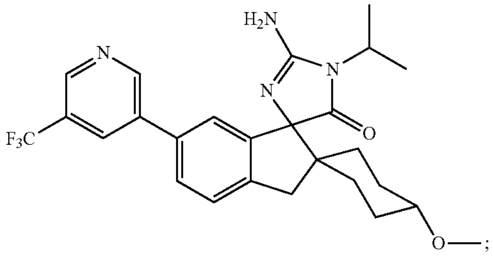
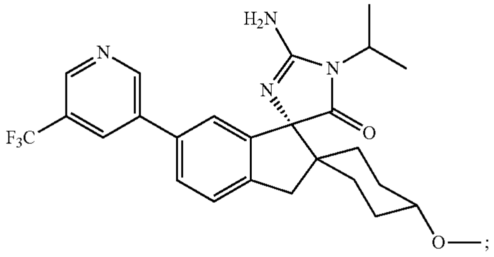
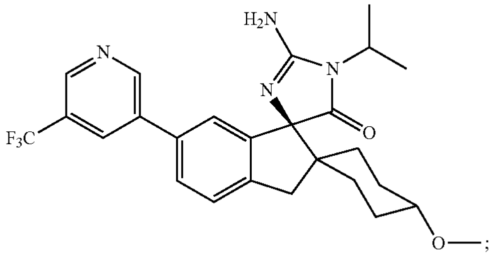
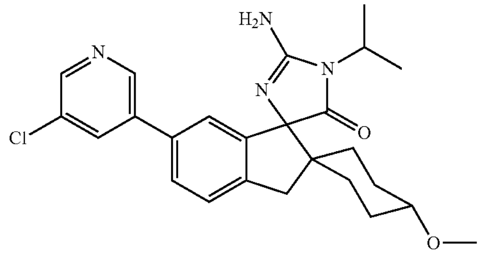
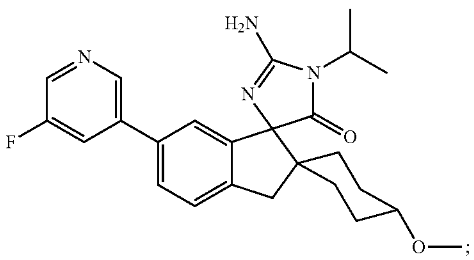

-continued
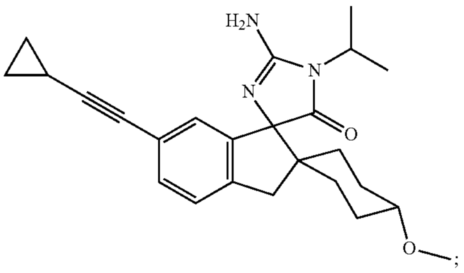
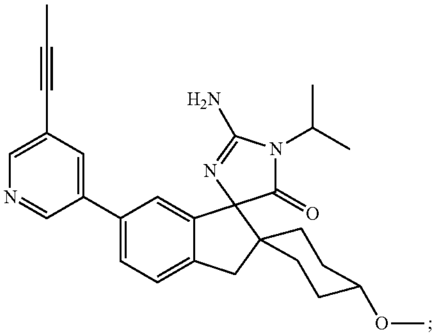
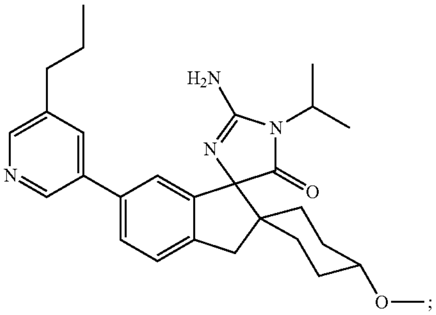
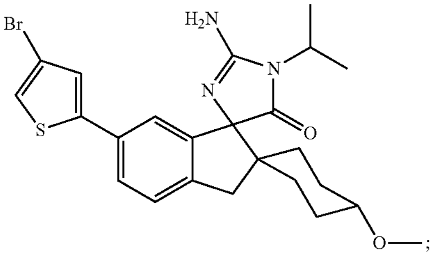
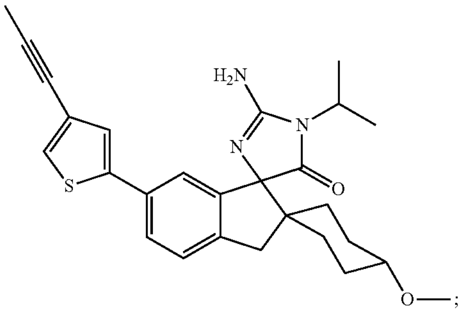
-continued
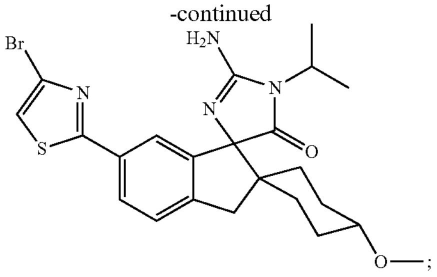
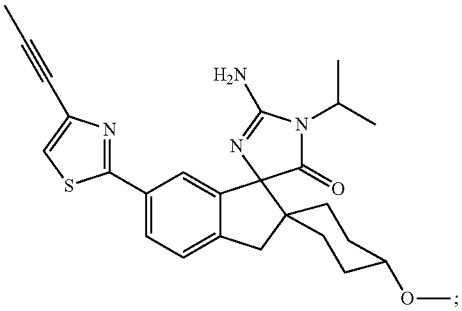
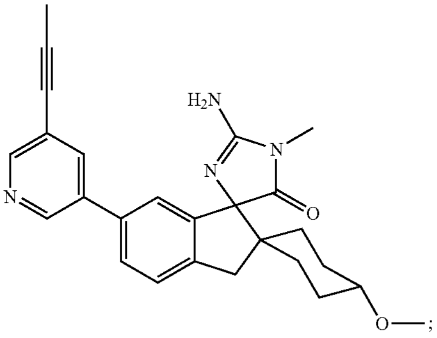
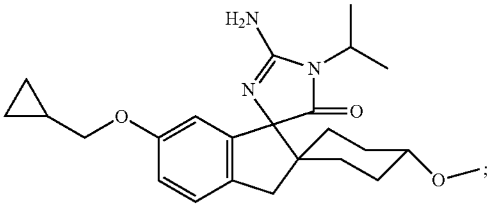
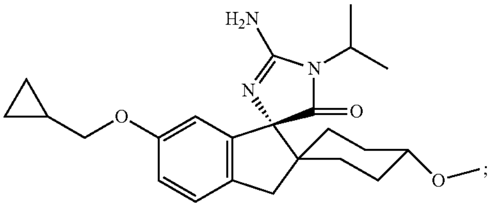
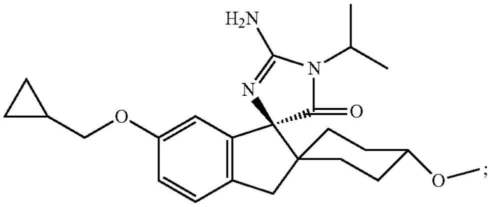
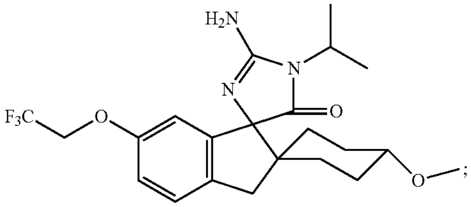

-continued
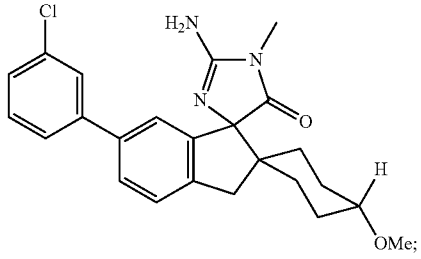
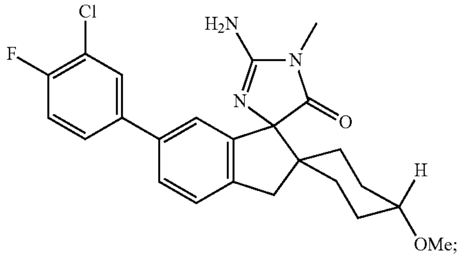
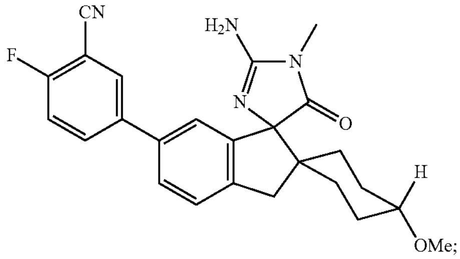
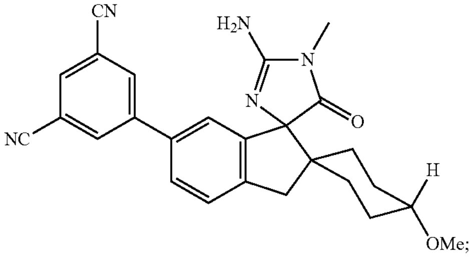
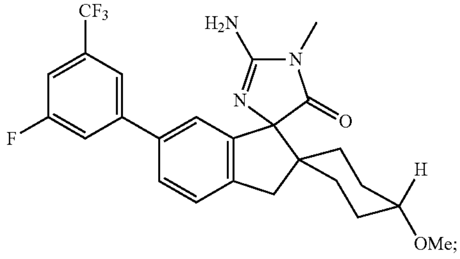
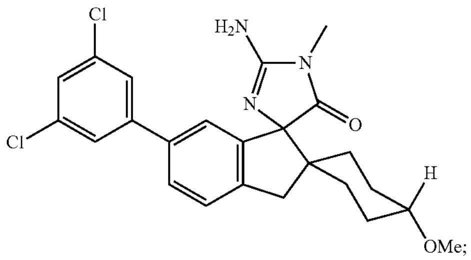
-continued
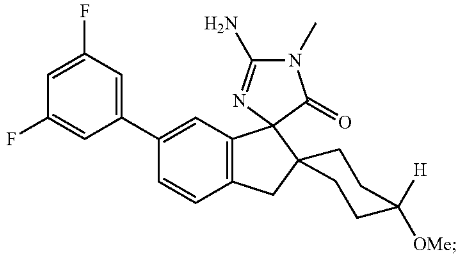
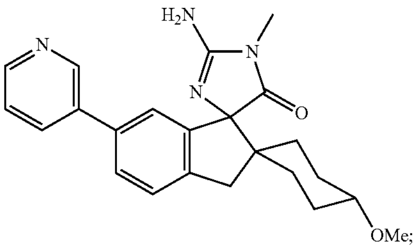
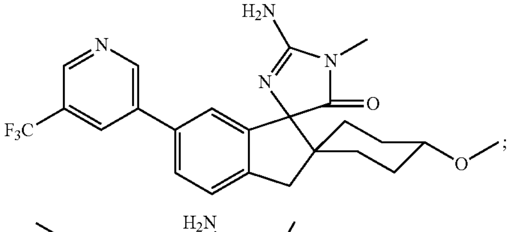
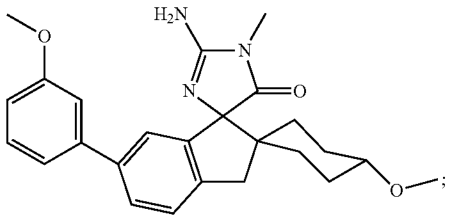
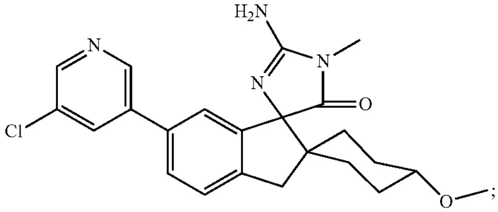
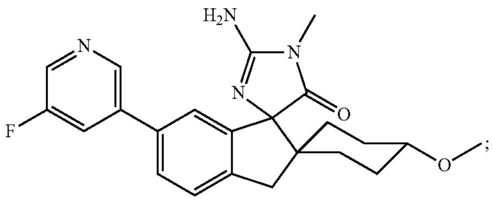
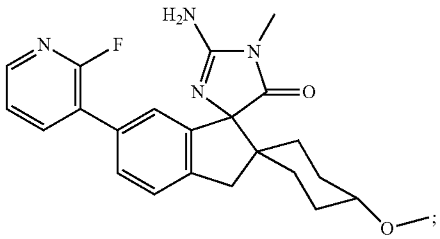

-continued
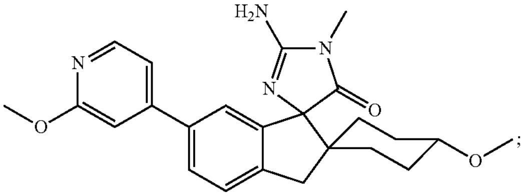
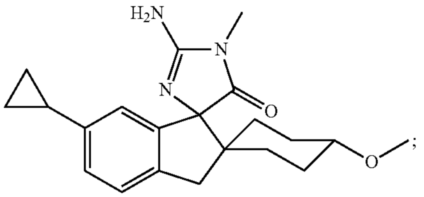
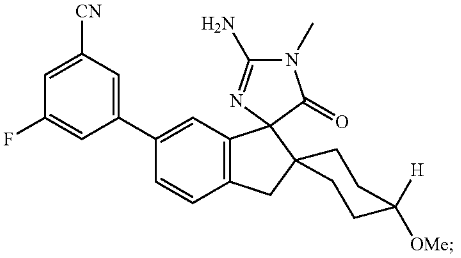
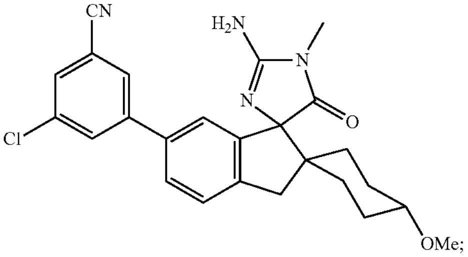
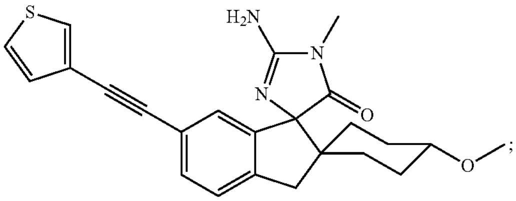
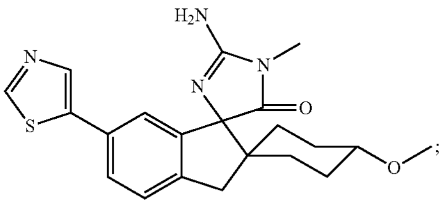
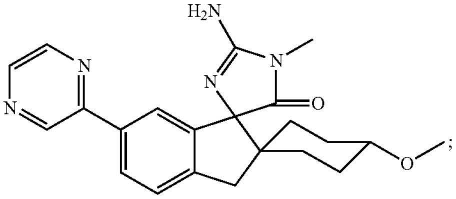
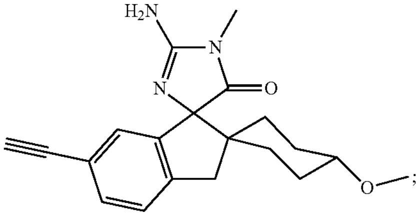
-continued
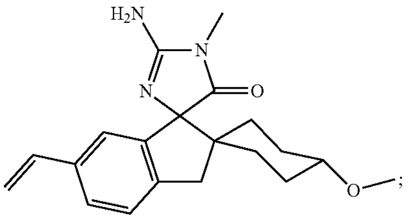
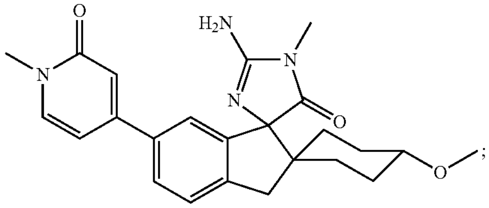
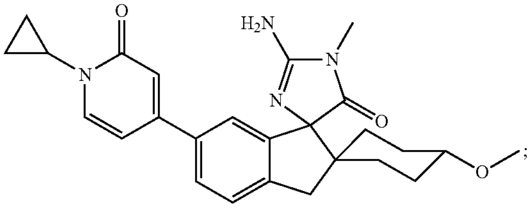
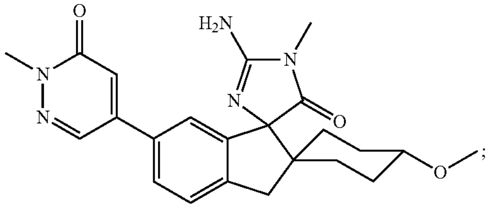
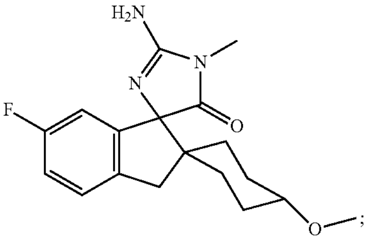
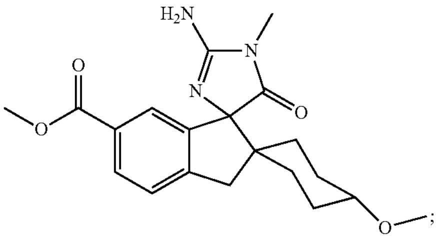
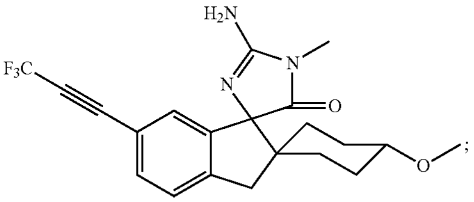

-continued
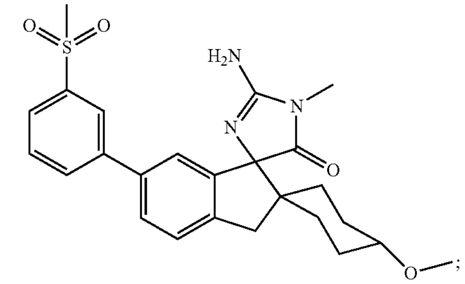
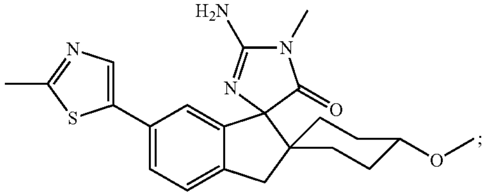
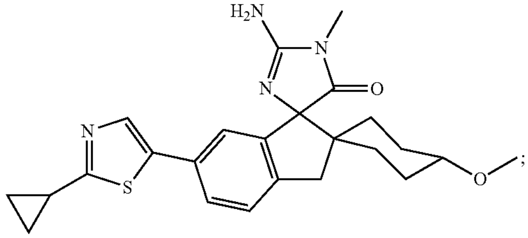
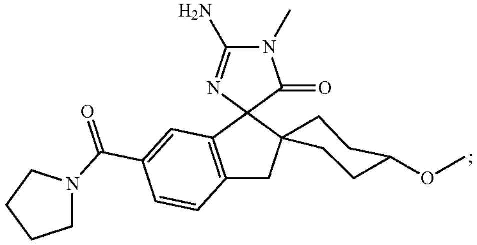
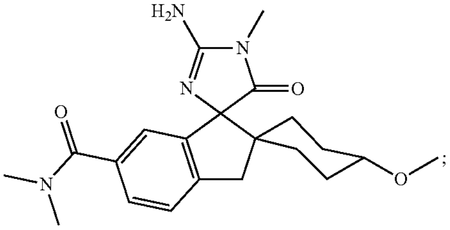
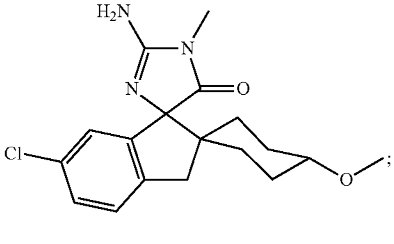
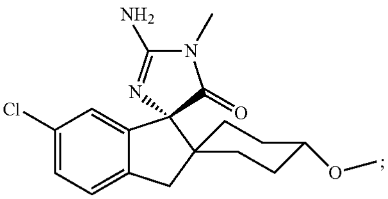
-continued
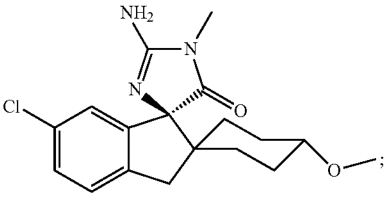
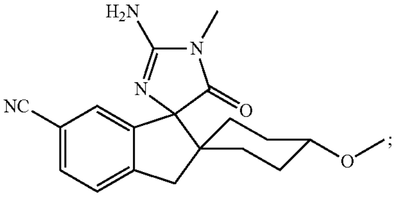
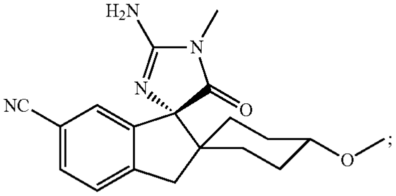
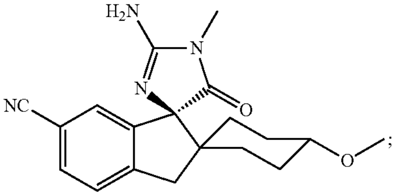
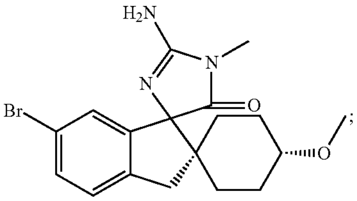
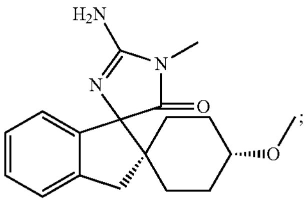
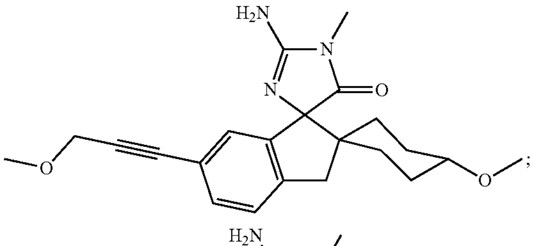
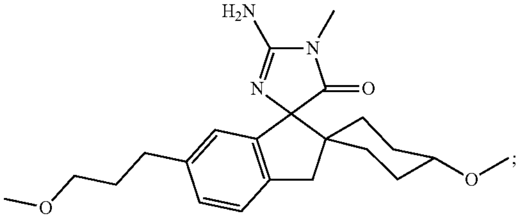

-continued
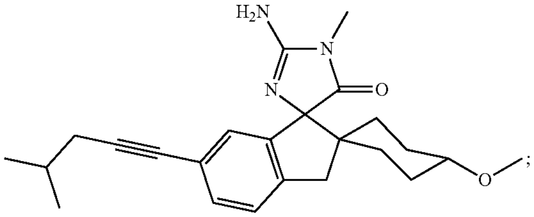
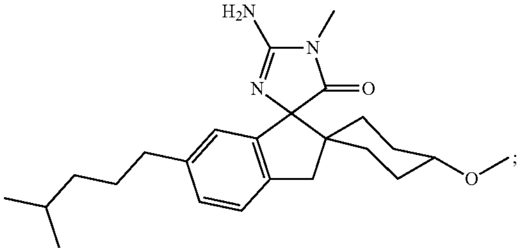
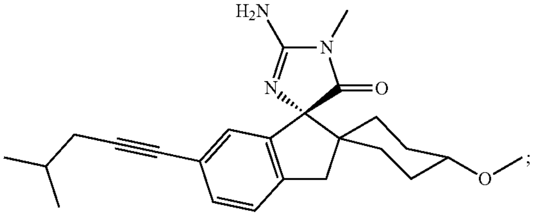
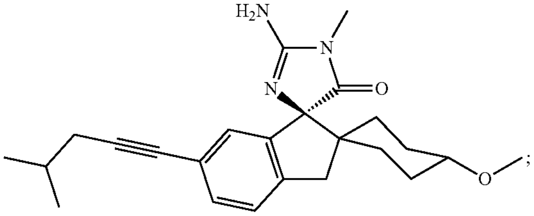
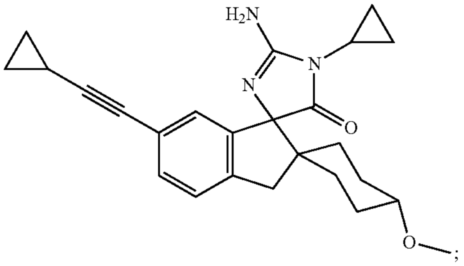
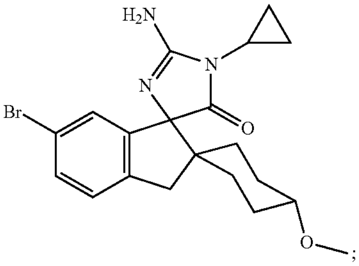
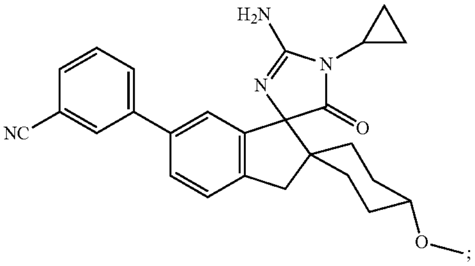
-continued
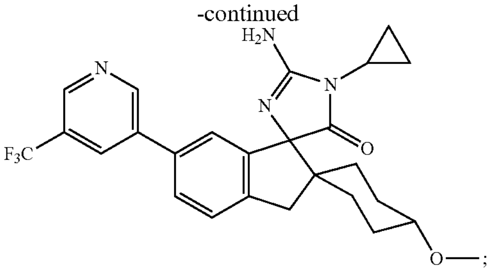
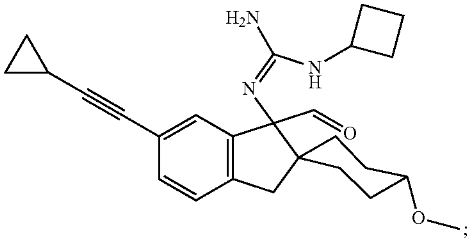
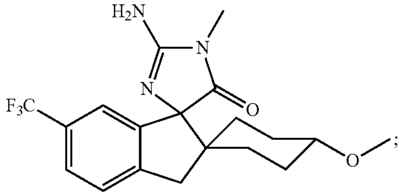
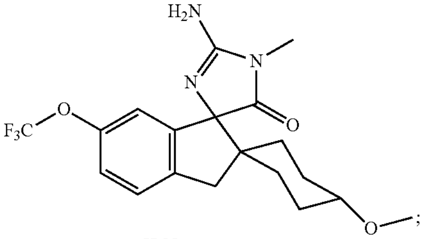
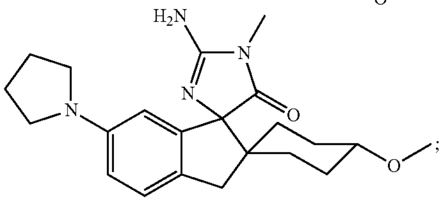
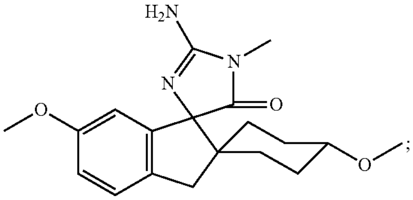
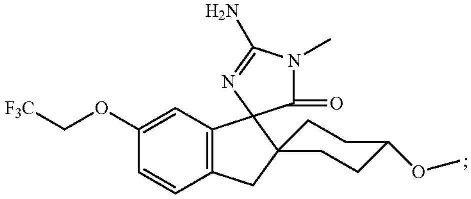
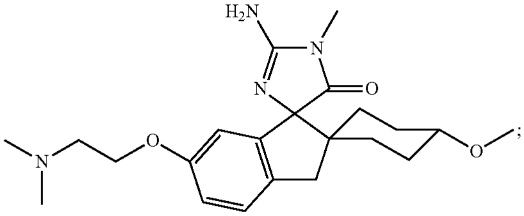

-continued
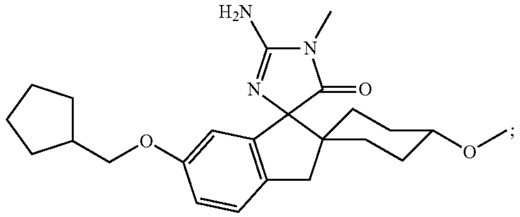
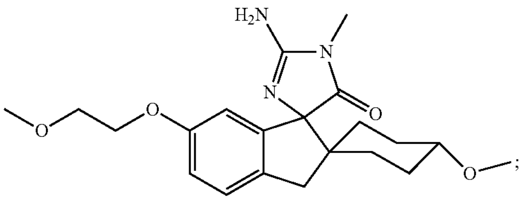
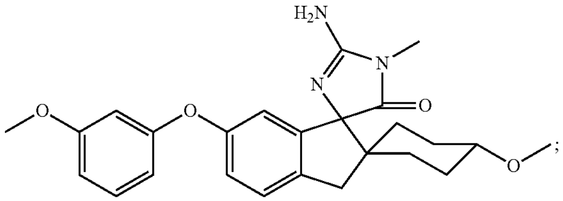
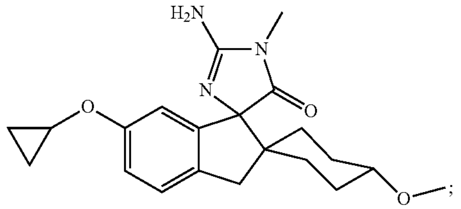
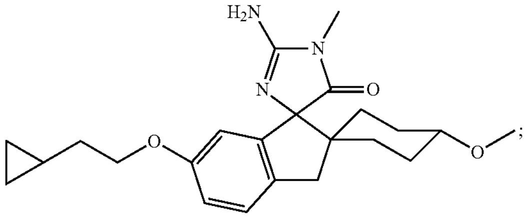
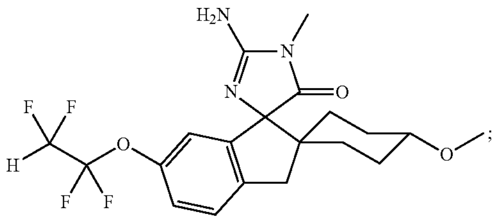
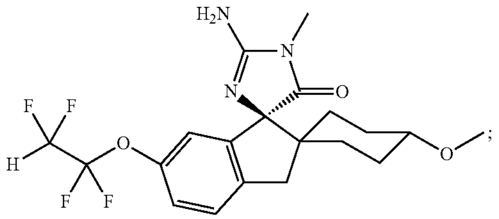
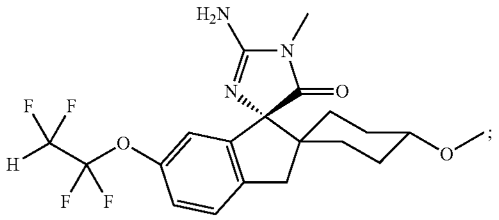
-continued
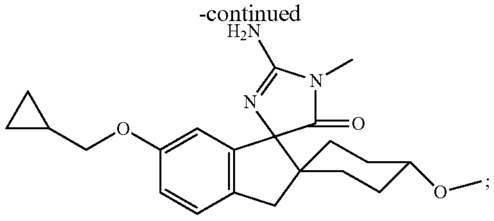
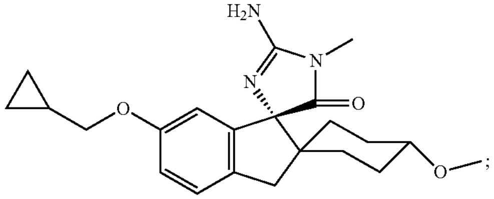
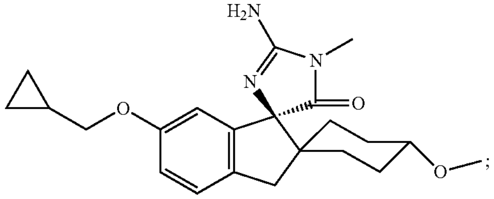
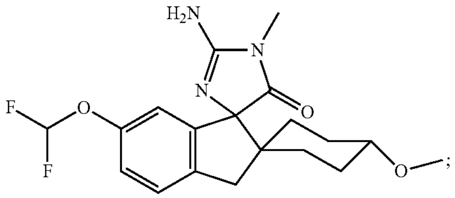
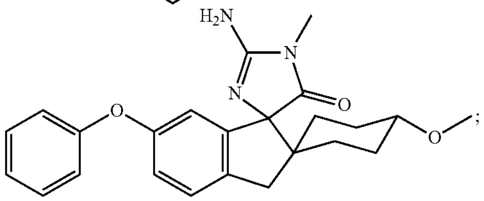
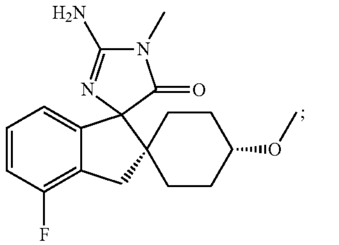
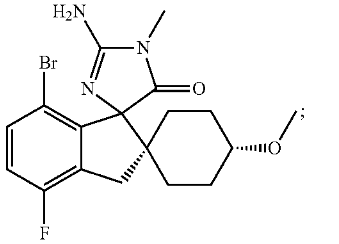
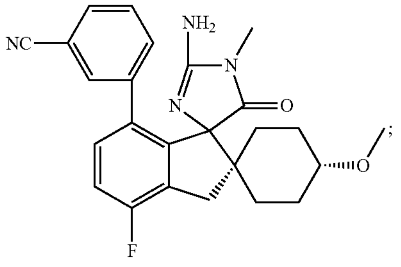

-continued
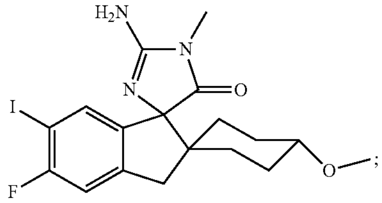
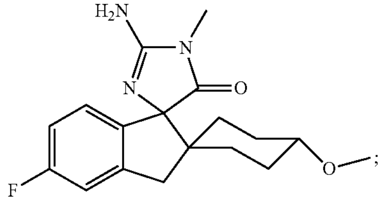
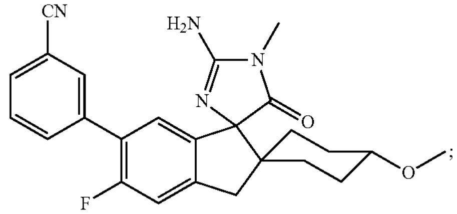
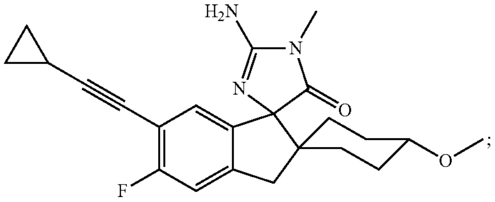
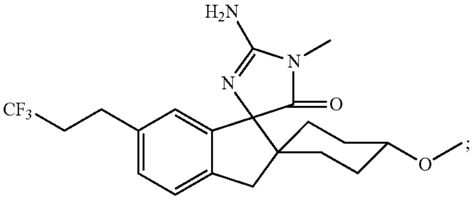
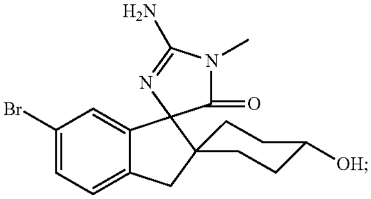
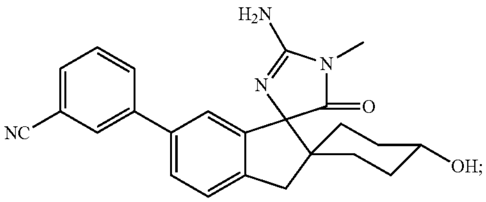
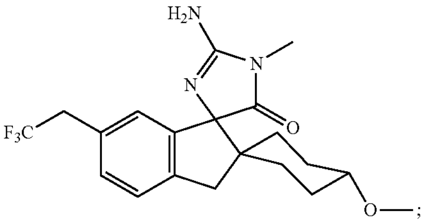
-continued
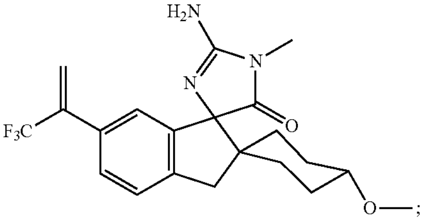
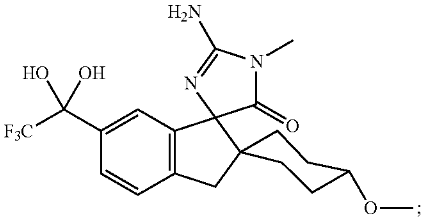
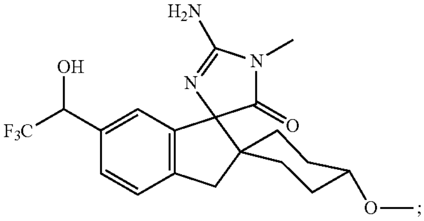
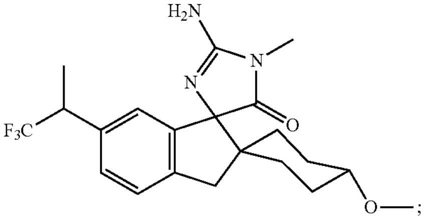
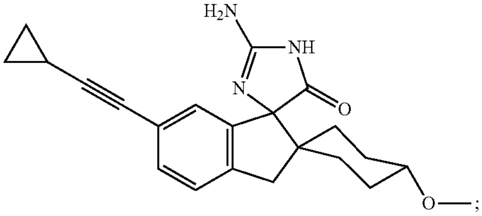
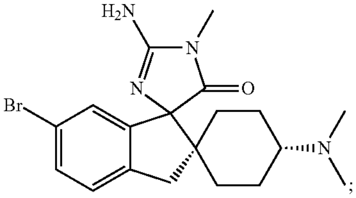
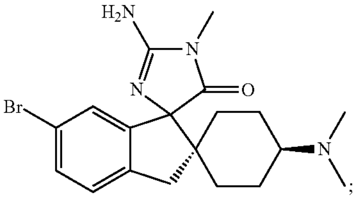
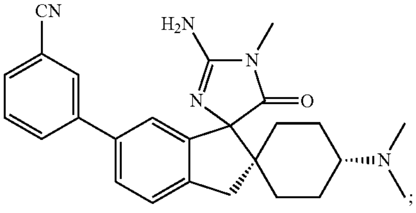

-continued
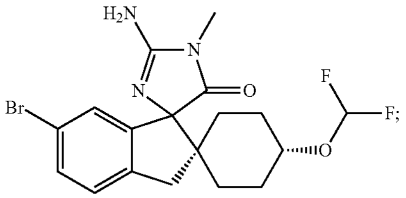
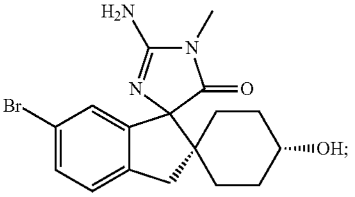
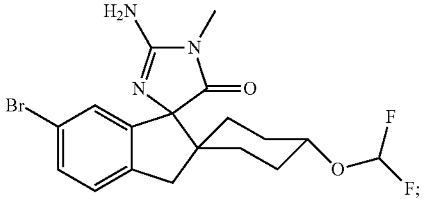
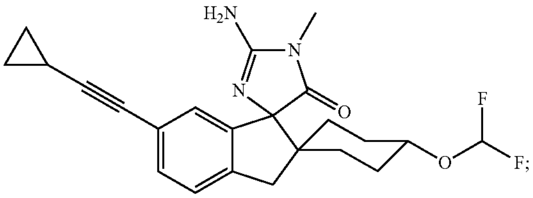
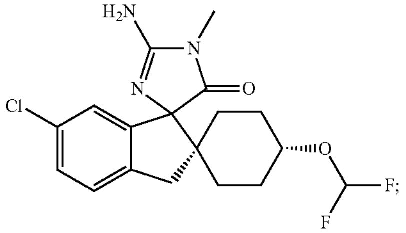
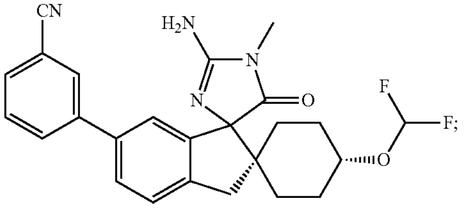
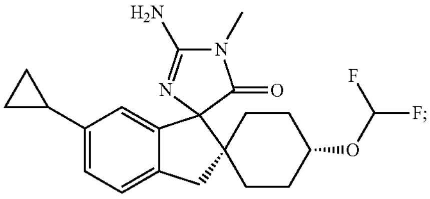
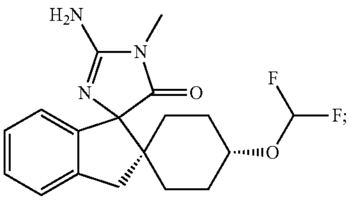
-continued
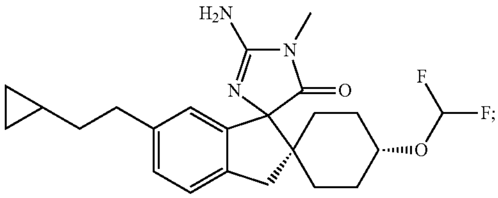
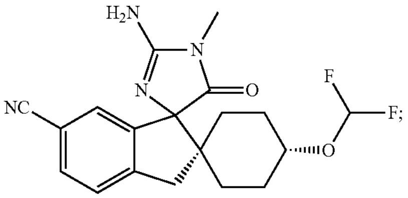
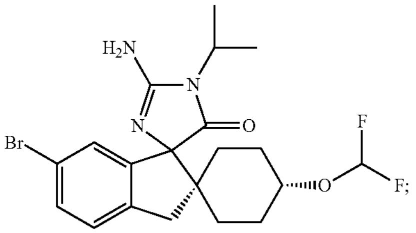
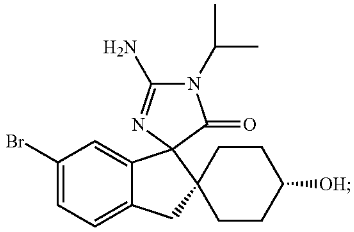
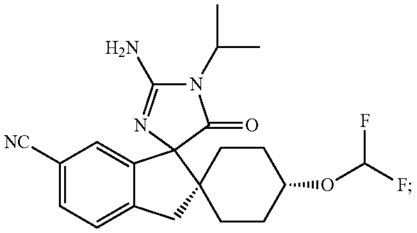
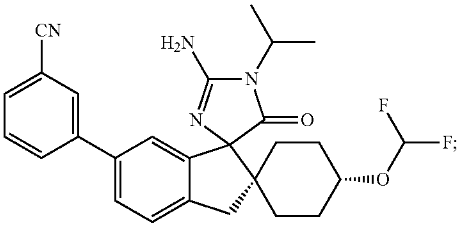
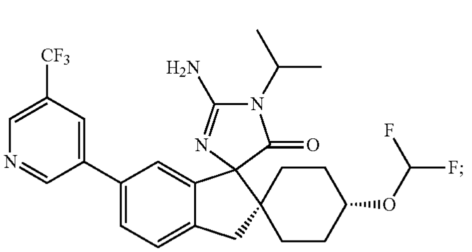

-continued
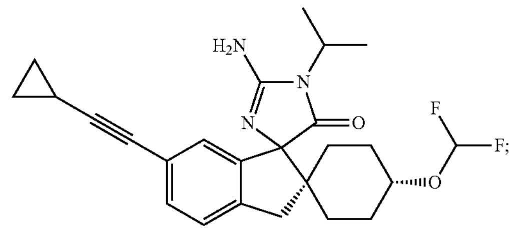
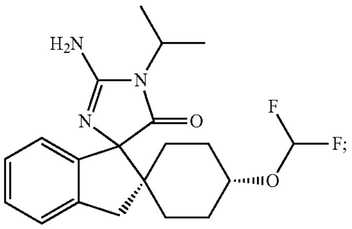
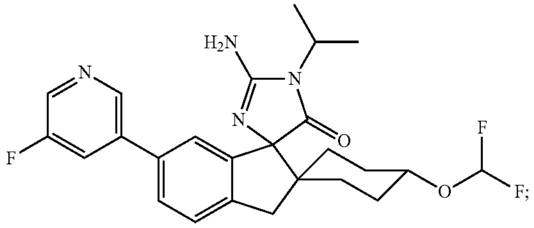
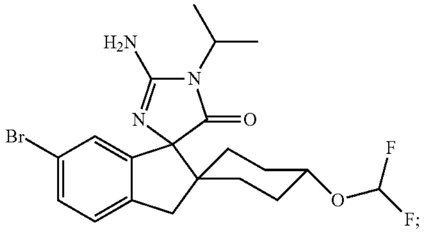
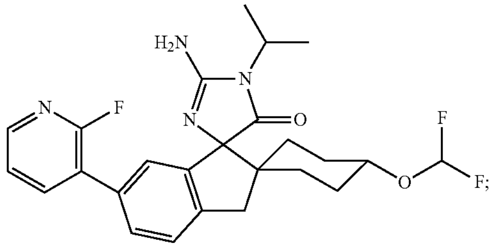
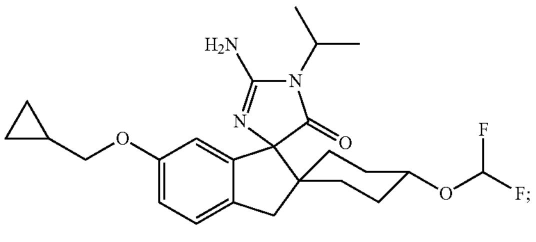
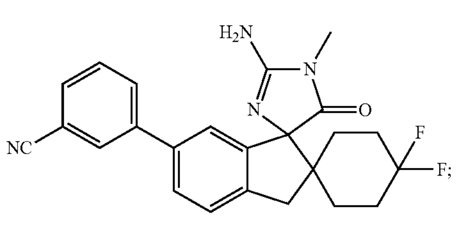
-continued
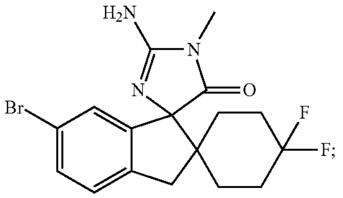
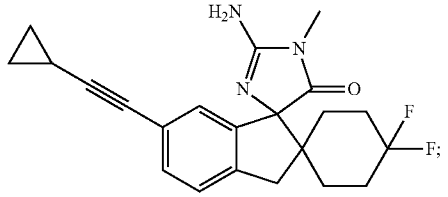
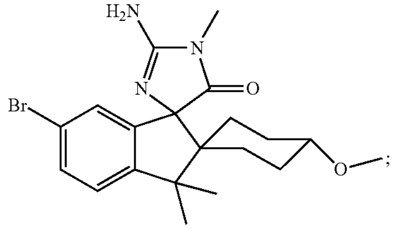
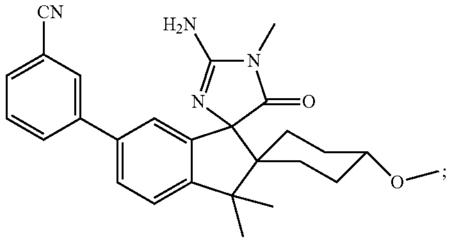
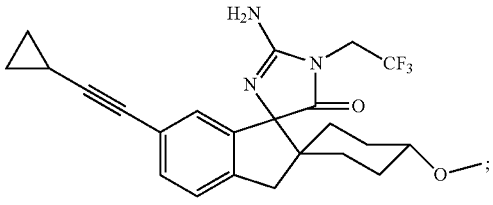
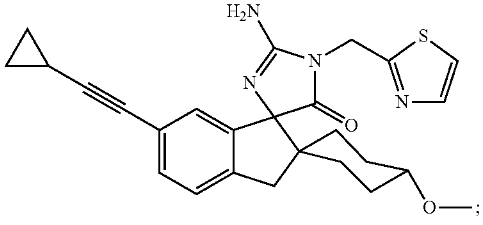
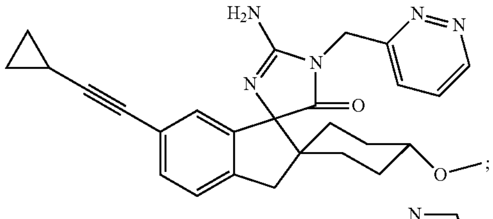
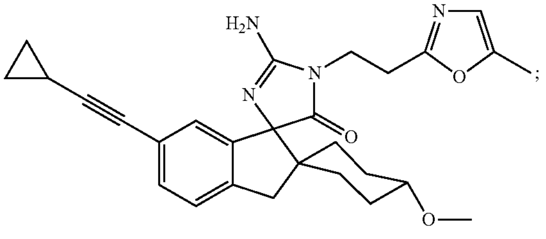

-continued
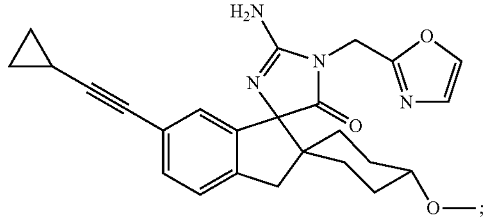
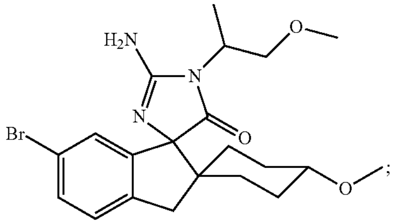
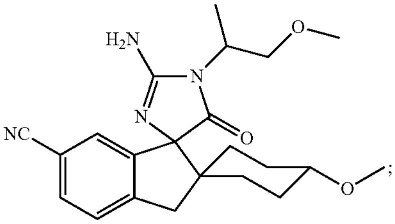
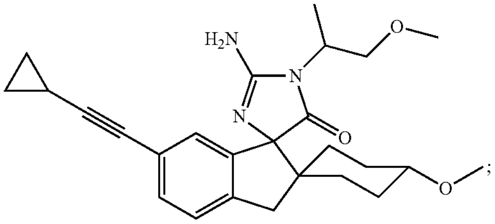
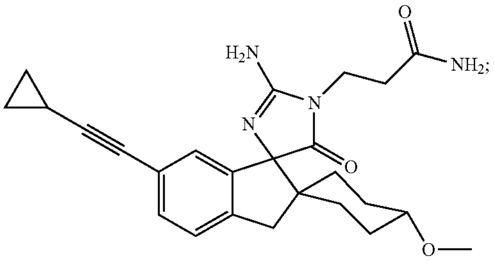
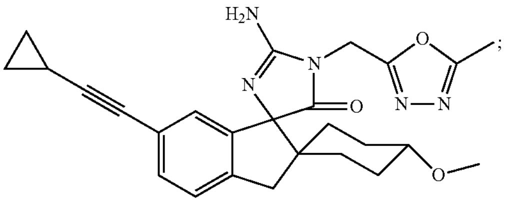
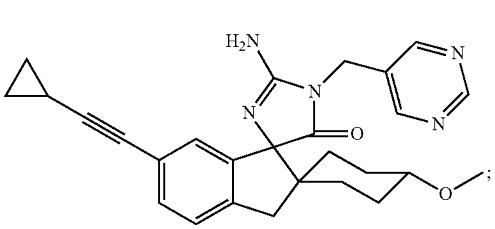
-continued
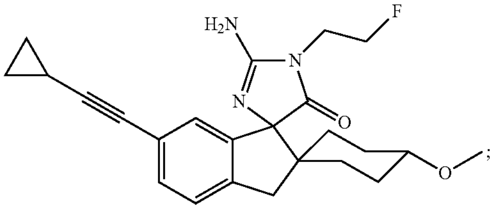
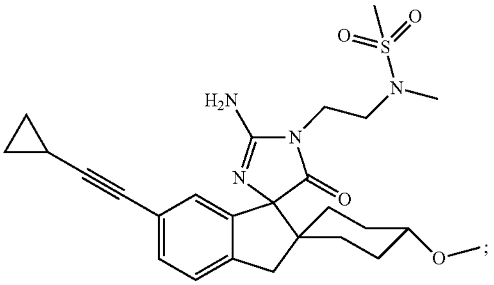
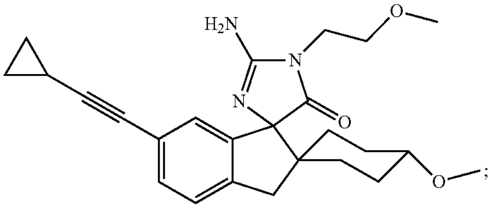
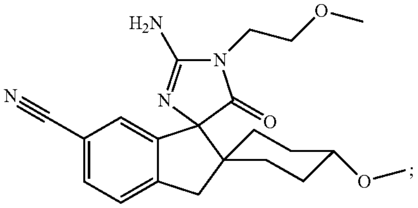
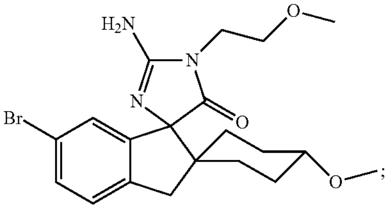
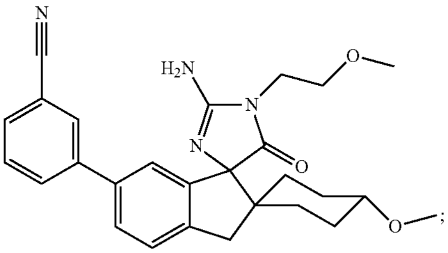
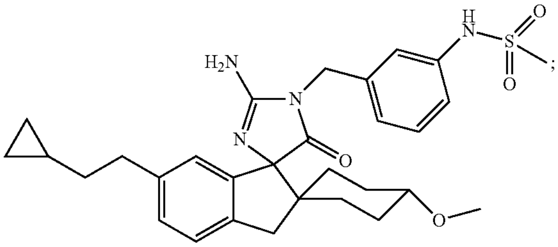

-continued
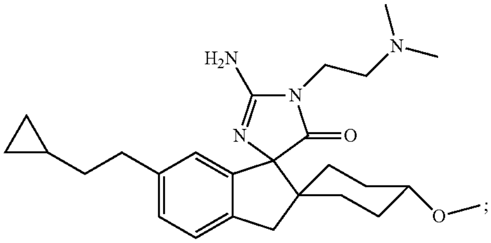
;
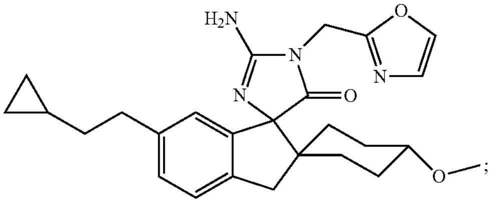
;
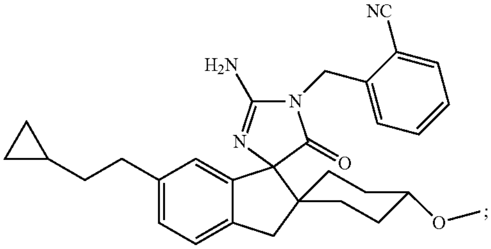
;
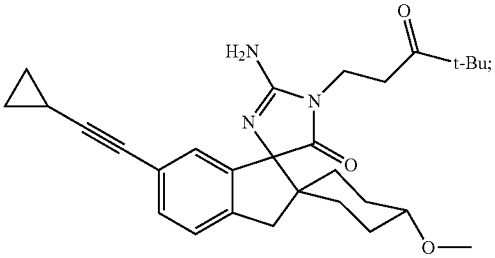
;
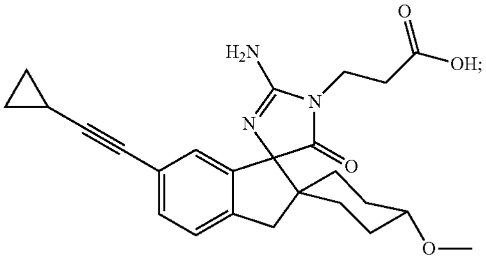
;
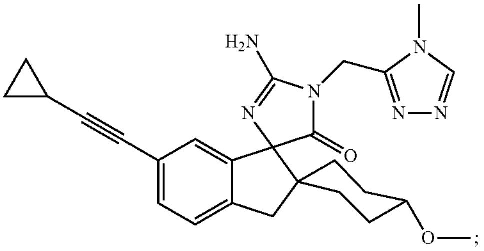
;
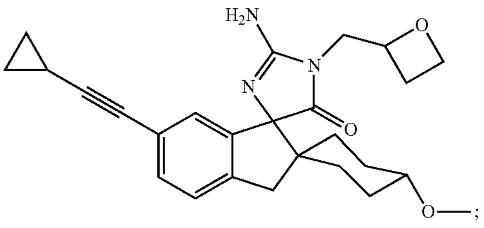
;
-continued
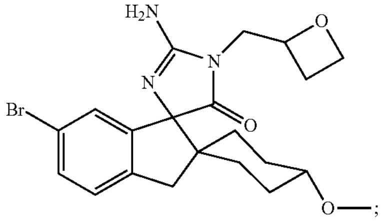
;
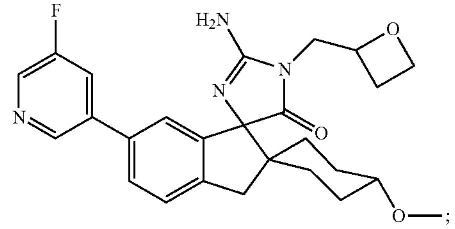
;
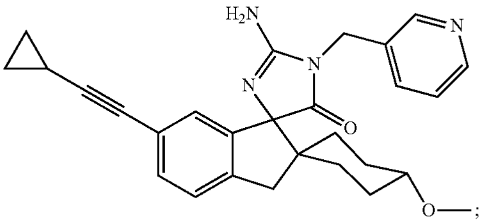
;
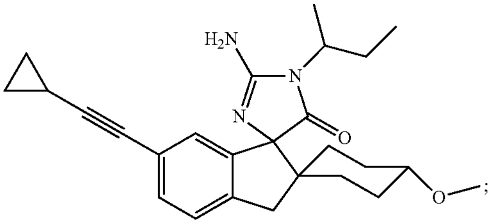
;
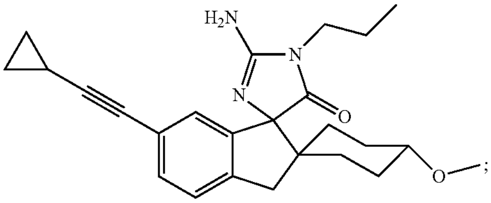
;
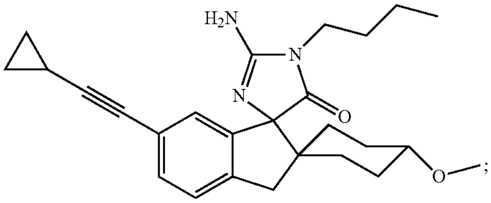
;
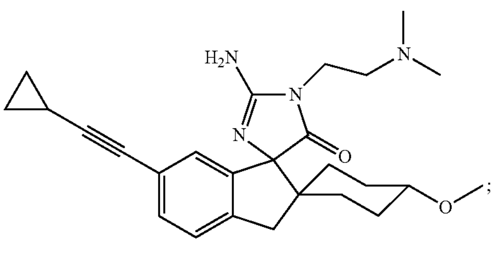
;

-continued
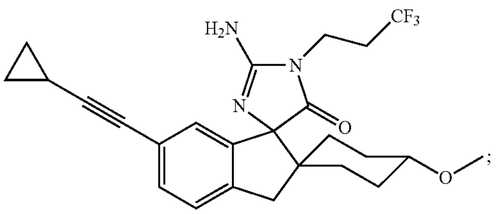
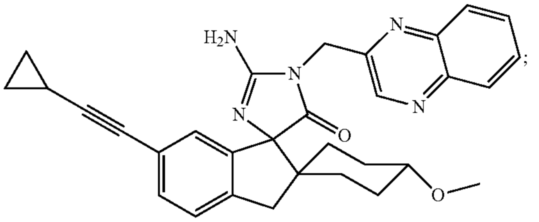
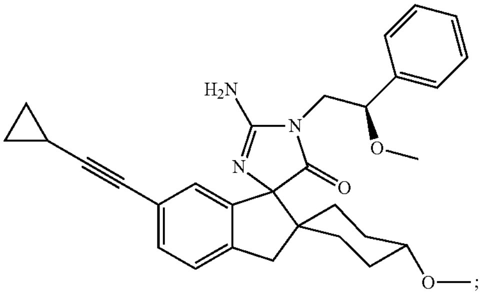
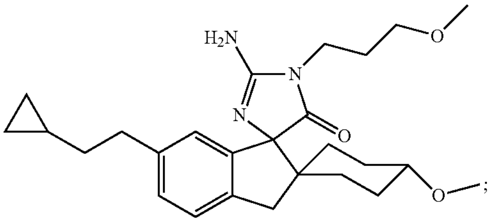
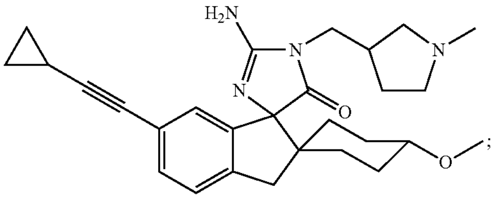
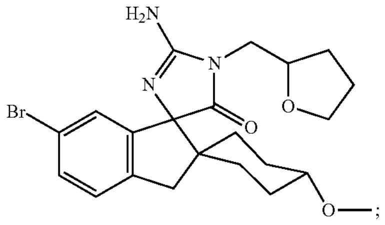
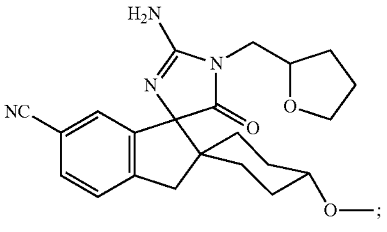
-continued
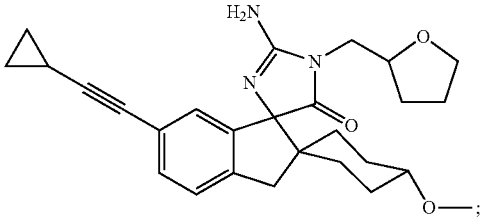
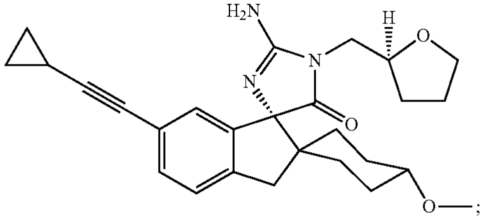
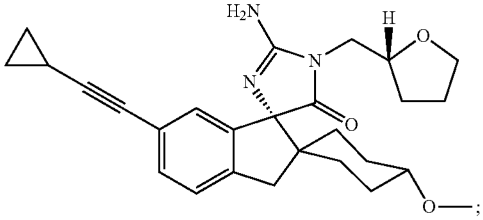
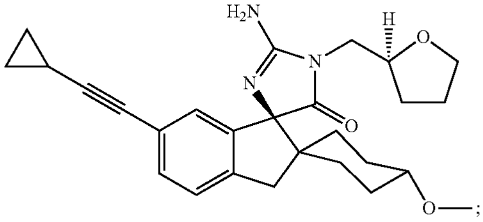
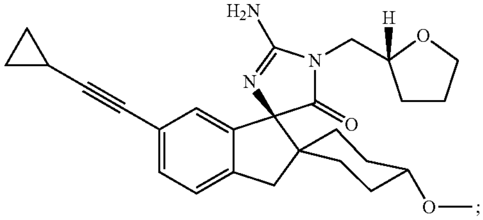
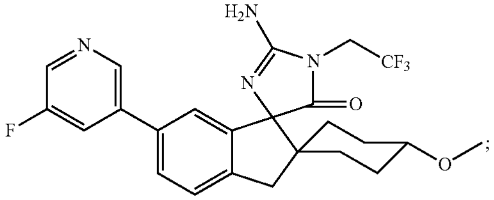
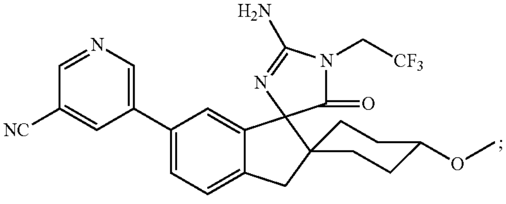
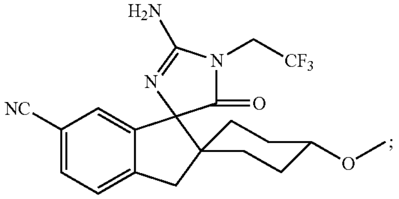

-continued
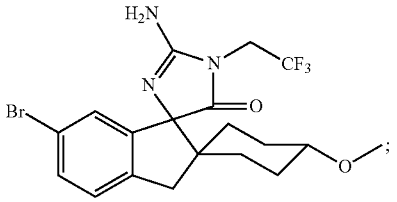
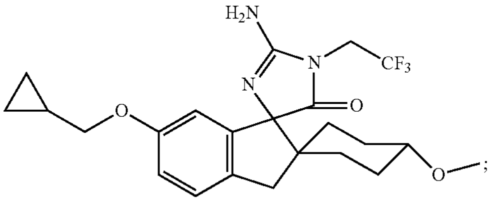
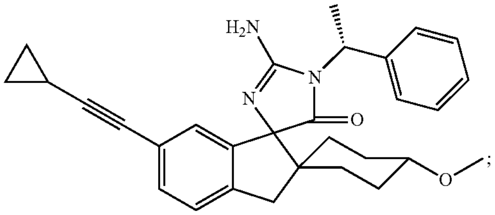
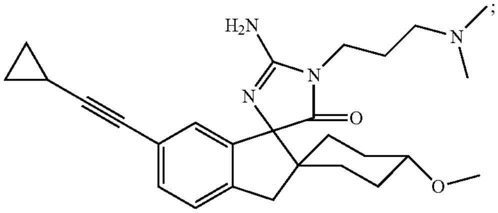
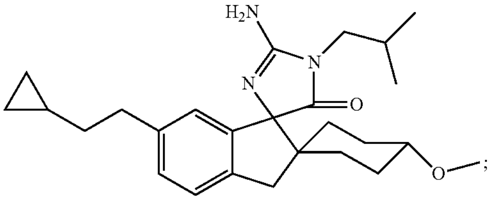
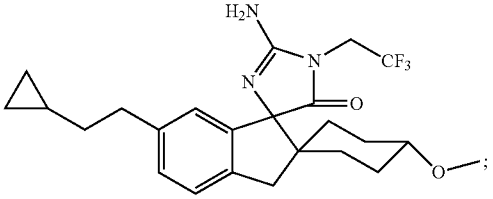
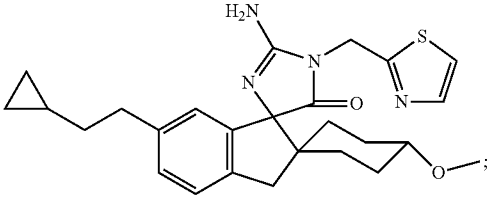
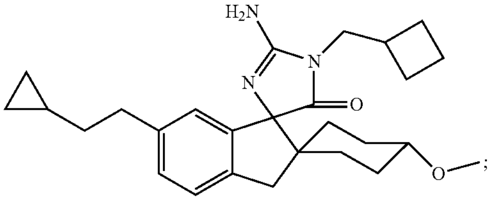
-continued
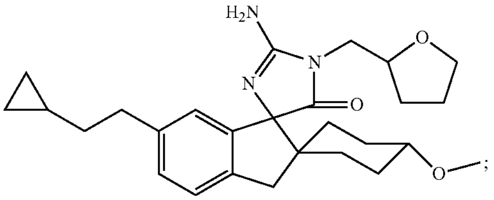
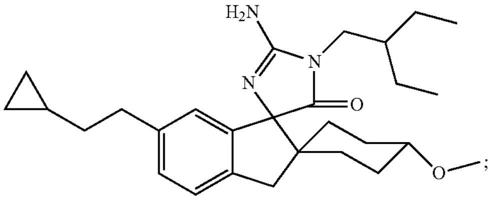
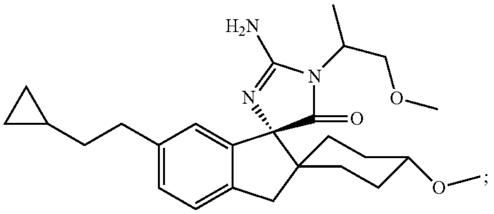
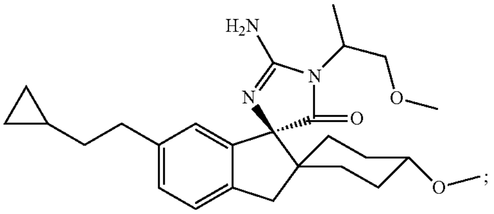
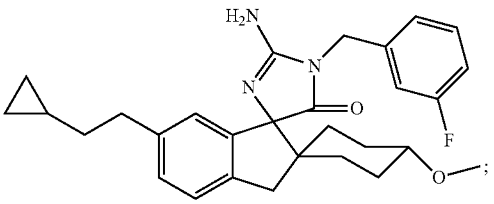
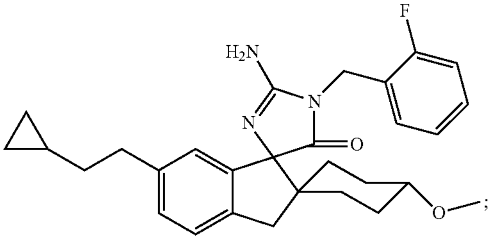
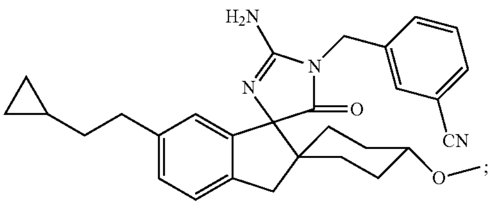

-continued
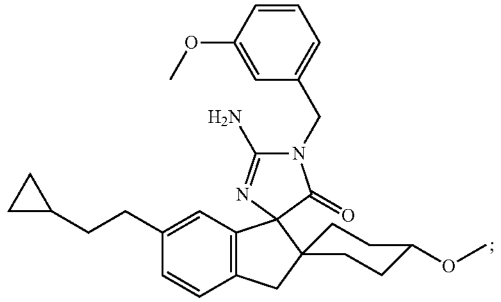
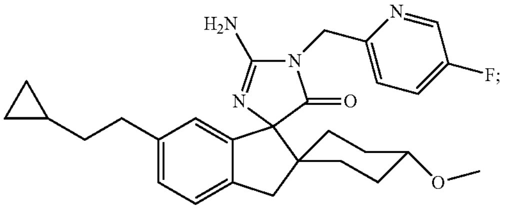
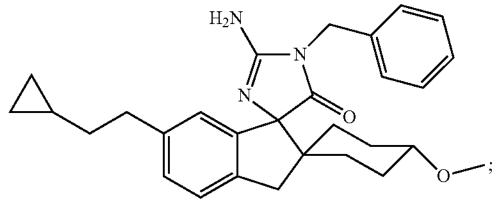
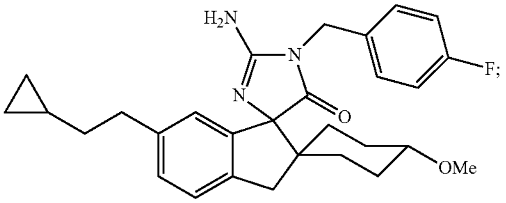
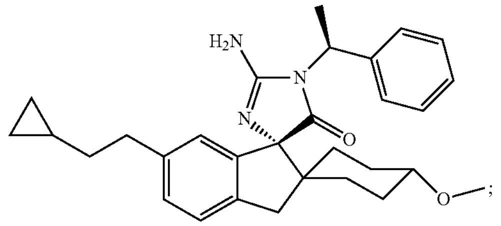
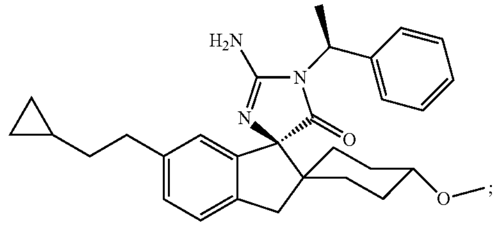
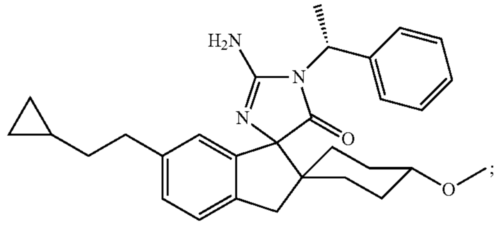
-continued
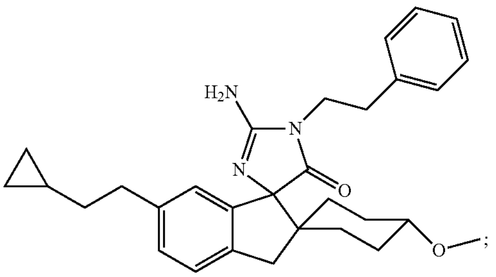
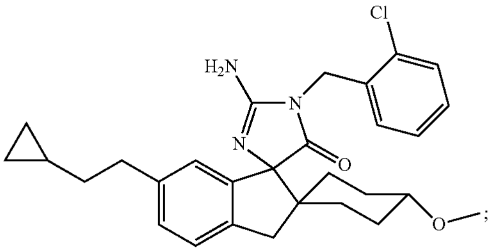
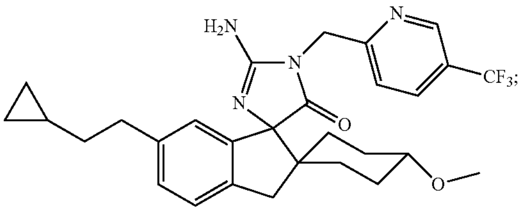
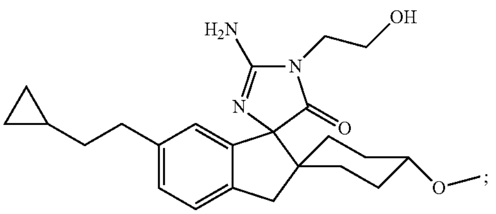
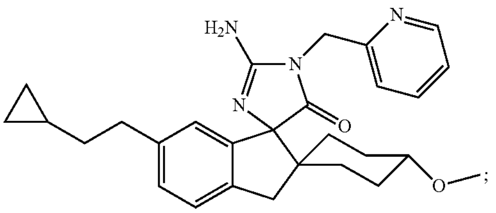
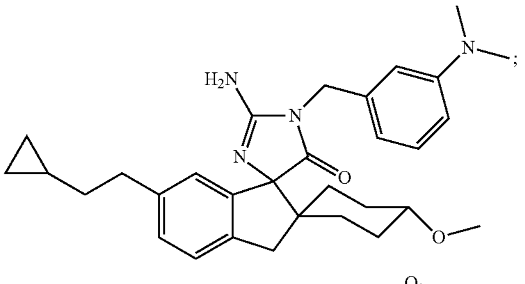
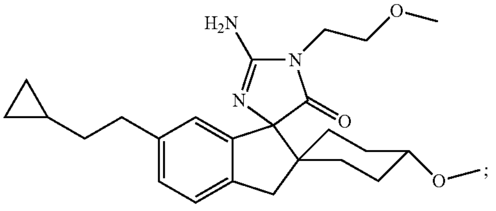

-continued
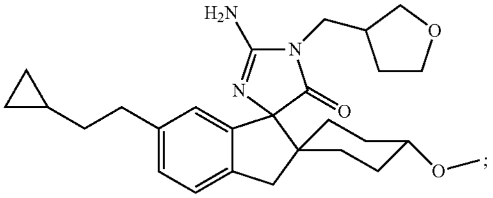
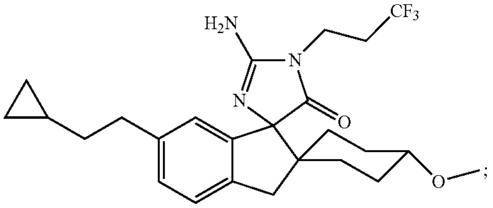
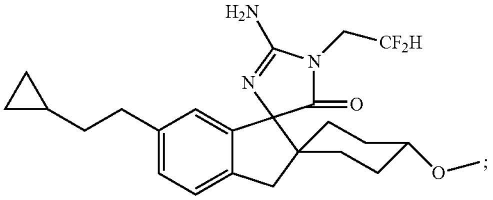
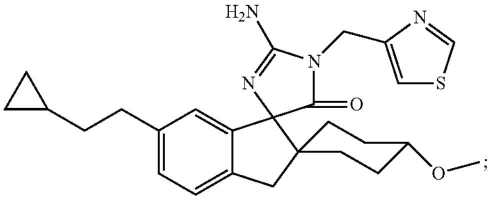
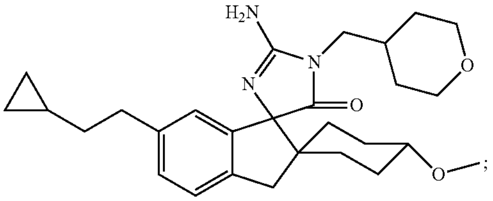
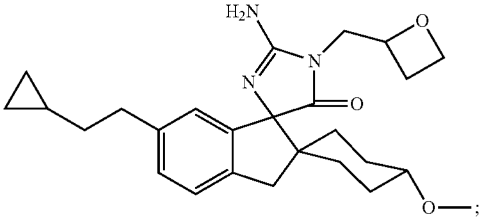
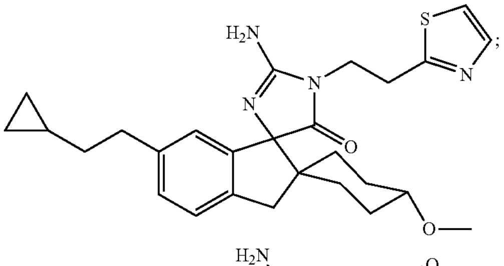
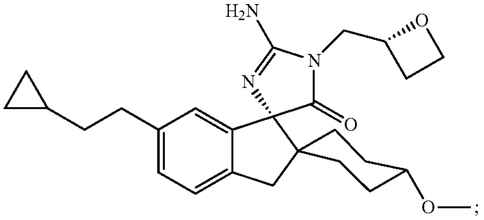
-continued
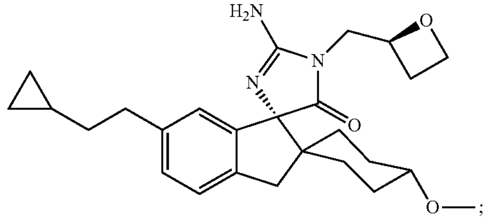
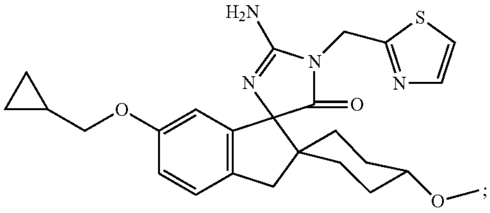
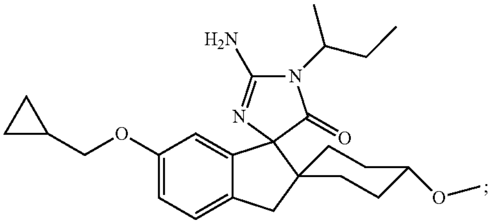
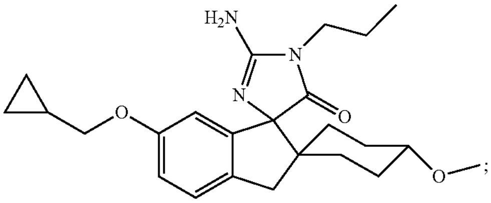
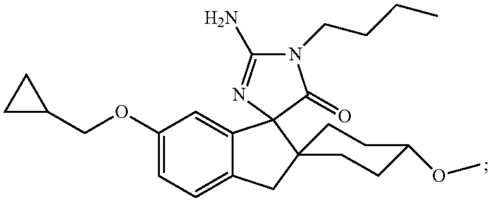
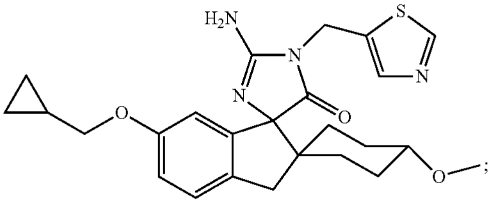
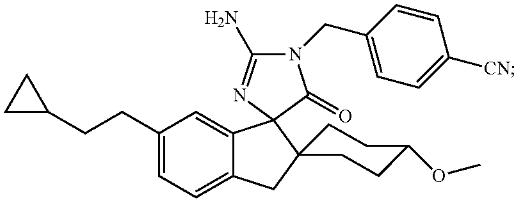
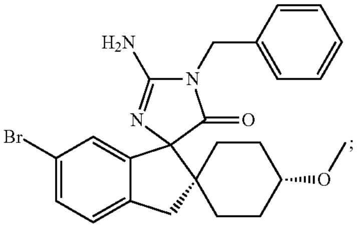

-continued
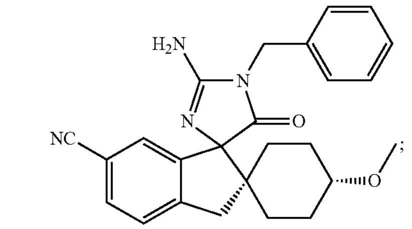
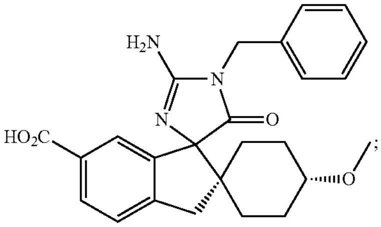
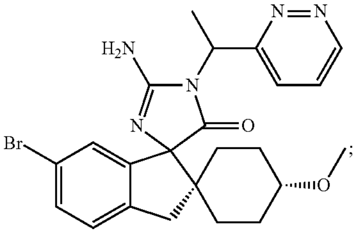
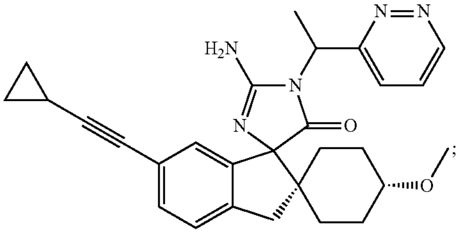
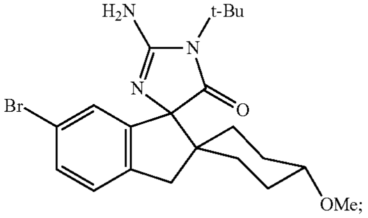
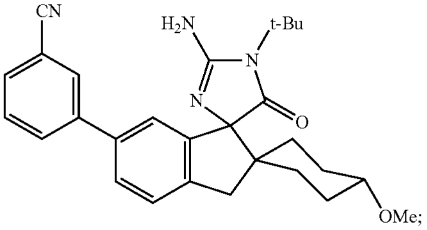
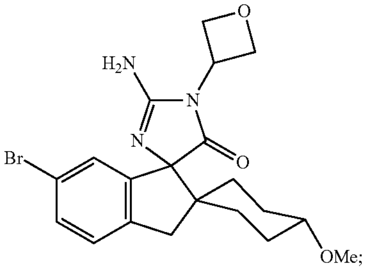
-continued
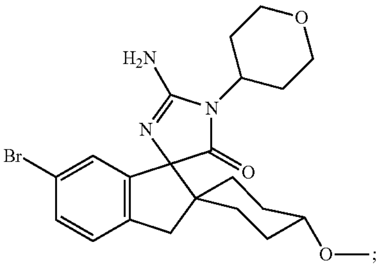
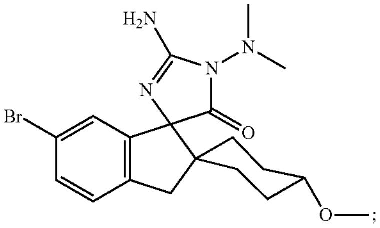
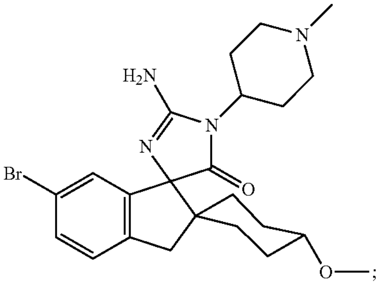
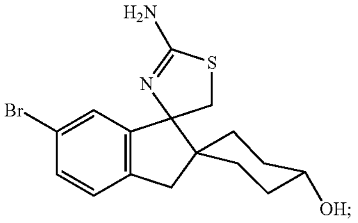
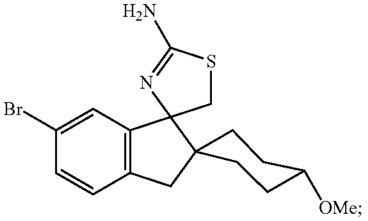
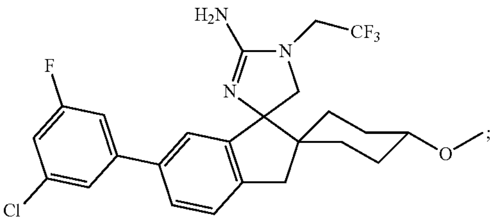
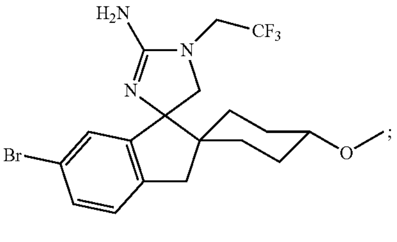

-continued
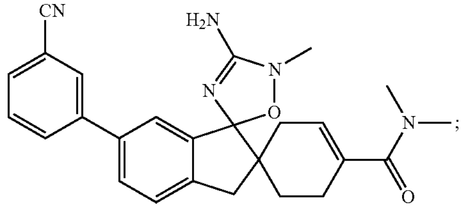
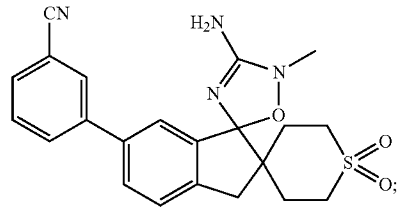
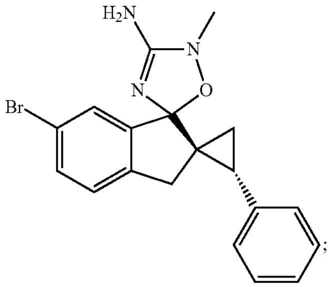
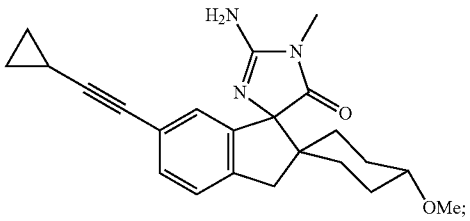
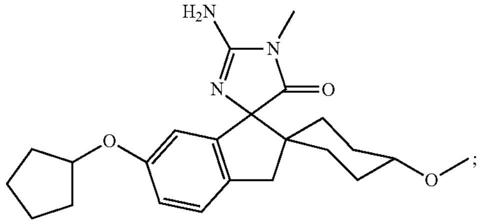
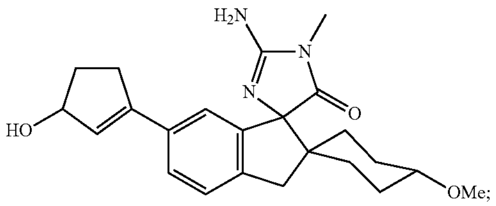
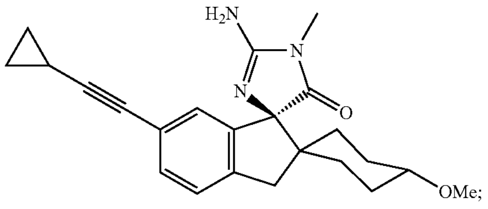
-continued
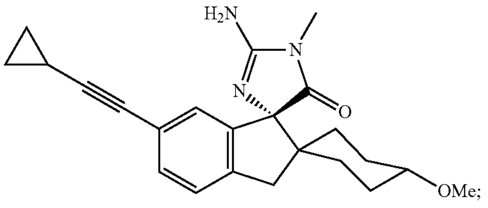
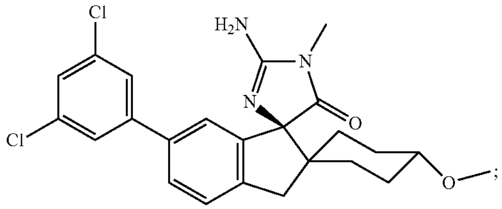
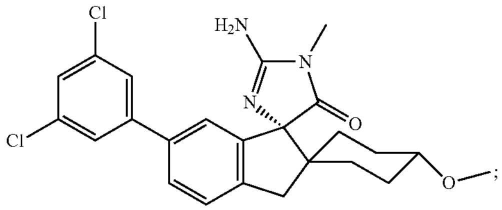
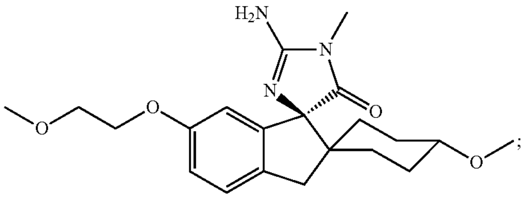
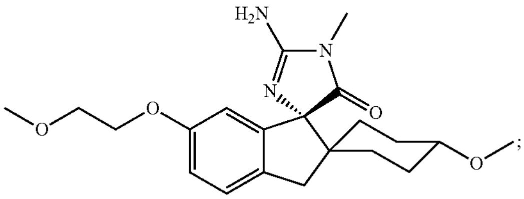
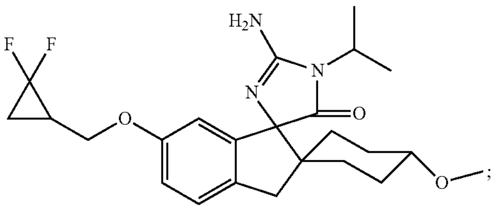
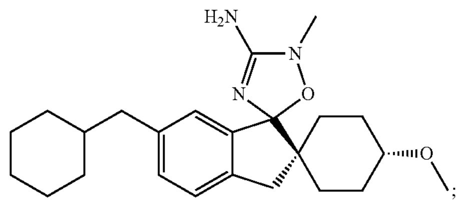
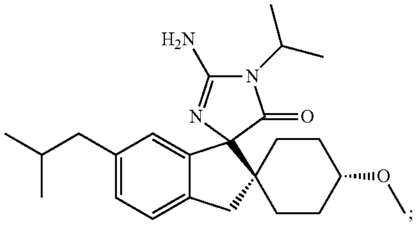

-continued
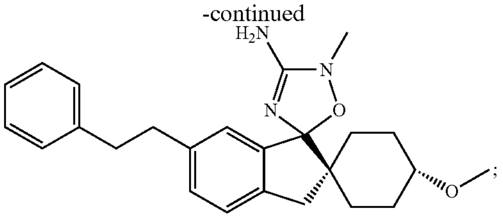
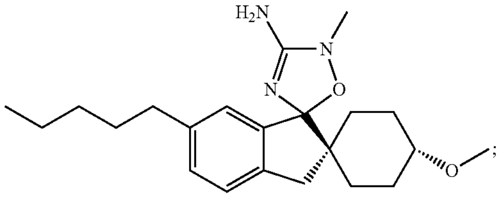
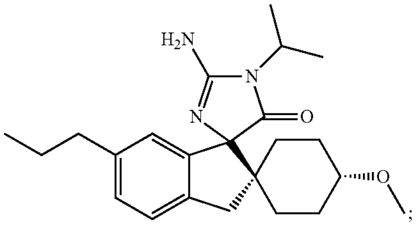
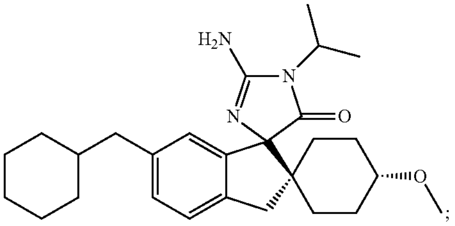
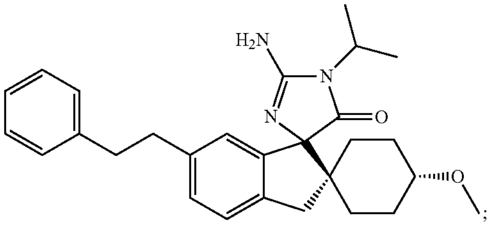
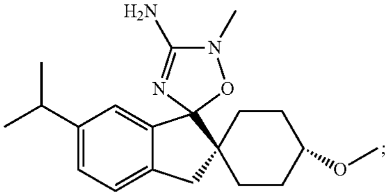
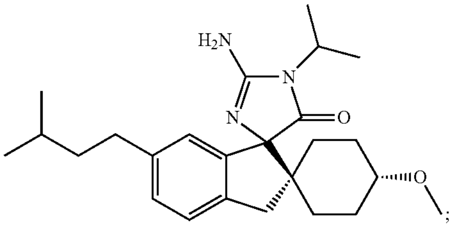
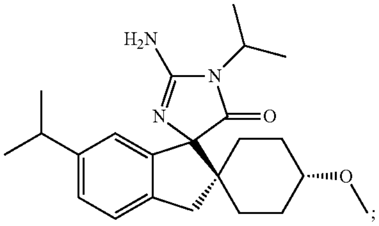
-continued
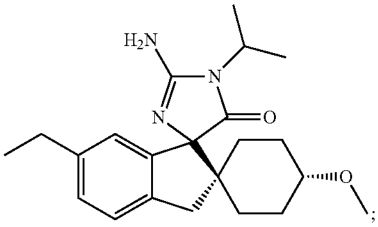
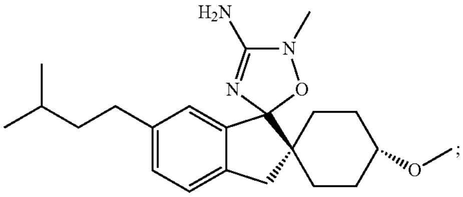
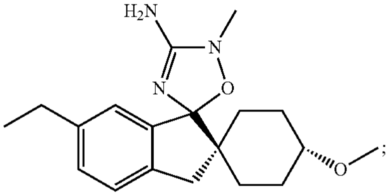
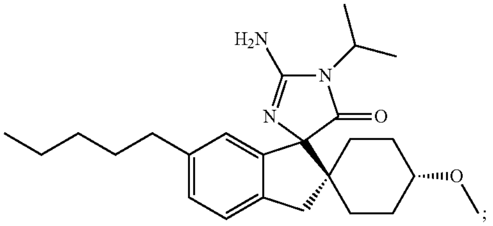
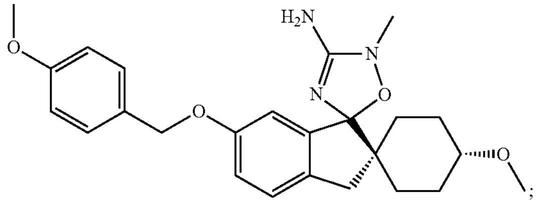
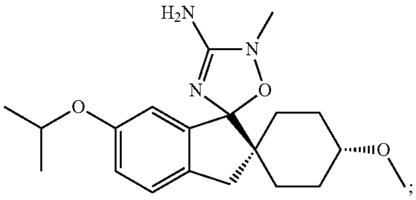
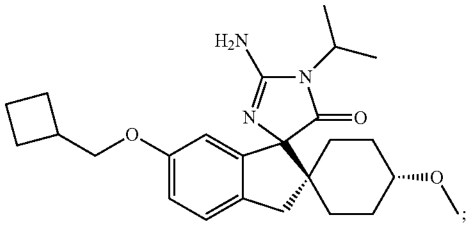
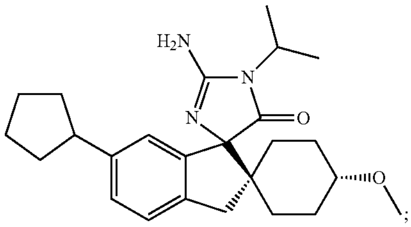

-continued
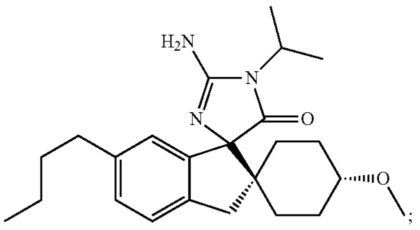
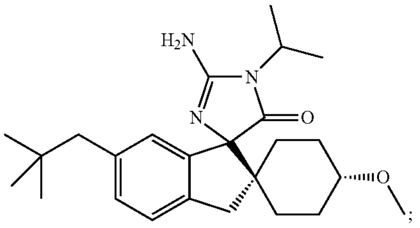
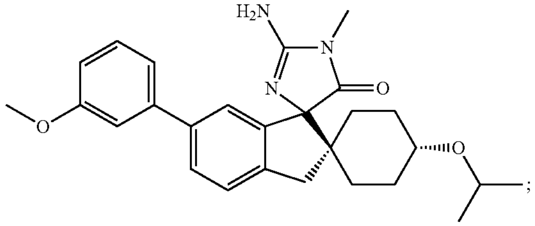
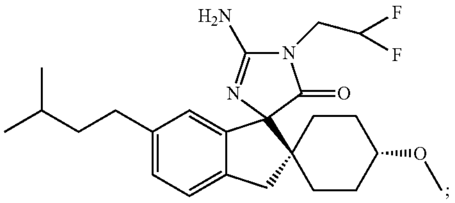
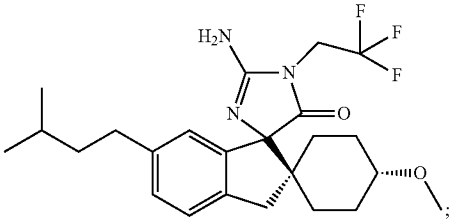
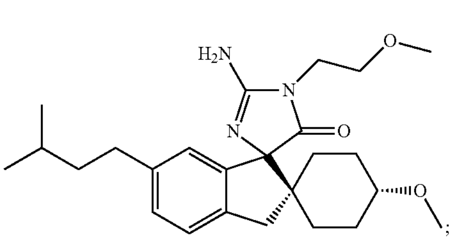
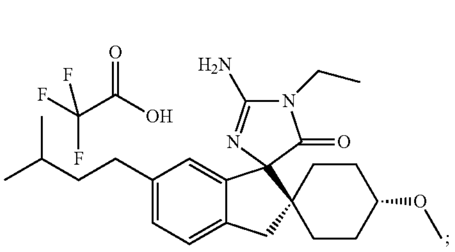
-continued
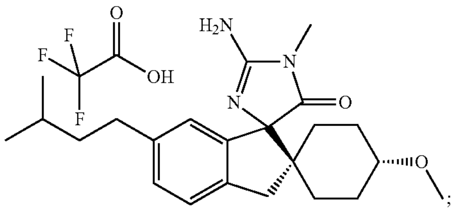
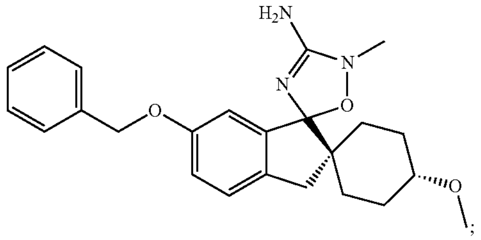
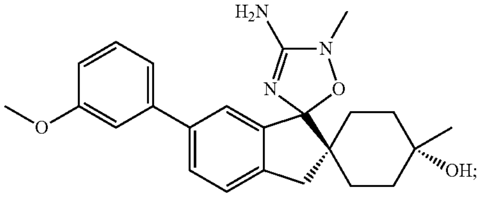
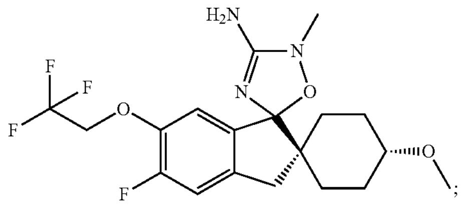
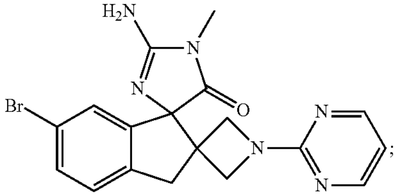
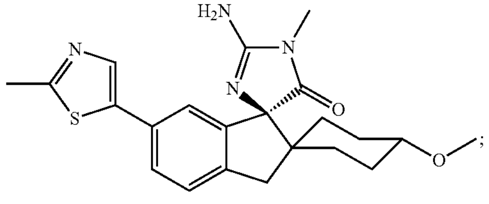
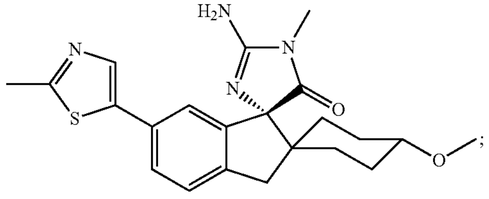
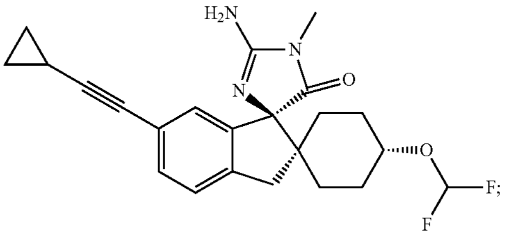

-continued
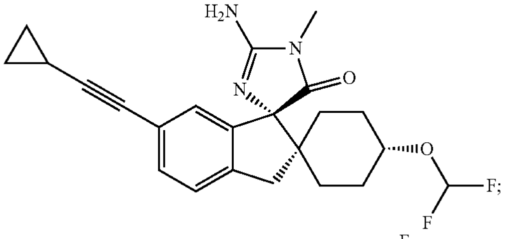
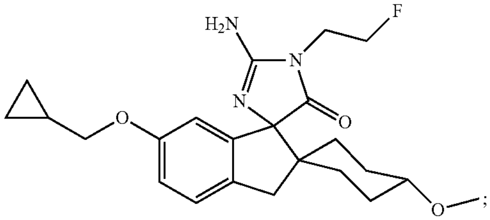
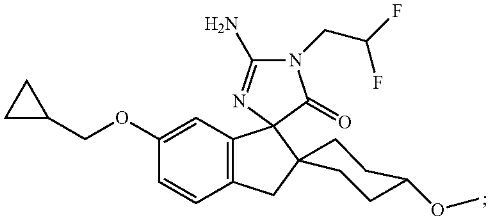
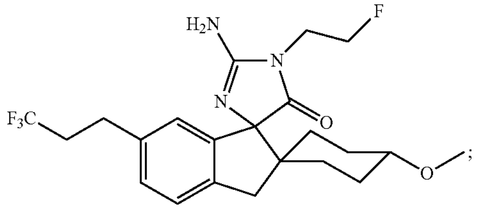
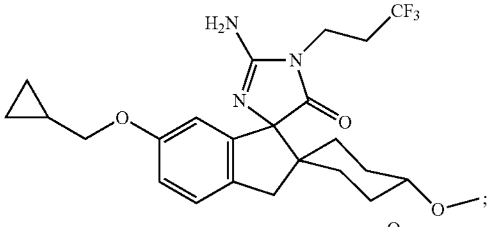
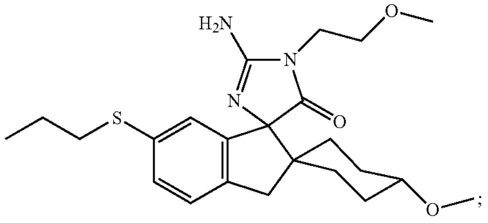
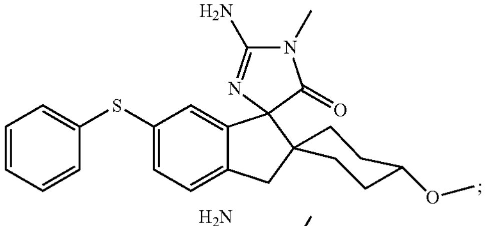
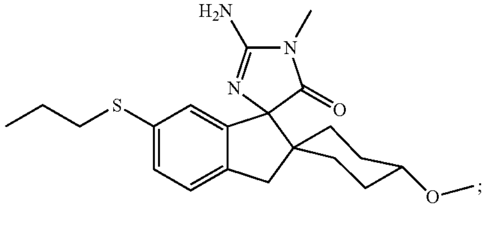
-continued
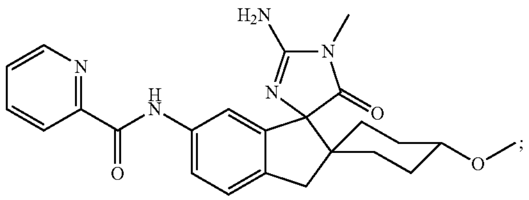
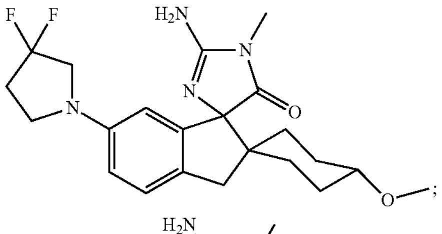
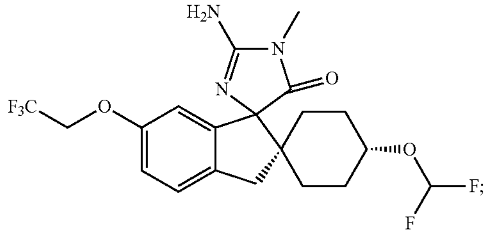
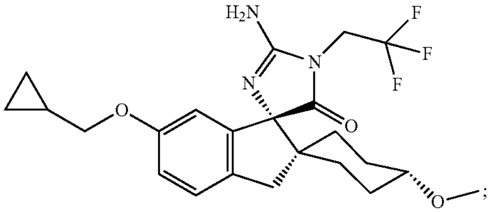
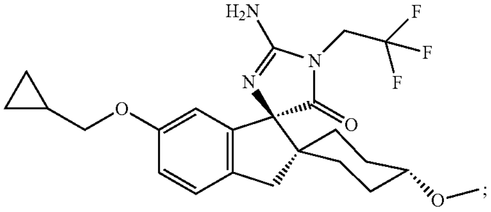
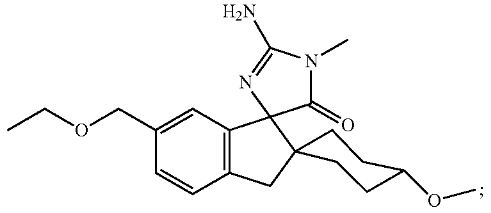
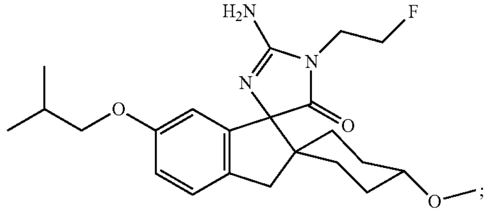
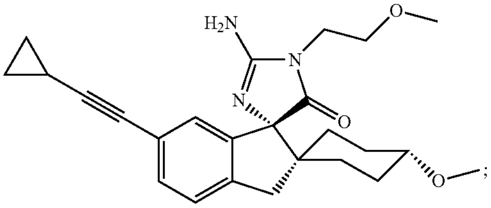

-continued
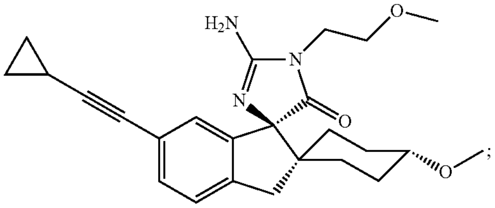
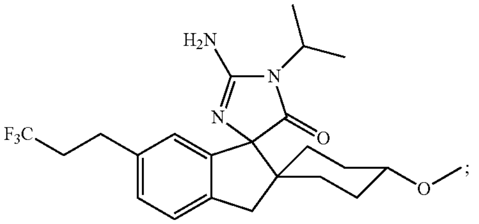
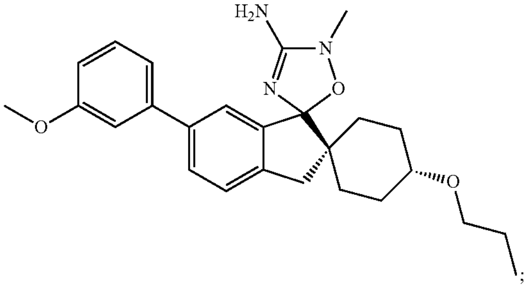
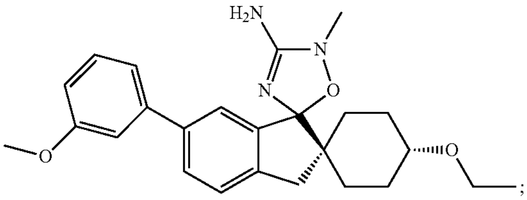
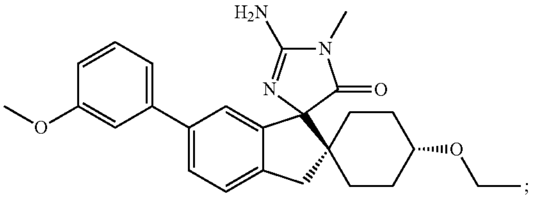
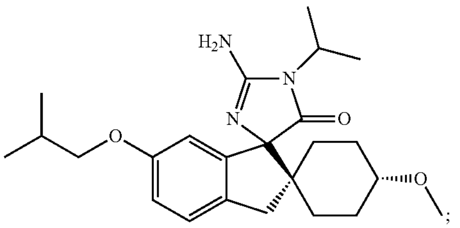
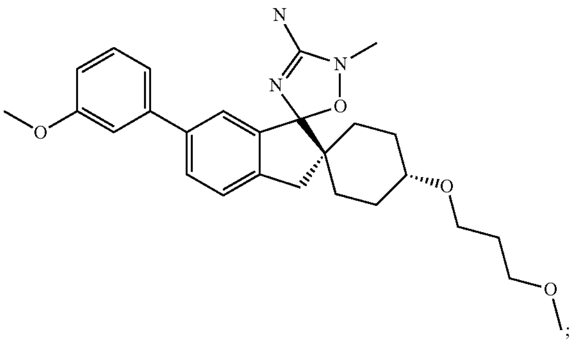
-continued
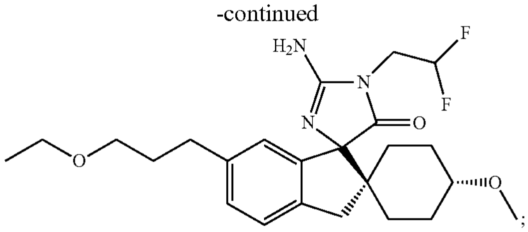
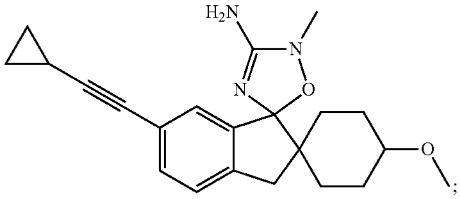
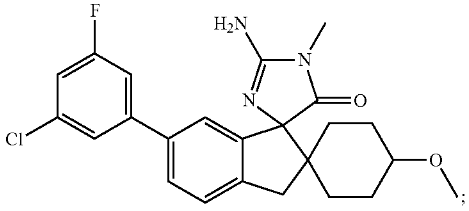
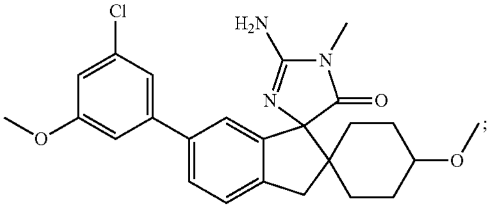
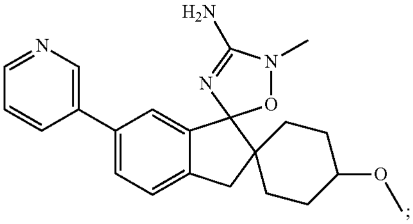
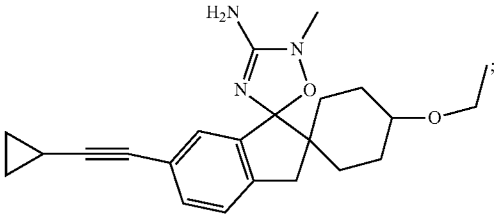
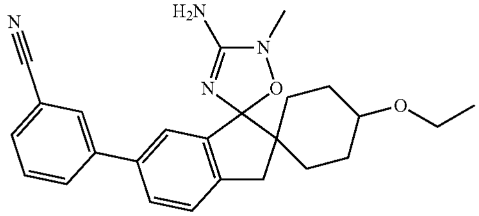
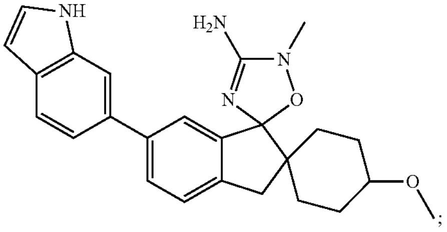

-continued
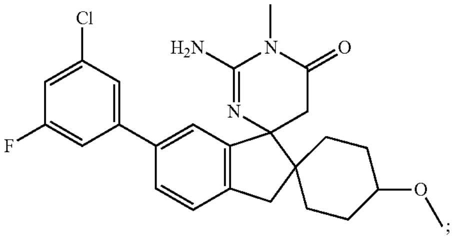
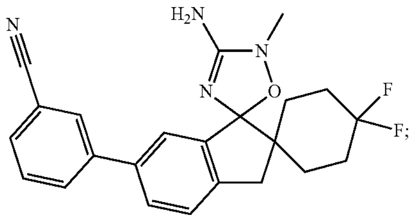
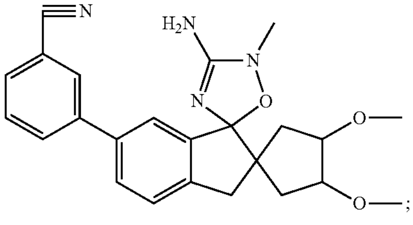
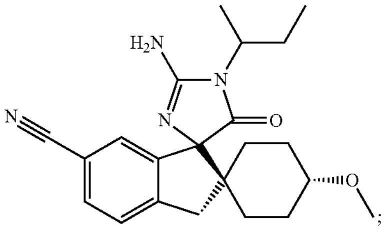
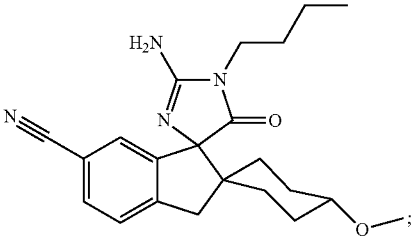
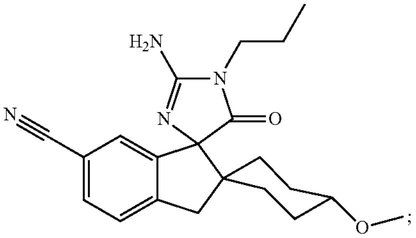
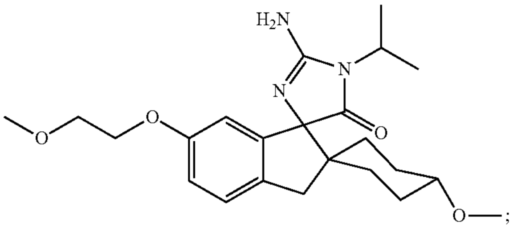
-continued
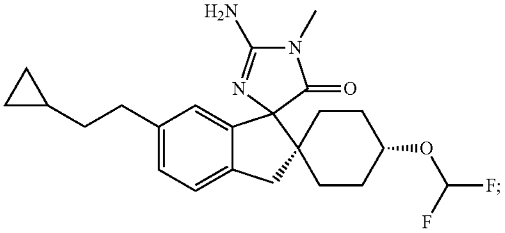
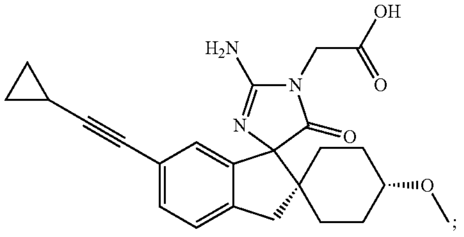
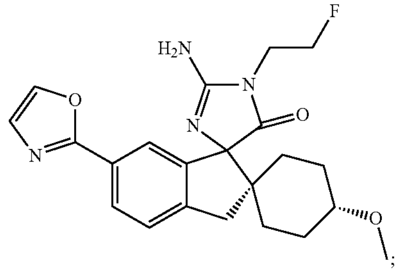
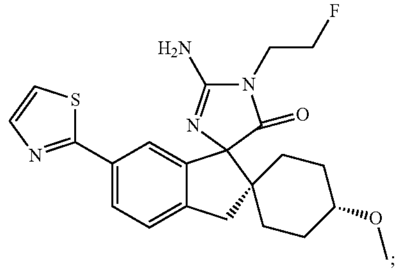
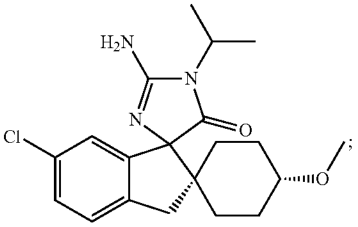
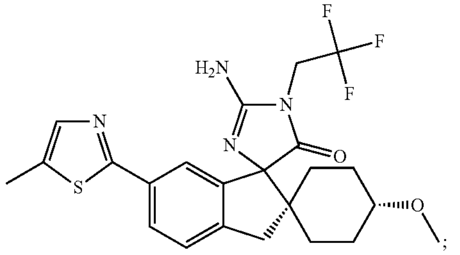
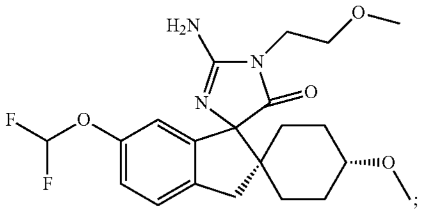

-continued
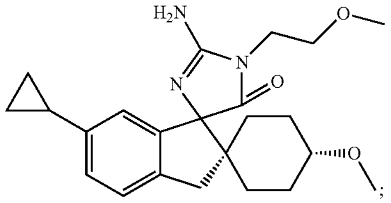
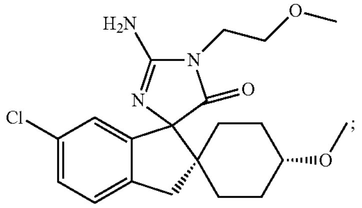
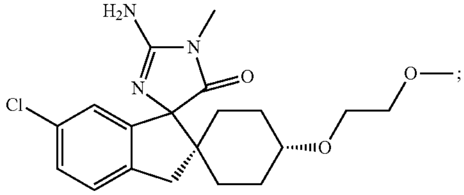
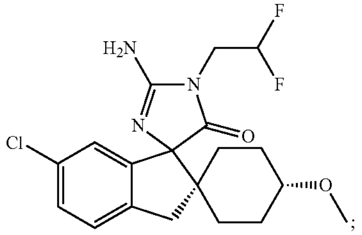
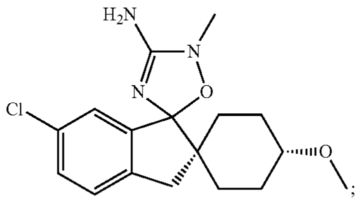
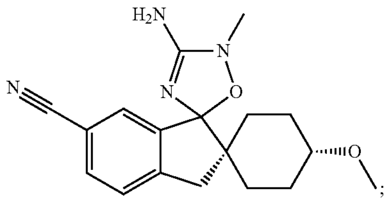
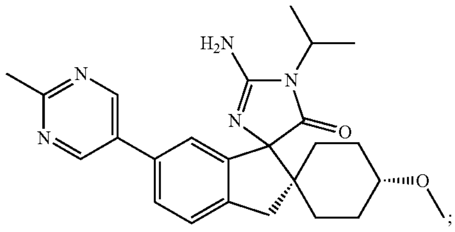
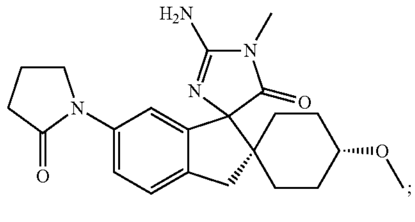
-continued
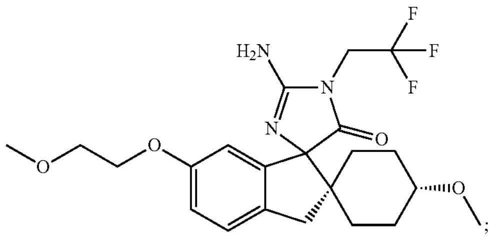
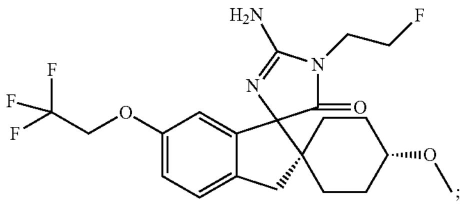
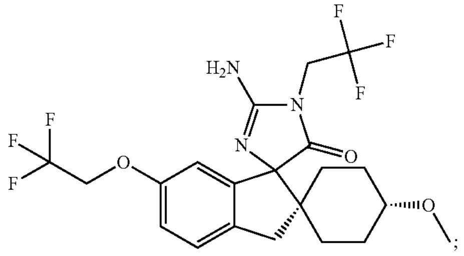
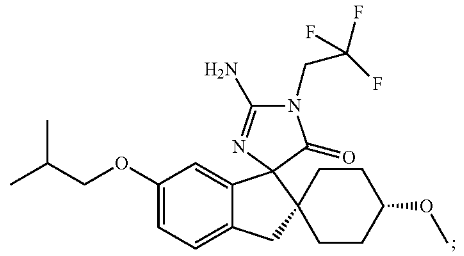
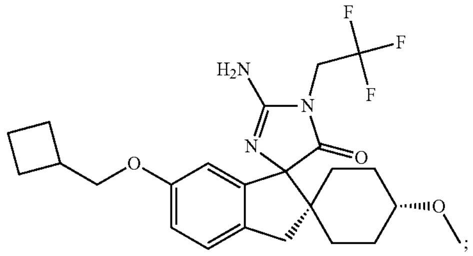
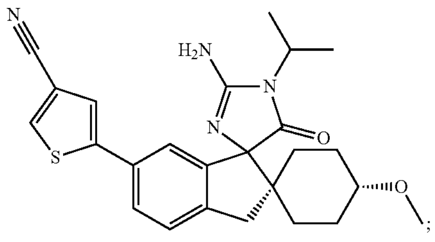
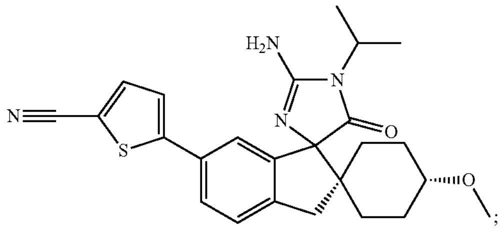

-continued
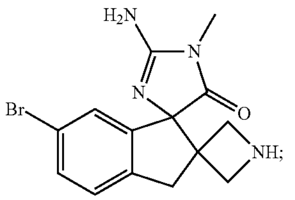
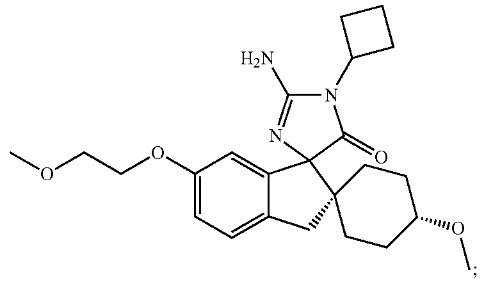
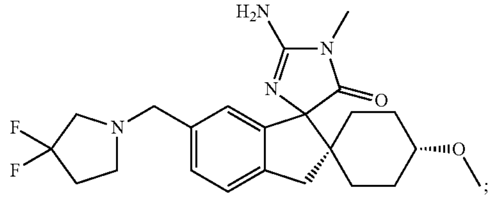
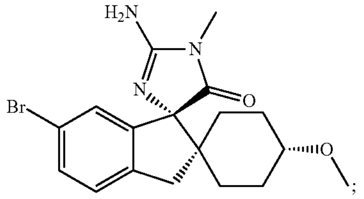
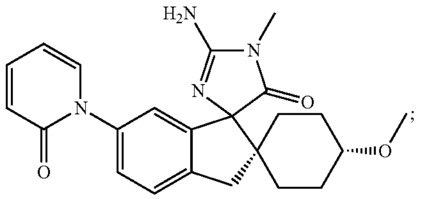
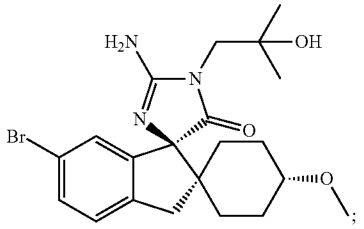
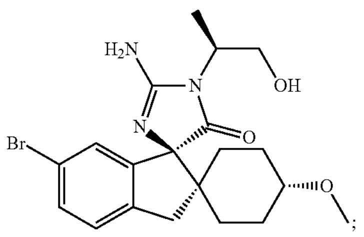
-continued
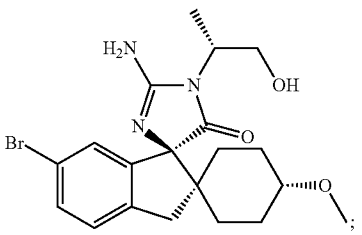
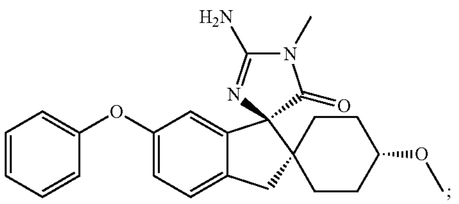
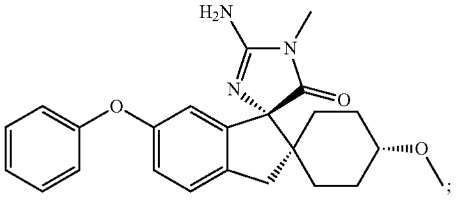
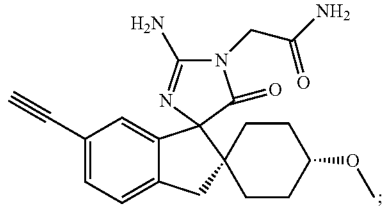
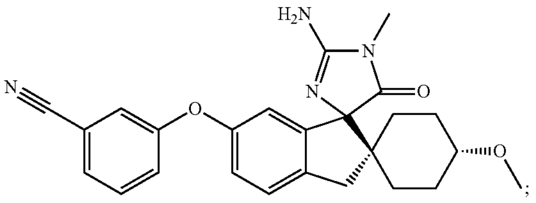
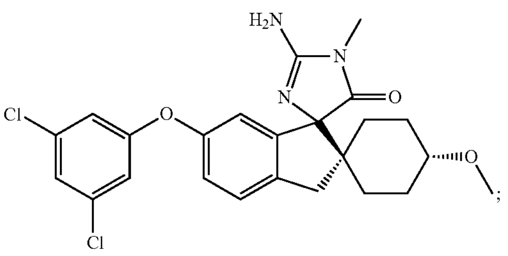
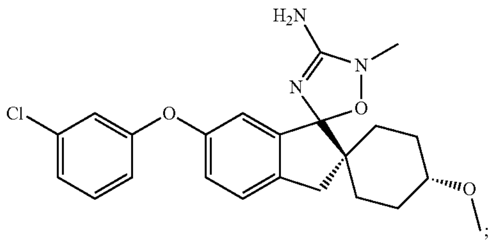

-continued
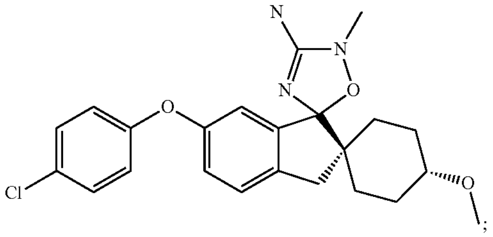
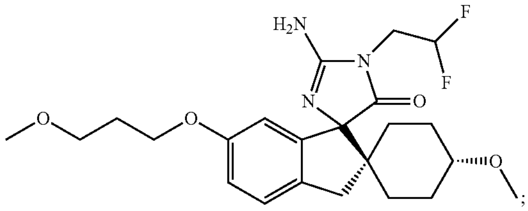
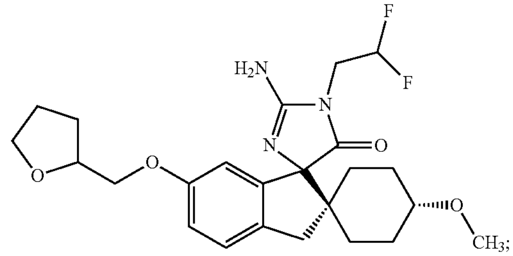
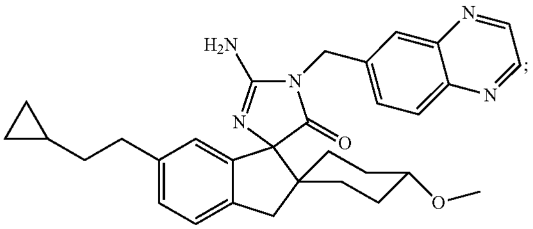
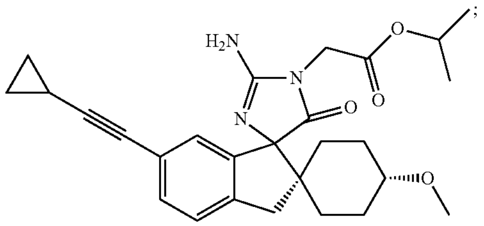
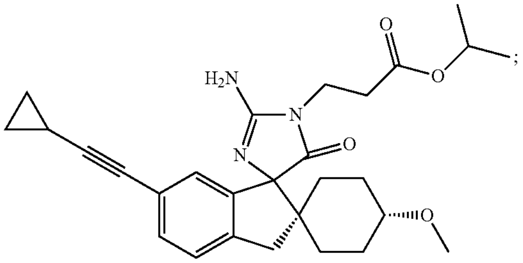
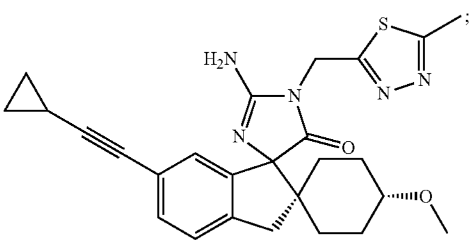
-continued
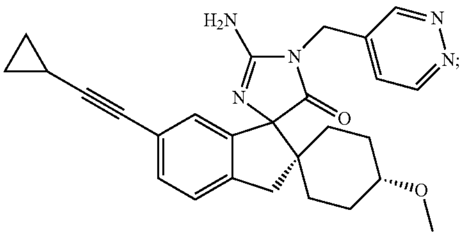
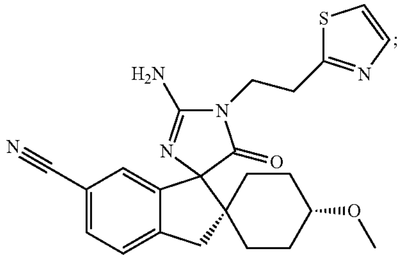
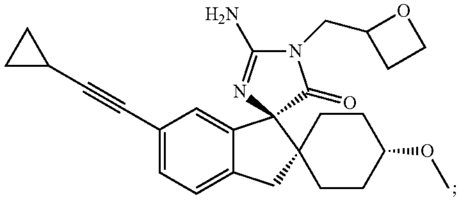
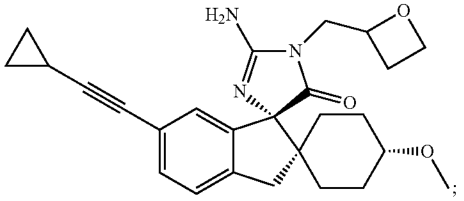
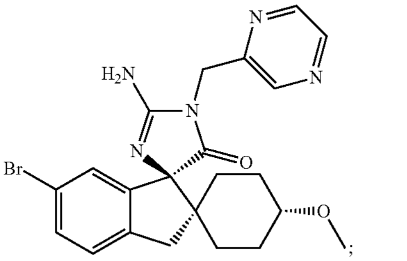
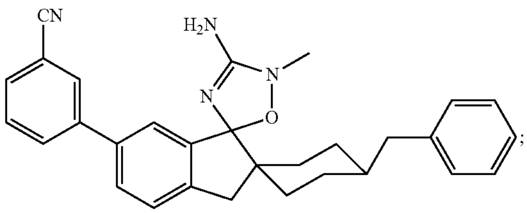
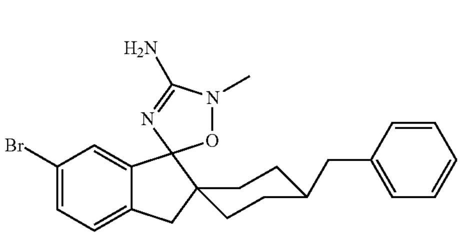

-continued
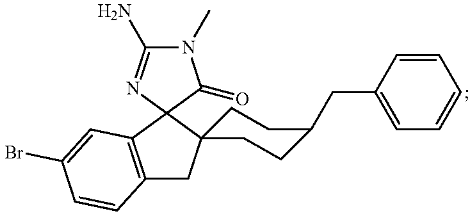
;
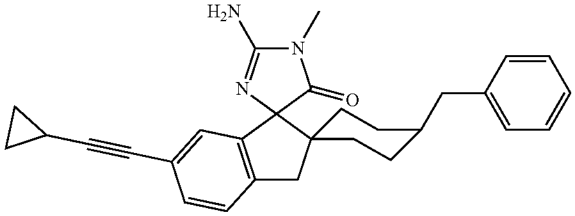
and
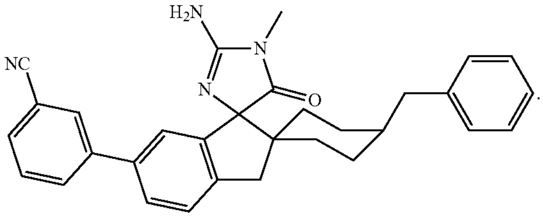
.
* * * * *